(12) United States Patent
Zhu

(10) Patent No.: US 6,589,758 B1
(45) Date of Patent: Jul. 8, 2003

(54) CRYSTAL OF A KINASE-LIGAND COMPLEX AND METHODS OF USE

(75) Inventor: Xiaotian Zhu, Watertown, MA (US)

(73) Assignee: Amgen Inc., Thousand Oaks, CA (US)

( * ) Notice: Subject to any disclaimer, the term of this patent is extended or adjusted under 35 U.S.C. 154(b) by 1 day.

(21) Appl. No.: 09/862,154

(22) Filed: May 21, 2001

Related U.S. Application Data

(60) Provisional application No. 60/205,510, filed on May 19, 2000.

(51) Int. Cl.$^7$ .............................. C12Q 1/48; C12Q 1/00; C07K 1/00
(52) U.S. Cl. .............................. 435/15; 435/4; 530/350
(58) Field of Search ........................ 435/15, 4; 530/350

(56) References Cited

FOREIGN PATENT DOCUMENTS

WO          WO 200070030 A1 *    5/2000

OTHER PUBLICATIONS

Ausubel, F.M., et al. *Current Protocols in Moleuclar Biology*, vol. 1, John Wiley & Sons, Inc.(1999).

Alberola–Ila, J., et al., *Differential signaling by lymphocyte antigen receptors, Annu. Rev. Immunol.* 15, 125–154, (1997).

Barber, E.K., et al. *The CD4 and CD8 antigens are coupled to a protein–tyrosine kinase (p561ck) that phosphorylates the CD3 complex, Proc. Natl. Acad. Sci. U S A* 86, 3277–3281 (1989).

Berridge, M.J., *Lymphocyte activation in health and disease, Critical reviews in Immunology*, 17, 155–178, (1997).

Bougeret, C. et al., *Detection of a physical and functional interaction between Csk and Lck which involved the SH2 domain of Csk and is mediated by autophosphorylation of Lck on tyrosine 394., J. Biol. Chem.* 271, 7465–7472 (1996).

Braunwalder, A.F., et al., *A solid–phase assay for the determination of protein tyrosine kinase activity of c–src using scintillating microtitration plates, Anal. Biochem.*, 234 (1): 23–26 (1996).

Brunet, *Akt promotes cell survival by phosphorylating and inhibiting a forkhead transcription factor, Cell* 96: 857–868 (1999).

Brunger, A. T., et al., *Slow–cooling protocols for crystallographic refinement by simulated annealing, Acta Crystallogr.* A 46, 585–593 (1990).

Buchdunger, E. et al., *Inhibition of the Abl protein –tyrosine kinase in vitro and in vivo by a 2–Phenylaminopyrimidine Derivative, Cancer Research*, 56, 100–104 (1996).

Bugg, C.E. et al., *Drugs by Design, Scientific American*, Dec.:92–98 (1993).

(List continued on next page.)

Primary Examiner—Louise N. Leary
(74) Attorney, Agent, or Firm—Mary Susan Howard; Ron K. Levy; Steven M. Odre

(57) ABSTRACT

The invention relates to the three-dimensional structure of a crystal of a kinase enzyme complexed with a ligand. The three-dimensional structure of a protein kinase-ligand complex is disclosed. The invention also relates to methods of preparing such crystals. Kinase-ligand crystal structures wherein the ligand is an inhibitor molecule are useful for providing structural information that may be integrated into drug screening and drug design processes. Thus, the invention also relates to methods of using the crystal structure of kinase enzyme-ligand complexes for identifying, designing, selecting, or testing inhibitors of kinase enzymes, such inhibitors being useful as therapeutics for the treatment or modulation of i) diseases; ii) disease symptoms; or iii) the effect of other physiological events mediated by kinases; having one or more kinase enzymes involved in their pathology.

36 Claims, 13 Drawing Sheets

(7 of 13 Drawing Sheet(s) Filed in Color)

OTHER PUBLICATIONS

Chalupny, N. J., et al., *Association of CD8 with p56lck is required for early T Cell signaling events*, Embo J. 10, 1201–1207 (1991).

Chan, A.C., et al., *The zeta chain is associated with a tyrosine kinase and upon T–cell antigen receptor stimulation associates with ZAP–70, a 70–kDa tyrosine*, Proc. Natl. Acad. Sci. U S A 88, 9166–9170, (1991).

Chan, A.C., et al., *Activation of ZAP–70 kinase activity by phosphorylation of tyrosine 493 is required for lymphocyte antigen receptor funtion*, Embo J. 4, (11), 2499–2508, (1995).

Chu, K. et. al., *Requirement for kinase activity of CD4–associated p56lck in antibody–triggered T cell signaling transduction*, , J. Biol. Chem 269, 24095–24101, (1994.

Dunbrack et al., *Meeting Review: the Second Meeting on the Critical Assessment of Techniques for Protein Structure Prediction* (CASP2), Folding & Design, (2) 2: R27–42 (1997).

Evans, S.V. SETOR: *hardware–lighted three–dimensional solid model representations of macromoleucles*, J. Mol. Graph. 11, 134–138, 127–128 (1993).

Fieser, L., et al., *Fieser & Fieser's Reagents for Organic Synthesis*, John Wiley & Sons (1994).

Gervais, F. G., et al., *The SH2 domain is required for stable phosphorylation of p56lck at tyrosine 505, the negative regulatory site*, Mol. Cell. Biol. 13, 7112–7121, (1993).

Gish et al., *Bacterial expression, purification and preliminary kinetic description of the kinase domain of v–fps*, Protein Engineering, (3) 6: 609–614, (1995).

Glover, D., ed, *DNA Cloning*, vols. I & II (1985).

Greene, T.W. et al., *Protective Groups in Organic Synthesis*, $2^{nd}$ Ed., John Wiley & Sons (1991).

Hames, B.D., et. al., eds. ,*Nucleic Acid Hybridization, A Practical Approach*, IRL Press (1985).

Hanke, J. H., et al., *Discovery of a novel, potent, and Src family–selective tyrosine kinase inhibitor. study of Lck– and FynT–dependent T cell activation*, J. Biol. Chem. 271, 695–701, (1996).

Hardie et al., *The Protein Kinase Facts Book*, I & II, Academic Press, San Diego, CA (1995).

Henning, S. W., et al., *p56lck signals for regulating thymocyte development can be distinguished by their dependency on Rho function*, J. Exp. Med. 188, 931–939 (1998).

Hubbard, S. R., *Crystal structure of the activated insulin receptor tyrosine kinase in complex with peptide substrate and ATP analog*, Embo J., 16, 5572–5581,(1997).

Huse, M., et al., *A $Zn^2+$ ion Links the cytoplasmic Tail of CD4 and the N–terminal Region of Lck*, J Biol. Chem. 273, 18729–18733 (1998).

Isakov, N., et al., *ZAP–70 Binding Specificity to T Cell Receptor Tyrosine–based Activation Motifs: The Tandem SH2 Domains of ZAP–70 Bind Distinct Tyrosine–based Activation Motifs with Varying Affinity*, J. Exp. Med., 181, 375–380 (1995).

Jullien, P., et al., *Tyr 394 and Tyr505 are autophosphorylated in recombinant Lck on protein–tyrosine kinase expressed in Escherichia coli*, Eur. J. Biochem., 224, 589–596(1994).

Kaga, S., Activation of p21–CDC42/Rac–activated kinases by CD28 signaling: p21–activated kinase (PAK) and MEK kinase 1 (MEKK1) may mediate the interplay between CD3 and CD28 signals, Journal of Immunology 160: 4182–4189 (1998).

Kersh, E. N., et al., Fidelity of T cell activation through multistep T cell receptor zeta phosphorylation, Science 281, 572–575 (1998).

Kim, Y.H., et al., Up–regulation of c–myc induces the gene expression of the murine homologues of $p34^{cdc2}$ and cyclin–dependent kinase–2 in T lymphocytes, J. Immunol. 152, 4328–4333 (1994).

Knighton, D. R., et al., Crystal structure of catalytic subunit of cyclic adenosine monophospate–dependent protein kinase, Science 253, 407–414 (1991).

Knighton, D. R., et al., Structure of a peptide inhibitor bound to the catalytic subunit of cyclic adenosine monophosphate–dependent protein kinase, Science 253, 414–420 (1991).

Kuduva, S. S., et al., Crystal Engineering Considerations and the Role of C–H O Hydrogen Bonds in Determining O–HO Networks., J. Am. Chem. Soc. 121, 1936–1944, (1999).

Lamers, M.B., et al., Structure of the protein tyrosine kinase domain of C–terminal Src kinase (CSK) in complex with staurosporine. J. Mol. Biol., 285, 713–725 () 1999.

Larock, R., *Comprehensive Organic Transformations*, VCH Publishers (1989).

Lawrie, A.M., et al., Protein kinase inhibition by staurosporine revealed in details of the molecular interaction with CDK2 Nat. Struct. Biol. 4, 796–801 (1997).

Lehr, R.V., et al., Production, purification and characterization of non–myristylated human T–cell protein tyrosine kinase in a baculovirus expression system, Gene 169 (2): 27527–27529 (1996).

Liu K.D., et al., Janus kinases in interleukin–2–mediated signaling: JAK1 and JAK3 are differentially regulated by tyrosine phosphorylation, Current Biology, 7 (11): 817–826 (1997).

Levin, S.D., et al., The protein tyrosine kinase p56lck regulates thymocyte development independently of its interaction with CD4 and CD8 coreceptors, J. Exp. Med. 178, 245–255 (1993).

Lin, R. S., et al., Zinc is essential for binding of p56(lck) to CD4 and CD8alpha, J Biol. Chem. 273, 18729–18733 (1998).

LoGrasso, P. V., et al., Mechanism of activation for Zap–70 catalytic activity, Proc. Natl. Acad. Sci. U S A, 93, 12165–12170 (1996).

Madrenas, J., et al. Zeta phosphorylation without ZAP–70 activation induced by TCR antagonists or partial agonists, Science 267, 515–518 (1995).

Meggio, F., et. al., Different susceptibility of protein kinases to staurosporine inhibition. Kinetic studies and molecular bases for the resistance of protein kinase CK2, Eur. J. Biochem, 234, 317–322, (1995).

Moarefi, I., et al., Activation of the Src–family tyrosine kinase Hck by SH3 domain displacement, Nature 385, 650–653 (1997).

Mohammadi, et al., Crystal structure of an angiogenesis inhibitor bound to the FGF receptor tyrosine kinase domain, Embo J. 17, 5896–5904, (1998).

Molina, T.J., et al., Profound block in thymocyte development in mice lacking p56lck, Nature 357, 161–164, (1992).

Molina, T.J., et al., Peripheral T cells in mice lacking p56lck do not express signficant antiviral effector functions, J. Immunol., 151, 699–706 (1993).

Morgenstern, K. A., et al. Complementary DNA cloning and kinetic characterization of a novel intracellular serine proteinase inhibitor: mechanism of action with trypsin and factor Xa as model proteinases, Biochemistry 33, 3432–3441 (1994).

Morgenstern, K. A., et al., Polynucleotide modulatin of the protease, nucleoside triphosphatase, and helicase activities of hepatitis C virus NS3–NS4A complex isolated from transftected COS cells., J. Virol. 71, 3767–3775 (1997).

Mustelin, T., et al., Dephosphorylation and activation of the T cell tyrosine kinase pp56lck by the leukocyte common antigen (CD45), Oncogene 5, 809–813 (1990).

Navaza, J., Amo Re: an Automated Package for Molecular Replacement, Acta Crystallographics, Section A, 157–163 (1994).

Nicholls, A., et al., Protein folding and association: insights from the interfacial and thermodynamic properties of hydrocarbons, Proteins, 11, 281–296.

Neumeister, E.N., et al., Binding of ZAP–70 to phosphorylated T–cell receptor zeta and eta enhances its autophosphorylation and generates specific binding sites for SH2 domain–containing proteins. Mol. Cell. Biol, 15, 3171–13178 (1995).

Olayioye, ErB–1 and ErbB–2 acquire distinct signaling properties dependent upon their dimerization partner, Molecular & Cellular Biology, 18 (9): 5042–5051 (1998).

Paquette, L., ed., *Encyclopedia Of Reagents For Organic Synthesis*, John Wiley & Sons (1995).

Prade, L., et al., Staurosporine–induced conformational changes of cAMP–dependent protein kinase catalytic subunit explain inhibitory potential, Structure 5, 1627–1637 (1997).

Qian, D., et al., T cell antigen receptor signal transduction, Curr. Opin. Cell Ciol., 9, 205–212 (1997).

Reynolds, P. J., Functional analysis of SH2 and SH3 domains of the lck tyrosine protein kinase, Oncogene 7, 1949–1955 (1992).

Rudd, C. E. Adaptors and molecular scaffolds in immune cell signaling, Cell, 96, 5–8 (1999).

Sambrok, J. et al., *Moleuclar Cloning: A Laboratory Manual*, Second Edition, (1989).

Satterthwaite, Independent and opposing roles for Btk and Lyn in B cell and myeloid signaling pathways, Journal of Exp. Med. 188 (5): 833–844 (1998).

Sicheri, F., et al., Crystal structure of the Src family tyrosine kinase Hck, Nature, 385, 602–609 (1997).

Stephan, Fc∈R1–induced protein tyrosine phosphorylation of pp72 in rat basophilic leukemia cells (RBL–2H3), Journal of Biological Chemistry, 267 (8): 5434–5441, (1992).

Straus, D. B., et al., Genetic evidence for the involvement of the lck tyrosine kinase in signal transduction through the T cell antigen receptor, Cell 70, 585–593, (1992).

Straus, D. B., et al, The CD3 chains of the T cell antigen receptor associate with the ZAP–70 tyrosine kinase and are tyrosine phosphorylated after receptor stimulation, J. Exp. Med., 178, 1523–1530 (1993).

Thome, M., et al., The $p56^{lck}$ SH2 domain mediates recruitment of $CD8/p56^{lck}$ to the activated T cell receptor/CD3/zeta complex, Eur. J. Immunol. 26, 2093–2100 (1996).

Toledo, L.M., et al., Structures of staurosporine bound to CDK2 and cAPK—new tools for structure–based design of protein kinase inhibitors., Structure 5, 1551–1556 (1997).

Tong, L., et al., A highly specific inhibitor of human p38 MAP kinase bonds in the ATP pocket, Structure 6, 1117–1128, (1997).

Traxler, P., Tyrosine kinase inhibitors in cancer treatment (Part II). Expert Opinion in Therapeutic Patents 8, 1599–1625, (1998).

van Oers, N.S., et al., Lck regulates the tyrosine phosphorylation of the T cell receptor subunits and ZAP–70 in murine thymocytes, J. Exp. Med. 183, 1053–1062.

Vinter, J.G. et al, *Molecular Modeling in Drug Design*, CRC Press (1996).

Wang, Z., et al., Structural basis of inhibitor selectivity in MAP kinases., Structure 6, 1117–1128 (1998).

Wange, R. L., et al., A tyrosine–phosphorylated 70–kDa protein binds a photoaffinity analogue of ATP and associates with both the zeta chain and CD3 components of activated T cell antigen receptor, J. Biol. Chem 267, 11685–11688 (1992).

Wange, R. L., et al., Tandem SH2 domains of ZAP–70 bind to T cell antigen receptor zeta and CD3 epsilon from activated Jurkat T cell, J. Biol. Chem., 268, 19797–19801 (1993).

Wange, R. L., et al., Activating and inhibitory mutations in adjacent tyrosines in the kinase domain of ZAP–70, J. Biol. Chem 270, 18730–18733 (1995).

Watts, J. D., Purification and initial characterization of the lymphocyte–specific protein–tyrosyl kinase p56lck from a baculovirus expression system., J. Biol. Chem, 267, 901–907 (1992).

Watts, J. D., et al., Identification by electorspray ionization mass spectrometry of the sites of tyrosine phosphorylation induced in activated Jurkat T cells on the protein tyrosine kinase ZAP–70, J. Biol. Chem, 269, 29520–29529 (1994).

West, M.L., et al., Targeting HIV–1 protease: a test of drug–design methodologies, Elesvier Science Ltd, TiPS—(vol. 16), Feb. 67–74, (1995).

Williams, J. C., et al., A crystal structure of the inactivated form of chicken Src: a dynamic molecule with multiple regulatory interactions., J. MI Biol. 274, 757–775 (1997).

Wilson, K. P., et al., The structural basis for the specificity of pyridinylimidazole inhibitors of p38 MAP kinase., Chem. & Biol. 4, 423–431 (1997).

Wong, J., et al., Genetic evidence of a role for Lck in T–cell receptor function independent or downstream of ZAP–70/Syk protein tyrosine kinases, Mol. Cell. Biol, 18, 2855–2866.

Xu, W., et al., Three–dimensional structure of the tyrosine kinase c–Src., Nature, 385, 595–602 (1997).

Yamaguchi, H., et al., Structural basis for activation of human lymphocyte kinase Lck upon tyrosine phosphorylation., Nature, (London), 384, 484–489 (1996).

Yoshida, A., et al., Differential endothelial migration and proliferation to basic fibroblast growth factor and vascular endothelial growth factor, Growth Factors 13: 57–64 (1996).

* cited by examiner

FIG. 5B

```
              αEF                    αF                           αG
              ─────                 ─────                        ───
LCK  394  YTAREGAKFPIKWTAPEAINYGTFT--IKSDVWSFGILLTEIVTHGRI-PYPGMTNPEVIQ
ZAP70     YTARSAGKWPLKWYAPECINFRKFS-SRSDVWSYGVTMWEALSYGQK-PYKKMKGPEVMA
EGFR      YHAE-GGKVPIKWMALESILHRIYT-HQSDVWSYGVTVWELMTFGSK-PYDGIPASEISS
PKA       WTLC----GTPEYLAPEIILSKGYNK-AVDWWALGVLIYEMAAGYPP--FFADQPIQIYE

αH                           αI
             ────                         ────
LCK  451  NLERG--YRMVRPDNCPEELYQLMRLCWKER-PEDRPTFDYLRSVLEDFFT------
ZAP70     FIEQG--KRMECPPECPPELYALMSDCWIYK-WEDRPDFLTVEQRMRACYY------
EGFR      ILEKG--ERLPQPPICTIDVYMIMVKCWMID-ADSRPKFRELIIEFSKMARDPQR---YL
PKA       KIVSG--KVRFPSHFSSDLKDLLRNLLQVD-LTKRFGNLKNGVN-DIKNHKWFATTDWI

LCK  500  ATEG--QYQ-PQP-------------------------------------------
ZAP70     SLAS--KVEGP-PGSTQKAEAACA---------------------------------
EGFR      VIQGDERMHLPSPTDSNFYRALMDEEDMDDVVDADEYLIPQQGFFSSPSTSRTPLLSSLS
PKA       AIYQR-KVEAPFIPKFKGPGDTSNFDDYEEEIRVSINEKCGKEFSEF----------
```

ND METHODS OF USE

SEQUENCE LISTING

<160> NUMBER OF SEQ ID NOS: 1

<210> SEQ ID NO 1
<211> LENGTH: 508
<212> TYPE: PRT
<213> ORGANISM: Homo sapiens

<400> SEQUENCE: 1

```
Gly Cys Gly Cys Ser Ser His Pro Glu Asp Asp Trp Met Glu Asn Ile
 1               5                  10                  15

Asp Val Cys Glu Asn Cys His Tyr Pro Ile Val Pro Leu Asp Gly Lys
            20                  25                  30

Gly Thr Leu Leu Ile Arg Asn Gly Ser Glu Val Arg Asp Pro Leu Val
        35                  40                  45

Thr Tyr Glu Gly Ser Asn Pro Pro Ala Ser Pro Leu Gln Asp Asn Leu
    50                  55                  60

Val Ile Ala Leu His Ser Tyr Glu Pro Ser His Asp Gly Asp Leu Gly
65                  70                  75                  80

Phe Glu Lys Gly Glu Gln Leu Arg Ile Leu Glu Gln Ser Gly Glu Trp
                85                  90                  95

Trp Lys Ala Gln Ser Leu Thr Thr Gly Gln Glu Gly Phe Ile Pro Phe
            100                 105                 110

Asn Phe Val Ala Lys Ala Asn Ser Leu Glu Pro Glu Pro Trp Phe Phe
        115                 120                 125

Lys Asn Leu Ser Arg Lys Asp Ala Glu Arg Gln Leu Leu Ala Pro Gly
    130                 135                 140

Asn Thr His Gly Ser Phe Leu Ile Arg Glu Ser Glu Ser Thr Ala Gly
145                 150                 155                 160
```

-continued

```
Ser Phe Ser Leu Ser Val Arg Asp Phe Asp Gln Asn Gln Gly Glu Val
            165                 170                 175

Val Lys His Tyr Lys Ile Arg Asn Leu Asp Asn Gly Gly Phe Tyr Ile
            180                 185                 190

Ser Pro Arg Ile Thr Phe Pro Gly Leu His Glu Leu Val Arg His Tyr
            195                 200                 205

Thr Asn Ala Ser Asp Gly Leu Cys Thr Arg Leu Ser Arg Pro Cys Gln
        210                 215                 220

Thr Gln Lys Pro Gln Lys Pro Trp Trp Glu Asp Glu Trp Glu Val Pro
225                 230                 235                 240

Arg Glu Thr Leu Lys Leu Val Glu Arg Leu Gly Ala Gly Gln Phe Gly
                245                 250                 255

Glu Val Trp Met Gly Tyr Tyr Asn Gly His Thr Lys Val Ala Val Lys
            260                 265                 270

Ser Leu Lys Gln Gly Ser Met Ser Pro Asp Ala Phe Leu Ala Glu Ala
            275                 280                 285

Asn Leu Met Lys Gln Leu Gln His Gln Arg Leu Val Arg Leu Tyr Ala
        290                 295                 300

Val Val Thr Gln Glu Pro Ile Tyr Ile Ile Thr Glu Tyr Met Glu Asn
305                 310                 315                 320

Gly Ser Leu Val Asp Phe Leu Lys Thr Pro Ser Gly Ile Lys Leu Thr
                325                 330                 335

Ile Asn Lys Leu Leu Asp Met Ala Ala Gln Ile Ala Glu Gly Met Ala
            340                 345                 350

Phe Ile Glu Glu Arg Asn Tyr Ile His Arg Asp Leu Arg Ala Ala Asn
            355                 360                 365

Ile Leu Val Ser Asp Thr Leu Ser Cys Lys Ile Ala Asp Phe Gly Leu
        370                 375                 380

Ala Arg Leu Ile Glu Asp Asn Glu Tyr Thr Ala Arg Glu Gly Ala Lys
385                 390                 395                 400

Phe Pro Ile Lys Trp Thr Ala Pro Glu Ala Ile Asn Tyr Gly Thr Phe
                405                 410                 415

Thr Ile Lys Ser Asp Val Trp Ser Phe Gly Ile Leu Leu Thr Glu Ile
            420                 425                 430

Val Thr His Gly Arg Ile Pro Tyr Pro Gly Met Thr Asn Pro Glu Val
        435                 440                 445

Ile Gln Asn Leu Glu Arg Gly Tyr Arg Met Val Arg Pro Asp Asn Cys
        450                 455                 460

Pro Glu Glu Leu Tyr Gln Leu Met Arg Leu Cys Trp Lys Glu Arg Pro
465                 470                 475                 480

Glu Asp Arg Pro Thr Phe Asp Tyr Leu Arg Ser Val Leu Glu Asp Phe
                485                 490                 495

Phe Thr Ala Thr Glu Gly Gln Tyr Gln Pro Gln Pro
                500                 505
```

CRYSTAL OF A KINASE-LIGAND COMPLEX AND METHODS OF USE

This application claims the benefit of U.S. Provisional Application No. 60/205,510 filed May 19, 2000, which is hereby incorporated by reference in its entirety.

BACKGROUND OF THE INVENTION

The invention relates to the three-dimensional structure of a crystal of a kinase enzyme complexed with a ligand. The three-dimensional structure of a protein kinase-ligand complex is disclosed. The invention also relates to methods of preparing such crystals. Kinase-ligand crystal structures wherein the ligand is an inhibitor molecule are useful for providing structural information that may be integrated into drug screening and drug design processes. Thus, the invention also relates to methods of using the crystal structure of kinase enzyme-ligand complexes for identifying, designing, selecting, or testing inhibitors of kinase enzymes, such inhibitors being useful as therapeutics for the treatment or modulation of i) diseases; ii) disease symptoms; or iii) the effect of other physiological events mediated by kinases; having one or more kinase enzymes involved in their pathology.

T-cell activation is a complex process that results from the integrated activation of multiple signal transduction pathways [1–3]. One of the earliest T-cell signaling events observed upon T-cell receptor (TCR)-ligand engagement is the CD4/CD8-dependent activation of lymphocyte kinase (Lck), a member of the non-receptor Src family of tyrosine kinases [4–8]. Lck phosphorylates and activates a number of substrates necessary for TCR signaling [9]. Perhaps the best understood activity of Lck is the phosphorylation of immunoreceptor tyrosine-based activation motifs (ITAMs) in the TCR ζ-subunit [4, 6, 9]. The extent of ζ-chain ITAM phosphorylation dictates the threshold for ligand-mediated TCR signaling and T-cell activation [10, 11]. Phosphorylated ITAMs serve as high affinity docking sites for the recruitment of additional signaling factors, particularly the Syk family tyrosine kinase ZAP-70 [12, 13]. Dual phosphorylation of tyrosines in the ITAMs by Lck is required for the binding of tandem ZAP-70 Src homology-2 (SH2) domains [14–16]. Co-localization of ZAP-70 and Lck to the TCR-ζ subunit-CD4/8 complex facilitates the Lck-mediated activation of ZAP-70 and subsequent ZAP-70 autophosphorylation [17–21]. Activated Lck and ZAP-70 perpetuate the TCR signaling cascade by providing additional docking sites for other SH2 containing kinases (including Fyn, Syk and Itk), adaptor proteins (including SLP-76, SHC, LAT, FyB and Grap), and transducing elements (including PLCγ, PI3-kinase and Rac/Rho) [2, 3, 22]. Biochemical information is then transmitted down multiple signaling pathways, including the Ras/mitogen-activated protein kinase pathway, the phosphatidylinositol pathway, and the Rho/Rac pathway [2]. Among other effects, TCR signaling up-regulates transcription and translation of IL-2 and IL-2 receptors which are prerequisites for T-cell proliferation.

Genetic studies have demonstrated that Lck expression is restricted to lymphocytes. Loss of Lck expression in human Jurkat T-cells results in a loss of signaling in response to TCR ligation [23, 24]. In addition, inactivation of the Lck gene, or expression of dominant negative transgenes in mice, results in early arrest of thymocyte maturation [25–27]. These and other biochemical studies have implicated Lck as an essential early mediator of the TCR signaling pathway. Lck therefore represents an attractive target for therapeutic intervention in T-cell mediated disorders such as autoimmune diseases and transplant rejection.

Lck is a modular protein consisting of a C-terminal catalytic domain, a single Src homology-2 (SH2) and a Src homology-3 (SH3) domain, and a unique N-terminal region. The N-terminal region is involved in anchoring Lck to CD4/8 through $Zn^{2+}$ coordination with conserved cysteine residues present in both proteins [28, 29]. The activity of Lck is regulated by autophosphorylation of Tyr-394 located in the catalytic domain activation loop [30] and by the phosphorylation of Tyr-505 by C-terminal Src kinase (Csk) [31–33]. Further understanding of the regulation of Lck has been provided by the crystal structures of two other Src family protein kinases, c-Src and Hck [34–36]. From these structures it can be delineated that the SH2 and SH3 domains function in part to negatively regulate Lck activity by forming intramolecular contacts that stabilize the catalytic domain in an inactive conformation [37]. The SH2 domain binds to phosphorylated Tyr-505 and the SH3 domain associates with a proline containing motif in a hinge region connecting the SH2 and catalytic domains [34–36]. Release of these intramolecular regulatory constraints by dephosphorylation of Tyr-505 [38] and/or the presence of competing SH3/SH2 ligands [39] results in the autophosphorylation of Tyr-394 in the activation loop and a catalytically active kinase [19]. A structural basis for Lck activation has been previously elucidated from the crystal structure of an autophosphorylated Lck catalytic domain [40].

Protein kinases have been implicated as potential targets for a variety of clinical applications. The identification of molecules, such as inhibitors, that bind to kinase enzymes, affect kinase activity and thereby influence pathological processes, is valuable for investigating potential therapeutics for disease, or disease symptoms, that are mediated by kinase enzymes. Such identification has been attempted using methods such as the screening of large numbers of random libraries of natural and/or synthetic compounds, hoping that some number of random compounds will demonstrate the desired biological activity. This method is inefficient in that it typically results in a small number of "hits" and it is constrained by the limitations imposed in actually screening large numbers of compounds in laboratory assays. An improved method of such identification is structure-based drug design ("SBDD"). SBDD comprises a number of integrated components, including, structural information (e.g., spectroscopic data such as X-ray or magnetic reasonance information, relating to enzyme structure and/or conformation, enzyme-ligand interactions, etc.), computer modeling, medicinal chemistry, and biological testing (both in vitro and in vivo). These components, each alone and in combination, are useful for accelerating the drug discovery process, for gaining insight into disease and disease processes, and for providing a more efficient method for identifying drug candidates.

Efforts to understand the molecular constraints necessary to achieve inhibitor potency and selectivity have been aided by an increasing number of crystal structures of different protein kinases complexed with ATP-competitive inhibitors. One such inhibitor is staurosporine, an alkaloid that has been previously shown to inhibit a broad range of tyrosine and serine/threonine kinases with nanomolar potency [41]. Crystal structures of staurosporine bound to the serine/threonine kinases protein kinase A (PKA) and the cyclin-dependent kinase 2 (CDK2) elucidated the binding mode of this inhibitor to protein kinases [42, 43] (reviewed in [44]). A similar binding mode has been reported in a recently solved structure of the tyrosine kinase Csk in complex with staurosporine [45]. Described herein are crystal structures of Lck complexed with staurosporine obtained from both soaking and co-crystallization experiments. Comparison of these two complexes and those previously reported further elucidates the structural basis for the high potency and poor selectivity of this inhibitor.

To date, the three-dimensional structures of Hck/AMP-PNP and Hck/Quercetin complexes have been reported, however, these ligands are not src-selective ligands. The three-dimensional structure of c-Src (apo form) has been elucidated, however, this structure lacks a ligand bound to the enzyme and therefor lacks critical information regarding the interaction of a ligand with the active site of the enzyme.

The role of Src family members Lck and Fyn in TCR activation has been studied with two related Src kinase inhibitors, PP1 and PP2 [51]. PP1 and PP2 are reported to se inhibit Lck and c-Src in vitro at concentrations much lower than is required to inhibit Zap-70, JAK2, EGF-R kinase and protein kinase A [51]. These compounds also inhibit anti-CD3-induced protein tyrosine phosphorylation and subsequent IL-2 gene activation in T lymphocytes [51]. Thus, it appears that PP1 and PP2 dissect a component of TCR signaling not distinguished by other immunosuppressive drugs such as cyclosporin and FK-506. The structural basis for the potency and selectivity of these compounds with the crystal structure of PP2 bound to Lck is described herein. This structure is a useful tool in the design of specific Lck inhibitors and aids in the tailoring of inhibitors, such as PP1 and PP2, to enhance their physical properties, including their therapeutic and pharmaco-kinetic properties.

There is a need for three-dimensional structures of kinase-ligand complexes in order to garner a better understanding of the important interactions between a kinase and its bound ligand, and to utilize this information for methods to identify, design and test molecules with improved binding affinity and molecules that would be useful as therapeutics and/or modulators of kinase-mediated physiological events.

SUMMARY OF THE INVENTION

The present invention provides crystals of kinase-ligand complexes suitable for X-ray diffraction analysis. The invention also relates to methods for preparing the crystals of kinase-ligand complexes, particularly where the ligand is an inhibitor of the kinase enzyme. The invention also relates to the detailed three-dimensional structural information of the protein-ligand complexes constituting these crystals, and use of the structure coordinates to reveal atomic details of the active site(s) and other physicochemical interactions that enhance interaction and/or association between the kinase and the ligand. It is also an object of this invention to use the kinase-ligand complex crystals, the three-dimensional structural information provided by the kinase-ligand complex crystals, and the structure coordinates of the kinase-ligand complex in methods to identify, design, select, and evaluate potential inhibitors of kinases that would be useful as therapeutics for diseases or symptoms of diseases that are associated with kinase-mediated physiological events. Such methods may also include use of computer modeling of potential inhibitors based on the the kinase-ligand complex crystals, the three-dimensional structural information of the kinase-ligand complex crystals, and the structure coordinates of the kinase-ligand complex crystals.

BRIEF DESCRIPTION OF THE DRAWINGS

This patent file contains at least one drawing executed in color. Copies of this patent with color drawings will be provided by the Patent Office upon request and payment of the necessary fee.

DETAILED DESCRIPTION OF THE INVENTION

In order that the invention described herein be more fully understood, the following detailed description is set forth. The interactions of a ligand (e.g., inhibitors AMP-PNP, staurosporine, PP2, damnacanthal, PD153035, and baicalein) with a kinase are delineated below. For an overview of kinases, see, *The Protein Kinase Facts Book I & II*, G. Hardie and S. Hanks, eds., Academic Press, (1995).

AMP-PNP Binding to the Lck Catalytic Domain

Figure 1A:
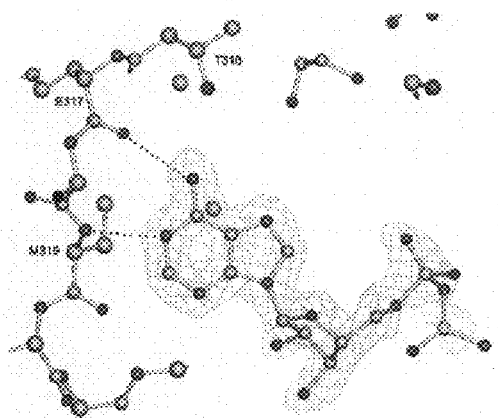
FIG. 1. Electron density maps of ligands bound to Lck. 2Fo-Fc electron density maps contoured at 1σ. The linker region between the N and C terminal lobe of the Lck kinase domain is shown on the left side of the bound ligands. Hydrogen bonds formed between ligands and the kinase linker region are represented by the purple dashed lines. A. AMP-PNP; B. staurosporine; C. PP2. D. PD153035; E. Baicalein; F. Damnacanthal.
Figure 2A:
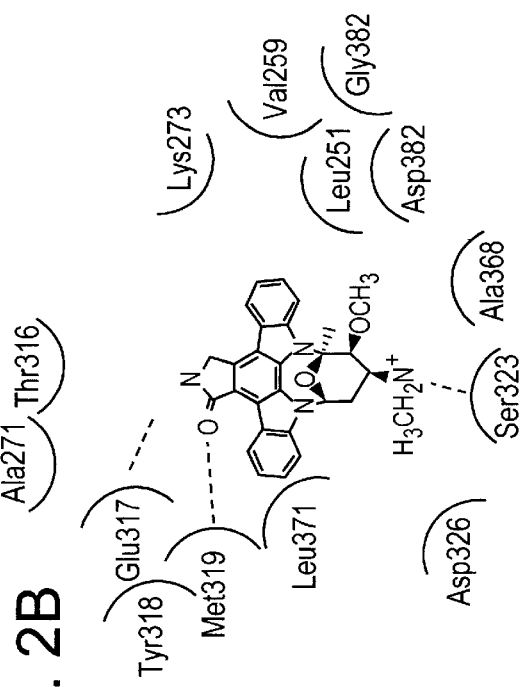
FIG. 2. Schematic representation of the hydrogen bonding interactions and van der Waals contacts between Lck and the ligands. Hydrogen bonds are represented with dashed lines. The residues of Lck in contact with the bound ligand are shown. A. AMP-PNP; B. staurosporine;C PP2; D. PD153035; E. Baicalein, F. Damnacanthal.

To provide a structural basis for understanding the interactions of ATP-competitive inhibitors with Lck, the Lck catalytic domain was co-crystallized with the non-hydrolyzable ATP analog AMP-PNP. Consistent with structures of other protein kinases in complex with ATP analogs [46–48], AMP-PNP binds in the cleft between the N- and C-terminal lobes of Lck, with a pair of conserved hydrogen bonds formed between the adenine base and the backbone of the kinase linker region (FIGS. 1A & 2A). The gamma phosphate of AMP-PNP is disordered in the binary complex, perhaps due to the absence of a substrate peptide or divalent cations. In ternary complexes of PKA with ATP and a substrate peptide inhibitor [46, 47], and IRK with AMP-PNP and a substrate peptide [48], the bound peptides appear to help anchor the gamma phosphate of ATP to the enzyme. Only small conformational changes are observed in the Lck:AMP-PNP complex relative to the previously reported apo Lck structure [40]. However, Ser323 undergoes a conformational change in the ribose binding pocket of Lck that appears to be important for AMP-PNP binding. In the apo structure, Ser323 adopts two partially occupied conformations. One conformation results in a hydrogen bond between Ser323 and Asp326. The other conformation results in Ser323 hydrogen bonding to the backbone carbonyl of Asp368. In both conformations, the Ser323 O$\gamma$ points away from the ATP binding cleft and faces the C-terminal lobe. In the Lck:AMP-PNP structure, the side chain of Ser323 is rotated more than 100 degrees about $\chi$1 and forms a hydrogen bond with the ribose oxygen of AMP-PNP (O$\gamma$:O2' distance 2.7 O). Ser323 of Lck is conserved among all known Src-family tyrosine kinases with the exception of Blk, which contains a cysteine at this position.

Staurosporine Binding to Lck

Figure 1B:
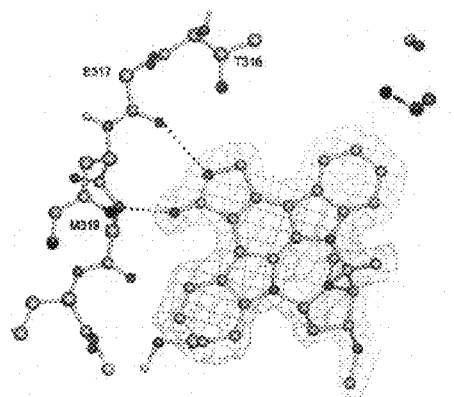
Figure 2B:
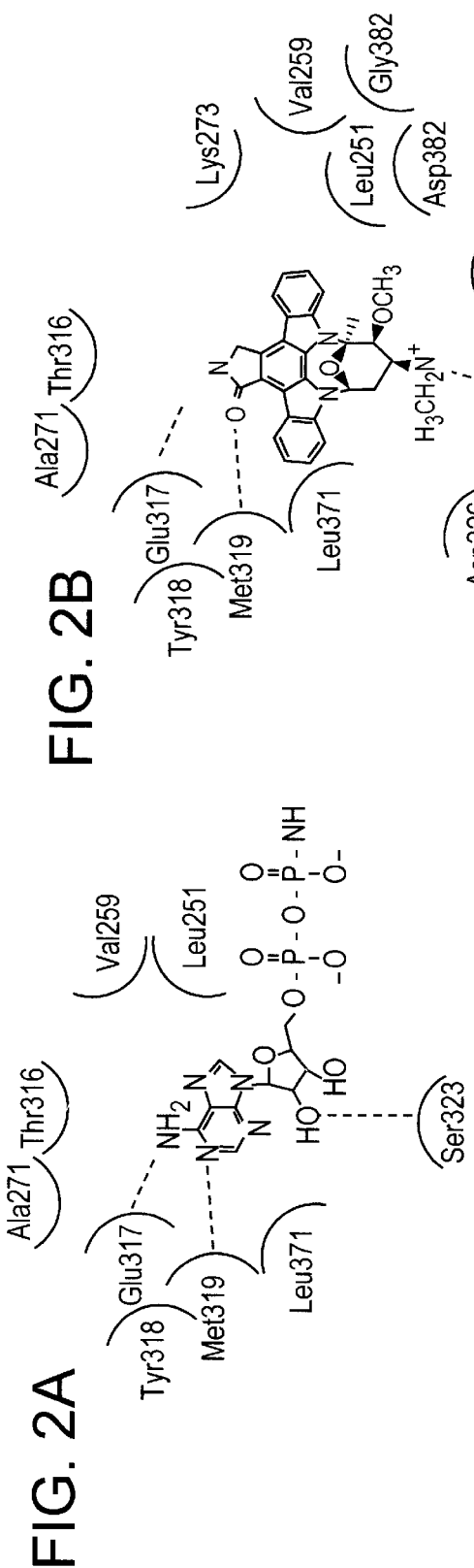

Structures of staurosporine bound to Lck were determined both from apo Lck crystals soaked with. In the Lck:staurosporine complex the inhibitor occupies the ATP binding site and forms three hydrogen bonds with the enzyme. The NH and keto oxygen of the lactam ring of staurosporine make a pair of hydrogen bonds with the carbonyl oxygen of Glu317 and the backbone NH of Met319, similar to those formed by the adenine ring of ATP (FIGS. 1B and 2B). The third hydrogen bond, which occurs in the ribose binding pocket of Lck, appears to be different in the two complexes. In the Lck:staurosporine complex derived from soaking, the methylamino substituent of the glycosidic ring participates in a hydrogen bond with Ser323 (N:O$\gamma$ distance 2.9 Å). This interaction is similar to the hydrogen bond observed between Ser323 and the ribose 2'-hydroxyl in the Lck:AMP-PNP complex.

Staurosporine also makes extensive van der Waals contacts with Lck. Seven residues from the N-terminal lobe (Leu251, Gly252, Val259, Ala271, Lys273, Thr316, and Tyr318) and six residues from the C-terminal lobe (Met319, Gly322, Ser323, Ala368, Leu371, and Asp382) of Lck contribute a total of 78 van der Waals contacts to the bound inhibitor. The majority of these contacts are to the fused carbazole moiety of staurosporine, which spans a plane of approximately 15×11 Å$^2$. In contrast, the glycosidic group of staurosporine spans only 6 Å in a direction perpendicular to the plane of carbazole ring system. Approximately half of the van der Waals interactions result from a large movement of the glycine rich loop of Lck, induced by staurosporine binding. .

Figure 4A:
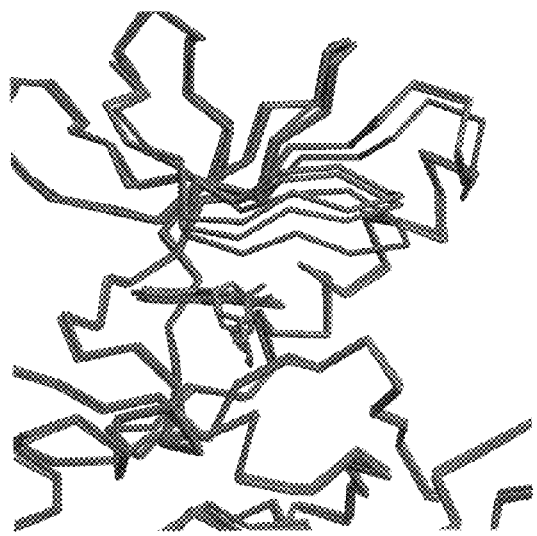
FIG. 4. Superposition of Lck (green), CDK2 (cyan) and PKA (yellow) in complex with staurosporine (purple). The structure alignment is based on the bound ligands. The Lck:staurosporine co-crystallized complex contains a loop conformation intermediate between the more open and closed positions observed in the CDK2 and PKA complexes.
Figure 4B:
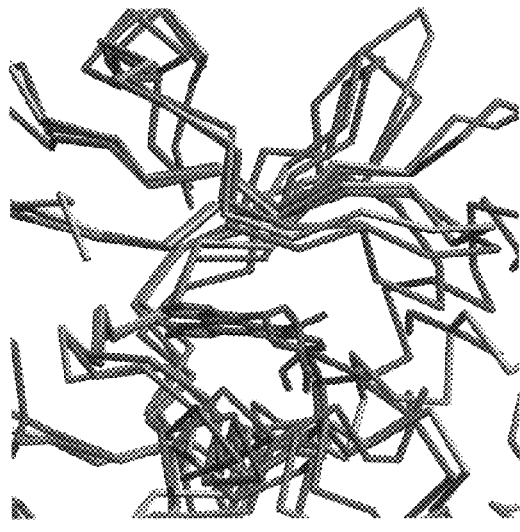

Crystal structures of the protein kinases CDK2, PKA and CSK in complex with staurosporine have also been reported [42, 43, 45]. The same hydrogen bonding pattern observed between the lactam of staurosporine and the linker region of Lck is observed in each of these crystal structures. Inspection of the PKA:staurosporine and CDK2:staurosporine complexes (CSK coordinates not available) reveals that the CH—O interaction described above for our two Lck:staurosporine structures is present as the closest contact between staurosporine and the glycine rich loop in these structures as well. Not only are the CH—O distances constant in the four complexes (3.5 Å), but the geometry of the interaction is similar as well. This type of CH—O interaction is well documented in small molecule crystal structures [49] and has also been observed in other biomolecular complexes [50]. Interestingly, both PKA and CDK2 undergo conformational changes in the glycine rich loop upon staurosporine binding, and while this loop contains additional conformational differences in the CDK2 complex (FIG. 4), the glycine C$\alpha$:glycosidic oxygen interaction is maintained. This emphasizes the importance of this interaction in complexes between staurosporine and Ser/Thr and tyrosine kinases. It appears that this interaction is critical for the potency of staurosporine binding to the ATP binding site of these kinases.

In both the Lck and CSK complexes a single hydrogen bond is formed between staurosporine and the ribose binding pocket [45]. In comparison, staurosporine has been observed to form two hydrogen bonds with this pocket in CDK2 and PKA [42, 43]. In these two complexes rotation about the C—N bond of the methylamino substituent allows the amine nitrogen to hydrogen bond to both a carbonyl oxygen from the catalytic loop and a side chain from the ribose binding pocket. Of the two methylamino hydrogen bonding interactions observed in our Lck:staurosporine complex, the contact with the carbonyl oxygen of Ala368 more closely resembles the interactions observed in the PKA and CDK2 complexes. The distance between this carbonyl oxygen and the C$\alpha$ of Gly252 is 10.3 Å for the Lck:staurosporine complexe. The equivalent distances in the PKA and CDK2 structures are 9.0 Å and 8.8 Å, respectively.

PP2 Binding to Lck

Figure 1C:
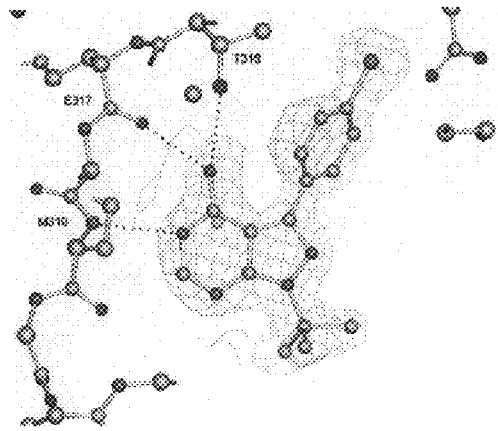
Figure 1D:
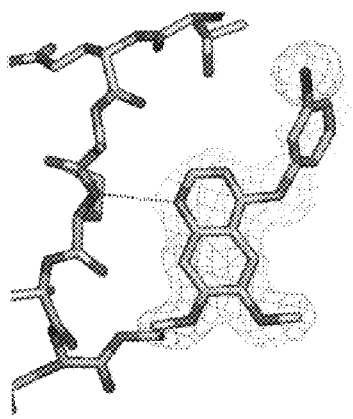
Figure 1E:
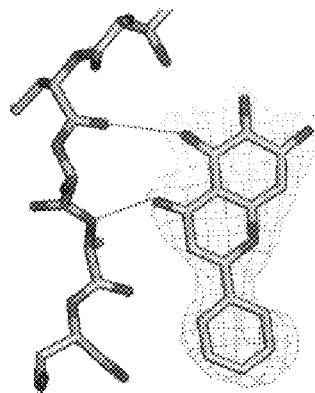
Figure 1F:
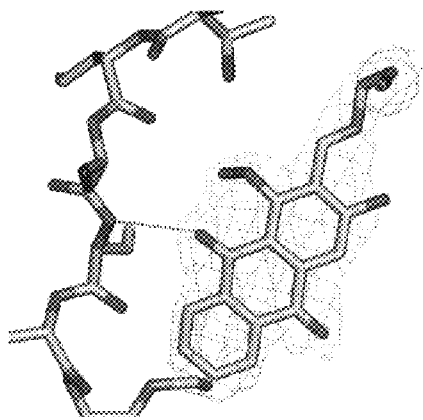
Figure 2C:
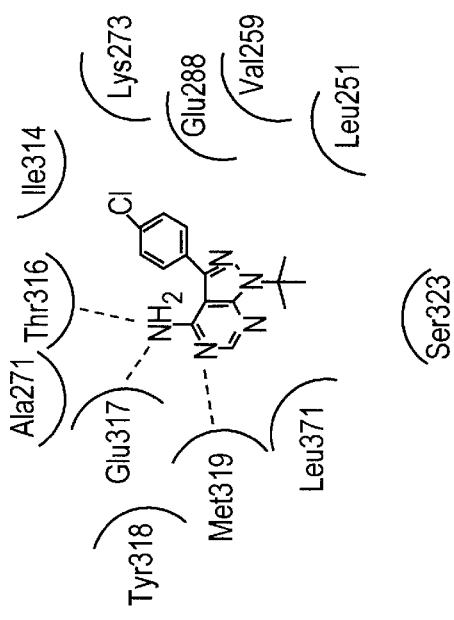
Figure 2D:
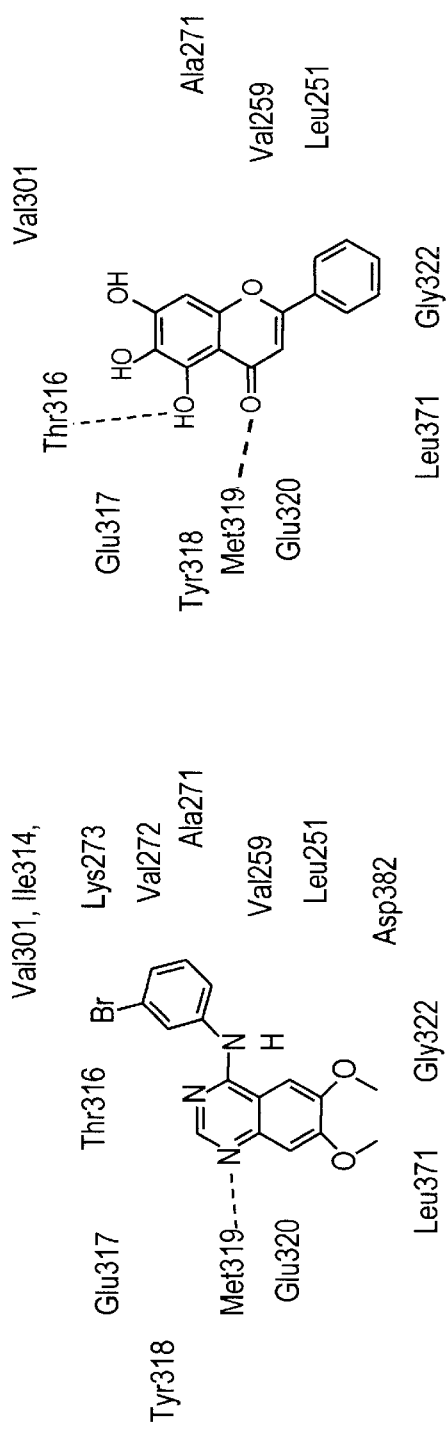
Figure 2E:
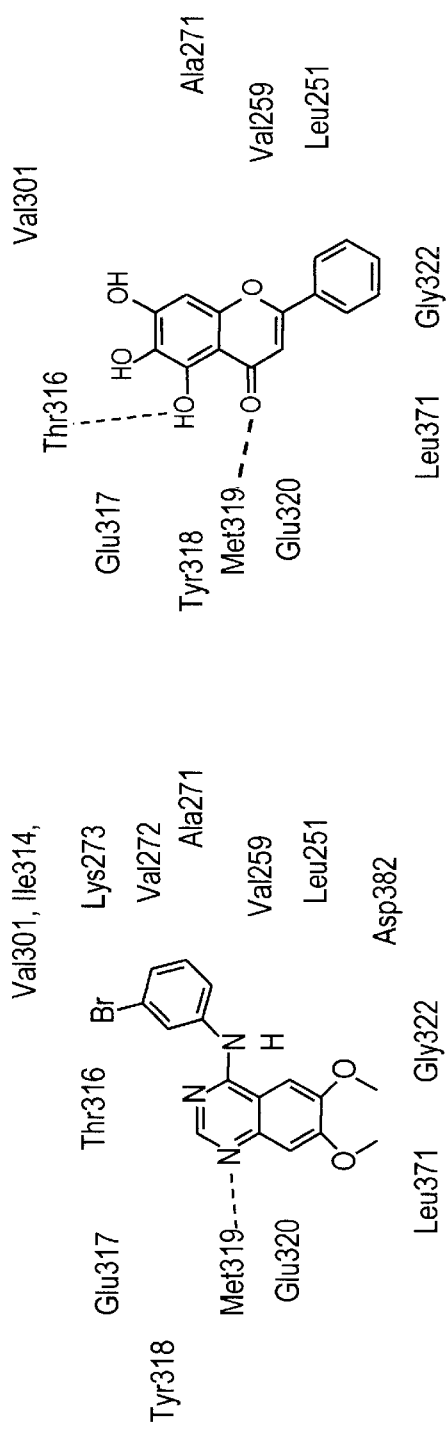
Figure 2F:
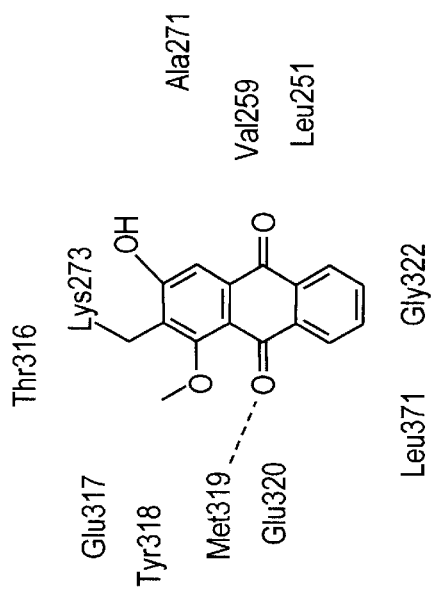
Figure 3A:
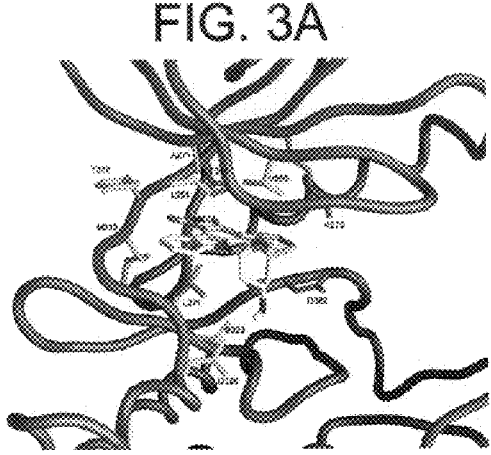
FIG. 3. Interactions of the ligands with Lck at the ATP binding cleft. . A & B. staurosporine; C & D. PP2. E & F. PD153035; G & H. Baicalein; I & J. Damnacanthal.
Figure 3C:
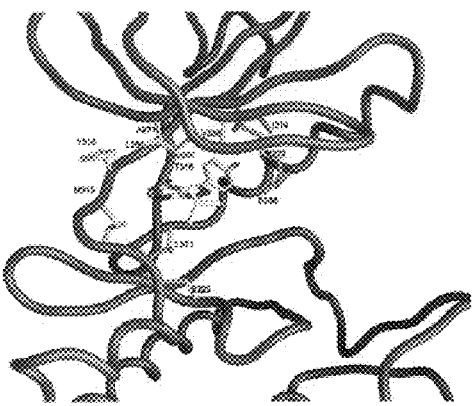
Figure 3B:
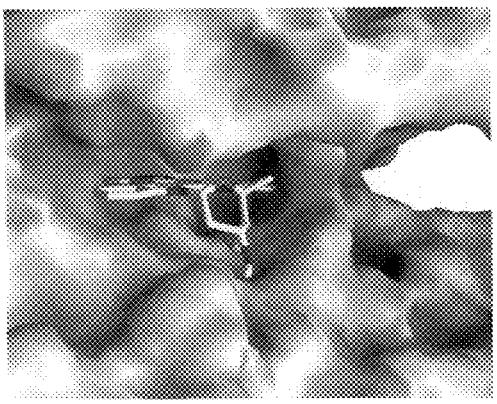
Figure 3D:
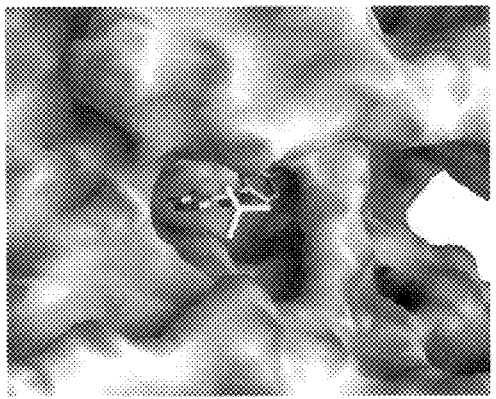
Figure 3E:
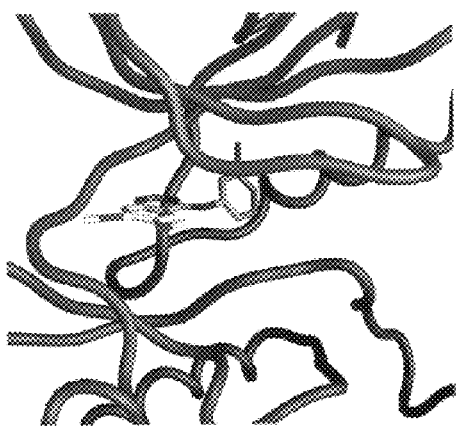
Figure 3F:
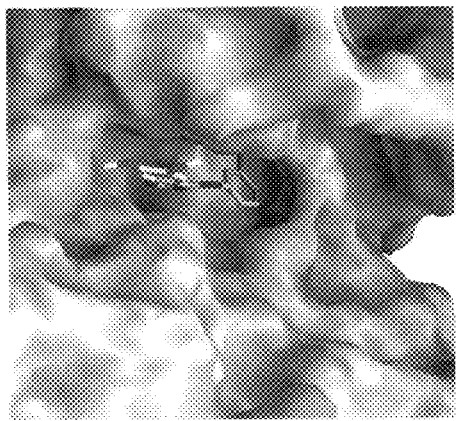
Figure 3G:
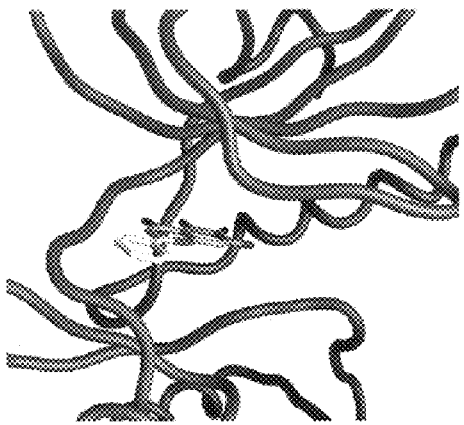
Figure 3H:
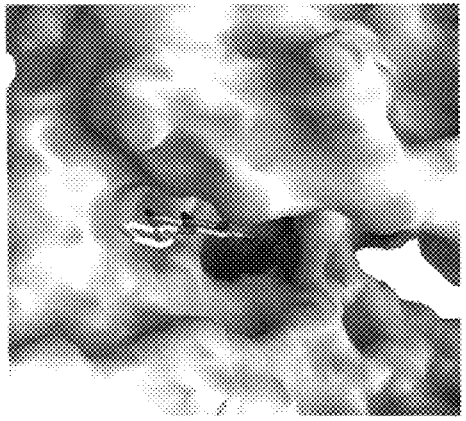
Figure 3I:
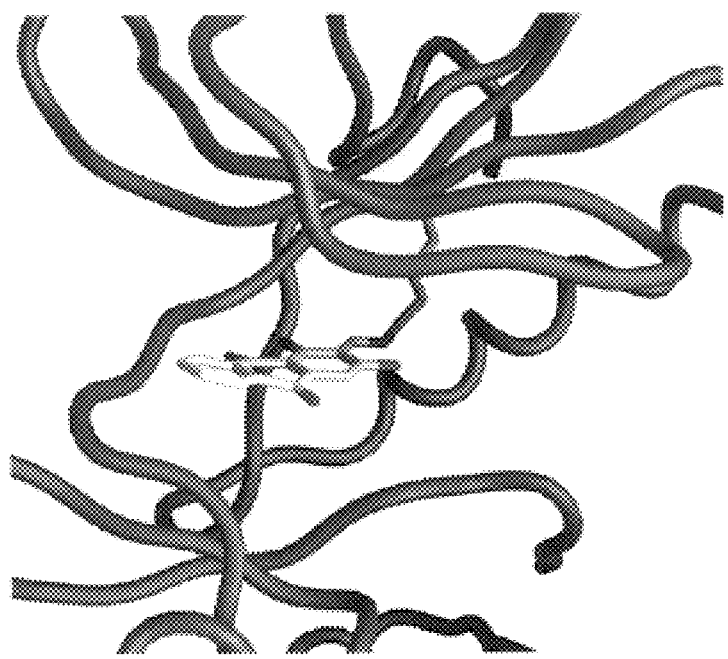
Figure 3J:
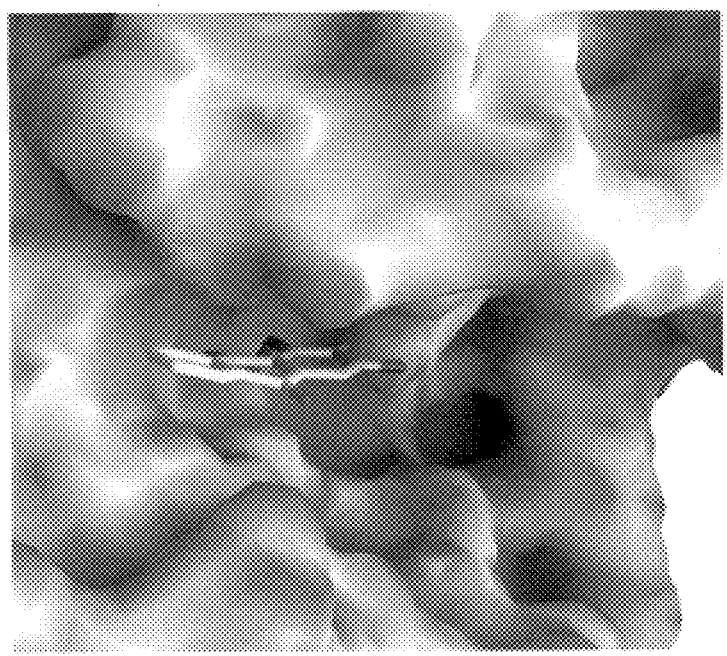

PP2 has been reported to be a potent Src family selective tyrosine kinase inhibitor [51]. This compound inhibits Lck with an IC$_{50}$ of 4 nM and Fyn with an IC$_{50}$ of 5 nM. slightly less potent against EGF-R (IC$_{50}$=0.45 $\mu$M) and inactive against ZAP-70 (IC$_{50}$=100 $\mu$M) [51]. PP1, an analog of PP2, shows approximately the same inhibitory activity against Lck [51]. To determine the structural basis for this selectivity, PP2 was co-crystallized with the kinase domain of Lck. This structure reveals that PP2 binds in the ATP binding site and induces little global conformational change in the enzyme. Superimposition of the Lck:PP2 and Lck:AMP-PNP structures yields an overall rms difference of 0.27 O for the 278 C$\alpha$ atoms. The pyrazolo-pyrimidine ring of PP2 occupies a similar position in the Lck ATP binding cleft as the adenine ring of AMP-PNP (FIGS. 1C & 2C). This binding mode places the 3-(4-chlorophenyl) substituent of PP2 in a hydrophobic pocket adjacent to the ATP binding cleft (FIGS. 3B & 3D). PP2 forms three hydrogen bonds with Lck, two of which are similar to those found in the Lck:AMP-PNP and Lck:staurosporine structures (FIGS. 1C & 2C). These are between the 4-amino group of PP2 and the backbone carbonyl of Glu317, and between the N5 of PP2 and the backbone NH of Met319. The third hydrogen bond, formed between the 4-amino group of PP2 and the side chain hydroxyl of Thr316, is unique in the structures reported here. The two conserved hydrogen bonds in the PP2:Lck complex are relatively long, with distances between donor and acceptor atoms of approximately 3.2 O. PP2 also makes thirty-eight van der Waals interactions with Lck. Nineteen of these contacts come from the 3-(4-chlorophenyl) substituent, which is deeply buried inside the hydrophobic pocket. The tert-butyl substituent of the pyrazolo-pyrimidine contributes four van der Waals contacts to the complex. This substituent is located at the entrance of the ATP binding pocket and contacts residues from both the N- and C-terminal lobes of Lck.

Figure 5A:
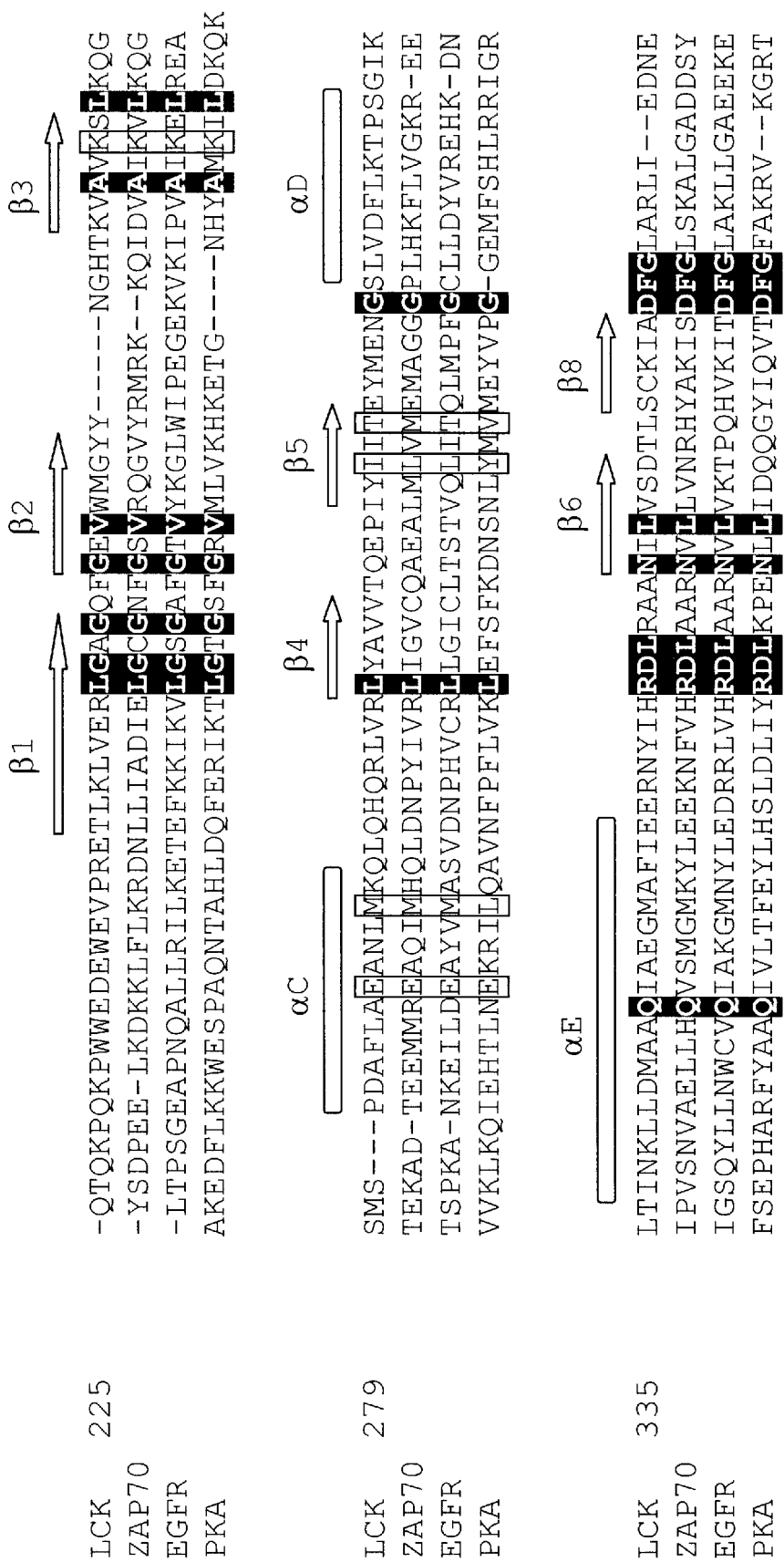
FIG. 5. Structure based sequence alignment of Lck, ZAP-70, the EGF receptor, and PKA. The conserved residues are highlighted in yellow. The amino acids in the hydrophobic pocket where PP2 binds are highlighted in black. Tyrosine 394 on the activation loop is highlighted in purple. The kinase lobe linker region and the catalytic region are labeled.

The hydrophobic pocket occupied by the 3-(4-chlorophenyl) substituent of PP2 is defined by residues Thr316, Ile314, Met292, Glu288 and Lys273. The this pocket appears to be unique to the Src family (FIG. 5). For instance, Thr316, which is located at the entrance of the hydrophobic pocket, is not conserved in other tyrosine kinase families. ZAP-70 contains a methionine at this position which is likely to block access of this pocket to PP2-like inhibitors. This is consistent with the 100 $\mu$M $IC_{50}$ previously reported for PP2 against ZAP-70 [51]. Like Lck, the EGF receptor kinase has a threonine at the entrance of the hydrophobic pocket and is inhibited moderately by PP2 ($IC_{50}$=0.45 $\mu$M) [51]. The hydrophobic pocket in EGFR differs from the Src kinases by having a leucine at the position equivalent to Ile314 in Lck. In the Lck:PP2 complex, Ile314 contacts the 4-chloro substituent of the 3-phenyl ring. The presence of a leucine at this position in EGFR could partially account for the weaker inhibition of this receptor tyrosine kinase by PP2.

Figure 6:
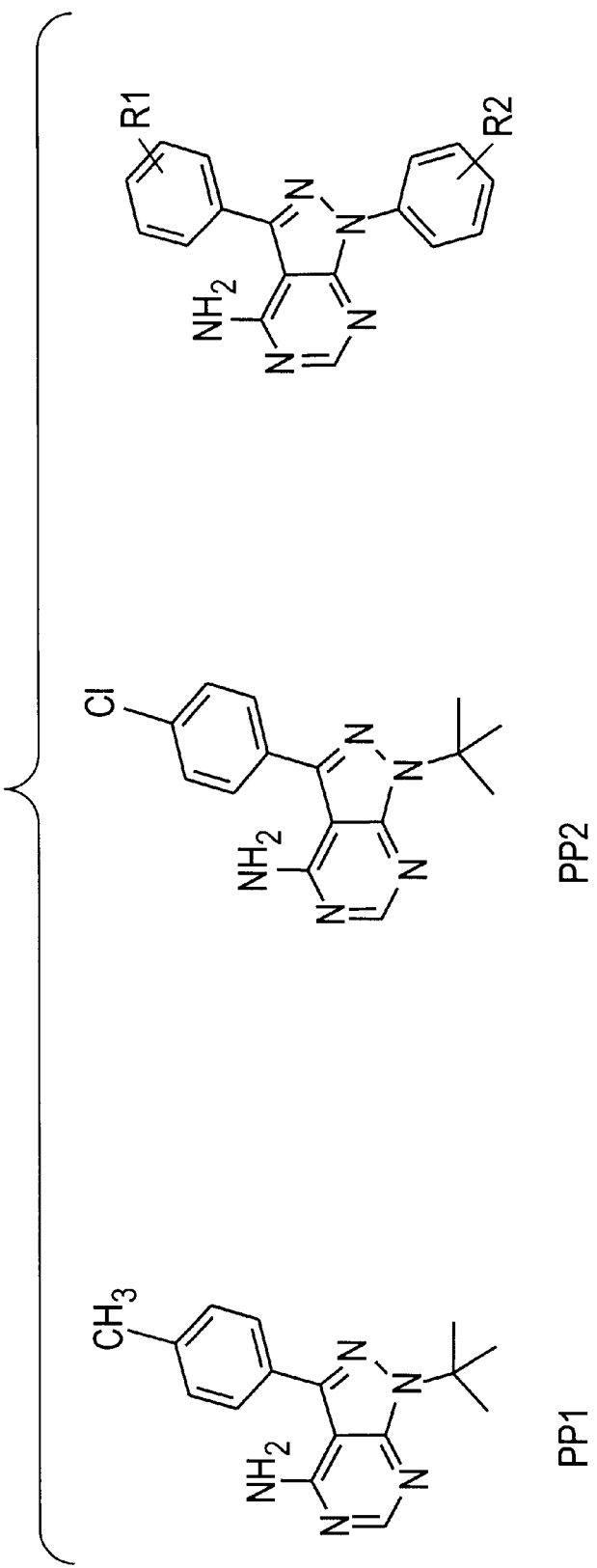
FIG. 6. Comparison of the ligand positions in the Lck complexes based on the superposition of the COs of Lck. A. AMP-PNP (purple) and staurosporine. B. AMP-PNP (purple) and PP2.

The structure of the Lck:PP2 complex helps explain the structure activity relationships (SAR) of a series of 4-Amino-1,3-diphenyl-pyrrolo[3,4d]pyrimidines that show a high degree of specificity towards c-Src [52]. The molecular structures of these compounds are analogous to PP2, but have a phenyl ring at the N1 position of the pyrrole instead of a tert-butyl group (FIG. 6C). A wide variety of polar moieties are well tolerated on this phenyl ring. The amino acid identity of the active sites of Lck and Src (defined as a 10 Å radius around ATP) is 89%. The amino acid composition of the ribose binding pocket within the Src family is completely conserved, while the hydrophobic pocket is less conserved. Superimposition of several of these compounds on our Lck:PP2 complex indicates that the polar groups on the N1-phenyl ring can interact favorably with hydrophilic residues in the ribose binding pocket (Ser343, Asp345), while the 3-phenyl group occupies the same region of the hydrophobic pocket as the 3-(4-chlorophenyl) group of PP2.

Damnacanthal Binding to Lck

Damnacanthal binds to Lck in the ATP binding site located between the N and C terminal domains. Enzyme:ligand van der Waals interactions are observed with residues 251, 259, 273, 271, 316, 317, 318, 319, 320, 371, 322, and 301. The inhibitor forms with Lck at the lobe linker region and forms one covalent bond with Lck through lysine 273 in what appears to be a previously unreported novel interaction. The covalent interaction between lysine 273 and damnacanthal is seen clearly in the continuous electron density located between lysine 273 and damnacanthal. There is a large conformational change of the side chain of lysine 273 compared with the structures of apo Lck. Lysine 273 forms hydrogen bonds with glutamate 288 located on the alpha helix C in the structure of apo Lck. In the structure of damnacanthal and Lck, however, these hydrogen bonding interactions are interrupted with a 4.5O movement of the side chain of lysine 273 towards the bound inhibitor. Lysine 273 and its homologous residues in other protein kinases are absolutely conserved in all the serine/threonine and tyrosine protein kinase families. It is a critical residue for kinases to bind to ATP by interacting with the phosphate groups of ATP. In addition, there are eight residues from the N terminal domain (Leu251, Val259, Ala271, Thr316, Glu317, Tyr318, Met319 and Glu320) and three residues from the C terminal domains (Gly322, Val301 and Leu371) which are in vdw contact with the ligand respectively.

PD153035 Binding to Lck

PD153035 binds to Lck in the ATP binding cleft located between the N and C terminal domains. Enzyme:ligand van der Waals interactions are observed with residues 251, 259, 273, 314, 316, 271, 318, 319, 317, 320, 371, 322, 301, 382, and 288. PD153035 forms forms only one hydrogen bond with Lck. This is between 1-N of the quinazoline and the backbone NH of Met319. In addition to the hydrogen bond interaction, PD153035 makes extensive van der Waals interactions with Lck. A total of seventy-two van der Waals contacts are made between Lck and the ligand (using a 4.2 O radius probe). Among them, fifty-four contacts are contributed by the N terminal domain of Lck (Leu251, Val259, Ala271, Val272, Lys273Val301, Ile314, Thr316, Glu317, Tyr318, Met319 and Glu320) while 18 contacts are added by interacting with the C terminal domain (Gly322, Leu371 and Glu382). The 4-amino-bromophenyl group is inserted into the hydrophobic pocket near the ATP binding site, interacting with Ala271, Lys273, Glu288, Ile314 and Glu382 and making eighteen vdw contacts. The composition of this pocket varies from kinase to kinase, and may be exploited for designing Lck specific inhibitors.

Baicalein Binding to Lck

Baicalein binds to Lck in the ATP binding cleft located between the N and C terminal domains. Enzyme:ligand van der Waals interactions are observed with residues 251, 259, 273, 271, 316, 317, 318, 319, 320, 371, 322, and 301. Baicalein forms three hydrogen bonds with Lck. These are between the 1-carbonyl group of baicalein and the backbone carbonyl of Glu317, and between the 8-hydroxyl group of baicalein and the backbone NH of Met319. The third hydrogen bond is formed between the 8-hydroxyl group and the side chain hydroxyl of Thr316. Baicalein also makes fifty-one van der Waals interactions with Lck (4.2 O radius probe). Among them, thirty-four contacts are contributed by the N terminal domain of Lck (Ala271, Val301, Thr316, Glu317, Tyr318, Met319 and contacts are added by interacting with the C terminal domain (Gly322 and Leu371). The 3-phenyl group is important for baicalein binding to Lck. It interacts with the linker region between the N and C terminal domains, making seventeen contacts, accounting for one third of the total van der Waals contacts made between Lck and baicalein. In addition, an ethylene glycol molecule was found to be located in the hydrophobic pocket near the ATP binding cleft. This ethylene glycol molecule interacts extensively with baicalein, making a total of five van der Waals contacts.

Comparison of Ligand Binding to Lck

Superimposition of the Lck:AMP-PNP, Lck:staurosporine and Lck:PP2 structures highlights similar features of inhibitor binding to the enzyme. The aromatic ring systems of the bound inhibitors occupy similar positions in the adenine binding pocket, as do their hydrogen bond donors and acceptors (FIGS. 6A & 6B). This results in a hydrogen bonding pattern to the backbone carbonyl of Glu317 and the amide of Met319 that is conserved in all three structures (FIGS. 1 & 2).

Staurosporine makes significantly more interactions with the glycine rich loop of Lck than does either AMP-PNP or PP2. The majority of these interactions are with residues that are highly conserved among protein kinases. These include Leu251, Gly252, Val259, Ala271, Lys273, Gly322 and Leu371, residues which are either absolutely or highly conserved among known tyrosine kinase sequences. PP2 by contrast, makes a number of interactions with residues that are specific to the Src family kinases by accessing a hydrophobic pocket neighboring the adenine binding region of Lck. This hydrophobic pocket exists in other kinases as well and has been exploited in the discovery of specific inhibitors. For example, the structures of FGF receptor and p38 MAP kinases bound with specific inhibitors show that the inhibitors gain both potency and specificity by placing substituents in this hydrophobic pocket of the enzyme [53–56]. However, the exact position and topology of the hydrophobic pockets of Lck, FGF-R, p38 and other kinases are likely to be defined not only by sequence but by additional factors, such as activation state or relative positioning of the kinase N- and C-terminal domains. This diversity around the ATP-binding site provides opportunities for the discovery or design of potent, selective, small molecule inhibitors for specific protein kinases.

Inhibition of Lck Activity and T-cell Receptor Signaling

Figure 7A:
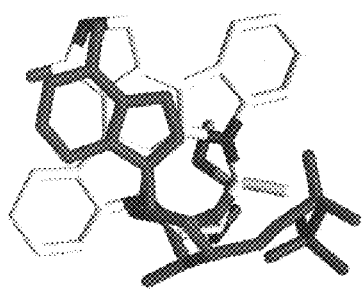
FIG. 7. A. Enzymatic assay. $IC_{50}$ titration curves for an Lck catalytic domain (squares) or the nearly full-length enzyme with SH2 and SH3 regulatory domains (circles). The Lck proteins were titrated with staurosporine (open symbols) and PP2 (filled symbols). B. Cellular assay. PP2 (filled diamonds) and staurosporine (filled triangles) inhibit TCR-induced IL-2 secretion from hPBL T-cells. C. Endogenous protein phosphorylation assay. PP2 and staurosporine inhibit TCR-induced increases in phosphotyrosine incorporation into the TCR p23 ζ-chain and a 70 kDa protein.

In the crystallographic studies presented here, the catalytic domain of Lck was used as a substitute for the full length protein. Previous studies have demonstrated that the Lck catalytic domain can be expressed and isolated as a constitutively active enzyme [40]. Nevertheless, a detailed comparison of the catalytic activities of Lck in the full length and truncated forms has not been reported. To provide a basis for the physiological relevance of our crystallographic studies, the $IC_{50}$ values of staurosporine and PP2 were measured against these two forms of Lck. The full-length and catalytic domains of Lck displayed comparable specific activities (10 and 15 nmoles/min/nM enzyme) when assayed using a poly-GluTyr substrate. Furthermore, staurosporine ($IC_{50}$ full length=34 nM, kinase domain=40 nM) and PP2 ($IC_{50}$ full length=19 nM, kinase domain=20 nM) each inhibited both the full length and truncated forms of Lck to a similar extent in an autophosphorylation assay (FIG. 7A).

Figure 7B:
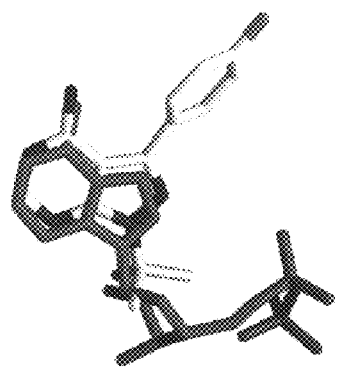
Figure 8A:
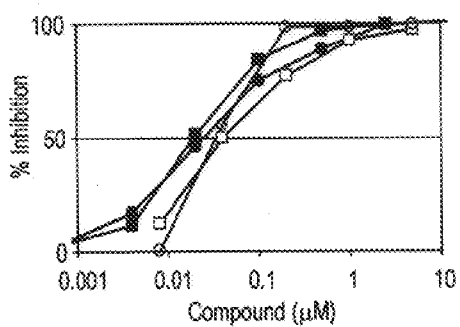
FIGS. 8A–8C. A. Enzymatic assay. $IC_{50}$ titration curves for an Lck catalytic domain (squares) or the nearly full-length enzyme with SH2 and SH3 regulatory domains (circles). The Lck proteins were titrated with staurosporine (open symbols) and PP2 (filled symbols). B. Cellular assay. PP2 (filled diamonds) and staurosporine (filled triangles) inhibit TCR-induced IL-2 secretion from hPBL T-cells. C. Endogenous protein phosphorylation assay. PP2 and staurosporine inhibit TCR-induced increases in phosphotyrosine incorporation into the TCR p23-chain and a 70 kDa protein.
Figure 8C:
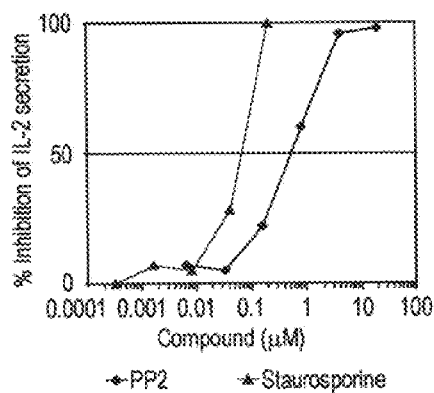
Figure 8B:
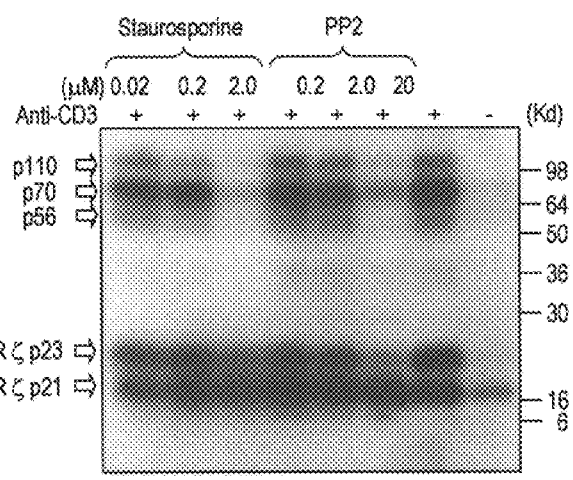

The effect of staurosporine and PP2 on Lck-mediated phosphorylation of TCR ζ-chain and IL-2 production in human T-cells was also investigated. Both inhibitors showed a dose-dependent inhibition of Lck-dependent phosphorylation of the TCR ζ-chain (p23), and also inhibited the phosphorylation of a 70 kD protein which is likely to be ZAP-70 (FIG. 7C). FIG. 7, panel B shows that staurosporine ($IC_{50}$=60 nM) and PP2 ($IC_{50}$=600 nM) also exhibited dose-dependent inhibition of IL-2 production in human T-cell cultures. The results of these in vitro and cellular studies suggests that the catalytic domain of Lck is a valid substitute for the full-length Lck as a molecular target for the development of new immunosuppressive therapeutic agents.

Biological Significance

The molecular targets of currently used immunosuppressive drugs such as FK-506 and cyclosporine are broadly expressed in many different tissues and cell types. The non-immunossuppressant toxicity profiles of such drugs can be traced to the inhibition of their targets in non-lymphoic tissues. Targeting Lck for the development of novel immunosuppressive drugs has promise as this enzyme is selectively expressed in T-cells and NK cells. Thus, agents that selectively inhibit Lck could lead to T-cell specific immunosuppression with improved therapeutic windows and broader clinical potential.

In the past few years much progress has been made in the design of selective kinase inhibitors. It has been established that highly specific ATP-competitive inhibitors can be obtained against a number of different kinases with clinical utility in oncology. In the present study, a comparison of several ligated Lck structures has provided valuable insight into the mode of binding of non-selective and Src family selective inhibitors. The structure of Lck in complex with AMP-PNP likely represents a conformation of Lck when ATP is bound prior to the binding of substrates and phosphotransfer. Analysis of the Lck:staurosporine complex reveals that binding of this inhibitor to Lck and other kinases induces a conformational change in the glycine rich loop, which helps maximize van der Waals interactions. This conformational change is mediated by a CH—O interaction that appears to be a common binding component for staurosporine with protein kinases. The non-selectivity of staurosporine may be explained by interactions with residues that are highly conserved in the ATP binding cleft. In contrast, the Src-selective inhibitor PP2 binds to Lck by accessing a hydrophobic pocket whose composition is unique to the Src family. The structures of these Lck complexes offer useful structural insights as they demonstrate binding modes that make differential use of various regions of the ATP binding cleft. Furthermore, these complexes indicate that kinase selectivity can be achieved with small molecule inhibitors that exploit subtle topological differences or sequence substitutions among protein kinases.

As used herein, the terms "sequence homology", or "homology", or "homologues", refers to the degree of identity or correspondence between nucleic acid or amino acid sequences of proteins. In a specific embodiment, two DNA sequences are "substantially homologous" or "substantially similar" when at least about 50% (preferably at least about 75% and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., [*Maniatis et al., Molecular Cloning: A Laboratory Manual*, Second Edition, (1989); *DNA Cloning*, Vols. I & II, (D. Glover, ed. 1985); Nucleic Acid Hybridization, B. D. Hames & S. J. Higgins, eds., (1985); *Current Protocols in Molecular Biology*, John Wiley & Sons, Inc. (1994); and references cited therein].

Similarly, in a particular embodiment, two amino acid sequences are "substantially homologous" or "substantially similar" when greater than about 30%, alternatively greater than about 70%, or alternatively greater than about 90% of the amino acids are identical, or when greater than about 60%, alternatively greater than about 75%, or alternatively greater than 90% are similar (functionally identical). Preferably, the similar or homologous sequences are identified by alignment using, for example, the GCG (Genetics Computer Group, Program Manual for the GCG Package, Version 7, Madison, Wis.) pileup program.

The term "active site" refers to any or all of the following: (i) the portion of the kinase sequence that binds to substrate, (ii) the portion of the kinase sequence that binds to an inhibitor, (iii) the portion of the kinase sequence that binds to ATP. The active site may also be characterized as comprising at least amino acid residues 259, 271, 371, 251, 323, 314, 292, 316, 288, 273, 318, 319, 301, 317, 320, 322 and 382 of SEQ ID NO: 1.

Due to the degeneracy of nucleotide coding sequences, other DNA sequences which encode substantially the same amino acid sequence as a kinase gene may be used in the practice of the present invention. These include but are not limited to allelic genes, homologous genes from other species, and nucleotide sequences comprising all or portions of kinase genes which are altered by the substitution of different codons that encode the same amino acid residue within the sequence, thus producing a silent change. Likewise, the kinase derivatives of the invention include, but are not limited to, those containing, as a primary amino acid sequence, all or part of the amino acid sequence of a kinase protein including altered sequences in which functionally equivalent amino acid residues are substituted for residues within the sequence resulting in a conservative amino acid substitution. For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, lysine, and histidine. The negatively charged (acidic) amino acids include aspartic acid and glutamic acid. Such alterations will not be expected to affect apparent molecular weight as determined by polyacrylamide gel electrophoresis, or isoelectric point. Abbreviations of amino acids are known in the art and are defined below:

| | |
|---|---|
| A = Ala = alanine | T = Thr = threonine |
| V = Val = valine | C = Cys = cysteine |
| L = Leu = leucine | Y = Tyr = tyrosine |
| I = Ile = isoleucine | N = Asn = asparagine |
| P = Pro = proline | Q = Gln = glutamine |
| F = Phe = phenylalanine | D = Asp = aspartic acid |
| W = Trp = tryptophan | E = Glu = glutamic acid |
| M = Met = methionine | K = Lys = lysine |
| G = Gly = glycine | R = Arg = arginine |
| S = Ser = serine | H = His = histidine |

The term "structure coordinates" refers to three-dimensional atomic coordinates derived from mathematical equations related to the experimentally measured intensities obtained upon diffraction of a mono- or polychromatic beam of X-rays by the atoms (scattering centers) of a kinase or kinase-ligand complex in crystal form. The diffraction data may be used to calculate an electron density map of the repeating unit of the crystal. The electron density maps can be used to establish the positions of the individual atoms within the unit cell of the crystal. Alternatively, computer programs such as XPLOR can be used to establish and refine the positions of individual atoms. Those of skill in the art understand that a set of structure coordinates determined by X-ray crystallography is not without error. For the purposes of this invention, any set of structure coordinates for a kinase, particularly a src-family kinase, and more particularly Lck, or Lck homologues, that have a root mean square deviation of equivalent protein backbone atoms (N, Cα, C and O) of less than about 1.50 Å, or alternatively less than about 1.00 Å when superimposed, using backbone atoms, on the structure coordinates listed herein shall be considered identical and within the scope of the invention.

The term "unit cell" refers to a basic parallelipiped shaped block. The entire volume of a crystal may be constructed by regular assembly of such blocks. Each unit cell comprises a complete representation of the unit of pattern, the repetition of which builds up the crystal.

The term "space group" refers to the arrangement of symmetry elements of a crystal.

The term "complex" refers to a kinase (or kinase truncation or homologue) in covalent or non-covalent association with a ligand, such ligand including, for example, a chemical entity, compound, or inhibitor, candidate drug, and the like. The term "association" refers to a condition of proximity between the ligand and the kinase, or their respective portions thereof, in any appropriate physicochemical interaction.

The term "kinase", unless expressly stated to the contrary, refers to full length as well as truncated protein sequences, or subsequences, and homologues.

The term "globular core" refers to the general spatial shape of the of the core of the kinase enzyme.

The invention relates to a crystal of a protein-ligand complex comprising a protein-ligand complex of a kinase and a ligand, wherein the crystal effectively diffracts X-rays for the determination of the atomic coordinates of the protein-ligand complex to a resolution of greater (meaning better as used in this context throughout) than 5.0 Angstroms, alternatively greater than 3.0 Angstroms, or alternatively greater than 2.0 Angstroms; and kinase comprises amino acids 225 to 508 of SEQ ID NO: 1 or an amino acid sequence that differs from amino acids 225 to 508 of SEQ ID NO: 1 by only conservative substitutions; alternatively, wherein said kinase comprises the active site as defined herein. The invention also relates to a crystal of a protein-ligand complex comprising a protein-ligand complex of a kinase and a ligand, wherein the crystal effectively diffracts X-rays for the determination of the atomic coordinates of the protein-ligand complex to a resolution of greater than 5.0 Angstroms, alternatively greater than 3.0 Angstroms, or alternatively greater than 2.0 Angstroms; and wherein the kinase: (a) comprises amino acids 225 to 508 of SEQ ID NO: 1 or an amino acid sequence that differs from amino acids 225 to 508 of SEQ ID NO: 1 by only conservative substitutions (or alternatively, wherein said kinase comprises the active site as defined herein); and (b) retains the globular core of the corresponding full-length kinase. Other embodiments include the crystals above wherein the kinase is alternatively a src-family kinase, or alternatively Lck, or alternatively a truncated Lck sequence; those crystals above wherein the ligand is AMP-PNP, staurosporine, PP2, baicalein, damnacanthal, or PD153035, or alternatively AMP-PNP, or alternatively staurosporine, or alternatively PP2, or alternatively baicalein, or alternatively damnacanthal, or alternatively PD153035; and those wherein the ligand is Lck and the ligand is AMP-PNP, staurosporine, PP2, baicalein, damnacanthal or PD153035, or alternatively AMP-PNP, or alternatively staurosporine, or alternatively PP2, or alternatively baicalein, or alternatively damnacanthal, or alternatively PD153035.

An alternate embodiment is the crystal of described above, wherein the kinase, or alternatively src-family kinase, or alternatively Lck, or alternatively truncated Lck, comprises an amino acid sequence of amino acids 251 to 371 of SEQ ID NO: 1, or an amino acid sequence that differs from amino acids 251 to 371 of SEQ ID NO: 1 by only conservative substitutions, or alternatively, wherein said kinase comprises the active site as defined herein. Other embodiments include such crystals wherein the kinase is alternatively a src-family kinase, or alternatively Lck, or alternatively a truncated Lck sequence; those crystals above wherein the ligand is AMP-PNP, staurosporine, PP2, baicalein, damnacanthal, or PD153035, or alternatively AMP-PNP, or alternatively staurosporine, or alternatively PP2, or alternatively baicalein, or alternatively damnacanthal, or alternatively PD153035; and those wherein the ligand is Lck and the ligand is AMP-PNP, staurosporine, PP2, baicalein, damnacanthal or PD153035, or alternatively AMP-PNP, or alternatively staurosporine, or alternatively PP2, or alternatively baicalein, or alternatively damnacanthal, or alternatively PD153035.

An alternate embodiment is the crystal described above wherein the kinase-ligand complex comprises AMP-PNP and having space group of $P2_12_12_1$ and a unit cell of dimensions of a=42.1 Å, b=73.7 Å, and c=91.7 Å.

An alternate embodiment is the crystal described above wherein the kinase-ligand complex comprises staurosporine and having space group of $P2_12_12_1$ and a unit cell of dimensions of a=42.2 Å, b=73.8 Å, and c=91.4 Å.

An alternate embodiment is the crystal described above wherein the kinase-ligand complex comprises staurosporine and having space group of $P2_12_12_1$ and a unit cell of dimensions of a=61.5 Å, b=69.0 Å, and c=73.7 Å.

An alternate embodiment is the crystal described above wherein the kinase-ligand complex comprises PP2 and having space group of $P2_12_12_1$ and a unit cell of dimensions of a=42.0 Å, b=73.7 Å, and c=91.6 Å.

An alternate embodiment is the crystal described above wherein the kinase-ligand complex comprises baicalein and having space group of $P22_12_1$ and a unit cell of dimensions of a=42.2 Å, b=73.9 Å, and c=91.7 Å.

An alternate embodiment is the crystal described above wherein the kinase-ligand complex comprises damnacanthal and having space group of $P2_12_12_1$ and a unit cell of dimensions of a=41.9 Å, b=73.6 Å, and c=92.3 Å.

An alternate embodiment is the crystal described above wherein the kinase-ligand complex comprises PD153035 and having space group of $P2_12_12_1$ and a unit cell of dimensions of a=42.1 Å, b=73.8 Å, and c=92.3 Å.

An alternate embodiment is the crystal described above wherein the kinase has secondary structural elements that include five beta strands and one helix in the N-terminal lobe (strands 1, 2, 3, 4 and 5 and alpha helix C), and two beta strands and seven alpha helices in the C-terminal domain (strands 6 & 8, and alpha helices D, E, EF, F, G, H and I).

Another embodiment is a method of using the kinase-ligand crystals described herein in an inhibitor screening assay comprising:
  (a) selecting a potential inhibitor by performing rational drug design with the three-dimensional structure determined for the crystal, wherein said selecting is performed in conjunction with computer modeling;
  (b) contacting the potential inhibitor with the kinase; and
  (c) detecting the ability of the potential inhibitor for inhibiting the kinase.

Alternate embodiments are those wherein the detecting the ability of the potential inhibitor for inhibiting the kinase in step (c) is performed using an enzyme inhibition assay, or alternatively those wherein the detecting the ability of the potential inhibitor for inhibiting the kinase in step (c) is performed using a cellular-based assay. A further embodiment is this method further comprising:
  (d) growing a supplemental crystal comprising a protein-ligand complex formed between the kinase and a first potential inhibitor from step (a), wherein the supplemental crystal effectively diffracts X-rays for the determination of the atomic coordinates of the protein-ligand complex to a resolution of greater than 5.0 Angstroms;
  (e) determining the three-dimensional structure of the supplemental crystal;
  (f) selecting a second potential inhibitor by performing rational drug design with the three-dimensional structure determined for the supplemental crystal, wherein said selecting is performed in conjunction with computer modeling;
  (g) contacting the second potential inhibitor with the kinase; and
  (h) detecting the ability of the second potential inhibitor for inhibiting the kinase.

In another embodiment, the invention relates to a method for identifying a potential inhibitor of kinase comprising:
  (a) selecting or designing a potential inhibitor by performing rational drug design with the three-dimensional structure coordinates of any of Tables 1–7, or alternatively any two or more of Tables 1–7, wherein said selecting is performed in conjunction with computer modeling;
  (b) contacting the potential inhibitor with the kinase; and
  (c) detecting the ability of the potential inhibitor for inhibiting the kinase.

Alternate embodiments are those wherein the detecting the ability of the potential inhibitor for inhibiting the kinase in step (c) is performed using an enzyme inhibition assay, or alternatively those wherein the detecting the ability of the potential inhibitor for inhibiting the kinase in step (c) is performed using a cellular-based assay. In another embodiment, the potential inhibitor is designed de novo. In yet another embodiment, the potential inhibitor is designed from a known inhibitor. A further embodiment is this method further comprising:
  (d) selecting an second potential inhibitor by performing rational drug design with the three-dimensional structure coordinates of any of Tables 1–7, or alternatively any combination of two or more of Tables 1–7, and the potential inhibitor of step (a), wherein said selecting is performed in conjunction with computer modeling;
  (e) contacting the potential inhibitor with a kinase; and
  (f) detecting the ability of the potential inhibitor for inhibiting the kinase.

In an alternate embodiment, the invention relates to a method of using the kinase to grow a crystal of a protein-ligand complex comprising:
  (a) contacting a kinase with a ligand, wherein the kinase forms a protein-ligand complex with the ligand; and
  (b) growing the crystal of the protein-ligand complex; wherein the crystal effectively diffracts X-rays for the determination of the atomic coordinates of the protein-ligand complex to a resolution of greater than 5.0 Angstroms.

An alternate embodiment is this method wherein said growing is performed by hanging drop vapor diffusion. Another embodiment is this method wherein said ligand is PP2, staurosporine, AMP-PNP, baicalein, damnacanthal, or PD153035, or alternatively, said ligand is baicalein, damnacanthal, or PD153035.

In an alternate embodiment, the invention relates to a method of using a kinase to produce a crystal of a protein-ligand complex comprising contacting a kinase crystal with a ligand, wherein the kinase forms a protein-ligand complex with the ligand within the crystal, and wherein the crystal effectively diffracts X-rays for the determination of the atomic coordinates of the protein-ligand complex to a resolution of greater than 5.0 Angstroms. Another embodiment is this method wherein said ligand is PP2, staurosporine, AMP-PNP, baicalein, damnacanthal, or PD153035, or alternatively, said ligand is baicalein, damnacanthal, or PD153035.

In an alternate embodiment, the invention relates to a method of growing a crystal of a kinase-ligand complex wherein the crystal effectively diffracts X-rays for the determination of the atomic coordinates of the protein-ligand complex to a resolution of greater than 5.0 Angstroms, comprising:
  (a) contacting a kinase solution with a ligand, wherein kinase forms a protein-ligand complex with the ligand; and
  (b) growing the crystal of the protein-ligand complex; wherein the crystal effectively diffracts X-rays for the determination of the atomic coordinates of the protein-ligand complex to a resolution of greater than 5.0 Angstroms.

An alternate embodiment is this method wherein said growing is performed by hanging drop vapor diffusion. Another embodiment is this method wherein said ligand is PP2, staurosporine, AMP-PNP, baicalein, damnacanthal, or PD153035, or alternatively, said ligand is baicalein, damnacanthal, or PD153035.

In another embodiment, this invention relates to a method of producing a crystal of a kinase-ligand complex wherein the crystal effectively diffracts X-rays for the determination of the atomic coordinates of the protein-ligand complex to a resolution of greater than 5.0 Angstroms, comprising contacting a kinase crystal with a ligand, wherein the kinase forms a protein-ligand complex with the ligand within the crystal, and wherein the crystal effectively diffracts X-rays for the determination of the atomic coordinates of the protein-ligand complex to a resolution of greater than 5.0 Angstroms. An alternate embodiment is this method wherein said ligand is PP2, staurosporine, AMP-PNP, baicalein, damnacanthal, or PD153035, or alternatively, said ligand is baicalein, damnacanthal, or PD153035.

Alternate embodiments of the invention are those crystals, and methods of using such crystals or structure coordinates thereof, described herein wherein the crystals further comprise a nucleoside or nucleotide cofactor or substrate, or further comprise any one of ATP, GTP, Mg, Mn, peptides or polymeric amino acids.

In each of the methods described herein, further embodiments are those wherein the kinase is a src-family kinase, alternatively Lck, or alternatively, truncated Lck.

In another embodiment, the invention relates to a method of using the three-dimensional structure coordinates of any one of Tables 1–7, or alternatively any combination of two or more of Tables 1–7, comprising:
  (a) Determining structure factors from the coordinates; and
  (b) Applying said structure factor information to a set of X-ray diffraction data obtained from a crystal of a protein homologous to SEQ ID NO: 1;
  (c) Solving the three-dimensional structure of the protein homologous to SEQ ID NO: 1.

In another embodiment, the invention relates to a method for identifying a potential inhibitor of a kinase that covalently binds with Lys 273 of SEQ ID NO.: 1 or a homologous lysine residue in a kinase comprising:
  (a) selecting or designing a potential inhibitor by performing rational drug design with the three-dimensional structure coordinates of Table 6, wherein said selecting is performed in conjunction with computer modeling;
  (b) contacting the potential inhibitor with a kinase; and
  (c) detecting the ability of the potential inhibitor for inhibiting the kinase.

A further embodiment is that wherein the three-dimensional structure coordinates in step (a) further comprise one or more structure coordinates of Tables 1–5 or 7.

In another embodiment, the invention relates to a computer-readable data storage medium ("CRM") comprising a data storage material encoded with computer readable data, which when used by a computer programmed with instructions for using such data, displays a three-dimensional graphical representation of a molecule or molecular complex comprising a binding pocket defined by structure coordinates of SEQ ID NO.: 1, or alternatively by structure coordinates of an active site as defined herein, or a homologue of said molecule or molecular complex, wherein said homologue comprises a binding pocket that has a root mean square deviation from the backbone atoms of said amino acids of less than about 1.50 Å, or alternatively less than about 100 Å. In another embodiment, the aforementioned structure coordinates are those of any one or more of Tables 1–7, or a subset thereof, including the coordinates relating to the active site as defined herein.

The computer may comprise a central processing unit ("CPU"), a working memory, for example, random access memory ("RAM") and/or storage memory in the form of one or more disk drives (e.g., floppy, Zip™, Jazz™), tape drives, CD-ROM drives, DVD drives, and the like, a display terminal such as for example, a cathode ray tube type display, and input and output lines for data transmission, including a keyboard and/or mouse controller. The computer may be a stand-alone, or connected to a network and/or shared server. Computer-readable data storage materials include, for example, hard drives, floppy, Zip™ and Jazz™ type disks, tapes, CDs, and DVDs.

In another embodiment, the invention relates to a computer readable data storage material encoded with computer readable data comprising structure coordinates of any one or more of Tables 1–7, or alternatively, encoded with computer readable data comprising structure coordinates of the active site of any one or more of Tables 1–7.

In another embodiment, the invention relates to a method for identifying a potential inhibitor of a kinase comprising:
  (a) selecting or designing a potential inhibitor by performing rational drug design with a computer readable data storage material encoded with computer readable data comprising structure coordinates of any one or more of Tables 1–7, wherein said selecting is performed in conjunction with computer modeling;
  (b) contacting the potential inhibitor with a kinase; and
  (c) detecting the ability of the potential inhibitor for inhibiting the kinase.;

In another embodiment, the computer readable data storage material in step (a) is encoded with computer readable data comprising structure coordinates of the active site of any one or more of Tables 1–7.

Table 1 contains the X-ray structure coordinates of an Lck:PP2 complex. Tables 2 and 3 contain the X-ray structure coordinates of an Lck:AMP-PNP complex. Table 4 contains the X-ray structure coordinates of an Lck:staurosporine complex. Table 5 contains the X-ray structure coordinates of an Lck:baicalein complex. Table 6 contains the X-ray structure coordinates of an Lck:damnacanthal complex. Table 7 contains the X-ray structure coordinates of an Lck:PD153035 complex. Tables 8 and 9 summarize the diffraction data and refined model of Tables 1–4 and 5–7, respectively.

Crystals of the kinase or kinase-ligand complex can be produced or grown by a number of techniques including batch crystallization, vapor diffusion (either by sitting drop or hanging drop), soaking, and by microdialysis. Seeding of the crystals in some instances is required to obtain X-ray quality crystals. Standard micro and/or macro seeding of crystals may therefore be used. Preferably, the crystal effectively diffracts X-rays for the determination of the atomic coordinates of the protein-ligand complex to a resolution greater than 5.0 Angstroms, alternatively greater than 3.0 Angstroms, or alternatively greater than 2.0 Angstroms. Exemplified in the Examples section below is the hanging-drop vapor diffusion procedure.

Once a crystal of the present invention is produced, X-ray diffraction data can be collected. The example below used standard cryogenic conditions for such X-ray diffraction data collection though alternative methods may also be used. For example, diffraction data can be collected by using X-rays produced in a conventional source (such as a sealed tube or rotating anode) or using a synchrotron source. Methods of X-ray data collection include, but are not limited to, precession photography, oscillation photography and diffractometer data collection. Data can be processed using packages including, for example, DENZO and SCALPACK (Z. Otwinowski and W. Minor) and the like.

The three-dimensional structure of the protein or protein-ligand complex constituting the crystal may be determined by conventional means as described herein. Where appropriate, the structure factors from the three-dimensional structure coordinates of a related protein may be utilized to aid the structure determination of the protein-ligand complex. Structure factors are mathematical expressions derived from three-dimensional structure coordinates of a molecule. These mathematical expressions include, for example, amplitude and phase information. The term "structure factors" is known to those of ordinary skill in the art. Alternatively, the three-dimensional structure of the protein-ligand complex may be determined using molecular replacement analysis. This analysis utilizes a known three-dimensional structure as a search model to determine the structure of a closely related protein-ligand complex. The measured X-ray diffraction intensities of the crystal are compared with the computed structure factors of the search model to determine the position and orientation of the protein in the protein-ligand complex crystal. Computer programs that can be used in such analyses include, for example, X-PLOR and AmoRe (J. Navaza, Acta Crystallographics ASO, 157–163 (1994)). Once the position and orientation are known, an electron density map may be calculated using the search model to provide X-ray phases. The electron density can be inspected for structural differences and the search model may be modified to conform to the new structure. Using this approach, one may use the structure of the kinase-ligand complex or complexes described herein to solve other kinase-ligand complex crystal structures, or other kinase crystal structures, particularly where the kinase is homologous to Lck. Computer programs that can be used in such analyses include, for example, QUANTA and the like.

Upon determination of the three-dimensional structure of a crystal of a kinase-ligand complex, a potential inhibitor may be evaluated by any of several methods, alone or in combination. Such evaluation may utilize visual inspection of a three-dimensional representation of the active site, based on the X-ray coordinates of a crystal described herein, on a computer screen. Evaluation, or modeling, may be accomplished through the use of computer modeling techniques, hardware, and software known to those of ordinary skill in the art. This may additionally involve model building, model docking, or other analysis of kinase-ligand interactions using software including, for example, QUANTA or SYBYL, followed by energy minimization and molecular dynamics with standard molecular mechanics forcefields including, for example, CHARMM and AMBER. The three-dimensional structural information of a kinase-ligand complex may also be utilized in conjunction with computer modeling to generate computer models of other kinase protein structures, particularly those with homology to the kinase from which the three-dimensional structural information was determined. Using the structure coordinates described herein, computer models of kinase protein structures of src-family kinases, or of kinases that share sequence homology in the kinase domain or the active site as compared to Lck, may be created using standard methods and techniques known to those of ordinary skill in the art, including software packages described herein.

Once the three-dimensional structure of a crystal comprising a protein-ligand complex formed between a kinase and a standard ligand for that kinase is determined, a potential ligand is examined through the use of computer modeling using a docking program such as FLEX X, DOCK, or AUTODOCK (see, Dunbrack et al., *Folding & Design*, 2:R27–42 (1997)), to identify potential ligands and/or inhibitors for kinases. This procedure can include computer fitting of potential ligands to the ligand binding site to ascertain how well the shape and the chemical structure of the potential ligand will complement the binding site. [Bugg et al., *Scientific American*, December:92–98 (1993); West et al., TIPS, 16:67–74 (1995)]. Computer programs can also be employed to estimate the attraction, repulsion, and steric hindrance of the two binding partners (i.e., the ligand-binding site and the potential ligand). Generally the tighter the fit, the lower the steric hindrances, and the greater the attractive forces, the more potent the potential drug since these properties are consistent with a tighter binding constant. Furthermore, the more specificity in the design of a potential drug, the more likely that the drug will not interact as well with other proteins. This will minimize potential side-effects due to unwanted interactions with other proteins.

A variety of methods are available to one skilled in the art for evaluating and virtually screening molecules or chemical fragments appropriate for associating with a protein, particularly a kinase enzyme. Such association may be in a variety of forms including, for example, steric interactions, van der Waals interactions, electrostatic interactions, solvation interactions, charge interactions, covalent bonding interactions, non-covalent bonding interactions (e.g., hydrogen-bonding interactions), entropically or enthalpically favorable interactions, and the like.

Numerous computer programs are available and suitable for rational drug design and the processes of computer modeling, model building, and computationally identifying, selecting and evaluating potential inhibitors in the methods described herein. These include, for example, GRID (available form Oxford University, UK), MCSS (available from Molecular Simulations Inc., Burlington, Mass.), AUTODOCK (available from Oxford Molecular Group), FLEX X (available from Tripos, St. Louis. Mo.), DOCK (available from University of California, San Francisco), CAVEAT (available from University of California, Berkeley), HOOK (available from Molecular Simulations Inc., Burlington, Mass.), and 3D database systems such as MACCS-3D (available from MDL Information Systems, San Leandro, Calif.), UNITY (available from Tripos, St. Louis. Mo.), and CATALYST (available from Molecular Simulations Inc., Burlington, Mass.). Potential inhibitors may also be computationally designed "de novo" using such software packages as LUDI (available from Biosym Technologies, San Diego, Calif.), LEGEND (available from Molecular Simulations Inc., Burlington, Mass.), and LEAP-FROG (Tripos Associates, St. Louis, Mo.). Compound deformation energy and electrostatic repulsion, may be evaluated using programs such as GAUSSIAN 92, AMBER, QUANTA/CHARMM, AND INSIGHT II/DISCOVER. These computer evaluation and modeling techniques may be performed on any suitable hardware including for example, workstations available from Silicon Graphics, Sun Microsystems, and the like. These techniques, methods, hardware and software packages are representative and are not intended to be comprehensive listing. Other modeling techniques known in the art may also be employed in accordance with this invention. See for example, N. C. Cohen, *Molecular Modeling in Drug Design*, Academic Press (1996) (and references therein), and software identified at internet sites including the CAOS/CAMM Center Cheminformatics Suite at http://www.caos.kun.nl/, and the NIH Molecular Modeling Home Page at http://www.fi.muni.cz/usr/mejzlik/mirrors/molbio.info.nih.gov/modeling/software list/.

A potential inhibitor is selected by performing rational drug design with the three-dimensional structure (or structures) determined for the crystal described herein, especially in conjunction with computer modeling and methods described above. The potential inhibitor is then obtained from commercial sources or is synthesized from readily available starting materials using standard synthetic techniques and methodologies known to those of ordinary skill in the art. The potential inhibitor is then assayed to determine its ability to inhibit the target enzyme and/or enzyme pathway as described above.

The potential inhibitor selected or identified by the aforementioned process may be assayed to determine its ability to inhibit the target enzyme and/or enzyme pathway. The assay may be in vitro or in vivo. Inhibition can be measured by various methods, including, for example, those methods illustrated in the examples below. The compounds described herein may be used in assays, including radiolabelled, antibody detection and fluorometric, for the isolation, identification, or structural or functional characterization of enzymes, peptides or polypeptides. Such assays include any assay wherein a nucleoside or nucleotide are cofactors or substrates of the peptide of interest, and particularly any assay involving phosphotransfer in which the substrates and or cofactors are ATP, GTP, Mg, Mn, peptides or polymeric amino acids. The assay may be an enzyme inhibition assay, utilizing a full length or truncated kinase, said enzyme having sequence homology with that of mammalian origin, including for example, human, murine, rat, and the like. The enzyme is contacted with the potential inhibitor and a measurement of the binding affinity of the potential inhibitor against a standard is determined. Such assays are known to one of ordinary skill in the art and are exemplified in the examples herein. The assay may also be a cell-based assay. The potential inhibitor is contacted with a cell and a measurement of inhibition of a standard marker produced in the cell is determined. Cells may be either isolated from an animal, including a transformed cultured cell, or may be in a living animal. Such assays are also known to one of ordinary skill in the art and are exemplified in the examples herein.

When suitable potential ligands are identified as described above, a supplemental crystal can be produced or grown (using techniques described herein) that comprises a protein-ligand complex formed between a kinase, src kinase, lck, or truncated lck and the potential ligand. Preferably, the crystal effectively diffracts X-rays for the determination of the atomic coordinates of the protein-ligand complex to a resolution greater than 5.0 Angstroms, alternatively greater than 3.0 Angstroms, or alternatively greater than 2.0 Angstroms. The three-dimensional structure of the protein-ligand complex constituting the supplemental crystal may be determined by conventional means such as those described herein.

A potential inhibitor is selected by performing rational drug design with the three-dimensional structure (or structures) determined for the supplemental crystal, especially in conjunction with computer modeling described above. The potential inhibitor is then obtained from commercial sources or is synthesized from readily available starting materials using standard synthetic techniques and methodologies known to those of ordinary skill in the art. The potential inhibitor is then assayed to determine its ability to inhibit the target enzyme and/or enzyme pathway as described above.

For all potential inhibitor assays described herein, further refinements to the structure of the potential inhibitor will generally be necessary and can be made by successive iterations of any/or all of the steps provided by the inhibitor screening assay.

The inhibitors identified by the methods described herein may also be useful for inhibition of kinase activity of one or more enzymes. Kinases include, for example, protein kinases, lipid kinases (e.g., phosphatidylinositol kinases PI-3, PI-4) and carbohydrate kinases. Kinases may be of prokaryotic, eukaryotic, bacterial, viral, fungal or archaea origin. Specifically, the compounds described herein are useful as inhibitors of tyrosine, serine/threonine or histidine protein kinases. Examples of kinases that are inhibited by the compounds and compositions described herein and against which the methods described herein are useful include, but are not limited to, LCK, IRK (=INSR=Insulin receptor), IGF-1 receptor, SYK, ZAP-70, IRAK1, IRAK2, BLK, BMX, BTK, FRK, FGR, FYN, HCK, ITK, LYN, TEC, TXK, YES, ABL, SRC, EGF-R (=ErbB-1), ErbB-2 (=NEU=HER2), ErbB-3, ErbB-4, FAK, FGF1R (=FGR-1), FGF2R (=FGR-2), IKK-1 (=IKK-ALPHA=CHUK), IKK-2 (=IKK-BETA), MET (=c-MET), NIK, PDGF receptor ALPHA, PDGF receptor BETA, TIE1, TIE2 (=TEK), VEGFR1 (=FLT-1), VEGFR2 (=KDR), FLT-3, FLT-4, KIT, CSK, JAK1, JAK2, JAK3, TYK2, RIP, RIP-2, LOK, TAK1, RET, ALK, MLK3, COT TRKA, PYK2, EPHB4, RON, GSK3, UL13, ORF47, ATM, CDK (including all subtypes), PKA, PKB (including all PKB subtypes) (=AKT-1, AKT-2, AKT-3), PKC (including all PKC subtypes), and bARK1 (=GRK2) (and other G-protein coupled receptor kinases (GRKs)), and all subtypes or isoforms of these kinases. The inhibitors identified by the methods described herein are suitable for use in the treatment of diseases and disease symptoms that involve one or more of the aforementioned protein kinases. In one embodiment, the inhibitors identified by the methods described herein are particularly suited for inhibition of or treatment of disease or disease symptoms mediated by src-family kinases. In an alternate embodiment, the inhibitors described herein are particularly suited for inhibition of LCK.

The inhibitors described herein are also useful for inhibiting the biological activity of any enzyme comprising greater than 90%, alternatively greater than 85%, or alternatively greater than 70% sequence homology with a kinase sequence, including the kinases mentioned herein. The inhibitors described herein are also useful for inhibiting the biological activity of any enzyme comprising a subsequence, or variant thereof, of any enzyme that comprises greater than 90%, alternatively greater than 85%, or alternatively greater than 70% sequence homology with a kinase subsequence, including subsequences of the kinases mentioned herein. Such subsequence preferably comprises greater than 90%, alternatively greater than 85%, or alternatively greater than 70% sequence homology with the sequence of an active site or subdomain of a kinase enzyme. The subsequences, or variants thereof, comprise at least about 250 amino acids, or alternatively at least about 120 amino acids.

The inhibitors described herein are useful for inhibiting the biological activity of any enzyme that binds ATP and thus for treating disease or disease symptoms mediated by any enzyme that binds ATP. The inhibitors described herein are also useful for inhibiting the biological activity of any enzyme that is involved in phosphotransfer and thus for treating disease or disease symptoms mediated by any enzyme that is involved in phosphotransfer. The inhibitors described herein are also useful for inhibiting the biological activity of a polypeptide or enzyme having sequence homology with a kinase sequence and thus for treating disease or disease symptoms mediated by such polypeptide or enzyme. Such polypeptides or enzymes may be identified by comparison of their sequence with kinase sequences and kinase catalytic domain sequences. For example, one method of comparison involves the database PROSITE (http://expasy.hcuge.ch), containing "signatures" or sequence patterns (or motifs) or profiles of protein families or domains. Thus, the inhibitors described herein are useful for inhibiting the biological activity of a polypeptide or enzyme comprising a sequence that comprises a "signature" or sequence pattern or profile derived for, and identified in PROSITE as relating to kinases, and for treating disease or disease symptoms mediated by such polypeptide or enzyme. Examples of such PROSITE motifs or consensus patterns identified as relating to kinases include PS00107, PS00108, PS00109, PS50011, PS00915, and PS00916. The term "kinases" as used in this application, unless expressly stated to the contrary, refers to protein sequences that comprise such signature, motif, or sequence or consensus patterns.

The inhibitors described herein are useful in inhibiting kinase activity. As such, the compounds, compositions and methods of this invention are useful in treating kinase-mediated disease or disease symptoms in a mammal, particularly a human. Kinase mediated diseases are those wherein a protein kinase is involved in signaling, mediation, modulation, or regulation of the disease process. Kinase mediated diseases are exemplified by the following disease classes: cancer, autoimmunological, metabolic, inflammatory, infection (bacterial, viral, yeast, fungal, etc.), central nervous system degenerative disease, allergy/asthma, angiogenesis, cardiovascular disease, and the like.

The inhibitors described herein are useful in treating or preventing diseases, including, transplant rejection (e.g., kidney, liver, heart, lung, pancreas (islet cells), bone marrow, cornea, small bowel, skin allografts or xenografts), graft versus host disease, osteoarthritis, rheumatoid arthritis, multiple sclerosis, juvenile diabetes, asthma, inflammatory bowel disease (Crohn's disease, ulcerative colitis), cachexia, septic shock, lupus, diabetes mellitus, myasthenia gravis, psoriasis, dermatitis, eczema, seborrhea, Alzheimer's disease, Parkinson's disease, stem cell protection during chemotherapy, ex vivo purging for autologous or allogeneic bone marrow transplantation, cancer (breast, lung, colorectal, ovary, prostate, renal, squamous cell, prostate, etc.), bacterial infections, viral infections, fungal infections and heart disease, including but not limited to, restenosis.

Synthetic chemistry transformations and protecting group methodologies (protection and deprotection) useful in synthesizing the inhibitor compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995).

The inhibitors described herein may contain one or more asymmetric centers and thus occur as racemates and racemic mixtures, single enantiomers, individual diastereomers and diastereomeric mixtures. All such isomeric forms of these compounds are expressly included in the present invention. The inhibitors described herein may also be represented in multiple tautomeric forms, all of which are included herein. The inhibitors may also occur in cis- or trans- or E- or Z-double bond isomeric forms. All such isomeric forms of such inhibitors are expressly included in the present invention. All crystal forms of the inhibitors described herein are expressly included in the present invention.

All references cited herein, whether in print, electronic, computer readable storage media or other form, are expressly incorporated by reference in their entirety, including but not limited to, abstracts, articles, journals, publications, texts, treatises, internet web sites, databases, software packages, patents, and patent publications.

In order that the invention described herein may be more readily understood, the following examples are set forth. It should be understood that these examples are for illustrative purposes only and are not to be construed as limiting this invention in any manner.

EXAMPLES

Example 1

Construct design, protein expression and purification. Full-length LCK cDNA (gift of T. Roberts, DFCI) was used as a template for PCR amplification of a 879 bp fragment encoding amino acid residues 225 to 509 of the Lck catalytic domain. The PCR product was cloned into the Bam HI and Eco RI sites of the plasmid vector pFastBacl(Gibco/BRL) modified to contain the coding region for GST and a thrombin cleavage site upstream of the multiple cloning site. Recombinant baculovirus was obtained using the Bac-to-Bac expression system (Gibco/BRL). After two rounds of amplification in Sf9 insect cells (*Spodoptera frugiperda*)

cultured in Hink's modification of Graces media, the virus was used to infect High Five insect cells (*trichoplusia ni*) cells grown in Ex-cell 405 media for protein production.

Recombinant GST-Lck (225–509) was purified from baculovirus cells essentially as previously described [40], except that the first step involved fractionating cell lysates on glutathione Sepharose (Pharmacia Biotech). The GST-Lck bound to the resin was eluted with 30 mM glutathione and cleaved overnight at 4° C. with the fusion protein at 0.5 mg/ml and α-thrombin added at a 1:1000 ratio (w/w). A protease inhibitor cocktail was then added and the protein sample was incubated for 30 min at 25° C. The inhibition of thrombin was confirmed in a spectrophotometric assay as described [57, 58]. The cleaved GST and Lck were separated by anion exchange chromatography essentially as described for the separation of Lck phosphorylation species [40]. The pooled fraction of Lck was then concentrated in a centriprep-10 and size fractionated on a column of Superdex-75. The monomeric fraction appeared homogeneous by SDS and native polyacrylamide gel electrophoresis.

Example 2

Structural determination. Crystals of the Lck kinase domain in complex with AMP-PNP/Mg (5mM) were grown from 1.6M ammonium sulfate in 0.1M bisTris (pH6.5) by hanging drop method. These crystals are isomorphous to the apo Lck [40]. Crystals of apo Lck were obtained under the same condition as described above by microseeding the apo protein sample with the crystals of Lck:AMP-PNP. These crystals were subsequently soaked for three days in a solution containing 1.6M ammonium sulfate, 0.1M bisTris (pH6.5) and 0.3 mM staurosporine. Lck:PP2 crystals are obtained by similar methods.

Crystals of Lck:AMP-PNP and Lck:staurosporine (soaked) were equilibrated against a solution containing 1.6M ammonium sulfate, 0.1M bisTris and 20% ethylene glycol and frozen at 100K for data collection. Diffraction data of the crystals of Lck:AMP-PNP were collected at the X4A beamline at Brookhaven National Laboratory using an Raxis-IV image plate detector or were collected on an Raxis-II image plate detector mounted on the RU300 generator. Diffraction data for Lck:PP2 was collected on an Raxis-II image plate detector mounted on the RU300 generator. Lck:PP2 crystals were equilibrated as above prior to freezing,. Crystals of Lck:baicalein, Lck:damnacanthal, and Lck:PD153035 were obtained using essentially similar conditions to those described above and diffraction data on those crystals were collected on an Raxis-II image plate detector mounted on the RU300 generator. All data were processed using the HKL software package (Z. Otwinowski).

The structure of the Lck:staurosporine co-complex was solved by molecular replacement using the program AmoRe (J. Navaza). The apo Lck structure was used as a search model. The initial molecular replacement solution was subject to rigid body and positional refinement using XPLOR [59] (Molecular Simulations, Inc.)

Bound ligands were identified using the difference fourier method phased by the structure of the apo Lck [40]. Model building of protein and inhibitor into electron density maps were performed using the graphic program Quanta (Molecular Simulations, Inc.), and the structures were refined using XPLOR [59]. The graphic figures were made by using Grasp [60] and Setor [61].

Example 3

Kinase activity assays. Protein kinase activity was measured in two different in vitro assays. In the first assay, the kinase of interest was incubated with [$^{33}$P]-ATP in a 96-well plate previously coated with substrate (i.e. poly[Glu, Tyr] 4:1) and the kinase activity determined in a Microbeta, Wallac Top-Count (Packard Instruments). In the second assay, protein kinase autophosphorylation was examined. GST fused Lck proteins consisting of either the kinase domain (Residues 225–509) or nearly full length (Residues 66–509) sequences were incubated in 10 mM $Mg^{2+}$, 25 mM Tris 7.5, 1 mM DTT, 1 μM ATP (10 μCi/ml [$^{33}$P]ATP) for 5 minutes at room temperature with the indicated concentration of compounds. The reaction was stopped by addition of one volume of 10% TCA and filtered through a millipore filter plate. After 3 washes with 200 μl 10% TCA, 50 μl of scintillation cocktail was added to each well and the plate was read in a microbeta scintillation counter (Wallach).

Example 4

T-cell activation. Whole blood was obtained from normal donors and human peripheral blood lymphocytes (hPBL) were isolated by ficol-hypaque density centrifugation. T-cells were then purified from the hPBL by negative selection using an R&D column following the manufacturers directions (R&D Systems, Minneapolis, Minn.). A 96-well flat-bottomed plate was coated with 10 μg/ml of goat anti-mouse (GAM)-$IgG_1$ (Caltag, Burlingame, Calif.) in PBS overnight at 4C. The GAM-coated plate was flicked out and anti-CD3 mAb (UCHT-1, Coulter/Immunotech, Miami, Fla.) is added at 0.2 μg/ml in AIMV medium (Gibco, Grand Island, N.Y.) for 3 hr. at 37C. Purified T-cells were pre-incubated at 1×10$^5$/well in AIM V with or without compound for 30 minutes then transferred to the anti-CD3 capture plate. Finally, anti-CD28 (Pharmingen, San Diego, Calif.) in AIMV (150 ng/ml final) was added to each well. Cells were incubated for 20 hours at 37C in 5% $CO_2$ then supernatants were tested by ELISA for cytokine levels (Endogen, Woburn, Mass.).

Example 5

Phosphotyrosine western blotting. Jurkat (ATCC, Manassas, Va.) cells (1×10$^7$) in RPMI-1640 (Gibco, Grand Island, N.Y.) containing 10% FCS (Sigma, St. Louis, Mo.) were incubated with or without anti-CD3 mAb (UCHT-1, 10 μg/ml) for 15 minutes on ice. Cells were washed in cold PBS then incubated with or without GAM-$IgG_1$ (10 μg /ml) in RPMI-1640 containing 10% FCS for 15 minutes on ice. Cells were then transferred to 37° C. water bath for 1 minute. Stimulation was stopped by the addition of 5 volumes of cold PBS containing 200 μM sodium orthovanadate. Cells were spun down and lysed in 150 mM Tris/10 mM HEPES buffer, pH 7.3, containing 1% Triton X-100 and Complete protease inhibitor cocktail (Boehringer Mannheim, Germany) for 30 minutes on ice. Whole cell lysates (2×10$^6$/cell equivalents per lane) were separated by 14% reducing SDS-PAGE and transferred to PVDF membrane. Blots were probed with anti-phosphotyrosine (4G10, Upstate Biotechnology, Inc., Saranac Lake, N.Y.) and developed using ECL-plus following the manufacturers directions (Amersham, Arlington Heights, Ill.).

Example 6

Kinases suitable for use in the following protocol to determine kinase activity of the compounds described herein include, but are not limited to: Lck, Lyn, Src, Fyn, Syk, Zap-70, Itk, Tec, Btk, EGFR, ErbB2, Kdr, Tek, c-Met, InsR.

Kinases are expressed as either kinase domains or full length constructs fused to glutathione S-transferase (GST) or polyHistidine tagged fusion proteins in either *E. coli* or Baculovirus-High Five expression systems. They are purified to near homogeneity by affinity chromatography essentially as previously described (Lehr et al., 1996; Gish et al., 1995). In some instances, kinases are co-expressed or mixed with purified or partially purified regulatory polypeptides prior to measurement of activity.

Kinase activity and inhibition are measured essentially by established protocols (Braunwalder et al., 1996). Briefly, The transfer of $^{33}Po_4$ from ATP to the synthetic substrates poly(Glu, Tyr) 4:1 or poly(Arg, Ser) 3:1 attached to the bioactive surface of microtiter plates serves as the basis to evaluate enzyme activity. After an incubation period, the amount of phosphate transferred is measured by first washing the plate with 0.5% phosphoric acid, adding liquid scintillant, and then counting in a liquid scintillation detector.

The $IC_{50}$ is determined by the concentration of compound that causes a 50% reduction in the amount of $^{33}P$ incorporated onto the substrate bound to the plate.

Other similar methods whereby phosphate is transferred to peptide or polypeptide substrate containing tyrosine, serine, threonine, or histidine, either alone, in combination, or in combination with other amino acids, in solution or immobilized (i.e., solid phase) are also useful. Alternatively, kinase activity can be measured using antibody-based methods whereby an antibody or polypeptide is used as a reagent to detect phosphorylated target polypeptide.

Example 6 References

Braunwalder A F, Yarwood D R, Hall T, Missbach M, Lipson K E, Sills M A. (1996). A solid-phase assay for the determination of protein tyrosine kinase activity of c-src using scintillating microtitration plates. *Anal. Biochem.* 234 (1):23–26.

Gish G, McGlone M L, Pawson T, Adams J A. (1995). Bacterial expression, purification and preliminary kinetic description of the kinase domain of v-fps. *Protein Eng.* 8(6):609–614.

Lehr R V, Ma Y G, Kratz D, Brake P G, Wang S, Faltynek C R, Wang X M, Stevis P E (1996). Production, purification and characterization of non-myristylated human T-cell protein tyrosine kinase in a baculovirus expression system. *Gene* 169(2):27527–9.

Example 7

The cellular activities of the inhibitor compounds described herein may be assessed in a number of assays known to those skilled in the art, some of which are exemplified as described below. Typical sources for cells include, but are not limited to, human bone marrow or peripheral blood lymphocytes, or their equivalents, or rodent spleen cells. Transformed cell lines that have been reported as cytokine- and growth factor-dependent cells are available from standard cell banks such as The American Type Culture Collection (Bethesda, Md.). Cells genetically manipulated to express a particular kinase or kinases are also suitable for use in assaying cellular activity. These cells are grown in various standard tissue culture media available from suppliers such as GIBCO/BRL (Grand Island, N.Y.) supplemented with fetal bovine serum. Cellular activity may also be measured using bacterial, yeast, or virally infected mammalian cells. Standard inhibitors of cell activation include mycophenolic acid (SIGMA, St. Louis, Mo.), staurosporine (Calbiochem, San Diego, Calif.), wortmannin (Calbiochem), cyclosporine, FK-506, and steroids (e.g., corticosteroids).

The compound(s) are tested for activity in cellular assays of T or B cell activation. For example, the receptor-induced production of cytokines and/or cell proliferation is a useful measure. This assay is performed similarly to techniques described in the literature (1,2), and involves antibody-, antigen-, mitogen-, or antigen presenting cell-mediated crosslinking of the T cell or B cell receptor with or without engagement of co-stimulatory receptors.

The compound(s) are tested for activity in cellular assays of allergic mediator release. For example, the receptor-induced degranulation in mast cells or basophils leading to histamine release and the production of cytokines is a useful measure. This assay is performed similarly to techniques described in the literature (3), and involves crosslinking of antigen-specific IgE on cells leading to degranulation and or cytokine production.

The compound(s) are tested for activity in cellular assays of growth factor effects. For example, growth factor receptor-induced signaling in a cell leading to intracellular signaling events such as kinase autophosphorylation, phosphorylation of relevant kinase substrates, phosphorylation of MAP kinases, or induction of gene expression. Also, for example, growth factor-induced functional events in cells such as DNA synthesis, proliferation, migration, or apoptosis. These assays are performed similarly to techniques described in the literature (4–7), and involve addition of growth factor to responsive cells followed by monitoring of signaling or functional events.

The compound(s) are tested for activity in cellular assays of cytokine activation. For example, cytokine-induced intracellular signaling events and/or cell proliferation and/or cytokine production are a useful measure. This assay is performed similarly to techniques described in the literature (8), and involves addition of cytokine to responsive cells followed by monitoring intracellular signaling events and/or cell proliferation and/or cytokine production.

Example 7 References

1. Shuji, K., et al. Activation of p21-CDC42/Rac-activated kinases by CD28 signaling: p21-activated kinase (PAK) and MEK kinase 1 (MEKK1) may mediate the interplay between CD3 and CD28 signals. *J. Immunol.* 160: 4182–4189 (1998).
2. Satterthwaite, A. B., et al., Independent and opposing roles for Btk and Lyn in B cell and myeloid signaling pathways. *J. Exp. Med.* 188: 833–844 (1998).
3. Stephan, V., et al. FcεR1-induced protein tyrosine phosphorylation of pp72 in rat basophilic leukemia cells (RBL-2H3). *J. Biol. Chem.* 267 (8): 5434–5441 (1992).
4. Olayioye, M. A., et al. ErbB-1 and ErbB-2 acquire distinct signaling properties dependent upon their dimerization partner. *Molecular and Cellular Biology.* 18(9): 5042–5051 (1998).
5. Buchdunger, E., et al. Inhibition of the Abl protein-tyrosine kinase in vitro and in vivo by a 2-phenylaminopyrimidine derivative. *Cancer Res.* 56;101–104 (1996).
6. Yoshida, A. et al., Differential endothelial migration and proliferation to basic fibroblast growth factor and vascular endothelial growth factor. *Growth Factors.* 13:57–64 (1996).
7. Brunet, A., et al., Akt promotes cell survival by phosphorylating and inhibiting forkhead transcription factor. *Cell.* 96:857–868 (1999).

8. Liu, K. D., et al. Janus kinases in interleukin-2-mediated signaling: JAK1 and JAK3 are differentially regulated by tyrosine phosphorylation. *Current Biology*. 7 (11): 817-826 (1997).

While we have described a number of embodiments of this invention, it is apparent that our basic examples may be altered to provide other embodiments that utilize the products and processes of this invention. Therefore, it will be appreciated that the scope of this invention is to be defined by the claims rather than by the specific embodiments that have been represented by way of example.

REFERENCES

1. Alberola-Ila, J., Takaki, S., Kemer, J. D. & Perlmutter, R. M. (1997). Differential signaling by lymphocyte antigen receptors. *Annu. Rev. Immunol.* 15, 125–154.

2. Berridge, M. J. (1997). Lymphocyte activation in health and disease. *Critical S Reviews in Immunology* 17, 155–178.

3. Qian, D & Weiss, A. (1997). T cell antigen receptor signal transduction. *Curr. Opin. Cell Biol.* 9, 205–212.

4. Barber, E. K., Dasgupta, J. D., Schlossman, S. F., Trevillyan, J. M. & Rudd, C. E. (1989). The CD4 and CD8 antigens are coupled to a protein-tyrosine kinase (p56lck) that phosphorylates the CD3 complex. *Proc. Natl. Acad. Sci. USA* 86, 3277–3281.

5. Wong, J., Straus, D. & Chan, A. C. (1998). Genetic evidence of a role for Lck in T-cell receptor finction independent or downstream of ZAP-70/Syk protein tyrosine kinases. *Mol. Cell. Biol.* 18, 2855–2866.

6. Thome, M., Germain, V., DiSanto, J. P. & Acuto, O. (1996). The p56lck SH2 domain mediates recruitment of CD8/pS6lck to the activated T cell receptor/CD3/zeta complex. *Eur. J. Immunol.* 26, 2093–2100.

7. Chu, K. & Littman, D. R. (1994). Requirement for kinase activity of CD4-associated p56lck in antibody-triggered T cell signal transduction. *J. Biol. Chem.* 269, 24095–24101.

8. Chalupny, N. J., Ledbetter, J. A. & Kavathas, P. (1991). Association of CD8 with p56lck is required for early T cell signaling events. *Embo J.* 10, 1201–1207.

9. van Oers, N. S., Killeen, N. & Weiss, A. (1996). Lck regulates the tyrosine phosphorylation of the T cell receptor subunits and ZAP-70 in murine thymocytes. *J Exp. Med.* 183, 1053–1062.

10. Kersh, E. N., Shaw, A. S. & Allen, P. M. (1998). Fidelity of T cell activation through multistep T cell receptor zeta phosphorylation. *Science* 281, 572–575.

11. Madrenas, J., Wange, R. L., Wang, J. L., Isakov, N., Samelson, L. E. & Germain, R. N. (1995). Zeta phosphorylation without ZAP-70 activation induced by TCR antagonists or partial agonists. *Science* 267, 515–518.

12. Straus, D. B. & Weiss, A. (1993). The CD3 chains of the T cell antigen receptor associate with the ZAP-70 tyrosine kinase and are tyrosine phosphorylated after receptor stimulation. *J. Exp. Med.* 178, 1523–1530.

13. Wange, R. L., Kong, A. N. & Samelson, L. E. (1992). A tyrosine-phosphorylated 70-kDa protein binds a photoaffinity analogue of ATP and associates with both the zeta chain and CD3 components of the activated T cell antigen receptor. *J. Biol. Chem.* 267, 11685–11688.

14. Chan, A. C., Irving, B. A., Fraser, J. D. & Weiss, A. (1991). The zeta chain is associated with a tyrosine kinase and upon T-cell antigen receptor stimulation associates with ZAP-70, a 70-kDa tyrosine phosphoprotein. *Proc. Natl. Acad. Sci. USA* 88, 9166–9170.

15. Isakov, N., Wange, R. L., Burgess, W. H., Watts, J. D., Aebersold, R. & Samelson, L. E. (1995). ZAP-70 binding specificity to T cell receptor tyrosine-based activation motifs: the tandem SH2 domains of ZAP-70 bind distinct tyrosine-based activation motifs with varying affinity. *J. Exp. Med.* 181, 375–380.

16. Wange, R. L., Malek, S. N., Desiderio, S. & Samelson, L. E. (1993). Tandem SH2 domains of ZAP-70 bind to T cell antigen receptor zeta and CD3 epsilon from activated Jurkat T cells. *J. Biol. Chem.* 268, 19797–19801.

17. Chan, A. C. et. al. & Kurosaki, T. (1995). Activation of ZAP-70 kinase activity by phosphorylation of tyrosine 493 is required for lymphocyte antigen receptor function. *Embo J.* 14, 2499–24508.

18. Neumeister, E. N., Zhu, Y., Richard, S., Terhorst, C., Chan, A. C. & Shaw, A. S. (1995). Binding of ZAP-70 to phosphorylated T-cell receptor zeta and eta enhances its autophosphorylation and generates specific binding sites for SH2 domain-containing proteins. *Mol. Cell. Biol.* 15, 3171–3178.

19. Watts, J. D., Affolter, M., Krebs, D. L., Wange, R. L., Samelson, L. E. & Aebersold, R. (1994). Identification by electrospray ionization mass spectrometry of the sites of tyrosine phosphorylation induced in activated Jurkat T cells on the protein tyrosine kinase ZAP-70. *J. Biol. Chem.* 269, 29520–29529.

20. LoGrasso, P. V., Hawkins, J., Frank, L. J., Wisniewski, D. & Marcy, A. (1996). Mechanism of activation for Zap-70 catalytic activity. *Proc. Natl. Acad. Sci. U S A* 93, 12165–12170.

21. Wange, R. L., Guitian, R., Isakov, N., Watts, J. D., Aebersold, R. & Samelson, L. E. (1995). Activating and inhibitory mutations in adjacent tyrosines in the kinase domain of ZAP-70. *J. Biol. Chem.* 270, 18730–18733.

22. Rudd, C. E. (1999). Adaptors and molecular scaffolds in immune cell signaling. *Cell* 96, 5–8.

23. Straus, D. B. & Weiss, A. (1992). Genetic evidence for the involvement of the lck tyrosine kinase in signal transduction through the T cell antigen receptor. *Cell* 70, 585–593.

24. Henning, S. W. & Cantrell, D. A. (1998). p56lck signals for regulating thymocyte development can be distinguished by their dependency on Rho function. *J. Exp. Med.* 188, 931–939.

25. Levin, S. D., Abraham, K. M., Anderson, S. J., Forbush, K. A. & Perlmutter, R. M. (1993). The protein tyrosine kinase pS6lck regulates thymocyte development independently of its interaction with CD4 and CD8 coreceptors [corrected] [published erratum appears in J Exp Med 1993 Sep 1;178(3):1135]. *J. Exp. Med.* 178, 245–255.

26. Molina, T. J., et. al. Veillette A,& (1992). Profound block in thymocyte development in mice lacking pS6lck. *Nature* 357, 161–164.

27. Molina, T. J., Bachmann, M. F., Kundig, T. M., Zinkemagel, R. M. & Mak, T. W. (1993). Peripheral T cells in mice lacking pS6lck do not express significant antiviral effector functions. *J. Immunol.* 151, 699–706.

28. Lin, R. S., Rodriguez, C., Veillette, A. & Lodish, H. F. (1998). Zinc is essential for binding of p56(lck) to CD4 and CD8alpha. *J. Biol. Chem.* 273, 32878–328.

29. Huse, M., Eck, M. J. & Harrison, S. C. (1998). A Zn2+ ion links the cytoplasmic tail of CD4 and the N-terminal region of Lck. *J. Biol. Chem.* 273, 18729–18733.

30. Watts, J. D., Wilson, G. M., Ettenhadieh, E., Clark Lewis, I., Kubanek, C. A., Astell, C. R., Marth, J. D. &

Aebersold, R. (1992). Purification and initial characterization of the lymphocyte-specific protein-tyrosyl kinase pS6lck from a baculovirus expression system. *J. Biol. Chem.* 267, 901–907.

31. Gervais, F. G., Chow, L. M., Lee, J. M., Branton, P. E. & Veillette, A. (1993). The SH2 domain is required for stable phosphorylation of pS6lck at tyrosine 505, the negative regulatory site. *Mol. Cell. Biol.* 13, 7112–7121.

32. Bougeret, C., et. al., & Fischer, S. (1996). Detection of a physical and functional interaction between Csk and Lck which involves the SH2 domain of Csk and is mediated by autophosphorylation of Lck on tyrosine 394. *J. Biol. Chem.* 271, 7465–7472.

33. Jullien, P., et. al., & Benarous, R. (1994). Tyr394 and Tyr505 are autophosphorylated in recombinant Lck protein-tyrosine kinase expressed in *Escherichia coli*. *Eur. J. Biochem.* 224, 589–596.

34. Williams, J. C., et. al., & Wierenga, R. K. (1997). The 2.35. A crystal structure of the inactivated form of chicken Src: a dynamic molecule with multiple regulatory interactions. *J. Mol. Biol.* 274, 757–775.

35. Sicheri, F., Moarefi, I. & Kuriyan, J. (1997). Crystal structure of the Src family tyrosine kinase Hck. *Nature* 385, 602–609.

36. Xu, W., Harrison, S. C. & Eck, M. J. (1997). Three-dimensional structure of the tyrosine kinase c-Src. *Nature* 385, 595–602.

37. Reynolds, P. J., Hurley, T. R. & Sefton, B. M. (1992). Functional analysis of the SH2 and SH3 domains of the lck tyrosine protein kinase. *Oncogene* 7, 1949–1955.

38. Mustelin, T. & Altman, A. (1990). Dephosphorylation and activation of the T cell tyrosine kinase pp56lck by the leukocyte common antigen (CD45). *Oncogene* 5, 809–813.

39. Moarefi, I., et. al. & Miller, W. T. (1997). Activation of the Src-family tyrosine kinase Hck by SH3 domain displacement. *Nature* 385, 650–653.

40. Yamaguchi, H. & Hendrickson, W. A. (1996). Structural basis for activation of human lymphocyte kinase Lck upon tyrosine phosphorylation. *Nature* 384, 484–489.

41. Meggio, D., et. al., & Furet, P.(1995). Different susceptibility of protein kinases to staurosporine inhibition. Kinetic studies and molecular bases for the resistance of protein kinase CK2. *Eur. J. Biochem.* 234, 317–322.

42. Prade, L., Engh, R. A., Girod, A., Kinzel, V., Huber, R., & Bossemeyer, D. (1997). Staurosporine-induced conformational changes of cAMP-dependent protein kinase catalytic subunit explain inhibitory potential. *Structure* 5, 1627–1637.

43. Lawrie, A. M., Noble, M. E., Tunnah, P., Brown, N. R., Johnson, L. N., and Endicott, J. A. (1997). Protein kinase inhibition by staurosporine revealed in details of the molecular interaction with CDK2 [letter]. *Nat. Struct. Biol.* 4, 796–801.

44. Toledo, L. M. & Lydon, N. B. (1997). Structures of staurosporine bound to CDK2 and cAPK-new tools for structure-based design of protein kinase inhibitors. *Structure* 5, 1551–1556.

45. Lamers, M. B., Antson, A. A., Hubbard, R. E., Scott, R. K. & Williams, D. H. (1999). Structure of the protein tyrosine kinase domain of C-terminal Src kinase (CSK) in complex with staurosporine. *J. Mol. Biol.* 285, 713–725.

46. Knighton, D. R., et. al. & Sowadski, J. M. (1991). Crystal structure of the catalytic subunit of cyclic adenosine monophosphate-dependent protein kinase. *Science* 253, 407–414.

47. Knighton, D. R., et. al. & Sowadski, J. M. (1991). Structure of a peptide inhibitor bound to the catalytic subunit of cyclic adenosine monophosphate-dependent protein kinase. *Science* 253, 414–420.

48. Hubbard, S. R. (1997). Crystal structure of the activated insulin receptor tyrosine kinase in complex with peptide substrate and ATP analog. *Embo J.* 16, 5572–5581.

49. Srinivasan S. Kuduva, Donald C. Craig, Ashwini Nangia & Gautam R. (1999). Cubanecarboxylic Acids. Crystal Engineering Considerations and the Role of C—H Hydrogen Bonds in Determining O—H O Networks. *J. Am. Chem. Soc.* 121, 1936–1944.

50. Kim, Y. H., Buchholz, M. A., Chrest, F. J. & Nordin, A. A. (1994). Up-regulation of c-myc induces the gene expression of the murine homologues of p34cdc2 and cyclin-dependent kinase-2 in T lymphocytes. *J.Immunol.* 152, 4328–4333.

51. Hanke, J. H., et. al. & Connelly, P. A. (1996). Discovery of a novel, potent, and Src family-selective tyrosine kinase inhibitor. Study of Lck- and FynT-dependent T cell activation. *J. Biol. Chem.* 271, 695–701.

52. Traxler, P. (1998). Tyrosine kinase inhibitors in cancer treatment (Part II). *Expert Opinion in Therapeutic Patents* 8, 1599–1625.

53. Mohammadi, et. al. & Hubbard, S. R. (1998). Crystal structure of an angiogenesis inhibitor bound to the FGF receptor tyrosine kinase domain. *Embo J.* 17, 5896–5904.

54. Tong, L., Pav, S., White, D. M., Rogers, S., Crane, K. M., Cywin, C. L., Brown, M. L., and Pargellis, C. A. (1997). A highly specific inhibitor of human p38 MAP kinase binds in the ATP pocket. *Nat. Struct. Biol.* 4, 311–316.

55. Wilson, K. P., et. al. & Su, M. S. S. (1997). The structural basis for the specificity of pyridinylimidazole inhibitors of p38 MAP kinase. *Chem. & Biol.* 4, 423–431.

56. Wang, Z., et. al. & Goldsmith, E. J. (1998). Structural basis of inhibitor selectivity in MAP kinases. *Structure* 6, 1117–1128.

57. Morgenstern, K. A., et. al. & Kisiel, W. (1994). Complementary DNA cloning and kinetic characterization of a novel intracellular serine proteinase inhibitor: mechanism of action with trypsin and factor Xa as niodel proteinases. *Biochemistry* 33, 3432–3441.

58. Morgenstern, K. A., et. al. & Thomson, J. A. (1997). Polynucleotide modulation of the protease, nucleoside triphosphatase, and helicase activities of a hepatitis C virus NS3-NS4A complex isolated from transfected COS cells. *J. Virol.* 71, 3767–3775.

59. Brunger, A. T., Krukowski, A. & Erickson, J. W. (1990). Slow-cooling protocols for crystallographic refinement by simulated annealing. *Acta Crystallogr.* A 46, 585–593.

60. Nicholls, A., Sharp, K. A. & Honig, B. (1991). Protein folding and association: insights from the interfacial and thermodynamic properties of hydrocarbons. *Proteins* 11, 281–296.

61. Evans, S. V. (1993). SETOR: hardware-lighted three-dimensional solid model representations of macromolecules. *J Mol. Graph.* 11, 134–138, 127–128.

TABLE 1

Coordinates of Lck bound with PP2

| | | Atom Type | Res | # | X | Y | Z | Occ | B |
|---|---|---|---|---|---|---|---|---|---|
| ATOM | 1 | CB | LYS | 231 | 0.991 | 26.799 | 89.459 | 1.00 | 35.40 |
| ATOM | 2 | CG | LYS | 231 | 0.374 | 26.962 | 88.107 | 1.00 | 37.62 |
| ATOM | 3 | CD | LYS | 231 | 0.905 | 25.834 | 87.245 | 1.00 | 39.89 |
| ATOM | 4 | CE | LYS | 231 | 0.214 | 25.740 | 85.904 | 1.00 | 41.37 |
| ATOM | 5 | NZ | LYS | 231 | 0.933 | 24.716 | 85.076 | 1.00 | 41.65 |
| ATOM | 9 | C | LYS | 231 | 1.694 | 27.685 | 91.603 | 1.00 | 31.30 |
| ATOM | 10 | O | LYS | 231 | 2.774 | 28.259 | 91.645 | 1.00 | 31.13 |
| ATOM | 13 | N | LYS | 231 | 1.184 | 29.238 | 89.851 | 1.00 | 34.51 |
| ATOM | 15 | CA | LYS | 231 | 0.763 | 27.931 | 90.450 | 1.00 | 32.98 |
| ATOM | 16 | N | PRO | 232 | 1.278 | 26.851 | 92.579 | 1.00 | 30.24 |
| ATOM | 17 | CD | PRO | 232 | −0.033 | 26.192 | 92.746 | 1.00 | 29.57 |
| ATOM | 18 | CA | PRO | 232 | 2.148 | 26.560 | 93.722 | 1.00 | 26.98 |
| ATOM | 19 | CB | PRO | 232 | 1.277 | 25.633 | 94.590 | 1.00 | 26.85 |
| ATOM | 20 | CG | PRO | 232 | 0.321 | 25.045 | 93.658 | 1.00 | 28.72 |
| ATOM | 21 | C | PRO | 232 | 3.410 | 25.870 | 93.180 | 1.00 | 24.72 |
| ATOM | 22 | O | PRO | 232 | 3.411 | 25.249 | 92.127 | 1.00 | 23.36 |
| ATOM | 23 | N | TRP | 233 | 4.506 | 26.024 | 93.896 | 1.00 | 25.48 |
| ATOM | 25 | CA | TRP | 233 | 5.793 | 25.473 | 93.470 | 1.00 | 23.55 |
| ATOM | 26 | CB | TRP | 233 | 6.878 | 25.761 | 94.535 | 1.00 | 23.19 |
| ATOM | 27 | CG | TRP | 233 | 6.731 | 24.980 | 95.839 | 1.00 | 22.23 |
| ATOM | 28 | CD2 | TRP | 233 | 7.153 | 23.624 | 96.113 | 1.00 | 21.73 |
| ATOM | 29 | CE2 | TRP | 233 | 6.845 | 23.357 | 97.461 | 1.00 | 22.74 |
| ATOM | 30 | CE3 | TRP | 233 | 7.762 | 22.615 | 95.347 | 1.00 | 22.69 |
| ATOM | 31 | CD1 | TRP | 233 | 6.203 | 25.451 | 96.995 | 1.00 | 20.43 |
| ATOM | 32 | NE1 | TRP | 233 | 6.276 | 24.494 | 97.972 | 1.00 | 22.28 |
| ATOM | 34 | CZ2 | TRP | 233 | 7.113 | 22.112 | 98.076 | 1.00 | 22.05 |
| ATOM | 35 | CZ3 | TRP | 233 | 8.037 | 21.372 | 95.957 | 1.00 | 20.26 |
| ATOM | 36 | CH2 | TRP | 233 | 7.709 | 21.139 | 97.306 | 1.00 | 21.81 |
| ATOM | 37 | C | TRP | 233 | 5.775 | 23.976 | 93.115 | 1.00 | 24.28 |
| ATOM | 38 | O | TRP | 233 | 6.474 | 23.542 | 92.186 | 1.00 | 21.45 |
| ATOM | 39 | N | TRP | 234 | 4.970 | 23.184 | 93.825 | 1.00 | 23.01 |
| ATOM | 41 | CA | TRP | 234 | 4.914 | 21.748 | 93.540 | 1.00 | 22.90 |
| ATOM | 42 | CB | TRP | 234 | 4.259 | 20.990 | 94.714 | 1.00 | 20.97 |
| ATOM | 43 | CG | TRP | 234 | 2.862 | 21.453 | 95.077 | 1.00 | 19.50 |
| ATOM | 44 | CD2 | TRP | 234 | 2.505 | 22.370 | 96.124 | 1.00 | 18.76 |
| ATOM | 45 | CE2 | TRP | 234 | 1.087 | 22.439 | 96.155 | 1.00 | 18.03 |
| ATOM | 46 | CE3 | TRP | 234 | 3.240 | 23.139 | 97.028 | 1.00 | 20.40 |
| ATOM | 47 | CD1 | TRP | 234 | 1.685 | 21.028 | 94.523 | 1.00 | 19.50 |
| ATOM | 48 | NE1 | TRP | 234 | 0.614 | 21.613 | 95.176 | 1.00 | 18.89 |
| ATOM | 50 | CZ2 | TRP | 234 | 0.395 | 23.241 | 97.060 | 1.00 | 19.36 |
| ATOM | 51 | CZ3 | TRP | 234 | 2.545 | 23.950 | 97.937 | 1.00 | 21.59 |
| ATOM | 52 | CH2 | TRP | 234 | 1.132 | 23.988 | 97.942 | 1.00 | 21.04 |
| ATOM | 53 | C | TRP | 234 | 4.257 | 21.405 | 92.192 | 1.00 | 23.16 |
| ATOM | 54 | O | TRP | 234 | 4.442 | 20.316 | 91.630 | 1.00 | 21.44 |
| ATOM | 55 | N | GLU | 235 | 3.474 | 22.340 | 91.674 | 1.00 | 24.87 |
| ATOM | 57 | CA | GLU | 235 | 2.809 | 22.169 | 90.381 | 1.00 | 27.37 |
| ATOM | 58 | CB | GLU | 235 | 1.348 | 22.612 | 90.486 | 1.00 | 29.65 |
| ATOM | 59 | CG | GLU | 235 | 0.498 | 21.741 | 91.387 | 1.00 | 31.86 |
| ATOM | 60 | CD | GLU | 235 | −0.983 | 22.049 | 91.281 | 1.00 | 36.12 |
| ATOM | 61 | OE1 | GLU | 235 | −1.358 | 23.128 | 90.777 | 1.00 | 37.74 |
| ATOM | 62 | OE2 | GLU | 235 | −1.783 | 21.197 | 91.705 | 1.00 | 37.52 |
| ATOM | 63 | C | GLU | 235 | 3.502 | 22.998 | 89.296 | 1.00 | 28.36 |
| ATOM | 64 | O | GLU | 235 | 3.177 | 22.923 | 88.115 | 1.00 | 30.14 |
| ATOM | 65 | N | ASP | 236 | 4.431 | 23.833 | 89.736 | 1.00 | 30.43 |
| ATOM | 67 | CA | ASP | 236 | 5.190 | 24.741 | 88.885 | 1.00 | 31.53 |
| ATOM | 68 | CB | ASP | 236 | 6.014 | 25.637 | 89.822 | 1.00 | 34.01 |
| ATOM | 69 | CG | ASP | 236 | 6.359 | 26.961 | 89.231 | 1.00 | 35.33 |
| ATOM | 70 | OD1 | ASP | 236 | 5.874 | 27.298 | 88.124 | 1.00 | 37.56 |
| ATOM | 71 | OD2 | ASP | 236 | 7.123 | 27.677 | 89.902 | 1.00 | 36.77 |
| ATOM | 72 | C | ASP | 236 | 6.153 | 24.035 | 87.922 | 1.00 | 30.91 |
| ATOM | 73 | O | ASP | 236 | 6.873 | 23.102 | 88.283 | 1.00 | 31.33 |
| ATOM | 74 | N | GLU | 237 | 6.259 | 24.583 | 86.723 | 1.00 | 29.27 |
| ATOM | 76 | CA | GLU | 237 | 7.179 | 24.066 | 85.733 | 1.00 | 28.93 |
| ATOM | 77 | CB | GLU | 237 | 6.734 | 24.482 | 84.324 | 1.00 | 31.31 |
| ATOM | 78 | CG | GLU | 237 | 6.005 | 25.839 | 84.237 | 1.00 | 33.53 |
| ATOM | 79 | CD | GLU | 237 | 4.581 | 25.803 | 84.834 | 1.00 | 36.26 |
| ATOM | 80 | OE1 | GLU | 237 | 3.821 | 24.860 | 84.486 | 1.00 | 40.24 |
| ATOM | 81 | OE2 | GLU | 237 | 4.233 | 26.674 | 85.672 | 1.00 | 35.72 |
| ATOM | 82 | C | GLU | 237 | 8.603 | 24.578 | 85.993 | 1.00 | 29.26 |
| ATOM | 83 | O | GLU | 237 | 9.568 | 24.075 | 85.418 | 1.00 | 30.63 |
| ATOM | 84 | N | TRP | 238 | 8.748 | 25.546 | 86.896 | 1.00 | 26.50 |
| ATOM | 86 | CA | TRP | 238 | 10.048 | 26.122 | 87.169 | 1.00 | 24.60 |
| ATOM | 87 | CB | TRP | 238 | 9.965 | 27.639 | 87.065 | 1.00 | 27.03 |
| ATOM | 88 | CG | TRP | 238 | 9.900 | 28.103 | 85.638 | 1.00 | 28.24 |

TABLE 1-continued

Coordinates of Lck bound with PP2

| | | Atom Type | Res | # | X | Y | Z | Occ | B |
|---|---|---|---|---|---|---|---|---|---|
| ATOM | 89 | CD2 | TRP | 238 | 8.744 | 28.547 | 84.944 | 1.00 | 30.29 |
| ATOM | 90 | CE2 | TRP | 238 | 9.134 | 28.864 | 83.621 | 1.00 | 30.52 |
| ATOM | 91 | CE3 | TRP | 238 | 7.405 | 28.704 | 85.313 | 1.00 | 29.46 |
| ATOM | 92 | CD1 | TRP | 238 | 10.928 | 28.160 | 84.738 | 1.00 | 29.31 |
| ATOM | 93 | NE1 | TRP | 238 | 10.480 | 28.615 | 83.518 | 1.00 | 30.13 |
| ATOM | 95 | CZ2 | TRP | 238 | 8.254 | 29.323 | 82.679 | 1.00 | 30.01 |
| ATOM | 96 | CZ3 | TRP | 238 | 6.532 | 29.155 | 84.385 | 1.00 | 32.47 |
| ATOM | 97 | CH2 | TRP | 238 | 6.950 | 29.465 | 83.073 | 1.00 | 33.11 |
| ATOM | 98 | C | TRP | 238 | 10.802 | 25.724 | 88.437 | 1.00 | 22.43 |
| ATOM | 99 | O | TRP | 238 | 12.026 | 25.856 | 88.468 | 1.00 | 22.74 |
| ATOM | 100 | N | GLU | 239 | 10.100 | 25.313 | 89.496 | 1.00 | 17.81 |
| ATOM | 102 | CA | GLU | 239 | 10.786 | 24.906 | 90.714 | 1.00 | 16.97 |
| ATOM | 103 | CB | GLU | 239 | 9.840 | 24.545 | 91.854 | 1.00 | 16.07 |
| ATOM | 104 | CG | GLU | 239 | 10.586 | 24.476 | 93.186 | 1.00 | 18.77 |
| ATOM | 105 | CD | GLU | 239 | 10.861 | 25.851 | 93.816 | 1.00 | 19.99 |
| ATOM | 106 | OE1 | GLU | 239 | 10.154 | 26.835 | 93.468 | 1.00 | 20.95 |
| ATOM | 107 | OE2 | GLU | 239 | 11.728 | 25.937 | 94.716 | 1.00 | 15.13 |
| ATOM | 108 | C | GLU | 239 | 11.687 | 23.726 | 90.414 | 1.00 | 16.51 |
| ATOM | 109 | O | GLU | 239 | 11.341 | 22.831 | 89.641 | 1.00 | 16.73 |
| ATOM | 110 | N | VAL | 240 | 12.826 | 23.709 | 91.080 | 1.00 | 15.81 |
| ATOM | 112 | CA | VAL | 240 | 13.813 | 22.696 | 90.842 | 1.00 | 15.66 |
| ATOM | 113 | CB | VAL | 240 | 14.747 | 23.268 | 89.731 | 1.00 | 18.62 |
| ATOM | 114 | CG1 | VAL | 240 | 16.140 | 23.706 | 90.292 | 1.00 | 15.18 |
| ATOM | 115 | CG2 | VAL | 240 | 14.747 | 22.424 | 88.517 | 1.00 | 16.45 |
| ATOM | 116 | C | VAL | 240 | 14.542 | 22.479 | 92.151 | 1.00 | 15.04 |
| ATOM | 117 | O | VAL | 240 | 14.746 | 23.427 | 92.934 | 1.00 | 15.18 |
| ATOM | 118 | N | PRO | 241 | 14.832 | 21.202 | 92.492 | 1.00 | 14.96 |
| ATOM | 119 | CD | PRO | 241 | 14.389 | 19.967 | 91.794 | 1.00 | 12.45 |
| ATOM | 120 | CA | PRO | 241 | 15.556 | 20.883 | 93.738 | 1.00 | 14.57 |
| ATOM | 121 | CB | PRO | 241 | 15.730 | 19.351 | 93.637 | 1.00 | 14.89 |
| ATOM | 122 | CG | PRO | 241 | 14.449 | 18.932 | 92.879 | 1.00 | 13.42 |
| ATOM | 123 | C | PRO | 241 | 16.923 | 21.561 | 93.662 | 1.00 | 14.29 |
| ATOM | 124 | O | PRO | 241 | 17.539 | 21.562 | 92.615 | 1.00 | 13.35 |
| ATOM | 125 | N | ARG | 242 | 17.388 | 22.157 | 94.752 | 1.00 | 14.32 |
| ATOM | 127 | CA | ARG | 242 | 18.667 | 22.826 | 94.736 | 1.00 | 16.02 |
| ATOM | 128 | CB | ARG | 242 | 18.911 | 23.549 | 96.047 | 1.00 | 17.39 |
| ATOM | 129 | CG | ARG | 242 | 19.954 | 24.664 | 95.915 | 1.00 | 19.83 |
| ATOM | 130 | CD | ARG | 242 | 20.484 | 25.107 | 97.287 | 1.00 | 18.48 |
| ATOM | 131 | NE | ARG | 242 | 19.438 | 25.621 | 98.178 | 1.00 | 18.30 |
| ATOM | 133 | CZ | ARG | 242 | 18.850 | 26.802 | 98.030 | 1.00 | 20.27 |
| ATOM | 134 | NH1 | ARG | 242 | 19.188 | 27.590 | 97.017 | 1.00 | 19.01 |
| ATOM | 137 | NH2 | ARG | 242 | 17.928 | 27.199 | 98.887 | 1.00 | 19.75 |
| ATOM | 140 | C | ARG | 242 | 19.852 | 21.889 | 94.423 | 1.00 | 17.15 |
| ATOM | 141 | O | ARG | 242 | 20.885 | 22.343 | 93.904 | 1.00 | 13.41 |
| ATOM | 142 | N | GLU | 243 | 19.663 | 20.581 | 94.660 | 1.00 | 15.70 |
| ATOM | 144 | CA | GLU | 243 | 20.690 | 19.555 | 94.391 | 1.00 | 17.46 |
| ATOM | 145 | CB | GLU | 243 | 20.219 | 18.157 | 94.879 | 1.00 | 21.17 |
| ATOM | 146 | CG | GLU | 243 | 20.101 | 18.009 | 96.375 | 1.00 | 26.41 |
| ATOM | 147 | CD | GLU | 243 | 18.891 | 18.731 | 96.906 | 1.00 | 29.87 |
| ATOM | 148 | OE1 | GLU | 243 | 17.830 | 18.651 | 96.261 | 1.00 | 30.02 |
| ATOM | 149 | OE2 | GLU | 243 | 19.008 | 19.380 | 97.961 | 1.00 | 33.72 |
| ATOM | 150 | C | GLU | 243 | 21.019 | 19.437 | 92.896 | 1.00 | 15.84 |
| ATOM | 151 | O | GLU | 243 | 22.073 | 18.886 | 92.509 | 1.00 | 13.74 |
| ATOM | 152 | N | THR | 244 | 20.105 | 19.899 | 92.045 | 1.00 | 13.19 |
| ATOM | 154 | CA | THR | 244 | 20.340 | 19.829 | 90.618 | 1.00 | 12.84 |
| ATOM | 155 | CB | THR | 244 | 19.062 | 20.179 | 89.836 | 1.00 | 12.93 |
| ATOM | 156 | OG1 | THR | 244 | 18.614 | 21.497 | 90.225 | 1.00 | 15.83 |
| ATOM | 158 | CG2 | THR | 244 | 17.960 | 19.145 | 90.108 | 1.00 | 12.75 |
| ATOM | 159 | C | THR | 244 | 21.416 | 20.810 | 90.189 | 1.00 | 12.09 |
| ATOM | 160 | O | THR | 244 | 21.919 | 20.756 | 89.082 | 1.00 | 12.81 |
| ATOM | 161 | N | LEU | 245 | 21.827 | 21.686 | 91.093 | 1.00 | 13.36 |
| ATOM | 163 | CA | LEU | 245 | 22.766 | 22.728 | 90.715 | 1.00 | 14.88 |
| ATOM | 164 | CB | LEU | 245 | 22.119 | 24.089 | 91.047 | 1.00 | 14.94 |
| ATOM | 165 | CG | LEU | 245 | 20.787 | 24.385 | 90.349 | 1.00 | 15.32 |
| ATOM | 166 | CD1 | LEU | 245 | 20.038 | 25.475 | 91.120 | 1.00 | 15.68 |
| ATOM | 167 | CD2 | LEU | 245 | 21.098 | 24.810 | 88.914 | 1.00 | 12.08 |
| ATOM | 168 | C | LEU | 245 | 24.130 | 22.735 | 91.350 | 1.00 | 15.36 |
| ATOM | 169 | O | LEU | 245 | 24.268 | 22.590 | 92.555 | 1.00 | 17.11 |
| ATOM | 170 | N | LYS | 246 | 25.128 | 23.086 | 90.552 | 1.00 | 14.82 |
| ATOM | 172 | CA | LYS | 246 | 26.475 | 23.179 | 91.087 | 1.00 | 15.04 |
| ATOM | 173 | CB | LYS | 246 | 27.414 | 22.108 | 90.531 | 1.00 | 15.31 |
| ATOM | 174 | CG | LYS | 246 | 28.807 | 22.160 | 91.193 | 1.00 | 21.90 |
| ATOM | 175 | CD | LYS | 246 | 29.832 | 21.342 | 90.371 | 1.00 | 27.51 |
| ATOM | 176 | CE | LYS | 246 | 31.226 | 21.291 | 91.023 | 1.00 | 31.22 |

TABLE 1-continued

Coordinates of Lck bound with PP2

| | | Atom Type | Res | # | X | Y | Z | Occ | B |
|---|---|---|---|---|---|---|---|---|---|
| ATOM | 177 | NZ | LYS | 246 | 32.180 | 20.493 | 90.158 | 1.00 | 33.21 |
| ATOM | 181 | C | LYS | 246 | 26.984 | 24.530 | 90.684 | 1.00 | 12.78 |
| ATOM | 182 | O | LYS | 246 | 27.078 | 24.829 | 89.501 | 1.00 | 14.00 |
| ATOM | 183 | N | LEU | 247 | 27.237 | 25.370 | 91.675 | 0.60 | 11.60 |
| ATOM | 185 | CA | LEU | 247 | 27.771 | 26.724 | 91.457 | 0.60 | 10.36 |
| ATOM | 186 | CB | LEU | 247 | 27.335 | 27.623 | 92.609 | 0.60 | 10.23 |
| ATOM | 187 | CG | LEU | 247 | 25.898 | 28.184 | 92.519 | 0.60 | 12.95 |
| ATOM | 188 | CD1 | LEU | 247 | 24.840 | 27.109 | 92.272 | 0.60 | 14.45 |
| ATOM | 189 | CD2 | LEU | 247 | 25.570 | 28.997 | 93.772 | 0.60 | 10.02 |
| ATOM | 190 | C | LEU | 247 | 29.294 | 26.632 | 91.316 | 0.60 | 10.78 |
| ATOM | 191 | O | LEU | 247 | 30.009 | 26.119 | 92.179 | 0.60 | 9.14 |
| ATOM | 192 | N | VAL | 248 | 29.796 | 27.083 | 90.169 | 1.00 | 14.86 |
| ATOM | 194 | CA | VAL | 248 | 31.219 | 26.980 | 89.862 | 1.00 | 17.81 |
| ATOM | 195 | CB | VAL | 248 | 31.431 | 26.331 | 88.473 | 1.00 | 17.07 |
| ATOM | 196 | CG1 | VAL | 248 | 32.879 | 26.479 | 87.998 | 1.00 | 23.15 |
| ATOM | 197 | CG2 | VAL | 248 | 31.075 | 24.888 | 88.540 | 1.00 | 17.53 |
| ATOM | 198 | C | VAL | 248 | 32.046 | 28.243 | 89.913 | 1.00 | 19.58 |
| ATOM | 199 | O | VAL | 248 | 33.172 | 28.227 | 90.405 | 1.00 | 21.76 |
| ATOM | 200 | N | GLU | 249 | 31.512 | 29.350 | 89.423 | 1.00 | 19.48 |
| ATOM | 202 | CA | GLU | 249 | 32.321 | 30.567 | 89.400 | 1.00 | 20.59 |
| ATOM | 203 | CB | GLU | 249 | 33.008 | 30.694 | 88.031 | 1.00 | 21.97 |
| ATOM | 204 | CG | GLU | 249 | 33.795 | 32.009 | 87.893 | 1.00 | 28.98 |
| ATOM | 205 | CD | GLU | 249 | 34.442 | 32.223 | 86.528 | 1.00 | 29.46 |
| ATOM | 206 | OE1 | GLU | 249 | 34.138 | 31.491 | 85.563 | 1.00 | 33.62 |
| ATOM | 207 | OE2 | GLU | 249 | 35.240 | 33.166 | 86.412 | 1.00 | 31.65 |
| ATOM | 208 | C | GLU | 249 | 31.461 | 31.798 | 89.645 | 1.00 | 20.64 |
| ATOM | 209 | O | GLU | 249 | 30.462 | 32.002 | 88.978 | 1.00 | 18.22 |
| ATOM | 210 | N | ARG | 250 | 31.801 | 32.566 | 90.673 | 1.00 | 21.11 |
| ATOM | 212 | CA | ARG | 250 | 31.062 | 33.781 | 90.949 | 1.00 | 20.75 |
| ATOM | 213 | CB | ARG | 250 | 31.368 | 34.301 | 92.352 | 1.00 | 22.14 |
| ATOM | 214 | CG | ARG | 250 | 30.624 | 35.594 | 92.672 | 1.00 | 25.03 |
| ATOM | 215 | CD | ARG | 250 | 30.841 | 36.072 | 94.117 | 1.00 | 28.48 |
| ATOM | 216 | NE | ARG | 250 | 32.219 | 35.928 | 94.541 | 1.00 | 30.65 |
| ATOM | 218 | CZ | ARG | 250 | 32.668 | 36.245 | 95.748 | 1.00 | 36.29 |
| ATOM | 219 | NH1 | ARG | 250 | 31.833 | 36.738 | 96.666 | 1.00 | 38.58 |
| ATOM | 222 | NH2 | ARG | 250 | 33.960 | 36.072 | 96.039 | 1.00 | 36.92 |
| ATOM | 225 | C | ARG | 250 | 31.497 | 34.770 | 89.879 | 1.00 | 19.46 |
| ATOM | 226 | O | ARG | 250 | 32.685 | 34.953 | 89.604 | 1.00 | 19.15 |
| ATOM | 227 | N | LEU | 251 | 30.521 | 35.363 | 89.207 | 1.00 | 18.03 |
| ATOM | 229 | CA | LEU | 251 | 30.790 | 36.308 | 88.139 | 1.00 | 17.17 |
| ATOM | 230 | CB | LEU | 251 | 29.872 | 36.026 | 86.942 | 1.00 | 15.71 |
| ATOM | 231 | CG | LEU | 251 | 29.883 | 34.605 | 86.399 | 1.00 | 16.81 |
| ATOM | 232 | CD1 | LEU | 251 | 28.811 | 34.429 | 85.350 | 1.00 | 15.28 |
| ATOM | 233 | CD2 | LEU | 251 | 31.259 | 34.297 | 85.808 | 1.00 | 14.89 |
| ATOM | 234 | C | LEU | 251 | 30.544 | 37.724 | 88.609 | 1.00 | 19.19 |
| ATOM | 235 | O | LEU | 251 | 31.048 | 38.683 | 88.020 | 1.00 | 21.50 |
| ATOM | 236 | N | GLY | 252 | 29.708 | 37.850 | 89.633 | 1.00 | 18.74 |
| ATOM | 238 | CA | GLY | 252 | 29.352 | 39.152 | 90.150 | 1.00 | 19.05 |
| ATOM | 239 | C | GLY | 252 | 28.758 | 39.061 | 91.531 | 1.00 | 18.73 |
| ATOM | 240 | O | GLY | 252 | 28.194 | 38.019 | 91.930 | 1.00 | 16.57 |
| ATOM | 241 | N | ALA | 253 | 28.899 | 40.154 | 92.278 | 1.00 | 19.10 |
| ATOM | 243 | CA | ALA | 253 | 28.415 | 40.215 | 93.641 | 1.00 | 19.46 |
| ATOM | 244 | CB | ALA | 253 | 29.460 | 39.647 | 94.584 | 1.00 | 20.66 |
| ATOM | 245 | C | ALA | 253 | 28.095 | 41.666 | 94.010 | 1.00 | 19.86 |
| ATOM | 246 | O | ALA | 253 | 28.797 | 42.583 | 93.648 | 1.00 | 18.61 |
| ATOM | 247 | N | GLY | 254 | 26.978 | 41.858 | 94.696 | 1.00 | 19.85 |
| ATOM | 249 | CA | GLY | 254 | 26.577 | 43.195 | 95.080 | 1.00 | 20.71 |
| ATOM | 250 | C | GLY | 254 | 25.766 | 43.113 | 96.338 | 1.00 | 20.71 |
| ATOM | 251 | O | GLY | 254 | 25.714 | 42.062 | 96.991 | 1.00 | 21.09 |
| ATOM | 252 | N | GLN | 255 | 25.081 | 44.211 | 96.627 | 1.00 | 21.69 |
| ATOM | 254 | CA | GLN | 255 | 24.238 | 44.399 | 97.805 | 1.00 | 22.87 |
| ATOM | 255 | CB | GLN | 255 | 23.678 | 45.842 | 97.768 | 1.00 | 24.44 |
| ATOM | 256 | CG | GLN | 255 | 23.066 | 46.343 | 99.090 | 1.00 | 27.91 |
| ATOM | 257 | CD | GLN | 255 | 22.530 | 47.773 | 98.983 | 1.00 | 28.66 |
| ATOM | 258 | OE1 | GLN | 255 | 21.679 | 48.167 | 99.756 | 1.00 | 32.42 |
| ATOM | 259 | NE2 | GLN | 255 | 23.013 | 48.531 | 98.005 | 1.00 | 28.11 |
| ATOM | 262 | C | GLN | 255 | 23.070 | 43.417 | 97.932 | 1.00 | 22.21 |
| ATOM | 263 | O | GLN | 255 | 22.684 | 42.998 | 99.038 | 1.00 | 20.67 |
| ATOM | 264 | N | PHE | 256 | 22.492 | 43.044 | 96.798 | 1.00 | 22.10 |
| ATOM | 266 | CA | PHE | 256 | 21.330 | 42.141 | 96.832 | 1.00 | 22.26 |
| ATOM | 267 | CB | PHE | 256 | 20.233 | 42.692 | 95.934 | 1.00 | 22.35 |
| ATOM | 268 | CG | PHE | 256 | 19.919 | 44.131 | 96.211 | 1.00 | 22.39 |
| ATOM | 269 | CD1 | PHE | 256 | 19.430 | 44.503 | 97.450 | 1.00 | 20.34 |
| ATOM | 270 | CD2 | PHE | 256 | 20.225 | 45.119 | 95.277 | 1.00 | 22.22 |

TABLE 1-continued

Coordinates of Lck bound with PP2

| | | Atom Type | Res | # | X | Y | Z | Occ | B |
|---|---|---|---|---|---|---|---|---|---|
| ATOM | 271 | CE1 | PHE | 256 | 19.261 | 45.827 | 97.774 | 1.00 | 22.81 |
| ATOM | 272 | CE2 | PHE | 256 | 20.062 | 46.462 | 95.597 | 1.00 | 22.65 |
| ATOM | 273 | CZ | PHE | 256 | 19.585 | 46.820 | 96.841 | 1.00 | 22.73 |
| ATOM | 274 | C | PHE | 256 | 21.586 | 40.667 | 96.529 | 1.00 | 21.89 |
| ATOM | 275 | O | PHE | 256 | 20.677 | 39.852 | 96.579 | 1.00 | 19.84 |
| ATOM | 276 | N | GLY | 257 | 22.848 | 40.312 | 96.294 | 1.00 | 21.14 |
| ATOM | 278 | CA | GLY | 257 | 23.146 | 38.924 | 95.985 | 1.00 | 21.14 |
| ATOM | 279 | C | GLY | 257 | 24.351 | 38.728 | 95.090 | 1.00 | 20.30 |
| ATOM | 280 | O | GLY | 257 | 25.188 | 39.643 | 94.922 | 1.00 | 18.68 |
| ATOM | 281 | N | GLU | 258 | 24.404 | 37.561 | 94.445 | 1.00 | 17.66 |
| ATOM | 283 | CA | GLU | 258 | 25.517 | 37.227 | 93.589 | 1.00 | 16.20 |
| ATOM | 284 | CB | GLU | 258 | 26.463 | 36.241 | 94.307 | 1.00 | 18.61 |
| ATOM | 285 | CG | GLU | 258 | 26.931 | 36.680 | 95.701 | 1.00 | 24.08 |
| ATOM | 286 | CD | GLU | 258 | 27.827 | 35.638 | 96.385 | 1.00 | 29.32 |
| ATOM | 287 | OE1 | GLU | 258 | 27.455 | 34.436 | 96.441 | 1.00 | 30.55 |
| ATOM | 288 | OE2 | GLU | 258 | 28.919 | 36.011 | 96.858 | 1.00 | 32.64 |
| ATOM | 289 | C | GLU | 258 | 25.009 | 36.582 | 92.317 | 1.00 | 15.13 |
| ATOM | 290 | O | GLU | 258 | 23.854 | 36.183 | 92.224 | 1.00 | 13.97 |
| ATOM | 291 | N | VAL | 259 | 25.878 | 36.545 | 91.322 | 0.77 | 11.50 |
| ATOM | 293 | CA | VAL | 259 | 25.565 | 35.918 | 90.054 | 0.77 | 11.87 |
| ATOM | 294 | CB | VAL | 259 | 25.458 | 36.944 | 88.918 | 0.77 | 10.59 |
| ATOM | 295 | CG1 | VAL | 259 | 25.195 | 36.196 | 87.577 | 0.77 | 11.39 |
| ATOM | 296 | CG2 | VAL | 259 | 24.300 | 37.950 | 89.231 | 0.77 | 12.35 |
| ATOM | 297 | C | VAL | 259 | 26.721 | 34.951 | 89.791 | 0.77 | 11.07 |
| ATOM | 298 | O | VAL | 259 | 27.878 | 35.340 | 89.806 | 0.77 | 7.65 |
| ATOM | 299 | N | TRP | 260 | 26.374 | 33.688 | 89.570 | 1.00 | 12.75 |
| ATOM | 301 | CA | TRP | 260 | 27.355 | 32.634 | 89.339 | 1.00 | 12.57 |
| ATOM | 302 | CB | TRP | 260 | 27.223 | 31.564 | 90.422 | 1.00 | 13.64 |
| ATOM | 303 | CG | TRP | 260 | 27.624 | 31.962 | 91.839 | 1.00 | 15.49 |
| ATOM | 304 | CD2 | TRP | 260 | 28.768 | 31.510 | 92.549 | 1.00 | 16.17 |
| ATOM | 305 | CE2 | TRP | 260 | 28.693 | 32.051 | 93.849 | 1.00 | 19.28 |
| ATOM | 306 | CE3 | TRP | 260 | 29.857 | 30.699 | 92.215 | 1.00 | 18.93 |
| ATOM | 307 | CD1 | TRP | 260 | 26.917 | 32.752 | 92.710 | 1.00 | 13.42 |
| ATOM | 308 | NE1 | TRP | 260 | 27.547 | 32.806 | 93.911 | 1.00 | 16.08 |
| ATOM | 310 | CZ2 | TRP | 260 | 29.664 | 31.811 | 94.816 | 1.00 | 19.80 |
| ATOM | 311 | CZ3 | TRP | 260 | 30.836 | 30.463 | 93.179 | 1.00 | 21.11 |
| ATOM | 312 | CH2 | TRP | 260 | 30.733 | 31.017 | 94.463 | 1.00 | 20.39 |
| ATOM | 313 | C | TRP | 260 | 27.110 | 31.896 | 88.057 | 1.00 | 14.42 |
| ATOM | 314 | O | TRP | 260 | 25.977 | 31.874 | 87.544 | 1.00 | 12.42 |
| ATOM | 315 | N | MET | 261 | 28.187 | 31.306 | 87.534 | 1.00 | 12.57 |
| ATOM | 317 | CA | MET | 261 | 28.125 | 30.398 | 86.383 | 1.00 | 14.05 |
| ATOM | 318 | CB | MET | 261 | 29.426 | 30.446 | 85.540 | 1.00 | 14.46 |
| ATOM | 319 | CG | MET | 261 | 29.467 | 29.449 | 84.368 | 1.00 | 17.51 |
| ATOM | 320 | SD | MET | 261 | 29.909 | 27.732 | 84.824 | 1.00 | 18.15 |
| ATOM | 321 | CE | MET | 261 | 31.650 | 27.952 | 84.794 | 1.00 | 21.26 |
| ATOM | 322 | C | MET | 261 | 28.058 | 29.049 | 87.114 | 1.00 | 12.89 |
| ATOM | 323 | O | MET | 261 | 28.746 | 28.843 | 88.098 | 1.00 | 12.76 |
| ATOM | 324 | N | GLY | 262 | 27.192 | 28.148 | 86.669 | 1.00 | 12.57 |
| ATOM | 326 | CA | GLY | 262 | 27.092 | 26.863 | 87.334 | 1.00 | 12.10 |
| ATOM | 327 | C | GLY | 262 | 26.605 | 25.802 | 86.361 | 1.00 | 10.09 |
| ATOM | 328 | O | GLY | 262 | 26.539 | 26.068 | 85.161 | 1.00 | 10.85 |
| ATOM | 329 | N | TYR | 263 | 26.312 | 24.595 | 86.840 | 1.00 | 9.97 |
| ATOM | 331 | CA | TYR | 263 | 25.798 | 23.571 | 85.929 | 1.00 | 8.96 |
| ATOM | 332 | CB | TYR | 263 | 26.803 | 22.422 | 85.749 | 1.00 | 12.15 |
| ATOM | 333 | CG | TYR | 263 | 27.970 | 22.824 | 84.895 | 1.00 | 15.43 |
| ATOM | 334 | CD1 | TYR | 263 | 27.909 | 22.695 | 83.507 | 1.00 | 17.03 |
| ATOM | 335 | CE1 | TYR | 263 | 28.929 | 23.120 | 82.711 | 1.00 | 19.78 |
| ATOM | 336 | CD2 | TYR | 263 | 29.105 | 23.381 | 85.459 | 1.00 | 18.36 |
| ATOM | 337 | CE2 | TYR | 263 | 30.149 | 23.816 | 84.667 | 1.00 | 19.33 |
| ATOM | 338 | CZ | TYR | 263 | 30.057 | 23.676 | 83.295 | 1.00 | 22.04 |
| ATOM | 339 | OH | TYR | 263 | 31.100 | 24.070 | 82.483 | 1.00 | 22.57 |
| ATOM | 341 | C | TYR | 263 | 24.518 | 23.001 | 86.512 | 1.00 | 8.52 |
| ATOM | 342 | O | TYR | 263 | 24.410 | 22.801 | 87.719 | 1.00 | 9.40 |
| ATOM | 343 | N | TYR | 264 | 23.567 | 22.702 | 85.639 | 1.00 | 8.93 |
| ATOM | 345 | CA | TYR | 264 | 22.288 | 22.121 | 86.049 | 1.00 | 10.98 |
| ATOM | 346 | CB | TYR | 264 | 21.113 | 22.820 | 85.320 | 1.00 | 11.56 |
| ATOM | 347 | CG | TYR | 264 | 19.774 | 22.108 | 85.499 | 1.00 | 11.28 |
| ATOM | 348 | CD1 | TYR | 264 | 19.069 | 22.217 | 86.688 | 1.00 | 9.42 |
| ATOM | 349 | CE1 | TYR | 264 | 17.861 | 21.577 | 86.872 | 1.00 | 15.83 |
| ATOM | 350 | CD2 | TYR | 264 | 19.244 | 21.331 | 84.482 | 1.00 | 14.76 |
| ATOM | 351 | CE2 | TYR | 264 | 18.028 | 20.658 | 84.641 | 1.00 | 16.70 |
| ATOM | 352 | CZ | TYR | 264 | 17.342 | 20.787 | 85.851 | 1.00 | 16.43 |
| ATOM | 353 | OH | TYR | 264 | 16.194 | 20.076 | 86.066 | 1.00 | 16.99 |
| ATOM | 355 | C | TYR | 264 | 22.362 | 20.632 | 85.640 | 1.00 | 9.72 |

TABLE 1-continued

Coordinates of Lck bound with PP2

| | | Atom Type | Res | # | X | Y | Z | Occ | B |
|---|---|---|---|---|---|---|---|---|---|
| ATOM | 356 | O | TYR | 264 | 22.630 | 20.326 | 84.523 | 1.00 | 8.37 |
| ATOM | 357 | N | ASN | 265 | 22.131 | 19.742 | 86.583 | 1.00 | 12.41 |
| ATOM | 359 | CA | ASN | 265 | 22.168 | 18.281 | 86.351 | 1.00 | 15.00 |
| ATOM | 360 | CB | ASN | 265 | 20.931 | 17.835 | 85.542 | 1.00 | 14.45 |
| ATOM | 361 | CG | ASN | 265 | 19.697 | 17.631 | 86.409 | 1.00 | 16.46 |
| ATOM | 362 | OD1 | ASN | 265 | 19.684 | 17.960 | 87.593 | 1.00 | 18.43 |
| ATOM | 363 | ND2 | ASN | 265 | 18.646 | 17.085 | 85.811 | 1.00 | 19.57 |
| ATOM | 366 | C | ASN | 265 | 23.480 | 17.833 | 85.671 | 1.00 | 13.32 |
| ATOM | 367 | O | ASN | 265 | 23.479 | 17.112 | 84.669 | 1.00 | 13.22 |
| ATOM | 368 | N | GLY | 266 | 24.576 | 18.441 | 86.134 | 1.00 | 13.42 |
| ATOM | 370 | CA | GLY | 266 | 25.903 | 18.157 | 85.627 | 1.00 | 10.69 |
| ATOM | 371 | C | GLY | 266 | 26.370 | 18.683 | 84.291 | 1.00 | 10.57 |
| ATOM | 372 | O | GLY | 266 | 27.497 | 19.190 | 84.188 | 1.00 | 13.73 |
| ATOM | 373 | N | HIS | 267 | 25.524 | 18.672 | 83.278 | 0.49 | 6.58 |
| ATOM | 375 | CA | HIS | 267 | 25.959 | 19.032 | 81.930 | 0.49 | 4.52 |
| ATOM | 376 | CB | HIS | 267 | 25.519 | 17.906 | 80.982 | 0.49 | 2.00 |
| ATOM | 377 | CG | HIS | 267 | 26.142 | 16.579 | 81.298 | 0.49 | 2.01 |
| ATOM | 378 | CD2 | HIS | 267 | 27.443 | 16.220 | 81.373 | 0.49 | 2.00 |
| ATOM | 379 | ND1 | HIS | 267 | 25.404 | 15.465 | 81.622 | 0.49 | 3.59 |
| ATOM | 381 | CE1 | HIS | 267 | 26.233 | 14.460 | 81.887 | 0.49 | 2.00 |
| ATOM | 382 | NE2 | HIS | 267 | 27.465 | 14.892 | 81.741 | 0.49 | 4.45 |
| ATOM | 384 | C | HIS | 267 | 25.565 | 20.347 | 81.277 | 0.49 | 4.81 |
| ATOM | 385 | O | HIS | 267 | 26.133 | 20.755 | 80.290 | 0.49 | 2.00 |
| ATOM | 386 | N | THR | 268 | 24.595 | 21.015 | 81.863 | 1.00 | 8.43 |
| ATOM | 388 | CA | THR | 268 | 24.045 | 22.241 | 81.271 | 1.00 | 9.66 |
| ATOM | 389 | CB | THR | 268 | 22.495 | 22.190 | 81.312 | 1.00 | 9.51 |
| ATOM | 390 | OG1 | THR | 268 | 22.064 | 21.009 | 80.609 | 1.00 | 11.36 |
| ATOM | 392 | CG2 | THR | 268 | 21.869 | 23.479 | 80.588 | 1.00 | 7.84 |
| ATOM | 393 | C | THR | 268 | 24.508 | 23.484 | 81.978 | 1.00 | 10.26 |
| ATOM | 394 | O | THR | 268 | 24.201 | 23.690 | 83.109 | 1.00 | 8.95 |
| ATOM | 395 | N | LYS | 269 | 25.226 | 24.322 | 81.256 | 1.00 | 8.44 |
| ATOM | 397 | CA | LYS | 269 | 25.758 | 25.539 | 81.820 | 1.00 | 10.73 |
| ATOM | 398 | CB | LYS | 269 | 26.793 | 26.085 | 80.844 | 1.00 | 14.43 |
| ATOM | 399 | CG | LYS | 269 | 27.857 | 26.927 | 81.456 | 1.00 | 20.68 |
| ATOM | 400 | CD | LYS | 269 | 28.940 | 27.198 | 80.418 | 1.00 | 22.81 |
| ATOM | 401 | CE | LYS | 269 | 30.165 | 27.822 | 81.080 | 1.00 | 25.97 |
| ATOM | 402 | NZ | LYS | 269 | 31.365 | 27.979 | 80.165 | 1.00 | 28.11 |
| ATOM | 406 | C | LYS | 269 | 24.610 | 26.538 | 82.010 | 1.00 | 9.94 |
| ATGM | 407 | O | LYS | 269 | 23.766 | 26.713 | 81.133 | 1.00 | 9.80 |
| ATOM | 408 | N | VAL | 270 | 24.565 | 27.161 | 83.184 | 1.00 | 9.86 |
| ATOM | 410 | CA | VAL | 270 | 23.523 | 28.127 | 83.507 | 1.00 | 10.05 |
| ATOM | 411 | CB | VAL | 270 | 22.407 | 27.471 | 84.453 | 1.00 | 9.92 |
| ATOM | 412 | CG1 | VAL | 270 | 21.595 | 26.382 | 83.716 | 1.00 | 7.56 |
| ATOM | 413 | CG2 | VAL | 270 | 23.040 | 26.947 | 85.730 | 1.00 | 7.92 |
| ATOM | 414 | C | VAL | 270 | 24.112 | 29.285 | 84.304 | 1.00 | 8.92 |
| ATOM | 415 | O | VAL | 270 | 25.244 | 29.215 | 84.820 | 1.00 | 6.48 |
| ATOM | 416 | N | ALA | 271 | 23.347 | 30.375 | 84.386 | 1.00 | 9.98 |
| ATOM | 418 | CA | ALA | 271 | 23.721 | 31.526 | 85.230 | 1.00 | 6.96 |
| ATOM | 419 | CB | ALA | 271 | 23.429 | 32.850 | 84.490 | 1.00 | 12.05 |
| ATOM | 420 | C | ALA | 271 | 22.781 | 31.390 | 86.436 | 1.00 | 8.72 |
| ATOM | 421 | O | ALA | 271 | 21.607 | 31.007 | 86.300 | 1.00 | 8.81 |
| ATOM | 422 | N | VAL | 272 | 23.283 | 31.634 | 87.640 | 1.00 | 9.04 |
| ATOM | 424 | CA | VAL | 272 | 22.452 | 31.523 | 88.852 | 1.00 | 10.61 |
| ATOM | 425 | CB | VAL | 272 | 22.906 | 30.305 | 89.770 | 1.00 | 12.04 |
| ATOM | 426 | CG1 | VAL | 272 | 22.058 | 30.206 | 91.013 | 1.00 | 10.75 |
| ATOM | 427 | CG2 | VAL | 272 | 22.791 | 28.965 | 88.987 | 1.00 | 8.55 |
| ATOM | 428 | C | VAL | 272 | 22.586 | 32.866 | 89.624 | 1.00 | 13.45 |
| ATOM | 429 | O | VAL | 272 | 23.720 | 33.334 | 89.901 | 1.00 | 14.83 |
| ATOM | 430 | N | LYS | 273 | 21.452 | 33.535 | 89.854 | 1.00 | 12.70 |
| ATOM | 432 | CA | LYS | 273 | 21.409 | 34.801 | 90.618 | 1.00 | 12.28 |
| ATOM | 433 | CB | LYS | 273 | 20.508 | 35.828 | 89.921 | 1.00 | 13.97 |
| ATOM | 434 | CG | LYS | 273 | 20.492 | 37.206 | 90.606 | 1.00 | 17.88 |
| ATOM | 435 | CD | LYS | 273 | 19.981 | 38.243 | 89.611 | 1.00 | 20.07 |
| ATOM | 436 | CE | LYS | 273 | 19.348 | 39.440 | 90.304 | 1.00 | 19.77 |
| ATOM | 437 | NZ | LYS | 273 | 18.869 | 40.401 | 89.268 | 1.00 | 18.18 |
| ATOM | 441 | C | LYS | 273 | 20.840 | 34.426 | 91.959 | 1.00 | 8.80 |
| ATOM | 442 | O | LYS | 273 | 19.733 | 33.857 | 92.030 | 1.00 | 10.19 |
| ATOM | 443 | N | SER | 274 | 21.585 | 34.687 | 93.022 | 0.65 | 6.09 |
| ATOM | 445 | CA | SER | 274 | 21.164 | 34.319 | 94.360 | 0.65 | 8.59 |
| ATOM | 446 | CB | SER | 274 | 22.258 | 33.490 | 95.032 | 0.65 | 10.55 |
| ATOM | 447 | OG | SER | 274 | 23.470 | 34.234 | 95.063 | 0.65 | 10.38 |
| ATOM | 449 | C | SER | 274 | 20.891 | 35.535 | 95.198 | 0.65 | 10.30 |
| ATOM | 450 | O | SER | 274 | 21.649 | 36.495 | 95.187 | 0.65 | 5.65 |
| ATOM | 451 | N | LEU | 275 | 19.804 | 35.465 | 95.967 | 1.00 | 15.24 |

TABLE 1-continued

Coordinates of Lck bound with PP2

| | | Atom Type | Res | # | X | Y | Z | Occ | B |
|---|---|---|---|---|---|---|---|---|---|
| ATOM | 453 | CA | LEU | 275 | 19.389 | 36.573 | 96.821 | 1.00 | 17.33 |
| ATOM | 454 | CB | LEU | 275 | 17.864 | 36.490 | 97.091 | 1.00 | 17.49 |
| ATOM | 455 | CG | LEU | 275 | 17.236 | 37.430 | 98.139 | 1.00 | 19.44 |
| ATOM | 456 | CD1 | LEU | 275 | 17.369 | 38.895 | 97.688 | 1.00 | 18.21 |
| ATOM | 457 | CD2 | LEU | 275 | 15.735 | 37.045 | 98.373 | 1.00 | 19.11 |
| ATOM | 458 | C | LEU | 275 | 20.118 | 36.561 | 98.149 | 1.00 | 19.37 |
| ATOM | 459 | O | LEU | 275 | 20.134 | 35.559 | 98.860 | 1.00 | 21.32 |
| ATOM | 460 | N | LYS | 276 | 20.707 | 37.699 | 98.496 | 1.00 | 21.66 |
| ATOM | 462 | CA | LYS | 276 | 21.371 | 37.849 | 99.781 | 1.00 | 23.47 |
| ATOM | 463 | CB | LYS | 276 | 22.256 | 39.097 | 99.809 | 1.00 | 22.50 |
| ATOM | 464 | CG | LYS | 276 | 22.803 | 39.370 | 101.182 | 1.00 | 25.85 |
| ATOM | 465 | CD | LYS | 276 | 23.761 | 40.521 | 101.196 | 1.00 | 30.61 |
| ATOM | 466 | CE | LYS | 276 | 24.215 | 40.799 | 102.616 | 1.00 | 32.42 |
| ATOM | 467 | NZ | LYS | 276 | 25.396 | 41.724 | 102.623 | 1.00 | 36.15 |
| ATOM | 471 | C | LYS | 276 | 20.240 | 38.032 | 100.774 | 1.00 | 22.87 |
| ATOM | 472 | O | LYS | 276 | 19.562 | 39.024 | 100.744 | 1.00 | 22.78 |
| ATOM | 473 | N | ALA | 277 | 20.035 | 37.047 | 101.637 | 1.00 | 26.43 |
| ATOM | 475 | CA | ALA | 277 | 18.964 | 37.093 | 102.631 | 1.00 | 29.92 |
| ATOM | 476 | CB | ALA | 277 | 19.031 | 35.875 | 103.560 | 1.00 | 29.37 |
| ATOM | 477 | C | ALA | 277 | 18.984 | 38.383 | 103.449 | 1.00 | 29.68 |
| ATOM | 478 | O | ALA | 277 | 20.035 | 38.841 | 103.908 | 1.00 | 32.15 |
| ATOM | 479 | N | GLY | 278 | 17.802 | 38.981 | 103.586 | 1.00 | 29.88 |
| ATOM | 481 | CA | GLY | 278 | 17.646 | 40.212 | 104.332 | 1.00 | 27.48 |
| ATOM | 482 | C | GLY | 278 | 17.983 | 41.489 | 103.571 | 1.00 | 27.11 |
| ATOM | 483 | O | GLY | 278 | 17.649 | 42.563 | 104.050 | 1.00 | 26.26 |
| ATOM | 484 | N | SER | 279 | 18.621 | 41.396 | 102.399 | 1.00 | 24.86 |
| ATOM | 486 | CA | SER | 279 | 18.972 | 42.600 | 101.640 | 1.00 | 22.90 |
| ATOM | 487 | CB | SER | 279 | 20.068 | 42.286 | 100.630 | 1.00 | 22.71 |
| ATOM | 488 | OG | SER | 279 | 19.618 | 41.387 | 99.616 | 1.00 | 20.28 |
| ATOM | 490 | C | SER | 279 | 17.784 | 43.230 | 100.933 | 1.00 | 23.27 |
| ATOM | 491 | O | SER | 279 | 17.783 | 44.413 | 100.562 | 1.00 | 23.91 |
| ATOM | 492 | N | MET | 280 | 16.762 | 42.413 | 100.711 | 1.00 | 21.45 |
| ATOM | 494 | CA | MET | 280 | 15.561 | 42.865 | 100.034 | 1.00 | 19.30 |
| ATOM | 495 | CB | MET | 280 | 15.819 | 43.181 | 98.549 | 1.00 | 20.90 |
| ATOM | 496 | CG | MET | 280 | 16.054 | 41.973 | 97.620 | 1.00 | 19.17 |
| ATOM | 497 | SD | MET | 280 | 16.469 | 42.390 | 95.878 | 1.00 | 21.32 |
| ATOM | 498 | CE | MET | 280 | 14.834 | 42.654 | 95.202 | 1.00 | 16.33 |
| ATOM | 499 | C | MET | 280 | 14.514 | 41.760 | 100.192 | 1.00 | 19.63 |
| ATOM | 500 | O | MET | 280 | 14.783 | 40.649 | 100.686 | 1.00 | 18.67 |
| ATOM | 501 | N | SER | 281 | 13.290 | 42.111 | 99.850 | 1.00 | 16.87 |
| ATOM | 503 | CA | SER | 281 | 12.181 | 41.205 | 99.953 | 1.00 | 17.53 |
| ATOM | 504 | CB | SER | 281 | 10.902 | 41.995 | 99.604 | 1.00 | 18.68 |
| ATOM | 505 | OG | SER | 281 | 9.840 | 41.144 | 99.299 | 1.00 | 16.36 |
| ATOM | 507 | C | SER | 281 | 12.304 | 40.006 | 99.010 | 1.00 | 13.43 |
| ATOM | 508 | O | SER | 281 | 12.602 | 40.179 | 97.814 | 1.00 | 16.07 |
| ATOM | 509 | N | PRO | 282 | 12.052 | 38.791 | 99.518 | 0.51 | 10.91 |
| ATOM | 510 | CD | PRO | 282 | 11.934 | 38.421 | 100.939 | 0.51 | 10.92 |
| ATOM | 511 | CA | PRO | 282 | 12.131 | 37.601 | 98.674 | 0.51 | 10.05 |
| ATOM | 512 | CB | PRO | 282 | 11.791 | 36.460 | 99.646 | 0.51 | 9.74 |
| ATOM | 513 | CG | PRO | 282 | 12.321 | 36.934 | 100.922 | 0.51 | 10.72 |
| ATOM | 514 | C | PRO | 282 | 11.079 | 37.742 | 97.567 | 0.51 | 9.74 |
| ATOM | 515 | O | PRO | 282 | 11.306 | 37.355 | 96.424 | 0.51 | 5.34 |
| ATOM | 516 | N | ASP | 283 | 9.929 | 38.339 | 97.913 | 1.00 | 12.36 |
| ATOM | 518 | CA | ASP | 283 | 8.872 | 38.566 | 96.909 | 1.00 | 12.64 |
| ATOM | 519 | CB | ASP | 283 | 7.597 | 39.111 | 97.536 | 1.00 | 14.44 |
| ATOM | 520 | CG | ASP | 283 | 6.486 | 39.284 | 96.498 | 1.00 | 19.62 |
| ATOM | 521 | OD1 | ASP | 283 | 6.159 | 38.285 | 95.831 | 1.00 | 20.34 |
| ATOM | 522 | OD2 | ASP | 283 | 5.951 | 40.398 | 96.294 | 1.00 | 17.83 |
| ATOM | 523 | C | ASP | 283 | 9.338 | 39.546 | 95.839 | 1.00 | 11.41 |
| ATOM | 524 | O | ASP | 283 | 9.038 | 39.402 | 94.664 | 1.00 | 10.24 |
| ATOM | 525 | N | ALA | 284 | 10.071 | 40.579 | 96.244 | 1.00 | 11.86 |
| ATOM | 527 | CA | ALA | 284 | 10.583 | 41.563 | 95.269 | 1.00 | 11.50 |
| ATOM | 528 | CB | ALA | 284 | 11.302 | 42.729 | 96.023 | 1.00 | 14.90 |
| ATOM | 529 | C | ALA | 284 | 11.599 | 40.856 | 94.365 | 1.00 | 9.71 |
| ATOM | 530 | O | ALA | 284 | 11.616 | 41.001 | 93.160 | 1.00 | 12.77 |
| ATOM | 531 | N | PHE | 285 | 12.482 | 40.081 | 94.968 | 1.00 | 12.36 |
| ATOM | 533 | CA | PHE | 285 | 13.497 | 39.363 | 94.170 | 1.00 | 11.93 |
| ATOM | 534 | CB | PHE | 285 | 14.400 | 38.560 | 95.107 | 1.00 | 12.00 |
| ATOM | 535 | CG | PHE | 285 | 15.470 | 37.766 | 94.398 | 1.00 | 11.48 |
| ATOM | 536 | CD1 | PHE | 285 | 16.658 | 38.372 | 94.029 | 1.00 | 11.61 |
| ATOM | 537 | CD2 | PHE | 285 | 15.306 | 36.366 | 94.188 | 1.00 | 12.64 |
| ATOM | 538 | CE1 | PHE | 285 | 17.723 | 37.603 | 93.469 | 1.00 | 15.09 |
| ATOM | 539 | CE2 | PHE | 285 | 16.342 | 35.582 | 93.634 | 1.00 | 11.94 |
| ATOM | 540 | CZ | PHE | 285 | 17.550 | 36.193 | 93.272 | 1.00 | 13.87 |

TABLE 1-continued

Coordinates of Lck bound with PP2

| | | Atom Type | Res | # | X | Y | Z | Occ | B |
|---|---|---|---|---|---|---|---|---|---|
| ATOM | 541 | C | PHE | 285 | 12.861 | 38.440 | 93.113 | 1.00 | 12.72 |
| ATOM | 542 | O | PHE | 285 | 13.187 | 38.502 | 91.937 | 1.00 | 13.64 |
| ATOM | 543 | N | LEU | 286 | 11.889 | 37.631 | 93.531 | 1.00 | 12.47 |
| ATOM | 545 | CA | LEU | 286 | 11.239 | 36.697 | 92.631 | 1.00 | 13.16 |
| ATOM | 546 | CB | LEU | 286 | 10.452 | 35.655 | 93.439 | 1.00 | 10.98 |
| ATOM | 547 | CG | LEU | 286 | 11.406 | 34.705 | 94.189 | 1.00 | 11.81 |
| ATOM | 548 | CD1 | LEU | 286 | 10.686 | 33.906 | 95.289 | 1.00 | 11.78 |
| ATOM | 549 | CD2 | LEU | 286 | 12.074 | 33.779 | 93.168 | 1.00 | 11.79 |
| ATOM | 550 | C | LEU | 286 | 10.373 | 37.335 | 91.549 | 1.00 | 13.30 |
| ATOM | 551 | O | LEU | 286 | 10.099 | 36.721 | 90.501 | 1.00 | 13.69 |
| ATOM | 552 | N | ALA | 287 | 9.980 | 38.595 | 91.753 | 1.00 | 14.22 |
| ATOM | 554 | CA | ALA | 287 | 9.164 | 39.275 | 90.744 | 1.00 | 12.79 |
| ATOM | 555 | CB | ALA | 287 | 8.747 | 40.716 | 91.227 | 1.00 | 14.01 |
| ATOM | 556 | C | ALA | 287 | 9.877 | 39.327 | 89.413 | 1.00 | 12.05 |
| ATOM | 557 | O | ALA | 287 | 9.263 | 39.236 | 88.375 | 1.00 | 14.50 |
| ATOM | 558 | N | GLU | 288 | 11.211 | 39.367 | 89.437 | 1.00 | 13.61 |
| ATOM | 560 | CA | GLU | 288 | 11.989 | 39.383 | 88.200 | 1.00 | 12.81 |
| ATOM | 561 | CB | GLU | 288 | 13.486 | 39.460 | 88.526 | 1.00 | 13.21 |
| ATOM | 562 | CG | GLU | 288 | 14.424 | 39.430 | 87.310 | 1.00 | 16.97 |
| ATOM | 563 | CD | GLU | 288 | 15.909 | 39.764 | 87.655 | 1.00 | 18.73 |
| ATOM | 564 | OE1 | GLU | 288 | 16.279 | 39.835 | 88.824 | 1.00 | 20.30 |
| ATOM | 565 | OE2 | GLU | 288 | 16.735 | 39.934 | 86.741 | 1.00 | 21.91 |
| ATOM | 566 | C | GLU | 288 | 11.732 | 38.075 | 87.439 | 1.00 | 11.20 |
| ATOM | 567 | O | GLU | 288 | 11.424 | 38.063 | 86.263 | 1.00 | 11.74 |
| ATOM | 568 | N | ALA | 289 | 11.813 | 36.962 | 88.169 | 1.00 | 10.96 |
| ATOM | 570 | CA | ALA | 289 | 11.597 | 35.633 | 87.566 | 1.00 | 9.73 |
| ATOM | 571 | CB | ALA | 289 | 11.872 | 34.542 | 88.603 | 1.00 | 8.45 |
| ATOM | 572 | C | ALA | 289 | 10.166 | 35.530 | 87.033 | 1.00 | 8.84 |
| ATOM | 573 | O | ALA | 289 | 9.934 | 35.052 | 85.914 | 1.00 | 9.57 |
| ATOM | 574 | N | ASN | 290 | 9.198 | 35.999 | 87.827 | 1.00 | 10.45 |
| ATOM | 576 | CA | ASN | 290 | 7.800 | 35.953 | 87.404 | 1.00 | 14.12 |
| ATOM | 577 | CB | ASN | 290 | 6.876 | 36.488 | 88.520 | 1.00 | 16.66 |
| ATOM | 578 | CG | ASN | 290 | 6.762 | 35.513 | 89.712 | 1.00 | 21.59 |
| ATOM | 579 | OD1 | ASN | 290 | 6.541 | 35.926 | 90.856 | 1.00 | 23.55 |
| ATOM | 580 | ND2 | ASN | 290 | 6.905 | 34.219 | 89.440 | 1.00 | 22.69 |
| ATOM | 583 | C | ASN | 290 | 7.584 | 36.726 | 86.085 | 1.00 | 14.97 |
| ATOM | 584 | O | ASN | 290 | 6.789 | 36.320 | 85.222 | 1.00 | 13.37 |
| ATOM | 585 | N | LEU | 291 | 8.285 | 37.854 | 85.928 | 1.00 | 17.47 |
| ATOM | 587 | CA | LEU | 291 | 8.199 | 38.648 | 84.697 | 1.00 | 17.29 |
| ATOM | 588 | CB | LEU | 291 | 9.003 | 39.971 | 84.821 | 1.00 | 20.19 |
| ATOM | 589 | CG | LEU | 291 | 8.472 | 41.392 | 85.179 | 1.00 | 24.74 |
| ATOM | 590 | CD1 | LEU | 291 | 6.997 | 41.521 | 84.889 | 1.00 | 22.61 |
| ATOM | 591 | CD2 | LEU | 291 | 8.806 | 41.810 | 86.644 | 1.00 | 22.09 |
| ATOM | 592 | C | LEU | 291 | 8.778 | 37.817 | 83.517 | 1.00 | 16.73 |
| ATOM | 593 | O | LEU | 291 | 8.221 | 37.803 | 82.417 | 1.00 | 15.61 |
| ATOM | 594 | N | MET | 292 | 9.939 | 37.179 | 83.730 | 1.00 | 13.77 |
| ATOM | 596 | CA | MET | 292 | 10.590 | 36.381 | 82.675 | 1.00 | 13.57 |
| ATOM | 597 | CB | MET | 292 | 11.966 | 35.896 | 83.117 | 1.00 | 13.10 |
| ATOM | 598 | CG | MET | 292 | 12.909 | 37.044 | 83.430 | 1.00 | 14.50 |
| ATOM | 599 | SD | MET | 292 | 14.439 | 36.550 | 84.164 | 1.00 | 15.15 |
| ATOM | 600 | CE | MET | 292 | 15.202 | 35.872 | 82.775 | 1.00 | 9.75 |
| ATOM | 601 | C | MET | 292 | 9.714 | 35.228 | 82.178 | 1.00 | 14.48 |
| ATOM | 602 | O | MET | 292 | 9.803 | 34.854 | 81.031 | 1.00 | 14.30 |
| ATOM | 603 | N | LYS | 293 | 8.866 | 34.686 | 83.058 | 1.00 | 15.91 |
| ATOM | 605 | CA | LYS | 293 | 7.902 | 33.660 | 82.670 | 1.00 | 19.35 |
| ATOM | 606 | CB | LYS | 293 | 7.013 | 33.269 | 83.859 | 1.00 | 18.02 |
| ATOM | 607 | CG | LYS | 293 | 7.721 | 32.508 | 84.966 | 1.00 | 19.31 |
| ATOM | 608 | CD | LYS | 293 | 6.813 | 32.324 | 86.197 | 1.00 | 21.14 |
| ATOM | 609 | CE | LYS | 293 | 7.610 | 31.749 | 87.383 | 1.00 | 23.15 |
| ATOM | 610 | NZ | LYS | 293 | 6.770 | 31.524 | 88.623 | 1.00 | 23.01 |
| ATOM | 614 | C | LYS | 293 | 6.978 | 34.180 | 81.547 | 1.00 | 20.23 |
| ATOM | 615 | O | LYS | 293 | 6.643 | 33.444 | 80.647 | 1.00 | 22.05 |
| ATOM | 616 | N | GLN | 294 | 6.639 | 35.471 | 81.571 | 1.00 | 22.80 |
| ATOM | 618 | CA | GLN | 294 | 5.734 | 36.086 | 80.563 | 1.00 | 23.80 |
| ATOM | 619 | CB | GLN | 294 | 4.932 | 37.226 | 81.188 | 1.00 | 23.71 |
| ATOM | 620 | CG | GLN | 294 | 4.115 | 36.880 | 82.410 | 1.00 | 25.12 |
| ATOM | 621 | CD | GLN | 294 | 3.137 | 35.733 | 82.183 | 1.00 | 25.84 |
| ATOM | 622 | OE1 | GLN | 294 | 2.564 | 35.563 | 81.087 | 1.00 | 27.13 |
| ATOM | 623 | NE2 | GLN | 294 | 2.908 | 34.962 | 83.232 | 1.00 | 25.33 |
| ATOM | 626 | C | GLN | 294 | 6.413 | 36.688 | 79.333 | 1.00 | 24.50 |
| ATOM | 627 | O | GLN | 294 | 5.755 | 37.279 | 78.443 | 1.00 | 24.11 |
| ATOM | 628 | N | LEU | 295 | 7.738 | 36.618 | 79.306 | 1.00 | 21.49 |
| ATOM | 630 | CA | LEU | 295 | 8.487 | 37.197 | 78.219 | 1.00 | 19.69 |
| ATOM | 631 | CB | LEU | 295 | 9.192 | 38.475 | 78.711 | 1.00 | 19.08 |

TABLE 1-continued

Coordinates of Lck bound with PP2

| | Atom Type | Res | # | X | Y | Z | Occ | B |
|---|---|---|---|---|---|---|---|---|
| ATOM | 632 | CG | LEU | 295 | 8.308 | 39.673 | 78.994 | 1.00 | 18.05 |
| ATOM | 633 | CD1 | LEU | 295 | 9.091 | 40.766 | 79.704 | 1.00 | 20.60 |
| ATOM | 634 | CD2 | LEU | 295 | 7.790 | 40.127 | 77.657 | 1.00 | 16.99 |
| ATOM | 635 | C | LEU | 295 | 9.500 | 36.220 | 77.709 | 1.00 | 18.25 |
| ATOM | 636 | O | LEU | 295 | 10.698 | 36.338 | 77.975 | 1.00 | 19.62 |
| ATOM | 637 | N | GLN | 296 | 9.035 | 35.260 | 76.928 | 1.00 | 17.39 |
| ATOM | 639 | CA | GLN | 296 | 9.951 | 34.250 | 76.416 | 1.00 | 18.14 |
| ATOM | 640 | CB | GLN | 296 | 9.420 | 32.832 | 76.700 | 1.00 | 15.45 |
| ATOM | 641 | CG | GLN | 296 | 9.288 | 32.539 | 78.179 | 1.00 | 19.02 |
| ATOM | 642 | CD | GLN | 296 | 8.794 | 31.115 | 78.413 | 1.00 | 20.14 |
| ATOM | 643 | OE1 | GLN | 296 | 9.206 | 30.199 | 77.725 | 1.00 | 22.06 |
| ATOM | 644 | NE2 | GLN | 296 | 7.912 | 30.942 | 79.361 | 1.00 | 20.10 |
| ATOM | 647 | C | GLN | 296 | 10.118 | 34.452 | 74.943 | 1.00 | 15.64 |
| ATOM | 648 | O | GLN | 296 | 9.150 | 34.458 | 74.215 | 1.00 | 15.34 |
| ATOM | 649 | N | HIS | 297 | 11.372 | 34.551 | 74.509 | 1.00 | 14.27 |
| ATOM | 651 | CA | HIS | 297 | 11.688 | 34.765 | 73.101 | 1.00 | 11.92 |
| ATOM | 652 | CB | HIS | 297 | 11.370 | 36.225 | 72.753 | 1.00 | 10.95 |
| ATOM | 653 | CG | HIS | 297 | 11.495 | 36.546 | 71.297 | 1.00 | 10.37 |
| ATOM | 654 | CD2 | HIS | 297 | 10.556 | 36.624 | 70.319 | 1.00 | 12.15 |
| ATOM | 655 | ND1 | HIS | 297 | 12.695 | 36.842 | 70.695 | 1.00 | 11.35 |
| ATOM | 657 | CE1 | HIS | 297 | 12.501 | 37.097 | 69.409 | 1.00 | 13.18 |
| ATOM | 658 | NE2 | HIS | 297 | 11.204 | 36.963 | 69.158 | 1.00 | 11.54 |
| ATOM | 660 | C | HIS | 297 | 13.173 | 34.498 | 72.928 | 1.00 | 11.34 |
| ATOM | 661 | O | HIS | 297 | 13.933 | 34.717 | 73.884 | 1.00 | 9.90 |
| ATOM | 662 | N | GLN | 298 | 13.604 | 34.113 | 71.716 | 1.00 | 11.48 |
| ATOM | 664 | CA | GLN | 298 | 15.036 | 33.841 | 71.439 | 1.00 | 12.13 |
| ATOM | 665 | CB | GLN | 298 | 15.289 | 33.479 | 69.963 | 1.00 | 13.49 |
| ATOM | 666 | CG | GLN | 298 | 14.906 | 32.112 | 69.500 | 1.00 | 15.33 |
| ATOM | 667 | CD | GLN | 298 | 15.696 | 30.957 | 70.148 | 1.00 | 15.54 |
| ATOM | 668 | OE1 | GLN | 298 | 16.995 | 30.917 | 70.199 | 1.00 | 16.95 |
| ATOM | 669 | NE2 | GLN | 298 | 14.949 | 29.994 | 70.610 | 1.00 | 12.02 |
| ATOM | 672 | C | GLN | 298 | 15.956 | 35.039 | 71.743 | 1.00 | 11.32 |
| ATOM | 673 | O | GLN | 298 | 17.119 | 34.891 | 72.078 | 1.00 | 11.14 |
| ATOM | 674 | N | ARG | 299 | 15.412 | 36.245 | 71.641 | 1.00 | 10.16 |
| ATOM | 676 | CA | ARG | 299 | 16.194 | 37.454 | 71.883 | 1.00 | 9.08 |
| ATOM | 677 | CB | ARG | 299 | 15.738 | 38.560 | 70.916 | 1.00 | 8.03 |
| ATOM | 678 | CG | ARG | 299 | 15.814 | 38.211 | 69.431 | 1.00 | 3.63 |
| ATOM | 679 | CD | ARG | 299 | 17.162 | 38.557 | 68.807 | 1.00 | 3.23 |
| ATOM | 680 | NE | ARG | 299 | 18.321 | 37.992 | 69.520 | 1.00 | 6.82 |
| ATOM | 682 | CZ | ARG | 299 | 18.788 | 36.758 | 69.370 | 1.00 | 8.67 |
| ATOM | 683 | NH1 | ARG | 299 | 18.174 | 35.912 | 68.556 | 1.00 | 8.24 |
| ATOM | 686 | NH2 | ARG | 299 | 19.910 | 36.390 | 70.007 | 1.00 | 8.32 |
| ATOM | 689 | C | ARG | 299 | 16.181 | 37.986 | 73.310 | 1.00 | 7.13 |
| ATOM | 690 | O | ARG | 299 | 16.643 | 39.079 | 73.549 | 1.00 | 9.74 |
| ATOM | 691 | N | LEU | 300 | 15.561 | 37.269 | 74.242 | 1.00 | 6.11 |
| ATOM | 693 | CA | LEU | 300 | 15.522 | 37.665 | 75.629 | 1.00 | 6.01 |
| ATOM | 694 | CB | LEU | 300 | 14.069 | 37.890 | 76.154 | 1.00 | 7.06 |
| ATOM | 695 | CG | LEU | 300 | 13.323 | 39.211 | 75.813 | 1.00 | 7.90 |
| ATOM | 696 | CD1 | LEU | 300 | 13.413 | 39.508 | 74.322 | 1.00 | 4.75 |
| ATOM | 697 | CD2 | LEU | 300 | 11.827 | 39.102 | 76.265 | 1.00 | 7.42 |
| ATOM | 698 | C | LEU | 300 | 16.142 | 36.506 | 76.406 | 1.00 | 8.93 |
| ATOM | 699 | O | LEU | 300 | 15.848 | 35.338 | 76.102 | 1.00 | 6.41 |
| ATOM | 700 | N | VAL | 301 | 16.966 | 36.841 | 77.410 | 1.00 | 6.55 |
| ATOM | 702 | CA | VAL | 301 | 17.619 | 35.855 | 78.245 | 1.00 | 8.81 |
| ATOM | 703 | CB | VAL | 301 | 18.539 | 36.531 | 79.288 | 1.00 | 8.90 |
| ATOM | 704 | CG1 | VAL | 301 | 19.124 | 35.519 | 80.295 | 1.00 | 12.65 |
| ATOM | 705 | CG2 | VAL | 301 | 19.711 | 37.185 | 78.520 | 1.00 | 9.85 |
| ATOM | 706 | C | VAL | 301 | 16.495 | 35.009 | 78.820 | 1.00 | 9.15 |
| ATOM | 707 | O | VAL | 301 | 15.511 | 35.520 | 79.376 | 1.00 | 8.93 |
| ATOM | 708 | N | ARG | 302 | 16.646 | 33.690 | 78.681 | 1.00 | 8.85 |
| ATOM | 710 | CA | ARG | 302 | 15.573 | 32.768 | 79.119 | 1.00 | 10.40 |
| ATOM | 711 | CB | ARG | 302 | 15.536 | 31.582 | 78.143 | 1.00 | 12.40 |
| ATOM | 712 | CG | ARG | 302 | 14.164 | 30.941 | 77.970 | 1.00 | 23.68 |
| ATOM | 713 | CD | ARG | 302 | 14.140 | 29.714 | 78.754 | 1.00 | 30.77 |
| ATOM | 714 | NE | ARG | 302 | 13.444 | 28.625 | 78.073 | 1.00 | 38.30 |
| ATOM | 716 | CZ | ARG | 302 | 13.393 | 27.385 | 78.542 | 1.00 | 40.51 |
| ATOM | 717 | NH1 | ARG | 302 | 13.996 | 27.096 | 79.696 | 1.00 | 39.82 |
| ATOM | 720 | NH2 | ARG | 302 | 12.752 | 26.447 | 77.855 | 1.00 | 41.42 |
| ATOM | 723 | C | ARG | 302 | 15.580 | 32.270 | 80.538 | 1.00 | 8.42 |
| ATOM | 724 | O | ARG | 302 | 16.607 | 31.798 | 81.060 | 1.00 | 7.98 |
| ATOM | 725 | N | LEU | 303 | 14.422 | 32.334 | 81.200 | 1.00 | 5.71 |
| ATOM | 727 | CA | LEU | 303 | 14.349 | 31.803 | 82.563 | 1.00 | 8.28 |
| ATOM | 728 | CB | LEU | 303 | 13.025 | 32.163 | 83.194 | 1.00 | 6.95 |
| ATOM | 729 | CG | LEU | 303 | 12.808 | 31.608 | 84.595 | 1.00 | 8.61 |

TABLE 1-continued

Coordinates of Lck bound with PP2

| | | Atom Type | Res | # | X | Y | Z | Occ | B |
|---|---|---|---|---|---|---|---|---|---|
| ATOM | 730 | CD1 | LEU | 303 | 13.812 | 32.220 | 85.529 | 1.00 | 5.11 |
| ATOM | 731 | CD2 | LEU | 303 | 11.355 | 31.903 | 85.056 | 1.00 | 7.06 |
| ATOM | 732 | C | LEU | 303 | 14.373 | 30.254 | 82.446 | 1.00 | 10.39 |
| ATOM | 733 | O | LEU | 303 | 13.822 | 29.694 | 81.516 | 1.00 | 9.86 |
| ATOM | 734 | N | TYR | 304 | 15.121 | 29.592 | 83.313 | 1.00 | 11.01 |
| ATOM | 736 | CA | TYR | 304 | 15.173 | 28.128 | 83.288 | 1.00 | 12.82 |
| ATOM | 737 | CB | TYR | 304 | 16.603 | 27.634 | 83.371 | 1.00 | 13.79 |
| ATOM | 738 | CG | TYR | 304 | 17.405 | 27.754 | 82.136 | 1.00 | 12.77 |
| ATOM | 739 | CD1 | TYR | 304 | 16.859 | 28.291 | 80.969 | 1.00 | 10.38 |
| ATOM | 740 | CE1 | TYR | 304 | 17.585 | 28.347 | 79.831 | 1.00 | 12.06 |
| ATOM | 741 | CD2 | TYR | 304 | 18.719 | 27.284 | 82.116 | 1.00 | 11.93 |
| ATOM | 742 | CE2 | TYR | 304 | 19.472 | 27.322 | 80.975 | 1.00 | 13.56 |
| ATOM | 743 | CZ | TYR | 304 | 18.905 | 27.849 | 79.818 | 1.00 | 12.06 |
| ATOM | 744 | OH | TYR | 304 | 19.613 | 27.789 | 78.641 | 1.00 | 11.27 |
| ATOM | 746 | C | TYR | 304 | 14.467 | 27.548 | 84.510 | 1.00 | 12.51 |
| ATOM | 747 | O | TYR | 304 | 13.698 | 26.601 | 84.397 | 1.00 | 13.97 |
| ATOM | 748 | N | ALA | 305 | 14.756 | 28.106 | 85.687 | 1.00 | 10.67 |
| ATOM | 750 | CA | ALA | 305 | 14.185 | 27.579 | 86.929 | 1.00 | 11.01 |
| ATOM | 751 | CB | ALA | 305 | 14.918 | 26.257 | 87.300 | 1.00 | 8.23 |
| ATOM | 752 | C | ALA | 305 | 14.335 | 28.548 | 88.086 | 1.00 | 9.42 |
| ATOM | 753 | O | ALA | 305 | 14.999 | 29.576 | 87.975 | 1.00 | 9.68 |
| ATOM | 754 | N | VAL | 306 | 13.764 | 28.160 | 89.216 | 0.75 | 8.59 |
| ATOM | 756 | CA | VAL | 306 | 13.840 | 28.902 | 90.474 | 0.75 | 8.69 |
| ATOM | 757 | CB | VAL | 306 | 12.566 | 29.770 | 90.740 | 0.75 | 9.62 |
| ATOM | 758 | CG1 | VAL | 306 | 12.431 | 30.827 | 89.666 | 0.75 | 10.69 |
| ATOM | 759 | CG2 | VAL | 306 | 11.261 | 28.883 | 90.800 | 0.75 | 9.31 |
| ATOM | 760 | C | VAL | 306 | 13.930 | 27.920 | 91.633 | 0.75 | 10.26 |
| ATOM | 761 | O | VAL | 306 | 13.482 | 26.785 | 91.510 | 0.75 | 7.84 |
| ATOM | 762 | N | VAL | 307 | 14.608 | 28.337 | 92.710 | 1.00 | 12.30 |
| ATOM | 764 | CA | VAL | 307 | 14.670 | 27.582 | 93.960 | 1.00 | 14.51 |
| ATOM | 765 | CB | VAL | 307 | 16.115 | 27.196 | 94.422 | 1.00 | 13.59 |
| ATOM | 766 | CG1 | VAL | 307 | 16.019 | 26.529 | 95.817 | 1.00 | 14.23 |
| ATOM | 767 | CG2 | VAL | 307 | 16.772 | 26.224 | 93.434 | 1.00 | 11.32 |
| ATOM | 768 | C | VAL | 307 | 14.092 | 28.645 | 94.910 | 1.00 | 17.91 |
| ATOM | 769 | O | VAL | 307 | 14.711 | 29.739 | 95.168 | 1.00 | 15.90 |
| ATOM | 770 | N | THR | 308 | 12.870 | 28.400 | 95.364 | 1.00 | 19.17 |
| ATOM | 772 | CA | THR | 308 | 12.176 | 29.380 | 96.205 | 1.00 | 22.29 |
| ATOM | 773 | CB | THR | 308 | 10.645 | 29.485 | 95.851 | 1.00 | 22.71 |
| ATOM | 774 | OG1 | THR | 308 | 10.057 | 28.188 | 95.749 | 1.00 | 21.78 |
| ATOM | 776 | CG2 | THR | 308 | 10.462 | 30.186 | 94.518 | 1.00 | 23.24 |
| ATOM | 777 | C | THR | 308 | 12.377 | 29.339 | 97.707 | 1.00 | 24.69 |
| ATOM | 778 | O | THR | 308 | 11.681 | 30.033 | 98.452 | 1.00 | 25.07 |
| ATOM | 779 | N | ALA | 309 | 13.304 | 28.499 | 98.162 | 1.00 | 26.35 |
| ATOM | 781 | CA | ALA | 309 | 13.617 | 28.424 | 99.580 | 1.00 | 27.81 |
| ATOM | 782 | CB | ALA | 309 | 13.673 | 26.977 | 100.049 | 1.00 | 29.53 |
| ATOM | 783 | C | ALA | 309 | 14.978 | 29.105 | 99.719 | 1.00 | 28.47 |
| ATOM | 784 | O | ALA | 309 | 15.822 | 29.050 | 98.800 | 1.00 | 26.56 |
| ATOM | 785 | N | GLU | 310 | 15.204 | 29.755 | 100.862 | 1.00 | 28.30 |
| ATOM | 787 | CA | GLU | 310 | 16.457 | 30.481 | 101.096 | 1.00 | 28.80 |
| ATOM | 788 | CB | GLU | 310 | 16.308 | 31.391 | 102.324 | 1.00 | 29.80 |
| ATOM | 789 | CG | GLU | 310 | 15.345 | 32.549 | 102.045 | 1.00 | 33.60 |
| ATOM | 790 | CD | GLU | 310 | 14.915 | 33.346 | 103.269 | 1.00 | 35.54 |
| ATOM | 791 | OE1 | GLU | 310 | 15.289 | 32.988 | 104.413 | 1.00 | 37.41 |
| ATOM | 792 | OE2 | GLU | 310 | 14.150 | 34.315 | 103.080 | 1.00 | 36.45 |
| ATOM | 793 | C | GLU | 310 | 17.748 | 29.655 | 101.157 | 1.00 | 28.31 |
| ATOM | 794 | O | GLU | 310 | 17.810 | 28.605 | 101.794 | 1.00 | 30.35 |
| ATOM | 795 | N | PRO | 311 | 18.811 | 30.121 | 100.486 | 1.00 | 26.38 |
| ATOM | 796 | CD | PRO | 311 | 20.162 | 29.534 | 100.647 | 1.00 | 26.11 |
| ATOM | 797 | CA | PRO | 311 | 18.853 | 31.351 | 99.688 | 1.00 | 23.53 |
| ATOM | 798 | CB | PRO | 311 | 20.363 | 31.610 | 99.503 | 1.00 | 24.89 |
| ATOM | 799 | CG | PRO | 311 | 20.967 | 30.221 | 99.565 | 1.00 | 26.08 |
| ATOM | 800 | C | PRO | 311 | 18.154 | 31.132 | 98.360 | 1.00 | 21.13 |
| ATOM | 801 | O | PRO | 311 | 18.378 | 30.165 | 97.673 | 1.00 | 18.55 |
| ATOM | 802 | N | ILE | 312 | 17.312 | 32.086 | 98.003 | 1.00 | 19.48 |
| ATOM | 804 | CA | ILE | 312 | 16.533 | 32.024 | 96.777 | 1.00 | 16.72 |
| ATOM | 805 | CB | ILE | 312 | 15.440 | 33.126 | 96.851 | 1.00 | 17.73 |
| ATOM | 806 | CG2 | ILE | 312 | 14.608 | 33.129 | 95.595 | 1.00 | 15.57 |
| ATOM | 807 | CG1 | ILE | 312 | 14.590 | 32.867 | 98.111 | 1.00 | 18.07 |
| ATOM | 808 | CD1 | ILE | 312 | 13.363 | 33.699 | 98.238 | 1.00 | 23.33 |
| ATOM | 809 | C | ILE | 312 | 17.381 | 32.167 | 95.524 | 1.00 | 15.13 |
| ATOM | 810 | O | ILE | 312 | 18.290 | 32.987 | 95.454 | 1.00 | 14.05 |
| ATOM | 811 | N | TYR | 313 | 17.132 | 31.311 | 94.543 | 1.00 | 14.30 |
| ATOM | 813 | CA | TYR | 313 | 17.875 | 31.382 | 93.278 | 1.00 | 13.21 |
| ATOM | 814 | CB | TYR | 313 | 18.621 | 30.069 | 92.976 | 1.00 | 12.11 |

TABLE 1-continued

Coordinates of Lck bound with PP2

| | | Atom Type | Res | # | X | Y | Z | Occ | B |
|---|---|---|---|---|---|---|---|---|---|
| ATOM | 815 | CG | TYR | 313 | 19.762 | 29.641 | 93.897 | 1.00 | 15.64 |
| ATOM | 816 | CD1 | TYR | 313 | 20.381 | 30.523 | 94.759 | 1.00 | 13.64 |
| ATOM | 817 | CE1 | TYR | 313 | 21.466 | 30.126 | 95.521 | 1.00 | 16.99 |
| ATOM | 818 | CD2 | TYR | 313 | 20.253 | 28.340 | 93.835 | 1.00 | 16.93 |
| ATOM | 819 | CE2 | TYR | 313 | 21.336 | 27.939 | 94.591 | 1.00 | 18.03 |
| ATOM | 820 | CZ | TYR | 313 | 21.940 | 28.824 | 95.421 | 1.00 | 17.94 |
| ATOM | 821 | OH | TYR | 313 | 23.057 | 28.416 | 96.101 | 1.00 | 19.83 |
| ATOM | 823 | C | TYR | 313 | 16.957 | 31.575 | 92.086 | 1.00 | 11.00 |
| ATOM | 824 | O | TYR | 313 | 15.887 | 31.020 | 92.043 | 1.00 | 12.08 |
| ATOM | 825 | N | ILE | 314 | 17.475 | 32.251 | 91.062 | 0.82 | 9.52 |
| ATOM | 827 | CA | ILE | 314 | 16.803 | 32.420 | 89.761 | 0.82 | 8.77 |
| ATOM | 828 | CB | ILE | 314 | 16.520 | 33.902 | 89.393 | 0.82 | 8.15 |
| ATOM | 829 | CG2 | ILE | 314 | 15.923 | 34.013 | 87.975 | 0.82 | 6.94 |
| ATOM | 830 | CG1 | ILE | 314 | 15.526 | 34.505 | 90.382 | 0.82 | 8.58 |
| ATOM | 831 | CD1 | ILE | 314 | 15.304 | 36.031 | 90.182 | 0.82 | 8.14 |
| ATOM | 832 | C | ILE | 314 | 17.860 | 31.869 | 88.807 | 0.82 | 5.81 |
| ATOM | 833 | O | ILE | 314 | 19.018 | 32.299 | 88.802 | 0.82 | 4.52 |
| ATOM | 834 | N | ILE | 315 | 17.485 | 30.858 | 88.041 | 1.00 | 8.34 |
| ATOM | 836 | CA | ILE | 315 | 18.410 | 30.182 | 87.127 | 1.00 | 8.77 |
| ATOM | 837 | CB | ILE | 315 | 18.393 | 28.646 | 87.369 | 1.00 | 12.61 |
| ATOM | 838 | CG2 | ILE | 315 | 19.323 | 27.932 | 86.355 | 1.00 | 8.22 |
| ATOM | 839 | CG1 | ILE | 315 | 18.811 | 28.341 | 88.832 | 1.00 | 11.62 |
| ATOM | 840 | CD1 | ILE | 315 | 17.659 | 28.147 | 89.775 | 1.00 | 11.79 |
| ATOM | 841 | C | ILE | 315 | 18.045 | 30.508 | 85.707 | 1.00 | 8.39 |
| ATOM | 842 | O | ILE | 315 | 16.885 | 30.338 | 85.318 | 1.00 | 6.04 |
| ATOM | 843 | N | THR | 316 | 19.021 | 30.986 | 84.913 | 1.00 | 5.83 |
| ATOM | 845 | CA | THR | 316 | 18.699 | 31.378 | 83.547 | 1.00 | 8.36 |
| ATOM | 846 | CB | THR | 316 | 18.750 | 32.954 | 83.344 | 1.00 | 9.42 |
| ATOM | 847 | OG1 | THR | 316 | 20.125 | 33.390 | 83.423 | 1.00 | 8.78 |
| ATOM | 849 | CG2 | THR | 316 | 17.943 | 33.736 | 84.402 | 1.00 | 5.91 |
| ATOM | 850 | C | THR | 316 | 19.723 | 30.856 | 82.557 | 1.00 | 8.42 |
| ATOM | 851 | O | THR | 316 | 20.764 | 30.284 | 82.913 | 1.00 | 8.32 |
| ATOM | 852 | N | GLU | 317 | 19.404 | 31.112 | 81.293 | 1.00 | 8.36 |
| ATOM | 854 | CA | GLU | 317 | 20.263 | 30.847 | 80.150 | 1.00 | 8.92 |
| ATOM | 855 | CB | GLU | 317 | 19.585 | 31.516 | 78.951 | 1.00 | 8.49 |
| ATOM | 856 | CG | GLU | 317 | 20.295 | 31.428 | 77.609 | 1.00 | 6.91 |
| ATOM | 857 | CD | GLU | 317 | 19.390 | 31.856 | 76.463 | 1.00 | 11.13 |
| ATOM | 858 | OE1 | GLU | 317 | 18.458 | 32.641 | 76.728 | 1.00 | 11.40 |
| ATOM | 859 | OE2 | GLU | 317 | 19.614 | 31.449 | 75.287 | 1.00 | 9.16 |
| ATOM | 860 | C | GLU | 317 | 21.620 | 31.563 | 80.429 | 1.00 | 9.37 |
| ATOM | 861 | O | GLU | 317 | 21.670 | 32.702 | 80.956 | 1.00 | 7.89 |
| ATOM | 862 | N | TYR | 318 | 22.717 | 30.885 | 80.134 | 1.00 | 9.26 |
| ATOM | 864 | CA | TYR | 318 | 24.049 | 31.441 | 80.377 | 1.00 | 9.46 |
| ATOM | 865 | CB | TYR | 318 | 25.008 | 30.340 | 80.828 | 1.00 | 10.67 |
| ATOM | 866 | CG | TYR | 318 | 26.398 | 30.870 | 81.120 | 1.00 | 13.70 |
| ATOM | 867 | CD1 | TYR | 318 | 26.616 | 31.658 | 82.229 | 1.00 | 13.98 |
| ATOM | 868 | CE1 | TYR | 318 | 27.864 | 32.130 | 82.529 | 1.00 | 18.18 |
| ATOM | 869 | CD2 | TYR | 318 | 27.487 | 30.564 | 80.291 | 1.00 | 14.21 |
| ATOM | 870 | CE2 | TYR | 318 | 28.764 | 31.049 | 80.592 | 1.00 | 14.28 |
| ATOM | 871 | CZ | TYR | 318 | 28.933 | 31.822 | 81.710 | 1.00 | 15.79 |
| ATOM | 872 | OH | TYR | 318 | 30.161 | 32.311 | 82.066 | 1.00 | 19.16 |
| ATOM | 874 | C | TYR | 318 | 24.561 | 32.132 | 79.110 | 1.00 | 9.19 |
| ATOM | 875 | O | TYR | 318 | 24.480 | 31.588 | 78.010 | 1.00 | 9.33 |
| ATOM | 876 | N | MET | 319 | 24.978 | 33.390 | 79.243 | 1.00 | 8.48 |
| ATOM | 878 | CA | MET | 319 | 25.453 | 34.147 | 78.066 | 1.00 | 9.42 |
| ATOM | 879 | CB | MET | 319 | 24.787 | 35.524 | 78.046 | 1.00 | 10.85 |
| ATOM | 880 | CG | MET | 319 | 23.237 | 35.423 | 77.946 | 1.00 | 11.71 |
| ATOM | 881 | SD | MET | 319 | 22.750 | 34.629 | 76.411 | 1.00 | 13.99 |
| ATOM | 882 | CE | MET | 319 | 23.254 | 35.844 | 75.227 | 1.00 | 8.87 |
| ATOM | 883 | C | MET | 319 | 26.968 | 34.254 | 78.250 | 1.00 | 9.69 |
| ATOM | 884 | O | MET | 319 | 27.462 | 35.031 | 79.087 | 1.00 | 7.90 |
| ATOM | 885 | N | GLU | 320 | 27.684 | 33.493 | 77.435 | 1.00 | 6.36 |
| ATOM | 887 | CA | GLU | 320 | 29.135 | 33.342 | 77.540 | 1.00 | 10.55 |
| ATOM | 888 | CB | GLU | 320 | 29.642 | 32.303 | 76.508 | 1.00 | 11.97 |
| ATOM | 889 | CG | GLU | 320 | 31.146 | 31.906 | 76.652 | 1.00 | 20.65 |
| ATOM | 890 | CD | GLU | 320 | 31.485 | 31.222 | 77.983 | 1.00 | 24.26 |
| ATOM | 891 | OE1 | GLU | 320 | 31.327 | 29.988 | 78.068 | 1.00 | 27.15 |
| ATOM | 892 | OE2 | GLU | 320 | 31.922 | 31.915 | 78.944 | 1.00 | 28.40 |
| ATOM | 893 | C | GLU | 320 | 30.005 | 34.588 | 77.524 | 1.00 | 11.16 |
| ATOM | 894 | O | GLU | 320 | 31.031 | 34.639 | 78.213 | 1.00 | 12.37 |
| ATOM | 895 | N | ASN | 321 | 29.628 | 35.555 | 76.695 | 1.00 | 11.28 |
| ATOM | 897 | CA | ASN | 321 | 30.374 | 36.782 | 76.561 | 1.00 | 11.02 |
| ATOM | 898 | CB | ASN | 321 | 30.451 | 37.230 | 75.093 | 1.00 | 12.54 |
| ATOM | 899 | CG | ASN | 321 | 31.520 | 36.474 | 74.337 | 1.00 | 13.58 |

TABLE 1-continued

Coordinates of Lck bound with PP2

| | | Atom Type | Res | # | X | Y | Z | Occ | B |
|---|---|---|---|---|---|---|---|---|---|
| ATOM | 900 | OD1 | ASN | 321 | 32.638 | 36.338 | 74.833 | 1.00 | 12.04 |
| ATOM | 901 | ND2 | ASN | 321 | 31.171 | 35.921 | 73.195 | 1.00 | 11.91 |
| ATOM | 904 | C | ASN | 321 | 29.917 | 37.887 | 77.473 | 1.00 | 11.39 |
| ATOM | 905 | O | ASN | 321 | 30.356 | 39.014 | 77.315 | 1.00 | 12.51 |
| ATOM | 906 | N | GLY | 322 | 29.017 | 37.536 | 78.403 | 1.00 | 8.41 |
| ATOM | 908 | CA | GLY | 322 | 28.528 | 38.421 | 79.427 | 1.00 | 6.95 |
| ATOM | 909 | C | GLY | 322 | 27.900 | 39.733 | 78.973 | 1.00 | 6.87 |
| ATOM | 910 | O | GLY | 322 | 27.255 | 39.785 | 77.923 | 1.00 | 7.74 |
| ATOM | 911 | N | SER | 323 | 28.125 | 40.794 | 79.731 | 0.43 | 2.00 |
| ATOM | 913 | CA | SER | 323 | 27.539 | 42.086 | 79.394 | 0.43 | 2.39 |
| ATOM | 914 | CB | SER | 323 | 27.636 | 42.956 | 80.635 | 0.43 | 2.00 |
| ATOM | 915 | OG | SER | 323 | 27.155 | 44.230 | 80.416 | 0.43 | 2.00 |
| ATOM | 917 | C | SER | 323 | 28.122 | 42.789 | 78.147 | 0.43 | 4.13 |
| ATOM | 918 | O | SER | 323 | 29.336 | 42.891 | 77.969 | 0.43 | 2.00 |
| ATOM | 919 | N | LEU | 324 | 27.239 | 43.287 | 77.279 | 1.00 | 7.40 |
| ATOM | 921 | CA | LEU | 324 | 27.659 | 43.959 | 76.056 | 1.00 | 8.58 |
| ATOM | 922 | CB | LEU | 324 | 26.460 | 44.460 | 75.264 | 1.00 | 7.55 |
| ATOM | 923 | CG | LEU | 324 | 26.757 | 45.294 | 74.010 | 1.00 | 8.52 |
| ATOM | 924 | CD1 | LEU | 324 | 27.410 | 44.434 | 72.917 | 1.00 | 8.10 |
| ATOM | 925 | CD2 | LEU | 324 | 25.382 | 45.839 | 73.496 | 1.00 | 7.07 |
| ATOM | 926 | C | LEU | 324 | 28.586 | 45.151 | 76.367 | 1.00 | 8.58 |
| ATOM | 927 | O | LEU | 324 | 29.549 | 45.352 | 75.682 | 1.00 | 9.01 |
| ATOM | 928 | N | VAL | 325 | 28.264 | 45.917 | 77.398 | 1.00 | 9.65 |
| ATOM | 930 | CA | VAL | 325 | 29.091 | 47.041 | 77.763 | 1.00 | 12.45 |
| ATOM | 931 | CB | VAL | 325 | 28.433 | 47.877 | 78.896 | 1.00 | 10.82 |
| ATOM | 932 | CG1 | VAL | 325 | 28.708 | 47.274 | 80.325 | 1.00 | 10.26 |
| ATOM | 933 | CG2 | VAL | 325 | 28.931 | 49.339 | 78.773 | 1.00 | 14.55 |
| ATOM | 934 | C | VAL | 325 | 30.535 | 46.567 | 78.096 | 1.00 | 14.06 |
| ATOM | 935 | O | VAL | 325 | 31.517 | 47.235 | 77.720 | 1.00 | 15.13 |
| ATOM | 936 | N | ASP | 326 | 30.673 | 45.387 | 78.718 | 1.00 | 12.37 |
| ATOM | 938 | CA | ASP | 326 | 32.016 | 44.853 | 79.026 | 1.00 | 11.79 |
| ATOM | 939 | CB | ASP | 326 | 32.000 | 43.837 | 80.173 | 1.00 | 12.18 |
| ATOM | 940 | CG | ASP | 326 | 31.535 | 44.411 | 81.453 | 1.00 | 15.66 |
| ATOM | 941 | OD1 | ASP | 326 | 31.852 | 45.571 | 81.744 | 1.00 | 17.87 |
| ATOM | 942 | OD2 | ASP | 326 | 30.858 | 43.685 | 82.212 | 1.00 | 15.29 |
| ATOM | 943 | C | ASP | 326 | 32.637 | 44.163 | 77.814 | 1.00 | 9.96 |
| ATOM | 944 | O | ASP | 326 | 33.831 | 44.319 | 77.505 | 1.00 | 11.59 |
| ATOM | 945 | N | PHE | 327 | 31.824 | 43.432 | 77.071 | 1.00 | 9.51 |
| ATOM | 947 | CA | PHE | 327 | 32.316 | 42.701 | 75.916 | 1.00 | 9.01 |
| ATOM | 948 | CB | PHE | 327 | 31.214 | 41.835 | 75.309 | 1.00 | 8.68 |
| ATOM | 949 | CG | PHE | 327 | 31.612 | 41.231 | 73.975 | 1.00 | 12.74 |
| ATOM | 950 | CD1 | PHE | 327 | 32.505 | 40.144 | 73.926 | 1.00 | 9.77 |
| ATOM | 951 | CD2 | PHE | 327 | 31.163 | 41.782 | 72.780 | 1.00 | 9.21 |
| ATOM | 952 | CE1 | PHE | 327 | 32.936 | 39.628 | 72.731 | 1.00 | 9.36 |
| ATOM | 953 | CE2 | PHE | 327 | 31.586 | 41.283 | 71.557 | 1.00 | 12.46 |
| ATOM | 954 | CZ | PHE | 327 | 32.500 | 40.177 | 71.527 | 1.00 | 13.61 |
| ATOM | 955 | C | PHE | 327 | 32.926 | 43.614 | 74.805 | 1.00 | 9.16 |
| ATOM | 956 | O | PHE | 327 | 33.917 | 43.268 | 74.158 | 1.00 | 6.44 |
| ATOM | 957 | N | LEU | 328 | 32.333 | 44.793 | 74.602 | 0.40 | 3.00 |
| ATOM | 959 | CA | LEU | 328 | 32.806 | 45.699 | 73.566 | 0.40 | 3.56 |
| ATOM | 960 | CB | LEU | 328 | 31.804 | 46.853 | 73.418 | 0.40 | 2.90 |
| ATOM | 961 | CG | LEU | 328 | 30.746 | 46.915 | 72.301 | 0.40 | 2.00 |
| ATOM | 962 | CD1 | LEU | 328 | 30.559 | 45.669 | 71.533 | 0.40 | 2.00 |
| ATOM | 963 | CD2 | LEU | 328 | 29.472 | 47.450 | 72.887 | 0.40 | 3.15 |
| ATOM | 964 | C | LEU | 328 | 34.220 | 46.262 | 73.819 | 0.40 | 4.10 |
| ATOM | 965 | O | LEU | 328 | 34.886 | 46.785 | 72.935 | 0.40 | 2.00 |
| ATOM | 966 | N | LYS | 329 | 34.640 | 46.172 | 75.069 | 1.00 | 8.38 |
| ATOM | 968 | CA | LYS | 329 | 35.947 | 46.662 | 75.537 | 1.00 | 12.01 |
| ATOM | 969 | CB | LYS | 329 | 35.810 | 47.192 | 76.963 | 1.00 | 11.97 |
| ATOM | 970 | CG | LYS | 329 | 34.926 | 48.431 | 77.072 | 1.00 | 11.78 |
| ATOM | 971 | CD | LYS | 329 | 34.774 | 48.868 | 78.519 | 1.00 | 9.98 |
| ATOM | 972 | CE | LYS | 329 | 33.652 | 49.917 | 78.635 | 1.00 | 13.45 |
| ATOM | 973 | NZ | LYS | 329 | 33.460 | 50.307 | 80.062 | 1.00 | 15.31 |
| ATOM | 977 | C | LYS | 329 | 37.049 | 45.608 | 75.486 | 1.00 | 14.87 |
| ATOM | 978 | O | LYS | 329 | 38.235 | 45.940 | 75.621 | 1.00 | 16.51 |
| ATOM | 979 | N | THR | 330 | 36.670 | 44.349 | 75.254 | 1.00 | 13.19 |
| ATOM | 981 | CA | THR | 330 | 37.649 | 43.250 | 75.198 | 1.00 | 11.60 |
| ATOM | 982 | CB | THR | 330 | 36.942 | 41.856 | 75.342 | 1.00 | 7.69 |
| ATOM | 983 | OG1 | THR | 330 | 36.045 | 41.654 | 74.260 | 1.00 | 5.64 |
| ATOM | 985 | CG2 | THR | 330 | 36.173 | 41.737 | 76.601 | 1.00 | 8.84 |
| ATOM | 986 | C | THR | 330 | 38.311 | 43.273 | 73.803 | 1.00 | 12.19 |
| ATOM | 987 | O | THR | 330 | 37.808 | 43.897 | 72.863 | 1.00 | 15.01 |
| ATOM | 988 | N | PRO | 331 | 39.429 | 42.542 | 73.628 | 1.00 | 13.69 |
| ATOM | 989 | CD | PRO | 331 | 40.235 | 41.842 | 74.656 | 1.00 | 13.18 |

TABLE 1-continued

Coordinates of Lck bound with PP2

| | | Atom Type | Res | # | X | Y | Z | Occ | B |
|---|---|---|---|---|---|---|---|---|---|
| ATOM | 990 | CA | PRO | 331 | 40.097 | 42.512 | 72.323 | 1.00 | 13.57 |
| ATOM | 991 | CB | PRO | 331 | 41.247 | 41.522 | 72.562 | 1.00 | 12.36 |
| ATOM | 992 | CG | PRO | 331 | 41.598 | 41.771 | 73.979 | 1.00 | 12.02 |
| ATOM | 993 | C | PRO | 331 | 39.143 | 42.046 | 71.197 | 1.00 | 14.37 |
| ATOM | 994 | O | PRO | 331 | 39.223 | 42.517 | 70.063 | 1.00 | 15.73 |
| ATOM | 995 | N | SER | 332 | 38.238 | 41.108 | 71.488 | 1.00 | 13.66 |
| ATOM | 997 | CA | SER | 332 | 37.310 | 40.655 | 70.431 | 1.00 | 15.74 |
| ATOM | 998 | CB | SER | 332 | 36.532 | 39.391 | 70.863 | 1.00 | 14.92 |
| ATOM | 999 | OG | SER | 332 | 37.433 | 38.325 | 71.143 | 1.00 | 20.31 |
| ATOM | 1001 | C | SER | 332 | 36.311 | 41.746 | 70.053 | 1.00 | 14.88 |
| ATOM | 1002 | O | SER | 332 | 36.038 | 41.960 | 68.881 | 1.00 | 17.21 |
| ATOM | 1003 | N | GLY | 333 | 35.726 | 42.389 | 71.059 | 1.00 | 14.09 |
| ATOM | 1005 | CA | GLY | 333 | 34.763 | 43.457 | 70.818 | 1.00 | 15.72 |
| ATOM | 1006 | C | GLY | 333 | 35.393 | 44.613 | 70.033 | 1.00 | 15.81 |
| ATOM | 1007 | O | GLY | 333 | 34.794 | 45.122 | 69.089 | 1.00 | 15.33 |
| ATOM | 1008 | N | ILE | 334 | 36.608 | 45.004 | 70.414 | 1.00 | 16.19 |
| ATOM | 1010 | CA | ILE | 334 | 37.340 | 46.096 | 69.746 | 1.00 | 16.93 |
| ATOM | 1011 | CB | ILE | 334 | 38.718 | 46.326 | 70.430 | 1.00 | 18.36 |
| ATOM | 1012 | CG2 | ILE | 334 | 39.584 | 47.319 | 69.606 | 1.00 | 19.31 |
| ATOM | 1013 | CG1 | ILE | 334 | 38.476 | 46.832 | 71.855 | 1.00 | 18.58 |
| ATOM | 1014 | CD1 | ILE | 334 | 39.750 | 46.931 | 72.714 | 1.00 | 21.36 |
| ATOM | 1015 | C | ILE | 334 | 37.528 | 45.878 | 68.259 | 1.00 | 17.57 |
| ATOM | 1016 | O | ILE | 334 | 37.469 | 46.798 | 67.474 | 1.00 | 18.66 |
| ATOM | 1017 | N | LYS | 335 | 37.752 | 44.640 | 67.850 | 1.00 | 19.23 |
| ATOM | 1019 | CA | LYS | 335 | 37.936 | 44.350 | 66.446 | 1.00 | 19.72 |
| ATOM | 1020 | CB | LYS | 335 | 38.745 | 43.076 | 66.305 | 1.00 | 23.00 |
| ATOM | 1021 | CG | LYS | 335 | 40.107 | 43.204 | 66.963 | 1.00 | 27.33 |
| ATOM | 1022 | CD | LYS | 335 | 40.692 | 41.872 | 67.270 | 1.00 | 30.63 |
| ATOM | 1023 | CE | LYS | 335 | 41.873 | 42.040 | 68.182 | 1.00 | 31.48 |
| ATOM | 1024 | NZ | LYS | 335 | 42.292 | 40.723 | 68.592 | 1.00 | 31.57 |
| ATOM | 1028 | C | LYS | 335 | 36.628 | 44.242 | 65.628 | 1.00 | 18.64 |
| ATOM | 1029 | O | LYS | 335 | 36.655 | 44.080 | 64.417 | 1.00 | 16.73 |
| ATOM | 1030 | N | LEU | 336 | 35.480 | 44.410 | 66.269 | 1.00 | 16.82 |
| ATOM | 1032 | CA | LEU | 336 | 34.210 | 44.297 | 65.520 | 1.00 | 15.13 |
| ATOM | 1033 | CB | LEU | 336 | 33.015 | 44.291 | 66.470 | 1.00 | 15.27 |
| ATOM | 1034 | CG | LEU | 336 | 32.912 | 43.123 | 67.484 | 1.00 | 18.77 |
| ATOM | 1035 | CD1 | LEU | 336 | 31.580 | 43.183 | 68.225 | 1.00 | 17.54 |
| ATOM | 1036 | CD2 | LEU | 336 | 33.070 | 41.761 | 66.812 | 1.00 | 13.51 |
| ATOM | 1037 | C | LEU | 336 | 34.045 | 45.428 | 64.522 | 1.00 | 16.15 |
| ATOM | 1038 | O | LEU | 336 | 34.293 | 46.566 | 64.858 | 1.00 | 17.28 |
| ATOM | 1039 | N | THR | 337 | 33.595 | 45.103 | 63.301 | 1.00 | 17.02 |
| ATOM | 1041 | CA | THR | 337 | 33.375 | 46.095 | 62.260 | 1.00 | 17.40 |
| ATOM | 1042 | CB | THR | 337 | 33.280 | 45.449 | 60.901 | 1.00 | 17.62 |
| ATOM | 1043 | OG1 | THR | 337 | 32.197 | 44.481 | 60.893 | 1.00 | 19.04 |
| ATOM | 1045 | CG2 | THR | 337 | 34.638 | 44.736 | 60.559 | 1.00 | 21.95 |
| ATOM | 1046 | C | THR | 337 | 32.056 | 46.827 | 62.515 | 1.00 | 16.83 |
| ATOM | 1047 | O | THR | 337 | 31.185 | 46.334 | 63.289 | 1.00 | 15.94 |
| ATOM | 1048 | N | ILE | 338 | 31.873 | 47.975 | 61.859 | 1.00 | 14.47 |
| ATOM | 1050 | CA | ILE | 338 | 30.628 | 48.715 | 62.042 | 1.00 | 13.03 |
| ATOM | 1051 | CB | ILE | 338 | 30.579 | 50.047 | 61.246 | 1.00 | 12.67 |
| ATOM | 1052 | CG2 | ILE | 338 | 30.812 | 49.779 | 59.745 | 1.00 | 13.10 |
| ATOM | 1053 | CG1 | ILE | 338 | 29.248 | 50.761 | 61.561 | 1.00 | 11.18 |
| ATOM | 1054 | CD1 | ILE | 338 | 29.074 | 51.054 | 63.101 | 1.00 | 9.52 |
| ATOM | 1055 | C | ILE | 338 | 29.456 | 47.820 | 61.624 | 1.00 | 11.79 |
| ATOM | 1056 | O | ILE | 338 | 28.400 | 47.872 | 62.208 | 1.00 | 11.62 |
| ATOM | 1057 | N | ASN | 339 | 29.703 | 46.940 | 60.647 | 1.00 | 11.95 |
| ATOM | 1059 | CA | ASN | 339 | 28.697 | 46.004 | 60.140 | 1.00 | 14.07 |
| ATOM | 1060 | CB | ASN | 339 | 29.293 | 45.192 | 58.963 | 1.00 | 17.39 |
| ATOM | 1061 | CG | ASN | 339 | 28.391 | 44.043 | 58.510 | 1.00 | 24.54 |
| ATOM | 1062 | OD1 | ASN | 339 | 28.660 | 42.860 | 58.826 | 1.00 | 26.23 |
| ATOM | 1063 | ND2 | ASN | 339 | 27.328 | 44.365 | 57.761 | 1.00 | 23.79 |
| ATOM | 1066 | C | ASN | 339 | 28.155 | 45.087 | 61.240 | 1.00 | 12.19 |
| ATOM | 1067 | O | ASN | 339 | 26.929 | 44.936 | 61.424 | 1.00 | 9.91 |
| ATOM | 1068 | N | LYS | 340 | 29.065 | 44.515 | 62.028 | 1.00 | 10.14 |
| ATOM | 1070 | CA | LYS | 340 | 28.660 | 43.623 | 63.090 | 1.00 | 8.13 |
| ATOM | 1071 | CB | LYS | 340 | 29.841 | 42.738 | 63.522 | 1.00 | 8.27 |
| ATOM | 1072 | CG | LYS | 340 | 29.559 | 41.849 | 64.749 | 1.00 | 5.54 |
| ATOM | 1073 | CD | LYS | 340 | 28.492 | 40.798 | 64.448 | 1.00 | 7.28 |
| ATOM | 1074 | CE | LYS | 340 | 28.114 | 39.995 | 65.721 | 1.00 | 7.51 |
| ATOM | 1075 | NZ | LYS | 340 | 27.019 | 39.000 | 65.349 | 1.00 | 10.96 |
| ATOM | 1079 | C | LYS | 340 | 28.030 | 44.410 | 64.260 | 1.00 | 7.62 |
| ATOM | 1080 | O | LYS | 340 | 27.116 | 43.947 | 64.943 | 1.00 | 7.08 |
| ATOM | 1081 | N | LEU | 341 | 28.461 | 45.644 | 64.477 | 1.00 | 6.47 |
| ATOM | 1083 | CA | LEU | 341 | 27.845 | 46.435 | 65.569 | 1.00 | 5.96 |

TABLE 1-continued

Coordinates of Lck bound with PP2

| | Atom Type | Res | # | X | Y | Z | Occ | B |
|---|---|---|---|---|---|---|---|---|
| ATOM | 1084 | CB | LEU | 341 | 28.621 | 47.727 | 65.862 | 1.00 | 4.03 |
| ATOM | 1085 | CG | LEU | 341 | 30.109 | 47.507 | 66.294 | 1.00 | 7.36 |
| ATOM | 1086 | CD1 | LEU | 341 | 30.826 | 48.855 | 66.323 | 1.00 | 6.06 |
| ATOM | 1087 | CD2 | LEU | 341 | 30.217 | 46.836 | 67.674 | 1.00 | 7.12 |
| ATOM | 1088 | C | LEU | 341 | 26.400 | 46.770 | 65.202 | 1.00 | 3.96 |
| ATOM | 1089 | O | LEU | 341 | 25.529 | 46.844 | 66.082 | 1.00 | 6.11 |
| ATOM | 1090 | N | LEU | 342 | 26.156 | 47.004 | 63.920 | 1.00 | 6.18 |
| ATOM | 1092 | CA | LEU | 342 | 24.815 | 47.310 | 63.419 | 1.00 | 7.59 |
| ATOM | 1093 | CB | LEU | 342 | 24.885 | 47.755 | 61.956 | 1.00 | 8.88 |
| ATOM | 1094 | CG | LEU | 342 | 25.484 | 49.180 | 61.797 | 1.00 | 11.62 |
| ATOM | 1095 | CD1 | LEU | 342 | 25.823 | 49.430 | 60.312 | 1.00 | 10.17 |
| ATOM | 1096 | CD2 | LEU | 342 | 24.493 | 50.268 | 62.373 | 1.00 | 7.90 |
| ATOM | 1097 | C | LEU | 342 | 23.909 | 46.080 | 63.537 | 1.00 | 7.74 |
| ATOM | 1098 | O | LEU | 342 | 22.686 | 46.172 | 63.764 | 1.00 | 8.65 |
| ATOM | 1099 | N | ASP | 343 | 24.505 | 44.936 | 63.238 | 1.00 | 9.65 |
| ATOM | 1101 | CA | ASP | 343 | 23.823 | 43.621 | 63.312 | 1.00 | 8.35 |
| ATOM | 1102 | CB | ASP | 343 | 24.860 | 42.510 | 62.947 | 1.00 | 7.51 |
| ATOM | 1103 | CG | ASP | 343 | 24.387 | 41.116 | 63.308 | 1.00 | 10.12 |
| ATOM | 1104 | OD1 | ASP | 343 | 23.166 | 40.929 | 63.483 | 1.00 | 8.76 |
| ATOM | 1105 | OD2 | ASP | 343 | 25.234 | 40.206 | 63.368 | 1.00 | 10.74 |
| ATOM | 1106 | C | ASP | 343 | 23.333 | 43.500 | 64.763 | 1.00 | 7.81 |
| ATOM | 1107 | O | ASP | 343 | 22.134 | 43.420 | 65.022 | 1.00 | 8.47 |
| ATOM | 1108 | N | MET | 344 | 24.259 | 43.572 | 65.710 | 1.00 | 8.09 |
| ATOM | 1110 | CA | MET | 344 | 23.919 | 43.525 | 67.133 | 1.00 | 10.16 |
| ATOM | 1111 | CB | MET | 344 | 25.168 | 43.775 | 67.997 | 1.00 | 10.84 |
| ATOM | 1112 | CG | MET | 344 | 26.224 | 42.685 | 67.796 | 1.00 | 15.39 |
| ATOM | 1113 | SD | MET | 344 | 27.746 | 43.042 | 68.667 | 1.00 | 20.54 |
| ATOM | 1114 | CE | MET | 344 | 27.504 | 42.221 | 70.052 | 1.00 | 13.40 |
| ATOM | 1115 | C | MET | 344 | 22.844 | 44.544 | 67.503 | 1.00 | 8.86 |
| ATOM | 1116 | O | MET | 344 | 21.957 | 44.225 | 68.265 | 1.00 | 7.44 |
| ATOM | 1117 | N | ALA | 345 | 23.006 | 45.808 | 67.087 | 1.00 | 7.26 |
| ATOM | 1119 | CA | ALA | 345 | 21.959 | 46.828 | 67.380 | 1.00 | 5.67 |
| ATOM | 1120 | CB | ALA | 345 | 22.290 | 48.136 | 66.681 | 1.00 | 4.54 |
| ATOM | 1121 | C | ALA | 345 | 20.590 | 46.309 | 66.889 | 1.00 | 5.23 |
| ATOM | 1122 | O | ALA | 345 | 19.589 | 46.445 | 67.587 | 1.00 | 3.90 |
| ATOM | 1123 | N | ALA | 346 | 20.545 | 45.783 | 65.662 | 1.00 | 5.10 |
| ATOM | 1125 | CA | ALA | 346 | 19.305 | 45.238 | 65.119 | 1.00 | 7.13 |
| ATOM | 1126 | CB | ALA | 346 | 19.459 | 44.810 | 63.656 | 1.00 | 8.22 |
| ATOM | 1127 | C | ALA | 346 | 18.766 | 44.079 | 65.974 | 1.00 | 7.97 |
| ATOM | 1128 | O | ALA | 346 | 17.529 | 43.993 | 66.187 | 1.00 | 8.44 |
| ATOM | 1129 | N | GLN | 347 | 19.643 | 43.170 | 66.451 | 1.00 | 8.27 |
| ATOM | 1131 | CA | GLN | 347 | 19.202 | 42.062 | 67.330 | 1.00 | 8.51 |
| ATOM | 1132 | CB | GLN | 347 | 20.367 | 41.169 | 67.763 | 1.00 | 5.95 |
| ATOM | 1133 | CG | GLN | 347 | 21.081 | 40.521 | 66.547 | 1.00 | 6.80 |
| ATOM | 1134 | CD | GLN | 347 | 22.118 | 39.500 | 66.933 | 1.00 | 5.32 |
| ATOM | 1135 | OE1 | GLN | 347 | 22.064 | 38.966 | 68.019 | 1.00 | 7.59 |
| ATOM | 1136 | NE2 | GLN | 347 | 23.057 | 39.196 | 66.016 | 1.00 | 8.42 |
| ATOM | 1139 | C | GLN | 347 | 18.522 | 42.623 | 68.566 | 1.00 | 8.39 |
| ATOM | 1140 | O | GLN | 347 | 17.477 | 42.131 | 69.008 | 1.00 | 9.27 |
| ATOM | 1141 | N | ILE | 348 | 19.099 | 43.676 | 69.133 | 1.00 | 5.65 |
| ATOM | 1143 | CA | ILE | 348 | 18.502 | 44.278 | 70.327 | 1.00 | 7.21 |
| ATOM | 1144 | CB | ILE | 348 | 19.440 | 45.351 | 70.966 | 1.00 | 5.99 |
| ATOM | 1145 | CG2 | ILE | 348 | 18.820 | 45.942 | 72.262 | 1.00 | 6.69 |
| ATOM | 1146 | CG1 | ILE | 348 | 20.761 | 44.628 | 71.411 | 1.00 | 9.42 |
| ATOM | 1147 | CD1 | ILE | 348 | 21.921 | 45.569 | 71.586 | 1.00 | 11.33 |
| ATOM | 1148 | C | ILE | 348 | 17.131 | 44.880 | 70.028 | 1.00 | 5.07 |
| ATOM | 1149 | O | ILE | 348 | 16.247 | 44.767 | 70.856 | 1.00 | 4.61 |
| ATOM | 1150 | N | ALA | 349 | 16.994 | 45.538 | 68.865 | 1.00 | 7.16 |
| ATOM | 1152 | CA | ALA | 349 | 15.724 | 46.206 | 68.493 | 1.00 | 9.08 |
| ATOM | 1153 | CB | ALA | 349 | 15.871 | 47.041 | 67.216 | 1.00 | 6.01 |
| ATOM | 1154 | C | ALA | 349 | 14.687 | 45.087 | 68.274 | 1.00 | 9.02 |
| ATOM | 1155 | O | ALA | 349 | 13.523 | 45.231 | 68.595 | 1.00 | 4.41 |
| ATOM | 1156 | N | GLU | 350 | 15.179 | 43.954 | 67.774 | 1.00 | 7.05 |
| ATOM | 1158 | CA | GLU | 350 | 14.339 | 42.778 | 67.527 | 1.00 | 8.60 |
| ATOM | 1159 | CB | GLU | 350 | 15.143 | 41.692 | 66.794 | 1.00 | 9.61 |
| ATOM | 1160 | CG | GLU | 350 | 14.353 | 40.388 | 66.563 | 1.00 | 12.76 |
| ATOM | 1161 | CD | GLU | 350 | 15.117 | 39.374 | 65.703 | 1.00 | 14.23 |
| ATOM | 1162 | OE1 | GLU | 350 | 16.121 | 39.721 | 65.028 | 1.00 | 11.84 |
| ATOM | 1163 | OE2 | GLU | 350 | 14.649 | 38.234 | 65.655 | 1.00 | 15.86 |
| ATOM | 1164 | C | GLU | 350 | 13.773 | 42.270 | 68.839 | 1.00 | 7.48 |
| ATOM | 1165 | O | GLU | 350 | 12.564 | 42.004 | 68.956 | 1.00 | 8.86 |
| ATOM | 1166 | N | GLY | 351 | 14.616 | 42.185 | 69.853 | 1.00 | 5.37 |
| ATOM | 1168 | CA | GLY | 351 | 14.183 | 41.757 | 71.173 | 1.00 | 5.89 |
| ATOM | 1169 | C | GLY | 351 | 13.196 | 42.777 | 71.765 | 1.00 | 7.42 |

TABLE 1-continued

Coordinates of Lck bound with PP2

| | | Atom Type | Res | # | X | Y | Z | Occ | B |
|---|---|---|---|---|---|---|---|---|---|
| ATOM | 1170 | O | GLY | 351 | 12.149 | 42.414 | 72.368 | 1.00 | 6.11 |
| ATOM | 1171 | N | MET | 352 | 13.522 | 44.055 | 71.628 | 1.00 | 4.75 |
| ATOM | 1173 | CA | MET | 352 | 12.617 | 45.113 | 72.122 | 1.00 | 6.41 |
| ATOM | 1174 | CB | MET | 352 | 13.287 | 46.490 | 72.111 | 1.00 | 5.29 |
| ATOM | 1175 | CG | MET | 352 | 14.426 | 46.629 | 73.178 | 1.00 | 6.68 |
| ATOM | 1176 | SD | MET | 352 | 13.960 | 46.322 | 74.854 | 1.00 | 9.97 |
| ATOM | 1177 | CE | MET | 352 | 12.604 | 47.517 | 75.127 | 1.00 | 9.15 |
| ATOM | 1178 | C | MET | 352 | 11.290 | 45.173 | 71.332 | 1.00 | 7.01 |
| ATOM | 1179 | O | MET | 352 | 10.292 | 45.583 | 71.906 | 1.00 | 8.77 |
| ATOM | 1180 | N | ALA | 353 | 11.263 | 44.738 | 70.064 | 1.00 | 8.07 |
| ATOM | 1182 | CA | ALA | 353 | 10.020 | 44.738 | 69.279 | 1.00 | 5.88 |
| ATOM | 1183 | CB | ALA | 353 | 10.291 | 44.491 | 67.828 | 1.00 | 7.39 |
| ATOM | 1184 | C | ALA | 353 | 9.090 | 43.646 | 69.840 | 1.00 | 9.76 |
| ATOM | 1185 | O | ALA | 353 | 7.869 | 43.788 | 69.823 | 1.00 | 7.82 |
| ATOM | 1186 | N | PHE | 354 | 9.669 | 42.551 | 70.362 | 1.00 | 9.39 |
| ATOM | 1188 | CA | PHE | 354 | 8.853 | 41.481 | 70.978 | 1.00 | 9.75 |
| ATOM | 1189 | CB | PHE | 354 | 9.693 | 40.227 | 71.299 | 1.00 | 8.22 |
| ATOM | 1190 | CG | PHE | 354 | 8.974 | 39.223 | 72.218 | 1.00 | 9.88 |
| ATOM | 1191 | CD1 | PHE | 354 | 7.912 | 38.441 | 71.738 | 1.00 | 12.19 |
| ATOM | 1192 | CD2 | PHE | 354 | 9.311 | 39.119 | 73.547 | 1.00 | 10.85 |
| ATOM | 1193 | CE1 | PHE | 354 | 7.202 | 37.566 | 72.617 | 1.00 | 9.37 |
| ATOM | 1194 | CE2 | PHE | 354 | 8.605 | 38.254 | 74.435 | 1.00 | 12.35 |
| ATOM | 1195 | CZ | PHE | 354 | 7.558 | 37.488 | 73.953 | 1.00 | 10.17 |
| ATOM | 1196 | C | PHE | 354 | 8.261 | 42.030 | 72.284 | 1.00 | 6.25 |
| ATOM | 1197 | O | PHE | 354 | 7.094 | 41.874 | 72.566 | 1.00 | 7.01 |
| ATOM | 1198 | N | ILE | 355 | 9.092 | 42.739 | 73.058 | 1.00 | 6.36 |
| ATOM | 1200 | CA | ILE | 355 | 8.659 | 43.342 | 74.331 | 1.00 | 8.20 |
| ATOM | 1201 | CB | ILE | 355 | 9.866 | 43.958 | 75.089 | 1.00 | 6.84 |
| ATOM | 1202 | CG2 | ILE | 355 | 9.418 | 44.825 | 76.269 | 1.00 | 8.30 |
| ATOM | 1203 | CG1 | ILE | 355 | 10.754 | 42.822 | 75.583 | 1.00 | 7.74 |
| ATOM | 1204 | CD1 | ILE | 355 | 11.983 | 43.271 | 76.310 | 1.00 | 5.93 |
| ATOM | 1205 | C | ILE | 355 | 7.512 | 44.343 | 74.094 | 1.00 | 6.49 |
| ATOM | 1206 | O | ILE | 355 | 6.490 | 44.314 | 74.750 | 1.00 | 6.90 |
| ATOM | 1207 | N | GLU | 356 | 7.710 | 45.180 | 73.091 | 1.00 | 8.41 |
| ATOM | 1209 | CA | GLU | 356 | 6.764 | 46.190 | 72.643 | 1.00 | 8.52 |
| ATOM | 1210 | CB | GLU | 356 | 7.404 | 46.906 | 71.442 | 1.00 | 10.94 |
| ATOM | 1211 | CG | GLU | 356 | 6.454 | 47.665 | 70.479 | 1.00 | 13.83 |
| ATOM | 1212 | CD | GLU | 356 | 7.254 | 48.392 | 69.370 | 1.00 | 13.44 |
| ATOM | 1213 | OE1 | GLU | 356 | 7.847 | 49.387 | 69.756 | 1.00 | 14.28 |
| ATOM | 1214 | OE2 | GLU | 356 | 7.325 | 47.968 | 68.147 | 1.00 | 15.54 |
| ATOM | 1215 | C | GLU | 356 | 5.430 | 45.503 | 72.239 | 1.00 | 9.09 |
| ATOM | 1216 | O | GLU | 356 | 4.346 | 45.884 | 72.696 | 1.00 | 7.12 |
| ATOM | 1217 | N | GLU | 357 | 5.519 | 44.442 | 71.446 | 0.36 | 2.80 |
| ATOM | 1219 | CA | GLU | 357 | 4.326 | 43.725 | 71.021 | 0.36 | 3.40 |
| ATOM | 1220 | CB | GLU | 357 | 4.695 | 42.730 | 69.894 | 0.36 | 2.45 |
| ATOM | 1221 | CG | GLU | 357 | 3.553 | 41.917 | 69.325 | 0.36 | 4.19 |
| ATOM | 1222 | CD | GLU | 357 | 3.246 | 40.699 | 70.168 | 0.36 | 6.13 |
| ATOM | 1223 | OE1 | GLU | 357 | 4.126 | 40.269 | 70.946 | 0.36 | 6.48 |
| ATOM | 1224 | OE2 | GLU | 357 | 2.125 | 40.154 | 70.084 | 0.36 | 10.01 |
| ATOM | 1225 | C | GLU | 357 | 3.533 | 43.067 | 72.169 | 0.36 | 4.04 |
| ATOM | 1226 | O | GLU | 357 | 2.308 | 43.006 | 72.126 | 0.36 | 2.00 |
| ATOM | 1227 | N | ARG | 358 | 4.227 | 42.632 | 73.225 | 1.00 | 7.81 |
| ATOM | 1229 | CA | ARG | 358 | 3.576 | 41.991 | 74.384 | 1.00 | 9.23 |
| ATOM | 1230 | CB | ARG | 358 | 4.553 | 41.053 | 75.146 | 1.00 | 10.13 |
| ATOM | 1231 | CG | ARG | 358 | 5.072 | 39.858 | 74.336 | 1.00 | 12.15 |
| ATOM | 1232 | CD | ARG | 358 | 3.926 | 39.058 | 73.620 | 1.00 | 17.62 |
| ATOM | 1233 | NE | ARG | 358 | 2.936 | 38.578 | 74.565 | 1.00 | 20.90 |
| ATOM | 1235 | CZ | ARG | 358 | 1.667 | 38.272 | 74.262 | 1.00 | 23.73 |
| ATOM | 1236 | NH1 | ARG | 358 | 1.205 | 38.382 | 73.027 | 1.00 | 22.10 |
| ATOM | 1239 | NH2 | ARG | 358 | 0.849 | 37.875 | 75.216 | 1.00 | 23.38 |
| ATOM | 1242 | C | ARG | 358 | 2.981 | 42.972 | 75.372 | 1.00 | 8.80 |
| ATOM | 1243 | O | ARG | 358 | 2.491 | 42.582 | 76.428 | 1.00 | 8.51 |
| ATOM | 1244 | N | ASN | 359 | 3.069 | 44.265 | 75.044 | 1.00 | 11.15 |
| ATOM | 1246 | CA | ASN | 359 | 2.553 | 45.318 | 75.904 | 1.00 | 11.08 |
| ATOM | 1247 | CB | ASN | 359 | 1.087 | 45.040 | 76.266 | 1.00 | 12.23 |
| ATOM | 1248 | CG | ASN | 359 | 0.166 | 45.474 | 75.167 | 1.00 | 13.91 |
| ATOM | 1249 | OD1 | ASN | 359 | 0.623 | 45.997 | 74.195 | 1.00 | 15.68 |
| ATOM | 1250 | ND2 | ASN | 359 | −1.155 | 45.286 | 75.340 | 1.00 | 15.64 |
| ATOM | 1253 | C | ASN | 359 | 3.386 | 45.571 | 77.130 | 1.00 | 11.57 |
| ATOM | 1254 | O | ASN | 359 | 2.889 | 46.060 | 78.149 | 1.00 | 9.73 |
| ATOM | 1255 | N | TYR | 360 | 4.671 | 45.185 | 77.063 | 1.00 | 9.79 |
| ATOM | 1257 | CA | TYR | 360 | 5.546 | 45.422 | 78.204 | 1.00 | 9.21 |
| ATOM | 1258 | CB | TYR | 360 | 6.419 | 44.185 | 78.492 | 1.00 | 10.72 |
| ATOM | 1259 | CG | TYR | 360 | 5.739 | 43.135 | 79.337 | 1.00 | 12.72 |

TABLE 1-continued

Coordinates of Lck bound with PP2

| | | Atom Type | Res | # | X | Y | Z | Occ | B |
|---|---|---|---|---|---|---|---|---|---|
| ATOM | 1260 | CD1 | TYR | 360 | 6.013 | 43.026 | 80.680 | 1.00 | 14.34 |
| ATOM | 1261 | CE1 | TYR | 360 | 5.384 | 42.030 | 81.474 | 1.00 | 16.48 |
| ATOM | 1262 | CD2 | TYR | 360 | 4.827 | 42.262 | 78.776 | 1.00 | 14.33 |
| ATOM | 1263 | CE2 | TYR | 360 | 4.201 | 41.275 | 79.548 | 1.00 | 16.68 |
| ATOM | 1264 | CZ | TYR | 360 | 4.485 | 41.174 | 80.888 | 1.00 | 15.37 |
| ATOM | 1265 | OH | TYR | 360 | 3.883 | 40.198 | 81.637 | 1.00 | 18.48 |
| ATOM | 1267 | C | TYR | 360 | 6.497 | 46.577 | 77.919 | 1.00 | 7.60 |
| ATOM | 1268 | O | TYR | 360 | 6.607 | 47.058 | 76.807 | 1.00 | 7.26 |
| ATOM | 1269 | N | ILE | 361 | 7.168 | 47.026 | 78.969 | 1.00 | 9.03 |
| ATOM | 1271 | CA | ILE | 361 | 8.203 | 48.037 | 78.812 | 1.00 | 9.74 |
| ATOM | 1272 | CB | ILE | 361 | 7.832 | 49.459 | 79.382 | 1.00 | 9.50 |
| ATOM | 1273 | CG2 | ILE | 361 | 6.744 | 50.166 | 78.488 | 1.00 | 11.71 |
| ATOM | 1274 | CG1 | ILE | 361 | 7.386 | 49.365 | 80.828 | 1.00 | 12.15 |
| ATOM | 1275 | CD1 | ILE | 361 | 6.910 | 50.681 | 81.374 | 1.00 | 15.27 |
| ATOM | 1276 | C | ILE | 361 | 9.331 | 47.424 | 79.625 | 1.00 | 8.68 |
| ATOM | 1277 | O | ILE | 361 | 9.099 | 46.637 | 80.511 | 1.00 | 10.97 |
| ATOM | 1278 | N | HIS | 362 | 10.543 | 47.913 | 79.424 | 1.00 | 8.96 |
| ATOM | 1280 | CA | HIS | 362 | 11.694 | 47.388 | 80.151 | 1.00 | 7.95 |
| ATOM | 1281 | CB | HIS | 362 | 12.803 | 47.084 | 79.099 | 1.00 | 8.38 |
| ATOM | 1282 | CG | HIS | 362 | 14.005 | 46.405 | 79.671 | 1.00 | 9.73 |
| ATOM | 1283 | CD2 | HIS | 362 | 14.377 | 45.108 | 79.655 | 1.00 | 7.39 |
| ATOM | 1284 | ND1 | HIS | 362 | 14.963 | 47.070 | 80.419 | 1.00 | 6.36 |
| ATOM | 1286 | CE1 | HIS | 362 | 15.874 | 46.209 | 80.825 | 1.00 | 9.86 |
| ATOM | 1287 | NE2 | HIS | 362 | 15.536 | 45.003 | 80.378 | 1.00 | 10.13 |
| ATOM | 1289 | C | HIS | 362 | 12.156 | 48.394 | 81.208 | 1.00 | 7.43 |
| ATOM | 1290 | O | HIS | 362 | 12.404 | 48.038 | 82.372 | 1.00 | 7.91 |
| ATOM | 1291 | N | ARG | 363 | 12.324 | 49.657 | 80.794 | 1.00 | 8.44 |
| ATOM | 1293 | CA | ARG | 363 | 12.763 | 50.776 | 81.671 | 1.00 | 8.08 |
| ATOM | 1294 | CB | ARG | 363 | 11.876 | 50.937 | 82.919 | 1.00 | 9.73 |
| ATOM | 1295 | CG | ARG | 363 | 10.387 | 51.082 | 82.599 | 1.00 | 13.47 |
| ATOM | 1296 | CD | ARG | 363 | 9.586 | 51.484 | 83.839 | 1.00 | 13.85 |
| ATOM | 1297 | NE | ARG | 363 | 9.685 | 50.538 | 84.930 | 1.00 | 13.20 |
| ATOM | 1299 | CZ | ARG | 363 | 9.722 | 50.888 | 86.212 | 1.00 | 15.35 |
| ATOM | 1300 | NH1 | ARG | 363 | 9.674 | 52.171 | 86.564 | 1.00 | 14.95 |
| ATOM | 1303 | NH2 | ARG | 363 | 9.738 | 49.956 | 87.151 | 1.00 | 14.46 |
| ATOM | 1306 | C | ARG | 363 | 14.223 | 50.794 | 82.112 | 1.00 | 9.76 |
| ATOM | 1307 | O | ARG | 363 | 14.650 | 51.732 | 82.791 | 1.00 | 9.55 |
| ATOM | 1308 | N | ASP | 364 | 15.026 | 49.830 | 81.665 | 1.00 | 9.49 |
| ATOM | 1310 | CA | ASP | 364 | 16.451 | 49.811 | 82.066 | 1.00 | 10.04 |
| ATOM | 1311 | CB | ASP | 364 | 16.639 | 48.836 | 83.240 | 1.00 | 9.98 |
| ATOM | 1312 | CG | ASP | 364 | 17.888 | 49.148 | 84.107 | 1.00 | 14.26 |
| ATOM | 1313 | OD1 | ASP | 364 | 18.594 | 50.156 | 83.889 | 1.00 | 14.89 |
| ATOM | 1314 | OD2 | ASP | 364 | 18.129 | 48.394 | 85.062 | 1.00 | 13.47 |
| ATOM | 1315 | C | ASP | 364 | 17.262 | 49.368 | 80.858 | 1.00 | 9.74 |
| ATOM | 1316 | O | ASP | 364 | 18.196 | 48.554 | 80.943 | 1.00 | 8.70 |
| ATOM | 1317 | N | LEU | 365 | 16.825 | 49.827 | 79.689 | 1.00 | 7.97 |
| ATOM | 1319 | CA | LEU | 365 | 17.483 | 49.485 | 78.455 | 1.00 | 8.00 |
| ATOM | 1320 | CB | LEU | 365 | 16.568 | 49.811 | 77.255 | 1.00 | 7.28 |
| ATOM | 1321 | CG | LEU | 365 | 17.078 | 49.446 | 75.865 | 1.00 | 8.56 |
| ATOM | 1322 | CD1 | LEU | 365 | 17.582 | 47.986 | 75.822 | 1.00 | 11.42 |
| ATOM | 1323 | CD2 | LEU | 365 | 15.960 | 49.617 | 74.849 | 1.00 | 11.34 |
| ATOM | 1324 | C | LEU | 365 | 18.818 | 50.270 | 78.340 | 1.00 | 10.93 |
| ATOM | 1325 | O | LEU | 365 | 18.840 | 51.495 | 78.137 | 1.00 | 13.74 |
| ATOM | 1326 | N | ARG | 366 | 19.924 | 49.544 | 78.418 | 1.00 | 8.54 |
| ATOM | 1328 | CA | ARG | 366 | 21.264 | 50.124 | 78.320 | 1.00 | 10.81 |
| ATOM | 1329 | CB | ARG | 366 | 21.658 | 50.813 | 79.638 | 1.00 | 10.58 |
| ATOM | 1330 | CG | ARG | 366 | 21.516 | 49.930 | 80.844 | 1.00 | 13.47 |
| ATOM | 1331 | CD | ARG | 366 | 21.725 | 50.740 | 82.138 | 1.00 | 18.51 |
| ATOM | 1332 | NE | ARG | 366 | 23.068 | 51.312 | 82.233 | 1.00 | 18.31 |
| ATOM | 1334 | CZ | ARG | 366 | 23.459 | 52.090 | 83.234 | 1.00 | 20.91 |
| ATOM | 1335 | NH1 | ARG | 366 | 22.610 | 52.392 | 84.208 | 1.00 | 21.08 |
| ATOM | 1338 | NH2 | ARG | 366 | 24.696 | 52.554 | 83.279 | 1.00 | 21.60 |
| ATOM | 1341 | C | ARG | 366 | 22.190 | 48.951 | 78.021 | 1.00 | 11.69 |
| ATOM | 1342 | O | ARG | 366 | 21.838 | 47.814 | 78.289 | 1.00 | 6.35 |
| ATOM | 1343 | N | ALA | 367 | 23.355 | 49.245 | 77.439 | 1.00 | 9.93 |
| ATOM | 1345 | CA | ALA | 367 | 24.324 | 48.205 | 77.065 | 1.00 | 9.46 |
| ATOM | 1346 | CB | ALA | 367 | 25.569 | 48.855 | 76.478 | 1.00 | 8.97 |
| ATOM | 1347 | C | ALA | 367 | 24.707 | 47.242 | 78.203 | 1.00 | 9.81 |
| ATOM | 1348 | O | ALA | 367 | 25.001 | 46.038 | 77.968 | 1.00 | 10.18 |
| ATOM | 1349 | N | ALA | 368 | 24.676 | 47.737 | 79.435 | 1.00 | 7.59 |
| ATOM | 1351 | CA | ALA | 368 | 24.992 | 46.897 | 80.570 | 1.00 | 9.89 |
| ATOM | 1352 | CB | ALA | 368 | 24.928 | 47.694 | 81.854 | 1.00 | 8.37 |
| ATOM | 1353 | C | ALA | 368 | 23.979 | 45.752 | 80.670 | 1.00 | 11.64 |
| ATOM | 1354 | O | ALA | 368 | 24.293 | 44.629 | 81.180 | 1.00 | 8.73 |

TABLE 1-continued

Coordinates of Lck bound with PP2

| | | Atom Type | Res | # | X | Y | Z | Occ | B |
|---|---|---|---|---|---|---|---|---|---|
| ATOM | 1355 | N | ASN | 369 | 22.771 | 46.039 | 80.198 | 1.00 | 7.92 |
| ATOM | 1357 | CA | ASN | 369 | 21.687 | 45.091 | 80.307 | 1.00 | 9.98 |
| ATOM | 1358 | CB | ASN | 369 | 20.453 | 45.804 | 80.894 | 1.00 | 7.16 |
| ATOM | 1359 | CG | ASN | 369 | 20.658 | 46.204 | 82.338 | 1.00 | 9.70 |
| ATOM | 1360 | OD1 | ASN | 369 | 21.472 | 45.576 | 83.079 | 1.00 | 9.63 |
| ATOM | 1361 | ND2 | ASN | 369 | 19.954 | 47.251 | 82.775 | 1.00 | 7.25 |
| ATOM | 1364 | C | ASN | 369 | 21.381 | 44.285 | 79.055 | 1.00 | 8.69 |
| ATOM | 1365 | O | ASN | 369 | 20.265 | 43.723 | 78.901 | 1.00 | 10.46 |
| ATOM | 1366 | N | ILE | 370 | 22.374 | 44.223 | 78.162 | 1.00 | 7.57 |
| ATOM | 1368 | CA | ILE | 370 | 22.296 | 43.411 | 76.948 | 1.00 | 6.61 |
| ATOM | 1369 | CB | ILE | 370 | 22.648 | 44.186 | 75.646 | 1.00 | 4.56 |
| ATOM | 1370 | CG2 | ILE | 370 | 22.640 | 43.224 | 74.430 | 1.00 | 2.00 |
| ATOM | 1371 | CG1 | ILE | 370 | 21.621 | 45.314 | 75.369 | 1.00 | 3.78 |
| ATOM | 1372 | CD1 | ILE | 370 | 20.045 | 44.954 | 75.518 | 1.00 | 5.14 |
| ATOM | 1373 | C | ILE | 370 | 23.388 | 42.327 | 77.185 | 1.00 | 9.06 |
| ATOM | 1374 | O | ILE | 370 | 24.530 | 42.660 | 77.608 | 1.00 | 7.80 |
| ATOM | 1375 | N | LEU | 371 | 23.043 | 41.047 | 77.024 | 1.00 | 8.95 |
| ATOM | 1377 | CA | LEU | 371 | 24.063 | 39.964 | 77.236 | 1.00 | 7.58 |
| ATOM | 1378 | CB | LEU | 371 | 23.569 | 38.835 | 78.156 | 1.00 | 5.07 |
| ATOM | 1379 | CG | LEU | 371 | 23.229 | 39.260 | 79.587 | 1.00 | 6.83 |
| ATOM | 1380 | CD1 | LEU | 371 | 22.753 | 38.058 | 80.450 | 1.00 | 9.45 |
| ATOM | 1381 | CD2 | LEU | 371 | 24.465 | 40.010 | 80.243 | 1.00 | 8.95 |
| ATOM | 1382 | C | LEU | 371 | 24.470 | 39.428 | 75.882 | 1.00 | 7.66 |
| ATOM | 1383 | O | LEU | 371 | 23.703 | 39.510 | 74.940 | 1.00 | 8.35 |
| ATOM | 1384 | N | VAL | 372 | 25.717 | 38.957 | 75.780 | 1.00 | 7.21 |
| ATOM | 1386 | CA | VAL | 372 | 26.263 | 38.476 | 74.528 | 1.00 | 9.26 |
| ATOM | 1387 | CB | VAL | 372 | 27.536 | 39.268 | 74.150 | 1.00 | 10.89 |
| ATOM | 1388 | CG1 | VAL | 372 | 27.996 | 38.831 | 72.754 | 1.00 | 8.47 |
| ATOM | 1389 | CG2 | VAL | 372 | 27.271 | 40.866 | 74.213 | 1.00 | 5.59 |
| ATOM | 1390 | C | VAL | 372 | 26.594 | 36.970 | 74.660 | 1.00 | 7.83 |
| ATOM | 1391 | O | VAL | 372 | 27.185 | 36.548 | 75.643 | 1.00 | 8.91 |
| ATOM | 1392 | N | SER | 373 | 26.205 | 36.218 | 73.637 | 1.00 | 7.24 |
| ATOM | 1394 | CA | SER | 373 | 26.384 | 34.760 | 73.579 | 1.00 | 9.76 |
| ATOM | 1395 | CB | SER | 373 | 25.342 | 34.107 | 72.660 | 1.00 | 5.50 |
| ATOM | 1396 | OG | SER | 373 | 25.745 | 34.322 | 71.320 | 1.00 | 8.32 |
| ATOM | 1398 | C | SER | 373 | 27.744 | 34.446 | 72.996 | 1.00 | 9.94 |
| ATOM | 1399 | O | SER | 373 | 28.465 | 35.340 | 72.475 | 1.00 | 7.48 |
| ATOM | 1400 | N | ASP | 374 | 28.094 | 33.165 | 73.062 | 1.00 | 10.41 |
| ATOM | 1402 | CA | ASP | 374 | 29.371 | 32.686 | 72.546 | 1.00 | 12.58 |
| ATOM | 1403 | CB | ASP | 374 | 29.578 | 31.214 | 72.933 | 1.00 | 16.92 |
| ATOM | 1404 | CG | ASP | 374 | 28.619 | 30.307 | 72.212 | 1.00 | 21.38 |
| ATOM | 1405 | OD1 | ASP | 374 | 27.403 | 30.535 | 72.324 | 1.00 | 22.32 |
| ATOM | 1406 | OD2 | ASP | 374 | 29.071 | 29.434 | 71.444 | 1.00 | 27.84 |
| ATOM | 1407 | C | ASP | 374 | 29.397 | 32.866 | 71.016 | 1.00 | 14.92 |
| ATOM | 1408 | O | ASP | 374 | 30.467 | 32.919 | 70.405 | 1.00 | 13.69 |
| ATOM | 1409 | N | THR | 375 | 28.229 | 32.954 | 70.365 | 1.00 | 12.20 |
| ATOM | 1411 | CA | THR | 375 | 28.238 | 33.202 | 68.910 | 1.00 | 11.93 |
| ATOM | 1412 | CB | THR | 375 | 27.130 | 32.433 | 68.162 | 1.00 | 12.01 |
| ATOM | 1413 | OG1 | THR | 375 | 25.856 | 32.721 | 68.763 | 1.00 | 11.68 |
| ATOM | 1415 | CG2 | THR | 375 | 27.397 | 30.929 | 68.211 | 1.00 | 13.26 |
| ATOM | 1416 | C | THR | 375 | 28.084 | 34.695 | 68.569 | 1.00 | 11.66 |
| ATOM | 1417 | O | THR | 375 | 27.801 | 35.064 | 67.430 | 1.00 | 12.15 |
| ATOM | 1418 | N | LEU | 376 | 28.233 | 35.560 | 69.565 | 1.00 | 11.08 |
| ATOM | 1420 | CA | LEU | 376 | 28.072 | 37.019 | 69.352 | 1.00 | 11.90 |
| ATOM | 1421 | CB | LEU | 376 | 29.142 | 37.609 | 68.399 | 1.00 | 11.87 |
| ATOM | 1422 | CG | LEU | 376 | 30.631 | 37.276 | 68.729 | 1.00 | 14.72 |
| ATOM | 1423 | CD1 | LEU | 376 | 31.563 | 38.234 | 67.934 | 1.00 | 14.52 |
| ATOM | 1424 | CD2 | LEU | 376 | 30.918 | 37.377 | 70.198 | 1.00 | 11.76 |
| ATOM | 1425 | C | LEU | 376 | 26.650 | 37.416 | 68.889 | 1.00 | 11.62 |
| ATOM | 1426 | O | LEU | 376 | 26.465 | 38.175 | 67.929 | 1.00 | 12.23 |
| ATOM | 1427 | N | SER | 377 | 25.653 | 36.778 | 69.498 | 1.00 | 8.91 |
| ATOM | 1429 | CA | SER | 377 | 24.281 | 37.152 | 69.246 | 1.00 | 8.75 |
| ATOM | 1430 | CB | SER | 377 | 23.395 | 35.931 | 68.944 | 1.00 | 6.43 |
| ATOM | 1431 | OG | SER | 377 | 23.392 | 35.061 | 70.052 | 1.00 | 7.78 |
| ATOM | 1433 | C | SER | 377 | 23.949 | 37.847 | 70.595 | 1.00 | 8.80 |
| ATOM | 1434 | O | SER | 377 | 24.573 | 37.565 | 71.663 | 1.00 | 7.17 |
| ATOM | 1435 | N | CYS | 378 | 22.997 | 38.780 | 70.553 | 1.00 | 8.01 |
| ATOM | 1437 | CA | CYS | 378 | 22.639 | 39.570 | 71.724 | 1.00 | 8.87 |
| ATOM | 1438 | CB | CYS | 378 | 22.712 | 41.064 | 71.359 | 1.00 | 11.38 |
| ATOM | 1439 | SG | CYS | 378 | 24.361 | 41.659 | 70.914 | 1.00 | 14.14 |
| ATOM | 1440 | C | CYS | 378 | 21.227 | 39.276 | 72.218 | 1.00 | 8.65 |
| ATOM | 1441 | O | CYS | 378 | 20.335 | 39.062 | 71.414 | 1.00 | 10.46 |
| ATOM | 1442 | N | LYS | 379 | 21.057 | 39.286 | 73.537 | 1.00 | 7.74 |
| ATOM | 1444 | CA | LYS | 379 | 19.748 | 39.098 | 74.188 | 1.00 | 9.78 |

TABLE 1-continued

Coordinates of Lck bound with PP2

| | Atom Type | Res | # | X | Y | Z | Occ | B |
|---|---|---|---|---|---|---|---|---|
| ATOM | 1445 | CB | LYS | 379 | 19.635 | 37.717 | 74.845 | 1.00 | 5.83 |
| ATOM | 1446 | CG | LYS | 379 | 19.907 | 36.610 | 73.796 | 1.00 | 7.52 |
| ATOM | 1447 | CD | LYS | 379 | 19.441 | 35.258 | 74.203 | 1.00 | 5.35 |
| ATOM | 1448 | CE | LYS | 379 | 19.825 | 34.309 | 73.066 | 1.00 | 8.53 |
| ATOM | 1449 | NZ | LYS | 379 | 19.129 | 33.014 | 73.109 | 1.00 | 7.32 |
| ATOM | 1453 | C | LYS | 379 | 19.470 | 40.162 | 75.244 | 1.00 | 8.89 |
| ATOM | 1454 | O | LYS | 379 | 20.363 | 40.551 | 76.014 | 1.00 | 10.66 |
| ATOM | 1455 | N | ILE | 380 | 18.210 | 40.581 | 75.337 | 1.00 | 7.78 |
| ATOM | 1457 | CA | ILE | 380 | 17.808 | 41.558 | 76.359 | 1.00 | 6.62 |
| ATOM | 1458 | CB | ILE | 380 | 16.334 | 42.064 | 76.148 | 1.00 | 5.67 |
| ATOM | 1459 | CG2 | ILE | 380 | 15.981 | 43.131 | 77.237 | 1.00 | 7.47 |
| ATOM | 1460 | CG1 | ILE | 380 | 16.065 | 42.543 | 74.719 | 1.00 | 8.91 |
| ATOM | 1461 | CD1 | ILE | 380 | 17.119 | 43.535 | 74.160 | 1.00 | 8.08 |
| ATOM | 1462 | C | ILE | 380 | 17.825 | 40.803 | 77.706 | 1.00 | 7.03 |
| ATOM | 1463 | O | ILE | 380 | 17.416 | 39.619 | 77.776 | 1.00 | 7.34 |
| ATOM | 1464 | N | ALA | 381 | 18.230 | 41.493 | 78.784 | 1.00 | 6.85 |
| ATOM | 1466 | CA | ALA | 381 | 18.329 | 40.932 | 80.112 | 1.00 | 8.40 |
| ATOM | 1467 | CB | ALA | 381 | 19.772 | 40.496 | 80.365 | 1.00 | 10.10 |
| ATOM | 1468 | C | ALA | 381 | 17.904 | 41.940 | 81.181 | 1.00 | 10.96 |
| ATOM | 1469 | O | ALA | 381 | 17.528 | 43.064 | 80.865 | 1.00 | 9.25 |
| ATOM | 1470 | N | ASP | 382 | 17.974 | 41.525 | 82.455 | 1.00 | 13.46 |
| ATOM | 1472 | CA | ASP | 382 | 17.659 | 42.358 | 83.628 | 1.00 | 16.25 |
| ATOM | 1473 | CB | ASP | 382 | 18.723 | 43.436 | 83.849 | 1.00 | 21.02 |
| ATOM | 1474 | CG | ASP | 382 | 19.811 | 42.987 | 84.821 | 1.00 | 29.16 |
| ATOM | 1475 | OD1 | ASP | 382 | 20.331 | 41.856 | 84.688 | 1.00 | 31.18 |
| ATOM | 1476 | OD2 | ASP | 382 | 20.125 | 43.756 | 85.749 | 1.00 | 32.56 |
| ATOM | 1477 | C | ASP | 382 | 16.283 | 42.994 | 83.587 | 1.00 | 16.63 |
| ATOM | 1478 | O | ASP | 382 | 16.115 | 44.215 | 83.506 | 1.00 | 14.95 |
| ATOM | 1479 | N | PHE | 383 | 15.289 | 42.126 | 83.681 | 1.00 | 15.23 |
| ATOM | 1481 | CA | PHE | 383 | 13.897 | 42.495 | 83.607 | 1.00 | 14.42 |
| ATOM | 1482 | CB | PHE | 383 | 13.135 | 41.269 | 83.123 | 1.00 | 13.10 |
| ATOM | 1483 | CG | PHE | 383 | 13.552 | 40.824 | 81.756 | 1.00 | 11.15 |
| ATOM | 1484 | CD1 | PHE | 383 | 13.092 | 41.491 | 80.634 | 1.00 | 11.32 |
| ATOM | 1485 | CD2 | PHE | 383 | 14.479 | 39.797 | 81.591 | 1.00 | 11.61 |
| ATOM | 1486 | CE1 | PHE | 383 | 13.559 | 41.145 | 79.387 | 1.00 | 9.59 |
| ATOM | 1487 | CE2 | PHE | 383 | 14.951 | 39.452 | 80.330 | 1.00 | 5.95 |
| ATOM | 1488 | CZ | PHE | 383 | 14.507 | 40.102 | 79.248 | 1.00 | 6.03 |
| ATOM | 1489 | C | PHE | 383 | 13.306 | 42.959 | 84.914 | 1.00 | 14.50 |
| ATOM | 1490 | O | PHE | 383 | 12.112 | 43.049 | 85.035 | 1.00 | 15.77 |
| ATOM | 1491 | N | GLY | 384 | 14.149 | 43.290 | 85.880 | 1.00 | 14.37 |
| ATOM | 1493 | CA | GLY | 384 | 13.677 | 43.701 | 87.189 | 1.00 | 14.45 |
| ATOM | 1494 | C | GLY | 384 | 12.722 | 44.873 | 87.230 | 1.00 | 14.19 |
| ATOM | 1495 | O | GLY | 384 | 11.838 | 44.934 | 88.115 | 1.00 | 13.20 |
| ATOM | 1496 | N | LEU | 385 | 12.920 | 45.828 | 86.326 | 1.00 | 12.95 |
| ATOM | 1498 | CA | LEU | 385 | 12.053 | 47.005 | 86.300 | 1.00 | 13.18 |
| ATOM | 1499 | CB | LEU | 385 | 12.886 | 48.281 | 86.023 | 1.00 | 13.68 |
| ATOM | 1500 | CG | LEU | 385 | 13.867 | 48.544 | 87.165 | 1.00 | 17.86 |
| ATOM | 1501 | CD1 | LEU | 385 | 14.944 | 49.590 | 86.734 | 1.00 | 20.90 |
| ATOM | 1502 | CD2 | LEU | 385 | 13.095 | 49.015 | 88.401 | 1.00 | 18.99 |
| ATOM | 1503 | C | LEU | 385 | 10.988 | 46.867 | 85.253 | 1.00 | 11.66 |
| ATOM | 1504 | O | LEU | 385 | 10.221 | 47.755 | 85.089 | 1.00 | 12.38 |
| ATOM | 1505 | N | ALA | 386 | 10.953 | 45.748 | 84.523 | 1.00 | 13.67 |
| ATOM | 1507 | CA | ALA | 386 | 9.965 | 45.580 | 83.454 | 1.00 | 13.66 |
| ATOM | 1508 | CB | ALA | 386 | 10.243 | 44.316 | 82.652 | 1.00 | 13.42 |
| ATOM | 1509 | C | ALA | 386 | 8.522 | 45.549 | 83.999 | 1.00 | 13.70 |
| ATOM | 1510 | O | ALA | 386 | 8.262 | 45.036 | 85.069 | 1.00 | 14.67 |
| ATOM | 1511 | N | ARG | 387 | 7.595 | 46.094 | 83.234 | 1.00 | 14.30 |
| ATOM | 1513 | CA | ARG | 387 | 6.206 | 46.142 | 83.679 | 1.00 | 15.35 |
| ATOM | 1514 | CB | ARG | 387 | 5.880 | 47.488 | 84.315 | 1.00 | 14.74 |
| ATOM | 1515 | CG | ARG | 387 | 6.758 | 47.859 | 85.514 | 1.00 | 17.36 |
| ATOM | 1516 | CD | ARG | 387 | 6.533 | 46.935 | 86.696 | 1.00 | 12.99 |
| ATOM | 1517 | NE | ARG | 387 | 7.249 | 47.427 | 87.855 | 1.00 | 14.52 |
| ATOM | 1519 | CZ | ARG | 387 | 8.366 | 46.878 | 88.316 | 1.00 | 16.69 |
| ATOM | 1520 | NH1 | ARG | 387 | 8.891 | 45.796 | 87.702 | 1.00 | 14.56 |
| ATOM | 1523 | NH2 | ARG | 387 | 8.955 | 47.396 | 89.373 | 1.00 | 13.33 |
| ATOM | 1526 | C | ARG | 387 | 5.272 | 45.969 | 82.523 | 1.00 | 15.31 |
| ATOM | 1527 | O | ARG | 387 | 5.515 | 46.467 | 81.415 | 1.00 | 13.91 |
| ATOM | 1528 | N | LEU | 388 | 4.176 | 45.272 | 82.811 | 1.00 | 17.64 |
| ATOM | 1530 | CA | LEU | 388 | 3.129 | 45.049 | 81.846 | 1.00 | 20.19 |
| ATOM | 1531 | CB | LEU | 388 | 2.219 | 43.891 | 82.280 | 1.00 | 21.96 |
| ATOM | 1532 | CG | LEU | 388 | 1.040 | 43.441 | 81.406 | 1.00 | 21.86 |
| ATOM | 1533 | CD1 | LEU | 388 | −0.225 | 44.187 | 81.738 | 1.00 | 26.99 |
| ATOM | 1534 | CD2 | LEU | 388 | 1.340 | 43.579 | 79.946 | 1.00 | 24.42 |
| ATOM | 1535 | C | LEU | 388 | 2.346 | 46.339 | 81.883 | 1.00 | 22.45 |

TABLE 1-continued

Coordinates of Lck bound with PP2

| | | Atom Type | Res | # | X | Y | Z | Occ | B |
|---|---|---|---|---|---|---|---|---|---|
| ATOM | 1536 | O | LEU | 388 | 1.939 | 46.799 | 82.934 | 1.00 | 22.82 |
| ATOM | 1537 | N | ILE | 389 | 2.126 | 46.903 | 80.710 | 1.00 | 25.77 |
| ATOM | 1539 | CA | ILE | 389 | 1.391 | 48.147 | 80.569 | 1.00 | 31.17 |
| ATOM | 1540 | CB | ILE | 389 | 2.007 | 48.973 | 79.406 | 1.00 | 32.68 |
| ATOM | 1541 | CG2 | ILE | 389 | 0.977 | 49.811 | 78.700 | 1.00 | 35.18 |
| ATOM | 1542 | CG1 | ILE | 389 | 3.199 | 49.793 | 79.906 | 1.00 | 33.70 |
| ATOM | 1543 | CD1 | ILE | 389 | 3.234 | 50.008 | 81.385 | 1.00 | 33.09 |
| ATOM | 1544 | C | ILE | 389 | −0.082 | 47.830 | 80.310 | 1.00 | 33.94 |
| ATOM | 1545 | O | ILE | 389 | −0.479 | 47.374 | 79.223 | 1.00 | 33.18 |
| ATOM | 1546 | N | GLU | 390 | −0.884 | 48.033 | 81.343 | 1.00 | 37.88 |
| ATOM | 1548 | CA | GLU | 390 | −2.326 | 47.791 | 81.277 | 1.00 | 42.55 |
| ATOM | 1549 | CB | GLU | 390 | −2.922 | 47.974 | 82.674 | 1.00 | 45.03 |
| ATOM | 1550 | CG | GLU | 390 | −1.924 | 47.709 | 83.827 | 1.00 | 47.42 |
| ATOM | 1551 | CD | GLU | 390 | −1.907 | 46.263 | 84.320 | 1.00 | 49.42 |
| ATOM | 1552 | OE1 | GLU | 390 | −2.865 | 45.504 | 84.044 | 1.00 | 52.67 |
| ATOM | 1553 | OE2 | GLU | 390 | −0.941 | 45.888 | 85.023 | 1.00 | 49.76 |
| ATOM | 1554 | C | GLU | 390 | −2.891 | 48.829 | 80.297 | 1.00 | 44.19 |
| ATOM | 1555 | O | GLU | 390 | −3.263 | 48.501 | 79.169 | 1.00 | 45.01 |
| ATOM | 1556 | N | ASP | 391 | −2.899 | 50.094 | 80.727 | 1.00 | 45.67 |
| ATOM | 1558 | CA | ASP | 391 | −3.348 | 51.230 | 79.909 | 1.00 | 46.27 |
| ATOM | 1559 | CB | ASP | 391 | −4.036 | 52.278 | 80.795 | 1.00 | 46.38 |
| ATOM | 1560 | CG | ASP | 391 | −5.096 | 51.673 | 81.721 | 1.00 | 46.67 |
| ATOM | 1561 | OD1 | ASP | 391 | −4.768 | 50.776 | 82.530 | 1.00 | 45.67 |
| ATOM | 1562 | OD2 | ASP | 391 | −6.254 | 52.123 | 81.663 | 1.00 | 47.09 |
| ATOM | 1563 | C | ASP | 391 | −2.027 | 51.786 | 79.353 | 1.00 | 46.49 |
| ATOM | 1564 | O | ASP | 391 | −0.983 | 51.277 | 79.719 | 1.00 | 49.17 |
| ATOM | 1565 | N | ASN | 392 | −2.035 | 52.861 | 78.563 | 1.00 | 45.78 |
| ATOM | 1567 | CA | ASN | 392 | −0.785 | 53.403 | 77.968 | 1.00 | 44.41 |
| ATOM | 1568 | CB | ASN | 392 | −1.056 | 54.720 | 77.217 | 1.00 | 46.14 |
| ATOM | 1569 | CG | ASN | 392 | 0.185 | 55.244 | 76.462 | 1.00 | 47.37 |
| ATOM | 1570 | OD1 | ASN | 392 | 0.403 | 56.459 | 76.344 | 1.00 | 47.96 |
| ATOM | 1571 | ND2 | ASN | 392 | 1.001 | 54.325 | 75.958 | 1.00 | 48.86 |
| ATOM | 1574 | C | ASN | 392 | 0.508 | 53.579 | 78.775 | 1.00 | 42.14 |
| ATOM | 1575 | O | ASN | 392 | 1.602 | 53.302 | 78.249 | 1.00 | 43.11 |
| ATOM | 1576 | N | GLU | 393 | 0.439 | 54.012 | 80.033 | 1.00 | 39.10 |
| ATOM | 1578 | CA | GLU | 393 | 1.686 | 54.237 | 80.765 | 1.00 | 36.60 |
| ATOM | 1579 | CB | GLU | 393 | 2.077 | 55.731 | 80.683 | 1.00 | 36.66 |
| ATOM | 1580 | CG | GLU | 393 | 1.148 | 56.694 | 81.381 | 1.00 | 39.54 |
| ATOM | 1581 | CD | GLU | 393 | 1.588 | 58.158 | 81.306 | 1.00 | 42.34 |
| ATOM | 1582 | OE1 | GLU | 393 | 1.618 | 58.811 | 82.369 | 1.00 | 42.59 |
| ATOM | 1583 | OE2 | GLU | 393 | 1.862 | 58.676 | 80.197 | 1.00 | 44.17 |
| ATOM | 1584 | C | GLU | 393 | 1.715 | 53.797 | 82.253 | 1.00 | 34.46 |
| ATOM | 1585 | O | GLU | 393 | 0.769 | 53.675 | 82.965 | 1.00 | 35.21 |
| ATOM | 1586 | N | PTR | 394 | 3.001 | 53.540 | 82.661 | 1.00 | 29.11 |
| ATOM | 1587 | CA | PTR | 394 | 3.298 | 53.169 | 84.025 | 1.00 | 26.42 |
| ATOM | 1588 | C | PTR | 394 | 3.931 | 54.436 | 84.666 | 1.00 | 24.90 |
| ATOM | 1589 | O | PTR | 394 | 4.763 | 55.076 | 84.070 | 1.00 | 23.07 |
| ATOM | 1590 | CB | PTR | 394 | 4.362 | 52.061 | 83.972 | 1.00 | 23.81 |
| ATOM | 1591 | CG | PTR | 394 | 4.671 | 51.487 | 85.340 | 1.00 | 25.37 |
| ATOM | 1592 | CD1 | PTR | 394 | 3.906 | 50.463 | 85.860 | 1.00 | 25.42 |
| ATOM | 1593 | CD2 | PTR | 394 | 5.728 | 51.987 | 86.078 | 1.00 | 26.36 |
| ATOM | 1594 | CE1 | PTR | 394 | 4.220 | 49.955 | 87.118 | 1.00 | 28.45 |
| ATOM | 1595 | CE2 | PTR | 394 | 6.061 | 51.496 | 87.341 | 1.00 | 29.97 |
| ATOM | 1596 | CZ | PTR | 394 | 5.286 | 50.470 | 87.832 | 1.00 | 30.84 |
| ATOM | 1597 | OH | PTR | 394 | 5.638 | 49.945 | 89.136 | 1.00 | 38.55 |
| ATOM | 1598 | P | PTR | 394 | 6.362 | 50.808 | 90.275 | 1.00 | 40.34 |
| ATOM | 1599 | O1P | PTR | 394 | 7.387 | 51.592 | 89.615 | 1.00 | 41.04 |
| ATOM | 1600 | O2P | PTR | 394 | 6.976 | 49.958 | 91.281 | 1.00 | 41.13 |
| ATOM | 1601 | O3P | PTR | 394 | 5.391 | 51.756 | 90.903 | 1.00 | 44.63 |
| ATOM | 1602 | N | THR | 395 | 3.561 | 54.729 | 85.902 | 1.00 | 25.26 |
| ATOM | 1604 | CA | THR | 395 | 4.088 | 55.931 | 86.611 | 1.00 | 26.22 |
| ATOM | 1605 | CB | THR | 395 | 2.923 | 56.896 | 87.089 | 1.00 | 27.32 |
| ATOM | 1606 | OG1 | THR | 395 | 2.050 | 57.159 | 85.991 | 1.00 | 24.61 |
| ATOM | 1608 | CG2 | THR | 395 | 3.476 | 58.262 | 87.597 | 1.00 | 26.90 |
| ATOM | 1609 | C | THR | 395 | 4.783 | 55.378 | 87.821 | 1.00 | 27.47 |
| ATOM | 1610 | O | THR | 395 | 4.163 | 54.678 | 88.622 | 1.00 | 28.67 |
| ATOM | 1611 | N | ALA | 396 | 6.082 | 55.628 | 87.937 | 1.00 | 28.84 |
| ATOM | 1613 | CA | ALA | 396 | 6.859 | 55.130 | 89.085 | 1.00 | 31.81 |
| ATOM | 1614 | CB | ALA | 396 | 8.350 | 55.325 | 88.839 | 1.00 | 30.56 |
| ATOM | 1615 | C | ALA | 396 | 6.460 | 55.843 | 90.382 | 1.00 | 34.00 |
| ATOM | 1616 | O | ALA | 396 | 5.639 | 56.762 | 90.363 | 1.00 | 33.88 |
| ATOM | 1617 | N | ALA | 397 | 7.058 | 55.432 | 91.500 | 1.00 | 37.57 |
| ATOM | 1619 | CA | ALA | 397 | 6.773 | 56.045 | 92.803 | 1.00 | 40.37 |
| ATOM | 1620 | CB | ALA | 397 | 7.104 | 55.068 | 93.922 | 1.00 | 42.31 |

TABLE 1-continued

Coordinates of Lck bound with PP2

| | Atom Type | Res | # | X | Y | Z | Occ | B |
|---|---|---|---|---|---|---|---|---|
| ATOM | 1621 | C | ALA | 397 | 7.583 | 57.335 | 92.944 | 1.00 | 42.80 |
| ATOM | 1622 | O | ALA | 397 | 8.743 | 57.405 | 92.539 | 1.00 | 42.60 |
| ATOM | 1623 | N | GLU | 398 | 6.970 | 58.362 | 93.528 | 1.00 | 45.77 |
| ATOM | 1625 | CA | GLU | 398 | 7.610 | 59.683 | 93.673 | 1.00 | 47.84 |
| ATOM | 1626 | CB | GLU | 398 | 6.734 | 60.601 | 94.523 | 1.00 | 50.12 |
| ATOM | 1627 | CG | GLU | 398 | 5.373 | 60.880 | 93.884 | 1.00 | 53.67 |
| ATOM | 1628 | CD | GLU | 398 | 5.490 | 61.473 | 92.490 | 1.00 | 55.50 |
| ATOM | 1629 | OE1 | GLU | 398 | 5.992 | 62.612 | 92.377 | 1.00 | 56.86 |
| ATOM | 1630 | OE2 | GLU | 398 | 5.085 | 60.805 | 91.512 | 1.00 | 56.88 |
| ATOM | 1631 | C | GLU | 398 | 9.082 | 59.802 | 94.094 | 1.00 | 47.14 |
| ATOM | 1632 | O | GLU | 398 | 9.768 | 60.765 | 93.719 | 1.00 | 48.42 |
| ATOM | 1633 | N | GLY | 399 | 9.585 | 58.839 | 94.859 | 1.00 | 46.48 |
| ATOM | 1635 | CA | GLY | 399 | 10.982 | 58.891 | 95.266 | 1.00 | 44.00 |
| ATOM | 1636 | C | GLY | 399 | 11.881 | 58.026 | 94.394 | 1.00 | 41.93 |
| ATOM | 1637 | O | GLY | 399 | 13.058 | 57.832 | 94.698 | 1.00 | 43.45 |
| ATOM | 1638 | N | ALA | 400 | 11.335 | 57.512 | 93.296 | 1.00 | 40.42 |
| ATOM | 1640 | CA | ALA | 400 | 12.093 | 56.644 | 92.391 | 1.00 | 38.09 |
| ATOM | 1641 | CB | ALA | 400 | 11.142 | 55.857 | 91.493 | 1.00 | 38.53 |
| ATOM | 1642 | C | ALA | 400 | 13.103 | 57.412 | 91.554 | 1.00 | 34.64 |
| ATOM | 1643 | O | ALA | 400 | 12.784 | 58.434 | 90.969 | 1.00 | 35.67 |
| ATOM | 1644 | N | ALA | 401 | 14.338 | 56.925 | 91.529 | 1.00 | 31.89 |
| ATOM | 1646 | CA | ALA | 401 | 15.406 | 57.567 | 90.768 | 1.00 | 29.60 |
| ATOM | 1647 | CB | ALA | 401 | 16.568 | 57.955 | 91.704 | 1.00 | 29.17 |
| ATOM | 1648 | C | ALA | 401 | 15.888 | 56.645 | 89.639 | 1.00 | 27.73 |
| ATOM | 1649 | O | ALA | 401 | 15.948 | 55.412 | 89.786 | 1.00 | 29.01 |
| ATOM | 1650 | N | PHE | 402 | 16.194 | 57.245 | 88.496 | 1.00 | 24.12 |
| ATOM | 1652 | CA | PHE | 402 | 16.642 | 56.507 | 87.307 | 1.00 | 22.37 |
| ATOM | 1653 | CB | PHE | 402 | 15.519 | 56.502 | 86.279 | 1.00 | 22.95 |
| ATOM | 1654 | CG | PHE | 402 | 14.274 | 55.838 | 86.781 | 1.00 | 24.95 |
| ATOM | 1655 | CD1 | PHE | 402 | 14.171 | 54.443 | 86.775 | 1.00 | 25.08 |
| ATOM | 1656 | CD2 | PHE | 402 | 13.238 | 56.598 | 87.349 | 1.00 | 25.66 |
| ATOM | 1657 | CE1 | PHE | 402 | 13.056 | 53.804 | 87.336 | 1.00 | 26.56 |
| ATOM | 1658 | CE2 | PHE | 402 | 12.117 | 55.971 | 87.918 | 1.00 | 25.82 |
| ATOM | 1659 | CZ | PHE | 402 | 12.028 | 54.572 | 87.910 | 1.00 | 26.72 |
| ATOM | 1660 | C | PHE | 402 | 17.903 | 57.126 | 86.736 | 1.00 | 19.57 |
| ATOM | 1661 | O | PHE | 402 | 18.177 | 58.296 | 86.994 | 1.00 | 20.18 |
| ATOM | 1662 | N | PRO | 403 | 18.722 | 56.338 | 86.020 | 1.00 | 17.47 |
| ATOM | 1663 | CD | PRO | 403 | 18.495 | 54.940 | 85.630 | 1.00 | 18.55 |
| ATOM | 1664 | CA | PRO | 403 | 19.966 | 56.858 | 85.428 | 1.00 | 16.70 |
| ATOM | 1665 | CB | PRO | 403 | 20.540 | 55.657 | 84.674 | 1.00 | 16.97 |
| ATOM | 1666 | CG | PRO | 403 | 19.910 | 54.447 | 85.358 | 1.00 | 20.19 |
| ATOM | 1667 | C | PRO | 403 | 19.587 | 57.948 | 84.451 | 1.00 | 15.54 |
| ATOM | 1668 | O | PRO | 403 | 18.954 | 57.698 | 83.415 | 1.00 | 14.87 |
| ATOM | 1669 | N | ILE | 404 | 19.946 | 59.173 | 84.797 | 1.00 | 14.66 |
| ATOM | 1671 | CA | ILE | 404 | 19.611 | 60.333 | 83.977 | 1.00 | 13.68 |
| ATOM | 1672 | CB | ILE | 404 | 20.166 | 61.635 | 84.611 | 1.00 | 13.64 |
| ATOM | 1673 | CG2 | ILE | 404 | 20.070 | 62.847 | 83.635 | 1.00 | 13.49 |
| ATOM | 1674 | CG1 | ILE | 404 | 19.452 | 61.908 | 85.942 | 1.00 | 14.28 |
| ATOM | 1675 | CD1 | ILE | 404 | 17.965 | 61.923 | 85.854 | 1.00 | 21.89 |
| ATOM | 1676 | C | ILE | 404 | 19.988 | 60.283 | 82.514 | 1.00 | 10.49 |
| ATOM | 1677 | O | ILE | 404 | 19.189 | 60.623 | 81.657 | 1.00 | 13.39 |
| ATOM | 1678 | N | LYS | 405 | 21.211 | 59.857 | 82.213 | 1.00 | 10.10 |
| ATOM | 1680 | CA | LYS | 405 | 21.691 | 59.833 | 80.819 | 1.00 | 8.60 |
| ATOM | 1681 | CB | LYS | 405 | 23.200 | 59.603 | 80.798 | 1.00 | 8.67 |
| ATOM | 1682 | CG | LYS | 405 | 24.036 | 60.751 | 81.412 | 1.00 | 11.05 |
| ATOM | 1683 | CD | LYS | 405 | 25.544 | 60.429 | 81.442 | 1.00 | 15.41 |
| ATOM | 1684 | CE | LYS | 405 | 26.382 | 61.629 | 81.950 | 1.00 | 18.38 |
| ATOM | 1685 | NZ | LYS | 405 | 27.786 | 61.702 | 81.303 | 1.00 | 23.91 |
| ATOM | 1689 | C | LYS | 405 | 21.000 | 58.872 | 79.872 | 1.00 | 7.88 |
| ATOM | 1690 | O | LYS | 405 | 21.058 | 59.069 | 78.644 | 1.00 | 7.04 |
| ATOM | 1691 | N | TRP | 406 | 20.400 | 57.804 | 80.412 | 1.00 | 8.72 |
| ATOM | 1693 | CA | TRP | 406 | 19.698 | 56.811 | 79.573 | 1.00 | 9.83 |
| ATOM | 1694 | CB | TRP | 406 | 20.016 | 55.381 | 80.039 | 1.00 | 11.56 |
| ATOM | 1695 | CG | TRP | 406 | 21.358 | 54.884 | 79.663 | 1.00 | 10.68 |
| ATOM | 1696 | CD2 | TRP | 406 | 22.573 | 55.093 | 80.384 | 1.00 | 10.60 |
| ATOM | 1697 | CE2 | TRP | 406 | 23.582 | 54.422 | 79.676 | 1.00 | 10.53 |
| ATOM | 1698 | CE3 | TRP | 406 | 22.896 | 55.786 | 81.554 | 1.00 | 7.38 |
| ATOM | 1699 | CD1 | TRP | 406 | 21.666 | 54.138 | 78.588 | 1.00 | 13.93 |
| ATOM | 1700 | NE1 | TRP | 406 | 23.006 | 53.854 | 78.585 | 1.00 | 14.24 |
| ATOM | 1702 | CZ2 | TRP | 406 | 24.907 | 54.424 | 80.098 | 1.00 | 11.04 |
| ATOM | 1703 | CZ3 | TRP | 406 | 24.215 | 55.786 | 81.984 | 1.00 | 10.50 |
| ATOM | 1704 | CH2 | TRP | 406 | 25.208 | 55.112 | 81.261 | 1.00 | 7.77 |
| ATOM | 1705 | C | TRP | 406 | 18.181 | 56.919 | 79.606 | 1.00 | 11.42 |
| ATOM | 1706 | O | TRP | 406 | 17.497 | 56.267 | 78.824 | 1.00 | 11.43 |

TABLE 1-continued

Coordinates of Lck bound with PP2

| | | Atom Type | Res | # | X | Y | Z | Occ | B |
|---|---|---|---|---|---|---|---|---|---|
| ATOM | 1707 | N | THR | 407 | 17.652 | 57.725 | 80.524 | 1.00 | 10.56 |
| ATOM | 1709 | CA | THR | 407 | 16.222 | 57.848 | 80.706 | 1.00 | 11.52 |
| ATOM | 1710 | CB | THR | 407 | 15.911 | 57.899 | 82.231 | 1.00 | 10.98 |
| ATOM | 1711 | OG1 | THR | 407 | 16.569 | 56.798 | 82.877 | 1.00 | 12.19 |
| ATOM | 1713 | CG2 | THR | 407 | 14.412 | 57.806 | 82.508 | 1.00 | 11.63 |
| ATOM | 1714 | C | THR | 407 | 15.555 | 59.015 | 79.938 | 1.00 | 11.66 |
| ATOM | 1715 | O | THR | 407 | 16.073 | 60.099 | 79.919 | 1.00 | 12.05 |
| ATOM | 1716 | N | ALA | 408 | 14.409 | 58.746 | 79.304 | 1.00 | 9.19 |
| ATOM | 1718 | CA | ALA | 408 | 13.645 | 59.741 | 78.507 | 1.00 | 9.76 |
| ATOM | 1719 | CB | ALA | 408 | 12.411 | 59.090 | 77.897 | 1.00 | 10.54 |
| ATOM | 1720 | C | ALA | 408 | 13.209 | 60.874 | 79.419 | 1.00 | 9.45 |
| ATOM | 1721 | O | ALA | 408 | 12.950 | 60.646 | 80.558 | 1.00 | 10.32 |
| ATOM | 1722 | N | PRO | 409 | 13.132 | 62.115 | 78.907 | 1.00 | 10.88 |
| ATOM | 1723 | CD | PRO | 409 | 13.410 | 62.579 | 77.551 | 1.00 | 11.22 |
| ATOM | 1724 | CA | PRO | 409 | 12.731 | 63.248 | 79.731 | 1.00 | 13.35 |
| ATOM | 1725 | CB | PRO | 409 | 12.683 | 64.396 | 78.716 | 1.00 | 13.57 |
| ATOM | 1726 | CG | PRO | 409 | 13.756 | 63.998 | 77.791 | 1.00 | 15.33 |
| ATOM | 1727 | C | PRO | 409 | 11.422 | 63.084 | 80.469 | 1.00 | 13.71 |
| ATOM | 1728 | O | PRO | 409 | 11.356 | 63.418 | 81.654 | 1.00 | 13.85 |
| ATOM | 1729 | N | GLU | 410 | 10.392 | 62.555 | 79.789 | 1.00 | 14.45 |
| ATOM | 1731 | CA | GLU | 410 | 9.074 | 62.375 | 80.435 | 1.00 | 15.87 |
| ATOM | 1732 | CB | GLU | 410 | 7.999 | 61.873 | 79.451 | 1.00 | 15.43 |
| ATOM | 1733 | CG | GLU | 410 | 8.163 | 60.399 | 78.938 | 1.00 | 16.98 |
| ATOM | 1734 | CD | GLU | 410 | 9.074 | 60.243 | 77.711 | 1.00 | 16.27 |
| ATOM | 1735 | OE1 | GLU | 410 | 9.822 | 61.196 | 77.351 | 1.00 | 17.12 |
| ATOM | 1736 | OE2 | GLU | 410 | 9.054 | 59.155 | 77.094 | 1.00 | 14.45 |
| ATOM | 1737 | C | GLU | 410 | 9.163 | 61.485 | 81.641 | 1.00 | 16.20 |
| ATOM | 1738 | O | GLU | 410 | 8.487 | 61.725 | 82.641 | 1.00 | 15.55 |
| ATOM | 1739 | N | ALA | 411 | 10.064 | 60.490 | 81.597 | 1.00 | 16.98 |
| ATOM | 1741 | CA | ALA | 411 | 10.245 | 59.586 | 82.743 | 1.00 | 18.93 |
| ATOM | 1742 | CB | ALA | 411 | 11.019 | 58.316 | 82.320 | 1.00 | 18.93 |
| ATOM | 1743 | C | ALA | 411 | 10.995 | 60.298 | 83.877 | 1.00 | 20.04 |
| ATOM | 1744 | O | ALA | 411 | 10.733 | 60.065 | 85.080 | 1.00 | 20.20 |
| ATOM | 1745 | N | ILE | 412 | 12.000 | 61.102 | 83.513 | 1.00 | 19.47 |
| ATOM | 1747 | CA | ILE | 412 | 12.764 | 61.853 | 84.542 | 1.00 | 19.22 |
| ATOM | 1748 | CB | ILE | 412 | 14.015 | 62.534 | 83.940 | 1.00 | 19.14 |
| ATOM | 1749 | CG2 | ILE | 412 | 14.636 | 63.570 | 84.938 | 1.00 | 19.48 |
| ATOM | 1750 | CG1 | ILE | 412 | 15.000 | 61.489 | 83.436 | 1.00 | 16.00 |
| ATOM | 1751 | CD1 | ILE | 412 | 15.987 | 62.079 | 82.388 | 1.00 | 17.37 |
| ATOM | 1752 | C | ILE | 412 | 11.896 | 62.964 | 85.178 | 1.00 | 18.91 |
| ATOM | 1753 | O | ILE | 412 | 11.864 | 63.141 | 86.391 | 1.00 | 19.37 |
| ATOM | 1754 | N | ASN | 413 | 11.172 | 63.700 | 84.353 | 1.00 | 19.40 |
| ATOM | 1756 | CA | ASN | 413 | 10.334 | 64.805 | 84.878 | 1.00 | 21.43 |
| ATOM | 1757 | CB | ASN | 413 | 10.085 | 65.819 | 83.770 | 1.00 | 18.83 |
| ATOM | 1758 | CG | ASN | 413 | 11.381 | 66.386 | 83.221 | 1.00 | 19.10 |
| ATOM | 1759 | OD1 | ASN | 413 | 12.332 | 66.515 | 83.933 | 1.00 | 19.65 |
| ATOM | 1760 | ND2 | ASN | 413 | 11.409 | 66.692 | 81.955 | 1.00 | 20.84 |
| ATOM | 1763 | C | ASN | 413 | 8.990 | 64.407 | 85.524 | 1.00 | 22.30 |
| ATOM | 1764 | O | ASN | 413 | 8.527 | 65.040 | 86.478 | 1.00 | 22.79 |
| ATOM | 1765 | N | TYR | 414 | 8.402 | 63.303 | 85.060 | 1.00 | 22.84 |
| ATOM | 1767 | CA | TYR | 414 | 7.105 | 62.891 | 85.555 | 1.00 | 23.38 |
| ATOM | 1768 | CB | TYR | 414 | 6.085 | 63.121 | 84.441 | 1.00 | 25.46 |
| ATOM | 1769 | CG | TYR | 414 | 6.276 | 64.428 | 83.670 | 1.00 | 29.64 |
| ATOM | 1770 | CD1 | TYR | 414 | 6.421 | 65.649 | 84.338 | 1.00 | 30.70 |
| ATOM | 1771 | CE1 | TYR | 414 | 6.547 | 66.856 | 83.632 | 1.00 | 31.19 |
| ATOM | 1772 | CD2 | TYR | 414 | 6.267 | 64.439 | 82.278 | 1.00 | 29.95 |
| ATOM | 1773 | CE2 | TYR | 414 | 6.385 | 65.621 | 81.566 | 1.00 | 32.57 |
| ATOM | 1774 | CZ | TYR | 414 | 6.522 | 66.831 | 82.247 | 1.00 | 33.21 |
| ATOM | 1775 | OH | TYR | 414 | 6.616 | 68.018 | 81.534 | 1.00 | 34.76 |
| ATOM | 1777 | C | TYR | 414 | 6.934 | 61.478 | 86.102 | 1.00 | 23.24 |
| ATOM | 1778 | O | TYR | 414 | 5.872 | 61.162 | 86.566 | 1.00 | 25.90 |
| ATOM | 1779 | N | GLY | 415 | 7.962 | 60.634 | 86.046 | 1.00 | 21.41 |
| ATOM | 1781 | CA | GLY | 415 | 7.819 | 59.265 | 86.524 | 1.00 | 21.21 |
| ATOM | 1782 | C | GLY | 415 | 7.029 | 58.446 | 85.492 | 1.00 | 20.23 |
| ATOM | 1783 | O | GLY | 415 | 6.758 | 57.279 | 85.671 | 1.00 | 21.38 |
| ATOM | 1784 | N | THR | 416 | 6.787 | 59.049 | 84.349 | 1.00 | 20.26 |
| ATOM | 1786 | CA | THR | 416 | 6.014 | 58.442 | 83.285 | 1.00 | 21.50 |
| ATOM | 1787 | CB | THR | 416 | 5.163 | 59.566 | 82.611 | 1.00 | 23.40 |
| ATOM | 1788 | OG1 | THR | 416 | 3.916 | 59.688 | 83.329 | 1.00 | 27.04 |
| ATOM | 1790 | CG2 | THR | 416 | 4.890 | 59.281 | 81.162 | 1.00 | 26.75 |
| ATOM | 1791 | C | THR | 416 | 6.836 | 57.629 | 82.252 | 1.00 | 19.43 |
| ATOM | 1792 | O | THR | 416 | 7.646 | 58.184 | 81.497 | 1.00 | 16.41 |
| ATOM | 1793 | N | PHE | 417 | 6.575 | 56.320 | 82.209 | 1.00 | 16.02 |
| ATOM | 1795 | CA | PHE | 417 | 7.259 | 55.414 | 81.278 | 1.00 | 14.98 |

TABLE 1-continued

Coordinates of Lck bound with PP2

| | | Atom Type | Res | # | X | Y | Z | Occ | B |
|---|---|---|---|---|---|---|---|---|---|
| ATOM | 1796 | CB | PHE | 417 | 7.953 | 54.294 | 82.034 | 1.00 | 14.22 |
| ATOM | 1797 | CG | PHE | 417 | 9.114 | 54.722 | 82.869 | 1.00 | 13.32 |
| ATOM | 1798 | CD1 | PHE | 417 | 8.929 | 55.042 | 84.205 | 1.00 | 12.88 |
| ATOM | 1799 | CD2 | PHE | 417 | 10.414 | 54.690 | 82.352 | 1.00 | 11.83 |
| ATOM | 1800 | CE1 | PHE | 417 | 10.029 | 55.315 | 85.024 | 1.00 | 16.16 |
| ATOM | 1801 | CE2 | PHE | 417 | 11.500 | 54.953 | 83.152 | 1.00 | 9.52 |
| ATOM | 1802 | CZ | PHE | 417 | 11.322 | 55.264 | 84.488 | 1.00 | 12.45 |
| ATOM | 1803 | C | PHE | 417 | 6.333 | 54.716 | 80.290 | 1.00 | 14.56 |
| ATOM | 1804 | O | PHE | 417 | 5.238 | 54.220 | 80.662 | 1.00 | 14.80 |
| ATOM | 1805 | N | THR | 418 | 6.727 | 54.697 | 79.023 | 1.00 | 13.23 |
| ATOM | 1807 | CA | THR | 418 | 5.959 | 53.962 | 78.016 | 1.00 | 13.01 |
| ATOM | 1808 | CB | THR | 418 | 5.059 | 54.873 | 77.061 | 1.00 | 14.60 |
| ATOM | 1809 | OG1 | THR | 418 | 5.907 | 55.558 | 76.151 | 1.00 | 16.70 |
| ATOM | 1811 | CG2 | THR | 418 | 4.217 | 55.892 | 77.866 | 1.00 | 11.08 |
| ATOM | 1812 | C | THR | 418 | 7.003 | 53.283 | 77.163 | 1.00 | 11.75 |
| ATOM | 1813 | O | THR | 418 | 8.216 | 53.410 | 77.403 | 1.00 | 11.33 |
| ATOM | 1814 | N | ILE | 419 | 6.555 | 52.534 | 76.167 | 1.00 | 11.63 |
| ATOM | 1816 | CA | ILE | 419 | 7.501 | 51.869 | 75.297 | 1.00 | 10.87 |
| ATOM | 1817 | CB | ILE | 419 | 6.801 | 50.910 | 74.297 | 1.00 | 12.79 |
| ATOM | 1818 | CG2 | ILE | 419 | 5.976 | 51.677 | 73.171 | 1.00 | 9.94 |
| ATOM | 1819 | CG1 | ILE | 419 | 7.857 | 49.987 | 73.647 | 1.00 | 9.84 |
| ATOM | 1820 | CD1 | ILE | 419 | 8.638 | 49.121 | 74.690 | 1.00 | 9.11 |
| ATOM | 1821 | C | ILE | 419 | 8.363 | 52.931 | 74.574 | 1.00 | 12.14 |
| ATOM | 1822 | O | ILE | 419 | 9.524 | 52.659 | 74.185 | 1.00 | 11.23 |
| ATOM | 1823 | N | LYS | 420 | 7.826 | 54.154 | 74.460 | 1.00 | 8.11 |
| ATOM | 1825 | CA | LYS | 420 | 8.552 | 55.237 | 73.788 | 1.00 | 7.87 |
| ATOM | 1826 | CB | LYS | 420 | 7.615 | 56.403 | 73.489 | 1.00 | 6.52 |
| ATOM | 1827 | CG | LYS | 420 | 6.541 | 56.046 | 72.445 | 1.00 | 5.66 |
| ATOM | 1828 | CD | LYS | 420 | 7.131 | 55.633 | 71.125 | 1.00 | 5.00 |
| ATOM | 1829 | CE | LYS | 420 | 5.982 | 55.321 | 70.158 | 1.00 | 4.07 |
| ATOM | 1830 | NZ | LYS | 420 | 6.425 | 54.699 | 68.865 | 1.00 | 5.92 |
| ATOM | 1834 | C | LYS | 420 | 9.711 | 55.725 | 74.645 | 1.00 | 6.25 |
| ATOM | 1835 | O | LYS | 420 | 10.633 | 56.357 | 74.124 | 1.00 | 9.15 |
| ATOM | 1836 | N | SER | 421 | 9.622 | 55.508 | 75.954 | 0.84 | 3.44 |
| ATOM | 1838 | CA | SER | 421 | 10.712 | 55.855 | 76.853 | 0.84 | 7.00 |
| ATOM | 1839 | CB | SER | 421 | 10.320 | 55.736 | 78.334 | 0.84 | 5.36 |
| ATOM | 1840 | OG | SER | 421 | 9.199 | 56.532 | 78.638 | 0.84 | 11.88 |
| ATOM | 1842 | C | SER | 421 | 11.825 | 54.875 | 76.566 | 0.84 | 6.33 |
| ATOM | 1843 | O | SER | 421 | 12.967 | 55.220 | 76.622 | 0.84 | 5.12 |
| ATOM | 1844 | N | ASP | 422 | 11.484 | 53.607 | 76.334 | 1.00 | 9.14 |
| ATOM | 1846 | CA | ASP | 422 | 12.517 | 52.597 | 76.025 | 1.00 | 8.70 |
| ATOM | 1847 | CB | ASP | 422 | 11.885 | 51.196 | 75.904 | 1.00 | 12.07 |
| ATOM | 1848 | CG | ASP | 422 | 11.572 | 50.563 | 77.259 | 1.00 | 12.39 |
| ATOM | 1849 | OD1 | ASP | 422 | 12.056 | 51.022 | 78.327 | 1.00 | 10.34 |
| ATOM | 1850 | OD2 | ASP | 422 | 10.816 | 49.582 | 77.246 | 1.00 | 11.32 |
| ATOM | 1851 | C | ASP | 422 | 13.184 | 52.950 | 74.686 | 1.00 | 6.58 |
| ATOM | 1852 | O | ASP | 422 | 14.369 | 52.729 | 74.503 | 1.00 | 8.49 |
| ATOM | 1853 | N | VAL | 423 | 12.406 | 53.490 | 73.743 | 1.00 | 5.50 |
| ATOM | 1855 | CA | VAL | 423 | 12.958 | 53.869 | 72.455 | 1.00 | 6.60 |
| ATOM | 1856 | CB | VAL | 423 | 11.861 | 54.360 | 71.466 | 1.00 | 5.46 |
| ATOM | 1857 | CG1 | VAL | 423 | 12.489 | 55.077 | 70.272 | 1.00 | 6.60 |
| ATOM | 1858 | CG2 | VAL | 423 | 11.039 | 53.179 | 70.942 | 1.00 | 7.26 |
| ATOM | 1859 | C | VAL | 423 | 14.038 | 54.958 | 72.656 | 1.00 | 7.12 |
| ATOM | 1860 | O | VAL | 423 | 15.065 | 54.917 | 72.020 | 1.00 | 5.42 |
| ATOM | 1861 | N | TRP | 424 | 13.783 | 55.910 | 73.554 | 1.00 | 6.23 |
| ATOM | 1863 | CA | TRP | 424 | 14.763 | 56.979 | 73.845 | 1.00 | 6.55 |
| ATOM | 1864 | CB | TRP | 424 | 14.208 | 57.882 | 74.954 | 1.00 | 5.57 |
| ATOM | 1865 | CG | TRP | 424 | 15.192 | 58.959 | 75.346 | 1.00 | 7.05 |
| ATOM | 1866 | CD2 | TRP | 424 | 15.151 | 60.335 | 74.967 | 1.00 | 6.30 |
| ATOM | 1867 | CE2 | TRP | 424 | 16.308 | 60.951 | 75.529 | 1.00 | 8.37 |
| ATOM | 1868 | CE3 | TRP | 424 | 14.245 | 61.121 | 74.229 | 1.00 | 7.64 |
| ATOM | 1869 | CD1 | TRP | 424 | 16.318 | 58.800 | 76.109 | 1.00 | 5.60 |
| ATOM | 1870 | NE1 | TRP | 424 | 16.980 | 59.990 | 76.219 | 1.00 | 5.35 |
| ATOM | 1872 | CZ2 | TRP | 424 | 16.590 | 62.315 | 75.375 | 1.00 | 10.22 |
| ATOM | 1873 | CZ3 | TRP | 424 | 14.518 | 62.503 | 74.075 | 1.00 | 9.61 |
| ATOM | 1874 | CH2 | TRP | 424 | 15.680 | 63.078 | 74.643 | 1.00 | 7.29 |
| ATOM | 1875 | C | TRP | 424 | 16.060 | 56.280 | 74.363 | 1.00 | 6.20 |
| ATOM | 1876 | O | TRP | 424 | 17.158 | 56.541 | 73.879 | 1.00 | 7.99 |
| ATOM | 1877 | N | SER | 425 | 15.885 | 55.412 | 75.355 | 0.74 | 3.20 |
| ATOM | 1879 | CA | SER | 425 | 16.990 | 54.663 | 75.922 | 0.74 | 4.31 |
| ATOM | 1880 | CB | SER | 425 | 16.495 | 53.701 | 77.008 | 0.74 | 2.00 |
| ATOM | 1881 | OG | SER | 425 | 15.803 | 54.395 | 78.026 | 0.74 | 2.00 |
| ATOM | 1883 | C | SER | 425 | 17.737 | 53.913 | 74.846 | 0.74 | 3.33 |
| ATOM | 1884 | O | SER | 425 | 18.950 | 53.850 | 74.888 | 0.74 | 2.42 |

TABLE 1-continued

Coordinates of Lck bound with PP2

| | Atom Type | Res | # | X | Y | Z | Occ | B |
|---|---|---|---|---|---|---|---|---|
| ATOM | 1885 | N | PHE | 426 | 17.007 | 53.293 | 73.903 | 1.00 | 5.45 |
| ATOM | 1887 | CA | PHE | 426 | 17.657 | 52.573 | 72.797 | 1.00 | 6.49 |
| ATOM | 1888 | CB | PHE | 426 | 16.623 | 51.923 | 71.873 | 1.00 | 4.63 |
| ATOM | 1889 | CG | PHE | 426 | 17.220 | 51.113 | 70.753 | 1.00 | 7.25 |
| ATOM | 1890 | CD1 | PHE | 426 | 17.757 | 49.839 | 70.993 | 1.00 | 7.49 |
| ATOM | 1891 | CD2 | PHE | 426 | 17.257 | 51.607 | 69.464 | 1.00 | 5.54 |
| ATOM | 1892 | CE1 | PHE | 426 | 18.321 | 49.102 | 69.956 | 1.00 | 7.13 |
| ATOM | 1893 | CE2 | PHE | 426 | 17.820 | 50.860 | 68.434 | 1.00 | 7.86 |
| ATOM | 1894 | CZ | PHE | 426 | 18.354 | 49.600 | 68.698 | 1.00 | 5.60 |
| ATOM | 1895 | C | PHE | 426 | 18.584 | 53.554 | 72.015 | 1.00 | 8.58 |
| ATOM | 1896 | O | PHE | 426 | 19.686 | 53.185 | 71.563 | 1.00 | 5.97 |
| ATOM | 1897 | N | GLY | 427 | 18.113 | 54.784 | 71.810 | 1.00 | 6.15 |
| ATOM | 1899 | CA | GLY | 427 | 18.949 | 55.784 | 71.131 | 1.00 | 6.03 |
| ATOM | 1900 | C | GLY | 427 | 20.276 | 55.953 | 71.872 | 1.00 | 4.54 |
| ATOM | 1901 | O | GLY | 427 | 21.341 | 55.962 | 71.238 | 1.00 | 5.34 |
| ATOM | 1902 | N | ILE | 428 | 20.215 | 56.014 | 73.195 | 1.00 | 4.21 |
| ATOM | 1904 | CA | ILE | 428 | 21.401 | 56.164 | 74.015 | 1.00 | 3.97 |
| ATOM | 1905 | CB | ILE | 428 | 21.090 | 56.406 | 75.483 | 1.00 | 4.96 |
| ATOM | 1906 | CG2 | ILE | 428 | 22.463 | 56.522 | 76.258 | 1.00 | 2.19 |
| ATOM | 1907 | CG1 | ILE | 428 | 20.164 | 57.671 | 75.681 | 1.00 | 7.36 |
| ATOM | 1908 | CD1 | ILE | 428 | 20.782 | 58.976 | 75.203 | 1.00 | 3.13 |
| ATOM | 1909 | C | ILE | 428 | 22.297 | 54.873 | 73.914 | 1.00 | 8.27 |
| ATOM | 1910 | O | ILE | 428 | 23.547 | 54.933 | 73.888 | 1.00 | 4.68 |
| ATOM | 1911 | N | LEU | 429 | 21.637 | 53.711 | 73.972 | 1.00 | 7.27 |
| ATOM | 1913 | CA | LEU | 429 | 22.327 | 52.410 | 73.827 | 1.00 | 6.62 |
| ATOM | 1914 | CB | LEU | 429 | 21.296 | 51.253 | 73.959 | 1.00 | 6.35 |
| ATOM | 1915 | CG | LEU | 429 | 21.845 | 49.877 | 74.329 | 1.00 | 11.27 |
| ATOM | 1916 | CD1 | LEU | 429 | 20.673 | 48.933 | 74.756 | 1.00 | 8.31 |
| ATOM | 1917 | CD2 | LEU | 429 | 22.560 | 49.308 | 73.139 | 1.00 | 12.01 |
| ATOM | 1918 | C | LEU | 429 | 23.106 | 52.375 | 72.491 | 1.00 | 6.20 |
| ATOM | 1919 | O | LEU | 429 | 24.256 | 51.910 | 72.453 | 1.00 | 5.46 |
| ATOM | 1920 | N | LEU | 430 | 22.530 | 52.859 | 71.384 | 1.00 | 6.35 |
| ATOM | 1922 | CA | LEU | 430 | 23.257 | 52.883 | 70.118 | 1.00 | 7.66 |
| ATOM | 1923 | CB | LEU | 430 | 22.405 | 53.531 | 69.001 | 1.00 | 9.11 |
| ATOM | 1924 | CG | LEU | 430 | 21.088 | 52.860 | 68.575 | 1.00 | 12.71 |
| ATOM | 1925 | CD1 | LEU | 430 | 20.402 | 53.710 | 67.469 | 1.00 | 12.19 |
| ATOM | 1926 | CD2 | LEU | 430 | 21.364 | 51.433 | 68.038 | 1.00 | 11.08 |
| ATOM | 1927 | C | LEU | 430 | 24.609 | 53.674 | 70.239 | 1.00 | 8.68 |
| ATOM | 1928 | O | LEU | 430 | 25.574 | 53.393 | 69.501 | 1.00 | 7.43 |
| ATOM | 1929 | N | THR | 431 | 24.651 | 54.720 | 71.075 | 1.00 | 8.14 |
| ATOM | 1931 | CA | THR | 431 | 25.921 | 55.506 | 71.257 | 1.00 | 8.38 |
| ATOM | 1932 | CB | THR | 431 | 25.741 | 56.859 | 72.021 | 1.00 | 4.90 |
| ATOM | 1933 | OG1 | THR | 431 | 25.469 | 56.643 | 73.392 | 1.00 | 3.60 |
| ATOM | 1935 | CG2 | THR | 431 | 24.529 | 57.704 | 71.425 | 1.00 | 5.55 |
| ATOM | 1936 | C | THR | 431 | 26.923 | 54.631 | 72.005 | 1.00 | 8.62 |
| ATOM | 1937 | O | THR | 431 | 28.125 | 54.631 | 71.695 | 1.00 | 9.17 |
| ATOM | 1938 | N | GLU | 432 | 26.424 | 53.860 | 72.967 | 1.00 | 7.90 |
| ATOM | 1940 | CA | GLU | 432 | 27.328 | 52.951 | 73.694 | 1.00 | 10.08 |
| ATOM | 1941 | CB | GLU | 432 | 26.627 | 52.186 | 74.815 | 1.00 | 5.99 |
| ATOM | 1942 | CG | GLU | 432 | 26.143 | 53.057 | 75.932 | 1.00 | 10.88 |
| ATOM | 1943 | CD | GLU | 432 | 25.363 | 52.313 | 76.946 | 1.00 | 9.59 |
| ATOM | 1944 | OE1 | GLU | 432 | 24.175 | 52.004 | 76.677 | 1.00 | 10.03 |
| ATOM | 1945 | OE2 | GLU | 432 | 25.905 | 52.072 | 78.050 | 1.00 | 11.37 |
| ATOM | 1946 | C | GLU | 432 | 27.926 | 51.942 | 72.745 | 1.00 | 8.62 |
| ATOM | 1947 | O | GLU | 432 | 29.097 | 51.536 | 72.916 | 1.00 | 11.14 |
| ATOM | 1948 | N | ILE | 433 | 27.137 | 51.487 | 71.778 | 1.00 | 8.61 |
| ATOM | 1950 | CA | ILE | 433 | 27.604 | 50.462 | 70.831 | 1.00 | 10.01 |
| ATOM | 1951 | CB | ILE | 433 | 26.413 | 49.891 | 69.976 | 1.00 | 10.36 |
| ATOM | 1952 | CG2 | ILE | 433 | 26.928 | 49.148 | 68.750 | 1.00 | 9.69 |
| ATOM | 1953 | CG1 | ILE | 433 | 25.555 | 48.915 | 79.793 | 1.00 | 7.16 |
| ATOM | 1954 | CD1 | ILE | 433 | 24.341 | 48.431 | 69.943 | 1.00 | 9.87 |
| ATOM | 1955 | C | ILE | 433 | 28.702 | 50.975 | 69.916 | 1.00 | 13.45 |
| ATOM | 1956 | O | ILE | 433 | 29.819 | 50.391 | 69.800 | 1.00 | 13.31 |
| ATOM | 1957 | N | VAL | 434 | 28.426 | 52.119 | 69.304 | 1.00 | 10.37 |
| ATOM | 1959 | CA | VAL | 434 | 29.357 | 52.736 | 68.363 | 1.00 | 13.65 |
| ATOM | 1960 | CB | VAL | 434 | 28.624 | 53.819 | 67.515 | 1.00 | 14.15 |
| ATOM | 1961 | CG1 | VAL | 434 | 28.526 | 55.101 | 68.291 | 1.00 | 12.09 |
| ATOM | 1962 | CG2 | VAL | 434 | 29.335 | 54.029 | 66.212 | 1.00 | 17.74 |
| ATOM | 1963 | C | VAL | 434 | 30.635 | 53.329 | 69.002 | 1.00 | 12.97 |
| ATOM | 1964 | O | VAL | 434 | 31.570 | 53.674 | 68.308 | 1.00 | 17.99 |
| ATOM | 1965 | N | THR | 435 | 30.646 | 53.500 | 70.314 | 1.00 | 11.64 |
| ATOM | 1967 | CA | THR | 435 | 31.815 | 54.028 | 70.993 | 1.00 | 11.78 |
| ATOM | 1968 | CB | THR | 435 | 31.458 | 55.206 | 71.945 | 1.00 | 12.27 |
| ATOM | 1969 | OG1 | THR | 435 | 30.573 | 54.737 | 72.967 | 1.00 | 10.57 |

TABLE 1-continued

Coordinates of Lck bound with PP2

| | Atom Type | Res | # | X | Y | Z | Occ | B |
|---|---|---|---|---|---|---|---|---|
| ATOM | 1971 | CG2 | THR | 435 | 30.795 | 56.338 | 71.192 | 1.00 | 8.79 |
| ATOM | 1972 | C | THR | 435 | 32.475 | 52.911 | 71.816 | 1.00 | 12.81 |
| ATOM | 1973 | O | THR | 435 | 33.285 | 53.166 | 72.710 | 1.00 | 10.66 |
| ATOM | 1974 | N | HIS | 436 | 32.037 | 51.667 | 71.581 | 1.00 | 12.55 |
| ATOM | 1976 | CA | HIS | 436 | 32.599 | 50.520 | 72.294 | 1.00 | 13.21 |
| ATOM | 1977 | CB | HIS | 436 | 34.044 | 50.249 | 71.838 | 1.00 | 16.87 |
| ATOM | 1978 | CG | HIS | 436 | 34.139 | 49.679 | 70.445 | 1.00 | 18.59 |
| ATOM | 1979 | CD2 | HIS | 436 | 34.228 | 50.288 | 69.233 | 1.00 | 20.86 |
| ATOM | 1980 | ND1 | HIS | 436 | 34.148 | 48.318 | 70.189 | 1.00 | 20.34 |
| ATOM | 1982 | CE1 | HIS | 436 | 34.241 | 48.112 | 68.884 | 1.00 | 19.64 |
| ATOM | 1983 | NE2 | HIS | 436 | 34.287 | 49.287 | 68.280 | 1.00 | 21.05 |
| ATOM | 1985 | C | HIS | 436 | 32.485 | 50.659 | 73.793 | 1.00 | 13.02 |
| ATOM | 1986 | O | HIS | 436 | 33.406 | 50.445 | 74.542 | 1.00 | 12.87 |
| ATOM | 1987 | N | GLY | 437 | 31.297 | 51.065 | 74.231 | 1.00 | 9.87 |
| ATOM | 1989 | CA | GLY | 437 | 31.041 | 51.176 | 75.644 | 1.00 | 9.32 |
| ATOM | 1990 | C | GLY | 437 | 31.324 | 52.449 | 76.409 | 1.00 | 10.65 |
| ATOM | 1991 | O | GLY | 437 | 31.235 | 52.408 | 77.628 | 1.00 | 14.03 |
| ATOM | 1992 | N | ARG | 438 | 31.619 | 53.559 | 75.744 | 0.58 | 7.95 |
| ATOM | 1994 | CA | ARG | 438 | 31.865 | 54.845 | 76.434 | 0.58 | 9.13 |
| ATOM | 1995 | CB | ARG | 438 | 32.379 | 55.911 | 75.427 | 0.58 | 7.13 |
| ATOM | 1996 | CG | ARG | 438 | 32.767 | 57.291 | 76.016 | 0.58 | 13.47 |
| ATOM | 1997 | CD | ARG | 438 | 33.308 | 58.331 | 74.947 | 0.58 | 15.92 |
| ATOM | 1998 | NE | ARG | 438 | 34.144 | 59.360 | 75.592 | 0.58 | 20.59 |
| ATOM | 2000 | CZ | ARG | 438 | 34.649 | 60.453 | 75.009 | 0.58 | 22.05 |
| ATOM | 2001 | NH1 | ARG | 438 | 34.425 | 60.731 | 73.733 | 0.58 | 24.21 |
| ATOM | 2004 | NH2 | ARG | 438 | 35.402 | 61.282 | 75.713 | 0.58 | 24.37 |
| ATOM | 2007 | C | ARG | 438 | 30.587 | 55.365 | 77.100 | 0.58 | 8.53 |
| ATOM | 2008 | O | ARG | 438 | 29.498 | 55.128 | 76.627 | 0.58 | 7.09 |
| ATOM | 2009 | N | ILE | 439 | 30.752 | 56.178 | 78.145 | 1.00 | 10.66 |
| ATOM | 2011 | CA | ILE | 439 | 29.627 | 56.760 | 78.878 | 1.00 | 10.11 |
| ATOM | 2012 | CB | ILE | 439 | 30.081 | 57.320 | 80.241 | 1.00 | 12.96 |
| ATOM | 2013 | CG2 | ILE | 439 | 28.968 | 58.213 | 80.913 | 1.00 | 10.12 |
| ATOM | 2014 | CG1 | ILE | 439 | 30.427 | 56.146 | 81.159 | 1.00 | 14.57 |
| ATOM | 2015 | CD1 | ILE | 439 | 30.995 | 56.620 | 82.485 | 1.00 | 21.31 |
| ATOM | 2016 | C | ILE | 439 | 29.009 | 57.863 | 78.018 | 1.00 | 8.83 |
| ATOM | 2017 | O | ILE | 439 | 29.737 | 58.628 | 77.301 | 1.00 | 6.52 |
| ATOM | 2018 | N | PRO | 440 | 27.664 | 57.830 | 77.895 | 0.43 | 4.21 |
| ATOM | 2019 | CD | PRO | 440 | 26.757 | 56.807 | 78.445 | 0.43 | 3.42 |
| ATOM | 2020 | CA | PRO | 440 | 26.944 | 58.828 | 77.097 | 0.43 | 2.93 |
| ATOM | 2021 | CB | PRO | 440 | 25.470 | 58.376 | 77.180 | 0.43 | 2.42 |
| ATOM | 2022 | CG | PRO | 440 | 25.406 | 57.469 | 78.330 | 0.43 | 3.41 |
| ATOM | 2023 | C | PRO | 440 | 27.162 | 60.255 | 77.570 | 0.43 | 4.35 |
| ATOM | 2024 | O | PRO | 440 | 27.467 | 60.519 | 78.721 | 0.43 | 2.00 |
| ATOM | 2025 | N | TYR | 441 | 27.030 | 61.180 | 76.626 | 1.00 | 8.70 |
| ATOM | 2027 | CA | TYR | 441 | 27.242 | 62.604 | 76.875 | 1.00 | 11.22 |
| ATOM | 2028 | CB | TYR | 441 | 26.141 | 63.160 | 77.783 | 1.00 | 7.10 |
| ATOM | 2029 | CG | TYR | 441 | 24.737 | 62.959 | 77.225 | 1.00 | 8.04 |
| ATOM | 2030 | CD1 | TYR | 441 | 24.199 | 63.851 | 76.299 | 1.00 | 5.02 |
| ATOM | 2031 | CE1 | TYR | 441 | 22.838 | 63.713 | 75.834 | 1.00 | 6.62 |
| ATOM | 2032 | CD2 | TYR | 441 | 23.922 | 61.910 | 77.693 | 1.00 | 8.69 |
| ATOM | 2033 | CE2 | TYR | 441 | 22.585 | 61.771 | 77.265 | 1.00 | 6.35 |
| ATOM | 2034 | CZ | TYR | 441 | 22.062 | 62.690 | 76.327 | 1.00 | 3.59 |
| ATOM | 2035 | OH | TYR | 441 | 20.791 | 62.567 | 75.906 | 1.00 | 5.76 |
| ATOM | 2037 | C | TYR | 441 | 28.648 | 62.832 | 77.480 | 1.00 | 13.13 |
| ATOM | 2038 | O | TYR | 441 | 28.782 | 63.363 | 78.580 | 1.00 | 13.31 |
| ATOM | 2039 | N | PRO | 442 | 29.708 | 62.474 | 76.720 | 1.00 | 16.46 |
| ATOM | 2040 | CD | PRO | 442 | 29.650 | 62.023 | 75.305 | 1.00 | 16.07 |
| ATOM | 2041 | CA | PRO | 442 | 31.099 | 62.634 | 77.171 | 1.00 | 18.90 |
| ATOM | 2042 | CB | PRO | 442 | 31.912 | 62.369 | 75.896 | 1.00 | 18.71 |
| ATOM | 2043 | CG | PRO | 442 | 31.026 | 61.506 | 75.056 | 1.00 | 17.72 |
| ATOM | 2044 | C | PRO | 442 | 31.408 | 64.054 | 77.734 | 1.00 | 17.44 |
| ATOM | 2045 | O | PRO | 442 | 30.973 | 65.047 | 77.201 | 1.00 | 20.36 |
| ATOM | 2046 | N | GLY | 443 | 31.989 | 64.100 | 78.923 | 1.00 | 19.95 |
| ATOM | 2048 | CA | GLY | 443 | 32.369 | 65.379 | 79.530 | 1.00 | 18.74 |
| ATOM | 2049 | C | GLY | 443 | 31.240 | 66.180 | 80.156 | 1.00 | 18.63 |
| ATOM | 2050 | O | GLY | 443 | 31.448 | 67.364 | 80.517 | 1.00 | 17.80 |
| ATOM | 2051 | N | MET | 444 | 30.074 | 65.556 | 80.346 | 1.00 | 14.22 |
| ATOM | 2053 | CA | MET | 444 | 28.943 | 66.262 | 80.933 | 1.00 | 13.92 |
| ATOM | 2054 | CB | MET | 444 | 27.822 | 66.473 | 79.889 | 1.00 | 12.80 |
| ATOM | 2055 | CG | MET | 444 | 28.284 | 67.080 | 78.562 | 1.00 | 12.70 |
| ATOM | 2056 | SD | MET | 444 | 27.057 | 67.124 | 77.232 | 1.00 | 16.71 |
| ATOM | 2057 | CE | MET | 444 | 25.673 | 67.839 | 78.021 | 1.00 | 14.85 |
| ATOM | 2058 | C | MET | 444 | 28.368 | 65.584 | 82.168 | 1.00 | 12.83 |
| ATOM | 2059 | O | MET | 444 | 28.274 | 64.353 | 82.236 | 1.00 | 13.52 |

TABLE 1-continued

Coordinates of Lck bound with PP2

| | Atom Type | Res | # | X | Y | Z | Occ | B |
|---|---|---|---|---|---|---|---|---|
| ATOM | 2060 | N | THR | 445 | 28.003 | 66.408 | 83.154 | 1.00 | 9.18 |
| ATOM | 2062 | CA | THR | 445 | 27.357 | 65.947 | 84.366 | 1.00 | 9.96 |
| ATOM | 2063 | CB | THR | 445 | 27.543 | 66.962 | 85.483 | 1.00 | 12.35 |
| ATOM | 2064 | OG1 | THR | 445 | 26.889 | 68.200 | 85.111 | 1.00 | 10.49 |
| ATOM | 2066 | CG2 | THR | 445 | 29.034 | 67.191 | 85.707 | 1.00 | 11.76 |
| ATOM | 2067 | C | THR | 445 | 25.858 | 65.853 | 84.049 | 1.00 | 9.07 |
| ATOM | 2068 | O | THR | 445 | 25.413 | 66.299 | 83.020 | 1.00 | 7.89 |
| ATOM | 2069 | N | ASN | 446 | 25.096 | 65.245 | 84.931 | 1.00 | 8.86 |
| ATOM | 2071 | CA | ASN | 446 | 23.646 | 65.121 | 84.749 | 1.00 | 11.83 |
| ATOM | 2072 | CB | ASN | 446 | 23.056 | 64.281 | 85.904 | 1.00 | 12.92 |
| ATOM | 2073 | CG | ASN | 446 | 23.418 | 62.783 | 85.799 | 1.00 | 13.53 |
| ATOM | 2074 | OD1 | ASN | 446 | 23.732 | 62.290 | 84.737 | 1.00 | 14.11 |
| ATOM | 2075 | ND2 | ASN | 446 | 23.300 | 62.072 | 86.888 | 1.00 | 13.23 |
| ATOM | 2078 | C | ASN | 446 | 22.927 | 66.489 | 84.591 | 1.00 | 11.18 |
| ATOM | 2079 | O | ASN | 446 | 22.005 | 66.609 | 83.781 | 1.00 | 12.97 |
| ATOM | 2080 | N | PRO | 447 | 23.260 | 67.502 | 85.440 | 1.00 | 12.38 |
| ATOM | 2081 | CD | PRO | 447 | 23.968 | 67.358 | 86.733 | 1.00 | 10.34 |
| ATOM | 2082 | CA | PRO | 447 | 22.629 | 68.832 | 85.325 | 1.00 | 11.77 |
| ATOM | 2083 | CB | PRO | 447 | 23.305 | 69.620 | 86.456 | 1.00 | 14.03 |
| ATOM | 2084 | CG | PRO | 447 | 23.500 | 68.549 | 87.537 | 1.00 | 12.63 |
| ATOM | 2085 | C | PRO | 447 | 22.883 | 69.452 | 83.932 | 1.00 | 10.06 |
| ATOM | 2086 | O | PRO | 447 | 21.989 | 70.096 | 83.348 | 1.00 | 10.62 |
| ATOM | 2087 | N | GLU | 448 | 24.095 | 69.261 | 83.379 | 1.00 | 9.60 |
| ATOM | 2089 | CA | GLU | 448 | 24.435 | 69.741 | 82.037 | 1.00 | 9.02 |
| ATOM | 2090 | CB | GLU | 448 | 25.922 | 69.533 | 81.737 | 1.00 | 11.92 |
| ATOM | 2091 | CG | GLU | 448 | 26.842 | 70.583 | 82.471 | 1.00 | 14.25 |
| ATOM | 2092 | CD | GLU | 448 | 28.303 | 70.263 | 82.243 | 1.00 | 17.10 |
| ATOM | 2093 | OE1 | GLU | 448 | 28.746 | 69.091 | 82.455 | 1.00 | 15.79 |
| ATOM | 2094 | OE2 | GLU | 448 | 29.014 | 71.173 | 81.795 | 1.00 | 20.35 |
| ATOM | 2095 | C | GLU | 448 | 23.633 | 69.041 | 80.944 | 1.00 | 8.80 |
| ATOM | 2096 | O | GLU | 448 | 23.277 | 69.617 | 79.909 | 1.00 | 7.80 |
| ATOM | 2097 | N | VAL | 449 | 23.446 | 67.733 | 81.115 | 1.00 | 8.54 |
| ATOM | 2099 | CA | VAL | 449 | 22.674 | 66.953 | 80.127 | 1.00 | 8.45 |
| ATOM | 2100 | CB | VAL | 449 | 22.727 | 65.414 | 80.492 | 1.00 | 7.43 |
| ATOM | 2101 | CG1 | VAL | 449 | 21.663 | 64.624 | 79.728 | 1.00 | 9.15 |
| ATOM | 2102 | CG2 | VAL | 449 | 24.090 | 64.862 | 80.141 | 1.00 | 11.63 |
| ATOM | 2103 | C | VAL | 449 | 21.218 | 67.497 | 80.157 | 1.00 | 5.64 |
| ATOM | 2104 | O | VAL | 449 | 20.650 | 67.845 | 79.138 | 1.00 | 7.70 |
| ATOM | 2105 | N | ILE | 450 | 20.649 | 67.631 | 81.337 | 0.60 | 2.91 |
| ATOM | 2107 | CA | ILE | 450 | 19.274 | 68.141 | 81.460 | 0.60 | 4.78 |
| ATOM | 2108 | CB | ILE | 450 | 18.870 | 68.177 | 82.962 | 0.60 | 3.17 |
| ATOM | 2109 | CG2 | ILE | 450 | 17.538 | 68.969 | 83.185 | 0.60 | 4.56 |
| ATOM | 2110 | CG1 | ILE | 450 | 18.733 | 66.721 | 83.454 | 0.60 | 3.56 |
| ATOM | 2111 | CD1 | ILE | 450 | 18.783 | 66.570 | 84.923 | 0.60 | 4.70 |
| ATOM | 2112 | C | ILE | 450 | 19.061 | 69.514 | 80.798 | 0.60 | 5.71 |
| ATOM | 2113 | O | ILE | 450 | 18.146 | 69.734 | 79.987 | 0.60 | 2.44 |
| ATOM | 2114 | N | GLN | 451 | 20.027 | 70.377 | 81.055 | 1.00 | 9.36 |
| ATOM | 2116 | CA | GLN | 451 | 20.053 | 71.754 | 80.559 | 1.00 | 14.03 |
| ATOM | 2117 | CB | GLN | 451 | 21.248 | 72.487 | 81.211 | 1.00 | 19.90 |
| ATOM | 2118 | CG | GLN | 451 | 21.416 | 73.981 | 80.917 | 1.00 | 28.98 |
| ATOM | 2119 | CD | GLN | 451 | 22.705 | 74.544 | 81.557 | 1.00 | 34.25 |
| ATOM | 2120 | OE1 | GLN | 451 | 23.830 | 74.071 | 81.261 | 1.00 | 36.31 |
| ATOM | 2121 | NE2 | GLN | 451 | 22.553 | 75.546 | 82.431 | 1.00 | 36.66 |
| ATOM | 2124 | C | GLN | 451 | 20.166 | 71.714 | 79.049 | 1.00 | 12.84 |
| ATOM | 2125 | O | GLN | 451 | 19.441 | 72.402 | 78.335 | 1.00 | 11.56 |
| ATOM | 2126 | N | ASN | 452 | 21.069 | 70.891 | 78.527 | 1.00 | 11.36 |
| ATOM | 2128 | CA | ASN | 452 | 21.196 | 70.819 | 77.083 | 1.00 | 10.00 |
| ATOM | 2129 | CB | ASN | 452 | 22.424 | 70.010 | 76.693 | 1.00 | 12.65 |
| ATOM | 2130 | CG | ASN | 452 | 23.683 | 70.865 | 76.564 | 1.00 | 16.71 |
| ATOM | 2131 | OD1 | ASN | 452 | 24.578 | 70.539 | 75.787 | 1.00 | 23.16 |
| ATOM | 2132 | ND2 | ASN | 452 | 23.759 | 71.937 | 77.308 | 1.00 | 18.51 |
| ATOM | 2135 | C | ASN | 452 | 19.917 | 70.251 | 76.435 | 1.00 | 9.75 |
| ATOM | 2136 | O | ASN | 452 | 19.387 | 70.768 | 75.401 | 1.00 | 8.53 |
| ATOM | 2137 | N | LEU | 453 | 19.386 | 69.174 | 77.007 | 1.00 | 9.20 |
| ATOM | 2139 | CA | LEU | 453 | 18.160 | 68.612 | 76.436 | 1.00 | 8.71 |
| ATOM | 2140 | CB | LEU | 453 | 17.687 | 67.411 | 77.236 | 1.00 | 9.28 |
| ATOM | 2141 | CG | LEU | 453 | 18.624 | 66.186 | 77.152 | 1.00 | 9.86 |
| ATOM | 2142 | CD1 | LEU | 453 | 18.104 | 65.089 | 78.051 | 1.00 | 7.88 |
| ATOM | 2143 | CD2 | LEU | 453 | 18.697 | 65.762 | 75.664 | 1.00 | 11.07 |
| ATOM | 2144 | C | LEU | 453 | 17.046 | 69.650 | 76.404 | 1.00 | 8.57 |
| ATOM | 2145 | O | LEU | 453 | 16.381 | 69.785 | 75.435 | 1.00 | 10.42 |
| ATOM | 2146 | N | GLU | 454 | 16.875 | 70.396 | 77.490 | 1.00 | 11.11 |
| ATOM | 2148 | CA | GLU | 454 | 15.798 | 71.398 | 77.560 | 1.00 | 11.88 |
| ATOM | 2149 | CB | GLU | 454 | 15.629 | 71.866 | 79.011 | 1.00 | 15.37 |

TABLE 1-continued

Coordinates of Lck bound with PP2

| | Atom Type | Res | # | X | Y | Z | Occ | B |
|---|---|---|---|---|---|---|---|---|
| ATOM | 2150 | CG | GLU | 454 | 15.194 | 70.672 | 79.903 | 1.00 | 18.92 |
| ATOM | 2151 | CD | GLU | 454 | 14.980 | 70.997 | 81.371 | 1.00 | 23.60 |
| ATOM | 2152 | OE1 | GLU | 454 | 15.583 | 71.964 | 81.885 | 1.00 | 26.49 |
| ATOM | 2153 | OE2 | GLU | 454 | 14.211 | 70.241 | 82.038 | 1.00 | 25.97 |
| ATOM | 2154 | C | GLU | 454 | 15.913 | 72.548 | 76.534 | 1.00 | 11.10 |
| ATOM | 2155 | O | GLU | 454 | 14.905 | 73.160 | 76.138 | 1.00 | 12.14 |
| ATOM | 2156 | N | ARG | 455 | 17.115 | 72.728 | 75.985 | 1.00 | 9.92 |
| ATOM | 2158 | CA | ARG | 455 | 17.394 | 73.739 | 74.943 | 1.00 | 9.09 |
| ATOM | 2159 | CB | ARG | 455 | 18.904 | 74.071 | 74.933 | 1.00 | 11.52 |
| ATOM | 2160 | CG | ARG | 455 | 19.385 | 74.722 | 76.196 | 1.00 | 13.92 |
| ATOM | 2161 | CD | ARG | 455 | 20.793 | 75.252 | 76.049 | 1.00 | 15.24 |
| ATOM | 2162 | NE | ARG | 455 | 20.845 | 76.406 | 75.150 | 1.00 | 12.95 |
| ATOM | 2164 | CZ | ARG | 455 | 21.958 | 77.079 | 74.862 | 1.00 | 12.76 |
| ATOM | 2165 | NH1 | ARG | 455 | 23.121 | 76.705 | 75.392 | 1.00 | 11.45 |
| ATOM | 2168 | NH2 | ARG | 455 | 21.906 | 78.149 | 74.069 | 1.00 | 11.06 |
| ATOM | 2171 | C | ARG | 455 | 17.070 | 73.160 | 73.571 | 1.00 | 9.53 |
| ATOM | 2172 | O | ARG | 455 | 17.085 | 73.844 | 72.551 | 1.00 | 11.25 |
| ATOM | 2173 | N | GLY | 456 | 16.808 | 71.853 | 73.529 | 1.00 | 8.70 |
| ATOM | 2175 | CA | GLY | 456 | 16.561 | 71.205 | 72.263 | 1.00 | 6.55 |
| ATOM | 2176 | C | GLY | 456 | 17.796 | 70.526 | 71.681 | 1.00 | 5.96 |
| ATOM | 2177 | O | GLY | 456 | 17.750 | 70.047 | 70.562 | 1.00 | 8.41 |
| ATOM | 2178 | N | TYR | 457 | 18.922 | 70.530 | 72.390 | 1.00 | 7.30 |
| ATOM | 2180 | CA | TYR | 457 | 20.131 | 69.880 | 71.858 | 1.00 | 7.68 |
| ATOM | 2181 | CB | TYR | 457 | 21.401 | 70.324 | 72.579 | 1.00 | 7.52 |
| ATOM | 2182 | CG | TYR | 457 | 21.840 | 71.776 | 72.424 | 1.00 | 9.01 |
| ATOM | 2183 | CD1 | TYR | 457 | 21.454 | 72.534 | 71.331 | 1.00 | 10.16 |
| ATOM | 2184 | CE1 | TYR | 457 | 21.989 | 73.844 | 71.097 | 1.00 | 10.10 |
| ATOM | 2185 | CD2 | TYR | 457 | 22.751 | 72.319 | 73.310 | 1.00 | 11.27 |
| ATOM | 2186 | CE2 | TYR | 457 | 23.290 | 73.622 | 73.108 | 1.00 | 12.24 |
| ATOM | 2187 | CZ | TYR | 457 | 22.897 | 74.360 | 71.996 | 1.00 | 11.69 |
| ATOM | 2188 | OH | TYR | 457 | 23.426 | 75.627 | 71.811 | 1.00 | 10.39 |
| ATOM | 2190 | C | TYR | 457 | 20.004 | 68.416 | 72.217 | 1.00 | 7.71 |
| ATOM | 2191 | O | TYR | 457 | 19.218 | 68.070 | 73.085 | 1.00 | 5.65 |
| ATOM | 2192 | N | ARG | 458 | 20.804 | 67.586 | 71.565 | 1.00 | 6.53 |
| ATOM | 2194 | CA | ARG | 458 | 20.848 | 66.148 | 71.900 | 1.00 | 7.08 |
| ATOM | 2195 | CB | ARG | 458 | 20.196 | 65.324 | 70.798 | 1.00 | 4.26 |
| ATOM | 2196 | CG | ARG | 458 | 18.641 | 65.551 | 70.676 | 1.00 | 7.42 |
| ATOM | 2197 | CD | ARG | 458 | 17.955 | 65.113 | 71.973 | 1.00 | 5.42 |
| ATOM | 2198 | NE | ARG | 458 | 16.498 | 65.301 | 71.900 | 1.00 | 4.88 |
| ATOM | 2200 | CZ | ARG | 458 | 15.829 | 66.318 | 72.442 | 1.00 | 9.16 |
| ATOM | 2201 | NH1 | ARG | 458 | 16.486 | 67.283 | 73.103 | 1.00 | 9.98 |
| ATOM | 2204 | NH2 | ARG | 458 | 14.483 | 66.325 | 72.396 | 1.00 | 5.17 |
| ATOM | 2207 | C | ARG | 458 | 22.343 | 65.863 | 71.951 | 1.00 | 9.32 |
| ATOM | 2208 | O | ARG | 458 | 23.171 | 66.756 | 71.695 | 1.00 | 7.42 |
| ATOM | 2209 | N | MET | 459 | 22.705 | 64.617 | 72.272 | 1.00 | 8.38 |
| ATOM | 2211 | CA | MET | 459 | 24.122 | 64.237 | 72.331 | 1.00 | 8.96 |
| ATOM | 2212 | CB | MET | 459 | 24.260 | 62.724 | 72.596 | 1.00 | 6.66 |
| ATOM | 2213 | CG | MET | 459 | 25.577 | 62.369 | 73.205 | 1.00 | 8.80 |
| ATOM | 2214 | SD | MET | 459 | 25.707 | 60.524 | 73.364 | 1.00 | 9.21 |
| ATOM | 2215 | CE | MET | 459 | 24.390 | 60.196 | 74.315 | 1.00 | 9.63 |
| ATOM | 2216 | C | MET | 459 | 24.880 | 64.547 | 71.059 | 1.00 | 7.14 |
| ATOM | 2217 | O | MET | 459 | 24.436 | 64.284 | 69.955 | 1.00 | 7.18 |
| ATOM | 2218 | N | VAL | 460 | 26.067 | 65.113 | 71.243 | 1.00 | 8.38 |
| ATOM | 2220 | CA | VAL | 460 | 26.977 | 65.433 | 70.167 | 1.00 | 10.29 |
| ATOM | 2221 | CB | VAL | 460 | 28.318 | 65.999 | 70.764 | 1.00 | 13.33 |
| ATOM | 2222 | CG1 | VAL | 460 | 29.387 | 66.083 | 69.725 | 1.00 | 12.10 |
| ATOM | 2223 | CG2 | VAL | 460 | 28.070 | 67.394 | 71.423 | 1.00 | 16.34 |
| ATOM | 2224 | C | VAL | 460 | 27.275 | 64.124 | 69.428 | 1.00 | 11.62 |
| ATOM | 2225 | O | VAL | 460 | 27.376 | 63.081 | 70.059 | 1.00 | 13.62 |
| ATOM | 2226 | N | ARG | 461 | 27.414 | 64.195 | 68.108 | 1.00 | 11.56 |
| ATOM | 2228 | CA | ARG | 461 | 27.748 | 63.033 | 67.276 | 1.00 | 14.53 |
| ATOM | 2229 | CB | ARG | 461 | 28.101 | 63.456 | 65.828 | 1.00 | 14.99 |
| ATOM | 2230 | CG | ARG | 461 | 26.963 | 64.094 | 65.000 | 1.00 | 14.92 |
| ATOM | 2231 | CD | ARG | 461 | 27.431 | 64.655 | 63.638 | 1.00 | 17.39 |
| ATOM | 2232 | NE | ARG | 461 | 26.286 | 64.991 | 62.776 | 1.00 | 13.44 |
| ATOM | 2234 | CZ | ARG | 461 | 25.599 | 66.141 | 62.785 | 1.00 | 17.27 |
| ATOM | 2235 | NH1 | ARG | 461 | 25.901 | 67.139 | 63.624 | 1.00 | 15.13 |
| ATOM | 2238 | NH2 | ARG | 461 | 24.618 | 66.322 | 61.901 | 1.00 | 12.90 |
| ATOM | 2241 | C | ARG | 461 | 28.994 | 62.358 | 67.822 | 1.00 | 16.47 |
| ATOM | 2242 | O | ART | 461 | 30.049 | 63.002 | 67.966 | 1.00 | 15.87 |
| ATOM | 2243 | N | PRO | 462 | 28.887 | 61.062 | 68.179 | 1.00 | 14.68 |
| ATOM | 2244 | CD | PRO | 462 | 27.675 | 60.227 | 68.325 | 1.00 | 15.13 |
| ATOM | 2245 | CA | PRO | 462 | 30.075 | 60.385 | 68.697 | 1.00 | 16.27 |
| ATOM | 2246 | CB | PRO | 462 | 29.536 | 58.998 | 69.123 | 1.00 | 14.87 |

TABLE 1-continued

Coordinates of Lck bound with PP2

| | Atom Type | Res | # | X | Y | Z | Occ | B |
|---|---|---|---|---|---|---|---|---|
| ATOM | 2247 | CG | PRO | 462 | 28.058 | 59.285 | 69.459 | 1.00 | 15.13 |
| ATOM | 2248 | C | PRO | 462 | 31.118 | 60.275 | 67.600 | 1.00 | 17.36 |
| ATOM | 2249 | O | PRO | 462 | 30.816 | 60.340 | 66.414 | 1.00 | 14.94 |
| ATOM | 2250 | N | ASP | 463 | 32.380 | 60.214 | 68.025 | 1.00 | 21.83 |
| ATOM | 2252 | CA | ASP | 463 | 33.503 | 60.072 | 67.108 | 1.00 | 23.79 |
| ATOM | 2253 | CB | ASP | 463 | 34.808 | 59.889 | 67.883 | 1.00 | 27.14 |
| ATOM | 2254 | CG | ASP | 463 | 35.214 | 61.133 | 68.627 | 1.00 | 31.66 |
| ATOM | 2255 | OD1 | ASP | 463 | 34.823 | 62.242 | 68.175 | 1.00 | 32.60 |
| ATOM | 2256 | OD2 | ASP | 463 | 35.918 | 60.996 | 69.662 | 1.00 | 34.15 |
| ATOM | 2257 | C | ASP | 463 | 33.265 | 58.833 | 66.293 | 1.00 | 24.03 |
| ATOM | 2258 | O | ASP | 463 | 32.772 | 57.838 | 66.820 | 1.00 | 25.01 |
| ATOM | 2259 | N | ASN | 464 | 33.574 | 58.926 | 65.003 | 1.00 | 23.24 |
| ATOM | 2261 | CA | ASN | 464 | 33.421 | 57.834 | 64.064 | 1.00 | 24.48 |
| ATOM | 2262 | CB | ASN | 464 | 34.449 | 56.752 | 64.387 | 1.00 | 29.50 |
| ATOM | 2263 | CG | ASN | 464 | 35.856 | 57.299 | 64.371 | 1.00 | 30.61 |
| ATOM | 2264 | OD1 | ASN | 464 | 36.233 | 58.041 | 63.460 | 1.00 | 33.47 |
| ATOM | 2265 | ND2 | ASN | 464 | 36.594 | 57.036 | 65.416 | 1.00 | 32.95 |
| ATOM | 2268 | C | ASN | 464 | 32.023 | 57.235 | 63.914 | 1.00 | 22.41 |
| ATOM | 2269 | O | ASN | 464 | 31.879 | 56.143 | 63.420 | 1.00 | 24.37 |
| ATOM | 2270 | N | CYS | 465 | 30.991 | 57.933 | 64.375 | 1.00 | 19.98 |
| ATOM | 2272 | CA | CYS | 465 | 29.613 | 57.417 | 64.210 | 1.00 | 19.12 |
| ATOM | 2273 | CB | CYS | 465 | 28.680 | 58.077 | 65.244 | 1.00 | 18.06 |
| ATOM | 2274 | SG | CYS | 465 | 26.961 | 57.543 | 65.229 | 1.00 | 16.47 |
| ATOM | 2275 | C | CYS | 465 | 29.095 | 57.739 | 62.792 | 1.00 | 17.54 |
| ATOM | 2276 | O | CYS | 465 | 29.175 | 58.877 | 62.353 | 1.00 | 17.92 |
| ATOM | 2277 | N | PRO | 466 | 28.613 | 56.723 | 62.037 | 1.00 | 15.82 |
| ATOM | 2278 | CD | PRO | 466 | 28.607 | 55.275 | 62.326 | 1.00 | 15.22 |
| ATOM | 2279 | CA | PRO | 466 | 28.090 | 56.994 | 60.694 | 1.00 | 14.66 |
| ATOM | 2280 | CB | PRO | 466 | 27.629 | 55.624 | 60.214 | 1.00 | 15.65 |
| ATOM | 2281 | CG | PRO | 466 | 28.554 | 54.659 | 60.957 | 1.00 | 16.18 |
| ATOM | 2282 | C | PRO | 466 | 26.864 | 57.933 | 60.846 | 1.00 | 14.65 |
| ATOM | 2283 | O | PRO | 466 | 26.012 | 57.759 | 61.757 | 1.00 | 10.18 |
| ATOM | 2284 | N | GLU | 467 | 26.797 | 58.937 | 59.971 | 1.00 | 11.67 |
| ATOM | 2286 | CA | GLU | 467 | 25.696 | 59.912 | 60.010 | 1.00 | 10.18 |
| ATOM | 2287 | CB | GLU | 467 | 25.910 | 60.972 | 58.915 | 1.00 | 9.33 |
| ATOM | 2288 | CG | GLU | 467 | 24.920 | 62.171 | 59.002 | 1.00 | 9.53 |
| ATOM | 2289 | CD | GLU | 467 | 24.934 | 62.883 | 60.360 | 1.00 | 9.62 |
| ATOM | 2290 | OE1 | GLU | 467 | 25.913 | 62.769 | 61.119 | 1.00 | 8.00 |
| ATOM | 2291 | OE2 | GLU | 467 | 23.941 | 63.560 | 60.690 | 1.00 | 11.06 |
| ATOM | 2292 | C | GLU | 467 | 24.284 | 59.256 | 59.915 | 1.00 | 7.67 |
| ATOM | 2293 | O | GLU | 467 | 23.358 | 59.649 | 60.633 | 1.00 | 7.21 |
| ATOM | 2294 | N | GLU | 468 | 24.136 | 58.199 | 59.122 | 0.51 | 3.25 |
| ATOM | 2296 | CA | GLU | 468 | 22.835 | 57.497 | 59.036 | 0.51 | 3.63 |
| ATOM | 2297 | CB | GLU | 468 | 22.901 | 56.340 | 58.038 | 0.51 | 2.00 |
| ATOM | 2298 | CG | GLU | 468 | 23.184 | 56.814 | 56.640 | 0.51 | 3.78 |
| ATOM | 2299 | CD | GLU | 468 | 23.598 | 55.704 | 55.734 | 0.51 | 5.17 |
| ATOM | 2300 | OE1 | GLU | 468 | 22.700 | 55.024 | 55.182 | 0.51 | 3.58 |
| ATOM | 2301 | OE2 | GLU | 468 | 24.826 | 55.518 | 55.577 | 0.51 | 5.21 |
| ATOM | 2302 | C | GLU | 468 | 22.378 | 56.955 | 60.386 | 0.51 | 2.00 |
| ATOM | 2303 | O | GLU | 468 | 21.223 | 57.045 | 60.754 | 0.51 | 2.00 |
| ATOM | 2304 | N | LEU | 469 | 23.326 | 56.408 | 61.142 | 1.00 | 4.11 |
| ATOM | 2306 | CA | LEU | 469 | 23.040 | 55.864 | 62.475 | 1.00 | 5.94 |
| ATOM | 2307 | CB | LEU | 469 | 24.210 | 55.035 | 63.024 | 1.00 | 8.41 |
| ATOM | 2308 | CG | LEU | 469 | 23.924 | 54.377 | 64.411 | 1.00 | 9.32 |
| ATOM | 2309 | CD1 | LEU | 469 | 22.854 | 53.295 | 64.270 | 1.00 | 9.52 |
| ATOM | 2310 | CD2 | LEU | 469 | 25.225 | 53.755 | 64.965 | 1.00 | 9.76 |
| ATOM | 2311 | C | LEU | 469 | 22.741 | 56.996 | 63.456 | 1.00 | 7.74 |
| ATOM | 2312 | O | LEU | 469 | 21.808 | 56.935 | 64.250 | 1.00 | 8.18 |
| ATOM | 2313 | N | TYR | 470 | 23.528 | 58.079 | 63.376 | 1.00 | 7.64 |
| ATOM | 2315 | CA | TYR | 470 | 23.299 | 59.211 | 64.257 | 1.00 | 6.10 |
| ATOM | 2316 | CB | TYR | 470 | 24.370 | 60.325 | 64.013 | 1.00 | 7.72 |
| ATOM | 2317 | CG | TYR | 470 | 24.174 | 61.538 | 64.921 | 1.00 | 6.53 |
| ATOM | 2318 | CD1 | TYR | 470 | 24.304 | 61.421 | 66.298 | 1.00 | 8.09 |
| ATOM | 2319 | CE1 | TYR | 470 | 24.154 | 62.522 | 67.136 | 1.00 | 8.81 |
| ATOM | 2320 | CD2 | TYR | 470 | 23.876 | 62.807 | 64.388 | 1.00 | 7.03 |
| ATOM | 2321 | CE2 | TYR | 470 | 23.712 | 63.923 | 65.213 | 1.00 | 6.75 |
| ATOM | 2322 | CZ | TYR | 470 | 23.857 | 63.782 | 66.587 | 1.00 | 9.17 |
| ATOM | 2323 | OH | TYR | 470 | 23.757 | 64.879 | 67.455 | 1.00 | 8.33 |
| ATOM | 2325 | C | TYR | 470 | 21.879 | 59.764 | 63.976 | 1.00 | 5.88 |
| ATOM | 2326 | O | TYR | 470 | 21.188 | 60.109 | 64.910 | 1.00 | 8.89 |
| ATOM | 2327 | N | GLN | 471 | 21.464 | 59.905 | 62.704 | 1.00 | 6.37 |
| ATOM | 2329 | CA | GLN | 471 | 20.089 | 60.396 | 62.401 | 1.00 | 5.98 |
| ATOM | 2330 | CB | GLN | 471 | 19.902 | 60.709 | 60.903 | 1.00 | 7.06 |
| ATOM | 2331 | CG | GLN | 471 | 20.667 | 62.016 | 60.488 | 1.00 | 8.39 |

TABLE 1-continued

Coordinates of Lck bound with PP2

| Atom Type | Res | # | X | Y | Z | Occ | B |
|---|---|---|---|---|---|---|---|
| ATOM 2332 CD | GLN | 471 | 20.303 | 63.192 | 61.403 | 1.00 | 10.48 |
| ATOM 2333 OE1 | GLN | 471 | 19.102 | 63.454 | 61.641 | 1.00 | 9.64 |
| ATOM 2334 NE2 | GLN | 471 | 21.313 | 63.932 | 61.888 | 1.00 | 8.49 |
| ATOM 2337 C | GLN | 471 | 19.023 | 59.381 | 62.912 | 1.00 | 6.80 |
| ATOM 2338 O | GLN | 471 | 17.924 | 59.746 | 63.251 | 1.00 | 8.94 |
| ATOM 2339 N | LEU | 472 | 19.372 | 58.097 | 63.006 | 1.00 | 7.17 |
| ATOM 2341 CA | LEU | 472 | 18.409 | 57.129 | 63.579 | 1.00 | 6.73 |
| ATOM 2342 CB | LEU | 472 | 18.837 | 55.684 | 63.305 | 1.00 | 7.36 |
| ATOM 2343 CG | LEU | 472 | 17.751 | 54.633 | 63.568 | 1.00 | 4.99 |
| ATOM 2344 CD1 | LEU | 472 | 16.608 | 54.835 | 62.580 | 1.00 | 6.17 |
| ATOM 2345 CD2 | LEU | 472 | 18.386 | 53.219 | 63.432 | 1.00 | 5.99 |
| ATOM 2346 C | LEU | 472 | 18.296 | 57.380 | 65.105 | 1.00 | 7.03 |
| ATOM 2347 O | LEU | 472 | 17.217 | 57.333 | 65.696 | 1.00 | 7.74 |
| ATOM 2348 N | MET | 473 | 19.418 | 57.672 | 65.765 | 1.00 | 8.81 |
| ATOM 2350 CA | MET | 473 | 19.375 | 57.957 | 67.205 | 1.00 | 7.49 |
| ATOM 2351 CB | MET | 473 | 20.772 | 58.193 | 67.738 | 1.00 | 6.97 |
| ATOM 2352 CG | MET | 473 | 21.833 | 57.105 | 67.411 | 1.00 | 8.95 |
| ATOM 2353 SD | MET | 473 | 23.482 | 57.869 | 67.764 | 1.00 | 9.18 |
| ATOM 2354 CE | MET | 473 | 24.667 | 56.454 | 67.716 | 1.00 | 6.33 |
| ATOM 2355 C | MET | 473 | 18.533 | 59.225 | 67.463 | 1.00 | 7.22 |
| ATOM 2356 O | MET | 473 | 17.774 | 59.310 | 68.434 | 1.00 | 6.41 |
| ATOM 2357 N | ARG | 474 | 18.678 | 60.214 | 66.589 | 1.00 | 5.53 |
| ATOM 2359 CA | ARG | 474 | 17.923 | 61.481 | 66.739 | 1.00 | 8.24 |
| ATOM 2360 CB | ARG | 474 | 18.260 | 62.503 | 65.609 | 1.00 | 9.46 |
| ATOM 2361 CG | ARG | 474 | 19.713 | 62.862 | 65.471 | 1.00 | 12.37 |
| ATOM 2362 CD | ARG | 474 | 20.229 | 63.720 | 66.655 | 1.00 | 19.09 |
| ATOM 2363 NE | ARG | 474 | 19.508 | 64.990 | 66.825 | 1.00 | 20.33 |
| ATOM 2365 CZ | ARG | 474 | 20.060 | 66.126 | 67.244 | 1.00 | 16.96 |
| ATOM 2366 NH1 | ARG | 474 | 21.372 | 66.206 | 67.494 | 1.00 | 12.13 |
| ATOM 2369 NH2 | ARG | 474 | 19.260 | 67.108 | 67.667 | 1.00 | 16.09 |
| ATOM 2372 C | ARG | 474 | 16.415 | 61.194 | 66.676 | 1.00 | 8.17 |
| ATOM 2373 O | ARG | 474 | 15.665 | 61.824 | 67.401 | 1.00 | 9.22 |
| ATOM 2374 N | LEU | 475 | 15.985 | 60.220 | 65.863 | 1.00 | 6.83 |
| ATOM 2376 CA | LEU | 475 | 14.522 | 59.853 | 65.826 | 1.00 | 8.75 |
| ATOM 2377 CB | LEU | 475 | 14.148 | 58.791 | 64.774 | 1.00 | 8.07 |
| ATOM 2378 CG | LEU | 475 | 14.378 | 59.002 | 63.303 | 1.00 | 12.69 |
| ATOM 2379 CD1 | LEU | 475 | 13.634 | 57.895 | 62.566 | 1.00 | 14.03 |
| ATOM 2380 CD2 | LEU | 475 | 13.856 | 60.359 | 62.846 | 1.00 | 13.04 |
| ATOM 2381 C | LEU | 475 | 14.111 | 59.298 | 67.164 | 1.00 | 8.19 |
| ATOM 2382 O | LEU | 475 | 12.992 | 59.568 | 67.637 | 1.00 | 8.29 |
| ATOM 2383 N | CYS | 476 | 15.009 | 58.535 | 67.805 | 1.00 | 8.96 |
| ATOM 2385 CA | CYS | 476 | 14.702 | 58.001 | 69.132 | 1.00 | 9.13 |
| ATOM 2386 CB | CYS | 476 | 15.797 | 57.005 | 69.593 | 1.00 | 9.64 |
| ATOM 2387 SG | CYS | 476 | 15.970 | 55.547 | 68.497 | 1.00 | 10.31 |
| ATOM 2388 C | CYS | 476 | 14.593 | 59.093 | 70.173 | 1.00 | 9.15 |
| ATOM 2389 O | CYS | 476 | 14.021 | 58.889 | 71.243 | 1.00 | 8.58 |
| ATOM 2390 N | TRP | 477 | 15.245 | 60.241 | 69.909 | 1.00 | 11.52 |
| ATOM 2392 CA | TRP | 477 | 15.237 | 61.331 | 70.874 | 1.00 | 11.66 |
| ATOM 2393 CB | TRP | 477 | 16.652 | 61.910 | 71.060 | 1.00 | 10.91 |
| ATOM 2394 CG | TRP | 477 | 17.729 | 60.905 | 71.477 | 1.00 | 10.69 |
| ATOM 2395 CD2 | TRP | 477 | 19.090 | 60.880 | 71.014 | 1.00 | 8.06 |
| ATOM 2396 CE2 | TRP | 477 | 19.706 | 59.737 | 71.582 | 1.00 | 10.51 |
| ATOM 2397 CE3 | TRP | 477 | 19.849 | 61.715 | 70.169 | 1.00 | 6.59 |
| ATOM 2398 CD1 | TRP | 477 | 17.583 | 59.810 | 72.312 | 1.00 | 7.36 |
| ATOM 2399 NE1 | TRP | 477 | 18.759 | 59.116 | 72.367 | 1.00 | 9.93 |
| ATOM 2401 CZ2 | TRP | 477 | 21.065 | 59.391 | 71.329 | 1.00 | 8.71 |
| ATOM 2402 CZ3 | TRP | 477 | 21.191 | 61.381 | 69.914 | 1.00 | 7.45 |
| ATOM 2403 CH2 | TRP | 477 | 21.783 | 60.232 | 70.493 | 1.00 | 8.83 |
| ATOM 2404 C | TRP | 477 | 14.251 | 62.466 | 70.550 | 1.00 | 12.97 |
| ATOM 2405 O | TRP | 477 | 14.387 | 63.589 | 71.018 | 1.00 | 12.53 |
| ATOM 2406 N | LYS | 478 | 13.210 | 62.153 | 69.796 | 1.00 | 15.35 |
| ATOM 2408 CA | LYS | 478 | 12.215 | 63.162 | 69.475 | 1.00 | 14.26 |
| ATOM 2409 CB | LYS | 478 | 11.233 | 62.647 | 68.415 | 1.00 | 16.83 |
| ATOM 2410 CG | LYS | 478 | 11.865 | 62.697 | 67.038 | 1.00 | 19.68 |
| ATOM 2411 CD | LYS | 478 | 10.898 | 62.366 | 65.969 | 1.00 | 24.32 |
| ATOM 2412 CE | LYS | 478 | 11.468 | 62.669 | 64.598 | 1.00 | 24.58 |
| ATOM 2413 NZ | LYS | 478 | 11.720 | 64.104 | 64.481 | 1.00 | 29.10 |
| ATOM 2417 C | LYS | 478 | 11.555 | 63.619 | 70.739 | 1.00 | 12.48 |
| ATOM 2418 O | LYS | 478 | 11.399 | 62.871 | 71.705 | 1.00 | 11.24 |
| ATOM 2419 N | GLU | 479 | 11.335 | 64.926 | 70.818 | 1.00 | 12.24 |
| ATOM 2421 CA | GLU | 479 | 10.719 | 65.500 | 72.014 | 1.00 | 13.61 |
| ATOM 2422 CB | GLU | 479 | 10.430 | 66.996 | 71.763 | 1.00 | 16.26 |
| ATOM 2423 CG | GLU | 479 | 9.854 | 67.725 | 72.953 | 1.00 | 20.83 |
| ATOM 2424 CD | GLU | 479 | 10.848 | 67.847 | 74.081 | 1.00 | 26.33 |

TABLE 1-continued

Coordinates of Lck bound with PP2

| | Atom Type | Res | # | X | Y | Z | Occ | B |
|---|---|---|---|---|---|---|---|---|
| ATOM | 2425 | OE1 | GLU | 479 | 12.068 | 67.605 | 73.841 | 1.00 | 27.22 |
| ATOM | 2426 | OE2 | GLU | 479 | 10.415 | 68.188 | 75.210 | 1.00 | 27.42 |
| ATOM | 2427 | C | GLU | 479 | 9.419 | 64.788 | 72.399 | 1.00 | 13.09 |
| ATOM | 2428 | O | GLU | 479 | 9.211 | 64.409 | 73.548 | 1.00 | 13.68 |
| ATOM | 2429 | N | ARG | 480 | 8.485 | 64.679 | 71.461 | 1.00 | 12.69 |
| ATOM | 2431 | CA | ARG | 480 | 7.219 | 64.006 | 71.831 | 1.00 | 15.85 |
| ATOM | 2432 | CB | ARG | 480 | 6.046 | 64.466 | 70.948 | 1.00 | 16.94 |
| ATOM | 2433 | CG | ARG | 480 | 5.859 | 65.995 | 70.946 | 1.00 | 23.39 |
| ATOM | 2434 | CD | ARG | 480 | 4.530 | 66.365 | 70.332 | 1.00 | 27.67 |
| ATOM | 2435 | NE | ARG | 480 | 4.493 | 66.092 | 68.904 | 1.00 | 33.64 |
| ATOM | 2437 | CZ | ARG | 480 | 3.398 | 65.729 | 68.234 | 1.00 | 36.96 |
| ATOM | 2438 | NH1 | ARG | 480 | 2.243 | 65.585 | 68.881 | 1.00 | 38.79 |
| ATOM | 2441 | NH2 | ARG | 480 | 3.443 | 65.565 | 66.910 | 1.00 | 35.83 |
| ATOM | 2444 | C | ARG | 480 | 7.376 | 62.500 | 71.731 | 1.00 | 12.27 |
| ATOM | 2445 | O | ARG | 480 | 7.801 | 61.997 | 70.723 | 1.00 | 12.79 |
| ATOM | 2446 | N | PRO | 481 | 7.021 | 61.777 | 72.788 | 1.00 | 11.66 |
| ATOM | 2447 | CD | PRO | 481 | 6.505 | 62.310 | 74.063 | 1.00 | 12.06 |
| ATOM | 2448 | CA | PRO | 481 | 7.124 | 60.311 | 72.817 | 1.00 | 12.25 |
| ATOM | 2449 | CB | PRO | 481 | 6.349 | 59.943 | 74.090 | 1.00 | 12.06 |
| ATOM | 2450 | CG | PRO | 481 | 6.596 | 61.112 | 74.988 | 1.00 | 12.05 |
| ATOM | 2451 | C | PRO | 481 | 6.467 | 59.690 | 71.595 | 1.00 | 12.62 |
| ATOM | 2452 | O | PRO | 481 | 7.070 | 58.886 | 70.870 | 1.00 | 10.95 |
| ATOM | 2453 | N | GLU | 482 | 5.267 | 60.179 | 71.262 | 1.00 | 13.13 |
| ATOM | 2455 | CA | GLU | 482 | 4.518 | 59.631 | 70.138 | 1.00 | 15.42 |
| ATOM | 2456 | CB | GLU | 482 | 3.068 | 60.178 | 70.141 | 1.00 | 21.05 |
| ATOM | 2457 | CG | GLU | 482 | 2.960 | 61.678 | 69.884 | 1.00 | 27.58 |
| ATOM | 2458 | CD | GLU | 482 | 2.981 | 62.568 | 71.132 | 1.00 | 30.23 |
| ATOM | 2459 | OE1 | GLU | 482 | 3.405 | 62.151 | 72.254 | 1.00 | 28.76 |
| ATOM | 2460 | OE2 | GLU | 482 | 2.544 | 63.730 | 70.955 | 1.00 | 32.94 |
| ATOM | 2461 | C | GLU | 482 | 5.175 | 59.766 | 68.767 | 1.00 | 12.59 |
| ATOM | 2462 | O | GLU | 482 | 4.865 | 59.019 | 67.819 | 1.00 | 10.03 |
| ATOM | 2463 | N | ASP | 483 | 6.149 | 60.676 | 68.653 | 1.00 | 13.06 |
| ATOM | 2465 | CA | ASP | 483 | 6.854 | 60.865 | 67.389 | 1.00 | 11.42 |
| ATOM | 2466 | CB | ASP | 483 | 7.410 | 62.289 | 67.257 | 1.00 | 14.02 |
| ATOM | 2467 | CG | ASP | 483 | 6.303 | 63.353 | 67.128 | 1.00 | 19.29 |
| ATOM | 2468 | OD1 | ASP | 483 | 5.155 | 63.000 | 66.796 | 1.00 | 18.01 |
| ATOM | 2469 | OD2 | ASP | 483 | 6.604 | 64.526 | 67.389 | 1.00 | 18.98 |
| ATOM | 2470 | C | ASP | 483 | 8.019 | 59.913 | 67.212 | 1.00 | 9.88 |
| ATOM | 2471 | O | ASP | 483 | 8.552 | 59.772 | 66.108 | 1.00 | 10.53 |
| ATOM | 2472 | N | ARG | 484 | 8.465 | 59.324 | 68.311 | 1.00 | 8.99 |
| ATOM | 2474 | CA | ARG | 484 | 9.599 | 58.377 | 68.286 | 1.00 | 8.84 |
| ATOM | 2475 | CB | ARG | 484 | 10.047 | 58.081 | 69.714 | 1.00 | 9.56 |
| ATOM | 2476 | CG | ARG | 484 | 10.416 | 59.331 | 70.509 | 1.00 | 6.73 |
| ATOM | 2477 | CD | ARG | 484 | 10.875 | 59.035 | 71.914 | 1.00 | 8.41 |
| ATOM | 2478 | NE | ARG | 484 | 10.877 | 60.273 | 72.686 | 1.00 | 7.26 |
| ATOM | 2480 | CZ | ARG | 484 | 10.694 | 60.357 | 74.003 | 1.00 | 10.06 |
| ATOM | 2481 | NH1 | ARG | 484 | 10.524 | 59.253 | 74.736 | 1.00 | 9.41 |
| ATOM | 2484 | NH2 | ARG | 484 | 10.557 | 61.561 | 74.583 | 1.00 | 7.76 |
| ATOM | 2487 | C | ARG | 484 | 9.079 | 57.105 | 67.577 | 1.00 | 9.79 |
| ATOM | 2488 | O | ARG | 484 | 7.927 | 56.744 | 67.719 | 1.00 | 8.30 |
| ATOM | 2489 | N | PRO | 485 | 9.940 | 56.427 | 66.811 | 1.00 | 8.28 |
| ATOM | 2490 | CD | PRO | 485 | 11.404 | 56.680 | 66.780 | 1.00 | 7.46 |
| ATOM | 2491 | CA | PRO | 485 | 9.582 | 55.219 | 66.057 | 1.00 | 8.60 |
| ATOM | 2492 | CB | PRO | 485 | 10.809 | 55.012 | 65.157 | 1.00 | 7.26 |
| ATOM | 2493 | CG | PRO | 485 | 11.953 | 55.476 | 66.042 | 1.00 | 7.83 |
| ATOM | 2494 | C | PRO | 485 | 9.312 | 54.001 | 66.905 | 1.00 | 8.39 |
| ATOM | 2495 | O | PRO | 485 | 9.562 | 53.983 | 68.104 | 1.00 | 8.61 |
| ATOM | 2496 | N | THR | 486 | 8.751 | 52.978 | 66.267 | 1.00 | 10.14 |
| ATOM | 2498 | CA | THR | 486 | 8.525 | 51.716 | 66.975 | 1.00 | 9.93 |
| ATOM | 2499 | CB | THR | 486 | 7.432 | 50.894 | 66.285 | 1.00 | 11.71 |
| ATOM | 2500 | OG1 | THR | 486 | 7.883 | 50.576 | 64.963 | 1.00 | 9.31 |
| ATOM | 2502 | CG2 | THR | 486 | 6.094 | 51.712 | 66.212 | 1.00 | 10.77 |
| ATOM | 2503 | C | THR | 486 | 9.821 | 50.891 | 66.906 | 1.00 | 9.76 |
| ATOM | 2504 | O | THR | 486 | 10.720 | 51.106 | 66.036 | 1.00 | 9.57 |
| ATOM | 2505 | N | PHE | 487 | 9.894 | 49.880 | 67.764 | 1.00 | 8.81 |
| ATOM | 2507 | CA | PHE | 487 | 11.043 | 49.002 | 67.758 | 1.00 | 9.30 |
| ATOM | 2508 | CB | PHE | 487 | 11.124 | 48.168 | 69.050 | 1.00 | 7.15 |
| ATOM | 2509 | CG | PHE | 487 | 11.748 | 48.908 | 70.162 | 1.00 | 6.74 |
| ATOM | 2510 | CD1 | PHE | 487 | 13.118 | 49.181 | 70.141 | 1.00 | 5.25 |
| ATOM | 2511 | CD2 | PHE | 487 | 10.988 | 49.333 | 71.240 | 1.00 | 6.74 |
| ATOM | 2512 | CE1 | PHE | 487 | 13.716 | 49.878 | 71.224 | 1.00 | 5.38 |
| ATOM | 2513 | CE2 | PHE | 487 | 11.561 | 50.015 | 72.281 | 1.00 | 7.47 |
| ATOM | 2514 | CZ | PHE | 487 | 12.953 | 50.287 | 72.278 | 1.00 | 7.99 |
| ATOM | 2515 | C | PHE | 487 | 11.083 | 48.182 | 66.505 | 1.00 | 9.64 |

TABLE 1-continued

Coordinates of Lck bound with PP2

| | Atom Type | Res | # | X | Y | Z | Occ | B |
|---|---|---|---|---|---|---|---|---|
| ATOM | 2516 | O | PHE | 487 | 12.155 | 47.935 | 65.950 | 1.00 | 8.29 |
| ATOM | 2517 | N | ASP | 488 | 9.911 | 47.850 | 65.966 | 1.00 | 11.10 |
| ATOM | 2519 | CA | ASP | 488 | 9.909 | 47.132 | 64.699 | 1.00 | 10.80 |
| ATOM | 2520 | CB | ASP | 488 | 8.510 | 46.673 | 64.306 | 1.00 | 17.60 |
| ATOM | 2521 | CG | ASP | 488 | 8.565 | 45.552 | 63.286 | 1.00 | 22.53 |
| ATOM | 2522 | OD1 | ASP | 488 | 9.381 | 44.630 | 63.479 | 1.00 | 26.33 |
| ATOM | 2523 | OD2 | ASP | 488 | 7.857 | 45.617 | 62.281 | 1.00 | 25.89 |
| ATOM | 2524 | C | ASP | 488 | 10.504 | 48.007 | 63.566 | 1.00 | 10.95 |
| ATOM | 2525 | O | ASP | 488 | 11.268 | 47.505 | 62.680 | 1.00 | 9.83 |
| ATOM | 2526 | N | TYR | 489 | 10.155 | 49.307 | 63.554 | 1.00 | 7.53 |
| ATOM | 2528 | CA | TYR | 489 | 10.703 | 50.218 | 62.527 | 1.00 | 8.33 |
| ATOM | 2529 | CB | TYR | 489 | 10.162 | 51.673 | 62.706 | 1.00 | 6.41 |
| ATOM | 2530 | CG | TYR | 489 | 10.787 | 52.671 | 61.761 | 1.00 | 12.54 |
| ATOM | 2531 | CD1 | TYR | 489 | 10.319 | 52.830 | 60.467 | 1.00 | 11.81 |
| ATOM | 2532 | CE1 | TYR | 489 | 10.952 | 53.702 | 59.580 | 1.00 | 12.33 |
| ATOM | 2533 | CD2 | TYR | 489 | 11.918 | 53.433 | 62.155 | 1.00 | 13.93 |
| ATOM | 2534 | CE2 | TYR | 489 | 12.537 | 54.307 | 61.272 | 1.00 | 12.86 |
| ATOM | 2535 | CZ | TYR | 489 | 12.061 | 54.431 | 60.003 | 1.00 | 12.57 |
| ATOM | 2536 | OH | TYR | 489 | 12.683 | 55.295 | 59.134 | 1.00 | 10.28 |
| ATOM | 2538 | C | TYR | 489 | 12.250 | 50.223 | 62.661 | 1.00 | 6.43 |
| ATOM | 2539 | O | TYR | 489 | 12.966 | 50.046 | 61.708 | 1.00 | 9.95 |
| ATOM | 2540 | N | LEU | 490 | 12.715 | 50.448 | 63.868 | 1.00 | 9.44 |
| ATOM | 2542 | CA | LEU | 490 | 14.144 | 50.483 | 64.208 | 1.00 | 10.56 |
| ATOM | 2543 | CB | LEU | 490 | 14.319 | 50.711 | 65.723 | 1.00 | 9.09 |
| ATOM | 2544 | CG | LEU | 490 | 13.938 | 52.108 | 66.222 | 1.00 | 9.40 |
| ATOM | 2545 | CD1 | LEU | 490 | 13.737 | 52.138 | 67.750 | 1.00 | 10.17 |
| ATOM | 2546 | CD2 | LEU | 490 | 15.035 | 53.094 | 65.804 | 1.00 | 11.51 |
| ATOM | 2547 | C | LEU | 490 | 14.855 | 49.192 | 63.768 | 1.00 | 9.22 |
| ATOM | 2548 | O | LEU | 490 | 15.841 | 49.242 | 63.113 | 1.00 | 9.40 |
| ATOM | 2549 | N | ARG | 491 | 14.278 | 48.035 | 64.074 | 1.00 | 9.85 |
| ATOM | 2551 | CA | ARG | 491 | 14.891 | 46.758 | 63.686 | 1.00 | 8.29 |
| ATOM | 2552 | CB | ARG | 491 | 14.014 | 45.575 | 64.163 | 1.00 | 8.09 |
| ATOM | 2553 | CG | ARG | 491 | 14.557 | 44.214 | 63.601 | 1.00 | 9.21 |
| ATOM | 2554 | CD | ARG | 491 | 13.455 | 43.119 | 63.545 | 1.00 | 14.63 |
| ATOM | 2555 | NE | ARG | 491 | 12.249 | 43.619 | 62.861 | 1.00 | 17.86 |
| ATOM | 2557 | CZ | ARG | 491 | 12.054 | 43.689 | 61.541 | 1.00 | 17.59 |
| ATOM | 2558 | NH1 | ARG | 491 | 12.975 | 43.279 | 60.674 | 1.00 | 18.87 |
| ATOM | 2561 | NH2 | ARG | 491 | 10.917 | 44.213 | 61.089 | 1.00 | 16.93 |
| ATOM | 2564 | C | ARG | 491 | 15.078 | 46.682 | 62.175 | 1.00 | 9.76 |
| ATOM | 2565 | O | ARG | 491 | 16.145 | 46.355 | 61.644 | 1.00 | 10.85 |
| ATOM | 2566 | N | SER | 492 | 14.026 | 47.078 | 61.468 | 0.71 | 8.11 |
| ATOM | 2568 | CA | SER | 492 | 14.006 | 47.054 | 60.027 | 0.71 | 6.86 |
| ATOM | 2569 | CB | SER | 492 | 12.597 | 47.458 | 59.546 | 0.71 | 7.55 |
| ATOM | 2570 | OG | SER | 492 | 12.518 | 47.367 | 58.156 | 0.71 | 11.29 |
| ATOM | 2572 | C | SER | 492 | 15.050 | 47.977 | 59.406 | 0.71 | 7.68 |
| ATOM | 2573 | O | SER | 492 | 15.724 | 47.620 | 58.456 | 0.71 | 3.32 |
| ATOM | 2574 | N | VAL | 493 | 15.155 | 49.204 | 59.912 | 1.00 | 8.81 |
| ATOM | 2576 | CA | VAL | 493 | 16.151 | 50.128 | 59.343 | 1.00 | 10.14 |
| ATOM | 2577 | CB | VAL | 493 | 16.023 | 51.549 | 59.943 | 1.00 | 9.81 |
| ATOM | 2578 | CG1 | VAL | 493 | 17.238 | 52.441 | 59.508 | 1.00 | 7.77 |
| ATOM | 2579 | CG2 | VAL | 493 | 14.693 | 52.175 | 59.516 | 1.00 | 8.92 |
| ATOM | 2580 | C | VAL | 493 | 17.554 | 49.594 | 59.670 | 1.00 | 8.53 |
| ATOM | 2581 | O | VAL | 493 | 18.448 | 49.650 | 58.842 | 1.00 | 10.58 |
| ATOM | 2582 | N | LEU | 494 | 17.747 | 49.139 | 60.906 | 1.00 | 9.18 |
| ATOM | 2584 | CA | LEU | 494 | 19.058 | 48.622 | 61.318 | 1.00 | 9.12 |
| ATOM | 2585 | CB | LEU | 494 | 19.096 | 48.364 | 62.816 | 1.00 | 9.94 |
| ATOM | 2586 | CG | LEU | 494 | 19.261 | 49.601 | 63.715 | 1.00 | 8.16 |
| ATOM | 2587 | CD1 | LEU | 494 | 18.790 | 49.288 | 65.090 | 1.00 | 4.70 |
| ATOM | 2588 | CD2 | LEU | 494 | 20.702 | 50.179 | 63.717 | 1.00 | 2.75 |
| ATOM | 2589 | C | LEU | 494 | 19.490 | 47.425 | 60.497 | 1.00 | 11.22 |
| ATOM | 2590 | O | LEU | 494 | 20.683 | 47.290 | 60.169 | 1.00 | 11.13 |
| ATOM | 2591 | N | GLU | 495 | 18.539 | 46.541 | 60.144 | 1.00 | 11.26 |
| ATOM | 2593 | CA | GLU | 495 | 18.878 | 45.407 | 59.279 | 1.00 | 11.66 |
| ATOM | 2594 | CB | GLU | 495 | 17.679 | 44.444 | 59.133 | 1.00 | 13.61 |
| ATOM | 2595 | CG | GLU | 495 | 17.503 | 43.566 | 60.380 | 1.00 | 11.89 |
| ATOM | 2596 | CD | GLU | 495 | 16.260 | 42.687 | 60.369 | 1.00 | 17.24 |
| ATOM | 2597 | OE1 | GLU | 495 | 15.562 | 42.579 | 59.346 | 1.00 | 18.35 |
| ATOM | 2598 | OE2 | GLU | 495 | 15.955 | 42.113 | 61.429 | 1.00 | 18.05 |
| ATOM | 2599 | C | GLU | 495 | 19.321 | 45.903 | 57.874 | 1.00 | 11.87 |
| ATOM | 2600 | O | GLU | 495 | 20.172 | 45.319 | 57.237 | 1.00 | 11.52 |
| ATOM | 2601 | N | ASP | 496 | 18.661 | 46.934 | 57.362 | 1.00 | 9.31 |
| ATOM | 2603 | CA | ASP | 496 | 19.032 | 47.490 | 56.081 | 1.00 | 10.10 |
| ATOM | 2604 | CB | ASP | 496 | 18.012 | 48.585 | 55.663 | 1.00 | 12.32 |
| ATOM | 2605 | CG | ASP | 496 | 16.755 | 47.995 | 55.058 | 1.00 | 16.14 |

TABLE 1-continued

Coordinates of Lck bound with PP2

| | Atom Type | Res | # | X | Y | Z | Occ | B |
|---|---|---|---|---|---|---|---|---|
| ATOM | 2606 | OD1 | ASP | 496 | 16.753 | 46.774 | 54.763 | 1.00 | 15.24 |
| ATOM | 2607 | OD2 | ASP | 496 | 15.767 | 48.716 | 54.884 | 1.00 | 14.19 |
| ATOM | 2608 | C | ASP | 496 | 20.429 | 48.085 | 56.167 | 1.00 | 10.00 |
| ATOM | 2609 | O | ASP | 496 | 21.251 | 47.896 | 55.286 | 1.00 | 10.81 |
| ATOM | 2610 | N | PHE | 497 | 20.722 | 48.775 | 57.268 | 1.00 | 10.93 |
| ATOM | 2612 | CA | PHE | 497 | 22.039 | 49.389 | 57.412 | 1.00 | 12.83 |
| ATOM | 2613 | CB | PHE | 497 | 22.131 | 50.120 | 58.753 | 1.00 | 12.07 |
| ATOM | 2614 | CG | PHE | 497 | 21.398 | 51.445 | 58.801 | 1.00 | 9.10 |
| ATOM | 2615 | CD1 | PHE | 497 | 20.706 | 51.925 | 57.697 | 1.00 | 11.06 |
| ATOM | 2616 | CD2 | PHE | 497 | 21.452 | 52.221 | 59.957 | 1.00 | 9.30 |
| ATOM | 2617 | CE1 | PHE | 497 | 20.068 | 53.232 | 57.737 | 1.00 | 11.14 |
| ATOM | 2618 | CE2 | PHE | 497 | 20.836 | 53.481 | 60.012 | 1.00 | 10.69 |
| ATOM | 2619 | CZ | PHE | 497 | 20.148 | 53.981 | 58.893 | 1.00 | 9.81 |
| ATOM | 2620 | C | PHE | 497 | 23.124 | 48.288 | 57.352 | 1.00 | 16.73 |
| ATOM | 2621 | O | PHE | 497 | 24.127 | 48.408 | 56.636 | 1.00 | 14.67 |
| ATOM | 2622 | N | PHE | 498 | 22.847 | 47.184 | 58.053 | 1.00 | 19.32 |
| ATOM | 2624 | CA | PHE | 498 | 23.738 | 46.021 | 58.150 | 1.00 | 24.72 |
| ATOM | 2625 | CB | PHE | 498 | 23.138 | 45.044 | 59.210 | 1.00 | 28.15 |
| ATOM | 2626 | CG | PHE | 498 | 23.691 | 43.637 | 59.189 | 1.00 | 29.02 |
| ATOM | 2627 | CD1 | PHE | 498 | 25.046 | 43.393 | 59.165 | 1.00 | 32.59 |
| ATOM | 2628 | CD2 | PHE | 498 | 22.824 | 42.549 | 59.274 | 1.00 | 34.85 |
| ATOM | 2629 | CE1 | PHE | 498 | 25.547 | 42.077 | 59.227 | 1.00 | 33.04 |
| ATOM | 2630 | CE2 | PHE | 498 | 23.298 | 41.231 | 59.338 | 1.00 | 32.20 |
| ATOM | 2631 | CZ | PHE | 498 | 24.670 | 41.003 | 59.313 | 1.00 | 35.12 |
| ATOM | 2632 | C | PHE | 498 | 23.914 | 45.348 | 56.797 | 1.00 | 26.82 |
| ATOM | 2633 | O | PHE | 498 | 25.036 | 45.093 | 56.358 | 1.00 | 27.45 |
| ATOM | 2634 | N | THR | 499 | 22.795 | 45.074 | 56.130 | 1.00 | 28.64 |
| ATOM | 2636 | CA | THR | 499 | 22.820 | 44.387 | 54.844 | 1.00 | 32.01 |
| ATOM | 2637 | CB | THR | 499 | 21.409 | 43.887 | 54.410 | 1.00 | 31.10 |
| ATOM | 2638 | OG1 | THR | 499 | 20.471 | 44.961 | 54.452 | 1.00 | 33.42 |
| ATOM | 2640 | CG2 | THR | 499 | 20.925 | 42.811 | 55.340 | 1.00 | 32.06 |
| ATOM | 2641 | C | THR | 499 | 23.464 | 45.193 | 53.736 | 1.00 | 34.11 |
| ATOM | 2642 | O | THR | 499 | 23.686 | 44.677 | 52.648 | 1.00 | 36.15 |
| ATOM | 2643 | N | ALA | 500 | 23.781 | 46.454 | 54.026 | 1.00 | 35.54 |
| ATOM | 2645 | CA | ALA | 500 | 24.417 | 47.346 | 53.062 | 1.00 | 37.58 |
| ATOM | 2646 | CB | ALA | 500 | 23.808 | 48.744 | 53.152 | 1.00 | 37.42 |
| ATOM | 2647 | C | ALA | 500 | 25.920 | 47.409 | 53.343 | 1.00 | 38.52 |
| ATOM | 2648 | O | ALA | 500 | 26.746 | 47.377 | 52.411 | 1.00 | 39.26 |
| ATOM | 2649 | N | THR | 501 | 26.278 | 47.516 | 54.625 | 1.00 | 37.64 |
| ATOM | 2651 | CA | THR | 501 | 27.684 | 47.556 | 55.016 | 1.00 | 38.55 |
| ATOM | 2652 | CB | THR | 501 | 27.898 | 48.237 | 56.416 | 1.00 | 38.57 |
| ATOM | 2653 | OG1 | THR | 501 | 27.373 | 47.410 | 57.466 | 1.00 | 34.01 |
| ATOM | 2655 | CG2 | THR | 501 | 27.241 | 49.626 | 56.465 | 1.00 | 36.76 |
| ATOM | 2656 | C | THR | 501 | 28.236 | 46.119 | 55.047 | 1.00 | 39.81 |
| ATOM | 2657 | O | THR | 501 | 27.714 | 45.260 | 54.289 | 1.00 | 40.00 |
| ATOM | 2658 | OT | THR | 501 | 29.166 | 45.854 | 55.848 | 1.00 | 40.98 |
| ATOM | 2659 | OH2 | TIP | 1 | 21.607 | 29.808 | 74.673 | 1.00 | 13.25 |
| ATOM | 2662 | OH2 | TIP | 6 | 16.481 | 32.964 | 74.773 | 1.00 | 8.18 |
| ATOM | 2665 | OH2 | TIP | 7 | 24.345 | 68.868 | 70.468 | 1.00 | 8.60 |
| ATOM | 2668 | OH2 | TIP | 8 | 3.800 | 16.878 | 94.895 | 1.00 | 8.12 |
| ATOM | 2671 | OH2 | TIP | 9 | 18.122 | 62.115 | 79.618 | 1.00 | 9.07 |
| ATOM | 2674 | OH2 | TIP | 10 | 16.780 | 62.091 | 62.320 | 1.00 | 17.42 |
| ATOM | 2677 | OH2 | TIP | 11 | 25.046 | 50.597 | 80.016 | 1.00 | 3.72 |
| ATOM | 2680 | OH2 | TIP | 12 | 26.577 | 31.808 | 75.342 | 1.00 | 7.12 |
| ATOM | 2683 | OH2 | TIP | 13 | 25.262 | 21.524 | 76.974 | 1.00 | 7.12 |
| ATOM | 2686 | OH2 | TIP | 14 | 3.750 | 51.832 | 76.137 | 1.00 | 13.69 |
| ATOM | 2689 | OH2 | TIP | 15 | 32.763 | 40.036 | 77.507 | 1.00 | 22.70 |
| ATOM | 2692 | OH2 | TIP | 16 | 23.035 | 20.546 | 78.042 | 1.00 | 13.17 |
| ATOM | 2695 | OH2 | TIP | 17 | 7.604 | 53.997 | 63.857 | 1.00 | 20.48 |
| ATOM | 2698 | OH2 | TIP | 18 | 28.104 | 56.401 | 74.609 | 1.00 | 12.66 |
| ATOM | 2701 | OH2 | TIP | 19 | 22.067 | 18.830 | 82.221 | 1.00 | 13.82 |
| ATOM | 2704 | OH2 | TIP | 20 | 13.310 | 34.312 | 76.774 | 1.00 | 8.87 |
| ATOM | 2707 | OH2 | TIP | 21 | 7.119 | 57.296 | 104.332 | 1.00 | 7.40 |
| ATOM | 2710 | OH2 | TIP | 22 | 35.615 | 44.422 | 79.595 | 1.00 | 21.54 |
| ATOM | 2713 | OH2 | TIP | 23 | 8.611 | 65.581 | 68.778 | 1.00 | 13.66 |
| ATOM | 2716 | OH2 | TIP | 24 | 22.334 | 28.244 | 79.140 | 1.00 | 9.70 |
| ATOM | 2719 | OH2 | TIP | 25 | 14.002 | 69.197 | 73.540 | 1.00 | 21.31 |
| ATOM | 2722 | OH2 | TIP | 26 | 13.645 | 55.624 | 79.426 | 1.00 | 11.16 |
| ATOM | 2725 | OH2 | TIP | 27 | 4.291 | 54.619 | 67.027 | 1.00 | 14.97 |
| ATOM | 2728 | OH2 | TIP | 28 | 6.648 | 45.172 | 67.946 | 1.00 | 11.87 |
| ATOM | 2731 | OH2 | TIP | 29 | 24.617 | 78.613 | 73.803 | 1.00 | 7.20 |
| ATOM | 2734 | OH2 | TIP | 30 | 30.105 | 59.806 | 72.375 | 1.00 | 22.68 |
| ATOM | 2737 | OH2 | TIP | 31 | 25.906 | 23.633 | 78.474 | 1.00 | 14.97 |
| ATOM | 2740 | OH2 | TIP | 32 | 3.150 | 56.882 | 67.884 | 1.00 | 18.06 |

TABLE 1-continued

Coordinates of Lck bound with PP2

| | Atom Type | Res | # | X | Y | Z | Occ | B |
|---|---|---|---|---|---|---|---|---|
| ATOM | 2743 | OH2 | TIP | 33 | 6.452 | 52.073 | 70.077 | 1.00 | 23.60 |
| ATOM | 2746 | OH2 | TIP | 34 | 25.999 | 70.637 | 71.770 | 1.00 | 16.40 |
| ATOM | 2749 | OH2 | TIP | 35 | 30.439 | 41.016 | 81.578 | 1.00 | 8.11 |
| ATOM | 2752 | OH2 | TIP | 36 | 13.101 | 71.537 | 72.323 | 1.00 | 14.42 |
| ATOM | 2755 | OH2 | TIP | 37 | 29.388 | 17.926 | 80.825 | 1.00 | 23.02 |
| ATOM | 2758 | OH2 | TIP | 38 | 35.887 | 38.783 | 74.498 | 1.00 | 23.64 |
| ATOM | 2761 | OH2 | TIP | 39 | 29.565 | 66.029 | 74.889 | 1.00 | 20.03 |
| ATOM | 2764 | OH2 | TIP | 40 | 16.396 | 52.686 | 84.622 | 1.00 | 15.35 |
| ATOM | 2767 | OH2 | TIP | 41 | 4.038 | 43.999 | 85.648 | 1.00 | 13.56 |
| ATOM | 2770 | OH2 | TIP | 42 | 29.895 | 58.350 | 74.470 | 1.00 | 12.85 |
| ATOM | 2773 | OH2 | TIP | 43 | 16.006 | 20.021 | 80.032 | 1.00 | 17.93 |
| ATOM | 2776 | OH2 | TIP | 44 | 4.726 | 47.653 | 74.993 | 1.00 | 23.30 |
| ATOM | 2779 | OH2 | TIP | 45 | 15.082 | 76.736 | 76.273 | 1.00 | 14.21 |
| ATOM | 2782 | OH2 | TIP | 46 | 6.212 | 59.954 | 101.185 | 1.00 | 14.52 |
| ATOM | 2785 | OH2 | TIP | 47 | 14.038 | 45.946 | 83.586 | 1.00 | 10.46 |
| ATOM | 2788 | OH2 | TIP | 48 | 14.035 | 25.017 | 81.228 | 1.00 | 29.03 |
| ATOM | 2791 | OH2 | TIP | 49 | 10.652 | 40.732 | 67.376 | 1.00 | 10.79 |
| ATOM | 2794 | OH2 | TIP | 50 | 33.261 | 42.026 | 62.917 | 1.00 | 19.02 |
| ATOM | 2797 | OH2 | TIP | 51 | 6.599 | 57.993 | 76.906 | 1.00 | 15.26 |
| ATOM | 2800 | OH2 | TIP | 53 | 6.156 | 57.374 | 65.551 | 1.00 | 27.15 |
| ATOM | 2803 | OH2 | TIP | 54 | 17.644 | 53.001 | 80.698 | 1.00 | 14.74 |
| ATOM | 2806 | OH2 | TIP | 55 | 11.433 | 33.376 | 69.389 | 1.00 | 22.38 |
| ATOM | 2809 | OH2 | TIP | 56 | 12.863 | 36.165 | 79.302 | 1.00 | 28.40 |
| ATOM | 2812 | OH2 | TIP | 57 | 39.996 | 43.532 | 77.556 | 1.00 | 30.23 |
| ATOM | 2815 | OH2 | TIP | 58 | 3.108 | 18.092 | 92.566 | 1.00 | 23.01 |
| ATOM | 2818 | OH2 | TIP | 59 | 13.400 | 23.825 | 95.215 | 1.00 | 15.83 |
| ATOM | 2821 | OH2 | TIP | 60 | 12.144 | 38.120 | 66.081 | 1.00 | 28.53 |
| ATOM | 2824 | OH2 | TIP | 61 | 24.488 | 67.388 | 74.369 | 1.00 | 19.91 |
| ATOM | 2827 | OH2 | TIP | 62 | 43.447 | 40.286 | 77.519 | 1.00 | 23.20 |
| ATOM | 2830 | OH2 | TIP | 63 | 1.187 | 21.662 | 100.301 | 1.00 | 25.85 |
| ATOM | 2833 | OH2 | TIP | 64 | 11.268 | 66.563 | 68.304 | 1.00 | 18.84 |
| ATOM | 2836 | OH2 | TIP | 65 | 4.560 | 48.311 | 66.937 | 1.00 | 30.17 |
| ATOM | 2839 | OH2 | TIP | 66 | 23.895 | 29.206 | 76.838 | 1.00 | 21.66 |
| ATOM | 2842 | OH2 | TIP | 67 | 13.775 | 73.914 | 73.721 | 1.00 | 15.70 |
| ATOM | 2845 | OH2 | TIP | 68 | 15.313 | 54.443 | 81.542 | 1.00 | 19.77 |
| ATOM | 2848 | OH2 | TIP | 69 | 35.474 | 54.860 | 72.471 | 1.00 | 31.09 |
| ATOM | 2851 | OH2 | TIP | 70 | 25.667 | 52.892 | 57.948 | 1.00 | 45.86 |
| ATOM | 2854 | OH2 | TIP | 71 | 14.679 | 45.561 | 56.799 | 1.00 | 23.99 |
| ATOM | 2857 | OH2 | TIP | 73 | 24.498 | 26.195 | 78.508 | 1.00 | 45.19 |
| ATOM | 2860 | OH2 | TIP | 74 | 17.843 | 34.155 | 99.866 | 1.00 | 21.03 |
| ATOM | 2863 | OH2 | TIP | 76 | 29.878 | 33.436 | 98.172 | 1.00 | 51.49 |
| ATOM | 2866 | OH2 | TIP | 77 | 26.142 | 72.935 | 70.592 | 1.00 | 14.89 |
| ATOM | 2869 | OH2 | TIP | 78 | 12.087 | 33.784 | 80.125 | 1.00 | 15.78 |
| ATOM | 2872 | OH2 | TIP | 79 | 29.070 | 62.498 | 72.146 | 1.00 | 11.81 |
| ATOM | 2875 | OH2 | TIP | 80 | 26.762 | 65.659 | 74.219 | 1.00 | 15.76 |
| ATOM | 2878 | OH2 | TIP | 81 | 27.244 | 19.850 | 78.029 | 1.00 | 21.65 |
| ATOM | 2881 | OH2 | TIP | 82 | 29.140 | 36.797 | 82.374 | 1.00 | 17.60 |
| ATOM | 2884 | OH2 | TIP | 84 | 18.796 | 52.521 | 83.123 | 1.00 | 18.72 |
| ATOM | 2887 | OH2 | TIP | 85 | 27.251 | 24.541 | 94.370 | 1.00 | 25.70 |
| ATOM | 2890 | OH2 | TIP | 86 | −1.545 | 21.255 | 100.340 | 1.00 | 17.73 |
| ATOM | 2893 | OH2 | TIP | 87 | 15.837 | 35.644 | 101.482 | 1.00 | 27.51 |
| ATOM | 2896 | OH2 | TIP | 88 | 34.284 | 38.018 | 76.564 | 1.00 | 26.44 |
| ATOM | 2899 | OH2 | TIP | 89 | 24.213 | 74.301 | 76.721 | 1.00 | 26.05 |
| ATOM | 2902 | OH2 | TIP | 90 | 13.037 | 22.464 | 79.577 | 1.00 | 20.22 |
| ATOM | 2905 | OH2 | TIP | 91 | 9.767 | 52.390 | 79.457 | 1.00 | 18.86 |
| ATOM | 2908 | OH2 | TIP | 92 | 20.238 | 71.139 | 85.112 | 1.00 | 19.98 |
| ATOM | 2911 | OH2 | TIP | 93 | 4.599 | 59.491 | 77.668 | 1.00 | 22.03 |
| ATOM | 2914 | OH2 | TIP | 94 | 10.448 | 58.867 | 64.309 | 1.00 | 37.46 |
| ATOM | 2917 | OH2 | TIP | 95 | 17.150 | 52.061 | 87.312 | 1.00 | 28.30 |
| ATOM | 2920 | OH2 | TIP | 96 | 14.944 | 19.298 | 88.358 | 1.00 | 23.01 |
| ATOM | 2923 | OH2 | TIP | 98 | 22.606 | 31.977 | 72.585 | 1.00 | 30.76 |
| ATOM | 2926 | OH2 | TIP | 99 | 16.389 | 46.097 | 85.748 | 1.00 | 31.74 |
| ATOM | 2929 | OH2 | TIP | 100 | 32.467 | 60.047 | 71.069 | 1.00 | 22.28 |
| ATOM | 2932 | OH2 | TIP | 101 | 12.570 | 44.846 | 99.291 | 1.00 | 24.56 |
| ATOM | 2935 | OH2 | TIP | 102 | 15.465 | 38.546 | 102.263 | 1.00 | 23.51 |
| ATOM | 2938 | OH2 | TIP | 103 | −2.147 | 21.190 | 94.409 | 1.00 | 34.08 |
| ATOM | 2941 | OH2 | TIP | 104 | 23.412 | 43.123 | 93.986 | 1.00 | 20.69 |
| ATOM | 2944 | OH2 | TIP | 106 | 32.275 | 63.542 | 69.259 | 1.00 | 35.11 |
| ATOM | 2947 | OH2 | TIP | 109 | 27.641 | 29.169 | 75.550 | 1.00 | 42.12 |
| ATOM | 2950 | OH2 | TIP | 110 | 34.288 | 32.152 | 91.932 | 1.00 | 35.49 |
| ATOM | 2953 | OH2 | TIP | 111 | 5.812 | 50.212 | 63.249 | 1.00 | 19.89 |
| ATOM | 2956 | OH2 | TIP | 112 | 8.168 | 28.072 | 92.374 | 1.00 | 26.50 |
| ATOM | 2959 | OH2 | TIP | 114 | 11.901 | 21.456 | 95.373 | 1.00 | 35.24 |
| ATOM | 2962 | OH2 | TIP | 115 | −5.840 | 20.011 | 93.287 | 1.00 | 34.92 |

TABLE 1-continued

Coordinates of Lck bound with PP2

| | Atom Type | Res | # | X | Y | Z | Occ | B |
|---|---|---|---|---|---|---|---|---|
| ATOM | 2965 | OH2 | TIP | 116 | 34.337 | 49.043 | 60.740 | 1.00 | 24.03 |
| ATOM | 2968 | OH2 | TIP | 117 | 15.413 | 40.101 | 91.364 | 1.00 | 15.29 |
| ATOM | 2971 | OH2 | TIP | 119 | 13.005 | 30.660 | 72.127 | 1.00 | 31.18 |
| ATOM | 2974 | OH2 | TIP | 120 | 29.150 | 70.914 | 70.714 | 1.00 | 37.66 |
| ATOM | 2977 | OH2 | TIP | 121 | 6.283 | 34.776 | 76.059 | 1.00 | 18.99 |
| ATOM | 2980 | OH2 | TIP | 122 | 26.184 | 75.068 | 74.889 | 1.00 | 33.22 |
| ATOM | 2983 | OH2 | TIP | 123 | 40.357 | 38.872 | 69.510 | 1.00 | 42.15 |
| ATOM | 2986 | OH2 | TIP | 125 | 24.270 | 25.656 | 95.508 | 1.00 | 23.81 |
| ATOM | 2989 | OH2 | TIP | 126 | 26.877 | 26.802 | 73.517 | 1.00 | 25.85 |
| ATOM | 2992 | OH2 | TIP | 127 | 34.779 | 35.873 | 70.723 | 1.00 | 29.26 |
| ATOM | 2995 | OH2 | TIP | 133 | 23.187 | 58.759 | 84.297 | 1.00 | 26.34 |
| ATOM | 2998 | OH2 | TIP | 134 | 23.576 | 54.423 | 85.628 | 1.00 | 37.02 |
| ATOM | 3001 | OH2 | TIP | 136 | 19.455 | 59.322 | 89.181 | 1.00 | 38.92 |
| ATOM | 3004 | OH2 | TIP | 137 | 11.696 | 59.602 | 87.696 | 1.00 | 32.60 |
| ATOM | 3007 | OH2 | TIP | 138 | 12.636 | 69.530 | 76.584 | 1.00 | 37.94 |
| ATOM | 3010 | OH2 | TIP | 140 | 26.613 | 28.113 | 77.816 | 1.00 | 25.26 |
| ATOM | 3013 | OH2 | TIP | 142 | 27.818 | 61.288 | 62.778 | 1.00 | 30.40 |
| ATOM | 3016 | OH2 | TIP | 143 | 3.206 | 49.856 | 71.371 | 1.00 | 42.17 |
| ATOM | 3019 | OH2 | TIP | 146 | 2.534 | 52.633 | 67.963 | 1.00 | 43.02 |
| ATOM | 3022 | OH2 | TIP | 147 | 25.577 | 46.460 | 95.088 | 1.00 | 33.95 |
| ATOM | 3025 | OH2 | TIP | 149 | 9.759 | 51.941 | 89.536 | 1.00 | 35.56 |
| ATOM | 3028 | OH2 | TIP | 150 | 12.752 | 31.552 | 74.994 | 1.00 | 27.35 |
| ATOM | 3031 | OH2 | TIP | 151 | 12.093 | 29.315 | 75.972 | 1.00 | 25.75 |
| ATOM | 3034 | OH2 | TIP | 152 | 21.842 | 59.026 | 87.281 | 1.00 | 31.48 |
| ATOM | 3037 | OH2 | TIP | 153 | 11.270 | 44.335 | 57.695 | 1.00 | 27.59 |
| ATOM | 3040 | OH2 | TIP | 154 | 14.539 | 59.954 | 88.025 | 1.00 | 30.50 |
| ATOM | 3043 | OH2 | TIP | 156 | 4.272 | 28.080 | 96.025 | 1.00 | 47.65 |
| ATOM | 3046 | OH2 | TIP | 157 | 17.859 | 42.053 | 92.196 | 1.00 | 29.57 |
| ATOM | 3049 | OH2 | TIP | 158 | 22.647 | 41.349 | 83.263 | 1.00 | 39.70 |
| ATOM | 3052 | OH2 | TIP | 159 | 11.322 | 46.623 | 90.716 | 1.00 | 31.92 |
| ATOM | 3055 | OH2 | TIP | 161 | 2.712 | 52.383 | 89.710 | 1.00 | 33.22 |
| ATOM | 3058 | OH2 | TIP | 162 | 1.287 | 52.867 | 87.116 | 1.00 | 44.83 |
| ATOM | 3061 | OH2 | TIP | 165 | 27.002 | 63.572 | 86.923 | 1.00 | 29.86 |
| ATOM | 3064 | OH2 | TIP | 166 | 16.412 | 64.181 | 68.052 | 1.00 | 15.25 |
| ATOM | 3067 | OH2 | TIP | 167 | 6.518 | 17.919 | 94.625 | 1.00 | 22.60 |
| ATOM | 3070 | OH2 | TIP | 168 | 3.236 | 56.796 | 74.190 | 1.00 | 24.04 |
| ATOM | 3073 | OH2 | TIP | 170 | 22.853 | 45.908 | 85.283 | 1.00 | 31.68 |
| ATOM | 3076 | OH2 | TIP | 171 | 23.845 | 31.720 | 74.930 | 1.00 | 24.61 |
| ATOM | 3079 | OH2 | TIP | 173 | 12.173 | 62.934 | 61.143 | 1.00 | 35.38 |
| ATOM | 3082 | OH2 | TIP | 174 | 7.573 | 21.577 | 91.113 | 1.00 | 25.92 |
| ATOM | 3085 | OH2 | TIP | 175 | 6.408 | 34.865 | 93.539 | 1.00 | 25.00 |
| ATOM | 3088 | OH2 | TIP | 176 | 6.879 | 44.086 | 90.136 | 1.00 | 52.52 |
| ATOM | 3091 | OH2 | TIP | 178 | 0.615 | 45.299 | 71.526 | 1.00 | 33.57 |
| ATOM | 3094 | OH2 | TIP | 182 | 20.199 | 39.536 | 93.672 | 1.00 | 32.42 |
| ATOM | 3097 | OH2 | TIP | 183 | −0.763 | 50.856 | 82.292 | 1.00 | 42.39 |
| ATOM | 3100 | OH2 | TIP | 188 | 34.519 | 25.551 | 92.081 | 1.00 | 43.60 |
| ATOM | 3103 | OH2 | TIP | 189 | 33.409 | 56.361 | 79.281 | 1.00 | 22.55 |
| ATOM | 3106 | OH2 | TIP | 192 | 35.529 | 52.146 | 76.123 | 1.00 | 33.38 |
| ATOM | 3109 | OH2 | TIP | 198 | 8.143 | 34.005 | 71.774 | 1.00 | 35.46 |
| ATOM | 3112 | OH2 | TIP | 205 | 11.395 | 37.978 | 80.175 | 1.00 | 52.83 |
| ATOM | 3115 | OH2 | TIP | 206 | 13.568 | 38.792 | 104.153 | 1.00 | 43.36 |
| ATOM | 3118 | OH2 | TIP | 209 | 28.674 | 52.942 | 57.817 | 1.00 | 43.27 |
| ATOM | 3121 | OH2 | TIP | 210 | 27.341 | 25.580 | 77.094 | 1.00 | 40.43 |
| ATOM | 3124 | OH2 | TIP | 211 | 33.895 | 35.700 | 78.552 | 1.00 | 31.26 |
| ATOM | 3127 | OH2 | TIP | 213 | 36.039 | 41.473 | 62.983 | 1.00 | 36.60 |
| ATOM | 3130 | OH2 | TIP | 215 | 3.114 | 32.257 | 85.950 | 1.00 | 40.38 |
| ATOM | 3133 | OH2 | TIP | 216 | 29.196 | 19.501 | 86.311 | 1.00 | 27.87 |
| ATOM | 3136 | OH2 | TIP | 217 | 1.734 | 38.940 | 80.274 | 1.00 | 29.80 |
| ATOM | 3139 | OH2 | TIP | 218 | 13.815 | 67.086 | 76.838 | 1.00 | 49.80 |
| ATOM | 3142 | OH2 | TIP | 219 | 6.229 | 43.091 | 87.714 | 1.00 | 46.16 |
| ATOM | 3145 | OH2 | TIP | 221 | 15.410 | 51.944 | 90.086 | 1.00 | 36.89 |
| ATOM | 3148 | OH2 | TIP | 225 | 7.645 | 32.694 | 69.299 | 1.00 | 49.48 |
| ATOM | 3151 | OH2 | TIP | 232 | 38.235 | 43.952 | 79.309 | 1.00 | 34.31 |
| ATOM | 3154 | OH2 | TIP | 233 | 16.673 | 67.605 | 66.736 | 1.00 | 42.44 |
| ATOM | 3157 | OH2 | TIP | 238 | 31.695 | 33.929 | 65.363 | 1.00 | 37.59 |
| ATOM | 3160 | OH2 | TIP | 239 | 39.136 | 48.319 | 75.756 | 1.00 | 30.95 |
| ATOM | 3163 | OH2 | TIP | 246 | 13.766 | 42.285 | 91.193 | 1.00 | 37.06 |
| ATOM | 3166 | OH2 | TIP | 250 | 10.830 | 20.805 | 92.924 | 1.00 | 42.77 |
| ATOM | 3169 | OH2 | TIP | 253 | 15.397 | 18.714 | 83.768 | 1.00 | 52.46 |
| ATOM | 3172 | OH2 | TIP | 904 | 20.775 | 41.091 | 87.469 | 1.00 | 26.19 |
| ATOM | 3175 | OH2 | TIP | 905 | 14.259 | 45.126 | 90.442 | 1.00 | 33.83 |
| ATOM | 3178 | OH2 | TIP | 906 | 19.912 | 46.870 | 90.941 | 1.00 | 32.08 |
| ATOM | 3181 | OH2 | TIP | 907 | 19.475 | 44.746 | 88.140 | 1.00 | 34.56 |
| ATOM | 3184 | OH2 | TIP | 908 | 23.007 | 45.712 | 92.056 | 1.00 | 27.28 |

TABLE 1-continued

Coordinates of Lck bound with PP2

| | | Atom Type | Res | # | X | Y | Z | Occ | B |
|---|---|---|---|---|---|---|---|---|---|
| ATOM | 3187 | OH2 | TIP | 909 | 16.243 | 39.301 | 84.268 | 1.00 | 13.29 |
| ATOM | 3190 | OH2 | TIP | 910 | 30.673 | 39.068 | 83.162 | 1.00 | 20.89 |
| ATOM | 3193 | OH2 | TIP | 911 | 32.869 | 40.494 | 79.855 | 1.00 | 30.39 |
| ATOM | 3196 | OH2 | TIP | 912 | 34.067 | 33.748 | 75.534 | 1.00 | 31.62 |
| ATOM | 3199 | S | SO4 | 901 | 20.211 | 32.729 | 69.365 | 1.00 | 11.83 |
| ATOM | 3200 | O1 | SO4 | 901 | 19.917 | 32.055 | 70.576 | 1.00 | 8.25 |
| ATOM | 3201 | O2 | SO4 | 901 | 18.988 | 33.154 | 68.793 | 1.00 | 11.09 |
| ATOM | 3202 | O3 | SO4 | 901 | 21.079 | 33.859 | 69.664 | 1.00 | 9.69 |
| ATOM | 3203 | O4 | SO4 | 901 | 20.891 | 31.903 | 68.483 | 1.00 | 8.29 |
| ATOM | 3204 | S | SO4 | 902 | 39.416 | 37.847 | 73.393 | 1.00 | 33.31 |
| ATOM | 3205 | O1 | SO4 | 902 | 38.532 | 36.720 | 73.276 | 1.00 | 36.88 |
| ATOM | 3206 | O2 | SO4 | 902 | 40.315 | 37.846 | 72.295 | 1.00 | 30.80 |
| ATOM | 3207 | O3 | SO4 | 902 | 38.625 | 39.033 | 73.415 | 1.00 | 32.33 |
| ATOM | 3208 | O4 | SO4 | 902 | 40.103 | 37.742 | 74.636 | 1.00 | 30.64 |
| ATOM | 3209 | S | SO4 | 903 | 14.903 | 66.497 | 81.052 | 1.00 | 45.64 |
| ATOM | 3210 | O1 | SO4 | 903 | 14.611 | 65.314 | 80.325 | 1.00 | 45.40 |
| ATOM | 3211 | O2 | SO4 | 903 | 13.851 | 67.466 | 80.876 | 1.00 | 39.04 |
| ATOM | 3212 | O3 | SO4 | 903 | 15.056 | 66.123 | 82.449 | 1.00 | 41.16 |
| ATOM | 3213 | O4 | SO4 | 903 | 16.087 | 67.039 | 80.513 | 1.00 | 42.64 |
| ATOM | 3214 | C1 | TES | 1 | 25.406 | 37.409 | 83.740 | 1.00 | 18.65 |
| ATOM | 3215 | N2 | TES | 1 | 26.303 | 36.893 | 82.876 | 1.00 | 17.59 |
| ATOM | 3216 | C3 | TES | 1 | 26.063 | 35.914 | 82.050 | 1.00 | 16.60 |
| ATOM | 3217 | N4 | TES | 1 | 24.789 | 35.339 | 82.066 | 1.00 | 17.34 |
| ATOM | 3218 | C5 | TES | 1 | 23.880 | 35.860 | 82.935 | 1.00 | 17.94 |
| ATOM | 3219 | C6 | TES | 1 | 24.124 | 36.952 | 83.843 | 1.00 | 19.34 |
| ATOM | 3220 | C8 | TES | 1 | 23.433 | 37.629 | 84.848 | 1.00 | 20.90 |
| ATOM | 3221 | N9 | TES | 1 | 24.295 | 38.548 | 85.351 | 1.00 | 23.47 |
| ATOM | 3222 | N10 | TES | 1 | 25.526 | 38.402 | 84.658 | 1.00 | 20.41 |
| ATOM | 3223 | C11 | TES | 1 | 22.064 | 37.416 | 85.360 | 1.00 | 24.35 |
| ATOM | 3224 | C12 | TES | 1 | 21.559 | 36.094 | 85.645 | 1.00 | 21.75 |
| ATOM | 3225 | C13 | TES | 1 | 20.245 | 35.936 | 86.147 | 1.00 | 19.80 |
| ATOM | 3226 | C14 | TES | 1 | 19.451 | 37.077 | 86.345 | 1.00 | 21.04 |
| ATOM | 3227 | C15 | TES | 1 | 19.913 | 38.376 | 86.105 | 1.00 | 24.23 |
| ATOM | 3228 | C16 | TES | 1 | 21.245 | 38.551 | 85.600 | 1.00 | 24.86 |
| ATOM | 3229 | CL2 | TES | 1 | 17.843 | 36.693 | 86.919 | 1.00 | 24.39 |
| ATOM | 3230 | C22 | TES | 1 | 26.723 | 39.233 | 85.003 | 1.00 | 21.28 |
| ATOM | 3231 | C23 | TES | 1 | 27.086 | 40.186 | 83.849 | 1.00 | 22.71 |
| ATOM | 3232 | C27 | TES | 1 | 27.859 | 38.378 | 85.381 | 1.00 | 19.02 |
| ATOM | 3233 | C31 | TES | 1 | 26.327 | 40.092 | 86.267 | 1.00 | 20.75 |
| ATOM | 3234 | N35 | TES | 1 | 22.684 | 35.170 | 82.804 | 1.00 | 17.59 |
| ATOM | 3235 | H1 | TES | 1 | 24.169 | 39.201 | 86.141 | 1.00 | 20.00 |
| ATOM | 3236 | H2 | TES | 1 | 21.917 | 35.543 | 83.360 | 1.00 | 20.00 |
| ATOM | 3237 | H3 | TES | 1 | 22.707 | 34.421 | 82.235 | 1.00 | 20.00 |
| END | | | | | | | | | |

TABLE 2

Coordinates of Lck bound with AMP-PNP

| | | Atom Type | Res | # | X | Y | Z | Occ | B |
|---|---|---|---|---|---|---|---|---|---|
| ATOM | 1 | CB | LYS | 231 | 1.530 | 26.649 | 88.787 | 1.00 | 37.83 |
| ATOM | 2 | CG | LYS | 231 | 0.717 | 26.584 | 87.564 | 1.00 | 37.44 |
| ATOM | 3 | CD | LYS | 231 | 1.283 | 25.595 | 86.606 | 1.00 | 38.84 |
| ATOM | 4 | CE | LYS | 231 | 0.371 | 25.484 | 85.401 | 1.00 | 43.58 |
| ATOM | 5 | NZ | LYS | 231 | 0.880 | 24.421 | 84.468 | 1.00 | 44.98 |
| ATOM | 9 | C | LYS | 231 | 1.837 | 27.516 | 91.023 | 1.00 | 35.81 |
| ATOM | 10 | O | LYS | 231 | 2.856 | 28.159 | 91.228 | 1.00 | 33.83 |
| ATOM | 13 | N | LYS | 231 | 1.192 | 29.091 | 89.212 | 1.00 | 39.11 |
| ATOM | 15 | CA | LYS | 231 | 1.048 | 27.708 | 89.771 | 1.00 | 36.90 |
| ATOM | 16 | N | PRO | 232 | 1.341 | 26.653 | 91.909 | 1.00 | 35.23 |
| ATOM | 17 | CD | PRO | 232 | 0.047 | 25.938 | 91.884 | 1.00 | 36.98 |
| ATOM | 18 | CA | PRO | 232 | 2.077 | 26.404 | 93.149 | 1.00 | 32.73 |
| ATOM | 19 | CB | PRO | 232 | 1.147 | 25.423 | 93.888 | 1.00 | 32.14 |
| ATOM | 20 | CG | PRO | 232 | 0.326 | 24.779 | 92.787 | 1.00 | 35.96 |
| ATOM | 21 | C | PRO | 232 | 3.482 | 25.814 | 92.739 | 1.00 | 31.15 |
| ATOM | 22 | O | PRO | 232 | 3.577 | 25.249 | 91.649 | 1.00 | 27.60 |
| ATOM | 23 | N | TRP | 233 | 4.559 | 26.010 | 93.532 | 1.00 | 31.09 |
| ATOM | 25 | CA | TRP | 233 | 5.943 | 25.510 | 93.202 | 1.00 | 30.95 |
| ATOM | 26 | CB | TRP | 233 | 7.057 | 25.851 | 94.244 | 1.00 | 28.05 |

TABLE 2-continued

Coordinates of Lck bound with AMP-PNP

| | Atom Type | Res | # | X | Y | Z | Occ | B |
|---|---|---|---|---|---|---|---|---|
| ATOM | 27 | CG | TRP | 233 | 6.983 | 25.142 | 95.538 | 1.00 | 25.65 |
| ATOM | 28 | CD2 | TRP | 233 | 7.393 | 23.796 | 95.821 | 1.00 | 24.06 |
| ATOM | 29 | CE2 | TRP | 233 | 7.102 | 23.557 | 97.170 | 1.00 | 24.26 |
| ATOM | 30 | CE3 | TRP | 233 | 7.972 | 22.773 | 95.049 | 1.00 | 21.80 |
| ATOM | 31 | CD1 | TRP | 233 | 6.491 | 25.638 | 96.677 | 1.00 | 26.39 |
| ATOM | 32 | NE1 | TRP | 233 | 6.552 | 24.700 | 97.673 | 1.00 | 26.21 |
| ATOM | 34 | CZ2 | TRP | 233 | 7.361 | 22.322 | 97.800 | 1.00 | 24.85 |
| ATOM | 35 | CZ3 | TRP | 233 | 8.232 | 21.532 | 95.675 | 1.00 | 20.36 |
| ATOM | 36 | CH2 | TRP | 233 | 7.922 | 21.324 | 97.044 | 1.00 | 19.92 |
| ATOM | 37 | C | TRP | 233 | 6.015 | 24.011 | 92.831 | 1.00 | 31.74 |
| ATOM | 38 | O | TRP | 233 | 6.824 | 23.632 | 91.973 | 1.00 | 30.34 |
| ATOM | 39 | N | TRP | 234 | 5.101 | 23.199 | 93.409 | 1.00 | 33.48 |
| ATOM | 41 | CA | TRP | 234 | 5.018 | 21.725 | 93.154 | 1.00 | 33.75 |
| ATOM | 42 | CB | TRP | 234 | 4.216 | 20.921 | 94.207 | 1.00 | 31.16 |
| ATOM | 43 | CG | TRP | 234 | 2.776 | 21.333 | 94.488 | 1.00 | 28.34 |
| ATOM | 44 | CD2 | TRP | 234 | 2.398 | 22.201 | 95.524 | 1.00 | 26.29 |
| ATOM | 45 | CE2 | TRP | 234 | 0.986 | 22.293 | 95.534 | 1.00 | 26.45 |
| ATOM | 46 | CE3 | TRP | 234 | 3.139 | 22.935 | 96.456 | 1.00 | 26.00 |
| ATOM | 47 | CD1 | TRP | 234 | 1.607 | 20.920 | 93.881 | 1.00 | 26.78 |
| ATOM | 48 | NE1 | TRP | 234 | 0.539 | 21.498 | 94.515 | 1.00 | 27.76 |
| ATOM | 50 | CZ2 | TRP | 234 | 0.295 | 23.095 | 96.450 | 1.00 | 27.03 |
| ATOM | 51 | CZ3 | TRP | 234 | 2.474 | 23.722 | 97.353 | 1.00 | 28.64 |
| ATOM | 52 | CH2 | TRP | 234 | 1.051 | 23.802 | 97.354 | 1.00 | 27.62 |
| ATOM | 53 | C | TRP | 234 | 4.401 | 21.432 | 91.833 | 1.00 | 34.53 |
| ATOM | 54 | O | TRP | 234 | 4.297 | 20.267 | 91.391 | 1.00 | 33.15 |
| ATOM | 55 | N | GLU | 235 | 3.889 | 22.479 | 91.240 | 1.00 | 36.00 |
| ATOM | 57 | CA | GLU | 235 | 3.290 | 22.335 | 89.953 | 1.00 | 38.26 |
| ATOM | 58 | CB | GLU | 235 | 1.819 | 22.698 | 90.017 | 1.00 | 38.59 |
| ATOM | 59 | CG | GLU | 235 | 0.981 | 21.786 | 90.873 | 1.00 | 39.84 |
| ATOM | 60 | CD | GLU | 235 | −0.510 | 21.994 | 90.638 | 1.00 | 42.45 |
| ATOM | 61 | OE1 | GLU | 235 | −0.852 | 22.819 | 89.772 | 1.00 | 42.87 |
| ATOM | 62 | OE2 | GLU | 235 | −1.345 | 21.334 | 91.302 | 1.00 | 43.99 |
| ATOM | 63 | C | GLU | 235 | 4.016 | 23.215 | 88.938 | 1.00 | 39.64 |
| ATOM | 64 | O | GLU | 235 | 3.917 | 22.999 | 87.735 | 1.00 | 38.07 |
| ATOM | 65 | N | ASP | 236 | 4.736 | 24.216 | 89.429 | 1.00 | 42.18 |
| ATOM | 67 | CA | ASP | 236 | 5.441 | 25.112 | 88.536 | 1.00 | 43.34 |
| ATOM | 68 | CB | ASP | 236 | 6.114 | 26.227 | 89.346 | 1.00 | 45.25 |
| ATOM | 69 | CG | ASP | 236 | 6.619 | 27.343 | 88.470 | 1.00 | 47.09 |
| ATOM | 70 | OD1 | ASP | 236 | 5.786 | 28.160 | 88.049 | 1.00 | 52.49 |
| ATOM | 71 | OD2 | ASP | 236 | 7.821 | 27.369 | 88.144 | 1.00 | 47.48 |
| ATOM | 72 | C | ASP | 236 | 6.478 | 24.368 | 87.662 | 1.00 | 42.58 |
| ATOM | 73 | O | ASP | 236 | 7.409 | 23.729 | 88.171 | 1.00 | 44.15 |
| ATOM | 74 | N | GLU | 237 | 6.365 | 24.526 | 86.356 | 1.00 | 38.06 |
| ATOM | 76 | CA | GLU | 237 | 7.300 | 23.894 | 85.439 | 1.00 | 36.59 |
| ATOM | 77 | CB | GLU | 237 | 6.800 | 24.046 | 84.009 | 1.00 | 36.46 |
| ATOM | 78 | CG | GLU | 237 | 6.123 | 25.389 | 83.715 | 1.00 | 43.75 |
| ATOM | 79 | CD | GLU | 237 | 4.751 | 25.561 | 84.434 | 1.00 | 46.78 |
| ATOM | 80 | OE1 | GLU | 237 | 3.951 | 24.594 | 84.433 | 1.00 | 47.53 |
| ATOM | 81 | OE2 | GLU | 237 | 4.538 | 26.619 | 85.093 | 1.00 | 47.26 |
| ATOM | 82 | C | GLU | 237 | 8.765 | 24.357 | 85.526 | 1.00 | 36.28 |
| ATOM | 83 | O | GLU | 237 | 9.645 | 23.675 | 85.022 | 1.00 | 36.06 |
| ATOM | 84 | N | TRP | 238 | 9.022 | 25.506 | 86.153 | 1.00 | 35.21 |
| ATOM | 86 | CA | TRP | 238 | 10.378 | 26.006 | 86.255 | 1.00 | 31.93 |
| ATOM | 87 | CB | TRP | 238 | 10.415 | 27.504 | 86.030 | 1.00 | 28.95 |
| ATOM | 88 | CG | TRP | 238 | 10.089 | 27.881 | 84.648 | 1.00 | 24.79 |
| ATOM | 89 | CD2 | TRP | 238 | 8.795 | 28.214 | 84.154 | 1.00 | 25.38 |
| ATOM | 90 | CE2 | TRP | 238 | 8.955 | 28.675 | 82.835 | 1.00 | 26.85 |
| ATOM | 91 | CE3 | TRP | 238 | 7.518 | 28.167 | 84.703 | 1.00 | 21.63 |
| ATOM | 92 | CD1 | TRP | 238 | 10.963 | 28.112 | 83.628 | 1.00 | 23.77 |
| ATOM | 93 | NE1 | TRP | 238 | 10.297 | 28.600 | 82.543 | 1.00 | 26.71 |
| ATOM | 95 | CZ2 | TRP | 238 | 7.884 | 29.088 | 82.060 | 1.00 | 30.52 |
| ATOM | 96 | CZ3 | TRP | 238 | 6.468 | 28.567 | 83.946 | 1.00 | 26.61 |
| ATOM | 97 | CH2 | TRP | 238 | 6.639 | 29.024 | 82.633 | 1.00 | 30.73 |
| ATOM | 98 | C | TRP | 238 | 11.090 | 25.653 | 87.544 | 1.00 | 31.26 |
| ATOM | 99 | O | TRP | 238 | 12.303 | 25.692 | 87.607 | 1.00 | 30.87 |
| ATOM | 100 | N | GLU | 239 | 10.341 | 25.230 | 88.553 | 1.00 | 30.15 |
| ATOM | 102 | CA | GLU | 239 | 10.937 | 24.880 | 89.825 | 1.00 | 29.70 |
| ATOM | 103 | CB | GLU | 239 | 9.813 | 24.679 | 90.828 | 1.00 | 31.38 |
| ATOM | 104 | CG | GLU | 239 | 10.070 | 25.020 | 92.294 | 1.00 | 38.59 |
| ATOM | 105 | CD | GLU | 239 | 10.220 | 26.411 | 92.781 | 1.00 | 44.86 |
| ATOM | 106 | OE1 | GLU | 239 | 10.022 | 27.301 | 92.330 | 1.00 | 49.26 |
| ATOM | 107 | OE2 | GLU | 239 | 10.944 | 26.554 | 93.684 | 1.00 | 46.75 |
| ATOM | 108 | C | GLU | 239 | 11.820 | 23.606 | 89.719 | 1.00 | 29.69 |
| ATOM | 109 | O | GLU | 239 | 11.423 | 22.617 | 89.105 | 1.00 | 31.42 |

TABLE 2-continued

Coordinates of Lck bound with AMP-PNP

| | | Atom Type | Res | # | X | Y | Z | Occ | B |
|---|---|---|---|---|---|---|---|---|---|
| ATOM | 110 | N | VAL | 240 | 13.029 | 23.667 | 90.268 | 1.00 | 26.63 |
| ATOM | 112 | CA | VAL | 240 | 13.895 | 22.515 | 90.225 | 1.00 | 24.23 |
| ATOM | 113 | CB | VAL | 240 | 15.051 | 22.623 | 89.200 | 1.00 | 24.53 |
| ATOM | 114 | CG1 | VAL | 240 | 14.515 | 22.722 | 87.795 | 1.00 | 22.09 |
| ATOM | 115 | CG2 | VAL | 240 | 16.014 | 23.755 | 89.573 | 1.00 | 23.29 |
| ATOM | 116 | C | VAL | 240 | 14.536 | 22.314 | 91.560 | 1.00 | 23.64 |
| ATOM | 117 | O | VAL | 240 | 14.713 | 23.257 | 92.343 | 1.00 | 22.01 |
| ATOM | 118 | N | PRO | 241 | 14.831 | 21.056 | 91.875 | 1.00 | 22.17 |
| ATOM | 119 | CD | PRO | 241 | 14.386 | 19.838 | 91.140 | 1.00 | 21.25 |
| ATOM | 120 | CA | PRO | 241 | 15.470 | 20.731 | 93.144 | 1.00 | 20.23 |
| ATOM | 121 | CB | PRO | 241 | 15.609 | 19.216 | 93.056 | 1.00 | 19.32 |
| ATOM | 122 | CG | PRO | 241 | 14.392 | 18.797 | 92.217 | 1.00 | 18.66 |
| ATOM | 123 | C | PRO | 241 | 16.844 | 21.447 | 93.139 | 1.00 | 21.05 |
| ATOM | 124 | O | PRO | 241 | 17.469 | 21.530 | 92.084 | 1.00 | 20.90 |
| ATOM | 125 | N | ARG | 242 | 17.309 | 21.945 | 94.280 | 1.00 | 20.76 |
| ATOM | 127 | CA | ARG | 242 | 18.578 | 22.668 | 94.334 | 1.00 | 23.13 |
| ATOM | 128 | CB | ARG | 242 | 18.785 | 23.378 | 95.671 | 1.00 | 22.78 |
| ATOM | 129 | CG | ARG | 242 | 19.866 | 24.477 | 95.614 | 1.00 | 25.41 |
| ATOM | 130 | CD | ARG | 242 | 20.298 | 24.961 | 96.983 | 1.00 | 27.06 |
| ATOM | 131 | NE | ARG | 242 | 19.164 | 25.381 | 97.805 | 1.00 | 33.41 |
| ATOM | 133 | CZ | ARG | 242 | 18.606 | 26.587 | 97.755 | 1.00 | 30.59 |
| ATOM | 134 | NH1 | ARG | 242 | 19.084 | 27.491 | 96.913 | 1.00 | 29.32 |
| ATOM | 137 | NH2 | ARG | 242 | 17.573 | 26.883 | 98.537 | 1.00 | 28.47 |
| ATOM | 140 | C | ARG | 242 | 19.771 | 21.756 | 94.062 | 1.00 | 25.38 |
| ATOM | 141 | O | ARG | 242 | 20.826 | 22.221 | 93.588 | 1.00 | 24.61 |
| ATOM | 142 | N | GLU | 243 | 19.579 | 20.460 | 94.289 | 1.00 | 25.40 |
| ATOM | 144 | CA | GLU | 243 | 20.616 | 19.463 | 94.059 | 1.00 | 25.43 |
| ATOM | 145 | CB | GLU | 243 | 20.187 | 18.071 | 94.594 | 1.00 | 27.61 |
| ATOM | 146 | CG | GLU | 243 | 20.021 | 17.995 | 96.094 | 1.00 | 34.52 |
| ATOM | 147 | CD | GLU | 243 | 18.757 | 18.664 | 96.591 | 1.00 | 37.01 |
| ATOM | 148 | OE1 | GLU | 243 | 17.840 | 18.855 | 95.774 | 1.00 | 35.85 |
| ATOM | 149 | OE2 | GLU | 243 | 18.673 | 18.959 | 97.802 | 1.00 | 41.46 |
| ATOM | 150 | C | GLU | 243 | 20.935 | 19.324 | 92.577 | 1.00 | 24.43 |
| ATOM | 151 | O | GLU | 243 | 21.954 | 18.771 | 92.215 | 1.00 | 24.98 |
| ATOM | 152 | N | THR | 244 | 20.064 | 19.801 | 91.708 | 1.00 | 23.29 |
| ATOM | 154 | CA | THR | 244 | 20.327 | 19.671 | 90.282 | 1.00 | 23.34 |
| ATOM | 155 | CB | THR | 244 | 19.039 | 19.875 | 89.465 | 1.00 | 24.16 |
| ATOM | 156 | OG1 | THR | 244 | 18.630 | 21.238 | 89.603 | 1.00 | 21.58 |
| ATOM | 158 | CG2 | THR | 244 | 17.915 | 18.920 | 89.940 | 1.00 | 22.81 |
| ATOM | 159 | C | THR | 244 | 21.357 | 20.705 | 89.811 | 1.00 | 21.94 |
| ATOM | 160 | O | THR | 244 | 21.788 | 20.701 | 88.666 | 1.00 | 21.51 |
| ATOM | 161 | N | LEU | 245 | 21.789 | 21.564 | 90.722 | 1.00 | 20.26 |
| ATOM | 163 | CA | LEU | 245 | 22.690 | 22.632 | 90.349 | 1.00 | 20.18 |
| ATOM | 164 | CB | LEU | 245 | 22.052 | 24.023 | 90.633 | 1.00 | 18.93 |
| ATOM | 165 | CG | LEU | 245 | 20.724 | 24.367 | 89.916 | 1.00 | 16.80 |
| ATOM | 166 | CD1 | LEU | 245 | 20.043 | 25.508 | 90.638 | 1.00 | 15.50 |
| ATOM | 167 | CD2 | LEU | 245 | 20.982 | 24.715 | 88.479 | 1.00 | 15.07 |
| ATOM | 168 | C | LEU | 245 | 24.036 | 22.623 | 91.016 | 1.00 | 21.46 |
| ATOM | 169 | O | LEU | 245 | 24.169 | 22.329 | 92.198 | 1.00 | 24.16 |
| ATOM | 170 | N | LYS | 246 | 25.051 | 22.993 | 90.254 | 1.00 | 23.10 |
| ATOM | 172 | CA | LYS | 246 | 26.392 | 23.085 | 90.808 | 1.00 | 23.12 |
| ATOM | 173 | CB | LYS | 246 | 27.313 | 22.016 | 90.237 | 1.00 | 24.89 |
| ATOM | 174 | CG | LYS | 246 | 28.652 | 22.045 | 90.899 | 1.00 | 30.08 |
| ATOM | 175 | CD | LYS | 246 | 29.686 | 21.303 | 90.095 | 1.00 | 36.11 |
| ATOM | 176 | CE | LYS | 246 | 31.042 | 21.386 | 90.774 | 1.00 | 40.50 |
| ATOM | 177 | NZ | LYS | 246 | 32.093 | 20.897 | 89.831 | 1.00 | 45.53 |
| ATOM | 181 | C | LYS | 246 | 26.934 | 24.456 | 90.410 | 1.00 | 22.14 |
| ATOM | 182 | O | LYS | 246 | 27.057 | 24.716 | 89.224 | 1.00 | 23.00 |
| ATOM | 183 | N | LEU | 247 | 27.241 | 25.324 | 91.381 | 0.60 | 20.92 |
| ATOM | 185 | CA | LEU | 247 | 27.773 | 26.656 | 91.056 | 0.60 | 18.66 |
| ATOM | 186 | CB | LEU | 247 | 27.342 | 27.740 | 92.060 | 0.60 | 14.86 |
| ATOM | 187 | CG | LEU | 247 | 25.951 | 27.816 | 92.744 | 0.60 | 10.67 |
| ATOM | 188 | CD1 | LEU | 247 | 25.806 | 29.118 | 93.471 | 0.60 | 11.61 |
| ATOM | 189 | CD2 | LEU | 247 | 24.758 | 27.644 | 91.820 | 0.60 | 10.00 |
| ATOM | 190 | C | LEU | 247 | 29.284 | 26.537 | 90.968 | 0.60 | 19.26 |
| ATOM | 191 | O | LEU | 247 | 29.980 | 26.146 | 91.902 | 0.60 | 17.61 |
| ATOM | 192 | N | VAL | 248 | 29.785 | 26.861 | 89.793 | 1.00 | 21.68 |
| ATOM | 194 | CA | VAL | 248 | 31.188 | 26.704 | 89.567 | 1.00 | 25.27 |
| ATOM | 195 | CB | VAL | 248 | 31.398 | 25.950 | 88.256 | 1.00 | 23.58 |
| ATOM | 196 | CG1 | VAL | 248 | 32.861 | 25.815 | 87.968 | 1.00 | 25.11 |
| ATOM | 197 | CG2 | VAL | 248 | 30.759 | 24.565 | 88.369 | 1.00 | 26.69 |
| ATOM | 198 | C | VAL | 248 | 32.074 | 27.942 | 89.644 | 1.00 | 25.79 |
| ATOM | 199 | O | VAL | 248 | 33.111 | 27.907 | 90.275 | 1.00 | 26.29 |
| ATOM | 200 | N | GLU | 249 | 31.646 | 29.054 | 89.079 | 1.00 | 27.89 |

TABLE 2-continued

Coordinates of Lck bound with AMP-PNP

| | | Atom Type | Res | # | X | Y | Z | Occ | B |
|---|---|---|---|---|---|---|---|---|---|
| ATOM | 202 | CA | GLU | 249 | 32.473 | 30.247 | 89.039 | 1.00 | 27.88 |
| ATOM | 203 | CB | GLU | 249 | 33.126 | 30.296 | 87.632 | 1.00 | 31.84 |
| ATOM | 204 | CG | GLU | 249 | 33.990 | 31.504 | 87.319 | 1.00 | 37.38 |
| ATOM | 205 | CD | GLU | 249 | 34.481 | 31.683 | 85.847 | 1.00 | 41.34 |
| ATOM | 206 | OE1 | GLU | 249 | 34.082 | 31.024 | 84.840 | 1.00 | 43.62 |
| ATOM | 207 | OE2 | GLU | 249 | 35.291 | 32.617 | 85.738 | 1.00 | 44.93 |
| ATOM | 208 | C | GLU | 249 | 31.600 | 31.510 | 89.332 | 1.00 | 28.46 |
| ATOM | 209 | O | GLU | 249 | 30.566 | 31.718 | 88.722 | 1.00 | 26.68 |
| ATOM | 210 | N | ARG | 250 | 32.005 | 32.335 | 90.296 | 1.00 | 28.83 |
| ATOM | 212 | CA | ARG | 250 | 31.226 | 33.534 | 90.635 | 1.00 | 28.81 |
| ATOM | 213 | CB | ARG | 250 | 31.476 | 33.970 | 92.113 | 1.00 | 30.75 |
| ATOM | 214 | CG | ARG | 250 | 30.613 | 35.195 | 92.619 | 1.00 | 35.96 |
| ATOM | 215 | CD | ARG | 250 | 31.015 | 35.934 | 93.982 | 1.00 | 41.14 |
| ATOM | 216 | NE | ARG | 250 | 32.500 | 35.855 | 94.222 | 1.00 | 50.47 |
| ATOM | 218 | CZ | ARG | 250 | 33.085 | 35.446 | 95.148 | 1.00 | 53.39 |
| ATOM | 219 | NH1 | ARG | 250 | 32.207 | 35.230 | 95.611 | 1.00 | 55.04 |
| ATOM | 222 | NH2 | ARG | 250 | 34.231 | 35.113 | 95.622 | 1.00 | 56.01 |
| ATOM | 225 | C | ARG | 250 | 31.543 | 34.651 | 89.635 | 1.00 | 27.28 |
| ATOM | 226 | O | ARG | 250 | 32.696 | 35.018 | 89.404 | 1.00 | 27.02 |
| ATOM | 227 | N | LEU | 251 | 30.514 | 35.114 | 88.953 | 1.00 | 24.93 |
| ATOM | 229 | CA | LEU | 251 | 30.719 | 36.123 | 87.965 | 1.00 | 24.60 |
| ATOM | 230 | CB | LEU | 251 | 29.761 | 35.937 | 86.754 | 1.00 | 22.78 |
| ATOM | 231 | CG | LEU | 251 | 29.636 | 34.579 | 85.991 | 1.00 | 21.71 |
| ATOM | 232 | CD1 | LEU | 251 | 28.622 | 34.418 | 84.848 | 1.00 | 22.72 |
| ATOM | 233 | CD2 | LEU | 251 | 31.012 | 34.340 | 85.428 | 1.00 | 20.58 |
| ATOM | 234 | C | LEU | 251 | 30.502 | 37.514 | 88.575 | 1.00 | 25.88 |
| ATOM | 235 | O | LEU | 251 | 31.101 | 38.489 | 88.127 | 1.00 | 26.29 |
| ATOM | 236 | N | GLY | 252 | 29.687 | 37.579 | 89.619 | 1.00 | 25.94 |
| ATOM | 238 | CA | GLY | 252 | 29.428 | 38.861 | 90.223 | 1.00 | 25.27 |
| ATOM | 239 | C | GLY | 252 | 28.814 | 38.745 | 91.589 | 1.00 | 27.18 |
| ATOM | 240 | O | GLY | 252 | 28.179 | 37.737 | 91.904 | 1.00 | 27.65 |
| ATOM | 241 | N | ALA | 253 | 29.132 | 39.722 | 92.433 | 1.00 | 26.87 |
| ATOM | 243 | CA | ALA | 253 | 28.619 | 39.799 | 93.789 | 1.00 | 28.35 |
| ATOM | 244 | CB | ALA | 253 | 29.645 | 39.354 | 94.803 | 1.00 | 28.60 |
| ATOM | 245 | C | ALA | 253 | 28.228 | 41.244 | 94.039 | 1.00 | 28.94 |
| ATOM | 246 | O | ALA | 253 | 28.929 | 42.159 | 93.662 | 1.00 | 27.71 |
| ATOM | 247 | N | GLY | 254 | 27.070 | 41.433 | 94.651 | 1.00 | 30.03 |
| ATOM | 249 | CA | GLY | 254 | 26.590 | 42.763 | 94.929 | 1.00 | 27.78 |
| ATOM | 250 | C | GLY | 254 | 25.759 | 42.786 | 96.191 | 1.00 | 28.67 |
| ATOM | 251 | O | GLY | 254 | 25.642 | 41.805 | 96.946 | 1.00 | 27.16 |
| ATOM | 252 | N | GLN | 255 | 25.172 | 43.944 | 96.404 | 1.00 | 30.78 |
| ATOM | 254 | CA | GLN | 255 | 24.330 | 44.191 | 97.568 | 1.00 | 35.15 |
| ATOM | 255 | CB | GLN | 255 | 23.782 | 45.613 | 97.465 | 1.00 | 35.64 |
| ATOM | 256 | CG | GLN | 255 | 23.052 | 46.111 | 98.684 | 1.00 | 36.07 |
| ATOM | 257 | CD | GLN | 255 | 22.563 | 47.548 | 98.502 | 1.00 | 38.63 |
| ATOM | 258 | OE1 | GLN | 255 | 22.941 | 48.261 | 97.544 | 1.00 | 36.80 |
| ATOM | 259 | NE2 | GLN | 255 | 21.672 | 47.957 | 99.392 | 1.00 | 40.92 |
| ATOM | 262 | C | GLN | 255 | 23.145 | 43.199 | 97.698 | 1.00 | 37.01 |
| ATOM | 263 | O | GLN | 255 | 22.739 | 42.828 | 98.808 | 1.00 | 38.82 |
| ATOM | 264 | N | PHE | 256 | 22.618 | 42.734 | 96.575 | 1.00 | 35.08 |
| ATOM | 266 | CA | PHE | 256 | 21.452 | 41.858 | 96.652 | 1.00 | 34.39 |
| ATOM | 267 | CB | PHE | 256 | 20.399 | 42.381 | 95.704 | 1.00 | 33.93 |
| ATOM | 268 | CG | PHE | 256 | 20.120 | 43.841 | 95.887 | 1.00 | 35.82 |
| ATOM | 269 | CD1 | PHE | 256 | 19.590 | 44.310 | 97.084 | 1.00 | 37.69 |
| ATOM | 270 | CD2 | PHE | 256 | 20.417 | 44.751 | 94.882 | 1.00 | 37.17 |
| ATOM | 271 | CE1 | PHE | 256 | 19.366 | 45.658 | 97.269 | 1.00 | 39.52 |
| ATOM | 272 | CE2 | PHE | 256 | 20.190 | 46.117 | 95.065 | 1.00 | 37.23 |
| ATOM | 273 | CZ | PHE | 256 | 19.668 | 46.569 | 96.253 | 1.00 | 38.55 |
| ATOM | 274 | C | PHE | 256 | 21.690 | 40.393 | 96.391 | 1.00 | 35.30 |
| ATOM | 275 | O | PHE | 256 | 20.742 | 39.606 | 96.244 | 1.00 | 34.61 |
| ATOM | 276 | N | GLY | 257 | 22.957 | 40.020 | 96.287 | 1.00 | 35.29 |
| ATOM | 278 | CA | GLY | 257 | 23.243 | 38.632 | 96.046 | 1.00 | 33.59 |
| ATOM | 279 | C | GLY | 257 | 24.363 | 38.465 | 95.062 | 1.00 | 32.61 |
| ATOM | 280 | O | GLY | 257 | 25.185 | 39.363 | 94.849 | 1.00 | 33.22 |
| ATOM | 281 | N | GLU | 258 | 24.323 | 37.349 | 94.367 | 1.00 | 30.90 |
| ATOM | 283 | CA | GLU | 258 | 25.397 | 37.071 | 93.465 | 1.00 | 29.26 |
| ATOM | 284 | CB | GLU | 258 | 26.401 | 36.157 | 94.173 | 1.00 | 32.05 |
| ATOM | 285 | CG | GLU | 258 | 26.959 | 36.587 | 95.536 | 1.00 | 37.52 |
| ATOM | 286 | CD | GLU | 258 | 27.842 | 35.474 | 96.175 | 1.00 | 41.31 |
| ATOM | 287 | OE1 | GLU | 258 | 27.699 | 34.261 | 95.888 | 1.00 | 44.11 |
| ATOM | 288 | OE2 | GLU | 258 | 28.717 | 35.811 | 96.976 | 1.00 | 43.94 |
| ATOM | 289 | C | GLU | 258 | 24.958 | 36.383 | 92.171 | 1.00 | 26.26 |
| ATOM | 290 | O | GLU | 258 | 23.794 | 35.968 | 92.045 | 1.00 | 25.25 |
| ATOM | 291 | N | VAL | 259 | 25.878 | 36.354 | 91.209 | 0.77 | 22.42 |

TABLE 2-continued

Coordinates of Lck bound with AMP-PNP

| | | Atom Type | Res | # | X | Y | Z | Occ | B |
|---|---|---|---|---|---|---|---|---|---|
| ATOM | 293 | CA | VAL | 259 | 25.746 | 35.693 | 89.893 | 0.77 | 22.25 |
| ATOM | 294 | CB | VAL | 259 | 25.768 | 36.645 | 88.669 | 0.77 | 21.14 |
| ATOM | 295 | CG1 | VAL | 259 | 25.740 | 35.819 | 87.320 | 0.77 | 19.21 |
| ATOM | 296 | CG2 | VAL | 259 | 24.592 | 37.543 | 88.746 | 0.77 | 20.54 |
| ATOM | 297 | C | VAL | 259 | 26.869 | 34.696 | 89.690 | 0.77 | 21.14 |
| ATOM | 298 | O | VAL | 259 | 28.041 | 35.005 | 89.827 | 0.77 | 19.78 |
| ATOM | 299 | N | TRP | 260 | 26.429 | 33.502 | 89.315 | 1.00 | 21.25 |
| ATOM | 301 | CA | TRP | 260 | 27.279 | 32.369 | 89.092 | 1.00 | 20.50 |
| ATOM | 302 | CB | TRP | 260 | 26.947 | 31.368 | 90.160 | 1.00 | 21.50 |
| ATOM | 303 | CG | TRP | 260 | 27.438 | 31.859 | 91.376 | 1.00 | 22.22 |
| ATOM | 304 | CD2 | TRP | 260 | 28.564 | 31.372 | 92.069 | 1.00 | 23.17 |
| ATOM | 305 | CE2 | TRP | 260 | 28.614 | 32.046 | 93.302 | 1.00 | 23.80 |
| ATOM | 306 | CE3 | TRP | 260 | 29.537 | 30.393 | 91.791 | 1.00 | 24.27 |
| ATOM | 307 | CD1 | TRP | 260 | 26.872 | 32.818 | 92.163 | 1.00 | 24.11 |
| ATOM | 308 | NE1 | TRP | 260 | 27.573 | 32.931 | 93.336 | 1.00 | 22.67 |
| ATOM | 310 | CZ2 | TRP | 260 | 29.594 | 31.773 | 94.274 | 1.00 | 27.01 |
| ATOM | 311 | CZ3 | TRP | 260 | 30.514 | 30.117 | 92.748 | 1.00 | 25.33 |
| ATOM | 312 | CH2 | TRP | 260 | 30.541 | 30.804 | 93.988 | 1.00 | 25.33 |
| ATOM | 313 | C | TRP | 260 | 27.186 | 31.645 | 87.789 | 1.00 | 20.66 |
| ATOM | 314 | O | TRP | 260 | 26.122 | 31.642 | 87.135 | 1.00 | 17.41 |
| ATOM | 315 | N | MET | 261 | 28.338 | 31.155 | 87.330 | 1.00 | 22.38 |
| ATOM | 317 | CA | MET | 261 | 28.302 | 30.271 | 86.172 | 1.00 | 22.42 |
| ATOM | 318 | CB | MET | 261 | 29.507 | 30.278 | 85.251 | 1.00 | 24.52 |
| ATOM | 319 | CG | MET | 261 | 29.443 | 29.097 | 84.252 | 1.00 | 26.58 |
| ATOM | 320 | SD | MET | 261 | 30.476 | 27.739 | 84.446 | 1.00 | 30.59 |
| ATOM | 321 | CE | MET | 261 | 29.455 | 26.614 | 84.399 | 1.00 | 32.94 |
| ATOM | 322 | C | MET | 261 | 28.214 | 28.899 | 86.802 | 1.00 | 21.77 |
| ATOM | 323 | O | MET | 261 | 28.940 | 28.571 | 87.748 | 1.00 | 22.16 |
| ATOM | 324 | N | GLY | 262 | 27.242 | 28.150 | 86.320 | 1.00 | 21.66 |
| ATOM | 326 | CA | GLY | 262 | 27.052 | 26.820 | 86.849 | 1.00 | 17.56 |
| ATOM | 327 | C | GLY | 262 | 26.566 | 25.840 | 85.828 | 1.00 | 19.07 |
| ATOM | 328 | O | GLY | 262 | 26.451 | 26.139 | 84.634 | 1.00 | 17.94 |
| ATOM | 329 | N | TYR | 263 | 26.303 | 24.646 | 86.348 | 1.00 | 18.76 |
| ATOM | 331 | CA | TYR | 263 | 25.796 | 23.497 | 85.560 | 1.00 | 18.48 |
| ATOM | 332 | CB | TYR | 263 | 26.866 | 22.398 | 85.444 | 1.00 | 16.81 |
| ATOM | 333 | CG | TYR | 263 | 28.033 | 22.802 | 84.624 | 1.00 | 19.76 |
| ATOM | 334 | CD1 | TYR | 263 | 27.972 | 22.759 | 83.238 | 1.00 | 19.56 |
| ATOM | 335 | CE1 | TYR | 263 | 29.010 | 23.209 | 82.469 | 1.00 | 23.28 |
| ATOM | 336 | CD2 | TYR | 263 | 29.175 | 23.295 | 85.223 | 1.00 | 19.69 |
| ATOM | 337 | CE2 | TYR | 263 | 30.247 | 23.745 | 84.467 | 1.00 | 21.11 |
| ATOM | 338 | CZ | TYR | 263 | 30.157 | 23.703 | 83.088 | 1.00 | 23.30 |
| ATOM | 339 | OH | TYR | 263 | 31.184 | 24.173 | 82.298 | 1.00 | 26.58 |
| ATOM | 341 | C | TYR | 263 | 24.531 | 22.867 | 86.172 | 1.00 | 17.60 |
| ATOM | 342 | O | TYR | 263 | 24.411 | 22.682 | 87.377 | 1.00 | 16.26 |
| ATOM | 343 | N | TYR | 264 | 23.585 | 22.583 | 85.298 | 1.00 | 20.34 |
| ATOM | 345 | CA | TYR | 264 | 22.347 | 21.915 | 85.695 | 1.00 | 22.16 |
| ATOM | 346 | CB | TYR | 264 | 21.151 | 22.594 | 85.035 | 1.00 | 21.31 |
| ATOM | 347 | CG | TYR | 264 | 19.877 | 21.798 | 85.192 | 1.00 | 23.68 |
| ATOM | 348 | CD1 | TYR | 264 | 19.096 | 21.950 | 86.306 | 1.00 | 20.71 |
| ATOM | 349 | CE1 | TYR | 264 | 17.928 | 21.188 | 86.481 | 1.00 | 23.19 |
| ATOM | 350 | CD2 | TYR | 264 | 19.486 | 20.866 | 84.226 | 1.00 | 25.63 |
| ATOM | 351 | CE2 | TYR | 264 | 18.327 | 20.092 | 84.386 | 1.00 | 25.62 |
| ATOM | 352 | CZ | TYR | 264 | 17.563 | 20.267 | 85.520 | 1.00 | 24.58 |
| ATOM | 353 | OH | TYR | 264 | 16.414 | 19.531 | 85.714 | 1.00 | 27.93 |
| ATOM | 355 | C | TYR | 264 | 22.483 | 20.458 | 85.193 | 1.00 | 20.81 |
| ATOM | 356 | O | TYR | 264 | 22.757 | 20.253 | 84.010 | 1.00 | 18.48 |
| ATOM | 357 | N | ASN | 265 | 22.239 | 19.493 | 86.097 | 1.00 | 21.28 |
| ATOM | 359 | CA | ASN | 265 | 22.364 | 18.007 | 85.828 | 1.00 | 21.74 |
| ATOM | 360 | CB | ASN | 265 | 21.200 | 17.448 | 85.009 | 1.00 | 22.19 |
| ATOM | 361 | CG | ASN | 265 | 19.870 | 17.305 | 85.774 | 1.00 | 24.59 |
| ATOM | 362 | OD1 | ASN | 265 | 19.729 | 17.368 | 86.984 | 1.00 | 23.92 |
| ATOM | 363 | ND2 | ASN | 265 | 18.837 | 17.117 | 84.962 | 1.00 | 25.24 |
| ATOM | 366 | C | ASN | 265 | 23.678 | 17.680 | 85.114 | 1.00 | 18.48 |
| ATOM | 367 | O | ASN | 265 | 23.726 | 16.939 | 84.110 | 1.00 | 19.13 |
| ATOM | 368 | N | GLY | 266 | 24.712 | 18.282 | 85.692 | 1.00 | 16.90 |
| ATOM | 370 | CA | GLY | 266 | 26.101 | 18.152 | 85.289 | 1.00 | 13.15 |
| ATOM | 371 | C | GLY | 266 | 26.539 | 18.642 | 83.944 | 1.00 | 11.08 |
| ATOM | 372 | O | GLY | 266 | 27.651 | 19.128 | 83.813 | 1.00 | 16.72 |
| ATOM | 373 | N | HIS | 267 | 25.661 | 18.613 | 82.964 | 0.49 | 8.78 |
| ATOM | 375 | CA | HIS | 267 | 26.045 | 18.997 | 81.629 | 0.49 | 8.54 |
| ATOM | 376 | CB | HIS | 267 | 25.636 | 17.878 | 80.655 | 0.49 | 7.49 |
| ATOM | 377 | CG | HIS | 267 | 26.316 | 16.573 | 80.920 | 0.49 | 6.75 |
| ATOM | 378 | CD2 | HIS | 267 | 27.618 | 16.222 | 80.867 | 0.49 | 6.15 |
| ATOM | 379 | ND1 | HIS | 267 | 25.626 | 15.438 | 81.294 | 0.49 | 5.87 |

TABLE 2-continued

Coordinates of Lck bound with AMP-PNP

| | Atom Type | Res | # | X | Y | Z | Occ | B |
|---|---|---|---|---|---|---|---|---|
| ATOM | 381 | CE1 | HIS | 267 | 26.479 | 14.441 | 81.449 | 0.49 | 6.87 |
| ATOM | 382 | NE2 | HIS | 267 | 27.692 | 14.892 | 81.202 | 0.49 | 9.37 |
| ATOM | 384 | C | HIS | 267 | 25.592 | 20.337 | 81.061 | 0.49 | 10.78 |
| ATOM | 385 | O | HIS | 267 | 26.192 | 20.829 | 80.109 | 0.49 | 6.89 |
| ATOM | 386 | N | THR | 268 | 24.576 | 20.949 | 81.652 | 1.00 | 15.33 |
| ATOM | 388 | CA | THR | 268 | 24.031 | 22.195 | 81.098 | 1.00 | 19.30 |
| ATOM | 389 | CB | THR | 268 | 22.481 | 22.144 | 81.017 | 1.00 | 22.06 |
| ATOM | 390 | OG1 | THR | 268 | 22.131 | 20.956 | 80.294 | 1.00 | 20.10 |
| ATOM | 392 | CG2 | THR | 268 | 21.922 | 23.393 | 80.235 | 1.00 | 18.68 |
| ATOM | 393 | C | THR | 268 | 24.486 | 23.467 | 81.759 | 1.00 | 16.30 |
| ATOM | 394 | O | THR | 268 | 24.114 | 23.738 | 82.876 | 1.00 | 15.99 |
| ATOM | 395 | N | LYS | 269 | 25.315 | 24.197 | 81.034 | 1.00 | 16.63 |
| ATOM | 397 | CA | LYS | 269 | 25.886 | 25.461 | 81.521 | 1.00 | 19.51 |
| ATOM | 398 | CB | LYS | 269 | 27.043 | 25.966 | 80.594 | 1.00 | 19.25 |
| ATOM | 399 | CG | LYS | 269 | 28.043 | 27.034 | 81.191 | 1.00 | 23.75 |
| ATOM | 400 | CD | LYS | 269 | 29.474 | 26.916 | 80.493 | 1.00 | 26.70 |
| ATOM | 401 | CE | LYS | 269 | 30.463 | 28.100 | 80.604 | 1.00 | 31.11 |
| ATOM | 402 | NZ | LYS | 269 | 31.737 | 27.815 | 79.807 | 1.00 | 32.76 |
| ATOM | 406 | C | LYS | 269 | 24.772 | 26.489 | 81.643 | 1.00 | 16.84 |
| ATOM | 407 | O | LYS | 269 | 23.996 | 26.713 | 80.736 | 1.00 | 15.56 |
| ATOM | 408 | N | VAL | 270 | 24.657 | 27.044 | 82.842 | 1.00 | 16.32 |
| ATOM | 410 | CA | VAL | 270 | 23.629 | 28.040 | 83.104 | 1.00 | 16.17 |
| ATOM | 411 | CB | VAL | 270 | 22.429 | 27.383 | 83.834 | 1.00 | 14.53 |
| ATOM | 412 | CG1 | VAL | 270 | 21.785 | 26.336 | 82.951 | 1.00 | 14.57 |
| ATOM | 413 | CG2 | VAL | 270 | 22.898 | 26.770 | 85.156 | 1.00 | 12.27 |
| ATOM | 414 | C | VAL | 270 | 24.148 | 29.162 | 84.005 | 1.00 | 16.24 |
| ATOM | 415 | O | VAL | 270 | 25.216 | 29.036 | 84.615 | 1.00 | 14.64 |
| ATOM | 416 | N | ALA | 271 | 23.411 | 30.271 | 84.052 | 1.00 | 16.15 |
| ATOM | 418 | CA | ALA | 271 | 23.758 | 31.380 | 84.957 | 1.00 | 17.09 |
| ATOM | 419 | CB | ALA | 271 | 23.518 | 32.713 | 84.259 | 1.00 | 16.89 |
| ATOM | 420 | C | ALA | 271 | 22.852 | 31.261 | 86.171 | 1.00 | 15.23 |
| ATOM | 421 | O | ALA | 271 | 21.674 | 30.947 | 85.996 | 1.00 | 15.43 |
| ATOM | 422 | N | VAL | 272 | 23.359 | 31.494 | 87.391 | 1.00 | 16.62 |
| ATOM | 424 | CA | VAL | 272 | 22.554 | 31.406 | 88.606 | 1.00 | 17.94 |
| ATOM | 425 | CB | VAL | 272 | 22.975 | 30.235 | 89.532 | 1.00 | 17.38 |
| ATOM | 426 | CG1 | VAL | 272 | 22.120 | 30.200 | 90.800 | 1.00 | 13.54 |
| ATOM | 427 | CG2 | VAL | 272 | 22.887 | 28.925 | 88.771 | 1.00 | 18.41 |
| ATOM | 428 | C | VAL | 272 | 22.630 | 32.686 | 89.422 | 1.00 | 20.75 |
| ATOM | 429 | O | VAL | 272 | 23.697 | 33.090 | 89.885 | 1.00 | 22.07 |
| ATOM | 430 | N | LYS | 273 | 21.497 | 33.335 | 89.600 | 1.00 | 22.94 |
| ATOM | 432 | CA | LYS | 273 | 21.501 | 34.571 | 90.378 | 1.00 | 23.64 |
| ATOM | 433 | CB | LYS | 273 | 20.729 | 35.642 | 89.606 | 1.00 | 24.86 |
| ATOM | 434 | CG | LYS | 273 | 20.744 | 37.112 | 90.077 | 1.00 | 30.01 |
| ATOM | 435 | CD | LYS | 273 | 19.453 | 37.572 | 89.439 | 1.00 | 34.96 |
| ATOM | 436 | CE | LYS | 273 | 19.213 | 38.982 | 89.008 | 1.00 | 36.43 |
| ATOM | 437 | NZ | LYS | 273 | 17.744 | 38.858 | 88.903 | 1.00 | 42.94 |
| ATOM | 441 | C | LYS | 273 | 20.855 | 34.209 | 91.695 | 1.00 | 20.45 |
| ATOM | 442 | O | LYS | 273 | 19.780 | 33.648 | 91.711 | 1.00 | 20.86 |
| ATOM | 443 | N | SER | 274 | 21.529 | 34.514 | 92.791 | 0.65 | 18.76 |
| ATOM | 445 | CA | SER | 274 | 21.021 | 34.171 | 94.098 | 0.65 | 19.42 |
| ATOM | 446 | CB | SER | 274 | 22.065 | 33.395 | 94.881 | 0.65 | 21.93 |
| ATOM | 447 | OG | SER | 274 | 23.236 | 34.180 | 95.068 | 0.65 | 27.20 |
| ATOM | 449 | C | SER | 274 | 20.678 | 35.410 | 94.865 | 0.65 | 21.38 |
| ATOM | 450 | O | SER | 274 | 21.346 | 36.432 | 94.773 | 0.65 | 19.86 |
| ATOM | 451 | N | LEU | 275 | 19.683 | 35.281 | 95.719 | 1.00 | 25.45 |
| ATOM | 453 | CA | LEU | 275 | 19.254 | 36.416 | 96.476 | 1.00 | 27.40 |
| ATOM | 454 | CB | LEU | 275 | 17.711 | 36.464 | 96.564 | 1.00 | 27.49 |
| ATOM | 455 | CG | LEU | 275 | 16.867 | 37.412 | 97.463 | 1.00 | 28.09 |
| ATOM | 456 | CD1 | LEU | 275 | 16.942 | 38.885 | 97.101 | 1.00 | 25.93 |
| ATOM | 457 | CD2 | LEU | 275 | 15.416 | 36.936 | 97.377 | 1.00 | 27.55 |
| ATOM | 458 | C | LEU | 275 | 19.907 | 36.445 | 97.833 | 1.00 | 27.78 |
| ATOM | 459 | O | LEU | 275 | 19.924 | 35.448 | 98.541 | 1.00 | 29.52 |
| ATOM | 460 | N | LYS | 276 | 20.457 | 37.600 | 98.179 | 1.00 | 29.98 |
| ATOM | 462 | CA | LYS | 276 | 21.077 | 37.802 | 99.476 | 1.00 | 32.68 |
| ATOM | 463 | CB | LYS | 276 | 21.982 | 39.031 | 99.481 | 1.00 | 33.96 |
| ATOM | 464 | CG | LYS | 276 | 22.616 | 39.278 | 100.832 | 1.00 | 36.49 |
| ATOM | 465 | CD | LYS | 276 | 23.659 | 40.320 | 100.731 | 1.00 | 42.22 |
| ATOM | 466 | CE | LYS | 276 | 24.215 | 40.606 | 102.123 | 1.00 | 47.21 |
| ATOM | 467 | NZ | LYS | 276 | 25.344 | 41.588 | 102.053 | 1.00 | 51.35 |
| ATOM | 471 | C | LYS | 276 | 19.979 | 37.963 | 100.515 | 1.00 | 32.85 |
| ATOM | 472 | O | LYS | 276 | 19.207 | 38.917 | 100.458 | 1.00 | 33.52 |
| ATOM | 473 | N | ALA | 277 | 19.946 | 37.078 | 101.504 | 1.00 | 34.58 |
| ATOM | 475 | CA | ALA | 277 | 18.855 | 37.188 | 102.460 | 1.00 | 34.05 |
| ATOM | 476 | CB | ALA | 277 | 18.590 | 35.935 | 103.315 | 1.00 | 35.34 |

TABLE 2-continued

Coordinates of Lck bound with AMP-PNP

| | Atom Type | Res | # | X | Y | Z | Occ | B |
|---|---|---|---|---|---|---|---|---|
| ATOM | 477 | C | ALA | 277 | 18.837 | 38.420 | 103.250 | 1.00 | 34.04 |
| ATOM | 478 | O | ALA | 277 | 19.822 | 38.880 | 103.840 | 1.00 | 38.07 |
| ATOM | 479 | N | GLY | 278 | 17.657 | 38.987 | 103.145 | 1.00 | 32.76 |
| ATOM | 481 | CA | GLY | 278 | 17.389 | 40.217 | 103.795 | 1.00 | 30.78 |
| ATOM | 482 | C | GLY | 278 | 17.837 | 41.403 | 102.975 | 1.00 | 30.85 |
| ATOM | 483 | O | GLY | 278 | 17.515 | 42.505 | 103.365 | 1.00 | 31.24 |
| ATOM | 484 | N | SER | 279 | 18.526 | 41.242 | 101.852 | 1.00 | 29.47 |
| ATOM | 486 | CA | SER | 279 | 18.926 | 42.435 | 101.139 | 1.00 | 28.75 |
| ATOM | 487 | CB | SER | 279 | 19.994 | 42.091 | 100.127 | 1.00 | 27.18 |
| ATOM | 488 | OG | SER | 279 | 19.457 | 41.248 | 99.136 | 1.00 | 23.79 |
| ATOM | 490 | C | SER | 279 | 17.741 | 43.107 | 100.434 | 1.00 | 30.73 |
| ATOM | 491 | O | SER | 279 | 17.805 | 44.300 | 100.089 | 1.00 | 33.17 |
| ATOM | 492 | N | MET | 280 | 16.697 | 42.325 | 100.140 | 1.00 | 27.39 |
| ATOM | 494 | CA | MET | 280 | 15.542 | 42.858 | 99.442 | 1.00 | 23.62 |
| ATOM | 495 | CB | MET | 280 | 15.864 | 43.127 | 97.984 | 1.00 | 24.43 |
| ATOM | 496 | CG | MET | 280 | 16.214 | 41.890 | 97.209 | 1.00 | 23.94 |
| ATOM | 497 | SD | MET | 280 | 16.460 | 42.155 | 95.478 | 1.00 | 28.79 |
| ATOM | 498 | CE | MET | 280 | 14.806 | 42.233 | 94.886 | 1.00 | 23.16 |
| ATOM | 499 | C | MET | 280 | 14.446 | 41.837 | 99.528 | 1.00 | 23.80 |
| ATOM | 500 | O | MET | 280 | 14.652 | 40.717 | 100.010 | 1.00 | 24.10 |
| ATOM | 501 | N | SER | 281 | 13.269 | 42.198 | 99.030 | 1.00 | 22.93 |
| ATOM | 503 | CA | SER | 281 | 12.151 | 41.289 | 99.102 | 1.00 | 20.64 |
| ATOM | 504 | CB | SER | 281 | 10.853 | 41.981 | 98.725 | 1.00 | 21.35 |
| ATOM | 505 | OG | SER | 281 | 9.789 | 41.050 | 98.602 | 1.00 | 21.47 |
| ATOM | 507 | C | SER | 281 | 12.275 | 40.068 | 98.223 | 1.00 | 18.82 |
| ATOM | 508 | O | SER | 281 | 12.547 | 40.172 | 97.032 | 1.00 | 20.53 |
| ATOM | 509 | N | PRO | 282 | 12.106 | 38.907 | 98.828 | 0.51 | 14.57 |
| ATOM | 510 | CD | PRO | 282 | 12.078 | 38.605 | 100.266 | 0.51 | 13.40 |
| ATOM | 511 | CA | PRO | 282 | 12.195 | 37.703 | 98.034 | 0.51 | 12.57 |
| ATOM | 512 | CB | PRO | 282 | 12.245 | 36.600 | 99.092 | 0.51 | 11.19 |
| ATOM | 513 | CG | PRO | 282 | 11.579 | 37.204 | 100.266 | 0.51 | 10.35 |
| ATOM | 514 | C | PRO | 282 | 10.992 | 37.691 | 97.044 | 0.51 | 13.41 |
| ATOM | 515 | O | PRO | 282 | 11.091 | 37.097 | 95.979 | 0.51 | 9.01 |
| ATOM | 516 | N | ASP | 283 | 9.903 | 38.442 | 97.324 | 1.00 | 18.15 |
| ATOM | 518 | CA | ASP | 283 | 8.762 | 38.551 | 96.392 | 1.00 | 17.76 |
| ATOM | 519 | CB | ASP | 283 | 7.525 | 39.193 | 97.049 | 1.00 | 22.85 |
| ATOM | 520 | CG | ASP | 283 | 6.351 | 39.362 | 96.061 | 1.00 | 26.42 |
| ATOM | 521 | OD1 | ASP | 283 | 5.871 | 38.330 | 95.582 | 1.00 | 29.45 |
| ATOM | 522 | OD2 | ASP | 283 | 5.942 | 40.486 | 95.723 | 1.00 | 27.03 |
| ATOM | 523 | C | ASP | 283 | 9.170 | 39.388 | 95.208 | 1.00 | 18.60 |
| ATOM | 524 | O | ASP | 283 | 8.874 | 39.069 | 94.056 | 1.00 | 17.98 |
| ATOM | 525 | N | ALA | 284 | 9.882 | 40.483 | 95.495 | 1.00 | 19.23 |
| ATOM | 527 | CA | ALA | 284 | 10.369 | 41.385 | 94.446 | 1.00 | 20.69 |
| ATOM | 528 | CB | ALA | 284 | 10.904 | 42.671 | 95.096 | 1.00 | 18.76 |
| ATOM | 529 | C | ALA | 284 | 11.474 | 40.702 | 93.642 | 1.00 | 19.76 |
| ATOM | 530 | O | ALA | 284 | 11.659 | 40.978 | 92.463 | 1.00 | 21.88 |
| ATOM | 531 | N | PHE | 285 | 12.256 | 39.869 | 94.296 | 1.00 | 21.00 |
| ATOM | 533 | CA | PHE | 285 | 13.304 | 39.153 | 93.568 | 1.00 | 19.86 |
| ATOM | 534 | CB | PHE | 285 | 14.156 | 38.362 | 94.576 | 1.00 | 21.58 |
| ATOM | 535 | CG | PHE | 285 | 15.271 | 37.599 | 93.938 | 1.00 | 21.81 |
| ATOM | 536 | CD1 | PHE | 285 | 16.415 | 38.254 | 93.505 | 1.00 | 21.74 |
| ATOM | 537 | CD2 | PHE | 285 | 15.188 | 36.219 | 93.807 | 1.00 | 20.96 |
| ATOM | 538 | CE1 | PHE | 285 | 17.485 | 37.517 | 92.945 | 1.00 | 25.30 |
| ATOM | 539 | CE2 | PHE | 285 | 16.225 | 35.459 | 93.260 | 1.00 | 19.10 |
| ATOM | 540 | CZ | PHE | 285 | 17.382 | 36.100 | 92.823 | 1.00 | 23.29 |
| ATOM | 541 | C | PHE | 285 | 12.627 | 38.204 | 92.574 | 1.00 | 19.96 |
| ATOM | 542 | O | PHE | 285 | 12.892 | 38.261 | 91.367 | 1.00 | 19.45 |
| ATOM | 543 | N | LEU | 286 | 11.662 | 37.418 | 93.051 | 1.00 | 17.20 |
| ATOM | 545 | CA | LEU | 286 | 11.009 | 36.439 | 92.166 | 1.00 | 17.90 |
| ATOM | 546 | CB | LEU | 286 | 10.276 | 35.373 | 92.997 | 1.00 | 19.19 |
| ATOM | 547 | CG | LEU | 286 | 11.177 | 34.438 | 93.824 | 1.00 | 19.01 |
| ATOM | 548 | CD1 | LEU | 286 | 10.332 | 33.564 | 94.734 | 1.00 | 18.18 |
| ATOM | 549 | CD2 | LEU | 286 | 11.998 | 33.593 | 92.853 | 1.00 | 20.50 |
| ATOM | 550 | C | LEU | 286 | 10.095 | 37.006 | 91.112 | 1.00 | 18.94 |
| ATOM | 551 | O | LEU | 286 | 9.796 | 36.344 | 90.095 | 1.00 | 18.97 |
| ATOM | 552 | N | ALA | 287 | 9.588 | 38.217 | 91.340 | 1.00 | 20.47 |
| ATOM | 554 | CA | ALA | 287 | 8.729 | 38.846 | 90.353 | 1.00 | 19.43 |
| ATOM | 555 | CB | ALA | 287 | 8.328 | 40.262 | 90.816 | 1.00 | 21.51 |
| ATOM | 556 | C | ALA | 287 | 9.406 | 38.916 | 88.981 | 1.00 | 19.24 |
| ATOM | 557 | O | ALA | 287 | 8.761 | 38.846 | 87.945 | 1.00 | 21.16 |
| ATOM | 558 | N | GLU | 288 | 10.713 | 39.052 | 88.974 | 1.00 | 21.50 |
| ATOM | 560 | CA | GLU | 288 | 11.430 | 39.108 | 87.711 | 1.00 | 21.69 |
| ATOM | 561 | CB | GLU | 288 | 12.918 | 39.398 | 87.932 | 1.00 | 20.35 |
| ATOM | 562 | CG | GLU | 288 | 13.645 | 39.463 | 86.597 | 1.00 | 20.74 |

TABLE 2-continued

Coordinates of Lck bound with AMP-PNP

| | | Atom Type | Res | # | X | Y | Z | Occ | B |
|---|---|---|---|---|---|---|---|---|---|
| ATOM | 563 | CD | GLU | 288 | 15.132 | 39.628 | 86.723 | 1.00 | 20.43 |
| ATOM | 564 | OE1 | GLU | 288 | 15.674 | 39.496 | 87.832 | 1.00 | 21.79 |
| ATOM | 565 | OE2 | GLU | 288 | 15.744 | 39.903 | 85.689 | 1.00 | 25.80 |
| ATOM | 566 | C | GLU | 288 | 11.289 | 37.771 | 86.982 | 1.00 | 21.41 |
| ATOM | 567 | O | GLU | 288 | 11.076 | 37.738 | 85.775 | 1.00 | 19.82 |
| ATOM | 568 | N | ALA | 289 | 11.425 | 36.672 | 87.720 | 1.00 | 23.03 |
| ATOM | 570 | CA | ALA | 289 | 11.298 | 35.339 | 87.103 | 1.00 | 26.06 |
| ATOM | 571 | CB | ALA | 289 | 11.664 | 34.239 | 88.119 | 1.00 | 25.97 |
| ATOM | 572 | C | ALA | 289 | 9.851 | 35.144 | 86.582 | 1.00 | 26.33 |
| ATOM | 573 | O | ALA | 289 | 9.638 | 34.651 | 85.467 | 1.00 | 24.08 |
| ATOM | 574 | N | ASN | 290 | 8.866 | 35.549 | 87.372 | 1.00 | 26.78 |
| ATOM | 576 | CA | ASN | 290 | 7.483 | 35.426 | 86.911 | 1.00 | 28.16 |
| ATOM | 577 | CB | ASN | 290 | 6.521 | 35.896 | 87.992 | 1.00 | 31.30 |
| ATOM | 578 | CG | ASN | 290 | 6.545 | 34.976 | 89.195 | 1.00 | 34.57 |
| ATOM | 579 | OD1 | ASN | 290 | 6.896 | 33.794 | 89.070 | 1.00 | 37.25 |
| ATOM | 580 | ND2 | ASN | 290 | 6.218 | 35.503 | 90.363 | 1.00 | 34.64 |
| ATOM | 583 | C | ASN | 290 | 7.237 | 36.170 | 85.607 | 1.00 | 28.72 |
| ATOM | 584 | O | ASN | 290 | 6.569 | 35.665 | 84.709 | 1.00 | 29.41 |
| ATOM | 585 | N | LEU | 291 | 7.809 | 37.362 | 85.487 | 1.00 | 28.18 |
| ATOM | 587 | CA | LEU | 291 | 7.664 | 38.119 | 84.240 | 1.00 | 25.84 |
| ATOM | 588 | CB | LEU | 291 | 8.223 | 39.546 | 84.437 | 1.00 | 26.13 |
| ATOM | 589 | CG | LEU | 291 | 8.169 | 40.485 | 83.236 | 1.00 | 26.10 |
| ATOM | 590 | CD1 | LEU | 291 | 8.014 | 41.938 | 83.754 | 1.00 | 24.19 |
| ATOM | 591 | CD2 | LEU | 291 | 9.437 | 40.315 | 82.403 | 1.00 | 25.70 |
| ATOM | 592 | C | LEU | 291 | 8.366 | 37.411 | 83.085 | 1.00 | 23.49 |
| ATOM | 593 | O | LEU | 291 | 7.844 | 37.383 | 81.992 | 1.00 | 23.93 |
| ATOM | 594 | N | MET | 292 | 9.561 | 36.863 | 83.321 | 1.00 | 24.90 |
| ATOM | 596 | CA | MET | 292 | 10.305 | 36.165 | 82.260 | 1.00 | 24.87 |
| ATOM | 597 | CB | MET | 292 | 11.686 | 35.687 | 82.745 | 1.00 | 25.73 |
| ATOM | 598 | CG | MET | 292 | 12.792 | 36.757 | 82.932 | 1.00 | 25.22 |
| ATOM | 599 | SD | MET | 292 | 14.277 | 36.170 | 83.568 | 1.00 | 24.22 |
| ATOM | 600 | CE | MET | 292 | 14.270 | 36.727 | 85.291 | 1.00 | 31.98 |
| ATOM | 601 | C | MET | 292 | 9.499 | 34.964 | 81.724 | 1.00 | 24.23 |
| ATOM | 602 | O | MET | 292 | 9.625 | 34.616 | 80.557 | 1.00 | 25.70 |
| ATOM | 603 | N | LYS | 293 | 8.677 | 34.329 | 82.561 | 1.00 | 23.39 |
| ATOM | 605 | CA | LYS | 293 | 7.841 | 33.210 | 82.072 | 1.00 | 24.49 |
| ATOM | 606 | CB | LYS | 293 | 6.979 | 32.614 | 83.193 | 1.00 | 22.46 |
| ATOM | 607 | CG | LYS | 293 | 7.721 | 31.947 | 84.349 | 1.00 | 25.48 |
| ATOM | 608 | CD | LYS | 293 | 6.832 | 31.844 | 85.573 | 1.00 | 25.08 |
| ATOM | 609 | CE | LYS | 293 | 7.556 | 31.097 | 86.636 | 1.00 | 25.94 |
| ATOM | 610 | NZ | LYS | 293 | 6.747 | 31.053 | 87.900 | 1.00 | 28.18 |
| ATOM | 614 | C | LYS | 293 | 6.920 | 33.656 | 80.922 | 1.00 | 25.40 |
| ATOM | 615 | O | LYS | 293 | 6.600 | 32.875 | 80.031 | 1.00 | 26.85 |
| ATOM | 616 | N | GLN | 294 | 6.533 | 34.931 | 80.894 | 1.00 | 25.66 |
| ATOM | 618 | CA | GLN | 294 | 5.656 | 35.392 | 79.822 | 1.00 | 24.99 |
| ATOM | 619 | CB | GLN | 294 | 4.719 | 36.481 | 80.333 | 1.00 | 25.55 |
| ATOM | 620 | CG | GLN | 294 | 3.972 | 36.097 | 81.601 | 1.00 | 23.62 |
| ATOM | 621 | CD | GLN | 294 | 3.143 | 34.849 | 81.413 | 1.00 | 27.88 |
| ATOM | 622 | OE1 | GLN | 294 | 2.618 | 34.623 | 80.337 | 1.00 | 31.73 |
| ATOM | 623 | NE2 | GLN | 294 | 3.025 | 34.026 | 82.465 | 1.00 | 30.15 |
| ATOM | 626 | C | GLN | 294 | 6.381 | 35.945 | 78.632 | 1.00 | 26.64 |
| ATOM | 627 | O | GLN | 294 | 5.752 | 36.231 | 77.623 | 1.00 | 27.61 |
| ATOM | 628 | N | LEU | 295 | 7.671 | 36.191 | 78.776 | 1.00 | 27.07 |
| ATOM | 630 | CA | LEU | 295 | 8.445 | 36.748 | 77.682 | 1.00 | 24.82 |
| ATOM | 631 | CB | LEU | 295 | 9.037 | 38.101 | 78.078 | 1.00 | 25.86 |
| ATOM | 632 | CG | LEU | 295 | 8.053 | 39.234 | 78.210 | 1.00 | 24.00 |
| ATOM | 633 | CD1 | LEU | 295 | 8.764 | 40.471 | 78.728 | 1.00 | 23.30 |
| ATOM | 634 | CD2 | LEU | 295 | 7.403 | 39.478 | 76.853 | 1.00 | 23.01 |
| ATOM | 635 | C | LEU | 295 | 9.532 | 35.825 | 77.212 | 1.00 | 23.86 |
| ATOM | 636 | O | LEU | 295 | 10.719 | 36.061 | 77.458 | 1.00 | 26.71 |
| ATOM | 637 | N | GLN | 296 | 9.102 | 34.838 | 76.429 | 1.00 | 21.39 |
| ATOM | 639 | CA | GLN | 296 | 9.994 | 33.827 | 75.893 | 1.00 | 18.39 |
| ATOM | 640 | CB | GLN | 296 | 9.385 | 32.438 | 76.121 | 1.00 | 22.05 |
| ATOM | 641 | CG | GLN | 296 | 9.167 | 32.095 | 77.578 | 1.00 | 23.35 |
| ATOM | 642 | CD | GLN | 296 | 8.581 | 30.699 | 77.779 | 1.00 | 27.58 |
| ATOM | 643 | OE1 | GLN | 296 | 9.000 | 29.747 | 77.149 | 1.00 | 34.77 |
| ATOM | 644 | NE2 | GLN | 296 | 7.616 | 30.580 | 78.676 | 1.00 | 29.64 |
| ATOM | 647 | C | GLN | 296 | 10.155 | 34.084 | 74.428 | 1.00 | 17.06 |
| ATOM | 648 | O | GLN | 296 | 9.192 | 34.066 | 73.690 | 1.00 | 17.47 |
| ATOM | 649 | N | HIS | 297 | 11.401 | 34.301 | 74.008 | 1.00 | 13.82 |
| ATOM | 651 | CA | HIS | 297 | 11.703 | 34.575 | 72.613 | 1.00 | 12.19 |
| ATOM | 652 | CB | HIS | 297 | 11.385 | 36.056 | 72.315 | 1.00 | 10.71 |
| ATOM | 653 | CG | HIS | 297 | 11.467 | 36.409 | 70.878 | 1.00 | 6.59 |
| ATOM | 654 | CD2 | HIS | 297 | 10.512 | 36.487 | 69.917 | 1.00 | 5.42 |

TABLE 2-continued

Coordinates of Lck bound with AMP-PNP

| | | Atom Type | Res | # | X | Y | Z | Occ | B |
|---|---|---|---|---|---|---|---|---|---|
| ATOM | 655 | ND1 | HIS | 297 | 12.659 | 36.713 | 70.260 | 1.00 | 10.13 |
| ATOM | 657 | CE1 | HIS | 297 | 12.434 | 36.968 | 68.973 | 1.00 | 12.03 |
| ATOM | 658 | NE2 | HIS | 297 | 11.139 | 36.833 | 68.738 | 1.00 | 8.83 |
| ATOM | 660 | C | HIS | 297 | 13.205 | 34.340 | 72.404 | 1.00 | 12.25 |
| ATOM | 661 | O | HIS | 297 | 13.968 | 34.478 | 73.319 | 1.00 | 13.62 |
| ATOM | 662 | N | GLN | 298 | 13.626 | 34.045 | 71.186 | 1.00 | 12.61 |
| ATOM | 664 | CA | GLN | 298 | 15.030 | 33.831 | 70.931 | 1.00 | 16.77 |
| ATOM | 665 | CB | GLN | 298 | 15.313 | 33.498 | 69.461 | 1.00 | 16.56 |
| ATOM | 666 | CG | GLN | 298 | 14.897 | 32.149 | 68.971 | 1.00 | 21.12 |
| ATOM | 667 | CD | GLN | 298 | 15.538 | 30.934 | 69.743 | 1.00 | 21.61 |
| ATOM | 668 | OE1 | GLN | 298 | 14.816 | 30.067 | 70.243 | 1.00 | 19.75 |
| ATOM | 669 | NE2 | GLN | 298 | 16.865 | 30.882 | 69.820 | 1.00 | 18.05 |
| ATOM | 672 | C | GLN | 298 | 15.919 | 35.012 | 71.275 | 1.00 | 16.39 |
| ATOM | 673 | O | GLN | 298 | 17.060 | 34.817 | 71.616 | 1.00 | 18.14 |
| ATOM | 674 | N | ARG | 299 | 15.395 | 36.228 | 71.128 | 1.00 | 18.02 |
| ATOM | 676 | CA | ARG | 299 | 16.177 | 37.424 | 71.393 | 1.00 | 14.74 |
| ATOM | 677 | CB | ARG | 299 | 15.751 | 38.528 | 70.447 | 1.00 | 12.85 |
| ATOM | 678 | CG | ARG | 299 | 15.842 | 38.137 | 68.986 | 1.00 | 11.65 |
| ATOM | 679 | CD | ARG | 299 | 17.134 | 38.532 | 68.353 | 1.00 | 9.41 |
| ATOM | 680 | NE | ARG | 299 | 18.297 | 37.997 | 69.070 | 1.00 | 14.53 |
| ATOM | 682 | CZ | ARG | 299 | 18.737 | 36.729 | 68.969 | 1.00 | 15.60 |
| ATOM | 683 | NH1 | ARG | 299 | 18.116 | 35.845 | 68.191 | 1.00 | 8.73 |
| ATOM | 686 | NH2 | ARG | 299 | 19.814 | 36.334 | 69.638 | 1.00 | 14.55 |
| ATOM | 689 | C | ARG | 299 | 16.175 | 37.896 | 72.821 | 1.00 | 12.76 |
| ATOM | 690 | O | ARG | 299 | 16.688 | 38.958 | 73.094 | 1.00 | 12.91 |
| ATOM | 691 | N | LEU | 300 | 15.598 | 37.130 | 73.729 | 1.00 | 14.57 |
| ATOM | 693 | CA | LEU | 300 | 15.541 | 37.516 | 75.134 | 1.00 | 15.73 |
| ATOM | 694 | CB | LEU | 300 | 14.067 | 37.756 | 75.559 | 1.00 | 15.13 |
| ATOM | 695 | CG | LEU | 300 | 13.391 | 39.110 | 75.214 | 1.00 | 15.54 |
| ATOM | 696 | CD1 | LEU | 300 | 13.400 | 39.375 | 73.735 | 1.00 | 9.79 |
| ATOM | 697 | CD2 | LEU | 300 | 11.951 | 39.110 | 75.789 | 1.00 | 14.31 |
| ATOM | 698 | C | LEU | 300 | 16.125 | 36.387 | 75.998 | 1.00 | 15.89 |
| ATOM | 699 | O | LEU | 300 | 15.796 | 35.224 | 75.783 | 1.00 | 17.98 |
| ATOM | 700 | N | VAL | 301 | 16.961 | 36.732 | 76.963 | 1.00 | 15.52 |
| ATOM | 702 | CA | VAL | 301 | 17.561 | 35.760 | 77.855 | 1.00 | 15.64 |
| ATOM | 703 | CB | VAL | 301 | 18.371 | 36.443 | 78.934 | 1.00 | 15.52 |
| ATOM | 704 | CG1 | VAL | 301 | 18.748 | 35.486 | 80.060 | 1.00 | 14.98 |
| ATOM | 705 | CG2 | VAL | 301 | 19.639 | 36.991 | 78.339 | 1.00 | 15.35 |
| ATOM | 706 | C | VAL | 301 | 16.425 | 34.913 | 78.442 | 1.00 | 18.94 |
| ATOM | 707 | O | VAL | 301 | 15.475 | 35.449 | 79.034 | 1.00 | 20.49 |
| ATOM | 708 | N | ARG | 302 | 16.538 | 33.582 | 78.268 | 1.00 | 19.16 |
| ATOM | 710 | CA | ARG | 302 | 15.476 | 32.635 | 78.699 | 1.00 | 18.40 |
| ATOM | 711 | CB | ARG | 302 | 15.498 | 31.397 | 77.767 | 1.00 | 24.28 |
| ATOM | 712 | CG | ARG | 302 | 14.178 | 30.536 | 77.655 | 1.00 | 29.32 |
| ATOM | 713 | CD | ARG | 302 | 14.447 | 28.965 | 77.667 | 1.00 | 36.19 |
| ATOM | 714 | NE | ARG | 302 | 13.268 | 28.086 | 77.463 | 1.00 | 41.02 |
| ATOM | 716 | CZ | ARG | 302 | 12.895 | 27.024 | 78.191 | 1.00 | 43.23 |
| ATOM | 717 | NH1 | ARG | 302 | 13.534 | 26.611 | 79.299 | 1.00 | 43.30 |
| ATOM | 720 | NH2 | ARG | 302 | 12.133 | 26.125 | 77.565 | 1.00 | 47.92 |
| ATOM | 723 | C | ARG | 302 | 15.539 | 32.194 | 80.151 | 1.00 | 15.80 |
| ATOM | 724 | O | ARG | 302 | 16.619 | 31.892 | 80.661 | 1.00 | 14.82 |
| ATOM | 725 | N | LEU | 303 | 14.411 | 32.212 | 80.859 | 1.00 | 11.55 |
| ATOM | 727 | CA | LEU | 303 | 14.399 | 31.709 | 82.233 | 1.00 | 14.00 |
| ATOM | 728 | CB | LEU | 303 | 13.075 | 32.001 | 82.892 | 1.00 | 14.73 |
| ATOM | 729 | CG | LEU | 303 | 12.928 | 31.481 | 84.331 | 1.00 | 16.56 |
| ATOM | 730 | CD1 | LEU | 303 | 13.913 | 32.167 | 85.251 | 1.00 | 13.83 |
| ATOM | 731 | CD2 | LEU | 303 | 11.462 | 31.725 | 84.820 | 1.00 | 10.17 |
| ATOM | 732 | C | LEU | 303 | 14.569 | 30.168 | 82.150 | 1.00 | 17.81 |
| ATOM | 733 | O | LEU | 303 | 13.848 | 29.483 | 81.420 | 1.00 | 17.00 |
| ATOM | 734 | N | TYR | 304 | 15.552 | 29.637 | 82.854 | 1.00 | 20.52 |
| ATOM | 736 | CA | TYR | 304 | 15.831 | 28.198 | 82.809 | 1.00 | 21.34 |
| ATOM | 737 | CB | TYR | 304 | 17.339 | 27.989 | 82.930 | 1.00 | 23.44 |
| ATOM | 738 | CG | TYR | 304 | 17.786 | 26.607 | 82.640 | 1.00 | 27.68 |
| ATOM | 739 | CD1 | TYR | 304 | 17.696 | 25.605 | 83.614 | 1.00 | 32.52 |
| ATOM | 740 | CE1 | TYR | 304 | 18.063 | 24.290 | 83.343 | 1.00 | 31.28 |
| ATOM | 741 | CD2 | TYR | 304 | 18.265 | 26.265 | 81.385 | 1.00 | 30.83 |
| ATOM | 742 | CE2 | TYR | 304 | 18.636 | 24.943 | 81.103 | 1.00 | 34.15 |
| ATOM | 743 | CZ | TYR | 304 | 18.530 | 23.974 | 82.093 | 1.00 | 33.90 |
| ATOM | 744 | OH | TYR | 304 | 18.926 | 22.706 | 81.819 | 1.00 | 36.03 |
| ATOM | 746 | C | TYR | 304 | 15.099 | 27.500 | 83.964 | 1.00 | 21.96 |
| ATOM | 747 | O | TYR | 304 | 14.425 | 26.499 | 83.764 | 1.00 | 22.13 |
| ATOM | 748 | N | ALA | 305 | 15.209 | 28.053 | 85.170 | 1.00 | 20.64 |
| ATOM | 750 | CA | ALA | 305 | 14.570 | 27.441 | 86.312 | 1.00 | 18.28 |
| ATOM | 751 | CB | ALA | 305 | 15.304 | 26.148 | 86.694 | 1.00 | 16.59 |

TABLE 2-continued

Coordinates of Lck bound with AMP-PNP

| | Atom Type | Res | # | X | Y | Z | Occ | B |
|---|---|---|---|---|---|---|---|---|
| ATOM | 752 | C | ALA | 305 | 14.577 | 28.379 | 87.504 | 1.00 | 18.49 |
| ATOM | 753 | O | ALA | 305 | 15.163 | 29.456 | 87.448 | 1.00 | 19.05 |
| ATOM | 754 | N | VAL | 306 | 14.007 | 27.905 | 88.607 | 0.75 | 16.83 |
| ATOM | 756 | CA | VAL | 306 | 13.954 | 28.661 | 89.842 | 0.75 | 15.19 |
| ATOM | 757 | CB | VAL | 306 | 12.764 | 29.710 | 89.803 | 0.75 | 15.23 |
| ATOM | 758 | CG1 | VAL | 306 | 11.927 | 29.459 | 88.605 | 0.75 | 20.64 |
| ATOM | 759 | CG2 | VAL | 306 | 11.921 | 29.725 | 91.030 | 0.75 | 13.94 |
| ATOM | 760 | C | VAL | 306 | 13.940 | 27.741 | 91.044 | 0.75 | 16.10 |
| ATOM | 761 | O | VAL | 306 | 13.514 | 26.582 | 90.963 | 0.75 | 15.63 |
| ATOM | 762 | N | VAL | 307 | 14.561 | 28.206 | 92.116 | 1.00 | 17.75 |
| ATOM | 764 | CA | VAL | 307 | 14.597 | 27.467 | 93.373 | 1.00 | 21.46 |
| ATOM | 765 | CB | VAL | 307 | 16.049 | 27.043 | 93.786 | 1.00 | 21.01 |
| ATOM | 766 | CG1 | VAL | 307 | 16.040 | 26.413 | 95.148 | 1.00 | 19.40 |
| ATOM | 767 | CG2 | VAL | 307 | 16.626 | 26.084 | 92.774 | 1.00 | 21.25 |
| ATOM | 768 | C | VAL | 307 | 14.007 | 28.478 | 94.364 | 1.00 | 25.12 |
| ATOM | 769 | O | VAL | 307 | 14.662 | 29.445 | 94.772 | 1.00 | 26.63 |
| ATOM | 770 | N | THR | 308 | 12.746 | 28.257 | 94.690 | 1.00 | 27.40 |
| ATOM | 772 | CA | THR | 308 | 11.950 | 29.075 | 95.580 | 1.00 | 29.59 |
| ATOM | 773 | CB | THR | 308 | 10.419 | 28.814 | 95.309 | 1.00 | 29.83 |
| ATOM | 774 | OG1 | THR | 308 | 10.049 | 29.395 | 94.049 | 1.00 | 33.86 |
| ATOM | 776 | CG2 | THR | 308 | 9.547 | 29.357 | 96.404 | 1.00 | 36.10 |
| ATOM | 777 | C | THR | 308 | 12.277 | 29.040 | 97.098 | 1.00 | 29.95 |
| ATOM | 778 | O | THR | 308 | 11.854 | 29.954 | 97.798 | 1.00 | 31.04 |
| ATOM | 779 | N | ALA | 309 | 12.912 | 27.991 | 97.643 | 1.00 | 29.60 |
| ATOM | 781 | CA | ALA | 309 | 13.238 | 28.074 | 99.079 | 1.00 | 30.23 |
| ATOM | 782 | CB | ALA | 309 | 13.392 | 26.727 | 99.771 | 1.00 | 29.90 |
| ATOM | 783 | C | ALA | 309 | 14.515 | 28.884 | 99.226 | 1.00 | 31.24 |
| ATOM | 784 | O | ALA | 309 | 15.291 | 29.062 | 98.277 | 1.00 | 29.98 |
| ATOM | 785 | N | GLU | 310 | 14.854 | 29.175 | 100.460 | 1.00 | 33.02 |
| ATOM | 787 | CA | GLU | 310 | 16.004 | 30.011 | 100.692 | 1.00 | 35.30 |
| ATOM | 788 | CB | GLU | 310 | 15.656 | 30.948 | 101.789 | 1.00 | 36.75 |
| ATOM | 789 | CG | GLU | 310 | 15.201 | 32.303 | 101.410 | 1.00 | 41.03 |
| ATOM | 790 | CD | GLU | 310 | 14.844 | 33.028 | 102.675 | 1.00 | 45.51 |
| ATOM | 791 | OE1 | GLU | 310 | 15.311 | 32.566 | 103.742 | 1.00 | 49.70 |
| ATOM | 792 | OE2 | GLU | 310 | 14.057 | 33.996 | 102.629 | 1.00 | 45.61 |
| ATOM | 793 | C | GLU | 310 | 17.339 | 29.341 | 101.019 | 1.00 | 36.39 |
| ATOM | 794 | O | GLU | 310 | 17.375 | 28.495 | 101.942 | 1.00 | 36.98 |
| ATOM | 795 | N | PRO | 311 | 18.463 | 29.858 | 100.389 | 1.00 | 35.12 |
| ATOM | 796 | CD | PRO | 311 | 19.811 | 29.252 | 100.425 | 1.00 | 35.52 |
| ATOM | 797 | CA | PRO | 311 | 18.465 | 31.010 | 99.427 | 1.00 | 34.76 |
| ATOM | 798 | CB | PRO | 311 | 19.946 | 31.334 | 99.245 | 1.00 | 35.47 |
| ATOM | 799 | CG | PRO | 311 | 20.559 | 30.004 | 99.238 | 1.00 | 35.08 |
| ATOM | 800 | C | PRO | 311 | 17.796 | 30.904 | 98.018 | 1.00 | 34.02 |
| ATOM | 801 | O | PRO | 311 | 18.086 | 29.989 | 97.268 | 1.00 | 35.15 |
| ATOM | 802 | N | ILE | 312 | 17.030 | 31.923 | 97.614 | 1.00 | 30.57 |
| ATOM | 804 | CA | ILE | 312 | 16.329 | 31.878 | 96.329 | 1.00 | 26.24 |
| ATOM | 805 | CB | ILE | 312 | 15.206 | 32.953 | 96.298 | 1.00 | 27.45 |
| ATOM | 806 | CG2 | ILE | 312 | 14.435 | 32.869 | 95.015 | 1.00 | 25.33 |
| ATOM | 807 | CG1 | ILE | 312 | 14.310 | 32.765 | 97.536 | 1.00 | 27.69 |
| ATOM | 808 | CD1 | ILE | 312 | 13.197 | 33.782 | 97.633 | 1.00 | 31.84 |
| ATOM | 809 | C | ILE | 312 | 17.210 | 31.993 | 95.106 | 1.00 | 23.75 |
| ATOM | 810 | O | ILE | 312 | 18.114 | 32.837 | 95.061 | 1.00 | 21.09 |
| ATOM | 811 | N | TYR | 313 | 16.984 | 31.136 | 94.126 | 1.00 | 21.51 |
| ATOM | 813 | CA | TYR | 313 | 17.798 | 31.205 | 92.910 | 1.00 | 21.71 |
| ATOM | 814 | CB | TYR | 313 | 18.534 | 29.892 | 92.611 | 1.00 | 22.23 |
| ATOM | 815 | CG | TYR | 313 | 19.668 | 29.443 | 93.513 | 1.00 | 24.22 |
| ATOM | 816 | CD1 | TYR | 313 | 20.291 | 30.304 | 94.391 | 1.00 | 21.28 |
| ATOM | 817 | CE1 | TYR | 313 | 21.336 | 29.863 | 95.178 | 1.00 | 24.77 |
| ATOM | 818 | CD2 | TYR | 313 | 20.119 | 28.124 | 93.449 | 1.00 | 27.05 |
| ATOM | 819 | CE2 | TYR | 313 | 21.154 | 27.670 | 94.238 | 1.00 | 27.82 |
| ATOM | 820 | CZ | TYR | 313 | 21.759 | 28.542 | 95.101 | 1.00 | 26.54 |
| ATOM | 821 | OH | TYR | 313 | 22.766 | 28.079 | 95.906 | 1.00 | 26.31 |
| ATOM | 823 | C | TYR | 313 | 16.960 | 31.436 | 91.681 | 1.00 | 19.02 |
| ATOM | 824 | O | TYR | 313 | 15.892 | 30.860 | 91.547 | 1.00 | 19.71 |
| ATOM | 825 | N | ILE | 314 | 17.465 | 32.248 | 90.770 | 0.82 | 17.24 |
| ATOM | 827 | CA | ILE | 314 | 16.833 | 32.432 | 89.477 | 0.82 | 16.18 |
| ATOM | 828 | CB | ILE | 314 | 16.489 | 33.910 | 89.160 | 0.82 | 14.02 |
| ATOM | 829 | CG2 | ILE | 314 | 16.144 | 34.043 | 87.694 | 0.82 | 14.53 |
| ATOM | 830 | CG1 | ILE | 314 | 15.335 | 34.371 | 90.031 | 0.82 | 15.31 |
| ATOM | 831 | CD1 | ILE | 314 | 14.958 | 35.856 | 89.855 | 0.82 | 13.93 |
| ATOM | 832 | C | ILE | 314 | 17.912 | 31.927 | 88.488 | 0.82 | 15.65 |
| ATOM | 833 | O | ILE | 314 | 19.013 | 32.499 | 88.391 | 0.82 | 13.85 |
| ATOM | 834 | N | ILE | 315 | 17.600 | 30.874 | 87.748 | 1.00 | 15.03 |
| ATOM | 836 | CA | ILE | 315 | 18.543 | 30.294 | 86.817 | 1.00 | 13.64 |

TABLE 2-continued

Coordinates of Lck bound with AMP-PNP

| | | Atom Type | Res | # | X | Y | Z | Occ | B |
|---|---|---|---|---|---|---|---|---|---|
| ATOM | 837 | CB | ILE | 315 | 18.589 | 28.746 | 86.947 | 1.00 | 13.73 |
| ATOM | 838 | CG2 | ILE | 315 | 19.637 | 28.154 | 85.991 | 1.00 | 9.69 |
| ATOM | 839 | CG1 | ILE | 315 | 18.915 | 28.335 | 88.393 | 1.00 | 13.21 |
| ATOM | 840 | CD1 | ILE | 315 | 17.711 | 28.255 | 89.330 | 1.00 | 9.79 |
| ATOM | 841 | C | ILE | 315 | 18.192 | 30.690 | 85.403 | 1.00 | 14.14 |
| ATOM | 842 | O | ILE | 315 | 17.040 | 30.544 | 84.997 | 1.00 | 14.62 |
| ATOM | 843 | N | THR | 316 | 19.173 | 31.165 | 84.631 | 1.00 | 14.85 |
| ATOM | 845 | CA | THR | 316 | 18.872 | 31.595 | 83.277 | 1.00 | 14.14 |
| ATOM | 846 | CB | THR | 316 | 18.878 | 33.143 | 83.201 | 1.00 | 13.98 |
| ATOM | 847 | OG1 | THR | 316 | 20.169 | 33.618 | 83.616 | 1.00 | 17.04 |
| ATOM | 849 | CG2 | THR | 316 | 17.800 | 33.726 | 84.118 | 1.00 | 8.17 |
| ATOM | 850 | C | THR | 316 | 19.839 | 31.078 | 82.216 | 1.00 | 16.85 |
| ATOM | 851 | O | THR | 316 | 20.845 | 30.456 | 82.534 | 1.00 | 17.57 |
| ATOM | 852 | N | GLU | 317 | 19.486 | 31.332 | 80.957 | 1.00 | 16.91 |
| ATOM | 854 | CA | GLU | 317 | 20.277 | 31.008 | 79.791 | 1.00 | 16.67 |
| ATOM | 855 | CB | GLU | 317 | 19.564 | 31.541 | 78.567 | 1.00 | 17.21 |
| ATOM | 856 | CG | GLU | 317 | 20.222 | 31.261 | 77.252 | 1.00 | 14.43 |
| ATOM | 857 | CD | GLU | 317 | 19.353 | 31.727 | 76.087 | 1.00 | 18.13 |
| ATOM | 858 | OE1 | GLU | 317 | 18.398 | 32.537 | 76.315 | 1.00 | 14.82 |
| ATOM | 859 | OE2 | GLU | 317 | 19.576 | 31.266 | 74.961 | 1.00 | 13.42 |
| ATOM | 860 | C | GLU | 317 | 21.673 | 31.664 | 79.890 | 1.00 | 19.07 |
| ATOM | 861 | O | GLU | 317 | 21.806 | 32.899 | 80.004 | 1.00 | 20.58 |
| ATOM | 862 | N | TYR | 318 | 22.704 | 30.838 | 79.797 | 1.00 | 18.98 |
| ATOM | 864 | CA | TYR | 318 | 24.067 | 31.333 | 79.909 | 1.00 | 18.22 |
| ATOM | 865 | CB | TYR | 318 | 25.030 | 30.186 | 80.223 | 1.00 | 19.73 |
| ATOM | 866 | CG | TYR | 318 | 26.358 | 30.706 | 80.707 | 1.00 | 19.63 |
| ATOM | 867 | CD1 | TYR | 318 | 26.476 | 31.214 | 81.987 | 1.00 | 22.75 |
| ATOM | 868 | CE1 | TYR | 318 | 27.677 | 31.676 | 82.465 | 1.00 | 24.78 |
| ATOM | 869 | CD2 | TYR | 318 | 27.479 | 30.673 | 79.884 | 1.00 | 19.43 |
| ATOM | 870 | CE2 | TYR | 318 | 28.709 | 31.150 | 80.353 | 1.00 | 20.22 |
| ATOM | 871 | CZ | TYR | 318 | 28.804 | 31.645 | 81.639 | 1.00 | 24.87 |
| ATOM | 872 | OH | TYR | 318 | 30.005 | 32.114 | 82.121 | 1.00 | 27.76 |
| ATOM | 874 | C | TYR | 318 | 24.499 | 32.037 | 78.642 | 1.00 | 18.73 |
| ATOM | 875 | O | TYR | 318 | 24.244 | 31.551 | 77.538 | 1.00 | 18.36 |
| ATOM | 876 | N | MET | 319 | 25.140 | 33.194 | 78.786 | 1.00 | 18.80 |
| ATOM | 878 | CA | MET | 319 | 25.580 | 33.945 | 77.595 | 1.00 | 18.78 |
| ATOM | 879 | CB | MET | 319 | 24.855 | 35.289 | 77.554 | 1.00 | 18.67 |
| ATOM | 880 | CG | MET | 319 | 23.322 | 35.146 | 77.365 | 1.00 | 13.13 |
| ATOM | 881 | SD | MET | 319 | 22.872 | 34.497 | 75.765 | 1.00 | 14.87 |
| ATOM | 882 | CE | MET | 319 | 23.121 | 35.815 | 74.681 | 1.00 | 11.13 |
| ATOM | 883 | C | MET | 319 | 27.101 | 34.078 | 77.686 | 1.00 | 20.76 |
| ATOM | 884 | O | MET | 319 | 27.637 | 34.830 | 78.490 | 1.00 | 22.04 |
| ATOM | 885 | N | GLU | 320 | 27.775 | 33.343 | 76.825 | 1.00 | 22.41 |
| ATOM | 887 | CA | GLU | 320 | 29.220 | 33.251 | 76.844 | 1.00 | 23.90 |
| ATOM | 888 | CB | GLU | 320 | 29.736 | 32.30 | 75.714 | 1.00 | 27.88 |
| ATOM | 889 | CG | GLU | 320 | 31.143 | 31.847 | 75.990 | 1.00 | 36.74 |
| ATOM | 890 | CD | GLU | 320 | 31.169 | 30.929 | 77.210 | 1.00 | 43.00 |
| ATOM | 891 | OE1 | GLU | 320 | 30.333 | 29.992 | 77.268 | 1.00 | 46.34 |
| ATOM | 892 | OE2 | GLU | 320 | 32.004 | 31.132 | 78.135 | 1.00 | 46.76 |
| ATOM | 893 | C | GLU | 320 | 30.042 | 34.514 | 76.872 | 1.00 | 22.26 |
| ATOM | 894 | O | GLU | 320 | 31.014 | 34.546 | 77.606 | 1.00 | 19.88 |
| ATOM | 895 | N | ASN | 321 | 29.643 | 35.531 | 76.115 | 1.00 | 21.61 |
| ATOM | 897 | CA | ASN | 321 | 30.434 | 36.739 | 76.062 | 1.00 | 20.96 |
| ATOM | 898 | CB | ASN | 321 | 30.647 | 37.164 | 74.591 | 1.00 | 22.07 |
| ATOM | 899 | CG | ASN | 321 | 31.705 | 36.304 | 73.903 | 1.00 | 22.87 |
| ATOM | 900 | OD1 | ASN | 321 | 31.523 | 35.816 | 72.784 | 1.00 | 24.57 |
| ATOM | 901 | ND2 | ASN | 321 | 32.796 | 36.080 | 74.608 | 1.00 | 19.26 |
| ATOM | 904 | C | ASN | 321 | 30.012 | 37.866 | 76.966 | 1.00 | 18.96 |
| ATOM | 905 | O | ASN | 321 | 30.377 | 39.016 | 76.738 | 1.00 | 20.52 |
| ATOM | 906 | N | GLY | 322 | 29.231 | 37.519 | 77.975 | 1.00 | 16.99 |
| ATOM | 908 | CA | GLY | 322 | 28.769 | 38.471 | 78.979 | 1.00 | 16.93 |
| ATOM | 909 | C | GLY | 322 | 28.044 | 39.711 | 78.495 | 1.00 | 14.71 |
| ATOM | 910 | O | GLY | 322 | 27.388 | 39.631 | 77.460 | 1.00 | 15.91 |
| ATOM | 911 | N | SER | 323 | 28.327 | 40.851 | 79.105 | 0.43 | 12.37 |
| ATOM | 913 | CA | SER | 323 | 27.646 | 42.064 | 78.698 | 0.43 | 11.44 |
| ATOM | 914 | CB | SER | 323 | 27.596 | 43.084 | 79.841 | 0.43 | 12.56 |
| ATOM | 915 | OG | SER | 323 | 28.794 | 43.830 | 79.919 | 0.43 | 22.42 |
| ATOM | 917 | C | SER | 323 | 28.189 | 42.694 | 77.472 | 0.43 | 9.75 |
| ATOM | 918 | O | SER | 323 | 29.388 | 42.697 | 77.253 | 0.43 | 7.93 |
| ATOM | 919 | N | LEU | 324 | 27.272 | 43.230 | 76.680 | 1.00 | 12.31 |
| ATOM | 921 | CA | LEU | 324 | 27.636 | 43.886 | 75.441 | 1.00 | 13.53 |
| ATOM | 922 | CB | LEU | 324 | 26.431 | 44.378 | 74.643 | 1.00 | 11.33 |
| ATOM | 923 | CG | LEU | 324 | 26.783 | 45.050 | 73.315 | 1.00 | 11.74 |
| ATOM | 924 | CD1 | LEU | 324 | 27.129 | 44.114 | 72.137 | 1.00 | 11.30 |

TABLE 2-continued

Coordinates of Lck bound with AMP-PNP

| | | Atom Type | Res | # | X | Y | Z | Occ | B |
|---|---|---|---|---|---|---|---|---|---|
| ATOM | 925 | CD2 | LEU | 324 | 25.487 | 45.831 | 72.929 | 1.00 | 13.50 |
| ATOM | 926 | C | LEU | 324 | 28.560 | 45.053 | 75.824 | 1.00 | 14.72 |
| ATOM | 927 | O | LEU | 324 | 29.626 | 45.171 | 75.249 | 1.00 | 15.57 |
| ATOM | 928 | N | VAL | 325 | 28.226 | 45.764 | 76.882 | 1.00 | 14.93 |
| ATOM | 930 | CA | VAL | 325 | 29.051 | 46.873 | 77.264 | 1.00 | 16.29 |
| ATOM | 931 | CB | VAL | 325 | 28.448 | 47.689 | 78.401 | 1.00 | 13.59 |
| ATOM | 932 | CG1 | VAL | 325 | 28.612 | 47.004 | 79.724 | 1.00 | 14.56 |
| ATOM | 933 | CG2 | VAL | 325 | 29.095 | 49.059 | 78.404 | 1.00 | 15.75 |
| ATOM | 934 | C | VAL | 325 | 30.488 | 46.427 | 77.590 | 1.00 | 19.59 |
| ATOM | 935 | O | VAL | 325 | 31.457 | 47.137 | 77.313 | 1.00 | 19.46 |
| ATOM | 936 | N | ASP | 326 | 30.635 | 45.209 | 78.126 | 1.00 | 18.89 |
| ATOM | 938 | CA | ASP | 326 | 31.969 | 44.711 | 78.426 | 1.00 | 16.74 |
| ATOM | 939 | CB | ASP | 326 | 31.937 | 43.714 | 79.539 | 1.00 | 15.36 |
| ATOM | 940 | CG | ASP | 326 | 31.595 | 44.321 | 80.855 | 1.00 | 18.53 |
| ATOM | 941 | OD1 | ASP | 326 | 31.915 | 45.501 | 81.089 | 1.00 | 22.26 |
| ATOM | 942 | OD2 | ASP | 326 | 31.004 | 43.623 | 81.697 | 1.00 | 21.60 |
| ATOM | 943 | C | ASP | 326 | 32.603 | 44.066 | 77.218 | 1.00 | 17.28 |
| ATOM | 944 | O | ASP | 326 | 33.792 | 44.270 | 76.924 | 1.00 | 19.53 |
| ATOM | 945 | N | PHE | 327 | 31.807 | 43.309 | 76.487 | 1.00 | 16.77 |
| ATOM | 947 | CA | PHE | 327 | 32.300 | 42.609 | 75.305 | 1.00 | 15.42 |
| ATOM | 948 | CB | PHE | 327 | 31.167 | 41.806 | 74.651 | 1.00 | 16.38 |
| ATOM | 949 | CG | PHE | 327 | 31.582 | 41.145 | 73.377 | 1.00 | 18.43 |
| ATOM | 950 | CD1 | PHE | 327 | 32.504 | 40.079 | 73.406 | 1.00 | 17.80 |
| ATOM | 951 | CD2 | PHE | 327 | 31.133 | 41.595 | 72.172 | 1.00 | 19.13 |
| ATOM | 952 | CE1 | PHE | 327 | 32.956 | 39.501 | 72.254 | 1.00 | 17.90 |
| ATOM | 953 | CE2 | PHE | 327 | 31.575 | 41.019 | 70.983 | 1.00 | 18.88 |
| ATOM | 954 | CZ | PHE | 327 | 32.491 | 39.971 | 71.022 | 1.00 | 20.02 |
| ATOM | 955 | C | PHE | 327 | 32.925 | 43.534 | 74.257 | 1.00 | 14.46 |
| ATOM | 956 | O | PHE | 327 | 33.924 | 43.143 | 73.608 | 1.00 | 15.79 |
| ATOM | 957 | N | LEU | 328 | 32.331 | 44.711 | 74.078 | 0.40 | 10.06 |
| ATOM | 959 | CA | LEU | 328 | 32.798 | 45.658 | 73.078 | 0.40 | 7.95 |
| ATOM | 960 | CB | LEU | 328 | 31.793 | 46.801 | 72.949 | 0.40 | 5.19 |
| ATOM | 961 | CG | LEU | 328 | 30.499 | 46.422 | 72.223 | 0.40 | 2.00 |
| ATOM | 962 | CD1 | LEU | 328 | 29.622 | 47.623 | 72.147 | 0.40 | 2.00 |
| ATOM | 963 | CD2 | LEU | 328 | 30.823 | 45.921 | 70.838 | 0.40 | 2.00 |
| ATOM | 964 | C | LEU | 328 | 34.172 | 46.227 | 73.360 | 0.40 | 8.30 |
| ATOM | 965 | O | LEU | 328 | 34.786 | 46.852 | 72.507 | 0.40 | 5.91 |
| ATOM | 966 | N | LYS | 329 | 34.650 | 46.004 | 74.569 | 1.00 | 13.67 |
| ATOM | 968 | CA | LYS | 329 | 35.946 | 46.510 | 74.960 | 1.00 | 17.41 |
| ATOM | 969 | CB | LYS | 329 | 35.886 | 47.085 | 76.365 | 1.00 | 14.37 |
| ATOM | 970 | CG | LYS | 329 | 34.906 | 48.185 | 76.494 | 1.00 | 15.62 |
| ATOM | 971 | CD | LYS | 329 | 34.845 | 48.643 | 77.935 | 1.00 | 16.67 |
| ATOM | 972 | CE | LYS | 329 | 33.757 | 49.685 | 78.082 | 1.00 | 17.36 |
| ATOM | 973 | NZ | LYS | 329 | 33.631 | 50.022 | 79.532 | 1.00 | 20.17 |
| ATOM | 977 | C | LYS | 329 | 37.026 | 45.430 | 74.893 | 1.00 | 20.20 |
| ATOM | 978 | O | LYS | 329 | 38.195 | 45.707 | 75.091 | 1.00 | 25.35 |
| ATOM | 979 | N | THR | 330 | 36.646 | 44.192 | 74.618 | 1.00 | 18.94 |
| ATOM | 981 | CA | THR | 330 | 37.630 | 43.131 | 74.547 | 1.00 | 14.51 |
| ATOM | 982 | CB | THR | 330 | 36.957 | 41.722 | 74.733 | 1.00 | 11.78 |
| ATOM | 983 | OG1 | THR | 330 | 36.088 | 41.483 | 73.653 | 1.00 | 14.69 |
| ATOM | 985 | CG2 | THR | 330 | 36.167 | 41.654 | 76.008 | 1.00 | 8.84 |
| ATOM | 986 | C | THR | 330 | 38.279 | 43.175 | 73.184 | 1.00 | 15.86 |
| ATOM | 987 | O | THR | 330 | 37.781 | 43.845 | 72.271 | 1.00 | 20.22 |
| ATOM | 988 | N | PRO | 331 | 39.413 | 42.461 | 73.015 | 1.00 | 15.75 |
| ATOM | 989 | CD | PRO | 331 | 40.192 | 41.763 | 74.059 | 1.00 | 11.93 |
| ATOM | 990 | CA | PRO | 331 | 40.109 | 42.429 | 71.725 | 1.00 | 14.76 |
| ATOM | 991 | CB | PRO | 331 | 41.241 | 41.424 | 71.979 | 1.00 | 12.37 |
| ATOM | 992 | CG | PRO | 331 | 41.562 | 41.646 | 73.417 | 1.00 | 11.73 |
| ATOM | 993 | C | PRO | 331 | 39.166 | 41.993 | 70.607 | 1.00 | 16.66 |
| ATOM | 994 | O | PRO | 331 | 39.208 | 42.526 | 69.507 | 1.00 | 18.42 |
| ATOM | 995 | N | SER | 332 | 38.283 | 41.033 | 70.884 | 1.00 | 19.45 |
| ATOM | 997 | CA | SER | 332 | 37.333 | 40.590 | 69.866 | 1.00 | 21.00 |
| ATOM | 998 | CB | SER | 332 | 36.594 | 39.321 | 70.309 | 1.00 | 24.09 |
| ATOM | 999 | OG | SER | 332 | 37.486 | 38.231 | 70.423 | 1.00 | 31.13 |
| ATOM | 1001 | C | SER | 332 | 36.309 | 41.670 | 69.588 | 1.00 | 19.06 |
| ATOM | 1002 | O | SER | 332 | 35.994 | 41.908 | 68.446 | 1.00 | 21.97 |
| ATOM | 1003 | N | GLY | 333 | 35.759 | 42.271 | 70.639 | 1.00 | 20.79 |
| ATOM | 1005 | CA | GLY | 333 | 34.769 | 43.330 | 70.447 | 1.00 | 22.67 |
| ATOM | 1006 | C | GLY | 333 | 35.350 | 44.503 | 69.650 | 1.00 | 22.18 |
| ATOM | 1007 | O | GLY | 333 | 34.730 | 44.985 | 68.705 | 1.00 | 21.13 |
| ATOM | 1008 | N | ILE | 334 | 36.576 | 44.890 | 70.002 | 1.00 | 22.89 |
| ATOM | 1010 | CA | ILE | 334 | 37.236 | 46.007 | 69.329 | 1.00 | 23.12 |
| ATOM | 1011 | CB | ILE | 334 | 38.631 | 46.354 | 69.928 | 1.00 | 23.80 |
| ATOM | 1012 | CG2 | ILE | 334 | 39.113 | 47.598 | 69.248 | 1.00 | 25.22 |

TABLE 2-continued

Coordinates of Lck bound with AMP-PNP

| | Atom Type | Res | # | X | Y | Z | Occ | B |
|---|---|---|---|---|---|---|---|---|
| ATOM | 1013 | CG1 | ILE | 334 | 38.582 | 46.603 | 71.458 | 1.00 | 22.41 |
| ATOM | 1014 | CD1 | ILE | 334 | 39.990 | 46.590 | 72.189 | 1.00 | 21.59 |
| ATOM | 1015 | C | ILE | 334 | 37.407 | 45.787 | 67.815 | 1.00 | 23.63 |
| ATOM | 1016 | O | ILE | 334 | 37.290 | 46.710 | 67.047 | 1.00 | 24.35 |
| ATOM | 1017 | N | LYS | 335 | 37.648 | 44.555 | 67.381 | 1.00 | 26.06 |
| ATOM | 1019 | CA | LYS | 335 | 37.830 | 44.292 | 65.969 | 1.00 | 27.33 |
| ATOM | 1020 | CB | LYS | 335 | 38.616 | 43.001 | 65.763 | 1.00 | 30.12 |
| ATOM | 1021 | CG | LYS | 335 | 40.007 | 43.052 | 66.331 | 1.00 | 36.81 |
| ATOM | 1022 | CD | LYS | 335 | 40.582 | 41.644 | 66.546 | 1.00 | 40.63 |
| ATOM | 1023 | CE | LYS | 335 | 41.918 | 41.735 | 67.231 | 1.00 | 41.34 |
| ATOM | 1024 | NZ | LYS | 335 | 42.211 | 40.491 | 67.953 | 1.00 | 40.29 |
| ATOM | 1028 | C | LYS | 335 | 36.558 | 44.225 | 65.137 | 1.00 | 25.83 |
| ATOM | 1029 | O | LYS | 335 | 36.629 | 44.133 | 63.919 | 1.00 | 24.93 |
| ATOM | 1030 | N | LEU | 336 | 35.408 | 44.292 | 65.787 | 1.00 | 25.22 |
| ATOM | 1032 | CA | LEU | 336 | 34.145 | 44.197 | 65.047 | 1.00 | 25.55 |
| ATOM | 1033 | CB | LEU | 336 | 32.954 | 44.138 | 66.034 | 1.00 | 26.91 |
| ATOM | 1034 | CG | LEU | 336 | 32.907 | 42.865 | 66.938 | 1.00 | 25.49 |
| ATOM | 1035 | CD1 | LEU | 336 | 31.774 | 42.861 | 67.935 | 1.00 | 28.40 |
| ATOM | 1036 | CD2 | LEU | 336 | 32.872 | 41.599 | 66.116 | 1.00 | 22.50 |
| ATOM | 1037 | C | LEU | 336 | 33.971 | 45.282 | 63.993 | 1.00 | 25.58 |
| ATOM | 1038 | O | LEU | 336 | 34.276 | 46.428 | 64.259 | 1.00 | 28.02 |
| ATOM | 1039 | N | THR | 337 | 33.495 | 44.910 | 62.802 | 1.00 | 25.27 |
| ATOM | 1041 | CA | THR | 337 | 33.241 | 45.891 | 61.742 | 1.00 | 25.86 |
| ATOM | 1042 | CB | THR | 337 | 33.166 | 45.222 | 60.318 | 1.00 | 25.88 |
| ATOM | 1043 | OG1 | THR | 337 | 31.993 | 44.387 | 60.185 | 1.00 | 26.06 |
| ATOM | 1045 | CG2 | THR | 337 | 34.417 | 44.369 | 60.091 | 1.00 | 26.41 |
| ATOM | 1046 | C | THR | 337 | 31.935 | 46.648 | 62.062 | 1.00 | 25.21 |
| ATOM | 1047 | O | THR | 337 | 31.162 | 46.183 | 62.910 | 1.00 | 24.24 |
| ATOM | 1048 | N | ILE | 338 | 31.728 | 47.795 | 61.416 | 1.00 | 22.87 |
| ATOM | 1050 | CA | ILE | 338 | 30.489 | 48.561 | 61.632 | 1.00 | 23.64 |
| ATOM | 1051 | CB | ILE | 338 | 30.484 | 49.881 | 60.824 | 1.00 | 20.07 |
| ATOM | 1052 | CG2 | ILE | 338 | 30.632 | 49.557 | 59.351 | 1.00 | 19.98 |
| ATOM | 1053 | CG1 | ILE | 338 | 29.217 | 50.695 | 61.122 | 1.00 | 19.49 |
| ATOM | 1054 | CD1 | ILE | 338 | 29.044 | 51.055 | 62.619 | 1.00 | 16.21 |
| ATOM | 1055 | C | ILE | 338 | 29.331 | 47.675 | 61.187 | 1.00 | 22.37 |
| ATOM | 1056 | O | ILE | 338 | 28.240 | 47.755 | 61.744 | 1.00 | 25.54 |
| ATOM | 1057 | N | ASN | 339 | 29.605 | 46.806 | 60.223 | 1.00 | 22.72 |
| ATOM | 1059 | CA | ASN | 339 | 28.605 | 45.869 | 59.704 | 1.00 | 22.70 |
| ATOM | 1060 | CB | ASN | 339 | 29.225 | 45.059 | 58.566 | 1.00 | 27.00 |
| ATOM | 1061 | CG | ASN | 339 | 28.571 | 43.704 | 58.390 | 1.00 | 35.39 |
| ATOM | 1062 | OD1 | ASN | 339 | 27.387 | 43.636 | 58.127 | 1.00 | 38.99 |
| ATOM | 1063 | ND2 | ASN | 339 | 29.346 | 42.623 | 58.527 | 1.00 | 37.08 |
| ATOM | 1066 | C | ASN | 339 | 28.060 | 44.948 | 60.802 | 1.00 | 21.63 |
| ATOM | 1067 | O | ASN | 339 | 26.857 | 44.795 | 60.961 | 1.00 | 20.41 |
| ATOM | 1068 | N | LYS | 340 | 28.961 | 44.369 | 61.595 | 1.00 | 21.18 |
| ATOM | 1070 | CA | LYS | 340 | 28.552 | 43.474 | 62.664 | 1.00 | 20.62 |
| ATOM | 1071 | CB | LYS | 340 | 29.731 | 42.654 | 63.179 | 1.00 | 17.18 |
| ATOM | 1072 | CG | LYS | 340 | 29.389 | 41.735 | 64.356 | 1.00 | 17.20 |
| ATOM | 1073 | CD | LYS | 340 | 28.338 | 40.693 | 63.958 | 1.00 | 17.23 |
| ATOM | 1074 | CE | LYS | 340 | 27.957 | 39.875 | 65.176 | 1.00 | 19.05 |
| ATOM | 1075 | NZ | LYS | 340 | 26.872 | 38.871 | 64.846 | 1.00 | 18.26 |
| ATOM | 1079 | C | LYS | 340 | 27.892 | 44.265 | 63.807 | 1.00 | 20.56 |
| ATOM | 1080 | O | LYS | 340 | 26.996 | 43.754 | 64.499 | 1.00 | 19.99 |
| ATOM | 1081 | N | LEU | 341 | 28.372 | 45.485 | 64.038 | 1.00 | 18.72 |
| ATOM | 1083 | CA | LEU | 341 | 27.760 | 46.309 | 65.067 | 1.00 | 18.01 |
| ATOM | 1084 | CB | LEU | 341 | 28.547 | 47.598 | 65.242 | 1.00 | 18.92 |
| ATOM | 1085 | CG | LEU | 341 | 29.977 | 47.455 | 65.749 | 1.00 | 20.09 |
| ATOM | 1086 | CD1 | LEU | 341 | 30.629 | 48.814 | 65.891 | 1.00 | 19.43 |
| ATOM | 1087 | CD2 | LEU | 341 | 29.977 | 46.775 | 67.103 | 1.00 | 20.52 |
| ATOM | 1088 | C | LEU | 341 | 26.303 | 46.661 | 64.694 | 1.00 | 17.59 |
| ATOM | 1089 | O | LEU | 341 | 25.457 | 46.724 | 65.559 | 1.00 | 18.31 |
| ATOM | 1090 | N | LEU | 342 | 26.044 | 46.864 | 63.411 | 1.00 | 17.36 |
| ATOM | 1092 | CA | LEU | 342 | 24.716 | 47.210 | 62.932 | 1.00 | 18.37 |
| ATOM | 1093 | CB | LEU | 342 | 24.805 | 57.753 | 61.496 | 1.00 | 16.74 |
| ATOM | 1094 | CG | LEU | 342 | 25.497 | 49.147 | 61.460 | 1.00 | 18.05 |
| ATOM | 1095 | CD1 | LEU | 342 | 25.819 | 49.476 | 60.011 | 1.00 | 13.77 |
| ATOM | 1096 | CD2 | LEU | 342 | 24.607 | 50.233 | 62.125 | 1.00 | 13.53 |
| ATOM | 1097 | C | LEU | 342 | 23.833 | 45.961 | 63.031 | 1.00 | 18.66 |
| ATOM | 1098 | O | LEU | 342 | 22.634 | 46.049 | 63.299 | 1.00 | 17.97 |
| ATOM | 1099 | N | ASP | 343 | 24.491 | 44.816 | 62.914 | 1.00 | 20.90 |
| ATOM | 1101 | CA | ASP | 343 | 23.867 | 43.494 | 63.017 | 1.00 | 20.25 |
| ATOM | 1102 | CB | ASP | 343 | 24.896 | 42.395 | 62.683 | 1.00 | 19.73 |
| ATOM | 1103 | CG | ASP | 343 | 24.417 | 40.993 | 63.026 | 1.00 | 18.77 |
| ATOM | 1104 | OD1 | ASP | 343 | 23.220 | 40.755 | 63.221 | 1.00 | 18.48 |

TABLE 2-continued

Coordinates of Lck bound with AMP-PNP

| | | Atom Type | Res | # | X | Y | Z | Occ | B |
|---|---|---|---|---|---|---|---|---|---|
| ATOM | 1105 | OD2 | ASP | 343 | 25.268 | 40.100 | 63.076 | 1.00 | 19.66 |
| ATOM | 1106 | C | ASP | 343 | 23.402 | 43.353 | 64.438 | 1.00 | 17.56 |
| ATOM | 1107 | O | ASP | 343 | 22.227 | 43.126 | 64.696 | 1.00 | 17.02 |
| ATOM | 1108 | N | MET | 344 | 24.337 | 43.525 | 65.363 | 1.00 | 17.57 |
| ATOM | 1110 | CA | MET | 344 | 23.940 | 43.438 | 66.754 | 1.00 | 18.94 |
| ATOM | 1111 | CB | MET | 344 | 25.159 | 43.614 | 67.636 | 1.00 | 22.04 |
| ATOM | 1112 | CG | MET | 344 | 26.205 | 42.564 | 67.317 | 1.00 | 20.27 |
| ATOM | 1113 | SD | MET | 344 | 27.702 | 42.778 | 68.340 | 1.00 | 25.96 |
| ATOM | 1114 | CE | MET | 344 | 27.750 | 41.447 | 69.307 | 1.00 | 22.39 |
| ATOM | 1115 | C | MET | 344 | 22.832 | 44.414 | 67.132 | 1.00 | 16.14 |
| ATOM | 1116 | O | MET | 344 | 21.929 | 44.037 | 67.828 | 1.00 | 16.41 |
| ATOM | 1117 | N | ALA | 345 | 22.904 | 45.652 | 66.647 | 1.00 | 16.35 |
| ATOM | 1119 | CA | ALA | 345 | 21.848 | 46.656 | 66.952 | 1.00 | 16.04 |
| ATOM | 1120 | CB | ALA | 345 | 22.196 | 48.009 | 66.306 | 1.00 | 15.38 |
| ATOM | 1121 | C | ALA | 345 | 20.475 | 46.163 | 66.481 | 1.00 | 12.30 |
| ATOM | 1122 | O | ALA | 345 | 19.496 | 46.319 | 67.209 | 1.00 | 13.10 |
| ATOM | 1123 | N | ALA | 346 | 20.414 | 45.615 | 65.273 | 1.00 | 12.19 |
| ATOM | 1125 | CA | ALA | 346 | 19.153 | 45.072 | 64.749 | 1.00 | 15.73 |
| ATOM | 1126 | CB | ALA | 346 | 19.336 | 44.622 | 63.306 | 1.00 | 14.07 |
| ATOM | 1127 | C | ALA | 346 | 18.625 | 43.928 | 65.615 | 1.00 | 17.64 |
| ATOM | 1128 | O | ALA | 346 | 17.436 | 43.843 | 65.851 | 1.00 | 21.71 |
| ATOM | 1129 | N | GLN | 347 | 19.527 | 43.064 | 66.118 | 1.00 | 18.84 |
| ATOM | 1131 | CA | GLN | 347 | 19.121 | 41.930 | 66.947 | 1.00 | 17.03 |
| ATOM | 1132 | CB | GLN | 347 | 20.318 | 41.035 | 67.320 | 1.00 | 13.90 |
| ATOM | 1133 | CG | GLN | 347 | 21.028 | 40.452 | 66.101 | 1.00 | 17.33 |
| ATOM | 1134 | CD | GLN | 347 | 22.086 | 39.395 | 66.450 | 1.00 | 15.74 |
| ATOM | 1135 | OE1 | GLN | 347 | 22.058 | 38.793 | 67.527 | 1.00 | 13.53 |
| ATOM | 1136 | NE2 | GLN | 347 | 23.009 | 39.142 | 65.508 | 1.00 | 13.32 |
| ATOM | 1139 | C | GLN | 347 | 18.461 | 42.434 | 68.214 | 1.00 | 17.85 |
| ATOM | 1140 | O | GLN | 347 | 17.469 | 41.872 | 68.650 | 1.00 | 18.87 |
| ATOM | 1141 | N | ILE | 348 | 19.026 | 43.474 | 68.796 | 1.00 | 17.10 |
| ATOM | 1143 | CA | ILE | 348 | 18.501 | 44.082 | 70.018 | 1.00 | 17.32 |
| ATOM | 1144 | CB | ILE | 348 | 19.469 | 45.204 | 70.508 | 1.00 | 16.99 |
| ATOM | 1145 | CG2 | ILE | 348 | 18.892 | 45.990 | 71.694 | 1.00 | 12.02 |
| ATOM | 1146 | CG1 | ILE | 348 | 20.791 | 44.532 | 70.895 | 1.00 | 17.04 |
| ATOM | 1147 | CD1 | ILE | 348 | 21.913 | 45.483 | 71.171 | 1.00 | 15.48 |
| ATOM | 1148 | C | ILE | 348 | 17.142 | 44.691 | 69.701 | 1.00 | 16.91 |
| ATOM | 1149 | O | ILE | 348 | 16.212 | 44.525 | 70.447 | 1.00 | 16.81 |
| ATOM | 1150 | N | ALA | 349 | 17.071 | 45.393 | 68.584 | 1.00 | 16.01 |
| ATOM | 1152 | CA | ALA | 349 | 15.852 | 46.024 | 68.152 | 1.00 | 15.43 |
| ATOM | 1153 | CB | ALA | 349 | 16.080 | 46.841 | 66.879 | 1.00 | 9.59 |
| ATOM | 1154 | C | ALA | 349 | 14.772 | 44.936 | 67.910 | 1.00 | 15.31 |
| ATOM | 1155 | O | ALA | 349 | 13.602 | 5.173 | 68.183 | 1.00 | 13.86 |
| ATOM | 1156 | N | GLU | 350 | 15.174 | 43.746 | 67.460 | 1.00 | 15.50 |
| ATOM | 1158 | CA | GLU | 350 | 14.238 | 42.630 | 67.221 | 1.00 | 16.08 |
| ATOM | 1159 | CB | GLU | 350 | 14.964 | 41.524 | 66.455 | 1.00 | 17.84 |
| ATOM | 1160 | CG | GLU | 350 | 14.132 | 40.344 | 66.101 | 1.00 | 21.98 |
| ATOM | 1161 | CD | GLU | 350 | 14.942 | 39.274 | 65.337 | 1.00 | 26.03 |
| ATOM | 1162 | OE1 | GLU | 350 | 15.942 | 39.592 | 64.646 | 1.00 | 25.60 |
| ATOM | 1163 | OE2 | GLU | 350 | 14.546 | 38.095 | 65.408 | 1.00 | 29.09 |
| ATOM | 1164 | C | GLU | 350 | 13.695 | 42.103 | 68.531 | 1.00 | 15.26 |
| ATOM | 1165 | O | GLU | 350 | 12.516 | 41.770 | 68.622 | 1.00 | 13.24 |
| ATOM | 1166 | N | GLY | 351 | 14.574 | 41.999 | 69.540 | 1.00 | 14.92 |
| ATOM | 1168 | CA | GLY | 351 | 14.124 | 41.554 | 70.855 | 1.00 | 15.10 |
| ATOM | 1169 | C | GLY | 351 | 13.134 | 42.578 | 71.418 | 1.00 | 17.07 |
| ATOM | 1170 | O | GLY | 351 | 12.089 | 42.209 | 71.970 | 1.00 | 19.38 |
| ATOM | 1171 | N | MET | 352 | 13.462 | 43.860 | 71.291 | 1.00 | 16.33 |
| ATOM | 1173 | CA | MET | 352 | 12.575 | 44.898 | 71.824 | 1.00 | 14.83 |
| ATOM | 1174 | CB | MET | 352 | 13.274 | 46.268 | 71.799 | 1.00 | 17.15 |
| ATOM | 1175 | CG | MET | 352 | 14.404 | 46.402 | 72.806 | 1.00 | 12.62 |
| ATOM | 1176 | SD | MET | 352 | 13.996 | 46.063 | 74.508 | 1.00 | 15.26 |
| ATOM | 1177 | CE | MET | 352 | 12.540 | 47.225 | 75.678 | 1.00 | 13.35 |
| ATOM | 1178 | C | MET | 352 | 11.256 | 44.956 | 71.072 | 1.00 | 13.44 |
| ATOM | 1179 | O | MET | 352 | 10.261 | 45.337 | 71.647 | 1.00 | 14.17 |
| ATOM | 1180 | N | ALA | 353 | 11.240 | 44.567 | 69.790 | 1.00 | 11.98 |
| ATOM | 1182 | CA | ALA | 353 | 10.001 | 44.558 | 69.022 | 1.00 | 11.64 |
| ATOM | 1183 | CB | ALA | 353 | 10.267 | 44.268 | 67.587 | 1.00 | 10.76 |
| ATOM | 1184 | C | ALA | 353 | 9.076 | 43.504 | 69.584 | 1.00 | 15.00 |
| ATOM | 1185 | O | ALA | 353 | 7.852 | 43.658 | 69.546 | 1.00 | 17.11 |
| ATOM | 1186 | N | PHE | 354 | 9.672 | 42.420 | 70.085 | 1.00 | 17.52 |
| ATOM | 1188 | CA | PHE | 354 | 8.931 | 41.346 | 70.696 | 1.00 | 15.71 |
| ATOM | 1189 | CB | PHE | 354 | 9.852 | 40.157 | 71.024 | 1.00 | 16.79 |
| ATOM | 1190 | CG | PHE | 354 | 9.167 | 39.089 | 71.803 | 1.00 | 15.49 |
| ATOM | 1191 | CD1 | PHE | 354 | 8.110 | 38.438 | 71.216 | 1.00 | 16.89 |

TABLE 2-continued

Coordinates of Lck bound with AMP-PNP

| | Atom Type | Res | # | X | Y | Z | Occ | B |
|---|---|---|---|---|---|---|---|---|
| ATOM | 1192 | CD2 | PHE | 354 | 9.468 | 38.821 | 73.124 | 1.00 | 14.96 |
| ATOM | 1193 | CE1 | PHE | 354 | 7.334 | 37.548 | 71.915 | 1.00 | 15.69 |
| ATOM | 1194 | CE2 | PHE | 354 | 8.687 | 37.907 | 73.856 | 1.00 | 16.25 |
| ATOM | 1195 | CZ | PHE | 354 | 7.613 | 37.279 | 73.233 | 1.00 | 14.21 |
| ATOM | 1196 | C | PHE | 354 | 8.295 | 41.890 | 71.973 | 1.00 | 14.98 |
| ATOM | 1197 | O | PHE | 354 | 7.097 | 41.709 | 72.180 | 1.00 | 15.65 |
| ATOM | 1198 | N | ILE | 355 | 9.100 | 42.516 | 72.831 | 1.00 | 13.91 |
| ATOM | 1200 | CA | ILE | 355 | 8.610 | 43.093 | 74.083 | 1.00 | 15.69 |
| ATOM | 1201 | CB | ILE | 355 | 9.780 | 43.731 | 74.800 | 1.00 | 14.98 |
| ATOM | 1202 | CG2 | ILE | 355 | 9.306 | 44.671 | 75.941 | 1.00 | 15.02 |
| ATOM | 1203 | CG1 | ILE | 355 | 10.713 | 42.635 | 75.290 | 1.00 | 13.68 |
| ATOM | 1204 | CD1 | ILE | 355 | 11.981 | 43.106 | 76.050 | 1.00 | 13.62 |
| ATOM | 1205 | C | ILE | 355 | 7.459 | 44.101 | 73.798 | 1.00 | 15.54 |
| ATOM | 1206 | O | ILE | 355 | 6.414 | 44.063 | 74.408 | 1.00 | 15.57 |
| ATOM | 1207 | N | GLU | 356 | 7.645 | 44.880 | 72.751 | 1.00 | 16.21 |
| ATOM | 1209 | CA | GLU | 356 | 6.691 | 45.881 | 72.326 | 1.00 | 17.55 |
| ATOM | 1210 | CB | GLU | 356 | 7.289 | 46.645 | 71.150 | 1.00 | 17.46 |
| ATOM | 1211 | CG | GLU | 356 | 6.388 | 47.565 | 70.371 | 1.00 | 20.93 |
| ATOM | 1212 | CD | GLU | 356 | 7.166 | 48.283 | 69.248 | 1.00 | 25.88 |
| ATOM | 1213 | OE1 | GLU | 356 | 7.312 | 47.785 | 68.095 | 1.00 | 26.40 |
| ATOM | 1214 | OE2 | GLU | 356 | 7.667 | 49.364 | 69.519 | 1.00 | 28.48 |
| ATOM | 1215 | C | GLU | 356 | 5.356 | 45.242 | 71.936 | 1.00 | 17.60 |
| ATOM | 1216 | O | GLU | 356 | 4.325 | 45.698 | 72.383 | 1.00 | 19.61 |
| ATOM | 1217 | N | GLU | 357 | 5.415 | 44.192 | 71.118 | 0.36 | 14.79 |
| ATOM | 1219 | CA | GLU | 357 | 4.242 | 43.456 | 70.661 | 0.36 | 12.79 |
| ATOM | 1220 | CB | GLU | 357 | 4.727 | 42.434 | 69.605 | 0.36 | 12.71 |
| ATOM | 1221 | CG | GLU | 357 | 3.842 | 41.280 | 69.204 | 0.36 | 16.32 |
| ATOM | 1222 | CD | GLU | 357 | 4.647 | 40.034 | 68.710 | 0.36 | 21.70 |
| ATOM | 1223 | OE1 | GLU | 357 | 5.869 | 40.104 | 68.400 | 0.36 | 23.32 |
| ATOM | 1224 | OE2 | GLU | 357 | 4.033 | 38.948 | 68.665 | 0.36 | 25.20 |
| ATOM | 1225 | C | GLU | 357 | 3.470 | 42.803 | 71.823 | 0.36 | 10.96 |
| ATOM | 1226 | O | GLU | 357 | 2.255 | 42.749 | 71.813 | 0.36 | 8.17 |
| ATOM | 1227 | N | ARG | 358 | 4.174 | 42.404 | 72.866 | 1.00 | 14.43 |
| ATOM | 1229 | CA | ARG | 358 | 3.531 | 41.750 | 74.016 | 1.00 | 14.57 |
| ATOM | 1230 | CB | ARG | 358 | 4.523 | 40.756 | 74.676 | 1.00 | 15.08 |
| ATOM | 1231 | CG | ARG | 358 | 5.074 | 39.682 | 73.719 | 1.00 | 15.68 |
| ATOM | 1232 | CD | ARG | 358 | 3.940 | 38.859 | 73.095 | 1.00 | 16.35 |
| ATOM | 1233 | NE | ARG | 358 | 2.986 | 38.399 | 74.097 | 1.00 | 20.96 |
| ATOM | 1235 | CZ | ARG | 358 | 1.710 | 38.155 | 73.826 | 1.00 | 22.73 |
| ATOM | 1236 | NH1 | ARG | 358 | 1.270 | 38.313 | 72.594 | 1.00 | 19.50 |
| ATOM | 1239 | NH2 | ARG | 358 | 0.860 | 37.789 | 74.773 | 1.00 | 25.50 |
| ATOM | 1242 | C | ARG | 358 | 3.005 | 42.728 | 75.054 | 1.00 | 14.70 |
| ATOM | 1243 | O | ARG | 358 | 2.633 | 42.324 | 76.146 | 1.00 | 16.87 |
| ATOM | 1244 | N | ASN | 359 | 3.036 | 44.025 | 74.755 | 1.00 | 16.35 |
| ATOM | 1246 | CA | ASN | 359 | 2.580 | 45.025 | 75.741 | 1.00 | 16.01 |
| ATOM | 1247 | CB | ASN | 359 | 1.121 | 44.772 | 76.134 | 1.00 | 17.72 |
| ATOM | 1248 | CG | ASN | 359 | 0.162 | 45.263 | 75.077 | 1.00 | 20.99 |
| ATOM | 1249 | OD1 | ASN | 359 | 0.591 | 45.886 | 74.139 | 1.00 | 23.16 |
| ATOM | 1250 | ND2 | ASN | 359 | −1.126 | 44.936 | 75.193 | 1.00 | 23.65 |
| ATOM | 1253 | C | ASN | 359 | 3.441 | 45.185 | 76.985 | 1.00 | 16.43 |
| ATOM | 1254 | O | ASN | 359 | 2.945 | 45.523 | 78.062 | 1.00 | 17.27 |
| ATOM | 1255 | N | TYR | 360 | 4.731 | 44.912 | 76.859 | 1.00 | 17.35 |
| ATOM | 1257 | CA | TYR | 360 | 5.618 | 45.104 | 78.010 | 1.00 | 18.37 |
| ATOM | 1258 | CB | TYR | 360 | 6.487 | 43.865 | 78.282 | 1.00 | 17.76 |
| ATOM | 1259 | CG | TYR | 360 | 5.782 | 42.747 | 78.996 | 1.00 | 16.41 |
| ATOM | 1260 | CD1 | TYR | 360 | 4.982 | 41.863 | 78.290 | 1.00 | 18.58 |
| ATOM | 1261 | CE1 | TYR | 360 | 4.323 | 40.835 | 78.945 | 1.00 | 20.66 |
| ATOM | 1262 | CD2 | TYR | 360 | 5.910 | 42.581 | 80.355 | 1.00 | 17.13 |
| ATOM | 1263 | CE2 | TYR | 360 | 5.253 | 41.560 | 81.023 | 1.00 | 20.21 |
| ATOM | 1264 | CZ | TYR | 360 | 4.463 | 40.700 | 80.314 | 1.00 | 19.85 |
| ATOM | 1265 | OH | TYR | 360 | 3.743 | 39.736 | 80.985 | 1.00 | 26.09 |
| ATOM | 1267 | C | TYR | 360 | 6.572 | 46.266 | 77.723 | 1.00 | 17.97 |
| ATOM | 1268 | O | TYR | 360 | 6.696 | 46.727 | 76.596 | 1.00 | 14.07 |
| ATOM | 1269 | N | ILE | 361 | 7.198 | 46.752 | 78.782 | 1.00 | 18.53 |
| ATOM | 1271 | CA | ILE | 361 | 8.219 | 47.755 | 78.665 | 1.00 | 20.70 |
| ATOM | 1272 | CB | ILE | 361 | 7.779 | 49.180 | 79.175 | 1.00 | 20.42 |
| ATOM | 1273 | CG2 | ILE | 361 | 6.761 | 49.799 | 78.224 | 1.00 | 20.38 |
| ATOM | 1274 | CG1 | ILE | 361 | 7.310 | 49.121 | 80.610 | 1.00 | 20.54 |
| ATOM | 1275 | CD1 | ILE | 361 | 7.026 | 50.483 | 81.187 | 1.00 | 24.78 |
| ATOM | 1276 | C | ILE | 361 | 9.382 | 47.205 | 79.488 | 1.00 | 21.11 |
| ATOM | 1277 | O | ILE | 361 | 9.184 | 46.410 | 80.408 | 1.00 | 23.36 |
| ATOM | 1278 | N | HIS | 362 | 10.587 | 47.659 | 79.183 | 1.00 | 20.32 |
| ATOM | 1280 | CA | HIS | 362 | 11.778 | 47.195 | 79.900 | 1.00 | 18.13 |
| ATOM | 1281 | CB | HIS | 362 | 12.876 | 46.935 | 78.865 | 1.00 | 17.63 |

TABLE 2-continued

Coordinates of Lck bound with AMP-PNP

| | Atom Type | Res | # | X | Y | Z | Occ | B |
|---|---|---|---|---|---|---|---|---|
| ATOM | 1282 | CG | HIS | 362 | 14.083 | 46.232 | 79.419 | 1.00 | 18.12 |
| ATOM | 1283 | CD2 | HIS | 362 | 14.479 | 44.945 | 79.323 | 1.00 | 18.04 |
| ATOM | 1284 | ND1 | HIS | 362 | 15.052 | 46.880 | 80.162 | 1.00 | 17.47 |
| ATOM | 1286 | CE1 | HIS | 362 | 15.995 | 46.017 | 80.494 | 1.00 | 19.69 |
| ATOM | 1287 | NE2 | HIS | 362 | 15.669 | 44.837 | 80.002 | 1.00 | 19.55 |
| ATOM | 1289 | C | HIS | 362 | 12.250 | 48.182 | 80.953 | 1.00 | 16.38 |
| ATOM | 1290 | O | HIS | 362 | 12.533 | 47.820 | 82.077 | 1.00 | 16.56 |
| ATOM | 1291 | N | ARG | 363 | 12.384 | 49.442 | 80.541 | 1.00 | 18.87 |
| ATOM | 1293 | CA | ARG | 363 | 12.795 | 50.537 | 81.437 | 1.00 | 19.55 |
| ATOM | 1294 | CB | ARG | 363 | 11.940 | 50.584 | 82.703 | 1.00 | 16.82 |
| ATOM | 1295 | CG | ARG | 363 | 10.450 | 50.871 | 82.432 | 1.00 | 15.69 |
| ATOM | 1296 | CD | ARG | 363 | 9.746 | 51.332 | 83.693 | 1.00 | 12.82 |
| ATOM | 1297 | NE | ARG | 363 | 9.807 | 50.377 | 84.769 | 1.00 | 16.17 |
| ATOM | 1299 | CZ | ARG | 363 | 9.719 | 50.708 | 86.044 | 1.00 | 16.47 |
| ATOM | 1300 | NH1 | ARG | 363 | 9.575 | 51.976 | 86.373 | 1.00 | 21.41 |
| ATOM | 1303 | NH2 | ARG | 363 | 9.731 | 49.787 | 86.988 | 1.00 | 19.50 |
| ATOM | 1306 | C | ARG | 363 | 14.258 | 50.557 | 81.853 | 1.00 | 20.13 |
| ATOM | 1307 | O | ARG | 363 | 14.649 | 51.438 | 82.576 | 1.00 | 23.91 |
| ATOM | 1308 | N | ASP | 364 | 15.058 | 49.579 | 81.441 | 1.00 | 19.03 |
| ATOM | 1310 | CA | ASP | 364 | 16.485 | 49.567 | 81.836 | 1.00 | 16.53 |
| ATOM | 1311 | CB | ASP | 364 | 16.697 | 48.592 | 82.978 | 1.00 | 19.77 |
| ATOM | 1312 | CG | ASP | 364 | 17.928 | 48.901 | 83.840 | 1.00 | 23.49 |
| ATOM | 1313 | OD1 | ASP | 364 | 18.660 | 49.876 | 83.582 | 1.00 | 24.42 |
| ATOM | 1314 | OD2 | ASP | 364 | 18.153 | 48.176 | 84.825 | 1.00 | 27.26 |
| ATOM | 1315 | C | ASP | 364 | 17.296 | 49.147 | 80.620 | 1.00 | 16.47 |
| ATOM | 1316 | O | ASP | 364 | 18.284 | 48.424 | 80.741 | 1.00 | 17.58 |
| ATOM | 1317 | N | LEU | 365 | 16.851 | 49.560 | 79.447 | 1.00 | 12.32 |
| ATOM | 1319 | CA | LEU | 365 | 17.519 | 49.247 | 78.203 | 1.00 | 14.67 |
| ATOM | 1320 | CB | LEU | 365 | 16.595 | 49.479 | 77.026 | 1.00 | 12.87 |
| ATOM | 1321 | CG | LEU | 365 | 17.089 | 49.116 | 75.630 | 1.00 | 11.40 |
| ATOM | 1322 | CD1 | LEU | 365 | 17.468 | 47.618 | 75.584 | 1.00 | 14.03 |
| ATOM | 1323 | CD2 | LEU | 365 | 16.067 | 49.428 | 74.583 | 1.00 | 7.20 |
| ATOM | 1324 | C | LEU | 365 | 18.831 | 50.090 | 78.034 | 1.00 | 19.62 |
| ATOM | 1325 | O | LEU | 365 | 18.811 | 51.329 | 77.861 | 1.00 | 21.35 |
| ATOM | 1326 | N | ARG | 366 | 19.948 | 49.382 | 78.017 | 1.00 | 18.38 |
| ATOM | 1328 | CA | ARG | 366 | 21.273 | 49.955 | 77.887 | 1.00 | 18.62 |
| ATOM | 1329 | CB | ARG | 366 | 21.668 | 50.625 | 79.207 | 1.00 | 17.23 |
| ATOM | 1330 | CG | ARG | 366 | 21.584 | 49.703 | 80.386 | 1.00 | 21.00 |
| ATOM | 1331 | CD | ARG | 366 | 21.786 | 50.457 | 81.719 | 1.00 | 23.24 |
| ATOM | 1332 | NE | ARG | 366 | 23.106 | 51.061 | 81.783 | 1.00 | 29.88 |
| ATOM | 1334 | CZ | ARG | 366 | 23.437 | 52.001 | 82.672 | 1.00 | 35.16 |
| ATOM | 1335 | NH1 | ARG | 366 | 22.541 | 52.419 | 83.566 | 1.00 | 34.83 |
| ATOM | 1338 | NH2 | ARG | 366 | 24.663 | 52.527 | 82.653 | 1.00 | 35.29 |
| ATOM | 1341 | C | ARG | 366 | 22.244 | 48.773 | 77.568 | 1.00 | 19.27 |
| ATOM | 1342 | O | ARG | 366 | 21.917 | 47.574 | 77.794 | 1.00 | 18.61 |
| ATOM | 1343 | N | ALA | 367 | 23.420 | 49.085 | 77.066 | 1.00 | 17.16 |
| ATOM | 1345 | CA | ALA | 367 | 24.361 | 48.059 | 76.699 | 1.00 | 14.91 |
| ATOM | 1346 | CB | ALA | 367 | 25.589 | 48.643 | 76.078 | 1.00 | 15.47 |
| ATOM | 1347 | C | ALA | 367 | 24.738 | 47.110 | 77.830 | 1.00 | 15.64 |
| ATOM | 1348 | O | ALA | 367 | 25.034 | 45.945 | 77.562 | 1.00 | 16.83 |
| ATOM | 1349 | N | ALA | 368 | 24.702 | 47.574 | 79.072 | 1.00 | 13.84 |
| ATOM | 1351 | CA | ALA | 368 | 25.020 | 46.728 | 80.192 | 1.00 | 14.87 |
| ATOM | 1352 | CB | ALA | 368 | 25.095 | 47.516 | 81.477 | 1.00 | 12.42 |
| ATOM | 1353 | C | ALA | 368 | 23.978 | 45.603 | 80.353 | 1.00 | 18.21 |
| ATOM | 1354 | O | ALA | 368 | 24.299 | 44.532 | 80.936 | 1.00 | 19.57 |
| ATOM | 1355 | N | ASN | 369 | 22.773 | 45.840 | 79.835 | 1.00 | 16.57 |
| ATOM | 1357 | CA | ASN | 369 | 21.707 | 44.868 | 79.962 | 1.00 | 17.13 |
| ATOM | 1358 | CB | ASN | 369 | 20.457 | 45.543 | 80.521 | 1.00 | 17.43 |
| ATOM | 1359 | CG | ASN | 369 | 20.656 | 45.924 | 81.965 | 1.00 | 18.16 |
| ATOM | 1360 | OD1 | ASN | 369 | 21.446 | 45.275 | 82.672 | 1.00 | 18.99 |
| ATOM | 1361 | ND2 | ASN | 369 | 19.982 | 46.986 | 82.416 | 1.00 | 20.31 |
| ATOM | 1364 | C | ASN | 369 | 21.429 | 44.042 | 78.706 | 1.00 | 17.54 |
| ATOM | 1365 | O | ASN | 369 | 20.324 | 43.535 | 78.510 | 1.00 | 20.01 |
| ATOM | 1366 | N | ILE | 370 | 22.392 | 44.022 | 77.805 | 1.00 | 16.12 |
| ATOM | 1368 | CA | ILE | 370 | 22.285 | 43.213 | 76.621 | 1.00 | 15.43 |
| ATOM | 1369 | CB | ILE | 370 | 22.616 | 43.996 | 75.347 | 1.00 | 13.08 |
| ATOM | 1370 | CG2 | ILE | 370 | 22.685 | 43.061 | 74.163 | 1.00 | 12.36 |
| ATOM | 1371 | CG1 | ILE | 370 | 21.605 | 45.120 | 75.127 | 1.00 | 14.37 |
| ATOM | 1372 | CD1 | ILE | 370 | 20.119 | 44.695 | 75.114 | 1.00 | 15.62 |
| ATOM | 1373 | C | ILE | 370 | 23.389 | 42.142 | 76.825 | 1.00 | 16.79 |
| ATOM | 1374 | O | ILE | 370 | 24.515 | 42.470 | 77.255 | 1.00 | 17.04 |
| ATOM | 1375 | N | LEU | 371 | 23.062 | 40.857 | 76.617 | 1.00 | 16.45 |
| ATOM | 1377 | CA | LEU | 371 | 24.086 | 39.814 | 76.783 | 1.00 | 13.91 |
| ATOM | 1378 | CB | LEU | 371 | 23.629 | 38.718 | 77.718 | 1.00 | 11.51 |

TABLE 2-continued

Coordinates of Lck bound with AMP-PNP

| | Atom Type | Res | # | X | Y | Z | Occ | B |
|---|---|---|---|---|---|---|---|---|
| ATOM | 1379 | CG | LEU | 371 | 23.385 | 39.151 | 79.162 | 1.00 | 11.65 |
| ATOM | 1380 | CD1 | LEU | 371 | 23.017 | 37.974 | 80.030 | 1.00 | 9.30 |
| ATOM | 1381 | CD2 | LEU | 371 | 24.623 | 39.845 | 79.736 | 1.00 | 13.96 |
| ATOM | 1382 | C | LEU | 371 | 24.515 | 39.273 | 75.435 | 1.00 | 15.55 |
| ATOM | 1383 | O | LEU | 371 | 23.743 | 39.310 | 74.498 | 1.00 | 14.88 |
| ATOM | 1384 | N | VAL | 372 | 25.753 | 38.805 | 75.323 | 1.00 | 16.05 |
| ATOM | 1386 | CA | VAL | 372 | 26.276 | 38.352 | 74.048 | 1.00 | 16.97 |
| ATOM | 1387 | CB | VAL | 372 | 27.483 | 39.238 | 73.661 | 1.00 | 15.86 |
| ATOM | 1388 | CG1 | VAL | 372 | 28.019 | 38.915 | 72.278 | 1.00 | 14.22 |
| ATOM | 1389 | CG2 | VAL | 372 | 27.015 | 40.717 | 73.765 | 1.00 | 16.22 |
| ATOM | 1390 | C | VAL | 372 | 26.662 | 36.860 | 74.136 | 1.00 | 19.00 |
| ATOM | 1391 | O | VAL | 372 | 27.310 | 36.425 | 75.091 | 1.00 | 16.67 |
| ATOM | 1392 | N | SER | 373 | 26.176 | 36.084 | 73.171 | 1.00 | 17.20 |
| ATOM | 1394 | CA | SER | 373 | 26.443 | 34.661 | 73.173 | 1.00 | 16.49 |
| ATOM | 1395 | CB | SER | 373 | 25.401 | 33.903 | 72.382 | 1.00 | 9.61 |
| ATOM | 1396 | OG | SER | 373 | 25.609 | 34.133 | 71.002 | 1.00 | 12.51 |
| ATOM | 1398 | C | SER | 373 | 27.818 | 34.328 | 72.567 | 1.00 | 19.20 |
| ATOM | 1399 | O | SER | 373 | 28.515 | 35.194 | 71.993 | 1.00 | 18.05 |
| ATOM | 1400 | N | ASP | 374 | 28.132 | 33.030 | 72.589 | 1.00 | 19.95 |
| ATOM | 1402 | CA | ASP | 374 | 29.372 | 32.544 | 72.033 | 1.00 | 20.00 |
| ATOM | 1403 | CB | ASP | 374 | 29.589 | 31.078 | 72.391 | 1.00 | 26.17 |
| ATOM | 1404 | CG | ASP | 374 | 28.545 | 30.163 | 71.772 | 1.00 | 31.48 |
| ATOM | 1405 | OD1 | ASP | 374 | 27.331 | 30.389 | 71.978 | 1.00 | 38.05 |
| ATOM | 1406 | OD2 | ASP | 374 | 28.943 | 29.237 | 71.042 | 1.00 | 34.24 |
| ATOM | 1407 | C | ASP | 374 | 29.393 | 32.722 | 70.530 | 1.00 | 20.11 |
| ATOM | 1408 | O | ASP | 374 | 30.473 | 32.770 | 69.956 | 1.00 | 20.54 |
| ATOM | 1409 | N | THR | 375 | 28.233 | 32.821 | 69.871 | 1.00 | 19.69 |
| ATOM | 1411 | CA | THR | 375 | 28.237 | 33.030 | 68.402 | 1.00 | 19.16 |
| ATOM | 1412 | CB | THR | 375 | 27.161 | 32.200 | 67.721 | 1.00 | 18.19 |
| ATOM | 1413 | OG1 | THR | 375 | 25.884 | 32.473 | 68.337 | 1.00 | 21.03 |
| ATOM | 1415 | CG2 | THR | 375 | 27.480 | 30.704 | 67.854 | 1.00 | 22.62 |
| ATOM | 1416 | C | THR | 375 | 28.050 | 34.530 | 68.047 | 1.00 | 18.52 |
| ATOM | 1417 | O | THR | 375 | 27.761 | 34.892 | 66.912 | 1.00 | 16.67 |
| ATOM | 1418 | N | LEU | 376 | 28.207 | 35.375 | 69.055 | 1.00 | 17.98 |
| ATOM | 1420 | CA | LEU | 376 | 28.055 | 36.815 | 68.877 | 1.00 | 19.87 |
| ATOM | 1421 | CB | LEU | 376 | 29.050 | 37.365 | 67.846 | 1.00 | 16.55 |
| ATOM | 1422 | CG | LEU | 376 | 30.530 | 37.043 | 68.128 | 1.00 | 19.39 |
| ATOM | 1423 | CD1 | LEU | 376 | 31.407 | 38.002 | 67.298 | 1.00 | 17.27 |
| ATOM | 1424 | CD2 | LEU | 376 | 30.879 | 37.163 | 69.594 | 1.00 | 18.10 |
| ATOM | 1425 | C | LEU | 376 | 26.628 | 37.226 | 68.523 | 1.00 | 19.40 |
| ATOM | 1426 | O | LEU | 376 | 26.403 | 38.075 | 67.668 | 1.00 | 20.81 |
| ATOM | 1427 | N | SER | 377 | 25.674 | 36.563 | 69.154 | 1.00 | 17.62 |
| ATOM | 1429 | CA | SER | 377 | 24.280 | 36.930 | 68.974 | 1.00 | 16.30 |
| ATOM | 1430 | CB | SER | 377 | 23.370 | 35.697 | 68.723 | 1.00 | 10.40 |
| ATOM | 1431 | OG | SER | 377 | 23.443 | 34.763 | 69.780 | 1.00 | 11.26 |
| ATOM | 1433 | C | SER | 377 | 23.928 | 37.681 | 70.273 | 1.00 | 16.38 |
| ATOM | 1434 | O | SER | 377 | 24.550 | 37.456 | 71.330 | 1.00 | 14.77 |
| ATOM | 1435 | N | CYS | 378 | 22.993 | 38.632 | 70.165 | 1.00 | 16.82 |
| ATOM | 1437 | CA | CYS | 378 | 22.615 | 39.439 | 71.319 | 1.00 | 17.69 |
| ATOM | 1438 | CB | CYS | 378 | 22.723 | 40.941 | 70.982 | 1.00 | 18.25 |
| ATOM | 1439 | SG | CYS | 378 | 24.427 | 41.428 | 70.519 | 1.00 | 15.71 |
| ATOM | 1440 | C | CYS | 378 | 21.252 | 39.151 | 71.879 | 1.00 | 15.25 |
| ATOM | 1441 | O | CYS | 378 | 20.327 | 38.899 | 71.148 | 1.00 | 15.90 |
| ATOM | 1442 | N | LYS | 379 | 21.130 | 39.258 | 73.195 | 1.00 | 15.87 |
| ATOM | 1444 | CA | LYS | 379 | 19.873 | 39.054 | 73.836 | 1.00 | 15.83 |
| ATOM | 1445 | CB | LYS | 379 | 19.812 | 37.666 | 74.496 | 1.00 | 15.60 |
| ATOM | 1446 | CG | LYS | 379 | 20.037 | 36.561 | 73.480 | 1.00 | 19.59 |
| ATOM | 1447 | CD | LYS | 379 | 19.703 | 35.184 | 74.000 | 1.00 | 16.05 |
| ATOM | 1448 | CE | LYS | 379 | 20.029 | 34.207 | 72.859 | 1.00 | 16.48 |
| ATOM | 1449 | NZ | LYS | 379 | 19.249 | 32.982 | 72.931 | 1.00 | 14.49 |
| ATOM | 1453 | C | LYS | 379 | 19.584 | 40.120 | 74.910 | 1.00 | 15.54 |
| ATOM | 1454 | O | LYS | 379 | 20.485 | 40.554 | 75.630 | 1.00 | 14.31 |
| ATOM | 1455 | N | ILE | 380 | 18.295 | 40.466 | 75.022 | 1.00 | 14.13 |
| ATOM | 1457 | CA | ILE | 380 | 17.854 | 41.414 | 76.044 | 1.00 | 11.75 |
| ATOM | 1458 | CB | ILE | 380 | 16.375 | 41.897 | 75.825 | 1.00 | 14.77 |
| ATOM | 1459 | CG2 | ILE | 380 | 16.038 | 43.003 | 76.826 | 1.00 | 12.38 |
| ATOM | 1460 | CG1 | ILE | 380 | 16.131 | 42.369 | 74.372 | 1.00 | 12.86 |
| ATOM | 1461 | CD1 | ILE | 380 | 17.049 | 43.459 | 73.920 | 1.00 | 15.77 |
| ATOM | 1462 | C | ILE | 380 | 17.899 | 40.623 | 77.352 | 1.00 | 12.43 |
| ATOM | 1463 | O | ILE | 380 | 17.428 | 39.476 | 77.425 | 1.00 | 11.43 |
| ATOM | 1464 | N | ALA | 381 | 18.410 | 41.245 | 78.388 | 1.00 | 12.03 |
| ATOM | 1466 | CA | ALA | 381 | 18.540 | 40.652 | 79.684 | 1.00 | 13.59 |
| ATOM | 1467 | CB | ALA | 381 | 19.984 | 40.229 | 79.914 | 1.00 | 12.83 |
| ATOM | 1468 | C | ALA | 381 | 18.103 | 41.691 | 80.759 | 1.00 | 16.54 |

TABLE 2-continued

Coordinates of Lck bound with AMP-PNP

| | Atom Type | Res | # | X | Y | Z | Occ | B |
|---|---|---|---|---|---|---|---|---|
| ATOM | 1469 | O | ALA | 381 | 17.777 | 42.833 | 80.432 | 1.00 | 17.99 |
| ATOM | 1470 | N | ASP | 382 | 18.145 | 41.285 | 82.023 | 1.00 | 17.83 |
| ATOM | 1472 | CA | ASP | 382 | 17.758 | 42.113 | 83.173 | 1.00 | 22.61 |
| ATOM | 1473 | CB | ASP | 382 | 18.782 | 43.206 | 83.523 | 1.00 | 24.19 |
| ATOM | 1474 | CG | ASP | 382 | 18.593 | 43.704 | 84.956 | 1.00 | 28.24 |
| ATOM | 1475 | OD1 | ASP | 382 | 17.492 | 43.502 | 85.538 | 1.00 | 29.43 |
| ATOM | 1476 | OD2 | ASP | 382 | 19.545 | 44.237 | 85.533 | 1.00 | 33.21 |
| ATOM | 1477 | C | ASP | 382 | 16.346 | 42.720 | 83.100 | 1.00 | 23.47 |
| ATOM | 1478 | O | ASP | 382 | 16.156 | 43.929 | 82.857 | 1.00 | 26.04 |
| ATOM | 1479 | N | PHE | 383 | 15.374 | 41.876 | 83.437 | 1.00 | 20.99 |
| ATOM | 1481 | CA | PHE | 383 | 13.971 | 42.238 | 83.431 | 1.00 | 17.65 |
| ATOM | 1482 | CB | PHE | 383 | 13.146 | 41.066 | 82.908 | 1.00 | 15.74 |
| ATOM | 1483 | CG | PHE | 383 | 13.539 | 40.611 | 81.531 | 1.00 | 11.79 |
| ATOM | 1484 | CD1 | PHE | 383 | 13.033 | 41.254 | 80.412 | 1.00 | 10.41 |
| ATOM | 1485 | CD2 | PHE | 383 | 14.474 | 39.598 | 81.355 | 1.00 | 6.82 |
| ATOM | 1486 | CE1 | PHE | 383 | 13.449 | 40.905 | 79.140 | 1.00 | 10.63 |
| ATOM | 1487 | CE2 | PHE | 383 | 14.900 | 39.245 | 80.081 | 1.00 | 7.13 |
| ATOM | 1488 | CZ | PHE | 383 | 14.401 | 39.887 | 78.985 | 1.00 | 7.27 |
| ATOM | 1489 | C | PHE | 383 | 13.441 | 42.694 | 84.793 | 1.00 | 18.53 |
| ATOM | 1490 | O | PHE | 383 | 12.226 | 42.734 | 85.010 | 1.00 | 18.76 |
| ATOM | 1491 | N | GLY | 384 | 14.340 | 43.042 | 85.696 | 1.00 | 19.19 |
| ATOM | 1493 | CA | GLY | 384 | 13.939 | 43.509 | 87.021 | 1.00 | 21.04 |
| ATOM | 1494 | C | GLY | 384 | 12.973 | 44.703 | 87.032 | 1.00 | 22.23 |
| ATOM | 1495 | O | GLY | 384 | 12.091 | 44.791 | 87.890 | 1.00 | 22.56 |
| ATOM | 1496 | N | LEU | 385 | 13.121 | 45.606 | 86.060 | 1.00 | 21.19 |
| ATOM | 1498 | CA | LEU | 385 | 12.234 | 46.774 | 86.004 | 1.00 | 21.56 |
| ATOM | 1499 | CB | LEU | 385 | 13.032 | 48.048 | 85.706 | 1.00 | 19.23 |
| ATOM | 1500 | CG | LEU | 385 | 13.985 | 48.510 | 86.806 | 1.00 | 19.18 |
| ATOM | 1501 | CD1 | LEU | 385 | 14.780 | 39.751 | 86.306 | 1.00 | 21.36 |
| ATOM | 1502 | CD2 | LEU | 385 | 13.200 | 48.842 | 88.046 | 1.00 | 14.38 |
| ATOM | 1503 | C | LEU | 385 | 11.150 | 46.625 | 84.962 | 1.00 | 20.62 |
| ATOM | 1504 | O | LEU | 385 | 10.322 | 47.522 | 84.802 | 1.00 | 21.37 |
| ATOM | 1505 | N | ALA | 386 | 11.191 | 45.528 | 84.211 | 1.00 | 21.92 |
| ATOM | 1507 | CA | ALA | 386 | 10.208 | 45.302 | 83.150 | 1.00 | 22.38 |
| ATOM | 1508 | CB | ALA | 386 | 10.536 | 44.062 | 82.366 | 1.00 | 21.60 |
| ATOM | 1509 | C | ALA | 386 | 8.781 | 45.234 | 83.718 | 1.00 | 22.56 |
| ATOM | 1510 | O | ALA | 386 | 8.565 | 44.759 | 84.837 | 1.00 | 22.02 |
| ATOM | 1511 | N | ARG | 387 | 7.815 | 45.709 | 82.937 | 1.00 | 22.00 |
| ATOM | 1513 | CA | ARG | 387 | 6.418 | 45.730 | 83.394 | 1.00 | 21.42 |
| ATOM | 1514 | CB | ARG | 387 | 6.052 | 47.080 | 84.021 | 1.00 | 20.93 |
| ATOM | 1515 | CG | ARG | 387 | 6.878 | 47.511 | 85.195 | 1.00 | 22.36 |
| ATOM | 1516 | CD | ARG | 387 | 6.644 | 46.657 | 86.383 | 1.00 | 20.81 |
| ATOM | 1517 | NE | ARG | 387 | 7.346 | 47.194 | 87.533 | 1.00 | 22.93 |
| ATOM | 1519 | CZ | ARG | 387 | 8.504 | 46.731 | 87.993 | 1.00 | 26.61 |
| ATOM | 1520 | NH1 | ARG | 387 | 9.108 | 45.704 | 87.388 | 1.00 | 26.75 |
| ATOM | 1523 | NH2 | ARG | 387 | 9.044 | 47.253 | 89.088 | 1.00 | 25.49 |
| ATOM | 1526 | C | ARG | 387 | 5.411 | 45.490 | 82.282 | 1.00 | 20.65 |
| ATOM | 1527 | O | ARG | 387 | 5.638 | 45.837 | 81.108 | 1.00 | 15.93 |
| ATOM | 1528 | N | LEU | 388 | 4.299 | 44.859 | 82.655 | 1.00 | 22.37 |
| ATOM | 1530 | CA | LEU | 388 | 3.256 | 44.638 | 81.689 | 1.00 | 25.26 |
| ATOM | 1531 | CB | LEU | 388 | 2.387 | 43.430 | 82.041 | 1.00 | 27.00 |
| ATOM | 1532 | CG | LEU | 388 | 1.550 | 43.223 | 80.779 | 1.00 | 25.08 |
| ATOM | 1533 | CD1 | LEU | 388 | 1.705 | 41.941 | 79.981 | 1.00 | 26.36 |
| ATOM | 1534 | CD2 | LEU | 388 | 0.247 | 43.295 | 81.355 | 1.00 | 25.06 |
| ATOM | 1535 | C | LEU | 388 | 2.457 | 45.939 | 81.683 | 1.00 | 26.73 |
| ATOM | 1536 | O | LEU | 388 | 2.148 | 46.495 | 82.723 | 1.00 | 25.72 |
| ATOM | 1537 | N | ILE | 389 | 2.160 | 46.425 | 80.496 | 1.00 | 29.26 |
| ATOM | 1539 | CA | ILE | 389 | 1.470 | 47.676 | 80.350 | 1.00 | 34.27 |
| ATOM | 1540 | CB | ILE | 389 | 2.196 | 48.499 | 79.297 | 1.00 | 35.09 |
| ATOM | 1541 | CG2 | ILE | 389 | 1.467 | 49.72 | 78.935 | 1.00 | 36.03 |
| ATOM | 1542 | CG1 | ILE | 389 | 3.563 | 48.869 | 79.864 | 1.00 | 36.24 |
| ATOM | 1543 | CD1 | ILE | 389 | 3.507 | 49.506 | 81.264 | 1.00 | 33.80 |
| ATOM | 1544 | C | ILE | 389 | 0.018 | 47.434 | 80.058 | 1.00 | 37.44 |
| ATOM | 1545 | O | ILE | 389 | −0.390 | 47.106 | 78.946 | 1.00 | 38.29 |
| ATOM | 1546 | N | GLU | 390 | −0.765 | 47.653 | 81.088 | 1.00 | 40.80 |
| ATOM | 1548 | CA | GLU | 390 | −2.186 | 47.422 | 81.022 | 1.00 | 46.41 |
| ATOM | 1549 | CB | GLU | 390 | −2.712 | 47.356 | 82.459 | 1.00 | 48.77 |
| ATOM | 1550 | CG | GLU | 390 | −1.681 | 46.711 | 83.434 | 1.00 | 51.74 |
| ATOM | 1551 | CD | GLU | 390 | −1.810 | 45.193 | 83.740 | 1.00 | 55.50 |
| ATOM | 1552 | OE1 | GLU | 390 | −2.641 | 44.416 | 83.175 | 1.00 | 57.31 |
| ATOM | 1553 | OE2 | GLU | 390 | −0.984 | 44.799 | 84.598 | 1.00 | 56.71 |
| ATOM | 1554 | C | GLU | 390 | −2.896 | 48.444 | 80.068 | 1.00 | 48.64 |
| ATOM | 1555 | O | GLU | 390 | −3.560 | 48.015 | 79.119 | 1.00 | 50.05 |
| ATOM | 1556 | N | ASP | 391 | −2.589 | 49.746 | 80.236 | 1.00 | 49.94 |

TABLE 2-continued

Coordinates of Lck bound with AMP-PNP

| | Atom Type | Res | # | X | Y | Z | Occ | B |
|---|---|---|---|---|---|---|---|---|
| ATOM | 1558 | CA | ASP | 391 | -3.062 | 50.943 | 79.463 | 1.00 | 52.09 |
| ATOM | 1559 | CB | ASP | 391 | -3.704 | 51.868 | 80.517 | 1.00 | 53.43 |
| ATOM | 1560 | CG | ASP | 391 | -5.190 | 51.599 | 80.683 | 1.00 | 54.64 |
| ATOM | 1561 | OD1 | ASP | 391 | -5.816 | 51.546 | 79.605 | 1.00 | 57.00 |
| ATOM | 1562 | OD2 | ASP | 391 | -5.720 | 51.446 | 81.813 | 1.00 | 55.68 |
| ATOM | 1563 | C | ASP | 391 | -1.720 | 51.530 | 78.813 | 1.00 | 54.45 |
| ATOM | 1564 | O | ASP | 391 | -0.734 | 50.989 | 79.216 | 1.00 | 57.78 |
| ATOM | 1565 | N | ASN | 392 | -1.601 | 52.563 | 77.923 | 1.00 | 54.74 |
| ATOM | 1567 | CA | ASN | 392 | -0.222 | 53.004 | 77.344 | 1.00 | 54.25 |
| ATOM | 1568 | CB | ASN | 392 | -0.281 | 54.412 | 76.624 | 1.00 | 57.84 |
| ATOM | 1569 | CG | ASN | 392 | 0.774 | 54.671 | 75.390 | 1.00 | 61.35 |
| ATOM | 1570 | OD1 | ASN | 392 | 1.285 | 53.777 | 74.659 | 1.00 | 63.64 |
| ATOM | 1571 | ND2 | ASN | 392 | 0.926 | 55.982 | 75.103 | 1.00 | 64.17 |
| ATOM | 1574 | C | ASN | 392 | 0.909 | 53.201 | 78.360 | 1.00 | 51.44 |
| ATOM | 1575 | O | ASN | 392 | 2.071 | 53.027 | 78.005 | 1.00 | 50.36 |
| ATOM | 1576 | N | GLU | 393 | 0.598 | 53.413 | 79.630 | 1.00 | 48.28 |
| ATOM | 1578 | CA | GLU | 393 | 1.703 | 53.844 | 80.469 | 1.00 | 46.79 |
| ATOM | 1579 | CB | GLU | 393 | 1.505 | 55.343 | 80.475 | 1.00 | 46.89 |
| ATOM | 1580 | CG | GLU | 393 | 2.546 | 56.345 | 80.691 | 1.00 | 46.44 |
| ATOM | 1581 | CD | GLU | 393 | 1.801 | 57.659 | 80.529 | 1.00 | 46.39 |
| ATOM | 1582 | OE1 | GLU | 393 | 1.063 | 58.050 | 81.476 | 1.00 | 45.21 |
| ATOM | 1583 | OE2 | GLU | 393 | 1.773 | 58.175 | 79.384 | 1.00 | 45.38 |
| ATOM | 1584 | C | GLU | 393 | 1.852 | 53.352 | 81.891 | 1.00 | 46.03 |
| ATOM | 1585 | O | GLU | 393 | 0.867 | 53.073 | 82.583 | 1.00 | 47.03 |
| ATOM | 1586 | N | TYR | 394 | 3.106 | 53.298 | 82.336 | 1.00 | 43.40 |
| ATOM | 1588 | CA | TYR | 394 | 3.368 | 52.883 | 83.697 | 1.00 | 40.15 |
| ATOM | 1589 | CB | TYR | 394 | 4.177 | 51.595 | 83.765 | 1.00 | 38.62 |
| ATOM | 1590 | CG | TYR | 394 | 4.416 | 51.044 | 85.153 | 1.00 | 38.07 |
| ATOM | 1591 | CD1 | TYR | 394 | 5.245 | 51.714 | 86.025 | 1.00 | 39.62 |
| ATOM | 1592 | CE1 | TYR | 394 | 5.630 | 51.162 | 87.222 | 1.00 | 42.24 |
| ATOM | 1593 | CD2 | TYR | 394 | 3.946 | 49.783 | 85.532 | 1.00 | 40.01 |
| ATOM | 1594 | CE2 | TYR | 394 | 4.328 | 49.204 | 86.751 | 1.00 | 40.87 |
| ATOM | 1595 | CZ | TYR | 394 | 5.186 | 49.907 | 87.591 | 1.00 | 43.04 |
| ATOM | 1596 | OH | TYR | 394 | 5.669 | 49.391 | 88.778 | 1.00 | 46.90 |
| ATOM | 1598 | C | TYR | 394 | 4.027 | 54.037 | 84.428 | 1.00 | 40.06 |
| ATOM | 1599 | O | TYR | 394 | 5.016 | 54.637 | 83.968 | 1.00 | 40.48 |
| ATOM | 1600 | N | THR | 395 | 3.494 | 54.314 | 85.605 | 1.00 | 40.62 |
| ATOM | 1602 | CA | THR | 395 | 3.996 | 55.420 | 86.394 | 1.00 | 39.68 |
| ATOM | 1603 | CB | THR | 395 | 2.833 | 56.407 | 86.622 | 1.00 | 36.39 |
| ATOM | 1604 | OG1 | THR | 395 | 2.416 | 56.900 | 85.345 | 1.00 | 35.31 |
| ATOM | 1606 | CG2 | THR | 395 | 3.269 | 57.568 | 87.421 | 1.00 | 34.94 |
| ATOM | 1607 | C | THR | 395 | 4.793 | 55.021 | 87.646 | 1.00 | 40.23 |
| ATOM | 1608 | O | THR | 395 | 4.261 | 54.422 | 88.561 | 1.00 | 42.34 |
| ATOM | 1609 | N | ALA | 396 | 6.094 | 55.301 | 87.652 | 1.00 | 40.72 |
| ATOM | 1611 | CA | ALA | 396 | 6.936 | 54.917 | 88.793 | 1.00 | 42.94 |
| ATOM | 1612 | CB | ALA | 396 | 8.401 | 55.095 | 88.459 | 1.00 | 42.40 |
| ATOM | 1613 | C | ALA | 396 | 6.652 | 55.661 | 90.064 | 1.00 | 45.64 |
| ATOM | 1614 | O | ALA | 396 | 5.918 | 56.635 | 90.044 | 1.00 | 47.05 |
| ATOM | 1615 | N | ARG | 397 | 7.312 | 55.274 | 91.152 | 1.00 | 48.85 |
| ATOM | 1617 | CA | ARG | 397 | 7.118 | 55.986 | 92.409 | 1.00 | 52.23 |
| ATOM | 1618 | CB | ARG | 397 | 7.631 | 55.177 | 93.578 | 1.00 | 51.92 |
| ATOM | 1619 | CG | ARG | 397 | 7.441 | 55.909 | 94.893 | 1.00 | 56.10 |
| ATOM | 1620 | CD | ARG | 397 | 7.539 | 54.933 | 96.067 | 1.00 | 57.82 |
| ATOM | 1621 | NE | ARG | 397 | 7.418 | 55.586 | 97.366 | 1.00 | 56.39 |
| ATOM | 1623 | CZ | ARG | 397 | 6.985 | 54.972 | 98.459 | 1.00 | 55.20 |
| ATOM | 1624 | NH1 | ARG | 397 | 6.624 | 53.694 | 98.400 | 1.00 | 53.82 |
| ATOM | 1627 | NH2 | ARG | 397 | 6.934 | 55.634 | 99.602 | 1.00 | 55.03 |
| ATOM | 1630 | C | ARG | 397 | 7.816 | 57.358 | 92.363 | 1.00 | 54.99 |
| ATOM | 1631 | O | ARG | 397 | 8.851 | 57.505 | 91.714 | 1.00 | 55.96 |
| ATOM | 1632 | N | GLU | 398 | 7.239 | 58.380 | 92.988 | 1.00 | 56.91 |
| ATOM | 1634 | CA | GLU | 398 | 7.884 | 59.688 | 92.932 | 1.00 | 59.37 |
| ATOM | 1635 | CB | GLU | 398 | 7.106 | 60.765 | 93.703 | 1.00 | 62.54 |
| ATOM | 1636 | CG | GLU | 398 | 5.719 | 61.103 | 93.140 | 1.00 | 66.92 |
| ATOM | 1637 | CD | GLU | 398 | 4.758 | 61.532 | 91.681 | 1.00 | 70.31 |
| ATOM | 1638 | OE1 | GLU | 398 | 6.843 | 61.954 | 91.212 | 1.00 | 74.49 |
| ATOM | 1639 | OE2 | GLU | 398 | 4.703 | 61.414 | 91.022 | 1.00 | 71.70 |
| ATOM | 1640 | C | GLU | 398 | 9.298 | 59.578 | 93.469 | 1.00 | 59.04 |
| ATOM | 1641 | O | GLU | 398 | 10.211 | 60.249 | 92.988 | 1.00 | 58.64 |
| ATOM | 1642 | N | GLY | 399 | 9.482 | 58.692 | 94.444 | 1.00 | 57.92 |
| ATOM | 1644 | CA | GLY | 399 | 10.799 | 58.527 | 95.010 | 1.00 | 55.73 |
| ATOM | 1645 | C | GLY | 399 | 11.724 | 57.759 | 94.081 | 1.00 | 53.26 |
| ATOM | 1646 | O | GLY | 399 | 12.920 | 57.684 | 94.327 | 1.00 | 54.49 |
| ATOM | 1647 | N | ALA | 400 | 11.182 | 57.195 | 93.011 | 1.00 | 50.53 |
| ATOM | 1649 | CA | ALA | 400 | 12.004 | 56.401 | 92.092 | 1.00 | 49.36 |

TABLE 2-continued

Coordinates of Lck bound with AMP-PNP

| | | Atom Type | Res | # | X | Y | Z | Occ | B |
|---|---|---|---|---|---|---|---|---|---|
| ATOM | 1650 | CB | ALA | 400 | 11.126 | 55.624 | 91.107 | 1.00 | 47.55 |
| ATOM | 1651 | C | ALA | 400 | 12.988 | 57.254 | 91.331 | 1.00 | 48.46 |
| ATOM | 1652 | O | ALA | 400 | 12.627 | 48.312 | 90.838 | 1.00 | 51.06 |
| ATOM | 1653 | N | ALA | 401 | 14.170 | 56.724 | 91.100 | 1.00 | 46.01 |
| ATOM | 1655 | CA | ALA | 401 | 15.170 | 57.496 | 90.478 | 1.00 | 44.15 |
| ATOM | 1656 | CB | ALA | 401 | 16.096 | 57.908 | 91.591 | 1.00 | 45.07 |
| ATOM | 1657 | C | ALA | 401 | 15.864 | 56.589 | 89.359 | 1.00 | 41.57 |
| ATOM | 1658 | O | ALA | 401 | 16.039 | 44.375 | 89.578 | 1.00 | 40.99 |
| ATOM | 1659 | N | PHE | 402 | 16.052 | 57.085 | 88.130 | 1.00 | 38.21 |
| ATOM | 1661 | CA | PHE | 402 | 16.627 | 56.248 | 87.072 | 1.00 | 35.49 |
| ATOM | 1662 | CB | PHE | 402 | 15.606 | 55.988 | 85.941 | 1.00 | 35.98 |
| ATOM | 1663 | CG | PHE | 402 | 14.368 | 55.247 | 86.382 | 1.00 | 39.61 |
| ATOM | 1664 | CD1 | PHE | 402 | 14.299 | 53.843 | 86.361 | 1.00 | 40.06 |
| ATOM | 1665 | CD2 | PHE | 402 | 13.289 | 55.959 | 86.919 | .00 | 41.14 |
| ATOM | 1666 | CE1 | PHE | 402 | 13.161 | 53.164 | 86.893 | 1.00 | 40.16 |
| ATOM | 1667 | CE2 | PHE | 402 | 12.155 | 55.293 | 87.446 | 1.00 | 40.96 |
| ATOM | 1668 | CZ | PHE | 402 | 12.098 | 53.899 | 87.436 | 1.00 | 41.14 |
| ATOM | 1669 | C | PHE | 402 | 17.865 | 56.933 | 86.483 | 1.00 | 34.30 |
| ATOM | 1670 | O | PHE | 402 | 18.058 | 58.136 | 86.674 | 1.00 | 36.67 |
| ATOM | 1671 | N | PRO | 403 | 18.722 | 56.166 | 85.781 | 1.00 | 30.75 |
| ATOM | 1672 | CD | PRO | 403 | 18.577 | 54.718 | 85.543 | 1.00 | 30.65 |
| ATOM | 1673 | CA | PRO | 403 | 19.951 | 56.689 | 85.159 | 1.00 | 28.50 |
| ATOM | 1674 | CB | PRO | 403 | 20.524 | 55.465 | 84.409 | 1.00 | 29.37 |
| ATOM | 1675 | CG | PRO | 403 | 19.990 | 43.288 | 85.229 | 1.00 | 30.78 |
| ATOM | 1676 | C | PRO | 403 | 19.567 | 57.772 | 84.181 | 1.00 | 26.46 |
| ATOM | 1677 | O | PRO | 403 | 18.963 | 57.493 | 83.152 | 1.00 | 26.61 |
| ATOM | 1678 | N | ILE | 404 | 19.941 | 59.004 | 84.496 | 1.00 | 24.48 |
| ATOM | 1580 | CA | ILE | 404 | 19.627 | 60.141 | 83.673 | 1.00 | 20.10 |
| ATOM | 1681 | CB | ILE | 404 | 20.211 | 61.446 | 84.297 | 1.00 | 22.53 |
| ATOM | 1682 | CG2 | ILE | 404 | 20.006 | 62.648 | 83.363 | 1.00 | 19.44 |
| ATOM | 1683 | CG1 | ILE | 404 | 19.574 | 61.677 | 85.652 | 1.00 | 24.54 |
| ATOM | 1684 | CD1 | ILE | 404 | 18.040 | 61.803 | 85.603 | 1.00 | 27.14 |
| ATOM | 1685 | C | ILE | 404 | 20.051 | 60.036 | 82.228 | 1.00 | 18.42 |
| ATOM | 1686 | O | ILE | 404 | 19.273 | 60.342 | 81.342 | 1.00 | 19.08 |
| ATOM | 1687 | N | LYS | 405 | 21.274 | 59.613 | 81.968 | 1.00 | 19.47 |
| ATOM | 1689 | CA | LYS | 405 | 21.741 | 59.560 | 80.575 | 1.00 | 17.69 |
| ATOM | 1690 | CB | LYS | 405 | 23.244 | 59.319 | 80.543 | 1.00 | 19.78 |
| ATOM | 1691 | CG | LYS | 405 | 24.007 | 60.419 | 81.214 | 1.00 | 20.91 |
| ATOM | 1692 | CD | LYS | 405 | 25.504 | 60.285 | 81.004 | 1.00 | 25.68 |
| ATOM | 1693 | CE | LYS | 405 | 26.228 | 61.491 | 81.594 | 1.00 | 25.97 |
| ATOM | 1694 | NZ | LYS | 405 | 27.619 | 61.628 | 81.058 | 1.00 | 30.78 |
| ATOM | 1698 | C | LYS | 405 | 21.024 | 58.584 | 79.649 | 1.00 | 17.59 |
| ATOM | 1699 | O | LYS | 405 | 20.997 | 58.781 | 78.447 | 1.00 | 17.74 |
| ATOM | 1700 | N | TRP | 406 | 20.439 | 57.533 | 80.198 | 1.00 | 17.75 |
| ATOM | 1702 | CA | TRP | 406 | 19.742 | 56.538 | 79.383 | 1.00 | 18.37 |
| ATOM | 1703 | CB | TRP | 406 | 20.066 | 55.132 | 79.897 | 1.00 | 19.40 |
| ATOM | 1704 | CG | TRP | 406 | 21.359 | 54.653 | 79.472 | 1.00 | 18.94 |
| ATOM | 1705 | CD2 | TRP | 406 | 22.628 | 54.844 | 80.12 | 1.00 | 19.38 |
| ATOM | 1706 | CE2 | TRP | 406 | 23.589 | 54.168 | 79.342 | 1.00 | 18.92 |
| ATOM | 1707 | CE3 | TRP | 406 | 23.035 | 55.510 | 81.292 | 1.00 | 17.63 |
| ATOM | 1708 | CD1 | TRP | 406 | 21.603 | 53.907 | 78.360 | 1.00 | 18.56 |
| ATOM | 1709 | NE1 | TRP | 406 | 22.938 | 53.613 | 78.272 | 1.00 | 18.76 |
| ATOM | 1711 | CZ2 | TRP | 406 | 24.934 | 54.135 | 79.684 | 1.00 | 18.38 |
| ATOM | 1712 | CZ3 | TRP | 406 | 24.373 | 55.472 | 81.631 | 1.00 | 18.43 |
| ATOM | 1713 | CH2 | TRP | 406 | 25.313 | 54.790 | 80.827 | 1.00 | 20.51 |
| ATOM | 1714 | C | TRP | 406 | 18.221 | 56.667 | 79.414 | 1.00 | 20.12 |
| ATOM | 1715 | O | TRP | 406 | 17.529 | 56.117 | 78.571 | 1.00 | 19.54 |
| ATOM | 1716 | N | THR | 407 | 17.701 | 57.377 | 80.400 | 1.00 | 21.90 |
| ATOM | 1718 | CA | THR | 407 | 16.273 | 57.481 | 80.565 | 1.00 | 20.95 |
| ATOM | 1719 | CB | THR | 407 | 15.975 | 57.565 | 82.053 | 1.00 | 21.49 |
| ATOM | 1720 | OG1 | THR | 407 | 16.5472 | 56.449 | 82.731 | 1.00 | 21.33 |
| ATOM | 1722 | CG2 | THR | 407 | 14.463 | 57.568 | 82.320 | 1.00 | 20.08 |
| ATOM | 1723 | C | THR | 407 | 15.595 | 58.637 | 79.784 | 1.00 | 21.99 |
| ATOM | 1724 | O | THR | 407 | 16.066 | 59.766 | 79.777 | 1.00 | 21.47 |
| ATOM | 1725 | N | ALA | 408 | 14.453 | 58.355 | 79.160 | 1.00 | 21.85 |
| ATOM | 1727 | CA | ALA | 408 | 13.698 | 59.383 | 78.403 | 1.00 | 21.61 |
| ATOM | 1728 | CB | ALA | 408 | 12.470 | 58.761 | 77.725 | 1.00 | 22.58 |
| ATOM | 1729 | C | ALA | 408 | 13.260 | 60.533 | 79.311 | 1.00 | 21.12 |
| ATOM | 1730 | O | ALA | 408 | 12.942 | 60.343 | 80.479 | 1.00 | 22.30 |
| ATOM | 1731 | N | PRO | 409 | 13.197 | 51.739 | 78.768 | 1.00 | 22.37 |
| ATOM | 1732 | CD | PRO | 409 | 13.479 | 62.088 | 77.367 | 1.00 | 21.70 |
| ATOM | 1733 | CA | PRO | 409 | 12.799 | 62.939 | 79.540 | 1.00 | 22.65 |
| ATOM | 1734 | CB | PRO | 409 | 12.767 | 64.041 | 78.477 | 1.00 | 21.61 |
| ATOM | 1735 | CG | PRO | 409 | 13.763 | 63.578 | 77.460 | 1.00 | 21.10 |

TABLE 2-continued

Coordinates of Lck bound with AMP-PNP

| | Atom Type | Res | # | X | Y | Z | Occ | B |
|---|---|---|---|---|---|---|---|---|
| ATOM | 1736 | C | PRO | 409 | 11.448 | 62.800 | 80.264 | 1.00 | 23.34 |
| ATOM | 1737 | O | PRO | 409 | 11.357 | 63.092 | 81.452 | 1.00 | 23.23 |
| ATOM | 1738 | N | GLU | 410 | 10.435 | 62.271 | 79.586 | 1.00 | 24.26 |
| ATOM | 1740 | CA | GLU | 410 | 9.136 | 62.137 | 80.239 | 1.00 | 23.57 |
| ATOM | 1741 | CB | GLU | 410 | 8.043 | 61.687 | 79.274 | 1.00 | 23.95 |
| ATOM | 1742 | CG | GLU | 410 | 8.173 | 60.240 | 78.775 | 1.00 | 25.44 |
| ATOM | 1743 | CD | GLU | 410 | 9.123 | 60.042 | 77.597 | 1.00 | 27.31 |
| ATOM | 1744 | OE1 | GLU | 410 | 9.817 | 60.995 | 77.159 | 1.00 | 26.56 |
| ATOM | 1745 | OE2 | GLU | 410 | 9.158 | 58.915 | 77.064 | 1.00 | 27.58 |
| ATOM | 1746 | C | GLU | 410 | 9.210 | 61.207 | 81.415 | 1.00 | 24.83 |
| ATOM | 1747 | O | GLU | 410 | 8.489 | 61.424 | 82.394 | 1.00 | 28.35 |
| ATOM | 1748 | CA | ALA | 411 | 10.090 | 60.204 | 81.361 | 1.00 | 24.70 |
| ATOM | 1750 | CA | ALA | 411 | 10.232 | 59.291 | 82.489 | 1.00 | 24.06 |
| ATOM | 1751 | CB | ALA | 411 | 10.948 | 58.015 | 82.063 | 1.00 | 23.48 |
| ATOM | 1752 | C | ALA | 411 | 10.989 | 59.983 | 83.600 | 1.00 | 22.89 |
| ATOM | 1753 | O | ALA | 411 | 10.670 | 59.809 | 84.759 | 1.00 | 23.57 |
| ATOM | 1754 | N | ILE | 412 | 12.036 | 60.730 | 83.251 | 1.00 | 23.82 |
| ATOM | 1756 | CA | ILE | 412 | 12.805 | 61.463 | 84.279 | 1.00 | 24.62 |
| ATOM | 1757 | CB | ILE | 412 | 14.035 | 62.160 | 83.657 | 1.00 | 26.65 |
| ATOM | 1758 | CG2 | ILE | 412 | 14.670 | 63.166 | 84.650 | 1.00 | 24.30 |
| ATOM | 1759 | CG1 | ILE | 412 | 15.068 | 61.128 | 83.198 | 1.00 | 26.80 |
| ATOM | 1760 | CD1 | ILE | 412 | 16.199 | 61.747 | 82.363 | 1.00 | 29.02 |
| ATOM | 1761 | C | ILE | 412 | 11.929 | 62.559 | 84.948 | 1.00 | 23.45 |
| ATOM | 1762 | O | ILE | 412 | 11.891 | 62.693 | 86.161 | 1.00 | 21.71 |
| ATOM | 1763 | N | ASN | 413 | 11.191 | 63.292 | 84.129 | 1.00 | 23.22 |
| ATOM | 1765 | CA | ASN | 413 | 10.351 | 64.386 | 84.611 | 1.00 | 27.01 |
| ATOM | 1766 | CB | ASN | 413 | 10.090 | 65.380 | 83.455 | 1.00 | 25.92 |
| ATOM | 1767 | CG | ASN | 413 | 11.326 | 66.208 | 83.129 | 1.00 | 25.74 |
| ATOM | 1768 | OD1 | ASN | 413 | 12.269 | 66.197 | 83.880 | 1.00 | 27.88 |
| ATOM | 1769 | ND2 | ASN | 413 | 11.268 | 66.991 | 82.074 | 1.00 | 28.60 |
| ATOM | 1772 | C | ASN | 413 | 9.013 | 64.013 | 85.297 | 1.00 | 28.43 |
| ATOM | 1773 | O | ASN | 413 | 8.657 | 64.566 | 86.337 | 1.00 | 28.15 |
| ATOM | 1774 | N | TYR | 414 | 8.315 | 63.038 | 84.722 | 1.00 | 30.08 |
| ATOM | 1776 | CA | TYR | 414 | 7.026 | 62.645 | 85.253 | 1.00 | 30.85 |
| ATOM | 1777 | CB | TYR | 414 | 5.985 | 62.791 | 84.173 | 1.00 | 29.88 |
| ATOM | 1778 | CG | TYR | 414 | 6.134 | 64.027 | 83.348 | 1.00 | 32.03 |
| ATOM | 1779 | CD1 | TYR | 414 | 6.387 | 65.269 | 83.946 | 1.00 | 33.46 |
| ATOM | 1780 | CE1 | TYR | 414 | 6.507 | 66.424 | 83.184 | 1.00 | 33.49 |
| ATOM | 1781 | CD2 | TYR | 414 | 6.012 | 63.984 | 81.971 | 1.00 | 33.51 |
| ATOM | 1782 | CE2 | TYR | 414 | 6.130 | 65.131 | 81.202 | 1.00 | 34.46 |
| ATOM | 1783 | CZ | TYR | 414 | 6.376 | 66.344 | 81.814 | 1.00 | 35.28 |
| ATOM | 1784 | OH | TYR | 414 | 6.487 | 67.473 | 81.042 | 1.00 | 37.44 |
| ATOM | 1786 | C | TYR | 414 | 6.946 | 61.239 | 85.810 | 1.00 | 30.61 |
| ATOM | 1787 | O | TYR | 414 | 5.931 | 60.884 | 86.397 | 1.00 | 32.49 |
| ATOM | 1788 | N | GLY | 415 | 8.002 | 60.450 | 85.633 | 1.00 | 29.99 |
| ATOM | 1790 | CA | GLY | 415 | 7.966 | 59.086 | 86.132 | 1.00 | 28.82 |
| ATOM | 1791 | C | GLY | 415 | 7.089 | 58.242 | 85.206 | 1.00 | 28.52 |
| ATOM | 1792 | O | GLY | 415 | 6.753 | 57.092 | 85.481 | 1.00 | 27.98 |
| ATOM | 1793 | N | THR | 416 | 6.798 | 58.817 | 84.057 | 1.00 | 27.94 |
| ATOM | 1795 | CA | THR | 416 | 5.954 | 58.204 | 83.076 | 1.00 | 29.92 |
| ATOM | 1796 | CB | THR | 416 | 5.011 | 59.322 | 82.598 | 1.00 | 32.60 |
| ATOM | 1797 | OG1 | THR | 416 | 3.682 | 58.995 | 83.011 | 1.00 | 37.83 |
| ATOM | 1799 | CG2 | THR | 416 | 5.107 | 59.645 | 81.141 | 1.00 | 34.29 |
| ATOM | 1800 | C | THR | 416 | 6.735 | 57.382 | 81.997 | 1.00 | 28.19 |
| ATOM | 1801 | O | THR | 416 | 7.563 | 57.923 | 81.263 | 1.00 | 28.30 |
| ATOM | 1802 | N | PHE | 417 | 6.534 | 56.058 | 81.996 | 1.00 | 25.95 |
| ATOM | 1804 | CA | PHE | 417 | 7.252 | 55.157 | 81.088 | 1.00 | 22.72 |
| ATOM | 1805 | CB | PHE | 417 | 7.960 | 54.053 | 81.929 | 1.00 | 22.06 |
| ATOM | 1806 | CG | PHE | 417 | 9.240 | 54.463 | 82.623 | 1.00 | 19.89 |
| ATOM | 1807 | CD1 | PHE | 417 | 10.423 | 54.495 | 81.896 | 1.00 | 20.48 |
| ATOM | 1808 | CD2 | PHE | 417 | 9.318 | 54.638 | 84.014 | 1.00 | 19.95 |
| ATOM | 1809 | CE1 | PHE | 417 | 11.633 | 54.672 | 82.495 | 1.00 | 18.79 |
| ATOM | 1810 | CE2 | PHE | 417 | 10.607 | 54.820 | 84.620 | 1.00 | 20.32 |
| ATOM | 1811 | CZ | PHE | 417 | 11.732 | 43.828 | 83.830 | 1.00 | 20.05 |
| ATOM | 1812 | C | PHE | 417 | 6.343 | 54.447 | 80.051 | 1.00 | 21.56 |
| ATOM | 1813 | O | PHE | 417 | 5.266 | 53.981 | 80.389 | 1.00 | 20.78 |
| ATOM | 1814 | N | THR | 418 | 6.747 | 54.431 | 78.783 | 1.00 | 19.69 |
| ATOM | 1816 | CA | THR | 418 | 6.007 | 53.693 | 77.764 | 1.00 | 20.67 |
| ATOM | 1817 | CB | THR | 418 | 5.148 | 54.590 | 76.854 | 1.00 | 20.26 |
| ATOM | 1818 | OG1 | THR | 418 | 6.015 | 55.312 | 76.008 | 1.00 | 25.33 |
| ATOM | 1820 | CG2 | THR | 418 | 4.271 | 55.562 | 77.684 | 1.00 | 21.05 |
| ATOM | 1821 | C | THR | 418 | 7.056 | 52.981 | 76.873 | 1.00 | 20.77 |
| ATOM | 1822 | O | THR | 418 | 8.262 | 53.163 | 77.050 | 1.00 | 20.46 |
| ATOM | 1823 | N | ILE | 419 | 6.628 | 52.204 | 75.894 | 1.00 | 19.91 |

TABLE 2-continued

Coordinates of Lck bound with AMP-PNP

| | Atom Type | Res | # | X | Y | Z | Occ | B |
|---|---|---|---|---|---|---|---|---|
| ATOM | 1825 | CA | ILE | 419 | 7.596 | 51.546 | 75.059 | 1.00 | 19.28 |
| ATOM | 1826 | CB | ILE | 419 | 6.906 | 50.615 | 74.033 | 1.00 | 19.61 |
| ATOM | 1827 | CG2 | ILE | 419 | 6.084 | 51.447 | 73.012 | 1.00 | 17.68 |
| ATOM | 1828 | CG1 | ILE | 419 | 7.932 | 49.725 | 73.275 | 1.00 | 16.37 |
| ATOM | 1829 | CD1 | ILE | 419 | 8.633 | 48.748 | 74.143 | 1.00 | 11.47 |
| ATOM | 1830 | C | ILE | 419 | 8.439 | 52.641 | 74.341 | 1.00 | 20.48 |
| ATOM | 1831 | O | ILE | 419 | 9.552 | 52.369 | 73.871 | 1.00 | 19.11 |
| ATOM | 1832 | N | LYS | 420 | 7.866 | 53.847 | 74.198 | 1.00 | 19.01 |
| ATOM | 1834 | CA | LYS | 420 | 8.554 | 54.973 | 73.550 | 1.00 | 16.10 |
| ATOM | 1835 | CB | LYS | 420 | 7.588 | 56.126 | 73.250 | 1.00 | 15.15 |
| ATOM | 1836 | CG | LYS | 420 | 6.484 | 55.787 | 72.239 | 1.00 | 15.77 |
| ATOM | 1837 | CD | LYS | 420 | 7.047 | 55.221 | 70.937 | 1.00 | 14.36 |
| ATOM | 1838 | CE | LYS | 420 | 5.948 | 55.081 | 69.907 | 1.00 | 7.71 |
| ATOM | 1839 | NZ | LYS | 420 | 6.454 | 54.493 | 68.641 | 1.00 | 12.60 |
| ATOM | 1843 | C | LYS | 420 | 9.713 | 55.474 | 74.404 | 1.00 | 14.10 |
| ATOM | 1844 | O | LYS | 420 | 10.612 | 56.062 | 73.882 | 1.00 | 15.75 |
| ATOM | 1845 | N | SER | 421 | 9.634 | 55.280 | 75.719 | 0.84 | 11.80 |
| ATOM | 1847 | CA | SER | 421 | 10.705 | 55.605 | 76.605 | 0.84 | 11.53 |
| ATOM | 1848 | CB | SER | 421 | 10.288 | 55.456 | 78.074 | 0.84 | 10.22 |
| ATOM | 1849 | OG | SER | 421 | 9.162 | 56.223 | 78.370 | 0.84 | 13.84 |
| ATOM | 1851 | C | SER | 421 | 11.856 | 54.618 | 76.329 | 0.84 | 13.00 |
| ATOM | 1852 | O | SER | 421 | 13.032 | 54.979 | 76.449 | 0.84 | 11.53 |
| ATOM | 1853 | N | ASP | 422 | 11.528 | 53.348 | 76.074 | 1.00 | 15.55 |
| ATOM | 1855 | CA | ASP | 422 | 12.561 | 52.353 | 75.775 | 1.00 | 14.65 |
| ATOM | 1856 | CB | ASP | 422 | 11.968 | 50.948 | 75.674 | 1.00 | 15.84 |
| ATOM | 1857 | CG | ASP | 422 | 11.668 | 50.329 | 77.007 | 1.00 | 17.56 |
| ATOM | 1858 | OD1 | ASP | 422 | 12.194 | 50.768 | 78.064 | 1.00 | 17.02 |
| ATOM | 1859 | OD2 | ASP | 422 | 10.879 | 49.371 | 76.982 | 1.00 | 18.39 |
| ATOM | 1860 | C | ASP | 422 | 13.211 | 52.708 | 74.447 | 1.00 | 15.67 |
| ATOM | 1861 | O | ASP | 422 | 14.403 | 52.482 | 74.256 | 1.00 | 18.05 |
| ATOM | 1862 | N | VAL | 423 | 12.419 | 53.237 | 73.518 | 1.00 | 14.52 |
| ATOM | 1864 | CA | VAL | 423 | 12.956 | 53.641 | 72.215 | 1.00 | 14.96 |
| ATOM | 1865 | CB | VAL | 423 | 11.852 | 54.135 | 71.290 | 1.00 | 13.71 |
| ATOM | 1866 | CG1 | VAL | 423 | 12.434 | 54.804 | 70.050 | 1.00 | 11.97 |
| ATOM | 1867 | CG2 | VAL | 423 | 10.995 | 52.940 | 70.853 | 1.00 | 11.91 |
| ATOM | 1868 | C | VAL | 423 | 14.042 | 54.737 | 72.400 | 1.00 | 15.31 |
| ATOM | 1869 | O | VAL | 423 | 15.084 | 54.665 | 71.765 | 1.00 | 16.48 |
| ATOM | 1870 | N | TRP | 424 | 13.786 | 55.679 | 73.309 | 1.00 | 14.64 |
| ATOM | 1872 | CA | TRP | 424 | 14.778 | 56.726 | 73.584 | 1.00 | 16.07 |
| ATOM | 1873 | CB | TRP | 424 | 14.29 | 57.698 | 74.643 | 1.00 | 16.52 |
| ATOM | 1874 | CG | TRP | 424 | 15.185 | 58.718 | 75.027 | 1.00 | 18.45 |
| ATOM | 1875 | CD2 | TRP | 424 | 15.141 | 60.102 | 74.685 | 1.00 | 18.79 |
| ATOM | 1876 | CE2 | TRP | 424 | 16.277 | 60.700 | 75.259 | 1.00 | 19.83 |
| ATOM | 1877 | CE3 | TRP | 424 | 14.239 | 60.887 | 73.958 | 1.00 | 20.12 |
| ATOM | 1878 | CD1 | TRP | 424 | 16.312 | 58.548 | 75.780 | 1.00 | 18.97 |
| ATOM | 1879 | NE1 | TRP | 424 | 16.961 | 59.724 | 75.931 | 1.00 | 16.31 |
| ATOM | 1881 | CZ2 | TRP | 424 | 16.561 | 62.081 | 75.122 | 1.00 | 20.80 |
| ATOM | 1882 | CZ3 | TRP | 424 | 14.506 | 62.268 | 73.824 | 1.00 | 19.39 |
| ATOM | 1883 | CH2 | TRP | 424 | 15.655 | 62.840 | 74.397 | 1.00 | 19.97 |
| ATOM | 1884 | C | TRP | 424 | 16.060 | 56.041 | 74.127 | 1.00 | 12.71 |
| ATOM | 1885 | O | TRP | 424 | 17.176 | 56.337 | 73.641 | 1.00 | 11.08 |
| ATOM | 1886 | N | SER | 425 | 15.884 | 55.140 | 75.103 | 1.00 | 8.75 |
| ATOM | 1888 | CA | SER | 425 | 17.020 | 54.421 | 75.678 | 0.74 | 10.92 |
| ATOM | 1889 | CB | SER | 425 | 16.555 | 53.443 | 76.749 | 0.74 | 12.58 |
| ATOM | 1890 | OG | SER | 425 | 15.843 | 54.097 | 77.763 | 0.74 | 14.72 |
| ATOM | 1892 | C | SER | 425 | 17.785 | 53.651 | 74.607 | 0.74 | 10.97 |
| ATOM | 1893 | O | SER | 425 | 19.010 | 53.594 | 74.636 | 0.74 | 12.46 |
| ATOM | 1894 | N | PHE | 426 | 17.057 | 53.069 | 73.661 | 1.00 | 11.96 |
| ATOM | 1896 | CA | PHE | 426 | 17.696 | 52.350 | 72.579 | 1.00 | 13.86 |
| ATOM | 1897 | CB | PHE | 426 | 16.674 | 51.731 | 71.656 | 1.00 | 11.32 |
| ATOM | 1898 | CG | PHE | 426 | 17.268 | 50.930 | 70.536 | 1.00 | 12.43 |
| ATOM | 1899 | CD1 | PHE | 426 | 17.850 | 49.676 | 70.798 | 1.00 | 11.39 |
| ATOM | 1900 | CD2 | PHE | 426 | 17.279 | 51.424 | 69.249 | 1.00 | 11.59 |
| ATOM | 1901 | CE1 | PHE | 426 | 18.419 | 48.961 | 69.779 | 1.00 | 10.37 |
| ATOM | 1902 | CE2 | PHE | 426 | 17.866 | 50.689 | 68.215 | 1.00 | 11.36 |
| ATOM | 1903 | CZ | PHE | 426 | 18.430 | 49.456 | 68.498 | 1.00 | 9.95 |
| ATOM | 1904 | C | PHE | 426 | 18.619 | 53.298 | 71.807 | 1.00 | 14.91 |
| ATOM | 1905 | O | PHE | 426 | 19.710 | 52.881 | 71.379 | 1.00 | 16.79 |
| ATOM | 1906 | N | GLY | 427 | 18.175 | 54.530 | 71.574 | 1.00 | 15.14 |
| ATOM | 1908 | CA | GLY | 427 | 19.005 | 55.494 | 70.858 | 1.00 | 16.07 |
| ATOM | 1909 | C | GLY | 427 | 20.333 | 55.675 | 71.592 | 1.00 | 15.29 |
| ATOM | 1910 | O | GLY | 427 | 21.367 | 55.736 | 70.961 | 1.00 | 15.59 |
| ATOM | 1911 | N | ILE | 428 | 20.274 | 55.821 | 72.915 | 1.00 | 13.04 |
| ATOM | 1913 | CA | ILE | 428 | 21.435 | 55.958 | 73.739 | 1.00 | 13.65 |

TABLE 2-continued

Coordinates of Lck bound with AMP-PNP

| | Atom Type | Res | # | X | Y | Z | Occ | B |
|---|---|---|---|---|---|---|---|---|
| ATOM | 1914 | CB | ILE | 428 | 21.042 | 56.193 | 75.213 | 1.00 | 15.69 |
| ATOM | 1915 | CG2 | ILE | 428 | 22.306 | 56.236 | 76.077 | 1.00 | 14.46 |
| ATOM | 1916 | CG1 | ILE | 428 | 20.175 | 57.467 | 75.342 | 1.00 | 17.63 |
| ATOM | 1917 | CD1 | ILE | 428 | 20.855 | 58.757 | 74.831 | 1.00 | 15.45 |
| ATOM | 1918 | C | ILE | 428 | 22.304 | 54.666 | 73.630 | 1.00 | 16.99 |
| ATOM | 1919 | O | ILE | 428 | 23.523 | 53.728 | 73.492 | 1.00 | 14.96 |
| ATOM | 1920 | N | LEU | 429 | 21.654 | 53.513 | 73.675 | 1.00 | 18.20 |
| ATOM | 1922 | CA | LEU | 429 | 22.349 | 52.229 | 73.557 | 1.00 | 18.84 |
| ATOM | 1923 | CB | LEU | 429 | 21.344 | 51.066 | 73.695 | 1.00 | 19.87 |
| ATOM | 1924 | CG | LEU | 429 | 21.890 | 49.653 | 73.876 | 1.00 | 20.75 |
| ATOM | 1925 | CD1 | LEU | 429 | 20.791 | 48.727 | 74.436 | 1.00 | 18.75 |
| ATOM | 1926 | CD2 | LEU | 429 | 22.409 | 49.128 | 72.549 | 1.00 | 21.10 |
| ATOM | 1927 | C | LEU | 429 | 23.113 | 52.182 | 72.238 | 1.00 | 17.14 |
| ATOM | 1928 | O | LEU | 429 | 24.239 | 51.706 | 72.197 | 1.00 | 17.44 |
| ATOM | 1929 | N | LEU | 430 | 22.525 | 52.706 | 71.164 | 1.00 | 15.39 |
| ATOM | 1931 | CA | LEU | 430 | 23.241 | 52.725 | 69.908 | 1.00 | 15.10 |
| ATOM | 1932 | CB | LEU | 430 | 22.412 | 53.360 | 68.800 | 1.00 | 15.61 |
| ATOM | 1933 | CG | LEU | 430 | 21.155 | 52.641 | 68.351 | 1.00 | 18.59 |
| ATOM | 1934 | CD1 | LEU | 430 | 20.470 | 53.464 | 67.278 | 1.00 | 14.20 |
| ATOM | 1935 | CD2 | LEU | 430 | 21.518 | 51.242 | 67.828 | 1.00 | 16.64 |
| ATOM | 1936 | C | LEU | 430 | 24.587 | 53.492 | 70.017 | 1.00 | 16.62 |
| ATOM | 1937 | O | LEU | 430 | 25.539 | 53.148 | 69.330 | 1.00 | 15.61 |
| ATOM | 1938 | N | THR | 431 | 24.644 | 54.537 | 70.847 | 1.00 | 19.39 |
| ATOM | 1940 | CA | THR | 431 | 25.901 | 55.294 | 71.008 | 1.00 | 19.11 |
| ATOM | 1941 | CB | THR | 431 | 25.742 | 56.667 | 71.758 | 1.00 | 15.34 |
| ATOM | 1942 | OG1 | THR | 431 | 25.465 | 56.469 | 73.143 | 1.00 | 12.80 |
| ATOM | 1944 | CG2 | THR | 431 | 24.640 | 57.456 | 71.164 | 1.00 | 13.08 |
| ATOM | 1945 | C | THR | 431 | 26.909 | 54.411 | 71.733 | 1.00 | 19.79 |
| atom | 1946 | o | thr | 431 | 28.105 | 54.447 | 71.414 | 1.00 | 20.57 |
| ATOM | 1947 | N | GLU | 432 | 26.444 | 53.600 | 72.693 | 1.00 | 19.43 |
| ATOM | 1949 | CA | GLU | 432 | 27.361 | 52.697 | 73.389 | 1.00 | 18.07 |
| ATOM | 1950 | CB | GLU | 432 | 26.665 | 51.930 | 74.493 | 1.00 | 19.17 |
| ATOM | 1951 | CG | GLU | 432 | 26.127 | 52.805 | 75.603 | 1.00 | 17.14 |
| ATOM | 1952 | CD | GLU | 432 | 25.461 | 52.018 | 76.673 | 1.00 | 17.70 |
| ATOM | 1953 | OE1 | GLU | 432 | 24.287 | 51.671 | 76.452 | 1.00 | 15.03 |
| ATOM | 1954 | OE2 | GLU | 432 | 26.089 | 51.738 | 77.711 | 1.00 | 21.38 |
| ATOM | 1955 | C | GLU | 432 | 27.935 | 51.673 | 72.387 | 1.00 | 20.42 |
| ATOM | 1956 | O | GLU | 432 | 29.117 | 51.311 | 72.447 | 1.00 | 21.99 |
| ATOM | 1957 | N | ILE | 433 | 27.124 | 51.244 | 71.442 | 1.00 | 17.57 |
| ATOM | 1959 | CA | ILE | 433 | 27.610 | 50.277 | 70.481 | 1.00 | 17.15 |
| ATOM | 1960 | CB | ILE | 433 | 26.456 | 49.748 | 69.615 | 1.00 | 13.48 |
| ATOM | 1961 | CG2 | ILE | 433 | 26.969 | 49.056 | 68.369 | 1.00 | 14.99 |
| ATOM | 1962 | CG1 | ILE | 433 | 25.569 | 48.827 | 70.453 | 1.00 | 14.70 |
| ATOM | 1963 | CD1 | ILE | 433 | 24.356 | 48.293 | 69.661 | 1.00 | 15.32 |
| ATOM | 1964 | C | ILE | 433 | 28.712 | 50.851 | 69.583 | 1.00 | 19.95 |
| ATOM | 1965 | O | ILE | 433 | 29.805 | 50.280 | 69.460 | 1.00 | 21.11 |
| ATOM | 1966 | N | VAL | 434 | 28.420 | 51.988 | 68.953 | 1.00 | 20.59 |
| ATOM | 1968 | CA | VAL | 434 | 29.353 | 52.602 | 68.038 | 1.00 | 19.04 |
| ATOM | 1969 | CB | VAL | 434 | 28.610 | 53.644 | 67.140 | 1.00 | 19.75 |
| ATOM | 1970 | CG1 | VAL | 434 | 28.609 | 55.040 | 67.759 | 1.00 | 16.22 |
| ATOM | 1971 | CG2 | VAL | 434 | 29.164 | 53.625 | 65.724 | 1.00 | 22.03 |
| ATOM | 1972 | C | VAL | 434 | 30.650 | 53.137 | 68.721 | 1.00 | 18.85 |
| ATOM | 1973 | O | VAL | 434 | 31.668 | 53.256 | 68.078 | 1.00 | 21.33 |
| ATOM | 1974 | N | THR | 435 | 30.626 | 53.364 | 70.026 | 1.00 | 18.23 |
| ATOM | 1976 | CA | THR | 435 | 31.824 | 53.837 | 70.716 | 1.00 | 18.93 |
| ATOM | 1977 | CB | THR | 435 | 31.495 | 54.993 | 71.674 | 1.00 | 16.49 |
| ATOM | 1978 | OG1 | THR | 435 | 30.641 | 54.492 | 72.693 | 1.00 | 16.60 |
| ATOM | 1980 | CG2 | THR | 435 | 30.795 | 56.146 | 70.909 | 1.00 | 12.43 |
| ATOM | 1981 | C | THR | 435 | 32.485 | 52.714 | 71.546 | 1.00 | 21.45 |
| ATOM | 1982 | O | THR | 435 | 33.347 | 52.938 | 72.400 | 1.00 | 20.04 |
| ATOM | 1983 | N | HIS | 436 | 32.077 | 51.460 | 71.293 | 1.00 | 20.62 |
| ATOM | 1985 | CA | HIS | 436 | 32.610 | 50.333 | 72.044 | 1.00 | 19.62 |
| ATOM | 1986 | CB | HIS | 436 | 34.038 | 50.024 | 71.638 | 1.00 | 23.29 |
| ATOM | 1987 | CG | HIS | 436 | 34.155 | 49.533 | 70.236 | 1.00 | 25.16 |
| ATOM | 1988 | CD2 | HIS | 436 | 34.147 | 50.195 | 69.060 | 1.00 | 26.06 |
| ATOM | 1989 | ND1 | HIS | 436 | 34.209 | 48.184 | 69.919 | 1.00 | 26.86 |
| ATOM | 1991 | CE1 | HIS | 436 | 34.212 | 48.047 | 68.596 | 1.00 | 24.56 |
| ATOM | 1992 | NE2 | HIS | 436 | 34.174 | 49.251 | 68.056 | 1.00 | 26.47 |
| ATOM | 1994 | C | HIS | 436 | 32.515 | 50.473 | 73.540 | 1.00 | 18.57 |
| ATOM | 1995 | O | HIS | 436 | 33.474 | 50.250 | 74.248 | 1.00 | 19.06 |
| ATOM | 1996 | N | GLY | 437 | 31.342 | 50.884 | 74.001 | 1.00 | 19.54 |
| ATOM | 1998 | CA | GLY | 437 | 31.109 | 50.994 | 75.427 | 1.00 | 18.07 |
| ATOM | 1999 | C | GLY | 437 | 31.368 | 52.280 | 76.155 | 1.00 | 19.71 |
| ATOM | 2000 | O | GLY | 437 | 31.265 | 52.264 | 77.382 | 1.00 | 23.18 |

TABLE 2-continued

Coordinates of Lck bound with AMP-PNP

| | Atom Type | Res | # | X | Y | Z | Occ | B |
|---|---|---|---|---|---|---|---|---|
| ATOM | 2001 | N | ARG | 438 | 31.625 | 53.379 | 75.451 | 0.58 | 17.74 |
| ATOM | 2003 | CA | ARG | 438 | 31.863 | 54.659 | 76.118 | 0.48 | 16.96 |
| ATOM | 2004 | CB | ARG | 438 | 32.322 | 55.699 | 75.072 | 0.58 | 18.69 |
| ATOM | 2005 | CG | ARG | 438 | 32.916 | 56.962 | 75.643 | 0.58 | 24.05 |
| ATOM | 2006 | CD | ARG | 438 | 33.318 | 57.941 | 74.525 | 0.58 | 24.65 |
| ATOM | 2007 | NE | ARG | 438 | 34.286 | 58.933 | 74.994 | 0.58 | 30.19 |
| ATOM | 2009 | CZ | ARG | 438 | 34.556 | 60.070 | 74.353 | 0.58 | 31.90 |
| ATOM | 2010 | NH1 | ARG | 438 | 33.936 | 60.369 | 73.228 | 0.58 | 34.48 |
| ATOM | 2013 | NH2 | ARG | 438 | 35.437 | 60.923 | 74.844 | 0.58 | 34.48 |
| ATOM | 2016 | C | ARG | 438 | 30.591 | 55.152 | 76.810 | 0.58 | 15.26 |
| ATOM | 2017 | O | ARG | 438 | 29.497 | 54.837 | 76.393 | 0.58 | 13.56 |
| ATOM | 2018 | N | ILE | 439 | 30.735 | 55.878 | 77.901 | 1.00 | 16.65 |
| ATOM | 2020 | CA | ILE | 439 | 29.608 | 56.467 | 78.618 | 1.00 | 17.06 |
| ATOM | 2021 | CB | ILE | 439 | 30.086 | 57.074 | 79.945 | 1.00 | 20.85 |
| ATOM | 2022 | CG2 | ILE | 439 | 28.983 | 57.937 | 80.589 | 1.00 | 21.06 |
| ATOM | 2023 | CG1 | ILE | 439 | 30.501 | 55.933 | 80.883 | 1.00 | 21.92 |
| ATOM | 2024 | CD1 | ILE | 439 | 31.070 | 56.392 | 82.180 | 1.00 | 22.55 |
| ATOM | 2025 | C | ILE | 439 | 29.001 | 57.572 | 77.748 | 1.00 | 15.41 |
| ATOM | 2026 | O | ILE | 439 | 29.752 | 58.391 | 77.165 | 1.00 | 16.20 |
| ATOM | 2027 | N | PRO | 440 | 27.665 | 57.580 | 77.594 | 0.43 | 10.45 |
| ATOM | 2028 | CD | PRO | 440 | 26.703 | 56.670 | 78.229 | 0.43 | 5.92 |
| ATOM | 2029 | CA | PRO | 440 | 26.983 | 58.587 | 76.776 | 0.43 | 9.30 |
| ATOM | 2030 | CB | PRO | 440 | 25.516 | 58.151 | 76.850 | 0.43 | 7.88 |
| ATOM | 2031 | CG | PRO | 440 | 25.433 | 57.460 | 78.165 | 0.43 | 7.57 |
| ATOM | 2032 | C | PRO | 440 | 27.190 | 60.024 | 77.272 | 0.43 | 8.71 |
| ATOM | 2033 | O | PRO | 440 | 27.501 | 60.252 | 78.432 | 0.43 | 6.28 |
| ATOM | 2034 | N | TYR | 441 | 27.103 | 60.972 | 76.359 | 1.00 | 11.99 |
| ATOM | 2036 | CA | TYR | 441 | 27.259 | 62.401 | 76.693 | 1.00 | 16.68 |
| ATOM | 2037 | CB | TYR | 441 | 26.179 | 62.876 | 77.658 | 1.00 | 14.19 |
| ATOM | 2038 | CG | TYR | 441 | 24.789 | 62.722 | 77.105 | 1.00 | 16.13 |
| ATOM | 2039 | CD1 | TYR | 441 | 24.265 | 63.645 | 76.185 | 1.00 | 13.76 |
| ATOM | 2040 | CE1 | TYR | 441 | 22.966 | 63.522 | 75.713 | 1.00 | 14.57 |
| ATOM | 2041 | CD2 | TYR | 441 | 23.973 | 61.666 | 77.526 | 1.00 | 15.68 |
| ATOM | 2042 | CE2 | TYR | 441 | 22.671 | 61.524 | 77.057 | 1.00 | 14.69 |
| ATOM | 2043 | CZ | TYR | 441 | 22.168 | 62.465 | 76.146 | 1.00 | 16.03 |
| ATOM | 2044 | OH | TYR | 441 | 20.870 | 62.338 | 75.699 | 1.00 | 16.22 |
| ATOM | 2046 | C | TYR | 441 | 28.635 | 62.642 | 77.299 | 1.00 | 19.83 |
| ATOM | 2047 | O | TYR | 441 | 28.761 | 63.055 | 78.433 | 1.00 | 22.48 |
| ATOM | 2048 | N | PRO | 442 | 29.683 | 62.308 | 76.550 | 1.00 | 21.96 |
| ATOM | 2049 | CD | PRO | 442 | 29.621 | 61.815 | 75.149 | 1.00 | 23.72 |
| ATOM | 2050 | CA | PRO | 442 | 31.058 | 62.478 | 76.991 | 1.00 | 24.18 |
| ATOM | 2051 | CB | PRO | 442 | 31.849 | 62.276 | 75.687 | 1.00 | 23.93 |
| ATOM | 2052 | CG | PRO | 442 | 30.987 | 61.262 | 74.932 | 1.00 | 23.15 |
| ATOM | 2053 | C | PRO | 442 | 31.353 | 63.888 | 77.593 | 1.00 | 23.56 |
| ATOM | 2054 | O | PRO | 442 | 30.954 | 64.906 | 77.047 | 1.00 | 22.74 |
| ATOM | 2055 | N | GLY | 443 | 31.984 | 63.889 | 78.751 | 1.00 | 23.98 |
| ATOM | 2057 | CA | GLY | 443 | 32.365 | 65.116 | 79.423 | 1.00 | 25.02 |
| ATOM | 2058 | C | GLY | 443 | 31.223 | 65.938 | 80.001 | 1.00 | 25.31 |
| ATOM | 2059 | O | GLY | 443 | 31.427 | 67.108 | 80.330 | 1.00 | 27.52 |
| ATOM | 2060 | N | MET | 444 | 30.040 | 65.347 | 80.141 | 1.00 | 22.78 |
| ATOM | 2062 | CA | MET | 444 | 28.904 | 66.081 | 80.676 | 1.00 | 19.38 |
| ATOM | 2063 | CB | MET | 444 | 27.804 | 66.213 | 79.642 | 1.00 | 17.92 |
| ATOM | 2064 | CG | MET | 444 | 28.205 | 66.965 | 78.383 | 1.00 | 15.75 |
| ATOM | 2065 | SD | MET | 444 | 27.016 | 66.876 | 77.050 | 1.00 | 20.93 |
| ATOM | 2066 | CE | MET | 444 | 25.610 | 67.571 | 77.794 | 1.00 | 15.12 |
| ATOM | 2067 | C | MET | 444 | 28.330 | 65.475 | 81.935 | 1.00 | 20.07 |
| ATOM | 2068 | O | MET | 444 | 28.210 | 64.248 | 82.042 | 1.00 | 22.27 |
| ATOM | 2069 | N | THR | 445 | 27.978 | 66.348 | 82.880 | 1.00 | 19.84 |
| ATOM | 2071 | CA | THR | 445 | 27.372 | 65.932 | 84.106 | 1.00 | 19.22 |
| ATOM | 2072 | CB | THR | 445 | 27.576 | 66.964 | 85.238 | 1.00 | 23.06 |
| ATOM | 2073 | OG1 | THR | 445 | 26.830 | 68.164 | 84.943 | 1.00 | 23.49 |
| ATOM | 2075 | CG2 | THR | 445 | 29.102 | 67.271 | 85.392 | 1.00 | 24.46 |
| ATOM | 2076 | C | THR | 445 | 25.881 | 65.741 | 83.788 | 1.00 | 18.15 |
| ATOM | 2077 | O | THR | 445 | 25.388 | 66.088 | 82.718 | 1.00 | 17.17 |
| ATOM | 2078 | N | ASN | 446 | 25.163 | 65.120 | 84.684 | 1.00 | 18.92 |
| ATOM | 2080 | CA | ASN | 446 | 23.757 | 64.962 | 84.384 | 1.00 | 22.14 |
| ATOM | 2081 | CB | ASN | 446 | 23.118 | 64.029 | 85.368 | 1.00 | 22.94 |
| ATOM | 2082 | CG | ASN | 446 | 23.520 | 62.605 | 85.162 | 1.00 | 23.33 |
| ATOM | 2083 | OD1 | ASN | 446 | 23.620 | 62.087 | 84.063 | 1.00 | 27.45 |
| ATOM | 2084 | ND2 | ASN | 446 | 23.650 | 61.925 | 86.254 | 1.00 | 20.08 |
| ATOM | 2087 | C | ASN | 446 | 22.998 | 66.279 | 84.316 | 1.00 | 21.36 |
| ATOM | 2088 | O | ASN | 446 | 22.103 | 66.415 | 83.504 | 1.00 | 22.94 |
| ATOM | 2089 | N | PRO | 447 | 23.291 | 67.216 | 85.237 | 1.00 | 21.41 |
| ATOM | 2090 | CD | PRO | 447 | 24.006 | 67.063 | 86.516 | 1.00 | 19.28 |

TABLE 2-continued

Coordinates of Lck bound with AMP-PNP

| | Atom Type | Res | # | X | Y | Z | Occ | B |
|---|---|---|---|---|---|---|---|---|
| ATOM | 2091 | CA | PRO | 447 | 22.599 | 68.504 | 85.173 | 1.00 | 19.53 |
| ATOM | 2092 | CB | PRO | 447 | 23.242 | 69.293 | 86.331 | 1.00 | 20.05 |
| ATOM | 2093 | CG | PRO | 447 | 23.430 | 68.199 | 87.372 | 1.00 | 20.54 |
| ATOM | 2094 | C | PRO | 447 | 22.884 | 69.115 | 83.783 | 1.00 | 18.40 |
| ATOM | 2095 | O | PRO | 447 | 21.982 | 69.684 | 83.162 | 1.00 | 18.87 |
| ATOM | 2096 | N | GLU | 448 | 24.079 | 68.932 | 83.241 | 1.00 | 17.60 |
| ATOM | 2098 | CA | GLU | 448 | 24.383 | 69.494 | 81.888 | 1.00 | 17.50 |
| ATOM | 2099 | CB | GLU | 448 | 25.875 | 69.386 | 81.562 | 1.00 | 17.69 |
| ATOM | 2100 | CG | GLU | 448 | 26.730 | 70.197 | 82.503 | 1.00 | 20.35 |
| ATOM | 2101 | CD | GLU | 448 | 28.202 | 70.065 | 82.200 | 1.00 | 22.71 |
| ATOM | 2102 | OE1 | GLU | 448 | 28.742 | 68.945 | 82.274 | 1.00 | 21.71 |
| ATOM | 2103 | OE2 | GLU | 448 | 28.838 | 71.083 | 81.865 | 1.00 | 29.91 |
| ATOM | 2104 | C | GLU | 448 | 23.601 | 68.769 | 80.802 | 1.00 | 18.43 |
| ATOM | 2105 | O | GLU | 448 | 23.234 | 69.358 | 79.781 | 1.00 | 17.96 |
| ATOM | 2106 | N | VAL | 449 | 23.444 | 67.446 | 80.976 | 1.00 | 19.16 |
| ATOM | 2108 | CA | VAL | 449 | 22.649 | 66.685 | 80.003 | 1.00 | 19.42 |
| ATOM | 2109 | CB | VAL | 449 | 22.680 | 65.134 | 80.205 | 1.00 | 18.44 |
| ATOM | 2110 | CG1 | VAL | 449 | 21.890 | 64.507 | 79.102 | 1.00 | 18.24 |
| ATOM | 2111 | CG2 | VAL | 449 | 24.106 | 64.594 | 80.094 | 1.00 | 16.28 |
| ATOM | 2112 | C | VAL | 449 | 21.188 | 67.190 | 80.005 | 1.00 | 16.19 |
| ATOM | 2113 | O | VAL | 449 | 20.644 | 67.474 | 78.956 | 1.00 | 18.65 |
| ATOM | 2114 | N | ILE | 450 | 20.608 | 67.337 | 81.179 | 0.60 | 14.24 |
| ATOM | 2116 | CA | ILE | 450 | 19.246 | 67.835 | 81.301 | 0.60 | 15.95 |
| ATOM | 2117 | CB | ILE | 450 | 18.850 | 67.860 | 82.769 | 0.60 | 14.74 |
| ATOM | 2118 | CG2 | ILE | 450 | 17.535 | 68.649 | 82.967 | 0.60 | 11.72 |
| ATOM | 2119 | CG1 | ILE | 450 | 18.714 | 66.416 | 83.280 | 0.60 | 13.82 |
| ATOM | 2120 | CD1 | ILE | 450 | 18.473 | 66.323 | 84.762 | 0.60 | 16.21 |
| ATOM | 2121 | C | ILE | 450 | 19.102 | 69.240 | 80.680 | 0.60 | 17.69 |
| ATOM | 2122 | O | ILE | 450 | 18.164 | 69.498 | 79.944 | 0.60 | 16.19 |
| ATOM | 2123 | N | GLN | 451 | 20.052 | 70.123 | 80.972 | 1.00 | 22.22 |
| ATOM | 2125 | CA | GLN | 451 | 20.038 | 71.469 | 80.438 | 1.00 | 23.33 |
| ATOM | 2126 | CB | GLN | 451 | 21.165 | 72.291 | 81.113 | 1.00 | 29.28 |
| ATOM | 2127 | CG | GLN | 451 | 21.698 | 73.572 | 80.452 | 1.00 | 38.30 |
| ATOM | 2128 | CD | GLN | 451 | 23.250 | 73.598 | 80.516 | 1.00 | 44.81 |
| ATOM | 2129 | OE1 | GLN | 451 | 23.870 | 73.579 | 81.599 | 1.00 | 47.60 |
| ATOM | 2130 | NE2 | GLN | 451 | 23.871 | 73.533 | 79.341 | 1.00 | 47.62 |
| ATOM | 2133 | C | GLN | 451 | 20.112 | 71.447 | 78.914 | 1.00 | 22.37 |
| ATOM | 2134 | O | GLN | 451 | 19.300 | 72.094 | 78.265 | 1.00 | 21.86 |
| ATOM | 2135 | N | ASN | 452 | 20.998 | 70.644 | 78.346 | 1.00 | 21.50 |
| ATOM | 2137 | CA | ASN | 452 | 21.105 | 70.604 | 76.893 | 1.00 | 23.60 |
| ATOM | 2138 | CB | ASN | 452 | 22.291 | 69.730 | 76.475 | 1.00 | 30.33 |
| ATOM | 2139 | CG | ASN | 452 | 23.620 | 70.476 | 76.472 | 1.00 | 33.45 |
| ATOM | 2140 | OD1 | ASN | 452 | 24.582 | 70.027 | 75.827 | 1.00 | 38.19 |
| ATOM | 2141 | ND2 | ASN | 452 | 23.688 | 71.601 | 77.179 | 1.00 | 33.08 |
| ATOM | 2144 | C | ASN | 452 | 19.840 | 70.063 | 76.224 | 1.00 | 24.20 |
| ATOM | 2145 | O | ASN | 452 | 19.408 | 70.546 | 75.168 | 1.00 | 25.63 |
| ATOM | 2146 | N | LEU | 453 | 19.298 | 68.988 | 76.787 | 1.00 | 22.63 |
| ATOM | 2148 | CA | LEU | 453 | 18.111 | 68.402 | 76.191 | 1.00 | 20.88 |
| ATOM | 2149 | CB | LEU | 453 | 17.735 | 67.131 | 76.911 | 1.00 | 19.15 |
| ATOM | 2150 | CG | LEU | 453 | 18.640 | 66.041 | 76.303 | 1.00 | 20.09 |
| ATOM | 2151 | CD1 | LEU | 453 | 18.704 | 65.061 | 77.381 | 1.00 | 19.24 |
| ATOM | 2152 | CD2 | LEU | 453 | 18.171 | 65.442 | 74.999 | 1.00 | 19.91 |
| ATOM | 2153 | C | LEU | 453 | 16.953 | 69.359 | 76.154 | 1.00 | 20.98 |
| ATOM | 2154 | O | LEU | 453 | 16.247 | 69.482 | 75.150 | 1.00 | 20.40 |
| ATOM | 2155 | N | GLU | 454 | 16.849 | 70.134 | 77.215 | 1.00 | 20.29 |
| ATOM | 2157 | CA | GLU | 454 | 15.777 | 71.091 | 77.333 | 1.00 | 20.69 |
| ATOM | 2158 | CB | GLU | 454 | 15.636 | 71.460 | 78.808 | 1.00 | 22.44 |
| ATOM | 2159 | CG | GLU | 454 | 14.691 | 70.571 | 79.652 | 1.00 | 26.95 |
| ATOM | 2160 | CD | GLU | 454 | 14.860 | 70.937 | 81.103 | 1.00 | 32.80 |
| ATOM | 2161 | OE1 | GLU | 454 | 15.655 | 71.869 | 81.371 | 1.00 | 35.24 |
| ATOM | 2162 | OE2 | GLU | 454 | 14.234 | 70.303 | 81.985 | 1.00 | 36.29 |
| ATOM | 2163 | C | GLU | 454 | 15.940 | 72.301 | 76.361 | 1.00 | 19.99 |
| ATOM | 2164 | O | GLU | 454 | 14.950 | 72.951 | 76.027 | 1.00 | 19.52 |
| ATOM | 2165 | N | ARG | 455 | 17.141 | 72.486 | 75.781 | 1.00 | 17.70 |
| ATOM | 2167 | CA | ARG | 455 | 17.386 | 73.552 | 74.782 | 1.00 | 17.77 |
| ATOM | 2168 | CB | ARG | 455 | 18.844 | 74.021 | 74.771 | 1.00 | 18.95 |
| ATOM | 2169 | CG | ARG | 455 | 19.356 | 74.547 | 76.074 | 1.00 | 22.96 |
| ATOM | 2170 | CD | ARG | 455 | 20.763 | 75.090 | 75.932 | 1.00 | 23.08 |
| ATOM | 2171 | NE | ARG | 455 | 20.833 | 76.222 | 75.012 | 1.00 | 25.12 |
| ATOM | 2173 | CZ | ARG | 455 | 21.969 | 76.855 | 74.680 | 1.00 | 24.77 |
| ATOM | 2174 | NH1 | ARG | 455 | 23.139 | 76.455 | 75.192 | 1.00 | 22.66 |
| ATOM | 2177 | NH2 | ARG | 455 | 21.926 | 77.913 | 73.881 | 1.00 | 19.61 |
| ATOM | 2180 | C | ARG | 455 | 17.114 | 73.011 | 73.385 | 1.00 | 18.74 |
| ATOM | 2181 | O | ARG | 455 | 17.200 | 73.728 | 72.402 | 1.00 | 18.28 |

TABLE 2-continued

Coordinates of Lck bound with AMP-PNP

| | Atom Type | Res | # | X | Y | Z | Occ | B |
|---|---|---|---|---|---|---|---|---|
| ATOM | 2182 | N | GLY | 456 | 16.807 | 71.716 | 73.285 | 1.00 | 20.31 |
| ATOM | 2184 | CA | GLY | 456 | 16.597 | 71.101 | 71.977 | 1.00 | 18.59 |
| ATOM | 2185 | C | GLY | 456 | 17.849 | 70.367 | 71.487 | 1.00 | 18.02 |
| ATOM | 2186 | O | GLY | 456 | 17.828 | 69.804 | 70.405 | 1.00 | 17.58 |
| ATOM | 2187 | N | TYR | 457 | 18.945 | 70.432 | 72.210 | 1.00 | 18.14 |
| ATOM | 2189 | CA | TYR | 457 | 20.149 | 69.747 | 71.750 | 1.00 | 19.56 |
| ATOM | 2190 | CB | TYR | 457 | 21.385 | 70.191 | 72.541 | 1.00 | 17.10 |
| ATOM | 2191 | CG | TYR | 457 | 21.894 | 71.591 | 72.302 | 1.00 | 17.96 |
| ATOM | 2192 | CD1 | TYR | 457 | 21.478 | 72.352 | 71.226 | 1.00 | 19.20 |
| ATOM | 2193 | CE1 | TYR | 457 | 21.992 | 73.637 | 71.008 | 1.00 | 19.38 |
| ATOM | 2194 | CD2 | TYR | 457 | 22.836 | 72.138 | 73.170 | 1.00 | 20.40 |
| ATOM | 2195 | CE2 | TYR | 457 | 23.347 | 73.404 | 72.960 | 1.00 | 19.97 |
| ATOM | 2196 | CZ | TYR | 457 | 22.920 | 74.135 | 71.879 | 1.00 | 17.83 |
| ATOM | 2197 | OH | TYR | 457 | 23.472 | 75.385 | 71.675 | 1.00 | 17.07 |
| ATOM | 2199 | C | TYR | 457 | 20.021 | 68.246 | 72.034 | 1.00 | 20.03 |
| ATOM | 2200 | O | TYR | 457 | 19.221 | 67.828 | 72.870 | 1.00 | 18.91 |
| ATOM | 2201 | N | ARG | 458 | 20.819 | 67.445 | 71.340 | 1.00 | 20.26 |
| ATOM | 2203 | CA | ARG | 458 | 20.854 | 66.013 | 71.608 | 1.00 | 19.25 |
| ATOM | 2204 | CB | ARG | 458 | 20.175 | 65.210 | 70.495 | 1.00 | 17.50 |
| ATOM | 2205 | CG | ARG | 458 | 18.652 | 65.394 | 70.441 | 1.00 | 14.01 |
| ATOM | 2206 | CD | ARG | 458 | 17.986 | 65.025 | 71.777 | 1.00 | 13.72 |
| ATOM | 2207 | NE | ARG | 458 | 16.528 | 65.083 | 71.689 | 1.00 | 15.54 |
| ATOM | 2209 | CZ | ARG | 458 | 15.776 | 66.071 | 72.199 | 1.00 | 17.63 |
| ATOM | 2210 | NH1 | ARG | 458 | 16.347 | 67.098 | 72.825 | 1.00 | 18.53 |
| ATOM | 2213 | NH2 | ARG | 458 | 14.444 | 66.012 | 72.092 | 1.00 | 14.13 |
| ATOM | 2216 | C | ARG | 458 | 22.325 | 65.657 | 71.718 | 1.00 | 19.83 |
| ATOM | 2217 | O | ARG | 458 | 23.195 | 66.530 | 71.557 | 1.00 | 17.44 |
| ATOM | 2218 | N | MET | 459 | 22.628 | 64.380 | 71.961 | 1.00 | 17.91 |
| ATOM | 2220 | CA | MET | 459 | 24.043 | 64.001 | 72.101 | 1.00 | 15.97 |
| ATOM | 2221 | CB | MET | 459 | 24.199 | 62.503 | 72.377 | 1.00 | 15.95 |
| ATOM | 2222 | CG | MET | 459 | 25.568 | 62.127 | 72.906 | 1.00 | 15.08 |
| ATOM | 2223 | SD | MET | 459 | 25.816 | 60.318 | 73.149 | 1.00 | 19.19 |
| ATOM | 2224 | CE | MET | 459 | 24.291 | 59.886 | 73.995 | 1.00 | 17.66 |
| ATOM | 2225 | C | MET | 459 | 24.854 | 64.341 | 70.872 | 1.00 | 15.70 |
| ATOM | 2226 | O | MET | 459 | 24.419 | 64.145 | 69.726 | 1.00 | 14.70 |
| ATOM | 2227 | N | VAL | 460 | 26.046 | 64.885 | 71.098 | 1.00 | 15.83 |
| ATOM | 2229 | CA | VAL | 460 | 26.935 | 65.234 | 70.021 | 1.00 | 14.18 |
| ATOM | 2230 | CB | VAL | 460 | 28.245 | 65.833 | 70.624 | 1.00 | 17.78 |
| ATOM | 2231 | CG1 | VAL | 460 | 29.355 | 65.930 | 69.544 | 1.00 | 19.44 |
| ATOM | 2232 | CG2 | VAL | 460 | 27.956 | 67.209 | 71.227 | 1.00 | 15.84 |
| ATOM | 2233 | C | VAL | 460 | 27.295 | 63.950 | 69.235 | 1.00 | 15.35 |
| ATOM | 2234 | O | VAL | 460 | 27.398 | 62.886 | 69.833 | 1.00 | 17.60 |
| ATOM | 2235 | N | ARG | 461 | 27.463 | 64.046 | 67.924 | 1.00 | 14.74 |
| ATOM | 2237 | CA | ARG | 461 | 27.858 | 62.899 | 67.114 | 1.00 | 20.91 |
| ATOM | 2238 | CB | ARG | 461 | 28.214 | 63.364 | 65.695 | 1.00 | 17.94 |
| ATOM | 2239 | CG | ARG | 461 | 27.058 | 63.957 | 64.917 | 1.00 | 17.02 |
| ATOM | 2240 | CD | ARG | 461 | 27.500 | 64.354 | 63.533 | 1.00 | 14.96 |
| ATOM | 2241 | NE | ARG | 461 | 26.364 | 64.666 | 62.692 | 1.00 | 17.42 |
| ATOM | 2243 | CZ | ARG | 461 | 25.687 | 65.829 | 62.692 | 1.00 | 18.25 |
| ATOM | 2244 | NH1 | ARG | 461 | 26.03 | 66.825 | 63.493 | 1.00 | 18.39 |
| ATOM | 2247 | NH2 | ARG | 461 | 24.645 | 65.985 | 61.881 | 1.00 | 17.39 |
| ATOM | 2250 | C | ARG | 461 | 29.093 | 62.172 | 67.672 | 1.00 | 24.64 |
| ATOM | 2251 | O | ARG | 461 | 30.143 | 62.800 | 67.840 | 1.00 | 26.86 |
| ATOM | 2252 | N | PRO | 462 | 28.974 | 60.863 | 68.043 | 1.00 | 25.97 |
| ATOM | 2253 | CD | PRO | 462 | 27.723 | 60.100 | 68.164 | 1.00 | 26.62 |
| ATOM | 2254 | CA | PRO | 462 | 30.105 | 60.075 | 68.580 | 1.00 | 26.30 |
| ATOM | 2255 | CB | PRO | 462 | 29.478 | 58.706 | 68.855 | 1.00 | 25.21 |
| ATOM | 2256 | CG | PRO | 462 | 28.091 | 59.044 | 69.225 | 1.00 | 27.71 |
| ATOM | 2257 | C | PRO | 462 | 31.186 | 59.973 | 67.531 | 1.00 | 27.36 |
| ATOM | 2258 | O | PRO | 462 | 30.887 | 60.074 | 66.349 | 1.00 | 22.85 |
| ATOM | 2259 | N | ASP | 463 | 32.440 | 59.856 | 67.976 | 1.00 | 33.07 |
| ATOM | 2261 | CA | ASP | 463 | 33.542 | 59.724 | 67.037 | 1.00 | 36.40 |
| ATOM | 2262 | CB | ASP | 463 | 34.905 | 59.513 | 67.731 | 1.00 | 42.61 |
| ATOM | 2263 | CG | ASP | 463 | 35.486 | 60.802 | 68.343 | 1.00 | 46.87 |
| ATOM | 2264 | OD1 | ASP | 463 | 35.313 | 61.884 | 67.723 | 1.00 | 52.92 |
| ATOM | 2265 | OD2 | ASP | 463 | 36.113 | 60.733 | 69.440 | 1.00 | 48.62 |
| ATOM | 2266 | C | ASP | 463 | 33.249 | 58.565 | 66.102 | 1.00 | 36.01 |
| ATOM | 2267 | O | ASP | 463 | 32.726 | 57.512 | 66.506 | 1.00 | 38.21 |
| ATOM | 2268 | N | ASN | 464 | 33.364 | 58.858 | 64.826 | 1.00 | 34.27 |
| ATOM | 2270 | CA | ASN | 464 | 33.164 | 57.823 | 63.884 | 1.00 | 33.69 |
| ATOM | 2271 | CB | ASN | 464 | 34.310 | 56.892 | 64.024 | 1.00 | 37.65 |
| ATOM | 2272 | CG | ASN | 464 | 35.421 | 57.411 | 63.277 | 1.00 | 41.02 |
| ATOM | 2273 | OD1 | ASN | 464 | 36.530 | 57.497 | 63.748 | 1.00 | 42.34 |
| ATOM | 2274 | ND2 | ASN | 464 | 35.092 | 57.962 | 62.114 | 1.00 | 46.22 |

TABLE 2-continued

Coordinates of Lck bound with AMP-PNP

| | Atom Type | Res | # | X | Y | Z | Occ | B |
|---|---|---|---|---|---|---|---|---|
| ATOM | 2277 | C | ASN | 464 | 31.858 | 57.103 | 63.742 | 1.00 | 31.02 |
| ATOM | 2278 | O | ASN | 464 | 31.769 | 55.942 | 63.346 | 1.00 | 33.21 |
| ATOM | 2279 | N | CYS | 465 | 30.831 | 57.839 | 64.091 | 1.00 | 28.20 |
| ATOM | 2281 | CA | CYS | 465 | 29.512 | 57.312 | 63.948 | 1.00 | 23.77 |
| ATOM | 2282 | CB | CYS | 465 | 28.624 | 57.996 | 64.957 | 1.00 | 22.59 |
| ATOM | 2283 | SG | CYS | 465 | 26.940 | 57.347 | 64.922 | 1.00 | 20.23 |
| ATOM | 2284 | C | CYS | 465 | 29.009 | 57.609 | 62.534 | 1.00 | 20.29 |
| ATOM | 2285 | O | CYS | 465 | 29.113 | 58.722 | 62.076 | 1.00 | 20.20 |
| ATOM | 2286 | N | PRO | 466 | 28.580 | 56.571 | 61.785 | 1.00 | 19.54 |
| ATOM | 2287 | CD | PRO | 466 | 28.614 | 55.148 | 62.170 | 1.00 | 18.45 |
| ATOM | 2288 | CA | PRO | 466 | 28.044 | 56.745 | 60.424 | 1.00 | 17.34 |
| ATOM | 2289 | CB | PRO | 466 | 27.528 | 55.340 | 60.086 | 1.00 | 17.76 |
| ATOM | 2290 | CG | PRO | 466 | 28.454 | 54.452 | 60.853 | 1.00 | 18.34 |
| ATOM | 2291 | C | PRO | 466 | 26.833 | 57.713 | 60.603 | 1.00 | 17.27 |
| ATOM | 2292 | O | PRO | 466 | 26.087 | 57.593 | 61.573 | 1.00 | 15.23 |
| ATOM | 2293 | N | GLU | 467 | 26.693 | 58.678 | 59.702 | 1.00 | 18.48 |
| ATOM | 2295 | CA | GLU | 467 | 25.622 | 59.652 | 59.830 | 1.00 | 18.82 |
| ATOM | 2296 | CB | GLU | 467 | 25.850 | 60.793 | 58.830 | 1.00 | 17.73 |
| ATOM | 2297 | CG | GLU | 467 | 25.269 | 62.174 | 59.193 | 1.00 | 17.92 |
| ATOM | 2298 | CD | GLU | 467 | 25.281 | 62.575 | 60.623 | 1.00 | 16.81 |
| ATOM | 2299 | OE1 | GLU | 467 | 26.239 | 62.494 | 61.391 | 1.00 | 20.48 |
| ATOM | 2300 | OE2 | GLU | 467 | 24.245 | 63.097 | 60.907 | 1.00 | 19.26 |
| ATOM | 2301 | C | GLU | 467 | 24.233 | 59.009 | 59.717 | 1.00 | 16.25 |
| ATOM | 2302 | O | GLU | 467 | 23.296 | 59.473 | 60.377 | 1.00 | 18.45 |
| ATOM | 2303 | N | GLU | 468 | 24.109 | 57.933 | 58.948 | 0.51 | 12.70 |
| ATOM | 2305 | CA | GLU | 468 | 22.824 | 57.230 | 58.840 | 0.51 | 9.87 |
| ATOM | 2306 | CB | GLU | 468 | 22.881 | 56.084 | 67.826 | 0.51 | 9.75 |
| ATOM | 2307 | CG | GLU | 468 | 22.768 | 56.476 | 56.373 | 0.51 | 12.87 |
| ATOM | 2308 | CD | GLU | 468 | 23.600 | 55.604 | 55.454 | 0.51 | 16.73 |
| ATOM | 2309 | OE1 | GLU | 468 | 24.697 | 55.613 | 55.289 | 0.51 | 21.01 |
| ATOM | 2310 | OE2 | GLU | 468 | 23.104 | 54.806 | 54.715 | 0.51 | 19.71 |
| ATOM | 2311 | C | GLU | 468 | 22.427 | 56.693 | 60.208 | 0.51 | 7.61 |
| ATOM | 2312 | O | GLU | 468 | 21.285 | 56.793 | 60.593 | 0.51 | 5.14 |
| ATOM | 2313 | N | LEU | 469 | 23.383 | 56.173 | 60.961 | 1.00 | 11.98 |
| ATOM | 2315 | CA | LEU | 469 | 23.088 | 55.669 | 62.295 | 1.00 | 13.45 |
| ATOM | 2316 | CB | LEU | 469 | 24.255 | 54.815 | 62.821 | 1.00 | 16.09 |
| ATOM | 2317 | CG | LEU | 469 | 24.011 | 54.128 | 64.188 | 1.00 | 18.21 |
| ATOM | 2318 | CD1 | LEU | 469 | 22.896 | 53.133 | 64.027 | 1.00 | 19.45 |
| ATOM | 2319 | CD2 | LEU | 469 | 25.309 | 53.401 | 64.621 | 1.00 | 20.80 |
| ATOM | 2320 | C | LEU | 469 | 22.810 | 56.829 | 63.234 | 1.00 | 14.50 |
| ATOM | 2321 | O | LEU | 469 | 21.922 | 56.748 | 64.097 | 1.00 | 13.69 |
| ATOM | 2322 | N | TYR | 470 | 23.556 | 57.925 | 63.087 | 1.00 | 15.76 |
| ATOM | 2324 | CA | TYR | 470 | 23.330 | 59.070 | 63.961 | 1.00 | 15.69 |
| ATOM | 2325 | CB | TYR | 470 | 24.347 | 60.190 | 63.676 | 1.00 | 15.77 |
| ATOM | 2326 | CG | TYR | 470 | 24.177 | 61.346 | 64.628 | 1.00 | 13.26 |
| ATOM | 2327 | CD1 | TYR | 470 | 24.383 | 61.192 | 65.989 | 1.00 | 11.67 |
| ATOM | 2328 | CE1 | TYR | 470 | 25.238 | 62.237 | 66.860 | 1.00 | 14.86 |
| ATOM | 2329 | CD2 | TYR | 470 | 23.799 | 62.610 | 64.152 | 1.00 | 14.80 |
| ATOM | 2330 | CE2 | TYR | 470 | 23.648 | 63.674 | 65.007 | 1.00 | 11.49 |
| ATOM | 2331 | CZ | TYR | 470 | 23.876 | 63.487 | 66.360 | 1.00 | 14.26 |
| ATOM | 2332 | OH | TYR | 470 | 23.829 | 64.533 | 67.259 | 1.00 | 13.59 |
| ATOM | 2334 | C | TYR | 470 | 21.897 | 59.622 | 63.790 | 1.00 | 15.89 |
| ATOM | 2335 | O | TYR | 470 | 21.222 | 59.948 | 64.748 | 1.00 | 16.07 |
| ATOM | 2336 | N | GLN | 471 | 21.458 | 59.722 | 62.563 | 1.00 | 17.58 |
| ATOM | 2338 | CA | GLN | 471 | 20.122 | 60.197 | 62.267 | 1.00 | 19.32 |
| ATOM | 2339 | CB | GLN | 471 | 20.095 | 60.406 | 60.776 | 1.00 | 20.31 |
| ATOM | 2340 | CG | GLN | 471 | 20.193 | 61.875 | 60.292 | 1.00 | 27.33 |
| ATOM | 2341 | CD | GLN | 471 | 20.883 | 62.897 | 61.206 | 1.00 | 28.92 |
| ATOM | 2342 | OE1 | GLN | 471 | 22.072 | 62.990 | 61.296 | 1.00 | 36.59 |
| ATOM | 2343 | NE2 | GLN | 471 | 20.103 | 63.750 | 61.758 | 1.00 | 28.48 |
| ATOM | 2346 | C | GLN | 471 | 19.025 | 59.212 | 62.785 | 1.00 | 21.02 |
| ATOM | 2347 | O | GLN | 471 | 17.942 | 59.640 | 63.223 | 1.00 | 22.52 |
| ATOM | 2348 | N | LEU | 472 | 19.337 | 57.916 | 62.835 | 1.00 | 19.39 |
| ATOM | 2350 | CA | LEU | 472 | 18.398 | 56.945 | 63.388 | 1.00 | 19.13 |
| ATOM | 2351 | CB | LEU | 472 | 18.851 | 55.510 | 63.099 | 1.00 | 22.09 |
| ATOM | 2352 | CG | LEU | 472 | 17.826 | 54.393 | 63.372 | 1.00 | 21.25 |
| ATOM | 2353 | CD1 | LEU | 472 | 16.645 | 54.578 | 62.419 | 1.00 | 21.50 |
| ATOM | 2354 | CD2 | LEU | 472 | 18.486 | 53.021 | 63.134 | 1.00 | 16.29 |
| ATOM | 2355 | C | LEU | 472 | 18.313 | 57.183 | 64.917 | 1.00 | 18.02 |
| ATOM | 2356 | O | LEU | 472 | 17.232 | 57.104 | 65.524 | 1.00 | 19.05 |
| ATOM | 2357 | N | MET | 473 | 19.448 | 57.491 | 65.539 | 1.00 | 18.25 |
| ATOM | 2359 | CA | MET | 473 | 19.449 | 57.813 | 66.976 | 1.00 | 17.95 |
| ATOM | 2360 | CB | MET | 473 | 20.836 | 58.137 | 67.466 | 1.00 | 18.39 |
| ATOM | 2361 | CG | MET | 473 | 21.885 | 57.043 | 67.296 | 1.00 | 19.12 |

TABLE 2-continued

Coordinates of Lck bound with AMP-PNP

| | Atom Type | Res | # | X | Y | Z | Occ | B |
|---|---|---|---|---|---|---|---|---|
| ATOM | 2362 | SD | MET | 473 | 23.579 | 57.734 | 67.549 | 1.00 | 17.70 |
| ATOM | 2363 | CE | MET | 473 | 24.541 | 56.279 | 67.611 | 1.00 | 21.24 |
| ATOM | 2364 | C | MET | 473 | 18.567 | 59.055 | 67.233 | 1.00 | 17.42 |
| ATOM | 2365 | O | MET | 473 | 17.826 | 59.099 | 68.220 | 1.00 | 17.21 |
| ATOM | 2366 | N | ARG | 474 | 18.648 | 60.043 | 66.342 | 1.00 | 17.08 |
| ATOM | 2368 | CA | ARG | 474 | 17.892 | 61.290 | 66.513 | 1.00 | 16.18 |
| ATOM | 2369 | CB | ARG | 474 | 18.240 | 62.345 | 65.407 | 1.00 | 16.13 |
| ATOM | 2370 | CG | ARG | 474 | 19.678 | 62.878 | 65.264 | 1.00 | 15.54 |
| ATOM | 2371 | CD | ARG | 474 | 20.206 | 63.766 | 66.340 | 1.00 | 17.62 |
| ATOM | 2372 | NE | ARG | 474 | 19.690 | 65.108 | 66.507 | 1.00 | 25.22 |
| ATOM | 2374 | CZ | ARG | 474 | 20.451 | 66.074 | 66.989 | 1.00 | 24.91 |
| ATOM | 2375 | NH1 | ARG | 474 | 21.737 | 65.854 | 67.244 | 1.00 | 21.73 |
| ATOM | 2378 | NH2 | ARG | 474 | 19.827 | 67.067 | 67.594 | 1.00 | 28.65 |
| ATOM | 2381 | C | ARG | 474 | 16.374 | 60.982 | 66.462 | 1.00 | 15.94 |
| ATOM | 2382 | O | ARG | 474 | 15.613 | 61.602 | 67.148 | 1.00 | 18.86 |
| ATOM | 2383 | N | LEU | 475 | 15.933 | 60.061 | 65.611 | 1.00 | 16.10 |
| ATOM | 2385 | CA | LEU | 475 | 14.507 | 59.688 | 65.596 | 1.00 | 17.16 |
| ATOM | 2386 | CB | LEU | 475 | 14.201 | 58.641 | 64.522 | 1.00 | 16.67 |
| ATOM | 2387 | CG | LEU | 475 | 14.260 | 58.919 | 63.031 | 1.00 | 18.23 |
| ATOM | 2388 | CD1 | LEU | 475 | 13.551 | 57.692 | 62.447 | 1.00 | 20.24 |
| ATOM | 2389 | CD2 | LEU | 475 | 13.537 | 60.190 | 62.620 | 1.00 | 19.21 |
| ATOM | 2390 | C | LEU | 475 | 14.103 | 59.119 | 66.949 | 1.00 | 16.79 |
| ATOM | 2391 | O | LEU | 475 | 13.025 | 59.451 | 67.477 | 1.00 | 17.89 |
| ATOM | 2392 | N | CYS | 476 | 15.007 | 58.382 | 67.581 | 1.00 | 16.31 |
| ATOM | 2394 | CA | CYS | 476 | 14.718 | 57.793 | 68.896 | 1.00 | 16.85 |
| ATOM | 2395 | CB | CYS | 476 | 15.831 | 56.780 | 69.277 | 1.00 | 15.55 |
| ATOM | 2396 | SG | CYS | 476 | 15.969 | 55.406 | 68.118 | 1.00 | 14.96 |
| ATOM | 2397 | C | CYS | 476 | 14.650 | 58.840 | 69.980 | 1.00 | 17.41 |
| ATOM | 2398 | O | CYS | 476 | 14.159 | 58.563 | 71.058 | 1.00 | 20.02 |
| ATOM | 2399 | N | TRP | 477 | 15.236 | 60.016 | 69.704 | 1.00 | 20.22 |
| ATOM | 2401 | CA | TRP | 477 | 15.284 | 61.111 | 70.682 | 1.00 | 19.77 |
| ATOM | 2402 | CB | TRP | 477 | 16.689 | 61.668 | 70.808 | 1.00 | 19.85 |
| ATOM | 2403 | CG | TRP | 477 | 17.712 | 60.646 | 71.178 | 1.00 | 19.63 |
| ATOM | 2404 | CD2 | TRP | 477 | 19.084 | 60.628 | 70.782 | 1.00 | 18.71 |
| ATOM | 2405 | CE2 | TRP | 477 | 19.682 | 59.507 | 71.392 | 1.00 | 20.22 |
| ATOM | 2406 | CE3 | TRP | 477 | 19.869 | 61.469 | 69.963 | 1.00 | 18.45 |
| ATOM | 2407 | CD1 | TRP | 477 | 17.537 | 59.565 | 71.995 | 1.00 | 20.69 |
| ATOM | 2408 | NE1 | TRP | 477 | 18.721 | 58.877 | 72.136 | 1.00 | 17.19 |
| ATOM | 2410 | CZ2 | TRP | 477 | 21.060 | 59.190 | 71.216 | 1.00 | 16.34 |
| ATOM | 2411 | CZ3 | TRP | 477 | 21.222 | 61.159 | 69.786 | 1.00 | 15.37 |
| ATOM | 2412 | CH2 | TRP | 477 | 21.796 | 60.035 | 70.416 | 1.00 | 15.60 |
| ATOM | 2413 | C | TRP | 477 | 14.305 | 62.251 | 70.376 | 1.00 | 19.98 |
| ATOM | 2414 | O | TRP | 477 | 14.498 | 63.69 | 70.825 | 1.00 | 17.04 |
| ATOM | 2415 | N | LYS | 478 | 13.280 | 61.974 | 69.572 | 1.00 | 18.53 |
| ATOM | 2417 | CA | LYS | 478 | 12.302 | 63.005 | 69.296 | 1.00 | 17.79 |
| ATOM | 2418 | CB | LYS | 478 | 11.276 | 62.549 | 68.282 | 1.00 | 18.06 |
| ATOM | 2419 | CG | LYS | 478 | 11.831 | 62.577 | 66.881 | 1.00 | 17.26 |
| ATOM | 2420 | CD | LYS | 478 | 10.816 | 62.102 | 65.915 | 1.00 | 19.20 |
| ATOM | 2421 | CE | LYS | 478 | 11.309 | 62.303 | 64.503 | 1.00 | 22.29 |
| ATOM | 2422 | NZ | LYS | 478 | 11.573 | 63.737 | 64.240 | 1.00 | 27.75 |
| ATOM | 2426 | C | LYS | 478 | 11.615 | 63.452 | 70.576 | 1.00 | 18.94 |
| ATOM | 2427 | O | LYS | 478 | 11.429 | 62.677 | 71.516 | 1.00 | 19.46 |
| ATOM | 2428 | N | GLU | 479 | 11.319 | 64.743 | 70.658 | 1.00 | 19.78 |
| ATOM | 2430 | CA | GLU | 479 | 10.695 | 65.284 | 71.852 | 1.00 | 22.45 |
| ATOM | 2431 | CB | GLU | 479 | 10.434 | 66.767 | 71.627 | 1.00 | 27.45 |
| ATOM | 2432 | CG | GLU | 479 | 9.843 | 67.518 | 72.816 | 1.00 | 33.27 |
| ATOM | 2433 | CD | GLU | 479 | 10.791 | 67.878 | 73.971 | 1.00 | 38.31 |
| ATOM | 2434 | OE1 | GLU | 479 | 12.044 | 67.900 | 73.903 | 1.00 | 44.43 |
| ATOM | 2435 | OE2 | GLU | 479 | 10.187 | 68.204 | 75.002 | 1.00 | 39.74 |
| ATOM | 2436 | C | GLU | 479 | 9.394 | 64.549 | 72.287 | 1.00 | 22.57 |
| ATOM | 2437 | O | GLU | 479 | 9.264 | 64.065 | 73.415 | 1.00 | 21.17 |
| ATOM | 2438 | N | ARG | 480 | 8.427 | 64.469 | 71.387 | 1.00 | 21.63 |
| ATOM | 2440 | CA | ARG | 480 | 7.194 | 63.785 | 71.746 | 1.00 | 25.32 |
| ATOM | 2441 | CB | ARG | 480 | 6.053 | 64.222 | 70.837 | 1.00 | 27.02 |
| ATOM | 2442 | CG | ARG | 480 | 5.329 | 65.427 | 71.242 | 1.00 | 34.46 |
| ATOM | 2443 | CD | ARG | 480 | 4.500 | 65.812 | 70.100 | 1.00 | 35.70 |
| ATOM | 2444 | NE | ARG | 480 | 4.865 | 65.561 | 68.688 | 1.00 | 41.57 |
| ATOM | 2446 | CZ | ARG | 480 | 3.848 | 65.369 | 67.862 | 1.00 | 43.95 |
| ATOM | 2447 | NH1 | ARG | 480 | 2.706 | 65.400 | 68.498 | 1.00 | 46.80 |
| ATOM | 2450 | NH2 | ARG | 480 | 3.857 | 65.388 | 66.521 | 1.00 | 43.75 |
| ATOM | 2453 | C | ARG | 480 | 7.361 | 62.274 | 71.585 | 1.00 | 22.03 |
| ATOM | 2454 | O | ARG | 480 | 7.707 | 61.799 | 70.526 | 1.00 | 21.78 |
| ATOM | 2455 | N | PRO | 481 | 7.088 | 61.510 | 72.641 | 1.00 | 20.56 |
| ATOM | 2456 | CD | PRO | 481 | 6.601 | 61.978 | 73.953 | 1.00 | 19.52 |

TABLE 2-continued

Coordinates of Lck bound with AMP-PNP

| | Atom Type | Res | # | X | Y | Z | Occ | B |
|---|---|---|---|---|---|---|---|---|
| ATOM | 2457 | CA | PRO | 481 | 7.203 | 60.043 | 72.606 | 1.00 | 20.01 |
| ATOM | 2458 | CB | PRO | 481 | 6.566 | 59.619 | 73.916 | 1.00 | 19.09 |
| ATOM | 2459 | CG | PRO | 481 | 6.859 | 60.763 | 74.832 | 1.00 | 18.91 |
| ATOM | 2460 | C | PRO | 481 | 6.489 | 59.426 | 71.414 | 1.00 | 22.36 |
| ATOM | 2461 | O | PRO | 481 | 7.057 | 58.599 | 70.701 | 1.00 | 24.56 |
| ATOM | 2462 | N | GLU | 482 | 5.289 | 59.920 | 71.100 | 1.00 | 23.76 |
| ATOM | 2464 | CA | GLU | 482 | 4.527 | 59.365 | 69.977 | 1.00 | 22.80 |
| ATOM | 2465 | CB | GLU | 482 | 3.101 | 59.928 | 69.970 | 1.00 | 26.56 |
| ATOM | 2466 | CG | GLU | 482 | 3.088 | 61.434 | 69.770 | 1.00 | 34.44 |
| ATOM | 2467 | CD | GLU | 482 | 2.854 | 62.240 | 71.068 | 1.00 | 37.15 |
| ATOM | 2468 | OE1 | GLU | 482 | 3.373 | 62.884 | 72.176 | 1.00 | 32.95 |
| ATOM | 2469 | OE2 | GLU | 482 | 2.104 | 63.231 | 70.949 | 1.00 | 44.38 |
| ATOM | 2470 | C | GLU | 482 | 5.182 | 59.557 | 68.626 | 1.00 | 20.97 |
| ATOM | 2471 | O | GLU | 482 | 4.835 | 58.870 | 67.667 | 1.00 | 20.58 |
| ATOM | 2472 | N | ASP | 483 | 6.108 | 60.502 | 68.520 | 1.00 | 20.69 |
| ATOM | 2474 | CA | ASP | 483 | 6.810 | 60.707 | 67.247 | 1.00 | 17.73 |
| ATOM | 2475 | CB | ASP | 483 | 7.313 | 62.132 | 67.113 | 1.00 | 21.92 |
| ATOM | 2476 | CG | ASP | 483 | 6.201 | 63.123 | 66.952 | 1.00 | 23.99 |
| ATOM | 2477 | OD1 | ASP | 483 | 5.090 | 62.749 | 66.535 | 1.00 | 26.48 |
| ATOM | 2478 | OD2 | ASP | 483 | 6.476 | 64.279 | 67.256 | 1.00 | 26.05 |
| ATOM | 2479 | C | ASP | 483 | 7.994 | 59.779 | 67.074 | 1.00 | 16.37 |
| ATOM | 2480 | O | ASP | 483 | 8.529 | 59.663 | 65.984 | 1.00 | 13.59 |
| ATOM | 2481 | N | ARG | 484 | 8.409 | 59.133 | 68.151 | 1.00 | 16.89 |
| ATOM | 2483 | CA | ARG | 484 | 9.556 | 58.206 | 68.083 | 1.00 | 17.09 |
| ATOM | 2484 | CB | ARG | 484 | 10.054 | 57.871 | 69.488 | 1.00 | 13.85 |
| ATOM | 2485 | CG | ARG | 484 | 10.487 | 59.103 | 70.255 | 1.00 | 11.02 |
| ATOM | 2486 | CD | ARG | 484 | 10.824 | 58.769 | 71.676 | 1.00 | 12.58 |
| ATOM | 2487 | NE | ARG | 484 | 10.898 | 59.984 | 72.449 | 1.00 | 14.20 |
| ATOM | 2489 | CZ | ARG | 484 | 10.673 | 60.073 | 73.746 | 1.00 | 21.54 |
| ATOM | 2490 | NH1 | ARG | 484 | 10.373 | 58.989 | 74.443 | 1.00 | 20.98 |
| ATOM | 2493 | NH2 | ARG | 484 | 10.632 | 61.286 | 74.357 | 1.00 | 23.02 |
| ATOM | 2496 | C | ARG | 484 | 9.079 | 56.942 | 67.337 | 1.00 | 19.02 |
| ATOM | 2497 | O | ARG | 484 | 7.918 | 56.565 | 67.419 | 1.00 | 20.65 |
| ATOM | 2498 | N | PRO | 485 | 9.981 | 56.307 | 66.584 | 1.00 | 17.88 |
| ATOM | 2499 | CD | PRO | 485 | 11.424 | 56.601 | 66.551 | 1.00 | 17.09 |
| ATOM | 2500 | CA | PRO | 485 | 9.680 | 55.098 | 65.809 | 1.00 | 16.95 |
| ATOM | 2501 | CB | PRO | 485 | 10.935 | 54.941 | 64.982 | 1.00 | 15.97 |
| ATOM | 2502 | CG | PRO | 485 | 12.002 | 55.366 | 65.916 | 1.00 | 14.91 |
| ATOM | 2503 | C | PRO | 485 | 9.387 | 53.845 | 66.653 | 1.00 | 15.71 |
| ATOM | 2504 | O | PRO | 485 | 9.619 | 53.806 | 67.838 | 1.00 | 14.43 |
| ATOM | 2505 | N | THR | 486 | 8.768 | 52.861 | 66.025 | 1.00 | 16.25 |
| ATOM | 2507 | CA | THR | 486 | 8.504 | 51.581 | 66.722 | 1.00 | 17.14 |
| ATOM | 2508 | CB | THR | 486 | 7.417 | 50.779 | 66.033 | 1.00 | 16.41 |
| ATOM | 2509 | OG1 | THR | 486 | 7.829 | 51.558 | 66.000 | 1.00 | 16.20 |
| ATOM | 2511 | CG2 | THR | 486 | 6.058 | 51.558 | 66.000 | 1.00 | 15.66 |
| ATOM | 2512 | C | THR | 486 | 9.779 | 50.747 | 66.664 | 1.00 | 16.65 |
| ATOM | 2513 | O | THR | 486 | 10.647 | 50.987 | 65.824 | 1.00 | 17.35 |
| ATOM | 2514 | N | PHE | 487 | 9.891 | 49.752 | 67.531 | 1.00 | 16.93 |
| ATOM | 2516 | CA | PHE | 487 | 11.080 | 48.887 | 67.487 | 1.00 | 15.50 |
| ATOM | 2517 | CB | PHE | 487 | 11.174 | 48.036 | 68.741 | 1.00 | 12.76 |
| ATOM | 2518 | CG | PHE | 487 | 11.758 | 48.741 | 69.884 | 1.00 | 12.18 |
| ATOM | 2519 | CD1 | PHE | 487 | 13.138 | 49.069 | 69.879 | 1.00 | 11.67 |
| ATOM | 2520 | CD2 | PHE | 487 | 10.987 | 49.065 | 70.985 | 1.00 | 12.34 |
| ATOM | 2521 | CE1 | PHE | 487 | 13.709 | 49.708 | 70.975 | 1.00 | 12.23 |
| ATOM | 2522 | CE2 | PHE | 487 | 11.552 | 49.727 | 72.097 | 1.00 | 13.42 |
| ATOM | 2523 | CZ | PHE | 487 | 12.937 | 50.044 | 72.075 | 1.00 | 12.97 |
| ATOM | 2524 | C | PHE | 487 | 11.076 | 48.043 | 66.241 | 1.00 | 17.36 |
| ATOM | 2525 | O | PHE | 487 | 12.130 | 47.704 | 65.711 | 1.00 | 18.27 |
| ATOM | 2526 | N | ASP | 488 | 9.905 | 47.728 | 65.719 | 1.00 | 19.57 |
| ATOM | 2528 | CA | ASP | 488 | 9.892 | 46.945 | 64.483 | 1.00 | 20.13 |
| ATOM | 2529 | CB | ASP | 488 | 8.470 | 46.499 | 64.106 | 1.00 | 24.27 |
| ATOM | 2530 | CG | ASP | 488 | 8.496 | 45.499 | 62.992 | 1.00 | 29.59 |
| ATOM | 2531 | OD1 | ASP | 488 | 9.131 | 44.444 | 63.191 | 1.00 | 36.24 |
| ATOM | 2532 | OD2 | ASP | 488 | 7.964 | 45.752 | 61.907 | 1.00 | 33.69 |
| ATOM | 2533 | C | ASP | 488 | 10.488 | 47.784 | 63.346 | 1.00 | 18.94 |
| ATOM | 2534 | O | ASP | 488 | 11.215 | 47.273 | 62.444 | 1.00 | 16.23 |
| ATOM | 2535 | N | TYR | 489 | 10.150 | 49.082 | 63.347 | 1.00 | 17.75 |
| ATOM | 2537 | CA | TYR | 489 | 10.712 | 49.989 | 62.324 | 1.00 | 17.95 |
| ATOM | 2538 | CB | TYR | 489 | 10.131 | 51.399 | 62.490 | 1.00 | 17.00 |
| ATOM | 2539 | CG | TYR | 489 | 10.784 | 52.406 | 61.612 | 1.00 | 15.28 |
| ATOM | 2540 | CD1 | TYR | 489 | 10.356 | 52.584 | 60.313 | 1.00 | 14.83 |
| ATOM | 2541 | CE1 | TYR | 489 | 10.989 | 53.458 | 59.479 | 1.00 | 15.97 |
| ATOM | 2542 | CD2 | TYR | 489 | 11.877 | 53.158 | 62.063 | 1.00 | 15.71 |
| ATOM | 2543 | CE2 | TYR | 489 | 12.511 | 54.063 | 61.209 | 1.00 | 14.92 |

TABLE 2-continued

Coordinates of Lck bound with AMP-PNP

| | Atom Type | Res | # | X | Y | Z | Occ | B |
|---|---|---|---|---|---|---|---|---|
| ATOM | 2544 | CZ | TYR | 489 | 12.065 | 54.201 | 59.929 | 1.00 | 15.91 |
| ATOM | 2545 | OH | TYR | 489 | 12.646 | 55.117 | 59.055 | 1.00 | 17.58 |
| ATOM | 2547 | C | TYR | 489 | 12.258 | 50.052 | 62.496 | 1.00 | 16.42 |
| ATOM | 2548 | O | TYR | 489 | 13.005 | 50.000 | 61.532 | 1.00 | 15.86 |
| ATOM | 2549 | N | LEU | 490 | 12.702 | 50.223 | 63.726 | 1.00 | 16.20 |
| ATOM | 2551 | CA | LEU | 490 | 14.130 | 50.318 | 63.992 | 1.00 | 17.33 |
| ATOM | 2552 | CB | LEU | 490 | 14.357 | 50.563 | 65.480 | 1.00 | 15.71 |
| ATOM | 2553 | CG | LEU | 490 | 13.988 | 51.980 | 65.957 | 1.00 | 18.53 |
| ATOM | 2554 | CD1 | LEU | 490 | 13.929 | 52.008 | 67.486 | 1.00 | 13.48 |
| ATOM | 2555 | CD2 | LEU | 490 | 15.081 | 52.997 | 65.466 | 1.00 | 13.64 |
| ATOM | 2556 | C | LEU | 490 | 14.848 | 49.036 | 63.546 | 1.00 | 17.72 |
| ATOM | 2557 | O | LEU | 490 | 15.904 | 49.116 | 62.933 | 1.00 | 17.65 |
| ATOM | 2558 | N | ARG | 491 | 14.249 | 47.881 | 63.824 | 1.00 | 18.78 |
| ATOM | 2560 | CA | ARG | 491 | 14.840 | 46.616 | 63.419 | 1.00 | 17.34 |
| ATOM | 2561 | CB | ARG | 491 | 13.982 | 45.428 | 63.875 | 1.00 | 17.59 |
| ATOM | 2562 | CG | ARG | 491 | 14.540 | 44.136 | 63.232 | 1.00 | 24.17 |
| ATOM | 2563 | CD | ARG | 491 | 13.523 | 43.026 | 63.167 | 1.00 | 22.99 |
| ATOM | 2564 | NE | ARG | 491 | 12.284 | 43.481 | 62.543 | 1.00 | 25.56 |
| ATOM | 2566 | CZ | ARG | 491 | 12.064 | 43.567 | 61.239 | 1.00 | 22.13 |
| ATOM | 2567 | NH1 | ARG | 491 | 12.999 | 43.225 | 60.371 | 1.00 | 20.13 |
| ATOM | 2570 | NH2 | ARG | 491 | 10.894 | 44.032 | 60.802 | 1.00 | 22.56 |
| ATOM | 2573 | C | ARG | 491 | 14.987 | 46.543 | 61.911 | 1.00 | 15.82 |
| ATOM | 2574 | O | ARG | 491 | 16.047 | 46.194 | 61.391 | 1.00 | 17.69 |
| ATOM | 2575 | N | SER | 492 | 13.929 | 46.895 | 61.201 | 0.71 | 14.44 |
| ATOM | 2577 | CA | SER | 492 | 13.948 | 46.832 | 59.751 | 0.71 | 12.85 |
| ATOM | 2578 | CB | SER | 492 | 12.560 | 47.197 | 59.208 | 0.71 | 10.21 |
| ATOM | 2579 | OG | SER | 492 | 12.535 | 47.140 | 57.800 | 0.71 | 13.48 |
| ATOM | 2581 | C | SER | 492 | 15.009 | 47.747 | 59.152 | 0.71 | 12.75 |
| ATOM | 2582 | O | SER | 492 | 15.688 | 47.387 | 58.208 | 0.71 | 12.67 |
| ATOM | 2583 | N | VAL | 493 | 15.128 | 48.946 | 59.687 | 1.00 | 15.45 |
| ATOM | 2585 | CA | VAL | 493 | 16.101 | 49.895 | 59.178 | 1.00 | 15.94 |
| ATOM | 2586 | CB | VAL | 493 | 15.912 | 51.314 | 59.829 | 1.00 | 18.03 |
| ATOM | 2587 | CG1 | VAL | 493 | 17.062 | 52.223 | 59.447 | 1.00 | 15.50 |
| ATOM | 2588 | CG2 | VAL | 493 | 14.587 | 51.931 | 59.354 | 1.00 | 14.02 |
| ATOM | 2589 | C | VAL | 493 | 17.520 | 49.389 | 59.452 | 1.00 | 12.14 |
| ATOM | 2590 | O | VAL | 493 | 18.341 | 49.419 | 58.586 | 1.00 | 11.76 |
| ATOM | 2591 | N | LEU | 494 | 17.766 | 48.933 | 60.667 | 1.00 | 13.03 |
| ATOM | 2593 | CA | LEU | 494 | 19.086 | 48.432 | 61.028 | 1.00 | 14.71 |
| ATOM | 2594 | CB | LEU | 494 | 19.157 | 48.159 | 62.520 | 1.00 | 10.71 |
| ATOM | 2595 | CG | LEU | 494 | 19.173 | 49.410 | 63.390 | 1.00 | 8.89 |
| ATOM | 2596 | CD1 | LEU | 494 | 18.912 | 49.063 | 64.858 | 1.00 | 2.00 |
| ATOM | 2597 | CD2 | LEU | 494 | 20.551 | 50.101 | 63.290 | 1.00 | 12.44 |
| ATOM | 2598 | C | LEU | 494 | 19.502 | 47.218 | 60.180 | 1.00 | 17.11 |
| ATOM | 2599 | O | LEU | 494 | 20.666 | 47.111 | 59.803 | 1.00 | 16.73 |
| ATOM | 2600 | N | GLU | 495 | 18.559 | 46.339 | 59.844 | 1.00 | 20.35 |
| ATOM | 2602 | CA | GLU | 495 | 18.876 | 45.198 | 58.999 | 1.00 | 21.31 |
| ATOM | 2603 | CB | GLU | 495 | 17.669 | 44.245 | 58.899 | 1.00 | 23.20 |
| ATOM | 2604 | CG | GLU | 495 | 17.373 | 43.530 | 60.206 | 1.00 | 25.30 |
| ATOM | 2605 | CD | GLU | 495 | 16.180 | 42.595 | 60.127 | 1.00 | 27.48 |
| ATOM | 2606 | OE1 | GLU | 495 | 15.434 | 42.595 | 59.123 | 1.00 | 29.73 |
| ATOM | 2607 | OE2 | GLU | 495 | 15.960 | 41.852 | 61.083 | 1.00 | 31.46 |
| ATOM | 2608 | C | GLU | 495 | 19.270 | 45.711 | 57.611 | 1.00 | 22.77 |
| ATOM | 2609 | O | GLU | 495 | 20.174 | 45.168 | 56.954 | 1.00 | 22.87 |
| ATOM | 2610 | N | ASP | 496 | 18.574 | 46.740 | 57.126 | 1.00 | 22.86 |
| ATOM | 2612 | CA | ASP | 496 | 18.915 | 47.313 | 55.831 | 1.00 | 22.17 |
| ATOM | 2613 | CB | ASP | 496 | 17.885 | 58.377 | 55.400 | 1.00 | 23.72 |
| ATOM | 2614 | CG | ASP | 496 | 16.620 | 47.773 | 54.828 | 1.00 | 24.62 |
| ATOM | 2615 | OD1 | ASP | 496 | 16.584 | 46.547 | 54.539 | 1.00 | 27.54 |
| ATOM | 2616 | OD2 | ASP | 496 | 15.644 | 48.526 | 43.664 | 1.00 | 23.63 |
| ATOM | 2617 | C | ASP | 496 | 20.303 | 47.935 | 55.898 | 1.00 | 20.74 |
| ATOM | 2618 | O | ASP | 496 | 21.034 | 47.881 | 54.941 | 1.00 | 20.45 |
| ATOM | 2619 | N | PHE | 497 | 20.653 | 48.551 | 57.031 | 1.00 | 22.83 |
| ATOM | 2621 | CA | PHE | 497 | 21.990 | 49.160 | 57.185 | 1.00 | 23.54 |
| ATOM | 2622 | CB | PHE | 497 | 22.107 | 49.907 | 58.534 | 1.00 | 22.41 |
| ATOM | 2623 | CG | PHE | 497 | 21.396 | 51.257 | 58.593 | 1.00 | 19.41 |
| ATOM | 2624 | CD1 | PHE | 47 | 20.699 | 51.789 | 57.504 | 1.00 | 16.87 |
| ATOM | 2625 | CD2 | PHE | 497 | 21.446 | 51.973 | 59.761 | 1.00 | 17.79 |
| ATOM | 2626 | CE1 | PHE | 497 | 20.042 | 53.066 | 57.611 | 1.00 | 15.59 |
| ATOM | 2627 | CE2 | PHE | 497 | 20.808 | 53.213 | 59.83 | 1.00 | 16.89 |
| ATOM | 2628 | CZ | PHE | 497 | 20.107 | 53.751 | 58.799 | 1.00 | 15.28 |
| ATOM | 2629 | C | PHE | 497 | 23.144 | 48.119 | 57.079 | 1.00 | 26.43 |
| ATOM | 2630 | O | PHE | 497 | 24.132 | 48.361 | 56.405 | 1.00 | 24.05 |
| ATOM | 2631 | N | PHE | 498 | 22.995 | 46.993 | 57.786 | 1.00 | 31.81 |
| ATOM | 2633 | CA | PHE | 498 | 23.937 | 45.847 | 57.839 | 1.00 | 34.53 |

TABLE 2-continued

Coordinates of Lck bound with AMP-PNP

| | | Atom Type | Res | # | X | Y | Z | Occ | B |
|---|---|---|---|---|---|---|---|---|---|
| ATOM | 2634 | CB | PHE | 498 | 23.410 | 44.895 | 58.970 | 1.00 | 38.33 |
| ATOM | 2635 | CG | PHE | 498 | 23.812 | 43.440 | 58.870 | 1.00 | 42.97 |
| ATOM | 2636 | CD1 | PHE | 498 | 25.128 | 43.061 | 58.962 | 1.00 | 44.23 |
| ATOM | 2637 | CD2 | PHE | 498 | 22.841 | 42.441 | 58.808 | 1.00 | 45.57 |
| ATOM | 2638 | CE1 | PHE | 498 | 25.494 | 41.718 | 59.002 | 1.00 | 45.32 |
| ATOM | 2639 | CE2 | PHE | 498 | 23.194 | 41.084 | 58.846 | 1.00 | 45.40 |
| ATOM | 2640 | CZ | PHE | 498 | 24.536 | 40.728 | 58.947 | 1.00 | 45.26 |
| ATOM | 2641 | C | PHE | 498 | 23.986 | 45.174 | 56.452 | 1.00 | 34.71 |
| ATOM | 2642 | O | PHE | 498 | 25.078 | 44.797 | 55.999 | 1.00 | 34.04 |
| ATOM | 2643 | N | THR | 499 | 22.861 | 45.066 | 55.747 | 1.00 | 36.17 |
| ATOM | 2645 | CA | THR | 499 | 22.929 | 44.395 | 54.446 | 1.00 | 39.53 |
| ATOM | 2646 | CB | THR | 499 | 21.599 | 43.788 | 53.879 | 1.00 | 38.32 |
| ATOM | 2647 | OG1 | THR | 499 | 20.731 | 44.827 | 53.457 | 1.00 | 40.33 |
| ATOM | 2649 | CG2 | THR | 499 | 20.883 | 42.893 | 54.883 | 1.00 | 38.45 |
| ATOM | 2650 | C | THR | 499 | 23.610 | 45.230 | 53.394 | 1.00 | 42.57 |
| ATOM | 2651 | O | THR | 499 | 24.254 | 44.701 | 52.449 | 1.00 | 45.02 |
| ATOM | 2652 | N | ALA | 500 | 23.561 | 46.542 | 53.566 | 1.00 | 46.24 |
| ATOM | 2654 | CA | ALA | 500 | 24.251 | 47.406 | 52.624 | 1.00 | 48.43 |
| ATOM | 2655 | CB | ALA | 500 | 23.704 | 48.821 | 52.716 | 1.00 | 48.43 |
| ATOM | 2656 | C | ALA | 500 | 25.755 | 47.359 | 52.979 | 1.00 | 48.93 |
| ATOM | 2657 | O | ALA | 500 | 26.588 | 47.243 | 52.081 | 1.00 | 51.02 |
| ATOM | 2658 | N | THR | 501 | 26.087 | 47.447 | 54.280 | 1.00 | 49.00 |
| ATOM | 2660 | CA | THR | 501 | 27.489 | 47.375 | 54.745 | 1.00 | 50.41 |
| ATOM | 2661 | CB | THR | 501 | 27.729 | 47.812 | 56.242 | 1.00 | 50.29 |
| ATOM | 2662 | OG1 | THR | 501 | 27.170 | 46.843 | 57.145 | 1.00 | 51.73 |
| ATOM | 2664 | CG2 | THR | 501 | 27.211 | 49.187 | 56.529 | 1.00 | 48.41 |
| ATOM | 2665 | C | THR | 501 | 28.051 | 45.942 | 54.648 | 1.00 | 51.23 |
| ATOM | 2666 | O | THR | 501 | 27.291 | 45.008 | 54.304 | 1.00 | 50.34 |
| ATOM | 2667 | OT | THR | 501 | 29.271 | 45.796 | 54.838 | 1.00 | 53.71 |
| ATOM | 2668 | S | SO4 | 901 | 20.240 | 32.671 | 68.950 | 1.00 | 20.54 |
| ATOM | 2669 | O1 | SO4 | 901 | 20.164 | 32.039 | 70.208 | 1.00 | 18.75 |
| ATOM | 2670 | O2 | SO4 | 901 | 18.884 | 33.001 | 68.524 | 1.00 | 21.22 |
| ATOM | 2671 | O3 | SO4 | 901 | 21.012 | 33.903 | 69.104 | 1.00 | 22.65 |
| ATOM | 2672 | O4 | SO4 | 901 | 20.810 | 31.783 | 68.019 | 1.00 | 20.07 |
| ATOM | 2673 | PA | ANP | 1 | 25.168 | 41.602 | 88.040 | 1.00 | 59.70 |
| ATOM | 2674 | O1A | ANP | 1 | 25.690 | 41.585 | 89.452 | 1.00 | 62.05 |
| ATOM | 2675 | O2A | ANP | 1 | 23.870 | 40.964 | 87.774 | 1.00 | 60.10 |
| ATOM | 2676 | O5' | ANP | 1 | 26.271 | 40.936 | 87.075 | 1.00 | 55.58 |
| ATOM | 2677 | O3A | ANP | 1 | 25.238 | 43.072 | 87.395 | 1.00 | 58.85 |
| ATOM | 2678 | C5' | ANP | 1 | 27.126 | 39.813 | 87.313 | 1.00 | 47.85 |
| ATOM | 2679 | O4' | ANP | 1 | 27.811 | 39.435 | 85.961 | 1.00 | 42.19 |
| ATOM | 2680 | O4' | ANP | 1 | 27.328 | 38.181 | 85.485 | 1.00 | 39.82 |
| ATOM | 2681 | C1' | ANP | 1 | 27.393 | 38.245 | 84.067 | 1.00 | 34.30 |
| ATOM | 2682 | N9 | ANP | 1 | 26.168 | 37.720 | 83.671 | 1.00 | 29.49 |
| ATOM | 2683 | C4 | ANP | 1 | 25.987 | 36.620 | 82.839 | 1.00 | 27.56 |
| ATOM | 2684 | N3 | ANP | 1 | 26.971 | 35.962 | 82.079 | 1.00 | 25.59 |
| ATOM | 2685 | C2 | ANP | 1 | 26.430 | 34.902 | 81.461 | 1.00 | 25.56 |
| ATOM | 2686 | N1 | ANP | 1 | 25.142 | 34.566 | 81.317 | 1.00 | 22.28 |
| ATOM | 2687 | C6 | ANP | 1 | 24.205 | 35.236 | 82.032 | 1.00 | 24.41 |
| ATOM | 2688 | N6 | ANP | 1 | 22.887 | 34.873 | 81.858 | 1.00 | 23.00 |
| ATOM | 2689 | C5 | ANP | 1 | 24.642 | 36.295 | 82.892 | 1.00 | 27.32 |
| ATOM | 2690 | N7 | ANP | 1 | 23.958 | 37.069 | 83.756 | 1.00 | 27.18 |
| ATOM | 2691 | C8 | ANP | 1 | 24.888 | 37.892 | 84.271 | 1.00 | 29.52 |
| ATOM | 2692 | C2' | ANP | 1 | 27.365 | 39.606 | 83.480 | 1.00 | 37.32 |
| ATOM | 2693 | O2' | ANP | 1 | 27.402 | 39.564 | 81.930 | 1.00 | 37.60 |
| ATOM | 2694 | C3' | ANP | 1 | 28.466 | 39.860 | 84.536 | 1.00 | 41.10 |
| ATOM | 2695 | O3' | ANP | 1 | 29.648 | 40.806 | 84.396 | 1.00 | 40.76 |
| ATOM | 2696 | OH2 | TIP | 1 | 21.636 | 29.682 | 74.788 | 1.00 | 24.70 |
| ATOM | 2699 | OH2 | TIP | 2 | 19.421 | 27.894 | 78.845 | 1.00 | 15.80 |
| ATOM | 2702 | OH2 | TIP | 3 | 14.819 | 51.729 | 79.254 | 1.00 | 11.50 |
| ATOM | 2705 | OH2 | TIP | 4 | 19.432 | 60.733 | 77.592 | 1.00 | 22.33 |
| ATOM | 2708 | OH2 | TIP | 5 | 20.635 | 62.747 | 73.259 | 1.00 | 21.30 |
| ATOM | 2711 | OH2 | TIP | 6 | 16.552 | 32.841 | 74.619 | 1.00 | 25.56 |
| ATOM | 2714 | OH2 | TIP | 7 | 24.548 | 68.842 | 70.700 | 1.00 | 20.10 |
| ATOM | 2717 | OH2 | TIP | 8 | 3.895 | 16.823 | 94.898 | 1.00 | 13.20 |
| ATOM | 2720 | OH2 | TIP | 9 | 18.109 | 61.908 | 79.708 | 1.00 | 27.65 |
| ATOM | 2723 | OH2 | TIP | 10 | 16.726 | 62.080 | 62.427 | 1.00 | 20.90 |
| ATOM | 2726 | OH2 | TIP | 11 | 25.219 | 50.449 | 80.027 | 1.00 | 19.51 |
| ATOM | 2729 | OH2 | TIP | 12 | 26.686 | 31.635 | 75.090 | 1.00 | 13.82 |
| ATOM | 2732 | OH2 | TIP | 13 | 25.361 | 21.684 | 76.987 | 1.00 | 26.96 |
| ATOM | 2735 | OH2 | TIP | 14 | 3.847 | 51.668 | 76.148 | 1.00 | 22.21 |
| ATOM | 2738 | OH2 | TIP | 15 | 33.052 | 40.009 | 77.678 | 1.00 | 32.58 |
| ATOM | 2741 | OH2 | TIP | 16 | 23.215 | 20.551 | 78.038 | 1.00 | 29.80 |
| ATOM | 2744 | OH2 | TIP | 17 | 7.654 | 54028 | 63.788 | 1.00 | 34.59 |

TABLE 2-continued

Coordinates of Lck bound with AMP-PNP

| | | Atom Type | Res | # | X | Y | Z | Occ | B |
|---|---|---|---|---|---|---|---|---|---|
| ATOM | 2747 | OH2 | TIP | 18 | 28.141 | 56.263 | 74.474 | 1.00 | 22.00 |
| ATOM | 2750 | OH2 | TIP | 19 | 22.179 | 18.839 | 82.211 | 1.00 | 26.18 |
| ATOM | 2753 | OH2 | TIP | 20 | 13.275 | 34.109 | 76.607 | 1.00 | 22.45 |
| ATOM | 2756 | OH2 | TIP | 21 | 7.198 | 57.427 | 104.428 | 1.00 | 22.43 |
| ATOM | 2759 | OH2 | TIP | 22 | 35.735 | 44.087 | 79.480 | 1.00 | 33.94 |
| ATOM | 2762 | OH2 | TIP | 23 | 8.540 | 65.595 | 69.023 | 1.00 | 24.56 |
| ATOM | 2765 | OH2 | TIP | 24 | 22.270 | 28.066 | 79.324 | 1.00 | 22.91 |
| ATOM | 2768 | OH2 | TIP | 25 | 14.107 | 69.026 | 73.845 | 1.00 | 31.41 |
| ATOM | 2771 | OH2 | TIP | 26 | 13.696 | 55.586 | 79.458 | 1.00 | 22.90 |
| ATOM | 2774 | OH2 | TIP | 27 | 4.349 | 54.682 | 67.141 | 1.00 | 45.29 |
| ATOM | 2777 | OH2 | TIP | 28 | 6.680 | 45.227 | 67.941 | 1.00 | 43.31 |
| ATOM | 2780 | OH2 | TIP | 29 | 24.714 | 78.648 | 73.916 | 1.00 | 17.34 |
| ATOM | 2783 | OH2 | TIP | 30 | 30.134 | 59.806 | 72.383 | 1.00 | 29.23 |
| ATOM | 2786 | OH2 | TIP | 31 | 26.035 | 23.821 | 78.463 | 1.00 | 21.36 |
| ATOM | 2789 | OH2 | TIP | 32 | 3.066 | 56.997 | 68.078 | 1.00 | 28.45 |
| ATOM | 2792 | OH2 | TIP | 33 | 6.610 | 51.972 | 70.152 | 1.00 | 23.35 |
| ATOM | 2795 | OH2 | TIP | 34 | 26.470 | 70.439 | 71.773 | 1.00 | 36.32 |
| ATOM | 2798 | OH2 | TIP | 35 | 30.259 | 41.069 | 81.623 | 1.00 | 23.00 |
| ATOM | 2801 | OH2 | TIP | 36 | 13.095 | 71.374 | 72.576 | 1.00 | 42.40 |
| ATOM | 2804 | OH2 | TIP | 37 | 29.729 | 18.036 | 80.754 | 1.00 | 33.66 |
| ATOM | 2807 | OH2 | TIP | 38 | 36.082 | 38.615 | 74.443 | 1.00 | 37.20 |
| ATOM | 2810 | OH2 | TIP | 39 | 29.667 | 65.962 | 75.095 | 1.00 | 56.18 |
| ATOM | 2813 | OH2 | TIP | 40 | 16.535 | 52.578 | 84.855 | 1.00 | 32.05 |
| ATOM | 2816 | OH2 | TIP | 41 | 4.169 | 43.760 | 85.732 | 1.00 | 30.89 |
| ATOM | 2819 | OH2 | TIP | 42 | 29.884 | 58.322 | 74.618 | 1.00 | 17.65 |
| ATOM | 2822 | OH2 | TIP | 43 | 15.951 | 20.096 | 79.975 | 1.00 | 25.65 |
| ATOM | 2825 | OH2 | TIP | 44 | 4.646 | 47.648 | 75.172 | 1.00 | 35.85 |
| ATOM | 2828 | OH2 | TIP | 45 | 15.058 | 76.771 | 76.303 | 1.00 | 30.45 |
| ATOM | 2831 | OH2 | TIP | 46 | 6.244 | 59.942 | 101.309 | 1.00 | 35.15 |
| ATOM | 2834 | OH2 | TIP | 47 | 14.040 | 45.715 | 83.639 | 1.00 | 18.86 |
| ATOM | 2837 | OH2 | TIP | 48 | 14.202 | 25.165 | 81.284 | 1.00 | 34.29 |
| ATOM | 2840 | OH2 | TIP | 49 | 10.663 | 40.652 | 67.185 | 1.00 | 26.39 |
| ATOM | 2843 | OH2 | TIP | 50 | 33.301 | 41.942 | 62.513 | 1.00 | 35.25 |
| ATOM | 2846 | OH2 | TIP | 51 | 6.527 | 57.868 | 77.114 | 1.00 | 53.32 |
| ATOM | 2849 | OH2 | TIP | 52 | 17.044 | 28.731 | 80.298 | 1.00 | 36.84 |
| ATOM | 2852 | OH2 | TIP | 53 | 6.062 | 57.571 | 65.730 | 1.00 | 30.27 |
| ATOM | 2855 | OH2 | TIP | 54 | 17.822 | 52.756 | 80.733 | 1.00 | 34.91 |
| ATOM | 2858 | OH2 | TIP | 55 | 11.552 | 33.271 | 69.618 | 1.00 | 32.40 |
| ATOM | 2861 | OH2 | TIP | 56 | 12.856 | 35.833 | 79.201 | 1.00 | 22.14 |
| ATOM | 2864 | OH2 | TIP | 57 | 40.066 | 43.507 | 77.613 | 1.00 | 50.14 |
| ATOM | 2867 | OH2 | TIP | 58 | 2.995 | 17.966 | 92.504 | 1.00 | 37.28 |
| ATOM | 2870 | OH2 | TIP | 59 | 13.311 | 23.566 | 95.035 | 1.00 | 47.12 |
| ATOM | 2873 | OH2 | TIP | 60 | 11.795 | 37.974 | 66.135 | 1.00 | 36.11 |
| ATOM | 2876 | OH2 | TIP | 61 | 24.504 | 67.408 | 74.469 | 1.00 | 35.25 |
| ATOM | 2879 | OH2 | TIP | 62 | 43.357 | 40.085 | 77.338 | 1.00 | 51.90 |
| ATOM | 2882 | OH2 | TIP | 63 | 1.393 | 21.671 | 100.291 | 1.00 | 33.39 |
| ATOM | 2885 | OH2 | TIP | 64 | 11.280 | 66.450 | 68.597 | 1.00 | 31.52 |
| ATOM | 2888 | OH2 | TIP | 65 | 4.661 | 48.407 | 66.893 | 1.00 | 31.00 |
| ATOM | 2891 | OH2 | TIP | 66 | 23.517 | 29.080 | 77.018 | 1.00 | 31.18 |
| ATOM | 2894 | OH2 | TIP | 67 | 13.747 | 73.842 | 73.889 | 1.00 | 26.91 |
| ATOM | 2897 | OH2 | TIP | 68 | 15.378 | 54.181 | 81.664 | 1.00 | 19.28 |
| ATOM | 2900 | OH2 | TIP | 69 | 35.556 | 54.625 | 72.574 | 1.00 | 56.78 |
| ATOM | 2903 | OH2 | TIP | 70 | 25.738 | 53.333 | 58.018 | 1.00 | 44.39 |
| ATOM | 2906 | OH2 | TIP | 71 | 14.505 | 45.522 | 57.007 | 1.00 | 52.07 |
| ATOM | 2909 | OH2 | TIP | 72 | 9.631 | 42.340 | 87.085 | 1.00 | 47.28 |
| ATOM | 2912 | OH2 | TIP | 73 | 24.646 | 26.338 | 78.448 | 1.00 | 50.23 |
| ATOM | 2915 | OH2 | TIP | 74 | 17.613 | 34.219 | 99.904 | 1.00 | 41.24 |
| ATOM | 2918 | OH2 | TIP | 75 | 31.787 | 33.945 | 97.250 | 1.00 | 76.43 |
| ATOM | 2921 | OH2 | TIP | 76 | 29.710 | 33.429 | 98.446 | 1.00 | 67.00 |
| ATOM | 2924 | OH2 | TIP | 77 | 26.300 | 72.730 | 70.717 | 1.00 | 25.94 |
| ATOM | 2927 | OH2 | TIP | 78 | 11.976 | 33.414 | 80.103 | 1.00 | 24.71 |
| ATOM | 2930 | OH2 | TIP | 79 | 29.259 | 62.469 | 72.136 | 1.00 | 30.42 |
| ATOM | 2933 | OH2 | TIP | 80 | 26.839 | 65.527 | 74.362 | 1.00 | 40.02 |
| ATOM | 2936 | OH2 | TIP | 81 | 27.257 | 19.893 | 78.082 | 1.00 | 32.57 |
| ATOM | 2939 | OH2 | TIP | 82 | 29.912 | 36.264 | 82.030 | 1.00 | 41.11 |
| ATOM | 2942 | OH2 | TIP | 84 | 18.856 | 52.421 | 83.223 | 1.00 | 30.89 |
| ATOM | 2945 | OH2 | TIP | 85 | 27.449 | 24.537 | 94.644 | 1.00 | 62.62 |
| ATOM | 2948 | OH2 | TIP | 86 | −1.546 | 21.109 | 100.288 | 1.00 | 51.77 |
| ATOM | 2951 | OH2 | TIP | 87 | 15.729 | 35.403 | 101.377 | 1.00 | 39.68 |
| ATOM | 2954 | OH2 | TIP | 88 | 34.403 | 37.880 | 76.403 | 1.00 | 28.62 |
| ATOM | 2957 | OH2 | TIP | 89 | 24.265 | 74.217 | 76.897 | 1.00 | 33.70 |
| ATOM | 2960 | OH2 | TIP | 90 | 13.249 | 22.449 | 79.551 | 1.00 | 32.00 |
| ATOM | 2963 | OH2 | TIP | 91 | 9.902 | 52.146 | 79.592 | 1.00 | 40.91 |
| ATOM | 2966 | OH2 | TIP | 92 | 20.101 | 71.150 | 85.234 | 1.00 | 42.55 |

TABLE 2-continued

Coordinates of Lck bound with AMP-PNP

| | | Atom Type | Res | # | X | Y | Z | Occ | B |
|---|---|---|---|---|---|---|---|---|---|
| ATOM | 2969 | OH2 | TIP | 93 | 4.608 | 59.409 | 77.922 | 1.00 | 43.45 |
| ATOM | 2972 | OH2 | TIP | 94 | 10.440 | 59.077 | 64.328 | 1.00 | 40.61 |
| ATOM | 2975 | OH2 | TIP | 95 | 17.443 | 51.837 | 87.380 | 1.00 | 44.75 |
| ATOM | 2978 | OH2 | TIP | 96 | 14.747 | 19.195 | 88.163 | 1.00 | 32.29 |
| ATOM | 2981 | OH2 | TIP | 98 | 22.641 | 31.842 | 72.909 | 1.00 | 68.73 |
| ATOM | 2984 | OH2 | TIP | 99 | 16.410 | 46.201 | 86.092 | 1.00 | 35.14 |
| ATOM | 2987 | OH2 | TIP | 100 | 32.717 | 59.893 | 71.213 | 1.00 | 53.13 |
| ATOM | 2990 | OH2 | TIP | 101 | 12.529 | 44.995 | 98.969 | 1.00 | 36.54 |
| ATOM | 2993 | OH2 | TIP | 102 | 15.282 | 38.471 | 102.107 | 1.00 | 36.81 |
| ATOM | 2996 | OH2 | TIP | 103 | −1.910 | 21.152 | 94.291 | 1.00 | 36.76 |
| ATOM | 2999 | OH2 | TIP | 104 | 23.386 | 43.084 | 94.045 | 1.00 | 37.19 |
| ATOM | 3002 | OH2 | TIP | 105 | 24.169 | 18.508 | 94.575 | 1.00 | 54.05 |
| ATOM | 3005 | OH2 | TIP | 106 | 32.547 | 63.480 | 69.339 | 1.00 | 62.31 |
| ATOM | 3008 | OH2 | TIP | 107 | 32.770 | 33.673 | 71.653 | 1.00 | 36.53 |
| ATOM | 3011 | OH2 | TIP | 108 | 6.133 | 39.983 | 88.066 | 1.00 | 48.22 |
| ATOM | 3014 | OH2 | TIP | 109 | 27.593 | 29.189 | 75.515 | 1.00 | 52.79 |
| ATOM | 3017 | OH2 | TIP | 110 | 34.714 | 32.216 | 91.918 | 1.00 | 32.03 |
| ATOM | 3020 | OH2 | TIP | 111 | 5.948 | 50.113 | 63.208 | 1.00 | 47.91 |
| ATOM | 3023 | OH2 | TIP | 112 | 7.211 | 28.277 | 92.069 | 1.00 | 58.25 |
| ATOM | 3026 | OH2 | TIP | 113 | 4.659 | 62.123 | 78.278 | 1.00 | 65.10 |
| ATOM | 3029 | OH2 | TIP | 114 | 12.092 | 21.414 | 95.200 | 1.00 | 45.95 |
| ATOM | 3032 | OH2 | TIP | 115 | −5.762 | 20.102 | 93.377 | 1.00 | 54.02 |
| ATOM | 3035 | OH2 | TIP | 116 | 34.368 | 49.023 | 60.476 | 1.00 | 48.95 |
| ATOM | 3038 | OH2 | TIP | 117 | 15.264 | 39.756 | 90.933 | 1.00 | 50.11 |
| ATOM | 3041 | OH2 | TIP | 118 | 20.473 | 34.315 | 86.628 | 1.00 | 35.15 |
| ATOM | 3044 | OH2 | TIP | 119 | 12.962 | 30.648 | 72.355 | 1.00 | 42.72 |
| ATOM | 3047 | OH2 | TIP | 120 | 29.284 | 70.894 | 70.767 | 1.00 | 60.04 |
| ATOM | 3050 | OH2 | TIP | 121 | 6.144 | 34.703 | 75.934 | 1.00 | 47.46 |
| ATOM | 3053 | OH2 | TIP | 122 | 26.483 | 75.969 | 74.981 | 1.00 | 62.56 |
| ATOM | 3056 | OH2 | TIP | 123 | 40.678 | 38.708 | 69.386 | 1.00 | 42.80 |
| ATOM | 3059 | OH2 | TIP | 124 | 18.287 | 74.826 | 79.516 | 1.00 | 35.33 |
| ATOM | 3062 | OH2 | TIP | 125 | 24.227 | 25.786 | 95.606 | 1.00 | 45.47 |
| ATOM | 3065 | OH2 | TIP | 126 | 26.975 | 26.962 | 73.533 | 1.00 | 31.23 |
| ATOM | 3068 | OH2 | TIP | 127 | 34.377 | 35.809 | 70.653 | 1.00 | 42.79 |
| ATOM | 3071 | OH2 | TIP | 128 | 9.420 | 66.131 | 80.020 | 1.00 | 41.85 |
| ATOM | 3074 | OH2 | TIP | 129 | 5.913 | 42.023 | 93.982 | 1.00 | 37.93 |

TABLE 3

Coordinates of Lck bound with AMP-PNP

| | | Atom Type | Res | # | X | Y | Z | Occ | B |
|---|---|---|---|---|---|---|---|---|---|
| ATOM | 1 | CB | LYS | 231 | 1.385 | 26.773 | 89.461 | 1.00 | 21.34 |
| ATOM | 2 | CG | LYS | 231 | 0.537 | 26.769 | 88.245 | 1.00 | 21.51 |
| ATOM | 3 | CD | LYS | 231 | 1.065 | 25.734 | 87.277 | 1.00 | 23.65 |
| ATOM | 4 | CE | LYS | 231 | 0.120 | 25.565 | 86.108 | 1.00 | 23.61 |
| ATOM | 5 | NZ | LYS | 231 | 0.728 | 24.648 | 85.080 | 1.00 | 25.65 |
| ATOM | 6 | HZ1 | LYS | 231 | 0.915 | 23.722 | 85.493 | 1.00 | 0.00 |
| ATOM | 7 | HZ2 | LYS | 231 | 1.620 | 25.071 | 84.742 | 1.00 | 0.00 |
| ATOM | 8 | HZ3 | LYS | 231 | 0.075 | 24.561 | 84.274 | 1.00 | 0.00 |
| ATOM | 9 | C | LYS | 231 | 1.988 | 27.638 | 91.652 | 1.00 | 19.85 |
| ATOM | 10 | O | LYS | 231 | 3.059 | 28.227 | 91.744 | 1.00 | 20.43 |
| ATOM | 11 | HT1 | LYS | 231 | 2.338 | 29.252 | 89.546 | 1.00 | 0.00 |
| ATOM | 12 | HT2 | LYS | 231 | 1.183 | 29.956 | 90.579 | 1.00 | 0.00 |
| ATOM | 13 | N | LYS | 231 | 1.355 | 29.219 | 89.879 | 1.00 | 20.87 |
| ATOM | 14 | HT3 | LYS | 231 | 0.717 | 29.358 | 89.057 | 1.00 | 0.00 |
| ATOM | 15 | CA | LYS | 231 | 1.088 | 27.870 | 90.472 | 1.00 | 20.91 |
| ATOM | 16 | N | PRO | 232 | 1.597 | 26.726 | 92.561 | 1.00 | 18.80 |
| ATOM | 17 | CD | PRO | 232 | 0.390 | 25.885 | 92.560 | 1.00 | 18.99 |
| ATOM | 18 | CA | PRO | 232 | 2.435 | 26.437 | 93.733 | 1.00 | 17.40 |
| ATOM | 19 | CB | PRO | 232 | 1.579 | 25.470 | 94.538 | 1.00 | 18.29 |
| ATOM | 20 | CG | PRO | 232 | 0.814 | 24.761 | 93.509 | 1.00 | 19.28 |
| ATOM | 21 | C | PRO | 232 | 3.705 | 25.766 | 93.253 | 1.00 | 15.67 |
| ATOM | 22 | O | PRO | 232 | 3.737 | 25.184 | 92.178 | 1.00 | 15.72 |
| ATOM | 23 | N | TRP | 233 | 4.744 | 25.851 | 94.063 | 1.00 | 15.43 |
| ATOM | 24 | H | TRP | 233 | 4.653 | 26.278 | 94.938 | 1.00 | 0.00 |
| ATOM | 25 | CA | TRP | 233 | 6.049 | 25.336 | 93.653 | 1.00 | 14.16 |
| ATOM | 26 | CB | TRP | 233 | 7.123 | 25.646 | 94.713 | 1.00 | 13.93 |
| ATOM | 27 | CG | TRP | 233 | 6.954 | 24.883 | 96.024 | 1.00 | 13.67 |

TABLE 3-continued

Coordinates of Lck bound with AMP-PNP

| | | Atom Type | Res | # | X | Y | Z | Occ | B |
|---|---|---|---|---|---|---|---|---|---|
| ATOM | 28 | CD2 | TRP | 233 | 7.354 | 23.532 | 96.282 | 1.00 | 13.44 |
| ATOM | 29 | CE2 | TRP | 233 | 7.057 | 23.264 | 97.626 | 1.00 | 13.68 |
| ATOM | 30 | CE3 | TRP | 233 | 7.945 | 22.518 | 95.485 | 1.00 | 13.97 |
| ATOM | 31 | CD1 | TRP | 233 | 6.443 | 25.356 | 97.181 | 1.00 | 13.30 |
| ATOM | 32 | NE1 | TRP | 233 | 6.510 | 24.402 | 98.161 | 1.00 | 12.97 |
| ATOM | 33 | HE1 | TRP | 233 | 6.237 | 24.512 | 99.089 | 1.00 | 0.00 |
| ATOM | 34 | CZ2 | TRP | 233 | 7.313 | 22.031 | 98.220 | 1.00 | 12.53 |
| ATOM | 35 | CZ3 | TRP | 233 | 8.207 | 21.261 | 96.095 | 1.00 | 12.04 |
| ATOM | 36 | CH2 | TRP | 233 | 7.884 | 21.044 | 97.449 | 1.00 | 12.52 |
| ATOM | 37 | C | TRP | 233 | 6.030 | 23.858 | 93.280 | 1.00 | 14.34 |
| ATOM | 38 | O | TRP | 233 | 6.738 | 23.462 | 92.380 | 1.00 | 13.58 |
| ATOM | 39 | N | TRP | 234 | 5.163 | 23.064 | 93.912 | 1.00 | 13.99 |
| ATOM | 40 | H | TRP | 234 | 4.556 | 23.452 | 94.570 | 1.00 | 0.00 |
| ATOM | 41 | CA | TRP | 234 | 5.112 | 21.632 | 93.603 | 1.00 | 14.92 |
| ATOM | 42 | CB | TRP | 234 | 4.507 | 20.854 | 94.790 | 1.00 | 13.19 |
| ATOM | 43 | CG | TRP | 234 | 3.124 | 21.289 | 95.147 | 1.00 | 12.51 |
| ATOM | 44 | CD2 | TRP | 234 | 2.755 | 22.231 | 96.158 | 1.00 | 12.55 |
| ATOM | 45 | CE2 | TRP | 234 | 1.346 | 22.370 | 96.127 | 1.00 | 13.35 |
| ATOM | 46 | CE3 | TRP | 234 | 3.488 | 22.980 | 97.079 | 1.00 | 14.36 |
| ATOM | 47 | CD1 | TRP | 234 | 1.938 | 20.883 | 94.555 | 1.00 | 12.11 |
| ATOM | 48 | NE1 | TRP | 234 | 0.874 | 21.538 | 95.149 | 1.00 | 11.94 |
| ATOM | 49 | HE1 | TRP | 234 | −0.056 | 21.431 | 94.898 | 1.00 | 0.00 |
| ATOM | 50 | CZ2 | TRP | 234 | 0.644 | 23.231 | 96.982 | 1.00 | 13.79 |
| ATOM | 51 | CZ3 | TRP | 234 | 2.786 | 23.866 | 97.946 | 1.00 | 16.07 |
| ATOM | 52 | CH2 | TRP | 234 | 1.373 | 23.975 | 97.886 | 1.00 | 16.13 |
| ATOM | 53 | C | TRP | 234 | 4.405 | 21.300 | 92.295 | 1.00 | 15.64 |
| ATOM | 54 | O | TRP | 234 | 4.413 | 20.139 | 91.829 | 1.00 | 15.96 |
| ATOM | 55 | N | CLU | 235 | 3.820 | 22.323 | 91.686 | 1.00 | 16.35 |
| ATOM | 56 | H | GLU | 235 | 3.838 | 23.203 | 92.107 | 1.00 | 0.00 |
| ATOM | 57 | CA | GLU | 235 | 3.152 | 22.179 | 90.402 | 1.00 | 18.95 |
| ATOM | 58 | CB | GLU | 235 | 1.672 | 22.623 | 90.489 | 1.00 | 19.45 |
| ATOM | 59 | CG | GLU | 235 | 0.789 | 21.713 | 91.394 | 1.00 | 21.99 |
| ATOM | 60 | CD | GLU | 235 | −0.684 | 21.852 | 91.119 | 1.00 | 24.05 |
| ATOM | 61 | OE1 | GLU | 235 | −1.084 | 22.883 | 90.512 | 1.00 | 26.95 |
| ATOM | 62 | OE2 | GLU | 235 | −1.450 | 20.942 | 91.542 | 1.00 | 24.79 |
| ATOM | 63 | C | GLU | 235 | 3.885 | 23.036 | 89.360 | 1.00 | 19.29 |
| ATOM | 64 | O | GLU | 235 | 3.701 | 22.834 | 88.169 | 1.00 | 20.91 |
| ATOM | 65 | N | ASP | 236 | 4.691 | 23.997 | 89.811 | 1.00 | 19.88 |
| ATOM | 66 | H | ASP | 236 | 4.823 | 24.117 | 90.773 | 1.00 | 0.00 |
| ATOM | 67 | CA | ASP | 236 | 5.384 | 24.897 | 88.880 | 1.00 | 20.52 |
| ATOM | 68 | CB | ASP | 236 | 5.972 | 26.104 | 89.645 | 1.00 | 21.88 |
| ATOM | 69 | CG | ASP | 236 | 6.438 | 27.211 | 88.724 | 1.00 | 24.16 |
| ATOM | 70 | OD1 | ASP | 236 | 5.609 | 27.763 | 87.958 | 1.00 | 25.94 |
| ATOM | 71 | OD2 | ASP | 236 | 7.641 | 27.543 | 88.786 | 1.00 | 26.72 |
| ATOM | 72 | C | ASP | 236 | 6.465 | 24.212 | 88.035 | 1.00 | 19.94 |
| ATOM | 73 | O | ASP | 236 | 7.405 | 23.589 | 88.560 | 1.00 | 20.22 |
| ATOM | 74 | N | GLU | 237 | 6.363 | 24.421 | 86.726 | 1.00 | 19.19 |
| ATOM | 75 | H | GLU | 237 | 5.643 | 24.976 | 86.428 | 1.00 | 0.00 |
| ATOM | 76 | CA | GLU | 237 | 7.291 | 23.876 | 85.759 | 1.00 | 18.93 |
| ATOM | 77 | CB | GLU | 237 | 6.767 | 24.171 | 84.336 | 1.00 | 21.53 |
| ATOM | 78 | CG | GLU | 237 | 5.949 | 25.481 | 84.159 | 1.00 | 25.16 |
| ATOM | 79 | CD | GLU | 237 | 4.521 | 25.450 | 84.779 | 1.00 | 26.69 |
| ATOM | 80 | OE1 | GLU | 237 | 3.679 | 24.578 | 84.402 | 1.00 | 28.81 |
| ATOM | 81 | OE2 | GLU | 237 | 4.253 | 26.327 | 85.629 | 1.00 | 28.14 |
| ATOM | 82 | C | GLU | 237 | 8.740 | 24.369 | 85.919 | 1.00 | 18.12 |
| ATOM | 83 | O | GLU | 237 | 9.684 | 23.709 | 85.466 | 1.00 | 18.57 |
| ATOM | 84 | N | TRP | 238 | 8.924 | 25.472 | 86.635 | 1.00 | 16.91 |
| ATOM | 85 | H | TRP | 238 | 8.164 | 25.919 | 87.048 | 1.00 | 0.00 |
| ATOM | 86 | CA | TRP | 238 | 10.266 | 26.021 | 86.808 | 1.00 | 16.06 |
| ATOM | 87 | CB | TRP | 238 | 10.289 | 27.557 | 86.586 | 1.00 | 16.99 |
| ATOM | 88 | CG | TRP | 238 | 10.110 | 28.031 | 85.147 | 1.00 | 18.25 |
| ATOM | 89 | CD2 | TRP | 238 | 8.886 | 28.388 | 84.524 | 1.00 | 19.01 |
| ATOM | 90 | CE2 | TRP | 238 | 9.200 | 28.819 | 83.207 | 1.00 | 18.54 |
| ATOM | 91 | CE3 | TRP | 238 | 7.547 | 28.380 | 84.949 | 1.00 | 18.64 |
| ATOM | 92 | CD1 | TRP | 238 | 11.090 | 28.244 | 84.221 | 1.00 | 17.51 |
| ATGM | 93 | NE1 | TRP | 238 | 10.558 | 28.711 | 83.052 | 1.00 | 18.52 |
| ATOM | 94 | HE1 | TRP | 238 | 11.049 | 28.951 | 82.237 | 1.00 | 0.00 |
| ATOM | 95 | CZ2 | TRP | 238 | 8.216 | 29.244 | 82.317 | 1.00 | 20.29 |
| ATOM | 96 | CZ3 | TRP | 238 | 6.582 | 28.790 | 84.075 | 1.00 | 20.70 |
| ATOM | 97 | CH2 | TRP | 238 | 6.908 | 29.220 | 82.767 | 1.00 | 20.69 |
| ATOM | 98 | C | TRP | 238 | 10.976 | 25.689 | 88.109 | 1.00 | 14.67 |
| ATOM | 99 | O | TRP | 238 | 12.196 | 25.840 | 88.205 | 1.00 | 14.18 |
| ATOM | 100 | N | GLU | 239 | 10.264 | 25.185 | 89.119 | 1.00 | 13.40 |
| ATOM | 101 | H | GLU | 239 | 9.309 | 25.008 | 89.012 | 1.00 | 0.00 |

TABLE 3-continued

Coordinates of Lck bound with AMP-PNP

| | | Atom Type | Res | # | X | Y | Z | Occ | B |
|---|---|---|---|---|---|---|---|---|---|
| ATOM | 102 | CA | GLU | 239 | 10.915 | 24.882 | 90.388 | 1.00 | 12.41 |
| ATOM | 103 | CB | GLU | 239 | 9.893 | 24.602 | 91.513 | 1.00 | 13.82 |
| ATOM | 104 | CG | GLU | 239 | 10.526 | 24.406 | 92.876 | 1.00 | 13.92 |
| ATOM | 105 | CD | GLU | 239 | 10.802 | 25.700 | 93.640 | 1.00 | 15.04 |
| ATOM | 106 | OE1 | GLU | 239 | 10.143 | 26.716 | 93.321 | 1.00 | 15.02 |
| ATOM | 107 | OE2 | GLU | 239 | 11.666 | 25.716 | 94.544 | 1.00 | 14.50 |
| ATOM | 108 | C | GLU | 239 | 11.804 | 23.648 | 90.233 | 1.00 | 12.24 |
| ATOM | 109 | O | GLU | 239 | 11.391 | 22.668 | 89.611 | 1.00 | 13.77 |
| ATOM | 110 | N | VAL | 240 | 13.023 | 23.735 | 90.766 | 1.00 | 11.71 |
| ATOM | 111 | H | VAL | 240 | 13.299 | 24.560 | 91.203 | 1.00 | 0.00 |
| ATOM | 112 | CA | VAL | 240 | 13.945 | 22.598 | 90.744 | 1.00 | 12.51 |
| ATOM | 113 | CB | VAL | 240 | 15.105 | 22.733 | 89.670 | 1.00 | 12.10 |
| ATOM | 114 | CG1 | VAL | 240 | 14.585 | 22.850 | 88.277 | 1.00 | 13.18 |
| ATOM | 115 | CG2 | VAL | 240 | 16.071 | 23.859 | 90.061 | 1.00 | 10.76 |
| ATOM | 116 | C | VAL | 240 | 14.616 | 22.422 | 92.110 | 1.00 | 12.39 |
| ATOM | 117 | O | VAL | 240 | 14.841 | 23.375 | 92.870 | 1.00 | 12.42 |
| ATOM | 118 | N | PRO | 241 | 14.908 | 21.154 | 92.491 | 1.00 | 11.86 |
| ATOM | 119 | CD | PRO | 241 | 14.473 | 19.902 | 91.840 | 1.00 | 12.24 |
| ATOM | 120 | CA | PRO | 241 | 15.568 | 20.912 | 93.767 | 1.00 | 12.65 |
| ATOM | 121 | CB | PRO | 241 | 15.730 | 19.372 | 93.775 | 1.00 | 11.78 |
| ATOM | 122 | CG | PRO | 241 | 14.565 | 18.895 | 92.974 | 1.00 | 12.22 |
| ATOM | 123 | C | PRO | 241 | 16.962 | 21.570 | 93.740 | 1.00 | 11.85 |
| ATOM | 124 | O | PRO | 241 | 17.620 | 21.555 | 92.693 | 1.00 | 12.46 |
| ATOM | 125 | N | ARG | 242 | 17.384 | 22.198 | 94.832 | 1.00 | 12.89 |
| ATOM | 126 | H | ARG | 242 | 16.795 | 22.250 | 95.619 | 1.00 | 0.00 |
| ATOM | 127 | CA | ARG | 242 | 18.708 | 22.830 | 94.861 | 1.00 | 12.40 |
| ATOM | 128 | CB | ARG | 242 | 18.950 | 23.533 | 96.193 | 1.00 | 14.75 |
| ATOM | 129 | CG | ARG | 242 | 20.091 | 24.535 | 96.113 | 1.00 | 15.25 |
| ATOM | 130 | CD | ARG | 242 | 20.541 | 25.070 | 97.460 | 1.00 | 17.56 |
| ATOM | 131 | NE | ARG | 242 | 19.422 | 25.556 | 98.268 | 1.00 | 18.07 |
| ATOM | 132 | HE | ARG | 242 | 19.107 | 24.977 | 98.985 | 1.00 | 0.00 |
| ATOM | 133 | CZ | ARG | 242 | 18.799 | 26.724 | 98.110 | 1.00 | 19.12 |
| ATOM | 134 | NH1 | ARG | 242 | 19.166 | 27.577 | 97.161 | 1.00 | 19.73 |
| ATOM | 135 | HH11 | ARG | 242 | 19.915 | 27.339 | 96.534 | 1.00 | 0.00 |
| ATOM | 136 | HH12 | ARG | 242 | 18.676 | 28.436 | 97.031 | 1.00 | 0.00 |
| ATOM | 137 | NH2 | ARG | 242 | 17.780 | 27.032 | 98.902 | 1.00 | 18.83 |
| ATOM | 138 | HH21 | ARG | 242 | 17.506 | 26.405 | 99.623 | 1.00 | 0.00 |
| ATOM | 139 | HH22 | ARG | 242 | 17.312 | 27.908 | 98.781 | 1.00 | 0.00 |
| ATOM | 140 | C | ARG | 242 | 19.895 | 21.875 | 94.555 | 1.00 | 12.95 |
| ATOM | 141 | O | ARG | 242 | 20.894 | 22.277 | 93.987 | 1.00 | 11.99 |
| ATOM | 142 | N | GLU | 243 | 19.697 | 20.585 | 94.822 | 1.00 | 13.41 |
| ATOM | 143 | H | GLU | 243 | 18.842 | 20.286 | 95.170 | 1.00 | 0.00 |
| ATOM | 144 | CA | GLU | 243 | 20.754 | 19.606 | 94.572 | 1.00 | 14.21 |
| ATOM | 145 | CB | GLU | 243 | 20.342 | 18.237 | 95.178 | 1.00 | 16.12 |
| ATOM | 146 | CG | GLU | 243 | 20.061 | 18.260 | 96.691 | 1.00 | 21.22 |
| ATOM | 147 | CD | GLU | 243 | 18.709 | 18.847 | 97.095 | 1.00 | 22.86 |
| ATOM | 148 | OE1 | GLU | 243 | 17.795 | 18.975 | 96.259 | 1.00 | 22.70 |
| ATOM | 149 | OE2 | GLU | 243 | 18.539 | 19.103 | 98.316 | 1.00 | 25.06 |
| ATOM | 150 | C | GLU | 243 | 21.102 | 19.446 | 93.076 | 1.00 | 12.77 |
| ATOM | 151 | O | GLU | 243 | 22.152 | 18.874 | 92.721 | 1.00 | 12.70 |
| ATOM | 152 | N | THR | 244 | 20.240 | 19.959 | 92.200 | 1.00 | 11.90 |
| ATOM | 153 | H | THR | 244 | 19.429 | 20.393 | 92.526 | 1.00 | 0.00 |
| ATOM | 154 | CA | THR | 244 | 20.480 | 19.869 | 90.761 | 1.00 | 11.33 |
| ATOM | 155 | CB | THR | 244 | 19.178 | 20.061 | 89.922 | 1.00 | 11.58 |
| ATOM | 156 | OG1 | THR | 244 | 18.722 | 21.409 | 90.111 | 1.00 | 12.20 |
| ATOM | 157 | HG1 | THR | 244 | 18.543 | 21.529 | 91.048 | 1.00 | 0.00 |
| ATOM | 158 | CG2 | THR | 244 | 18.068 | 19.018 | 90.329 | 1.00 | 11.12 |
| ATOM | 159 | C | THR | 244 | 21.513 | 20.905 | 90.309 | 1.00 | 10.60 |
| ATOM | 160 | O | THR | 244 | 22.005 | 20.841 | 89.187 | 1.00 | 9.84 |
| ATOM | 161 | N | LEU | 245 | 21.893 | 21.813 | 91.196 | 1.00 | 10.02 |
| ATOM | 162 | H | LEU | 245 | 21.570 | 21.783 | 92.115 | 1.00 | 0.00 |
| ATOM | 163 | CA | LEU | 245 | 22.835 | 22.865 | 90.806 | 1.00 | 10.44 |
| ATOM | 164 | CB | LEU | 245 | 22.179 | 24.221 | 91.148 | 1.00 | 9.40 |
| ATOM | 165 | CG | LEU | 245 | 20.838 | 24.462 | 90.428 | 1.00 | 10.29 |
| ATOM | 166 | CD1 | LEU | 245 | 20.055 | 25.579 | 91.158 | 1.00 | 11.97 |
| ATOM | 167 | CD2 | LEU | 245 | 21.079 | 24.863 | 88.989 | 1.00 | 11.52 |
| ATOM | 168 | C | LEU | 245 | 24.183 | 22.828 | 91.494 | 1.00 | 11.15 |
| ATOM | 169 | O | LEU | 245 | 24.257 | 22.514 | 92.699 | 1.00 | 13.40 |
| ATOM | 170 | N | LYS | 246 | 25.230 | 23.052 | 90.715 | 1.00 | 10.77 |
| ATOM | 171 | H | LYS | 246 | 25.086 | 23.177 | 89.756 | 1.00 | 0.00 |
| ATOM | 172 | CA | LYS | 246 | 26.597 | 23.139 | 91.215 | 1.00 | 12.14 |
| ATOM | 173 | CB | LYS | 246 | 27.528 | 22.118 | 90.572 | 1.00 | 13.85 |
| ATOM | 174 | CG | LYS | 246 | 28.935 | 22.225 | 91.133 | 1.00 | 16.33 |
| ATOM | 175 | CD | LYS | 246 | 29.970 | 21.564 | 90.205 | 1.00 | 19.11 |

TABLE 3-continued

Coordinates of Lck bound with AMP-PNP

| | | Atom Type | Res | # | X | Y | Z | Occ | B |
|---|---|---|---|---|---|---|---|---|---|
| ATOM | 176 | CE | LYS | 246 | 31.305 | 21.487 | 90.910 | 1.00 | 20.77 |
| ATOM | 177 | NZ | LYS | 246 | 32.177 | 20.585 | 90.041 | 1.00 | 22.87 |
| ATOM | 178 | HZ1 | LYS | 246 | 32.285 | 20.988 | 89.106 | 1.00 | 0.00 |
| ATOM | 179 | HZ2 | LYS | 246 | 31.712 | 19.652 | 89.977 | 1.00 | 0.00 |
| ATOM | 180 | HZ3 | LYS | 246 | 33.102 | 20.464 | 90.502 | 1.00 | 0.00 |
| ATOM | 181 | C | LYS | 246 | 27.051 | 24.538 | 90.814 | 1.00 | 10.91 |
| ATOM | 182 | O | LYS | 246 | 27.037 | 24.876 | 89.642 | 1.00 | 10.91 |
| ATOM | 183 | N | LEU | 247 | 27.367 | 25.383 | 91.798 | 0.60 | 9.61 |
| ATOM | 184 | H | LEU | 247 | 27.319 | 25.075 | 92.714 | 1.00 | 0.00 |
| ATOM | 185 | CA | LEU | 247 | 27.815 | 26.761 | 91.532 | 0.60 | 9.63 |
| ATOM | 186 | CB | LEU | 247 | 27.348 | 27.712 | 92.652 | 0.60 | 9.83 |
| ATOM | 187 | CG | LEU | 247 | 25.846 | 28.129 | 92.642 | 0.60 | 10.31 |
| ATOM | 188 | CD1 | LEU | 247 | 24.882 | 26.939 | 92.630 | 0.60 | 13.23 |
| ATOM | 189 | CD2 | LEU | 247 | 25.564 | 29.031 | 93.833 | 0.60 | 11.95 |
| ATOM | 190 | C | LEU | 247 | 29.327 | 26.666 | 91.428 | 0.60 | 10.71 |
| ATOM | 191 | O | LEU | 247 | 29.973 | 26.180 | 92.342 | 0.60 | 10.43 |
| ATOM | 192 | N | VAL | 248 | 29.873 | 27.137 | 90.313 | 1.00 | 11.88 |
| ATOM | 193 | H | VAL | 248 | 29.310 | 27.614 | 89.675 | 1.00 | 0.00 |
| ATOM | 194 | CA | VAL | 248 | 31.310 | 26.991 | 90.003 | 1.00 | 13.11 |
| ATOM | 195 | CB | VAL | 248 | 31.498 | 26.319 | 88.602 | 1.00 | 13.53 |
| ATOM | 196 | CG1 | VAL | 248 | 32.978 | 26.241 | 88.210 | 1.00 | 14.85 |
| ATOM | 197 | CG2 | VAL | 248 | 30.899 | 24.899 | 88.605 | 1.00 | 14.81 |
| ATOM | 198 | C | VAL | 248 | 32.186 | 28.216 | 90.080 | 1.00 | 14.16 |
| ATOM | 199 | O | VAL | 248 | 33.270 | 28.175 | 90.679 | 1.00 | 14.80 |
| ATOM | 200 | N | GLU | 249 | 31.725 | 29.312 | 89.495 | 1.00 | 13.26 |
| ATOM | 201 | H | GLU | 249 | 30.834 | 29.309 | 89.093 | 1.00 | 0.00 |
| ATOM | 202 | CA | GLU | 249 | 32.508 | 30.530 | 89.468 | 1.00 | 13.80 |
| ATOM | 203 | CB | GLU | 249 | 33.134 | 30.677 | 88.091 | 1.00 | 15.55 |
| ATOM | 204 | CG | GLU | 249 | 34.014 | 31.912 | 87.944 | 1.00 | 18.90 |
| ATOM | 205 | CD | GLU | 249 | 34.405 | 32.210 | 86.510 | 1.00 | 21.24 |
| ATOM | 206 | OE1 | GLU | 249 | 34.135 | 31.393 | 85.593 | 1.00 | 24.08 |
| ATOM | 207 | OE2 | GLU | 249 | 34.913 | 33.319 | 86.265 | 1.00 | 22.80 |
| ATOM | 208 | C | GLU | 249 | 31.631 | 31.727 | 89.746 | 1.00 | 13.85 |
| ATOM | 209 | O | GLU | 249 | 30.599 | 31.893 | 89.107 | 1.00 | 13.22 |
| ATOM | 210 | N | ARG | 250 | 32.032 | 32.565 | 90.691 | 1.00 | 13.43 |
| ATOM | 211 | H | ARG | 250 | 32.845 | 32.390 | 91.203 | 1.00 | 0.00 |
| ATOM | 212 | CA | ARG | 250 | 31.238 | 33.756 | 90.975 | 1.00 | 13.91 |
| ATOM | 213 | CB | ARG | 250 | 31.424 | 34.209 | 92.429 | 1.00 | 15.62 |
| ATOM | 214 | CG | ARG | 250 | 30.454 | 35.361 | 92.785 | 1.00 | 18.83 |
| ATOM | 215 | CD | ARG | 250 | 30.548 | 35.864 | 94.224 | 1.00 | 21.47 |
| ATOM | 216 | NE | ARG | 250 | 31.929 | 35.904 | 94.643 | 1.00 | 24.18 |
| ATOM | 217 | HE | ARG | 250 | 32.576 | 35.446 | 94.077 | 1.00 | 0.00 |
| ATOM | 218 | CZ | ARG | 250 | 32.379 | 36.480 | 95.742 | 1.00 | 25.74 |
| ATOM | 219 | NH1 | ARG | 250 | 31.558 | 37.136 | 96.561 | 1.00 | 27.48 |
| ATOM | 220 | HH11 | ARG | 250 | 30.581 | 37.188 | 96.376 | 1.00 | 0.00 |
| ATOM | 221 | HH12 | ARG | 250 | 31.927 | 37.552 | 97.403 | 1.00 | 0.00 |
| ATOM | 222 | NH2 | ARG | 250 | 33.593 | 36.137 | 96.166 | 1.00 | 28.18 |
| ATOM | 223 | HH21 | ARG | 250 | 34.096 | 35.413 | 95.681 | 1.00 | 0.00 |
| ATOM | 224 | HH22 | ARG | 250 | 33.955 | 36.514 | 97.011 | 1.00 | 0.00 |
| ATOM | 225 | C | ARG | 250 | 31.596 | 34.847 | 89.970 | 1.00 | 13.66 |
| ATOM | 226 | O | ARG | 250 | 32.789 | 35.114 | 89.719 | 1.00 | 15.10 |
| ATOM | 227 | N | LEU | 251 | 30.567 | 35.378 | 89.300 | 1.00 | 12.58 |
| ATOM | 228 | H | LEU | 251 | 29.669 | 35.062 | 89.490 | 1.00 | 0.00 |
| ATOM | 229 | CA | LEU | 251 | 30.723 | 36.409 | 88.295 | 1.00 | 11.75 |
| ATOM | 230 | CB | LEU | 251 | 29.719 | 36.195 | 87.157 | 1.00 | 12.32 |
| ATOM | 231 | CG | LEU | 251 | 29.810 | 34.803 | 86.565 | 1.00 | 11.37 |
| ATOM | 232 | CD1 | LEU | 251 | 28.787 | 34.682 | 85.487 | 1.00 | 11.33 |
| ATOM | 233 | CD2 | LEU | 251 | 31.198 | 34.554 | 86.008 | 1.00 | 12.76 |
| ATOM | 234 | C | LEU | 251 | 30.524 | 37.797 | 88.874 | 1.00 | 12.74 |
| ATOM | 235 | O | LEU | 251 | 31.043 | 38.767 | 88.320 | 1.00 | 13.60 |
| ATOM | 236 | N | GLY | 252 | 29.736 | 37.884 | 89.939 | 1.00 | 12.51 |
| ATOM | 237 | H | GLY | 252 | 29.333 | 37.075 | 90.321 | 1.00 | 0.00 |
| ATOM | 238 | CA | GLY | 252 | 29.458 | 39.185 | 90.521 | 1.00 | 13.79 |
| ATOM | 239 | C | GLY | 252 | 28.902 | 39.056 | 91.900 | 1.00 | 13.34 |
| ATOM | 240 | O | GLY | 252 | 28.356 | 38.030 | 92.292 | 1.00 | 13.87 |
| ATOM | 241 | N | ALA | 253 | 29.086 | 40.120 | 92.672 | 1.00 | 14.74 |
| ATOM | 242 | H | ALA | 253 | 29.577 | 40.898 | 92.327 | 1.00 | 0.00 |
| ATOM | 243 | CA | ALA | 253 | 28.596 | 40.172 | 94.040 | 1.00 | 16.13 |
| ATOM | 244 | CB | ALA | 253 | 29.648 | 39.731 | 95.035 | 1.00 | 15.97 |
| ATOM | 245 | C | ALA | 253 | 28.179 | 41.593 | 94.332 | 1.00 | 17.39 |
| ATOM | 246 | O | ALA | 253 | 28.882 | 42.558 | 94.005 | 1.00 | 17.53 |
| ATOM | 247 | N | GLY | 254 | 27.033 | 41.707 | 94.977 | 1.00 | 17.78 |
| ATOM | 248 | H | GLY | 254 | 26.551 | 40.907 | 95.239 | 1.00 | 0.00 |
| ATOM | 249 | CA | GLY | 254 | 26.517 | 43.011 | 95.317 | 1.00 | 18.08 |

TABLE 3-continued

Coordinates of Lck bound with AMP-PNP

| | | Atom Type | Res | # | X | Y | Z | Occ | B |
|---|---|---|---|---|---|---|---|---|---|
| ATOM | 250 | C | GLY | 254 | 25.728 | 42.948 | 96.598 | 1.00 | 17.45 |
| ATOM | 251 | O | GLY | 254 | 25.644 | 41.956 | 97.325 | 1.00 | 17.19 |
| ATOM | 252 | N | GLN | 255 | 25.101 | 44.066 | 96.868 | 1.00 | 18.33 |
| ATOM | 253 | H | GLN | 255 | 25.164 | 44.813 | 96.258 | 1.00 | 0.00 |
| ATOM | 254 | CA | GLN | 255 | 24.301 | 44.213 | 98.045 | 1.00 | 19.13 |
| ATOM | 255 | CB | GLN | 255 | 23.771 | 45.594 | 97.946 | 1.00 | 19.95 |
| ATOM | 256 | CG | GLN | 255 | 23.078 | 46.146 | 99.052 | 1.00 | 22.32 |
| ATOM | 257 | CD | GLN | 255 | 22.847 | 47.590 | 98.718 | 1.00 | 24.50 |
| ATOM | 258 | OE1 | GLN | 255 | 22.188 | 48.281 | 99.453 | 1.00 | 26.43 |
| ATOM | 259 | NE2 | GLN | 255 | 23.403 | 48.048 | 97.588 | 1.00 | 26.54 |
| ATOM | 260 | HE21 | GLN | 255 | 23.980 | 47.407 | 97.016 | 1.00 | 0.00 |
| ATOM | 261 | HE22 | GLN | 255 | 23.348 | 48.942 | 97.308 | 1.00 | 0.00 |
| ATOM | 262 | C | GLN | 255 | 23.114 | 43.280 | 98.164 | 1.00 | 18.89 |
| ATOM | 263 | O | GLN | 255 | 22.715 | 42.912 | 99.277 | 1.00 | 18.97 |
| ATOM | 264 | N | PHE | 256 | 22.566 | 42.891 | 97.016 | 1.00 | 18.57 |
| ATOM | 265 | H | PHE | 256 | 22.967 | 43.162 | 96.160 | 1.00 | 0.00 |
| ATOM | 266 | CA | PHE | 256 | 21.387 | 42.039 | 97.045 | 1.00 | 18.53 |
| ATOM | 267 | CB | PHE | 256 | 20.361 | 42.561 | 96.047 | 1.00 | 18.42 |
| ATOM | 268 | CG | PHE | 256 | 20.043 | 44.006 | 96.223 | 1.00 | 19.55 |
| ATOM | 269 | CD1 | PHE | 256 | 19.660 | 44.487 | 97.462 | 1.00 | 19.76 |
| ATOM | 270 | CD2 | PHE | 256 | 20.163 | 44.889 | 95.149 | 1.00 | 19.70 |
| ATOM | 271 | CE1 | PHE | 256 | 19.391 | 45.854 | 97.651 | 1.00 | 20.60 |
| ATOM | 272 | CE2 | PHE | 256 | 19.905 | 46.252 | 95.312 | 1.00 | 20.72 |
| ATOM | 273 | CZ | PHE | 256 | 19.517 | 46.734 | 96.572 | 1.00 | 21.23 |
| ATOM | 274 | C | PHE | 256 | 21.689 | 40.589 | 96.752 | 1.00 | 18.00 |
| ATOM | 275 | O | PHE | 256 | 20.764 | 39.761 | 96.636 | 1.00 | 16.87 |
| ATOM | 276 | N | GLY | 257 | 22.973 | 40.284 | 96.577 | 1.00 | 17.57 |
| ATOM | 277 | H | GLY | 257 | 23.667 | 40.987 | 96.619 | 1.00 | 0.00 |
| ATOM | 278 | CA | GLY | 257 | 23.337 | 38.913 | 96.293 | 1.00 | 17.34 |
| ATOM | 279 | C | GLY | 257 | 24.491 | 38.688 | 95.333 | 1.00 | 17.02 |
| ATOM | 280 | O | GLY | 257 | 25.258 | 39.602 | 95.011 | 1.00 | 17.68 |
| ATOM | 281 | N | GLU | 258 | 24.501 | 37.481 | 94.753 | 1.00 | 14.48 |
| ATOM | 282 | H | GLU | 258 | 23.782 | 36.853 | 94.960 | 1.00 | 0.00 |
| ATOM | 283 | CA | GLU | 258 | 25.569 | 37.077 | 93.856 | 1.00 | 14.43 |
| ATOM | 284 | CB | GLU | 258 | 26.448 | 36.038 | 94.559 | 1.00 | 15.81 |
| ATOM | 285 | CG | GLU | 258 | 27.085 | 36.578 | 95.872 | 1.00 | 19.83 |
| ATOM | 286 | CD | GLU | 258 | 28.011 | 35.584 | 96.576 | 1.00 | 22.41 |
| ATOM | 287 | OE1 | GLU | 258 | 27.731 | 34.360 | 96.582 | 1.00 | 24.84 |
| ATOM | 288 | OE2 | GLU | 258 | 29.021 | 36.035 | 97.165 | 1.00 | 26.85 |
| ATOM | 289 | C | GLU | 258 | 25.069 | 36.481 | 92.551 | 1.00 | 12.27 |
| ATOM | 290 | O | GLU | 258 | 23.942 | 36.024 | 92.462 | 1.00 | 12.35 |
| ATOM | 291 | N | VAL | 259 | 25.939 | 36.480 | 91.562 | 0.77 | 9.83 |
| ATOM | 292 | H | VAL | 259 | 26.806 | 36.897 | 91.710 | 1.00 | 0.00 |
| ATOM | 293 | CA | VAL | 259 | 25.657 | 35.863 | 90.262 | 0.77 | 8.93 |
| ATOM | 294 | CB | VAL | 259 | 25.650 | 36.867 | 89.108 | 0.77 | 9.26 |
| ATOM | 295 | CG1 | VAL | 259 | 25.414 | 36.115 | 87.754 | 0.77 | 8.23 |
| ATOM | 296 | CG2 | VAL | 259 | 24.500 | 37.872 | 89.347 | 0.77 | 10.50 |
| ATOM | 297 | C | VAL | 259 | 26.795 | 34.888 | 90.038 | 0.77 | 8.47 |
| ATOM | 298 | O | VAL | 259 | 27.958 | 35.272 | 90.143 | 0.77 | 7.91 |
| ATOM | 299 | N | TRP | 260 | 26.454 | 33.642 | 89.724 | 1.00 | 7.79 |
| ATOM | 300 | H | TRP | 260 | 25.509 | 33.403 | 89.658 | 1.00 | 0.00 |
| ATOM | 301 | CA | TRP | 260 | 27.449 | 32.614 | 89.503 | 1.00 | 8.79 |
| ATOM | 302 | CB | TRP | 260 | 27.298 | 31.522 | 90.561 | 1.00 | 10.03 |
| ATOM | 303 | CG | TRP | 260 | 27.700 | 31.898 | 91.938 | 1.00 | 12.72 |
| ATOM | 304 | CD2 | TRP | 260 | 28.837 | 31.392 | 92.653 | 1.00 | 13.43 |
| ATOM | 305 | CE2 | TRP | 260 | 28.838 | 32.008 | 93.918 | 1.00 | 15.26 |
| ATOM | 306 | CE3 | TRP | 260 | 29.836 | 30.464 | 92.335 | 1.00 | 14.66 |
| ATOM | 307 | CD1 | TRP | 260 | 27.066 | 32.770 | 92.780 | 1.00 | 12.67 |
| ATOM | 308 | NE1 | TRP | 260 | 27.763 | 32.834 | 93.984 | 1.00 | 15.10 |
| ATOM | 309 | HE1 | TRP | 260 | 27.518 | 33.395 | 94.742 | 1.00 | 0.00 |
| ATOM | 310 | CZ2 | TRP | 260 | 29.825 | 31.723 | 94.876 | 1.00 | 16.09 |
| ATOM | 311 | CZ3 | TRP | 260 | 30.813 | 30.188 | 93.297 | 1.00 | 16.92 |
| ATOM | 312 | CH2 | TRP | 260 | 30.796 | 30.815 | 94.547 | 1.00 | 16.41 |
| ATOM | 313 | C | TRP | 260 | 27.242 | 31.864 | 88.202 | 1.00 | 8.56 |
| ATOM | 314 | O | TRP | 260 | 26.132 | 31.790 | 87.674 | 1.00 | 9.60 |
| ATOM | 315 | N | MET | 261 | 28.341 | 31.349 | 87.662 | 1.00 | 8.43 |
| ATOM | 316 | H | MET | 261 | 29.227 | 31.596 | 87.991 | 1.00 | 0.00 |
| ATOM | 317 | CA | MET | 261 | 28.222 | 30.439 | 86.541 | 1.00 | 7.71 |
| ATOM | 318 | CB | MET | 261 | 29.469 | 30.486 | 85.644 | 1.00 | 9.06 |
| ATOM | 319 | CG | MET | 261 | 29.476 | 29.473 | 84.493 | 1.00 | 9.93 |
| ATOM | 320 | SD | MET | 261 | 30.097 | 27.818 | 85.014 | 1.00 | 12.84 |
| ATOM | 321 | CE | MET | 261 | 31.911 | 28.132 | 85.302 | 1.00 | 15.22 |
| ATOM | 322 | C | MET | 261 | 28.150 | 29.077 | 87.245 | 1.00 | 8.44 |
| ATOM | 323 | O | MET | 261 | 28.814 | 28.856 | 88.244 | 1.00 | 8.95 |

TABLE 3-continued

Coordinates of Lck bound with AMP-PNP

| | | Atom Type | Res | # | X | Y | Z | Occ | B |
|---|---|---|---|---|---|---|---|---|---|
| ATOM | 324 | N | GLY | 262 | 27.295 | 28.195 | 86.773 | 1.00 | 8.18 |
| ATOM | 325 | H | GLY | 262 | 26.731 | 28.417 | 86.018 | 1.00 | 0.00 |
| ATOM | 326 | CA | GLY | 262 | 27.203 | 26.878 | 87.413 | 1.00 | 8.32 |
| ATOM | 327 | C | GLY | 262 | 26.648 | 25.894 | 86.401 | 1.00 | 5.91 |
| ATOM | 328 | O | GLY | 262 | 26.517 | 26.175 | 85.206 | 1.00 | 5.98 |
| ATOM | 329 | N | TYR | 263 | 26.415 | 24.666 | 86.875 | 1.00 | 6.89 |
| ATOM | 330 | H | TYR | 263 | 26.583 | 24.448 | 87.807 | 1.00 | 0.00 |
| ATOM | 331 | CA | TYR | 263 | 25.861 | 23.637 | 85.987 | 1.00 | 7.28 |
| ATOM | 332 | CB | TYR | 263 | 26.889 | 22.496 | 85.841 | 1.00 | 8.06 |
| ATOM | 333 | CG | TYR | 263 | 28.080 | 22.924 | 85.048 | 1.00 | 10.09 |
| ATOM | 334 | CD1 | TYR | 263 | 28.044 | 22.868 | 83.662 | 1.00 | 10.54 |
| ATOM | 335 | CE1 | TYR | 263 | 29.066 | 23.364 | 82.901 | 1.00 | 14.47 |
| ATOM | 336 | CD2 | TYR | 263 | 29.184 | 23.476 | 85.673 | 1.00 | 12.72 |
| ATOM | 337 | CE2 | TYR | 263 | 30.221 | 23.978 | 84.935 | 1.00 | 14.68 |
| ATOM | 338 | CZ | TYR | 263 | 30.160 | 23.926 | 83.547 | 1.00 | 15.68 |
| ATOM | 339 | OH | TYR | 263 | 31.170 | 24.487 | 82.778 | 1.00 | 20.07 |
| ATOM | 340 | HH | TYR | 263 | 30.989 | 24.389 | 81.857 | 1.00 | 0.00 |
| ATOM | 341 | C | TYR | 263 | 24.615 | 23.016 | 86.596 | 1.00 | 6.81 |
| ATOM | 342 | O | TYR | 263 | 24.563 | 22.811 | 87.826 | 1.00 | 8.23 |
| ATOM | 343 | N | TYR | 264 | 23.617 | 22.767 | 85.750 | 1.00 | 7.63 |
| ATOM | 344 | H | TYR | 264 | 23.733 | 23.013 | 84.815 | 1.00 | 0.00 |
| ATOM | 345 | CA | TYR | 264 | 22.369 | 22.110 | 86.128 | 1.00 | 8.60 |
| ATOM | 346 | CB | TYR | 264 | 21.156 | 22.808 | 85.446 | 1.00 | 9.34 |
| ATOM | 347 | CG | TYR | 264 | 19.866 | 22.028 | 85.585 | 1.00 | 9.75 |
| ATOM | 348 | CD1 | TYR | 264 | 19.102 | 22.129 | 86.754 | 1.00 | 10.24 |
| ATOM | 349 | CE1 | TYR | 264 | 17.959 | 21.354 | 86.929 | 1.00 | 10.67 |
| ATOM | 350 | CD2 | TYR | 264 | 19.453 | 21.136 | 84.586 | 1.00 | 11.81 |
| ATOM | 351 | CE2 | TYR | 264 | 18.282 | 20.337 | 84.756 | 1.00 | 11.92 |
| ATOM | 352 | CZ | TYR | 264 | 17.562 | 20.474 | 85.941 | 1.00 | 12.03 |
| ATOM | 353 | OH | TYR | 264 | 16.420 | 19.720 | 86.154 | 1.00 | 14.04 |
| ATOM | 354 | HH | TYR | 264 | 16.040 | 19.932 | 86.999 | 1.00 | 0.00 |
| ATOM | 355 | C | TYR | 264 | 22.492 | 20.651 | 85.665 | 1.00 | 8.08 |
| ATOM | 356 | O | TYR | 264 | 22.826 | 20.368 | 84.513 | 1.00 | 7.72 |
| ATOM | 357 | N | ASN | 265 | 22.291 | 19.749 | 86.621 | 1.00 | 8.42 |
| ATOM | 358 | H | ASN | 265 | 22.114 | 20.076 | 87.520 | 1.00 | 0.00 |
| ATOM | 359 | CA | ASN | 265 | 22.350 | 18.290 | 86.352 | 1.00 | 8.83 |
| ATOM | 360 | CB | ASN | 265 | 21.111 | 17.794 | 85.571 | 1.00 | 10.23 |
| ATOM | 361 | CG | ASN | 265 | 19.909 | 17.513 | 86.449 | 1.00 | 12.04 |
| ATOM | 362 | OD1 | ASN | 265 | 18.922 | 16.924 | 85.971 | 1.00 | 16.27 |
| ATOM | 363 | ND2 | ASN | 265 | 19.987 | 17.846 | 87.700 | 1.00 | 10.60 |
| ATOM | 364 | HD21 | ASN | 265 | 20.791 | 18.278 | 88.040 | 1.00 | 0.00 |
| ATOM | 365 | HD22 | ASN | 265 | 19.200 | 17.675 | 88.263 | 1.00 | 0.00 |
| ATOM | 366 | C | ASN | 265 | 23.655 | 17.896 | 85.654 | 1.00 | 8.05 |
| ATOM | 367 | O | ASN | 265 | 23.664 | 17.133 | 84.672 | 1.00 | 9.88 |
| ATOM | 368 | N | GLY | 266 | 24.734 | 18.494 | 86.141 | 1.00 | 7.83 |
| ATOM | 369 | H | GLY | 266 | 24.621 | 19.165 | 86.832 | 1.00 | 0.00 |
| ATOM | 370 | CA | GLY | 266 | 26.076 | 18.161 | 85.677 | 1.00 | 6.92 |
| ATOM | 371 | C | GLY | 266 | 26.558 | 18.718 | 84.367 | 1.00 | 6.25 |
| ATOM | 372 | O | GLY | 266 | 27.690 | 19.215 | 84.313 | 1.00 | 9.19 |
| ATOM | 373 | N | HIS | 267 | 25.705 | 18.747 | 83.348 | 0.49 | 2.00 |
| ATOM | 374 | H | HIS | 267 | 24.768 | 18.516 | 83.488 | 1.00 | 0.00 |
| ATOM | 375 | CA | HIS | 267 | 26.132 | 19.118 | 82.007 | 0.49 | 2.00 |
| ATOM | 376 | CB | HIS | 267 | 25.644 | 18.007 | 81.071 | 0.49 | 2.00 |
| ATOM | 377 | CG | HIS | 267 | 26.288 | 16.707 | 81.346 | 0.49 | 2.00 |
| ATOM | 378 | CD2 | HIS | 267 | 27.610 | 16.377 | 81.362 | 0.49 | 2.00 |
| ATOM | 379 | ND1 | HIS | 267 | 25.611 | 15.575 | 81.738 | 0.49 | 2.60 |
| ATOM | 380 | HD1 | HIS | 267 | 24.637 | 15.483 | 81.811 | 1.00 | 0.00 |
| ATOM | 381 | CE1 | HIS | 267 | 26.481 | 14.607 | 81.990 | 0.49 | 2.00 |
| ATOM | 382 | NE2 | HIS | 267 | 27.697 | 15.089 | 81.760 | 0.49 | 3.36 |
| ATOM | 383 | HE2 | HIS | 267 | 28.533 | 14.590 | 81.874 | 1.00 | 0.00 |
| ATOM | 384 | C | HIS | 267 | 25.678 | 20.418 | 81.398 | 0.49 | 2.00 |
| ATOM | 385 | O | HIS | 267 | 26.213 | 20.808 | 80.365 | 0.49 | 2.30 |
| ATOM | 386 | N | THR | 268 | 24.710 | 21.092 | 82.013 | 1.00 | 5.29 |
| ATOM | 387 | H | THR | 268 | 24.397 | 20.822 | 82.896 | 1.00 | 0.00 |
| ATOM | 388 | CA | THR | 268 | 24.145 | 22.270 | 81.320 | 1.00 | 6.10 |
| ATOM | 389 | CB | THR | 268 | 22.609 | 22.169 | 81.303 | 1.00 | 7.20 |
| ATOM | 390 | OG1 | THR | 268 | 22.235 | 20.980 | 80.601 | 1.00 | 7.82 |
| ATOM | 391 | HG1 | THR | 268 | 22.598 | 20.214 | 81.047 | 1.00 | 0.00 |
| ATOM | 392 | CG2 | THR | 268 | 22.010 | 23.369 | 80.495 | 1.00 | 7.70 |
| ATOM | 393 | C | THR | 268 | 24.549 | 23.551 | 82.050 | 1.00 | 5.45 |
| ATOM | 394 | O | THR | 268 | 24.164 | 23.747 | 83.189 | 1.00 | 6.14 |
| ATOM | 395 | N | LYS | 269 | 25.347 | 24.370 | 81.356 | 1.00 | 6.47 |
| ATOM | 396 | H | LYS | 269 | 25.557 | 24.141 | 80.425 | 1.00 | 0.00 |
| ATOM | 397 | CA | LYS | 269 | 25.901 | 25.592 | 81.925 | 1.00 | 6.35 |

TABLE 3-continued

Coordinates of Lck bound with AMP-PNP

| | | Atom Type | Res | # | X | Y | Z | Occ | B |
|---|---|---|---|---|---|---|---|---|---|
| ATOM | 398 | CB | LYS | 269 | 26.940 | 26.166 | 80.973 | 1.00 | 7.90 |
| ATOM | 399 | CG | LYS | 269 | 27.866 | 27.140 | 81.613 | 1.00 | 10.78 |
| ATOM | 400 | CD | LYS | 269 | 29.023 | 27.358 | 80.618 | 1.00 | 13.81 |
| ATOM | 401 | CE | LYS | 269 | 30.233 | 27.795 | 81.340 | 1.00 | 17.11 |
| ATOM | 402 | NZ | LYS | 269 | 31.390 | 27.884 | 80.376 | 1.00 | 19.10 |
| ATOM | 403 | HZ1 | LYS | 269 | 31.172 | 28.567 | 79.641 | 1.00 | 0.00 |
| ATOM | 404 | HZ2 | LYS | 269 | 31.566 | 26.944 | 79.962 | 1.00 | 0.00 |
| ATOM | 405 | HZ3 | LYS | 269 | 32.243 | 28.180 | 80.907 | 1.00 | 0.00 |
| ATOM | 406 | C | LYS | 269 | 24.753 | 26.567 | 82.074 | 1.00 | 7.04 |
| ATOM | 407 | O | LYS | 269 | 23.952 | 26.722 | 81.169 | 1.00 | 7.34 |
| ATOM | 408 | N | VAL | 270 | 24.690 | 27.205 | 83.238 | 1.00 | 5.91 |
| ATOM | 409 | H | VAL | 270 | 25.398 | 27.048 | 83.893 | 1.00 | 0.00 |
| ATOM | 410 | CA | VAL | 270 | 23.629 | 28.177 | 83.546 | 1.00 | 6.63 |
| ATOM | 411 | CB | VAL | 270 | 22.509 | 27.481 | 84.400 | 1.00 | 6.46 |
| ATOM | 412 | CG1 | VAL | 270 | 21.803 | 26.405 | 83.568 | 1.00 | 7.32 |
| ATOM | 413 | CG2 | VAL | 270 | 23.083 | 26.839 | 85.698 | 1.00 | 7.53 |
| ATOM | 414 | C | VAL | 270 | 24.182 | 29.316 | 84.395 | 1.00 | 6.17 |
| ATOM | 415 | O | VAL | 270 | 25.268 | 29.240 | 84.916 | 1.00 | 6.51 |
| ATOM | 416 | N | ALA | 271 | 23.443 | 30.426 | 84.450 | 1.00 | 6.02 |
| ATOM | 417 | H | ALA | 271 | 22.644 | 30.496 | 83.891 | 1.00 | 0.00 |
| ATOM | 418 | CA | ALA | 271 | 23.788 | 31.527 | 85.338 | 1.00 | 5.74 |
| ATOM | 419 | CB | ALA | 271 | 23.574 | 32.853 | 84.648 | 1.00 | 5.67 |
| ATOM | 420 | C | ALA | 271 | 22.814 | 31.423 | 86.540 | 1.00 | 5.85 |
| ATOM | 421 | O | ALA | 271 | 21.608 | 31.142 | 86.381 | 1.00 | 7.29 |
| ATOM | 422 | N | VAL | 272 | 23.318 | 31.635 | 87.747 | 1.00 | 7.39 |
| ATOM | 423 | H | VAL | 272 | 24.267 | 31.833 | 87.843 | 1.00 | 0.00 |
| ATOM | 424 | CA | VAL | 272 | 22.475 | 31.543 | 88.936 | 1.00 | 8.08 |
| ATOM | 425 | CB | VAL | 272 | 22.969 | 30.428 | 89.899 | 1.00 | 8.79 |
| ATOM | 426 | CG1 | VAL | 272 | 22.070 | 30.343 | 91.136 | 1.00 | 9.68 |
| ATOM | 427 | CG2 | VAL | 272 | 23.015 | 29.076 | 89.131 | 1.00 | 9.63 |
| ATOM | 428 | C | VAL | 272 | 22.581 | 32.834 | 89.722 | 1.00 | 9.60 |
| ATOM | 429 | O | VAL | 272 | 23.684 | 33.284 | 89.989 | 1.00 | 11.01 |
| ATOM | 430 | N | LYS | 273 | 21.451 | 33.495 | 89.956 | 1.00 | 9.34 |
| ATOM | 431 | H | LYS | 273 | 20.623 | 33.163 | 89.587 | 1.00 | 0.00 |
| ATOM | 432 | CA | LYS | 273 | 21.441 | 34.713 | 90.766 | 1.00 | 9.94 |
| ATOM | 433 | CB | LYS | 273 | 20.613 | 35.821 | 90.094 | 1.00 | 13.05 |
| ATOM | 434 | CG | LYS | 273 | 20.444 | 36.981 | 91.030 | 1.00 | 16.55 |
| ATOM | 435 | CD | LYS | 273 | 20.241 | 38.260 | 90.283 | 1.00 | 18.34 |
| ATOM | 436 | CE | LYS | 273 | 18.990 | 38.229 | 89.471 | 1.00 | 18.99 |
| ATOM | 437 | NZ | LYS | 273 | 18.646 | 39.634 | 89.043 | 1.00 | 21.97 |
| ATOM | 438 | HZ1 | LYS | 273 | 19.448 | 40.027 | 88.524 | 1.00 | 0.00 |
| ATOM | 439 | HZ2 | LYS | 273 | 18.496 | 40.175 | 89.925 | 1.00 | 0.00 |
| ATOM | 440 | HZ3 | LYS | 273 | 17.792 | 39.616 | 88.478 | 1.00 | 0.00 |
| ATOM | 441 | C | LYS | 273 | 20.871 | 34.330 | 92.124 | 1.00 | 10.21 |
| ATOM | 442 | O | LYS | 273 | 19.781 | 33.769 | 92.200 | 1.00 | 10.49 |
| ATOM | 443 | N | SER | 274 | 21.606 | 34.614 | 93.188 | 0.65 | 8.89 |
| ATOM | 444 | H | SER | 274 | 22.451 | 35.070 | 93.082 | 1.00 | 0.00 |
| ATOM | 445 | CA | SER | 274 | 21.170 | 34.262 | 94.530 | 0.65 | 10.39 |
| ATOM | 446 | CB | SER | 274 | 22.290 | 33.526 | 95.266 | 0.65 | 10.95 |
| ATOM | 447 | OG | SER | 274 | 23.412 | 34.386 | 95.458 | 0.65 | 12.46 |
| ATOM | 448 | HG | SER | 274 | 23.734 | 34.694 | 94.615 | 1.00 | 0.00 |
| ATOM | 449 | C | SER | 274 | 20.827 | 35.531 | 95.287 | 0.65 | 10.72 |
| ATOM | 450 | O | SER | 274 | 21.436 | 36.556 | 95.060 | 0.65 | 11.54 |
| ATOM | 451 | N | LEU | 275 | 19.802 | 35.439 | 96.128 | 1.00 | 12.75 |
| ATOM | 452 | H | LEU | 275 | 19.341 | 34.581 | 96.220 | 1.00 | 0.00 |
| ATOM | 453 | CA | LEU | 275 | 19.322 | 36.539 | 96.946 | 1.00 | 14.16 |
| ATOM | 454 | CB | LEU | 275 | 17.799 | 36.441 | 97.131 | 1.00 | 14.72 |
| ATOM | 455 | CG | LEU | 275 | 17.126 | 37.358 | 98.176 | 1.00 | 15.26 |
| ATOM | 456 | CD1 | LEU | 275 | 17.373 | 38.810 | 97.880 | 1.00 | 14.76 |
| ATOM | 457 | CD2 | LEU | 275 | 15.642 | 37.071 | 98.223 | 1.00 | 15.40 |
| ATOM | 458 | C | LEU | 275 | 19.957 | 36.461 | 98.300 | 1.00 | 14.90 |
| ATOM | 459 | O | LEU | 275 | 19.884 | 35.439 | 98.984 | 1.00 | 15.55 |
| ATOM | 460 | N | LYS | 276 | 20.560 | 37.570 | 98.687 | 1.00 | 16.04 |
| ATOM | 461 | H | LYS | 276 | 20.585 | 38.337 | 98.075 | 1.00 | 0.00 |
| ATOM | 462 | CA | LYS | 276 | 21.161 | 37.698 | 100.008 | 1.00 | 18.12 |
| ATOM | 463 | CB | LYS | 276 | 22.041 | 38.935 | 100.022 | 1.00 | 17.89 |
| ATOM | 464 | CG | LYS | 276 | 22.544 | 39.200 | 101.420 | 1.00 | 20.43 |
| ATOM | 465 | CD | LYS | 276 | 23.537 | 40.284 | 101.422 | 1.00 | 21.32 |
| ATOM | 466 | CE | LYS | 276 | 24.127 | 40.343 | 102.800 | 1.00 | 23.30 |
| ATOM | 467 | NZ | LYS | 276 | 25.301 | 41.227 | 102.750 | 1.00 | 23.81 |
| ATOM | 468 | HZ1 | LYS | 276 | 25.023 | 42.181 | 102.440 | 1.00 | 0.00 |
| ATOM | 469 | HZ2 | LYS | 276 | 25.992 | 40.837 | 102.068 | 1.00 | 0.00 |
| ATOM | 470 | HZ3 | LYS | 276 | 25.742 | 41.282 | 103.688 | 1.00 | 0.00 |
| ATOM | 471 | C | LYS | 276 | 20.010 | 37.870 | 100.986 | 1.00 | 18.63 |

TABLE 3-continued

Coordinates of Lck bound with AMP-PNP

| | | Atom Type | Res | # | X | Y | Z | Occ | B |
|---|---|---|---|---|---|---|---|---|---|
| ATOM | 472 | O | LYS | 276 | 19.317 | 38.883 | 100.927 | 1.00 | 18.34 |
| ATOM | 473 | N | ALA | 277 | 19.804 | 36.878 | 101.854 | 1.00 | 20.10 |
| ATOM | 474 | H | ALA | 277 | 20.411 | 36.106 | 101.843 | 1.00 | 0.00 |
| ATOM | 475 | CA | ALA | 277 | 18.696 | 36.896 | 102.809 | 1.00 | 21.51 |
| ATOM | 476 | CB | ALA | 277 | 18.744 | 35.672 | 103.740 | 1.00 | 21.27 |
| ATOM | 477 | C | ALA | 277 | 18.662 | 38.192 | 103.608 | 1.00 | 21.38 |
| ATOM | 478 | O | ALA | 277 | 19.689 | 38.632 | 104.114 | 1.00 | 23.46 |
| ATOM | 479 | N | GLY | 278 | 17.498 | 38.841 | 103.623 | 1.00 | 21.75 |
| ATOM | 480 | H | GLY | 278 | 16.742 | 38.457 | 103.137 | 1.00 | 0.00 |
| ATOM | 481 | CA | GLY | 278 | 17.335 | 40.098 | 104.345 | 1.00 | 21.96 |
| ATOM | 482 | C | GLY | 278 | 17.703 | 41.377 | 103.617 | 1.00 | 21.14 |
| ATOM | 483 | O | GLY | 278 | 17.305 | 42.473 | 104.045 | 1.00 | 22.05 |
| ATOM | 484 | N | SER | 279 | 18.394 | 41.263 | 102.487 | 1.00 | 20.64 |
| ATOM | 485 | H | SER | 279 | 18.644 | 40.372 | 102.161 | 1.00 | 0.00 |
| ATOM | 486 | CA | SER | 279 | 18.819 | 42.442 | 101.738 | 1.00 | 19.52 |
| ATOM | 487 | CB | SER | 279 | 19.972 | 42.078 | 100.785 | 1.00 | 19.84 |
| ATOM | 488 | OG | SER | 279 | 19.440 | 41.327 | 99.694 | 1.00 | 18.98 |
| ATOM | 489 | HG | SER | 279 | 20.154 | 41.097 | 99.086 | 1.00 | 0.00 |
| ATOM | 490 | C | SER | 279 | 17.712 | 43.126 | 100.952 | 1.00 | 19.74 |
| ATOM | 491 | O | SER | 279 | 17.835 | 44.293 | 100.568 | 1.00 | 20.02 |
| ATOM | 492 | N | MET | 280 | 16.637 | 42.390 | 100.700 | 1.00 | 17.85 |
| ATOM | 493 | H | MET | 280 | 16.594 | 41.465 | 101.047 | 1.00 | 0.00 |
| ATOM | 494 | CA | MET | 280 | 15.489 | 42.901 | 99.956 | 1.00 | 16.89 |
| ATOM | 495 | CB | MET | 280 | 15.839 | 43.178 | 98.496 | 1.00 | 17.51 |
| ATOM | 496 | CG | MET | 280 | 16.225 | 41.950 | 97.688 | 1.00 | 17.40 |
| ATOM | 497 | SD | MET | 280 | 16.460 | 42.297 | 95.951 | 1.00 | 18.85 |
| ATOM | 498 | CE | MET | 280 | 14.770 | 42.465 | 95.400 | 1.00 | 16.54 |
| ATOM | 499 | C | MET | 280 | 14.422 | 41.828 | 100.044 | 1.00 | 15.88 |
| ATOM | 500 | O | MET | 280 | 14.692 | 40.713 | 100.422 | 1.00 | 16.00 |
| ATOM | 501 | N | SER | 281 | 13.194 | 42.197 | 99.739 | 1.00 | 14.52 |
| ATOM | 502 | H | SER | 281 | 13.024 | 43.121 | 99.473 | 1.00 | 0.00 |
| ATOM | 503 | CA | SER | 281 | 12.100 | 41.271 | 99.799 | 1.00 | 14.28 |
| ATOM | 504 | CB | SER | 281 | 10.811 | 42.032 | 99.436 | 1.00 | 15.24 |
| ATOM | 505 | OG | SER | 281 | 9.768 | 41.133 | 99.163 | 1.00 | 16.19 |
| ATOM | 506 | HG | SER | 281 | 10.032 | 40.550 | 98.442 | 1.00 | 0.00 |
| ATOM | 507 | C | SER | 281 | 12.231 | 40.062 | 98.869 | 1.00 | 12.89 |
| ATOM | 508 | O | SER | 281 | 12.536 | 40.225 | 97.691 | 1.00 | 12.83 |
| ATOM | 509 | N | PRO | 282 | 11.948 | 38.860 | 99.374 | 0.51 | 11.26 |
| ATOM | 510 | CD | PRO | 282 | 11.412 | 38.488 | 100.692 | 0.51 | 10.63 |
| ATOM | 511 | CA | PRO | 282 | 12.044 | 37.698 | 98.489 | 0.51 | 9.61 |
| ATOM | 512 | CB | PRO | 282 | 11.828 | 36.511 | 99.427 | 0.51 | 9.95 |
| ATOM | 513 | CG | PRO | 282 | 11.890 | 37.067 | 100.820 | 0.51 | 10.91 |
| ATOM | 514 | C | PRO | 282 | 10.938 | 37.789 | 97.410 | 0.51 | 8.61 |
| ATOM | 515 | O | PRO | 282 | 11.081 | 37.265 | 96.317 | 0.51 | 5.03 |
| ATOM | 516 | N | ASP | 283 | 9.820 | 38.444 | 97.734 | 1.00 | 10.53 |
| ATOM | 517 | H | ASP | 283 | 9.710 | 38.821 | 98.636 | 1.00 | 0.00 |
| ATOM | 518 | CA | ASP | 283 | 8.752 | 38.607 | 96.773 | 1.00 | 11.00 |
| ATOM | 519 | CB | ASP | 283 | 7.477 | 39.171 | 97.472 | 1.00 | 13.39 |
| ATOM | 520 | CG | ASP | 283 | 6.286 | 39.334 | 96.495 | 1.00 | 16.20 |
| ATOM | 521 | OD1 | ASP | 283 | 5.792 | 38.307 | 95.941 | 1.00 | 18.15 |
| ATOM | 522 | OD2 | ASP | 283 | 5.810 | 40.470 | 96.263 | 1.00 | 16.68 |
| ATOM | 523 | C | ASP | 283 | 9.237 | 39.535 | 95.651 | 1.00 | 10.60 |
| ATOM | 524 | O | ASP | 283 | 9.008 | 39.267 | 94.491 | 1.00 | 11.89 |
| ATOM | 525 | N | ALA | 284 | 9.901 | 40.638 | 96.000 | 1.00 | 12.01 |
| ATOM | 526 | H | ALA | 284 | 10.073 | 40.837 | 96.948 | 1.00 | 0.00 |
| ATOM | 527 | CA | ALA | 284 | 10.402 | 41.553 | 94.983 | 1.00 | 11.82 |
| ATOM | 528 | CB | ALA | 284 | 11.085 | 42.782 | 95.643 | 1.00 | 12.76 |
| ATOM | 529 | C | ALA | 284 | 11.421 | 40.824 | 94.112 | 1.00 | 11.34 |
| ATOM | 530 | O | ALA | 284 | 11.451 | 40.994 | 92.910 | 1.00 | 12.67 |
| ATOM | 531 | N | PHE | 285 | 12.292 | 40.068 | 94.752 | 1.00 | 11.20 |
| ATOM | 532 | H | PHE | 285 | 12.230 | 40.005 | 95.726 | 1.00 | 0.00 |
| ATOM | 533 | CA | PHE | 285 | 13.324 | 39.315 | 94.027 | 1.00 | 10.80 |
| ATOM | 534 | CB | PHE | 285 | 14.185 | 38.521 | 95.038 | 1.00 | 10.15 |
| ATOM | 535 | CG | PHE | 285 | 15.303 | 37.735 | 94.414 | 1.00 | 10.28 |
| ATOM | 536 | CD1 | PHE | 285 | 16.477 | 38.381 | 94.036 | 1.00 | 10.36 |
| ATOM | 537 | CD2 | PHE | 285 | 15.182 | 36.358 | 94.211 | 1.00 | 10.04 |
| ATOM | 538 | CE1 | PHE | 285 | 17.557 | 37.626 | 93.439 | 1.00 | 11.72 |
| ATOM | 539 | CE2 | PHE | 285 | 16.240 | 35.612 | 93.622 | 1.00 | 9.70 |
| ATOM | 540 | CZ | PHE | 285 | 17.408 | 36.252 | 93.244 | 1.00 | 9.67 |
| ATOM | 541 | C | PHE | 285 | 12.667 | 38.349 | 93.011 | 1.00 | 10.63 |
| ATOM | 542 | O | PHE | 285 | 13.036 | 38.328 | 91.833 | 1.00 | 11.66 |
| ATOM | 543 | N | LEU | 286 | 11.680 | 37.574 | 93.453 | 1.00 | 9.81 |
| ATOM | 544 | H | LEU | 286 | 11.360 | 37.667 | 94.365 | 1.00 | 0.00 |
| ATOM | 545 | CA | LEU | 286 | 11.055 | 36.582 | 92.565 | 1.00 | 11.19 |

TABLE 3-continued

Coordinates of Lck bound with AMP-PNP

| | | Atom Type | Res | # | X | Y | Z | Occ | B |
|---|---|---|---|---|---|---|---|---|---|
| ATOM | 546 | CB | LEU | 286 | 10.354 | 35.491 | 93.373 | 1.00 | 11.45 |
| ATOM | 547 | CG | LEU | 286 | 11.324 | 34.522 | 94.080 | 1.00 | 11.02 |
| ATOM | 548 | CD1 | LEU | 286 | 10.594 | 33.757 | 95.126 | 1.00 | 12.70 |
| ATOM | 549 | CD2 | LEU | 286 | 12.004 | 33.545 | 93.081 | 1.00 | 10.79 |
| ATOM | 550 | C | LEU | 286 | 10.129 | 37.149 | 91.534 | 1.00 | 11.27 |
| ATOM | 551 | O | LEU | 286 | 9.775 | 36.501 | 90.559 | 1.00 | 11.78 |
| ATOM | 552 | N | ALA | 287 | 9.690 | 38.381 | 91.767 | 1.00 | 11.65 |
| ATOM | 553 | H | ALA | 287 | 9.917 | 38.858 | 92.592 | 1.00 | 0.00 |
| ATOM | 554 | CA | ALA | 287 | 8.820 | 39.011 | 90.792 | 1.00 | 11.64 |
| ATOM | 555 | CB | ALA | 287 | 8.409 | 40.422 | 91.276 | 1.00 | 12.67 |
| ATOM | 556 | C | ALA | 287 | 9.434 | 39.050 | 89.383 | 1.00 | 10.99 |
| ATOM | 557 | O | ALA | 287 | 8.716 | 38.900 | 88.365 | 1.00 | 10.96 |
| ATOM | 558 | N | GLU | 288 | 10.765 | 39.146 | 89.327 | 1.00 | 10.68 |
| ATOM | 559 | H | GLU | 288 | 11.299 | 39.193 | 90.148 | 1.00 | 0.00 |
| ATOM | 560 | CA | GLU | 288 | 11.453 | 39.191 | 88.051 | 1.00 | 10.51 |
| ATOM | 561 | CB | GLU | 288 | 12.935 | 39.481 | 88.257 | 1.00 | 11.55 |
| ATOM | 562 | CG | GLU | 288 | 13.663 | 39.445 | 86.924 | 1.00 | 13.55 |
| ATOM | 563 | CD | GLU | 288 | 15.124 | 39.777 | 87.027 | 1.00 | 15.93 |
| ATOM | 564 | OE1 | GLU | 288 | 15.689 | 39.843 | 88.151 | 1.00 | 17.97 |
| ATOM | 565 | OE2 | GLU | 288 | 15.723 | 39.984 | 85.959 | 1.00 | 16.29 |
| ATOM | 566 | C | GLU | 288 | 11.309 | 37.847 | 87.345 | 1.00 | 9.59 |
| ATON | 567 | O | GLU | 288 | 11.052 | 37.767 | 86.153 | 1.00 | 9.75 |
| ATOM | 568 | N | ALA | 289 | 11.496 | 36.774 | 88.104 | 1.00 | 9.45 |
| ATOM | 569 | H | ALA | 289 | 11.702 | 36.863 | 89.059 | 1.00 | 0.00 |
| ATOM | 570 | CA | ALA | 289 | 11.352 | 35.449 | 87.502 | 1.00 | 9.52 |
| ATOM | 571 | CB | ALA | 289 | 11.724 | 34.414 | 88.530 | 1.00 | 9.44 |
| ATOM | 572 | C | ALA | 289 | 9.905 | 35.216 | 86.997 | 1.00 | 9.32 |
| ATOM | 573 | O | ALA | 289 | 9.695 | 34.740 | 85.884 | 1.00 | 9.28 |
| ATOM | 574 | N | ASN | 290 | 8.912 | 35.647 | 87.780 | 1.00 | 11.14 |
| ATOM | 575 | H | ASN | 290 | 9.101 | 36.050 | 88.649 | 1.00 | 0.00 |
| ATOM | 576 | CA | ASN | 290 | 7.516 | 35.468 | 87.357 | 1.00 | 11.56 |
| ATOM | 577 | CB | ASN | 290 | 6.569 | 35.952 | 88.466 | 1.00 | 14.37 |
| ATOM | 578 | CG | ASN | 290 | 6.655 | 35.081 | 89.739 | 1.00 | 17.32 |
| ATOM | 579 | OD1 | ASN | 290 | 7.075 | 33.943 | 89.680 | 1.00 | 19.80 |
| ATOM | 580 | ND2 | ASN | 290 | 6.187 | 35.593 | 90.851 | 1.00 | 17.51 |
| ATOM | 581 | HD21 | ASN | 290 | 5.786 | 36.481 | 90.850 | 1.00 | 0.00 |
| ATOM | 582 | HD22 | ASN | 290 | 6.275 | 35.050 | 91.644 | 1.00 | 0.00 |
| ATOM | 583 | C | ASN | 290 | 7.251 | 36.199 | 86.033 | 1.00 | 11.86 |
| ATOM | 584 | O | ASN | 290 | 6.587 | 35.677 | 85.153 | 1.00 | 11.62 |
| ATOM | 585 | N | LEU | 291 | 7.836 | 37.387 | 85.868 | 1.00 | 11.22 |
| ATOM | 586 | H | LEU | 291 | 8.374 | 37.768 | 86.595 | 1.00 | 0.00 |
| ATOM | 587 | CA | LEU | 291 | 7.656 | 38.133 | 84.625 | 1.00 | 11.75 |
| ATOM | 588 | CB | LEU | 291 | 8.282 | 39.535 | 84.751 | 1.00 | 12.23 |
| ATOM | 589 | CG | LEU | 291 | 8.185 | 40.373 | 83.467 | 1.00 | 13.03 |
| ATOM | 590 | CD1 | LEU | 291 | 7.868 | 41.815 | 83.829 | 1.00 | 15.64 |
| ATOM | 591 | CD2 | LEU | 291 | 9.504 | 40.288 | 82.637 | 1.00 | 14.61 |
| ATOM | 592 | C | LEU | 291 | 8.309 | 37.393 | 83.472 | 1.00 | 11.60 |
| ATOM | 593 | O | LEU | 291 | 7.775 | 37.337 | 82.375 | 1.00 | 11.66 |
| ATOM | 594 | N | MET | 292 | 9.492 | 36.843 | 83.729 | 1.00 | 10.84 |
| ATOM | 595 | H | MET | 292 | 9.873 | 36.893 | 84.632 | 1.00 | 0.00 |
| ATOM | 596 | CA | MET | 292 | 10.214 | 36.128 | 82.669 | 1.00 | 11.69 |
| ATOM | 597 | CB | MET | 292 | 11.631 | 35.762 | 83.112 | 1.00 | 10.20 |
| ATOM | 598 | CG | MET | 292 | 12.483 | 37.020 | 83.427 | 1.00 | 10.33 |
| ATOM | 599 | SD | MET | 292 | 14.091 | 36.510 | 84.073 | 1.00 | 10.40 |
| ATOM | 600 | CE | MET | 292 | 14.866 | 35.881 | 82.607 | 1.00 | 9.86 |
| ATOM | 601 | C | MET | 292 | 9.475 | 34.907 | 82.156 | 1.00 | 12.23 |
| ATOM | 602 | O | MET | 292 | 9.647 | 34.562 | 80.981 | 1.00 | 13.03 |
| ATOM | 603 | N | LYS | 293 | 8.584 | 34.350 | 82.985 | 1.00 | 13.02 |
| ATOM | 604 | H | LYS | 293 | 8.486 | 34.720 | 83.884 | 1.00 | 0.00 |
| ATOM | 605 | CA | LYS | 293 | 7.762 | 33.188 | 82.564 | 1.00 | 15.14 |
| ATOM | 606 | CB | LYS | 293 | 6.948 | 32.663 | 83.747 | 1.00 | 14.94 |
| ATOM | 607 | CG | LYS | 293 | 7.766 | 32.128 | 84.906 | 1.00 | 15.08 |
| ATOM | 608 | CD | LYS | 293 | 6.890 | 31.761 | 86.085 | 1.00 | 17.22 |
| ATOM | 609 | CE | LYS | 293 | 7.726 | 31.376 | 87.286 | 1.00 | 18.51 |
| ATOM | 610 | NZ | LYS | 293 | 6.887 | 30.902 | 88.479 | 1.00 | 19.83 |
| ATOM | 611 | HZ1 | LYS | 293 | 6.333 | 30.066 | 88.185 | 1.00 | 0.00 |
| ATOM | 612 | HZ2 | LYS | 293 | 6.239 | 31.661 | 88.760 | 1.00 | 0.00 |
| ATOM | 613 | HZ3 | LYS | 293 | 7.507 | 30.647 | 89.620 | 1.00 | 0.00 |
| ATOM | 614 | C | LYS | 293 | 6.829 | 33.606 | 81.421 | 1.00 | 16.53 |
| ATOM | 615 | O | LYS | 293 | 6.545 | 32.823 | 80.534 | 1.00 | 17.55 |
| ATOM | 616 | N | GLN | 294 | 6.420 | 34.875 | 81.424 | 1.00 | 18.04 |
| ATOM | 617 | H | GLN | 294 | 6.719 | 35.469 | 82.143 | 1.00 | 0.00 |
| ATOM | 618 | CA | GLN | 294 | 5.544 | 35.451 | 80.385 | 1.00 | 19.92 |
| ATOM | 619 | CB | GLN | 294 | 4.688 | 36.565 | 80.996 | 1.00 | 21.19 |

TABLE 3-continued

Coordinates of Lck bound with AMP-PNP

| | | Atom Type | Res | # | X | Y | Z | Occ | B |
|---|---|---|---|---|---|---|---|---|---|
| ATOM | 620 | CG | GLN | 294 | 3.862 | 36.130 | 82.160 | 1.00 | 23.42 |
| ATOM | 621 | CD | GLN | 294 | 3.053 | 34.911 | 81.850 | 1.00 | 24.85 |
| ATOM | 622 | OE1 | GLN | 294 | 2.605 | 34.705 | 80.711 | 1.00 | 27.15 |
| ATOM | 623 | NE2 | GLN | 294 | 2.836 | 34.090 | 82.865 | 1.00 | 27.14 |
| ATOM | 624 | HE21 | GLN | 294 | 3.177 | 34.317 | 83.740 | 1.00 | 0.00 |
| ATOM | 625 | HE22 | GLN | 294 | 2.292 | 33.291 | 82.678 | 1.00 | 0.00 |
| ATOM | 626 | C | GLN | 294 | 6.235 | 36.049 | 79.174 | 1.00 | 19.86 |
| ATOM | 627 | O | GLN | 294 | 5.586 | 36.469 | 78.184 | 1.00 | 21.52 |
| ATOM | 628 | N | LEU | 295 | 7.538 | 36.240 | 79.273 | 1.00 | 17.72 |
| ATOM | 629 | H | LEU | 295 | 8.005 | 35.994 | 80.100 | 1.00 | 0.00 |
| ATOM | 630 | CA | LEU | 295 | 8.259 | 36.856 | 78.183 | 1.00 | 17.44 |
| ATOM | 631 | CB | LEU | 295 | 8.899 | 38.174 | 78.633 | 1.00 | 18.33 |
| ATOM | 632 | CG | LEU | 295 | 8.089 | 39.439 | 78.537 | 1.00 | 19.10 |
| ATOM | 633 | CD1 | LEU | 295 | 8.952 | 40.578 | 79.056 | 1.00 | 17.86 |
| ATOM | 634 | CD2 | LEU | 295 | 7.638 | 39.671 | 77.075 | 1.00 | 18.70 |
| ATOM | 635 | C | LEU | 295 | 9.343 | 35.957 | 77.700 | 1.00 | 16.74 |
| ATOM | 636 | O | LEU | 295 | 10.523 | 36.204 | 77.934 | 1.00 | 18.51 |
| ATOM | 637 | N | GLN | 296 | 8.954 | 35.007 | 76.784 | 1.00 | 14.87 |
| ATOM | 638 | H | GLN | 296 | 8.013 | 34.951 | 76.608 | 1.00 | 0.00 |
| ATOM | 639 | CS | GLN | 296 | 9.889 | 34.056 | 76.344 | 1.00 | 13.05 |
| ATOM | 640 | CB | GLN | 296 | 9.391 | 32.620 | 76.593 | 1.00 | 14.33 |
| ATOM | 641 | CG | GLN | 296 | 9.240 | 32.242 | 78.076 | 1.00 | 15.73 |
| ATOM | 642 | CD | GLN | 296 | 8.678 | 30.784 | 78.185 | 1.00 | 16.79 |
| ATOM | 643 | OE1 | GLN | 296 | 9.296 | 29.906 | 77.494 | 1.00 | 18.93 |
| ATOM | 644 | NE2 | GLN | 296 | 7.762 | 30.529 | 79.014 | 1.00 | 16.78 |
| ATOM | 645 | HE21 | GLN | 296 | 7.353 | 31.246 | 79.528 | 1.00 | 0.00 |
| ATOM | 646 | HE22 | GLN | 296 | 7.461 | 29.594 | 79.074 | 1.00 | 0.00 |
| ATOM | 647 | C | GLN | 296 | 10.094 | 34.290 | 74.857 | 1.00 | 11.48 |
| ATOM | 648 | O | GLN | 296 | 9.158 | 32.239 | 74.065 | 1.00 | 12.22 |
| ATOM | 649 | N | HIS | 297 | 11.349 | 34.490 | 74.857 | 1.00 | 11.48 |
| ATOM | 650 | H | HIS | 297 | 12.070 | 34.506 | 75.110 | 1.00 | 0.00 |
| ATOM | 651 | CA | HIS | 297 | 11.667 | 34.709 | 73.042 | 1.00 | 7.88 |
| ATOM | 652 | CB | HIS | 297 | 11.381 | 36.185 | 72.696 | 1.00 | 7.64 |
| ATOM | 653 | CG | HIS | 297 | 11.478 | 36.523 | 71.250 | 1.00 | 7.02 |
| ATOM | 654 | CD2 | HIS | 297 | 10.499 | 36.614 | 70.288 | 1.00 | 6.74 |
| ATOM | 655 | ND1 | HIS | 297 | 12.645 | 36.853 | 70.603 | 1.00 | 8.34 |
| ATOM | 656 | HD1 | HIS | 297 | 13.531 | 36.897 | 71.018 | 1.00 | 0.00 |
| ATOM | 657 | CE1 | HIS | 297 | 12.413 | 37.105 | 69.324 | 1.00 | 8.54 |
| ATOM | 658 | NE2 | HIS | 297 | 11.101 | 36.960 | 69.130 | 1.00 | 9.52 |
| ATOM | 659 | HE2 | HIS | 297 | 10.657 | 37.102 | 68.264 | 1.00 | 0.00 |
| ATOM | 660 | C | HIS | 297 | 13.175 | 34.449 | 72.851 | 1.00 | 7.79 |
| ATOM | 661 | O | HIS | 297 | 13.956 | 34.573 | 73.811 | 1.00 | 7.26 |
| ATOM | 662 | N | GLN | 298 | 13.573 | 34.036 | 71.657 | 1.00 | 7.65 |
| ATOM | 663 | H | GLN | 298 | 12.903 | 33.866 | 70.970 | 1.00 | 0.00 |
| ATOM | 664 | CA | GLN | 298 | 15.013 | 33.818 | 71.377 | 1.00 | 7.64 |
| ATOM | 665 | CB | GLN | 298 | 15.300 | 33.484 | 69.903 | 1.00 | 10.16 |
| ATOM | 666 | CG | GLN | 298 | 14.997 | 32.104 | 69.355 | 1.00 | 11.96 |
| ATOM | 667 | CD | GLN | 298 | 15.649 | 30.957 | 70.130 | 1.00 | 8.58 |
| ATOM | 668 | OE1 | GLN | 298 | 14.935 | 30.145 | 70.613 | 1.00 | 8.87 |
| ATOM | 669 | NE2 | GLN | 298 | 17.002 | 30.904 | 70.237 | 1.00 | 8.67 |
| ATOM | 670 | HE21 | GLN | 298 | 17.535 | 31.617 | 69.798 | 1.00 | 0.00 |
| ATOM | 671 | HE22 | GLN | 298 | 17.380 | 30.158 | 70.698 | 1.00 | 0.00 |
| ATOM | 672 | C | GLN | 298 | 15.925 | 34.990 | 71.685 | 1.00 | 7.38 |
| ATOM | 673 | O | GLN | 298 | 17.099 | 34.823 | 72.012 | 1.00 | 7.02 |
| ATOM | 674 | H | ARG | 299 | 15.389 | 36.199 | 71.564 | 1.00 | 5.08 |
| ATOM | 675 | H | ARG | 299 | 14.460 | 36.275 | 71.341 | 1.00 | 0.00 |
| ATOM | 676 | CA | ARG | 299 | 16.191 | 37.381 | 71.783 | 1.00 | 4.55 |
| ATOM | 677 | CB | ARG | 299 | 15.713 | 38.518 | 70.482 | 1.00 | 4.18 |
| ATOM | 678 | CG | ARG | 299 | 15.844 | 38.163 | 59.343 | 1.00 | 5.31 |
| ATOM | 679 | CD | ARG | 299 | 17.190 | 38.627 | 68.732 | 1.00 | 5.70 |
| ATOM | 680 | NE | ARG | 299 | 18.367 | 38.057 | 69.401 | 1.00 | 4.85 |
| ATOM | 681 | HE | ARG | 299 | 18.907 | 38.669 | 69.940 | 1.00 | 0.00 |
| ATOM | 682 | CA | ARG | 299 | 18.762 | 36.772 | 69.325 | 1.00 | 5.72 |
| ATOM | 683 | NH1 | ARG | 299 | 18.072 | 35.895 | 68.613 | 1.00 | 5.30 |
| ATOM | 684 | HH11 | ARG | 299 | 17.246 | 36.191 | 68.136 | 1.00 | 0.00 |
| ATOM | 685 | HH12 | ARG | 299 | 18.357 | 34.942 | 68.573 | 1.00 | 0.00 |
| ATOM | 686 | NH2 | ARG | 299 | 19.887 | 36.428 | 69.941 | 1.00 | 5.26 |
| ATOM | 687 | HH21 | ARG | 299 | 20.424 | 37.131 | 70.406 | 1.00 | 0.00 |
| ATOM | 688 | HH22 | ARG | 299 | 20.218 | 35.491 | 69.900 | 1.00 | 0.00 |
| ATOM | 689 | C | ARG | 299 | 16.170 | 37.909 | 73.213 | 1.00 | 3.99 |
| ATOM | 690 | O | ARG | 299 | 16.721 | 38.978 | 73.459 | 1.00 | 4.46 |
| ATOM | 691 | N | LEU | 300 | 15.570 | 37.189 | 74.152 | 1.00 | 3.70 |
| ATOM | 692 | H | LEU | 300 | 15.123 | 36.350 | 73.885 | 1.00 | 0.00 |
| ATOM | 693 | CA | LEU | 300 | 15.532 | 37.609 | 75.547 | 1.00 | 2.76 |

TABLE 3-continued

Coordinates of Lck bound with AMP-PNP

| | | Atom Type | Res | # | X | Y | Z | Occ | B |
|---|---|---|---|---|---|---|---|---|---|
| ATOM | 694 | CB | LEU | 300 | 14.065 | 37.745 | 75.990 | 1.00 | 4.76 |
| ATOM | 695 | CG | LEU | 300 | 13.374 | 39.107 | 75.659 | 1.00 | 4.91 |
| ATOM | 696 | CD1 | LEU | 300 | 13.310 | 39.464 | 74.206 | 1.00 | 5.95 |
| ATOM | 697 | CD2 | LEU | 300 | 11.966 | 39.016 | 76.303 | 1.00 | 6.21 |
| ATOM | 698 | C | LEU | 300 | 16.165 | 36.473 | 76.369 | 1.00 | 4.75 |
| ATOM | 699 | O | LEU | 300 | 15.872 | 35.398 | 76.102 | 1.00 | 4.95 |
| ATOM | 700 | N | VAL | 301 | 16.977 | 36.818 | 77.352 | 1.00 | 4.59 |
| ATOM | 701 | H | VAL | 301 | 17.165 | 47.766 | 77.515 | 1.00 | 0.00 |
| ATOM | 702 | CA | VAL | 301 | 17.610 | 35.808 | 78.204 | 1.00 | 5.27 |
| ATOM | 703 | CB | VAL | 301 | 18.486 | 36.503 | 79.257 | 1.00 | 6.48 |
| ATOM | 704 | CG1 | VAL | 301 | 18.941 | 35.466 | 80.295 | 1.00 | 9.38 |
| ATOM | 705 | CG2 | VAL | 301 | 19.709 | 37.060 | 78.572 | 1.00 | 7.92 |
| ATOM | 706 | C | VAL | 301 | 16.469 | 34.980 | 78.818 | 1.00 | 5.74 |
| ATOM | 707 | O | VAL | 301 | 15.562 | 35.524 | 79.433 | 1.00 | 6.67 |
| ATOM | 708 | N | ARG | 302 | 16.551 | 33.666 | 78.661 | 1.00 | 4.72 |
| ATOM | 709 | H | ARG | 302 | 17.335 | 33.285 | 78.214 | 1.00 | 0.00 |
| ATOM | 710 | CA | ARG | 302 | 15.474 | 32.770 | 79.103 | 1.00 | 5.24 |
| ATOM | 711 | AC | ARG | 302 | 15.495 | 31.526 | 78.171 | 1.00 | 6.58 |
| ATOM | 712 | CG | ARG | 302 | 14.401 | 30.467 | 78.475 | 1.00 | 8.38 |
| ATOM | 713 | CD | ARG | 302 | 14.573 | 29.236 | 77.581 | 1.00 | 13.26 |
| ATOM | 714 | NE | ARG | 302 | 13.573 | 28.193 | 77.840 | 1.00 | 17.18 |
| ATOM | 715 | HE | ARG | 302 | 12.760 | 28.179 | 77.302 | 1.00 | 0.00 |
| ATOM | 716 | CA | ARG | 302 | 13.720 | 27.260 | 78.785 | 1.00 | 18.72 |
| ATOM | 717 | NH1 | ARG | 302 | 14.804 | 27.265 | 79.575 | 1.00 | 18.61 |
| ATOM | 718 | HH11 | ARG | 302 | 15.491 | 29.975 | 79.465 | 1.00 | 0.00 |
| ATOM | 719 | HH12 | ARG | 302 | 14.899 | 26.571 | 80.282 | 1.00 | 0.00 |
| ATOM | 720 | NH2 | ARG | 302 | 12.828 | 26.268 | 78.880 | 1.00 | 20.90 |
| ATOM | 721 | HH21 | ARG | 302 | 12.071 | 26.223 | 78.242 | 1.00 | 0.00 |
| ATOM | 722 | HH22 | ARG | 302 | 12.944 | 25.566 | 79.586 | 1.00 | 0.00 |
| ATOM | 723 | C | ARG | 302 | 15.565 | 32.306 | 80.554 | 1.00 | 4.86 |
| ATOM | 724 | O | ARG | 302 | 16.632 | 31.867 | 81.009 | 1.00 | 5.51 |
| ATOM | 725 | N | LEU | 303 | 14.441 | 32.352 | 81.265 | 1.00 | 4.43 |
| ATOM | 726 | H | LEU | 303 | 13.645 | 32.794 | 80.920 | 1.00 | 0.00 |
| ATOM | 727 | CA | LEU | 303 | 14.409 | 31.771 | 82.615 | 1.00 | 5.26 |
| ATOM | 728 | CB | LEU | 303 | 13.068 | 32.048 | 82.282 | 1.00 | 5.82 |
| ATOM | 729 | CG | LEU | 303 | 12.908 | 31.501 | 84.712 | 1.00 | 6.58 |
| ATOM | 730 | CD1 | LEU | 303 | 13.851 | 32.214 | 85.728 | 1.00 | 6.78 |
| ATOM | 731 | CD2 | LEU | 303 | 11.436 | 31.724 | 85.122 | 1.00 | 7.19 |
| ATOM | 732 | C | LEU | 303 | 14.513 | 30.233 | 82.472 | 1.00 | 7.27 |
| ATOM | 733 | O | LEU | 303 | 13.777 | 29.602 | 81.666 | 1.00 | 8.97 |
| ATOM | 734 | N | TYR | 304 | 15.381 | 29.645 | 83.287 | 1.00 | 7.38 |
| ATOM | 735 | H | TYR | 304 | 15.846 | 30.185 | 83.941 | 1.00 | 0.00 |
| ATOM | 736 | CA | TYR | 304 | 15.628 | 28.207 | 83.279 | 1.00 | 9.20 |
| ATOM | 737 | CB | TYR | 304 | 17.137 | 28.013 | 83.439 | 1.00 | 12.10 |
| ATOM | 738 | CG | TYR | 304 | 17.668 | 26.670 | 83.106 | 1.00 | 16.90 |
| ATOM | 739 | CD1 | TYR | 304 | 17.486 | 25.595 | 83.981 | 1.00 | 18.59 |
| ATOM | 740 | CE1 | TYR | 304 | 17.901 | 24.310 | 83.645 | 1.00 | 19.46 |
| ATOM | 741 | CD2 | TYR | 304 | 18.291 | 26.442 | 81.891 | 1.00 | 17.15 |
| ATOM | 742 | CE2 | TYR | 304 | 18.692 | 25.155 | 81.538 | 1.00 | 18.38 |
| ATOM | 743 | CA | TYR | 304 | 18.485 | 24.105 | 82.417 | 1.00 | 19.88 |
| ATOM | 744 | OH | TYR | 304 | 18.825 | 22.837 | 82.035 | 1.00 | 20.68 |
| ATOM | 745 | HH | TYR | 304 | 19.174 | 22.852 | 81.144 | 1.00 | 0.00 |
| ATOM | 746 | C | TYR | 304 | 14.886 | 27.530 | 84.432 | 1.00 | 8.76 |
| ATOM | 747 | O | TYR | 304 | 14.244 | 26.497 | 82.245 | 1.00 | 10.19 |
| ATOM | 748 | N | ALA | 305 | 15.007 | 28.085 | 85.626 | 1.00 | 7.54 |
| ATOM | 749 | H | ALA | 305 | 15.518 | 28.913 | 85.713 | 1.00 | 0.00 |
| ATOM | 750 | CA | ALA | 305 | 14.432 | 27.492 | 86.836 | 1.00 | 7.28 |
| ATOM | 751 | CB | ALA | 305 | 15.277 | 26.210 | 87.229 | 1.00 | 7.36 |
| ATOM | 752 | C | ALA | 305 | 14.479 | 28.472 | 88.005 | 1.00 | 7.58 |
| ATOM | 753 | O | ALA | 305 | 15.133 | 29.507 | 87.920 | 1.00 | 7.76 |
| ATOM | 754 | N | VAL | 306 | 13.877 | 28.072 | 89.125 | 0.75 | 6.33 |
| ATOM | 755 | H | VAL | 306 | 13.386 | 27.221 | 89.127 | 1.00 | 0.00 |
| ATOM | 756 | CA | VAL | 306 | 13.908 | 28.858 | 90.345 | 0.75 | 6.60 |
| ATOM | 757 | CB | VAL | 306 | 12.613 | 29.756 | 90.564 | 0.75 | 7.65 |
| ATOM | 758 | CG1 | VAL | 306 | 12.500 | 30.825 | 89.492 | 0.75 | 8.43 |
| ATOM | 759 | CG2 | VAL | 306 | 11.329 | 28.906 | 90.578 | 0.75 | 8.63 |
| ATOM | 760 | C | VAL | 306 | 13.983 | 27.880 | 91.509 | 0.75 | 7.64 |
| ATOM | 761 | O | VAL | 306 | 13.627 | 26.699 | 91.337 | 0.75 | 6.81 |
| ATOM | 762 | N | VAL | 306 | 14.564 | 28.341 | 92.605 | 1.00 | 9.85 |
| ATOM | 763 | H | VAL | 307 | 14.951 | 29.233 | 92.585 | 1.00 | 0.00 |
| ATOM | 764 | CA | VAL | 307 | 14.620 | 25.575 | 93.860 | 1.00 | 11.28 |
| ATOM | 765 | CB | VAL | 307 | 16.043 | 27.209 | 94.300 | 1.00 | 11.93 |
| ATOM | 766 | CG1 | VAL | 307 | 16.011 | 26.526 | 95.654 | 1.00 | 12.96 |
| ATOM | 767 | CG2 | VAL | 307 | 16.650 | 26.243 | 93.283 | 1.00 | 11.76 |

TABLE 3-continued

Coordinates of Lck bound with AMP-PNP

| | | Atom Type | Res | # | X | Y | Z | Occ | B |
|---|---|---|---|---|---|---|---|---|---|
| ATOM | 768 | C | VAL | 307 | 14.013 | 28.581 | 94.817 | 1.00 | 13.39 |
| ATOM | 769 | O | VAL | 307 | 14.649 | 29.603 | 95.136 | 1.00 | 12.71 |
| ATOM | 770 | N | THR | 308 | 13.790 | 288.294 | 95.284 | 1.00 | 15.11 |
| ATOM | 771 | H | THR | 308 | 12.360 | 27.452 | 95.070 | 1.00 | 0.00 |
| ATOM | 772 | CA | THR | 308 | 12.107 | 29.269 | 96.140 | 1.00 | 18.31 |
| ATOM | 773 | CB | THR | 308 | 10.638 | 29.453 | 95.709 | 1.00 | 19.28 |
| ATOM | 774 | OG1 | THR | 308 | 9.966 | 28.193 | 95.726 | 1.00 | 19.76 |
| ATOM | 775 | HG1 | THR | 308 | 9.056 | 28.301 | 95.466 | 1.00 | 0.00 |
| ATOM | 776 | CG2 | THR | 308 | 10.559 | 30.056 | 94.312 | 1.00 | 20.08 |
| ATOM | 777 | C | THR | 208 | 12.246 | 29.193 | 97.661 | 1.00 | 20.02 |
| ATOM | 778 | O | THR | 208 | 11.514 | 29.872 | 98.398 | 1.00 | 21.39 |
| ATOM | 779 | N | ALA | 309 | 13.143 | 28.337 | 98.137 | 1.00 | 21.32 |
| ATOM | 780 | H | ALA | 309 | 13.617 | 27.761 | 97.503 | 1.00 | 0.00 |
| ATOM | 781 | CA | ALA | 309 | 13.454 | 28.233 | 99.561 | 1.00 | 20.86 |
| ATOM | 782 | CB | ALA | 309 | 13.646 | 26.766 | 99.968 | 1.00 | 21.75 |
| ATOM | 783 | C | ALA | 309 | 14.754 | 29.016 | 99.768 | 1.00 | 21.92 |
| ATOM | 784 | O | ALA | 309 | 15.649 | 28.989 | 98.908 | 1.00 | 21.32 |
| ATOM | 785 | N | GLU | 310 | 14.873 | 29.734 | 100.883 | 1.00 | 21.30 |
| ATOM | 786 | H | GLU | 310 | 14.137 | 29.741 | 101.543 | 1.00 | 0.00 |
| ATOM | 787 | CA | GLU | 310 | 16.090 | 30.529 | 101.126 | 1.00 | 22.49 |
| ATOM | 788 | CB | GLU | 310 | 15.886 | 31.446 | 102.349 | 1.00 | 23.46 |
| ATOM | 789 | CG | GLU | 310 | 14.771 | 32.487 | 102.104 | 1.00 | 25.11 |
| ATOM | 790 | CD | GLU | 310 | 14.451 | 33.374 | 103.292 | 1.00 | 26.08 |
| ATOM | 791 | OE1 | GLU | 310 | 14.946 | 33.092 | 104.411 | 1.00 | 27.45 |
| ATOM | 792 | OE2 | GLU | 310 | 13.643 | 34.314 | 103.123 | 1.00 | 27.13 |
| ATOM | 793 | C | GLU | 310 | 17.389 | 29.683 | 101.245 | 1.00 | 22.09 |
| ATOM | 794 | O | GLU | 310 | 17.290 | 28.618 | 101.859 | 1.00 | 23.35 |
| ATOM | 795 | N | PRO | 311 | 18.495 | 30.125 | 100.602 | 1.00 | 20.88 |
| ATOM | 796 | CD | PRO | 311 | 19.781 | 29.296 | 100.672 | 1.00 | 20.86 |
| ATOM | 797 | CA | PRO | 311 | 18.626 | 31.337 | 99.782 | 1.00 | 20.02 |
| ATOM | 798 | CB | PRO | 311 | 20.140 | 31.514 | 99.653 | 1.00 | 20.24 |
| ATOM | 799 | CG | PRO | 311 | 20.638 | 30.083 | 99.618 | 1.00 | 21.06 |
| ATOM | 800 | C | PRO | 311 | 17.991 | 31.101 | 98.417 | 1.00 | 18.54 |
| ATOM | 801 | O | PRO | 311 | 18.334 | 30.173 | 97.705 | 1.00 | 18.90 |
| ATOM | 802 | N | ILE | 312 | 17.156 | 32.032 | 98.027 | 1.00 | 15.99 |
| ATOM | 803 | H | ILE | 312 | 17.013 | 32.821 | 98.586 | 1.00 | 0.00 |
| ATOM | 804 | CA | ILE | 312 | 16.428 | 31.941 | 96.785 | 1.00 | 14.13 |
| ATOM | 805 | CB | ILE | 312 | 15.357 | 33.048 | 96.802 | 1.00 | 15.35 |
| ATOM | 806 | CG2 | ILE | 312 | 14.599 | 33.109 | 85.489 | 1.00 | 15.68 |
| ATOM | 807 | CG1 | ILE | 312 | 14.445 | 32.807 | 98.025 | 1.00 | 17.79 |
| ATOM | 808 | CD1 | ILE | 312 | 13.416 | 33.839 | 98.227 | 1.00 | 19.19 |
| ATOM | 809 | C | ILE | 312 | 17.317 | 32.084 | 95.575 | 1.00 | 11.69 |
| ATOM | 810 | O | ILE | 312 | 18.233 | 32.918 | 95.556 | 1.00 | 11.84 |
| ATOM | 811 | N | TYR | 313 | 17.095 | 31.223 | 94.585 | 1.00 | 9.45 |
| ATOM | 812 | H | TYR | 313 | 16.400 | 30.545 | 94.679 | 1.00 | 0.00 |
| ATOM | 813 | CA | TYR | 313 | 17.861 | 31.336 | 93.345 | 1.00 | 8.37 |
| ATOM | 814 | CB | TYR | 313 | 18.624 | 30.041 | 93.016 | 1.00 | 8.55 |
| ATOM | 815 | CG | TYR | 313 | 19.756 | 29.586 | 93.920 | 1.00 | 12.63 |
| ATOM | 816 | CD1 | TYR | 313 | 20.370 | 30.425 | 94.826 | 1.00 | 12.91 |
| ATOM | 817 | CE1 | TYR | 313 | 21.426 | 29.985 | 95.632 | 1.00 | 14.23 |
| ATOM | 818 | CD2 | TYR | 313 | 20.223 | 28.273 | 93.828 | 1.00 | 14.27 |
| ATOM | 819 | CE2 | TYR | 313 | 21.280 | 27.829 | 94.626 | 1.00 | 14.90 |
| ATOM | 820 | CA | TYR | 313 | 21.870 | 28.689 | 95.520 | 1.00 | 15.27 |
| ATOM | 821 | OH | TYR | 313 | 22.910 | 28.240 | 96.314 | 1.00 | 17.23 |
| ATOM | 822 | HH | TYR | 313 | 23.083 | 27.319 | 96.125 | 1.00 | 0.00 |
| ATOM | 823 | C | TYR | 313 | 16.971 | 31.540 | 92.137 | 1.00 | 7.36 |
| ATOM | 824 | O | TYR | 313 | 15.893 | 30.996 | 92.046 | 1.00 | 7.60 |
| ATOM | 825 | N | ILE | 314 | 17.457 | 32.334 | 91.189 | 0.82 | 5.30 |
| ATOM | 826 | H | ILE | 314 | 19.265 | 32.853 | 91.366 | 1.00 | 0.00 |
| ATOM | 827 | CA | ILE | 314 | 16.818 | 32.465 | 89.871 | 0.82 | 5.28 |
| ATOM | 828 | CB | ILE | 314 | 16.487 | 33.917 | 89.505 | 0.82 | 3.82 |
| ATOM | 829 | CG2 | ILE | 314 | 16.118 | 34.031 | 88.022 | 0.82 | 5.97 |
| ATOM | 830 | CG1 | ILE | 314 | 15.353 | 34.373 | 90.376 | 0.82 | 6.17 |
| ATOM | 831 | CD1 | ILE | 314 | 15.075 | 35.885 | 90.228 | 0.82 | 6.59 |
| ATOM | 832 | C | ILE | 314 | 17.912 | 31.956 | 88.901 | 0.82 | 5.34 |
| ATOM | 833 | O | ILE | 314 | 19.054 | 32.440 | 88.919 | 0.82 | 6.05 |
| ATOM | 834 | N | ILE | 314 | 17.590 | 30.941 | 88.112 | 1.00 | 4.96 |
| ATOM | 835 | H | ILE | 314 | 16.681 | 30.583 | 88.145 | 1.00 | 0.00 |
| ATOM | 836 | CA | ILE | 314 | 18.555 | 30.342 | 87.177 | 1.00 | 5.21 |
| ATOM | 837 | CB | ILE | 314 | 18.584 | 28.786 | 87.389 | 1.00 | 6.45 |
| ATOM | 838 | CG2 | ILE | 314 | 19.648 | 28.161 | 86.489 | 1.00 | 6.91 |
| ATOM | 839 | CG1 | ILE | 314 | 18.928 | 28.480 | 88.858 | 1.00 | 7.39 |
| ATOM | 840 | CD1 | ILE | 314 | 17.755 | 28.248 | 89.842 | 1.00 | 8.45 |
| ATOM | 841 | C | ILE | 315 | 18.159 | 30.700 | 85.767 | 1.00 | 5.40 |

TABLE 3-continued

Coordinates of Lck bound with AMP-PNP

| | | Atom Type | Res | # | X | Y | Z | Occ | B |
|---|---|---|---|---|---|---|---|---|---|
| ATOM | 842 | O | ILE | 315 | 16.995 | 30.576 | 85.409 | 1.00 | 4.96 |
| ATOM | 843 | N | THR | 316 | 19.129 | 31.176 | 84.970 | 1.00 | 5.62 |
| ATOM | 844 | H | THR | 316 | 20.044 | 31.248 | 85.291 | 1.00 | 0.00 |
| ATOM | 845 | CA | THR | 316 | 18.824 | 31.575 | 83.165 | 1.00 | 5.76 |
| ATOM | 846 | CB | THR | 316 | 18.829 | 33.131 | 83.474 | 1.00 | 8.03 |
| ATOM | 847 | OG1 | THR | 316 | 20.137 | 33.649 | 83.793 | 1.00 | 9.42 |
| ATOM | 848 | HG1 | THR | 316 | 20.126 | 34.596 | 83.708 | 1.00 | 0.00 |
| ATOM | 849 | CG2 | THR | 316 | 17.897 | 33.731 | 84.491 | 1.00 | 7.19 |
| ATOM | 850 | C | THR | 316 | 19.792 | 31.052 | 82.580 | 1.00 | 5.99 |
| ATOM | 851 | O | THR | 316 | 20.860 | 30.501 | 82.906 | 1.00 | 5.90 |
| ATOM | 852 | N | GLU | 317 | 19.445 | 31.314 | 81.342 | 1.00 | 5.22 |
| ATOM | 853 | H | GLU | 317 | 18.592 | 31.745 | 81.162 | 1.00 | 0.00 |
| ATOM | 854 | CA | GLU | 317 | 20.295 | 30.965 | 81.189 | 1.00 | 5.30 |
| ATOM | 855 | CB | GLU | 317 | 19.618 | 31.546 | 78.960 | 1.00 | 5.70 |
| ATOM | 856 | CG | GLU | 317 | 20.307 | 31.327 | 77.643 | 1.00 | 6.11 |
| ATOM | 857 | CD | GLU | 317 | 19.459 | 31.830 | 76.475 | 1.00 | 6.55 |
| ATOM | 858 | OE1 | GLU | 317 | 18.499 | 32.609 | 76.704 | 1.00 | 6.40 |
| ATOM | 859 | OE2 | GLU | 317 | 19.715 | 31.435 | 75.323 | 1.00 | 7.06 |
| ATOM | 860 | C | GLU | 317 | 21.690 | 31.631 | 80.355 | 1.00 | 7.29 |
| ATOM | 861 | O | GLU | 317 | 21.794 | 32.387 | 80.668 | 1.00 | 8.69 |
| ATOM | 862 | N | TYR | 318 | 22.754 | 30.866 | 80.133 | 1.00 | 6.02 |
| ATOM | 863 | H | TYR | 318 | 22.648 | 29.938 | 79.891 | 1.00 | 0.00 |
| ATOM | 864 | CA | TYR | 318 | 24.114 | 31.411 | 80.272 | 1.00 | 5.54 |
| ATOM | 865 | CB | TYR | 318 | 25.078 | 30.268 | 80.623 | 1.00 | 6.33 |
| ATOM | 866 | CG | TYR | 318 | 26.452 | 30.764 | 81.010 | 1.00 | 7.47 |
| ATOM | 867 | CD1 | TYR | 318 | 26.643 | 31.354 | 82.258 | 1.00 | 10.12 |
| ATOM | 868 | CE1 | TYR | 318 | 27.862 | 31.866 | 82.636 | 1.00 | 13.41 |
| ATOM | 869 | CD2 | TYR | 318 | 27.509 | 30.672 | 80.143 | 1.00 | 9.46 |
| ATOM | 870 | CE2 | TYR | 318 | 28.766 | 31.208 | 80.518 | 1.00 | 11.26 |
| ATOM | 871 | CZ | TYR | 318 | 28.909 | 31.787 | 81.756 | 1.00 | 12.20 |
| ATOM | 872 | OH | TYR | 318 | 30.143 | 32.302 | 82.179 | 1.00 | 16.24 |
| ATOM | 873 | HH | TYR | 318 | 30.059 | 32.690 | 83.047 | 1.00 | 0.00 |
| ATOM | 874 | C | TYR | 318 | 24.554 | 32.041 | 78.950 | 1.00 | 5.01 |
| ATOM | 875 | O | TYR | 318 | 24.367 | 31.482 | 77.835 | 1.00 | 5.85 |
| ATOM | 876 | N | MET | 319 | 25.165 | 33.233 | 79.080 | 1.00 | 5.48 |
| ATOM | 877 | H | MET | 319 | 25.292 | 33.625 | 79.961 | 1.00 | 0.00 |
| ATOM | 878 | CA | MET | 319 | 25.612 | 33.975 | 77.904 | 1.00 | 5.51 |
| ATOM | 879 | CB | MET | 319 | 24.888 | 35.332 | 77.889 | 1.00 | 6.85 |
| ATOM | 880 | CG | MET | 319 | 23.344 | 35.195 | 77.705 | 1.00 | 8.12 |
| ATOM | 881 | SD | MET | 319 | 22.849 | 34.471 | 76.173 | 1.00 | 11.98 |
| ATOM | 882 | CE | MET | 319 | 23.062 | 35.837 | 75.041 | 1.00 | 9.53 |
| ATOM | 883 | C | MET | 319 | 27.129 | 34.107 | 78.064 | 1.00 | 5.87 |
| ATOM | 884 | O | MET | 319 | 27.615 | 34.858 | 78.897 | 1.00 | 6.85 |
| ATOM | 885 | N | GLU | 320 | 27.858 | 33.407 | 77.216 | 1.00 | 6.56 |
| ATOM | 886 | H | GLU | 320 | 27.431 | 32.956 | 76.543 | 1.00 | 0.00 |
| ATOM | 887 | CA | GLU | 320 | 29.299 | 33.269 | 77.406 | 1.00 | 7.66 |
| ATOM | 888 | CB | GLU | 320 | 29.898 | 32.327 | 76.362 | 1.00 | 10.83 |
| ATOM | 889 | CG | GLU | 320 | 31.367 | 31.957 | 76.669 | 1.00 | 16.03 |
| ATOM | 890 | CD | GLU | 320 | 31.475 | 31.047 | 77.891 | 1.00 | 19.05 |
| ATOM | 891 | OE1 | GLU | 320 | 30.758 | 30.025 | 77.939 | 1.00 | 22.54 |
| ATOM | 892 | OE2 | GLU | 320 | 32.235 | 31.369 | 78.834 | 1.00 | 23.91 |
| ATOM | 893 | C | GLU | 320 | 30.115 | 34.513 | 77.416 | 1.00 | 7.80 |
| ATOM | 894 | O | GLU | 320 | 31.104 | 34.568 | 78.145 | 1.00 | 9.31 |
| ATOM | 895 | N | ASN | 321 | 29.705 | 35.490 | 76.621 | 1.00 | 6.37 |
| ATOM | 896 | H | ASN | 321 | 28.871 | 35.388 | 76.113 | 1.00 | 0.00 |
| ATOM | 897 | CA | ASN | 321 | 30.480 | 36.772 | 76.512 | 1.00 | 6.88 |
| ATOM | 898 | CB | ASN | 321 | 30.615 | 37.140 | 75.058 | 1.00 | 6.80 |
| ATOM | 899 | CG | ASN | 321 | 31.689 | 36.332 | 74.348 | 1.00 | 8.90 |
| ATOM | 900 | OD1 | ASN | 321 | 32.864 | 36.282 | 74.820 | 1.00 | 9.89 |
| ATOM | 901 | ND2 | ASN | 321 | 31.354 | 35.755 | 73.224 | 1.00 | 9.37 |
| ATOM | 902 | HD21 | ASN | 321 | 30.446 | 35.848 | 72.879 | 1.00 | 0.00 |
| ATOM | 903 | HD22 | ASN | 321 | 32.049 | 35.235 | 72.766 | 1.00 | 0.00 |
| ATOM | 904 | C | ASN | 321 | 30.011 | 37.837 | 77.428 | 1.00 | 6.75 |
| ATOM | 905 | O | ASN | 321 | 30.506 | 38.975 | 77.292 | 1.00 | 8.29 |
| ATOM | 906 | N | GLY | 322 | 29.095 | 37.528 | 78.344 | 1.00 | 5.34 |
| ATOM | 907 | H | GLY | 322 | 28.692 | 36.642 | 78.339 | 1.00 | 0.00 |
| ATOM | 908 | CA | GLY | 322 | 28.722 | 38.495 | 79.367 | 1.00 | 5.22 |
| ATOM | 909 | C | GLY | 322 | 28.008 | 39.730 | 78.849 | 1.00 | 4.77 |
| ATOM | 910 | O | GLY | 322 | 27.372 | 39.690 | 77.799 | 1.00 | 6.29 |
| ATOM | 911 | N | SER | 323 | 28.143 | 40.835 | 79.574 | 0.43 | 2.00 |
| ATOM | 912 | H | SER | 323 | 28.719 | 40.843 | 80.360 | 1.00 | 0.00 |
| ATOM | 913 | CA | SER | 323 | 27.423 | 42.054 | 79.182 | 0.43 | 2.00 |
| ATOM | 914 | CB | SER | 323 | 27.333 | 43.044 | 80.361 | 0.32 | 2.00 |
| ATOM | 915 | OG | SER | 323 | 26.946 | 42.392 | 81.552 | 0.43 | 6.27 |

TABLE 3-continued

Coordinates of Lck bound with AMP-PNP

| | | Atom Type | Res | # | X | Y | Z | Occ | B |
|---|---|---|---|---|---|---|---|---|---|
| ATOM | 916 | HG | SER | 323 | 27.645 | 41.822 | 81.868 | 1.00 | 0.00 |
| ATOM | 917 | C | SER | 323 | 28.091 | 42.710 | 77.994 | 0.43 | 2.00 |
| ATOM | 918 | O | SER | 323 | 29.304 | 42.734 | 77.877 | 0.43 | 2.00 |
| ATOM | 919 | N | LEU | 324 | 27.267 | 43.285 | 77.135 | 1.00 | 3.87 |
| ATOM | 920 | H | LEU | 324 | 26.301 | 43.285 | 77.318 | 1.00 | 0.00 |
| ATOM | 921 | CA | LEU | 324 | 27.726 | 43.918 | 75.930 | 1.00 | 4.10 |
| ATOM | 922 | CB | LEU | 324 | 26.494 | 44.494 | 75.178 | 1.00 | 4.53 |
| ATOM | 923 | CG | LEU | 324 | 26.823 | 45.237 | 73.867 | 1.00 | 4.60 |
| ATOM | 924 | CD1 | LEU | 324 | 27.447 | 44.359 | 72.828 | 1.00 | 5.61 |
| ATOM | 925 | CD2 | LEU | 324 | 25.467 | 45.865 | 73.307 | 1.00 | 6.42 |
| ATOM | 926 | C | LEU | 324 | 28.697 | 45.076 | 76.272 | 1.00 | 5.16 |
| ATOM | 927 | O | LEU | 324 | 29.666 | 45.282 | 75.511 | 1.00 | 5.89 |
| ATOM | 928 | N | VAL | 325 | 28.386 | 45.855 | 77.306 | 1.00 | 6.46 |
| ATOM | 929 | H | VAL | 325 | 25.573 | 45.668 | 77.824 | 1.00 | 0.00 |
| ATOM | 930 | CA | VAL | 325 | 29.240 | 47.000 | 77.669 | 1.00 | 8.87 |
| ATOM | 931 | CB | VAL | 325 | 28.594 | 47.840 | 78.795 | 1.00 | 8.19 |
| ATOM | 932 | CG1 | VAL | 325 | 28.717 | 47.195 | 80.138 | 1.00 | 8.51 |
| ATOM | 933 | CG2 | VAL | 325 | 29.247 | 49.268 | 78.848 | 1.00 | 11.08 |
| ATOM | 934 | C | VAL | 325 | 30.653 | 46.530 | 77.989 | 1.00 | 9.20 |
| ATOM | 935 | O | VAL | 325 | 31.614 | 47.255 | 77.670 | 1.00 | 11.08 |
| ATOM | 936 | N | ASP | 326 | 30.798 | 45.323 | 78.552 | 1.00 | 8.70 |
| ATOM | 937 | H | ASP | 326 | 30.003 | 44.804 | 78.767 | 1.00 | 0.00 |
| ATOM | 938 | CA | ASP | 326 | 32.135 | 44.776 | 78.853 | 1.00 | 8.66 |
| ATOM | 939 | CB | ASP | 326 | 32.033 | 43.765 | 79.992 | 1.00 | 11.02 |
| ATOM | 940 | CG | ASP | 326 | 31.631 | 44.377 | 81.309 | 1.00 | 14.01 |
| ATOM | 941 | OD1 | ASP | 326 | 32.006 | 45.532 | 81.614 | 1.00 | 15.85 |
| ATOM | 942 | OD2 | ASP | 326 | 30.940 | 43.688 | 82.095 | 1.00 | 16.51 |
| ATOM | 943 | C | ASP | 326 | 32.740 | 44.091 | 77.626 | 1.00 | 7.60 |
| ATOM | 944 | O | ASP | 326 | 33.933 | 44.221 | 77.324 | 1.00 | 8.08 |
| ATOM | 945 | N | PHE | 327 | 31.911 | 43.400 | 76.853 | 1.00 | 5.80 |
| ATOM | 946 | H | PHE | 327 | 30.967 | 43.364 | 77.068 | 1.00 | 0.00 |
| ATOM | 947 | CA | PHE | 327 | 32.412 | 42.674 | 75.693 | 1.00 | 4.85 |
| ATOM | 948 | CB | PHE | 327 | 31.272 | 41.827 | 75.089 | 1.00 | 4.73 |
| ATOM | 949 | CG | PHE | 327 | 31.670 | 41.144 | 73.836 | 1.00 | 7.13 |
| ATOM | 950 | CD1 | PHE | 327 | 32.580 | 40.068 | 73.870 | 1.00 | 6.58 |
| ATOM | 951 | CD2 | PHE | 327 | 31.242 | 41.615 | 72.603 | 1.00 | 6.43 |
| ATOM | 952 | CE1 | PHE | 327 | 33.025 | 39.514 | 72.679 | 1.00 | 8.02 |
| ATOM | 953 | CE2 | PHE | 327 | 31.691 | 41.057 | 71.426 | 1.00 | 8.54 |
| ATOM | 954 | CA | PHE | 327 | 32.602 | 39.986 | 71.473 | 1.00 | 9.43 |
| ATOM | 955 | C | PHE | 327 | 33.044 | 43.581 | 74.630 | 1.00 | 4.40 |
| ATOM | 956 | O | PHE | 327 | 34.078 | 43.278 | 74.031 | 1.00 | 5.80 |
| ATOM | 957 | N | LEU | 328 | 32.413 | 44.736 | 74.421 | 0.40 | 2.00 |
| ATOM | 958 | H | LEU | 328 | 31.613 | 44.967 | 74.941 | 1.00 | 0.00 |
| ATOM | 959 | CA | LEU | 328 | 32.891 | 45.667 | 73.412 | 0.40 | 2.00 |
| ATOM | 960 | CB | LEU | 328 | 31.909 | 46.819 | 73.264 | 0.40 | 2.00 |
| ATOM | 961 | CG | LEU | 328 | 30.604 | 46.413 | 72.573 | 0.40 | 2.00 |
| ATOM | 962 | CD1 | LEU | 328 | 29.676 | 47.610 | 72.679 | 0.40 | 4.11 |
| ATOM | 963 | CD2 | LEU | 328 | 30.861 | 46.004 | 71.134 | 0.40 | 3.16 |
| ATOM | 964 | C | LEU | 328 | 34.267 | 46.218 | 73.721 | 0.40 | 2.00 |
| ATOM | 965 | O | LEU | 328 | 34.888 | 46.790 | 72.383 | 0.40 | 2.00 |
| ATOM | 966 | N | LYS | 329 | 34.707 | 46.049 | 74.966 | 1.00 | 6.15 |
| ATOM | 967 | H | LYS | 329 | 34.127 | 45.597 | 75.611 | 1.00 | 0.00 |
| ATOM | 968 | CA | LYS | 329 | 36.042 | 46.538 | 75.410 | 1.00 | 7.57 |
| ATOM | 969 | CB | LYS | 329 | 35.972 | 47.085 | 76.825 | 1.00 | 9.39 |
| ATOM | 970 | CG | LYS | 329 | 35.055 | 48.293 | 76.956 | 1.00 | 10.53 |
| ATOM | 971 | CD | LYS | 329 | 35.034 | 48.771 | 78.369 | 1.00 | 12.08 |
| ATOM | 972 | CE | LYS | 329 | 33.924 | 49.783 | 78.604 | 1.00 | 14.72 |
| ATOM | 973 | NZ | LYS | 329 | 33.813 | 50.022 | 80.065 | 1.00 | 17.45 |
| ATOM | 974 | HZ1 | LYS | 329 | 34.725 | 50.386 | 80.430 | 1.00 | 0.00 |
| ATOM | 975 | HZ2 | LYS | 329 | 33.609 | 49.124 | 80.554 | 1.00 | 0.00 |
| ATOM | 976 | HZ3 | LYS | 329 | 33.073 | 50.696 | 80.273 | 1.00 | 0.00 |
| ATOM | 977 | C | LYS | 329 | 37.121 | 45.460 | 75.332 | 1.00 | 9.59 |
| ATOM | 978 | O | LYS | 329 | 38.304 | 45.760 | 75.515 | 1.00 | 12.01 |
| ATOM | 979 | N | THR | 330 | 36.727 | 44.203 | 75.186 | 1.00 | 8.85 |
| ATOM | 980 | H | THR | 330 | 35.777 | 43.995 | 75.152 | 1.00 | 0.00 |
| ATOM | 981 | CA | THR | 330 | 37.733 | 43.124 | 75.084 | 1.00 | 9.09 |
| ATOM | 982 | CB | THR | 330 | 37.013 | 41.756 | 75.236 | 1.00 | 8.50 |
| ATOM | 983 | OG1 | THR | 330 | 36.187 | 41.541 | 74.094 | 1.00 | 9.34 |
| ATOM | 984 | HG1 | THR | 330 | 35.742 | 40.698 | 74.178 | 1.00 | 0.00 |
| ATOM | 985 | CG2 | THR | 330 | 36.275 | 41.705 | 76.534 | 1.00 | 10.85 |
| ATOM | 986 | C | THR | 330 | 38.400 | 43.168 | 73.699 | 1.00 | 8.83 |
| ATOM | 987 | O | THR | 330 | 37.948 | 43.804 | 72.771 | 1.00 | 8.36 |
| ATOM | 988 | N | PRO | 331 | 39.528 | 42.451 | 73.511 | 1.00 | 9.77 |
| ATOM | 989 | CD | PRO | 331 | 40.331 | 41.767 | 74.521 | 1.00 | 9.22 |

TABLE 3-continued

Coordinates of Lck bound with AMP-PNP

| | | Atom Type | Res | # | X | Y | Z | Occ | B |
|---|---|---|---|---|---|---|---|---|---|
| ATOM | 990 | CA | PRO | 331 | 40.169 | 42.453 | 72.195 | 1.00 | 10.20 |
| ATOM | 991 | CB | PRO | 331 | 41.304 | 41.427 | 72.382 | 1.00 | 9.14 |
| ATOM | 992 | CG | PRO | 331 | 41.688 | 41.634 | 73.771 | 1.00 | 8.46 |
| ATOM | 993 | C | PRO | 331 | 39.251 | 42.048 | 71.037 | 1.00 | 11.30 |
| ATOM | 994 | O | PRO | 331 | 39.314 | 42.623 | 69.952 | 1.00 | 12.41 |
| ATOM | 995 | N | SER | 332 | 38.424 | 41.026 | 71.272 | 1.00 | 11.84 |
| ATOM | 996 | H | SER | 332 | 38.455 | 40.584 | 72.144 | 1.00 | 0.00 |
| ATOM | 997 | CA | SER | 332 | 37.483 | 40.542 | 70.269 | 1.00 | 13.69 |
| ATOM | 998 | CB | SER | 332 | 36.732 | 39.300 | 70.805 | 1.00 | 15.15 |
| ATOM | 999 | OG | SER | 332 | 37.613 | 38.194 | 70.960 | 1.00 | 19.85 |
| ATOM | 1000 | HG | SER | 332 | 37.137 | 37.436 | 71.296 | 1.00 | 0.00 |
| ATOM | 1001 | C | SER | 332 | 36.462 | 41.632 | 69.986 | 1.00 | 13.44 |
| ATOM | 1002 | O | SER | 332 | 36.191 | 41.946 | 68.825 | 1.00 | 14.86 |
| ATOM | 1003 | N | GLY | 333 | 35.990 | 42.268 | 71.047 | 1.00 | 11.92 |
| ATOM | 1004 | H | GLY | 333 | 36.314 | 42.035 | 71.940 | 1.00 | 0.00 |
| ATOM | 1005 | CA | GLY | 333 | 34.997 | 43.333 | 70.888 | 1.00 | 11.53 |
| ATOM | 1006 | C | GLY | 333 | 35.575 | 44.519 | 70.120 | 1.00 | 11.96 |
| ATOM | 1007 | O | GLY | 333 | 34.911 | 45.094 | 69.240 | 1.00 | 11.03 |
| ATOM | 1008 | N | ILE | 334 | 36.797 | 44.903 | 70.471 | 1.00 | 11.99 |
| ATOM | 1009 | G | ILE | 334 | 37.279 | 44.425 | 71.166 | 1.00 | 0.00 |
| ATOM | 1010 | CA | ILE | 334 | 37.443 | 46.025 | 69.790 | 1.00 | 13.87 |
| ATOM | 1011 | CB | ILE | 334 | 38.796 | 46.304 | 70.469 | 1.00 | 13.07 |
| ATOM | 1012 | CG2 | ILE | 334 | 39.668 | 47.275 | 65.591 | 1.00 | 13.30 |
| ATOM | 1013 | CG1 | ILE | 334 | 38.540 | 46.807 | 71.885 | 1.00 | 13.93 |
| ATOM | 1014 | CD1 | ILE | 334 | 39.823 | 46.948 | 72.735 | 1.00 | 16.85 |
| ATOM | 1015 | C | ILE | 334 | 37.616 | 45.791 | 68.283 | 1.00 | 14.82 |
| ATOM | 1016 | O | ILE | 334 | 37.479 | 46.715 | 67.484 | 1.00 | 16.68 |
| ATOM | 1017 | N | LYS | 335 | 37.793 | 44.551 | 67.856 | 1.00 | 14.68 |
| ATOM | 1018 | H | LYS | 335 | 37.797 | 43.806 | 68.481 | 1.00 | 0.00 |
| ATOM | 1019 | CA | LYS | 335 | 37.985 | 44.319 | 66.427 | 1.00 | 15.73 |
| ATOM | 1020 | CB | LYS | 335 | 38.809 | 43.057 | 66.222 | 1.00 | 17.96 |
| ATOM | 1021 | CG | LYS | 335 | 40.132 | 43.083 | 66.978 | 1.00 | 20.04 |
| ATOM | 1022 | CD | LYS | 335 | 40.829 | 41.736 | 66.884 | 1.00 | 22.10 |
| ATOM | 1023 | CE | LYS | 335 | 42.093 | 41.738 | 67.703 | 1.00 | 24.01 |
| ATOM | 1024 | NX | LYS | 335 | 42.309 | 40.417 | 68.327 | 1.00 | 24.11 |
| ATOM | 1025 | HZ2 | LYS | 335 | 42.361 | 39.679 | 67.590 | 1.00 | 0.00 |
| ATOM | 1026 | HZ2 | LYS | 335 | 41.507 | 40.217 | 68.952 | 1.00 | 0.00 |
| ATOM | 1027 | HZ3 | LYS | 335 | 43.165 | 40.435 | 68.859 | 1.00 | 0.00 |
| ATOM | 1028 | C | LYS | 335 | 36.698 | 44.429 | 65.595 | 1.00 | 15.48 |
| ATOM | 1029 | O | LYS | 335 | 36.747 | 44.062 | 64.372 | 1.00 | 15.26 |
| ATOM | 1030 | N | LEU | 336 | 35.541 | 44.409 | 66.242 | 1.00 | 14.77 |
| ATOM | 1031 | H | LEU | 336 | 35.513 | 44.579 | 67.208 | 1.00 | 0.00 |
| ATOM | 1032 | CA | LEU | 336 | 34.296 | 44.313 | 65.460 | 2.00 | 23.70 |
| ATOM | 1033 | CB | LEU | 336 | 33.082 | 44.291 | 66.380 | 1.00 | 14.27 |
| ATOM | 1034 | CG | LEU | 336 | 33.028 | 43.099 | 67.363 | 1.00 | 15.32 |
| ATOM | 1035 | CD1 | LEU | 336 | 31.767 | 43.228 | 68.222 | 1.00 | 15.81 |
| ATOM | 1036 | CD2 | LEU | 336 | 33.067 | 41.753 | 66.636 | 1.00 | 16.91 |
| ATOM | 1037 | C | LEU | 336 | 34.122 | 45.410 | 64.448 | 1.00 | 13.32 |
| ATOM | 1038 | O | LEU | 336 | 34.392 | 46.582 | 64.763 | 1.00 | 15.25 |
| ATOM | 1039 | N | THR | 337 | 33.599 | 45.022 | 63.280 | 1.00 | 12.95 |
| ATOM | 1040 | H | THR | 337 | 33.359 | 44.105 | 63.153 | 1.00 | 0.00 |
| ATOM | 1041 | CA | THR | 337 | 33.353 | 45.967 | 62.202 | 1.00 | 11.61 |
| ATOM | 1042 | CB | THR | 337 | 33.161 | 45.237 | 60.836 | 1.00 | 11.98 |
| ATOM | 1043 | OG1 | THR | 337 | 32.050 | 44.309 | 60.907 | 1.00 | 12.22 |
| ATOM | 1044 | HG1 | THR | 337 | 31.248 | 44.779 | 61.143 | 1.00 | 0.00 |
| ATOM | 1045 | CG2 | THR | 337 | 34.450 | 44.424 | 60.453 | 1.00 | 13.51 |
| ATOM | 1046 | C | THR | 337 | 32.064 | 46.729 | 62.483 | 1.00 | 10.80 |
| ATOM | 1047 | O | THR | 337 | 31.255 | 46.279 | 63.309 | 1.00 | 9.51 |
| ATOM | 1048 | N | ILE | 338 | 31.890 | 47.892 | 61.843 | 1.00 | 9.90 |
| ATOM | 1049 | H | ILE | 338 | 32.595 | 48.249 | 61.262 | 1.00 | 0.00 |
| ATOM | 1050 | CA | ILE | 338 | 30.642 | 48.642 | 61.011 | 1.00 | 9.68 |
| ATOM | 1051 | CB | ILE | 338 | 30.677 | 50.012 | 61.253 | 1.00 | 10.93 |
| ATOM | 1052 | CG2 | ILE | 338 | 30.808 | 49.794 | 59.770 | 1.00 | 12.49 |
| ATOM | 1053 | CG1 | ILE | 338 | 29.417 | 50.842 | 61.559 | 1.00 | 12.18 |
| ATOM | 1054 | CD1 | ILE | 338 | 29.136 | 51.150 | 63.028 | 1.00 | 11.90 |
| ATOM | 1055 | C | ILE | 338 | 29.464 | 47.740 | 61.567 | 1.00 | 9.09 |
| ATOM | 1056 | O | ILE | 338 | 28.409 | 47.791 | 61.162 | 1.00 | 9.09 |
| ATOM | 1057 | N | ASN | 339 | 29.659 | 46.905 | 60.551 | 1.00 | 8.89 |
| ATOM | 1058 | H | ASN | 339 | 30.527 | 46.858 | 60.092 | 1.00 | 0.00 |
| ATOM | 1059 | CA | ASN | 339 | 28.595 | 46.012 | 60.093 | 1.00 | 10.04 |
| ATOM | 1060 | CB | ASN | 339 | 29.121 | 45.182 | 58.914 | 1.00 | 14.13 |
| ATOM | 1061 | CG | ASN | 339 | 28.369 | 43.872 | 58.706 | 1.00 | 19.41 |
| ATOM | 1062 | OD1 | ASN | 339 | 27.830 | 43.641 | 57.641 | 1.00 | 24.95 |
| ATOM | 1063 | ND2 | ASM | 339 | 28.340 | 43.013 | 59.728 | 1.00 | 24.26 |

TABLE 3-continued

Coordinates of Lck bound with AMP-PNP

| | | Atom Type | Res | # | X | Y | Z | Occ | B |
|---|---|---|---|---|---|---|---|---|---|
| ATOM | 1064 | HD21 | ASN | 339 | 28.774 | 43.262 | 60.586 | 1.00 | 0.00 |
| ATOM | 1065 | HD22 | ASN | 339 | 27.885 | 42.176 | 59.646 | 1.00 | 0.00 |
| ATOM | 1066 | C | ASN | 339 | 28.169 | 45.097 | 61.245 | 1.00 | 8.87 |
| ATOM | 1067 | O | ASN | 339 | 26.975 | 44.847 | 61.433 | 1.00 | 7.55 |
| ATOM | 1068 | N | LYS | 340 | 29.133 | 44.511 | 61.967 | 1.00 | 7.56 |
| ATOM | 1069 | H | LYS | 340 | 30.077 | 44.690 | 61.773 | 1.00 | 0.00 |
| ATOM | 1070 | CA | LYS | 340 | 28.726 | 43.588 | 63.029 | 1.00 | 6.70 |
| ATOM | 1071 | CB | LYS | 340 | 29.915 | 42.776 | 63.573 | 1.00 | 5.88 |
| ATOM | 1072 | CG | LYS | 340 | 29.586 | 41.835 | 64.698 | 1.00 | 6.19 |
| ATOM | 1073 | CS | LYS | 340 | 28.473 | 40.804 | 64.263 | 1.00 | 6.70 |
| ATOM | 1074 | CE | LYS | 340 | 28.199 | 39.920 | 65.468 | 1.00 | 7.59 |
| ATOM | 1075 | NZ | LYS | 340 | 27.010 | 38.984 | 65.151 | 1.00 | 9.23 |
| ATOM | 1076 | HZ1 | LYS | 340 | 27.244 | 38.385 | 64.353 | 1.00 | 0.00 |
| ATOM | 1077 | HZ2 | LYS | 340 | 26.167 | 39.561 | 64.935 | 1.00 | 0.00 |
| ATOM | 1078 | HZ3 | LYS | 340 | 26.803 | 38.402 | 65.992 | 1.00 | 0.00 |
| ATOM | 1079 | C | LYS | 340 | 28.046 | 44.352 | 64.150 | 1.00 | 6.91 |
| ATOM | 1080 | O | LYS | 340 | 27.097 | 43.838 | 64.795 | 1.00 | 7.61 |
| ATOM | 1081 | N | LEU | 341 | 28.526 | 45.576 | 64.420 | 1.00 | 5.67 |
| ATOM | 1082 | N | LEU | 341 | 29.266 | 45.945 | 63.925 | 1.00 | 0.00 |
| ATOM | 1083 | CA | LEU | 341 | 27.903 | 46.378 | 65.460 | 1.00 | 5.04 |
| ATOM | 1084 | CB | LEU | 341 | 28.692 | 47.686 | 65.712 | 1.00 | 6.51 |
| ATOM | 1085 | CG | LEU | 341 | 30.121 | 47.465 | 66.221 | 1.00 | 7.32 |
| ATOM | 1086 | CD1 | LEU | 341 | 30.775 | 48.870 | 66.357 | 1.00 | 8.50 |
| ATOM | 1087 | CD2 | LEU | 341 | 30.140 | 46.820 | 67.570 | 1.00 | 8.70 |
| ATOM | 1088 | C | LEU | 341 | 26.437 | 46.699 | 65.075 | 1.00 | 4.38 |
| ATOM | 1089 | O | LEU | 341 | 25.582 | 46.706 | 65.945 | 1.00 | 5.27 |
| ATOM | 1090 | N | LEU | 342 | 26.176 | 46.960 | 63.798 | 1.00 | 5.97 |
| ATOM | 1091 | H | LEU | 342 | 26.913 | 46.945 | 63.154 | 1.00 | 0.00 |
| ATOM | 1092 | CA | LEU | 342 | 24.816 | 47.279 | 63.312 | 1.00 | 4.84 |
| ATOM | 1093 | CB | LEU | 342 | 24.850 | 47.754 | 61.845 | 1.00 | 6.19 |
| ATOM | 1094 | CG | LEU | 342 | 25.448 | 49.182 | 61.674 | 1.00 | 8.40 |
| ATOM | 1095 | CD1 | LEU | 342 | 25.731 | 49.410 | 60.184 | 1.00 | 9.05 |
| ATOM | 1096 | CD2 | LEU | 342 | 24.536 | 50.273 | 62.284 | 1.00 | 10.59 |
| ATOM | 1097 | C | LEU | 342 | 23.957 | 46.020 | 63.435 | 1.00 | 6.56 |
| ATOM | 1098 | O | LEU | 342 | 22.808 | 46.088 | 63.844 | 1.00 | 6.05 |
| ATOM | 1099 | N | ASP | 343 | 24.562 | 44.872 | 63.129 | 1.00 | 6.36 |
| ATOM | 1100 | H | ASP | 343 | 25.477 | 44.873 | 62.804 | 1.00 | 0.00 |
| ATOM | 1101 | CA | ASP | 343 | 23.846 | 43.589 | 63.289 | 1.00 | 6.77 |
| ATOM | 1102 | CB | ASP | 343 | 24.814 | 42.473 | 62.870 | 1.00 | 5.62 |
| ATOM | 1103 | CG | ASP | 343 | 24.355 | 41.091 | 63.252 | 1.00 | 7.43 |
| ATOM | 1104 | OD1 | ASP | 343 | 23.150 | 40.853 | 63.435 | 1.00 | 8.26 |
| ATOM | 1105 | OD2 | ASP | 343 | 25.262 | 40.231 | 63.270 | 1.00 | 5.62 |
| ATOM | 1106 | C | ASP | 343 | 23.417 | 43.439 | 64.747 | 1.00 | 5.67 |
| ATOM | 1107 | O | ASP | 343 | 22.232 | 43.177 | 65.021 | 1.00 | 6.41 |
| ATOM | 1108 | N | MET | 344 | 24.343 | 43.555 | 65.699 | 1.00 | 5.54 |
| ATOM | 1109 | H | MET | 344 | 25.277 | 43.704 | 65.454 | 1.00 | 0.00 |
| ATOM | 1110 | CA | MET | 344 | 24.003 | 43.452 | 67.114 | 1.00 | 6.12 |
| ATOM | 1111 | CB | MET | 344 | 25.242 | 43.644 | 67.977 | 1.00 | 8.61 |
| ATOM | 1112 | CG | MET | 344 | 26.221 | 42.513 | 67.682 | 1.00 | 9.80 |
| ATOM | 1113 | SD | MET | 344 | 27.833 | 42.796 | 68.536 | 1.00 | 17.00 |
| ATOM | 1114 | CE | MET | 344 | 27.976 | 41.510 | 69.671 | 1.00 | 16.18 |
| ATOM | 1115 | C | MET | 344 | 22.911 | 44.461 | 67.503 | 1.00 | 5.89 |
| ATOM | 1116 | O | MET | 344 | 22.029 | 44.124 | 68.265 | 1.00 | 5.58 |
| ATOM | 1117 | N | ALA | 345 | 23.003 | 45.696 | 66.990 | 1.00 | 4.96 |
| ATOM | 1118 | H | ALA | 345 | 23.774 | 45.923 | 66.423 | 1.00 | 0.00 |
| ATOM | 1119 | CA | ALA | 345 | 21.995 | 46.729 | 67.266 | 1.00 | 4.58 |
| ATOM | 1120 | CB | ALA | 345 | 22.376 | 48.034 | 66.577 | 1.00 | 5.20 |
| ATOM | 1121 | C | ALA | 345 | 20.603 | 46.244 | 66.804 | 1.00 | 4.22 |
| ATOM | 1122 | O | ALA | 345 | 19.646 | 46.454 | 67.563 | 1.00 | 5.43 |
| ATOM | 1123 | N | ALA | 346 | 20.525 | 45.688 | 65.597 | 1.00 | 3.54 |
| ATOM | 1124 | H | ALA | 346 | 21.323 | 45.645 | 65.043 | 1.00 | 0.00 |
| ATOM | 1125 | CA | ALA | 346 | 19.257 | 45.140 | 65.059 | 1.00 | 4.63 |
| ATOM | 1126 | CB | ALA | 346 | 19.422 | 44.694 | 63.647 | 1.00 | 4.56 |
| ATOM | 1127 | C | ALA | 346 | 18.769 | 43.992 | 65.925 | 1.00 | 4.94 |
| ATOM | 1128 | O | ALA | 346 | 17.562 | 43.865 | 66.158 | 1.00 | 4.62 |
| ATOM | 1129 | N | GLN | 347 | 19.691 | 43.149 | 66.415 | 1.00 | 4.26 |
| ATOM | 1130 | H | GLN | 347 | 20.630 | 43.255 | 66.203 | 1.00 | 0.00 |
| ATOM | 1131 | CA | GLN | 347 | 19.253 | 42.039 | 67.287 | 1.00 | 4.61 |
| ATOM | 1132 | CB | GLN | 347 | 20.437 | 41.123 | 67.668 | 1.00 | 4.27 |
| ATOM | 1133 | CG | GLN | 347 | 21.120 | 40.527 | 66.475 | 1.00 | 5.36 |
| ATOM | 1134 | CD | GLN | 347 | 22.162 | 39.471 | 66.822 | 1.00 | 5.82 |
| ATOM | 1135 | OE1 | GLN | 347 | 22.130 | 39.918 | 67.891 | 1.00 | 7.06 |
| ATOM | 1136 | NE2 | GLN | 347 | 23.104 | 39.223 | 65.904 | 1.00 | 6.44 |
| ATOM | 1137 | HE21 | GLN | 347 | 23.095 | 39.715 | 65.057 | 1.00 | 0.00 |

TABLE 3-continued

Coordinates of Lck bound with AMP-PNP

| | | Atom Type | Res | # | X | Y | Z | Occ | B |
|---|---|---|---|---|---|---|---|---|---|
| ATOM | 1138 | HE22 | GLN | 347 | 23.763 | 38.532 | 66.098 | 1.00 | 0.00 |
| ATOM | 1139 | C | GLN | 347 | 18.558 | 42.542 | 68.524 | 1.00 | 5.59 |
| ATOM | 1140 | O | GLN | 347 | 17.563 | 41.999 | 68.987 | 1.00 | 6.38 |
| ATOM | 1141 | N | ILE | 348 | 19.117 | 43.599 | 69.139 | 1.00 | 4.36 |
| ATOM | 1142 | H | ILE | 348 | 19.933 | 43.999 | 68.752 | 1.00 | 0.00 |
| ATOM | 1143 | CA | ILE | 348 | 18.547 | 44.163 | 70.321 | 1.00 | 4.40 |
| ATOM | 1144 | CB | ILE | 348 | 19.507 | 45.237 | 70.855 | 1.00 | 4.00 |
| ATOM | 1145 | CG2 | ILE | 348 | 18.896 | 45.944 | 72.083 | 1.00 | 5.56 |
| ATOM | 1146 | CG1 | ILE | 348 | 20.815 | 44.547 | 71.279 | 1.00 | 3.40 |
| ATOM | 1147 | CD1 | ILE | 348 | 21.972 | 45.521 | 71.478 | 1.00 | 5.25 |
| ATOM | 1148 | C | ILE | 348 | 17.192 | 44.797 | 69.794 | 1.00 | 3.38 |
| ATOM | 1149 | O | ILE | 348 | 16.287 | 44.658 | 70.794 | 1.00 | 4.01 |
| ATOM | 1150 | N | ALA | 349 | 17.111 | 45.518 | 68.857 | 1.00 | 4.79 |
| ATOM | 1151 | H | ALA | 349 | 17.902 | 45.617 | 68.285 | 1.00 | 0.00 |
| ATOM | 1152 | CA | ALA | 349 | 15.827 | 46.147 | 68.447 | 1.00 | 3.81 |
| ATOM | 1153 | CB | ALA | 349 | 15.972 | 46.914 | 67.148 | 1.00 | 4.46 |
| ATOM | 1154 | C | ALA | 349 | 14.788 | 45.007 | 68.242 | 1.00 | 4.00 |
| ATOM | 1155 | O | ALA | 349 | 13.606 | 45.193 | 68.604 | 1.00 | 4.66 |
| ATOM | 1156 | N | GLU | 350 | 15.226 | 43.862 | 67.717 | 1.00 | 5.02 |
| ATOM | 1157 | H | GLU | 350 | 16.162 | 43.769 | 67.465 | 1.00 | 0.00 |
| ATOM | 1158 | CA | GLU | 350 | 14.295 | 42.747 | 67.499 | 1.00 | 4.86 |
| ATOM | 1159 | CB | GLU | 350 | 15.011 | 41.626 | 66.771 | 1.00 | 5.41 |
| ATOM | 1160 | CG | GLU | 350 | 14.139 | 40.436 | 66.419 | 1.00 | 7.13 |
| ATOM | 1161 | CD | GLU | 350 | 14.948 | 39.349 | 65.710 | 1.00 | 10.34 |
| ATOM | 1162 | OE1 | GLU | 350 | 15.991 | 39.637 | 65.025 | 1.00 | 10.86 |
| ATOM | 1163 | OE2 | GLU | 350 | 14.466 | 38.181 | 65.764 | 1.00 | 12.13 |
| ATOM | 1164 | C | GLU | 350 | 13.768 | 42.342 | 68.854 | 1.00 | 5.26 |
| ATOM | 1165 | O | GLU | 350 | 12.563 | 41.921 | 68.985 | 1.00 | 5.78 |
| ATOM | 1166 | N | GLY | 351 | 14.641 | 42.113 | 69.868 | 1.00 | 3.72 |
| ATOM | 1167 | H | GLY | 351 | 15.593 | 42.271 | 69.705 | 1.00 | 0.00 |
| ATOM | 1168 | CA | GLY | 351 | 14.167 | 41.705 | 71.183 | 1.00 | 3.50 |
| ATOM | 1169 | C | GLY | 351 | 13.200 | 42.739 | 71.741 | 1.00 | 4.23 |
| ATOM | 1170 | O | GLY | 351 | 12.202 | 42.405 | 72.322 | 1.00 | 5.58 |
| ATOM | 1171 | N | MET | 352 | 13.560 | 44.009 | 71.611 | 1.00 | 3.47 |
| ATOM | 1172 | H | MET | 352 | 14.420 | 44.241 | 71.190 | 1.00 | 0.00 |
| ATOM | 1173 | CA | MET | 352 | 12.665 | 45.019 | 72.130 | 1.00 | 3.42 |
| ATOM | 1174 | CB | MET | 352 | 13.342 | 46.392 | 72.110 | 1.00 | 2.72 |
| ATOM | 1175 | CG | MET | 352 | 14.467 | 46.506 | 73.158 | 1.00 | 5.58 |
| ATOM | 1176 | SD | MET | 352 | 14.003 | 46.180 | 74.852 | 1.00 | 5.58 |
| ATOM | 1177 | CE | MET | 352 | 12.489 | 47.318 | 75.041 | 1.00 | 7.43 |
| ATOM | 1178 | C | MET | 352 | 11.337 | 45.091 | 71.369 | 1.00 | 3.73 |
| ATOM | 1179 | O | MET | 352 | 10.372 | 45.485 | 72.023 | 1.00 | 4.83 |
| ATOM | 1180 | N | ALA | 353 | 11.275 | 44.680 | 70.093 | 1.00 | 4.70 |
| ATOM | 1181 | H | ALA | 353 | 12.092 | 44.390 | 69.637 | 1.00 | 0.00 |
| ATOM | 1182 | CA | ALA | 353 | 10.014 | 44.713 | 69.327 | 1.00 | 3.95 |
| ATOM | 1183 | CB | ALA | 353 | 10.251 | 44.482 | 67.888 | 1.00 | 5.05 |
| ATOM | 1184 | C | ALA | 353 | 9.116 | 43.633 | 69.914 | 1.00 | 5.68 |
| ATOM | 1185 | O | ALA | 353 | 7.888 | 43.816 | 69.920 | 1.00 | 5.65 |
| ATOM | 1186 | N | PHE | 354 | 9.703 | 42.527 | 70.378 | 1.00 | 5.57 |
| ATOM | 1187 | H | PHE | 354 | 10.677 | 42.415 | 70.297 | 1.00 | 0.00 |
| ATOM | 1188 | CA | PHE | 354 | 8.871 | 41.487 | 71.010 | 1.00 | 5.74 |
| ATOM | 1189 | CB | PHE | 354 | 9.690 | 40.193 | 71.276 | 1.00 | 5.64 |
| ATOM | 1190 | CG | PHE | 354 | 8.963 | 39.190 | 72.137 | 1.00 | 7.49 |
| ATOM | 1191 | CD1 | PHE | 354 | 7.954 | 38.421 | 71.583 | 1.00 | 9.77 |
| ATOM | 1192 | CD2 | PHE | 354 | 9.284 | 39.033 | 73.477 | 1.00 | 7.95 |
| ATOM | 1193 | CE1 | PHE | 354 | 7.269 | 37.494 | 72.416 | 1.00 | 7.85 |
| ATOM | 1194 | CE2 | PHE | 354 | 8.600 | 38.106 | 74.307 | 1.00 | 10.41 |
| ATOM | 1195 | CZ | PHE | 354 | 7.606 | 37.365 | 73.731 | 1.00 | 8.21 |
| ATOM | 1196 | C | PHE | 354 | 8.262 | 42.040 | 72.300 | 1.00 | 5.21 |
| ATOM | 1197 | O | PHE | 354 | 7.074 | 41.882 | 72.542 | 1.00 | 6.94 |
| ATOM | 1198 | N | ILE | 355 | 9.066 | 42.707 | 73.146 | 1.00 | 3.91 |
| ATOM | 1199 | H | ILE | 355 | 10.007 | 42.383 | 72.897 | 1.00 | 0.00 |
| ATOM | 1200 | CA | ILE | 355 | 8.624 | 43.274 | 74.422 | 1.00 | 4.64 |
| ATOM | 1201 | CB | ILE | 355 | 9.858 | 43.897 | 75.121 | 1.00 | 4.64 |
| ATOM | 1202 | CG2 | ILE | 355 | 9.429 | 44.817 | 76.257 | 1.00 | 5.51 |
| ATOM | 1203 | CG1 | ILE | 355 | 10.689 | 42.748 | 75.698 | 1.00 | 5.02 |
| ATOM | 1204 | CD1 | ILE | 355 | 12.039 | 43.224 | 76.336 | 1.00 | 5.07 |
| ATOM | 1205 | C | ILE | 355 | 7.507 | 44.302 | 74.145 | 1.00 | 5.18 |
| ATOM | 1206 | O | ILE | 355 | 6.471 | 44.277 | 74.821 | 1.00 | 6.36 |
| ATOM | 1207 | N | GLU | 356 | 7.688 | 45.052 | 73.072 | 1.00 | 5.48 |
| ATOM | 1208 | H | GLU | 356 | 8.499 | 44.926 | 72.549 | 1.00 | 0.00 |
| ATOM | 1209 | CA | GLU | 356 | 6.730 | 46.066 | 72.633 | 1.00 | 5.56 |
| ATOM | 1210 | CB | GLU | 356 | 7.309 | 46.792 | 71.413 | 1.00 | 6.65 |
| ATOM | 1211 | CG | GLU | 356 | 6.392 | 47.776 | 70.567 | 1.00 | 9.77 |

TABLE 3-continued

Coordinates of Lck bound with AMP-PNP

| | | Atom Type | Res | # | X | Y | Z | Occ | B |
|---|---|---|---|---|---|---|---|---|---|
| ATOM | 1212 | CD | GLU | 356 | 7.256 | 48.348 | 69.382 | 1.00 | 11.17 |
| ATOM | 1213 | OE1 | GLU | 356 | 7.380 | 47.805 | 68.206 | 1.00 | 14.46 |
| ATOM | 1214 | OE2 | GLU | 356 | 7.863 | 49.347 | 69.707 | 1.00 | 13.36 |
| ATOM | 1215 | C | GLU | 356 | 5.411 | 45.370 | 72.284 | 1.00 | 5.36 |
| ATOM | 1216 | O | GLU | 356 | 4.348 | 45.812 | 72.733 | 1.00 | 6.62 |
| ATOM | 1217 | N | GLU | 357 | 5.482 | 44.359 | 71.428 | 0.36 | 2.07 |
| ATOM | 1218 | H | GLU | 357 | 6.356 | 44.046 | 71.111 | 1.00 | 0.00 |
| ATOM | 1219 | CA | GLU | 357 | 4.260 | 42.690 | 70.981 | 0.36 | 2.00 |
| ATOM | 1220 | CB | GLU | 357 | 4.593 | 42.734 | 69.845 | 0.36 | 3.32 |
| ATOM | 1221 | CG | GLU | 357 | 3.419 | 41.918 | 69.332 | 0.36 | 6.37 |
| ATOM | 1222 | CD | GLU | 357 | 3.244 | 40.629 | 70.091 | 0.36 | 9.12 |
| ATOM | 1223 | OE1 | GLU | 357 | 4.082 | 40.326 | 70.953 | 0.36 | 10.81 |
| ATOM | 1224 | OE2 | GLU | 357 | 2.264 | 39.897 | 72.841 | 0.36 | 12.18 |
| ATOM | 1225 | C | GLU | 357 | 3.495 | 43.010 | 72.096 | 0.36 | 2.09 |
| ATOM | 1226 | O | GLU | 357 | 2.254 | 42.897 | 72.064 | 0.36 | 2.00 |
| ATOM | 1227 | N | ARG | 358 | 4.215 | 42.578 | 73.112 | 1.00 | 5.24 |
| ATOM | 1228 | H | ARG | 358 | 5.184 | 42.724 | 73.114 | 1.00 | 0.00 |
| ATOM | 1229 | CA | ARG | 358 | 3.568 | 41.888 | 74.246 | 1.00 | 6.65 |
| ATOM | 1230 | CB | ARG | 358 | 4.542 | 40.861 | 74.891 | 1.00 | 9.04 |
| ATOM | 1231 | CG | ARG | 358 | 5.014 | 39.746 | 73.965 | 1.00 | 10.38 |
| ATOM | 1232 | CD | ARG | 358 | 3.832 | 38.910 | 73.377 | 1.00 | 13.95 |
| ATOM | 1233 | NE | ARG | 358 | 2.952 | 38.513 | 74.438 | 1.00 | 17.47 |
| ATOM | 1234 | HE | ARG | 358 | 3.314 | 38.471 | 75.342 | 1.00 | 0.00 |
| ATOM | 1235 | CA | ARG | 358 | 1.678 | 38.213 | 74.227 | 1.00 | 17.45 |
| ATOM | 1236 | NH1 | ARG | 358 | 1.200 | 38.277 | 72.985 | 1.00 | 19.34 |
| ATOM | 1237 | HH11 | ARG | 358 | 1.801 | 38.543 | 72.242 | 1.00 | 0.00 |
| ATOM | 1238 | HH12 | ARG | 358 | 0.241 | 38.050 | 72.811 | 1.00 | 0.00 |
| ATOM | 1239 | NH2 | ARG | 358 | 0.897 | 37.937 | 75.262 | 1.00 | 19.28 |
| ATOM | 1240 | HH21 | ARG | 358 | 1.289 | 37.929 | 76.190 | 1.00 | 0.00 |
| ATOM | 1241 | C | ARG | 358 | −0.055 | 37.691 | 75.122 | 1.00 | 0.00 |
| ATOM | 1242 | C | ARG | 358 | 3.040 | 42.803 | 75.341 | 1.00 | 6.80 |
| ATOM | 1243 | O | ARG | 358 | 2.581 | 42.352 | 76.383 | 1.00 | 9.44 |
| ATOM | 1244 | N | ASN | 359 | 3.113 | 44.120 | 75.095 | 1.00 | 7.42 |
| ATOM | 1245 | H | ASN | 359 | 3.472 | 44.423 | 74.234 | 1.00 | 0.00 |
| ATOM | 1246 | CA | ASN | 359 | 2.661 | 45.128 | 76.047 | 1.00 | 8.33 |
| ATOM | 1247 | CB | ASN | 359 | 1.161 | 44.997 | 76.418 | 1.00 | 8.38 |
| ATOM | 1248 | CG | ASN | 359 | 0.249 | 45.452 | 75.301 | 1.00 | 9.65 |
| ATOM | 1249 | OD1 | ASN | 359 | 0.661 | 46.058 | 74.325 | 1.00 | 12.69 |
| ATOM | 1250 | ND2 | ASN | 359 | −1.031 | 45.100 | 75.428 | 1.00 | 12.89 |
| ATOM | 1251 | HD22 | ASN | 359 | −1.325 | 44.590 | 76.209 | 1.00 | 0.00 |
| ATOM | 1252 | HD22 | ASN | 359 | −1.663 | 45.395 | 74.733 | 1.00 | 0.00 |
| ATOM | 1253 | C | ASN | 359 | 3.477 | 45.300 | 77.298 | 1.00 | 7.53 |
| ATOM | 1254 | O | ASN | 359 | 2.976 | 45.618 | 78.353 | 1.00 | 9.21 |
| ATOM | 1255 | N | TYR | 360 | 4.786 | 45.023 | 77.207 | 1.00 | 6.45 |
| ATOM | 1256 | H | TYR | 360 | 5.185 | 44.692 | 76.374 | 1.00 | 0.00 |
| ATOM | 1257 | CA | TYR | 360 | 5.629 | 45.247 | 78.357 | 1.00 | 6.51 |
| ATOM | 1258 | CB | TYR | 360 | 6.540 | 44.026 | 78.603 | 1.00 | 6.47 |
| ATOM | 1259 | CB | TYR | 360 | 5.822 | 42.905 | 79.323 | 1.00 | 7.71 |
| ATOM | 1260 | CD1 | TYR | 360 | 5.025 | 42.040 | 78.627 | 1.00 | 11.10 |
| ATOM | 1261 | CE1 | TYR | 360 | 4.362 | 40.971 | 79.293 | 1.00 | 12.54 |
| ATOM | 1262 | CD2 | TYR | 360 | 5.976 | 42.726 | 80.686 | 1.00 | 9.28 |
| ATOM | 1263 | CE2 | TYR | 360 | 5.314 | 41.076 | 81.359 | 1.00 | 11.47 |
| ATOM | 1264 | CA | TYR | 360 | 4.526 | 40.842 | 80.651 | 1.00 | 13.14 |
| ATOM | 1265 | OH | TYR | 360 | 3.793 | 39.868 | 81.329 | 1.00 | 16.50 |
| ATOM | 1266 | HH | TYR | 360 | 3.298 | 39.348 | 80.701 | 1.00 | 0.00 |
| ATOM | 1267 | C | TYR | 360 | 6.552 | 46.413 | 78.061 | 1.00 | 5.30 |
| ATOM | 1268 | O | TYR | 360 | 6.622 | 46.880 | 76.936 | 1.00 | 6.46 |
| ATOM | 1269 | N | ILE | 361 | 7.170 | 46.882 | 79.125 | 1.00 | 6.46 |
| ATOM | 1270 | H | ILE | 361 | 6.925 | 46.527 | 80.001 | 1.00 | 0.00 |
| ATOM | 1271 | CA | ILE | 361 | 8.234 | 47.889 | 79.038 | 1.00 | 6.30 |
| ATOM | 1272 | CB | ILE | 361 | 7.795 | 49.281 | 79.548 | 1.00 | 7.47 |
| ATOM | 1273 | CG2 | ILE | 361 | 6.822 | 49.866 | 78.557 | 1.00 | 8.36 |
| ATOM | 1274 | CG1 | ILE | 361 | 7.283 | 49.192 | 80.974 | 1.00 | 7.63 |
| ATOM | 1275 | CD1 | ILE | 361 | 7.029 | 50.595 | 81.537 | 1.00 | 10.24 |
| ATOM | 1276 | C | ILE | 361 | 9.397 | 47.292 | 79.854 | 1.00 | 6.54 |
| ATOM | 1277 | O | ILE | 361 | 9.207 | 46.473 | 80.761 | 1.00 | 6.53 |
| ATOM | 1278 | N | HIS | 362 | 10.621 | 47.761 | 79.567 | 1.00 | 6.73 |
| ATOM | 1279 | H | HIS | 362 | 10.705 | 48.454 | 78.895 | 1.00 | 0.00 |
| ATOM | 1280 | CA | HIS | 362 | 11.806 | 47.232 | 80.245 | 1.00 | 6.25 |
| ATOM | 1281 | CB | HIS | 362 | 12.869 | 46.961 | 79.178 | 1.00 | 5.77 |
| ATOM | 1282 | CG | HIS | 362 | 14.092 | 46.248 | 79.690 | 1.00 | 5.45 |
| ATOM | 1283 | CD2 | HIS | 362 | 14.468 | 44.938 | 79.647 | 1.00 | 6.09 |
| ATOM | 1284 | ND1 | HIS | 362 | 15.077 | 46.892 | 80.397 | 1.00 | 6.86 |
| ATOM | 1285 | HD1 | HIS | 362 | 15.110 | 47.858 | 80.570 | 1.00 | 0.00 |

TABLE 3-continued

Coordinates of Lck bound with AMP-PNP

| | | Atom Type | Res | # | X | Y | Z | Occ | B |
|---|---|---|---|---|---|---|---|---|---|
| ATOM | 1286 | CE1 | HIS | 362 | 16.014 | 46.030 | 80.777 | 1.00 | 7.28 |
| ATOM | 1287 | NE2 | HIS | 362 | 15.650 | 44.829 | 80.321 | 1.00 | 6.66 |
| ATOM | 1288 | HE2 | HIS | 362 | 16.165 | 44.014 | 80.467 | 1.00 | 0.00 |
| ATOM | 1289 | C | HIS | 362 | 12.312 | 48.198 | 81.333 | 1.00 | 6.96 |
| ATOM | 1290 | O | HIS | 362 | 12.604 | 47.804 | 82.445 | 1.00 | 7.16 |
| ATOM | 1291 | N | ARG | 363 | 12.455 | 49.470 | 80.951 | 1.00 | 7.28 |
| ATOM | 1292 | H | ARG | 363 | 12.263 | 49.705 | 80.018 | 1.00 | 0.00 |
| ATOM | 1293 | CA | ARG | 363 | 12.869 | 50.559 | 81.843 | 1.00 | 7.20 |
| ATOM | 1294 | CB | ARG | 363 | 12.013 | 50.655 | 83.133 | 1.00 | 7.60 |
| ATOM | 1295 | CG | ARG | 363 | 10.522 | 50.776 | 82.802 | 1.00 | 7.72 |
| ATOM | 1296 | CD | ARG | 363 | 9.783 | 51.262 | 84.036 | 1.00 | 9.74 |
| ATOM | 1297 | NE | ARG | 363 | 9.869 | 50.343 | 85.152 | 1.00 | 10.57 |
| ATOM | 1298 | HE | ARG | 363 | 10.012 | 49.404 | 84.937 | 1.00 | 0.00 |
| ATOM | 1299 | CA | ARG | 363 | 9.750 | 50.683 | 86.428 | 1.00 | 12.41 |
| ATOM | 1300 | NH1 | ARG | 363 | 9.556 | 51.955 | 86.773 | 1.00 | 13.78 |
| ATOM | 1301 | HH11 | ARG | 363 | 9.518 | 52.662 | 86.073 | 1.00 | 0.00 |
| ATOM | 1302 | HH12 | ARG | 363 | 9.488 | 51.195 | 87.740 | 1.00 | 0.00 |
| ATOM | 1303 | NH2 | ARG | 363 | 9.784 | 49.752 | 87.368 | 1.00 | 12.55 |
| ATOM | 1304 | HH21 | ARG | 363 | 9.877 | 48.784 | 87.114 | 1.00 | 0.00 |
| ATOM | 1305 | HH22 | ARG | 363 | 9.691 | 50.004 | 88.328 | 1.00 | 0.00 |
| ATOM | 1306 | C | ARG | 363 | 14.314 | 50.619 | 82.248 | 1.00 | 8.08 |
| ATOM | 1307 | O | ARG | 363 | 14.715 | 51.571 | 82.927 | 1.00 | 10.09 |
| ATOM | 1308 | N | ASP | 364 | 15.106 | 49.633 | 81.845 | 1.00 | 7.43 |
| ATOM | 1309 | H | ASP | 364 | 14.739 | 48.926 | 81.296 | 1.00 | 0.00 |
| ATOM | 1310 | CA | ASP | 364 | 16.528 | 49.612 | 82.217 | 1.00 | 7.37 |
| ATOM | 1311 | CB | ASP | 364 | 16.718 | 48.600 | 83.369 | 1.00 | 9.33 |
| ATOM | 1312 | CG | ASP | 364 | 17.934 | 48.885 | 84.252 | 1.00 | 11.01 |
| ATOM | 1313 | OD1 | ASP | 364 | 18.666 | 49.855 | 83.985 | 1.00 | 14.23 |
| ATOM | 1314 | OD2 | ASP | 364 | 18.133 | 48.118 | 85.232 | 1.00 | 14.23 |
| ATOM | 1315 | C | ASP | 364 | 17.328 | 49.176 | 80.979 | 1.00 | 7.00 |
| ATOM | 1316 | O | ASP | 364 | 19.325 | 48.457 | 81.081 | 1.00 | 6.90 |
| ATOM | 1317 | N | LEU | 365 | 16.969 | 49.704 | 79.816 | 1.00 | 6.16 |
| ATOM | 1318 | H | LEU | 365 | 16.252 | 50.366 | 79.771 | 1.00 | 0.00 |
| ATOM | 1319 | CA | LEU | 365 | 17.626 | 49.321 | 78.591 | 1.00 | 5.80 |
| ATOM | 1320 | CB | LEU | 365 | 16.679 | 49.555 | 77.398 | 1.00 | 6.34 |
| ATOM | 1321 | CG | LEU | 365 | 17.204 | 49.239 | 75.995 | 1.00 | 5.69 |
| ATOM | 1322 | CD1 | LEU | 365 | 17.619 | 47.750 | 75.912 | 1.00 | 7.46 |
| ATOM | 1323 | CD2 | LEU | 365 | 16.103 | 49.465 | 75.001 | 1.00 | 7.06 |
| ATOM | 1324 | C | LEU | 365 | 18.919 | 50.133 | 78.461 | 1.00 | 7.96 |
| ATOM | 1325 | O | LEU | 365 | 18.889 | 51.344 | 78.362 | 1.00 | 8.00 |
| ATOM | 1326 | N | ARG | 366 | 20.036 | 49.436 | 78.454 | 1.00 | 6.41 |
| ATOM | 1327 | H | ARG | 366 | 19.967 | 48.457 | 78.536 | 1.00 | 0.00 |
| ATOM | 1328 | CA | ARG | 366 | 21.379 | 50.010 | 78.340 | 1.00 | 6.06 |
| ATOM | 1329 | CB | ARG | 366 | 21.798 | 50.631 | 79.664 | 1.00 | 6.83 |
| ATOM | 1330 | CG | ARG | 366 | 21.724 | 49.671 | 80.885 | 1.00 | 7.28 |
| ATOM | 1331 | CD | ARG | 366 | 21.889 | 50.431 | 79.664 | 1.00 | 6.83 |
| ATOM | 1332 | NE | ARG | 366 | 23.175 | 51.133 | 82.201 | 1.00 | 13.50 |
| ATOM | 1333 | HE | ARG | 366 | 23.818 | 50.985 | 81.487 | 1.00 | 0.00 |
| ATOM | 1334 | CA | ARG | 366 | 23.495 | 51.973 | 83.177 | 1.00 | 15.04 |
| ATOM | 1335 | NH1 | ARG | 366 | 22.631 | 52.211 | 84.154 | 1.00 | 18.15 |
| ATOM | 1336 | HH11 | ARG | 366 | 21.732 | 51.761 | 84.155 | 1.00 | 0.00 |
| ATOM | 1337 | HH12 | ARG | 366 | 22.860 | 52.847 | 84.888 | 1.00 | 0.00 |
| ATOM | 1338 | NH2 | ARG | 366 | 24.710 | 52.474 | 83.242 | 1.00 | 17.55 |
| ATOM | 1339 | HH21 | ARG | 366 | 25.390 | 52.220 | 82.560 | 1.00 | 0.00 |
| ATOM | 1340 | HH22 | ARG | 366 | 24.954 | 53.114 | 83.798 | 1.00 | 0.00 |
| ATOM | 1341 | C | ARG | 366 | 22.302 | 48.866 | 77.977 | 1.00 | 6.86 |
| ATOM | 1342 | O | ARG | 366 | 21.964 | 47.715 | 78.218 | 1.00 | 5.81 |
| ATOM | 1343 | N | ALA | 367 | 23.515 | 49.174 | 77.533 | 1.00 | 5.91 |
| ATOM | 1344 | H | ALA | 367 | 23.776 | 50.100 | 77.473 | 1.00 | 0.00 |
| ATOM | 1345 | CA | ALA | 367 | 24.423 | 48.087 | 77.137 | 1.00 | 5.11 |
| ATOM | 1346 | CB | ALA | 367 | 25.693 | 48.656 | 76.461 | 1.00 | 6.19 |
| ATOM | 1347 | C | ALA | 367 | 24.811 | 47.137 | 78.280 | 1.00 | 6.35 |
| ATOM | 1348 | O | ALA | 367 | 25.139 | 45.947 | 77.977 | 1.00 | 6.18 |
| ATOM | 1349 | N | ALA | 368 | 24.795 | 47.612 | 79.518 | 1.00 | 6.36 |
| ATOM | 1350 | H | ALA | 368 | 24.592 | 48.543 | 79.680 | 1.00 | 0.00 |
| ATOM | 1351 | CA | ALA | 368 | 25.095 | 46.734 | 80.647 | 1.00 | 6.76 |
| ATOM | 1352 | CB | ALA | 368 | 25.129 | 47.490 | 81.939 | 1.00 | 8.33 |
| ATOM | 1353 | C | ALA | 368 | 24.060 | 45.615 | 80.760 | 1.00 | 6.98 |
| ATOM | 1354 | O | ALA | 368 | 24.355 | 44.580 | 81.356 | 1.00 | 8.43 |
| ATOM | 1355 | N | ASN | 369 | 22.879 | 45.839 | 80.193 | 1.00 | 5.80 |
| ATOM | 1356 | H | ASN | 369 | 22.723 | 46.674 | 79.700 | 1.00 | 0.00 |
| ATOM | 1357 | CA | ASN | 369 | 21.773 | 44.877 | 80.321 | 1.00 | 6.07 |
| ATOM | 1358 | CB | ASN | 369 | 20.528 | 45.545 | 80.911 | 1.00 | 6.03 |
| ATOM | 1359 | CG | ASN | 369 | 20.736 | 45.949 | 82.373 | 1.00 | 7.00 |

TABLE 3-continued

Coordinates of Lck bound with AMP-PNP

| | | Atom Type | Res | # | X | Y | Z | Occ | B |
|---|---|---|---|---|---|---|---|---|---|
| ATOM | 1360 | OD1 | ASN | 369 | 21.510 | 35.292 | 83.117 | 1.00 | 8.89 |
| ATOM | 1361 | ND2 | ASN | 369 | 20.100 | 47.037 | 82.798 | 1.00 | 8.55 |
| ATOM | 1362 | HD21 | ASN | 369 | 19.516 | 47.524 | 82.189 | 1.00 | 0.00 |
| ATOM | 1363 | HD22 | ASN | 369 | 20.220 | 47.286 | 83.732 | 1.00 | 0.00 |
| ATOM | 1364 | C | ASN | 369 | 21.465 | 44.127 | 79.063 | 1.00 | 6.64 |
| ATOM | 1365 | O | ASN | 369 | 20.369 | 43.601 | 78.878 | 1.00 | 6.61 |
| ATOM | 1366 | N | ILE | 370 | 22.437 | 44.098 | 78.181 | 1.00 | 4.83 |
| ATOM | 1367 | H | ILE | 370 | 23.235 | 44.632 | 78.335 | 1.00 | 0.00 |
| ATOM | 1368 | CA | ILE | 370 | 22.369 | 43.243 | 76.985 | 1.00 | 4.37 |
| ATOM | 1369 | CB | ILE | 370 | 22.705 | 44.012 | 75.724 | 1.00 | 4.38 |
| ATOM | 1370 | CG2 | ILE | 370 | 22.787 | 43.118 | 74.492 | 1.00 | 5.49 |
| ATOM | 1371 | CG1 | ILE | 370 | 21.745 | 45.198 | 75.560 | 1.00 | 4.73 |
| ATOM | 1372 | CD1 | ILE | 370 | 20.210 | 44.713 | 75.543 | 1.00 | 6.97 |
| ATOM | 1373 | C | ILE | 370 | 23.478 | 42.202 | 77.193 | 1.00 | 5.68 |
| ATOM | 1374 | O | ILE | 370 | 24.572 | 42.529 | 77.592 | 1.00 | 6.20 |
| ATOM | 1375 | N | LEU | 371 | 23.127 | 40.935 | 77.039 | 1.00 | 4.58 |
| ATOM | 1376 | H | LEU | 371 | 22.204 | 40.693 | 76.821 | 1.00 | 0.00 |
| ATOM | 1377 | CA | LEU | 371 | 24.146 | 39.864 | 77.181 | 1.00 | 4.32 |
| ATOM | 1378 | CB | LEU | 371 | 23.603 | 38.761 | 78.096 | 1.00 | 3.54 |
| ATOM | 1379 | CG | LEU | 371 | 23.482 | 39.116 | 79.561 | 1.00 | 4.30 |
| ATOM | 1380 | CD2 | LEU | 371 | 22.880 | 38.001 | 80.367 | 1.00 | 6.65 |
| ATOM | 1381 | CD2 | LEU | 371 | 24.898 | 39.456 | 80.168 | 1.00 | 7.93 |
| ATOM | 1382 | C | LEU | 371 | 24.527 | 39.331 | 75.804 | 1.00 | 4.99 |
| ATOM | 1383 | O | LEU | 371 | 23.742 | 39.345 | 74.833 | 1.00 | 5.49 |
| ATOM | 1384 | N | VAL | 372 | 25.789 | 38.862 | 75.674 | 1.00 | 4.04 |
| ATOM | 1385 | H | VAL | 372 | 26.390 | 38.858 | 76.440 | 1.00 | 0.00 |
| ATOM | 1386 | CA | VAL | 372 | 26.310 | 38.403 | 74.401 | 1.00 | 4.69 |
| ATOM | 1387 | CB | VAL | 372 | 27.623 | 39.164 | 74.075 | 1.00 | 5.67 |
| ATOM | 1388 | CG1 | VAL | 372 | 28.146 | 38.812 | 72.722 | 1.00 | 6.43 |
| ATOM | 1389 | CG2 | VAL | 372 | 27.347 | 40.376 | 74.166 | 1.00 | 6.52 |
| ATOM | 1390 | C | VAL | 372 | 26.665 | 36.905 | 74.473 | 1.00 | 4.28 |
| ATOM | 1391 | O | VAL | 372 | 27.315 | 36.495 | 75.428 | 1.00 | 5.15 |
| ATOM | 1392 | N | SER | 373 | 26.214 | 36.144 | 73.480 | 1.00 | 4.34 |
| ATOM | 1393 | H | SER | 373 | 25.728 | 36.553 | 72.741 | 1.00 | 0.00 |
| ATOM | 1394 | CA | SER | 373 | 26.464 | 34.684 | 73.459 | 1.00 | 4.40 |
| ATOM | 1395 | CB | SER | 373 | 25.410 | 33.992 | 72.593 | 1.00 | 3.61 |
| ATOM | 1396 | OG | SER | 373 | 25.671 | 34.220 | 71.244 | 1.00 | 5.61 |
| ATOM | 1397 | HG | SER | 373 | 26.531 | 33.882 | 71.018 | 1.00 | 0.00 |
| ATOM | 1398 | C | SER | 373 | 27.827 | 34.351 | 72.900 | 1.00 | 6.57 |
| ATOM | 1399 | O | SER | 373 | 28.541 | 35.199 | 72.374 | 1.00 | 5.65 |
| ATOM | 1400 | N | ASP | 374 | 28.158 | 33.063 | 72.982 | 1.00 | 7.67 |
| ATOM | 1401 | H | ASP | 374 | 27.582 | 32.419 | 73.420 | 1.00 | 0.00 |
| ATOM | 1402 | CA | ASP | 374 | 29.401 | 32.633 | 72.405 | 1.00 | 9.72 |
| ATOM | 1403 | CB | ASP | 374 | 29.630 | 31.168 | 72.747 | 1.00 | 12.24 |
| ATOM | 1404 | CG | ASP | 374 | 28.651 | 30.288 | 72.094 | 1.00 | 16.64 |
| ATOM | 1405 | OD1 | ASP | 374 | 27.446 | 30.542 | 72.290 | 1.00 | 18.67 |
| ATOM | 1406 | OD2 | ASP | 374 | 29.066 | 29.426 | 71.278 | 1.00 | 20.28 |
| ATOM | 1407 | C | ASP | 374 | 29.476 | 32.827 | 70.891 | 1.00 | 9.29 |
| ATOM | 1408 | O | ASP | 374 | 30.554 | 32.831 | 70.344 | 1.00 | 11.15 |
| ATOM | 1409 | N | THR | 375 | 28.327 | 32.927 | 70.190 | 1.00 | 8.21 |
| ATOM | 1410 | H | THR | 375 | 27.459 | 32.875 | 70.657 | 1.00 | 0.00 |
| ATOM | 1411 | CA | THR | 375 | 28.306 | 33.120 | 68.755 | 1.00 | 8.40 |
| ATOM | 1412 | CB | THR | 375 | 27.238 | 32.260 | 68.056 | 1.00 | 8.35 |
| ATOM | 1413 | OG1 | THR | 375 | 25.982 | 32.561 | 68.672 | 1.00 | 9.12 |
| ATOM | 1414 | HG1 | THR | 375 | 25.806 | 33.510 | 68.563 | 1.00 | 0.00 |
| ATOM | 1415 | CG2 | THR | 375 | 27.485 | 30.719 | 68.176 | 1.00 | 11.28 |
| ATOM | 1416 | C | THR | 375 | 28.106 | 34.578 | 68.355 | 1.00 | 8.49 |
| ATOM | 1417 | O | THR | 375 | 27.811 | 34.903 | 67.226 | 1.00 | 8.72 |
| ATOM | 1418 | N | LEU | 376 | 28.203 | 35.436 | 69.353 | 1.00 | 7.19 |
| ATOM | 1419 | H | LEU | 376 | 28.346 | 35.101 | 70.256 | 1.00 | 0.00 |
| ATOM | 1420 | CA | LEU | 376 | 28.118 | 36.883 | 69.173 | 1.00 | 8.14 |
| ATOM | 1421 | CB | LEU | 376 | 29.149 | 37.407 | 68.161 | 1.00 | 10.40 |
| ATOM | 1422 | CG | LEU | 376 | 30.608 | 37.097 | 68.564 | 1.00 | 11.93 |
| ATOM | 1423 | CD1 | LEU | 376 | 31.457 | 38.031 | 67.671 | 1.00 | 13.62 |
| ATOM | 1424 | CD2 | LEU | 376 | 20.949 | 37.256 | 70.019 | 1.00 | 13.34 |
| ATOM | 1425 | C | LEU | 376 | 26.710 | 37.432 | 58.841 | 1.00 | 8.14 |
| ATOM | 1426 | O | LEU | 376 | 26.502 | 38.204 | 67.976 | 1.00 | 8.33 |
| ATOM | 1427 | N | SER | 377 | 25.742 | 36.609 | 69.371 | 1.00 | 6.49 |
| ATOM | 1428 | H | SER | 377 | 25.946 | 35.806 | 69.878 | 1.00 | 0.00 |
| ATOM | 1429 | CA | SER | 377 | 24.356 | 37.087 | 69.250 | 1.00 | 6.46 |
| ATOM | 1430 | CB | SER | 377 | 23.400 | 35.934 | 68.923 | 1.00 | 5.34 |
| ATOM | 1431 | OG | SER | 377 | 23.368 | 34.975 | 69.923 | 1.00 | 5.34 |
| ATOM | 1432 | HG | SER | 377 | 22.769 | 34.262 | 69.738 | 1.00 | 0.00 |
| ATOM | 1433 | C | SER | 377 | 24.012 | 37.791 | 70.588 | 1.00 | 5.46 |

TABLE 3-continued

Coordinates of Lck bound with AMP-PNP

| | | Atom Type | Res | # | X | Y | Z | Occ | B |
|---|---|---|---|---|---|---|---|---|---|
| ATOM | 1434 | O | SER | 377 | 24.592 | 37.566 | 71.649 | 1.00 | 6.09 |
| ATOM | 1435 | N | CYS | 378 | 23.032 | 38.684 | 70.544 | 1.00 | 5.11 |
| ATOM | 1436 | H | CYS | 378 | 22.529 | 38.848 | 69.724 | 1.00 | 0.00 |
| ATOM | 1437 | CA | CYS | 378 | 22.730 | 39.470 | 71.742 | 1.00 | 6.25 |
| ATOM | 1438 | CB | CYS | 378 | 22.741 | 40.969 | 71.406 | 1.00 | 6.45 |
| ATOM | 1439 | SG | CYS | 378 | 24.415 | 41.584 | 70.930 | 1.00 | 10.06 |
| ATOM | 1440 | C | CYS | 378 | 21.323 | 39.216 | 72.223 | 1.00 | 5.48 |
| ATOM | 1441 | O | CYS | 378 | 20.443 | 38.963 | 71.396 | 1.00 | 5.39 |
| ATOM | 1442 | N | LYS | 379 | 21.131 | 39.294 | 73.532 | 1.00 | 4.43 |
| ATOM | 1443 | H | LYS | 379 | 21.897 | 39.485 | 74.116 | 1.00 | 0.00 |
| ATOM | 1444 | CA | LYS | 379 | 19.808 | 39.073 | 74.131 | 1.00 | 4.63 |
| ATOM | 1445 | CB | LYS | 379 | 19.695 | 37.644 | 74.777 | 1.00 | 4.64 |
| ATOM | 1446 | CG | LYS | 379 | 19.810 | 36.618 | 73.678 | 1.00 | 4.87 |
| ATOM | 1447 | CD | LYS | 379 | 19.503 | 35.253 | 74.181 | 1.00 | 3.55 |
| ATOM | 1448 | CE | LYS | 379 | 19.881 | 34.280 | 73.053 | 1.00 | 4.66 |
| ATOM | 1449 | NZ | LYS | 379 | 19.074 | 32.964 | 73.127 | 1.00 | 6.09 |
| ATOM | 1450 | HZ1 | LYS | 379 | 18.062 | 33.166 | 73.034 | 1.00 | 0.00 |
| ATOM | 1451 | HZ2 | LYS | 379 | 19.248 | 32.493 | 74.028 | 1.00 | 0.00 |
| ATOM | 1452 | HZ3 | LYS | 379 | 19.372 | 32.341 | 72.353 | 1.00 | 0.00 |
| ATOM | 1453 | C | LYS | 379 | 19.553 | 40.113 | 75.210 | 1.00 | 4.75 |
| ATOM | 1454 | O | LYS | 379 | 20.444 | 40.544 | 75.950 | 1.00 | 5.82 |
| ATOM | 1455 | N | ILE | 380 | 18.281 | 40.504 | 75.338 | 1.00 | 3.76 |
| ATOM | 1456 | H | ILE | 389 | 17.617 | 40.153 | 74.718 | 1.00 | 0.00 |
| ATOM | 1457 | CA | ILE | 380 | 17.902 | 41.447 | 76.392 | 1.00 | 3.92 |
| ATOM | 1458 | CB | ILE | 380 | 16.439 | 41.933 | 76.175 | 1.00 | 5.30 |
| ATOM | 1459 | CG2 | ILE | 380 | 16.075 | 42.984 | 77.249 | 1.00 | 5.03 |
| ATOM | 1460 | CG1 | ILE | 380 | 16.168 | 42.431 | 74.744 | 1.00 | 8.04 |
| ATOM | 1461 | CD1 | ILE | 380 | 16.997 | 43.587 | 74.311 | 1.00 | 9.70 |
| ATOM | 1462 | C | ILE | 380 | 17.922 | 40.709 | 77.742 | 1.00 | 4.94 |
| ATOM | 1463 | O | ILE | 380 | 17.397 | 39.599 | 77.876 | 1.00 | 4.49 |
| ATOM | 1464 | N | ALA | 381 | 18.455 | 41.367 | 78.752 | 1.00 | 5.27 |
| ATOM | 1465 | H | ALA | 381 | 18.807 | 42.367 | 78.752 | 1.00 | 5.27 |
| ATOM | 1466 | CA | ALA | 381 | 18.528 | 40.803 | 80.077 | 1.00 | 5.60 |
| ATOM | 1467 | CB | ALA | 381 | 20.023 | 40.357 | 80.356 | 1.00 | 6.73 |
| ATOM | 1468 | C | ALA | 381 | 18.070 | 41.818 | 81.146 | 1.00 | 7.05 |
| ATOM | 1469 | O | ALA | 381 | 17.737 | 42.961 | 80.815 | 1.00 | 6.78 |
| ATOM | 1470 | N | ASP | 382 | 18.087 | 41.372 | 82.394 | 1.00 | 7.75 |
| ATOM | 1471 | H | ASP | 382 | 18.342 | 40.442 | 82.530 | 1.00 | 0.00 |
| ATOM | 1472 | CA | ASP | 382 | 17.73 | 42.160 | 83.573 | 1.00 | 8.33 |
| ATOM | 1473 | CB | ASP | 382 | 18.797 | 43.262 | 82.852 | 1.00 | 10.89 |
| ATOM | 1474 | CG | ASP | 382 | 18.620 | 43.868 | 85.256 | 1.00 | 14.13 |
| ATOM | 1475 | OD1 | ASP | 382 | 17.585 | 43.590 | 85.944 | 1.00 | 17.05 |
| ATOM | 1476 | OD2 | ASP | 382 | 19.563 | 44.563 | 85.725 | 1.00 | 17.44 |
| ATOM | 1477 | C | ASP | 382 | 16.365 | 42.738 | 83.523 | 1.00 | 8.68 |
| ATOM | 1478 | O | ASP | 382 | 16.140 | 43.927 | 83.251 | 1.00 | 9.78 |
| ATOM | 1479 | N | PHE | 383 | 15.419 | 41.900 | 83.924 | 1.00 | 7.70 |
| ATOM | 1480 | H | PHE | 383 | 15.675 | 41.030 | 84.282 | 1.00 | 0.00 |
| ATOM | 1481 | CA | PHE | 383 | 14.015 | 42.275 | 83.884 | 1.00 | 8.11 |
| ATOM | 1482 | CB | PHE | 383 | 13.235 | 41.053 | 83.392 | 1.00 | 7.97 |
| ATOM | 1483 | CG | PHE | 383 | 13.575 | 40.669 | 81.982 | 1.00 | 7.04 |
| ATOM | 1484 | CD1 | PHE | 383 | 13.019 | 41.341 | 80.899 | 1.00 | 6.87 |
| ATOM | 1485 | CD2 | PHE | 383 | 14.543 | 39.678 | 81.727 | 1.00 | 5.96 |
| ATOM | 1486 | CE1 | PHE | 383 | 13.419 | 41.040 | 79.600 | 1.00 | 5.83 |
| ATOM | 1487 | CE2 | PHE | 383 | 14.933 | 39.388 | 80.430 | 1.00 | 6.87 |
| ATOM | 1488 | CA | PHE | 383 | 14.397 | 40.045 | 79.374 | 1.00 | 6.24 |
| ATOM | 1489 | C | PHE | 383 | 13.457 | 42.771 | 85.216 | 1.00 | 8.69 |
| ATOM | 1490 | O | PHE | 383 | 12.227 | 42.854 | 85.411 | 1.00 | 9.48 |
| ATOM | 1491 | N | GLY | 384 | 14.344 | 43.214 | 86.096 | 1.00 | 9.32 |
| ATOM | 1492 | H | GLY | 384 | 15.292 | 43.213 | 85.846 | 1.00 | 0.00 |
| ATOM | 1493 | CA | GLY | 384 | 13.932 | 43.659 | 87.416 | 1.00 | 10.41 |
| ATOM | 1494 | C | GLY | 384 | 12.963 | 44.838 | 87.414 | 1.00 | 10.19 |
| ATOM | 1495 | O | GLY | 384 | 12.117 | 44.945 | 88.313 | 1.00 | 11.74 |
| ATOM | 1496 | N | LEU | 385 | 13.146 | 45.758 | 86.469 | 1.00 | 9.00 |
| ATOM | 1497 | H | LEU | 385 | 13.886 | 45.663 | 85.830 | 1.00 | 0.00 |
| ATOM | 1498 | CA | LEU | 385 | 12.259 | 46.925 | 86.389 | 1.00 | 9.26 |
| ATOM | 1499 | CB | LEU | 385 | 13.066 | 48.198 | 86.104 | 1.00 | 9.63 |
| ATOM | 1500 | CG | LEU | 385 | 13.971 | 48.641 | 87.249 | 1.00 | 12.22 |
| ATOM | 1501 | CD1 | LEU | 385 | 14.819 | 49.840 | 86.744 | 1.00 | 12.81 |
| ATOM | 1502 | CD2 | LEU | 385 | 13.169 | 48.985 | 88.509 | 1.00 | 13.55 |
| ATOM | 1503 | C | LEU | 385 | 11.197 | 46.759 | 85.349 | 1.00 | 8.64 |
| ATOM | 1504 | O | LEU | 385 | 10.364 | 47.645 | 85.173 | 1.00 | 8.68 |
| ATOM | 1505 | N | ALA | 386 | 11.185 | 45.634 | 84.630 | 1.00 | 7.47 |
| ATOM | 1506 | H | ALA | 386 | 11.848 | 44.929 | 84.838 | 1.00 | 0.00 |
| ATOM | 1507 | CA | ALA | 386 | 10.194 | 45.436 | 83.547 | 1.00 | 7.81 |

TABLE 3-continued

Coordinates of Lck bound with AMP-PNP

| | Atom Type | Res | # | X | Y | Z | Occ | B |
|---|---|---|---|---|---|---|---|---|
| ATOM | 1508 | CB | ALA | 386 | 10.579 | 44.228 | 82.723 | 1.00 | 8.06 |
| ATOM | 1509 | C | ALA | 386 | 8.783 | 45.304 | 84.065 | 1.00 | 8.67 |
| ATOM | 1510 | O | ALA | 386 | 8.597 | 44.840 | 85.166 | 1.00 | 9.09 |
| ATOM | 1511 | N | ARG | 387 | 7.810 | 45.773 | 83.293 | 1.00 | 9.55 |
| ATOM | 1512 | H | ARG | 387 | 8.034 | 46.133 | 82.404 | 1.00 | 0.00 |
| ATOM | 1513 | CA | ARG | 387 | 6.411 | 45.761 | 83.739 | 1.00 | 10.38 |
| ATOM | 1514 | CB | ARG | 387 | 6.041 | 47.127 | 84.382 | 1.00 | 9.95 |
| ATOM | 1515 | CG | ARG | 387 | 6.877 | 47.550 | 85.627 | 1.00 | 11.72 |
| ATOM | 1516 | CD | ARG | 387 | 6.626 | 46.683 | 86.843 | 1.00 | 11.98 |
| ATOM | 1517 | NE | ARG | 387 | 7.333 | 47.168 | 88.009 | 1.00 | 14.30 |
| ATOM | 1518 | HE | ARG | 387 | 6.881 | 47.843 | 88.543 | 1.00 | 0.00 |
| ATOM | 1519 | CA | ARG | 387 | 8.535 | 46.731 | 88.390 | 1.00 | 14.48 |
| ATOM | 1520 | NH1 | ARG | 387 | 9.165 | 45.782 | 87.704 | 1.00 | 14.82 |
| ATOM | 1521 | HH11 | ARG | 387 | 8.741 | 45.377 | 86.898 | 1.00 | 0.00 |
| ATOM | 1522 | HH12 | ARG | 387 | 10.064 | 45.463 | 88.010 | 1.00 | 0.00 |
| ATOM | 1523 | NH2 | ARG | 387 | 9.116 | 47.251 | 89.453 | 1.00 | 16.13 |
| ATOM | 1524 | HH21 | ARG | 387 | 9.645 | 47.969 | 89.975 | 1.00 | 0.00 |
| ATOM | 1525 | HH22 | ARG | 387 | 10.012 | 46.930 | 89.752 | 1.00 | 0.00 |
| ATOM | 1526 | C | ARG | 387 | 5.445 | 45.555 | 82.610 | 1.00 | 10.77 |
| ATOM | 1527 | O | ARG | 387 | 5.695 | 45.985 | 81.481 | 1.00 | 9.38 |
| ATOM | 1528 | N | LEU | 388 | 4.321 | 44.886 | 82.942 | 1.00 | 12.31 |
| ATOM | 1529 | H | LEU | 388 | 4.214 | 44.547 | 83.854 | 1.00 | 0.00 |
| ATOM | 1530 | CA | LEU | 388 | 3.233 | 44.681 | 82.000 | 1.00 | 15.61 |
| ATOM | 1531 | CB | LEU | 388 | 2.312 | 43.523 | 82.428 | 1.00 | 16.22 |
| ATOM | 1532 | CG | LEU | 388 | 1.164 | 43.180 | 81.444 | 1.00 | 16.99 |
| ATOM | 1533 | CD1 | LEU | 388 | 1.624 | 43.029 | 80.043 | 1.00 | 17.93 |
| ATOM | 1534 | CD2 | LEU | 388 | 0.454 | 41.881 | 81.908 | 1.00 | 19.04 |
| ATOM | 1535 | C | LEU | 388 | 2.444 | 45.977 | 83.079 | 1.00 | 17.76 |
| ATOM | 1536 | O | LEU | 388 | 2.023 | 46.406 | 83.162 | 1.00 | 18.30 |
| ATOM | 1537 | N | ILE | 389 | 2.211 | 46.542 | 80.910 | 1.00 | 19.03 |
| ATOM | 1538 | H | ILE | 389 | 2.498 | 46.080 | 80.106 | 1.00 | 0.00 |
| ATOM | 1539 | CA | ILE | 389 | 1.544 | 47.815 | 80.736 | 1.00 | 22.41 |
| ATOM | 1540 | CB | ILE | 389 | 2.540 | 48.673 | 79.801 | 1.00 | 22.90 |
| ATOM | 1541 | CG2 | ILE | 389 | 1.877 | 49.282 | 78.614 | 1.00 | 25.50 |
| ATOM | 1542 | CG1 | ILE | 389 | 3.364 | 49.629 | 80.675 | 1.00 | 24.32 |
| ATOM | 1543 | CD1 | ILE | 389 | 3.584 | 49.158 | 82.104 | 1.00 | 22.03 |
| ATOM | 1544 | C | ILE | 389 | 0.062 | 47.558 | 80.316 | 1.00 | 23.87 |
| ATOM | 1545 | O | ILE | 389 | −0.245 | 47.095 | 79.233 | 1.00 | 24.93 |
| ATOM | 1546 | N | GLU | 390 | −0.831 | 47.762 | 81.277 | 1.00 | 26.28 |
| ATOM | 1547 | H | GLU | 390 | −0.512 | 48.078 | 82.143 | 1.00 | 0.00 |
| ATOM | 1548 | CA | GLU | 390 | −2.289 | 47.561 | 81.120 | 1.00 | 27.19 |
| ATOM | 1549 | CB | GLU | 390 | −2.852 | 47.412 | 82.550 | 1.00 | 28.06 |
| ATOM | 1550 | CG | GLU | 390 | −1.738 | 46.634 | 83.317 | 1.00 | 29.36 |
| ATOM | 1551 | CD | GLU | 390 | −2.098 | 45.949 | 84.591 | 1.00 | 29.77 |
| ATOM | 1552 | OE1 | GLU | 390 | −2.656 | 44.821 | 84.536 | 1.00 | 33.71 |
| ATOM | 1553 | OE2 | GLU | 390 | −1.721 | 46.483 | 85.657 | 1.00 | 32.83 |
| ATOM | 1554 | C | GLU | 390 | −2.889 | 48.676 | 80.239 | 1.00 | 27.94 |
| ATOM | 1555 | O | GLU | 390 | −3.554 | 48.404 | 79.235 | 1.00 | 28.70 |
| ATOM | 1556 | N | ASP | 391 | −2.544 | 49.914 | 80.562 | 1.00 | 27.89 |
| ATOM | 1557 | H | ASP | 391 | −2.136 | 49.831 | 81.347 | 1.00 | 0.00 |
| ATOM | 1558 | CA | ASP | 391 | −2.912 | 51.113 | 79.835 | 1.00 | 27.88 |
| ATOM | 1559 | CB | ASP | 391 | −3.614 | 52.091 | 80.788 | 1.00 | 28.06 |
| ATOM | 1560 | CG | ASP | 391 | −4.958 | 51.566 | 81.269 | 1.00 | 28.78 |
| ATOM | 1561 | OD1 | ASP | 391 | −5.926 | 51.686 | 80.489 | 1.00 | 31.01 |
| ATOM | 1562 | OD2 | ASP | 391 | −5.055 | 51.010 | 82.382 | 1.00 | 30.51 |
| ATOM | 1563 | C | ASP | 391 | −1.566 | 51.661 | 79.319 | 1.00 | 28.40 |
| ATOM | 1564 | O | ASP | 391 | −0.498 | 51.332 | 79.861 | 1.00 | 30.70 |
| ATOM | 1565 | N | ASN | 392 | −1.584 | 52.451 | 78.264 | 1.00 | 27.86 |
| ATOM | 1566 | H | ASN | 392 | −2.449 | 52.738 | 77.912 | 1.00 | 0.00 |
| ATOM | 1567 | CA | ASN | 392 | −0.347 | 52.988 | 77.662 | 1.00 | 26.67 |
| ATOM | 1568 | CB | ASN | 392 | −0.749 | 54.151 | 76.702 | 1.00 | 27.44 |
| ATOM | 1569 | CG | ASN | 392 | 0.422 | 54.981 | 76.169 | 1.00 | 27.68 |
| ATOM | 1570 | OD1 | ASN | 392 | 0.624 | 55.099 | 74.941 | 1.00 | 30.22 |
| ATOM | 1571 | ND2 | ASN | 392 | 1.103 | 55.672 | 77.069 | 1.00 | 29.28 |
| ATOM | 1572 | HD21 | ASN | 392 | 0.826 | 55.624 | 78.013 | 1.00 | 0.00 |
| ATOM | 1573 | HD22 | ASN | 392 | 1.842 | 56.233 | 76.770 | 1.00 | 0.00 |
| ATOM | 1574 | C | ASN | 392 | 0.852 | 53.313 | 78.597 | 1.00 | 26.04 |
| ATOM | 1575 | O | ASN | 392 | 2.002 | 52.961 | 78.245 | 1.00 | 26.05 |
| ATOM | 1576 | N | GLU | 393 | 0.580 | 53.698 | 79.851 | 1.00 | 24.55 |
| ATOM | 1577 | H | GLU | 393 | −0.346 | 53.711 | 80.181 | 1.00 | 0.00 |
| ATOM | 1578 | CA | GLU | 393 | 1.659 | 54.131 | 80.765 | 1.00 | 24.24 |
| ATOM | 1579 | CB | GLU | 393 | 1.533 | 55.661 | 80.775 | 1.00 | 24.48 |
| ATOM | 1580 | CG | GLU | 393 | 2.497 | 56.482 | 81.537 | 1.00 | 26.69 |
| ATOM | 1581 | CD | GLU | 393 | 2.033 | 57.925 | 81.500 | 1.00 | 27.72 |

TABLE 3-continued

Coordinates of Lck bound with AMP-PNP

| | | Atom Type | Res | # | X | Y | Z | Occ | B |
|---|---|---|---|---|---|---|---|---|---|
| ATOM | 1582 | OE1 | GLU | 393 | 1.319 | 58.351 | 82.440 | 1.00 | 29.14 |
| ATOM | 1583 | OE2 | GLU | 393 | 2.348 | 58.613 | 80.499 | 1.00 | 30.45 |
| ATOM | 1584 | C | GLU | 393 | 1.838 | 53.569 | 82.213 | 1.00 | 23.01 |
| ATOM | 1585 | O | GLU | 393 | 0.853 | 53.231 | 82.901 | 1.00 | 24.00 |
| ATOM | 1586 | N | PTR | 394 | 3.101 | 53.425 | 82.647 | 1.00 | 20.84 |
| ATOM | 1587 | CA | PTR | 394 | 3.441 | 52.971 | 83.994 | 1.00 | 19.86 |
| ATOM | 1588 | C | PTR | 394 | 3.985 | 54.192 | 84.730 | 1.00 | 19.41 |
| ATOM | 1589 | O | PTR | 394 | 4.883 | 54.882 | 84.246 | 1.00 | 18.42 |
| ATOM | 1590 | CB | PTR | 394 | 4.521 | 51.850 | 83.989 | 1.00 | 19.64 |
| ATOM | 1591 | CG | PTR | 394 | 4.825 | 51.286 | 85.369 | 1.00 | 21.18 |
| ATOM | 1592 | CD2 | PTR | 394 | 3.984 | 50.326 | 85.920 | 1.00 | 22.60 |
| ATOM | 1593 | CD2 | PTR | 394 | 5.940 | 51.714 | 86.104 | 1.00 | 22.12 |
| ATOM | 1594 | CE1 | PTR | 394 | 4.263 | 49.820 | 87.180 | 1.00 | 25.56 |
| ATOM | 1595 | CE2 | PTR | 394 | 6.242 | 51.222 | 87.371 | 1.00 | 25.23 |
| ATOM | 1596 | CZ | PTR | 394 | 5.372 | 50.268 | 87.881 | 1.00 | 27.46 |
| ATOM | 1597 | OH | PTR | 394 | 5.671 | 49.754 | 89.196 | 1.00 | 32.26 |
| ATOM | 1598 | P | PTR | 394 | 6.483 | 50.612 | 90.322 | 1.00 | 35.99 |
| ATOM | 1599 | O1P | PTR | 394 | 7.817 | 50.767 | 90.802 | 1.00 | 35.74 |
| ATOM | 1600 | O2P | PTR | 394 | 6.596 | 49.898 | 91.619 | 1.00 | 35.31 |
| ATOM | 1601 | O3P | PTR | 394 | 5.885 | 52.009 | 90.479 | 1.00 | 36.41 |
| ATOM | 1602 | N | THR | 395 | 3.451 | 54.460 | 85.904 | 1.00 | 20.04 |
| ATOM | 1603 | H | THR | 395 | 2.745 | 53.891 | 86.266 | 1.00 | 0.00 |
| ATOM | 1604 | CA | THR | 395 | 3.920 | 55.583 | 86.693 | 1.00 | 20.75 |
| ATOM | 1605 | CB | THR | 395 | 2.722 | 56.526 | 87.037 | 1.00 | 20.90 |
| ATOM | 1606 | OG1 | THR | 395 | 2.160 | 57.062 | 85.828 | 1.00 | 21.39 |
| ATOM | 1607 | HG1 | THR | 395 | 1.897 | 56.368 | 85.193 | 1.00 | 0.00 |
| ATOM | 1608 | CG2 | THR | 395 | 3.200 | 57.691 | 87.864 | 1.00 | 22.70 |
| ATOM | 1609 | C | THR | 395 | 4.652 | 55.047 | 87.929 | 1.00 | 21.38 |
| ATOM | 1610 | O | THR | 395 | 4.100 | 54.294 | 88.718 | 1.00 | 22.13 |
| ATOM | 1611 | N | ALA | 396 | 5.943 | 55.339 | 88.035 | 1.00 | 21.97 |
| ATOM | 1612 | H | ALA | 396 | 6.350 | 55.856 | 87.315 | 1.00 | 0.00 |
| ATOM | 1613 | CA | ALA | 396 | 6.773 | 54.881 | 89.148 | 1.00 | 23.48 |
| ATOM | 1614 | CB | ALA | 396 | 8.240 | 55.170 | 88.811 | 1.00 | 22.84 |
| ATOM | 1615 | C | ALA | 396 | 6.403 | 55.520 | 90.512 | 1.00 | 24.59 |
| ATOM | 1616 | O | ALA | 396 | 5.348 | 56.123 | 90.650 | 1.00 | 25.45 |
| ATOM | 1617 | N | ALA | 397 | 7.319 | 55.433 | 91.486 | 1.00 | 26.07 |
| ATOM | 1618 | H | ALA | 397 | 8.126 | 54.926 | 91.281 | 1.00 | 0.00 |
| ATOM | 1619 | CA | ALA | 397 | 7.172 | 55.993 | 92.851 | 1.00 | 27.25 |
| ATOM | 1620 | CB | ALA | 397 | 7.836 | 55.050 | 93.486 | 1.00 | 26.07 |
| ATOM | 1621 | CB | ALA | 397 | 7.857 | 57.388 | 92.889 | 1.00 | 28.09 |
| ATOM | 1622 | O | ALA | 397 | 8.990 | 57.494 | 92.435 | 1.00 | 28.75 |
| ATOM | 1623 | N | GLU | 398 | 7.210 | 58.451 | 93.407 | 1.00 | 28.89 |
| ATOM | 1624 | H | GLU | 398 | 6.305 | 58.325 | 93.812 | 1.00 | 0.00 |
| ATOM | 1625 | CA | GLU | 398 | 7.837 | 59.794 | 93.419 | 1.00 | 29.61 |
| ATOM | 1626 | CB | GLU | 398 | 7.099 | 60.823 | 94.308 | 1.00 | 29.76 |
| ATOM | 1627 | CG | GLU | 398 | 5.801 | 61.413 | 93.737 | 1.00 | 31.04 |
| ATOM | 1628 | CD | GLU | 398 | 5.826 | 61.593 | 92.232 | 1.00 | 31.85 |
| ATOM | 1629 | OE1 | GLU | 398 | 6.686 | 62.342 | 91.720 | 1.00 | 32.63 |
| ATOM | 1630 | OE2 | GLU | 398 | 4.983 | 60.957 | 91.549 | 1.00 | 33.67 |
| ATOM | 1631 | C | GLU | 398 | 9.311 | 59.770 | 93.822 | 1.00 | 29.08 |
| ATOM | 1632 | O | GLU | 398 | 10.149 | 60.476 | 93.225 | 1.00 | 30.57 |
| ATOM | 1633 | N | GLY | 399 | 9.626 | 58.912 | 94.793 | 1.00 | 29.05 |
| ATOM | 1634 | H | GLY | 399 | 8.914 | 58.386 | 95.191 | 1.00 | 0.00 |
| ATOM | 1635 | CA | GLY | 399 | 10.993 | 58.770 | 95.265 | 1.00 | 27.68 |
| ATOM | 1636 | C | GLY | 399 | 11.902 | 58.917 | 94.392 | 1.00 | 27.05 |
| ATOM | 1637 | O | GLY | 399 | 13.124 | 58.061 | 93.489 | 1.00 | 28.08 |
| ATOM | 1638 | N | ALA | 400 | 11.343 | 57.016 | 93.575 | 1.00 | 25.80 |
| ATOM | 1639 | H | ALA | 400 | 10.365 | 56.937 | 93.574 | 1.00 | 0.00 |
| ATOM | 1640 | CA | ALA | 400 | 12.147 | 56.140 | 92.690 | 1.00 | 24.97 |
| ATOM | 1641 | CB | ALA | 400 | 11.230 | 55.264 | 91.820 | 1.00 | 25.88 |
| ATOM | 1642 | C | ALA | 400 | 13.072 | 56.964 | 91.796 | 1.00 | 24.08 |
| ATOM | 1643 | O | ALA | 400 | 12.653 | 57.972 | 91.231 | 1.00 | 23.69 |
| ATOM | 1644 | N | ALA | 401 | 14.325 | 56.527 | 91.684 | 1.00 | 22.58 |
| ATOM | 1645 | H | ALA | 401 | 14.587 | 55.709 | 92.161 | 1.00 | 0.00 |
| ATOM | 1646 | CA | ALA | 401 | 15.321 | 57.231 | 90.873 | 1.00 | 21.72 |
| ATOM | 1647 | CB | ALA | 401 | 16.440 | 57.756 | 91.750 | 1.00 | 21.84 |
| ATOM | 1648 | C | ALA | 401 | 15.898 | 56.360 | 89.770 | 1.00 | 21.42 |
| ATOM | 1649 | O | ALA | 401 | 16.135 | 55.160 | 89.962 | 1.00 | 22.02 |
| ATOM | 1650 | N | PHE | 402 | 16.136 | 56.968 | 88.606 | 1.00 | 20.24 |
| ATOM | 1651 | H | PHE | 402 | 15.926 | 57.920 | 88.525 | 1.00 | 0.00 |
| ATOM | 1652 | CA | PHE | 402 | 16.670 | 56.251 | 87.433 | 1.00 | 19.01 |
| ATOM | 1653 | CB | PHE | 402 | 15.592 | 56.187 | 86.349 | 1.00 | 19.03 |
| ATOM | 1654 | CG | PHE | 402 | 14.408 | 55.380 | 86.765 | 1.00 | 19.84 |
| ATOM | 1655 | CD2 | PHE | 402 | 13.389 | 55.961 | 87.520 | 1.00 | 20.91 |

TABLE 3-continued

Coordinates of Lck bound with AMP-PNP

| | | Atom Type | Res | # | X | Y | Z | Occ | B |
|---|---|---|---|---|---|---|---|---|---|
| ATOM | 1656 | CD2 | PHE | 402 | 14.343 | 54.026 | 86.462 | 1.00 | 21.47 |
| ATOM | 1657 | CE1 | PHE | 402 | 12.293 | 55.170 | 87.982 | 1.00 | 20.57 |
| ATOM | 1658 | CE2 | PHE | 402 | 13.290 | 53.251 | 86.902 | 1.00 | 23.31 |
| ATOM | 1659 | CA | PHE | 402 | 12.265 | 53.819 | 87.662 | 1.00 | 21.28 |
| ATOM | 1660 | C | PHE | 402 | 17.907 | 56.942 | 86.893 | 1.00 | 17.86 |
| ATOM | 1661 | N | PRO | 403 | 18.787 | 56.220 | 86.178 | 1.00 | 17.33 |
| ATOM | 1662 | N | PRO | 403 | 18.787 | 56.220 | 86.178 | 1.00 | 17.44 |
| ATOM | 1663 | CD | PRO | 403 | 18.730 | 54.779 | 85.882 | 1.00 | 18.18 |
| ATOM | 1664 | CA | PRO | 403 | 20.019 | 56.811 | 85.615 | 1.00 | 16.59 |
| ATOM | 1665 | CB | PRO | 403 | 20.691 | 55.627 | 84.911 | 1.00 | 17.23 |
| ATOM | 1666 | CG | PRO | 403 | 20.170 | 54.442 | 85.679 | 1.00 | 18.18 |
| ATOM | 1667 | C | PRO | 403 | 19.624 | 57.866 | 84.616 | 1.00 | 14.73 |
| ATOM | 1668 | O | PRO | 403 | 18.987 | 57.605 | 83.596 | 1.00 | 15.04 |
| ATOM | 1669 | N | ILE | 404 | 20.022 | 59.080 | 84.919 | 1.00 | 13.61 |
| ATOM | 1670 | H | ILE | 404 | 20.555 | 59.235 | 85.731 | 1.00 | 0.00 |
| ATOM | 1671 | CA | ILE | 404 | 19.660 | 60.194 | 84.091 | 1.00 | 12.30 |
| ATOM | 1672 | CB | ILE | 404 | 20.203 | 61.528 | 84.721 | 1.00 | 13.05 |
| ATOM | 1673 | CG2 | ILE | 404 | 20.079 | 72.721 | 83.745 | 1.00 | 13.72 |
| ATOM | 1674 | CG1 | ILE | 404 | 19.491 | 61.796 | 86.058 | 1.00 | 14.98 |
| ATOM | 1675 | CD1 | ILE | 404 | 18.033 | 61.960 | 85.911 | 1.00 | 17.98 |
| ATOM | 1676 | C | ILE | 404 | 20.085 | 60.106 | 82.647 | 1.00 | 11.12 |
| ATOM | 1677 | O | ILE | 404 | 19.278 | 60.367 | 81.756 | 1.00 | 11.56 |
| ATOM | 1678 | N | LYS | 405 | 21.318 | 59.670 | 82.381 | 1.00 | 9.07 |
| ATOM | 1679 | H | LYS | 405 | 21.925 | 59.426 | 83.106 | 1.00 | 0.00 |
| ATOM | 1680 | CA | LYS | 405 | 21.775 | 59.650 | 81.002 | 1.00 | 7.63 |
| ATOM | 1681 | CB | LYS | 405 | 23.300 | 59.453 | 80.911 | 1.00 | 8.28 |
| ATOM | 1682 | CG | LYS | 405 | 24.061 | 60.612 | 81.557 | 1.00 | 8.49 |
| ATOM | 1683 | CD | LYS | 405 | 25.564 | 60.423 | 81.441 | 1.00 | 11.13 |
| ATOM | 1684 | CE | LYS | 405 | 26.337 | 61.718 | 81.836 | 1.00 | 13.18 |
| ATOM | 1685 | NZ | LYS | 405 | 27.805 | 61.777 | 81.368 | 1.00 | 14.95 |
| ATOM | 1686 | HZ1 | LYS | 405 | 27.839 | 61.749 | 80.330 | 1.00 | 0.00 |
| ATOM | 1687 | HZ2 | LYS | 405 | 28.334 | 60.981 | 81.766 | 1.00 | 0.00 |
| ATOM | 1688 | HZ3 | LYS | 405 | 28.226 | 62.667 | 81.697 | 1.00 | 0.00 |
| ATOM | 1689 | C | LYS | 405 | 21.052 | 58.679 | 80.061 | 1.00 | 6.24 |
| ATOM | 1690 | O | LYS | 405 | 21.100 | 58.871 | 78.838 | 1.00 | 7.40 |
| ATOM | 1691 | N | TRP | 406 | 20.392 | 57.651 | 80.619 | 1.00 | 7.34 |
| ATOM | 1692 | H | TRP | 406 | 20.372 | 57.535 | 81.590 | 1.00 | 0.00 |
| ATOM | 1693 | CA | TRP | 406 | 19.728 | 56.699 | 79.731 | 1.00 | 8.49 |
| ATOM | 1694 | CB | TRP | 406 | 20.042 | 55.244 | 80.160 | 1.00 | 9.71 |
| ATOM | 1695 | CG | TRP | 406 | 21.321 | 54.748 | 79.711 | 1.00 | 10.18 |
| ATOM | 1696 | CD2 | TRP | 406 | 22.566 | 54.922 | 80.368 | 1.00 | 10.17 |
| ATOM | 1697 | CE2 | TRP | 406 | 23.535 | 54.241 | 79.595 | 1.00 | 9.32 |
| ATOM | 1698 | CE3 | TRP | 406 | 22.971 | 55.598 | 81.535 | 1.00 | 10.29 |
| ATOM | 1699 | CD1 | TRP | 406 | 21.558 | 54.016 | 78.589 | 1.00 | 10.80 |
| ATOM | 1700 | NE1 | TRP | 406 | 22.902 | 53.695 | 78.517 | 1.00 | 10.93 |
| ATOM | 1701 | HE1 | TRP | 406 | 23.320 | 53.164 | 77.823 | 1.00 | 0.00 |
| ATOM | 1702 | CZ2 | TRP | 406 | 24.874 | 54.205 | 79.959 | 1.00 | 11.02 |
| ATOM | 1703 | CZ3 | TRP | 406 | 24.319 | 55.569 | 81.909 | 1.00 | 11.88 |
| ATOM | 1704 | CH2 | TRP | 406 | 25.251 | 54.877 | 81.105 | 1.00 | 9.69 |
| ATOM | 1705 | C | TRP | 406 | 18.212 | 56.820 | 79.719 | 1.00 | 9.42 |
| ATOM | 1706 | O | TRP | 406 | 17.516 | 56.222 | 78.871 | 1.00 | 10.08 |
| ATOM | 1707 | N | THR | 407 | 17.706 | 57.613 | 80.652 | 1.00 | 9.02 |
| ATOM | 1708 | H | THR | 407 | 18.294 | 58.157 | 81.200 | 1.00 | 0.00 |
| ATOM | 1709 | CA | THR | 407 | 16.266 | 57.673 | 80.873 | 1.00 | 10.08 |
| ATOM | 1710 | CB | THR | 407 | 15.984 | 57.741 | 82.376 | 1.00 | 10.72 |
| ATOM | 1711 | OG1 | THR | 407 | 16.657 | 56.670 | 83.062 | 1.00 | 12.59 |
| ATOM | 1712 | HG1 | THR | 407 | 16.372 | 55.818 | 82.760 | 1.00 | 0.00 |
| ATOM | 1713 | CG2 | THR | 407 | 14.467 | 57.617 | 82.608 | 1.00 | 11.37 |
| ATOM | 1714 | C | THR | 407 | 15.592 | 58.819 | 80.107 | 1.00 | 9.61 |
| ATOM | 1715 | O | THR | 407 | 16.076 | 59.955 | 80.078 | 1.00 | 10.13 |
| ATOM | 1716 | N | ALA | 408 | 15.592 | 58.819 | 80.107 | 1.00 | 9.61 |
| ATOM | 1717 | H | ALA | 408 | 14.056 | 57.662 | 79.573 | 1.00 | 0.00 |
| ATOM | 1718 | CA | ALA | 408 | 13.718 | 59.566 | 78.744 | 1.00 | 9.33 |
| ATOM | 1719 | CB | ALA | 408 | 12.465 | 58.939 | 78.127 | 1.00 | 10.37 |
| ATOM | 1720 | C | ALA | 408 | 13.292 | 60.704 | 79.640 | 1.00 | 10.07 |
| ATOM | 1721 | O | ALA | 408 | 12.984 | 60.480 | 80.805 | 1.00 | 9.61 |
| ATOM | 1722 | N | PRO | 409 | 13.198 | 61.913 | 79.077 | 1.00 | 10.63 |
| ATOM | 1723 | CD | PRO | 409 | 13.575 | 62.330 | 77.706 | 1.00 | 11.82 |
| ATOM | 1724 | CA | PRO | 409 | 12.791 | 63.079 | 79.881 | 1.00 | 12.32 |
| ATOM | 1725 | CB | PRO | 409 | 12.689 | 64.185 | 78.827 | 1.00 | 12.27 |
| ATOM | 1726 | CG | PRO | 409 | 13.791 | 63.853 | 77.886 | 1.00 | 13.13 |
| ATOM | 1727 | C | PRO | 409 | 11.497 | 62.906 | 80.643 | 1.00 | 11.72 |
| ATOM | 1728 | O | PRO | 409 | 11.425 | 63.271 | 81.807 | 1.00 | 12.12 |
| ATOM | 1729 | N | GLU | 410 | 10.460 | 62.394 | 79.989 | 1.00 | 11.64 |

TABLE 3-continued

Coordinates of Lck bound with AMP-PNP

| | | Atom Type | Res | # | X | Y | Z | Occ | B |
|---|---|---|---|---|---|---|---|---|---|
| ATOM | 1730 | H | GLU | 410 | 10.569 | 62.124 | 79.053 | 1.00 | 0.00 |
| ATOM | 1731 | CA | GLU | 410 | 9.169 | 62.201 | 80.675 | 1.00 | 12.82 |
| ATOM | 1732 | CB | GLU | 410 | 8.100 | 61.709 | 79.705 | 1.00 | 13.13 |
| ATOM | 1733 | CG | GLU | 410 | 8.302 | 60.285 | 79.208 | 1.00 | 13.50 |
| ATOM | 1734 | CD | GLU | 410 | 9.158 | 60.157 | 77.949 | 1.00 | 14.16 |
| ATOM | 1735 | OE1 | GLU | 410 | 9.883 | 61.116 | 77.527 | 1.00 | 13.49 |
| ATOM | 1736 | OE2 | GLU | 410 | 9.065 | 59.066 | 77.439 | 1.00 | 12.30 |
| ATOM | 1737 | C | GLU | 410 | 9.271 | 61.294 | 81.893 | 1.00 | 13.03 |
| ATOM | 1738 | O | GLU | 410 | 8.546 | 61.457 | 82.992 | 1.00 | 12.80 |
| ATOM | 1739 | N | ALA | 411 | 10.166 | 60.309 | 81.848 | 1.00 | 12.07 |
| ATOM | 1740 | H | ALA | 411 | 10.709 | 60.180 | 81.049 | 1.00 | 0.00 |
| ATOM | 1741 | CA | ALA | 411 | 10.349 | 59.452 | 82.995 | 1.00 | 13.48 |
| ATOM | 1742 | CB | ALA | 411 | 11.013 | 58.115 | 82.544 | 1.00 | 11.89 |
| ATOM | 1743 | C | ALA | 411 | 11.148 | 60.152 | 84.098 | 1.00 | 13.86 |
| ATOM | 1744 | O | ALA | 411 | 10.810 | 60.060 | 85.261 | 1.00 | 14.48 |
| ATOM | 1745 | N | ILE | 412 | 12.181 | 60.902 | 83.730 | 1.00 | 14.47 |
| ATOM | 1746 | H | ILE | 412 | 12.449 | 60.948 | 82.784 | 1.00 | 0.00 |
| ATOM | 1747 | CA | ILE | 412 | 12.948 | 61.654 | 84.744 | 1.00 | 14.35 |
| ATOM | 1748 | CB | ILE | 412 | 14.113 | 62.409 | 84.064 | 1.00 | 14.57 |
| ATOM | 1749 | CG2 | ILE | 412 | 14.727 | 63.480 | 85.056 | 1.00 | 13.67 |
| ATOM | 1750 | CG1 | ILE | 412 | 15.170 | 61.407 | 83.604 | 1.00 | 14.89 |
| ATOM | 1751 | CD1 | ILE | 412 | 16.276 | 62.054 | 82.716 | 1.00 | 14.65 |
| ATOM | 1752 | C | ILE | 412 | 12.055 | 62.706 | 85.440 | 1.00 | 14.72 |
| ATOM | 1753 | O | ILE | 412 | 12.011 | 62.786 | 86.680 | 1.00 | 14.64 |
| ATOM | 1754 | N | ASN | 413 | 11.264 | 63.399 | 84.631 | 1.00 | 14.43 |
| ATOM | 1755 | H | ASN | 413 | 11.230 | 63.156 | 83.690 | 1.00 | 0.00 |
| ATOM | 1756 | CA | ASN | 413 | 10.414 | 64.489 | 85.121 | 1.00 | 15.79 |
| ATOM | 1757 | CB | ASN | 413 | 10.114 | 65.441 | 83.970 | 1.00 | 14.72 |
| ATOM | 1758 | CG | ASN | 413 | 11.378 | 66.139 | 83.446 | 1.00 | 15.01 |
| ATOM | 1759 | OD1 | ASN | 413 | 12.294 | 66.321 | 84.194 | 1.00 | 17.88 |
| ATOM | 1760 | ND2 | ASN | 413 | 11.434 | 66.458 | 82.163 | 1.00 | 16.83 |
| ATOM | 1761 | HD21 | ASN | 413 | 10.665 | 66.243 | 81.576 | 1.00 | 0.00 |
| ATOM | 1762 | HD22 | ASN | 413 | 12.214 | 66.918 | 81.835 | 1.00 | 0.00 |
| ATOM | 1763 | C | ASN | 413 | 9.123 | 64.113 | 85.824 | 1.00 | 16.85 |
| ATOM | 1764 | O | ASN | 413 | 8.785 | 64.680 | 86.890 | 1.00 | 17.54 |
| ATOM | 1765 | N | TYR | 414 | 8.403 | 63.169 | 85.228 | 1.00 | 17.67 |
| ATOM | 1766 | H | TYR | 414 | 8.738 | 62.752 | 84.418 | 1.00 | 0.00 |
| ATOM | 1767 | CA | TYR | 414 | 7.107 | 62.737 | 85.758 | 1.00 | 17.90 |
| ATOM | 1768 | CB | TYR | 414 | 6.048 | 62.839 | 84.688 | 1.00 | 19.12 |
| ATOM | 1769 | CG | TYR | 414 | 6.139 | 64.092 | 83.865 | 1.00 | 20.66 |
| ATOM | 1770 | CD1 | TYR | 414 | 6.223 | 65.333 | 84.472 | 1.00 | 22.51 |
| ATOM | 1771 | CE1 | TYR | 414 | 6.327 | 66.490 | 83.720 | 1.00 | 22.39 |
| ATOM | 1772 | CD2 | TYR | 414 | 6.149 | 64.043 | 82.495 | 1.00 | 21.40 |
| ATOM | 1773 | CE2 | TYR | 414 | 6.247 | 65.200 | 81.720 | 1.00 | 22.03 |
| ATOM | 1774 | CA | TYR | 414 | 6.336 | 66.425 | 82.358 | 1.00 | 23.14 |
| ATOM | 1775 | OH | TYR | 414 | 6.444 | 67.606 | 81.635 | 1.00 | 25.51 |
| ATOM | 1776 | HH | TYR | 414 | 6.465 | 68.348 | 82.243 | 1.00 | 0.00 |
| ATOM | 1777 | C | TYR | 414 | 7.038 | 61.353 | 86.348 | 1.00 | 17.97 |
| ATOM | 1778 | O | TYR | 414 | 6.048 | 61.020 | 87.011 | 1.00 | 18.36 |
| ATOM | 1779 | N | GLY | 415 | 8.045 | 60.530 | 86.081 | 1.00 | 16.60 |
| ATOM | 1780 | H | GLY | 415 | 8.790 | 60.830 | 85.527 | 1.00 | 0.00 |
| ATOM | 1781 | CA | GLY | 415 | 8.034 | 59.166 | 86.595 | 1.00 | 16.06 |
| ATOM | 1782 | C | GLY | 415 | 7.196 | 58.284 | 85.676 | 1.00 | 15.74 |
| ATOM | 1783 | O | GLY | 415 | 6.907 | 57.111 | 86.023 | 1.00 | 16.26 |
| ATOM | 1784 | N | THR | 416 | 6.808 | 58.837 | 84.532 | 1.00 | 14.68 |
| ATOM | 1785 | H | THR | 416 | 7.093 | 59.574 | 84.321 | 1.00 | 0.00 |
| ATOM | 1786 | CA | THR | 416 | 5.973 | 58.145 | 83.554 | 1.00 | 15.57 |
| ATOM | 1787 | CB | THR | 416 | 5.028 | 59.079 | 82.786 | 1.00 | 17.57 |
| ATOM | 1788 | OG1 | THR | 416 | 5.779 | 60.132 | 82.169 | 1.00 | 19.26 |
| ATOM | 1789 | HG1 | THR | 416 | 6.231 | 60.639 | 82.836 | 1.00 | 0.00 |
| ATOM | 1790 | CG2 | THR | 416 | 3.995 | 59.699 | 83.736 | 1.00 | 19.13 |
| ATOM | 1791 | C | THR | 416 | 6.800 | 57.401 | 82.524 | 1.00 | 14.21 |
| ATOM | 1792 | O | THR | 416 | 7.593 | 57.995 | 81.760 | 1.00 | 15.67 |
| ATOM | 1793 | N | PHE | 417 | 6.511 | 56.115 | 82.405 | 1.00 | 12.09 |
| ATOM | 1794 | H | PHE | 417 | 5.818 | 55.722 | 82.957 | 1.00 | 0.00 |
| ATOM | 1795 | CA | PHE | 417 | 7.231 | 55.271 | 81.441 | 1.00 | 11.30 |
| ATOM | 1796 | CB | PHE | 417 | 7.924 | 51.118 | 82.168 | 1.00 | 11.23 |
| ATOM | 1797 | CG | PHE | 417 | 9.090 | 54.535 | 82.997 | 1.00 | 10.41 |
| ATOM | 1798 | CD1 | PHE | 417 | 8.916 | 54.991 | 84.293 | 1.00 | 9.97 |
| ATOM | 1799 | CD2 | PHE | 417 | 10.388 | 54.409 | 82.486 | 1.00 | 9.23 |
| ATOM | 1800 | CE1 | PHE | 417 | 10.009 | 55.309 | 85.091 | 1.00 | 12.53 |
| ATOM | 1801 | CE2 | PHE | 417 | 11.462 | 54.713 | 83.243 | 1.00 | 9.51 |
| ATOM | 1802 | CZ | PHE | 417 | 11.311 | 55.166 | 84.558 | 1.00 | 9.78 |
| ATOM | 1803 | C | PHE | 417 | 6.300 | 54.610 | 80.450 | 1.00 | 11.10 |

TABLE 3-continued

Coordinates of Lck bound with AMP-PNP

| | | Atom Type | Res | # | X | Y | Z | Occ | B |
|---|---|---|---|---|---|---|---|---|---|
| ATOM | 1804 | O | PHE | 417 | 5.198 | 54.172 | 80.821 | 1.00 | 11.90 |
| ATOM | 1805 | N | THR | 418 | 6.715 | 54.593 | 79.183 | 1.00 | 10.15 |
| ATOM | 1806 | H | THR | 418 | 7.525 | 55.089 | 78.952 | 1.00 | 0.00 |
| ATOM | 1807 | CA | THR | 418 | 5.982 | 53.852 | 78.127 | 1.00 | 9.74 |
| ATOM | 1808 | CB | THR | 418 | 5.140 | 54.725 | 77.164 | 1.00 | 10.54 |
| ATOM | 1809 | OG1 | THR | 418 | 5.972 | 55.497 | 76.304 | 1.00 | 12.41 |
| ATOM | 1810 | HG1 | THR | 418 | 6.542 | 54.913 | 75.812 | 1.00 | 0.00 |
| ATOM | 1811 | CG2 | THR | 418 | 4.244 | 55.659 | 77.943 | 1.00 | 12.42 |
| ATOM | 1812 | C | THR | 418 | 7.019 | 53.150 | 77.269 | 1.00 | 8.07 |
| ATOM | 1813 | O | THR | 418 | 8.245 | 53.304 | 77.522 | 1.00 | 8.89 |
| ATOM | 1814 | N | ILE | 419 | 6.569 | 52.350 | 76.289 | 1.00 | 7.32 |
| ATOM | 1815 | H | ILE | 419 | 5.621 | 52.202 | 76.165 | 1.00 | 0.00 |
| ATOM | 1816 | CA | ILE | 419 | 7.551 | 51.741 | 75.415 | 1.00 | 6.24 |
| ATOM | 1817 | CB | ILE | 419 | 6.871 | 50.730 | 74.410 | 1.00 | 6.09 |
| ATOM | 1818 | CG2 | ILE | 419 | 6.082 | 51.511 | 73.346 | 1.00 | 5.86 |
| ATOM | 1819 | CG1 | ILE | 419 | 7.893 | 49.841 | 73.669 | 1.00 | 6.62 |
| ATOM | 1820 | CD1 | ILE | 419 | 8.604 | 48.853 | 74.599 | 1.00 | 7.43 |
| ATOM | 1821 | C | ILE | 419 | 8.387 | 52.838 | 74.702 | 1.00 | 6.54 |
| ATOM | 1822 | O | ILE | 419 | 9.534 | 52.607 | 74.300 | 1.00 | 6.86 |
| ATOM | 1823 | N | LYS | 420 | 7.813 | 54.056 | 74.546 | 1.00 | 7.02 |
| ATOM | 1824 | H | LYS | 420 | 6.898 | 51.194 | 74.832 | 1.00 | 0.00 |
| ATOM | 1825 | CA | LYS | 420 | 8.559 | 55.133 | 73.922 | 1.00 | 5.39 |
| ATOM | 1826 | CB | LYS | 420 | 7.616 | 56.295 | 73.620 | 1.00 | 6.87 |
| ATOM | 1827 | CG | LYS | 420 | 6.565 | 55.987 | 72.532 | 1.00 | 7.82 |
| ATOM | 1828 | CD | LYS | 420 | 7.083 | 55.455 | 71.200 | 1.00 | 7.78 |
| ATOM | 1829 | CE | LYS | 420 | 5.959 | 55.208 | 70.159 | 1.00 | 8.97 |
| ATOM | 1830 | NZ | LYS | 420 | 6.486 | 54.574 | 68.971 | 1.00 | 10.61 |
| ATOM | 1831 | HZ1 | LYS | 420 | 6.912 | 53.650 | 69.230 | 1.00 | 0.00 |
| ATOM | 1832 | HZ2 | LYS | 420 | 7.128 | 55.159 | 68.535 | 1.00 | 0.00 |
| ATOM | 1833 | HZ3 | LYS | 420 | 5.725 | 54.392 | 68.287 | 1.00 | 0.00 |
| ATOM | 1834 | C | LYS | 420 | 9.739 | 55.639 | 74.781 | 1.00 | 5.31 |
| ATOM | 1835 | O | LYS | 420 | 10.681 | 56.226 | 74.222 | 1.00 | 5.39 |
| ATOM | 1836 | N | SER | 421 | 9.680 | 55.442 | 76.096 | 0.84 | 4.39 |
| ATOM | 1837 | H | SER | 421 | 8.867 | 55.039 | 76.461 | 1.00 | 0.00 |
| ATOM | 1838 | CA | SER | 421 | 10.775 | 55.769 | 77.032 | 0.84 | 4.39 |
| ATOM | 1839 | CB | SER | 421 | 10.275 | 55.628 | 78.498 | 0.84 | 8.78 |
| ATOM | 1840 | OG | SER | 421 | 9.071 | 56.399 | 78.631 | 0.84 | 8.78 |
| ATOM | 1841 | HG | SER | 421 | 9.278 | 57.326 | 78.452 | 1.00 | 0.00 |
| ATOM | 1842 | C | SER | 421 | 11.898 | 54.774 | 76.723 | 0.84 | 4.17 |
| ATOM | 1843 | O | SER | 421 | 13.080 | 55.127 | 76.738 | 0.84 | 4.10 |
| ATOM | 1844 | N | ASP | 422 | 11.518 | 53.528 | 76.443 | 1.00 | 5.50 |
| ATOM | 1845 | H | ASP | 422 | 10.584 | 53.272 | 76.460 | 1.00 | 0.00 |
| ATOM | 1846 | CA | ASP | 422 | 12.551 | 52.540 | 76.115 | 1.00 | 4.75 |
| ATOM | 1847 | CB | ASP | 422 | 11.990 | 51.100 | 76.040 | 1.00 | 6.52 |
| ATOM | 1848 | CG | ASP | 422 | 11.724 | 50.489 | 77.392 | 1.00 | 7.22 |
| ATOM | 1849 | OD1 | ASP | 422 | 12.227 | 50.919 | 78.460 | 1.00 | 7.55 |
| ATOM | 1850 | OD2 | ASP | 422 | 10.893 | 49.543 | 77.380 | 1.00 | 9.72 |
| ATOM | 1851 | O | ASP | 422 | 13.207 | 52.883 | 73.792 | 1.00 | 4.30 |
| ATOM | 1852 | O | APS | 422 | 14.360 | 52.585 | 74.579 | 1.00 | 4.83 |
| ATOM | 1853 | N | VAL | 423 | 12.452 | 53.444 | 74.844 | 1.00 | 2.28 |
| ATOM | 1854 | H | VAL | 423 | 11.503 | 53.580 | 74.014 | 1.00 | 0.00 |
| ATOM | 1855 | CA | VAL | 423 | 12.995 | 53.847 | 72.548 | 1.00 | 3.14 |
| ATOM | 1856 | CB | VAL | 423 | 11.870 | 54.339 | 71.631 | 1.00 | 4.31 |
| ATOM | 1857 | CG1 | VAL | 423 | 12.411 | 55.008 | 70.401 | 1.00 | 4.11 |
| ATOM | 1858 | CG2 | VAL | 423 | 11.022 | 53.087 | 71.158 | 1.00 | 3.98 |
| ATOM | 1859 | C | VAL | 423 | 14.065 | 54.930 | 72.776 | 1.00 | 3.64 |
| ATOM | 1860 | O | VAL | 423 | 15.079 | 54.888 | 72.121 | 1.00 | 3.31 |
| ATOM | 1861 | N | TRP | 424 | 13.786 | 55.881 | 73.692 | 1.00 | 3.87 |
| ATOM | 1862 | H | TRP | 424 | 12.905 | 55.865 | 74.141 | 1.00 | 0.00 |
| ATOM | 1863 | CA | TRP | 424 | 14.793 | 56.897 | 74.008 | 1.00 | 4.26 |
| ATOM | 1864 | CB | TRP | 424 | 14.230 | 57.847 | 75.110 | 1.00 | 4.58 |
| ATOM | 1865 | CG | TRP | 424 | 15.218 | 58.908 | 75.524 | 1.00 | 5.10 |
| ATOM | 1866 | CD2 | TRP | 424 | 15.190 | 60.294 | 75.147 | 1.00 | 5.67 |
| ATOM | 1867 | CE2 | TRP | 424 | 16.342 | 60.888 | 75.701 | 1.00 | 5.11 |
| ATOM | 1868 | CE3 | TRP | 424 | 14.271 | 61.078 | 74.416 | 1.00 | 5.52 |
| ATOM | 1869 | CD1 | TRP | 424 | 16.339 | 58.728 | 76.275 | 1.00 | 5.45 |
| ATOM | 1870 | NE1 | TRP | 424 | 17.025 | 59.928 | 76.275 | 1.00 | 6.04 |
| ATOM | 1871 | HE1 | TRP | 424 | 17.870 | 60.056 | 76.863 | 1.00 | 0.00 |
| ATOM | 1872 | CZ2 | TRP | 424 | 16.629 | 62.268 | 75.548 | 1.00 | 4.89 |
| ATOM | 1873 | CZ3 | TRP | 424 | 14.539 | 62.462 | 74.268 | 1.00 | 5.83 |
| ATOM | 1874 | CH3 | TRP | 424 | 15.722 | 63.031 | 74.842 | 1.00 | 6.03 |
| ATOM | 1875 | C | TRP | 424 | 16.085 | 56.161 | 74.467 | 1.00 | 4.03 |
| ATOM | 1876 | O | TRP | 424 | 17.190 | 56.513 | 74.008 | 1.00 | 3.83 |
| ATOM | 1877 | N | SER | 425 | 15.925 | 55.282 | 75.435 | 0.74 | 2.00 |

TABLE 3-continued

Coordinates of Lck bound with AMP-PNP

| | | Atom Type | Res | # | X | Y | Z | Occ | B |
|---|---|---|---|---|---|---|---|---|---|
| ATOM | 1878 | H | SER | 425 | 15.019 | 55.122 | 75.789 | 1.00 | 0.00 |
| ATOM | 1879 | CA | SER | 425 | 17.053 | 54.56 | 76.005 | 0.74 | 2.00 |
| ATOM | 1880 | CB | SER | 425 | 16.530 | 53.590 | 77.044 | 0.74 | 2.00 |
| ATOM | 1881 | OG | SER | 425 | 15.918 | 54.259 | 78.131 | 0.74 | 3.21 |
| ATOM | 1882 | HG | SER | 425 | 15.179 | 54.793 | 77.793 | 1.00 | 0.00 |
| ATOM | 1883 | C | SER | 425 | 17.818 | 53.835 | 74.915 | 0.74 | 2.61 |
| ATOM | 1884 | O | SER | 425 | 19.051 | 53.752 | 74.965 | 0.74 | 2.00 |
| ATOM | 1885 | N | PHE | 426 | 17.094 | 53.193 | 73.991 | 1.00 | 3.61 |
| ATOM | 1886 | H | PHE | 426 | 16.127 | 53.188 | 74.079 | 1.00 | 0.00 |
| ATOM | 1887 | CA | PHE | 426 | 17.736 | 52.496 | 72.870 | 1.00 | 3.25 |
| ATOM | 1888 | CB | PHE | 426 | 16.676 | 51.897 | 71.952 | 1.00 | 3.78 |
| ATOM | 1889 | CG | PHE | 426 | 17.238 | 51.086 | 70.836 | 1.00 | 2.99 |
| ATOM | 1890 | CD1 | PHE | 426 | 17.786 | 49.829 | 71.097 | 1.00 | 3.53 |
| ATOM | 1891 | CD2 | PHE | 426 | 17.250 | 51.580 | 69.532 | 1.00 | 3.33 |
| ATOM | 1892 | CE2 | PHE | 426 | 18.341 | 49.085 | 70.044 | 1.00 | 3.60 |
| ATOM | 1893 | CE2 | PHE | 426 | 17.809 | 50.846 | 68.476 | 1.00 | 4.33 |
| ATOM | 1894 | CZ | PHE | 426 | 18.369 | 49.551 | 68.755 | 1.00 | 2.26 |
| ATOM | 1895 | C | PHE | 426 | 18.651 | 53.445 | 72.081 | 1.00 | 4.19 |
| ATOM | 1896 | O | PHE | 426 | 19.742 | 53.059 | 71.648 | 1.00 | 4.20 |
| ATOM | 1897 | N | GLY | 427 | 18.198 | 54.674 | 71.882 | 1.00 | 3.62 |
| ATOM | 1898 | H | GLY | 427 | 17.307 | 54.940 | 72.200 | 1.00 | 0.00 |
| ATOM | 1899 | CA | GLY | 427 | 19.084 | 55.593 | 71.185 | 1.00 | 4.54 |
| ATOM | 1901 | O | GLY | 427 | 21.434 | 55.911 | 71.318 | 1.00 | 3.03 |
| ATOM | 1902 | N | ILE | 427 | 20.319 | 55.912 | 73.279 | 1.00 | 2.87 |
| ATOM | 1903 | H | ILE | 427 | 19.437 | 55.901 | 73.706 | 1.00 | 0.00 |
| ATOM | 1904 | CA | ILE | 427 | 21.504 | 56.074 | 74.098 | 1.00 | 2.59 |
| ATOM | 1905 | CB | ILE | 427 | 21.141 | 56.366 | 75.562 | 1.00 | 3.04 |
| ATOM | 1906 | CG2 | ILE | 427 | 22.405 | 56.537 | 76.405 | 1.00 | 4.80 |
| ATOM | 1907 | CG1 | ILE | 427 | 20.191 | 57.589 | 75.641 | 1.00 | 3.89 |
| ATOM | 1908 | CD1 | ILE | 427 | 20.795 | 58.952 | 75.169 | 1.00 | 5.08 |
| ATOM | 1909 | C | ILE | 428 | 22.236 | 54.782 | 73.967 | 1.00 | 4.70 |
| ATOM | 1910 | O | ILE | 428 | 23.565 | 54.797 | 73.895 | 1.00 | 4.68 |
| ATOM | 1911 | N | LEU | 429 | 21.634 | 53.638 | 74.001 | 1.00 | 3.61 |
| ATOM | 1912 | H | LEU | 429 | 20.677 | 53.561 | 74.121 | 1.00 | 0.00 |
| ATOM | 1913 | CA | LEU | 429 | 22.384 | 52.370 | 73.868 | 1.00 | 4.69 |
| ATOM | 1914 | CB | LEU | 429 | 21.388 | 51.184 | 74.005 | 1.00 | 5.24 |
| ATOM | 1915 | CG | LEU | 429 | 21.962 | 49.763 | 74.217 | 1.00 | 7.89 |
| ATOM | 1916 | CD1 | LEU | 429 | 20.803 | 48.836 | 74.587 | 1.00 | 6.69 |
| ATOM | 1917 | CD2 | LEU | 429 | 22.640 | 49.187 | 73.029 | 1.00 | 11.59 |
| ATOM | 1918 | C | LEU | 429 | 23.177 | 52.328 | 72.528 | 1.00 | 5.16 |
| ATOM | 1919 | O | LEU | 429 | 24.305 | 51.787 | 72.453 | 1.00 | 6.28 |
| ATOM | 1920 | N | LEU | 430 | 22.593 | 52.823 | 71.446 | 1.00 | 4.85 |
| ATOM | 1921 | H | LEU | 430 | 21.691 | 53.201 | 71.500 | 1.00 | 0.00 |
| ATOM | 1922 | CA | LEU | 430 | 23.267 | 52.837 | 70.158 | 1.00 | 4.09 |
| ATOM | 1923 | CB | LEU | 430 | 22.427 | 53.499 | 69.089 | 1.00 | 4.96 |
| ATOM | 1924 | CG | LEU | 430 | 21.181 | 52.736 | 68.615 | 1.00 | 4.92 |
| ATOM | 1925 | CD1 | LEU | 430 | 20.499 | 53.563 | 67.511 | 1.00 | 5.50 |
| ATOM | 1926 | CD2 | LEU | 430 | 21.616 | 51.344 | 68.039 | 1.00 | 5.64 |
| ATOM | 1927 | C | LEU | 430 | 24.603 | 53.638 | 70.329 | 1.00 | 5.14 |
| ATOM | 1928 | O | LEU | 430 | 25.588 | 53.283 | 69.729 | 1.00 | 4.63 |
| ATOM | 1929 | N | THR | 431 | 24.631 | 54.686 | 71.143 | 1.00 | 4.15 |
| ATOM | 1930 | H | THR | 431 | 23.820 | 54.932 | 71.629 | 1.00 | 0.00 |
| ATOM | 1931 | CA | THR | 431 | 25.907 | 55.419 | 71.331 | 1.00 | 4.99 |
| ATOM | 1932 | CB | THR | 431 | 25.775 | 56.788 | 72.128 | 1.00 | 3.81 |
| ATOM | 1933 | OG1 | THR | 431 | 25.535 | 56.607 | 73.521 | 1.00 | 5.06 |
| ATOM | 1934 | HG1 | THR | 431 | 26.285 | 56.125 | 73.912 | 1.00 | 0.00 |
| ATOM | 1935 | CG2 | THR | 431 | 24.682 | 57.599 | 71.511 | 1.00 | 5.88 |
| ATOM | 1936 | C | THR | 431 | 26.916 | 54.513 | 72.030 | 1.00 | 5.33 |
| ATOM | 1937 | O | THR | 431 | 28.093 | 54.577 | 71.725 | 1.00 | 6.80 |
| ATOM | 1938 | N | GLU | 432 | 26.460 | 53.731 | 72.981 | 1.00 | 4.68 |
| ATOM | 1939 | H | GLU | 432 | 25.506 | 53.772 | 73.212 | 1.00 | 0.00 |
| ATOM | 1940 | CA | GLU | 432 | 27.364 | 52.789 | 73.682 | 1.00 | 5.06 |
| ATOM | 1941 | CB | GLU | 432 | 26.667 | 52.087 | 74.838 | 1.00 | 5.36 |
| ATOM | 1942 | CG | GLU | 432 | 26.109 | 52.989 | 75.912 | 1.00 | 5.97 |
| ATOM | 1943 | CD | GLU | 432 | 25.472 | 52.155 | 76.997 | 1.00 | 7.12 |
| ATOM | 1944 | OE1 | GLU | 432 | 24.291 | 51.757 | 76.844 | 1.00 | 7.06 |
| ATOM | 1945 | OE2 | GLU | 432 | 26.173 | 51.808 | 77.959 | 1.00 | 9.86 |
| ATOM | 1946 | C | GLU | 432 | 27.937 | 51.795 | 72.693 | 1.00 | 5.32 |
| ATOM | 1947 | O | GLU | 432 | 29.106 | 51.418 | 72.820 | 1.00 | 6.10 |
| ATOM | 1948 | N | ILE | 433 | 27.142 | 51.324 | 71.755 | 1.00 | 5.34 |
| ATOM | 1949 | H | ILE | 433 | 26.222 | 51.617 | 71.690 | 1.00 | 0.00 |
| ATOM | 1950 | CA | ILE | 433 | 27.658 | 50.357 | 70.802 | 1.00 | 6.31 |
| ATOM | 1951 | CB | ILE | 433 | 26.526 | 49.749 | 69.990 | 1.00 | 6.14 |
| ATOM | 1952 | CG2 | ILE | 433 | 27.062 | 49.005 | 68.759 | 1.00 | 8.93 |

TABLE 3-continued

Coordinates of Lck bound with AMP-PNP

| | | Atom Type | Res | # | X | Y | Z | Occ | B |
|---|---|---|---|---|---|---|---|---|---|
| ATOM | 1953 | CG1 | ILE | 433 | 25.675 | 48.945 | 70.934 | 1.00 | 7.33 |
| ATOM | 1954 | CD1 | ILE | 433 | 24.435 | 48.475 | 70.211 | 1.00 | 7.92 |
| ATOM | 1955 | C | ILE | 433 | 28.729 | 50.918 | 69.892 | 1.00 | 7.78 |
| ATOM | 1956 | O | ILE | 433 | 29.844 | 50.286 | 69.783 | 1.00 | 8.65 |
| ATOM | 1957 | N | VAL | 434 | 28.471 | 52.097 | 69.358 | 1.00 | 7.33 |
| ATOM | 1958 | H | VAL | 434 | 27.642 | 52.564 | 65.591 | 1.00 | 0.00 |
| ATOM | 1959 | CA | VAL | 434 | 29.398 | 52.699 | 68.407 | 1.00 | 10.01 |
| ATOM | 1960 | CB | VAL | 434 | 28.641 | 53.800 | 67.535 | 1.00 | 11.32 |
| ATOM | 1961 | CG1 | VAL | 434 | 28.540 | 55.063 | 68.298 | 1.00 | 12.92 |
| ATOM | 1962 | CG2 | VAL | 434 | 29.302 | 53.940 | 66.124 | 1.00 | 14.45 |
| ATOM | 1963 | C | VAL | 434 | 20.685 | 53.258 | 69.077 | 1.00 | 8.29 |
| ATOM | 1964 | O | VAL | 434 | 31.717 | 53.362 | 70.876 | 1.00 | 0.00 |
| ATOM | 1965 | N | THR | 435 | 30.662 | 53.505 | 70.374 | 1.00 | 8.17 |
| ATOM | 1966 | H | THR | 435 | 29.839 | 53.362 | 70.876 | 1.00 | 0.00 |
| ATOM | 1967 | CA | THR | 435 | 31.862 | 54.008 | 71.060 | 1.00 | 9.24 |
| ATOM | 1968 | CB | THR | 435 | 31.531 | 55.127 | 72.051 | 1.00 | 8.60 |
| ATOM | 1969 | OG1 | THR | 435 | 30.671 | 54.649 | 73.101 | 1.00 | 9.12 |
| ATOM | 1970 | HG1 | THR | 435 | 30.469 | 55.385 | 73.698 | 1.00 | 0.00 |
| ATOM | 1971 | CG2 | THR | 435 | 30.850 | 56.305 | 71.301 | 1.00 | 9.20 |
| ATOM | 1972 | C | THR | 435 | 32.545 | 52.895 | 71.865 | 1.00 | 10.34 |
| ATOM | 1973 | O | THR | 435 | 33.336 | 53.175 | 72.766 | 1.00 | 10.87 |
| ATOM | 1974 | N | HIS | 436 | 32.180 | 51.642 | 71.590 | 1.00 | 10.82 |
| ATOM | 1975 | H | HIS | 436 | 31.537 | 51.471 | 70.873 | 1.00 | 0.00 |
| ATOM | 1976 | CA | HIS | 436 | 32.744 | 50.530 | 72.347 | 1.00 | 11.46 |
| ATOM | 1977 | CB | HIS | 436 | 34.154 | 50.167 | 71.849 | 1.00 | 15.05 |
| ATOM | 1978 | CG | HIS | 436 | 34.179 | 49.627 | 70.461 | 1.00 | 16.72 |
| ATOM | 1979 | CD2 | HIS | 436 | 34.109 | 50.254 | 69.243 | 1.00 | 18.23 |
| ATOM | 1980 | ND1 | HIS | 436 | 34.283 | 48.283 | 70.183 | 1.00 | 18.71 |
| ATOM | 1981 | HD1 | HIS | 436 | 34.338 | 47.562 | 70.852 | 1.00 | 0.00 |
| ATOM | 1982 | CE1 | HIS | 436 | 34.284 | 48.090 | 68.872 | 1.00 | 17.96 |
| ATOM | 1983 | NE2 | HIS | 436 | 34.177 | 49.279 | 68.287 | 1.00 | 10.69 |
| ATOM | 1984 | HE2 | HIS | 436 | 34.183 | 49.421 | 67.315 | 1.00 | 0.00 |
| ATOM | 1985 | C | HIS | 436 | 32.630 | 50.659 | 73.865 | 1.00 | 10.91 |
| ATOM | 1986 | O | HIS | 436 | 33.569 | 50.410 | 74.667 | 1.00 | 12.67 |
| ATOM | 1987 | N | GLY | 437 | 31.418 | 51.025 | 74.291 | 1.00 | 9.46 |
| ATOM | 1988 | H | GLY | 437 | 30.733 | 51.246 | 73.653 | 1.00 | 0.00 |
| ATOM | 1989 | CA | GLY | 437 | 31.120 | 51.097 | 75.702 | 1.00 | 9.96 |
| ATOM | 1990 | C | GLY | 437 | 31.404 | 52.373 | 76.462 | 1.00 | 9.49 |
| ATOM | 1991 | O | GLY | 437 | 31.325 | 52.346 | 77.682 | 1.00 | 11.99 |
| ATOM | 1992 | N | ARG | 438 | 31.665 | 53.481 | 75.758 | 0.58 | 7.77 |
| ATOM | 1993 | H | ARG | 438 | 31.690 | 53.422 | 75.758 | 0.58 | 7.77 |
| ATOM | 1994 | CA | ARG | 438 | 31.923 | 54.759 | 76.429 | 0.58 | 8.40 |
| ATOM | 1995 | CB | ARG | 438 | 32.404 | 55.805 | 75.404 | 0.58 | 8.52 |
| ATOM | 1996 | CG | ARG | 438 | 33.030 | 57.083 | 75.974 | 0.58 | 11.45 |
| ATOM | 1997 | CD | ARG | 438 | 33.486 | 58.066 | 74.874 | 0.58 | 12.12 |
| ATOM | 1998 | NE | ARG | 438 | 34.280 | 59.175 | 75.424 | 0.58 | 15.11 |
| ATOM | 1999 | HE | ARG | 438 | 34.611 | 59.088 | 76.334 | 1.00 | 0.00 |
| ATOM | 2000 | CZ | ARG | 438 | 34.590 | 60.280 | 74.744 | 0.58 | 16.05 |
| ATOM | 2001 | NH1 | ARG | 438 | 34.178 | 60.439 | 73.497 | 0.58 | 17.29 |
| ATOM | 2002 | HH12 | ARG | 438 | 33.631 | 59.718 | 73.051 | 1.00 | 0.00 |
| ATOM | 2003 | HH12 | ARG | 438 | 34.407 | 61.263 | 72.984 | 1.00 | 0.00 |
| ATOM | 2004 | NH2 | ARG | 438 | 35.505 | 61.241 | 75.310 | 0.58 | 18.16 |
| ATOM | 2005 | HH21 | ARG | 438 | 35.597 | 61.150 | 76.254 | 1.00 | 0.00 |
| ATOM | 2006 | HH22 | ARG | 438 | 35.513 | 62.069 | 74.786 | 1.00 | 0.00 |
| ATOM | 2007 | C | ARG | 438 | 30.638 | 55.243 | 77.108 | 0.58 | 7.24 |
| ATOM | 2008 | O | ARG | 438 | 29.530 | 54.895 | 76.655 | 0.58 | 6.64 |
| ATOM | 2009 | N | ILE | 439 | 30.788 | 56.029 | 78.180 | 1.00 | 8.97 |
| ATOM | 2010 | H | ILE | 439 | 31.697 | 56.242 | 78.475 | 1.00 | 0.00 |
| AROM | 2011 | CA | ILE | 439 | 29.652 | 56.580 | 78.934 | 1.00 | 7.88 |
| ATOM | 2012 | CB | ILE | 439 | 30.127 | 57.170 | 80.287 | 1.00 | 11.18 |
| ATOM | 2013 | CG2 | ILE | 439 | 29.026 | 58.024 | 80.928 | 1.00 | 12.03 |
| ATOM | 2014 | CG1 | ILE | 439 | 30.520 | 56.025 | 81.211 | 1.00 | 11.96 |
| ATOM | 2015 | CD1 | ILE | 439 | 30.889 | 56.512 | 82.575 | 1.00 | 16.69 |
| ATOM | 2016 | C | ILE | 439 | 29.019 | 57.675 | 78.071 | 1.00 | 6.45 |
| ATOM | 2017 | O | ILE | 439 | 29.737 | 58.458 | 77.417 | 1.00 | 8.58 |
| ATOM | 2018 | N | PRO | 440 | 27.679 | 57.686 | 77.963 | 0.43 | 2.25 |
| ATOM | 2019 | CD | PRO | 440 | 26.708 | 56.716 | 78.495 | 0.43 | 2.56 |
| ATOM | 2020 | CA | PRO | 440 | 27.017 | 58.710 | 77.139 | 0.43 | 2.00 |
| ATOM | 2021 | CB | PRO | 440 | 25.524 | 58.333 | 77.243 | 0.43 | 2.00 |
| ATOM | 2022 | CG | PRO | 440 | 25.420 | 57.491 | 78.427 | 0.43 | 3.05 |
| ATOM | 2023 | C | PRO | 440 | 27.283 | 60.131 | 77.622 | 0.43 | 2.00 |
| ATOM | 2024 | O | PRO | 440 | 27.587 | 60.341 | 78.809 | 0.43 | 2.00 |
| ATOM | 2025 | N | TYR | 441 | 27.115 | 61.092 | 76.706 | 1.00 | 6.28 |
| ATOM | 2026 | H | TYR | 441 | 26.831 | 60.842 | 75.803 | 1.00 | 0.00 |

TABLE 3-continued

Coordinates of Lck bound with AMP-PNP

| | | Atom Type | Res | # | X | Y | Z | Occ | B |
|---|---|---|---|---|---|---|---|---|---|
| ATOM | 2027 | CA | TYR | 441 | 27.326 | 62.520 | 77.049 | 1.00 | 7.84 |
| ATOM | 2028 | CB | TYR | 441 | 26.252 | 63.053 | 77.985 | 1.00 | 7.07 |
| ATOM | 2029 | CG | TYR | 441 | 24.850 | 62.862 | 77.431 | 1.00 | 5.21 |
| ATOM | 2030 | CD1 | TYR | 441 | 24.301 | 63.763 | 76.504 | 1.00 | 5.50 |
| ATOM | 2031 | CE1 | TYR | 441 | 22.974 | 63.602 | 76.058 | 1.00 | 5.71 |
| ATOM | 2032 | CD2 | TYR | 441 | 24.055 | 61.788 | 77.859 | 1.00 | 6.20 |
| ATOM | 2033 | CE2 | TYR | 441 | 22.764 | 61.625 | 77.394 | 1.00 | 4.20 |
| ATOM | 2034 | CA | TYR | 441 | 22.220 | 62.538 | 76.516 | 1.00 | 5.80 |
| ATOM | 2035 | OH | TYR | 441 | 20.911 | 62.422 | 76.164 | 1.00 | 4.13 |
| ATOM | 2036 | HH | TYR | 441 | 20.531 | 61.671 | 76.616 | 1.00 | 0.00 |
| ATOM | 2037 | C | TYR | 441 | 28.682 | 62.737 | 77.679 | 1.00 | 10.50 |
| ATOM | 2038 | O | TYR | 441 | 28.786 | 63.196 | 78.818 | 1.00 | 9.67 |
| ATOM | 2039 | N | PRO | 442 | 29.724 | 62.483 | 76.898 | 1.00 | 11.93 |
| ATOM | 2040 | CD | PRO | 442 | 29.751 | 62.094 | 75.473 | 1.00 | 12.53 |
| ATOM | 2041 | CA | PRO | 442 | 31.074 | 62.657 | 77.425 | 1.00 | 14.05 |
| ATOM | 2042 | CB | PRO | 442 | 31.962 | 62.268 | 76.249 | 1.00 | 14.29 |
| ATOM | 2043 | CG | PRO | 442 | 31.118 | 61.497 | 75.363 | 1.00 | 13.87 |
| ATOM | 2044 | C | PRO | 442 | 31.424 | 64.044 | 77.967 | 1.00 | 13.17 |
| ATOM | 2045 | O | PRO | 442 | 31.135 | 65.008 | 77.356 | 1.00 | 14.67 |
| ATOM | 2046 | N | GLY | 443 | 31.980 | 64.003 | 79.166 | 1.00 | 14.90 |
| ATOM | 2047 | CA | GLY | 443 | 32.060 | 63.141 | 79.622 | 1.00 | 0.00 |
| ATOM | 2048 | CA | GLY | 443 | 32.438 | 65.214 | 79.838 | 1.00 | 13.50 |
| ATOM | 2049 | C | GLY | 443 | 31.325 | 66.026 | 80.453 | 1.00 | 15.21 |
| ATOM | 2050 | O | GLY | 443 | 31.535 | 67.204 | 80.844 | 1.00 | 15.80 |
| ATOM | 2051 | N | MET | 444 | 30.152 | 65.405 | 80.572 | 1.00 | 13.04 |
| ATOM | 2052 | H | MET | 444 | 30.072 | 64.473 | 80.280 | 1.00 | 0.00 |
| ATOM | 2053 | CA | MET | 444 | 29.011 | 66.110 | 81.133 | 1.00 | 12.08 |
| ATOM | 2054 | CB | MET | 444 | 27.904 | 66.247 | 80.081 | 1.00 | 12.69 |
| ATOM | 2055 | CG | MET | 444 | 28.365 | 66.809 | 78.745 | 1.00 | 14.01 |
| ATOM | 2056 | SD | MET | 444 | 27.083 | 66.990 | 77.487 | 1.00 | 13.68 |
| ATOM | 2057 | CE | MET | 444 | 25.864 | 67.933 | 78.292 | 1.00 | 13.90 |
| ATOM | 2058 | C | MET | 444 | 28.428 | 65.477 | 82.376 | 1.00 | 11.03 |
| ATOM | 2059 | O | MET | 444 | 28.302 | 64.250 | 82.459 | 1.00 | 11.68 |
| ATOM | 2060 | N | THR | 445 | 28.069 | 66.325 | 83.341 | 1.00 | 9.53 |
| ATOM | 2061 | H | THR | 445 | 28.272 | 67.272 | 83.235 | 1.00 | 0.00 |
| ATOM | 2062 | CA | THR | 445 | 27.399 | 65.870 | 84.550 | 1.00 | 9.56 |
| ATOM | 2063 | CB | THR | 445 | 27.493 | 66.906 | 85.671 | 1.00 | 11.45 |
| ATOM | 2064 | OG1 | THR | 445 | 26.787 | 68.112 | 85.278 | 1.00 | 11.07 |
| ATOM | 2065 | HG1 | THR | 445 | 27.181 | 68.455 | 84.470 | 1.00 | 0.00 |
| ATOM | 2066 | CG2 | THR | 445 | 28.985 | 67.231 | 85.975 | 1.00 | 13.08 |
| ATOM | 2067 | C | THR | 445 | 35.901 | 65.711 | 84.260 | 1.00 | 8.59 |
| ATOM | 2068 | O | THR | 445 | 25.408 | 66.221 | 83.254 | 1.00 | 8.79 |
| ATOM | 2069 | N | ASN | 446 | 25.168 | 65.098 | 85.182 | 1.00 | 9.38 |
| ATOM | 2070 | H | ASN | 446 | 25.593 | 64.726 | 85.988 | 1.00 | 0.00 |
| ATOM | 2071 | CA | ASN | 446 | 23.726 | 64.966 | 84.978 | 1.00 | 10.56 |
| ATOM | 2072 | CB | ASN | 446 | 23.111 | 64.095 | 86.052 | 1.00 | 12.38 |
| ATOM | 2073 | CG | ASN | 446 | 23.480 | 62.637 | 85.888 | 1.00 | 13.78 |
| ATOM | 2074 | OD1 | ASN | 446 | 23.862 | 62.184 | 84.813 | 1.00 | 14.64 |
| ATOM | 2075 | ND2 | ASN | 446 | 23.418 | 61.909 | 86.978 | 1.00 | 15.96 |
| ATOM | 2076 | HD21 | ASN | 446 | 23.185 | 62.332 | 87.802 | 1.00 | 0.00 |
| ATOM | 2077 | HD22 | ASN | 446 | 23.635 | 60.964 | 86.897 | 1.00 | 0.00 |
| ATOM | 2078 | C | ASN | 446 | 22.986 | 66.304 | 84.875 | 1.00 | 10.53 |
| ATOM | 2079 | O | ASN | 446 | 22.121 | 66.460 | 84.023 | 1.00 | 10.29 |
| ATOM | 2080 | N | PRO | 447 | 23.348 | 67.303 | 85.717 | 1.00 | 11.41 |
| ATOM | 2081 | CD | PRO | 447 | 24.130 | 67.277 | 86.969 | 1.00 | 11.07 |
| ATOM | 2082 | CA | PRO | 447 | 22.623 | 68.576 | 85.573 | 1.00 | 11.37 |
| ATOM | 2083 | CB | PRO | 447 | 23.188 | 69.426 | 86.729 | 1.00 | 11.98 |
| ATOM | 2084 | CG | PRO | 447 | 23.475 | 68.401 | 87.765 | 1.00 | 12.44 |
| ATOM | 2085 | C | PRO | 447 | 22.917 | 69.197 | 84.199 | 1.00 | 11.25 |
| ATOM | 2086 | O | PRO | 447 | 22.059 | 69.857 | 83.602 | 1.00 | 10.58 |
| ATOM | 2087 | N | GLU | 448 | 23.130 | 69.009 | 83.690 | 1.00 | 10.17 |
| ATOM | 2088 | H | GLU | 448 | 24.800 | 68.533 | 84.219 | 1.00 | 0.00 |
| ATOM | 2089 | CA | GLU | 448 | 24.477 | 69.552 | 82.365 | 1.00 | 9.24 |
| ATOM | 2090 | CB | GLU | 448 | 25.978 | 69.405 | 82.046 | 1.00 | 9.39 |
| ATOM | 2091 | CG | GLU | 448 | 26.812 | 70.398 | 82.851 | 1.00 | 12.36 |
| ATOM | 2092 | CD | GLU | 448 | 28.303 | 70.227 | 82.678 | 1.00 | 14.85 |
| ATOM | 2093 | OE1 | GLU | 448 | 28.849 | 69.096 | 82.698 | 1.00 | 12.78 |
| ATOM | 2094 | OE2 | GLU | 448 | 28.988 | 71.270 | 82.581 | 1.00 | 18.02 |
| ATOM | 2095 | C | GLU | 448 | 23.670 | 86.859 | 81.257 | 1.00 | 8.38 |
| ATOM | 2096 | O | GLU | 448 | 23.216 | 69.499 | 80.322 | 1.00 | 8.27 |
| ATOM | 2097 | N | VAL | 449 | 23.482 | 67.544 | 81.378 | 1.00 | 7.49 |
| ATOM | 2098 | H | VAL | 449 | 23.883 | 67.055 | 82.131 | 1.00 | 0.00 |
| ATOM | 2099 | CA | VAL | 449 | 22.714 | 66.799 | 80.376 | 1.00 | 6.61 |
| ATOM | 2100 | CB | VAL | 449 | 22.734 | 65.268 | 80.701 | 1.00 | 5.82 |

TABLE 3-continued

Coordinates of Lck bound with AMP-PNP

| | | Atom Type | Res | # | X | Y | Z | Occ | B |
|---|---|---|---|---|---|---|---|---|---|
| ATOM | 2101 | CG1 | VAL | 449 | 21.720 | 64.527 | 79.685 | 1.00 | 7.81 |
| ATOM | 2102 | CG2 | VAL | 449 | 24.134 | 64.734 | 80.451 | 1.00 | 7.31 |
| ATOM | 2103 | C | VAL | 449 | 21.285 | 67.318 | 80.384 | 1.00 | 5.47 |
| ATOM | 2104 | O | VAL | 449 | 20.748 | 67.638 | 79.333 | 1.00 | 6.04 |
| ATOM | 2105 | N | ILE | 450 | 20.735 | 67.486 | 81.573 | 0.60 | 3.36 |
| ATOM | 2106 | H | ILE | 450 | 21.259 | 67.331 | 82.377 | 0.60 | 0.00 |
| ATOM | 2107 | CA | ILE | 450 | 19.344 | 67.957 | 81.702 | 0.60 | 4.33 |
| ATOM | 2108 | CB | ILE | 450 | 18.921 | 67.934 | 83.180 | 0.60 | 4.13 |
| ATOM | 2109 | CG2 | ILE | 450 | 17.613 | 68.709 | 83.354 | 0.60 | 4.27 |
| ATOM | 2110 | CG1 | ILE | 450 | 18.739 | 66.471 | 83.617 | 0.60 | 4.38 |
| ATOM | 2111 | CD1 | ILE | 450 | 18.559 | 66.309 | 85.109 | 0.60 | 6.27 |
| ATOM | 2112 | C | ILE | 450 | 19.170 | 69.350 | 81.111 | 0.60 | 5.04 |
| ATOM | 2113 | O | ILE | 450 | 18.260 | 69.601 | 80.309 | 0.60 | 3.63 |
| ATOM | 2114 | N | GLN | 451 | 20.131 | 70.208 | 81.426 | 1.00 | 7.77 |
| ATOM | 2115 | H | GLN | 451 | 20.861 | 69.891 | 82.002 | 1.00 | 0.00 |
| ATOM | 2116 | CA | GLN | 451 | 20.122 | 71.594 | 80.937 | 1.00 | 10.54 |
| ATOM | 2117 | CB | GLN | 451 | 21.324 | 72.380 | 81.561 | 1.00 | 14.15 |
| ATOM | 2118 | CG | GLN | 451 | 21.528 | 73.883 | 81.175 | 1.00 | 20.16 |
| ATOM | 2119 | CD | GLN | 451 | 22.760 | 74.552 | 81.885 | 1.00 | 22.13 |
| ATOM | 2120 | OE1 | GLN | 451 | 22.612 | 75.605 | 82.517 | 1.00 | 26.32 |
| ATOM | 2121 | NE2 | GLN | 451 | 23.968 | 73.963 | 81.736 | 1.00 | 25.19 |
| ATOM | 2122 | HE21 | GLN | 451 | 24.064 | 73.148 | 81.192 | 1.00 | 0.00 |
| ATOM | 2123 | HE22 | GLN | 451 | 24.759 | 74.379 | 82.166 | 1.00 | 0.00 |
| ATOM | 2124 | C | GLN | 451 | 20.158 | 71.595 | 79.398 | 1.00 | 10.44 |
| ATOM | 2125 | O | GLN | 451 | 19.349 | 72.280 | 78.730 | 1.00 | 9.35 |
| ATOM | 2126 | N | ASN | 452 | 21.048 | 70.798 | 78.815 | 1.00 | 8.81 |
| ATOM | 2127 | H | ASN | 452 | 21.629 | 70.238 | 79.354 | 1.00 | 0.00 |
| ATOM | 2128 | CA | ASN | 452 | 21.198 | 70.776 | 77.359 | 1.00 | 8.91 |
| ATOM | 2129 | CB | ASN | 452 | 22.408 | 69.915 | 76.974 | 1.00 | 12.05 |
| ATOM | 2130 | CG | ASN | 452 | 23.700 | 70.670 | 76.921 | 1.00 | 15.97 |
| ATOM | 2131 | OD1 | ASN | 452 | 24.703 | 70.170 | 76.339 | 1.00 | 21.26 |
| ATOM | 2132 | ND2 | ASN | 452 | 23.708 | 71.858 | 77.460 | 1.00 | 16.96 |
| ATOM | 2133 | HD21 | ASN | 452 | 22.903 | 72.231 | 77.860 | 1.00 | 0.00 |
| ATOM | 2134 | HD22 | ASN | 452 | 24.554 | 72.362 | 77.417 | 1.00 | 0.00 |
| ATOM | 2135 | C | ASN | 452 | 19.941 | 70.203 | 76.681 | 1.00 | 7.97 |
| ATOM | 2136 | O | ASN | 452 | 19.478 | 70.736 | 75.669 | 1.00 | 7.99 |
| ATOM | 2137 | N | LEU | 453 | 19.412 | 69.105 | 77.224 | 1.00 | 7.30 |
| ATOM | 2138 | H | LEU | 453 | 19.813 | 68.691 | 78.019 | 1.00 | 0.00 |
| ATOM | 2139 | CA | LEU | 453 | 18.236 | 68.533 | 76.635 | 1.00 | 7.09 |
| ATOM | 2140 | CB | LEU | 453 | 17.793 | 67.274 | 77.383 | 1.00 | 7.90 |
| ATOM | 2141 | CG | LEU | 453 | 18.757 | 66.088 | 77.240 | 1.00 | 7.82 |
| ATOM | 2142 | CD1 | LEU | 453 | 18.258 | 64.959 | 78.206 | 1.00 | 8.30 |
| ATOM | 2143 | CD2 | LEU | 453 | 18.832 | 65.579 | 75.764 | 1.00 | 6.41 |
| ATOM | 2144 | C | LEU | 453 | 17.110 | 69.560 | 76.580 | 1.00 | 6.46 |
| ATOM | 2145 | O | LEU | 453 | 16.336 | 69.581 | 75.624 | 1.00 | 7.59 |
| ATOM | 2146 | N | GLU | 454 | 16.956 | 70.305 | 77.665 | 1.00 | 7.77 |
| ATOM | 2147 | H | GLU | 454 | 17.564 | 70.200 | 78.417 | 1.00 | 0.00 |
| ATOM | 2148 | CA | GLU | 454 | 15.883 | 71.291 | 77.719 | 1.00 | 9.34 |
| ATOM | 2149 | CB | GLU | 454 | 15.706 | 71.786 | 79.152 | 1.00 | 12.03 |
| ATOM | 2150 | CG | GLU | 454 | 15.054 | 70.656 | 79.968 | 1.00 | 17.04 |
| ATOM | 2151 | CD | GLU | 454 | 14.908 | 70.931 | 81.436 | 1.00 | 21.47 |
| ATOM | 2152 | OE1 | GLU | 454 | 15.423 | 71.959 | 81.918 | 1.00 | 23.68 |
| ATOM | 2153 | OE2 | GLU | 454 | 14.257 | 70.098 | 82.113 | 1.00 | 22.13 |
| ATOM | 2154 | C | GLU | 454 | 16.008 | 72.408 | 76.729 | 1.00 | 9.43 |
| ATOM | 2155 | O | GLU | 454 | 14.988 | 73.045 | 76.413 | 1.00 | 10.25 |
| ATOM | 2156 | N | ARG | 455 | 17.225 | 72.647 | 76.240 | 1.00 | 8.46 |
| ATOM | 2157 | H | ARG | 455 | 17.979 | 72.143 | 76.580 | 1.00 | 0.00 |
| ATOM | 2158 | CA | ARG | 455 | 17.474 | 73.668 | 75.208 | 1.00 | 7.95 |
| ATOM | 2159 | CB | ARG | 455 | 18.952 | 74.159 | 75.219 | 1.00 | 9.51 |
| ATOM | 2160 | CG | ARG | 455 | 19.395 | 74.768 | 76.525 | 1.00 | 11.91 |
| ATOM | 2161 | CD | ARG | 455 | 20.827 | 75.305 | 76.457 | 1.00 | 12.88 |
| ATOM | 2162 | NE | ARG | 455 | 20.908 | 76.335 | 75.408 | 1.00 | 10.71 |
| ATOM | 2163 | HE | ARG | 455 | 20.106 | 76.545 | 74.935 | 1.00 | 0.00 |
| ATOM | 2164 | CA | ARG | 455 | 22.038 | 76.973 | 75.060 | 1.00 | 10.70 |
| ATOM | 2165 | NH1 | ARG | 455 | 23.215 | 76.666 | 75.617 | 1.00 | 11.36 |
| ATOM | 2166 | HH11 | ARG | 455 | 23.266 | 75.965 | 76.330 | 1.00 | 0.00 |
| ATOM | 2167 | HH12 | ARG | 455 | 24.039 | 77.158 | 75.346 | 1.00 | 0.00 |
| ATOM | 2168 | NH2 | ARG | 455 | 21.945 | 78.048 | 74.293 | 1.00 | 7.80 |
| ATOM | 2169 | HH21 | ARG | 455 | 21.046 | 78.355 | 73.986 | 1.00 | 0.00 |
| ATOM | 2170 | HH22 | ARG | 455 | 22.769 | 78.538 | 74.007 | 1.00 | 0.00 |
| ATOM | 2171 | C | ARG | 455 | 17.179 | 73.119 | 73.811 | 1.00 | 7.19 |
| ATOM | 2172 | O | ARG | 455 | 17.216 | 73.811 | 72.829 | 1.00 | 7.14 |
| ATOM | 2173 | N | GLY | 456 | 16.969 | 71.797 | 73.694 | 1.00 | 6.37 |
| ATOM | 2174 | H | GLY | 456 | 16.986 | 71.232 | 74.489 | 1.00 | 0.00 |

TABLE 3-continued

Coordinates of Lck bound with AMP-PNP

| | | Atom Type | Res | # | X | Y | Z | Occ | B |
|---|---|---|---|---|---|---|---|---|---|
| ATOM | 2175 | CA | GLY | 456 | 16.732 | 71.194 | 72.404 | 1.00 | 6.14 |
| ATOM | 2176 | C | GLY | 456 | 17.969 | 70.497 | 71.856 | 1.00 | 5.95 |
| ATOM | 2177 | O | GLY | 456 | 17.942 | 69.907 | 70.766 | 1.00 | 7.78 |
| ATOM | 2178 | N | TYR | 457 | 19.402 | 70.542 | 72.619 | 1.00 | 5.47 |
| ATOM | 2179 | H | TYR | 457 | 19.023 | 71.005 | 73.485 | 1.00 | 0.00 |
| ATOM | 2180 | CA | TYR | 457 | 20.256 | 69.856 | 72.151 | 1.00 | 5.37 |
| ATOM | 2181 | CB | TYR | 457 | 21.503 | 70.284 | 72.933 | 1.00 | 5.38 |
| ATOM | 2182 | CG | TYR | 457 | 21.979 | 71.718 | 72.715 | 1.00 | 6.50 |
| ATOM | 2183 | CD1 | TYR | 457 | 21.495 | 72.490 | 71.683 | 1.00 | 7.95 |
| ATOM | 2184 | CE1 | TYR | 457 | 21.991 | 73.794 | 71.454 | 1.00 | 8.83 |
| ATOM | 2185 | CD2 | TYR | 457 | 22.957 | 72.246 | 73.530 | 1.00 | 8.19 |
| ATOM | 2186 | CE2 | TYR | 457 | 23.470 | 73.538 | 73.317 | 1.00 | 9.65 |
| ATOM | 2187 | CZ | TYR | 457 | 22.980 | 74.293 | 72.276 | 1.00 | 8.91 |
| ATOM | 2188 | OH | TYR | 457 | 23.541 | 75.554 | 72.010 | 1.00 | 9.80 |
| ATOM | 2189 | HH | TYR | 457 | 23.086 | 75.971 | 71.281 | 1.00 | 0.00 |
| ATOM | 2190 | C | TYR | 457 | 20.098 | 68.387 | 72.439 | 1.00 | 5.41 |
| ATOM | 2191 | O | TYR | 457 | 19.297 | 68.006 | 73.292 | 1.00 | 6.17 |
| ATOM | 2192 | N | ARG | 458 | 20.858 | 67.586 | 71.693 | 1.00 | 4.55 |
| ATOM | 2193 | H | ARG | 458 | 21.374 | 67.973 | 70.938 | 1.00 | 0.00 |
| ATOM | 2194 | CA | ARG | 458 | 20.935 | 66.138 | 71.975 | 1.00 | 4.84 |
| ATOM | 2195 | CB | ARG | 458 | 20.254 | 65.237 | 70.888 | 1.00 | 3.99 |
| ATOM | 2196 | CG | ARG | 458 | 18.701 | 65.543 | 70.874 | 1.00 | 4.20 |
| ATOM | 2197 | CD | ARG | 458 | 18.037 | 65.155 | 72.167 | 1.00 | 5.10 |
| ATOM | 2198 | NE | ARG | 458 | 15.566 | 65.315 | 72.102 | 1.00 | 5.88 |
| ATOM | 2199 | HE | ARG | 458 | 16.065 | 64.635 | 71.605 | 1.00 | 0.00 |
| ATOM | 2200 | CA | ARG | 458 | 15.875 | 66.325 | 72.467 | 1.00 | 7.42 |
| ATOM | 2201 | NH1 | ARG | 458 | 16.516 | 67.326 | 73.280 | 1.00 | 7.90 |
| ATOM | 2202 | HH11 | ARG | 458 | 17.507 | 67.309 | 73.327 | 1.00 | 0.00 |
| ATOM | 2203 | HH12 | ARG | 458 | 15.995 | 68.070 | 73.677 | 1.00 | 0.00 |
| ATOM | 2204 | NH2 | ARG | 458 | 14.532 | 66.252 | 72.469 | 1.00 | 7.34 |
| ATOM | 2205 | HH21 | ARG | 458 | 14.066 | 65.468 | 72.248 | 1.00 | 0.00 |
| ATOM | 2206 | HH22 | ARG | 458 | 13.996 | 66.998 | 73.052 | 1.00 | 0.00 |
| ATOM | 2207 | C | ARG | 458 | 22.412 | 65.805 | 72.031 | 1.00 | 6.43 |
| ATOM | 2208 | O | ARG | 458 | 23.290 | 66.676 | 71.861 | 1.00 | 7.40 |
| ATOM | 2209 | N | MET | 459 | 22.712 | 64.543 | 72.353 | 1.00 | 5.51 |
| ATOM | 2210 | H | MET | 459 | 22.005 | 63.887 | 72.532 | 1.00 | 0.00 |
| ATOM | 2211 | CA | MET | 459 | 24.111 | 64.152 | 72.485 | 1.00 | 5.59 |
| ATOM | 2212 | CB | MET | 459 | 24.216 | 62.643 | 72.743 | 1.00 | 6.59 |
| ATOM | 2213 | CG | MET | 459 | 25.571 | 62.339 | 73.338 | 1.00 | 7.84 |
| ATOM | 2214 | SD | MET | 459 | 25.818 | 60.536 | 73.560 | 1.00 | 6.28 |
| ATOM | 2215 | CE | MET | 459 | 24.337 | 60.011 | 74.236 | 1.00 | 6.82 |
| ATOM | 2216 | C | MET | 459 | 24.932 | 64.502 | 71.235 | 1.00 | 5.23 |
| ATOM | 2217 | O | MET | 459 | 24.508 | 64.251 | 70.107 | 1.00 | 5.48 |
| ATOM | 2218 | N | VAL | 460 | 26.145 | 65.055 | 71.436 | 1.00 | 5.55 |
| ATOM | 2219 | H | VAL | 460 | 26.446 | 65.223 | 72.340 | 1.00 | 0.00 |
| ATOM | 2220 | CA | VAL | 460 | 27.027 | 65.394 | 70.348 | 1.00 | 7.12 |
| ATOM | 2221 | CB | VAL | 460 | 28.303 | 66.024 | 70.947 | 1.00 | 7.96 |
| ATOM | 2222 | CG1 | VAL | 460 | 29.437 | 65.105 | 67.790 | 1.00 | 0.00 |
| ATOM | 2223 | CG2 | VAL | 460 | 27.916 | 67.395 | 71.546 | 1.00 | 9.72 |
| ATOM | 2224 | C | VAL | 460 | 27.385 | 64.139 | 69.536 | 1.00 | 6.92 |
| ATOM | 2225 | O | VAL | 460 | 27.514 | 63.072 | 70.135 | 1.00 | 7.43 |
| ATOM | 2226 | N | ARG | 461 | 27.522 | 64.250 | 68.228 | 1.00 | 7.25 |
| ATOM | 2227 | H | ARG | 461 | 27.347 | 65.105 | 67.790 | 1.00 | 0.00 |
| ATOM | 2228 | CA | ARG | 461 | 27.914 | 63.079 | 67.409 | 1.00 | 6.83 |
| ATOM | 2229 | CG | ARG | 461 | 28.282 | 63.474 | 65.983 | 1.00 | 7.15 |
| ATOM | 2230 | CG | ARG | 461 | 27.117 | 64.029 | 65.198 | 1.00 | 7.70 |
| ATOM | 2231 | CD | ARG | 461 | 27.573 | 64.576 | 63.843 | 1.00 | 8.56 |
| ATOM | 2232 | NE | ARG | 461 | 26.394 | 64.870 | 63.034 | 1.00 | 8.40 |
| ATOM | 2233 | HE | ARG | 461 | 26.059 | 64.166 | 62.465 | 1.00 | 0.00 |
| ATOM | 2234 | CA | ARG | 461 | 25.742 | 66.033 | 63.030 | 1.00 | 9.86 |
| ATOM | 2235 | NH1 | ARG | 461 | 26.151 | 67.061 | 63.803 | 1.00 | 8.75 |
| ATOM | 2236 | HH11 | ARG | 461 | 26.936 | 66.957 | 64.397 | 1.00 | 0.00 |
| ATOM | 2237 | HH12 | ARG | 461 | 25.636 | 67.921 | 63.781 | 1.00 | 0.00 |
| ATOM | 2238 | NH2 | ARG | 461 | 24.679 | 66.147 | 62.247 | 1.00 | 7.82 |
| ATOM | 2239 | HH21 | ARG | 461 | 24.374 | 65.365 | 61.712 | 1.00 | 0.00 |
| ATOM | 2240 | HH22 | ARG | 461 | 24.153 | 67.001 | 62.230 | 1.00 | 0.00 |
| ATOM | 2241 | C | ARG | 461 | 29.138 | 62.381 | 67.997 | 1.00 | 8.87 |
| ATOM | 2242 | O | ARG | 461 | 30.209 | 63.004 | 68.196 | 1.00 | 9.79 |
| ATOM | 2243 | N | PRO | 462 | 28.978 | 61.082 | 68.311 | 1.00 | 9.26 |
| ATOM | 2244 | CD | PRO | 462 | 27.722 | 60.309 | 68.426 | 1.00 | 9.57 |
| ATOM | 2245 | CA | PRO | 462 | 30.114 | 60.354 | 68.863 | 1.00 | 11.18 |
| ATOM | 2246 | CB | PRO | 462 | 29.536 | 58.948 | 69.103 | 1.00 | 9.51 |
| ATOM | 2247 | CG | PRO | 462 | 28.094 | 59.166 | 69.361 | 1.00 | 9.93 |
| ATOM | 2248 | C | PRO | 462 | 31.183 | 60.273 | 68.811 | 1.00 | 12.44 |

TABLE 3-continued

Coordinates of Lck bound with AMP-PNP

| | | Atom Type | Res | # | X | Y | Z | Occ | B |
|---|---|---|---|---|---|---|---|---|---|
| ATOM | 2249 | O | PRO | 462 | 20.902 | 60.304 | 66.613 | 1.00 | 12.97 |
| ATOM | 2250 | N | ASP | 463 | 32.429 | 60.068 | 68.249 | 1.00 | 15.65 |
| ATOM | 2251 | H | ASP | 463 | 32.611 | 60.028 | 69.194 | 1.00 | 0.00 |
| ATOM | 2252 | CA | ASP | 463 | 33.527 | 59.896 | 67.309 | 1.00 | 17.53 |
| ATOM | 2253 | CB | ASP | 463 | 34.846 | 59.645 | 68.056 | 1.00 | 19.87 |
| ATOM | 2254 | CG | ASP | 463 | 35.394 | 60.883 | 68.735 | 1.00 | 22.64 |
| ATOM | 2255 | OD1 | ASP | 463 | 35.069 | 62.011 | 68.287 | 1.00 | 26.57 |
| ATOM | 2256 | OD2 | ASP | 463 | 26.183 | 60.725 | 69.700 | 1.00 | 24.80 |
| ATOM | 2257 | C | ASP | 463 | 33.272 | 58.684 | 66.423 | 1.00 | 17.79 |
| ATOM | 2258 | O | ASP | 463 | 32.783 | 57.645 | 66.910 | 1.00 | 18.96 |
| ATOM | 2259 | N | ASN | 464 | 33.566 | 58.856 | 65.134 | 1.00 | 18.96 |
| ATOM | 2260 | H | ASN | 464 | 33.918 | 59.727 | 64.850 | 1.00 | 0.00 |
| ATOM | 2261 | CA | ASN | 464 | 33.426 | 57.827 | 64.104 | 1.00 | 19.94 |
| ATOM | 2262 | CB | ASN | 464 | 34.480 | 56.729 | 64.287 | 1.00 | 23.16 |
| ATOM | 2263 | CG | ASN | 464 | 35.902 | 57.252 | 64.087 | 1.00 | 25.19 |
| ATOM | 2264 | OD1 | ASN | 464 | 36.188 | 57.958 | 63.115 | 1.00 | 27.59 |
| ATOM | 2265 | ND2 | ASN | 464 | 36.778 | 56.955 | 65.040 | 1.00 | 26.98 |
| ATOM | 2266 | HD21 | ASN | 464 | 36.514 | 56.437 | 65.809 | 1.00 | 0.00 |
| ATOM | 2267 | HD22 | ASN | 464 | 37.700 | 57.286 | 64.893 | 1.00 | 0.00 |
| ATOM | 2268 | C | ASN | 464 | 32.055 | 57.184 | 63.998 | 1.00 | 18.39 |
| ATOM | 2269 | O | ASN | 464 | 31.927 | 56.007 | 63.639 | 1.00 | 20.77 |
| ATOM | 2270 | N | CYS | 465 | 31.017 | 57.920 | 64.342 | 1.00 | 16.37 |
| ATOM | 2271 | H | CYS | 465 | 31.151 | 58.841 | 64.656 | 1.00 | 0.00 |
| ATOM | 2272 | CA | CYS | 465 | 29.660 | 57.352 | 64.245 | 1.00 | 14.87 |
| ATOM | 2273 | CB | CYS | 465 | 28.795 | 58.006 | 65.308 | 1.00 | 14.20 |
| ATOM | 2274 | SG | CYS | 465 | 27.051 | 57.500 | 65.248 | 1.00 | 12.65 |
| ATOM | 2275 | C | CYS | 465 | 29.094 | 57.673 | 62.862 | 1.00 | 12.49 |
| ATOM | 2276 | O | CYS | 465 | 29.113 | 58.835 | 62.446 | 1.00 | 12.65 |
| ATOM | 2277 | N | PRO | 466 | 28.636 | 56.667 | 62.104 | 1.00 | 10.32 |
| ATOM | 2278 | CD | PRO | 466 | 28.670 | 55.217 | 62.425 | 1.00 | 11.10 |
| ATOM | 2279 | CA | PRO | 466 | 28.073 | 56.921 | 60.769 | 1.00 | 9.39 |
| ATOM | 2280 | CB | PRO | 466 | 27.566 | 55.548 | 60.319 | 1.00 | 10.25 |
| ATOM | 2281 | CG | PRO | 466 | 28.404 | 54.572 | 61.24 | 1.00 | 11.42 |
| ATOM | 2282 | C | PRO | 466 | 26.876 | 57.881 | 60.925 | 1.00 | 7.58 |
| ATOM | 2283 | O | PRO | 466 | 26.055 | 57.733 | 61.851 | 1.00 | 7.36 |
| ATOM | 2284 | N | GLU | 467 | 26.727 | 58.807 | 59.975 | 1.00 | 6.68 |
| ATOM | 2285 | H | GLU | 467 | 27.343 | 58.848 | 59.215 | 1.00 | 0.00 |
| ATOM | 2286 | CA | GLU | 467 | 25.652 | 59.781 | 60.100 | 1.00 | 6.04 |
| ATOM | 2287 | CB | GLU | 467 | 25.895 | 60.930 | 59.126 | 1.00 | 5.93 |
| ATOM | 2288 | CG | GLU | 467 | 24.827 | 62.033 | 59.276 | 1.00 | 7.61 |
| ATOM | 2289 | CD | GLU | 467 | 24.949 | 62.858 | 60.537 | 1.00 | 7.58 |
| ATOM | 2290 | OE1 | GLU | 467 | 25.929 | 61.714 | 61.289 | 1.00 | 8.06 |
| ATOM | 2291 | OE2 | GLU | 467 | 24.022 | 63.691 | 60.784 | 1.00 | 7.05 |
| ATOM | 2292 | C | GLU | 467 | 24.261 | 59.174 | 59.995 | 1.00 | 5.22 |
| ATOM | 2293 | O | GLU | 467 | 23.327 | 59.674 | 60.653 | 1.00 | 5.02 |
| ATOM | 2294 | N | GLU | 468 | 24.119 | 58.100 | 59.226 | 0.51 | 2.00 |
| ATOM | 2295 | H | GLU | 468 | 24.876 | 57.757 | 58.725 | 1.00 | 0.00 |
| ATOM | 2296 | CA | GLU | 468 | 22.823 | 57.436 | 59.143 | 0.51 | 2.00 |
| ATOM | 2297 | CB | GLU | 468 | 22.889 | 56.272 | 58.182 | 0.51 | 2.00 |
| ATOM | 2298 | CG | GLU | 468 | 23.077 | 56.743 | 56.747 | 0.51 | 2.53 |
| ATOM | 2299 | CD | GLU | 468 | 23.460 | 55.601 | 55.176 | 0.51 | 6.33 |
| ATOM | 2300 | OE1 | GLU | 468 | 22.553 | 55.026 | 55.176 | 0.51 | 7.50 |
| ATOM | 2301 | OE2 | GLU | 468 | 24.668 | 55.272 | 55.768 | 0.51 | 8.25 |
| ATOM | 2302 | C | GLU | 468 | 22.452 | 56.912 | 60.530 | 0.51 | 2.00 |
| ATOM | 2303 | O | GLU | 468 | 21.306 | 56.997 | 60.953 | 0.51 | 2.00 |
| ATOM | 2304 | N | LEU | 469 | 23.427 | 56.435 | 61.216 | 1.00 | 4.24 |
| ATOM | 2305 | H | LEU | 469 | 24.316 | 56.216 | 60.836 | 1.00 | 0.00 |
| ATOM | 2306 | CA | LEU | 469 | 23.123 | 55.853 | 62.550 | 1.00 | 3.84 |
| ATOM | 2307 | CB | LEU | 469 | 24.277 | 54.993 | 63.132 | 1.00 | 5.93 |
| ATOM | 2308 | CG | LEU | 469 | 23.972 | 54.287 | 64.459 | 1.00 | 7.66 |
| ATOM | 2309 | CD1 | LEU | 469 | 22.900 | 53.229 | 64.290 | 1.00 | 8.35 |
| ATOM | 2310 | CD2 | LEU | 469 | 25.272 | 53.663 | 64.991 | 1.00 | 10.08 |
| ATOM | 2311 | C | LEU | 469 | 22.788 | 57.015 | 63.497 | 1.00 | 4.40 |
| ATOM | 2312 | O | LEU | 469 | 21.912 | 56.929 | 64.358 | 1.00 | 4.94 |
| ATOM | 2313 | N | TYR | 470 | 23.556 | 58.113 | 63.385 | 1.00 | 4.82 |
| ATOM | 2314 | H | TYR | 470 | 24.279 | 58.161 | 62.740 | 1.00 | 0.00 |
| ATOM | 2315 | CA | TYR | 470 | 23.277 | 59.233 | 64.255 | 1.00 | 4.69 |
| ATOM | 2316 | CB | TYR | 470 | 24.308 | 60.364 | 64.027 | 1.00 | 3.97 |
| ATOM | 2317 | CG | TYR | 470 | 24.156 | 61.525 | 65.000 | 1.00 | 3.57 |
| ATOM | 2318 | CD1 | TYR | 470 | 24.403 | 61.380 | 66.367 | 1.00 | 3.84 |
| ATOM | 2319 | CE1 | TYR | 470 | 24.266 | 62.422 | 67.261 | 1.00 | 3.35 |
| ATOM | 2320 | CD2 | TYR | 470 | 23.773 | 62.770 | 64.530 | 1.00 | 5.04 |
| ATOM | 2321 | CE2 | TYR | 470 | 23.674 | 82.836 | 65.403 | 1.00 | 4.10 |
| ATOM | 2322 | CZ | TYR | 470 | 23.904 | 63.667 | 66.753 | 1.00 | 3.47 |

TABLE 3-continued

Coordinates of Lck bound with AMP-PNP

| | | Atom Type | Res | # | X | Y | Z | Occ | B |
|---|---|---|---|---|---|---|---|---|---|
| ATOM | 2323 | OG | TYR | 470 | 23.784 | 64.737 | 67.628 | 1.00 | 6.32 |
| ATOM | 2324 | HH | TYR | 470 | 23.979 | 64.406 | 68.492 | 1.00 | 0.00 |
| ATOM | 2325 | C | TYR | 470 | 21.862 | 59.774 | 64.035 | 1.00 | 4.18 |
| ATOM | 2326 | O | TYR | 470 | 21.175 | 60.125 | 65.030 | 1.00 | 4.33 |
| ATOM | 2327 | N | GLN | 471 | 21.427 | 59.837 | 62.764 | 1.00 | 4.39 |
| ATOM | 2328 | H | GLN | 471 | 22.002 | 59.548 | 62.038 | 1.00 | 0.00 |
| ATOM | 2329 | CA | GLN | 471 | 20.064 | 60.350 | 62.500 | 1.00 | 4.56 |
| ATOM | 2330 | CB | GLN | 471 | 19.868 | 60.703 | 61.031 | 1.00 | 5.08 |
| ATOM | 2331 | CG | GLN | 471 | 20.864 | 61.947 | 60.624 | 1.00 | 5.28 |
| ATOM | 2332 | CD | GLN | 471 | 20.329 | 63.136 | 61.492 | 1.00 | 7.09 |
| ATOM | 2333 | OE1 | GLN | 471 | 19.153 | 62.352 | 61.824 | 1.00 | 8.12 |
| ATOM | 2334 | NE2 | GLN | 471 | 21.326 | 63.940 | 61.856 | 1.00 | 6.37 |
| ATOM | 2335 | HE21 | GLN | 471 | 21.094 | 64.701 | 62.249 | 1.00 | 0.00 |
| ATOM | 2336 | HE22 | GLN | 471 | 21.094 | 64.701 | 62.429 | 1.00 | 0.00 |
| ATOM | 2337 | C | GLN | 471 | 18.995 | 59.350 | 63.008 | 1.00 | 4.46 |
| ATOM | 2338 | O | GLN | 471 | 17.929 | 59.765 | 63.467 | 1.00 | 6.58 |
| ATOM | 2339 | N | LEU | 472 | 19.363 | 58.068 | 63.149 | 1.00 | 5.67 |
| ATOM | 2340 | H | LEU | 472 | 20.238 | 57.765 | 62.845 | 1.00 | 0.00 |
| ATOM | 2341 | CA | LEU | 472 | 18.422 | 57.112 | 63.733 | 1.00 | 5.59 |
| ATOM | 2342 | CB | LEU | 472 | 18.847 | 55.677 | 63.423 | 1.00 | 5.95 |
| ATOM | 2343 | CG | LEU | 472 | 17.776 | 54.626 | 63.714 | 1.00 | 6.17 |
| ATOM | 2344 | CD1 | LEU | 472 | 16.699 | 54.732 | 62.640 | 1.00 | 8.40 |
| ATOM | 2345 | CD2 | LEU | 472 | 18.425 | 53.239 | 63.565 | 1.00 | 7.32 |
| ATOM | 2346 | C | LEU | 472 | 18.308 | 57.355 | 65.255 | 1.00 | 6.10 |
| ATOM | 2347 | O | LEU | 472 | 17.237 | 57.234 | 65.846 | 1.00 | 6.53 |
| ATOM | 2348 | N | MET | 473 | 19.454 | 57.647 | 65.908 | 1.00 | 5.16 |
| ATOM | 2349 | H | MET | 473 | 20.292 | 57.622 | 65.404 | 1.00 | 0.00 |
| ATOM | 2350 | CA | MET | 473 | 19.473 | 57.393 | 67.329 | 1.00 | 5.13 |
| ATOM | 2351 | CB | MET | 473 | 20.885 | 58.393 | 67.728 | 1.00 | 5.60 |
| ATOM | 2352 | CG | MET | 473 | 21.865 | 57.162 | 67.626 | 1.00 | 5.38 |
| ATOM | 2353 | SD | MET | 473 | 23.566 | 57.901 | 67.861 | 1.00 | 6.95 |
| ATOM | 2354 | CE | MET | 473 | 24.589 | 56.334 | 67.713 | 1.00 | 7.19 |
| ATOM | 2355 | C | MET | 473 | 18.596 | 59.224 | 67.515 | 1.00 | 5.07 |
| ATOM | 2356 | O | MET | 473 | 17.840 | 59.288 | 68.461 | 1.00 | 6.08 |
| ATOM | 2357 | N | ARG | 474 | 18.714 | 60.186 | 66.610 | 1.00 | 5.56 |
| ATOM | 2358 | H | ARG | 474 | 19.307 | 60.071 | 65.829 | 1.00 | 0.00 |
| ATOM | 2359 | CA | ARG | 474 | 17.907 | 61.417 | 66.799 | 1.00 | 5.66 |
| ATOM | 2360 | CB | ARG | 474 | 18.252 | 62.482 | 65.731 | 1.00 | 6.55 |
| ATOM | 2361 | CG | ARG | 474 | 19.756 | 62.944 | 65.715 | 1.00 | 8.15 |
| ATOM | 2362 | CD | ARG | 474 | 20.197 | 63.546 | 66.969 | 1.00 | 11.29 |
| ATOM | 2363 | NE | ARG | 474 | 19.469 | 64.769 | 67.278 | 1.00 | 13.35 |
| ATOM | 2364 | HE | ARG | 474 | 18.501 | 64.719 | 67.298 | 1.00 | 0.00 |
| ATOM | 2365 | CZ | ARG | 474 | 20.030 | 65.955 | 67.458 | 1.00 | 12.24 |
| ATOM | 2366 | NH1 | ARG | 474 | 21.344 | 66.132 | 67.458 | 1.00 | 8.11 |
| ATOM | 2367 | HH11 | ARG | 474 | 21.955 | 65.352 | 67.277 | 1.00 | 0.00 |
| ATOM | 2368 | HH12 | ARG | 474 | 21.745 | 67.030 | 67.635 | 1.00 | 0.00 |
| ATOM | 2369 | NH2 | ARG | 474 | 19.228 | 66.976 | 67.757 | 1.00 | 12.65 |
| ATOM | 2370 | HH21 | ARG | 474 | 18.246 | 66.849 | 67.753 | 1.00 | 0.00 |
| ATOM | 2371 | HH22 | ARG | 474 | 19.620 | 67.890 | 67.906 | 1.00 | 0.00 |
| ATOM | 2372 | C | ARG | 474 | 16.414 | 61.120 | 66.772 | 1.00 | 5.28 |
| ATOM | 2373 | O | ARG | 474 | 15.660 | 61.789 | 67.458 | 1.00 | 7.28 |
| ATOM | 2374 | N | LEU | 475 | 15.973 | 60.176 | 65.937 | 1.00 | 6.18 |
| ATOM | 2375 | H | LEU | 475 | 16.599 | 59.687 | 63.358 | 1.00 | 0.00 |
| ATOM | 2376 | CA | LEU | 475 | 14.535 | 59.833 | 65.918 | 1.00 | 5.65 |
| ATOM | 2377 | CB | LEU | 475 | 14.200 | 58.769 | 64.881 | 1.00 | 6.32 |
| ATOM | 2378 | CG | LEU | 475 | 14.438 | 59.049 | 63.423 | 1.00 | 8.27 |
| ATOM | 2379 | CD1 | LEU | 475 | 13.828 | 57.856 | 62.657 | 1.00 | 10.34 |
| ATOM | 2380 | CD2 | LEU | 475 | 13.761 | 60.340 | 63.023 | 1.00 | 10.06 |
| ATOM | 2381 | C | LEU | 475 | 14.119 | 59.292 | 67.288 | 1.00 | 5.62 |
| ATOM | 2382 | O | LEU | 475 | 13.021 | 59.578 | 67.798 | 1.00 | 6.38 |
| ATOM | 2383 | N | CYS | 476 | 15.010 | 58.527 | 67.943 | 1.00 | 5.04 |
| ATOM | 2384 | H | CYS | 476 | 15.872 | 58.323 | 67.538 | 1.00 | 0.00 |
| ATOM | 2385 | CA | CYS | 476 | 14.713 | 58.010 | 69.254 | 1.00 | 5.25 |
| ATOM | 2386 | CB | CYS | 476 | 15.827 | 57.034 | 69.670 | 1.00 | 4.89 |
| ATOM | 2387 | SG | CYS | 476 | 15.962 | 55.582 | 68.654 | 1.00 | 6.23 |
| ATOM | 2388 | C | CYS | 476 | 14.630 | 59.049 | 70.342 | 1.00 | 4.66 |
| ATOM | 2389 | O | CYS | 476 | 14.104 | 58.817 | 71.416 | 1.00 | 5.91 |
| ATOM | 2390 | N | TRP | 477 | 15.206 | 60.242 | 70.047 | 1.00 | 5.78 |
| ATOM | 2391 | H | TRP | 477 | 15.588 | 60.396 | 69.164 | 1.00 | 0.00 |
| ATOM | 2392 | CA | TRP | 477 | 15.261 | 61.296 | 71.025 | 1.00 | 5.87 |
| ATOM | 2393 | CB | TRP | 477 | 16.698 | 61.833 | 71.190 | 1.00 | 5.33 |
| ATOM | 2394 | CG | TRP | 477 | 17.736 | 60.770 | 71.568 | 1.00 | 4.82 |
| ATOM | 2395 | CD2 | TRP | 477 | 19.102 | 60.778 | 71.165 | 1.00 | 3.86 |
| ATOM | 2396 | CE2 | TRP | 477 | 19.728 | 59.628 | 71.752 | 1.00 | 5.21 |

TABLE 3-continued

Coordinates of Lck bound with AMP-PNP

| | | Atom Type | Res | # | X | Y | Z | Occ | B |
|---|---|---|---|---|---|---|---|---|---|
| ATOM | 2397 | CE3 | TRP | 477 | 19.871 | 61.642 | 70.361 | 1.00 | 4.16 |
| ATOM | 2398 | CD1 | TRP | 477 | 17.567 | 59.667 | 72.375 | 1.00 | 6.46 |
| ATOM | 2399 | NE1 | TRP | 477 | 18.785 | 58.969 | 72.482 | 1.00 | 4.91 |
| ATOM | 2400 | HE1 | TRP | 477 | 18.921 | 58.155 | 72.996 | 1.00 | 0.00 |
| ATOM | 2401 | CZ2 | TRP | 477 | 21.074 | 59.336 | 71.537 | 1.00 | 5.82 |
| ATOM | 2402 | CZ3 | TRP | 477 | 21.208 | 61.341 | 70.157 | 1.00 | 4.59 |
| ATOM | 2403 | CG2 | TRP | 477 | 21.786 | 60.209 | 70.741 | 1.00 | 4.52 |
| ATOM | 2404 | C | TRP | 477 | 14.331 | 62.432 | 70.728 | 1.00 | 7.18 |
| ATOM | 2405 | O | TRP | 477 | 14.519 | 62.536 | 71.231 | 1.00 | 7.39 |
| ATOM | 2406 | N | LYS | 478 | 13.291 | 61.161 | 69.961 | 1.00 | 6.00 |
| ATOM | 2407 | H | LYS | 478 | 13.180 | 61.274 | 69.565 | 1.00 | 0.00 |
| ATOM | 2408 | CA | LYS | 478 | 12.319 | 63.219 | 69.699 | 1.00 | 7.56 |
| ATOM | 2409 | CB | LYS | 478 | 11.293 | 62.731 | 68.679 | 1.00 | 8.32 |
| ATOM | 2410 | CG | LYS | 478 | 11.869 | 62.775 | 67.273 | 1.00 | 11.04 |
| ATOM | 2411 | CD | LYS | 478 | 10.927 | 62.299 | 66.234 | 1.00 | 14.78 |
| ATOM | 2412 | CE | LYS | 478 | 11.498 | 62.526 | 64.861 | 1.00 | 18.29 |
| ATOM | 2413 | NZ | LYS | 478 | 11.628 | 63.969 | 64.509 | 1.00 | 22.77 |
| ATOM | 2414 | HZ1 | LYS | 478 | 12.253 | 64.432 | 65.196 | 1.00 | 0.00 |
| ATOM | 2415 | HZ2 | LYS | 478 | 10.681 | 64.413 | 64.558 | 1.00 | 0.00 |
| ATOM | 2416 | HZ3 | LYS | 478 | 12.006 | 64.064 | 63.555 | 1.00 | 0.00 |
| ATOM | 2417 | C | LYS | 478 | 11.656 | 63.610 | 71.016 | 1.00 | 7.86 |
| ATOM | 2418 | O | LYS | 478 | 11.472 | 62.794 | 71.946 | 1.00 | 8.45 |
| ATOM | 2419 | N | GLU | 479 | 11.250 | 64.887 | 71.091 | 1.00 | 9.37 |
| ATOM | 2420 | H | GLU | 479 | 11.344 | 65.484 | 70.316 | 1.00 | 0.00 |
| ATOM | 2421 | CA | GLU | 479 | 10.683 | 65.403 | 72.316 | 1.00 | 10.56 |
| ATOM | 2422 | CB | GLU | 479 | 10.367 | 66.888 | 72.128 | 1.00 | 14.56 |
| ATOM | 2423 | CG | GLU | 479 | 9.793 | 67.492 | 73.360 | 1.00 | 18.93 |
| ATOM | 2424 | CD | GLU | 479 | 10.841 | 67.919 | 74.321 | 1.00 | 22.09 |
| ATOM | 2425 | OE1 | GLU | 479 | 12.025 | 67.617 | 74.055 | 1.00 | 23.23 |
| ATOM | 2426 | OE2 | GLU | 479 | 10.513 | 68.633 | 75.277 | 1.00 | 23.63 |
| ATOM | 2427 | C | GLU | 479 | 9.395 | 64.709 | 72.746 | 1.00 | 9.17 |
| ATOM | 2428 | O | GLU | 479 | 9.262 | 64.285 | 73.901 | 1.00 | 10.60 |
| ATOM | 2429 | N | ARG | 480 | 8.468 | 64.584 | 71.810 | 1.00 | 9.87 |
| ATOM | 2430 | H | ARG | 480 | 8.630 | 64.905 | 70.894 | 1.00 | 0.00 |
| ATOM | 2431 | CA | ARG | 480 | 7.183 | 63.956 | 72.149 | 1.00 | 10.88 |
| ATOM | 2432 | CB | ARG | 480 | 6.074 | 64.402 | 71.184 | 1.00 | 12.98 |
| ATOM | 2433 | CG | ARG | 480 | 5.722 | 65.877 | 71.254 | 1.00 | 17.39 |
| ATOM | 2434 | CD | ARG | 480 | 4.329 | 66.122 | 70.639 | 1.00 | 20.06 |
| ATOM | 2435 | NE | ARG | 480 | 4.354 | 65.998 | 69.186 | 1.00 | 24.35 |
| ATOM | 2436 | HE | ARG | 480 | 5.190 | 66.232 | 68.740 | 1.00 | 0.00 |
| ATOM | 2437 | CA | ARG | 480 | 3.316 | 65.616 | 68.436 | 1.00 | 24.98 |
| ATOM | 2438 | NH1 | ARG | 480 | 2.159 | 65.308 | 69.002 | 1.00 | 28.47 |
| ATOM | 2439 | HH11 | ARG | 480 | 2.071 | 65.319 | 69.990 | 1.00 | 0.00 |
| ATOM | 2440 | HH12 | ARG | 480 | 1.396 | 65.000 | 68.429 | 1.00 | 0.00 |
| ATOM | 2441 | NH2 | ARG | 480 | 3.427 | 65.577 | 67.109 | 1.00 | 27.22 |
| ATOM | 2442 | HH21 | ARG | 480 | 4.294 | 65.855 | 66.672 | 1.00 | 0.00 |
| ATOM | 2443 | HH22 | ARG | 480 | 2.657 | 65.305 | 66.549 | 1.00 | 0.00 |
| ATOM | 2444 | C | ARG | 480 | 7.347 | 62.458 | 72.013 | 1.00 | 9.30 |
| ATOM | 2445 | O | ARG | 480 | 7.697 | 62.010 | 70.935 | 1.00 | 10.00 |
| ATOM | 2446 | N | PRO | 481 | 7.033 | 61.699 | 73.085 | 1.00 | 9.78 |
| ATOM | 2447 | CD | PRO | 481 | 6.681 | 61.127 | 74.445 | 1.00 | 9.93 |
| ATOM | 2448 | CB | PRO | 481 | 7.161 | 60.240 | 73.019 | 1.00 | 9.85 |
| ATOM | 2449 | CB | PRO | 481 | 6.537 | 59.798 | 74.332 | 1.00 | 9.97 |
| ATOM | 2450 | CG | PRO | 481 | 6.910 | 60.886 | 75.309 | 1.00 | 11.62 |
| ATOM | 2451 | C | PRO | 481 | 6.450 | 59.638 | 71.819 | 1.00 | 10.02 |
| ATOM | 2452 | O | PRO | 481 | 7.016 | 58.825 | 71.071 | 1.00 | 10.13 |
| ATOM | 2453 | N | GLU | 482 | 5.238 | 60.133 | 71.512 | 1.00 | 10.63 |
| ATOM | 2454 | H | GLU | 482 | 4.858 | 60.861 | 72.027 | 1.00 | 0.00 |
| ATOM | 2455 | CA | GLU | 482 | 4.530 | 59.558 | 70.391 | 1.00 | 12.13 |
| ATOM | 2456 | CB | GLU | 482 | 3.077 | 60.045 | 70.404 | 1.00 | 14.96 |
| ATOM | 2457 | CG | GLU | 482 | 2.985 | 61.559 | 70.151 | 1.00 | 19.14 |
| ATOM | 2458 | CD | GLU | 482 | 2.948 | 62.440 | 71.417 | 1.00 | 21.01 |
| ATOM | 2459 | OE1 | GLU | 482 | 3.424 | 62.066 | 72.556 | 1.00 | 19.96 |
| ATOM | 2460 | OE2 | GLU | 482 | 2.392 | 63.564 | 71.233 | 1.00 | 24.17 |
| ATOM | 2461 | C | GLU | 482 | 5.175 | 59.758 | 69.003 | 1.00 | 10.16 |
| ATOM | 2462 | O | GLU | 482 | 4.799 | 59.108 | 68.013 | 1.00 | 11.74 |
| ATOM | 2463 | N | ASP | 483 | 6.164 | 60.663 | 68.908 | 1.00 | 9.21 |
| ATOM | 2464 | H | ASP | 483 | 6.436 | 61.169 | 69.691 | 1.00 | 0.00 |
| ATOM | 2465 | CA | ASP | 483 | 6.832 | 650.905 | 67.639 | 1.00 | 8.77 |
| ATOM | 2466 | CB | ASP | 483 | 7.347 | 62.347 | 67.567 | 1.00 | 10.30 |
| ATOM | 2467 | CG | ASP | 483 | 6.213 | 63.361 | 67.401 | 1.00 | 15.55 |
| ATOM | 2468 | OD1 | ASP | 483 | 5.094 | 62.959 | 66.996 | 1.00 | 16.29 |
| ATOM | 2469 | OD2 | ASP | 483 | 6.475 | 64.534 | 67.686 | 1.00 | 15.87 |
| ATOM | 2470 | C | ASP | 483 | 8.040 | 59.997 | 67.451 | 1.00 | 7.47 |

TABLE 3-continued

Coordinates of Lck bound with AMP-PNP

| | | Atom Type | Res | # | X | Y | Z | Occ | B |
|---|---|---|---|---|---|---|---|---|---|
| ATOM | 2471 | O | ASP | 483 | 8.606 | 59.932 | 66.358 | 1.00 | 9.55 |
| ATOM | 2472 | N | ARG | 484 | 8.425 | 59.305 | 68.515 | 1.00 | 7.27 |
| ATOM | 2473 | H | ARG | 484 | 7.950 | 59.423 | 69.358 | 1.00 | 0.00 |
| ATOM | 2474 | CA | ARG | 484 | 9.563 | 58.371 | 68.435 | 1.00 | 6.37 |
| ATOM | 2475 | CB | ARG | 484 | 10.038 | 58.016 | 69.835 | 1.00 | 5.61 |
| ATOM | 2476 | CG | ARG | 484 | 10.575 | 59.269 | 70.629 | 1.00 | 4.50 |
| ATOM | 2477 | CD | ARG | 484 | 10.822 | 58.932 | 72.045 | 1.00 | 5.79 |
| ATOM | 2478 | NE | ARG | 484 | 10.947 | 60.178 | 72.835 | 1.00 | 5.54 |
| ATOM | 2479 | HE | ARG | 484 | 11.163 | 60.995 | 72.370 | 1.00 | 0.00 |
| ATOM | 2480 | CA | ARG | 484 | 10.745 | 60.237 | 74.143 | 1.00 | 5.68 |
| ATOM | 2481 | NH1 | ARG | 484 | 10.435 | 59.130 | 74.890 | 1.00 | 6.19 |
| ATOM | 2482 | HH11 | ARG | 484 | 10.371 | 58.237 | 74.458 | 1.00 | 0.00 |
| ATOM | 2483 | HH12 | ARG | 484 | 10.304 | 59.233 | 75.870 | 1.00 | 0.00 |
| ATOM | 2484 | NH2 | ARG | 484 | 10.650 | 61.435 | 74.772 | 1.00 | 7.29 |
| ATOM | 2485 | HH21 | ARG | 484 | 10.726 | 62.276 | 74.240 | 1.00 | 0.00 |
| ATOM | 2486 | HH22 | ARG | 484 | 10.493 | 61.474 | 75.752 | 1.00 | 0.00 |
| ATOM | 2487 | C | ARG | 484 | 9.104 | 57.124 | 67.686 | 1.00 | 7.83 |
| ATOM | 2488 | O | ARG | 484 | 7.936 | 56.779 | 57.773 | 1.00 | 8.21 |
| ATOM | 2489 | N | PRO | 485 | 10.004 | 56.458 | 66.979 | 1.00 | 6.56 |
| ATOM | 2490 | CD | PRO | 485 | 11.455 | 56.804 | 66.892 | 1.00 | 6.14 |
| ATOM | 2491 | CA | PRO | 485 | 9.683 | 55.261 | 66.200 | 1.00 | 6.48 |
| ATOM | 2492 | CB | PRO | 485 | 10.958 | 55.027 | 65.380 | 1.00 | 6.21 |
| ATOM | 2493 | CG | PRO | 485 | 12.025 | 55.560 | 66.251 | 1.00 | 7.95 |
| ATOM | 2494 | C | PRO | 485 | 9.340 | 54.053 | 67.049 | 1.00 | 5.48 |
| ATOM | 2495 | O | PRO | 485 | 9.614 | 53.999 | 68.235 | 1.00 | 6.38 |
| ATOM | 2496 | N | THR | 486 | 8.778 | 53.043 | 66.388 | 1.00 | 6.76 |
| ATOM | 2497 | H | THR | 486 | 8.538 | 53.159 | 65.454 | 1.00 | 0.00 |
| ATOM | 2498 | CA | THR | 486 | 8.559 | 51.775 | 67.079 | 1.00 | 6.58 |
| ATOM | 2499 | CB | THR | 486 | 7.460 | 50.938 | 66.370 | 1.00 | 6.34 |
| ATOM | 2500 | OG1 | THR | 486 | 7.845 | 50.658 | 65.023 | 1.00 | 7.89 |
| ATOM | 2501 | HG1 | THR | 486 | 7.170 | 50.128 | 64.615 | 1.00 | 0.00 |
| ATOM | 2502 | CG2 | THR | 486 | 6.101 | 51.770 | 66.358 | 1.00 | 8.28 |
| ATOM | 2503 | C | THR | 486 | 9.829 | 50.953 | 66.980 | 1.00 | 6.42 |
| ATOM | 2504 | O | THR | 486 | 10.691 | 51.202 | 66.128 | 1.00 | 6.53 |
| ATOM | 2505 | N | PHE | 487 | 9.930 | 49.972 | 57.874 | 1.00 | 5.71 |
| ATOM | 2506 | H | PHE | 487 | 9.256 | 49.869 | 68.553 | 1.00 | 0.00 |
| ATOM | 2507 | CA | PHE | 487 | 11.060 | 49.050 | 67.789 | 1.00 | 5.66 |
| ATOM | 2508 | CB | PHE | 487 | 11.128 | 48.163 | 69.039 | 1.00 | 4.55 |
| ATOM | 2509 | CG | PHE | 487 | 11.765 | 48.852 | 70.218 | 1.00 | 3.64 |
| ATOM | 2510 | CD1 | PHE | 487 | 13.134 | 49.166 | 70.178 | 1.00 | 4.58 |
| ATOM | 2511 | CD2 | PHE | 487 | 11.025 | 49.199 | 71.350 | 1.00 | 3.94 |
| ATOM | 2512 | CE1 | PHE | 487 | 13.733 | 49.807 | 71.249 | 1.00 | 4.13 |
| AROM | 2513 | CE2 | PHE | 487 | 11.600 | 49.828 | 72.408 | 1.00 | 5.88 |
| ATOM | 2514 | CZ | PHE | 487 | 12.994 | 50.142 | 72.366 | 1.00 | 4.40 |
| ATOM | 2515 | C | PHE | 487 | 11.024 | 48.228 | 66.506 | 1.00 | 6.80 |
| ATOM | 2516 | O | PHE | 487 | 12.080 | 47.846 | 65.983 | 1.00 | 6.89 |
| ATOM | 2517 | N | ASP | 487 | 9.826 | 47.889 | 65.997 | 1.00 | 7.35 |
| ATOM | 2518 | H | ASP | 487 | 8.984 | 48.104 | 66.451 | 1.00 | 0.00 |
| ATOM | 2519 | CA | ASP | 487 | 9.836 | 47.177 | 64.727 | 1.00 | 9.30 |
| ATOM | 2520 | CB | ASP | 487 | 8.457 | 46.691 | 64.300 | 1.00 | 13.59 |
| ATOM | 2521 | CG | ASP | 487 | 8.569 | 45.639 | 63.185 | 1.00 | 18.00 |
| ATOM | 2522 | OD2 | ASP | 487 | 9.061 | 44.531 | 63.478 | 1.00 | 20.71 |
| ATOM | 2523 | OD2 | ASP | 487 | 8.328 | 45.959 | 62.005 | 1.00 | 23.96 |
| ATOM | 2524 | C | ASP | 488 | 10.447 | 48.019 | 63.607 | 1.00 | 7.89 |
| ATOM | 2525 | O | ASP | 488 | 11.202 | 47.492 | 62.081 | 1.00 | 8.16 |
| ATOM | 2526 | N | TYR | 489 | 10.154 | 49.338 | 63.599 | 1.00 | 6.57 |
| ATOM | 2527 | H | TYR | 489 | 9.501 | 49.680 | 64.240 | 1.00 | 0.00 |
| ATOM | 2528 | CA | TYR | 489 | 10.753 | 50.238 | 62.630 | 1.00 | 6.51 |
| ATOM | 2529 | CB | TYR | 489 | 10.198 | 51.661 | 62.797 | 1.00 | 5.83 |
| ATOM | 2530 | CG | TYR | 489 | 10.831 | 52.678 | 61.888 | 1.00 | 7.48 |
| ATOM | 2531 | CD1 | TYR | 489 | 10.412 | 52.820 | 60.575 | 1.00 | 8.56 |
| ATOM | 2532 | CE1 | TYR | 489 | 11.020 | 53.729 | 59.724 | 1.00 | 10.01 |
| ATOM | 2533 | CD2 | TYR | 489 | 11.898 | 53.460 | 62.347 | 1.00 | 6.56 |
| ATOM | 2534 | CE2 | TYR | 489 | 12.525 | 54.343 | 61.495 | 1.00 | 7.31 |
| ATOM | 2535 | CZ | TYR | 489 | 12.076 | 54.476 | 60.202 | 1.00 | 9.98 |
| ATOM | 2536 | OH | TYR | 489 | 12.677 | 55.392 | 59.366 | 1.00 | 11.46 |
| ATOM | 2537 | HH | TYR | 489 | 13.355 | 55.856 | 59.850 | 1.00 | 0.00 |
| ATOM | 2538 | C | TYR | 489 | 12.267 | 50.272 | 62.801 | 1.00 | 5.92 |
| ATOM | 2539 | O | TYR | 489 | 12.995 | 50.092 | 61.839 | 1.00 | 7.10 |
| ATOM | 2540 | N | LEU | 490 | 12.718 | 50.436 | 64.038 | 1.00 | 6.65 |
| ATOM | 2541 | H | LEU | 490 | 12.092 | 50.501 | 64.777 | 1.00 | 0.00 |
| ATOM | 2542 | CA | LEU | 490 | 14.165 | 50.492 | 64.347 | 1.00 | 6.42 |
| ATOM | 2543 | CB | LEU | 490 | 14.388 | 50.731 | 65.870 | 1.00 | 5.79 |
| ATOM | 2544 | CG | LEU | 490 | 13.989 | 52.132 | 66.373 | 1.00 | 7.48 |

TABLE 3-continued

Coordinates of Lck bound with AMP-PNP

| | | Atom Type | Res | # | X | Y | Z | Occ | B |
|---|---|---|---|---|---|---|---|---|---|
| ATOM | 2545 | CD1 | LEU | 490 | 13.931 | 52.235 | 67.878 | 1.00 | 6.61 |
| ATOM | 2546 | CD2 | LEU | 490 | 15.056 | 53.105 | 65.797 | 1.00 | 8.80 |
| ATOM | 2547 | C | LEU | 490 | 14.860 | 49.211 | 63.880 | 1.00 | 6.18 |
| ATOM | 2548 | O | LEU | 490 | 15.892 | 49.243 | 63.238 | 1.00 | 5.96 |
| ATOM | 2549 | N | ARG | 491 | 14.233 | 48.060 | 64.160 | 1.00 | 6.27 |
| ATOM | 2550 | H | ARG | 491 | 13.411 | 48.069 | 64.673 | 1.00 | 0.00 |
| ATOM | 2551 | CA | ARG | 491 | 14.815 | 46.795 | 63.721 | 1.00 | 6.31 |
| ATOM | 2552 | CB | ARG | 491 | 13.915 | 45.641 | 64.183 | 1.00 | 7.38 |
| ATOM | 2553 | CG | ARG | 491 | 14.470 | 44.283 | 63.688 | 1.00 | 9.31 |
| ATOM | 2554 | CD | ARG | 491 | 13.393 | 43.170 | 63.645 | 1.00 | 14.23 |
| ATOM | 2555 | NE | ARG | 491 | 12.172 | 43.958 | 62.930 | 1.00 | 15.07 |
| ATOM | 2556 | HE | ARG | 491 | 11.401 | 43.829 | 63.489 | 1.00 | 0.00 |
| ATOM | 2557 | CZ | ARG | 491 | 12.018 | 42.712 | 61.608 | 1.00 | 15.75 |
| ATOM | 2558 | NH1 | ARG | 491 | 12.982 | 43.434 | 60.746 | 1.00 | 15.02 |
| ATOM | 2559 | HH11 | ARG | 491 | 13.880 | 43.121 | 61.087 | 1.00 | 0.00 |
| ATOM | 2560 | HH12 | ARG | 491 | 12.829 | 43.535 | 59.774 | 1.00 | 0.00 |
| ATOM | 2561 | NH2 | ARG | 491 | 10.865 | 44.169 | 61.137 | 1.00 | 15.21 |
| ATOM | 2562 | HH21 | ARG | 491 | 10.135 | 44.416 | 61.771 | 1.00 | 0.00 |
| ATOM | 2563 | HH22 | ARG | 491 | 10.729 | 44.265 | 60.152 | 1.00 | 0.00 |
| ATOM | 2564 | C | ARG | 491 | 14.932 | 46.739 | 62.189 | 1.00 | 6.75 |
| ATOM | 2565 | O | ARG | 491 | 15.992 | 46.361 | 61.634 | 1.00 | 7.35 |
| ATOM | 2566 | N | SER | 492 | 13.879 | 47.186 | 61.492 | 0.71 | 4.54 |
| ATOM | 2567 | H | SER | 492 | 13.089 | 47.538 | 61.958 | 1.00 | 0.00 |
| ATOM | 2568 | CA | SER | 492 | 13.880 | 47.133 | 60.055 | 0.71 | 5.30 |
| ATOM | 2569 | CB | SER | 492 | 12.496 | 47.529 | 59.526 | 0.71 | 5.43 |
| ATOM | 2570 | OG | SER | 492 | 12.474 | 47.374 | 58.129 | 0.71 | 9.15 |
| ATOM | 2571 | HG | SER | 492 | 13.145 | 47.949 | 57.762 | 1.00 | 0.00 |
| ATOM | 2572 | C | SER | 492 | 14.962 | 48.008 | 59.439 | 0.71 | 4.32 |
| ATOM | 2573 | O | SER | 492 | 15.671 | 47.594 | 58.533 | 0.71 | 4.32 |
| ATOM | 2574 | N | VAL | 493 | 15.139 | 49.218 | 59.983 | 1.00 | 5.16 |
| ATOM | 2575 | H | VAL | 493 | 14.553 | 49.500 | 60.718 | 1.00 | 0.00 |
| ATOM | 2576 | CA | VAL | 493 | 16.138 | 50.119 | 59.443 | 1.00 | 6.43 |
| ATOM | 2577 | CB | VAL | 493 | 15.980 | 51.550 | 60.107 | 1.00 | 5.63 |
| ATOM | 2578 | CG1 | VAL | 493 | 17.159 | 52.455 | 59.652 | 1.00 | 8.00 |
| ATOM | 2579 | CG2 | VAL | 493 | 14.634 | 52.189 | 59.690 | 1.00 | 7.88 |
| ATOM | 2580 | C | VAL | 493 | 17.516 | 49.591 | 59.737 | 1.00 | 5.20 |
| ATOM | 2581 | O | VAL | 493 | 18.353 | 49.064 | 58.870 | 1.00 | 6.67 |
| ATOM | 2582 | N | LEU | 494 | 17.745 | 49.116 | 60.958 | 1.00 | 5.50 |
| ATOM | 2583 | H | LEU | 494 | 17.027 | 49.146 | 61.624 | 1.00 | 0.00 |
| ATOM | 2584 | CA | LEU | 494 | 19.094 | 48.609 | 61.333 | 1.00 | 6.34 |
| ATOM | 2585 | CB | LEU | 494 | 19.145 | 48.389 | 62.805 | 1.00 | 6.35 |
| ATOM | 2586 | CG | LEU | 494 | 19.171 | 49.514 | 63.713 | 1.00 | 5.07 |
| ATOM | 2587 | CD1 | LEU | 494 | 18.777 | 49.188 | 65.130 | 1.00 | 5.78 |
| ATOM | 2588 | CD2 | LEU | 494 | 20.588 | 50.169 | 63.619 | 1.00 | 6.58 |
| ATOM | 2589 | C | LEU | 494 | 19.489 | 47.393 | 60.482 | 1.00 | 7.76 |
| ATOM | 2590 | O | LEU | 494 | 20.648 | 47.259 | 60.094 | 1.00 | 8.54 |
| ATOM | 2591 | H | GLU | 495 | 18.498 | 46.580 | 60.118 | 1.00 | 8.30 |
| ATOM | 2592 | H | GLU | 495 | 17.585 | 46.751 | 60.430 | 1.00 | 0.00 |
| ATOM | 2593 | CA | GLU | 495 | 18.765 | 45.453 | 59.230 | 1.00 | 9.37 |
| ATOM | 2594 | CB | GLU | 495 | 17.566 | 44.502 | 59.139 | 1.00 | 10.30 |
| ATOM | 2595 | CG | GLU | 495 | 17.360 | 43.867 | 60.404 | 1.00 | 12.04 |
| ATOM | 2596 | CD | GLU | 495 | 16.133 | 42.795 | 60.346 | 1.00 | 14.75 |
| ATOM | 2597 | OE1 | GLU | 495 | 15.393 | 42.812 | 59.331 | 1.00 | 17.48 |
| ATOM | 2598 | OE2 | GLU | 495 | 15.858 | 42.105 | 61.362 | 1.00 | 15.95 |
| ATOM | 2599 | C | GLU | 495 | 19.195 | 45.944 | 57.850 | 1.00 | 9.75 |
| ATOM | 2600 | O | GLU | 495 | 20.099 | 45.395 | 57.222 | 1.00 | 9.88 |
| ATOM | 2601 | N | ASP | 496 | 18.574 | 47.016 | 57.385 | 1.00 | 8.31 |
| ATOM | 2602 | CA | ASP | 496 | 17.904 | 47.484 | 57.931 | 1.00 | 0.00 |
| ATOM | 2603 | CA | ASP | 496 | 18.930 | 47.551 | 56.084 | 1.00 | 9.40 |
| ATOM | 2604 | CB | ASP | 496 | 17.905 | 48.638 | 55.683 | 1.00 | 9.92 |
| ATOM | 2605 | CG | ASP | 496 | 16.633 | 48.068 | 55.109 | 1.00 | 10.66 |
| ATOM | 2606 | OD1 | ASP | 496 | 16.577 | 46.842 | 54.781 | 1.00 | 13.65 |
| ATOM | 2607 | OD2 | ASP | 496 | 15.618 | 48.817 | 54.976 | 1.00 | 10.73 |
| ATOM | 2608 | C | ASP | 496 | 20.344 | 48.131 | 56.130 | 1.00 | 9.26 |
| ATOM | 2609 | O | ASP | 496 | 21.085 | 48.049 | 55.169 | 1.00 | 10.67 |
| ATOM | 2610 | N | PHE | 497 | 20.864 | 48.787 | 57.241 | 1.00 | 9.18 |
| ATOM | 2611 | H | PHE | 497 | 20.045 | 48.836 | 57.979 | 1.00 | 0.00 |
| ATOM | 2612 | CA | PHE | 497 | 22.009 | 49.385 | 57.410 | 1.00 | 10.38 |
| ATOM | 2613 | CB | PHE | 497 | 22.103 | 50.110 | 58.765 | 1.00 | 9.42 |
| ATOM | 2614 | CG | PHE | 497 | 21.388 | 51.443 | 58.822 | 1.00 | 9.62 |
| ATOM | 2615 | CD1 | PHE | 497 | 20.736 | 51.943 | 57.722 | 1.00 | 9.72 |
| ATOM | 2616 | CD2 | PHE | 497 | 21.414 | 52.185 | 60.015 | 1.00 | 9.12 |
| ATOM | 2617 | CE1 | PHE | 497 | 20.102 | 53.192 | 57.800 | 1.00 | 9.37 |
| ATOM | 2618 | CE2 | PHE | 497 | 20.799 | 53.432 | 60.132 | 1.00 | 8.46 |

TABLE 3-continued

Coordinates of Lck bound with AMP-PNP

| | | Atom Type | Res | # | X | Y | Z | Occ | B |
|---|---|---|---|---|---|---|---|---|---|
| ATOM | 2619 | CA | PHE | 497 | 20.137 | 53.935 | 58.995 | 1.00 | 7.24 |
| ATOM | 2620 | C | PHE | 497 | 23.081 | 48.271 | 57.381 | 1.00 | 11.52 |
| ATOM | 2621 | O | PHE | 497 | 24.158 | 48.438 | 56.804 | 1.00 | 12.93 |
| ATOM | 2622 | N | PHE | 498 | 22.761 | 47.153 | 58.025 | 1.00 | 14.28 |
| ATOM | 2623 | H | PHE | 498 | 21.890 | 47.107 | 58.477 | 1.00 | 0.00 |
| ATOM | 2624 | CA | PHE | 498 | 23.660 | 45.986 | 58.085 | 1.00 | 16.98 |
| ATOM | 2625 | CB | PHE | 498 | 23.132 | 45.014 | 59.176 | 1.00 | 19.14 |
| ATOM | 2626 | CG | PHE | 498 | 23.659 | 43.596 | 59.107 | 1.00 | 20.38 |
| ATOM | 2627 | CD1 | PHE | 498 | 25.010 | 32.329 | 59.124 | 1.00 | 22.05 |
| ATOM | 2628 | CD2 | PHE | 498 | 22.758 | 42.525 | 59.125 | 1.00 | 22.64 |
| ATOM | 2629 | CE1 | PHE | 498 | 25.475 | 42.012 | 59.165 | 1.00 | 21.12 |
| ATOM | 2630 | CE2 | PHE | 498 | 23.202 | 41.203 | 59.168 | 1.00 | 22.55 |
| ATOM | 2631 | CA | PHE | 498 | 24.576 | 40.954 | 59.188 | 1.00 | 22.00 |
| ATOM | 2632 | C | PHE | 498 | 23.797 | 45.295 | 56.746 | 1.00 | 18.13 |
| ATOM | 2633 | O | PHE | 498 | 24.917 | 45.034 | 56.300 | 1.00 | 18.94 |
| ATOM | 2634 | N | THR | 499 | 22.687 | 45.073 | 56.055 | 1.00 | 20.19 |
| ATOM | 2635 | H | THR | 499 | 21.829 | 45.405 | 56.384 | 1.00 | 0.00 |
| ATOM | 2636 | CA | THR | 499 | 22.758 | 44.343 | 53.797 | 1.00 | 22.43 |
| ATOM | 2637 | CB | THR | 499 | 21.399 | 43.789 | 54.373 | 1.00 | 22.60 |
| ATOM | 2638 | OG1 | THR | 499 | 20.485 | 44.855 | 54.253 | 1.00 | 23.78 |
| ATOM | 2639 | HG1 | THR | 499 | 20.379 | 45.296 | 55.099 | 1.00 | 0.00 |
| ATOM | 2640 | CG2 | THR | 499 | 20.849 | 42.789 | 55.405 | 1.00 | 22.61 |
| ATOM | 2641 | C | THR | 499 | 23.419 | 45.195 | 53.736 | 1.00 | 23.72 |
| ATOM | 2642 | O | THR | 499 | 23.897 | 44.682 | 52.719 | 1.00 | 25.02 |
| ATOM | 2643 | N | ALA | 500 | 23.489 | 46.497 | 54.006 | 1.00 | 24.94 |
| ATOM | 2644 | H | ALA | 500 | 23.078 | 46.836 | 54.824 | 1.00 | 0.00 |
| ATOM | 2645 | CA | ALA | 500 | 24.153 | 47.432 | 53.125 | 1.00 | 26.58 |
| ATOM | 2646 | CB | ALA | 500 | 23.642 | 48.830 | 53.346 | 1.00 | 25.49 |
| ATOM | 2647 | C | ALA | 500 | 25.652 | 47.382 | 53.407 | 1.00 | 27.54 |
| ATOM | 2648 | N | THR | 501 | 26.428 | 47.114 | 52.491 | 1.00 | 28.68 |
| ATOM | 2649 | N | THR | 501 | 26.050 | 47.596 | 54.669 | 1.00 | 27.16 |
| ATOM | 2650 | H | THR | 501 | 25.364 | 47.778 | 55.345 | 1.00 | 0.00 |
| ATOM | 2651 | CA | THR | 501 | 27.474 | 47.577 | 55.072 | 1.00 | 26.85 |
| ATOM | 2652 | CB | THR | 501 | 27.687 | 48.037 | 56.555 | 1.00 | 26.63 |
| ATOM | 2653 | OG1 | THR | 501 | 26.993 | 47.162 | 57.454 | 1.00 | 26.89 |
| ATOM | 2654 | HG1 | THR | 501 | 26.037 | 47.169 | 57.270 | 1.00 | 0.00 |
| ATOM | 2655 | CG2 | THR | 501 | 27.224 | 49.498 | 56.773 | 1.00 | 25.38 |
| ATOM | 2656 | C | THR | 501 | 28.144 | 46.196 | 54.904 | 1.00 | 26.89 |
| ATOM | 2657 | O | THR | 501 | 27.647 | 45.353 | 54.112 | 1.00 | 27.80 |
| ATOM | 2658 | OT | THR | 501 | 29.172 | 45.942 | 55.594 | 1.00 | 28.37 |
| ATOM | 2659 | OH2 | TIP3 | 1 | 21.620 | 29.748 | 74.825 | 1.00 | 8.52 |
| ATOM | 2660 | H1 | TIP3 | 1 | 21.619 | 30.703 | 74.839 | 1.00 | 0.00 |
| ATOM | 2661 | H2 | TIP3 | 1 | 21.616 | 29.512 | 73.905 | 1.00 | 0.00 |
| ATOM | 2662 | OH2 | TIP3 | 2 | 19.448 | 27.888 | 78.810 | 1.00 | 8.93 |
| ATOM | 2663 | H1 | TIP3 | 2 | 19.438 | 28.841 | 78.818 | 1.00 | 0.00 |
| ATOM | 2664 | H2 | TIP3 | 2 | 19.446 | 27.649 | 77.893 | 1.00 | 0.00 |
| ATOM | 2665 | OH2 | TIP3 | 2 | 14.802 | 51.739 | 79.298 | 1.00 | 7.18 |
| ATOM | 2666 | H1 | TIP3 | 3 | 14.787 | 52.706 | 79.289 | 1.00 | 0.00 |
| ATOM | 2667 | H2 | TIP3 | 3 | 14.787 | 51.512 | 78.362 | 1.00 | 0.00 |
| ATOM | 2668 | OH2 | TIP3 | 4 | 19.440 | 60.726 | 77.700 | 1.00 | 6.25 |
| ATOM | 2669 | H1 | TIP3 | 4 | 19.463 | 61.675 | 77.720 | 1.00 | 0.00 |
| ATOM | 2670 | H2 | TIP3 | 4 | 19.463 | 61.675 | 77.720 | 1.00 | 0.00 |
| ATOM | 2671 | OH2 | TIP3 | 5 | 20.579 | 62.826 | 73.348 | 1.00 | 6.02 |
| ATOM | 2672 | H1 | TIP3 | 5 | 20.582 | 63.772 | 73.343 | 1.00 | 0.00 |
| ATOM | 2673 | H2 | TIP3 | 5 | 20.584 | 62.575 | 72.424 | 1.00 | 0.00 |
| ATOM | 2674 | OH2 | TIP3 | 6 | 16.627 | 32.849 | 74.682 | 1.00 | 6.62 |
| ATOM | 2675 | H1 | TIP3 | 6 | 16.613 | 33.808 | 74.673 | 1.00 | 0.00 |
| ATOM | 2676 | H2 | TIP3 | 6 | 16.613 | 32.606 | 73.751 | 1.00 | 0.00 |
| ATOM | 2677 | OH2 | TIP3 | 7 | 24.567 | 68.831 | 70.758 | 1.00 | 11.18 |
| ATOM | 2678 | H1 | TIP3 | 7 | 24.591 | 69.792 | 70.745 | 1.00 | 0.00 |
| ATOM | 2679 | H2 | TIP3 | 7 | 24.591 | 68.599 | 69.825 | 1.00 | 0.00 |
| ATOM | 2680 | OH2 | TIP3 | 8 | 3.910 | 16.814 | 94.936 | 1.00 | 8.70 |
| ATOM | 2681 | H1 | TIP3 | 8 | 3.914 | 17.769 | 94.934 | 1.00 | 0.00 |
| ATOM | 2682 | H2 | TIP3 | 8 | 3.914 | 16.574 | 94.006 | 1.00 | 0.00 |
| ATOM | 2683 | OH2 | TIP3 | 9 | 18.100 | 61.850 | 79.778 | 1.00 | 10.32 |
| ATOM | 2684 | H1 | TIP3 | 9 | 18.102 | 62.807 | 79.772 | 1.00 | 0.00 |
| ATOM | 2685 | H2 | TIP3 | 9 | 18.102 | 61.605 | 78.848 | 1.00 | 0.00 |
| ATOM | 2686 | OH2 | TIP3 | 10 | 16.772 | 62.110 | 62.500 | 1.00 | 12.69 |
| ATOM | 2687 | H1 | TIP3 | 10 | 16.756 | 63.066 | 62.499 | 1.00 | 0.00 |
| ATOM | 2688 | H2 | TIP3 | 10 | 16.749 | 61.901 | 61.567 | 1.00 | 0.00 |
| ATOM | 2689 | OH2 | TIP3 | 11 | 25.240 | 50.449 | 80.104 | 1.00 | 7.27 |
| ATOM | 2690 | H1 | TIP3 | 11 | 25.255 | 51.408 | 80.086 | 1.00 | 0.00 |
| ATOM | 2691 | H2 | TIP3 | 11 | 25.254 | 50.208 | 79.167 | 1.00 | 0.00 |
| ATOM | 2692 | OH2 | TIP3 | 12 | 26.659 | 31.622 | 75.084 | 1.00 | 8.62 |

TABLE 3-continued

Coordinates of Lck bound with AMP-PNP

| | | Atom Type | Res | # | X | Y | Z | Occ | B |
|---|---|---|---|---|---|---|---|---|---|
| ATOM | 2693 | H1 | TIP3 | 12 | 26.656 | 32.587 | 75.083 | 1.00 | 0.00 |
| ATOM | 2694 | H2 | TIP3 | 12 | 26.656 | 21.396 | 74.154 | 1.00 | 0.00 |
| ATOM | 2695 | OH2 | TIP3 | 13 | 25.383 | 21.709 | 76.987 | 1.00 | 9.37 |
| ATOM | 2696 | H1 | TIP3 | 13 | 25.381 | 22.678 | 76.989 | 1.00 | 0.00 |
| ATOM | 2697 | H2 | TIP3 | 13 | 25.381 | 21.489 | 76.055 | 1.00 | 0.00 |
| ATOM | 2698 | OH2 | TIP3 | 14 | 3.800 | 51.757 | 76.179 | 1.00 | 16.31 |
| ATOM | 2699 | H1 | TIP3 | 14 | 3.790 | 52.707 | 76.172 | 1.00 | 0.00 |
| ATOM | 2700 | H2 | TIP3 | 14 | 3.790 | 51.508 | 75.250 | 1.00 | 0.00 |
| ATOM | 2701 | OH2 | TIP3 | 15 | 33.014 | 39.952 | 77.627 | 1.00 | 15.59 |
| ATOM | 2702 | H1 | TIP3 | 15 | 33.021 | 40.918 | 77.633 | 1.00 | 0.00 |
| ATOM | 2703 | H2 | TIP3 | 15 | 33.021 | 39.720 | 76.707 | 1.00 | 0.00 |
| ATOM | 2704 | OH2 | TIP3 | 16 | 23.244 | 20.494 | 78.039 | 1.00 | 9.49 |
| ATOM | 2705 | H1 | TIP3 | 16 | 23.242 | 21.447 | 78.032 | 1.00 | 0.00 |
| ATOM | 2706 | H2 | TIP3 | 16 | 23.242 | 20.250 | 77.107 | 1.00 | 0.00 |
| ATOM | 2707 | OH2 | TIP3 | 17 | 7.671 | 53.984 | 63.752 | 1.00 | 12.47 |
| ATOM | 2708 | H1 | TIP3 | 17 | 7.669 | 54.938 | 63.759 | 1.00 | 0.00 |
| ATOM | 2709 | H2 | TIP3 | 17 | 7.669 | 53.747 | 62.829 | 1.00 | 0.00 |
| ATOM | 2710 | OH2 | TIP3 | 18 | 28.174 | 56.185 | 74.630 | 1.00 | 10.19 |
| ATOM | 2711 | H1 | TIP3 | 18 | 28.170 | 57.156 | 74.603 | 1.00 | 0.00 |
| ATOM | 2712 | H2 | TIP3 | 18 | 28.170 | 55.960 | 73.685 | 1.00 | 0.00 |
| ATOM | 2713 | OH2 | TIP3 | 19 | 22.146 | 18.808 | 82.244 | 1.00 | 9.68 |
| ATOM | 2714 | H1 | TIP3 | 19 | 22.146 | 19.771 | 82.246 | 1.00 | 0.00 |
| ATOM | 2715 | H2 | TIP3 | 19 | 22.148 | 18.581 | 82.320 | 1.00 | 0.00 |
| ATOM | 2716 | OH2 | TIP3 | 20 | 13.274 | 34.172 | 76.712 | 1.00 | 9.25 |
| ATOM | 2717 | H1 | TIP3 | 20 | 13.268 | 35.135 | 76.706 | 1.00 | 0.00 |
| ATOM | 2718 | H2 | TIP3 | 20 | 13.268 | 33.939 | 75.780 | 1.00 | 0.00 |
| ATOM | 2719 | OH2 | TIP3 | 21 | 7.239 | 57.436 | 104.519 | 1.00 | 13.95 |
| ATOM | 2720 | H1 | TIP3 | 21 | 7.217 | 58.400 | 104.524 | 1.00 | 0.00 |
| ATOM | 2721 | HE | TIP3 | 21 | 7.217 | 57.205 | 103.595 | 1.00 | 0.00 |
| ATOM | 2722 | OH2 | TIP3 | 22 | 35.743 | 44.113 | 79.494 | 1.00 | 19.75 |
| ATOM | 2723 | H1 | TIP3 | 22 | 35.762 | 45.067 | 79.489 | 1.00 | 0.00 |
| ATOM | 2724 | H2 | TIP3 | 22 | 35.762 | 45.067 | 79.489 | 1.00 | 0.00 |
| ATOM | 2725 | OH2 | TIP3 | 23 | 8.606 | 65.639 | 69.086 | 1.00 | 14.66 |
| ATOM | 2726 | H1 | TIP3 | 23 | 8.604 | 66.584 | 69.083 | 1.00 | 0.00 |
| ATOM | 2728 | OH2 | TIP3 | 24 | 22.220 | 28.061 | 79.375 | 1.00 | 12.39 |
| ATOM | 2729 | H1 | TIP3 | 24 | 22.229 | 29.002 | 79.345 | 1.00 | 0.00 |
| ATOM | 2730 | H2 | TIP3 | 24 | 22.240 | 27.824 | 78.438 | 1.00 | 0.00 |
| ATOM | 2731 | OH2 | TIP3 | 25 | 14.088 | 69.122 | 73.924 | 1.00 | 17.10 |
| ATOM | 2732 | H1 | TIP3 | 25 | 14.085 | 70.074 | 73.909 | 1.00 | 0.00 |
| ATOM | 2733 | H2 | TIP3 | 25 | 14.085 | 68.881 | 72.986 | 1.00 | 0.00 |
| ATOM | 2734 | OH2 | TIP3 | 26 | 13.661 | 55.614 | 79.562 | 1.00 | 10.12 |
| ATOM | 2735 | H1 | TIP3 | 26 | 13.655 | 56.564 | 79.554 | 1.00 | 0.00 |
| ATOM | 2736 | H2 | TIP3 | 26 | 13.666 | 55.383 | 78.629 | 1.00 | 0.00 |
| ATOM | 2737 | OH2 | TIP3 | 27 | 4.331 | 54.670 | 67.201 | 1.00 | 13.37 |
| ATOM | 2738 | H1 | TIP3 | 27 | 4.327 | 55.632 | 67.197 | 1.00 | 0.00 |
| ATOM | 2739 | H2 | TIP3 | 27 | 4.327 | 54.437 | 66.270 | 1.00 | 0.00 |
| ATOM | 2740 | OH2 | TIP3 | 28 | 6.632 | 45.326 | 67.982 | 1.00 | 11.48 |
| ATOM | 2741 | H1 | TIP3 | 28 | 6.608 | 46.242 | 67.924 | 1.00 | 0.00 |
| AOTM | 2742 | H2 | TIP3 | 28 | 6.631 | 45.075 | 67.039 | 1.00 | 0.00 |
| ATOM | 2743 | OH2 | TIP3 | 29 | 24.783 | 78.595 | 73.991 | 1.00 | 10.05 |
| ATOM | 2744 | H1 | TIP3 | 29 | 24.778 | 79.550 | 74.003 | 1.00 | 0.00 |
| ATOM | 2745 | H2 | TIP3 | 29 | 24.778 | 78.358 | 73.073 | 1.00 | 0.00 |
| ATOM | 2746 | OH2 | TIP3 | 30 | 30.152 | 59.848 | 72.332 | 1.00 | 12.11 |
| ATOM | 2748 | H2 | TIP3 | 30 | 30.157 | 59.604 | 71.413 | 1.00 | 0.00 |
| ATOM | 2749 | OH2 | TIP3 | 31 | 25.969 | 23.735 | 78.543 | 1.00 | 14.18 |
| ATOM | 2750 | H1 | TIP3 | 31 | 26.022 | 24.715 | 78.548 | 1.00 | 0.00 |
| ATOM | 2751 | H2 | TIP3 | 31 | 26.034 | 23.562 | 77.609 | 1.00 | 0.00 |
| ATOM | 2752 | OH2 | TIP3 | 32 | 3.073 | 56.966 | 68.148 | 1.00 | 18.92 |
| ATOM | 2753 | H1 | TIP3 | 32 | 3.062 | 57.921 | 68.149 | 1.00 | 0.00 |
| ATOM | 2754 | H2 | TIP3 | 32 | 3.064 | 56.716 | 67.222 | 1.00 | 0.00 |
| ATOM | 2755 | OH2 | TIP3 | 33 | 6.529 | 52.062 | 70.116 | 1.00 | 17.22 |
| ATOM | 2756 | H1 | TIP3 | 33 | 6.515 | 53.004 | 70.134 | 1.00 | 0.00 |
| ATOM | 2757 | H2 | TIP3 | 33 | 6.513 | 51.812 | 69.201 | 1.00 | 0.00 |
| ATOM | 2758 | OH2 | TIP3 | 34 | 26.402 | 70.378 | 71.831 | 1.00 | 17.50 |
| ATOM | 2759 | H1 | TIP3 | 34 | 26.425 | 71.335 | 71.835 | 1.00 | 0.00 |
| ATOM | 2760 | H2 | TIP3 | 34 | 26.425 | 71.335 | 71.835 | 1.00 | 0.00 |
| ATOM | 2761 | OH2 | TIP3 | 35 | 30.299 | 41.047 | 81.602 | 1.00 | 15.92 |
| ATOM | 2762 | H1 | TIP3 | 35 | 30.269 | 42.006 | 81.613 | 1.00 | 0.00 |
| ATOM | 2763 | H2 | TIP3 | 35 | 30.277 | 40.826 | 80.682 | 1.00 | 0.00 |
| ATOM | 2764 | OH2 | TIP3 | 36 | 13.099 | 71.465 | 72.644 | 1.00 | 13.79 |
| ATOM | 2765 | H1 | TIP3 | 36 | 13.094 | 72.419 | 72.624 | 1.00 | 0.00 |
| ATOM | 2766 | H2 | TIP3 | 36 | 13.088 | 71.217 | 71.707 | 1.00 | 0.00 |
| ATOM | 2767 | OH2 | TIP3 | 37 | 29.727 | 18.018 | 80.773 | 1.00 | 15.04 |
| ATOM | 2768 | H1 | TIP3 | 37 | 29.725 | 18.973 | 80.787 | 1.00 | 0.00 |

TABLE 3-continued

Coordinates of Lck bound with AMP-PNP

| | | Atom Type | Res | # | X | Y | Z | Occ | B |
|---|---|---|---|---|---|---|---|---|---|
| ATOM | 2769 | H2 | TIP3 | 37 | 29.726 | 17.774 | 79.864 | 1.00 | 0.00 |
| ATOM | 2770 | OH2 | TIP3 | 38 | 36.064 | 38.671 | 74.415 | 1.00 | 19.58 |
| ATOM | 2771 | H1 | TIP3 | 38 | 36.087 | 39.602 | 74.431 | 1.00 | 0.00 |
| ATOM | 2772 | H2 | TIP3 | 38 | 36.082 | 38.420 | 73.497 | 1.00 | 0.00 |
| ATOM | 2773 | OH2 | TIP3 | 39 | 29.627 | 65.885 | 75.019 | 1.00 | 21.09 |
| ATOM | 2774 | H1 | TIP3 | 39 | 29.655 | 66.852 | 75.030 | 1.00 | 0.00 |
| ATOM | 2775 | H2 | TIP3 | 39 | 29.655 | 65.661 | 74.098 | 1.00 | 0.00 |
| ATOM | 2776 | OH2 | TIP3 | 40 | 16.595 | 52.544 | 84.851 | 1.00 | 13.90 |
| ATOM | 2777 | H1 | TIP3 | 40 | 16.565 | 53.498 | 84.853 | 1.00 | 0.00 |
| ATOM | 2778 | H2 | TIP3 | 40 | 16.565 | 52.301 | 83.924 | 1.00 | 0.00 |
| ATOM | 2779 | OH2 | TIP3 | 41 | 4.206 | 43.642 | 85.694 | 1.00 | 20.52 |
| ATOM | 2780 | H1 | TIP3 | 41 | 4.220 | 44.619 | 85.718 | 1.00 | 0.00 |
| ATOM | 2781 | H2 | TIP3 | 41 | 4.220 | 42.432 | 84.778 | 1.00 | 0.00 |
| ATOM | 2782 | OH2 | TIP3 | 42 | 29.857 | 58.327 | 74.600 | 1.00 | 14.26 |
| ATOM | 2783 | H1 | TIP3 | 42 | 29.858 | 59.293 | 74.612 | 1.00 | 0.00 |
| ATOM | 2784 | H2 | TIP3 | 42 | 29.858 | 58.097 | 73.679 | 1.00 | 0.00 |
| ATOM | 2785 | OH2 | TIP3 | 43 | 16.161 | 19.916 | 80.183 | 1.00 | 13.92 |
| ATOM | 2786 | H1 | TIP3 | 43 | 16.152 | 20.873 | 80.195 | 1.00 | 0.00 |
| ATOM | 2787 | H2 | TIP3 | 43 | 16.152 | 19.673 | 79.264 | 1.00 | 0.00 |
| ATOM | 2788 | OH2 | TIP3 | 44 | 4.638 | 47.641 | 75.156 | 1.00 | 11.80 |
| ATOM | 2789 | H1 | TIP3 | 44 | 4.658 | 48.599 | 75.161 | 1.00 | 0.00 |
| ATOM | 2790 | H2 | TIP3 | 44 | 4.658 | 47.399 | 74.240 | 1.00 | 0.00 |
| ATOM | 2791 | OH2 | TIP3 | 45 | 15.020 | 76.683 | 76.321 | 1.00 | 15.07 |
| ATOM | 2792 | H1 | TIP3 | 45 | 15.022 | 77.651 | 76.323 | 1.00 | 0.00 |
| ATOM | 2793 | H2 | TIP3 | 45 | 15.022 | 76.454 | 75.392 | 1.00 | 0.00 |
| ATOM | 2794 | OH2 | TIP3 | 46 | 6.193 | 59.954 | 101.345 | 1.00 | 15.44 |
| ATOM | 2795 | H1 | TIP3 | 46 | 6.179 | 60.902 | 101.354 | 1.00 | 0.00 |
| ATOM | 2796 | H2 | TIP3 | 46 | 6.179 | 59.702 | 100.426 | 1.00 | 0.00 |
| ATOM | 2797 | OH2 | TIP3 | 47 | 14.081 | 45.728 | 83.666 | 1.00 | 10.14 |
| ATOM | 2798 | H1 | TIP3 | 47 | 14.071 | 46.678 | 83.675 | 1.00 | 0.00 |
| ATOM | 2799 | H2 | TIP3 | 47 | 14.071 | 45.475 | 82.745 | 1.00 | 0.00 |
| ATOM | 2800 | OH2 | TIP3 | 48 | 14.304 | 25.203 | 81.378 | 1.00 | 17.96 |
| ATOM | 2801 | H1 | TIP3 | 48 | 14.295 | 26.140 | 81.372 | 1.00 | 0.00 |
| ATOM | 2802 | H2 | TIP3 | 48 | 14.295 | 24.933 | 80.447 | 1.00 | 0.00 |
| ATOM | 2803 | OH2 | TIP3 | 49 | 10.646 | 40.704 | 67.208 | 1.00 | 16.11 |
| ATOM | 2804 | H1 | TIP3 | 49 | 10.619 | 41.662 | 67.206 | 1.00 | 0.00 |
| ATOM | 2805 | H1 | TIP3 | 49 | 10.619 | 40.464 | 66.278 | 1.00 | 0.00 |
| ATOM | 2806 | OH2 | TIP3 | 50 | 33.324 | 41.993 | 62.711 | 1.00 | 18.07 |
| ATOM | 2807 | H1 | TIP3 | 50 | 33.287 | 42.925 | 62.692 | 1.00 | 0.00 |
| ATOM | 2808 | H2 | TIP3 | 50 | 33.288 | 41.711 | 61.778 | 1.00 | 0.00 |
| ATOM | 2809 | OH2 | TIP3 | 51 | 6.569 | 57.850 | 77.095 | 1.00 | 16.85 |
| ATOM | 2810 | H1 | TIP3 | 51 | 6.578 | 5.806 | 77.099 | 1.00 | 0.00 |
| ATOM | 2811 | H2 | TIP3 | 51 | 6.578 | 58.806 | 77.099 | 1.00 | 0.00 |
| ATOM | 2812 | OH2 | TIP3 | 52 | 17.054 | 28.788 | 80.134 | 1.00 | 18.95 |
| ATOM | 2813 | H1 | TIP3 | 52 | 17.067 | 29.730 | 80.166 | 1.00 | 0.00 |
| ATOM | 2814 | H2 | TIP3 | 52 | 17.067 | 28.527 | 79.234 | 1.00 | 0.00 |
| ATOM | 2815 | OH2 | TIP3 | 53 | 6.065 | 57.530 | 65.648 | 1.00 | 23.77 |
| ATOM | 2816 | H1 | TIP3 | 53 | 6.086 | 58.499 | 65.665 | 1.00 | 0.00 |
| ATOM | 2817 | H2 | TIP3 | 53 | 6.086 | 57.308 | 64.732 | 1.00 | 0.00 |
| ATOM | 2818 | OH2 | TIP3 | 54 | 17.752 | 52.844 | 80.755 | 1.00 | 13.96 |
| ATOM | 2819 | H1 | TIP3 | 54 | 17.734 | 53.803 | 80.742 | 1.00 | 0.00 |
| ATOM | 2820 | H2 | TIP3 | 54 | 17.734 | 52.609 | 79.819 | 1.00 | 0.00 |
| ATOM | 2821 | OH2 | TIP3 | 55 | 11.753 | 33.295 | 69.481 | 1.00 | 17.77 |
| ATOM | 2822 | H1 | TIP3 | 55 | 11.721 | 34.247 | 69.504 | 1.00 | 0.00 |
| ATOM | 2823 | H2 | TIP3 | 55 | 11.721 | 34.247 | 69.504 | 1.00 | 0.00 |
| ATOM | 2824 | OH2 | TIP3 | 56 | 12.945 | 35.826 | 79.153 | 1.00 | 17.23 |
| ATOM | 2825 | H1 | TIP3 | 56 | 12.909 | 36.781 | 79.168 | 1.00 | 0.00 |
| ATOM | 2826 | H2 | TIP3 | 56 | 12.909 | 35.585 | 78.235 | 1.00 | 0.00 |
| ATOM | 2827 | OH2 | TIP3 | 57 | 40.075 | 43.408 | 77.618 | 1.00 | 25.03 |
| ATOM | 2828 | H1 | TIP3 | 57 | 40.050 | 44.376 | 77.632 | 1.00 | 0.00 |
| ATOM | 2829 | H2 | TIP3 | 57 | 40.050 | 43.185 | 76.701 | 1.00 | 0.00 |
| ATOM | 2830 | OH2 | TIP3 | 58 | 3.057 | 18.092 | 92.594 | 1.00 | 15.17 |
| ATOM | 2831 | H1 | TIP3 | 58 | 3.038 | 19.049 | 92.595 | 1.00 | 0.00 |
| ATOM | 2832 | H2 | TIP3 | 58 | 3.044 | 17.853 | 91.666 | 1.00 | 0.00 |
| ATOM | 2833 | OH2 | TIP3 | 59 | 13.402 | 23.676 | 95.191 | 1.00 | 18.92 |
| ATOM | 2834 | H1 | TIP3 | 59 | 13.392 | 24.628 | 95.178 | 1.00 | 0.00 |
| ATOM | 2835 | H2 | TIP3 | 59 | 13.388 | 23.427 | 94.259 | 1.00 | 0.00 |
| ATOM | 2836 | OH2 | TIP3 | 60 | 11.853 | 37.895 | 66.174 | 1.00 | 24.55 |
| ATOM | 2837 | H1 | TIP3 | 60 | 11.836 | 38.860 | 66.171 | 1.00 | 0.00 |
| ATOM | 2838 | H2 | TIP3 | 60 | 11.836 | 37.670 | 65.243 | 1.00 | 0.00 |
| ATOM | 2839 | OH2 | TIP3 | 61 | 24.411 | 67.363 | 74.598 | 1.00 | 19.56 |
| ATOM | 2840 | H1 | TIP3 | 61 | 24.434 | 68.332 | 74.589 | 1.00 | 0.00 |
| ATOM | 2841 | H2 | TIP3 | 61 | 24.434 | 67.144 | 73.661 | 1.00 | 0.00 |
| ATOM | 2842 | OH2 | TIP3 | 62 | 44.003 | 40.237 | 77.121 | 1.00 | 31.94 |

TABLE 3-continued

Coordinates of Lck bound with AMP-PNP

| | | Atom Type | Res | # | X | Y | Z | Occ | B |
|---|---|---|---|---|---|---|---|---|---|
| ATOM | 2843 | H1 | TIP3 | 62 | 43.457 | 41.037 | 77.326 | 1.00 | 0.00 |
| ATOM | 2844 | H2 | TIP3 | 62 | 43.436 | 39.913 | 76.436 | 1.00 | 0.00 |
| ATOM | 2845 | OH2 | TIP3 | 63 | 1.339 | 21.721 | 100.240 | 1.00 | 17.54 |
| ATOM | 2846 | H1 | TIP3 | 63 | 1.339 | 22.673 | 100.256 | 1.00 | 0.00 |
| ATOM | 2847 | H2 | TIP3 | 63 | 1.339 | 21.472 | 99.328 | 1.00 | 0.00 |
| ATOM | 2848 | OH2 | TIP3 | 64 | 11.283 | 66.503 | 68.672 | 1.00 | 18.27 |
| ATOM | 2849 | H1 | TIP3 | 64 | 11.300 | 67.456 | 68.667 | 1.00 | 0.00 |
| ATOM | 2850 | H2 | TIP3 | 64 | 11.300 | 66.356 | 67.742 | 1.00 | 0.00 |
| ATOM | 2851 | OH2 | TIP3 | 65 | 4.681 | 48.385 | 66.955 | 1.00 | 26.86 |
| ATOM | 2852 | H1 | TIP3 | 65 | 4.695 | 49.332 | 66.942 | 1.00 | 0.00 |
| ATOM | 2853 | H2 | TIP3 | 65 | 4.695 | 49.332 | 66.942 | 1.00 | 0.00 |
| ATOM | 2854 | OH2 | TIP3 | 66 | 23.486 | 29.111 | 77.108 | 1.00 | 18.25 |
| ATOM | 2855 | H1 | TIP3 | 66 | 23.490 | 30.049 | 77.092 | 1.00 | 0.00 |
| ATOM | 2856 | H2 | TIP3 | 66 | 23.496 | 28.856 | 76.174 | 1.00 | 0.00 |
| ATOM | 2857 | OH2 | TIP3 | 67 | 13.754 | 73.903 | 73.972 | 1.00 | 16.09 |
| ATOM | 2858 | H1 | TIP3 | 67 | 13.743 | 74.857 | 73.965 | 1.00 | 0.00 |
| ATOM | 2859 | H2 | TIP3 | 67 | 13.743 | 73.658 | 73.039 | 1.00 | 0.00 |
| ATOM | 2860 | OH2 | TIP3 | 68 | 15.325 | 54.153 | 81.648 | 1.00 | 15.14 |
| ATOM | 2861 | H1 | TIP3 | 68 | 15.321 | 55.104 | 81.648 | 1.00 | 0.00 |
| ATOM | 2862 | H2 | TIP3 | 68 | 15.321 | 53.903 | 80.723 | 1.00 | 0.00 |
| ATOM | 2863 | OH2 | TIP3 | 69 | 35.572 | 54.636 | 72.552 | 1.00 | 30.62 |
| ATOM | 2864 | H1 | TIP3 | 69 | 35.594 | 55.597 | 72.556 | 1.00 | 0.00 |
| ATOM | 2865 | H2 | TIP3 | 69 | 35.594 | 54.403 | 71.625 | 1.00 | 0.00 |
| ATOM | 2866 | OH2 | TIP3 | 70 | 25.795 | 53.197 | 58.018 | 1.00 | 33.10 |
| ATOM | 2867 | H1 | TIP3 | 70 | 25.769 | 54.178 | 58.023 | 1.00 | 0.00 |
| ATOM | 2868 | H2 | TIP3 | 70 | 25.659 | 52.994 | 57.086 | 1.00 | 0.00 |
| ATOM | 2869 | OH2 | TIP3 | 71 | 14.517 | 45.581 | 56.939 | 1.00 | 20.16 |
| ATOM | 2870 | H1 | TIP3 | 71 | 14.506 | 46.543 | 56.962 | 1.00 | 0.00 |
| ATOM | 2871 | H2 | TIP3 | 71 | 14.506 | 45.346 | 56.025 | 1.00 | 0.00 |
| ATOM | 2872 | OH2 | TIP3 | 72 | 9.677 | 42.302 | 87.127 | 1.00 | 22.96 |
| ATOM | 2873 | H1 | TIP3 | 72 | 9.690 | 43.260 | 87.147 | 1.00 | 0.00 |
| ATOM | 2874 | H2 | TIP3 | 72 | 9.690 | 42.060 | 86.212 | 1.00 | 0.00 |
| ATOM | 2875 | OH2 | TIP3 | 73 | 24.579 | 26.235 | 78.496 | 1.00 | 26.31 |
| ATOM | 2876 | H1 | TIP3 | 73 | 24.592 | 27.209 | 78.486 | 1.00 | 0.00 |
| ATOM | 2877 | H2 | TIP3 | 73 | 24.592 | 26.024 | 77.561 | 1.00 | 0.00 |
| ATOM | 2878 | OH2 | TIP3 | 74 | 17.567 | 34.269 | 99.900 | 1.00 | 24.15 |
| ATOM | 2879 | H1 | TIP3 | 74 | 17.549 | 35.217 | 99.899 | 1.00 | 0.00 |
| ATOM | 2880 | H2 | TIP3 | 74 | 17.550 | 34.016 | 98.977 | 1.00 | 0.00 |
| ATOM | 2881 | OH2 | TIP3 | 75 | 32.076 | 34.036 | 97.002 | 1.00 | 36.60 |
| ATOM | 2882 | H1 | TIP3 | 75 | 32.061 | 34.984 | 97.041 | 1.00 | 0.00 |
| ATOM | 2883 | H2 | TIP3 | 75 | 32.070 | 33.822 | 96.078 | 1.00 | 0.00 |
| ATOM | 2884 | OH2 | TIP3 | 76 | 29.996 | 33.471 | 98.371 | 1.00 | 32.47 |
| ATOM | 2885 | H1 | TIP3 | 76 | 30.003 | 34.432 | 98.365 | 1.00 | 0.00 |
| ATOM | 2886 | H2 | TIP3 | 76 | 30.003 | 33.240 | 97.440 | 1.00 | 0.00 |
| ATOM | 2887 | OH2 | TIP3 | 77 | 26.355 | 72.780 | 70.730 | 1.00 | 12.80 |
| ATOM | 2888 | H1 | TIP3 | 77 | 26.352 | 73.726 | 70.722 | 1.00 | 0.00 |
| ATOM | 2889 | H2 | TIP3 | 77 | 26.354 | 72.528 | 69.797 | 1.00 | 0.00 |
| ATOM | 2890 | OH2 | TIP3 | 78 | 12.021 | 33.492 | 80.130 | 1.00 | 11.11 |
| ATOM | 2891 | H1 | TIP3 | 78 | 12.012 | 34.444 | 80.131 | 1.00 | 0.00 |
| ATOM | 2892 | H2 | TIP3 | 78 | 12.012 | 33.245 | 79.207 | 1.00 | 0.00 |
| ATOM | 2893 | OH2 | TIP3 | 79 | 29.270 | 62.453 | 72.270 | 1.00 | 14.54 |
| ATOM | 2894 | H1 | TIP3 | 79 | 29.280 | 63.420 | 72.244 | 1.00 | 0.00 |
| ATOM | 2895 | H1 | TIP3 | 79 | 29.280 | 62.224 | 71.323 | 1.00 | 0.00 |
| ATOM | 2896 | OH2 | TIP3 | 80 | 26.858 | 65.447 | 74.374 | 1.00 | 14.48 |
| ATOM | 2897 | H1 | TIP3 | 80 | 26.860 | 66.399 | 74.373 | 1.00 | 0.00 |
| ATOM | 2898 | H2 | TIP3 | 80 | 26.866 | 65.196 | 73.462 | 1.00 | 0.00 |
| ATOM | 2899 | OH2 | TIP3 | 81 | 27.145 | 19.820 | 78.037 | 1.00 | 20.05 |
| ATOM | 2900 | H1 | TIP3 | 81 | 27.159 | 20.786 | 78.038 | 1.00 | 0.00 |
| ATOM | 2901 | H2 | TIP3 | 81 | 27.159 | 19.591 | 77.112 | 1.00 | 0.00 |
| ATOM | 2902 | OH2 | TIP3 | 82 | 29.828 | 36.381 | 82.139 | 1.00 | 22.88 |
| ATOM | 2903 | H1 | TIP3 | 82 | 29.845 | 27.338 | 82.130 | 1.00 | 0.00 |
| ATOM | 2904 | H2 | TIP3 | 82 | 29.845 | 36.141 | 81.206 | 1.00 | 0.00 |
| ATOM | 2905 | OH2 | TIP3 | 84 | 18.936 | 52.413 | 83.238 | 1.00 | 19.26 |
| ATOM | 2906 | H1 | TIP3 | 84 | 18.907 | 53.373 | 82.236 | 1.00 | 0.00 |
| ATOM | 2907 | H2 | TIP3 | 84 | 18.907 | 52.179 | 82.308 | 1.00 | 0.00 |
| ATOM | 2908 | OH2 | TIP3 | 85 | 27.489 | 24.446 | 94.600 | 1.00 | 23.28 |
| ATOM | 2909 | H1 | TIP3 | 85 | 27.449 | 25.406 | 94.617 | 1.00 | 0.00 |
| ATOM | 2910 | H2 | TIP3 | 85 | 27.449 | 24.207 | 93.689 | 1.00 | 0.00 |
| ATOM | 2911 | OH2 | TIP3 | 86 | −1.525 | 21.244 | 100.281 | 1.00 | 20.60 |
| ATOM | 2912 | H1 | TIP3 | 86 | −1.522 | 22.190 | 100.278 | 1.00 | 0.00 |
| ATOM | 2913 | H2 | TIP3 | 86 | −1.522 | 20.989 | 99.353 | 1.00 | 0.00 |
| ATOM | 2914 | OH2 | TIP3 | 87 | 15.694 | 35.478 | 101.363 | 1.00 | 21.69 |
| ATOM | 2915 | H1 | TIP3 | 87 | 15.706 | 36.430 | 101.284 | 1.00 | 0.00 |
| ATOM | 2916 | H2 | TIP3 | 87 | 15.706 | 35.236 | 100.447 | 1.00 | 0.00 |

TABLE 3-continued

Coordinates of Lck bound with AMP-PNP

| | | Atom Type | Res | # | X | Y | Z | Occ | B |
|---|---|---|---|---|---|---|---|---|---|
| ATOM | 2917 | OH2 | TIP3 | 88 | 34.425 | 37.817 | 76.435 | 1.00 | 19.28 |
| ATOM | 2918 | H1 | TIP3 | 88 | 34.435 | 38.779 | 76.430 | 1.00 | 0.00 |
| ATOM | 2919 | H2 | TIP3 | 88 | 34.435 | 37.591 | 75.503 | 1.00 | 0.00 |
| ATOM | 2920 | OH2 | TIP3 | 89 | 24.246 | 74.238 | 76.852 | 1.00 | 24.69 |
| ATOM | 2921 | H1 | TIP3 | 89 | 24.243 | 75.192 | 76.866 | 1.00 | 0.00 |
| ATOM | 2922 | H2 | TIP3 | 89 | 24.243 | 73.998 | 75.931 | 1.00 | 0.00 |
| ATOM | 2923 | OH2 | TIP3 | 90 | 13.178 | 22.440 | 79.586 | 1.00 | 20.65 |
| ATOM | 2924 | H1 | TIP3 | 90 | 13.179 | 23.405 | 79.587 | 1.00 | 0.00 |
| ATOM | 2925 | H1 | TIP3 | 90 | 13.179 | 22.206 | 78.661 | 1.00 | 0.00 |
| ATOM | 2926 | OH2 | TIP3 | 91 | 9.901 | 52.179 | 79.541 | 1.00 | 14.50 |
| ATOM | 2927 | H1 | TIP2 | 91 | 9.885 | 53.139 | 79.541 | 1.00 | 0.00 |
| ATOM | 2928 | H2 | TIP3 | 91 | 9.885 | 51.939 | 78.615 | 1.00 | 0.00 |
| ATOM | 2929 | OH2 | TIP3 | 92 | 20.065 | 71.147 | 85.203 | 1.00 | 24.37 |
| ATOM | 2930 | H1 | TIP3 | 92 | 20.041 | 72.108 | 85.216 | 1.00 | 0.00 |
| ATOM | 2931 | H2 | TIP3 | 92 | 20.041 | 70.911 | 84.282 | 1.00 | 0.00 |
| ATOM | 2932 | OH2 | TIP3 | 93 | 4.592 | 59.423 | 77.902 | 1.00 | 20.98 |
| ATOM | 2933 | H1 | TIP3 | 93 | 4.607 | 60.387 | 77.908 | 1.00 | 0.00 |
| ATOM | 2934 | H2 | TIP3 | 93 | 4.607 | 59.198 | 76.976 | 1.00 | 0.00 |
| ATOM | 2935 | OH2 | TIP3 | 94 | 10.454 | 59.113 | 64.371 | 1.00 | 20.16 |
| ATOM | 2936 | H1 | TIP3 | 94 | 10.456 | 60.064 | 64.357 | 1.00 | 0.00 |
| ATOM | 2937 | H2 | TIP3 | 94 | 10.456 | 58.865 | 63.346 | 1.00 | 0.00 |
| ATOM | 2938 | OH2 | TIP3 | 95 | 17.505 | 51.846 | 87.411 | 1.00 | 18.46 |
| ATOM | 2939 | H1 | TIP3 | 95 | 17.475 | 52.799 | 87.416 | 1.00 | 0.00 |
| ATOM | 2940 | H2 | TIP3 | 95 | 17.475 | 51.604 | 86.488 | 1.00 | 0.00 |
| ATOM | 2941 | OH2 | TIP3 | 96 | 14.817 | 19.185 | 88.279 | 1.00 | 20.43 |
| ATOM | 2942 | H1 | TIP3 | 96 | 14.808 | 20.144 | 88.264 | 1.00 | 0.00 |
| ATOM | 2943 | H2 | TIP3 | 96 | 14.808 | 18.951 | 87.347 | 1.00 | 0.00 |
| ATOM | 2944 | OH2 | TIP3 | 98 | 22.550 | 31.892 | 72.695 | 1.00 | 26.87 |
| ATOM | 2945 | H1 | TIP3 | 98 | 22.604 | 32.834 | 72.780 | 1.00 | 0.00 |
| ATOM | 2946 | H2 | TIP3 | 98 | 22.605 | 31.632 | 71.822 | 1.00 | 0.00 |
| ATOM | 2947 | OH2 | TIP3 | 99 | 16.431 | 46.142 | 86.054 | 1.00 | 19.46 |
| ATOM | 2948 | H1 | TIP3 | 99 | 16.410 | 47.101 | 86.053 | 1.00 | 0.00 |
| ATOM | 2949 | H2 | TIP3 | 99 | 16.412 | 45.907 | 85.128 | 1.00 | 0.00 |
| ATOM | 2950 | OH2 | TIP3 | 100 | 32.761 | 59.838 | 71.205 | 1.00 | 21.01 |
| ATOM | 2951 | H1 | TIP3 | 100 | 32.787 | 60.797 | 71.210 | 1.00 | 0.00 |
| ATOM | 2952 | H2 | TIP3 | 100 | 32.789 | 59.595 | 70.293 | 1.00 | 0.00 |
| ATOM | 2953 | OH2 | TIP3 | 101 | 12.534 | 45.025 | 99.009 | 1.00 | 24.38 |
| ATOM | 2954 | H1 | TIP3 | 101 | 12.550 | 45.969 | 99.012 | 1.00 | 0.00 |
| ATOM | 2955 | H2 | TIP3 | 101 | 12.550 | 45.969 | 99.012 | 1.00 | 0.00 |
| ATOM | 2956 | OH2 | TIP3 | 102 | 15.287 | 38.470 | 102.089 | 1.00 | 20.83 |
| ATOM | 2957 | H1 | TIP3 | 102 | 15.270 | 39.417 | 102.112 | 1.00 | 0.00 |
| ATOM | 2958 | H1 | TIP3 | 102 | 15.270 | 39.417 | 102.112 | 1.00 | 0.00 |
| ATOM | 2959 | OH2 | TIP3 | 103 | −1.791 | 21.163 | 94.344 | 1.00 | 19.97 |
| ATOM | 2960 | H1 | TIP3 | 103 | −1.773 | 22.122 | 94.336 | 1.00 | 0.00 |
| ATOM | 2961 | H2 | TIP3 | 103 | −1.775 | 20.933 | 93.418 | 1.00 | 0.00 |
| ATOM | 2962 | OH2 | TIP3 | 104 | 23.344 | 43.006 | 94.136 | 1.00 | 22.28 |
| ATOM | 2963 | H1 | TIP3 | 104 | 23.328 | 43.972 | 94.120 | 1.00 | 0.00 |
| ATOM | 2964 | H2 | TIP3 | 104 | 23.329 | 42.778 | 93.195 | 1.00 | 0.00 |
| ATOM | 2965 | OH2 | TIP3 | 105 | 24.245 | 18.434 | 94.544 | 1.00 | 24.15 |
| ATOM | 2966 | H1 | TIP3 | 105 | 24.232 | 19.393 | 94.540 | 1.00 | 0.00 |
| ATOM | 2967 | H2 | TIP3 | 105 | 24.232 | 18.194 | 93.617 | 1.00 | 0.00 |
| ATOM | 2968 | OH2 | TIP3 | 106 | 21.538 | 63.422 | 69.289 | 1.00 | 23.57 |
| ATOM | 2969 | H1 | TIP3 | 106 | 32.501 | 64.379 | 69.349 | 1.00 | 0.00 |
| ATOM | 2970 | H2 | TIP3 | 106 | 32.500 | 63.180 | 68.399 | 1.00 | 0.00 |
| ATOM | 2971 | OH2 | TIP3 | 107 | 32.847 | 33.726 | 71.640 | 1.00 | 22.75 |
| ATOM | 2972 | H1 | TIP3 | 107 | 32.482 | 34.676 | 71.651 | 1.00 | 0.00 |
| ATOM | 2973 | H2 | TIP3 | 107 | 32.842 | 33.471 | 70.723 | 1.00 | 0.00 |
| ATOM | 2974 | OH2 | TIP3 | 108 | 6.155 | 39.952 | 88.035 | 1.00 | 22.81 |
| ATOM | 2975 | H1 | TIP3 | 108 | 6.119 | 40.912 | 88.027 | 1.00 | 0.00 |
| ATOM | 2976 | H2 | TIP3 | 108 | 6.119 | 39.714 | 87.107 | 1.00 | 0.00 |
| ATOM | 2977 | OH2 | TIP3 | 109 | 27.765 | 29.208 | 75.507 | 1.00 | 27.86 |
| ATOM | 2978 | H1 | TIP3 | 109 | 27.701 | 30.128 | 75.507 | 1.00 | 0.00 |
| ATOM | 2979 | H2 | TIP3 | 109 | 27.702 | 28.917 | 74.585 | 1.00 | 0.00 |
| ATOM | 2980 | OH2 | TIP3 | 110 | 34.641 | 32.194 | 91.953 | 1.00 | 27.76 |
| ATOM | 2981 | H1 | TIP3 | 110 | 34.657 | 33.159 | 91.941 | 1.00 | 0.00 |
| ATOM | 2982 | H2 | TIP3 | 110 | 34.657 | 31.965 | 91.107 | 1.00 | 0.00 |
| ATOM | 2983 | OH2 | TIP3 | 111 | 5.934 | 50.021 | 63.248 | 1.00 | 22.40 |
| ATOM | 2984 | H1 | TIP3 | 111 | 5.943 | 50.984 | 63.248 | 1.00 | 0.00 |
| ATOM | 2985 | H2 | TIP3 | 111 | 5.943 | 49.791 | 62.317 | 1.00 | 0.00 |
| ATOM | 2986 | OH2 | TIP3 | 112 | 7.947 | 27.996 | 92.109 | 1.00 | 26.50 |
| ATOM | 2987 | H1 | TIP3 | 112 | 7.940 | 28.966 | 92.116 | 1.00 | 0.00 |
| ATOM | 2988 | H2 | TIP3 | 112 | 7.940 | 27.778 | 91.185 | 1.00 | 0.00 |
| ATOM | 2989 | OH2 | TIP3 | 113 | 4.672 | 62.116 | 78.254 | 1.00 | 20.82 |
| ATOM | 2990 | H1 | TIP3 | 113 | 4.662 | 63.064 | 78.251 | 1.00 | 0.00 |

TABLE 3-continued

Coordinates of Lck bound with AMP-PNP

| | | Atom Type | Res | # | X | Y | Z | Occ | B |
|---|---|---|---|---|---|---|---|---|---|
| ATOM | 2991 | H2 | TIP3 | 113 | 4.662 | 61.865 | 77.235 | 1.00 | 0.00 |
| ATOM | 2992 | OH2 | TIP3 | 114 | 12.054 | 21.331 | 95.197 | 1.00 | 26.63 |
| ATOM | 2993 | H1 | TIP3 | 114 | 12.049 | 22.291 | 95.167 | 1.00 | 0.00 |
| ATOM | 2994 | H2 | TIP3 | 114 | 12.052 | 21.095 | 94.252 | 1.00 | 0.00 |
| ATOM | 2995 | OH2 | TIP3 | 115 | −5.706 | 20.084 | 93.477 | 1.00 | 29.07 |
| ATOM | 2996 | H1 | TIP3 | 115 | −5.716 | 21.048 | 93.469 | 1.00 | 0.00 |
| ATOM | 2997 | H1 | TIP3 | 115 | −5.716 | 19.857 | 92.543 | 1.00 | 0.00 |
| ATOM | 2998 | OH2 | TIP3 | 116 | 24.383 | 48.971 | 60.475 | 1.00 | 24.24 |
| ATOM | 2999 | H1 | TIP3 | 116 | 34.275 | 49.932 | 60.475 | 1.00 | 0.00 |
| ATOM | 3000 | H2 | TIP3 | 116 | 34.275 | 48.735 | 59.548 | 1.00 | 0.00 |
| ATOM | 3001 | OH2 | TIP3 | 117 | 15.304 | 39.745 | 90.950 | 1.00 | 20.18 |
| ATOM | 3002 | H1 | TIP3 | 117 | 15.290 | 40.701 | 90.942 | 1.00 | 0.00 |
| ATOM | 3003 | H2 | TIP3 | 117 | 15.288 | 39.499 | 90.029 | 1.00 | 0.00 |
| ATOM | 3004 | OH2 | TIP3 | 118 | 20.425 | 34.287 | 86.652 | 1.00 | 21.38 |
| ATOM | 3005 | H1 | TIP3 | 118 | 20.420 | 34.057 | 85.722 | 1.00 | 0.00 |
| ATOM | 3006 | H2 | TIP3 | 118 | 20.420 | 34.057 | 85.722 | 1.00 | 0.00 |
| ATOM | 3007 | OH2 | TIP3 | 119 | 12.946 | 30.671 | 72.330 | 1.00 | 21.81 |
| ATOM | 3008 | H1 | TIP3 | 119 | 12.939 | 31.621 | 72.336 | 1.00 | 0.00 |
| ATOM | 3009 | H2 | TIP3 | 119 | 12.939 | 30.415 | 71.413 | 1.00 | 0.00 |
| ATOM | 3010 | OH2 | TIP3 | 120 | 29.267 | 70.890 | 70.793 | 1.00 | 22.48 |
| ATOM | 3011 | H1 | TIP3 | 120 | 29.268 | 71.844 | 70.799 | 1.00 | 0.00 |
| ATOM | 3012 | H2 | TIP3 | 120 | 29.268 | 70.649 | 69.867 | 1.00 | 0.00 |
| ATOM | 3013 | OH2 | TIP3 | 121 | 6.147 | 34.663 | 75.934 | 1.00 | 27.35 |
| ATOM | 3014 | H1 | TIP3 | 121 | 6.142 | 35.632 | 75.940 | 1.00 | 0.00 |
| ATOM | 3015 | H2 | TIP3 | 121 | 6.142 | 34.437 | 75.013 | 1.00 | 0.00 |
| ATOM | 3016 | OH2 | TIP3 | 122 | 26.574 | 74.898 | 74.914 | 1.00 | 24.47 |
| ATOM | 3017 | H1 | TIP3 | 122 | 26.584 | 75.856 | 74.919 | 1.00 | 0.00 |
| ATOM | 3018 | H2 | TIP3 | 122 | 26.584 | 74.655 | 73.993 | 1.00 | 0.00 |
| ATOM | 3019 | OH2 | TIP3 | 123 | 40.624 | 38.731 | 69.427 | 1.00 | 27.91 |
| ATOM | 3020 | H1 | TIP3 | 123 | 40.626 | 39.681 | 69.432 | 1.00 | 0.00 |
| ATOM | 3021 | H2 | TIP3 | 123 | 40.631 | 38.485 | 68.506 | 1.00 | 0.00 |
| ATOM | 3022 | OH2 | TIP3 | 124 | 18.335 | 74.758 | 79.540 | 1.00 | 23.98 |
| ATOM | 3023 | H1 | TIP3 | 124 | 18.311 | 75.515 | 79.532 | 1.00 | 0.00 |
| ATOM | 3024 | H2 | TIP3 | 124 | 18.309 | 74.518 | 78.613 | 1.00 | 0.00 |
| ATOM | 3025 | OH2 | TIP3 | 125 | 24.254 | 25.876 | 95.658 | 1.00 | 25.27 |
| ATOM | 3026 | H1 | TIP3 | 125 | 24.260 | 36.817 | 95.653 | 1.00 | 0.00 |
| ATOM | 3027 | H2 | TIP3 | 125 | 24.258 | 25.610 | 94.733 | 1.00 | 0.00 |
| ATOM | 3028 | OH2 | TIP3 | 126 | 27.246 | 26.940 | 73.274 | 1.00 | 26.51 |
| ATOM | 3029 | H1 | TIP3 | 126 | 27.105 | 27.879 | 73.539 | 1.00 | 0.00 |
| ATOM | 3030 | H2 | TIP3 | 126 | 27.084 | 26.684 | 72.509 | 1.00 | 0.00 |
| ATOM | 3031 | OH2 | TIP3 | 127 | 34.397 | 35.886 | 70.708 | 1.00 | 31.80 |
| ATOM | 3032 | H1 | TIP3 | 127 | 34.382 | 36.839 | 70.706 | 1.00 | 0.00 |
| ATOM | 3033 | H2 | TIP3 | 127 | 34.382 | 35.642 | 69.782 | 1.00 | 0.00 |
| ATOM | 3034 | OH2 | TIP3 | 128 | 9.465 | 66.059 | 80.174 | 1.00 | 30.85 |
| ATOM | 3035 | H1 | TIP3 | 128 | 9.469 | 67.026 | 80.156 | 1.00 | 0.00 |
| ATOM | 3036 | H2 | TIP3 | 128 | 9.469 | 65.836 | 79.229 | 1.00 | 0.00 |
| ATOM | 3037 | OH2 | TIP3 | 129 | 5.931 | 42.078 | 93.970 | 1.00 | 27.38 |
| ATOM | 3038 | H1 | TIP3 | 129 | 5.912 | 43.032 | 93.981 | 1.00 | 0.00 |
| ATOM | 3039 | H2 | TIP3 | 129 | 5.912 | 41.838 | 93.047 | 1.00 | 0.00 |
| ATOM | 3040 | OH2 | TIP3 | 130 | 20.620 | 40.016 | 85.891 | 1.00 | 38.29 |
| ATOM | 3041 | H1 | TIP3 | 130 | 20.594 | 40.972 | 85.901 | 1.00 | 0.00 |
| ATOM | 3042 | H2 | TIP3 | 130 | 20.594 | 39.776 | 84.970 | 1.00 | 0.00 |
| ATOM | 3043 | OH2 | TIP3 | 131 | 22.022 | 36.821 | 86.431 | 1.00 | 32.96 |
| ATOM | 3044 | H1 | TIP3 | 131 | 21.996 | 37.776 | 86.440 | 1.00 | 0.00 |
| ATOM | 3045 | H2 | TIP3 | 131 | 21.996 | 36.580 | 85.509 | 1.00 | 0.00 |
| ATOM | 3046 | OH2 | TIP3 | 132 | 20.893 | 36.741 | 83.379 | 1.00 | 22.74 |
| ATOM | 3047 | H1 | TIP3 | 132 | 20.877 | 37.688 | 83.396 | 1.00 | 0.00 |
| ATOM | 3048 | H2 | TIP3 | 132 | 20.877 | 36.485 | 82.465 | 1.00 | 0.00 |
| ATOM | 3049 | OH2 | TIP3 | 133 | 23.406 | 58.660 | 84.323 | 1.00 | 21.15 |
| ATOM | 3050 | H1 | TIP3 | 133 | 23.406 | 59.609 | 84.347 | 1.00 | 0.00 |
| ATOM | 3051 | H2 | TIP3 | 133 | 23.406 | 58.410 | 83.417 | 1.00 | 0.00 |
| ATOM | 3052 | OH2 | TIP3 | 134 | 23.629 | 54.392 | 85.766 | 1.00 | 36.35 |
| ATOM | 3053 | H1 | TIP3 | 134 | 23.628 | 55.363 | 85.762 | 1.00 | 0.00 |
| ATOM | 3054 | H2 | TIP3 | 134 | 23.630 | 51.174 | 84.835 | 1.00 | 0.00 |
| ATOM | 3055 | OH2 | TIP3 | 135 | 22.408 | 62.871 | 89.478 | 1.00 | 30.51 |
| ATOM | 3056 | H1 | TIP3 | 135 | 22.406 | 64.808 | 89.470 | 1.00 | 0.00 |
| ATOM | 3057 | H2 | TIP3 | 135 | 22.376 | 62.612 | 88.565 | 1.00 | 0.00 |
| ATOM | 3058 | OH2 | TIP3 | 136 | 19.425 | 59.372 | 89.140 | 1.00 | 30.89 |
| ATOM | 3059 | H1 | TIP3 | 136 | 19.425 | 60.328 | 89.123 | 1.00 | 0.00 |
| ATOM | 3060 | H2 | TIP3 | 136 | 19.427 | 59.136 | 88.202 | 1.00 | 0.00 |
| ATOM | 3061 | OH2 | TIP3 | 137 | 11.615 | 59.513 | 87.932 | 1.00 | 28.83 |
| ATOM | 3062 | H1 | TIP3 | 137 | 11.605 | 60.461 | 87.938 | 1.00 | 0.00 |
| ATOM | 3063 | H2 | TIP3 | 137 | 11.605 | 59.258 | 87.013 | 1.00 | 0.00 |
| ATOM | 3064 | OH2 | TIP3 | 138 | 12.694 | 69.504 | 76.549 | 1.00 | 29.32 |

TABLE 3-continued

Coordinates of Lck bound with AMP-PNP

| | | Atom Type | Res | # | X | Y | Z | Occ | B |
|---|---|---|---|---|---|---|---|---|---|
| ATOM | 3065 | H1 | TIP3 | 138 | 12.696 | 70.443 | 76.547 | 1.00 | 0.00 |
| ATOM | 3066 | H2 | TIP3 | 138 | 12.698 | 69.237 | 75.628 | 1.00 | 0.00 |
| ATOM | 3067 | OH2 | TIP3 | 139 | 32.023 | 33.237 | 67.973 | 1.00 | 28.64 |
| ATOM | 3068 | H1 | TIP3 | 139 | 32.002 | 33.008 | 67.035 | 1.00 | 0.00 |
| ATOM | 3069 | H2 | TIP3 | 139 | 32.022 | 33.008 | 67.035 | 1.00 | 0.00 |
| ATOM | 3070 | OH2 | TIP3 | 140 | 26.673 | 28.035 | 77.708 | 1.00 | 22.76 |
| ATOM | 3071 | H1 | TIP3 | 140 | 26.701 | 28.969 | 77.676 | 1.00 | 0.00 |
| ATOM | 3072 | H2 | TIP3 | 140 | 26.701 | 27.768 | 76.777 | 1.00 | 0.00 |
| ATOM | 3073 | OH2 | TIP3 | 141 | 32.465 | 52.473 | 65.827 | 1.00 | 30.71 |
| ATOM | 3074 | H1 | TIP3 | 141 | 32.493 | 53.434 | 65.832 | 1.00 | 0.00 |
| ATOM | 3075 | H2 | TIP3 | 141 | 32.493 | 52.238 | 64.904 | 1.00 | 0.0 |
| ATOM | 3076 | OH2 | TIP3 | 142 | 28.087 | 61.297 | 62.694 | 1.00 | 25.89 |
| ATOM | 3077 | H1 | TIP3 | 142 | 28.121 | 62.254 | 62.696 | 1.00 | 0.00 |
| ATOM | 3078 | H2 | TIP3 | 142 | 28.121 | 61.054 | 61.769 | 1.00 | 0.00 |
| ATOM | 3079 | OH2 | TIP3 | 143 | 3.030 | 49.726 | 71.581 | 1.00 | 29.32 |
| ATOM | 3080 | H1 | TIP3 | 143 | 3.019 | 50.689 | 71.562 | 1.00 | 0.00 |
| ATOM | 3081 | H2 | TIP3 | 143 | 3.019 | 49.500 | 70.637 | 1.00 | 0.00 |
| ATOM | 3082 | OH2 | TIP3 | 144 | 3.075 | 49.647 | 74.581 | 1.00 | 22.68 |
| ATOM | 3083 | H1 | TIP3 | 144 | 3.069 | 50.596 | 74.585 | 1.00 | 0.00 |
| ATOM | 3084 | H2 | TIP3 | 144 | 3.069 | 49.398 | 73.657 | 1.00 | 0.00 |
| ATOM | 3085 | OH2 | TIP3 | 145 | 5.155 | 55.012 | 64.654 | 1.00 | 25.00 |
| ATOM | 3086 | H1 | TIP3 | 145 | 5.114 | 55.977 | 64.654 | 1.00 | 0.00 |
| ATOM | 3087 | H2 | TIP3 | 145 | 5.114 | 54.783 | 63.725 | 1.00 | 0.00 |
| ATOM | 3088 | OH2 | TIP3 | 146 | 2.649 | 52.569 | 67.943 | 1.00 | 27.65 |
| ATOM | 3089 | H1 | TIP3 | 146 | 2.598 | 53.542 | 67.945 | 1.00 | 0.00 |
| ATOM | 3090 | H2 | TIP3 | 146 | 2.598 | 52.353 | 67.013 | 1.00 | 0.00 |
| ATOM | 3091 | OH2 | TIP3 | 147 | 25.491 | 46.315 | 95.161 | 1.00 | 23.75 |
| ATOM | 3092 | H1 | TIP3 | 147 | 25.505 | 47.272 | 95.167 | 1.00 | 0.00 |
| ATOM | 3093 | H2 | TIP3 | 147 | 25.505 | 46.074 | 94.235 | 1.00 | 0.00 |
| ATOM | 3094 | OH2 | TIP3 | 148 | 24.063 | 56.944 | 86.112 | 1.00 | 32.65 |
| ATOM | 3095 | H1 | TIP3 | 148 | 24.066 | 57.893 | 86.106 | 1.00 | 0.00 |
| ATOM | 3096 | H2 | TIP3 | 148 | 24.066 | 56.690 | 85.182 | 1.00 | 0.00 |
| ATOM | 3097 | OH2 | TIP3 | 149 | 9.768 | 51.724 | 89.764 | 1.00 | 30.10 |
| ATOM | 3098 | H1 | TIP3 | 149 | 9.550 | 52.635 | 89.797 | 1.00 | 0.00 |
| ATOM | 3099 | H2 | TIP3 | 149 | 9.559 | 51.416 | 88.881 | 1.00 | 0.00 |
| ATOM | 3100 | OH2 | TIP3 | 150 | 12.830 | 31.443 | 74.972 | 1.00 | 18.61 |
| ATOM | 3101 | H1 | TIP3 | 150 | 12.785 | 32.261 | 75.002 | 1.00 | 0.00 |
| ATOM | 3102 | H2 | TIP3 | 150 | 12.786 | 31.134 | 74.076 | 1.00 | 0.00 |
| ATOM | 3103 | OH2 | TIP3 | 151 | 12.058 | 29.386 | 75.911 | 1.00 | 26.41 |
| ATOM | 3104 | H1 | TIP3 | 151 | 12.139 | 30.373 | 75.907 | 1.00 | 0.00 |
| ATOM | 3105 | H2 | TIP3 | 151 | 12.148 | 29.211 | 74.698 | 1.00 | 0.00 |
| ATOM | 3106 | OH2 | TIP3 | 152 | 21.920 | 58.891 | 87.253 | 1.00 | 24.49 |
| ATOM | 3107 | H1 | TIP3 | 152 | 21.940 | 59.824 | 87.237 | 1.00 | 0.00 |
| ATOM | 3108 | H2 | TIP3 | 152 | 21.940 | 58.618 | 86.318 | 1.00 | 0.00 |
| ATOM | 3109 | OH2 | TIP3 | 153 | 10.991 | 44.408 | 57.618 | 1.00 | 30.05 |
| ATOM | 3110 | H1 | TIP3 | 153 | 11.001 | 45.351 | 57.616 | 1.00 | 0.00 |
| ATOM | 3111 | H2 | TIP3 | 153 | 11.001 | 44.143 | 56.693 | 1.00 | 0.00 |
| ATOM | 3112 | OH2 | TIP3 | 154 | 14.634 | 59.750 | 88.168 | 1.00 | 26.28 |
| ATOM | 3113 | H1 | TIP3 | 154 | 14.619 | 59.504 | 87.239 | 1.00 | 0.00 |
| ATOM | 3114 | H2 | TIP3 | 154 | 14.619 | 60.708 | 88.160 | 1.00 | 0.00 |
| ATOM | 3115 | OH2 | TIP3 | 155 | 3.782 | 51.970 | 70.479 | 1.00 | 31.90 |
| ATOM | 3116 | H1 | TIP3 | 155 | 3.755 | 52.919 | 70.475 | 1.00 | 0.00 |
| ATOM | 3117 | H2 | TIP3 | 155 | 3.755 | 51.716 | 69.553 | 1.00 | 0.00 |
| ATOM | 3118 | OH2 | TIP2 | 156 | 4.635 | 28.099 | 96.066 | 1.00 | 26.26 |
| ATOM | 3119 | H1 | TIP3 | 156 | 4.632 | 29.065 | 96.071 | 1.00 | 0.00 |
| ATOM | 3120 | H2 | TIP3 | 156 | 4.632 | 27.872 | 95.143 | 1.00 | 0.00 |
| ATOM | 3121 | OH2 | TIP3 | 157 | 18.575 | 41.802 | 92.535 | 1.00 | 36.30 |
| ATOM | 3122 | H1 | TIP3 | 157 | 18.614 | 42.757 | 92.517 | 1.00 | 0.00 |
| ATOM | 3123 | H2 | TIP3 | 157 | 18.614 | 41.555 | 91.599 | 1.00 | 0.00 |
| ATOM | 3124 | OH2 | TIP3 | 158 | 22.860 | 41.454 | 83.366 | 1.00 | 35.87 |
| ATOM | 3125 | H1 | TIP3 | 158 | 22.858 | 42.404 | 83.372 | 1.00 | 0.00 |
| ATOM | 3126 | H2 | TIP3 | 158 | 22.858 | 41.204 | 82.446 | 1.00 | 0.00 |
| ATOM | 3127 | OH2 | TIP3 | 159 | 11.591 | 46.630 | 90.976 | 1.00 | 25.90 |
| ATOM | 3128 | H1 | TIP3 | 159 | 11.624 | 47.583 | 91.014 | 1.00 | 0.00 |
| ATOM | 3129 | H2 | TIP3 | 159 | 11.624 | 46.384 | 90.077 | 1.00 | 0.00 |
| ATOM | 3130 | OH2 | TIP3 | 160 | 10.980 | 42.843 | 83.397 | 1.00 | 25.17 |
| ATOM | 3131 | H1 | TIP3 | 160 | 10.945 | 43.804 | 89.370 | 1.00 | 0.00 |
| ATOM | 3132 | H2 | TIP3 | 160 | 10.948 | 42.611 | 88.449 | 1.00 | 0.00 |
| ATOM | 3133 | OH2 | TIP3 | 161 | 2.899 | 52.279 | 89.567 | 1.00 | 35.93 |
| ATOM | 3134 | H1 | TIP3 | 161 | 2.875 | 53.239 | 89.576 | 1.00 | 0.00 |
| ATOM | 3135 | H2 | TIP3 | 161 | 2.884 | 52.048 | 88.642 | 1.00 | 0.00 |
| ATOM | 3136 | OH2 | TIP3 | 162 | 1.360 | 52.599 | 87.123 | 1.00 | 33.19 |
| ATOM | 3137 | H1 | TIP3 | 162 | 1.380 | 53.547 | 87.127 | 1.00 | 0.00 |
| ATOM | 3138 | H2 | TIP3 | 162 | 1.380 | 52.347 | 86.199 | 1.00 | 0.00 |

TABLE 3-continued

Coordinates of Lck bound with AMP-PNP

| | | Atom Type | Res | # | X | Y | Z | Occ | B |
|---|---|---|---|---|---|---|---|---|---|
| ATOM | 3139 | OH2 | TIP3 | 163 | 31.471 | 41.458 | 88.534 | 1.00 | 28.07 |
| ATOM | 3140 | H1 | TIP3 | 163 | 31.480 | 42.416 | 88.537 | 1.00 | 0.00 |
| ATOM | 3141 | H2 | TIP3 | 163 | 31.480 | 41.221 | 87.611 | 1.00 | 0.00 |
| ATOM | 3142 | OH2 | TIP3 | 164 | 31.236 | 37.995 | 83.715 | 1.00 | 35.98 |
| ATOM | 3143 | H1 | TIP3 | 164 | 31.244 | 38.937 | 83.680 | 1.00 | 0.00 |
| ATOM | 3144 | H2 | TIP3 | 164 | 31.244 | 27.740 | 82.766 | 1.00 | 0.00 |
| ATOM | 3145 | OH2 | TIP3 | 165 | 27.212 | 63.696 | 87.135 | 1.00 | 31.88 |
| ATOM | 3146 | H1 | TIP3 | 165 | 27.267 | 64.673 | 87.158 | 1.00 | 0.00 |
| ATOM | 3147 | H2 | TIP3 | 165 | 27.267 | 64.673 | 87.158 | 1.00 | 0.00 |
| ATOM | 3148 | OH2 | TIP3 | 166 | 16.681 | 64.326 | 68.227 | 1.00 | 14.19 |
| ATOM | 3149 | H1 | TIP3 | 166 | 16.644 | 65.299 | 68.243 | 1.00 | 0.00 |
| ATOM | 3150 | H2 | TIP3 | 166 | 16.644 | 64.102 | 67.313 | 1.00 | 0.00 |
| ATOM | 3151 | OH2 | TIP3 | 167 | 6.593 | 17.748 | 94.755 | 1.00 | 16.77 |
| ATOM | 3152 | H1 | TIP3 | 167 | 6.603 | 18.698 | 94.780 | 1.00 | 0.00 |
| ATOM | 3153 | H2 | TIP3 | 167 | 6.603 | 17.497 | 93.487 | 1.00 | 0.00 |
| ATOM | 3154 | OH2 | TIP3 | 168 | 3.319 | 56.318 | 74.128 | 1.00 | 35.41 |
| ATOM | 3155 | H1 | TIP3 | 168 | 3.338 | 57.270 | 74.09 | 1.00 | 0.00 |
| ATOM | 3156 | H2 | TIP3 | 168 | 3.338 | 56.073 | 73.190 | 1.00 | 0.00 |
| ATOM | 3157 | OH2 | TIP3 | 169 | 17.419 | 44.179 | 55.313 | 1.00 | 27.44 |
| ATOM | 3158 | H1 | TIP3 | 169 | 17.421 | 45.116 | 55.309 | 1.00 | 0.00 |
| ATOM | 3159 | H2 | TIP3 | 169 | 17.418 | 43.918 | 54.386 | 1.00 | 0.00 |
| ATOM | 3160 | OH2 | TIP3 | 170 | 23.116 | 45.953 | 85.369 | 1.00 | 30.99 |
| ATOM | 3161 | H1 | TIP3 | 170 | 23.152 | 46.921 | 85.402 | 1.00 | 0.00 |
| ATOM | 3162 | H2 | TIP3 | 170 | 23.155 | 45.744 | 84.459 | 1.00 | 0.00 |
| ATOM | 3163 | OH2 | TIP3 | 171 | 23.784 | 31.626 | 74.741 | 1.00 | 27.99 |
| ATOM | 3164 | H1 | TIP3 | 171 | 23.692 | 32.577 | 74.679 | 1.00 | 0.00 |
| ATOM | 3165 | H2 | TIP3 | 171 | 23.699 | 31.381 | 73.782 | 1.00 | 0.00 |
| ATOM | 3166 | OH2 | TIP3 | 172 | 29.228 | 23.854 | 78.309 | 1.00 | 33.69 |
| ATOM | 3167 | H1 | TIP3 | 172 | 29.203 | 24.821 | 78.316 | 1.00 | 0.00 |
| ATOM | 3168 | H2 | TIP3 | 172 | 29.203 | 23.628 | 77.385 | 1.00 | 0.00 |
| ATOM | 3169 | OH2 | TIP3 | 173 | 12.110 | 62.970 | 61.321 | 1.00 | 30.60 |
| ATOM | 3170 | H1 | TIP3 | 173 | 12.072 | 62.931 | 61.315 | 1.00 | 0.00 |
| ATOM | 3171 | H2 | TIP3 | 173 | 12.072 | 62.735 | 60.389 | 1.00 | 0.00 |
| ATOM | 3172 | OH2 | TIP3 | 174 | 7.496 | 21.769 | 90.909 | 1.00 | 29.01 |
| ATOM | 3173 | H1 | TIP3 | 174 | 7.519 | 22.745 | 90.874 | 1.00 | 0.00 |
| ATOM | 3174 | H2 | TIP3 | 174 | 7.514 | 21.560 | 89.967 | 1.00 | 0.00 |
| ATOM | 3175 | OH2 | TIP3 | 175 | 6.066 | 34.847 | 93.635 | 1.00 | 28.39 |
| ATOM | 3176 | H1 | TIP3 | 175 | 6.053 | 35.815 | 92.632 | 1.00 | 0.00 |
| ATOM | 3177 | H2 | TIP3 | 175 | 6.049 | 34.618 | 92.720 | 1.00 | 0.00 |
| ATOM | 3178 | OH2 | TIP3 | 176 | 6.593 | 44.033 | 89.946 | 1.00 | 33.99 |
| ATOM | 3179 | H1 | TIP3 | 176 | 6.575 | 44.965 | 89.812 | 1.00 | 0.00 |
| ATOM | 3180 | HE | TIP3 | 176 | 6.621 | 43.816 | 89.011 | 1.00 | 0.00 |
| ATOM | 3181 | OH2 | TIP3 | 177 | 10.295 | 25.226 | 82.030 | 1.00 | 32.08 |
| ATOM | 3182 | H1 | TIP3 | 177 | 10.182 | 26.172 | 82.011 | 1.00 | 0.00 |
| ATOM | 3183 | HE | TIP3 | 177 | 10.184 | 24.969 | 81.098 | 1.00 | 0.00 |
| ATOM | 3184 | OH2 | TIP3 | 178 | 0.809 | 45.203 | 71.524 | 1.00 | 25.10 |
| ATOM | 3185 | H1 | TIP3 | 178 | 0.842 | 46.181 | 71.532 | 1.00 | 0.00 |
| ATOM | 3186 | H2 | TIP3 | 178 | 0.842 | 44.995 | 70.597 | 1.00 | 0.00 |
| ATOM | 3187 | OH2 | TIP3 | 179 | 22.972 | 43.363 | 102.150 | 1.00 | 36.75 |
| ATOM | 3188 | H1 | TIP3 | 179 | 22.966 | 44.314 | 102.170 | 1.00 | 0.00 |
| ATOM | 3189 | H2 | TIP3 | 179 | 22.966 | 43.115 | 101.236 | 1.00 | 0.00 |
| ATOM | 3190 | OH2 | TIP3 | 180 | 23.237 | 48.451 | 85.106 | 1.00 | 35.30 |
| ATOM | 3191 | H1 | TIP3 | 180 | 23.257 | 49.383 | 85.127 | 1.00 | 0.00 |
| ATOM | 3192 | H2 | TIP3 | 180 | 23.257 | 48.176 | 84.197 | 1.00 | 0.00 |
| ATOM | 3193 | OH2 | TIP3 | 181 | 4.043 | 34.604 | 85.757 | 1.00 | 24.15 |
| ATOM | 3194 | H1 | TIP3 | 181 | 4.019 | 35.656 | 85.771 | 1.00 | 0.00 |
| ATOM | 3195 | H2 | TIP3 | 181 | 4.019 | 34.455 | 84.843 | 1.00 | 0.00 |
| ATOM | 3166 | OH2 | TIP3 | 172 | 29.228 | 23.854 | 78.308 | 1.00 | 33.69 |
| ATOM | 3167 | H1 | TIP3 | 172 | 29.203 | 24.821 | 78.316 | 1.00 | 0.00 |
| ATOM | 3168 | H1 | TIP3 | 172 | 29.203 | 23.628 | 77.385 | 1.00 | 0.00 |
| ATOM | 3169 | OH2 | TIP3 | 173 | 12.110 | 62.970 | 61.321 | 1.00 | 30.60 |
| ATOM | 3170 | H1 | TIP3 | 173 | 12.072 | 63.931 | 61.315 | 1.00 | 0.00 |
| ATOM | 3171 | H2 | TIP3 | 173 | 12.072 | 63.931 | 61.315 | 1.00 | 0.00 |
| ATOM | 3172 | OH2 | TIP3 | 174 | 7.496 | 21.769 | 90.909 | 1.00 | 29.01 |
| ATOM | 3173 | H1 | TIP3 | 174 | 7.519 | 22.745 | 90.874 | 1.00 | 0.00 |
| ATOM | 3174 | H2 | TIP3 | 174 | 7.514 | 21.560 | 89.967 | 1.00 | 0.00 |
| ATOM | 3175 | OH2 | TIP3 | 175 | 6.066 | 34.847 | 93.635 | 1.00 | 28.39 |
| ATOM | 3176 | H1 | TIP3 | 175 | 6.053 | 35.815 | 92.632 | 1.00 | 0.00 |
| ATOM | 3177 | H2 | TIP3 | 175 | 6.049 | 34.618 | 92.720 | 1.00 | 0.00 |
| ATOM | 3178 | OH2 | TIP3 | 176 | 6.593 | 44.033 | 89.946 | 1.00 | 33.99 |
| ATOM | 3179 | G1 | TIP3 | 176 | 6.575 | 44.965 | 89.812 | 1.00 | 0.00 |
| ATOM | 3180 | H2 | TIP3 | 176 | 6.621 | 43.816 | 89.011 | 1.00 | 0.00 |
| ATOM | 3181 | OH2 | TIP3 | 177 | 10.295 | 25.226 | 82.030 | 1.00 | 32.08 |
| ATOM | 3182 | H1 | TIP3 | 177 | 10.182 | 26.172 | 82.011 | 1.00 | 0.00 |

TABLE 3-continued

Coordinates of Lck bound with AMP-PNP

| | | Atom Type | Res | # | X | Y | Z | Occ | B |
|---|---|---|---|---|---|---|---|---|---|
| ATOM | 3183 | H2 | TIP3 | 177 | 10.184 | 24.969 | 81.098 | 1.00 | 0.00 |
| ATOM | 3184 | OH2 | TIP3 | 178 | 0.809 | 45.203 | 71.524 | 1.00 | 25.10 |
| ATOM | 3185 | H1 | TIP3 | 178 | 0.842 | 46.181 | 71.532 | 1.00 | 0.00 |
| ATOM | 3186 | H2 | TIP3 | 178 | 0.842 | 44.995 | 70.597 | 1.00 | 0.00 |
| ATOM | 3187 | OH2 | TIP3 | 179 | 22.972 | 43.363 | 102.150 | 1.00 | 36.75 |
| ATOM | 3188 | H1 | TIP3 | 179 | 22.966 | 44.314 | 102.170 | 1.00 | 0.00 |
| ATOM | 3189 | H2 | TIP3 | 179 | 22.966 | 43.115 | 101.236 | 1.00 | 0.00 |
| ATOM | 3190 | OH2 | TIP3 | 180 | 23.237 | 48.451 | 85.106 | 1.00 | 35.30 |
| ATOM | 3191 | H1 | TIP3 | 180 | 23.257 | 49.383 | 85.127 | 1.00 | 0.00 |
| ATOM | 3192 | H2 | TIP3 | 180 | 23.257 | 48.176 | 84.197 | 1.00 | 0.00 |
| ATOM | 3193 | OH2 | TIP3 | 181 | 4.043 | 34.705 | 85.757 | 1.00 | 24.15 |
| ATOM | 3194 | H1 | TIP3 | 181 | 4.019 | 35.656 | 85.771 | 1.00 | 0.00 |
| ATOM | 3195 | H2 | TIP3 | 181 | 4.019 | 34.455 | 84.843 | 1.00 | 0.00 |
| ATOM | 3196 | OH2 | TIP3 | 182 | 20.691 | 39.215 | 94.052 | 1.00 | 26.94 |
| ATOM | 3197 | H1 | TIP3 | 182 | 20.695 | 40.183 | 94.093 | 1.00 | 0.00 |
| ATOM | 3198 | H2 | TIP3 | 182 | 20.695 | 38.991 | 93.152 | 1.00 | 0.00 |
| ATOM | 3199 | OH2 | TIP3 | 183 | −1.097 | 50.890 | 82.306 | 1.00 | 33.75 |
| ATOM | 3200 | H1 | TIP3 | 183 | −1.253 | 51.786 | 82.212 | 1.00 | 0.00 |
| ATOM | 3201 | H2 | TIP3 | 183 | −1.081 | 50.37 | 81.373 | 1.00 | 0.00 |
| ATOM | 3202 | OH2 | TIP3 | 184 | 31.787 | 62.274 | 71.545 | 1.00 | 28.87 |
| ATOM | 3203 | H1 | TIP3 | 184 | 31.798 | 64.222 | 71.479 | 1.00 | 0.00 |
| ATOM | 3204 | H2 | TIP3 | 184 | 31.789 | 63.019 | 70.585 | 1.00 | 0.00 |
| ATOM | 3205 | OH2 | TIP3 | 185 | 14.762 | 22.784 | 82.023 | 1.00 | 32.79 |
| ATOM | 3206 | H1 | TIP3 | 185 | 14.723 | 23.746 | 82.025 | 1.00 | 0.00 |
| ATOM | 3207 | H2 | TIP3 | 185 | 14.721 | 22.557 | 81.094 | 1.00 | 0.00 |
| ATOM | 3208 | OH2 | TIP3 | 186 | 30.806 | 69.844 | 80.444 | 1.00 | 32.26 |
| ATOM | 3209 | H1 | TIP3 | 186 | 30.787 | 70.789 | 80.464 | 1.00 | 0.00 |
| ATOM | 3210 | H2 | TIP3 | 186 | 30.787 | 69.583 | 79.535 | 1.00 | 0.00 |
| ATOM | 3211 | OH2 | TIP3 | 187 | 18.427 | 72.812 | 83.951 | 1.00 | 27.54 |
| ATOM | 3213 | H2 | TIP3 | 187 | 18.458 | 72.563 | 83.028 | 1.00 | 0.00 |
| ATOM | 3214 | OH2 | TIP3 | 187 | 34.648 | 25.709 | 92.039 | 1.00 | 33.88 |
| ATOM | 3215 | H1 | TIP3 | 188 | 34.651 | 26.665 | 92.028 | 1.00 | 0.00 |
| ATOM | 3216 | H2 | TIP3 | 188 | 34.651 | 25.467 | 91.107 | 1.00 | 0.00 |
| ATOM | 3217 | OH2 | TIP3 | 188 | 33.550 | 56.144 | 79.255 | 1.00 | 25.78 |
| ATOM | 3218 | H1 | TIP3 | 189 | 33.568 | 57.112 | 79.229 | 1.00 | 0.00 |
| ATOM | 3219 | H2 | TIP3 | 189 | 33.568 | 55.923 | 78.308 | 1.00 | 0.00 |
| ATOM | 3220 | OH2 | TIP3 | 189 | 31.588 | 65.742 | 72.966 | 1.00 | 27.89 |
| ATOM | 3221 | H1 | TIP3 | 190 | 32.537 | 66.700 | 72.938 | 1.00 | 0.00 |
| ATOM | 3222 | H2 | TIP3 | 190 | 31.537 | 65.505 | 72.021 | 1.00 | 0.00 |
| ATOM | 3223 | HO2 | TIP3 | 191 | 34.007 | 49.937 | 64.148 | 1.00 | 36.57 |
| ATOM | 3224 | H1 | TIP3 | 191 | 34.017 | 50.889 | 64.136 | 1.00 | 0.00 |
| ATOM | 3225 | H2 | TIP3 | 191 | 34.017 | 49.704 | 63.211 | 1.00 | 0.00 |
| ATOM | 3226 | OH2 | TIP3 | 192 | 35.774 | 52.177 | 76.491 | 1.00 | 35.11 |
| ATOM | 3227 | H1 | TIP3 | 192 | 35.764 | 53.126 | 76.478 | 1.00 | 0.00 |
| ATOM | 3228 | H2 | TIP3 | 192 | 35.764 | 51.926 | 75.558 | 1.00 | 0.00 |
| ATOM | 3229 | OH2 | TIP3 | 193 | 14.266 | 18.832 | 81.850 | 1.00 | 42.65 |
| ATOM | 3230 | H1 | TIP3 | 193 | 14.506 | 19.737 | 82.028 | 1.00 | 0.00 |
| ATOM | 3231 | H2 | TIP3 | 193 | 14.529 | 18.531 | 81.024 | 1.00 | 0.00 |
| ATOM | 3233 | H1 | TIP3 | 194 | 1.557 | 58.563 | 65.337 | 1.00 | 0.00 |
| ATOM | 3234 | H2 | TIP3 | 194 | 1.557 | 57.638 | 64.404 | 1.00 | 0.00 |
| ATOM | 3235 | OH2 | TIP3 | 195 | 4.422 | 32.123 | 88.838 | 1.00 | 32.17 |
| ATOM | 3236 | H1 | TIP3 | 195 | 4.416 | 33.067 | 88.833 | 1.00 | 0.00 |
| ATOM | 3237 | H2 | TIP3 | 195 | 4.416 | 21.861 | 87.913 | 1.00 | 0.00 |
| ATOM | 3238 | OH2 | TIP3 | 196 | 14.003 | 45.749 | 53.783 | 1.00 | 31.04 |
| ATOM | 3239 | H1 | TIP3 | 196 | 13.997 | 46.724 | 53.783 | 1.00 | 0.00 |
| ATOM | 3240 | H2 | TIP3 | 196 | 13.997 | 45.534 | 52.856 | 1.00 | 0.00 |
| ATOM | 3241 | OH2 | TIP3 | 197 | 31.903 | 51.874 | 80.070 | 1.00 | 28.31 |
| ATOM | 3242 | HI | TIP3 | 197 | 31.894 | 52.799 | 80.038 | 1.00 | 0.00 |
| ATOM | 3243 | H2 | TIP3 | 197 | 31.902 | 51.577 | 79.144 | 1.00 | 0.00 |
| ATOM | 3244 | OH2 | TIP3 | 198 | 7.885 | 33.930 | 71.780 | 1.00 | 30.41 |
| ATOM | 3245 | H1 | TIP3 | 198 | 7.859 | 34.885 | 71.781 | 1.00 | 0.00 |
| ATOM | 3246 | H2 | TIP3 | 198 | 7.859 | 33.686 | 70.856 | 1.00 | 0.00 |
| ATOM | 3247 | OH2 | TIP3 | 199 | 2.175 | 52.836 | 74.373 | 1.00 | 36.70 |
| ATOM | 3248 | H1 | TIP3 | 199 | 2.210 | 53.787 | 74.386 | 1.00 | 0.00 |
| ATOM | 3249 | H2 | TIP3 | 199 | 2.209 | 52.586 | 73.455 | 1.00 | 0.00 |
| ATOM | 3250 | OH2 | TIP3 | 200 | 27.709 | 21.730 | 94.653 | 1.00 | 37.76 |
| ATOM | 3251 | H1 | TIP3 | 200 | 27.712 | 22.691 | 94.669 | 1.00 | 0.00 |
| ATOM | 3252 | H2 | TIP3 | 200 | 27.712 | 21.498 | 93.733 | 1.00 | 0.00 |
| ATOM | 3253 | OH2 | TIP3 | 201 | 6.824 | 43.909 | 85.895 | 1.00 | 38.46 |
| ATOM | 3254 | H1 | TIP3 | 201 | 6.800 | 44.826 | 85.981 | 1.00 | 0.00 |
| AOTM | 3255 | H2 | TIP3 | 201 | 6.797 | 43.646 | 85.033 | 1.00 | 0.00 |
| ATOM | 3256 | OH2 | TIP3 | 202 | 41.467 | 40.084 | 77.723 | 1.00 | 36.70 |
| ATOM | 3257 | H1 | TIP3 | 202 | 41.162 | 40.956 | 77.648 | 1.00 | 0.00 |
| ATOM | 3258 | H2 | TIP3 | 202 | 41.208 | 39.765 | 76.819 | 1.00 | 0.00 |

TABLE 3-continued

Coordinates of Lck bound with AMP-PNP

| | | Atom Type | Res | # | X | Y | Z | Occ | B |
|---|---|---|---|---|---|---|---|---|---|
| ATOM | 3259 | OH2 | TIP3 | 203 | 38.042 | 58.700 | 67.769 | 1.00 | 33.79 |
| ATOM | 3260 | H1 | TIP3 | 203 | 38.054 | 59.649 | 67.790 | 1.00 | 0.00 |
| ATOM | 3261 | H2 | TIP3 | 203 | 38.054 | 58.449 | 66.854 | 1.00 | 0.00 |
| ATOM | 3262 | OH2 | TIP3 | 204 | 28.693 | 45.564 | 82.956 | 1.00 | 35.59 |
| ATOM | 3263 | H1 | TIP3 | 204 | 28.704 | 46.535 | 82.980 | 1.00 | 0.00 |
| ATOM | 3264 | H2 | TIP3 | 204 | 28.704 | 45.329 | 82.041 | 1.00 | 0.00 |
| ATOM | 3265 | OH2 | TIP3 | 205 | 11.506 | 37.834 | 80.089 | 1.00 | 21.86 |
| ATOM | 3266 | H1 | TIP3 | 205 | 11.474 | 38.794 | 80.096 | 1.00 | 0.00 |
| ATOM | 3267 | H1 | TIP3 | 205 | 11.476 | 37.605 | 79.167 | 1.00 | 0.00 |
| ATOM | 3268 | OH2 | TIP3 | 206 | 13.581 | 38.686 | 104.175 | 1.00 | 33.01 |
| ATOM | 3269 | H1 | TIP3 | 206 | 13.577 | 39.652 | 104.176 | 1.00 | 0.00 |
| ATOM | 3270 | H2 | TIP3 | 206 | 13.577 | 38.461 | 103.247 | 1.00 | 0.00 |
| ATOM | 3271 | OH2 | TIP3 | 207 | 6.466 | 43.750 | 66.221 | 1.00 | 36.71 |
| ATOM | 3272 | H1 | TIP3 | 207 | 6.485 | 44.742 | 66.266 | 1.00 | 0.00 |
| ATOM | 3273 | H2 | TIP3 | 207 | 6.486 | 43.565 | 65.319 | 1.00 | 0.00 |
| ATOM | 3274 | H1 | TIP3 | 208 | 18.075 | 49.217 | 87.796 | 1.00 | 33.12 |
| ATOM | 3275 | H1 | TIP3 | 208 | 18.046 | 50.173 | 87.776 | 1.00 | 0.00 |
| ATOM | 3276 | H2 | TIP3 | 208 | 18.044 | 48.989 | 86.865 | 1.00 | 0.00 |
| ATOM | 3277 | OH2 | TIP3 | 209 | 28.496 | 52.689 | 58.003 | 1.00 | 35.36 |
| ATOM | 3278 | H1 | TIP3 | 209 | 28.443 | 53.649 | 58.016 | 1.00 | 0.00 |
| ATOM | 3279 | H2 | TIP3 | 209 | 28.443 | 53.456 | 57.082 | 1.00 | 0.00 |
| ATOM | 3280 | OH2 | TIP3 | 210 | 27.292 | 25.593 | 77.744 | 1.00 | 34.42 |
| ATOM | 3281 | H1 | TIP3 | 210 | 27.116 | 26.481 | 77.454 | 1.00 | 0.00 |
| ATOM | 3282 | H2 | TIP3 | 210 | 27.146 | 25.341 | 76.779 | 1.00 | 0.00 |
| ATOM | 3283 | OH2 | TIP3 | 211 | 33.979 | 35.777 | 78.853 | 1.00 | 32.89 |
| ATOM | 3284 | H1 | TIP3 | 211 | 34.015 | 36.734 | 78.857 | 1.00 | 0.00 |
| ATOM | 3285 | H2 | TIP3 | 211 | 34.015 | 35.532 | 77.931 | 1.00 | 0.00 |
| ATOM | 3286 | OH2 | TIP3 | 212 | 31.242 | 60.948 | 81.668 | 1.00 | 37.12 |
| ATOM | 3287 | H1 | TIP3 | 212 | 31.237 | 61.895 | 81.679 | 1.00 | 0.00 |
| ATOM | 3288 | H2 | TIP3 | 212 | 31.237 | 60.693 | 80.747 | 1.00 | 0.00 |
| ATOM | 3289 | OH2 | TIP3 | 213 | 35.836 | 41.528 | 63.005 | 1.00 | 34.19 |
| ATOM | 3290 | H1 | TIP3 | 213 | 35.833 | 42.482 | 63.033 | 1.00 | 0.00 |
| ATOM | 3291 | H2 | TIP3 | 213 | 35.833 | 41.285 | 62.095 | 1.00 | 0.00 |
| ATOM | 3292 | OH2 | TIP3 | 214 | −2.194 | 56.331 | 73.893 | 1.00 | 36.04 |
| ATOM | 3293 | H1 | TIP3 | 214 | −2.249 | 57.281 | 73.885 | 1.00 | 0.00 |
| ATOM | 3294 | H2 | TIP3 | 214 | −2.249 | 56.080 | 72.965 | 1.00 | 0.00 |
| ATOM | 3295 | OH2 | TIP3 | 215 | 3.099 | 32.353 | 85.937 | 1.00 | 36.12 |
| ATOM | 3296 | H1 | TIP3 | 215 | 3.140 | 33.324 | 85.937 | 1.00 | 0.00 |
| ATOM | 3297 | H2 | TIP3 | 215 | 3.143 | 32.141 | 85.004 | 1.00 | 0.00 |
| ATOM | 3298 | OH2 | TIP3 | 216 | 29.399 | 19.525 | 86.525 | 1.00 | 25.81 |
| ATOM | 3299 | H1 | TIP3 | 216 | 29.381 | 20.462 | 86.510 | 1.00 | 0.00 |
| ATOM | 3300 | H1 | TIP3 | 216 | 29.381 | 19.255 | 85.591 | 1.00 | 0.00 |
| ATOM | 3301 | OH2 | TIP3 | 217 | 1.615 | 38.832 | 79.927 | 1.00 | 28.39 |
| ATOM | 3302 | H1 | TIP3 | 217 | 1.622 | 39.783 | 79.929 | 1.00 | 0.00 |
| ATOM | 3303 | H2 | TIP3 | 217 | 1.622 | 39.783 | 79.929 | 1.00 | 0.00 |
| ATOM | 3304 | OH2 | TIP3 | 218 | 13.787 | 67.375 | 77.371 | 1.00 | 34.53 |
| ATOM | 3305 | H1 | TIP3 | 218 | 13.615 | 68.270 | 77.173 | 1.00 | 0.00 |
| ATOM | 3306 | H2 | TIP3 | 218 | 13.746 | 67.162 | 76.418 | 1.00 | 0.00 |
| ATOM | 3307 | OH2 | TIP3 | 219 | 6.177 | 43.017 | 87.892 | 1.00 | 32.18 |
| ATOM | 3308 | H1 | TIP3 | 219 | 6.255 | 44.059 | 87.926 | 1.00 | 0.00 |
| ATOM | 3309 | H2 | TIP3 | 219 | 6.260 | 42.938 | 86.951 | 1.00 | 0.00 |
| ATOM | 3310 | OH2 | TIP3 | 220 | 28.330 | 71.277 | 79.038 | 1.00 | 36.59 |
| ATOM | 3311 | H1 | TIP3 | 220 | 28.365 | 72.243 | 79.051 | 1.00 | 0.00 |
| ATOM | 3312 | H2 | TIP3 | 220 | 28.365 | 72.243 | 79.051 | 1.00 | 0.00 |
| ATOM | 3313 | OH2 | TIP3 | 221 | 15.295 | 51.964 | 90.082 | 1.00 | 35.46 |
| ATOM | 3314 | H1 | TIP3 | 221 | 15.297 | 52.918 | 90.087 | 1.00 | 0.00 |
| ATOM | 3315 | H2 | TIP3 | 221 | 15.297 | 51.720 | 89.159 | 1.00 | 0.00 |
| ATOM | 3316 | OH2 | TIP3 | 222 | 42.721 | 36.930 | 69.137 | 1.00 | 39.24 |
| ATOM | 3317 | H1 | TIP3 | 222 | 42.697 | 37.900 | 69.138 | 1.00 | 0.00 |
| ATOM | 3318 | H2 | TIP3 | 222 | 42.697 | 36.708 | 68.213 | 1.00 | 0.00 |
| ATOM | 3319 | OH2 | TIP3 | 223 | 9.299 | 64.027 | 76.973 | 1.00 | 34.30 |
| ATOM | 3320 | H1 | TIP3 | 223 | 9.283 | 64.978 | 76.989 | 1.00 | 0.00 |
| ATOM | 3321 | H2 | TIP3 | 223 | 9.283 | 63.775 | 76.057 | 1.00 | 0.00 |
| ATOM | 3322 | OH2 | TIP3 | 224 | −2.159 | 53.009 | 74.456 | 1.00 | 34.50 |
| ATOM | 3323 | H1 | TIP3 | 224 | −2.107 | 53.964 | 74.446 | 1.00 | 0.00 |
| ATOM | 3324 | H2 | TIP3 | 224 | −2.107 | 52.770 | 73.521 | 1.00 | 0.00 |
| ATOM | 3325 | H1 | TIP3 | 225 | 7.927 | 32.911 | 69.370 | 1.00 | 39.25 |
| ATOM | 3326 | H1 | TIP3 | 225 | 7.900 | 33.886 | 69.362 | 1.00 | 0.00 |
| ATOM | 3327 | H2 | TIP3 | 225 | 7.900 | 32.704 | 68.435 | 1.00 | 0.00 |
| ATOM | 3328 | OH2 | TIP3 | 226 | 35.674 | 33.002 | 69.346 | 1.00 | 37.41 |
| ATOM | 3329 | H1 | TIP3 | 226 | 35.675 | 33.963 | 69.341 | 1.00 | 0.00 |
| ATOM | 3330 | H2 | TIP3 | 226 | 35.675 | 33.963 | 69.341 | 1.00 | 0.00 |
| ATOM | 3331 | OH2 | TIP3 | 227 | 32.472 | 17.954 | 90.113 | 1.00 | 36.48 |
| ATOM | 3332 | H1 | TIP3 | 227 | 32.353 | 18.828 | 90.119 | 1.00 | 0.00 |

TABLE 3-continued

Coordinates of Lck bound with AMP-PNP

| | | Atom Type | Res | # | X | Y | Z | Occ | B |
|---|---|---|---|---|---|---|---|---|---|
| ATOM | 3333 | H2 | TIP3 | 227 | 32.363 | 17.557 | 89.235 | 1.00 | 0.00 |
| ATOM | 3334 | OH2 | TIP3 | 228 | 27.207 | 69.701 | 74.202 | 1.00 | 32.84 |
| ATOM | 3335 | H1 | TIP3 | 228 | 27.186 | 70.672 | 74.165 | 1.00 | 0.00 |
| ATOM | 3336 | H2 | TIP3 | 228 | 27.186 | 69.486 | 73.249 | 1.00 | 0.00 |
| ATOM | 3337 | OH2 | TIP3 | 229 | 27.479 | 45.093 | 68.178 | 1.00 | 37.84 |
| ATOM | 3338 | H1 | TIP3 | 229 | 27.483 | 46.021 | 68.187 | 1.00 | 0.00 |
| ATOM | 3339 | H2 | TIP3 | 229 | 27.483 | 44.816 | 67.258 | 1.00 | 0.00 |
| ATOM | 3340 | OH2 | TIP3 | 230 | 37.205 | 56.043 | 73.914 | 1.00 | 37.92 |
| ATOM | 3341 | H1 | TIP3 | 230 | 37.203 | 57.002 | 73.907 | 1.00 | 0.00 |
| ATOM | 3342 | HE | TIP3 | 230 | 37.203 | 55.806 | 72.981 | 1.00 | 0.00 |
| ATOM | 3343 | OH2 | TIP3 | 231 | 22.304 | 43.438 | 86.120 | 1.00 | 38.85 |
| ATOM | 3344 | H1 | TIP3 | 231 | 22.302 | 44.395 | 86.117 | 1.00 | 0.00 |
| ATOM | 3345 | H2 | TIP3 | 231 | 22.302 | 43.200 | 85.191 | 1.00 | 0.00 |
| ATOM | 3346 | OH2 | TIP3 | 232 | 38.333 | 43.976 | 79.336 | 1.00 | 35.69 |
| ATOM | 3347 | H1 | TIP3 | 232 | 38.328 | 44.928 | 79.294 | 1.00 | 0.00 |
| ATOM | 3348 | H2 | TIP3 | 232 | 38.328 | 43.733 | 78.380 | 1.00 | 0.00 |
| ATOM | 3349 | OH2 | TIP3 | 233 | 16.867 | 67.376 | 66.645 | 1.99 | 28.36 |
| ATOM | 3350 | H1 | TIP3 | 233 | 16.944 | 68.314 | 66.630 | 1.00 | 0.00 |
| ATOM | 3351 | H2 | TIP3 | 233 | 16.944 | 67.108 | 65.715 | 1.00 | 0.00 |
| ATOM | 3352 | OH2 | TIP3 | 234 | 32.553 | 48.070 | 81.478 | 1.00 | 33.63 |
| ATOM | 3353 | H1 | TIP3 | 234 | 32.529 | 49.029 | 81.495 | 1.00 | 0.00 |
| ATOM | 3354 | H2 | TIP3 | 234 | 32.529 | 47.836 | 80.558 | 1.00 | 0.00 |
| ATOM | 3355 | OH2 | TIP3 | 235 | 12.821 | 66.088 | 76.560 | 1.00 | 31.19 |
| ATOM | 3356 | H1 | TIP3 | 235 | 13.007 | 67.094 | 75.722 | 1.00 | 0.00 |
| ATOM | 3357 | H2 | TIP3 | 235 | 13.078 | 66.048 | 74.679 | 1.00 | 0.00 |
| ATOM | 3358 | OH2 | TIP3 | 236 | 6.843 | 46.881 | 60.307 | 1.00 | 35.24 |
| ATOM | 3359 | H1 | TIP3 | 236 | 6.894 | 47.835 | 60.307 | 1.00 | 0.00 |
| ATOM | 3360 | H1 | TIP3 | 236 | 6.894 | 46.639 | 59.380 | 1.00 | 0.00 |
| ATOM | 3361 | OH2 | TIP3 | 237 | 4.319 | 36.931 | 69.617 | 1.00 | 38.31 |
| ATOM | 3362 | H1 | TIP3 | 237 | 4.340 | 37.876 | 69.583 | 1.00 | 0.00 |
| ATOM | 3363 | H2 | TIP3 | 237 | 4.340 | 46.678 | 68.670 | 1.00 | 0.00 |
| ATOM | 3364 | OH2 | TIP3 | 238 | 31.451 | 33.832 | 65.405 | 1.00 | 35.68 |
| ATOM | 3365 | H1 | TIP3 | 238 | 31.412 | 34.791 | 65.419 | 1.00 | 0.00 |
| ATOM | 3366 | H2 | TIP3 | 238 | 31.412 | 33.596 | 64.486 | 1.00 | 0.00 |
| ATOM | 3367 | OH2 | TIP3 | 239 | 39.307 | 48.399 | 75.826 | 1.00 | 25.00 |
| ATOM | 3368 | H1 | TIP3 | 239 | 39.273 | 49.294 | 75.832 | 1.00 | 0.00 |
| ATOM | 3369 | H2 | TIP3 | 239 | 39.273 | 48.095 | 74.910 | 1.00 | 0.00 |
| ATOM | 3370 | OH2 | TIP3 | 240 | 32.144 | 39.954 | 63.110 | 1.00 | 36.62 |
| ATOM | 3371 | H1 | TIP3 | 240 | 32.196 | 40.964 | 63.098 | 1.00 | 0.00 |
| ATOM | 3372 | H2 | TIP3 | 240 | 32.207 | 39.809 | 62.162 | 1.00 | 0.00 |
| ATOM | 3373 | OH2 | TIP3 | 241 | 38.953 | 39.819 | 77.372 | 1.00 | 38.61 |
| ATOM | 3374 | H1 | TIP3 | 241 | 39.606 | 40.583 | 77.578 | 1.00 | 0.00 |
| ATOM | 3375 | H2 | TIP3 | 241 | 39.646 | 39.550 | 76.745 | 1.00 | 0.00 |
| ATOM | 3376 | OH2 | TIP3 | 242 | 27.548 | 59.716 | 72.066 | 1.00 | 38.18 |
| ATOM | 3377 | H1 | TIP3 | 242 | 27.587 | 60.647 | 71.978 | 1.00 | 0.00 |
| ATOM | 3378 | H2 | TIP3 | 242 | 27.512 | 59.450 | 71.210 | 1.00 | 0.00 |
| ATOM | 3379 | OH2 | TIP3 | 243 | 23.904 | 22.7566 | 95.445 | 1.00 | 34.40 |
| ATOM | 3380 | H1 | TIP3 | 243 | 23.928 | 23.706 | 95.440 | 1.00 | 0.00 |
| ATOM | 3381 | H2 | TIP3 | 243 | 23.926 | 22.505 | 94.522 | 1.00 | 0.00 |
| ATOM | 3382 | OH2 | TIP3 | 244 | 19.269 | 30.245 | 72.706 | 1.00 | 32.40 |
| ATOM | 3383 | H1 | TIP3 | 244 | 19.258 | 31.201 | 72.720 | 1.00 | 0.00 |
| ATOM | 3384 | H2 | TIP3 | 244 | 19.256 | 30.019 | 71.792 | 1.00 | 0.00 |
| ATOM | 3385 | OH2 | TIP3 | 245 | 0.514 | 52.634 | 68.623 | 1.00 | 34.70 |
| ATOM | 3386 | H1 | TIP3 | 245 | 0.583 | 54.583 | 68.603 | 1.00 | 0.00 |
| ATOM | 3387 | H2 | TIP3 | 245 | 0.583 | 53.384 | 67.682 | 1.00 | 0.00 |
| ATOM | 3388 | OH2 | TIP3 | 246 | 13.727 | 42.324 | 91.224 | 1.00 | 28.93 |
| ATOM | 3389 | H1 | TIP3 | 246 | 12.734 | 43.285 | 91.219 | 1.00 | 0.00 |
| ATOM | 3390 | H1 | TIP3 | 246 | 12.734 | 42.085 | 90.295 | 1.00 | 0.00 |
| ATOM | 3391 | OH2 | TIP3 | 247 | 12.121 | 26.078 | 76.245 | 1.00 | 35.21 |
| ATOM | 3392 | H1 | TIP3 | 247 | 12.115 | 27.032 | 76.248 | 1.00 | 0.00 |
| ATOM | 3393 | H2 | TIP3 | 247 | 12.115 | 25.828 | 75.321 | 1.00 | 0.00 |
| ATOM | 3394 | OH2 | TIP3 | 248 | 26.635 | 27.093 | 75.402 | 1.00 | 41.37 |
| ATOM | 3395 | H1 | TIP3 | 248 | 26.936 | 27.361 | 76.195 | 1.00 | 0.00 |
| ATOM | 3396 | H2 | TIP3 | 248 | 26.916 | 26.154 | 75.197 | 1.00 | 0.00 |
| ATOM | 3397 | OH2 | TIP3 | 249 | 4.453 | 30.792 | 80.479 | 1.00 | 34.61 |
| ATOM | 3398 | H1 | TIP3 | 249 | 4.440 | 31.767 | 80.478 | 1.00 | 0.00 |
| ATOM | 3399 | H2 | TIP3 | 249 | 4.440 | 30.581 | 79.550 | 1.00 | 0.00 |
| ATOM | 3400 | OH2 | TIP3 | 250 | 10.746 | 21.117 | 93.065 | 1.00 | 34.69 |
| ATOM | 3401 | H1 | TIP3 | 250 | 10.8982 | 22.015 | 93.131 | 1.00 | 0.00 |
| ATOM | 3402 | H2 | TIP3 | 250 | 10.869 | 20.735 | 92.219 | 1.00 | 0.00 |
| ATOM | 3403 | H2 | TIP3 | 251 | 10.306 | 56.959 | 61.376 | 1.00 | 39.18 |
| ATOM | 3404 | H1 | TIP3 | 251 | 10.344 | 57.906 | 61.368 | 1.00 | 0.00 |
| ATOM | 3405 | H2 | TIP3 | 251 | 10.344 | 56.703 | 60.446 | 1.00 | 0.00 |
| ATOM | 3406 | OH2 | TIP3 | 252 | 19.639 | 44.893 | 88.642 | 1.00 | 30.45 |

TABLE 3-continued

Coordinates of Lck bound with AMP-PNP

| | | Atom Type | Res | # | X | Y | Z | Occ | B |
|---|---|---|---|---|---|---|---|---|---|
| ATOM | 3407 | H1 | TIP3 | 252 | 19.629 | 45.858 | 88.629 | 1.00 | 0.00 |
| ATOM | 3408 | H2 | TIP3 | 252 | 19.629 | 44.668 | 87.710 | 1.00 | 0.00 |
| ATOM | 3409 | OH2 | TIP3 | 253 | 15.407 | 18.715 | 83.978 | 1.00 | 34.86 |
| ATOM | 3410 | H1 | TIP3 | 253 | 15.292 | 19.676 | 83.830 | 1.00 | 0.00 |
| ATOM | 3411 | H2 | TIP3 | 253 | 15.355 | 18.477 | 83.021 | 1.00 | 0.00 |
| ATOM | 3412 | OH2 | TIP3 | 254 | 9.191 | 21.414 | 89.085 | 1.00 | 31.02 |
| ATOM | 3413 | H1 | TIP3 | 254 | 9.127 | 22.355 | 89.110 | 1.00 | 0.00 |
| ATOM | 3414 | H2 | TIP3 | 254 | 9.127 | 21.152 | 88.178 | 1.00 | 0.00 |
| ATOM | 3415 | OH2 | TIP3 | 255 | 7.949 | 25.146 | 81.387 | 1.00 | 35.28 |
| ATOM | 3416 | H1 | TIP3 | 255 | 8.094 | 26.095 | 81.404 | 1.00 | 0.00 |
| ATOM | 3417 | H2 | TIP3 | 255 | 8.095 | 24.899 | 80.472 | 1.00 | 0.00 |
| ATOM | 3418 | OH2 | TIP3 | 256 | 34.958 | 38.845 | 64.354 | 1.00 | 35.59 |
| ATOM | 3419 | H1 | TIP3 | 256 | 35.003 | 39.804 | 65.364 | 1.00 | 0.00 |
| ATOM | 3420 | H2 | TIP3 | 256 | 35.003 | 38.611 | 64.433 | 1.00 | 0.00 |
| ATOM | 3421 | S | SO4 | 901 | 20.174 | 32.731 | 69.351 | 1.00 | 8.88 |
| ATOM | 3422 | O1 | SO4 | 901 | 19.784 | 32.048 | 70.522 | 1.00 | 8.66 |
| ATOM | 3423 | O2 | SO4 | 901 | 19.008 | 33.195 | 68.633 | 1.00 | 9.59 |
| ATOM | 3424 | O3 | SO4 | 901 | 20.991 | 33.872 | 69.811 | 1.00 | 8.42 |
| ATOM | 3425 | O4 | SO4 | 901 | 20.949 | 31.872 | 68.511 | 1.00 | 7.06 |
| ATOM | 3426 | S | SO4 | 902 | 39.464 | 37.832 | 73.382 | 1.00 | 27.67 |
| ATOM | 3427 | O1 | SO4 | 902 | 38.570 | 36.649 | 73.306 | 1.00 | 28.54 |
| ATOM | 3428 | O2 | SO4 | 902 | 40.301 | 37.833 | 72.264 | 1.00 | 26.97 |
| ATOM | 3429 | O3 | SO4 | 902 | 38.647 | 39.016 | 73.378 | 1.00 | 26.59 |
| ATOM | 3430 | O4 | SO4 | 902 | 40.168 | 37.757 | 74.605 | 1.00 | 27.31 |
| ATOM | 3431 | S | SO4 | 903 | 14.908 | 66.477 | 81.070 | 1.00 | 38.89 |
| ATOM | 3432 | O1 | SO4 | 903 | 14.636 | 65.291 | 80.341 | 1.00 | 39.87 |
| ATOM | 3433 | O2 | SO4 | 903 | 13.849 | 67.449 | 80.942 | 1.00 | 36.71 |
| ATOM | 3434 | O3 | SO3 | 903 | 15.068 | 66.086 | 82.452 | 1.00 | 37.21 |
| ATOM | 3435 | O4 | SO3 | 903 | 16.095 | 67.021 | 80.519 | 1.00 | 37.74 |
| ATOM | 3436 | PA | ANP | 1 | 24.843 | 41.888 | 87.844 | 1.00 | 36.02 |
| ATOM | 3437 | O1A | ANP | 1 | 25.011 | 41.910 | 89.325 | 1.00 | 36.27 |
| ATOM | 3438 | O2A | ANP | 1 | 23.696 | 41.181 | 87.286 | 1.00 | 35.82 |
| ATOM | 3439 | O5' | ANP | 1 | 26.156 | 41.369 | 87.121 | 1.00 | 33.31 |
| ATOM | 3440 | PB | ANP | 1 | 25.401 | 45.114 | 85.567 | 1.00 | 38.23 |
| ATOM | 3441 | O1B | ANP | 1 | 25.401 | 45.114 | 85.567 | 1.00 | 38.23 |
| ATOM | 3442 | O2B | ANP | 1 | 27.095 | 43.375 | 86.202 | 1.00 | 38.97 |
| ATOM | 3443 | O3A | ANP | 1 | 24.871 | 43.380 | 87.281 | 1.00 | 37.26 |
| ATOM | 3444 | N3B | ANP | 1 | 26.461 | 45.182 | 87.959 | 1.00 | 39.82 |
| ATOM | 3445 | C5' | ANP | 1 | 26.998 | 40.244 | 87.427 | 1.00 | 26.07 |
| ATOM | 3346 | C4' | ANP | 1 | 28.014 | 39.742 | 86.376 | 1.00 | 22.40 |
| ATOM | 3347 | O4' | ANP | 1 | 27.341 | 38.582 | 85.846 | 1.00 | 19.19 |
| ATOM | 3448 | C1' | ANP | 1 | 27.287 | 38.523 | 84.444 | 1.00 | 16.95 |
| ATOM | 3449 | N9 | ANP | 1 | 26.155 | 37.856 | 84.043 | 1.00 | 13.25 |
| ATOM | 3450 | C1 | ANP | 1 | 26.003 | 36.800 | 83.169 | 1.00 | 12.39 |
| ATOM | 3451 | N2 | ANP | 1 | 26.965 | 36.131 | 82.438 | 1.00 | 12.21 |
| ATOM | 3452 | C1 | ANP | 1 | 25.415 | 35.218 | 81.670 | 1.00 | 11.33 |
| ATOM | 3453 | N1 | ANP | 1 | 25.126 | 34.826 | 81.608 | 1.00 | 10.92 |
| ATOM | 3454 | C6 | ANP | 1 | 24.208 | 35.502 | 82.313 | 1.00 | 11.51 |
| ATOM | 3455 | N6 | ANP | 1 | 22.907 | 35.158 | 82.165 | 1.00 | 11.52 |
| ATOM | 3456 | C5 | ANP | 1 | 24.660 | 36.530 | 83.164 | 1.00 | 11.58 |
| ATOM | 3457 | N1 | ANP | 1 | 23.970 | 37.311 | 84.013 | 1.00 | 12.95 |
| ATOM | 3458 | C8 | ANP | 1 | 24.912 | 38.111 | 84.535 | 1.00 | 13.45 |
| ATOM | 3459 | C2' | ANP | 1 | 27.341 | 39.966 | 84.013 | 1.00 | 12.95 |
| ATOM | 3460 | O2' | ANP | 1 | 27.631 | 40.027 | 82.675 | 1.00 | 20.41 |
| ATOM | 3461 | C3' | ANP | 1 | 28.385 | 40.520 | 85.098 | 1.00 | 20.48 |
| ATOM | 3462 | O3' | ANP | 1 | 29.565 | 40.300 | 84.242 | 1.00 | 22.85 |
| ATOM | 3463 | C1 | DTT | 1 | 17.791 | 37.806 | 84.959 | 1.00 | 22.39 |
| ATOM | 3464 | C1 | DTT | 1 | 17.633 | 38.191 | 83.500 | 1.00 | 23.33 |
| ATOM | 3465 | O3 | DTT | 1 | 18.918 | 38.534 | 82.973 | 1.00 | 22.44 |
| ATOM | 3466 | O6 | ATT | 1 | 18.197 | 38.939 | 85.755 | 1.00 | 34.18 |
| END | | | | | | | | | |

TABLE 4

Coordinates of Lck bound with staurosporine (soaked)

| | | Atom Type | Res | # | X | Y | Z | Occ | B |
|---|---|---|---|---|---|---|---|---|---|
| ATOM | 1 | CB | LYS | 231 | 1.760 | 26.587 | 89.190 | 1.00 | 18.15 |
| ATOM | 2 | CG | LYS | 231 | 0.804 | 26.486 | 88.016 | 1.00 | 19.78 |

TABLE 4-continued

Coordinates of Lck bound with staurosporine (soaked)

| | Atom Type | Res | # | X | Y | Z | Occ | B |
|---|---|---|---|---|---|---|---|---|
| ATOM | 3 | CD | LYS | 231 | 1.297 | 25.440 | 87.044 | 1.00 | 21.94 |
| ATOM | 4 | CE | LYS | 231 | 0.737 | 25.667 | 85.678 | 1.00 | 21.71 |
| ATOM | 5 | NZ | LYS | 231 | 1.363 | 24.735 | 84.727 | 1.00 | 25.80 |
| ATOM | 9 | C | LYS | 231 | 2.208 | 27.249 | 91.505 | 1.00 | 16.44 |
| ATOM | 10 | O | LYS | 231 | 3.298 | 27.799 | 91.498 | 1.00 | 16.57 |
| ATOM | 13 | N | LYS | 231 | 1.232 | 28.896 | 89.968 | 1.00 | 18.23 |
| ATOM | 15 | CA | LYS | 231 | 1.255 | 27.440 | 90.349 | 1.00 | 17.63 |
| ATOM | 16 | N | PRO | 232 | 1.814 | 26.446 | 92.511 | 1.00 | 16.47 |
| ATOM | 17 | CD | PRO | 232 | 0.580 | 25.644 | 92.633 | 1.00 | 16.83 |
| ATOM | 18 | CA | PRO | 232 | 2.697 | 26.208 | 93.656 | 1.00 | 15.75 |
| ATOM | 19 | CB | PRO | 232 | 1.854 | 25.276 | 94.530 | 1.00 | 16.74 |
| ATOM | 20 | CG | PRO | 232 | 1.031 | 24.515 | 93.519 | 1.00 | 16.11 |
| ATOM | 21 | C | PRO | 232 | 3.957 | 25.516 | 93.146 | 1.00 | 15.08 |
| ATOM | 22 | O | PRO | 232 | 3.914 | 24.803 | 92.155 | 1.00 | 11.56 |
| ATOM | 23 | N | TRP | 233 | 5.061 | 25.660 | 93.878 | 1.00 | 14.93 |
| ATOM | 25 | CA | TRP | 233 | 6.315 | 25.098 | 93.442 | 1.00 | 15.30 |
| ATOM | 26 | CB | TRP | 233 | 7.432 | 25.348 | 94.482 | 1.00 | 16.73 |
| ATOM | 27 | CG | TRP | 233 | 7.278 | 24.559 | 95.770 | 1.00 | 15.82 |
| ATOM | 28 | CD2 | TRP | 233 | 7.695 | 23.204 | 96.006 | 1.00 | 16.47 |
| ATOM | 29 | CE2 | TRP | 233 | 7.336 | 22.873 | 97.331 | 1.00 | 16.40 |
| ATOM | 30 | CE3 | TRP | 233 | 8.344 | 22.232 | 95.222 | 1.00 | 16.08 |
| ATOM | 31 | CD1 | TRP | 233 | 6.707 | 24.989 | 96.926 | 1.00 | 15.21 |
| ATOM | 32 | NE1 | TRP | 233 | 6.741 | 23.982 | 97.877 | 1.00 | 15.51 |
| ATOM | 34 | CZ2 | TRP | 233 | 7.590 | 21.615 | 97.898 | 1.00 | 17.54 |
| ATOM | 35 | CZ3 | TRP | 233 | 8.600 | 20.980 | 95.785 | 1.00 | 16.04 |
| ATOM | 36 | CH2 | TRP | 233 | 8.217 | 20.684 | 97.112 | 1.00 | 17.08 |
| ATOM | 37 | C | TRP | 233 | 6.272 | 23.631 | 93.062 | 1.00 | 15.78 |
| ATOM | 38 | O | TRP | 233 | 6.950 | 23.237 | 92.114 | 1.00 | 16.43 |
| ATOM | 39 | N | TRP | 234 | 5.431 | 22.844 | 93.739 | 1.00 | 14.38 |
| ATOM | 41 | CA | TRP | 234 | 5.354 | 21.401 | 93.463 | 1.00 | 15.29 |
| ATOM | 42 | CB | TRP | 234 | 4.686 | 20.603 | 94.620 | 1.00 | 13.76 |
| ATOM | 43 | CG | TRP | 234 | 3.293 | 21.032 | 94.983 | 1.00 | 11.08 |
| ATOM | 44 | CD2 | TRP | 234 | 2.904 | 21.976 | 96.002 | 1.00 | 12.03 |
| ATOM | 45 | CE2 | TRP | 234 | 1.497 | 22.087 | 95.950 | 1.00 | 11.40 |
| ATOM | 46 | CE3 | TRP | 234 | 3.610 | 22.756 | 96.923 | 1.00 | 13.92 |
| ATOM | 47 | CD1 | TRP | 234 | 2.146 | 20.610 | 94.399 | 1.00 | 12.07 |
| ATOM | 48 | NE1 | TRP | 234 | 1.067 | 21.234 | 94.965 | 1.00 | 11.51 |
| ATOM | 50 | CZ2 | TRP | 234 | 0.765 | 22.914 | 96.804 | 1.00 | 13.55 |
| ATOM | 51 | CZ3 | TRP | 234 | 2.886 | 23.596 | 97.785 | 1.00 | 14.90 |
| ATOM | 52 | CH2 | TRP | 234 | 1.464 | 23.677 | 97.705 | 1.00 | 13.08 |
| ATOM | 53 | C | TRP | 234 | 4.718 | 21.054 | 92.135 | 1.00 | 15.90 |
| ATOM | 54 | O | TRP | 234 | 4.763 | 19.905 | 91.708 | 1.00 | 15.35 |
| ATOM | 55 | N | GLU | 235 | 4.076 | 22.030 | 91.508 | 1.00 | 16.06 |
| ATOM | 57 | CA | GLU | 235 | 3.483 | 21.823 | 90.182 | 1.00 | 17.45 |
| ATOM | 58 | CB | GLU | 235 | 1.978 | 22.133 | 90.187 | 1.00 | 18.24 |
| ATOM | 59 | CG | GLU | 235 | 1.124 | 21.155 | 90.988 | 1.00 | 20.36 |
| ATOM | 60 | CD | GLU | 235 | −0.372 | 21.423 | 90.895 | 1.00 | 23.76 |
| ATOM | 61 | OE1 | GLU | 235 | −0.814 | 22.410 | 90.254 | 1.00 | 25.31 |
| ATOM | 62 | OE2 | GLU | 235 | −1.122 | 20.611 | 91.457 | 1.00 | 23.55 |
| ATOM | 63 | C | GLU | 235 | 4.134 | 22.720 | 89.138 | 1.00 | 17.15 |
| ATOM | 64 | O | GLU | 235 | 3.820 | 22.648 | 87.952 | 1.00 | 18.56 |
| ATOM | 65 | N | ASP | 236 | 4.949 | 23.646 | 89.619 | 1.00 | 16.90 |
| ATOM | 67 | CA | ASP | 236 | 5.608 | 24.611 | 88.736 | 1.00 | 15.75 |
| ATOM | 68 | CB | ASP | 236 | 6.242 | 25.697 | 89.608 | 1.00 | 16.17 |
| ATOM | 69 | CG | ASP | 236 | 6.798 | 26.867 | 88.800 | 1.00 | 18.56 |
| ATOM | 70 | OD1 | ASP | 236 | 6.726 | 26.899 | 87.570 | 1.00 | 17.21 |
| ATOM | 71 | OD2 | ASP | 236 | 7.326 | 27.820 | 89.384 | 1.00 | 19.46 |
| ATOM | 72 | C | ASP | 236 | 6.651 | 23.950 | 87.841 | 1.00 | 15.80 |
| ATOM | 73 | O | ASP | 236 | 7.690 | 23.480 | 88.298 | 1.00 | 13.78 |
| ATOM | 74 | N | ALA | 237 | 6.393 | 23.961 | 86.543 | 1.00 | 14.20 |
| ATOM | 76 | CA | ALA | 237 | 7.356 | 23.384 | 85.605 | 1.00 | 15.78 |
| ATOM | 77 | CB | ALA | 237 | 6.829 | 23.514 | 84.163 | 1.00 | 15.97 |
| ATOM | 78 | C | ALA | 237 | 8.752 | 24.012 | 85.721 | 1.00 | 14.92 |
| ATOM | 79 | O | ALA | 237 | 9.723 | 23.383 | 85.391 | 1.00 | 14.31 |
| ATOM | 80 | N | TRP | 238 | 8.840 | 25.236 | 86.253 | 1.00 | 12.87 |
| ATOM | 82 | CA | TRP | 238 | 10.129 | 25.922 | 86.425 | 1.00 | 13.04 |
| ATOM | 83 | CB | TRP | 238 | 9.954 | 27.442 | 86.287 | 1.00 | 15.24 |
| ATOM | 84 | CG | TRP | 238 | 10.073 | 27.900 | 84.882 | 1.00 | 20.51 |
| ATOM | 85 | CD2 | TRP | 238 | 9.031 | 28.268 | 84.008 | 1.00 | 22.57 |
| ATOM | 86 | CE2 | TRP | 238 | 9.588 | 28.593 | 82.459 | 1.00 | 23.44 |
| ATOM | 87 | CE3 | TRP | 238 | 7.634 | 28.388 | 84.155 | 1.00 | 23.00 |
| ATOM | 88 | CD1 | TRP | 238 | 11.235 | 28.000 | 84.145 | 1.00 | 19.47 |
| ATOM | 89 | NE1 | TRP | 238 | 10.968 | 28.401 | 82.876 | 1.00 | 21.43 |
| ATOM | 91 | CZ2 | TRP | 238 | 8.864 | 28.997 | 81.674 | 1.00 | 24.52 |

TABLE 4-continued

Coordinates of Lck bound with staurosporine (soaked)

| | | Atom Type | Res | # | X | Y | Z | Occ | B |
|---|---|---|---|---|---|---|---|---|---|
| ATOM | 92 | CZ3 | TRP | 238 | 6.907 | 28.782 | 83.099 | 1.00 | 25.91 |
| ATOM | 93 | CH2 | TRP | 238 | 7.506 | 29.101 | 81.866 | 1.00 | 27.33 |
| ATOM | 94 | C | TRP | 238 | 10.953 | 25.631 | 87.693 | 1.00 | 12.20 |
| ATOM | 95 | O | TRP | 238 | 12.176 | 25.908 | 87.733 | 1.00 | 12.35 |
| ATOM | 96 | N | GLU | 239 | 10.315 | 25.146 | 88.747 | 1.00 | 10.34 |
| ATOM | 98 | CA | GLU | 239 | 11.049 | 24.844 | 89.979 | 1.00 | 10.08 |
| ATOM | 99 | CB | GLU | 239 | 10.073 | 24.461 | 91.128 | 1.00 | 9.78 |
| ATOM | 100 | CG | GLU | 239 | 10.736 | 24.336 | 92.513 | 1.00 | 11.32 |
| ATOM | 101 | CD | GLU | 239 | 10.896 | 25.689 | 93.246 | 1.00 | 11.67 |
| ATOM | 102 | OE1 | GLU | 239 | 10.190 | 26.651 | 92.913 | 1.00 | 11.98 |
| ATOM | 103 | OE2 | GLU | 239 | 11.718 | 25.788 | 94.189 | 1.00 | 13.38 |
| ATOM | 104 | C | GLU | 239 | 12.012 | 23.677 | 89.790 | 1.00 | 9.39 |
| ATOM | 105 | O | GLU | 239 | 11.657 | 22.701 | 89.136 | 1.00 | 10.05 |
| ATOM | 106 | N | VAL | 240 | 13.243 | 23.818 | 90.267 | 1.00 | 9.86 |
| ATOM | 108 | CA | VAL | 240 | 14.189 | 22.719 | 90.244 | 1.00 | 10.68 |
| ATOM | 109 | CB | VAL | 240 | 15.369 | 22.907 | 89.192 | 1.00 | 12.91 |
| ATOM | 110 | CG1 | VAL | 240 | 14.833 | 22.947 | 87.766 | 1.00 | 13.06 |
| ATOM | 111 | CG2 | VAL | 240 | 16.212 | 24.189 | 89.520 | 1.00 | 12.60 |
| ATOM | 112 | C | VAL | 240 | 14.832 | 22.564 | 91.629 | 1.00 | 12.37 |
| ATOM | 113 | O | VAL | 240 | 15.017 | 23.557 | 92.355 | 1.00 | 11.55 |
| ATOM | 114 | N | PRO | 241 | 15.155 | 21.317 | 92.027 | 1.00 | 12.09 |
| ATOM | 115 | CD | PRO | 241 | 14.718 | 20.058 | 91.401 | 1.00 | 12.63 |
| ATOM | 116 | CA | PRO | 241 | 15.799 | 21.069 | 93.321 | 1.00 | 12.13 |
| ATOM | 117 | CB | PRO | 241 | 15.978 | 19.546 | 93.314 | 1.00 | 12.25 |
| ATOM | 118 | CG | PRO | 241 | 14.760 | 19.070 | 92.581 | 1.00 | 14.30 |
| ATOM | 119 | C | PRO | 241 | 17.156 | 21.771 | 93.244 | 1.00 | 12.10 |
| ATOM | 120 | O | PRO | 241 | 17.823 | 21.782 | 92.183 | 1.00 | 8.60 |
| ATOM | 121 | N | ARG | 242 | 17.579 | 22.372 | 94.352 | 1.00 | 11.24 |
| ATOM | 123 | CA | ARG | 242 | 18.835 | 23.085 | 94.383 | 1.00 | 13.70 |
| ATOM | 124 | CB | ARG | 242 | 18.987 | 23.859 | 95.694 | 1.00 | 14.96 |
| ATOM | 125 | CG | ARG | 242 | 20.154 | 24.871 | 95.692 | 1.00 | 21.92 |
| ATOM | 126 | CD | ARG | 242 | 20.611 | 25.208 | 97.126 | 1.00 | 26.26 |
| ATOM | 127 | NE | ARG | 242 | 19.454 | 25.535 | 97.957 | 1.00 | 31.84 |
| ATOM | 129 | CZ | ARG | 242 | 18.881 | 26.725 | 97.964 | 1.00 | 31.27 |
| ATOM | 130 | NH1 | ARG | 242 | 19.384 | 27.680 | 97.214 | 1.00 | 33.78 |
| ATOM | 133 | NH2 | ARG | 242 | 17.727 | 26.903 | 98.588 | 1.00 | 34.79 |
| ATOM | 136 | C | ARG | 242 | 20.053 | 22.179 | 94.124 | 1.00 | 14.87 |
| ATOM | 137 | O | ARG | 242 | 21.111 | 22.641 | 93.681 | 1.00 | 13.69 |
| ATOM | 138 | N | GLU | 243 | 19.852 | 20.878 | 94.327 | 1.00 | 12.60 |
| ATOM | 140 | CA | GLU | 243 | 20.879 | 19.857 | 94.087 | 1.00 | 15.16 |
| ATOM | 141 | CB | GLU | 243 | 20.359 | 18.482 | 94.537 | 1.00 | 15.64 |
| ATOM | 142 | CG | GLU | 243 | 20.243 | 18.312 | 96.035 | 1.00 | 21.87 |
| ATOM | 143 | CD | GLU | 243 | 19.087 | 19.087 | 96.647 | 1.00 | 24.48 |
| ATOM | 144 | OE1 | GLU | 243 | 18.067 | 19.266 | 95.960 | 1.00 | 24.61 |
| ATOM | 145 | OE2 | GLU | 243 | 19.190 | 19.482 | 97.840 | 1.00 | 27.96 |
| ATOM | 146 | C | GLU | 243 | 21.282 | 19.754 | 92.604 | 1.00 | 14.70 |
| ATOM | 147 | O | GLU | 243 | 22.346 | 19.229 | 92.259 | 1.00 | 14.38 |
| ATOM | 148 | N | THR | 244 | 20.411 | 20.220 | 91.718 | 1.00 | 13.51 |
| ATOM | 150 | CA | THR | 244 | 20.699 | 20.168 | 90.280 | 1.00 | 12.07 |
| ATOM | 151 | CB | THR | 244 | 19.385 | 20.374 | 89.418 | 1.00 | 10.75 |
| ATOM | 152 | OG1 | THR | 244 | 18.888 | 21.707 | 89.565 | 1.00 | 10.55 |
| ATOM | 154 | CG2 | THR | 244 | 18.290 | 19.402 | 89.858 | 1.00 | 13.15 |
| ATOM | 155 | C | THR | 244 | 21.760 | 21.199 | 89.833 | 1.00 | 10.76 |
| ATOM | 156 | O | THR | 244 | 22.269 | 21.168 | 88.705 | 1.00 | 10.97 |
| ATOM | 157 | N | LEU | 245 | 22.148 | 22.077 | 90.746 | 1.00 | 8.88 |
| ATOM | 159 | CA | LEU | 245 | 23.061 | 23.165 | 90.379 | 1.00 | 9.31 |
| ATOM | 160 | CB | LEU | 245 | 22.368 | 24.506 | 90.651 | 1.00 | 10.49 |
| ATOM | 161 | CG | LEU | 245 | 20.914 | 24.742 | 90.150 | 1.00 | 11.43 |
| ATOM | 162 | CD1 | LEU | 245 | 20.382 | 26.019 | 90.797 | 1.00 | 13.57 |
| ATOM | 163 | CD2 | LEU | 245 | 20.877 | 24.853 | 88.650 | 1.00 | 11.87 |
| ATOM | 164 | C | LEU | 245 | 24.393 | 23.193 | 91.083 | 1.00 | 10.95 |
| ATOM | 165 | O | LEU | 245 | 24.495 | 22.971 | 92.300 | 1.00 | 9.05 |
| ATOM | 166 | N | LYS | 246 | 25.416 | 23.518 | 90.317 | 1.00 | 10.85 |
| ATOM | 168 | CA | LYS | 246 | 26.762 | 23.622 | 90.837 | 1.00 | 13.86 |
| ATOM | 169 | CB | LYS | 246 | 27.611 | 22.471 | 90.288 | 1.00 | 15.07 |
| ATOM | 170 | CG | LYS | 246 | 29.054 | 22.496 | 90.773 | 1.00 | 22.47 |
| ATOM | 171 | CD | LYS | 246 | 29.873 | 21.474 | 89.971 | 1.00 | 27.84 |
| ATOM | 172 | CE | LYS | 246 | 31.201 | 21.130 | 90.636 | 1.00 | 30.47 |
| ATOM | 173 | NZ | LYS | 246 | 31.003 | 20.227 | 91.823 | 1.00 | 34.63 |
| ATOM | 177 | C | LYS | 246 | 27.311 | 24.958 | 90.362 | 1.00 | 12.07 |
| ATOM | 178 | O | LYS | 246 | 27.438 | 25.151 | 89.148 | 1.00 | 14.04 |
| ATOM | 179 | N | LEU | 247 | 27.550 | 25.878 | 91.299 | 0.60 | 10.03 |
| ATOM | 181 | CA | LEU | 247 | 28.062 | 27.225 | 91.030 | 0.60 | 10.15 |
| ATOM | 182 | CB | LEU | 247 | 27.574 | 28.203 | 92.116 | 0.60 | 9.32 |

TABLE 4-continued

Coordinates of Lck bound with staurosporine (soaked)

| | Atom Type | Res | # | X | Y | Z | Occ | B |
|---|---|---|---|---|---|---|---|---|
| ATOM | 183 | CG | LEU | 247 | 26.175 | 28.846 | 92.001 | 0.60 | 10.50 |
| ATOM | 184 | CD1 | LEU | 247 | 25.107 | 27.817 | 91.828 | 0.60 | 10.50 |
| ATOM | 185 | CD2 | LEU | 247 | 25.882 | 29.702 | 93.248 | 0.60 | 10.58 |
| ATOM | 186 | C | LEU | 247 | 29.587 | 27.226 | 90.925 | 0.60 | 10.90 |
| ATOM | 187 | O | LEU | 247 | 30.281 | 26.783 | 91.830 | 0.60 | 9.54 |
| ATOM | 188 | N | VAL | 248 | 30.106 | 27.705 | 89.803 | 1.00 | 12.69 |
| ATOM | 190 | CA | VAL | 248 | 31.547 | 27.639 | 89.569 | 1.00 | 15.63 |
| ATOM | 191 | CB | VAL | 248 | 31.834 | 26.802 | 88.298 | 1.00 | 16.91 |
| ATOM | 192 | CG1 | VAL | 248 | 33.337 | 26.609 | 88.100 | 1.00 | 18.84 |
| ATOM | 193 | CG2 | VAL | 248 | 31.163 | 25.438 | 88.418 | 1.00 | 15.03 |
| ATOM | 194 | C | VAL | 248 | 32.328 | 28.947 | 89.556 | 1.00 | 16.65 |
| ATOM | 195 | O | VAL | 248 | 33.435 | 28.985 | 90.045 | 1.00 | 19.01 |
| ATOM | 196 | N | GLU | 249 | 31.759 | 30.034 | 89.046 | 1.00 | 16.72 |
| ATOM | 198 | CA | GLU | 249 | 32.487 | 31.249 | 88.985 | 1.00 | 16.72 |
| ATOM | 199 | CB | GLU | 249 | 33.278 | 31.332 | 87.659 | 1.00 | 20.55 |
| ATOM | 200 | CG | GLU | 249 | 34.366 | 32.418 | 87.599 | 1.00 | 26.95 |
| ATOM | 201 | CD | GLU | 249 | 34.77 | 32.796 | 86.158 | 1.00 | 29.78 |
| ATOM | 202 | OE1 | GLU | 249 | 34.916 | 31.893 | 85.301 | 1.00 | 32.71 |
| ATOM | 203 | OE2 | GLU | 249 | 34.963 | 34.03 | 85.879 | 1.00 | 31.08 |
| ATOM | 204 | C | GLU | 249 | 31.556 | 32.484 | 89.066 | 1.00 | 16.18 |
| ATOM | 205 | O | GLU | 249 | 30.524 | 32.519 | 88.422 | 1.00 | 14.44 |
| ATOM | 206 | N | ARG | 250 | 31.958 | 33.498 | 89.826 | 1.00 | 14.75 |
| ATOM | 208 | CB | ARG | 250 | 31.149 | 34.697 | 89.970 | 1.00 | 16.31 |
| ATOM | 209 | CB | ARG | 250 | 31.586 | 35.481 | 91.206 | 1.00 | 18.34 |
| ATOM | 210 | CG | ARG | 250 | 30.578 | 36.542 | 91.602 | 1.00 | 24.42 |
| ATOM | 211 | CD | ARG | 250 | 30.650 | 36.833 | 93.108 | 1.00 | 29.12 |
| ATOM | 212 | NE | ARG | 250 | 32.020 | 37.004 | 93.581 | 1.00 | 34.21 |
| ATOM | 214 | CZ | ARG | 250 | 32.474 | 36.540 | 94.752 | 1.00 | 38.12 |
| ATOM | 215 | NH1 | ARG | 250 | 31.658 | 35.886 | 95.591 | 1.00 | 38.43 |
| ATOM | 218 | NH2 | ARG | 250 | 33.760 | 36.673 | 95.064 | 1.00 | 38.12 |
| ATOM | 221 | C | ARG | 250 | 31.216 | 35.590 | 88.737 | 1.00 | 13.14 |
| ATOM | 222 | O | ARG | 250 | 32.285 | 35.858 | 88.232 | 1.00 | 13.08 |
| ATOM | 223 | N | LEU | 251 | 30.062 | 35.972 | 88.205 | 1.00 | 12.68 |
| ATOM | 224 | H | LEU | 251 | 29.248 | 35.608 | 88.573 | 1.00 | 20.00 |
| ATOM | 225 | CA | LEU | 251 | 30.012 | 36.833 | 87.024 | 1.00 | 11.57 |
| ATOM | 226 | CB | LEU | 251 | 28.920 | 36.356 | 86.071 | 1.00 | 10.45 |
| ATOM | 227 | CG | LEU | 251 | 29.000 | 34.881 | 85.622 | 1.00 | 10.47 |
| ATOM | 228 | CD1 | LEU | 251 | 27.692 | 34.513 | 84.926 | 1.00 | 10.51 |
| ATOM | 229 | CD2 | LEU | 251 | 30.194 | 34.549 | 84.674 | 1.00 | 9.63 |
| ATOM | 230 | C | LEU | 251 | 29.757 | 38.290 | 87.354 | 1.00 | 12.84 |
| ATOM | 231 | O | LEU | 251 | 30.110 | 39.141 | 86.586 | 1.00 | 12.85 |
| ATOM | 232 | N | GLY | 252 | 29.043 | 38.534 | 88.454 | 1.00 | 14.06 |
| ATOM | 234 | CA | GLY | 252 | 28.697 | 39.889 | 88.879 | 1.00 | 16.48 |
| ATOM | 235 | C | GLY | 252 | 28.247 | 39.871 | 90.337 | 1.00 | 18.50 |
| ATOM | 236 | O | GLY | 252 | 27.860 | 38.831 | 90.871 | 1.00 | 18.48 |
| ATOM | 237 | N | ALA | 253 | 28.377 | 40.997 | 91.032 | 1.00 | 20.36 |
| ATOM | 239 | CA | ALA | 253 | 27.977 | 41.046 | 92.430 | 1.00 | 22.25 |
| ATOM | 240 | CB | ALA | 253 | 29.170 | 40.793 | 93.359 | 1.00 | 22.29 |
| ATOM | 241 | C | ALA | 253 | 27.333 | 42.364 | 92.753 | 1.00 | 24.41 |
| ATOM | 242 | O | ALA | 253 | 27.654 | 43.386 | 92.154 | 1.00 | 25.47 |
| ATOM | 243 | N | GLY | 254 | 26.457 | 42.365 | 93.744 | 1.00 | 24.62 |
| ATOM | 245 | CA | GLY | 254 | 25.782 | 43.592 | 94.068 | 1.00 | 25.95 |
| ATOM | 246 | C | GLY | 254 | 25.166 | 43.611 | 95.431 | 1.00 | 25.48 |
| ATOM | 247 | O | GLY | 254 | 25.350 | 42.700 | 96.222 | 1.00 | 25.92 |
| ATOM | 248 | N | GLN | 255 | 24.527 | 44.737 | 95.722 | 1.00 | 26.31 |
| ATOM | 250 | CA | GLN | 255 | 23.874 | 44.957 | 96.998 | 1.00 | 26.64 |
| ATOM | 251 | CB | GLN | 255 | 23.446 | 46.419 | 97.064 | 1.00 | 29.75 |
| ATOM | 252 | CG | GLN | 255 | 22.747 | 46.856 | 98.322 | 1.00 | 34.10 |
| ATOM | 253 | CD | GLN | 255 | 22.017 | 48.171 | 98.121 | 1.00 | 36.38 |
| ATOM | 254 | OE1 | GLN | 255 | 21.131 | 48.519 | 98.905 | 1.00 | 38.79 |
| ATOM | 255 | NE2 | GLN | 255 | 22.362 | 48.896 | 97.053 | 1.00 | 36.30 |
| ATOM | 258 | C | GLN | 255 | 22.682 | 44.026 | 97.195 | 1.00 | 25.12 |
| ATOM | 259 | O | GLN | 255 | 22.359 | 43.641 | 98.325 | 1.00 | 25.75 |
| ATOM | 260 | N | ALA | 256 | 22.090 | 43.594 | 96.077 | 1.00 | 22.09 |
| ATOM | 261 | H | ALA | 256 | 22.487 | 43.881 | 95.233 | 1.00 | 20.00 |
| ATOM | 262 | CA | ALA | 256 | 20.935 | 42.685 | 96.077 | 1.00 | 21.90 |
| ATOM | 263 | CB | ALA | 256 | 19.911 | 43.108 | 94.982 | 1.00 | 20.60 |
| ATOM | 264 | C | ALA | 256 | 21.291 | 41.210 | 95.867 | 1.00 | 19.44 |
| ATOM | 265 | O | ALA | 256 | 20.440 | 40.347 | 95.964 | 1.00 | 15.55 |
| ATOM | 266 | N | GLY | 257 | 22.552 | 40.934 | 95.517 | 1.00 | 18.47 |
| ATOM | 268 | CA | GLY | 257 | 22.937 | 39.558 | 95.310 | 1.00 | 16.24 |
| ATOM | 269 | C | GLY | 257 | 24.099 | 39.430 | 94.354 | 1.00 | 15.18 |
| ATOM | 270 | O | GLY | 257 | 24.812 | 40.409 | 94.037 | 1.00 | 13.21 |
| ATOM | 271 | N | GLU | 258 | 24.241 | 38.212 | 93.832 | 1.00 | 13.24 |

TABLE 4-continued

Coordinates of Lck bound with staurosporine (soaked)

| | | Atom Type | Res | # | X | Y | Z | Occ | B |
|---|---|---|---|---|---|---|---|---|---|
| ATOM | 273 | CA | GLU | 258 | 25.292 | 37.891 | 92.911 | 1.00 | 13.69 |
| ATOM | 274 | CB | GLU | 258 | 26.321 | 37.003 | 93.639 | 1.00 | 14.93 |
| ATOM | 275 | CG | GLU | 258 | 26.843 | 37.599 | 94.953 | 1.00 | 19.82 |
| ATOM | 276 | CD | GLU | 258 | 28.028 | 36.822 | 95.491 | 1.00 | 21.99 |
| ATOM | 277 | OE1 | GLU | 258 | 27.927 | 35.579 | 95.638 | 1.00 | 22.59 |
| ATOM | 278 | OE2 | GLU | 258 | 29.072 | 37.457 | 95.699 | 1.00 | 23.01 |
| ATOM | 279 | C | GLU | 258 | 24.742 | 37.130 | 91.709 | 1.00 | 12.11 |
| ATOM | 280 | O | GLU | 258 | 23.557 | 36.707 | 91.717 | 1.00 | 12.35 |
| ATOM | 281 | N | VAL | 259 | 25.577 | 36.995 | 90.694 | 1.00 | 9.59 |
| ATOM | 282 | H | VAL | 259 | 26.474 | 37.374 | 90.786 | 1.00 | 20.00 |
| ATOM | 283 | CA | VAL | 259 | 25.275 | 36.217 | 89.519 | 1.00 | 10.11 |
| ATOM | 284 | CB | VAL | 259 | 24.980 | 37.045 | 88.216 | 1.00 | 11.85 |
| ATOM | 285 | CG1 | VAL | 259 | 24.607 | 36.055 | 87.038 | 1.00 | 9.66 |
| ATOM | 286 | CG2 | VAL | 259 | 23.823 | 38.034 | 88.430 | 1.00 | 10.23 |
| ATOM | 287 | C | VAL | 259 | 26.500 | 35.388 | 89.299 | 1.00 | 10.60 |
| ATOM | 288 | O | VAL | 259 | 27.644 | 35.919 | 89.313 | 1.00 | 10.25 |
| ATOM | 289 | N | TRP | 260 | 26.279 | 34.089 | 89.199 | 1.00 | 9.34 |
| ATOM | 291 | CA | TRP | 260 | 27.307 | 33.090 | 89.022 | 1.00 | 9.50 |
| ATOM | 292 | CB | TRP | 260 | 27.269 | 32.103 | 90.194 | 1.00 | 10.92 |
| ATOM | 293 | CG | TRP | 260 | 27.761 | 32.642 | 91.486 | 1.00 | 12.43 |
| ATOM | 294 | CD2 | TRP | 260 | 29.008 | 32.329 | 92.089 | 1.00 | 12.30 |
| ATOM | 295 | CE2 | TRP | 260 | 29.119 | 33.128 | 93.248 | 1.00 | 14.82 |
| ATOM | 296 | CE3 | TRP | 260 | 30.071 | 31.488 | 91.758 | 1.00 | 14.96 |
| ATOM | 297 | CD1 | TRP | 260 | 27.135 | 33.529 | 92.281 | 1.00 | 13.18 |
| ATOM | 298 | NE1 | TRP | 260 | 27.947 | 33.832 | 93.362 | 1.00 | 17.08 |
| ATOM | 300 | CZ2 | TRP | 260 | 30.238 | 33.081 | 94.093 | 1.00 | 17.64 |
| ATOM | 301 | CZ3 | TRP | 260 | 31.199 | 31.429 | 92.613 | 1.00 | 16.99 |
| ATOM | 302 | CH2 | TRP | 260 | 31.273 | 32.246 | 93.745 | 1.00 | 14.69 |
| ATOM | 303 | C | TRP | 260 | 27.080 | 32.231 | 87.800 | 1.00 | 9.88 |
| ATOM | 304 | O | TRP | 260 | 25.944 | 31.967 | 87.419 | 1.00 | 8.95 |
| ATOM | 305 | N | MET | 261 | 28.163 | 31.821 | 87.161 | 1.00 | 8.87 |
| ATOM | 307 | CA | MET | 261 | 28.038 | 30.878 | 86.085 | 1.00 | 10.46 |
| ATOM | 308 | CB | MET | 261 | 29.247 | 30.988 | 85.136 | 1.00 | 12.42 |
| ATOM | 309 | CG | MET | 261 | 29.262 | 29.954 | 83.987 | 1.00 | 16.57 |
| ATOM | 310 | SD | MET | 261 | 30.294 | 28.517 | 84.361 | 1.00 | 22.32 |
| ATOM | 311 | CE | MET | 261 | 29.294 | 27.235 | 83.989 | 1.00 | 23.08 |
| ATOM | 312 | C | MET | 261 | 28.056 | 29.525 | 86.781 | 1.00 | 9.83 |
| ATOM | 313 | O | MET | 261 | 28.834 | 29.330 | 87.742 | 1.00 | 9.64 |
| ATOM | 314 | N | GLY | 262 | 27.208 | 28.607 | 86.341 | 1.00 | 8.72 |
| ATOM | 316 | CA | GLY | 262 | 27.166 | 27.301 | 86.966 | 1.00 | 11.89 |
| ATOM | 317 | C | GLY | 262 | 26.724 | 26.246 | 85.969 | 1.00 | 10.57 |
| ATOM | 318 | O | GLY | 262 | 26.624 | 26.513 | 84.758 | 1.00 | 9.80 |
| ATOM | 319 | N | TYR | 263 | 26.497 | 25.042 | 86.465 | 1.00 | 9.01 |
| ATOM | 321 | CA | TYR | 263 | 26.035 | 23.960 | 85.621 | 1.00 | 11.02 |
| ATOM | 322 | CB | TYR | 263 | 27.097 | 22.855 | 85.485 | 1.00 | 12.51 |
| ATOM | 323 | CG | TYR | 263 | 28.293 | 23.213 | 84.655 | 1.00 | 14.55 |
| ATOM | 324 | CD1 | TYR | 263 | 29.438 | 23.724 | 85.239 | 1.00 | 18.08 |
| ATOM | 325 | CE1 | TYR | 263 | 30.546 | 24.079 | 84.461 | 1.00 | 20.09 |
| ATOM | 326 | CD2 | TYR | 263 | 28.269 | 23.049 | 83.277 | 1.00 | 18.00 |
| ATOM | 327 | CE2 | TYR | 263 | 29.333 | 23.398 | 82.502 | 1.00 | 19.77 |
| ATOM | 328 | CZ | TYR | 263 | 30.472 | 23.907 | 83.085 | 1.00 | 21.42 |
| ATOM | 329 | OH | TYR | 263 | 31.509 | 24.270 | 82.257 | 1.00 | 23.89 |
| ATOM | 331 | C | TYR | 263 | 24.802 | 23.330 | 86.196 | 1.00 | 10.30 |
| ATOM | 332 | O | TYR | 263 | 24.747 | 23.067 | 87.393 | 1.00 | 9.29 |
| ATOM | 333 | N | TYR | 264 | 23.829 | 23.092 | 85.327 | 1.00 | 9.14 |
| ATOM | 335 | CA | TYR | 264 | 22.598 | 22.418 | 85.668 | 1.00 | 9.25 |
| ATOM | 336 | CB | TYR | 264 | 21.389 | 23.039 | 84.904 | 1.00 | 8.14 |
| ATOM | 337 | CG | TYR | 264 | 20.125 | 22.250 | 85.107 | 1.00 | 8.30 |
| ATOM | 338 | CD1 | TYR | 264 | 19.414 | 22.336 | 86.296 | 1.00 | 9.38 |
| ATOM | 339 | CE1 | TYR | 264 | 18.277 | 21.535 | 86.521 | 1.00 | 10.86 |
| ATOM | 340 | CD2 | TYR | 264 | 19.660 | 21.345 | 84.113 | 1.00 | 10.42 |
| ATOM | 341 | CE2 | TYR | 264 | 18.504 | 20.541 | 84.338 | 1.00 | 11.07 |
| ATOM | 342 | CZ | TYR | 264 | 17.818 | 20.667 | 85.546 | 1.00 | 11.93 |
| ATOM | 343 | OH | TYR | 264 | 16.644 | 19.967 | 85.764 | 1.00 | 12.25 |
| ATOM | 345 | C | TYR | 264 | 22.755 | 20.991 | 85.244 | 1.00 | 7.93 |
| ATOM | 346 | O | TYR | 264 | 23.097 | 20.730 | 84.084 | 1.00 | 7.75 |
| ATOM | 347 | N | ASN | 265 | 22.556 | 20.068 | 86.177 | 1.00 | 8.78 |
| ATOM | 349 | CA | ASN | 265 | 22.656 | 18.630 | 85.940 | 1.00 | 7.73 |
| ATOM | 350 | CB | ASN | 265 | 21.432 | 18.107 | 85.138 | 1.00 | 9.37 |
| ATOM | 351 | CG | ASN | 265 | 20.195 | 17.820 | 86.027 | 1.00 | 10.68 |
| ATOM | 352 | OD1 | ASN | 265 | 19.201 | 17.236 | 85.555 | 1.00 | 14.15 |
| ATOM | 353 | ND2 | ASN | 265 | 20.277 | 18.151 | 87.295 | 1.00 | 6.80 |
| ATOM | 356 | C | ASN | 265 | 23.976 | 18.213 | 85.297 | 1.00 | 7.98 |
| ATOM | 357 | O | ASN | 265 | 24.000 | 17.505 | 84.261 | 1.00 | 7.72 |

TABLE 4-continued

Coordinates of Lck bound with staurosporine (soaked)

| | | Atom Type | Res | # | X | Y | Z | Occ | B |
|---|---|---|---|---|---|---|---|---|---|
| ATOM | 358 | N | GLY | 266 | 25.043 | 18.836 | 85.810 | 1.00 | 6.07 |
| ATOM | 360 | CA | GLY | 266 | 26.401 | 18.561 | 85.350 | 1.00 | 7.41 |
| ATOM | 361 | C | GLY | 266 | 26.851 | 19.058 | 83.986 | 1.00 | 7.01 |
| ATOM | 362 | O | GLY | 266 | 27.974 | 19.487 | 83.871 | 1.00 | 9.23 |
| ATOM | 363 | N | HIS | 267 | 25.968 | 19.138 | 83.003 | 0.49 | 2.00 |
| ATOM | 365 | CA | HIS | 267 | 26.385 | 19.498 | 81.649 | 0.49 | 2.00 |
| ATOM | 366 | CB | HIS | 267 | 25.879 | 18.404 | 80.711 | 0.49 | 2.00 |
| ATOM | 367 | CG | HIS | 267 | 26.427 | 17.062 | 81.012 | 0.49 | 2.00 |
| ATOM | 368 | CD2 | HIS | 267 | 25.850 | 15.925 | 81.413 | 0.49 | 2.00 |
| ATOM | 369 | ND1 | HIS | 267 | 27.795 | 16.791 | 80.933 | 0.49 | 2.00 |
| ATOM | 371 | CE1 | HIS | 267 | 27.995 | 15.546 | 81.278 | 0.49 | 2.00 |
| ATOM | 372 | NE2 | HIS | 267 | 26.840 | 14.982 | 81.578 | 0.49 | 2.00 |
| ATOM | 374 | C | HIS | 267 | 25.966 | 20.815 | 81.027 | 0.49 | 2.09 |
| ATOM | 375 | O | HIS | 267 | 26.543 | 21.266 | 80.034 | 0.49 | 2.00 |
| ATOM | 376 | N | THR | 268 | 24.935 | 21.423 | 81.586 | 1.00 | 4.73 |
| ATOM | 377 | H | THR | 268 | 24.525 | 21.095 | 82.409 | 1.00 | 20.00 |
| ATOM | 378 | CA | THR | 268 | 24.404 | 22.625 | 80.944 | 1.00 | 5.55 |
| ATOM | 379 | CB | THR | 268 | 22.859 | 22.525 | 80.846 | 1.00 | 7.68 |
| ATOM | 380 | OG1 | THR | 268 | 22.512 | 21.310 | 80.149 | 1.00 | 9.02 |
| ATOM | 382 | CG2 | THR | 268 | 22.274 | 23.755 | 80.100 | 1.00 | 5.22 |
| ATOM | 383 | C | THR | 268 | 24.803 | 23.892 | 81.652 | 1.00 | 6.63 |
| ATOM | 384 | O | THR | 268 | 24.513 | 24.093 | 82.850 | 1.00 | 6.37 |
| ATOM | 385 | N | LYS | 269 | 25.546 | 24.706 | 80.928 | 1.00 | 5.70 |
| ATOM | 387 | CA | LYS | 269 | 25.997 | 25.980 | 81.437 | 1.00 | 7.60 |
| ATOM | 388 | CB | LYS | 269 | 27.008 | 26.557 | 80.441 | 1.00 | 11.19 |
| ATOM | 389 | CG | LYS | 269 | 28.112 | 27.299 | 81.092 | 1.00 | 19.64 |
| ATOM | 390 | CD | LYS | 269 | 29.454 | 27.141 | 80.346 | 1.00 | 24.28 |
| ATOM | 391 | CE | LYS | 269 | 30.292 | 28.414 | 80.570 | 1.00 | 28.05 |
| ATOM | 392 | NZ | LYS | 269 | 31.712 | 28.462 | 80.031 | 1.00 | 29.11 |
| ATOM | 396 | C | LYS | 269 | 24.835 | 26.970 | 81.591 | 1.00 | 6.80 |
| ATOM | 397 | O | LYS | 269 | 24.107 | 27.215 | 80.617 | 1.00 | 4.51 |
| ATOM | 398 | N | VAL | 270 | 24.729 | 27.609 | 82.759 | 1.00 | 4.20 |
| ATOM | 400 | CA | VAL | 270 | 23.665 | 28.550 | 83.073 | 1.00 | 5.51 |
| ATOM | 401 | CB | VAL | 270 | 22.487 | 27.835 | 83.862 | 1.00 | 5.12 |
| ATOM | 402 | CG1 | VAL | 270 | 21.848 | 26.691 | 83.028 | 1.00 | 5.11 |
| ATOM | 403 | CG2 | VAL | 270 | 23.005 | 27.227 | 85.215 | 1.00 | 4.28 |
| ATOM | 404 | C | VAL | 270 | 24.196 | 29.670 | 83.985 | 1.00 | 4.46 |
| ATOM | 405 | O | VAL | 270 | 25.323 | 29.602 | 84.495 | 1.00 | 5.70 |
| ATOM | 406 | N | ALA | 271 | 23.427 | 30.735 | 84.117 | 1.00 | 4.49 |
| ATOM | 408 | CA | ALA | 271 | 23.749 | 31.844 | 85.016 | 1.00 | 5.32 |
| ATOM | 409 | CB | ALA | 271 | 23.510 | 33.201 | 84.315 | 1.00 | 5.88 |
| ATOM | 410 | C | ALA | 271 | 22.807 | 31.730 | 86.169 | 1.00 | 6.25 |
| ATOM | 411 | O | ALA | 271 | 21.619 | 31.496 | 85.963 | 1.00 | 6.40 |
| ATOM | 412 | N | VAL | 272 | 23.311 | 31.871 | 87.376 | 1.00 | 7.01 |
| ATOM | 414 | CA | VAL | 272 | 22.501 | 31.778 | 88.577 | 1.00 | 8.53 |
| ATOM | 415 | CB | VAL | 272 | 22.991 | 30.643 | 89.516 | 1.00 | 10.04 |
| ATOM | 416 | CG1 | VAL | 272 | 22.089 | 30.562 | 90.776 | 1.00 | 8.99 |
| ATOM | 417 | CG2 | VAL | 272 | 22.962 | 29.341 | 88.754 | 1.00 | 9.42 |
| ATOM | 418 | C | VAL | 272 | 22.551 | 33.066 | 89.373 | 1.00 | 8.99 |
| ATOM | 419 | O | VAL | 272 | 23.604 | 33.496 | 89.799 | 1.00 | 9.70 |
| ATOM | 420 | N | LYS | 273 | 21.397 | 33.713 | 89.473 | 1.00 | 10.49 |
| ATOM | 422 | CA | LYS | 273 | 21.250 | 34.941 | 90.240 | 1.00 | 12.00 |
| ATOM | 423 | CB | LYS | 273 | 20.196 | 35.824 | 89.540 | 1.00 | 14.81 |
| ATOM | 424 | CG | LYS | 273 | 20.151 | 37.282 | 90.025 | 1.00 | 20.98 |
| ATOM | 425 | CD | LYS | 273 | 19.145 | 38.096 | 89.197 | 1.00 | 21.51 |
| ATOM | 426 | CE | LYS | 273 | 19.180 | 39.574 | 89.551 | 1.00 | 25.70 |
| ATOM | 427 | NZ | LYS | 273 | 18.104 | 40.361 | 88.885 | 1.00 | 26.23 |
| ATOM | 431 | C | LYS | 273 | 20.778 | 34.571 | 91.660 | 1.00 | 12.95 |
| ATOM | 432 | O | LYS | 273 | 19.717 | 33.951 | 91.823 | 1.00 | 10.71 |
| ATOM | 433 | N | SER | 274 | 21.572 | 34.907 | 92.662 | 1.00 | 11.60 |
| ATOM | 435 | CA | SER | 274 | 21.239 | 34.619 | 94.053 | 1.00 | 14.29 |
| ATOM | 436 | CB | SER | 274 | 22.491 | 34.100 | 94.762 | 1.00 | 15.73 |
| ATOM | 437 | OG | SER | 274 | 23.481 | 35.139 | 94.783 | 1.00 | 18.57 |
| ATOM | 439 | C | SER | 274 | 20.792 | 35.880 | 94.777 | 1.00 | 16.33 |
| ATOM | 440 | O | SER | 274 | 21.347 | 36.931 | 94.557 | 1.00 | 16.75 |
| ATOM | 441 | N | LEU | 275 | 19.812 | 35.772 | 95.658 | 1.00 | 17.75 |
| ATOM | 443 | CA | LEU | 275 | 19.364 | 36.926 | 96.416 | 1.00 | 19.66 |
| ATOM | 444 | CB | LEU | 275 | 17.874 | 36.790 | 96.750 | 1.00 | 17.82 |
| ATOM | 445 | CG | LEU | 275 | 17.242 | 37.763 | 97.782 | 1.00 | 18.34 |
| ATOM | 446 | CD1 | LEU | 275 | 17.364 | 39.217 | 97.340 | 1.00 | 16.13 |
| ATOM | 447 | CD2 | LEU | 275 | 15.773 | 37.399 | 97.936 | 1.00 | 19.31 |
| ATOM | 448 | C | LEU | 275 | 20.136 | 37.100 | 97.708 | 1.00 | 20.05 |
| ATOM | 449 | O | LEU | 275 | 20.235 | 36.168 | 98.520 | 1.00 | 21.68 |
| ATOM | 450 | N | LYS | 276 | 20.678 | 38.291 | 97.915 | 1.00 | 21.85 |

TABLE 4-continued

Coordinates of Lck bound with staurosporine (soaked)

| | | Atom Type | Res | # | X | Y | Z | Occ | B |
|---|---|---|---|---|---|---|---|---|---|
| ATOM | 452 | CA | LYS | 276 | 21.344 | 38.566 | 99.161 | 1.00 | 22.31 |
| ATOM | 453 | CB | LYS | 276 | 22.108 | 39.880 | 99.083 | 1.00 | 22.82 |
| ATOM | 454 | CG | LYS | 276 | 22.633 | 40.254 | 100.446 | 1.00 | 23.68 |
| ATOM | 455 | CD | LYS | 276 | 23.468 | 41.476 | 100.398 | 1.00 | 23.56 |
| ATOM | 456 | CE | LYS | 276 | 24.054 | 41.658 | 101.760 | 1.00 | 26.66 |
| ATOM | 457 | NZ | LYS | 276 | 25.196 | 42.568 | 101.684 | 1.00 | 28.24 |
| ATOM | 461 | C | LYS | 276 | 20.266 | 38.685 | 100.241 | 1.00 | 23.91 |
| ATOM | 462 | O | LYS | 276 | 19.513 | 39.656 | 100.269 | 1.00 | 22.65 |
| ATOM | 463 | N | ALA | 277 | 20.162 | 37.673 | 101.091 | 1.00 | 25.44 |
| ATOM | 465 | CA | ALA | 277 | 19.147 | 37.644 | 102.135 | 1.00 | 28.36 |
| ATOM | 466 | CB | ALA | 277 | 19.387 | 36.469 | 103.085 | 1.00 | 27.71 |
| ATOM | 467 | C | ALA | 277 | 19.046 | 38.925 | 102.913 | 1.00 | 28.32 |
| ATOM | 468 | O | ALA | 277 | 20.033 | 39.430 | 103.427 | 1.00 | 31.33 |
| ATOM | 469 | N | GLY | 278 | 17.857 | 39.515 | 102.899 | 1.00 | 29.93 |
| ATOM | 471 | CA | GLY | 278 | 17.618 | 40.743 | 103.638 | 1.00 | 29.72 |
| ATOM | 472 | C | GLY | 278 | 17.743 | 42.014 | 102.841 | 1.00 | 30.31 |
| ATOM | 473 | O | GLY | 278 | 17.208 | 43.047 | 103.231 | 1.00 | 31.97 |
| ATOM | 474 | N | SER | 279 | 18.424 | 41.945 | 101.705 | 1.00 | 29.29 |
| ATOM | 476 | CA | SER | 279 | 18.618 | 43.119 | 100.863 | 1.00 | 27.22 |
| ATOM | 477 | CB | SER | 279 | 19.657 | 42.833 | 99.784 | 1.00 | 27.32 |
| ATOM | 478 | OG | SER | 279 | 19.144 | 41.896 | 98.846 | 1.00 | 27.64 |
| ATOM | 480 | C | SER | 279 | 17.359 | 43.602 | 100.183 | 1.00 | 26.04 |
| ATOM | 481 | O | SER | 279 | 17.230 | 44.747 | 99.832 | 1.00 | 26.50 |
| ATOM | 482 | N | MET | 280 | 16.492 | 42.668 | 99.844 | 1.00 | 24.08 |
| ATOM | 484 | CA | MET | 280 | 15.241 | 43.003 | 99.200 | 1.00 | 20.84 |
| ATOM | 485 | CB | MET | 280 | 15.440 | 43.303 | 97.712 | 1.00 | 22.08 |
| ATOM | 486 | CG | MET | 280 | 15.974 | 42.167 | 96.890 | 1.00 | 18.69 |
| ATOM | 487 | SD | MET | 280 | 15.987 | 42.519 | 95.137 | 1.00 | 22.52 |
| ATOM | 488 | CE | MET | 280 | 14.275 | 42.290 | 94.709 | 1.00 | 10.03 |
| ATOM | 489 | C | MET | 280 | 14.289 | 41.854 | 99.400 | 1.00 | 19.05 |
| ATOM | 490 | O | MET | 280 | 14.700 | 40.750 | 99.704 | 1.00 | 18.43 |
| ATOM | 491 | N | SER | 281 | 13.009 | 42.108 | 99.301 | 1.00 | 15.80 |
| ATOM | 493 | CA | SER | 281 | 12.032 | 41.073 | 99.498 | 1.00 | 15.96 |
| ATOM | 494 | CB | SER | 281 | 10.645 | 41.676 | 99.366 | 1.00 | 17.20 |
| ATOM | 495 | OG | SER | 281 | 9.725 | 40.685 | 98.991 | 1.00 | 16.98 |
| ATOM | 497 | C | SER | 281 | 12.156 | 39.928 | 98.493 | 1.00 | 14.42 |
| ATOM | 498 | O | SER | 281 | 12.369 | 40.178 | 97.303 | 1.00 | 15.13 |
| ATOM | 499 | N | PRO | 282 | 12.017 | 38.677 | 98.944 | 0.51 | 11.99 |
| ATOM | 500 | CD | PRO | 282 | 12.119 | 38.272 | 100.351 | 0.51 | 12.01 |
| ATOM | 501 | CA | PRO | 282 | 12.092 | 37.516 | 98.056 | 0.51 | 9.71 |
| ATOM | 502 | CB | PRO | 282 | 11.942 | 36.318 | 99.009 | 0.51 | 9.45 |
| ATOM | 503 | CG | PRO | 282 | 11.505 | 36.907 | 100.327 | 0.51 | 11.53 |
| ATOM | 504 | C | PRO | 282 | 10.971 | 37.570 | 97.000 | 0.51 | 8.44 |
| ATOM | 505 | O | PRO | 282 | 11.137 | 37.132 | 95.864 | 0.51 | 3.52 |
| ATOM | 506 | N | ASP | 283 | 9.801 | 38.069 | 97.408 | 1.00 | 9.84 |
| ATOM | 508 | CA | ASP | 283 | 8.689 | 38.252 | 96.484 | 1.00 | 10.75 |
| ATOM | 509 | CB | ASP | 283 | 7.478 | 38.857 | 97.209 | 1.00 | 15.31 |
| ATOM | 510 | CG | ASP | 283 | 6.276 | 39.016 | 96.301 | 1.00 | 18.52 |
| ATOM | 511 | OD1 | ASP | 283 | 5.791 | 37.972 | 95.818 | 1.00 | 18.82 |
| ATOM | 512 | OD2 | ASP | 283 | 5.809 | 40.169 | 96.061 | 1.00 | 19.91 |
| ATOM | 513 | C | ASP | 283 | 9.100 | 39.211 | 95.391 | 1.00 | 10.82 |
| ATOM | 514 | O | ASP | 283 | 8.812 | 38.997 | 94.250 | 1.00 | 10.24 |
| ATOM | 515 | N | ALA | 284 | 9.787 | 40.295 | 95.769 | 1.00 | 9.15 |
| ATOM | 517 | CA | ALA | 284 | 10.252 | 41.282 | 94.770 | 1.00 | 12.47 |
| ATOM | 518 | CB | ALA | 284 | 10.921 | 42.462 | 95.466 | 1.00 | 11.84 |
| ATOM | 519 | C | ALA | 284 | 11.250 | 40.642 | 93.803 | 1.00 | 12.12 |
| ATOM | 520 | O | ALA | 284 | 11.134 | 40.745 | 92.569 | 1.00 | 12.27 |
| ATOM | 521 | N | PHE | 285 | 12.176 | 39.881 | 94.384 | 1.00 | 13.53 |
| ATOM | 523 | CA | PHE | 285 | 13.198 | 39.163 | 93.620 | 1.00 | 12.88 |
| ATOM | 524 | CB | PHE | 285 | 14.092 | 38.404 | 94.615 | 1.00 | 10.02 |
| ATOM | 525 | CG | PHE | 285 | 15.241 | 37.657 | 93.979 | 1.00 | 9.97 |
| ATOM | 526 | CD1 | PHE | 285 | 16.388 | 38.312 | 93.585 | 1.00 | 11.33 |
| ATOM | 527 | CD2 | PHE | 285 | 15.171 | 36.266 | 93.824 | 1.00 | 10.09 |
| ATOM | 528 | CE1 | PHE | 285 | 17.468 | 37.590 | 93.037 | 1.00 | 12.01 |
| ATOM | 529 | CE2 | PHE | 285 | 16.222 | 35.561 | 93.297 | 1.00 | 8.91 |
| ATOM | 530 | CZ | PHE | 285 | 17.366 | 36.215 | 92.905 | 1.00 | 9.02 |
| ATOM | 531 | C | PHE | 285 | 12.551 | 38.230 | 92.597 | 1.00 | 13.34 |
| ATOM | 532 | O | PHE | 285 | 12.767 | 38.355 | 91.376 | 1.00 | 14.06 |
| ATOM | 533 | N | LEU | 286 | 11.645 | 37.378 | 93.082 | 1.00 | 13.73 |
| ATOM | 535 | CA | LEU | 286 | 10.950 | 36.406 | 92.251 | 1.00 | 13.26 |
| ATOM | 536 | CB | LEU | 286 | 10.195 | 35.405 | 93.118 | 1.00 | 13.89 |
| ATOM | 537 | CG | LEU | 286 | 11.161 | 34.471 | 93.851 | 1.00 | 14.02 |
| ATOM | 538 | CD1 | LEU | 286 | 10.336 | 33.449 | 94.581 | 1.00 | 15.09 |
| ATOM | 539 | CD2 | LEU | 286 | 12.141 | 33.772 | 92.882 | 1.00 | 14.06 |

TABLE 4-continued

Coordinates of Lck bound with staurosporine (soaked)

| | | Atom Type | Res | # | X | Y | Z | Occ | B |
|---|---|---|---|---|---|---|---|---|---|
| ATOM | 540 | C | LEU | 286 | 10.013 | 36.957 | 91.164 | 1.00 | 14.59 |
| ATOM | 541 | O | LEU | 286 | 9.770 | 36.292 | 90.126 | 1.00 | 12.36 |
| ATOM | 542 | N | ALA | 287 | 9.545 | 38.181 | 91.372 | 1.00 | 12.82 |
| ATOM | 544 | CA | ALA | 287 | 8.674 | 38.823 | 90.398 | 1.00 | 14.03 |
| ATOM | 545 | CB | ALA | 287 | 8.299 | 40.253 | 90.886 | 1.00 | 12.35 |
| ATOM | 546 | C | ALA | 287 | 9.309 | 38.885 | 89.011 | 1.00 | 12.11 |
| ATOM | 547 | O | ALA | 287 | 8.624 | 38.732 | 88.000 | 1.00 | 14.16 |
| ATOM | 548 | N | GLU | 288 | 1o.616 | 39.149 | 88.967 | 1.00 | 13.07 |
| ATOM | 550 | CA | GLU | 288 | 11.337 | 39.210 | 87.702 | 1.00 | 13.61 |
| ATOM | 551 | CB | GLU | 288 | 12.823 | 39.550 | 87.924 | 1.00 | 17.54 |
| ATOM | 552 | CG | GLU | 288 | 13.514 | 40.087 | 86.624 | 1.00 | 20.67 |
| ATOM | 553 | CD | GLU | 288 | 15.01o | 39.853 | 86.585 | 1.00 | 22.80 |
| ATOM | 554 | OE1 | GLU | 288 | 15.609 | 39.713 | 87.685 | 1.00 | 26.25 |
| ATOM | 555 | OE2 | GLU | 288 | 15.592 | 39.825 | 85.452 | 1.00 | 23.11 |
| ATOM | 556 | C | GLU | 288 | 11.243 | 37.890 | 86.941 | 1.00 | 14.04 |
| ATOM | 557 | O | GLU | 288 | 11.074 | 37.858 | 85.713 | 1.00 | 11.37 |
| ATOM | 558 | N | ALA | 289 | 11.356 | 36.776 | 87.677 | 1.00 | 13.32 |
| ATOM | 560 | CA | ALA | 289 | 11.255 | 35.459 | 87.014 | 1.00 | 12.33 |
| ATOM | 561 | CB | ALA | 289 | 11.609 | 34.340 | 87.987 | 1.00 | 9.97 |
| ATOM | 562 | C | ALA | 289 | 9.850 | 35.258 | 86.462 | 1.00 | 11.60 |
| ATOM | 563 | O | ALA | 289 | 9.653 | 34.800 | 85.348 | 1.00 | 11.52 |
| ATOM | 564 | N | ASN | 290 | 8.839 | 35.611 | 87.257 | 1.00 | 13.27 |
| ATOM | 566 | CA | ASN | 290 | 7.457 | 35.477 | 86.807 | 1.00 | 12.41 |
| ATOM | 567 | CB | ASN | 290 | 6.502 | 35.901 | 87.931 | 1.00 | 14.49 |
| ATOM | 568 | CG | ASN | 290 | 6.524 | 34.917 | 89.099 | 1.00 | 20.55 |
| ATOM | 569 | OD1 | ASN | 290 | 6.929 | 33.755 | 88.937 | 1.00 | 22.92 |
| ATOM | 570 | ND2 | ASN | 290 | 6.105 | 35.377 | 90.279 | 1.00 | 22.93 |
| ATOM | 573 | C | ASN | 290 | 7.213 | 36.292 | 85.530 | 1.00 | 12.76 |
| ATOM | 574 | O | ASN | 290 | 6.540 | 35.854 | 84.595 | 1.00 | 11.17 |
| ATOM | 575 | N | LEU | 291 | 7.795 | 37.485 | 85.456 | 1.00 | 11.61 |
| ATOM | 577 | CA | LEU | 291 | 7.626 | 38.259 | 84.224 | 1.00 | 11.64 |
| ATOM | 578 | CB | LEU | 291 | 8.169 | 39.673 | 84.422 | 1.00 | 9.96 |
| ATOM | 581 | CD2 | LEU | 291 | 9.451 | 40.583 | 82.529 | 1.00 | 14.59 |
| ATOM | 582 | C | LEU | 291 | 8.346 | 37.596 | 83.032 | 1.00 | 11.11 |
| ATOM | 583 | O | LEU | 291 | 7.835 | 37.568 | 81.936 | 1.00 | 8.95 |
| ATOM | 584 | N | MET | 292 | 9.556 | 37.084 | 83.258 | 1.00 | 10.78 |
| ATOM | 586 | CA | MET | 292 | 10.318 | 36.453 | 82.163 | 1.00 | 11.56 |
| ATOM | 587 | CB | MET | 292 | 11.703 | 36.016 | 82.636 | 1.00 | 10.22 |
| ATOM | 588 | CG | MET | 292 | 12.600 | 37.176 | 83.098 | 1.00 | 10.81 |
| ATOM | 589 | SD | MET | 292 | 14.110 | 36.571 | 83.937 | 1.00 | 12.07 |
| ATOM | 590 | CE | MET | 292 | 15.113 | 36.169 | 82.522 | 1.00 | 9.73 |
| ATOM | 591 | C | MET | 292 | 9.576 | 35.269 | 81.533 | 1.00 | 13.99 |
| ATOM | 592 | O | MET | 292 | 9.781 | 34.955 | 80.375 | 1.00 | 13.51 |
| ATOM | 593 | N | LYS | 293 | 8.747 | 34.600 | 82.326 | 1.00 | 14.27 |
| ATOM | 595 | CA | LYS | 293 | 7.927 | 33.505 | 81.810 | 1.00 | 18.20 |
| ATOM | 596 | CB | LYS | 293 | 7.059 | 32.889 | 82.918 | 1.00 | 17.91 |
| ATOM | 597 | CG | LYS | 293 | 7.788 | 32.069 | 83.956 | 1.00 | 19.57 |
| ATOM | 598 | CD | LYS | 293 | 6.832 | 31.655 | 85.125 | 1.00 | 22.28 |
| ATOM | 599 | CE | LYS | 293 | 7.630 | 31.258 | 86.369 | 1.00 | 24.15 |
| ATOM | 600 | NZ | LYS | 293 | 6.765 | 30.817 | 87.547 | 1.00 | 26.53 |
| ATOM | 604 | C | LYS | 293 | 7.027 | 33.985 | 80.642 | 1.00 | 17.56 |
| ATOM | 605 | O | LYS | 293 | 6.825 | 33.260 | 79.667 | 1.00 | 19.70 |
| ATOM | 606 | N | GLN | 294 | 6.569 | 35.232 | 80.725 | 1.00 | 18.40 |
| ATOM | 608 | CA | GLN | 294 | 5.715 | 35.871 | 79.692 | 1.00 | 18.61 |
| ATOM | 609 | CB | GLN | 294 | 4.932 | 37.056 | 80.299 | 1.00 | 18.33 |
| ATOM | 610 | CG | GLN | 294 | 4.157 | 36.753 | 81.587 | 1.00 | 18.95 |
| ATOM | 611 | CD | GLN | 294 | 3.299 | 35.548 | 81.445 | 1.00 | 21.42 |
| ATOM | 612 | OE1 | GLN | 294 | 2.661 | 35.330 | 80.392 | 1.00 | 25.23 |
| ATOM | 613 | NE2 | GLN | 294 | 3.288 | 34.712 | 82.470 | 1.00 | 23.40 |
| ATOM | 616 | C | GLN | 294 | 6.479 | 36.459 | 78.519 | 1.00 | 18.97 |
| ATOM | 617 | O | GLN | 294 | 5.883 | 37.021 | 77.573 | 1.00 | 20.23 |
| ATOM | 618 | N | LEU | 295 | 7.799 | 36.476 | 78.608 | 1.00 | 17.18 |
| ATOM | 620 | CA | LEU | 295 | 8.571 | 37.061 | 77.539 | 1.00 | 15.88 |
| ATOM | 621 | CB | LEU | 295 | 9.206 | 38.391 | 77.978 | 1.00 | 16.19 |
| ATOM | 622 | CG | LEU | 295 | 8.265 | 39.561 | 78.250 | 1.00 | 14.51 |
| ATOM | 623 | CD1 | LEU | 295 | 9.034 | 40.678 | 78.953 | 1.00 | 14.42 |
| ATOM | 624 | CD2 | LEU | 295 | 7.672 | 40.025 | 76.914 | 1.00 | 14.80 |
| ATOM | 625 | C | LEU | 295 | 9.634 | 36.148 | 77.051 | 1.00 | 15.46 |
| ATOM | 626 | O | LEU | 295 | 10.808 | 36.414 | 77.229 | 1.00 | 16.92 |
| ATOM | 627 | N | GLN | 296 | 9.217 | 35.076 | 76.402 | 1.00 | 13.87 |
| ATOM | 629 | CA | GLN | 296 | 10.166 | 34.124 | 75.882 | 1.00 | 12.14 |
| ATOM | 630 | CB | GLN | 296 | 9.622 | 32.698 | 76.060 | 1.00 | 12.02 |
| ATOM | 631 | CG | GLN | 296 | 9.503 | 32.296 | 77.521 | 1.00 | 13.14 |
| ATOM | 632 | CD | GLN | 296 | 8.863 | 30.942 | 77.698 | 1.00 | 13.95 |

TABLE 4-continued

Coordinates of Lck bound with staurosporine (soaked)

| | | Atom Type | Res | # | X | Y | Z | Occ | B |
|---|---|---|---|---|---|---|---|---|---|
| ATOM | 633 | OE1 | GLN | 296 | 9.306 | 29.989 | 77.113 | 1.00 | 14.90 |
| ATOM | 634 | NE2 | GLN | 296 | 7.815 | 30.863 | 78.526 | 1.00 | 11.25 |
| ATOM | 637 | C | GLN | 296 | 10.377 | 34.436 | 74.422 | 1.00 | 11.43 |
| ATOM | 638 | O | GLN | 296 | 9.420 | 34.517 | 73.667 | 1.00 | 10.56 |
| ATOM | 639 | N | HIS | 297 | 11.615 | 34.700 | 74.047 | 1.00 | 8.16 |
| ATOM | 641 | CA | HIS | 297 | 11.925 | 35.031 | 72.665 | 1.00 | 7.06 |
| ATOM | 642 | CB | HIS | 297 | 11.524 | 36.520 | 72.425 | 1.00 | 8.21 |
| ATOM | 643 | CG | HIS | 297 | 11.682 | 36.972 | 71.002 | 1.00 | 7.91 |
| ATOM | 644 | CD2 | HIS | 297 | 10.810 | 37.047 | 69.993 | 1.00 | 9.84 |
| ATOM | 645 | ND1 | HIS | 297 | 12.919 | 37.329 | 70.475 | 1.00 | 7.23 |
| ATOM | 647 | CE1 | HIS | 297 | 12.776 | 37.594 | 69.201 | 1.00 | 7.62 |
| ATOM | 648 | NE2 | HIS | 297 | 11.501 | 37.428 | 68.858 | 1.00 | 8.05 |
| ATOM | 650 | C | HIS | 297 | 13.408 | 34.835 | 72.494 | 1.00 | 5.69 |
| ATOM | 651 | O | HIS | 297 | 14.156 | 35.019 | 73.484 | 1.00 | 6.84 |
| ATOM | 652 | N | GLN | 298 | 13.888 | 34.501 | 71.297 | 1.00 | 5.85 |
| ATOM | 654 | CA | GLN | 298 | 15.348 | 34.304 | 71.124 | 1.00 | 5.85 |
| ATOM | 655 | CB | GLN | 298 | 15.751 | 33.937 | 69.688 | 1.00 | 7.17 |
| ATOM | 656 | CG | GLN | 298 | 15.283 | 32.622 | 69.181 | 1.00 | 7.62 |
| ATOM | 657 | CD | GLN | 298 | 15.876 | 31.431 | 69.900 | 1.00 | 5.57 |
| ATOM | 658 | OE1 | GLN | 298 | 15.131 | 30.570 | 70.307 | 1.00 | 6.33 |
| ATOM | 659 | NE2 | GLN | 298 | 17.232 | 31.341 | 69.984 | 1.00 | 3.89 |
| ATOM | 662 | C | GLN | 298 | 16.203 | 35.502 | 71.486 | 1.00 | 6.17 |
| ATOM | 663 | O | GLN | 298 | 17.357 | 35.340 | 71.902 | 1.00 | 4.21 |
| ATOM | 664 | N | ARG | 299 | 15.660 | 36.706 | 71.294 | 1.00 | 5.30 |
| ATOM | 666 | CA | ARG | 299 | 16.427 | 37.934 | 71.588 | 1.00 | 5.58 |
| ATOM | 667 | CB | ARG | 299 | 16.016 | 39.064 | 70.642 | 1.00 | 5.47 |
| ATOM | 668 | CG | ARG | 299 | 16.154 | 38.726 | 69.148 | 1.00 | 5.45 |
| ATOM | 669 | CD | ARG | 299 | 17.567 | 39.101 | 68.588 | 1.00 | 6.21 |
| ATOM | 670 | NE | ARG | 299 | 18.692 | 38.485 | 69.320 | 1.00 | 4.29 |
| ATOM | 672 | CZ | ARG | 299 | 19.049 | 37.196 | 69.256 | 1.00 | 6.38 |
| ATOM | 673 | NH1 | ARG | 299 | 18.364 | 36.337 | 68.501 | 1.00 | 2.92 |
| ATOM | 676 | NH2 | ARG | 299 | 20.162 | 36.791 | 69.863 | 1.00 | 2.41 |
| ATOM | 679 | C | ARG | 299 | 16.369 | 38.420 | 73.047 | 1.00 | 4.17 |
| ATOM | 680 | O | ARG | 299 | 16.849 | 39.506 | 73.342 | 1.00 | 2.82 |
| ATOM | 681 | N | LEU | 300 | 15.673 | 37.680 | 73.918 | 1.00 | 2.95 |
| ATOM | 683 | CA | LEU | 300 | 15.595 | 37.956 | 75.366 | 1.00 | 5.10 |
| ATOM | 684 | CB | LEU | 300 | 14.140 | 38.104 | 75.859 | 1.00 | 6.30 |
| ATOM | 685 | CG | LEU | 300 | 13.449 | 39.474 | 75.631 | 1.00 | 6.48 |
| ATOM | 686 | CD1 | LEU | 300 | 13.525 | 39.871 | 74.166 | 1.00 | 5.11 |
| ATOM | 687 | CD2 | LEU | 300 | 11.972 | 39.426 | 76.097 | 1.00 | 5.95 |
| ATOM | 688 | C | LEU | 300 | 16.261 | 36.823 | 76.189 | 1.00 | 5.43 |
| ATOM | 689 | O | LEU | 300 | 16.035 | 35.652 | 75.890 | 1.00 | 8.06 |
| ATOM | 690 | N | VAL | 301 | 17.114 | 37.172 | 77.153 | 1.00 | 3.26 |
| ATOM | 692 | CA | VAL | 301 | 17.729 | 36.170 | 78.009 | 1.00 | 4.14 |
| ATOM | 693 | CB | VAL | 301 | 18.612 | 36.847 | 79.115 | 1.00 | 5.85 |
| ATOM | 694 | CG1 | VAL | 301 | 18.976 | 35.830 | 80.239 | 1.00 | 6.95 |
| ATOM | 695 | CG2 | VAL | 301 | 19.908 | 37.376 | 78.452 | 1.00 | 4.28 |
| ATOM | 696 | C | VAL | 301 | 16.589 | 35.341 | 78.595 | 1.00 | 4.74 |
| ATOM | 697 | O | VAL | 301 | 15.607 | 35.898 | 79.118 | 1.00 | 3.76 |
| ATOM | 698 | N | ARG | 302 | 16.655 | 34.034 | 78.353 | 1.00 | 5.01 |
| ATOM | 700 | CA | ARG | 302 | 15.582 | 33.093 | 78.747 | 1.00 | 6.78 |
| ATOM | 701 | CB | ARG | 302 | 15.586 | 31.885 | 77.760 | 1.00 | 4.29 |
| ATOM | 702 | CG | ARG | 302 | 14.425 | 30.854 | 77.977 | 1.00 | 5.87 |
| ATOM | 703 | CD | ARG | 302 | 14.589 | 29.621 | 77.023 | 1.00 | 10.00 |
| ATOM | 704 | NE | ARG | 302 | 13.653 | 28.529 | 77.330 | 1.00 | 10.74 |
| ATOM | 706 | CZ | ARG | 302 | 13.839 | 27.642 | 78.306 | 1.00 | 13.16 |
| ATOM | 707 | NH1 | ARG | 302 | 14.931 | 27.696 | 79.064 | 1.00 | 10.13 |
| ATOM | 710 | NH2 | ARG | 302 | 12.917 | 26.721 | 78.546 | 1.00 | 14.10 |
| ATOM | 713 | C | ARG | 302 | 15.638 | 32.574 | 80.157 | 1.00 | 4.90 |
| ATOM | 714 | O | ARG | 302 | 16.711 | 32.175 | 80.623 | 1.00 | 4.69 |
| ATOM | 715 | N | LEU | 303 | 14.497 | 32.607 | 80.849 | 1.00 | 3.59 |
| ATOM | 717 | CA | LEU | 303 | 14.419 | 32.026 | 82.175 | 1.00 | 5.79 |
| ATOM | 718 | CB | LEU | 303 | 13.045 | 32.312 | 82.820 | 1.00 | 4.46 |
| ATOM | 719 | CG | LEU | 303 | 12.798 | 31.556 | 84.147 | 1.00 | 6.09 |
| ATOM | 720 | CD1 | LEU | 303 | 13.683 | 32.133 | 85.182 | 1.00 | 5.83 |
| ATOM | 721 | CD2 | LEU | 303 | 11.298 | 31.702 | 84.590 | 1.00 | 5.76 |
| ATOM | 722 | C | LEU | 303 | 14.597 | 30.495 | 82.033 | 1.00 | 6.12 |
| ATOM | 723 | O | LEU | 303 | 14.016 | 29.880 | 81.137 | 1.00 | 5.68 |
| ATOM | 724 | N | TYR | 304 | 15.467 | 29.939 | 82.854 | 1.00 | 6.67 |
| ATOM | 726 | CA | TYR | 304 | 15.760 | 28.519 | 82.853 | 1.00 | 10.36 |
| ATOM | 727 | CB | TYR | 304 | 17.291 | 28.358 | 83.016 | 1.00 | 12.58 |
| ATOM | 728 | CG | TYR | 304 | 17.822 | 26.995 | 82.695 | 1.00 | 18.48 |
| ATOM | 729 | CD1 | TYR | 304 | 17.631 | 25.921 | 83.579 | 1.00 | 18.80 |
| ATOM | 730 | CE1 | TYR | 304 | 18.052 | 24.647 | 83.257 | 1.00 | 20.58 |

TABLE 4-continued

Coordinates of Lck bound with staurosporine (soaked)

| | | Atom Type | Res | # | X | Y | Z | Occ | B |
|---|---|---|---|---|---|---|---|---|---|
| ATOM | 731 | CD2 | TYR | 304 | 18.451 | 26.747 | 81.479 | 1.00 | 19.27 |
| ATOM | 732 | CE2 | TYR | 304 | 18.876 | 25.452 | 81.134 | 1.00 | 18.54 |
| ATOM | 733 | CZ | TYR | 304 | 18.670 | 24.416 | 82.021 | 1.00 | 20.02 |
| ATOM | 734 | OH | TYR | 304 | 19.095 | 23.141 | 81.707 | 1.00 | 20.08 |
| ATOM | 736 | C | TYR | 304 | 15.001 | 27.749 | 83.976 | 1.00 | 9.73 |
| ATOM | 737 | O | TYR | 304 | 14.413 | 26.700 | 83.742 | 1.00 | 10.05 |
| ATOM | 738 | N | ALA | 305 | 15.004 | 28.302 | 85.185 | 1.00 | 7.52 |
| ATOM | 740 | CA | ALA | 305 | 14.384 | 27.634 | 86.321 | 1.00 | 9.06 |
| ATOM | 741 | CB | ALA | 305 | 15.183 | 26.340 | 86.675 | 1.00 | 9.73 |
| ATOM | 742 | C | ALA | 305 | 14.446 | 28.551 | 87.520 | 1.00 | 7.93 |
| ATOM | 743 | O | ALA | 305 | 15.064 | 29.608 | 87.437 | 1.00 | 5.51 |
| ATOM | 744 | N | VAL | 306 | 13.812 | 28.133 | 88.606 | 0.75 | 5.06 |
| ATOM | 746 | CA | VAL | 306 | 13.843 | 28.850 | 89.869 | 0.75 | 5.16 |
| ATOM | 747 | CB | VAL | 306 | 12.577 | 29.752 | 90.092 | 0.75 | 5.18 |
| ATOM | 748 | CG1 | VAL | 306 | 12.496 | 30.839 | 89.018 | 0.75 | 4.67 |
| ATOM | 749 | CG2 | VAL | 306 | 11.296 | 28.899 | 90.096 | 0.75 | 8.77 |
| ATOM | 750 | C | VAL | 306 | 13.890 | 27.878 | 91.033 | 0.75 | 7.22 |
| ATOM | 751 | O | VAL | 306 | 13.539 | 26.688 | 90.902 | 0.75 | 5.43 |
| ATOM | 752 | N | VAL | 307 | 14.463 | 28.359 | 92.125 | 1.00 | 10.68 |
| ATOM | 754 | CA | VAL | 307 | 14.508 | 27.659 | 93.397 | 1.00 | 12.59 |
| ATOM | 755 | CB | VAL | 307 | 15.958 | 27.351 | 93.812 | 1.00 | 13.79 |
| ATOM | 756 | CG1 | VAL | 307 | 16.007 | 26.697 | 95.200 | 1.00 | 13.71 |
| ATOM | 757 | CG2 | VAL | 307 | 16.608 | 26.402 | 92.743 | 1.00 | 14.06 |
| ATOM | 758 | C | VAL | 307 | 13.868 | 28.676 | 94.353 | 1.00 | 13.65 |
| ATOM | 759 | O | VAL | 307 | 14.442 | 29.722 | 94.622 | 1.00 | 13.40 |
| ATOM | 760 | N | THR | 308 | 12.636 | 28.409 | 94.744 | 1.00 | 14.36 |
| ATOM | 762 | CA | THR | 308 | 11.868 | 29.320 | 95.583 | 1.00 | 17.04 |
| ATOM | 763 | CB | THR | 308 | 10.423 | 29.408 | 95.087 | 1.00 | 17.52 |
| ATOM | 764 | OG1 | THR | 308 | 9.839 | 28.089 | 95.072 | 1.00 | 17.06 |
| ATOM | 766 | CG2 | THR | 308 | 10.407 | 29.988 | 93.650 | 1.00 | 14.81 |
| ATOM | 767 | C | THR | 308 | 11.915 | 29.139 | 97.116 | 1.00 | 20.73 |
| ATOM | 768 | O | THR | 308 | 11.151 | 29.785 | 97.843 | 1.00 | 20.55 |
| ATOM | 769 | N | ALA | 309 | 12.808 | 28.273 | 97.576 | 1.00 | 23.05 |
| ATOM | 771 | CA | ALA | 309 | 13.075 | 28.034 | 98.990 | 1.00 | 26.63 |
| ATOM | 772 | CB | ALA | 309 | 13.186 | 26.514 | 99.259 | 1.00 | 27.10 |
| ATOM | 773 | C | ALA | 309 | 14.400 | 28.710 | 99.259 | 1.00 | 27.06 |
| ATOM | 774 | O | ALA | 309 | 15.294 | 28.651 | 98.421 | 1.00 | 28.53 |
| ATOM | 775 | N | GLU | 310 | 14.528 | 29.426 | 100.372 | 1.00 | 29.16 |
| ATOM | 777 | CA | GLU | 310 | 15.768 | 30.145 | 100.684 | 1.00 | 29.78 |
| ATOM | 778 | CB | GLU | 310 | 15.524 | 31.083 | 101.885 | 1.00 | 32.43 |
| ATOM | 779 | CG | GLU | 310 | 14.395 | 32.120 | 101.619 | 1.00 | 37.17 |
| ATOM | 780 | CD | GLU | 310 | 14.264 | 33.233 | 102.677 | 1.00 | 40.15 |
| ATOM | 781 | OE1 | GLU | 310 | 15.052 | 33.274 | 103.659 | 1.00 | 41.14 |
| ATOM | 782 | OE2 | GLU | 310 | 13.356 | 34.084 | 102.516 | 1.00 | 41.13 |
| ATOM | 783 | C | GLU | 310 | 16.979 | 29.220 | 100.920 | 1.00 | 30.28 |
| ATOM | 784 | O | GLU | 310 | 16.810 | 28.135 | 101.475 | 1.00 | 30.28 |
| ATOM | 785 | N | PRO | 311 | 18.184 | 29.589 | 100.401 | 1.00 | 27.46 |
| ATOM | 786 | CD | PRO | 311 | 19.431 | 28.823 | 100.539 | 1.00 | 27.79 |
| ATOM | 787 | CA | PRO | 311 | 18.399 | 30.791 | 99.598 | 1.00 | 26.53 |
| ATOM | 788 | CB | PRO | 311 | 19.921 | 30.941 | 99.589 | 1.00 | 28.19 |
| ATOM | 789 | CG | PRO | 311 | 20.403 | 29.570 | 99.615 | 1.00 | 28.21 |
| ATOM | 790 | C | PRO | 311 | 17.793 | 30.569 | 98.210 | 1.00 | 25.22 |
| ATOM | 791 | O | PRO | 311 | 17.759 | 29.443 | 97.689 | 1.00 | 25.62 |
| ATOM | 792 | N | ILE | 312 | 17.237 | 31.642 | 97.668 | 1.00 | 20.59 |
| ATOM | 794 | CA | ILE | 312 | 16.521 | 31.626 | 96.409 | 1.00 | 18.53 |
| ATOM | 795 | CB | ILE | 312 | 15.394 | 32.689 | 96.474 | 1.00 | 20.69 |
| ATOM | 796 | CG2 | ILE | 312 | 14.560 | 32.665 | 95.198 | 1.00 | 23.02 |
| ATOM | 797 | CG1 | ILE | 312 | 14.486 | 32.398 | 97.690 | 1.00 | 23.23 |
| ATOM | 798 | CD1 | ILE | 312 | 13.437 | 33.459 | 97.930 | 1.00 | 25.11 |
| ATOM | 799 | C | ILE | 312 | 17.387 | 31.914 | 95.222 | 1.00 | 15.57 |
| ATOM | 800 | O | ILE | 312 | 18.319 | 32.702 | 95.295 | 1.00 | 13.64 |
| ATOM | 801 | N | TYR | 313 | 17.039 | 31.313 | 94.092 | 1.00 | 11.22 |
| ATOM | 803 | CA | TYR | 313 | 17.780 | 31.540 | 92.849 | 1.00 | 10.98 |
| ATOM | 804 | CB | TYR | 313 | 18.696 | 30.350 | 92.514 | 1.00 | 13.10 |
| ATOM | 805 | CG | TYR | 313 | 19.723 | 29.965 | 93.549 | 1.00 | 16.88 |
| ATOM | 806 | CD1 | TYR | 313 | 20.558 | 30.910 | 94.130 | 1.00 | 18.93 |
| ATOM | 807 | CE1 | TYR | 313 | 21.559 | 30.535 | 95.042 | 1.00 | 20.18 |
| ATOM | 808 | CD2 | TYR | 313 | 19.901 | 28.643 | 93.896 | 1.00 | 19.50 |
| ATOM | 809 | CE2 | TYR | 313 | 20.874 | 28.260 | 94.810 | 1.00 | 23.04 |
| ATOM | 810 | CZ | TYR | 313 | 21.700 | 29.198 | 95.382 | 1.00 | 22.50 |
| ATOM | 811 | OH | TYR | 313 | 22.615 | 28.780 | 96.334 | 1.00 | 23.90 |
| ATOM | 813 | C | TYR | 313 | 16.847 | 31.681 | 91.660 | 1.00 | 7.53 |
| ATOM | 814 | O | TYR | 313 | 15.759 | 31.147 | 91.663 | 1.00 | 7.59 |
| ATOM | 815 | N | ILE | 314 | 17.274 | 32.485 | 90.708 | 0.82 | 5.19 |

TABLE 4-continued

Coordinates of Lck bound with staurosporine (soaked)

| | | Atom Type | Res | # | X | Y | Z | Occ | B |
|---|---|---|---|---|---|---|---|---|---|
| ATOM | 817 | CA | ILE | 314 | 16.629 | 32.619 | 89.430 | 0.82 | 4.86 |
| ATOM | 818 | CB | ILE | 314 | 16.262 | 34.121 | 89.045 | 0.82 | 4.18 |
| ATOM | 819 | CG2 | ILE | 314 | 15.868 | 34.202 | 87.538 | 0.82 | 4.60 |
| ATOM | 820 | CG1 | ILE | 314 | 15.121 | 34.628 | 89.927 | 0.82 | 4.86 |
| ATOM | 821 | CD1 | ILE | 314 | 14.733 | 36.090 | 89.720 | 0.82 | 5.03 |
| ATOM | 822 | C | ILE | 314 | 17.709 | 32.110 | 88.468 | 0.82 | 3.70 |
| ATOM | 823 | O | ILE | 314 | 18.834 | 32.649 | 88.420 | 0.82 | 4.66 |
| ATOM | 824 | N | ILE | 315 | 17.421 | 31.047 | 87.742 | 1.00 | 3.50 |
| ATOM | 826 | CA | ILE | 315 | 18.429 | 30.500 | 86.833 | 1.00 | 4.82 |
| ATOM | 827 | CB | ILE | 315 | 18.532 | 28.945 | 86.945 | 1.00 | 6.00 |
| ATOM | 828 | CG2 | ILE | 315 | 19.664 | 28.420 | 86.046 | 1.00 | 2.00 |
| ATOM | 829 | CG1 | ILE | 315 | 18.799 | 28.533 | 88.401 | 1.00 | 7.08 |
| ATOM | 830 | CD1 | ILE | 315 | 17.513 | 28.158 | 89.123 | 1.00 | 9.51 |
| ATOM | 831 | C | ILE | 315 | 18.094 | 30.888 | 85.408 | 1.00 | 4.20 |
| ATOM | 832 | O | ILE | 315 | 16.958 | 30.735 | 84.988 | 1.00 | 3.76 |
| ATOM | 833 | N | THR | 316 | 19.069 | 31.406 | 84.672 | 1.00 | 3.78 |
| ATOM | 835 | CA | THR | 316 | 18.801 | 31.849 | 83.327 | 1.00 | 6.81 |
| ATOM | 836 | CB | THR | 316 | 18.795 | 33.443 | 83.208 | 1.00 | 10.74 |
| ATOM | 837 | OG1 | THR | 316 | 20.135 | 33.944 | 83.317 | 1.00 | 8.08 |
| ATOM | 839 | CG2 | THR | 316 | 17.941 | 34.094 | 84.309 | 1.00 | 7.54 |
| ATOM | 840 | C | THR | 316 | 19.836 | 31.360 | 82.341 | 1.00 | 8.02 |
| ATOM | 841 | O | THR | 316 | 20.829 | 30.707 | 82.705 | 1.00 | 7.95 |
| ATOM | 842 | N | GLU | 317 | 19.546 | 31.668 | 81.073 | 1.00 | 8.12 |
| ATOM | 844 | CA | GLU | 317 | 20.406 | 31.390 | 79.925 | 1.00 | 6.24 |
| ATOM | 845 | CB | GLU | 317 | 19.697 | 32.000 | 78.689 | 1.00 | 6.14 |
| ATOM | 846 | CG | GLU | 317 | 20.403 | 31.836 | 77.334 | 1.00 | 5.27 |
| ATOM | 847 | CD | GLU | 317 | 19.526 | 32.312 | 76.153 | 1.00 | 6.54 |
| ATOM | 848 | OE1 | GLU | 317 | 18.590 | 33.110 | 76.366 | 1.00 | 8.58 |
| ATOM | 849 | OE2 | GLU | 317 | 19.786 | 31.895 | 74.992 | 1.00 | 6.88 |
| ATOM | 850 | C | GLU | 317 | 21.746 | 32.105 | 80.164 | 1.00 | 6.62 |
| ATOM | 851 | O | GLU | 317 | 21.770 | 33.266 | 80.625 | 1.00 | 5.80 |
| ATOM | 852 | N | TYR | 318 | 22.845 | 31.425 | 79.833 | 1.00 | 4.84 |
| ATOM | 853 | H | TYR | 318 | 22.781 | 30.554 | 79.430 | 1.00 | 20.00 |
| ATOM | 854 | CA | TYR | 318 | 24.194 | 31.946 | 79.996 | 1.00 | 7.09 |
| ATOM | 855 | CB | TYR | 318 | 25.127 | 30.784 | 80.307 | 1.00 | 6.94 |
| ATOM | 856 | CG | TYR | 318 | 26.586 | 31.175 | 80.412 | 1.00 | 8.70 |
| ATOM | 857 | CD1 | TYR | 318 | 27.507 | 30.641 | 79.536 | 1.00 | 8.78 |
| ATOM | 858 | CE1 | TYR | 318 | 28.838 | 30.963 | 79.622 | 1.00 | 12.40 |
| ATOM | 859 | CD2 | TYR | 318 | 27.032 | 32.056 | 81.395 | 1.00 | 9.60 |
| ATOM | 860 | CE2 | TYR | 318 | 28.398 | 32.393 | 81.499 | 1.00 | 11.60 |
| ATOM | 861 | CZ | TYR | 318 | 29.282 | 31.831 | 80.592 | 1.00 | 12.34 |
| ATOM | 862 | OH | TYR | 318 | 30.605 | 32.172 | 80.614 | 1.00 | 13.65 |
| ATOM | 864 | C | TYR | 318 | 24.679 | 32.630 | 78.718 | 1.00 | 7.87 |
| ATOM | 865 | O | TYR | 318 | 24.588 | 32.055 | 77.646 | 1.00 | 7.67 |
| ATOM | 866 | N | MET | 319 | 25.230 | 33.826 | 78.851 | 1.00 | 7.03 |
| ATOM | 868 | CA | MET | 319 | 25.733 | 34.612 | 77.702 | 1.00 | 7.90 |
| ATOM | 869 | CB | MET | 319 | 24.936 | 35.929 | 77.662 | 1.00 | 7.45 |
| ATOM | 870 | CG | MET | 319 | 23.415 | 35.686 | 77.475 | 1.00 | 8.56 |
| ATOM | 871 | SD | MET | 319 | 23.081 | 34.959 | 75.864 | 1.00 | 11.41 |
| ATOM | 872 | CE | MET | 319 | 23.496 | 36.172 | 74.813 | 1.00 | 5.20 |
| ATOM | 873 | C | MET | 319 | 27.225 | 34.826 | 77.917 | 1.00 | 8.08 |
| ATOM | 874 | O | MET | 319 | 27.678 | 35.630 | 78.741 | 1.00 | 6.69 |
| ATOM | 875 | N | GLU | 320 | 27.998 | 34.004 | 77.225 | 1.00 | 7.13 |
| ATOM | 877 | CA | GLU | 320 | 29.433 | 33.933 | 77.394 | 1.00 | 10.02 |
| ATOM | 878 | CB | GLU | 320 | 29.989 | 32.986 | 76.317 | 1.00 | 15.75 |
| ATOM | 879 | CG | GLU | 320 | 31.462 | 32.922 | 76.271 | 1.00 | 23.94 |
| ATOM | 880 | CD | GLU | 320 | 31.934 | 31.545 | 76.529 | 1.00 | 29.33 |
| ATOM | 881 | OE1 | GLU | 320 | 32.143 | 31.198 | 77.738 | 1.00 | 33.76 |
| ATOM | 882 | OE2 | GLU | 320 | 31.959 | 30.741 | 75.562 | 1.00 | 27.05 |
| ATOM | 883 | C | GLU | 320 | 30.271 | 35.225 | 77.440 | 1.00 | 10.37 |
| ATOM | 884 | O | GLU | 320 | 31.225 | 35.342 | 78.238 | 1.00 | 8.73 |
| ATOM | 885 | N | ASN | 321 | 29.928 | 36.181 | 76.579 | 1.00 | 6.58 |
| ATOM | 887 | CA | ASN | 321 | 30.664 | 37.418 | 76.483 | 1.00 | 6.63 |
| ATOM | 888 | CB | ASN | 321 | 30.812 | 37.808 | 74.991 | 1.00 | 3.44 |
| ATOM | 889 | CG | ASN | 321 | 31.833 | 36.914 | 74.270 | 1.00 | 7.15 |
| ATOM | 890 | OD1 | ASN | 321 | 32.960 | 36.707 | 74.772 | 1.00 | 4.07 |
| ATOM | 891 | ND2 | ASN | 321 | 31.452 | 36.346 | 73.151 | 1.00 | 6.04 |
| ATOM | 894 | C | ASN | 321 | 30.173 | 38.555 | 77.364 | 1.00 | 6.86 |
| ATOM | 895 | O | ASN | 321 | 30.599 | 39.689 | 77.211 | 1.00 | 7.33 |
| ATOM | 896 | N | GLY | 322 | 29.238 | 38.237 | 78.269 | 1.00 | 5.72 |
| ATOM | 898 | CA | GLY | 322 | 28.783 | 39.238 | 79.235 | 1.00 | 5.81 |
| ATOM | 899 | C | GLY | 322 | 28.136 | 40.486 | 78.701 | 1.00 | 4.76 |
| ATOM | 900 | O | GLY | 322 | 27.537 | 40.429 | 77.649 | 1.00 | 4.07 |
| ATOM | 901 | N | SER | 323 | 28.234 | 41.597 | 79.422 | 1.00 | 4.07 |

TABLE 4-continued

Coordinates of Lck bound with staurosporine (soaked)

| | | Atom Type | Res | # | X | Y | Z | Occ | B |
|---|---|---|---|---|---|---|---|---|---|
| ATOM | 903 | CA | SER | 323 | 27.601 | 42.830 | 78.975 | 1.00 | 4.52 |
| ATOM | 904 | CB | SER | 323 | 27.551 | 43.892 | 80.118 | 1.00 | 5.64 |
| ATOM | 905 | OG | SER | 323 | 26.697 | 43.489 | 81.181 | 1.00 | 10.41 |
| ATOM | 907 | C | SER | 323 | 28.238 | 43.441 | 77.759 | 1.00 | 4.42 |
| ATOM | 908 | O | SER | 323 | 29.475 | 43.522 | 77.636 | 1.00 | 6.97 |
| ATOM | 909 | N | LEU | 324 | 27.387 | 43.900 | 76.853 | 1.00 | 2.28 |
| ATOM | 911 | CA | LEU | 324 | 27.840 | 44.535 | 75.644 | 1.00 | 5.27 |
| ATOM | 912 | CB | LEU | 324 | 26.642 | 45.033 | 74.833 | 1.00 | 3.48 |
| ATOM | 913 | CG | LEU | 324 | 26.955 | 45.780 | 73.529 | 1.00 | 5.04 |
| ATOM | 914 | CD1 | LEU | 324 | 27.664 | 44.823 | 72.523 | 1.00 | 6.71 |
| ATOM | 915 | CD2 | LEU | 324 | 25.617 | 46.220 | 72.922 | 1.00 | 8.47 |
| ATOM | 916 | C | LEU | 324 | 28.749 | 45.740 | 75.945 | 1.00 | 5.66 |
| ATOM | 917 | O | LEU | 324 | 29.777 | 45.913 | 75.288 | 1.00 | 6.05 |
| ATOM | 928 | N | VAL | 325 | 28.395 | 46.537 | 76.950 | 1.00 | 6.08 |
| ATOM | 920 | CA | VAL | 325 | 29.227 | 47.692 | 77.284 | 1.00 | 6.56 |
| ATOM | 921 | CB | VAL | 325 | 28.601 | 48.567 | 78.411 | 1.00 | 6.30 |
| ATOM | 922 | CG1 | VAL | 325 | 28.897 | 47.976 | 79.791 | 1.00 | 6.07 |
| ATOM | 923 | CG2 | VAL | 325 | 29.125 | 49.976 | 78.262 | 1.00 | 6.51 |
| ATOM | 924 | C | VAL | 325 | 30.668 | 47.301 | 77.634 | 1.00 | 8.74 |
| ATOM | 925 | O | VAL | 325 | 31.578 | 48.063 | 77.344 | 1.00 | 8.55 |
| ATOM | 926 | N | ASP | 326 | 30.850 | 46.118 | 78.250 | 1.00 | 8.86 |
| ATOM | 928 | CA | ASP | 326 | 32.183 | 45.599 | 78.576 | 1.00 | 9.40 |
| ATOM | 929 | CB | ASP | 326 | 32.137 | 44.627 | 79.786 | 1.00 | 10.79 |
| ATOM | 930 | CG | ASP | 326 | 31.682 | 45.308 | 81.073 | 1.00 | 15.23 |
| ATOM | 931 | OD1 | ASP | 326 | 31.907 | 46.527 | 81.226 | 1.00 | 17.45 |
| ATOM | 932 | OD2 | ASP | 326 | 31.114 | 44.620 | 81.945 | 1.00 | 15.65 |
| ATOM | 933 | C | ASP | 326 | 32.814 | 44.878 | 77.374 | 1.00 | 8.47 |
| ATOM | 934 | O | ASP | 326 | 34.010 | 45.097 | 77.041 | 1.00 | 8.70 |
| ATOM | 935 | N | PHE | 327 | 32.041 | 44.008 | 76.712 | 1.00 | 6.30 |
| ATOM | 937 | CA | PHE | 327 | 32.533 | 43.275 | 75.550 | 1.00 | 5.97 |
| ATOM | 938 | CB | PHE | 327 | 31.417 | 42.452 | 74.872 | 1.00 | 6.18 |
| ATOM | 939 | CG | PHE | 327 | 31.863 | 41.778 | 73.574 | 1.00 | 5.53 |
| ATOM | 940 | CD1 | PHE | 327 | 32.755 | 40.715 | 73.600 | 1.00 | 5.80 |
| ATOM | 941 | CD2 | PHE | 327 | 31.399 | 42.238 | 72.335 | 1.00 | 7.58 |
| ATOM | 942 | CE1 | PHE | 327 | 33.197 | 40.104 | 72.401 | 1.00 | 3.63 |
| ATOM | 943 | CE2 | PHE | 327 | 31.816 | 41.666 | 71.151 | 1.00 | 6.07 |
| ATOM | 944 | CZ | PHE | 327 | 32.733 | 40.585 | 71.193 | 1.00 | 6.92 |
| ATOM | 945 | C | PHE | 327 | 33.179 | 44.164 | 74.441 | 1.00 | 6.02 |
| ATOM | 946 | O | PHE | 327 | 34.170 | 43.765 | 73.827 | 1.00 | 4.71 |
| ATOM | 947 | N | LEU | 328 | 32.577 | 45.326 | 74.176 | 0.40 | 2.63 |
| ATOM | 949 | CA | LEU | 328 | 33.076 | 46.237 | 73.130 | 0.40 | 2.00 |
| ATOM | 950 | CB | LEU | 328 | 32.067 | 47.361 | 72.882 | 0.40 | 2.00 |
| ATOM | 951 | CG | LEU | 328 | 30.693 | 46.917 | 72.327 | 0.40 | 2.00 |
| ATOM | 952 | CD1 | LEU | 328 | 29.763 | 48.096 | 72.210 | 0.40 | 2.00 |
| ATOM | 953 | CD2 | LEU | 328 | 30.847 | 46.243 | 70.979 | 0.40 | 2.00 |
| ATOM | 954 | C | LEU | 328 | 34.476 | 46.819 | 73.373 | 0.40 | 3.02 |
| ATOM | 955 | O | LEU | 328 | 35.072 | 47.402 | 72.496 | 0.40 | 2.00 |
| ATOM | 956 | N | LYS | 329 | 34.916 | 46.745 | 74.625 | 1.00 | 6.19 |
| ATOM | 958 | CA | LYS | 329 | 36.245 | 47.196 | 75.057 | 1.00 | 8.81 |
| ATOM | 959 | CB | LYS | 329 | 36.190 | 47.773 | 76.477 | 1.00 | 9.48 |
| ATOM | 960 | CG | LYS | 329 | 35.251 | 48.970 | 76.589 | 1.00 | 10.04 |
| ATOM | 961 | CD | LYS | 329 | 35.080 | 49.401 | 78.016 | 1.00 | 9.54 |
| ATOM | 962 | CE | LYS | 329 | 33.808 | 50.288 | 78.100 | 1.00 | 11.11 |
| ATOM | 963 | NZ | LYS | 329 | 33.664 | 50.767 | 79.489 | 1.00 | 13.64 |
| ATOM | 967 | C | LYS | 329 | 37.304 | 46.104 | 75.026 | 1.00 | 7.62 |
| ATOM | 968 | O | LYS | 329 | 38.486 | 46.372 | 75.245 | 1.00 | 6.19 |
| ATOM | 969 | N | THR | 330 | 36.882 | 44.853 | 74.859 | 1.00 | 7.54 |
| ATOM | 971 | CA | THR | 330 | 37.876 | 43.765 | 74.792 | 1.00 | 8.64 |
| ATOM | 972 | CB | THR | 330 | 37.204 | 42.387 | 75.026 | 1.00 | 6.18 |
| ATOM | 973 | OG1 | THR | 330 | 36.302 | 42.117 | 73.957 | 1.00 | 8.72 |
| ATOM | 975 | CG2 | THR | 330 | 36.437 | 42.396 | 76.362 | 1.00 | 9.44 |
| ATOM | 976 | C | THR | 330 | 38.543 | 43.742 | 73.440 | 1.00 | 8.40 |
| ATOM | 977 | O | THR | 330 | 38.049 | 44.349 | 72.499 | 1.00 | 9.09 |
| ATOM | 978 | N | PRO | 331 | 39.628 | 42.958 | 73.281 | 1.00 | 10.04 |
| ATOM | 979 | CD | PRO | 331 | 40.423 | 42.266 | 74.324 | 1.00 | 8.53 |
| ATOM | 980 | CA | PRO | 331 | 40.318 | 42.890 | 71.989 | 1.00 | 10.41 |
| ATOM | 981 | CB | PRO | 331 | 41.418 | 41.849 | 72.247 | 1.00 | 8.90 |
| ATOM | 982 | CG | PRO | 331 | 41.784 | 42.165 | 73.621 | 1.00 | 10.95 |
| ATOM | 983 | C | PRO | 331 | 39.375 | 42.460 | 70.878 | 1.00 | 10.90 |
| ATOM | 984 | O | PRO | 331 | 39.397 | 43.019 | 69.779 | 1.00 | 11.98 |
| ATOM | 985 | N | SER | 332 | 38.515 | 41.491 | 71.162 | 1.00 | 9.20 |
| ATOM | 987 | CA | SER | 332 | 37.549 | 41.082 | 70.145 | 1.00 | 12.25 |
| ATOM | 988 | CB | SER | 332 | 36.719 | 39.902 | 70.646 | 1.00 | 10.86 |
| ATOM | 989 | OG | SER | 332 | 37.530 | 38.761 | 70.767 | 1.00 | 18.10 |

TABLE 4-continued

Coordinates of Lck bound with staurosporine (soaked)

| | | Atom Type | Res | # | X | Y | Z | Occ | B |
|---|---|---|---|---|---|---|---|---|---|
| ATOM | 991 | C | SER | 332 | 36.570 | 42.207 | 69.803 | 1.00 | 11.43 |
| ATOM | 992 | O | SER | 332 | 36.299 | 42.481 | 68.646 | 1.00 | 12.17 |
| ATOM | 993 | N | GLY | 333 | 36.022 | 42.826 | 70.837 | 1.00 | 9.65 |
| ATOM | 995 | CA | GLY | 333 | 35.047 | 43.887 | 70.619 | 1.00 | 11.87 |
| ATOM | 996 | C | GLY | 333 | 35.583 | 45.068 | 69.838 | 1.00 | 10.52 |
| ATOM | 997 | O | GLY | 333 | 34.919 | 45.600 | 68.942 | 1.00 | 9.33 |
| ATOM | 998 | N | ILE | 334 | 36.809 | 45.476 | 70.175 | 1.00 | 11.53 |
| ATOM | 1000 | CA | ILE | 334 | 37.456 | 46.609 | 69.508 | 1.00 | 12.33 |
| ATOM | 1001 | CB | ILE | 334 | 38.857 | 46.896 | 70.146 | 1.00 | 15.13 |
| ATOM | 1002 | CG2 | ILE | 334 | 39.623 | 47.990 | 69.348 | 1.00 | 16.44 |
| ATOM | 1003 | CG1 | ILE | 334 | 38.689 | 47.316 | 71.603 | 1.00 | 13.62 |
| ATOM | 1004 | CD1 | ILE | 334 | 40.003 | 47.491 | 72.392 | 1.00 | 16.24 |
| ATOM | 1005 | C | ILE | 334 | 37.581 | 46.407 | 68.010 | 1.00 | 13.92 |
| ATOM | 1006 | O | ILE | 334 | 37.397 | 47.319 | 67.228 | 1.00 | 17.25 |
| ATOM | 1007 | N | LYS | 335 | 37.860 | 45.181 | 67.609 | 1.00 | 14.22 |
| ATOM | 1009 | CA | LYS | 335 | 38.026 | 44.850 | 66.211 | 1.00 | 15.61 |
| ATOM | 1010 | CB | LYS | 335 | 38.742 | 43.501 | 66.098 | 1.00 | 18.74 |
| ATOM | 1011 | CG | LYS | 335 | 40.159 | 43.493 | 66.675 | 1.00 | 22.01 |
| ATOM | 1012 | CD | LYS | 335 | 40.737 | 42.086 | 66.747 | 1.00 | 27.64 |
| ATOM | 1013 | CE | LYS | 335 | 42.031 | 42.044 | 67.603 | 1.00 | 29.38 |
| ATOM | 1014 | NZ | LYS | 335 | 42.383 | 40.621 | 68.013 | 1.00 | 31.04 |
| ATOM | 1018 | C | LYS | 335 | 36.747 | 44.814 | 65.372 | 1.00 | 16.01 |
| ATOM | 1019 | O | LYS | 335 | 36.824 | 44.709 | 64.139 | 1.00 | 15.29 |
| ATOM | 1020 | N | LEU | 336 | 35.575 | 44.884 | 66.004 | 1.00 | 12.73 |
| ATOM | 1022 | CA | LEU | 336 | 34.317 | 44.804 | 65.218 | 1.00 | 11.81 |
| ATOM | 1023 | CB | LEU | 336 | 33.094 | 44.732 | 66.148 | 1.00 | 12.02 |
| ATOM | 1024 | CG | LEU | 336 | 33.012 | 43.570 | 67.175 | 1.00 | 13.35 |
| ATOM | 1025 | CD1 | LEU | 336 | 31.657 | 43.583 | 67.836 | 1.00 | 12.43 |
| ATOM | 1026 | CD2 | LEU | 336 | 33.251 | 42.218 | 66.515 | 1.00 | 14.13 |
| ATOM | 1027 | C | LEU | 336 | 34.117 | 45.968 | 64.252 | 1.00 | 10.72 |
| ATOM | 1028 | O | LEU | 336 | 34.325 | 47.107 | 64.598 | 1.00 | 13.53 |
| ATOM | 1029 | N | THR | 337 | 33.666 | 45.643 | 63.045 | 1.00 | 11.51 |
| ATOM | 1031 | CA | THR | 337 | 33.381 | 46.634 | 62.007 | 1.00 | 12.15 |
| ATOM | 1032 | CB | THR | 337 | 33.218 | 45.947 | 60.615 | 1.00 | 12.79 |
| ATOM | 1033 | OG1 | THR | 337 | 32.154 | 44.956 | 60.676 | 1.00 | 12.22 |
| ATOM | 1035 | CG2 | THR | 337 | 34.519 | 45.285 | 60.216 | 1.00 | 16.26 |
| ATOM | 1036 | C | THR | 337 | 32.057 | 47.342 | 62.297 | 1.00 | 10.27 |
| ATOM | 1037 | O | THR | 337 | 31.229 | 46.817 | 63.091 | 1.00 | 5.25 |
| ATOM | 1038 | N | ILE | 338 | 31.862 | 48.504 | 61.690 | 1.00 | 8.59 |
| ATOM | 1040 | CA | ILE | 338 | 30.615 | 49.200 | 61.846 | 1.00 | 7.74 |
| ATOM | 1041 | CB | ILE | 338 | 30.579 | 50.505 | 61.001 | 1.00 | 10.71 |
| ATOM | 1042 | CG2 | ILE | 338 | 30.765 | 50.197 | 59.517 | 1.00 | 11.93 |
| ATOM | 1043 | CG1 | ILE | 338 | 29.278 | 51.266 | 61.284 | 1.00 | 8.47 |
| ATOM | 1044 | CD1 | ILE | 338 | 29.254 | 51.745 | 62.769 | 1.00 | 12.52 |
| ATOM | 1045 | C | ILE | 338 | 29.467 | 48.298 | 61.413 | 1.00 | 6.40 |
| ATOM | 1046 | O | ILE | 338 | 28.363 | 48.402 | 61.924 | 1.00 | 5.38 |
| ATOM | 1047 | N | ASN | 339 | 29.695 | 47.468 | 60.386 | 1.00 | 7.04 |
| ATOM | 1049 | CA | ASN | 339 | 28.669 | 46.535 | 59.910 | 1.00 | 9.44 |
| ATOM | 1050 | CB | ASN | 339 | 29.214 | 45.704 | 58.744 | 1.00 | 12.90 |
| ATOM | 1051 | CG | ASN | 339 | 28.238 | 44.649 | 58.244 | 1.00 | 19.02 |
| ATOM | 1052 | OD1 | ASN | 339 | 28.450 | 43.440 | 58.443 | 1.00 | 21.28 |
| ATOM | 1053 | ND2 | ASN | 339 | 27.197 | 45.086 | 57.522 | 1.00 | 19.72 |
| ATOM | 1056 | C | ASN | 339 | 28.192 | 45.606 | 61.018 | 1.00 | 6.95 |
| ATOM | 1057 | O | ASN | 339 | 27.000 | 45.406 | 61.199 | 1.00 | 6.04 |
| ATOM | 1058 | N | LYS | 340 | 29.139 | 45.038 | 61.772 | 1.00 | 6.39 |
| ATOM | 1060 | CA | LYS | 340 | 28.769 | 44.129 | 62.873 | 1.00 | 6.76 |
| ATOM | 1061 | CB | LYS | 340 | 29.985 | 43.333 | 63.361 | 1.00 | 7.37 |
| ATOM | 1062 | CG | LYS | 340 | 29.723 | 42.361 | 64.575 | 1.00 | 7.98 |
| ATOM | 1063 | CD | LYS | 340 | 28.663 | 41.312 | 64.238 | 1.00 | 9.32 |
| ATOM | 1064 | CE | LYS | 340 | 28.325 | 40.403 | 65.435 | 1.00 | 7.68 |
| ATOM | 1065 | NZ | LYS | 340 | 27.121 | 39.561 | 65.006 | 1.00 | 11.81 |
| ATOM | 1069 | C | LYS | 340 | 28.090 | 44.877 | 64.015 | 1.00 | 6.46 |
| ATOM | 1070 | O | LYS | 340 | 27.180 | 44.361 | 64.669 | 1.00 | 7.41 |
| ATOM | 1071 | N | LEU | 341 | 28.524 | 46.122 | 64.273 | 1.00 | 4.91 |
| ATOM | 1073 | CA | LEU | 341 | 27.892 | 46.926 | 65.316 | 1.00 | 4.71 |
| ATOM | 1074 | CB | LEU | 341 | 28.662 | 48.275 | 65.487 | 1.00 | 6.87 |
| ATOM | 1075 | CG | LEU | 341 | 30.145 | 48.170 | 65.917 | 1.00 | 53.50 |
| ATOM | 1076 | CD1 | LEU | 341 | 30.792 | 49.563 | 66.144 | 1.00 | 7.84 |
| ATOM | 1077 | CD2 | LEU | 341 | 30.228 | 47.397 | 67.217 | 1.00 | 4.44 |
| ATOM | 1078 | C | LEU | 341 | 26.426 | 47.218 | 64.906 | 1.00 | 6.72 |
| ATOM | 1079 | O | LEU | 341 | 25.554 | 47.223 | 65.734 | 1.00 | 6.30 |
| ATOM | 1080 | N | LEU | 342 | 26.199 | 47.479 | 63.610 | 1.00 | 6.60 |
| ATOM | 1082 | CA | LEU | 342 | 24.852 | 47.780 | 63.101 | 1.00 | 8.16 |
| ATOM | 1083 | CB | LEU | 342 | 24.924 | 48.248 | 61.648 | 1.00 | 8.76 |

TABLE 4-continued

Coordinates of Lck bound with staurosporine (soaked)

| | Atom Type | Res | # | X | Y | Z | Occ | B |
|---|---|---|---|---|---|---|---|---|
| ATOM | 1084 | CG | LEU | 342 | 24.817 | 49.735 | 61.222 | 1.00 | 16.74 |
| ATOM | 1085 | CD1 | LEU | 342 | 24.670 | 50.708 | 62.352 | 1.00 | 13.92 |
| ATOM | 1086 | CD2 | LEU | 342 | 25.895 | 50.108 | 60.186 | 1.00 | 11.93 |
| ATOM | 1087 | C | LEU | 342 | 23.973 | 46.546 | 63.229 | 1.00 | 6.33 |
| ATOM | 1088 | O | LEU | 342 | 22.806 | 46.636 | 63.598 | 1.00 | 4.73 |
| ATOM | 1089 | N | ASP | 343 | 24.571 | 45.408 | 62.903 | 1.00 | 7.09 |
| ATOM | 1091 | CA | ASP | 343 | 23.914 | 44.099 | 63.063 | 1.00 | 7.37 |
| ATOM | 1092 | CB | ASP | 343 | 24.909 | 42.987 | 62.660 | 1.00 | 6.99 |
| ATOM | 1093 | CG | ASP | 343 | 24.466 | 41.581 | 63.110 | 1.00 | 7.27 |
| ATOM | 1094 | OD1 | ASP | 343 | 23.262 | 41.350 | 63.309 | 1.00 | 4.56 |
| ATOM | 1095 | OD2 | ASP | 343 | 25.337 | 40.719 | 63.252 | 1.00 | 6.70 |
| ATOM | 1096 | C | ASP | 343 | 23.501 | 43.949 | 64.529 | 1.00 | 7.54 |
| ATOM | 1097 | O | ASP | 343 | 22.342 | 43.697 | 64.838 | 1.00 | 7.54 |
| ATOM | 1098 | N | MET | 344 | 24.436 | 44.153 | 65.457 | 1.00 | 6.41 |
| ATOM | 1100 | CA | MET | 344 | 24.081 | 44.047 | 66.885 | 1.00 | 9.49 |
| ATOM | 1101 | CB | MET | 344 | 25.316 | 44.208 | 67.804 | 1.00 | 8.91 |
| ATOM | 1102 | CG | MET | 344 | 26.413 | 43.141 | 67.567 | 1.00 | 12.32 |
| ATOM | 1103 | SD | MET | 344 | 27.888 | 43.520 | 68.539 | 1.00 | 16.89 |
| ATOM | 1104 | CE | MET | 344 | 28.005 | 42.104 | 69.644 | 1.00 | 18.02 |
| ATOM | 1105 | C | MET | 344 | 22.962 | 45.016 | 67.328 | 1.00 | 7.42 |
| ATOM | 1106 | O | MET | 344 | 22.060 | 44.644 | 68.090 | 1.00 | 7.37 |
| ATOM | 1107 | N | ALA | 345 | 23.005 | 46.250 | 66.812 | 1.00 | 5.31 |
| ATOM | 1109 | CA | ALA | 345 | 21.943 | 47.219 | 67.162 | 1.00 | 2.94 |
| ATOM | 1110 | CB | ALA | 345 | 22.257 | 48.613 | 66.496 | 1.00 | 2.00 |
| ATOM | 1111 | C | ALA | 345 | 20.581 | 46.698 | 66.674 | 1.00 | 2.66 |
| ATOM | 1112 | O | ALA | 345 | 19.568 | 46.823 | 67.371 | 1.00 | 3.94 |
| ATOM | 1113 | N | ALA | 346 | 20.563 | 46.121 | 65.465 | 1.00 | 3.10 |
| ATOM | 1115 | CA | ALA | 346 | 19.353 | 45.540 | 64.894 | 1.00 | 5.34 |
| ATOM | 1116 | CB | ALA | 346 | 19.548 | 45.098 | 63.372 | 1.00 | 3.35 |
| ATOM | 1117 | C | ALA | 346 | 18.825 | 44.378 | 65.729 | 1.00 | 5.71 |
| ATOM | 1118 | O | ALA | 346 | 17.620 | 44.299 | 65.955 | 1.00 | 4.47 |
| ATOM | 1119 | N | GLN | 347 | 19.720 | 43.528 | 66.231 | 1.00 | 2.71 |
| ATOM | 1121 | CA | GLN | 347 | 19.307 | 42.428 | 67.141 | 1.00 | 4.60 |
| ATOM | 1122 | CB | GLN | 347 | 20.537 | 41.592 | 67.562 | 1.00 | 2.74 |
| ATOM | 1123 | CG | GLN | 347 | 21.216 | 40.940 | 66.362 | 1.00 | 5.37 |
| ATOM | 1124 | CD | GLN | 347 | 22.320 | 39.965 | 66.751 | 1.00 | 7.37 |
| ATOM | 1125 | OE1 | GLN | 347 | 22.353 | 39.486 | 67.855 | 1.00 | 8.75 |
| ATOM | 1126 | NE2 | GLN | 347 | 23.175 | 39.635 | 65.804 | 1.00 | 5.62 |
| ATOM | 1129 | C | GLN | 347 | 18.611 | 42.971 | 68.414 | 1.00 | 4.10 |
| ATOM | 1130 | O | GLN | 347 | 17.575 | 42.455 | 68.863 | 1.00 | 5.67 |
| ATOM | 1131 | N | ILE | 348 | 19.153 | 44.050 | 68.940 | 1.00 | 2.95 |
| ATOM | 1133 | CA | ILE | 348 | 18.628 | 44.666 | 70.150 | 1.00 | 4.54 |
| ATOM | 1134 | CB | ILE | 348 | 19.624 | 45.759 | 70.691 | 1.00 | 4.65 |
| ATOM | 1135 | CG2 | ILE | 348 | 19.039 | 46.538 | 71.882 | 1.00 | 3.08 |
| ATOM | 1136 | CG1 | ILE | 348 | 20.921 | 45.080 | 71.163 | 1.00 | 3.26 |
| ATOM | 1137 | CD1 | ILE | 348 | 22.039 | 46.103 | 71.381 | 1.00 | 5.43 |
| ATOM | 1138 | C | ILE | 348 | 17.268 | 45.264 | 69.885 | 1.00 | 5.36 |
| ATOM | 1139 | O | ILE | 348 | 16.338 | 45.032 | 70.674 | 1.00 | 4.39 |
| ATOM | 1140 | N | ALA | 349 | 17.137 | 45.971 | 68.750 | 1.00 | 4.26 |
| ATOM | 1142 | CA | ALA | 349 | 15.829 | 46.544 | 68.363 | 1.00 | 5.91 |
| ATOM | 1143 | CB | ALA | 349 | 15.966 | 47.377 | 67.099 | 1.00 | 3.48 |
| ATOM | 1144 | C | ALA | 349 | 14.794 | 45.409 | 68.122 | 1.00 | 5.32 |
| ATOM | 1145 | O | ALA | 349 | 13.601 | 45.564 | 68.351 | 1.00 | 4.56 |
| ATOM | 1146 | N | GLU | 350 | 15.282 | 44.267 | 67.641 | 1.00 | 5.83 |
| ATOM | 1148 | CA | GLU | 350 | 14.389 | 43.127 | 67.360 | 1.00 | 6.21 |
| ATOM | 1149 | CB | GLU | 350 | 15.156 | 42.033 | 66.591 | 1.00 | 8.90 |
| ATOM | 1150 | CG | GLU | 350 | 14.330 | 40.790 | 66.305 | 1.00 | 9.23 |
| ATOM | 1151 | CD | GLU | 350 | 15.141 | 39.730 | 65.550 | 1.00 | 12.88 |
| ATOM | 1152 | OE1 | GLU | 350 | 16.194 | 40.044 | 64.946 | 1.00 | 12.40 |
| ATOM | 1153 | OE2 | GLU | 350 | 14.724 | 38.558 | 65.564 | 1.00 | 13.17 |
| ATOM | 1154 | C | GLU | 350 | 13.807 | 42.575 | 68.648 | 1.00 | 3.70 |
| ATOM | 1155 | O | GLU | 350 | 12.576 | 42.238 | 68.754 | 1.00 | 3.99 |
| ATOM | 1156 | N | GLY | 351 | 14.664 | 42.494 | 69.666 | 1.00 | 3.72 |
| ATOM | 1158 | CA | GLY | 351 | 14.177 | 42.064 | 70.985 | 1.00 | 2.74 |
| ATOM | 1159 | C | GLY | 351 | 13.231 | 43.110 | 71.585 | 1.00 | 3.98 |
| ATOM | 1160 | O | GLY | 351 | 12.206 | 42.742 | 72.204 | 1.00 | 2.73 |
| ATOM | 1061 | N | MET | 352 | 13.563 | 44.402 | 71.478 | 1.00 | 3.10 |
| ATOM | 1163 | CA | MET | 352 | 12.672 | 45.431 | 72.017 | 1.00 | 3.20 |
| ATOM | 1164 | CB | MET | 352 | 13.346 | 46.839 | 71.992 | 1.00 | 4.15 |
| ATOM | 1165 | CG | MET | 352 | 14.463 | 46.987 | 73.003 | 1.00 | 2.46 |
| ATOM | 1166 | SD | MET | 352 | 13.963 | 46.634 | 74.672 | 1.00 | 8.88 |
| ATOM | 1167 | CE | MET | 352 | 12.466 | 47.792 | 74.796 | 1.00 | 7.85 |
| ATOM | 1168 | C | MET | 352 | 11.317 | 45.481 | 71.244 | 1.00 | 4.14 |
| ATOM | 1169 | O | MET | 352 | 10.298 | 45.901 | 71.790 | 1.00 | 4.32 |

TABLE 4-continued

Coordinates of Lck bound with staurosporine (soaked)

| | | Atom Type | Res | # | X | Y | Z | Occ | B |
|---|---|---|---|---|---|---|---|---|---|
| ATOM | 1170 | N | ALA | 353 | 11.345 | 45.131 | 69.947 | 1.00 | 4.31 |
| ATOM | 1172 | CA | ALA | 353 | 10.114 | 45.102 | 69.161 | 1.00 | 4.60 |
| ATOM | 1173 | CB | ALA | 353 | 10.433 | 44.852 | 67.643 | 1.00 | 4.58 |
| ATOM | 1174 | C | ALA | 353 | 9.184 | 44.019 | 69.694 | 1.00 | 5.84 |
| ATOM | 1175 | O | ALA | 353 | 7.950 | 44.175 | 69.740 | 1.00 | 4.41 |
| ATOM | 1176 | N | PHE | 354 | 9.773 | 42.911 | 70.170 | 1.00 | 6.70 |
| ATOM | 1178 | CA | PHE | 354 | 8.962 | 41.835 | 70.790 | 1.00 | 6.33 |
| ATOM | 1179 | CB | PHE | 354 | 9.811 | 40.577 | 71.057 | 1.00 | 6.88 |
| ATOM | 1180 | CG | PHE | 354 | 9.080 | 39.481 | 71.829 | 1.00 | 9.26 |
| ATOM | 1181 | CD1 | PHE | 354 | 8.023 | 38.781 | 71.242 | 1.00 | 9.54 |
| ATOM | 1182 | CD2 | PHE | 354 | 9.429 | 39.186 | 73.138 | 1.00 | 8.40 |
| ATOM | 1183 | CE1 | PHE | 354 | 7.346 | 37.781 | 71.957 | 1.00 | 11.15 |
| ATOM | 1184 | CE2 | PHE | 354 | 8.752 | 38.184 | 73.867 | 1.00 | 11.06 |
| ATOM | 1185 | CZ | PHE | 354 | 7.698 | 37.492 | 73.270 | 1.00 | 8.67 |
| ATOM | 1186 | C | PHE | 354 | 8.360 | 42.313 | 72.089 | 1.00 | 5.01 |
| ATOM | 1187 | O | PHE | 354 | 7.162 | 42.111 | 72.360 | 1.00 | 5.21 |
| ATOM | 1188 | N | ILE | 355 | 9.186 | 42.981 | 72.909 | 1.00 | 4.92 |
| ATOM | 1190 | CA | ILE | 355 | 8.725 | 43.546 | 74.191 | 1.00 | 3.39 |
| ATOM | 1191 | CB | ILE | 355 | 9.910 | 44.209 | 74.960 | 1.00 | 4.12 |
| ATOM | 1192 | CG2 | ILE | 355 | 9.446 | 45.113 | 76.167 | 1.00 | 3.25 |
| ATOM | 1193 | CG1 | ILE | 355 | 10.833 | 43.105 | 75.480 | 1.00 | 3.89 |
| ATOM | 1194 | CD1 | ILE | 355 | 12.153 | 43.638 | 76.042 | 1.00 | 6.62 |
| ATOM | 1195 | C | ILE | 355 | 7.597 | 44.548 | 73.950 | 1.00 | 4.30 |
| ATOM | 1196 | O | ILE | 355 | 6.566 | 44.533 | 74.627 | 1.00 | 2.05 |
| ATOM | 1197 | N | GLU | 356 | 7.783 | 45.361 | 72.917 | 1.00 | 5.49 |
| ATOM | 1199 | CA | GLU | 356 | 6.808 | 46.345 | 72.527 | 1.00 | 7.59 |
| ATOM | 1200 | CB | GLU | 356 | 7.382 | 47.158 | 71.359 | 1.00 | 8.33 |
| ATOM | 1201 | CG | GLU | 356 | 6.463 | 48.069 | 70.575 | 1.00 | 11.40 |
| ATOM | 1202 | CD | GLU | 356 | 7.238 | 48.763 | 69.411 | 1.00 | 13.48 |
| ATOM | 1203 | OE1 | GLU | 356 | 7.350 | 48.218 | 68.250 | 1.00 | 15.78 |
| ATOM | 1204 | OE2 | GLU | 356 | 7.756 | 49.864 | 69.664 | 1.00 | 14.27 |
| ATOM | 1205 | C | GLU | 356 | 5.475 | 45.692 | 72.132 | 1.00 | 8.84 |
| ATOM | 1206 | O | GLU | 356 | 4.424 | 46.054 | 72.629 | 1.00 | 7.97 |
| ATOM | 1207 | N | GLU | 357 | 5.517 | 44.734 | 71.225 | 1.00 | 10.18 |
| ATOM | 1209 | CA | GLU | 357 | 4.263 | 44.097 | 70.820 | 1.00 | 11.61 |
| ATOM | 1210 | CB | GLU | 357 | 4.408 | 43.355 | 49.495 | 1.00 | 16.07 |
| ATOM | 1211 | CG | GLU | 357 | 4.880 | 41.974 | 69.512 | 1.00 | 24.33 |
| ATOM | 1212 | CD | GLU | 357 | 3.799 | 40.973 | 69.812 | 1.00 | 28.19 |
| ATOM | 1213 | OE1 | GLU | 357 | 4.125 | 40.049 | 70.565 | 1.00 | 31.78 |
| ATOM | 1214 | OE2 | GLU | 357 | 2.649 | 41.078 | 69.322 | 1.00 | 30.15 |
| ATOM | 1215 | C | GLU | 357 | 3.501 | 43.309 | 71.911 | 1.00 | 10.18 |
| ATOM | 1216 | O | GLU | 357 | 2.289 | 43.180 | 71.842 | 1.00 | 9.51 |
| ATOM | 1217 | N | ARG | 358 | 4.205 | 42.869 | 72.956 | 1.00 | 6.49 |
| ATOM | 1219 | CA | ARG | 358 | 3.574 | 42.182 | 74.061 | 1.00 | 7.45 |
| ATOM | 1220 | CB | ARG | 358 | 4.592 | 41.215 | 74.730 | 1.00 | 8.83 |
| ATOM | 1221 | CG | ARG | 358 | 5.135 | 40.069 | 73.849 | 1.00 | 7.95 |
| ATOM | 1222 | CD | ARG | 358 | 3.999 | 39.232 | 73.218 | 1.00 | 12.64 |
| ATOM | 1223 | NE | ARG | 358 | 2.929 | 38.875 | 74.159 | 1.00 | 16.71 |
| ATOM | 1225 | CZ | ARG | 358 | 1.665 | 38.636 | 73.797 | 1.00 | 17.48 |
| ATOM | 1226 | NH1 | ARG | 358 | 1.296 | 38.710 | 72.515 | 1.00 | 16.26 |
| ATOM | 1229 | NH2 | ARG | 358 | 0.740 | 38.415 | 74.720 | 1.00 | 18.05 |
| ATOM | 1232 | C | ARG | 358 | 3.040 | 43.157 | 75.124 | 1.00 | 7.52 |
| ATOM | 1233 | O | ARG | 358 | 2.591 | 42.738 | 76.211 | 1.00 | 7.17 |
| ATOM | 1244 | N | ASN | 359 | 3.161 | 44.465 | 74.860 | 1.00 | 6.81 |
| ATOM | 1243 | CA | ASN | 359 | 2.694 | 45.491 | 75.800 | 1.00 | 8.64 |
| ATOM | 1240 | CB | ASN | 359 | 1.188 | 45.327 | 76.159 | 1.00 | 9.29 |
| ATOM | 1239 | CG | ASN | 359 | 0.300 | 45.844 | 75.061 | 1.00 | 10.37 |
| ATOM | 1238 | OD1 | ASN | 359 | 0.795 | 46.342 | 74.072 | 1.00 | 12.00 |
| ATOM | 1237 | ND2 | ASN | 359 | −1.018 | 45.678 | 75.204 | 1.00 | 12.20 |
| ATOM | 1236 | C | ASN | 359 | 3.511 | 45.652 | 77.050 | 1.00 | 8.02 |
| ATOM | 1234 | O | ASN | 359 | 2.995 | 46.046 | 78.108 | 1.00 | 9.17 |
| ATOM | 1245 | N | TYR | 360 | 4.801 | 45.314 | 76.963 | 1.00 | 5.75 |
| ATOM | 1247 | CA | TYR | 360 | 5.669 | 45.520 | 78.112 | 1.00 | 5.81 |
| ATOM | 1248 | CB | TYR | 360 | 6.541 | 44.275 | 78.342 | 1.00 | 6.39 |
| ATOM | 1249 | CG | TYR | 360 | 5.816 | 43.136 | 79.021 | 1.00 | 7.87 |
| ATOM | 1250 | CD1 | TYR | 360 | 5.033 | 42.243 | 78.288 | 1.00 | 9.17 |
| ATOM | 1251 | CE1 | TYR | 360 | 4.359 | 41.181 | 78.927 | 1.00 | 11.35 |
| ATOM | 1252 | CD2 | TYR | 360 | 5.909 | 42.967 | 80.389 | 1.00 | 9.95 |
| ATOM | 1253 | CE2 | TYR | 360 | 5.231 | 41.931 | 81.035 | 1.00 | 11.89 |
| ATOM | 1254 | CZ | TYR | 360 | 4.464 | 41.063 | 80.309 | 1.00 | 11.40 |
| ATOM | 1255 | OH | TYR | 360 | 3.752 | 40.116 | 81.010 | 1.00 | 13.18 |
| ATOM | 1257 | C | TYR | 360 | 6.621 | 46.687 | 77.853 | 1.00 | 5.77 |
| ATOM | 1258 | O | TYR | 360 | 6.719 | 47.189 | 76.730 | 1.00 | 5.39 |
| ATOM | 1259 | N | ILE | 361 | 7.307 | 47.122 | 78.909 | 1.00 | 6.08 |

TABLE 4-continued

Coordinates of Lck bound with staurosporine (soaked)

| | | Atom Type | Res | # | X | Y | Z | Occ | B |
|---|---|---|---|---|---|---|---|---|---|
| ATOM | 1261 | CA | ILE | 361 | 8.351 | 48.130 | 78.812 | 1.00 | 6.60 |
| ATOM | 1262 | CB | ILE | 361 | 7.949 | 49.538 | 79.349 | 1.00 | 7.46 |
| ATOM | 1263 | CG2 | ILE | 361 | 6.981 | 50.231 | 78.354 | 1.00 | 7.70 |
| ATOM | 1264 | CG1 | ILE | 361 | 7.350 | 49.430 | 80.744 | 1.00 | 7.66 |
| ATOM | 1265 | CD1 | ILE | 361 | 7.111 | 50.762 | 81.390 | 1.00 | 7.95 |
| ATOM | 1266 | C | ILE | 361 | 9.496 | 47.570 | 79.658 | 1.00 | 7.68 |
| ATOM | 1267 | O | ILE | 361 | 9.236 | 46.794 | 80.605 | 1.00 | 6.94 |
| ATOM | 1268 | N | HIS | 362 | 10.722 | 47.990 | 79.382 | 1.00 | 5.85 |
| ATOM | 1270 | CA | HIS | 362 | 11.865 | 47.457 | 80.114 | 1.00 | 6.16 |
| ATOM | 1271 | CB | HIS | 362 | 12.944 | 47.124 | 79.071 | 1.00 | 5.50 |
| ATOM | 1272 | CG | HIS | 362 | 14.150 | 46.453 | 79.609 | 1.00 | 7.36 |
| ATOM | 1273 | CD2 | HIS | 362 | 14.599 | 45.170 | 79.503 | 1.00 | 6.35 |
| ATOM | 1274 | ND1 | HIS | 362 | 15.119 | 47.120 | 80.343 | 1.00 | 7.52 |
| ATOM | 1276 | CE1 | HIS | 362 | 16.091 | 46.293 | 80.658 | 1.00 | 7.49 |
| ATOM | 1277 | NE2 | HIS | 362 | 15.807 | 45.106 | 80.156 | 1.00 | 6.81 |
| ATOM | 1279 | C | HIS | 362 | 12.371 | 48.418 | 81.211 | 1.00 | 4.64 |
| ATOM | 1280 | O | HIS | 362 | 12.588 | 48.033 | 82.369 | 1.00 | 5.59 |
| ATOM | 1281 | N | ARG | 363 | 12.491 | 49.679 | 80.831 | 1.00 | 7.45 |
| ATOM | 1283 | CA | ARG | 363 | 12.913 | 50.783 | 81.704 | 1.00 | 8.43 |
| ATOM | 1284 | CB | ARG | 363 | 12.035 | 50.835 | 82.970 | 1.00 | 7.51 |
| ATOM | 1285 | CG | ARG | 363 | 10.576 | 51.119 | 82.644 | 1.00 | 10.25 |
| ATOM | 1286 | CD | ARG | 363 | 9.897 | 51.683 | 83.914 | 1.00 | 10.59 |
| ATOM | 1287 | NE | ARG | 363 | 9.912 | 50.722 | 84.981 | 1.00 | 11.72 |
| ATOM | 1289 | CZ | ARG | 363 | 9.861 | 51.032 | 86.279 | 1.00 | 14.15 |
| ATOM | 1290 | NH1 | ARG | 363 | 9.808 | 52.301 | 86.646 | 1.00 | 13.54 |
| ATOM | 1293 | NH2 | ARG | 363 | 9.797 | 50.061 | 87.195 | 1.00 | 12.03 |
| ATOM | 1296 | C | ARG | 363 | 14.372 | 50.882 | 82.117 | 1.00 | 7.44 |
| ATOM | 1297 | O | ARG | 363 | 14.723 | 51.804 | 82.809 | 1.00 | 7.42 |
| ATOM | 1298 | N | ASP | 364 | 15.221 | 50.000 | 81.634 | 1.00 | 8.20 |
| ATOM | 1300 | CA | ASP | 364 | 16.643 | 50.002 | 82.025 | 1.00 | 7.94 |
| ATOM | 1301 | CB | ASP | 364 | 16.832 | 49.052 | 83.198 | 1.00 | 7.03 |
| ATOM | 1302 | CG | ASP | 364 | 18.059 | 49.370 | 84.068 | 1.00 | 11.50 |
| ATOM | 1303 | OD1 | ASP | 364 | 18.799 | 50.329 | 83.807 | 1.00 | 11.51 |
| ATOM | 1304 | OD2 | ASP | 364 | 18.264 | 48.627 | 85.043 | 1.00 | 12.82 |
| ATOM | 1305 | C | ASP | 364 | 17.473 | 49.590 | 80.842 | 1.00 | 6.20 |
| ATOM | 1306 | O | ASP | 364 | 18.410 | 48.799 | 80.968 | 1.00 | 5.54 |
| ATOM | 1307 | N | LEU | 365 | 17.034 | 50.044 | 79.663 | 1.00 | 5.04 |
| ATOM | 1309 | CA | LEU | 365 | 17.656 | 49.725 | 78.389 | 1.00 | 4.56 |
| ATOM | 1310 | CB | LEU | 365 | 16.672 | 50.008 | 77.222 | 1.00 | 3.62 |
| ATOM | 1311 | CG | LEU | 365 | 17.135 | 49.719 | 75.771 | 1.00 | 4.02 |
| ATOM | 1312 | CD1 | LEU | 365 | 17.593 | 48.293 | 75.631 | 1.00 | 4.75 |
| ATOM | 1313 | CD2 | LEU | 365 | 16.034 | 50.008 | 74.773 | 1.00 | 5.53 |
| ATOM | 1314 | C | LEU | 365 | 18.945 | 50.539 | 78.213 | 1.00 | 7.89 |
| ATOM | 1315 | O | LEU | 365 | 18.897 | 51.775 | 78.082 | 1.00 | 8.70 |
| ATOM | 1316 | N | ARG | 366 | 20.072 | 49.847 | 78.307 | 1.00 | 6.02 |
| ATOM | 1318 | CA | ARG | 366 | 21.398 | 50.414 | 78.170 | 1.00 | 7.65 |
| ATOM | 1319 | CB | ARG | 366 | 21.837 | 51.023 | 79.508 | 1.00 | 9.30 |
| ATOM | 1320 | CG | ARG | 366 | 21.673 | 50.061 | 80.689 | 1.00 | 12.26 |
| ATOM | 1321 | CD | ARG | 366 | 21.894 | 50.794 | 82.011 | 1.00 | 16.24 |
| ATOM | 1322 | NE | ARG | 366 | 23.214 | 51.410 | 82.088 | 1.00 | 19.64 |
| ATOM | 1324 | CZ | ARG | 366 | 23.503 | 52.394 | 82.930 | 1.00 | 23.12 |
| ATOM | 1325 | NH1 | ARG | 366 | 22.556 | 52.850 | 83.748 | 1.00 | 24.99 |
| ATOM | 1328 | NH2 | ARG | 366 | 24.715 | 52.926 | 82.955 | 1.00 | 22.43 |
| ATOM | 1331 | C | ARG | 366 | 22.324 | 49.265 | 77.787 | 1.00 | 7.09 |
| ATOM | 1332 | O | ARG | 366 | 21.982 | 48.103 | 78.058 | 1.00 | 6.44 |
| ATOM | 1333 | N | ALA | 367 | 23.516 | 49.586 | 77.286 | 1.00 | 6.74 |
| ATOM | 1335 | CA | ALA | 367 | 24.460 | 48.562 | 76.868 | 1.00 | 5.67 |
| ATOM | 1336 | CB | ALA | 367 | 25.733 | 49.199 | 76.238 | 1.00 | 3.81 |
| ATOM | 1337 | C | ALA | 367 | 24.852 | 47.653 | 78.034 | 1.00 | 6.22 |
| ATOM | 1338 | O | ALA | 367 | 25.191 | 46.502 | 77.806 | 1.00 | 8.48 |
| ATOM | 1339 | N | ALA | 368 | 24.815 | 48.157 | 79.278 | 1.00 | 4.60 |
| ATOM | 1341 | CA | ALA | 368 | 25.163 | 47.268 | 80.399 | 1.00 | 5.77 |
| ATOM | 1342 | CB | ALA | 368 | 25.235 | 48.038 | 81.749 | 1.00 | 7.66 |
| ATOM | 1343 | C | ALA | 368 | 24.161 | 46.098 | 80.500 | 1.00 | 5.40 |
| ATOM | 1344 | O | ALA | 368 | 24.511 | 44.968 | 80.918 | 1.00 | 6.12 |
| ATOM | 1345 | N | ASN | 369 | 22.935 | 46.343 | 80.058 | 1.00 | 5.01 |
| ATOM | 1347 | CA | ASN | 369 | 21.888 | 45.330 | 80.097 | 1.00 | 5.36 |
| ATOM | 1348 | CB | ASN | 369 | 20.623 | 45.916 | 80.696 | 1.00 | 4.47 |
| ATOM | 1349 | CG | ASN | 369 | 20.795 | 46.215 | 82.153 | 1.00 | 6.74 |
| ATOM | 1350 | OD1 | ASN | 369 | 21.544 | 45.516 | 82.817 | 1.00 | 5.37 |
| ATOM | 1351 | ND2 | ASN | 369 | 20.176 | 47.284 | 82.642 | 1.00 | 4.83 |
| ATOM | 1354 | C | ASN | 369 | 21.616 | 44.538 | 78.810 | 1.00 | 6.12 |
| ATOM | 1355 | O | ASN | 369 | 20.531 | 43.978 | 78.607 | 1.00 | 7.80 |
| ATOM | 1356 | N | ILE | 370 | 22.594 | 44.558 | 77.910 | 1.00 | 5.52 |

TABLE 4-continued

Coordinates of Lck bound with staurosporine (soaked)

| | | Atom Type | Res | # | X | Y | Z | Occ | B |
|---|---|---|---|---|---|---|---|---|---|
| ATOM | 1358 | CA | ILE | 370 | 22.513 | 43.978 | 78.607 | 1.00 | 7.80 |
| ATOM | 1359 | CB | ILE | 370 | 22.806 | 44.620 | 75.434 | 1.00 | 5.37 |
| ATOM | 1360 | CG2 | ILE | 370 | 22.870 | 43.667 | 74.213 | 1.00 | 2.00 |
| ATOM | 1361 | CG1 | ILE | 370 | 21.740 | 45.735 | 75.298 | 1.00 | 2.00 |
| ATOM | 1362 | CD1 | ILE | 370 | 20.271 | 45.186 | 75.440 | 1.00 | 2.00 |
| ATOM | 1363 | C | ILE | 370 | 23.630 | 42.766 | 76.896 | 1.00 | 5.96 |
| ATOM | 1364 | O | ILE | 370 | 24.759 | 43.164 | 77.265 | 1.00 | 5.26 |
| ATOM | 1365 | N | LEU | 371 | 23.310 | 41.491 | 76.754 | 1.00 | 6.77 |
| ATOM | 1366 | H | LEU | 371 | 22.404 | 41.249 | 76.524 | 1.00 | 20.00 |
| ATOM | 1366 | CA | LEU | 371 | 24.310 | 40.410 | 76.951 | 1.00 | 5.25 |
| ATOM | 1367 | CB | LEU | 371 | 23.697 | 39.300 | 77.849 | 1.00 | 5.80 |
| ATOM | 1368 | CG | LEU | 371 | 24.000 | 39.250 | 79.342 | 1.00 | 8.15 |
| ATOM | 1369 | CD1 | LEU | 371 | 24.465 | 40.553 | 79.905 | 1.00 | 8.54 |
| ATOM | 1370 | CD2 | LEU | 371 | 22.953 | 38.500 | 80.228 | 1.00 | 5.22 |
| ATOM | 1371 | C | LEU | 371 | 24.729 | 39.871 | 75.607 | 1.00 | 6.17 |
| ATOM | 1372 | O | LEU | 371 | 23.922 | 39.893 | 74.657 | 1.00 | 6.29 |
| ATOM | 1374 | N | VAL | 372 | 25.999 | 39.457 | 75.505 | 1.00 | 4.90 |
| ATOM | 1376 | CA | VAL | 372 | 26.568 | 38.935 | 74.275 | 1.00 | 6.66 |
| ATOM | 1377 | CB | VAL | 372 | 27.838 | 39.743 | 73.853 | 1.00 | 5.80 |
| ATOM | 1378 | CG1 | VAL | 372 | 28.259 | 39.341 | 72.425 | 1.00 | 5.19 |
| ATOM | 1379 | CG2 | VAL | 372 | 27.569 | 41.288 | 73.960 | 1.00 | 7.50 |
| ATOM | 1380 | C | VAL | 372 | 26.907 | 37.437 | 74.351 | 1.00 | 4.98 |
| ATOM | 1381 | O | VAL | 372 | 27.554 | 36.988 | 75.265 | 1.00 | 5.78 |
| ATOM | 1382 | N | SER | 373 | 26.434 | 36.672 | 73.372 | 1.00 | 7.12 |
| ATOM | 1384 | CA | SER | 373 | 26.662 | 35.231 | 73.320 | 1.00 | 7.38 |
| ATOM | 1385 | CB | SER | 373 | 25.583 | 34.524 | 72.455 | 1.00 | 7.48 |
| ATOM | 1386 | OG | SER | 373 | 25.791 | 34.804 | 71.073 | 1.00 | 5.48 |
| ATOM | 1388 | C | SER | 373 | 28.019 | 34.899 | 72.757 | 1.00 | 9.13 |
| ATOM | 1389 | O | SER | 373 | 28.723 | 35.753 | 72.197 | 1.00 | 8.18 |
| ATOM | 1390 | N | ASP | 374 | 28.359 | 33.619 | 72.805 | 1.00 | 8.64 |
| ATOM | 1392 | CA | ASP | 374 | 29.626 | 33.194 | 72.265 | 1.00 | 9.08 |
| ATOM | 1393 | CB | ASP | 374 | 29.854 | 31.727 | 72.644 | 1.00 | 9.32 |
| ATOM | 1394 | CG | ASP | 374 | 28.900 | 30.809 | 71.944 | 1.00 | 11.97 |
| ATOM | 1395 | OD1 | ASP | 374 | 27.709 | 31.136 | 71.917 | 1.00 | 14.88 |
| ATOM | 1396 | OD2 | ASP | 374 | 29.333 | 29.804 | 71.339 | 1.00 | 15.30 |
| ATOM | 1397 | C | ASP | 374 | 26.678 | 33.397 | 70.740 | 1.00 | 9.93 |
| ATOM | 1398 | O | ASP | 374 | 30.752 | 33.485 | 70.159 | 1.00 | 10.12 |
| ATOM | 1399 | N | THR | 375 | 28.519 | 33.487 | 70.070 | 1.00 | 7.98 |
| ATOM | 1401 | CA | THR | 375 | 28.509 | 33.720 | 68.613 | 1.00 | 8.27 |
| ATOM | 1402 | CB | THR | 375 | 27.415 | 32.873 | 67.900 | 1.00 | 8.75 |
| ATOM | 1403 | OG1 | THR | 375 | 26.127 | 33.281 | 68.402 | 1.00 | 10.07 |
| ATOM | 1450 | CG2 | THR | 375 | 27.566 | 31.382 | 68.169 | 1.00 | 7.62 |
| ATOM | 1406 | C | THR | 375 | 28.289 | 35.213 | 68.258 | 1.00 | 8.45 |
| ATOM | 1407 | O | THR | 375 | 27.968 | 35.566 | 67.137 | 1.00 | 8.09 |
| ATOM | 1408 | N | LEU | 376 | 28.468 | 36.088 | 69.248 | 1.00 | 8.22 |
| ATOM | 1410 | CA | LEU | 376 | 28.307 | 37.521 | 69.080 | 1.00 | 9.33 |
| ATOM | 1411 | CB | LEU | 376 | 29.290 | 38.110 | 68.046 | 1.00 | 8.40 |
| ATOM | 1412 | CG | LEU | 376 | 30.755 | 37.717 | 68.339 | 1.00 | 12.51 |
| ATOM | 1413 | CD1 | LEU | 376 | 31.719 | 38.480 | 67.387 | 1.00 | 14.37 |
| ATOM | 1414 | CD2 | LEU | 376 | 31.094 | 37.986 | 69.824 | 1.00 | 14.45 |
| ATOM | 1415 | C | LEU | 376 | 26.877 | 37.947 | 68.736 | 1.00 | 9.24 |
| ATOM | 1416 | O | LEU | 376 | 26.691 | 38.800 | 67.869 | 1.00 | 8.58 |
| ATOM | 1417 | N | SER | 377 | 25.898 | 37.206 | 69.255 | 1.00 | 6.91 |
| ATOM | 1419 | CA | SER | 377 | 24.507 | 37.607 | 69.085 | 1.00 | 6.35 |
| ATOM | 1420 | CB | SER | 377 | 23.568 | 36.419 | 68.736 | 1.00 | 3.06 |
| ATOM | 1421 | OG | SER | 377 | 23.581 | 35.453 | 69.779 | 1.00 | 7.61 |
| ATOM | 1423 | C | SER | 377 | 24.169 | 38.271 | 70.405 | 1.00 | 5.91 |
| ATOM | 1424 | O | SER | 377 | 24.836 | 37.965 | 71.457 | 1.00 | 5.71 |
| ATOM | 1425 | N | CYS | 378 | 23.247 | 39.227 | 70.371 | 1.00 | 4.65 |
| ATOM | 1427 | CA | CYS | 378 | 22.863 | 39.987 | 71.539 | 1.00 | 5.21 |
| ATOM | 1428 | CB | CYS | 378 | 22.851 | 41.492 | 71.171 | 1.00 | 6.09 |
| ATOM | 1429 | SG | CYS | 378 | 24.490 | 42.098 | 70.729 | 1.00 | 13.86 |
| ATOM | 1430 | C | CYS | 378 | 21.476 | 39.652 | 72.034 | 1.00 | 5.68 |
| ATOM | 1431 | O | CYS | 378 | 20.571 | 39.390 | 71.237 | 1.00 | 3.41 |
| ATOM | 1432 | N | LYS | 379 | 21.299 | 39.790 | 73.344 | 1.00 | 5.79 |
| ATOM | 1434 | CA | LYS | 379 | 20.028 | 39.568 | 73.979 | 1.00 | 6.15 |
| ATOM | 1435 | CB | LYS | 379 | 19.968 | 38.126 | 74.557 | 1.00 | 5.70 |
| ATOM | 1436 | CG | LYS | 379 | 20.024 | 37.069 | 73.428 | 1.00 | 5.57 |
| ATOM | 1437 | CD | LYS | 379 | 19.695 | 35.653 | 73.895 | 1.00 | 7.05 |
| ATOM | 1438 | CE | LYS | 379 | 19.965 | 34.712 | 72.713 | 1.00 | 8.56 |
| ATOM | 1439 | NZ | LYS | 379 | 19.168 | 33.450 | 72.774 | 1.00 | 5.14 |
| ATOM | 1443 | C | LYS | 379 | 17.774 | 40.570 | 75.101 | 1.00 | 6.59 |
| ATOM | 1444 | O | LYS | 379 | 20.688 | 41.019 | 75.798 | 1.00 | 6.88 |
| ATOM | 1445 | N | ILE | 380 | 18.503 | 40.923 | 75.260 | 1.00 | 6.01 |

TABLE 4-continued

Coordinates of Lck bound with staurosporine (soaked)

| | | Atom Type | Res | # | X | Y | Z | Occ | B |
|---|---|---|---|---|---|---|---|---|---|
| ATOM | 1447 | CA | ILE | 380 | 18.088 | 41.817 | 76.308 | 1.00 | 4.05 |
| ATOM | 1448 | CB | ILE | 380 | 16.676 | 42.413 | 75.983 | 1.00 | 4.23 |
| ATOM | 1449 | CG2 | ILE | 380 | 16.211 | 43.363 | 77.114 | 1.00 | 4.05 |
| ATOM | 1450 | CG1 | ILE | 380 | 16.740 | 43.090 | 74.596 | 1.00 | 7.39 |
| ATOM | 1451 | CD1 | ILE | 380 | 15.437 | 43.643 | 74.134 | 1.00 | 7.36 |
| ATOM | 1452 | C | ILE | 380 | 18.052 | 41.096 | 77.637 | 1.00 | 4.63 |
| ATOM | 1453 | O | ILE | 380 | 17.506 | 39.972 | 77.753 | 1.00 | 4.54 |
| ATOM | 1454 | N | ALA | 381 | 18.600 | 41.753 | 78.665 | 1.00 | 3.68 |
| ATOM | 1456 | CA | ALA | 381 | 18.646 | 41.193 | 79.985 | 1.00 | 5.86 |
| ATOM | 1457 | CB | ALA | 381 | 20.124 | 40.726 | 80.309 | 1.00 | 4.71 |
| ATOM | 1458 | C | ALA | 381 | 18.171 | 42.187 | 81.075 | 1.00 | 6.27 |
| ATOM | 1459 | O | ALA | 381 | 17.897 | 43.391 | 80.826 | 1.00 | 6.81 |
| ATOM | 1460 | N | ASP | 382 | 18.143 | 41.662 | 82.287 | 1.00 | 7.15 |
| ATOM | 1462 | CA | ASP | 382 | 17.753 | 42.393 | 83.495 | 1.00 | 6.71 |
| ATOM | 1463 | CB | ASP | 382 | 18.777 | 43.460 | 83.844 | 1.00 | 9.17 |
| ATOM | 1464 | CG | ASP | 382 | 18.576 | 44.005 | 85.266 | 1.00 | 12.95 |
| ATOM | 1465 | OD1 | ASP | 382 | 19.508 | 44.625 | 85.778 | 1.00 | 16.02 |
| ATOM | 1466 | OD2 | ASP | 382 | 17.515 | 43.747 | 85.882 | 1.00 | 12.88 |
| ATOM | 1467 | C | ASP | 382 | 16.390 | 43.016 | 83.401 | 1.00 | 8.02 |
| ATOM | 1468 | O | ASP | 382 | 16.241 | 44.204 | 83.113 | 1.00 | 8.10 |
| ATOM | 1469 | N | PHE | 383 | 15.384 | 42.209 | 83.699 | 1.00 | 7.98 |
| ATOM | 1471 | CA | PHE | 383 | 13.996 | 42.627 | 83.655 | 1.00 | 8.46 |
| ATOM | 1472 | CB | PHE | 383 | 13.180 | 41.433 | 83.124 | 1.00 | 8.36 |
| ATOM | 1473 | CG | PHE | 383 | 13.564 | 41.017 | 81.709 | 1.00 | 11.11 |
| ATOM | 1474 | CD1 | PHE | 383 | 12.949 | 41.607 | 80.607 | 1.00 | 11.02 |
| ATOM | 1475 | CD2 | PHE | 383 | 14.592 | 40.111 | 81.489 | 1.00 | 10.97 |
| ATOM | 1476 | CE1 | PHE | 383 | 13.380 | 41.293 | 79.283 | 1.00 | 11.05 |
| ATOM | 1477 | CE2 | PHE | 383 | 15.013 | 39.802 | 80.166 | 1.00 | 13.87 |
| ATOM | 1478 | CZ | PHE | 383 | 14.408 | 40.400 | 79.082 | 1.00 | 9.97 |
| ATOM | 1479 | C | PHE | 383 | 13.459 | 43.104 | 85.023 | 1.00 | 8.84 |
| ATOM | 1480 | O | PHE | 383 | 12.281 | 43.006 | 85.287 | 1.00 | 9.41 |
| ATOM | 1481 | N | GLY | 384 | 14.351 | 43.566 | 85.891 | 1.00 | 9.27 |
| ATOM | 1483 | CA | GLY | 384 | 13.939 | 44.014 | 87.221 | 1.00 | 9.87 |
| ATOM | 1484 | C | GLY | 384 | 12.934 | 45.151 | 87.217 | 1.00 | 11.29 |
| ATOM | 1485 | O | GLY | 384 | 11.997 | 45.191 | 88.033 | 1.00 | 8.71 |
| ATOM | 1486 | N | LEU | 385 | 13.131 | 46.103 | 86.303 | 1.00 | 9.04 |
| ATOM | 1488 | CA | LEU | 385 | 12.224 | 47.217 | 86.224 | 1.00 | 8.32 |
| ATOM | 1489 | CB | LEU | 385 | 13.035 | 48.490 | 85.924 | 1.00 | 9.56 |
| ATOM | 1490 | CG | LEU | 385 | 13.985 | 48.890 | 87.070 | 1.00 | 10.82 |
| ATOM | 1491 | CD1 | LEU | 385 | 14.808 | 50.197 | 86.660 | 1.00 | 13.00 |
| ATOM | 1492 | CD2 | LEU | 385 | 13.197 | 49.130 | 88.366 | 1.00 | 11.41 |
| ATOM | 1493 | C | LEU | 385 | 11.131 | 47.037 | 85.199 | 1.00 | 8.31 |
| ATOM | 1494 | O | LEU | 385 | 10.258 | 47.897 | 85.059 | 1.00 | 7.36 |
| ATOM | 1495 | N | ALA | 386 | 11.194 | 45.927 | 84.457 | 1.00 | 6.60 |
| ATOM | 1497 | CA | ALA | 386 | 10.224 | 45.678 | 83.384 | 1.00 | 8.27 |
| ATOM | 1498 | CB | ALA | 386 | 10.632 | 44.406 | 82.587 | 1.00 | 4.24 |
| ATOM | 1499 | C | ALA | 386 | 8.810 | 45.563 | 83.911 | 1.00 | 9.72 |
| ATOM | 1500 | O | ALA | 386 | 8.602 | 44.969 | 84.987 | 1.00 | 10.64 |
| ATOM | 1501 | N | ARG | 387 | 7.841 | 46.047 | 83.132 | 1.00 | 9.50 |
| ATOM | 1503 | CA | ARG | 387 | 6.430 | 46.084 | 83.531 | 1.00 | 11.62 |
| ATOM | 1504 | CB | ARG | 387 | 6.080 | 47.473 | 84.106 | 1.00 | 11.18 |
| ATOM | 1505 | CG | ARG | 387 | 6.824 | 47.881 | 85.379 | 1.00 | 16.85 |
| ATOM | 1506 | CD | ARG | 387 | 6.650 | 46.874 | 86.550 | 1.00 | 12.98 |
| ATOM | 1507 | NE | ARG | 387 | 7.323 | 47.389 | 87.733 | 1.00 | 14.69 |
| ATOM | 1509 | CZ | ARG | 387 | 8.473 | 46.964 | 88.256 | 1.00 | 14.33 |
| ATOM | 1510 | NH1 | ARG | 387 | 9.178 | 45.951 | 87.724 | 1.00 | 13.07 |
| ATOM | 1513 | NH2 | ARG | 387 | 8.928 | 47.575 | 89.352 | 1.00 | 14.51 |
| ATOM | 1516 | C | ARG | 387 | 5.446 | 45.880 | 82.394 | 1.00 | 11.46 |
| ATOM | 1517 | O | ARG | 387 | 5.706 | 46.265 | 81.267 | 1.00 | 9.12 |
| ATOM | 1518 | N | LEU | 388 | 4.324 | 45.227 | 82.714 | 1.00 | 12.72 |
| ATOM | 1520 | CA | LEU | 388 | 3.248 | 45.031 | 81.775 | 1.00 | 15.05 |
| ATOM | 1521 | CB | LEU | 388 | 2.345 | 43.844 | 82.196 | 1.00 | 14.65 |
| ATOM | 1522 | CG | LEU | 388 | 1.060 | 43.555 | 81.375 | 1.00 | 14.87 |
| ATOM | 1523 | CD1 | LEU | 388 | 1.351 | 43.464 | 79.893 | 1.00 | 13.38 |
| ATOM | 1524 | CD2 | LEU | 388 | 0.416 | 42.242 | 81.874 | 1.00 | 14.82 |
| ATOM | 1525 | C | LEU | 388 | 2.449 | 46.318 | 81.792 | 1.00 | 17.48 |
| ATOM | 1526 | O | LEU | 388 | 2.098 | 46.839 | 82.847 | 1.00 | 17.50 |
| ATOM | 1527 | N | ILE | 389 | 2.290 | 46.899 | 80.622 | 1.00 | 20.52 |
| ATOM | 1529 | CA | ILE | 389 | 1.560 | 48.120 | 80.420 | 1.00 | 24.70 |
| ATOM | 1530 | CB | ILE | 389 | 2.178 | 48.835 | 79.198 | 1.00 | 26.16 |
| ATOM | 1531 | CG2 | ILE | 389 | 1.254 | 49.885 | 78.627 | 1.00 | 27.35 |
| ATOM | 1532 | CG1 | ILE | 389 | 3.557 | 49.366 | 79.549 | 1.00 | 26.34 |
| ATOM | 1533 | CD1 | ILE | 389 | 3.586 | 50.174 | 80.857 | 1.00 | 27.98 |
| ATOM | 1534 | C | ILE | 389 | 0.061 | 47.828 | 80.162 | 1.00 | 27.71 |

TABLE 4-continued

Coordinates of Lck bound with staurosporine (soaked)

| | | Atom Type | Res | # | X | Y | Z | Occ | B |
|---|---|---|---|---|---|---|---|---|---|
| ATOM | 1535 | O | ILE | 389 | −0.322 | 47.340 | 79.089 | 1.00 | 28.01 |
| ATOM | 1536 | N | GLU | 390 | −0.774 | 48.060 | 81.166 | 1.00 | 29.07 |
| ATOM | 1538 | CA | GLU | 390 | −2.221 | 47.851 | 81.036 | 1.00 | 33.31 |
| ATOM | 1539 | CB | GLU | 390 | −2.858 | 47.921 | 82.428 | 1.00 | 35.64 |
| ATOM | 1540 | CG | GLU | 390 | −2.062 | 47.175 | 83.493 | 1.00 | 38.85 |
| ATOM | 1541 | CD | GLU | 390 | −2.423 | 45.698 | 83.589 | 1.00 | 41.95 |
| ATOM | 1542 | OE1 | GLU | 390 | −3.519 | 45.302 | 83.111 | 1.00 | 43.61 |
| ATOM | 1543 | OE2 | GLU | 390 | −1.623 | 44.934 | 84.182 | 1.00 | 44.08 |
| ATOM | 1544 | C | GLU | 390 | −2.847 | 48.913 | 80.102 | 1.00 | 35.51 |
| ATOM | 1545 | O | GLU | 390 | −3.491 | 48.588 | 79.107 | 1.00 | 34.45 |
| ATOM | 1546 | N | ASP | 391 | −2.695 | 50.191 | 80.464 | 1.00 | 36.04 |
| ATOM | 1548 | CA | ASP | 391 | −3.160 | 51.288 | 79.617 | 1.00 | 37.62 |
| ATOM | 1549 | CB | ASP | 391 | −3.698 | 52.456 | 80.450 | 1.00 | 39.24 |
| ATOM | 1550 | CG | ASP | 391 | −5.195 | 52.345 | 80.450 | 1.00 | 39.24 |
| ATOM | 1551 | OD1 | ASP | 391 | −5.570 | 52.062 | 81.881 | 1.00 | 41.07 |
| ATOM | 1552 | OD2 | ASP | 391 | −5.986 | 52.535 | 79.767 | 1.00 | 39.64 |
| ATOM | 1553 | C | ASP | 391 | −1.973 | 51.702 | 78.765 | 1.00 | 38.38 |
| ATOM | 1554 | O | ASP | 391 | −1.336 | 50.821 | 78.186 | 1.00 | 39.43 |
| ATOM | 1555 | N | ALA | 392 | −1.635 | 52.976 | 78.645 | 1.00 | 36.06 |
| ATOM | 1557 | CA | ALA | 392 | −0.445 | 53.263 | 77.842 | 1.00 | 35.60 |
| ATOM | 1558 | CB | ALA | 392 | −0.733 | 54.383 | 76.820 | 1.00 | 36.17 |
| ATOM | 1559 | C | ALA | 392 | 0.806 | 53.611 | 78.653 | 1.00 | 34.60 |
| ATOM | 1560 | O | ALA | 392 | 1.930 | 53.541 | 78.123 | 1.00 | 33.20 |
| ATOM | 1561 | N | GLU | 393 | 0.646 | 53.747 | 79.970 | 1.00 | 33.89 |
| ATOM | 1563 | CA | GLU | 393 | 1.740 | 54.243 | 80.795 | 1.00 | 34.08 |
| ATOM | 1564 | CB | GLU | 393 | 1.482 | 55.762 | 80.859 | 1.00 | 36.56 |
| ATOM | 1565 | CG | GLU | 393 | 2.562 | 56.693 | 81.308 | 1.00 | 41.00 |
| ATOM | 1566 | CD | GLU | 393 | 2.130 | 58.166 | 81.130 | 1.00 | 43.97 |
| ATOM | 1567 | OE1 | GLU | 393 | 1.076 | 58.563 | 81.679 | 1.00 | 44.55 |
| ATOM | 1568 | OE2 | GLU | 393 | 2.846 | 58.928 | 80.437 | 1.00 | 45.51 |
| ATOM | 1569 | C | GLU | 393 | 1.893 | 53.683 | 82.221 | 1.00 | 32.38 |
| ATOM | 1570 | O | GLU | 393 | 0.924 | 53.346 | 82.896 | 1.00 | 33.15 |
| ATOM | 1571 | N | PTR | 394 | 3.135 | 53.619 | 82.686 | 1.00 | 29.72 |
| ATOM | 1572 | CA | PTR | 394 | 3.450 | 43.199 | 84.044 | 1.00 | 28.19 |
| ATOM | 1573 | C | PTR | 394 | 4.041 | 54.513 | 84.728 | 1.00 | 26.93 |
| ATOM | 1574 | O | PTR | 394 | 4.806 | 55.192 | 84.107 | 1.00 | 26.68 |
| ATOM | 1575 | CB | PTR | 394 | 4.461 | 52.018 | 84.057 | 1.00 | 28.69 |
| ATOM | 1576 | CG | PTR | 394 | 4.947 | 51.604 | 85.475 | 1.00 | 30.42 |
| ATOM | 1577 | CD1 | PTR | 394 | 6.052 | 52.413 | 86.037 | 1.00 | 31.83 |
| ATOM | 1578 | CD2 | PTR | 394 | 4.438 | 50.580 | 86.206 | 1.00 | 32.13 |
| ATOM | 1579 | CE1 | PTR | 394 | 6.517 | 52.056 | 87.318 | 1.00 | 34.02 |
| ATOM | 1580 | CE2 | PTR | 394 | 4.903 | 50.219 | 87.487 | 1.00 | 32.68 |
| ATOM | 1581 | CZ | PTR | 394 | 5.976 | 50.995 | 88.021 | 1.00 | 34.04 |
| ATOM | 1582 | OH | PTR | 394 | 6.505 | 50.679 | 89.298 | 1.00 | 36.71 |
| ATOM | 1583 | P | PTR | 394 | 6.117 | 49.669 | 90.441 | 1.00 | 39.45 |
| ATOM | 1584 | O1P | PTR | 394 | 7.229 | 49.796 | 91.357 | 1.00 | 39.10 |
| ATOM | 1585 | O2P | PTR | 394 | 5.920 | 48.150 | 90.168 | 1.00 | 39.40 |
| ATOM | 1586 | O3P | PTR | 394 | 4.923 | 50.270 | 90.894 | 1.00 | 38.95 |
| ATOM | 1587 | N | THR | 395 | 3.590 | 54.670 | 85.950 | 1.00 | 26.11 |
| ATOM | 1589 | CA | THR | 395 | 4.088 | 55.800 | 86.722 | 1.00 | 25.74 |
| ATOM | 1590 | CB | THR | 395 | 2.918 | 56.697 | 87.183 | 1.00 | 24.73 |
| ATOM | 1591 | OG1 | THR | 395 | 2.191 | 57.126 | 86.018 | 1.00 | 24.08 |
| ATOM | 1593 | CG2 | THR | 395 | 3.438 | 57.927 | 87.934 | 1.00 | 25.09 |
| ATOM | 1594 | C | THR | 395 | 4.860 | 55.306 | 87.920 | 1.00 | 25.68 |
| ATOM | 1595 | O | THR | 395 | 4.342 | 54.492 | 88.695 | 1.00 | 24.31 |
| ATOM | 1596 | N | ALA | 396 | 6.140 | 55.668 | 87.984 | 1.00 | 26.54 |
| ATOM | 1598 | CA | ALA | 396 | 6.989 | 55.278 | 89.098 | 1.00 | 28.10 |
| ATOM | 1599 | CB | ALA | 396 | 8.464 | 55.588 | 88.771 | 1.00 | 27.74 |
| ATOM | 1600 | C | ALA | 396 | 6.547 | 56.073 | 90.312 | 1.00 | 29.65 |
| ATOM | 1601 | O | ALA | 396 | 5.877 | 57.104 | 90.150 | 1.00 | 31.08 |
| ATOM | 1602 | N | ARG | 397 | 6.911 | 55.663 | 91.519 | 1.00 | 31.81 |
| ATOM | 1604 | CA | ARG | 397 | 6.452 | 56.459 | 92.646 | 1.00 | 34.40 |
| ATOM | 1605 | CB | ARG | 397 | 5.970 | 55.570 | 93.780 | 1.00 | 35.57 |
| ATOM | 1606 | CG | ARG | 397 | 6.985 | 55.307 | 94.848 | 1.00 | 38.18 |
| ATOM | 1607 | CD | ARG | 397 | 6.817 | 56.289 | 96.038 | 1.00 | 40.04 |
| ATOM | 1608 | NE | ARG | 397 | 6.023 | 57.485 | 95.728 | 1.00 | 40.90 |
| ATOM | 1610 | CZ | ARG | 397 | 4.703 | 57.582 | 95.897 | 1.00 | 40.28 |
| ATOM | 1611 | NH1 | ARG | 387 | 4.018 | 56.556 | 96.373 | 1.00 | 40.76 |
| ATOM | 1614 | NH2 | ARG | 387 | 4.069 | 58.708 | 95.600 | 1.00 | 40.55 |
| ATOM | 1617 | C | ARG | 397 | 7.435 | 57.547 | 93.051 | 1.00 | 34.46 |
| ATOM | 1618 | O | ARG | 397 | 8.630 | 57.455 | 92.768 | 1.00 | 34.83 |
| ATOM | 1619 | N | ALA | 398 | 6.869 | 58.640 | 93.559 | 1.00 | 35.64 |
| ATOM | 1621 | CA | ALA | 398 | 7.548 | 59.886 | 93.948 | 1.00 | 35.34 |
| ATOM | 1622 | CB | ALA | 398 | 6.905 | 60.503 | 95.211 | 1.00 | 35.64 |

TABLE 4-continued

Coordinates of Lck bound with staurosporine (soaked)

| | | Atom Type | Res | # | X | Y | Z | Occ | B |
|---|---|---|---|---|---|---|---|---|---|
| ATOM | 1623 | C | ALA | 398 | 9.065 | 59.964 | 94.030 | 1.00 | 34.51 |
| ATOM | 1624 | O | ALA | 398 | 9.687 | 60.755 | 93.296 | 1.00 | 36.64 |
| ATOM | 1625 | N | GLY | 399 | 9.679 | 59.176 | 94.902 | 1.00 | 34.00 |
| ATOM | 1627 | CA | GLY | 399 | 11.124 | 59.263 | 95.047 | 1.00 | 32.81 |
| ATOM | 1628 | C | GLY | 399 | 11.992 | 58.359 | 94.192 | 1.00 | 31.38 |
| ATOM | 1629 | O | GLY | 399 | 13.204 | 58.293 | 94.413 | 1.00 | 31.87 |
| ATOM | 1630 | N | ALA | 400 | 11.390 | 57.672 | 93.227 | 1.00 | 28.96 |
| ATOM | 1632 | CA | ALA | 400 | 12.137 | 56.790 | 92.344 | 1.00 | 27.32 |
| ATOM | 1633 | CB | ALA | 400 | 11.174 | 56.056 | 91.394 | 1.00 | 26.93 |
| ATOM | 1634 | C | ALA | 400 | 13.176 | 57.556 | 91.544 | 1.00 | 25.78 |
| ATOM | 1635 | O | ALA | 400 | 12.899 | 58.602 | 90.986 | 1.00 | 26.61 |
| ATOM | 1636 | N | ALA | 401 | 14.402 | 57.059 | 91.524 | 1.00 | 25.56 |
| ATOM | 1638 | CA | ALA | 401 | 15.449 | 57.735 | 90.786 | 1.00 | 24.04 |
| ATOM | 1639 | CB | ALA | 401 | 16.606 | 58.096 | 91.755 | 1.00 | 2.91 |
| ATOM | 1640 | C | ALA | 401 | 15.933 | 56.851 | 89.634 | 1.00 | 23.70 |
| ATOM | 1641 | O | ALA | 401 | 15.934 | 55.619 | 89.771 | 1.00 | 24.65 |
| ATOM | 1642 | N | PHE | 402 | 16.272 | 57.449 | 88.495 | 1.00 | 21.51 |
| ATOM | 1644 | CA | PHE | 402 | 16.758 | 56.704 | 87.299 | 1.00 | 20.26 |
| ATOM | 1645 | CB | PHE | 402 | 15.642 | 56.605 | 86.236 | 1.00 | 19.45 |
| ATOM | 1646 | CG | PHE | 402 | 14.362 | 56.003 | 86.750 | 1.00 | 19.99 |
| ATOM | 1647 | CD1 | PHE | 402 | 13.375 | 56.818 | 87.331 | 1.00 | 18.30 |
| ATOM | 1648 | CD2 | PHE | 402 | 14.174 | 54.624 | 86.739 | 1.00 | 17.24 |
| ATOM | 1649 | CE1 | PHE | 402 | 12.214 | 56.264 | 87.885 | 1.00 | 18.60 |
| ATOM | 1650 | CE2 | PHE | 402 | 13.016 | 54.065 | 87.296 | 1.00 | 18.88 |
| ATOM | 1651 | CZ | PHE | 402 | 12.035 | 54.890 | 87.881 | 1.00 | 17.36 |
| ATOM | 1652 | C | PHE | 402 | 17.992 | 57.390 | 86.685 | 1.00 | 19.72 |
| ATOM | 1653 | O | PHE | 402 | 18.205 | 58.604 | 86.908 | 1.00 | 19.51 |
| ATOM | 1654 | N | PRO | 403 | 18.841 | 56.633 | 85.948 | 1.00 | 17.61 |
| ATOM | 1655 | CD | PRO | 403 | 18.654 | 55.224 | 85.565 | 1.00 | 17.37 |
| ATOM | 1656 | CA | PRO | 403 | 20.063 | 57.183 | 85.321 | 1.00 | 15.21 |
| ATOM | 1657 | CB | PRO | 403 | 20.615 | 55.998 | 84.521 | 1.00 | 14.52 |
| ATOM | 1658 | CG | PRO | 403 | 20.064 | 54.794 | 85.246 | 1.00 | 16.35 |
| ATOM | 1659 | C | PRO | 403 | 19.614 | 58.268 | 84.390 | 1.00 | 14.03 |
| ATOM | 1660 | O | PRO | 403 | 18.940 | 57.991 | 83.393 | 1.00 | 12.56 |
| ATOM | 1661 | N | ILE | 404 | 19.955 | 59.506 | 84.727 | 1.00 | 10.55 |
| ATOM | 1663 | CA | ILE | 404 | 19.548 | 60.642 | 83.932 | 1.00 | 9.23 |
| ATOM | 1664 | CB | ILE | 404 | 20.103 | 61.969 | 84.556 | 1.00 | 8.33 |
| ATOM | 1665 | CG2 | ILE | 404 | 19.856 | 63.198 | 83.614 | 1.00 | 7.22 |
| ATOM | 1666 | CG1 | ILE | 404 | 19.428 | 62.279 | 85.898 | 1.00 | 10.89 |
| ATOM | 1667 | CD1 | ILE | 404 | 18.045 | 62.761 | 85.740 | 1.00 | 15.61 |
| ATOM | 1668 | C | ILE | 404 | 19.958 | 60.551 | 82.463 | 1.00 | 9.05 |
| ATOM | 1669 | O | ILE | 404 | 19.168 | 60.830 | 81.581 | 1.00 | 10.29 |
| ATOM | 1670 | N | LYS | 405 | 21.218 | 60.216 | 82.199 | 1.00 | 7.51 |
| ATOM | 1672 | CA | LYS | 405 | 21.697 | 60.166 | 80.805 | 1.00 | 7.74 |
| ATOM | 1673 | CB | LYS | 405 | 23.199 | 59.976 | 80.757 | 1.00 | 7.91 |
| ATOM | 1674 | CG | LYS | 405 | 24.009 | 61.154 | 81.381 | 1.00 | 9.19 |
| ATOM | 1675 | CD | LYS | 405 | 25.544 | 60.934 | 81.284 | 1.00 | 12.01 |
| ATOM | 1676 | CE | LYS | 405 | 26.376 | 62.219 | 81.618 | 1.00 | 13.50 |
| ATOM | 1677 | NZ | LYS | 405 | 27.864 | 62.237 | 81.067 | 1.00 | 14.45 |
| ATOM | 1681 | C | LYS | 405 | 20.997 | 59.190 | 79.840 | 1.00 | 7.52 |
| ATOM | 1682 | O | LYS | 405 | 20.987 | 59.451 | 78.641 | 1.00 | 5.32 |
| ATOM | 1683 | N | TRP | 406 | 20.325 | 58.163 | 80.367 | 1.00 | 7.25 |
| ATOM | 1685 | CA | TRP | 406 | 19.631 | 57.158 | 79.533 | 1.00 | 10.21 |
| ATOM | 1686 | CB | TRP | 406 | 19.925 | 55.740 | 80.065 | 1.00 | 8.91 |
| ATOM | 1687 | CG | TRP | 406 | 21.236 | 55.217 | 79.637 | 1.00 | 10.41 |
| ATOM | 1688 | CD2 | TRP | 406 | 22.496 | 55.427 | 80.271 | 1.00 | 8.35 |
| ATOM | 1689 | CE2 | TRP | 406 | 23.476 | 54.814 | 79.452 | 1.00 | 9.11 |
| ATOM | 1690 | CE3 | TRP | 406 | 22.905 | 56.078 | 81.433 | 1.00 | 7.48 |
| ATOM | 1691 | CD1 | TRP | 406 | 21.484 | 54.492 | 78.508 | 1.00 | 10.63 |
| ATOM | 1692 | NE1 | TRP | 406 | 22.822 | 54.251 | 78.391 | 1.00 | 9.36 |
| ATOM | 1694 | CZ2 | TRP | 406 | 24.831 | 54.821 | 79.776 | 1.00 | 8.58 |
| ATOM | 1695 | CZ3 | TRP | 406 | 24.260 | 56.094 | 81.756 | 1.00 | 9.59 |
| ATOM | 1696 | CH2 | TRP | 406 | 25.210 | 55.475 | 80.918 | 1.00 | 8.77 |
| ATOM | 1697 | C | TRP | 406 | 18.106 | 57.292 | 79.568 | 1.00 | 11.44 |
| ATOM | 1698 | O | TRP | 406 | 17.387 | 56.668 | 78.809 | 1.00 | 12.49 |
| ATOM | 1699 | N | THR | 407 | 17.617 | 58.073 | 80.511 | 1.00 | 11.51 |
| ATOM | 1701 | CA | THR | 407 | 16.181 | 58.167 | 80.689 | 1.00 | 12.67 |
| ATOM | 1702 | CB | THR | 407 | 15.816 | 58.202 | 82.219 | 1.00 | 12.98 |
| ATOM | 1703 | OG1 | THR | 407 | 16.463 | 57.099 | 82.887 | 1.00 | 12.38 |
| ATOM | 1705 | CG2 | THR | 407 | 14.310 | 58.062 | 82.403 | 1.00 | 12.55 |
| ATOM | 1706 | C | THR | 407 | 15.504 | 59.303 | 79.948 | 1.00 | 12.08 |
| ATOM | 1707 | O | THR | 407 | 16.003 | 60.425 | 79.927 | 1.00 | 11.81 |
| ATOM | 1708 | N | ALA | 408 | 14.300 | 59.017 | 79.445 | 1.00 | 11.28 |
| ATOM | 1710 | CA | ALA | 408 | 13.510 | 59.970 | 78.686 | 1.00 | 10.42 |

TABLE 4-continued

Coordinates of Lck bound with staurosporine (soaked)

| | Atom Type | Res | # | X | Y | Z | Occ | B |
|---|---|---|---|---|---|---|---|---|
| ATOM | 1711 | CB | ALA | 408 | 12.267 | 59.252 | 78.095 | 1.00 | 8.62 |
| ATOM | 1712 | C | ALA | 408 | 13.090 | 61.129 | 79.566 | 1.00 | 10.45 |
| ATOM | 1713 | O | ALA | 408 | 12.737 | 60.925 | 80.724 | 1.00 | 10.17 |
| ATOM | 1714 | N | PRO | 409 | 13.067 | 62.356 | 79.035 | 1.00 | 12.06 |
| ATOM | 1715 | CD | PRO | 409 | 13.188 | 62.730 | 77.611 | 1.00 | 10.84 |
| ATOM | 1716 | CA | PRO | 409 | 12.681 | 63.524 | 79.862 | 1.00 | 12.48 |
| ATOM | 1717 | CB | PRO | 409 | 12.645 | 64.690 | 78.844 | 1.00 | 10.99 |
| ATOM | 1718 | CG | PRO | 409 | 13.517 | 64.202 | 77.677 | 1.00 | 9.44 |
| ATOM | 1719 | C | PRO | 409 | 11.341 | 63.395 | 80.598 | 1.00 | 13.51 |
| ATOM | 1720 | O | PRO | 409 | 11.274 | 63.733 | 81.780 | 1.00 | 13.39 |
| ATOM | 1720 | N | GLU | 410 | 10.309 | 62.825 | 79.950 | 1.00 | 13.66 |
| ATOM | 1721 | CA | GLU | 410 | 9.008 | 62.686 | 80.610 | 1.00 | 14.05 |
| ATOM | 1723 | CB | GLU | 410 | 7.929 | 62.164 | 79.618 | 1.00 | 14.74 |
| ATOM | 1724 | CG | GLU | 410 | 8.157 | 60.712 | 79.139 | 1.00 | 14.11 |
| ATOM | 1726 | CD | GLU | 410 | 9.006 | 60.589 | 77.855 | 1.00 | 13.92 |
| ATOM | 1727 | OE1 | GLU | 410 | 9.609 | 61.586 | 77.412 | 1.00 | 17.79 |
| ATOM | 1728 | OE2 | GLU | 410 | 9.055 | 59.487 | 77.268 | 1.00 | 10.94 |
| ATOM | 1729 | C | GLU | 410 | 9.096 | 61.754 | 81.789 | 1.00 | 15.51 |
| ATOM | 1730 | O | GLU | 410 | 8.327 | 61.851 | 82.762 | 1.00 | 15.28 |
| ATOM | 1731 | N | ALA | 411 | 10.070 | 60.839 | 81.740 | 1.00 | 13.77 |
| ATOM | 1733 | CA | ALA | 411 | 10.273 | 59.891 | 82.842 | 1.00 | 13.86 |
| ATOM | 1734 | CB | ALA | 411 | 10.993 | 58.635 | 82.349 | 1.00 | 11.70 |
| ATOM | 1735 | C | ALA | 411 | 11.038 | 60.542 | 83.979 | 1.00 | 15.69 |
| ATOM | 1736 | O | ALA | 411 | 10.800 | 60.260 | 85.160 | 1.00 | 16.64 |
| ATOM | 1737 | N | ILE | 412 | 12.015 | 61.375 | 83.623 | 1.00 | 17.12 |
| ATOM | 1739 | CA | ILE | 412 | 12.777 | 62.111 | 84.637 | 1.00 | 17.37 |
| ATOM | 1740 | CB | ILE | 412 | 13.973 | 62.899 | 83.992 | 1.00 | 17.17 |
| ATOM | 1741 | CG2 | ILE | 412 | 14.591 | 63.878 | 84.984 | 1.00 | 15.66 |
| ATOM | 1742 | CG1 | ILE | 412 | 15.060 | 61.930 | 83.462 | 1.00 | 17.50 |
| ATOM | 1743 | CD1 | ILE | 412 | 16.132 | 62.644 | 82.494 | 1.00 | 17.00 |
| ATOM | 1744 | C | ILE | 412 | 11.843 | 63.117 | 85.337 | 1.00 | 19.20 |
| ATOM | 1745 | O | ILE | 412 | 11.727 | 63.116 | 86.550 | 1.00 | 20.37 |
| ATOM | 1746 | N | ASN | 413 | 11.091 | 63.865 | 84.522 | 1.00 | 19.09 |
| ATOM | 1748 | CA | ASN | 413 | 10.193 | 64.901 | 84.980 | 1.00 | 22.25 |
| ATOM | 1749 | CB | ASN | 413 | 9.782 | 65.838 | 83.812 | 1.00 | 20.96 |
| ATOM | 1750 | CG | ASN | 413 | 10.949 | 66.645 | 83.252 | 1.00 | 23.09 |
| ATOM | 1751 | OD1 | ASN | 413 | 11.885 | 66.995 | 83.973 | 1.00 | 24.79 |
| ATOM | 1752 | ND2 | ASN | 413 | 10.902 | 66.945 | 81.961 | 1.00 | 24.01 |
| ATOM | 1755 | C | ASN | 413 | 8.921 | 64.436 | 85.696 | 1.00 | 22.36 |
| ATOM | 1756 | O | ASN | 413 | 8.634 | 64.894 | 86.796 | 1.00 | 25.00 |
| ATOM | 1757 | N | TYR | 414 | 8.177 | 63.525 | 85.073 | 1.00 | 24.57 |
| ATOM | 1759 | CA | TYR | 414 | 6.898 | 63.071 | 85.616 | 1.00 | 24.50 |
| ATOM | 1760 | CB | TYR | 414 | 5.790 | 63.345 | 84.593 | 1.00 | 24.84 |
| ATOM | 1761 | CG | TYR | 414 | 5.842 | 64.728 | 83.981 | 1.00 | 26.70 |
| ATOM | 1762 | CD1 | TYR | 414 | 5.987 | 65.875 | 84.772 | 1.00 | 28.30 |
| ATOM | 1763 | CE1 | TYR | 414 | 6.144 | 67.142 | 84.198 | 1.00 | 27.43 |
| ATOM | 1764 | CD2 | TYR | 414 | 5.821 | 64.896 | 82.605 | 1.00 | 29.06 |
| ATOM | 1765 | CE2 | TYR | 414 | 5.979 | 66.157 | 82.025 | 1.00 | 29.86 |
| ATOM | 1766 | CZ | TYR | 414 | 6.131 | 67.273 | 82.833 | 1.00 | 30.46 |
| ATOM | 1767 | OH | TYR | 414 | 6.329 | 68.528 | 82.252 | 1.00 | 32.92 |
| ATOM | 1769 | C | TYR | 414 | 6.825 | 61.638 | 86.113 | 1.00 | 23.44 |
| ATOM | 1770 | O | TYR | 414 | 5.803 | 61.207 | 86.625 | 1.00 | 25.42 |
| ATOM | 1771 | N | GLY | 415 | 7.928 | 60.899 | 86.015 | 1.00 | 22.95 |
| ATOM | 1773 | CA | GLY | 415 | 7.922 | 59.520 | 86.467 | 1.00 | 21.12 |
| ATOM | 1774 | C | GLY | 415 | 7.123 | 58.621 | 85.520 | 1.00 | 18.78 |
| ATOM | 1775 | O | GLY | 415 | 6.916 | 57.437 | 85.802 | 1.00 | 18.47 |
| ATOM | 1776 | N | THR | 416 | 6.722 | 59.172 | 84.383 | 1.00 | 18.49 |
| ATOM | 1778 | CA | THR | 416 | 5.939 | 58.434 | 83.396 | 1.00 | 18.76 |
| ATOM | 1779 | CB | THR | 416 | 4.974 | 59.380 | 82.694 | 1.00 | 19.70 |
| ATOM | 1780 | OG1 | THR | 416 | 5.715 | 60.494 | 82.206 | 1.00 | 25.21 |
| ATOM | 1782 | CG2 | THR | 416 | 3.918 | 59.920 | 83.703 | 1.00 | 23.33 |
| ATOM | 1783 | C | THR | 416 | 6.793 | 57.704 | 82.348 | 1.00 | 15.58 |
| ATOM | 1784 | O | THR | 416 | 7.590 | 58.312 | 81.606 | 1.00 | 15.63 |
| ATOM | 1785 | N | PHE | 417 | 6.559 | 56.397 | 82.263 | 1.00 | 14.22 |
| ATOM | 1787 | CA | PHE | 417 | 7.250 | 55.502 | 81.344 | 1.00 | 12.90 |
| ATOM | 1788 | CB | PHE | 417 | 7.911 | 56.364 | 82.118 | 1.00 | 12.43 |
| ATOM | 1789 | CG | PHE | 417 | 9.134 | 54.763 | 82.853 | 1.00 | 13.25 |
| ATOM | 1790 | CD1 | PHE | 417 | 9.057 | 55.226 | 84.174 | 1.00 | 12.35 |
| ATOM | 1791 | CD2 | PHE | 417 | 10.383 | 54.601 | 82.258 | 1.00 | 13.08 |
| ATOM | 1792 | CE1 | PHE | 417 | 10.217 | 55.598 | 84.848 | 1.00 | 14.79 |
| ATOM | 1793 | CE2 | PHE | 417 | 11.526 | 54.969 | 82.916 | 1.00 | 13.12 |
| ATOM | 1794 | CZ | PHE | 417 | 11.449 | 55.437 | 84.228 | 1.00 | 14.79 |
| ATOM | 1795 | C | PHE | 417 | 6.304 | 54.829 | 80.382 | 1.00 | 12.95 |
| ATOM | 1796 | O | PHE | 417 | 5.224 | 54.345 | 80.793 | 1.00 | 11.58 |

TABLE 4-continued

Coordinates of Lck bound with staurosporine (soaked)

| | | Atom Type | Res | # | X | Y | Z | Occ | B |
|---|---|---|---|---|---|---|---|---|---|
| ATOM | 1797 | N | THR | 418 | 6.686 | 54.787 | 79.118 | 1.00 | 9.37 |
| ATOM | 1799 | CA | THR | 418 | 5.913 | 54.095 | 78.072 | 1.00 | 9.20 |
| ATOM | 1800 | CB | THR | 418 | 5.073 | 55.056 | 77.147 | 1.00 | 11.14 |
| ATOM | 1801 | OG1 | THR | 418 | 5.959 | 55.769 | 76.311 | 1.00 | 12.07 |
| ATOM | 1803 | CG2 | THR | 418 | 4.246 | 56.057 | 77.952 | 1.00 | 12.81 |
| ATOM | 1804 | C | THR | 418 | 6.951 | 53.449 | 77.191 | 1.00 | 6.81 |
| ATOM | 1805 | O | THR | 418 | 8.154 | 53.657 | 77.387 | 1.00 | 8.90 |
| ATOM | 1806 | N | ILE | 419 | 5.642 | 52.686 | 76.204 | 1.00 | 6.90 |
| ATOM | 1808 | CA | ILE | 419 | 7.520 | 52.054 | 75.319 | 1.00 | 6.26 |
| ATOM | 1809 | CB | ILE | 419 | 6.799 | 51.100 | 74.313 | 1.00 | 6.92 |
| ATOM | 1810 | CG2 | ILE | 419 | 6.000 | 51.927 | 73.287 | 1.00 | 8.94 |
| ATOM | 1811 | CG1 | ILE | 419 | 7.798 | 50.165 | 73.599 | 1.00 | 5.41 |
| ATOM | 1812 | CD1 | ILE | 419 | 8.540 | 49.171 | 74.529 | 1.00 | 6.59 |
| ATOM | 1813 | C | ILE | 419 | 8.350 | 53.143 | 74.577 | 1.00 | 8.26 |
| ATOM | 1814 | O | ILE | 419 | 9.488 | 52.908 | 74.138 | 1.00 | 5.34 |
| ATOM | 1815 | N | LYS | 420 | 7.806 | 54.364 | 74.521 | 1.00 | 6.34 |
| ATOM | 1817 | CA | LYS | 420 | 8.520 | 55.484 | 73.854 | 1.00 | 4.08 |
| ATOM | 1818 | CB | LYS | 420 | 7.551 | 56.644 | 73.531 | 1.00 | 2.68 |
| ATOM | 1819 | CG | LYS | 420 | 6.438 | 56.270 | 72.514 | 1.00 | 3.67 |
| ATOM | 1820 | CD | LYS | 420 | 6.999 | 55.671 | 71.209 | 1.00 | 5.03 |
| ATOM | 1821 | CE | LYS | 420 | 5.953 | 55.772 | 70.043 | 1.00 | 6.23 |
| ATOM | 1822 | NZ | LYS | 420 | 6.424 | 54.981 | 68.875 | 1.00 | 7.07 |
| ATOM | 1826 | C | LYS | 420 | 9.676 | 55.986 | 74.697 | 1.00 | 4.79 |
| ATOM | 1827 | O | LYS | 420 | 10.576 | 56.650 | 74.186 | 1.00 | 6.52 |
| ATOM | 1828 | N | SER | 421 | 9.629 | 55.723 | 76.004 | 0.84 | 4.97 |
| ATOM | 1830 | CA | SER | 421 | 10.729 | 56.084 | 76.893 | 0.84 | 3.95 |
| ATOM | 1831 | CB | SER | 421 | 10.352 | 55.960 | 78.402 | 0.84 | 5.49 |
| ATOM | 1832 | OG | SER | 421 | 9.094 | 56.468 | 78.668 | 0.84 | 10.14 |
| ATOM | 1834 | C | SER | 421 | 11.856 | 55.117 | 76.617 | 0.84 | 3.16 |
| ATOM | 1835 | O | SER | 421 | 13.021 | 55.456 | 76.709 | 0.84 | 2.00 |
| ATOM | 1836 | N | ASP | 422 | 11.490 | 53.857 | 76.377 | 1.00 | 4.50 |
| ATOM | 1838 | CA | ASP | 422 | 12.512 | 52.860 | 76.032 | 1.00 | 5.52 |
| ATOM | 1839 | CB | ASP | 422 | 11.915 | 51.447 | 75.914 | 1.00 | 6.76 |
| ATOM | 1840 | CG | ASP | 422 | 11.665 | 50.773 | 77.266 | 1.00 | 9.09 |
| ATOM | 1841 | OD1 | ASP | 422 | 12.156 | 51.243 | 78.339 | 1.00 | 4.99 |
| ATOM | 1842 | OD2 | ASP | 422 | 10.963 | 49.730 | 77.229 | 1.00 | 9.59 |
| ATOM | 1843 | C | ASP | 422 | 13.142 | 53.267 | 74.694 | 1.00 | 3.86 |
| ATOM | 1844 | O | ASP | 422 | 14.361 | 53.122 | 74.463 | 1.00 | 2.91 |
| ATOM | 1845 | N | VAL | 423 | 12.304 | 53.759 | 73.783 | 1.00 | 4.15 |
| ATOM | 1847 | CA | VAL | 423 | 12.848 | 54.225 | 72.504 | 1.00 | 4.40 |
| ATOM | 1848 | CB | VAL | 423 | 11.735 | 54.766 | 71.550 | 1.00 | 5.29 |
| ATOM | 1849 | CG1 | VAL | 423 | 12.373 | 55.463 | 70.292 | 1.00 | 5.10 |
| ATOM | 1850 | CG2 | VAL | 423 | 10.844 | 53.619 | 71.040 | 1.00 | 4.81 |
| ATOM | 1851 | C | VAL | 423 | 13.944 | 55.267 | 72.711 | 1.00 | 3.42 |
| ATOM | 1852 | O | VAL | 423 | 15.025 | 55.180 | 72.099 | 1.00 | 3.11 |
| ATOM | 1853 | N | TRP | 424 | 13.687 | 56.245 | 73.583 | 1.00 | 4.34 |
| ATOM | 1855 | CA | TRP | 424 | 14.703 | 57.278 | 73.898 | 1.00 | 3.74 |
| ATOM | 1856 | CB | TRP | 424 | 14.186 | 58.216 | 75.004 | 1.00 | 3.96 |
| ATOM | 1857 | CG | TRP | 424 | 15.148 | 59.270 | 75.367 | 1.00 | 4.52 |
| ATOM | 1858 | CD2 | TRP | 424 | 15.071 | 60.663 | 75.021 | 1.00 | 4.48 |
| ATOM | 1859 | CE2 | TRP | 424 | 15.218 | 61.297 | 75.562 | 1.00 | 5.86 |
| ATOM | 1860 | CE3 | TRP | 424 | 14.137 | 61.450 | 74.307 | 1.00 | 6.03 |
| ATOM | 1861 | CD1 | TRP | 424 | 16.312 | 59.108 | 76.079 | 1.00 | 4.73 |
| ATOM | 1862 | NE1 | TRP | 424 | 16.952 | 60.329 | 76.206 | 1.00 | 2.83 |
| ATOM | 1864 | CZ2 | TRP | 424 | 16.470 | 62.682 | 75.422 | 1.00 | 5.37 |
| ATOM | 1865 | CZ3 | TRP | 424 | 14.387 | 62.856 | 74.166 | 1.00 | 6.25 |
| ATOM | 1866 | CH2 | TRP | 424 | 15.546 | 63.436 | 74.725 | 1.00 | 3.32 |
| ATOM | 1867 | C | TRP | 424 | 16.007 | 56.611 | 74.391 | 1.00 | 5.05 |
| ATOM | 1868 | O | TRP | 424 | 17.133 | 56.965 | 73.917 | 1.00 | 6.14 |
| ATOM | 1869 | N | SER | 425 | 15.858 | 55.672 | 75.338 | 0.74 | 2.00 |
| ATOM | 1871 | CA | SER | 425 | 16.988 | 54.915 | 75.894 | 0.74 | 2.00 |
| ATOM | 1872 | CB | SER | 425 | 16.515 | 53.928 | 76.981 | 0.74 | 2.95 |
| ATOM | 1873 | OG | SER | 425 | 15.796 | 54.605 | 78.015 | 0.74 | 2.82 |
| ATOM | 1875 | C | SER | 425 | 17.764 | 54.161 | 74.834 | 0.74 | 2.00 |
| ATOM | 1876 | O | SER | 425 | 18.976 | 54.040 | 74.889 | 0.74 | 2.00 |
| ATOM | 1877 | N | PHE | 426 | 17.38 | 53.644 | 73.857 | 1.00 | 2.05 |
| ATOM | 1879 | CA | PHE | 426 | 17.702 | 52.933 | 72.729 | 1.00 | 2.00 |
| ATOM | 1880 | CB | PHE | 426 | 16.643 | 52.335 | 71.789 | 1.00 | 2.00 |
| ATOM | 1881 | CG | PHE | 426 | 17.235 | 51.508 | 70.669 | 1.00 | 3.82 |
| ATOM | 1882 | CD1 | PHE | 426 | 17.777 | 50.261 | 70.941 | 1.00 | 3.04 |
| ATOM | 1883 | CD2 | PHE | 426 | 17.279 | 51.995 | 69.371 | 1.00 | 4.66 |
| ATOM | 1884 | CE1 | PHE | 426 | 18.346 | 49.516 | 69.918 | 1.00 | 5.20 |
| ATOM | 1885 | CE2 | PHE | 426 | 17.845 | 51.248 | 68.359 | 1.00 | 5.66 |
| ATOM | 1886 | CZ | PHE | 426 | 18.384 | 50.010 | 68.650 | 1.00 | 5.23 |

TABLE 4-continued

Coordinates of Lck bound with staurosporine (soaked)

| | | Atom Type | Res | # | X | Y | Z | Occ | B |
|---|---|---|---|---|---|---|---|---|---|
| ATOM | 1887 | C | PHE | 426 | 18.615 | 53.883 | 71.944 | 1.00 | 2.84 |
| ATOM | 1888 | O | PHE | 426 | 19.761 | 53.550 | 71.593 | 1.00 | 2.64 |
| ATOM | 1889 | N | GLY | 427 | 18.148 | 55.108 | 71.716 | 1.00 | 2.95 |
| ATOM | 1891 | CA | GLY | 427 | 19.003 | 56.051 | 70.975 | 1.00 | 2.56 |
| ATOM | 1892 | C | GLY | 427 | 20.309 | 56.268 | 71.740 | 1.00 | 3.41 |
| ATOM | 1893 | O | GLY | 427 | 21.375 | 56.316 | 71.143 | 1.00 | 5.01 |
| ATOM | 1894 | N | ILE | 428 | 20.218 | 56.398 | 73.062 | 1.00 | 2.32 |
| ATOM | 1896 | CA | ILE | 428 | 21.404 | 56.562 | 73.886 | 1.00 | 2.51 |
| ATOM | 1897 | CB | ILE | 428 | 21.044 | 56.798 | 75.385 | 1.00 | 2.00 |
| ATOM | 1898 | CG2 | ILE | 428 | 22.348 | 56.986 | 76.232 | 1.00 | 4.15 |
| ATOM | 1899 | CG1 | ILE | 428 | 20.075 | 58.015 | 75.551 | 1.00 | 3.53 |
| ATOM | 1900 | CD1 | ILE | 428 | 20.655 | 59.343 | 75.055 | 1.00 | 3.34 |
| ATOM | 1901 | C | ILE | 428 | 22.255 | 55.299 | 73.798 | 1.00 | 3.22 |
| ATOM | 1902 | O | ILE | 428 | 23.488 | 55.352 | 73.695 | 1.00 | 2.00 |
| ATOM | 1903 | N | LEU | 429 | 21.588 | 54.146 | 73.849 | 1.00 | 5.03 |
| ATOM | 1905 | CA | LEU | 429 | 22.300 | 52.873 | 73.737 | 1.00 | 4.88 |
| ATOM | 1906 | CB | LEU | 429 | 21.303 | 51.682 | 73.883 | 1.00 | 5.84 |
| ATOM | 1906 | CG | LEU | 429 | 21.893 | 50.289 | 74.195 | 1.00 | 8.89 |
| ATOM | 1908 | CD1 | LEU | 429 | 20.796 | 49.309 | 74.701 | 1.00 | 5.51 |
| ATOM | 1909 | CD2 | LEU | 429 | 22.507 | 49.742 | 72.917 | 1.00 | 10.48 |
| ATOM | 1910 | C | LEU | 429 | 23.134 | 52.812 | 72.436 | 1.00 | 3.30 |
| ATOM | 1911 | O | LEU | 429 | 24.248 | 52.361 | 72.435 | 1.00 | 3.13 |
| ATOM | 1912 | N | LEU | 430 | 22.571 | 53.297 | 71.326 | 1.00 | 4.74 |
| ATOM | 1914 | CA | LEU | 430 | 23.271 | 53.350 | 70.055 | 1.00 | 5.38 |
| ATOM | 1915 | CB | LEU | 430 | 22.407 | 53.988 | 68.973 | 1.00 | 4.05 |
| ATOM | 1916 | CG | LEU | 430 | 22.146 | 53.206 | 68.574 | 1.00 | 4.57 |
| ATOM | 1917 | CD1 | LEU | 430 | 20.360 | 54.072 | 67.628 | 1.00 | 5.38 |
| ATOM | 1918 | CD2 | LEU | 430 | 21.476 | 51.819 | 67.911 | 1.00 | 5.08 |
| ATOM | 1919 | C | LEU | 430 | 24.592 | 54.116 | 70.130 | 1.00 | 3.87 |
| ATOM | 1920 | O | LEU | 430 | 25.534 | 53.745 | 69.411 | 1.00 | 4.14 |
| ATOM | 1921 | N | THR | 431 | 24.627 | 55.186 | 70.943 | 1.00 | 3.19 |
| ATOM | 1923 | CA | THR | 431 | 25.866 | 55.948 | 71.123 | 1.00 | 4.13 |
| ATOM | 1924 | CB | THR | 431 | 25.674 | 57.329 | 71.881 | 1.00 | 6.10 |
| ATOM | 1925 | OG1 | THR | 431 | 25.431 | 57.085 | 73.283 | 1.00 | 4.45 |
| ATOM | 1927 | CG2 | THR | 431 | 24.482 | 58.149 | 71.271 | 1.00 | 3.43 |
| ATOM | 1928 | C | THR | 431 | 26.864 | 55.068 | 71.868 | 1.00 | 5.42 |
| ATOM | 1929 | O | THR | 431 | 28.063 | 55.066 | 71.547 | 1.00 | 5.41 |
| ATOM | 1930 | N | GLU | 432 | 26.376 | 54.264 | 72.816 | 1.00 | 5.58 |
| ATOM | 1932 | CA | GLU | 432 | 27.294 | 53.343 | 73.514 | 1.00 | 5.91 |
| ATOM | 1933 | CB | GLU | 432 | 26.601 | 52.587 | 74.663 | 1.00 | 4.77 |
| ATOM | 1934 | CG | GLU | 432 | 26.024 | 53.501 | 75.738 | 1.00 | 6.02 |
| ATOM | 1935 | CD | GLU | 432 | 25.312 | 52.690 | 76.824 | 1.00 | 8.30 |
| ATOM | 1936 | OE1 | GLU | 432 | 24.124 | 52.346 | 76.656 | 1.00 | 7.55 |
| ATOM | 1937 | OE2 | GLU | 432 | 25.984 | 52.327 | 77.812 | 1.00 | 8.54 |
| ATOM | 1938 | C | GLU | 432 | 27.876 | 52.314 | 72.562 | 1.00 | 4.75 |
| ATOM | 1939 | O | GLU | 432 | 29.063 | 51.880 | 72.721 | 1.00 | 7.57 |
| ATOM | 1940 | N | ILE | 433 | 27.067 | 51.895 | 71.580 | 1.00 | 4.02 |
| ATOM | 1942 | CA | ILE | 433 | 27.573 | 50.891 | 70.640 | 1.00 | 5.75 |
| ATOM | 1943 | CB | ILE | 433 | 26.434 | 50.278 | 69.789 | 1.00 | 5.46 |
| ATOM | 1944 | CG2 | ILE | 433 | 27.002 | 49.491 | 68.557 | 1.00 | 7.63 |
| ATOM | 1945 | CG1 | ILE | 433 | 25.621 | 49.330 | 70.667 | 1.00 | 3.44 |
| ATOM | 1946 | CD1 | ILE | 433 | 24.268 | 48.956 | 70.064 | 1.00 | 3.43 |
| ATOM | 1947 | C | ILE | 433 | 28.662 | 51.466 | 69.766 | 1.00 | 7.58 |
| ATOM | 1948 | O | ILE | 433 | 29.785 | 50.959 | 69.716 | 1.00 | 5.81 |
| ATOM | 1949 | N | VAL | 434 | 28.379 | 52.645 | 69.211 | 1.00 | 8.45 |
| ATOM | 1951 | CA | VAL | 434 | 29.334 | 53.291 | 68.302 | 1.00 | 10.29 |
| ATOM | 1952 | CB | VAL | 434 | 28.574 | 54.316 | 67.398 | 1.00 | 12.33 |
| ATOM | 1953 | CG1 | VAL | 434 | 28.572 | 55.699 | 68.013 | 1.00 | 10.36 |
| ATOM | 1954 | CG2 | VAL | 434 | 29.127 | 54.289 | 65.987 | 1.00 | 15.29 |
| ATOM | 1955 | C | VAL | 434 | 30.619 | 53.833 | 68.958 | 1.00 | 10.86 |
| ATOM | 1956 | O | VAL | 434 | 31.671 | 53.905 | 68.328 | 1.00 | 11.27 |
| ATOM | 1957 | N | THR | 435 | 30.578 | 54.184 | 70.235 | 1.00 | 9.46 |
| ATOM | 1959 | CA | THR | 435 | 31.790 | 54.635 | 70.917 | 1.00 | 10.41 |
| ATOM | 1960 | CB | THR | 435 | 31.459 | 55.722 | 71.927 | 1.00 | 9.86 |
| ATOM | 1961 | OG1 | THR | 435 | 30.628 | 55.153 | 72.922 | 1.00 | 10.21 |
| ATOM | 1963 | CG2 | THR | 435 | 30.747 | 56.926 | 71.238 | 1.00 | 5.06 |
| ATOM | 1964 | C | THR | 435 | 32.500 | 53.497 | 71.701 | 1.00 | 11.33 |
| ATOM | 1965 | O | THR | 435 | 33.333 | 53.724 | 72.552 | 1.00 | 9.52 |
| ATOM | 1966 | N | HIS | 436 | 32.095 | 52.255 | 71.426 | 1.00 | 10.76 |
| ATOM | 1968 | CA | HIS | 436 | 32.660 | 51.108 | 72.117 | 1.00 | 12.16 |
| ATOM | 1969 | CB | HIS | 436 | 34.093 | 50.771 | 71.622 | 1.00 | 14.36 |
| ATOM | 1970 | CG | HIS | 436 | 34.138 | 50.340 | 70.189 | 1.00 | 17.82 |
| ATOM | 1971 | CD2 | HIS | 436 | 34.040 | 51.008 | 69.028 | 1.00 | 18.01 |
| ATOM | 1972 | ND1 | HIS | 436 | 34.278 | 48.984 | 69.811 | 1.00 | 17.95 |

TABLE 4-continued

Coordinates of Lck bound with staurosporine (soaked)

| | | Atom Type | Res | # | X | Y | Z | Occ | B |
|---|---|---|---|---|---|---|---|---|---|
| ATOM | 1974 | CE1 | HIS | 436 | 34.249 | 48.894 | 68.515 | 1.00 | 16.78 |
| ATOM | 1975 | NE2 | HIS | 436 | 34.107 | 50.118 | 67.985 | 1.00 | 18.47 |
| ATOM | 1977 | C | HIS | 436 | 32.574 | 51.200 | 73.612 | 1.00 | 10.66 |
| ATOM | 1978 | O | HIS | 436 | 33.544 | 51.002 | 74.345 | 1.00 | 12.29 |
| ATOM | 1989 | N | GLY | 437 | 31.402 | 51.596 | 74.071 | 1.00 | 8.50 |
| ATOM | 1981 | CA | GLY | 437 | 31.165 | 51.663 | 75.495 | 1.00 | 9.22 |
| ATOM | 1982 | C | GLY | 437 | 31.423 | 52.924 | 76.259 | 1.00 | 8.30 |
| ATOM | 1983 | O | GLY | 437 | 31.442 | 52.845 | 77.479 | 1.00 | 10.50 |
| ATOM | 1984 | N | ARG | 438 | 31.604 | 54.072 | 75.605 | 0.58 | 4.33 |
| ATOM | 1986 | CA | ARG | 438 | 31.826 | 55.340 | 76.342 | 0.58 | 5.30 |
| ATOM | 1987 | CB | ARG | 438 | 32.316 | 56.432 | 75.375 | 0.58 | 5.27 |
| ATOM | 1988 | CG | ARG | 438 | 32.741 | 57.754 | 76.040 | 0.58 | 10.45 |
| ATOM | 1989 | CD | ARG | 438 | 33.316 | 58.745 | 75.006 | 0.58 | 12.08 |
| ATOM | 1990 | NE | ARG | 438 | 34.065 | 59.847 | 75.639 | 0.58 | 14.66 |
| ATOM | 1992 | CZ | ARG | 438 | 34.540 | 60.598 | 74.970 | 0.58 | 14.73 |
| ATOM | 1993 | NH1 | ARG | 438 | 34.337 | 60.986 | 73.670 | 0.58 | 16.77 |
| ATOM | 1996 | NH2 | ARG | 438 | 35.231 | 61.844 | 75.583 | 0.58 | 15.37 |
| ATOM | 1999 | C | ARG | 438 | 30.553 | 55.845 | 77.024 | 0.58 | 3.96 |
| ATOM | 2000 | O | ARG | 438 | 29.458 | 55.559 | 76.577 | 0.58 | 2.00 |
| ATOM | 2001 | N | ILE | 439 | 30.708 | 56.622 | 78.091 | 1.00 | 7.07 |
| ATOM | 2003 | CA | ILE | 439 | 29.595 | 57.199 | 78.814 | 1.00 | 4.89 |
| ATOM | 2004 | CB | ILE | 439 | 30.048 | 57.865 | 80.184 | 1.00 | 10.20 |
| ATOM | 2005 | CG2 | ILE | 439 | 28.834 | 58.496 | 80.938 | 1.00 | 8.12 |
| ATOM | 2006 | CG1 | ILE | 439 | 30.556 | 56.790 | 81.179 | 1.00 | 12.62 |
| ATOM | 2007 | CD1 | ILE | 439 | 31.474 | 57.384 | 82.326 | 1.00 | 13.55 |
| ATOM | 2008 | C | ILE | 439 | 28.975 | 58.227 | 77.894 | 1.00 | 4.63 |
| ATOM | 2009 | O | ILE | 439 | 29.710 | 58.973 | 77.199 | 1.00 | 5.97 |
| ATOM | 2010 | N | PRO | 440 | 27.646 | 58.251 | 77.788 | 0.43 | 2.00 |
| ATOM | 2011 | CD | PRO | 440 | 26.726 | 57.301 | 78.423 | 0.43 | 2.00 |
| ATOM | 2012 | CA | PRO | 440 | 26.959 | 59.219 | 76.917 | 0.43 | 2.00 |
| ATOM | 2013 | CB | PRO | 440 | 25.487 | 58.794 | 77.006 | 0.43 | 2.00 |
| ATOM | 2014 | CG | PRO | 440 | 25.386 | 57.918 | 78.191 | 0.43 | 2.00 |
| ATOM | 2015 | C | PRO | 440 | 27.155 | 60.671 | 77.359 | 0.43 | 2.00 |
| ATOM | 2016 | O | PRO | 440 | 27.480 | 60.906 | 78.521 | 0.43 | 2.00 |
| ATOM | 2017 | N | TYR | 441 | 26.950 | 61.622 | 76.415 | 1.00 | 4.34 |
| ATOM | 2019 | CA | TYR | 441 | 27.095 | 63.053 | 76.690 | 1.00 | 5.14 |
| ATOM | 2020 | CB | TYR | 441 | 26.031 | 63.549 | 77.709 | 1.00 | 3.68 |
| ATOM | 2021 | CG | TYR | 441 | 24.582 | 63.337 | 77.265 | 1.00 | 4.65 |
| ATOM | 2022 | CD1 | TYR | 441 | 24.002 | 64.215 | 76.326 | 1.00 | 3.69 |
| ATOM | 2023 | CE1 | TYR | 441 | 22.697 | 64.058 | 75.898 | 1.00 | 4.62 |
| ATOM | 2024 | CD2 | TYR | 441 | 23.804 | 62.283 | 77.756 | 1.00 | 4.82 |
| ATOM | 2025 | CE2 | TYR | 441 | 22.478 | 62.117 | 77.334 | 1.00 | 3.03 |
| ATOM | 2026 | CZ | TYR | 441 | 21.941 | 63.015 | 76.402 | 1.00 | 2.94 |
| ATOM | 2027 | OH | TYR | 441 | 20.669 | 62.919 | 75.948 | 1.00 | 2.71 |
| ATOM | 2029 | C | TYR | 441 | 28.467 | 63.298 | 77.309 | 1.00 | 9.44 |
| ATOM | 2030 | O | TYR | 441 | 28.565 | 63.832 | 78.399 | 1.00 | 10.66 |
| ATOM | 2031 | N | PRO | 442 | 29.540 | 62.948 | 76.597 | 1.00 | 11.17 |
| ATOM | 2032 | CD | PRO | 442 | 29.574 | 62.539 | 75.175 | 1.00 | 12.12 |
| ATOM | 2033 | CA | PRO | 442 | 30.906 | 63.125 | 77.120 | 1.00 | 12.86 |
| ATOM | 2034 | CB | PRO | 442 | 31.783 | 62.839 | 75.897 | 1.00 | 13.07 |
| ATOM | 2035 | CG | PRO | 442 | 30.897 | 61.871 | 75.065 | 1.00 | 11.80 |
| ATOM | 2036 | C | PRO | 442 | 31.234 | 64.500 | 77.078 | 1.00 | 11.90 |
| ATOM | 2037 | O | PRO | 442 | 30.916 | 65.527 | 77.134 | 1.00 | 12.98 |
| ATOM | 2038 | N | GLY | 443 | 31.778 | 64.492 | 78.917 | 1.00 | 13.61 |
| ATOM | 2040 | CA | GLY | 443 | 32.196 | 65.743 | 79.530 | 1.00 | 13.89 |
| ATOM | 2041 | C | GLY | 443 | 31.127 | 66.578 | 80.150 | 1.00 | 13.55 |
| ATOM | 2042 | O | GLY | 443 | 31.388 | 67.706 | 80.537 | 1.00 | 13.44 |
| ATOM | 2043 | N | MET | 444 | 29.914 | 66.029 | 80.245 | 1.00 | 11.91 |
| ATOM | 2045 | CA | MET | 444 | 28.784 | 66.748 | 80.829 | 1.00 | 10.61 |
| ATOM | 2046 | CB | MET | 444 | 27.659 | 66.840 | 79.774 | 1.00 | 12.90 |
| ATOM | 2047 | CG | MET | 444 | 28.124 | 67.442 | 78.447 | 1.00 | 10.70 |
| ATOM | 2048 | SD | MET | 444 | 26.904 | 67.475 | 77.084 | 1.00 | 14.53 |
| ATOM | 2049 | CE | MET | 444 | 25.403 | 68.138 | 77.901 | 1.00 | 12.34 |
| ATOM | 2050 | C | MET | 444 | 28.243 | 66.060 | 82.080 | 1.00 | 11.01 |
| ATOM | 2051 | O | MET | 444 | 28.173 | 64.826 | 82.151 | 1.00 | 9.30 |
| ATOM | 2052 | N | THR | 445 | 27.813 | 66.864 | 83.048 | 1.00 | 9.72 |
| ATOM | 2054 | CA | THR | 445 | 27.207 | 66.359 | 84.241 | 1.00 | 9.39 |
| ATOM | 2055 | CB | THR | 445 | 27.354 | 67.395 | 85.397 | 1.00 | 12.53 |
| ATOM | 2056 | OG1 | THR | 445 | 26.680 | 68.625 | 85.023 | 1.00 | 9.54 |
| ATOM | 2058 | CG2 | THR | 445 | 28.837 | 67.653 | 85.703 | 1.00 | 10.72 |
| ATOM | 2059 | C | THR | 445 | 25.714 | 66.202 | 83.969 | 1.00 | 9.34 |
| ATOM | 2060 | O | THR | 445 | 25.201 | 66.651 | 82.926 | 1.00 | 6.96 |
| ATOM | 2061 | N | ASN | 446 | 24.991 | 65.596 | 84.900 | 1.00 | 8.17 |
| ATOM | 2063 | CA | ASN | 446 | 23.549 | 65.438 | 84.723 | 1.00 | 10.10 |

TABLE 4-continued

Coordinates of Lck bound with staurosporine (soaked)

| | Atom Type | Res | # | X | Y | Z | Occ | B |
|---|---|---|---|---|---|---|---|---|
| ATOM | 2064 | CB | ASN | 446 | 22.950 | 64.647 | 85.888 | 1.00 | 11.33 |
| ATOM | 2065 | CG | ASN | 446 | 23.261 | 63.145 | 85.810 | 1.00 | 12.27 |
| ATOM | 2066 | OD1 | ASN | 446 | 23.738 | 62.652 | 84.779 | 1.00 | 13.46 |
| ATOM | 2067 | ND2 | ASN | 446 | 22.993 | 62.421 | 86.900 | 1.00 | 10.41 |
| ATOM | 2070 | C | ASN | 446 | 22.821 | 66.786 | 84.545 | 1.00 | 10.86 |
| ATOM | 2071 | O | ASN | 446 | 21.933 | 66.890 | 83.708 | 1.00 | 10.92 |
| ATOM | 2072 | N | PRO | 447 | 23.140 | 67.806 | 85.381 | 1.00 | 10.33 |
| ATOM | 2073 | CD | PRO | 447 | 23.818 | 67.712 | 86.697 | 1.00 | 11.30 |
| ATOM | 2074 | CA | PRO | 447 | 22.481 | 69.119 | 85.247 | 1.00 | 10.42 |
| ATOM | 2075 | CB | PRO | 447 | 23.137 | 69.936 | 86.370 | 1.00 | 12.22 |
| ATOM | 2076 | CG | PRO | 447 | 23.247 | 68.905 | 87.456 | 1.00 | 12.86 |
| ATOM | 2077 | C | PRO | 447 | 22.742 | 69.739 | 83.869 | 1.00 | 8.80 |
| ATOM | 2078 | O | PRO | 447 | 21.859 | 70.383 | 83.293 | 1.00 | 9.82 |
| ATOM | 2079 | N | GLU | 448 | 23.869 | 69.603 | 83.363 | 1.00 | 8.54 |
| ATOM | 2081 | CA | GLU | 448 | 24.300 | 70.112 | 82.029 | 1.00 | 8.10 |
| ATOM | 2082 | CB | GLU | 448 | 25.784 | 69.950 | 81.719 | 1.00 | 9.79 |
| ATOM | 2083 | CG | GLU | 448 | 26.674 | 71.007 | 82.384 | 1.00 | 13.23 |
| ATOM | 2084 | CD | GLU | 448 | 28.125 | 70.748 | 82.148 | 1.00 | 12.90 |
| ATOM | 2085 | OE1 | GLU | 448 | 28.746 | 71.586 | 81.484 | 1.00 | 16.44 |
| ATOM | 2086 | OE2 | GLU | 448 | 28.656 | 69.679 | 82.576 | 1.00 | 14.02 |
| ATOM | 2087 | C | GLU | 448 | 23.501 | 69.384 | 80.958 | 1.00 | 7.54 |
| ATOM | 2088 | O | GLU | 448 | 23.021 | 69.984 | 79.999 | 1.00 | 6.85 |
| ATOM | 2089 | N | VAL | 449 | 23.327 | 68.075 | 81.151 | 1.00 | 6.85 |
| ATOM | 2091 | CA | VAL | 449 | 22.532 | 67.273 | 80.174 | 1.00 | 6.66 |
| ATOM | 2092 | CB | VAL | 449 | 22.555 | 65.758 | 80.561 | 1.00 | 4.93 |
| ATOM | 2093 | CG1 | VAL | 449 | 21.562 | 64.982 | 79.702 | 1.00 | 9.91 |
| ATOM | 2094 | CG2 | VAL | 449 | 23.934 | 65.187 | 80.366 | 1.00 | 5.99 |
| ATOM | 2095 | C | VAL | 449 | 21.078 | 67.790 | 80.114 | 1.00 | 5.68 |
| ATOM | 2096 | O | VAL | 449 | 20.548 | 68.105 | 79.043 | 1.00 | 4.79 |
| ATOM | 2097 | N | ILE | 450 | 20.499 | 68.001 | 81.292 | 0.60 | 2.00 |
| ATOM | 2099 | CA | ILE | 450 | 19.152 | 68.451 | 81.399 | 0.60 | 3.50 |
| ATOM | 2100 | CB | ILE | 450 | 18.737 | 68.594 | 82.909 | 0.60 | 4.11 |
| ATOM | 2101 | CG2 | ILE | 450 | 17.459 | 69.395 | 83.108 | 0.60 | 2.00 |
| ATOM | 2102 | CG1 | ILE | 450 | 18.574 | 67.171 | 83.431 | 0.60 | 2.00 |
| ATOM | 2103 | CD1 | ILE | 450 | 18.374 | 67.130 | 84.893 | 0.60 | 6.46 |
| ATOM | 2104 | C | ILE | 450 | 19.050 | 69.938 | 80.778 | 0.60 | 3.55 |
| ATOM | 2105 | O | ILE | 450 | 18.145 | 70.230 | 79.999 | 0.60 | 2.00 |
| ATOM | 2106 | N | GLN | 451 | 20.020 | 70.787 | 81.097 | 1.00 | 6.56 |
| ATOM | 2108 | CA | GLN | 451 | 20.075 | 72.158 | 80.571 | 1.00 | 9.94 |
| ATOM | 2109 | CB | GLN | 451 | 21.341 | 72.877 | 81.075 | 1.00 | 13.77 |
| ATOM | 2110 | CG | GLN | 451 | 21.464 | 73.121 | 82.565 | 1.00 | 20.58 |
| ATOM | 2111 | CD | GLN | 451 | 22.831 | 73.739 | 82.890 | 1.00 | 25.24 |
| ATOM | 2112 | OE1 | GLN | 451 | 23.347 | 74.549 | 82.087 | 1.00 | 26.69 |
| ATOM | 2113 | NE2 | GLN | 451 | 23.453 | 73.326 | 83.996 | 1.00 | 24.98 |
| ATOM | 2116 | C | GLN | 451 | 20.101 | 72.153 | 79.034 | 1.00 | 8.45 |
| ATOM | 2117 | O | GLN | 451 | 19.308 | 72.814 | 78.354 | 1.00 | 8.08 |
| ATOM | 2118 | N | ASN | 452 | 20.995 | 71.335 | 78.488 | 1.00 | 8.61 |
| ATOM | 2120 | CA | ASN | 452 | 21.107 | 71.178 | 77.038 | 1.00 | 9.38 |
| ATOM | 2121 | CB | ASN | 452 | 22.292 | 70.283 | 76.654 | 1.00 | 10.95 |
| ATOM | 2122 | CG | ASN | 452 | 23.612 | 71.048 | 76.615 | 1.00 | 13.96 |
| ATOM | 2123 | OD1 | ASN | 452 | 24.486 | 70.740 | 75.827 | 1.00 | 18.85 |
| ATOM | 2124 | ND2 | ASN | 452 | 23.768 | 71.995 | 77.491 | 1.00 | 16.27 |
| ATOM | 2127 | C | ASN | 452 | 19.856 | 70.626 | 76.392 | 1.00 | 9.06 |
| ATOM | 2128 | O | ASN | 452 | 19.417 | 71.113 | 75.327 | 1.00 | 8.73 |
| ATOM | 2129 | N | LEU | 453 | 19.287 | 69.588 | 76.984 | 1.00 | 8.56 |
| ATOM | 2131 | CA | LEU | 453 | 18.080 | 69.022 | 76.418 | 1.00 | 7.19 |
| ATOM | 2132 | CB | LEU | 453 | 17.612 | 67.814 | 77.228 | 1.00 | 7.76 |
| ATOM | 2133 | CG | LEU | 453 | 18.532 | 66.609 | 77.142 | 1.00 | 6.00 |
| ATOM | 2134 | CD1 | LEU | 453 | 17.995 | 65.564 | 78.071 | 1.00 | 9.63 |
| ATOM | 2135 | CD2 | LEU | 453 | 18.615 | 66.104 | 75.679 | 1.00 | 6.63 |
| ATOM | 2136 | C | LEU | 453 | 16.953 | 70.050 | 76.352 | 1.00 | 8.52 |
| ATOM | 2137 | O | LEU | 453 | 16.224 | 70.124 | 75.364 | 1.00 | 9.41 |
| ATOM | 2138 | N | GLU | 454 | 16.787 | 70.812 | 77.437 | 1.00 | 7.13 |
| ATOM | 2140 | CA | GLU | 454 | 15.724 | 71.802 | 77.494 | 1.00 | 9.15 |
| ATOM | 2141 | CB | GLU | 454 | 15.458 | 72.265 | 78.953 | 1.00 | 10.57 |
| ATOM | 2142 | CG | GLU | 454 | 14.804 | 71.090 | 79.746 | 1.00 | 14.54 |
| ATOM | 2143 | CD | GLU | 454 | 14.678 | 71.302 | 81.259 | 1.00 | 18.39 |
| ATOM | 2144 | OE1 | GLU | 454 | 15.251 | 72.277 | 81.791 | 1.00 | 19.85 |
| ATOM | 2144 | OE2 | GLU | 454 | 14.003 | 70.466 | 81.910 | 1.00 | 18.65 |
| ATOM | 2146 | C | GLU | 454 | 15.876 | 72.937 | 76.516 | 1.00 | 8.75 |
| ATOM | 2147 | O | GLU | 454 | 14.915 | 73.603 | 76.173 | 1.00 | 9.11 |
| ATOM | 2148 | N | ARG | 455 | 17.102 | 73.132 | 76.038 | 1.00 | 8.42 |
| ATOM | 2150 | CA | ARG | 455 | 17.381 | 74.148 | 75.013 | 1.00 | 9.20 |
| ATOM | 2151 | CB | ARG | 455 | 18.884 | 74.503 | 74.997 | 1.00 | 10.05 |

TABLE 4-continued

Coordinates of Lck bound with staurosporine (soaked)

| | Atom Type | Res | # | X | Y | Z | Occ | B |
|---|---|---|---|---|---|---|---|---|
| ATOM | 2152 | CG | ARG | 455 | 19.347 | 75.201 | 76.209 | 1.00 | 12.72 |
| ATOM | 2153 | CD | ARG | 455 | 20.794 | 75.621 | 76.012 | 1.00 | 13.32 |
| ATOM | 2154 | NE | ARG | 455 | 20.862 | 76.749 | 75.073 | 1.00 | 12.24 |
| ATOM | 2156 | CZ | ARG | 455 | 21.999 | 77.383 | 74.764 | 1.00 | 11.80 |
| ATOM | 2157 | NH1 | ARG | 455 | 23.161 | 76.974 | 75.279 | 1.00 | 6.86 |
| ATOM | 2160 | NH2 | ARG | 455 | 21.932 | 78.547 | 74.123 | 1.00 | 7.34 |
| ATOM | 2163 | C | ARG | 455 | 17.062 | 73.632 | 73.619 | 1.00 | 9.77 |
| ATOM | 2164 | O | ARG | 455 | 17.047 | 74.409 | 72.682 | 1.00 | 9.32 |
| ATOM | 2165 | N | GLY | 456 | 16.814 | 72.318 | 73.483 | 1.00 | 8.29 |
| ATOM | 2167 | CA | GLY | 456 | 16.551 | 71.743 | 72.161 | 1.00 | 7.45 |
| ATOM | 2168 | C | GLY | 456 | 17.785 | 70.997 | 71.638 | 1.00 | 5.78 |
| ATOM | 2169 | O | GLY | 456 | 17.776 | 70.442 | 70.546 | 1.00 | 4.51 |
| ATOM | 2170 | N | TYR | 457 | 18.884 | 71.066 | 72.356 | 1.00 | 5.91 |
| ATOM | 2172 | CA | TYR | 457 | 20.077 | 70.333 | 71.918 | 1.00 | 5.76 |
| ATOM | 2173 | CB | TYR | 457 | 21.320 | 70.786 | 72.695 | 1.00 | 5.55 |
| ATOM | 2174 | CG | TYR | 457 | 21.816 | 72.215 | 72.470 | 1.00 | 4.70 |
| ATOM | 2175 | CD1 | TYR | 457 | 21.368 | 72.999 | 71.395 | 1.00 | 4.74 |
| ATOM | 2176 | CE1 | TYR | 457 | 21.910 | 74.291 | 71.166 | 1.00 | 5.80 |
| ATOM | 2177 | CD2 | TYR | 457 | 22.798 | 72.744 | 73.30 | 1.00 | 9.15 |
| ATOM | 2178 | CE2 | TYR | 457 | 23.348 | 73.99 | 73.075 | 1.00 | 7.40 |
| ATOM | 2179 | CZ | TYR | 457 | 22.905 | 74.770 | 72.012 | 1.00 | 6.58 |
| ATOM | 2180 | OH | TYR | 457 | 23.498 | 76.015 | 71.849 | 1.00 | 6.87 |
| ATOM | 2182 | C | TYR | 457 | 19.914 | 68.838 | 72.234 | 1.00 | 5.84 |
| ATOM | 2183 | O | TYR | 457 | 19.059 | 68.474 | 73.058 | 1.00 | 2.95 |
| ATOM | 2184 | N | ARG | 458 | 20.689 | 67.996 | 71.542 | 1.00 | 7.21 |
| ATOM | 2186 | CA | ARG | 458 | 20.741 | 66.581 | 71.849 | 1.00 | 5.55 |
| ATOM | 2187 | CB | ARG | 458 | 20.055 | 65.757 | 70.738 | 1.00 | 5.01 |
| ATOM | 2188 | CG | ARG | 458 | 18.511 | 65.956 | 70.669 | 1.00 | 3.95 |
| ATOM | 2189 | CD | ARG | 458 | 17.803 | 65.576 | 71.993 | 1.00 | 4.69 |
| ATOM | 2190 | NE | ARG | 458 | 16.318 | 65.689 | 71.959 | 1.00 | 4.48 |
| ATOM | 2192 | CZ | ARG | 458 | 15.581 | 66.711 | 72.411 | 1.00 | 8.02 |
| ATOM | 2193 | NH1 | ARG | 458 | 16.148 | 67.790 | 72.966 | 1.00 | 9.83 |
| ATOM | 2196 | NH2 | ARG | 458 | 14.256 | 66.681 | 72.293 | 1.00 | 6.51 |
| ATOM | 2199 | C | ARG | 458 | 22.222 | 66.237 | 71.976 | 1.00 | 6.38 |
| ATOM | 2200 | O | ARG | 458 | 23.090 | 67.126 | 71.790 | 1.00 | 5.47 |
| ATOM | 2201 | N | MET | 459 | 22.557 | 64.988 | 72.283 | 1.00 | 3.53 |
| ATOM | 2203 | CA | MET | 459 | 23.989 | 64.633 | 72.379 | 1.00 | 4.64 |
| ATOM | 2204 | CB | MET | 459 | 24.168 | 63.117 | 72.616 | 1.00 | 4.43 |
| ATOM | 2205 | CG | MET | 459 | 25.529 | 62.769 | 73.161 | 1.00 | 5.73 |
| ATOM | 2206 | SD | MET | 459 | 25.675 | 60.947 | 73.371 | 1.00 | 8.91 |
| ATOM | 2207 | CE | MET | 459 | 24.195 | 60.627 | 74.333 | 1.00 | 8.80 |
| ATOM | 2208 | C | MET | 459 | 24.762 | 64.997 | 71.127 | 1.00 | 4.68 |
| ATOM | 2209 | O | MET | 459 | 24.285 | 64.806 | 70.001 | 1.00 | 4.18 |
| ATOM | 2210 | N | VAL | 460 | 25.947 | 65.555 | 71.326 | 1.00 | 3.91 |
| ATOM | 2212 | CA | VAL | 460 | 26.849 | 65.922 | 70.239 | 1.00 | 6.53 |
| ATOM | 2213 | CB | VAL | 460 | 28.194 | 66.479 | 70.848 | 1.00 | 7.54 |
| ATOM | 2214 | CG1 | VAL | 460 | 29.230 | 66.668 | 69.784 | 1.00 | 8.61 |
| ATOM | 2215 | CG2 | VAL | 460 | 27.953 | 67.745 | 71.699 | 1.00 | 7.16 |
| ATOM | 2216 | C | VAL | 460 | 27.220 | 64.635 | 69.425 | 1.00 | 6.37 |
| ATOM | 2217 | O | VAL | 460 | 27.348 | 63.597 | 69.993 | 1.00 | 6.28 |
| ATOM | 2218 | N | ARG | 461 | 27.293 | 64.705 | 68.089 | 1.00 | 5.72 |
| ATOM | 2220 | CA | ARG | 461 | 27.713 | 63.538 | 67.294 | 1.00 | 8.25 |
| ATOM | 2221 | CB | ARG | 461 | 28.107 | 63.962 | 65.877 | 1.00 | 8.12 |
| ATOM | 2222 | CG | ARG | 461 | 26.973 | 64.465 | 65.084 | 1.00 | 7.53 |
| ATOM | 2223 | CD | ARG | 461 | 27.462 | 65.018 | 63.756 | 1.00 | 10.16 |
| ATOM | 2224 | NE | ARG | 461 | 26.283 | 65.256 | 62.928 | 1.00 | 7.37 |
| ATOM | 2226 | CZ | ARG | 461 | 25.641 | 66.421 | 62.865 | 1.00 | 8.20 |
| ATOM | 2227 | NH1 | ARG | 461 | 26.053 | 67.488 | 63.601 | 1.00 | 7.00 |
| ATOM | 2230 | NH2 | ARG | 461 | 24.632 | 66.538 | 62.011 | 1.00 | 3.52 |
| ATOM | 2233 | C | ARG | 461 | 28.937 | 62.826 | 67.834 | 1.00 | 9.83 |
| ATOM | 2234 | O | ARG | 461 | 29.988 | 63.453 | 68.008 | 1.00 | 8.35 |
| ATOM | 2235 | N | PRO | 462 | 28.823 | 61.513 | 68.167 | 1.00 | 10.04 |
| ATOM | 2236 | CD | PRO | 462 | 27.623 | 60.680 | 68.322 | 1.00 | 8.96 |
| ATOM | 2237 | CA | PRO | 462 | 30.016 | 60.825 | 68.694 | 1.00 | 11.37 |
| ATOM | 2238 | CB | PRO | 462 | 29.494 | 59.402 | 69.016 | 1.00 | 7.39 |
| ATOM | 2239 | CG | PRO | 462 | 28.069 | 59.631 | 69.369 | 1.00 | 8.81 |
| ATOM | 2240 | C | PRO | 462 | 31.052 | 60.732 | 67.606 | 1.00 | 12.74 |
| ATOM | 2241 | O | PRO | 462 | 30.740 | 60.793 | 66.416 | 1.00 | 10.85 |
| ATOM | 2242 | N | ASP | 463 | 32.300 | 60.581 | 68.029 | 1.00 | 17.47 |
| ATOM | 2244 | CA | ASP | 463 | 33.402 | 60.432 | 67.105 | 1.00 | 20.96 |
| ATOM | 2245 | CB | ASP | 463 | 34.736 | 60.286 | 67.870 | 1.00 | 25.18 |
| ATOM | 2246 | CG | ASP | 463 | 35.087 | 61.512 | 68.707 | 1.00 | 28.15 |
| ATOM | 2247 | OD1 | ASP | 463 | 34.495 | 62.597 | 68.500 | 1.00 | 29.78 |
| ATOM | 2248 | OD2 | ASP | 463 | 35.975 | 61.388 | 69.582 | 1.00 | 30.25 |

TABLE 4-continued

Coordinates of Lck bound with staurosporine (soaked)

| | Atom Type | Res | # | X | Y | Z | Occ | B |
|---|---|---|---|---|---|---|---|---|
| ATOM | 2249 | C | ASP | 463 | 33.178 | 59.198 | 66.262 | 1.00 | 21.24 |
| ATOM | 2250 | O | ASP | 463 | 32.636 | 58.191 | 66.749 | 1.00 | 21.61 |
| ATOM | 2251 | N | ASN | 464 | 33.463 | 59.319 | 64.973 | 1.00 | 22.32 |
| ATOM | 2253 | CA | ASN | 464 | 33.301 | 58.206 | 64.051 | 1.00 | 23.87 |
| ATOM | 2254 | CB | ASN | 464 | 34.451 | 57.226 | 64.261 | 1.00 | 26.43 |
| ATOM | 2255 | CG | ASN | 464 | 35.782 | 57.834 | 63.850 | 1.00 | 28.16 |
| ATOM | 2256 | OD1 | ASN | 464 | 36.029 | 58.025 | 62.660 | 1.00 | 32.70 |
| ATOM | 2257 | ND2 | ASN | 464 | 36.591 | 58.236 | 64.820 | 1.00 | 29.64 |
| ATOM | 2260 | C | ASN | 464 | 31.918 | 57.522 | 64.034 | 1.00 | 22.09 |
| ATOM | 2261 | O | ASN | 464 | 31.774 | 56.284 | 63.968 | 1.00 | 22.34 |
| ATOM | 2262 | N | CYS | 465 | 30.885 | 58.347 | 64.139 | 1.00 | 18.35 |
| ATOM | 2264 | CA | CYS | 465 | 29.505 | 57.849 | 64.079 | 1.00 | 13.90 |
| ATOM | 2265 | CB | CYS | 465 | 28.656 | 58.478 | 65.196 | 1.00 | 12.88 |
| ATOM | 2266 | SG | CYS | 465 | 26.904 | 58.015 | 65.072 | 1.00 | 13.96 |
| ATOM | 2267 | C | CYS | 465 | 28.941 | 58.185 | 62.702 | 1.00 | 14.12 |
| ATOM | 2268 | O | CYS | 465 | 29.052 | 59.332 | 62.251 | 1.00 | 13.81 |
| ATOM | 2269 | N | PRO | 466 | 28.501 | 57.172 | 61.945 | 1.00 | 12.80 |
| ATOM | 2270 | CD | PRO | 466 | 28.509 | 55.743 | 62.333 | 1.00 | 13.81 |
| ATOM | 2271 | CA | PRO | 466 | 27.930 | 57.356 | 60.609 | 1.00 | 11.16 |
| ATOM | 2272 | CB | PRO | 466 | 27.467 | 55.945 | 60.245 | 1.00 | 12.22 |
| ATOM | 2273 | CG | PRO | 466 | 28.424 | 55.059 | 61.038 | 1.00 | 11.55 |
| ATOM | 2274 | C | PRO | 466 | 26.735 | 58.304 | 60.781 | 1.00 | 8.89 |
| ATOM | 2275 | O | PRO | 466 | 25.944 | 58.167 | 61.759 | 1.00 | 5.97 |
| ATOM | 2276 | N | GLU | 467 | 26.651 | 59.303 | 59.900 | 1.00 | 5.38 |
| ATOM | 2278 | CA | GLU | 467 | 25.556 | 60.286 | 60.003 | 1.00 | 5.74 |
| ATOM | 2279 | CB | GLU | 467 | 25.705 | 61.399 | 58.937 | 1.00 | 5.77 |
| ATOM | 2280 | CG | GLU | 467 | 24.667 | 62.547 | 59.108 | 1.00 | 7.30 |
| ATOM | 2281 | CD | GLU | 467 | 24.772 | 63.304 | 60.430 | 1.00 | 8.60 |
| ATOM | 2282 | OE1 | GLU | 467 | 23.866 | 64.111 | 60.736 | 1.00 | 12.73 |
| ATOM | 2283 | OE2 | GLU | 467 | 25.779 | 63.148 | 61.157 | 1.00 | 8.79 |
| ATOM | 2284 | C | GLU | 467 | 24.172 | 59.647 | 59.928 | 1.00 | 3.94 |
| ATOM | 2285 | O | GLU | 467 | 23.238 | 60.090 | 60.610 | 1.00 | 2.54 |
| ATOM | 2286 | N | GLU | 468 | 24.018 | 58.578 | 59.144 | 0.51 | 2.00 |
| ATOM | 2288 | CA | GLU | 468 | 22.777 | 56.699 | 58.155 | 0.51 | 2.00 |
| ATOM | 2289 | CB | GLU | 468 | 22.728 | 57.056 | 56.720 | 0.51 | 2.00 |
| ATOM | 2290 | CG | GLU | 468 | 23.102 | 55.891 | 55.877 | 0.51 | 4.73 |
| ATOM | 2291 | CD | GLU | 468 | 24.312 | 55.744 | 55.699 | 0.51 | 6.19 |
| ATOM | 2292 | OE1 | GLU | 468 | 22.205 | 55.192 | 55.389 | 0.51 | 2.79 |
| ATOM | 2293 | OE2 | GLU | 468 | 22.274 | 57.412 | 60.486 | 0.51 | 2.00 |
| ATOM | 2294 | C | GLU | 468 | 21.133 | 57.557 | 60.870 | 0.51 | 2.00 |
| ATOM | 2295 | O | GLU | 468 | 21.133 | 57.557 | 60.870 | 0.51 | 2.00 |
| ATOM | 2296 | N | LEU | 469 | 23.211 | 56.804 | 61.206 | 1.00 | 2.68 |
| ATOM | 2298 | CA | LEU | 469 | 22.926 | 56.312 | 62.561 | 1.00 | 3.75 |
| ATOM | 2299 | CB | LEU | 469 | 24.119 | 55.501 | 63.087 | 1.00 | 5.21 |
| ATOM | 2300 | CG | LEU | 469 | 23.928 | 54.801 | 64.441 | 1.00 | 4.76 |
| ATOM | 2301 | CD1 | LEU | 469 | 22.855 | 53.731 | 64.304 | 1.00 | 6.81 |
| ATOM | 2302 | CD2 | LEU | 469 | 25.248 | 54.097 | 64.824 | 1.00 | 5.46 |
| ATOM | 2303 | C | LEU | 469 | 22.636 | 57.484 | 63.504 | 1.00 | 3.44 |
| ATOM | 2304 | O | LEU | 469 | 21.727 | 57.436 | 64.356 | 1.00 | 5.45 |
| ATOM | 2305 | N | TYR | 470 | 23.416 | 58.563 | 63.369 | 1.00 | 5.07 |
| ATOM | 2307 | CA | TYR | 470 | 23.161 | 59.732 | 64.240 | 1.00 | 4.26 |
| ATOM | 2308 | CB | TYR | 470 | 24.186 | 60.877 | 63.983 | 1.00 | 4.94 |
| ATOM | 2309 | CG | TYR | 470 | 24.024 | 62.070 | 64.944 | 1.00 | 3.71 |
| ATOM | 2310 | CD1 | TYR | 470 | 24.180 | 61.905 | 66.310 | 1.00 | 5.02 |
| ATOM | 2311 | CE1 | TYR | 470 | 24.036 | 62.998 | 67.192 | 1.00 | 5.96 |
| ATOM | 2312 | CD2 | TYR | 470 | 23.716 | 63.357 | 64.454 | 1.00 | 3.81 |
| ATOM | 2313 | CE2 | TYR | 470 | 23.588 | 64.425 | 65.296 | 1.00 | 5.55 |
| ATOM | 2314 | CZ | TYR | 470 | 23.746 | 64.245 | 66.668 | 1.00 | 6.06 |
| ATOM | 2315 | OH | TYR | 470 | 23.642 | 65.311 | 67.523 | 1.00 | 9.89 |
| ATOM | 2317 | C | TYR | 470 | 21.744 | 60.251 | 64.004 | 1.00 | 4.76 |
| ATOM | 2318 | O | TYR | 470 | 21.031 | 60.618 | 64.942 | 1.00 | 6.27 |
| ATOM | 2319 | N | GLN | 471 | 21.310 | 60.291 | 62.739 | 1.00 | 4.89 |
| ATOM | 2321 | CA | GLN | 471 | 19.956 | 60.783 | 62.482 | 1.00 | 4.63 |
| ATOM | 2322 | CB | GLN | 471 | 19.774 | 61.108 | 61.000 | 1.00 | 4.81 |
| ATOM | 2323 | CG | GLN | 471 | 20.553 | 62.364 | 50.572 | 1.00 | 5.80 |
| ATOM | 2324 | CD | GLN | 471 | 20.172 | 63.619 | 61.382 | 1.00 | 8.94 |
| ATOM | 2325 | OE1 | GLN | 471 | 18.992 | 63.860 | 61.704 | 1.00 | 6.43 |
| ATOM | 2326 | NE2 | GLN | 471 | 21.189 | 64.395 | 61.770 | 1.00 | 7.01 |
| ATOM | 2329 | C | GLN | 471 | 18.877 | 59.834 | 63.002 | 1.00 | 5.92 |
| ATOM | 2330 | O | GLN | 471 | 17.741 | 60.243 | 63.289 | 1.00 | 5.03 |
| ATOM | 2331 | N | LEU | 472 | 19.203 | 58.537 | 63.023 | 1.00 | 4.53 |
| ATOM | 2333 | CA | LEU | 472 | 18.277 | 57.547 | 63.597 | 1.00 | 5.41 |
| ATOM | 2334 | CB | LEU | 472 | 18.793 | 56.135 | 63.322 | 1.00 | 5.33 |
| ATOM | 2335 | CG | LEU | 472 | 17.748 | 55.057 | 63.605 | 1.00 | 6.16 |

TABLE 4-continued

Coordinates of Lck bound with staurosporine (soaked)

| | | Atom Type | Res | # | X | Y | Z | Occ | B |
|---|---|---|---|---|---|---|---|---|---|
| ATOM | 2336 | CD1 | LEU | 472 | 16.470 | 55.351 | 62.768 | 1.00 | 8.74 |
| ATOM | 2337 | CD2 | LEU | 472 | 18.332 | 53.678 | 63.277 | 1.00 | 5.70 |
| ATOM | 2338 | C | LEU | 472 | 18.160 | 57.793 | 65.129 | 1.00 | 4.27 |
| ATOM | 2339 | O | LEU | 472 | 17.074 | 57.806 | 65.685 | 1.00 | 6.39 |
| ATOM | 2340 | N | MET | 473 | 19.293 | 58.078 | 65.774 | 1.00 | 6.34 |
| ATOM | 2342 | CA | MET | 473 | 19.332 | 58.428 | 67.193 | 1.00 | 6.70 |
| ATOM | 2343 | CB | MET | 473 | 20.756 | 58.809 | 67.612 | 1.00 | 6.82 |
| ATOM | 2344 | CG | MET | 473 | 21.759 | 67.673 | 67.661 | 1.00 | 9.25 |
| ATOM | 2345 | SD | MET | 473 | 23.425 | 58.348 | 67.650 | 1.00 | 6.04 |
| ATOM | 2346 | CE | MET | 473 | 24.397 | 56.872 | 67.411 | 1.00 | 7.69 |
| ATOM | 2347 | C | MET | 473 | 18.452 | 59.648 | 67.459 | 1.00 | 4.98 |
| ATOM | 2348 | O | MET | 473 | 17.673 | 59.676 | 68.417 | 1.00 | 5.18 |
| ATOM | 2349 | N | ARG | 474 | 18.588 | 60.666 | 66.603 | 1.00 | 5.63 |
| ATOM | 2351 | CA | ARG | 474 | 17.775 | 61.881 | 66.772 | 1.00 | 6.92 |
| ATOM | 2352 | CB | ARG | 474 | 18.084 | 62.926 | 65.676 | 1.00 | 9.55 |
| ATOM | 2353 | CG | ARG | 474 | 19.539 | 63.314 | 65.490 | 1.00 | 11.83 |
| ATOM | 2354 | CD | ARG | 474 | 20.051 | 64.228 | 66.556 | 1.00 | 18.94 |
| ATOM | 2355 | NE | ARG | 474 | 19.308 | 65.498 | 66.637 | 1.00 | 20.37 |
| ATOM | 2357 | CZ | ARG | 474 | 19.840 | 66.644 | 67.043 | 1.00 | 17.59 |
| ATOM | 2358 | NH1 | ARG | 474 | 21.145 | 66.711 | 67.354 | 1.00 | 12.90 |
| ATOM | 2361 | NH2 | ARG | 474 | 19.018 | 67.646 | 67.381 | 1.00 | 17.79 |
| ATOM | 2364 | C | ARG | 474 | 16.280 | 61.538 | 66.722 | 1.00 | 6.79 |
| ATOM | 2365 | O | ARG | 474 | 15.492 | 62.135 | 67.418 | 1.00 | 5.98 |
| ATOM | 2366 | N | LEU | 475 | 15.888 | 60.572 | 65.882 | 1.00 | 4.98 |
| ATOM | 2368 | CA | LEU | 475 | 14.465 | 60.178 | 65.878 | 1.00 | 7.49 |
| ATOM | 2369 | CB | LEU | 475 | 14.167 | 59.090 | 64.817 | 1.00 | 8.16 |
| ATOM | 2370 | CG | LEU | 475 | 14.426 | 59.426 | 63.359 | 1.00 | 8.88 |
| ATOM | 2371 | CD1 | LEU | 475 | 13.760 | 58.322 | 62.500 | 1.00 | 10.43 |
| ATOM | 2372 | CD2 | LEU | 475 | 13.781 | 60.775 | 63.021 | 1.00 | 11.32 |
| ATOM | 2373 | C | LEU | 475 | 14.089 | 59.644 | 67.241 | 1.00 | 4.96 |
| ATOM | 2374 | O | LEU | 475 | 13.041 | 59.958 | 67.784 | 1.00 | 6.19 |
| ATOM | 2375 | N | CYS | 476 | 14.971 | 58.818 | 67.822 | 1.00 | 5.35 |
| ATOM | 2377 | CA | CYS | 476 | 14.706 | 58.295 | 69.168 | 1.00 | 6.09 |
| ATOM | 2378 | CB | CYS | 476 | 15.836 | 57.340 | 69.601 | 1.00 | 4.98 |
| ATOM | 2379 | SG | CYS | 476 | 15.937 | 55.886 | 68.514 | 1.00 | 7.06 |
| ATOM | 2380 | C | CYS | 476 | 14.576 | 59.387 | 70.217 | 1.00 | 5.88 |
| ATOM | 2381 | O | CYS | 476 | 13.911 | 59.207 | 71.247 | 1.00 | 4.37 |
| ATOM | 2382 | N | TRP | 477 | 15.169 | 60.555 | 69.925 | 1.00 | 6.18 |
| ATOM | 2384 | CA | TRP | 477 | 15.140 | 61.635 | 70.878 | 1.00 | 7.04 |
| ATOM | 2385 | CB | TRP | 477 | 16.555 | 62.215 | 71.094 | 1.00 | 5.80 |
| ATOM | 2386 | CG | TRP | 477 | 17.609 | 61.203 | 71.440 | 1.00 | 6.60 |
| ATOM | 2387 | CD2 | TRP | 477 | 18.978 | 61.225 | 71.020 | 1.00 | 6.30 |
| ATOM | 2388 | CE2 | TRP | 477 | 19.611 | 60.098 | 71.597 | 1.00 | 5.65 |
| ATOM | 2389 | CE3 | TRP | 477 | 19.732 | 62.080 | 70.200 | 1.00 | 4.69 |
| ATOM | 2390 | CD1 | TRP | 477 | 17.470 | 60.096 | 72.238 | 1.00 | 4.40 |
| ATOM | 2391 | NE1 | TRP | 477 | 18.673 | 59.442 | 72.341 | 1.00 | 6.25 |
| ATOM | 2393 | CZ2 | TRP | 477 | 20.972 | 59.816 | 71.411 | 1.00 | 7.14 |
| ATOM | 2394 | CZ3 | TRP | 477 | 21.096 | 61.802 | 70.012 | 1.00 | 6.66 |
| ATOM | 2395 | CH2 | TRP | 477 | 21.690 | 60.666 | 70.613 | 1.00 | 5.75 |
| ATOM | 2396 | C | TRP | 477 | 14.165 | 62.757 | 70.546 | 1.00 | 8.41 |
| ATOM | 2397 | O | TRP | 477 | 14.359 | 63.894 | 70.986 | 1.00 | 7.82 |
| ATOM | 2398 | N | LYS | 478 | 13.120 | 62.452 | 69.775 | 1.00 | 10.81 |
| ATOM | 2400 | CA | LYS | 478 | 12.105 | 63.471 | 69.495 | 1.00 | 11.81 |
| ATOM | 2401 | CB | LYS | 478 | 11.058 | 62.957 | 68.486 | 1.00 | 13.76 |
| ATOM | 2402 | CG | LYS | 478 | 11.632 | 63.105 | 67.055 | 1.00 | 15.00 |
| ATOM | 2403 | CD | LYS | 478 | 10.682 | 62.928 | 65.943 | 1.00 | 20.43 |
| ATOM | 2404 | CE | LYS | 478 | 11.383 | 63.220 | 64.623 | 1.00 | 19.86 |
| ATOM | 2405 | NZ | LYS | 478 | 11.498 | 64.682 | 64.302 | 1.00 | 24.89 |
| ATOM | 2409 | C | LYS | 478 | 11.483 | 63.966 | 70.785 | 1.00 | 10.75 |
| ATOM | 2410 | O | LYS | 478 | 11.411 | 63.245 | 71.774 | 1.00 | 10.57 |
| ATOM | 2411 | N | GLU | 479 | 11.136 | 65.245 | 70.830 | 1.00 | 11.76 |
| ATOM | 2413 | CA | GLU | 479 | 10.545 | 65.821 | 72.044 | 1.00 | 13.93 |
| ATOM | 2414 | CB | GLU | 479 | 10.230 | 67.310 | 71.834 | 1.00 | 16.32 |
| ATOM | 2415 | CG | GLU | 479 | 9.745 | 67.956 | 73.108 | 1.00 | 22.00 |
| ATOM | 2416 | CD | GLU | 479 | 10.869 | 68.064 | 74.118 | 1.00 | 26.69 |
| ATOM | 2417 | OE1 | GLU | 479 | 12.055 | 68.130 | 73.685 | 1.00 | 28.93 |
| ATOM | 2418 | OE2 | GLU | 479 | 10.589 | 68.082 | 75.338 | 1.00 | 29.48 |
| ATOM | 2419 | C | GLU | 479 | 9.272 | 65.117 | 72.511 | 1.00 | 12.78 |
| ATOM | 2420 | O | GLU | 479 | 9.128 | 64.715 | 73.663 | 1.00 | 11.58 |
| ATOM | 2421 | N | ARG | 480 | 8.306 | 65.011 | 71.606 | 1.00 | 13.56 |
| ATOM | 2423 | CA | ARG | 480 | 7.068 | 64.316 | 71.953 | 1.00 | 14.11 |
| ATOM | 2424 | CB | ARG | 480 | 5.920 | 64.768 | 71.023 | 1.00 | 16.76 |
| ATOM | 2425 | CG | ARG | 480 | 5.682 | 66.296 | 71.022 | 1.00 | 20.08 |
| ATOM | 2426 | CD | ARG | 480 | 4.356 | 66.616 | 70.378 | 1.00 | 25.32 |

TABLE 4-continued

Coordinates of Lck bound with staurosporine (soaked)

| | | Atom Type | Res | # | X | Y | Z | Occ | B |
|---|---|---|---|---|---|---|---|---|---|
| ATOM | 2427 | NE | ARG | 480 | 4.264 | 65.997 | 69.049 | 1.00 | 29.79 |
| ATOM | 2429 | CZ | ARG | 480 | 3.132 | 65.818 | 68.372 | 1.00 | 30.49 |
| ATOM | 2430 | NH1 | ARG | 480 | 1.981 | 66.214 | 68.906 | 1.00 | 33.45 |
| ATOM | 2433 | NH2 | ARG | 480 | 3.155 | 65.294 | 67.145 | 1.00 | 29.91 |
| ATOM | 2436 | C | ARG | 480 | 7.226 | 62.786 | 71.838 | 1.00 | 11.61 |
| ATOM | 2437 | O | ARG | 480 | 7.665 | 62.280 | 70.813 | 1.00 | 9.25 |
| ATOM | 2438 | N | PRO | 481 | 6.879 | 62.051 | 72.902 | 1.00 | 11.62 |
| ATOM | 2439 | CD | PRO | 481 | 6.473 | 62.568 | 74.214 | 1.00 | 11.47 |
| ATOM | 2440 | CA | PRO | 481 | 6.972 | 60.581 | 72.911 | 1.00 | 11.78 |
| ATOM | 2441 | CB | PRO | 481 | 6.221 | 60.207 | 74.172 | 1.00 | 11.23 |
| ATOM | 2442 | CG | PRO | 481 | 6.615 | 61.347 | 75.110 | 1.00 | 14.23 |
| ATOM | 2443 | C | PRO | 481 | 6.337 | 59.969 | 71.667 | 1.00 | 12.23 |
| ATOM | 2444 | O | PRO | 481 | 6.947 | 59.124 | 71.007 | 1.00 | 11.31 |
| ATOM | 2445 | N | GLU | 482 | 5.175 | 60.488 | 71.269 | 1.00 | 12.13 |
| ATOM | 2447 | CA | GLU | 482 | 4.447 | 59.979 | 70.091 | 1.00 | 12.86 |
| ATOM | 2448 | CB | GLU | 482 | 3.013 | 60.577 | 70.013 | 1.00 | 15.98 |
| ATOM | 2449 | CG | GLU | 482 | 2.982 | 62.087 | 70.078 | 1.00 | 20.93 |
| ATOM | 2450 | CD | GLU | 482 | 2.561 | 62.602 | 71.463 | 1.00 | 25.76 |
| ATOM | 2451 | OE1 | GLU | 482 | 1.399 | 63.103 | 71.539 | 1.00 | 30.37 |
| ATOM | 2452 | OE2 | GLU | 482 | 3.341 | 62.508 | 72.459 | 1.00 | 19.57 |
| ATOM | 2453 | C | GLU | 482 | 5.142 | 60.162 | 68.762 | 1.00 | 13.01 |
| ATOM | 2454 | O | GLU | 482 | 4.803 | 59.494 | 67.785 | 1.00 | 12.54 |
| ATOM | 2455 | N | ASP | 483 | 6.112 | 61.079 | 68.700 | 1.00 | 13.69 |
| ATOM | 2457 | CA | ASP | 483 | 6.858 | 61.286 | 67.463 | 1.00 | 11.91 |
| ATOM | 2458 | CB | ASP | 483 | 7.359 | 62.742 | 67.336 | 1.00 | 12.80 |
| ATOM | 2459 | CG | ASP | 483 | 6.242 | 63.738 | 67.122 | 1.00 | 16.80 |
| ATOM | 2460 | OD1 | ASP | 483 | 5.167 | 63.357 | 66.598 | 1.00 | 14.10 |
| ATOM | 2461 | OD2 | ASP | 483 | 6.434 | 64.909 | 67.523 | 1.00 | 18.37 |
| ATOM | 2462 | C | ASP | 483 | 8.040 | 60.333 | 67.313 | 1.00 | 9.87 |
| ATOM | 2463 | O | ASP | 483 | 8.668 | 60.268 | 66.246 | 1.00 | 11.58 |
| ATOM | 2464 | N | ARG | 484 | 8.393 | 59.643 | 68.404 | 1.00 | 8.94 |
| ATOM | 2466 | CA | ARG | 484 | 9.491 | 58.681 | 68.355 | 1.00 | 6.66 |
| ATOM | 2467 | CB | ARG | 484 | 9.964 | 58.350 | 69.776 | 1.00 | 7.83 |
| ATOM | 2468 | CG | ARG | 484 | 10.257 | 59.553 | 70.614 | 1.00 | 7.05 |
| ATOM | 2469 | CD | ARG | 484 | 10.649 | 59.211 | 72.052 | 1.00 | 6.98 |
| ATOM | 2470 | NE | ARG | 484 | 10.804 | 60.448 | 72.789 | 1.00 | 4.90 |
| ATOM | 2472 | CZ | ARG | 484 | 10.601 | 60.560 | 74.100 | 1.00 | 7.72 |
| ATOM | 2473 | NH1 | ARG | 484 | 10.308 | 59.488 | 74.824 | 1.00 | 5.26 |
| ATOM | 2476 | NH2 | ARG | 484 | 10.480 | 61.778 | 74.664 | 1.00 | 7.38 |
| ATOM | 2479 | C | ARG | 484 | 9.012 | 57.428 | 67.601 | 1.00 | 8.43 |
| ATOM | 2480 | O | ARG | 484 | 7.859 | 57.041 | 67.691 | 1.00 | 7.27 |
| ATOM | 2481 | N | PRO | 485 | 9.904 | 56.794 | 66.826 | 1.00 | 7.08 |
| ATOM | 2482 | CD | PRO | 485 | 11.361 | 57.012 | 66.755 | 1.00 | 5.37 |
| ATOM | 2483 | CA | PRO | 485 | 9.486 | 55.624 | 66.074 | 1.00 | 8.48 |
| ATOM | 2484 | CB | PRO | 485 | 10.647 | 55.404 | 65.103 | 1.00 | 6.52 |
| ATOM | 2485 | CG | PRO | 485 | 11.831 | 55.885 | 65.885 | 1.00 | 8.65 |
| ATOM | 2486 | C | PRO | 485 | 9.252 | 54.418 | 66.954 | 1.00 | 7.59 |
| ATOM | 2487 | O | PRO | 485 | 9.514 | 54.440 | 68.161 | 1.00 | 4.04 |
| ATOM | 2488 | N | THR | 486 | 8.685 | 53.379 | 66.341 | 1.00 | 6.13 |
| ATOM | 2490 | CA | THR | 486 | 8.509 | 52.125 | 67.031 | 1.00 | 6.49 |
| ATOM | 2491 | CB | THR | 486 | 7.424 | 51.227 | 66.336 | 1.00 | 7.20 |
| ATOM | 2492 | OG1 | THR | 486 | 7.836 | 50.985 | 64.982 | 1.00 | 5.76 |
| ATOM | 2494 | CG2 | THR | 486 | 6.033 | 51.934 | 66.341 | 1.00 | 9.07 |
| ATOM | 2495 | C | THR | 486 | 9.796 | 51.346 | 66.939 | 1.00 | 6.99 |
| ATOM | 2496 | O | THR | 486 | 10.661 | 51.612 | 66.071 | 1.00 | 5.95 |
| ATOM | 2497 | N | PHE | 487 | 9.895 | 50.303 | 67.768 | 1.00 | 7.41 |
| ATOM | 2499 | CA | PHE | 487 | 11.051 | 49.435 | 67.728 | 1.00 | 7.05 |
| ATOM | 2500 | CB | PHE | 487 | 11.099 | 48.583 | 69.028 | 1.00 | 5.13 |
| ATOM | 2501 | CG | PHE | 487 | 11.732 | 49.287 | 70.144 | 1.00 | 2.90 |
| ATOM | 2502 | CD1 | PHE | 487 | 13.112 | 49.564 | 70.101 | 1.00 | 3.27 |
| ATOM | 2503 | CD2 | PHE | 487 | 10.990 | 49.718 | 71.250 | 1.00 | 2.00 |
| ATOM | 2504 | CE1 | PHE | 487 | 13.721 | 50.242 | 71.155 | 1.00 | 2.00 |
| ATOM | 2505 | CE2 | PHE | 487 | 11.570 | 50.374 | 72.264 | 1.00 | 2.00 |
| ATOM | 2506 | CZ | PHE | 487 | 12.973 | 50.658 | 72.235 | 1.00 | 2.70 |
| ATOM | 2507 | C | PHE | 487 | 11.039 | 48.600 | 66.477 | 1.00 | 6.52 |
| ATOM | 2508 | O | PHE | 487 | 12.095 | 48.253 | 65.952 | 1.00 | 5.26 |
| ATOM | 2509 | N | ASP | 488 | 9.835 | 48.254 | 65.986 | 1.00 | 6.84 |
| ATOM | 2511 | CA | ASP | 488 | 9.791 | 47.504 | 64.736 | 1.00 | 10.14 |
| ATOM | 2512 | CB | ASP | 488 | 8.379 | 46.948 | 64.417 | 1.00 | 13.68 |
| ATOM | 2513 | CG | ASP | 488 | 8.419 | 45.877 | 63.300 | 1.00 | 18.95 |
| ATOM | 2514 | OD1 | ASP | 488 | 9.060 | 44.814 | 63.483 | 1.00 | 21.79 |
| ATOM | 2515 | OD2 | ASP | 488 | 7.859 | 46.115 | 62.225 | 1.00 | 23.85 |
| ATOM | 2516 | C | ASP | 488 | 10.344 | 48.378 | 63.576 | 1.00 | 8.80 |
| ATOM | 2517 | O | ASP | 488 | 11.00 | 47.882 | 62.677 | 1.00 | 9.13 |

TABLE 4-continued

Coordinates of Lck bound with staurosporine (soaked)

| | Atom Type | Res | # | X | Y | Z | Occ | B |
|---|---|---|---|---|---|---|---|---|
| ATOM | 2518 | N | TYR | 489 | 10.065 | 49.681 | 63.611 | 1.00 | 8.36 |
| ATOM | 2520 | CA | TYR | 489 | 10.648 | 50.587 | 62.606 | 1.00 | 7.68 |
| ATOM | 2521 | CB | TYR | 489 | 10.053 | 52.001 | 62.730 | 1.00 | 7.51 |
| ATOM | 2522 | CG | TYR | 489 | 10.712 | 53.012 | 61.813 | 1.00 | 9.26 |
| ATOM | 2523 | CD1 | TYR | 489 | 10.269 | 53.190 | 60.505 | 1.00 | 9.70 |
| ATOM | 2524 | CE1 | TYR | 489 | 10.858 | 54.146 | 59.666 | 1.00 | 10.43 |
| ATOM | 2525 | CD2 | TYR | 489 | 11.778 | 53.801 | 62.255 | 1.00 | 10.00 |
| ATOM | 2526 | CE2 | TYR | 489 | 12.382 | 54.748 | 61.421 | 1.00 | 11.07 |
| ATOM | 2527 | CZ | TYR | 489 | 11.922 | 54.913 | 60.122 | 1.00 | 11.40 |
| ATOM | 2528 | OH | TYR | 489 | 12.535 | 55.819 | 59.272 | 1.00 | 9.64 |
| ATOM | 2530 | C | TYR | 489 | 12.188 | 50.652 | 62.763 | 1.00 | 5.72 |
| ATOM | 2531 | O | TYR | 489 | 12.926 | 50.492 | 61.825 | 1.00 | 7.93 |
| ATOM | 2532 | N | LEU | 490 | 12.675 | 50.858 | 63.992 | 1.00 | 5.65 |
| ATOM | 2534 | CA | LEU | 490 | 14.116 | 50.877 | 64.228 | 1.00 | 4.64 |
| ATOM | 2535 | CB | LEU | 490 | 14.377 | 51.126 | 65.726 | 1.00 | 5.14 |
| ATOM | 2536 | CG | LEU | 490 | 13.994 | 52.554 | 66.205 | 1.00 | 3.68 |
| ATOM | 2537 | CD1 | LEU | 490 | 13.894 | 52.619 | 67.761 | 1.00 | 6.17 |
| ATOM | 2538 | CD2 | LEU | 490 | 15.121 | 53.481 | 65.721 | 1.00 | 5.67 |
| ATOM | 2539 | C | LEU | 490 | 14.795 | 49.575 | 63.763 | 1.00 | 6.45 |
| ATOM | 2540 | O | LEU | 490 | 15.853 | 49.569 | 63.139 | 1.00 | 4.40 |
| ATOM | 2541 | N | ARG | 491 | 14.150 | 48.438 | 64.049 | 1.00 | 6.90 |
| ATOM | 2543 | CA | ARG | 491 | 14.713 | 47.172 | 63.614 | 1.00 | 6.24 |
| ATOM | 2544 | CB | ARG | 491 | 13.804 | 46.024 | 64.085 | 1.00 | 7.39 |
| ATOM | 2545 | CG | ARG | 491 | 14.249 | 44.589 | 63.595 | 1.00 | 13.33 |
| ATOM | 2546 | CD | ARG | 491 | 13.006 | 43.783 | 63.232 | 1.00 | 16.63 |
| ATOM | 2547 | NE | ARG | 491 | 12.852 | 43.719 | 61.777 | 1.00 | 23.18 |
| ATOM | 2549 | CZ | ARG | 491 | 11.840 | 44.176 | 61.047 | 1.00 | 22.69 |
| ATOM | 2550 | NH1 | ARG | 491 | 10.783 | 44.798 | 61.560 | 1.00 | 23.32 |
| ATOM | 2553 | NH2 | ARG | 491 | 11.857 | 43.907 | 59.766 | 1.00 | 26.41 |
| ATOM | 2556 | C | ARG | 491 | 14.845 | 47.138 | 62.078 | 1.00 | 6.15 |
| ATOM | 2557 | O | ARG | 491 | 15.887 | 46.767 | 61.514 | 1.00 | 8.27 |
| ATOM | 2558 | N | SER | 492 | 13.781 | 47.533 | 61.401 | 0.71 | 5.72 |
| ATOM | 2560 | CA | SER | 492 | 13.771 | 47.514 | 59.941 | 0.71 | 5.48 |
| ATOM | 2561 | CB | SER | 492 | 12.379 | 47.952 | 59.447 | 0.71 | 7.19 |
| ATOM | 2562 | OG | SER | 492 | 12.296 | 47.757 | 58.055 | 0.71 | 11.62 |
| ATOM | 2564 | C | SER | 492 | 14.867 | 48.388 | 59.320 | 0.71 | 4.57 |
| ATOM | 2565 | O | SER | 492 | 15.580 | 47.991 | 58.402 | 0.71 | 2.00 |
| ATOM | 2566 | N | VAL | 493 | 14.996 | 49.609 | 59.845 | 1.00 | 5.21 |
| ATOM | 2568 | CA | VAL | 493 | 16.013 | 50.529 | 59.366 | 1.00 | 4.52 |
| ATOM | 2569 | CB | VAL | 493 | 15.809 | 51.921 | 60.073 | 1.00 | 5.78 |
| ATOM | 2570 | CG1 | VAL | 493 | 16.988 | 52.876 | 59.825 | 1.00 | 5.45 |
| ATOM | 2571 | CG2 | VAL | 493 | 14.535 | 52.548 | 59.627 | 1.00 | 7.49 |
| ATOM | 2572 | C | VAL | 493 | 17.436 | 50.006 | 59.632 | 1.00 | 3.86 |
| ATOM | 2573 | O | VAL | 493 | 18.299 | 50.059 | 58.791 | 1.00 | 5.74 |
| ATOM | 2574 | N | LEU | 494 | 17.693 | 49.544 | 60.857 | 1.00 | 4.14 |
| ATOM | 2576 | CA | LEU | 494 | 19.040 | 49.061 | 61.174 | 1.00 | 6.78 |
| ATOM | 2577 | CB | LEU | 494 | 19.186 | 48.810 | 62.671 | 1.00 | 4.46 |
| ATOM | 2578 | CG | LEU | 494 | 19.141 | 50.121 | 63.485 | 1.00 | 4.63 |
| ATOM | 2579 | CD1 | LEU | 494 | 18.661 | 49.807 | 64.958 | 1.00 | 4.58 |
| ATOM | 2580 | CD2 | LEU | 494 | 20.541 | 50.809 | 63.475 | 1.00 | 2.17 |
| ATOM | 2581 | C | LEU | 494 | 19.484 | 47.834 | 60.330 | 1.00 | 7.37 |
| ATOM | 2582 | O | LEU | 494 | 20.684 | 47.665 | 60.050 | 1.00 | 6.93 |
| ATOM | 2583 | N | GLU | 495 | 18.503 | 47.015 | 59.941 | 1.00 | 7.28 |
| ATOM | 2585 | CA | GLU | 495 | 18.770 | 45.865 | 59.055 | 1.00 | 10.08 |
| ATOM | 2586 | CB | GLU | 495 | 17.552 | 44.917 | 59.002 | 1.00 | 9.68 |
| ATOM | 2587 | CG | GLU | 495 | 17.314 | 44.174 | 60.318 | 1.00 | 12.01 |
| ATOM | 2588 | CD | GLU | 495 | 16.180 | 43.152 | 60.257 | 1.00 | 18.21 |
| ATOM | 2589 | OE1 | GLU | 495 | 15.568 | 42.977 | 59.163 | 1.00 | 17.97 |
| ATOM | 2590 | OE2 | GLU | 495 | 15.881 | 42.524 | 61.313 | 1.00 | 19.73 |
| ATOM | 2591 | C | GLU | 495 | 19.154 | 46.382 | 57.647 | 1.00 | 7.94 |
| ATOM | 2592 | O | GLU | 495 | 20.078 | 45.902 | 57.002 | 1.00 | 8.27 |
| ATOM | 2593 | N | ASP | 496 | 18.494 | 47.446 | 57.222 | 1.00 | 9.27 |
| ATOM | 2595 | CA | ASP | 496 | 18.840 | 48.047 | 55.932 | 1.00 | 9.40 |
| ATOM | 2596 | CB | ASP | 496 | 17.801 | 49.109 | 55.543 | 1.00 | 9.76 |
| ATOM | 2597 | CG | ASP | 496 | 16.529 | 48.508 | 55.005 | 1.00 | 9.08 |
| ATOM | 2598 | OD1 | ASP | 496 | 16.546 | 47.317 | 54.624 | 1.00 | 13.10 |
| ATOM | 2599 | OD2 | ASP | 496 | 15.506 | 49.203 | 54.934 | 1.00 | 8.40 |
| ATOM | 2600 | C | ASP | 496 | 20.231 | 48.655 | 56.023 | 1.00 | 9.38 |
| ATOM | 2601 | O | ASP | 496 | 21.073 | 48.442 | 55.132 | 1.00 | 9.97 |
| ATOM | 2602 | N | PHE | 497 | 20.533 | 49.304 | 57.151 | 1.00 | 9.58 |
| ATOM | 2604 | CA | PHE | 497 | 21.848 | 49.897 | 57.349 | 1.00 | 10.82 |
| ATOM | 2605 | CB | PHE | 497 | 21.947 | 50.567 | 58.730 | 1.00 | 10.33 |
| ATOM | 2606 | CG | PHE | 497 | 21.261 | 51.910 | 58.846 | 1.00 | 8.98 |
| ATOM | 2607 | CD1 | PHE | 497 | 20.500 | 52.438 | 57.804 | 1.00 | 9.24 |

TABLE 4-continued

Coordinates of Lck bound with staurosporine (soaked)

| | | Atom Type | Res | # | X | Y | Z | Occ | B |
|---|---|---|---|---|---|---|---|---|---|
| ATOM | 2608 | CD2 | PHE | 497 | 21.440 | 52.673 | 59.987 | 1.00 | 8.40 |
| ATOM | 2609 | CE1 | PHE | 497 | 19.829 | 53.667 | 57.950 | 1.00 | 9.15 |
| ATOM | 2610 | CE2 | PHE | 497 | 20.777 | 53.910 | 60.153 | 1.00 | 9.96 |
| ATOM | 2611 | CZ | PHE | 497 | 20.007 | 54.428 | 59.111 | 1.00 | 8.87 |
| ATOM | 2612 | C | PHE | 497 | 22.950 | 48.816 | 57.273 | 1.00 | 12.89 |
| ATOM | 2613 | O | PHE | 497 | 23.970 | 48.965 | 56.612 | 1.00 | 11.96 |
| ATOM | 2614 | N | PHE | 498 | 22.697 | 47.728 | 57.996 | 1.00 | 14.97 |
| ATOM | 2616 | CA | PHE | 498 | 23.598 | 46.574 | 58.066 | 1.00 | 20.02 |
| ATOM | 2617 | CB | PHE | 498 | 23.036 | 45.591 | 59.157 | 1.00 | 20.25 |
| ATOM | 2618 | CG | PHE | 498 | 23.576 | 44.196 | 59.110 | 1.00 | 22.23 |
| ATOM | 2619 | CD1 | PHE | 498 | 24.928 | 43.940 | 59.094 | 1.00 | 2.93 |
| ATOM | 2620 | CD2 | PHE | 498 | 22.695 | 43.118 | 59.149 | 1.00 | 26.01 |
| ATOM | 2621 | CE1 | PHE | 498 | 25.397 | 42.624 | 59.110 | 1.00 | 24.58 |
| ATOM | 2622 | CE2 | PHE | 498 | 23.147 | 41.813 | 59.165 | 1.00 | 24.88 |
| ATOM | 2623 | CZ | PHE | 498 | 24.497 | 41.560 | 59.147 | 1.00 | 24.56 |
| ATOM | 2624 | C | PHE | 498 | 23.762 | 45.903 | 56.700 | 1.00 | 21.85 |
| ATOM | 2625 | O | PHE | 498 | 24.864 | 45.729 | 56.220 | 1.00 | 22.72 |
| ATOM | 2626 | N | THR | 499 | 22.649 | 45.632 | 56.036 | 1.00 | 24.16 |
| ATOM | 2628 | CA | THR | 499 | 22.697 | 44.965 | 54.747 | 1.00 | 28.58 |
| ATOM | 2629 | CB | THR | 499 | 21.426 | 44.126 | 54.498 | 1.00 | 27.62 |
| ATOM | 2630 | OG1 | THR | 499 | 20.310 | 44.997 | 54.393 | 1.00 | 29.10 |
| ATOM | 2632 | CG2 | THR | 499 | 21.167 | 43.190 | 55.659 | 1.00 | 29.27 |
| ATOM | 2633 | C | THR | 499 | 22.932 | 45.913 | 53.594 | 1.00 | 32.13 |
| ATOM | 2634 | O | THR | 499 | 22.396 | 45.726 | 52.492 | 1.00 | 33.33 |
| ATOM | 2635 | N | ALA | 500 | 23.726 | 46.937 | 53.900 | 1.00 | 33.44 |
| ATOM | 2637 | CA | ALA | 500 | 24.182 | 48.016 | 53.028 | 1.00 | 35.24 |
| ATOM | 2638 | CB | ALA | 500 | 23.417 | 49.327 | 53.341 | 1.00 | 34.45 |
| ATOM | 2639 | C | ALA | 500 | 25.672 | 48.223 | 53.293 | 1.00 | 36.18 |
| ATOM | 2640 | O | ALA | 500 | 26.454 | 48.448 | 52.368 | 1.00 | 37.53 |
| ATOM | 2641 | N | THR | 501 | 26.062 | 48.167 | 54.575 | 1.00 | 35.49 |
| ATOM | 2643 | CA | THR | 501 | 27.477 | 48.285 | 54.968 | 1.00 | 35.21 |
| ATOM | 2644 | CB | THR | 501 | 27.660 | 48.803 | 56.434 | 1.00 | 34.98 |
| ATOM | 2645 | OG1 | THR | 501 | 27.065 | 47.864 | 57.335 | 1.00 | 34.15 |
| ATOM | 2647 | CG2 | THR | 501 | 27.027 | 50.190 | 56.633 | 1.00 | 33.83 |
| ATOM | 2648 | C | THR | 501 | 28.184 | 46.918 | 54.862 | 1.00 | 36.81 |
| ATOM | 2649 | O | THR | 501 | 27.963 | 46.234 | 53.833 | 1.00 | 36.26 |
| ATOM | 2650 | TO | THR | 501 | 28.927 | 46.526 | 55.809 | 1.00 | 37.49 |
| ATOM | 2651 | OH2 | TIP | 1 | 19.311 | 61.451 | 77.517 | 1.00 | 9.51 |
| ATOM | 2654 | OH2 | TIP | 2 | 21.927 | 30.146 | 74.495 | 1.00 | 10.87 |
| ATOM | 2657 | OH2 | TIP | 3 | 16.683 | 33.287 | 74.355 | 1.00 | 9.01 |
| ATOM | 2660 | OH2 | TIP | 4 | 39.739 | 38.338 | 73.029 | 1.00 | 16.54 |
| ATOM | 2663 | OH2 | TIP | 5 | 14.736 | 52.071 | 79.171 | 1.00 | 10.02 |
| ATOM | 2666 | OH2 | TIP | 6 | 20.566 | 63.204 | 73.067 | 1.00 | 10.44 |
| ATOM | 2669 | OH2 | TIP | 7 | 26.999 | 32.025 | 74.946 | 1.00 | 11.15 |
| ATOM | 2672 | OH2 | TIP | 8 | 24.523 | 79.325 | 73.707 | 1.00 | 12.34 |
| ATOM | 2675 | OH2 | TIP | 9 | 26.415 | 24.060 | 78.113 | 1.00 | 11.63 |
| ATOM | 2676 | OH2 | TIP | 10 | 25.241 | 50.846 | 79.942 | 1.00 | 4.37 |
| ATOM | 2681 | OH2 | TIP | 11 | 23.356 | 20.960 | 77.886 | 1.00 | 10.04 |
| ATOM | 2684 | OH2 | TIP | 12 | 26.225 | 73.383 | 70.539 | 1.00 | 11.22 |
| ATOM | 2686 | OH2 | TIP | 13 | 13.101 | 71.939 | 72.454 | 1.00 | 15.78 |
| ATOM | 2690 | OH2 | TIP | 14 | 28.040 | 56.696 | 74.337 | 1.00 | 10.46 |
| ATOM | 2693 | OH2 | TIP | 15 | 13.599 | 34.317 | 76.278 | 1.00 | 11.77 |
| ATOM | 2696 | OH2 | TIP | 16 | 14.407 | 25.394 | 81.101 | 1.00 | 12.52 |
| ATOM | 2699 | OH2 | TIP | 17 | 22.531 | 19.149 | 81.866 | 1.00 | 11.75 |
| ATOM | 2702 | OH2 | TIP | 18 | 3.993 | 51.772 | 76.108 | 1.00 | 12.20 |
| ATOM | 2705 | OH2 | TIP | 19 | 33.188 | 40.683 | 77.485 | 1.00 | 16.97 |
| ATOM | 2708 | OH2 | TIP | 20 | 30.131 | 18.456 | 80.658 | 1.00 | 11.69 |
| ATOM | 2711 | OH2 | TIP | 21 | 28.146 | 53.808 | 78.726 | 1.00 | 10.89 |
| ATOM | 2714 | OH2 | TIP | 22 | 5.966 | 57.823 | 65.467 | 1.00 | 25.51 |
| ATOM | 2717 | OH2 | TIP | 23 | 4.770 | 47.784 | 75.121 | 1.00 | 11.19 |
| ATOM | 2720 | OH2 | TIP | 24 | 29.430 | 62.780 | 71.874 | 1.00 | 12.30 |
| ATOM | 2723 | OH2 | TIP | 25 | 23.569 | 29.609 | 76.723 | 1.00 | 15.79 |
| ATOM | 2726 | OH2 | TIP | 26 | 19.387 | 28.532 | 78.780 | 1.00 | 11.30 |
| ATOM | 2729 | OH2 | TIP | 27 | 30.446 | 41.985 | 81.415 | 1.00 | 12.69 |
| ATOM | 2732 | OH2 | TIP | 28 | 26.750 | 65.828 | 74.084 | 1.00 | 12.12 |
| ATOM | 2735 | OH2 | TIP | 29 | 16.554 | 62.515 | 62.377 | 1.00 | 12.02 |
| ATOM | 2738 | OH2 | TIP | 30 | 4.250 | 54.927 | 67.119 | 1.00 | 11.65 |
| ATOM | 2741 | OH2 | TIP | 31 | 11.960 | 33.677 | 79.416 | 1.00 | 11.53 |
| ATOM | 2744 | OH2 | TIP | 32 | 17.879 | 62.427 | 79.648 | 1.00 | 12.18 |
| ATOM | 2747 | OH2 | TIP | 33 | 25.759 | 21.951 | 76.518 | 1.00 | 11.64 |
| ATOM | 2750 | OH2 | TIP | 34 | 4.279 | 16.551 | 94.706 | 1.00 | 8.69 |
| ATOM | 2753 | OH2 | TIP | 35 | 43.046 | 45.255 | 71.148 | 1.00 | 17.41 |
| ATOM | 2756 | OH2 | TIP | 36 | 33.552 | 42.873 | 62.416 | 1.00 | 12.80 |
| ATOM | 2759 | OH2 | TIP | 37 | 24.371 | 69.370 | 70.424 | 1.00 | 12.19 |

TABLE 4-continued

Coordinates of Lck bound with staurosporine (soaked)

| | | Atom Type | Res | # | X | Y | Z | Occ | B |
|---|---|---|---|---|---|---|---|---|---|
| ATOM | 2762 | OH2 | TIP | 38 | 8.595 | 65.929 | 68.815 | 1.00 | 10.23 |
| ATOM | 2765 | OH2 | TIP | 39 | 16.431 | 52.748 | 84.453 | 1.00 | 13.16 |
| ATOM | 2768 | OH2 | TIP | 40 | 26.298 | 70.965 | 71.663 | 1.00 | 16.76 |
| ATOM | 2771 | OH2 | TIP | 41 | 40.273 | 44.193 | 77.523 | 1.00 | 18.95 |
| ATOM | 2774 | OH2 | TIP | 42 | 11.838 | 33.972 | 69.173 | 1.00 | 15.53 |
| ATOM | 2777 | OH2 | TIP | 43 | 1.764 | 39.205 | 79.803 | 1.00 | 29.10 |
| ATOM | 2780 | OH2 | TIP | 44 | 13.713 | 56.017 | 79.376 | 1.00 | 14.52 |
| ATOM | 2783 | OH2 | TIP | 45 | 6.708 | 45.582 | 67.704 | 1.00 | 11.88 |
| ATOM | 2786 | OH2 | TIP | 46 | 17.978 | 38.720 | 82.589 | 1.00 | 19.42 |
| ATOM | 2789 | OH2 | TIP | 47 | 20.013 | 71.383 | 84.993 | 1.00 | 19.83 |
| ATOM | 2792 | OH2 | TIP | 48 | 23.308 | 59.317 | 84.264 | 1.00 | 13.60 |
| ATOM | 2795 | OH2 | TIP | 49 | 17.831 | 34.267 | 99.574 | 1.00 | 23.35 |
| ATOM | 2798 | OH2 | TIP | 50 | 15.163 | 19.433 | 87.833 | 1.00 | 14.39 |
| ATOM | 2801 | OH2 | TIP | 51 | 36.528 | 39.376 | 74.325 | 1.00 | 20.47 |
| ATOM | 2804 | OH2 | TIP | 52 | 30.957 | 70.019 | 72.459 | 1.00 | 31.69 |
| ATOM | 2807 | OH2 | TIP | 53 | 22.787 | 58.814 | 87.531 | 1.00 | 33.78 |
| ATOM | 2810 | OH2 | TIP | 54 | 3.052 | 57.417 | 68.084 | 1.00 | 19.58 |
| ATOM | 2813 | OH2 | TIP | 55 | 13.253 | 23.640 | 94.461 | 1.00 | 19.36 |
| ATOM | 2816 | OH2 | TIP | 56 | 35.613 | 44.620 | 79.222 | 1.00 | 27.49 |
| ATOM | 2819 | OH2 | TIP | 57 | 26.527 | 64.552 | 87.243 | 1.00 | 23.67 |
| ATOM | 2822 | OH2 | TIP | 58 | 28.903 | 71.148 | 70.501 | 1.00 | 17.76 |
| ATOM | 2825 | OH2 | TIP | 59 | 29.760 | 58.827 | 74.516 | 1.00 | 15.12 |
| ATOM | 2828 | OH2 | TIP | 60 | 43.367 | 40.547 | 77.280 | 1.00 | 18.72 |
| ATOM | 2831 | OH2 | TIP | 61 | 15.982 | 75.980 | 77.993 | 1.00 | 24.23 |
| ATOM | 2834 | OH2 | TIP | 62 | 32.897 | 34.167 | 71.680 | 1.00 | 27.51 |
| ATOM | 2837 | OH2 | TIP | 63 | 6.623 | 58.163 | 77.247 | 1.00 | 19.01 |
| ATOM | 2840 | OH2 | TIP | 64 | 30.113 | 60.394 | 72.292 | 1.00 | 15.41 |
| ATOM | 2843 | OH2 | TIP | 65 | 3.586 | 40.599 | 83.831 | 1.00 | 30.72 |
| ATOM | 2846 | OH2 | TIP | 66 | 27.441 | 51.105 | 81.647 | 1.00 | 19.30 |
| ATOM | 2849 | OH2 | TIP | 67 | 24.529 | 67.677 | 74.244 | 1.00 | 16.22 |
| ATOM | 2852 | OH2 | TIP | 68 | 19.038 | 52.615 | 83.053 | 1.00 | 24.52 |
| ATOM | 2855 | OH2 | TIP | 69 | 25.114 | 31.789 | 71.057 | 1.00 | 23.79 |
| ATOM | 2858 | OH2 | TIP | 70 | 9.969 | 59.436 | 64.059 | 1.00 | 17.72 |
| ATOM | 2861 | OH2 | TIP | 71 | 29.504 | 66.330 | 74.969 | 1.00 | 18.42 |
| ATOM | 2864 | OH2 | TIP | 72 | 6.497 | 52.369 | 69.874 | 1.00 | 12.22 |
| ATOM | 2867 | OH2 | TIP | 73 | 14.390 | 22.995 | 83.276 | 1.00 | 34.15 |
| ATOM | 2870 | OH2 | TIP | 74 | 27.616 | 25.173 | 94.161 | 1.00 | 19.72 |
| ATOM | 2873 | OH2 | TIP | 75 | −1.474 | 21.109 | 94.026 | 1.00 | 16.84 |
| ATOM | 2876 | OH2 | TIP | 76 | 7.073 | 27.726 | 99.566 | 1.00 | 29.78 |
| ATOM | 2879 | OH2 | TIP | 77 | 3.184 | 17.629 | 92.263 | 1.00 | 14.43 |
| ATOM | 2882 | OH2 | TIP | 78 | 10.524 | 41.239 | 67.027 | 1.00 | 18.23 |
| ATOM | 2885 | OH2 | TIP | 79 | 13.981 | 69.635 | 73.583 | 1.00 | 19.87 |
| ATOM | 2888 | OH2 | TIP | 80 | 15.009 | 39.727 | 90.769 | 1.00 | 19.18 |
| ATOM | 2891 | OH2 | TIP | 81 | 17.180 | 29.359 | 79.794 | 1.00 | 13.29 |
| ATOM | 2894 | OH2 | TIP | 82 | 8.570 | 33.844 | 71.005 | 1.00 | 30.33 |
| ATOM | 2897 | OH2 | TIP | 83 | 27.624 | 20.321 | 77.495 | 1.00 | 21.60 |
| ATOM | 2900 | OH2 | TIP | 84 | 14.470 | 25.077 | 74.515 | 1.00 | 22.43 |
| ATOM | 2903 | OH2 | TIP | 85 | 15.658 | 69.961 | 86.496 | 1.00 | 33.81 |
| ATOM | 2906 | OH2 | TIP | 86 | 4.347 | 43.749 | 85.189 | 1.00 | 18.89 |
| ATOM | 2909 | OH2 | TIP | 87 | 13.646 | 22.495 | 79.270 | 1.00 | 19.63 |
| ATOM | 2912 | OH2 | TIP | 88 | 34.351 | 49.689 | 60.577 | 1.00 | 22.73 |
| ATOM | 2915 | OH2 | TIP | 89 | 4.570 | 27.575 | 95.849 | 1.00 | 23.49 |
| ATOM | 2918 | OH2 | TIP | 90 | 14.488 | 65.973 | 82.024 | 1.00 | 33.95 |
| ATOM | 2921 | OH2 | TIP | 91 | 14.199 | 45.984 | 83.667 | 1.00 | 9.67 |
| ATOM | 2924 | OH2 | TIP | 92 | 12.650 | 36.289 | 79.191 | 1.00 | 28.99 |
| ATOM | 2927 | OH2 | TIP | 93 | 7.704 | 54.375 | 63.754 | 1.00 | 14.74 |
| ATOM | 2930 | OH2 | TIP | 94 | 41.632 | 44.586 | 69.191 | 1.00 | 13.30 |
| ATOM | 2933 | OH2 | TIP | 95 | 22.33 | 28.550 | 79.220 | 1.00 | 11.35 |
| ATOM | 2936 | OH2 | TIP | 96 | 3.508 | 56.701 | 74.135 | 1.00 | 40.43 |
| ATOM | 2939 | OH2 | TIP | 97 | 13.230 | 31.893 | 74.970 | 1.00 | 14.29 |
| ATOM | 2942 | OH2 | TIP | 98 | 30.226 | 70.647 | 76.992 | 1.00 | 36.97 |
| ATOM | 2945 | OH2 | TIP | 99 | 30.660 | 29.412 | 77.031 | 1.00 | 30.61 |
| ATOM | 2948 | OH2 | TIP | 100 | 3.867 | 29.346 | 100.830 | 1.00 | 35.05 |
| ATOM | 2951 | OH2 | TIP | 101 | 3.305 | 31.432 | 85.206 | 1.00 | 42.40 |
| ATOM | 2954 | OH2 | TIP | 102 | 19.769 | 33.131 | 97.641 | 1.00 | 34.70 |
| ATOM | 2957 | OH2 | TIP | 103 | 32.525 | 60.209 | 71.096 | 1.00 | 26.31 |
| ATOM | 2960 | OH2 | TIP | 104 | 14.385 | 18.965 | 81.633 | 1.00 | 39.40 |
| ATOM | 2963 | OH2 | TIP | 105 | 35.303 | 37.590 | 69.165 | 1.00 | 47.36 |
| ATOM | 2966 | OH2 | TIP | 106 | 12.150 | 44.315 | 98.941 | 1.00 | 27.18 |
| ATOM | 2969 | OH2 | TIP | 107 | 31.404 | 65.727 | 72.463 | 1.00 | 34.79 |
| ATOM | 2972 | OH2 | TIP | 108 | 1.407 | 57.920 | 64.929 | 1.00 | 48.77 |
| ATOM | 2975 | OH2 | TIP | 109 | 9.310 | 40.098 | 102.788 | 1.00 | 23.64 |
| ATOM | 2978 | OH2 | TIP | 110 | −0.848 | 51.009 | 82.212 | 1.00 | 38.03 |
| ATOM | 2981 | OH2 | TIP | 111 | 13.086 | 42.678 | 102.403 | 1.00 | 39.17 |

TABLE 4-continued

Coordinates of Lck bound with staurosporine (soaked)

| | | Atom Type | Res | # | X | Y | Z | Occ | B |
|---|---|---|---|---|---|---|---|---|---|
| ATOM | 2984 | OH2 | TIP | 112 | 1.621 | 52.914 | 87.041 | 1.00 | 27.63 |
| ATOM | 2987 | OH2 | TIP | 113 | 10.616 | 25.358 | 97.769 | 1.00 | 46.48 |
| ATOM | 2990 | OH2 | TIP | 114 | 2.753 | 32.296 | 80.523 | 1.00 | 54.81 |
| ATOM | 2993 | OH2 | TIP | 115 | 19.151 | 70.156 | 86.599 | 1.00 | 22.62 |
| ATOM | 2996 | OH2 | TIP | 116 | 3.297 | 33.113 | 89.038 | 1.00 | 44.00 |
| ATOM | 2999 | OH2 | TIP | 117 | 12.148 | 21.276 | 94.594 | 1.00 | 30.07 |
| ATOM | 3002 | OH2 | TIP | 118 | 9.743 | 70.112 | 82.946 | 1.00 | 25.91 |
| ATOM | 3005 | OH2 | TIP | 119 | 43.117 | 37.524 | 68.875 | 1.00 | 37.83 |
| ATOM | 3008 | OH2 | TIP | 120 | 22.806 | 32.177 | 72.420 | 1.00 | 27.17 |
| ATOM | 3011 | OH2 | TIP | 121 | 12.282 | 70.067 | 76.126 | 1.00 | 45.70 |
| ATOM | 3014 | OH2 | TIP | 122 | −0.783 | 32.259 | 88.769 | 1.00 | 33.61 |
| ATOM | 3017 | OH2 | TIP | 123 | 32.388 | 39.732 | 89.901 | 1.00 | 32.87 |
| ATOM | 3020 | OH2 | TIP | 124 | 7.556 | 27.635 | 71.724 | 1.00 | 31.46 |
| ATOM | 3023 | OH2 | TIP | 125 | 4.664 | 63.106 | 77.282 | 1.00 | 41.06 |
| ATOM | 3026 | OH2 | TIP | 126 | 7.065 | 70.330 | 72.529 | 1.00 | 49.77 |
| ATOM | 3029 | OH2 | TIP | 127 | 10.158 | 28.414 | 102.841 | 1.00 | 48.00 |
| ATOM | 3032 | OH2 | TIP | 128 | 17.158 | 52.424 | 87.288 | 1.00 | 19.66 |
| ATOM | 3035 | OH2 | TIP | 129 | 30.654 | 73.854 | 75.647 | 1.00 | 44.45 |
| ATOM | 3038 | OH2 | TIP | 130 | 8.181 | 21.129 | 91.405 | 1.00 | 19.36 |
| ATOM | 3041 | OH2 | TIP | 131 | 30.265 | 26.627 | 76.393 | 1.00 | 44.63 |
| ATOM | 3044 | OH2 | TIP | 132 | 1.404 | 36.670 | 96.617 | 1.00 | 37.69 |
| ATOM | 3047 | OH2 | TIP | 133 | 27.398 | 58.917 | 84.327 | 1.00 | 36.32 |
| ATOM | 3050 | OH2 | TIP | 134 | 26.579 | 75.000 | 74.442 | 1.00 | 23.63 |
| ATOM | 3053 | OH2 | TIP | 135 | 4.864 | 37.496 | 69.248 | 1.00 | 51.76 |
| ATOM | 3056 | OH2 | TIP | 136 | 38.759 | 60.728 | 66.988 | 1.00 | 46.94 |
| ATOM | 3059 | OH2 | TIP | 137 | 7.041 | 27.787 | 102.352 | 1.00 | 31.69 |
| ATOM | 3062 | OH2 | TIP | 138 | 1.044 | 56.406 | 73.837 | 1.00 | 54.98 |
| ATOM | 3065 | OH2 | TIP | 139 | 0.020 | 59.351 | 68.080 | 1.00 | 43.88 |
| ATOM | 3068 | OH2 | TIP | 140 | 24.025 | 74.725 | 76.829 | 1.00 | 25.03 |
| ATOM | 3071 | OH2 | TIP | 141 | 24.528 | 53.450 | 56.345 | 1.00 | 40.36 |
| ATOM | 3074 | OH2 | TIP | 142 | 32.470 | 40.634 | 63.102 | 1.00 | 43.71 |
| ATOM | 3077 | OH2 | TIP | 143 | 35.837 | 41.876 | 83.267 | 1.00 | 42.17 |
| ATOM | 3080 | OH2 | TIP | 144 | 13.772 | 74.524 | 73.842 | 1.00 | 21.66 |
| ATOM | 3083 | OH2 | TIP | 145 | 11.507 | 59.640 | 87.674 | 1.00 | 29.61 |
| ATOM | 3086 | OH2 | TIP | 146 | 35.527 | 33.428 | 69.247 | 1.00 | 55.37 |
| ATOM | 3089 | OH2 | TIP | 147 | −1.325 | 20.750 | 100.326 | 1.00 | 20.28 |
| ATOM | 3092 | OH2 | TIP | 148 | 8.007 | 41.733 | 67.424 | 1.00 | 42.05 |
| ATOM | 3095 | OH2 | TIP | 149 | −1.487 | 56.737 | 73.798 | 1.00 | 54.86 |
| ATOM | 3098 | OH2 | TIP | 150 | 6.452 | 37.420 | 92.986 | 1.00 | 37.34 |
| ATOM | 3101 | OH2 | TIP | 151 | 3.247 | 49.93 | 70.994 | 1.00 | 34.95 |
| ATOM | 3104 | S | SO4 | 901 | 20.457 | 33.124 | 69.153 | 1.00 | 10.65 |
| ATOM | 3105 | O1 | SO4 | 901 | 20.257 | 32.482 | 70.403 | 1.00 | 11.07 |
| ATOM | 3106 | O2 | SO4 | 901 | 19.170 | 33.561 | 68.666 | 1.00 | 10.55 |
| ATOM | 3107 | O3 | SO4 | 901 | 21.309 | 34.278 | 69.356 | 1.00 | 11.81 |
| ATOM | 3108 | O4 | SO4 | 901 | 21.109 | 32.174 | 68.216 | 1.00 | 8.82 |
| ATOM | 3109 | O4 | STU | 1 | 26.535 | 40.495 | 85.876 | 1.00 | 11.24 |
| ATOM | 3110 | C25 | STU | 1 | 27.502 | 40.339 | 84.840 | 1.00 | 9.72 |
| ATOM | 3111 | C24 | STU | 1 | 27.822 | 41.685 | 84.136 | 1.00 | 10.96 |
| ATOM | 3112 | C23 | STU | 1 | 26.945 | 42.806 | 84.728 | 1.00 | 12.11 |
| ATOM | 3113 | C22 | STU | 1 | 25.446 | 42.387 | 84.626 | 1.00 | 12.20 |
| ATOM | 3114 | C21 | STU | 1 | 25.305 | 41.210 | 85.651 | 1.00 | 11.74 |
| ATOM | 3115 | C26 | STU | 1 | 24.993 | 41.810 | 86.999 | 1.00 | 10.18 |
| ATOM | 3116 | N2 | STU | 1 | 24.278 | 40.197 | 85.248 | 1.00 | 8.64 |
| ATOM | 3117 | C18 | STU | 1 | 24.601 | 39.145 | 84.402 | 1.00 | 7.31 |
| ATOM | 3118 | C19 | STU | 1 | 25.764 | 38.773 | 83.853 | 1.00 | 8.67 |
| ATOM | 3119 | C6 | STU | 1 | 25.858 | 37.605 | 82.996 | 1.00 | 6.68 |
| ATOM | 3120 | C7 | STU | 1 | 24.603 | 36.902 | 82.801 | 1.00 | 5.78 |
| ATOM | 3121 | C10 | STU | 1 | 23.475 | 37.277 | 83.341 | 1.00 | 5.78 |
| ATOM | 3122 | C11 | STU | 1 | 23.380 | 38.427 | 84.169 | 1.00 | 7.21 |
| ATOM | 3123 | C12 | STU | 1 | 22.339 | 39.076 | 84.853 | 1.00 | 8.03 |
| ATOM | 3124 | C17 | STU | 1 | 22.898 | 40.224 | 85.534 | 1.00 | 7.47 |
| ATOM | 3125 | C16 | STU | 1 | 22.083 | 41.046 | 86.257 | 1.00 | 10.26 |
| ATOM | 3126 | C15 | STU | 1 | 20.716 | 40.769 | 86.371 | 1.00 | 7.20 |
| ATOM | 3127 | C14 | STU | 1 | 20.171 | 39.651 | 85.714 | 1.00 | 8.16 |
| ATOM | 3128 | C13 | STU | 1 | 20.895 | 38.816 | 84.968 | 1.00 | 7.93 |
| ATOM | 3129 | C9 | STU | 1 | 22.330 | 36.321 | 82.954 | 1.00 | 6.61 |
| ATOM | 3130 | N1 | STU | 1 | 23.082 | 35.431 | 82.089 | 1.00 | 7.37 |
| ATOM | 3131 | C8 | STU | 1 | 24.394 | 35.657 | 81.967 | 1.00 | 6.69 |
| ATOM | 3132 | O5 | STU | 1 | 25.212 | 35.024 | 81.341 | 1.00 | 9.35 |
| ATOM | 3133 | C5 | STU | 1 | 27.220 | 37.488 | 82.579 | 1.00 | 8.25 |
| ATOM | 3134 | C20 | STU | 1 | 27.911 | 38.565 | 83.172 | 1.00 | 8.48 |
| ATOM | 3135 | C1 | STU | 1 | 29.291 | 38.755 | 82.956 | 1.00 | 10.31 |
| ATOM | 3136 | C2 | STU | 1 | 29.958 | 37.837 | 82.165 | 1.00 | 7.16 |
| ATOM | 3137 | C3 | STU | 1 | 29.269 | 36.771 | 81.567 | 1.00 | 6.36 |

TABLE 4-continued

Coordinates of Lck bound with staurosporine (soaked)

| | | Atom Type | Res | # | X | Y | Z | Occ | B |
|---|---|---|---|---|---|---|---|---|---|
| ATOM | 3138 | C4 | STU | 1 | 27.892 | 36.595 | 81.781 | 1.00 | 6.70 |
| ATOM | 3139 | N3 | STU | 1 | 27.065 | 39.299 | 83.909 | 1.00 | 11.36 |
| ATOM | 3140 | O6 | STU | 1 | 25.269 | 41.898 | 83.285 | 1.00 | 15.68 |
| ATOM | 3141 | C27 | STU | 1 | 24.060 | 42.366 | 82.717 | 1.00 | 16.90 |
| ATOM | 3142 | N4 | STU | 1 | 27.204 | 44.135 | 83.925 | 1.00 | 14.54 |
| ATOM | 3143 | C28 | STU | 1 | 28.684 | 44.317 | 83.715 | 1.00 | 18.14 |

TABLE 5

Coordinates of Lck bound with baicalein

| | | Atom Type | Res | # | X | Y | Z | Occ | B |
|---|---|---|---|---|---|---|---|---|---|
| ATOM | 1 | CB | LYS | 231 | 1.292 | 26.841 | 89.344 | 1.00 | 29.33 |
| ATOM | 2 | CG | LYS | 231 | 0.672 | 27.077 | 87.978 | 1.00 | 31.74 |
| ATOM | 3 | CD | LYS | 231 | 0.810 | 25.829 | 87.123 | 1.00 | 32.04 |
| ATOM | 4 | CE | LYS | 231 | 0.103 | 26.050 | 85.794 | 1.00 | 35.11 |
| ATOM | 5 | NZ | LYS | 231 | 0.784 | 25.151 | 84.794 | 1.00 | 33.76 |
| ATOM | 6 | HZ1 | LYS | 231 | 0.686 | 24.180 | 85.135 | 1.00 | 0.00 |
| ATOM | 7 | HZ2 | LYS | 231 | 1.789 | 25.422 | 84.777 | 1.00 | 0.00 |
| ATOM | 8 | HZ3 | LYS | 231 | 0.350 | 25.280 | 83.882 | 1.00 | 0.00 |
| ATOM | 9 | C | LYS | 231 | 1.908 | 27.700 | 91.526 | 1.00 | 27.58 |
| ATOM | 10 | O | LYS | 231 | 3.013 | 28.303 | 91.664 | 1.00 | 27.64 |
| ATOM | 11 | HT1 | LYS | 231 | 2.367 | 29.332 | 89.461 | 1.00 | 0.00 |
| ATOM | 12 | HT2 | LYS | 231 | 1.221 | 30.057 | 90.482 | 1.00 | 0.00 |
| ATOM | 13 | N | LYS | 231 | 1.365 | 29.303 | 89.793 | 1.00 | 29.48 |
| ATOM | 14 | HT3 | LYS | 231 | 0.763 | 29.515 | 88.941 | 1.00 | 0.00 |
| ATOM | 15 | CA | LYS | 231 | 1.054 | 27.967 | 90.354 | 1.00 | 28.32 |
| ATOM | 16 | N | PRO | 232 | 1.505 | 26.815 | 92.446 | 1.00 | 26.98 |
| ATOM | 17 | CD | PRO | 232 | 0.246 | 26.009 | 92.397 | 1.00 | 26.43 |
| ATOM | 18 | CA | PRO | 232 | 2.321 | 26.491 | 93.656 | 1.00 | 25.55 |
| ATOM | 19 | CB | PRO | 232 | 1.348 | 25.551 | 94.418 | 1.00 | 25.93 |
| ATOM | 20 | CG | PRO | 232 | 0.540 | 24.917 | 93.368 | 1.00 | 26.91 |
| ATOM | 21 | C | PRO | 232 | 3.620 | 25.821 | 93.194 | 1.00 | 24.11 |
| ATOM | 22 | O | PRO | 232 | 3.678 | 25.288 | 92.068 | 1.00 | 23.35 |
| ATOM | 23 | N | TRP | 233 | 4.645 | 25.916 | 94.026 | 1.00 | 23.72 |
| ATOM | 24 | H | TRP | 233 | 4.546 | 26.336 | 94.887 | 1.00 | 0.00 |
| ATOM | 25 | CA | TRP | 233 | 5.977 | 25.357 | 93.679 | 1.00 | 24.39 |
| ATOM | 26 | CB | TRP | 233 | 7.036 | 25.656 | 94.789 | 1.00 | 23.59 |
| ATOM | 27 | CG | TRP | 233 | 6.877 | 24.919 | 96.083 | 1.00 | 24.63 |
| ATOM | 28 | CD2 | TRP | 233 | 7.301 | 23.557 | 96.406 | 1.00 | 24.94 |
| ATOM | 29 | CE2 | TRP | 233 | 6.976 | 23.326 | 97.762 | 1.00 | 25.05 |
| ATOM | 30 | CE3 | TRP | 233 | 7.933 | 22.531 | 95.677 | 1.00 | 25.10 |
| ATOM | 31 | CD1 | TRP | 233 | 6.340 | 25.421 | 97.225 | 1.00 | 23.37 |
| ATOM | 32 | NE1 | TRP | 233 | 6.400 | 24.477 | 98.244 | 1.00 | 25.04 |
| ATOM | 33 | HE1 | TRP | 233 | 6.093 | 24.612 | 99.146 | 1.00 | 0.00 |
| ATOM | 34 | CZ2 | TRP | 233 | 7.250 | 22.113 | 98.412 | 1.00 | 24.98 |
| ATOM | 35 | CZ3 | TRP | 233 | 8.208 | 21.331 | 96.327 | 1.00 | 25.30 |
| ATOM | 36 | CH2 | TRP | 233 | 7.860 | 21.136 | 97.693 | 1.00 | 25.14 |
| ATOM | 37 | C | TRP | 233 | 5.971 | 23.868 | 93.337 | 1.00 | 24.12 |
| ATOM | 38 | O | TRP | 233 | 6.750 | 23.433 | 92.463 | 1.00 | 24.17 |
| ATOM | 39 | N | TRP | 234 | 5.112 | 23.082 | 93.992 | 1.00 | 24.35 |
| ATOM | 40 | H | TRP | 234 | 4.543 | 23.486 | 94.673 | 1.00 | 0.00 |
| ATOM | 41 | CA | TRP | 234 | 5.047 | 21.667 | 93.652 | 1.00 | 24.69 |
| ATOM | 42 | CB | TRP | 234 | 4.429 | 20.810 | 94.827 | 1.00 | 22.35 |
| ATOM | 43 | CG | TRP | 234 | 3.058 | 21.228 | 95.215 | 1.00 | 19.34 |
| ATOM | 44 | CD2 | TRP | 234 | 2.690 | 22.198 | 96.215 | 1.00 | 18.40 |
| ATOM | 45 | CE2 | TRP | 234 | 1.298 | 22.335 | 96.168 | 1.00 | 17.94 |
| ATOM | 46 | CE3 | TRP | 234 | 3.437 | 22.970 | 97.130 | 1.00 | 18.54 |
| ATOM | 47 | CD1 | TRP | 234 | 1.903 | 20.827 | 94.634 | 1.00 | 18.11 |
| ATOM | 48 | NE1 | TRP | 234 | 0.829 | 21.491 | 95.197 | 1.00 | 17.61 |
| ATOM | 49 | HE1 | TRP | 234 | −0.090 | 21.396 | 94.924 | 1.00 | 0.00 |
| ATOM | 50 | CZ2 | TRP | 234 | 0.594 | 23.223 | 97.011 | 1.00 | 18.94 |
| ATOM | 51 | CZ3 | TRP | 234 | 2.762 | 23.860 | 97.963 | 1.00 | 19.16 |
| ATOM | 52 | CH2 | TRP | 234 | 1.341 | 23.989 | 97.905 | 1.00 | 19.55 |
| ATOM | 53 | C | TRP | 234 | 4.309 | 21.479 | 92.377 | 1.00 | 25.09 |
| ATOM | 54 | O | TRP | 234 | 4.319 | 20.385 | 91.790 | 1.00 | 25.09 |
| ATOM | 55 | N | GLU | 235 | 3.683 | 22.524 | 91.870 | 1.00 | 26.92 |
| ATOM | 56 | H | GLU | 235 | 3.676 | 23.396 | 92.399 | 1.00 | 0.00 |
| ATOM | 57 | CA | GLU | 235 | 2.978 | 22.482 | 90.583 | 1.00 | 28.87 |

TABLE 5-continued

Coordinates of Lck bound with baicalein

| | | Atom Type | Res | # | X | Y | Z | Occ | B |
|---|---|---|---|---|---|---|---|---|---|
| ATOM | 58 | CB | GLU | 235 | 1.520 | 22.909 | 90.705 | 1.00 | 29.65 |
| ATOM | 59 | CG | GLU | 235 | 0.674 | 21.967 | 91.546 | 1.00 | 31.81 |
| ATOM | 60 | CD | GLU | 235 | -0.809 | 21.948 | 91.184 | 1.00 | 33.39 |
| ATOM | 61 | OE1 | GLU | 235 | -1.284 | 22.856 | 90.462 | 1.00 | 33.53 |
| ATOM | 62 | OE2 | GLU | 235 | -1.482 | 20.979 | 91.632 | 1.00 | 34.15 |
| ATOM | 63 | C | GLU | 235 | 3.698 | 23.259 | 89.495 | 1.00 | 29.05 |
| ATOM | 64 | O | GLU | 235 | 3.432 | 23.068 | 88.316 | 1.00 | 29.17 |
| ATOM | 65 | N | ASP | 236 | 4.690 | 24.044 | 89.903 | 1.00 | 29.87 |
| ATOM | 66 | H | ASP | 236 | 5.009 | 24.036 | 90.802 | 1.00 | 0.00 |
| ATOM | 67 | CA | ASP | 236 | 5.398 | 24.898 | 88.924 | 1.00 | 30.07 |
| ATOM | 68 | CB | ASP | 236 | 6.014 | 26.091 | 89.684 | 1.00 | 31.50 |
| ATOM | 69 | CG | ASP | 236 | 6.502 | 27.140 | 88.840 | 1.00 | 33.75 |
| ATOM | 70 | OD1 | ASP | 236 | 5.829 | 27.436 | 87.977 | 1.00 | 35.74 |
| ATOM | 71 | OD2 | ASP | 236 | 7.578 | 27.633 | 88.872 | 1.00 | 37.03 |
| ATOM | 72 | C | ASP | 236 | 6.434 | 24.230 | 88.020 | 1.00 | 30.24 |
| ATOM | 73 | O | ASP | 236 | 7.355 | 23.546 | 88.481 | 1.00 | 29.74 |
| ATOM | 74 | N | GLU | 237 | 6.323 | 24.501 | 86.724 | 1.00 | 28.75 |
| ATOM | 75 | H | GLU | 237 | 5.622 | 25.089 | 86.434 | 1.00 | 0.00 |
| ATOM | 76 | CA | GLU | 237 | 7.256 | 23.974 | 85.731 | 1.00 | 28.69 |
| ATOM | 77 | CB | GLU | 237 | 6.781 | 24.293 | 84.319 | 1.00 | 29.58 |
| ATOM | 78 | CG | GLU | 237 | 5.996 | 25.626 | 84.132 | 1.00 | 32.06 |
| ATOM | 79 | CD | GLU | 237 | 4.564 | 25.595 | 84.726 | 1.00 | 32.98 |
| ATOM | 80 | OE1 | GLU | 237 | 3.757 | 24.719 | 84.383 | 1.00 | 35.34 |
| ATOM | 81 | OE2 | GLU | 237 | 4.282 | 26.384 | 85.580 | 1.00 | 33.35 |
| ATOM | 82 | C | GLU | 237 | 8.690 | 24.432 | 85.936 | 1.00 | 27.30 |
| ATOM | 83 | O | GLU | 237 | 9.613 | 23.784 | 85.455 | 1.00 | 27.39 |
| ATOM | 84 | N | TRP | 238 | 8.898 | 25.495 | 86.713 | 1.00 | 25.18 |
| ATOM | 85 | H | TRP | 238 | 8.131 | 25.898 | 87.167 | 1.00 | 0.00 |
| ATOM | 86 | CA | TRP | 238 | 10.235 | 26.046 | 86.901 | 1.00 | 23.25 |
| ATOM | 87 | CB | TRP | 238 | 10.237 | 27.569 | 86.716 | 1.00 | 22.94 |
| ATOM | 88 | CG | TRP | 238 | 10.057 | 28.028 | 85.304 | 1.00 | 21.91 |
| ATOM | 89 | CD2 | TRP | 238 | 8.810 | 28.367 | 84.657 | 1.00 | 22.48 |
| ATOM | 90 | CE2 | TRP | 238 | 9.119 | 28.780 | 83.331 | 1.00 | 22.81 |
| ATOM | 91 | CE3 | TRP | 238 | 7.471 | 28.368 | 85.071 | 1.00 | 22.40 |
| ATOM | 92 | CD1 | TRP | 238 | 11.028 | 28.237 | 84.384 | 1.00 | 21.53 |
| ATOM | 93 | NE1 | TRP | 238 | 10.478 | 28.694 | 83.186 | 1.00 | 22.29 |
| ATOM | 94 | HE1 | TRP | 238 | 10.976 | 28.925 | 82.382 | 1.00 | 0.00 |
| ATOM | 95 | CZ2 | TRP | 238 | 8.151 | 29.183 | 82.428 | 1.00 | 23.94 |
| ATOM | 96 | CZ3 | TRP | 238 | 6.520 | 28.757 | 84.200 | 1.00 | 23.24 |
| ATOM | 97 | CH2 | TRP | 238 | 6.842 | 29.162 | 82.883 | 1.00 | 24.85 |
| ATOM | 98 | C | TRP | 238 | 10.958 | 25.688 | 88.184 | 1.00 | 21.57 |
| ATOM | 99 | O | TRP | 238 | 12.155 | 25.876 | 88.270 | 1.00 | 21.19 |
| ATOM | 100 | N | GLU | 239 | 10.235 | 25.250 | 89.207 | 1.00 | 20.56 |
| ATOM | 101 | H | GLU | 239 | 9.255 | 25.182 | 89.129 | 1.00 | 0.00 |
| ATOM | 102 | CA | GLU | 239 | 10.886 | 24.892 | 90.481 | 1.00 | 19.62 |
| ATOM | 103 | CB | GLU | 239 | 9.861 | 24.584 | 91.574 | 1.00 | 19.70 |
| ATOM | 104 | CG | GLU | 239 | 10.490 | 24.377 | 92.976 | 1.00 | 17.68 |
| ATOM | 105 | CD | GLU | 239 | 10.763 | 25.727 | 93.701 | 1.00 | 17.87 |
| ATOM | 106 | OE1 | GLU | 239 | 10.011 | 26.702 | 93.441 | 1.00 | 17.40 |
| ATOM | 107 | OE2 | GLU | 239 | 11.693 | 25.807 | 94.549 | 1.00 | 14.89 |
| ATOM | 108 | C | GLU | 239 | 11.779 | 23.668 | 90.292 | 1.00 | 20.40 |
| ATOM | 109 | O | GLU | 239 | 11.352 | 22.681 | 89.671 | 1.00 | 21.39 |
| ATOM | 110 | N | VAL | 240 | 13.015 | 23.754 | 90.784 | 1.00 | 19.39 |
| ATOM | 111 | H | VAL | 240 | 13.311 | 24.591 | 91.163 | 1.00 | 0.00 |
| ATOM | 112 | CA | VAL | 240 | 13.921 | 22.616 | 90.746 | 1.00 | 18.62 |
| ATOM | 113 | CB | VAL | 240 | 15.073 | 22.752 | 89.717 | 1.00 | 19.14 |
| ATOM | 114 | CG1 | VAL | 240 | 14.523 | 22.874 | 88.301 | 1.00 | 19.24 |
| ATOM | 115 | CG2 | VAL | 240 | 16.036 | 23.915 | 90.110 | 1.00 | 19.83 |
| ATOM | 116 | C | VAL | 240 | 14.560 | 22.444 | 92.130 | 1.00 | 19.43 |
| ATOM | 117 | O | VAL | 240 | 14.687 | 23.407 | 92.887 | 1.00 | 19.29 |
| ATOM | 118 | N | PRO | 241 | 14.945 | 21.191 | 92.476 | 1.00 | 18.85 |
| ATOM | 119 | CD | PRO | 241 | 14.506 | 19.935 | 91.833 | 1.00 | 18.05 |
| ATOM | 120 | CA | PRO | 241 | 15.583 | 20.903 | 93.758 | 1.00 | 16.93 |
| ATOM | 121 | CB | PRO | 241 | 15.733 | 19.387 | 93.718 | 1.00 | 18.54 |
| ATOM | 122 | CG | PRO | 241 | 14.542 | 18.949 | 92.989 | 1.00 | 17.91 |
| ATOM | 123 | C | PRO | 241 | 16.962 | 21.587 | 93.736 | 1.00 | 17.86 |
| ATOM | 124 | O | PRO | 241 | 17.615 | 21.601 | 92.712 | 1.00 | 16.21 |
| ATOM | 125 | N | ARG | 242 | 17.402 | 22.164 | 94.853 | 1.00 | 17.40 |
| ATOM | 126 | H | ARG | 242 | 16.833 | 22.181 | 95.653 | 1.00 | 0.00 |
| ATOM | 127 | CA | ARG | 242 | 18.684 | 22.843 | 94.865 | 1.00 | 18.30 |
| ATOM | 128 | CB | ARG | 242 | 18.913 | 23.580 | 96.178 | 1.00 | 19.27 |
| ATOM | 129 | CG | ARG | 242 | 20.070 | 24.614 | 96.082 | 1.00 | 20.79 |
| ATOM | 130 | CD | ARG | 242 | 20.546 | 25.133 | 97.438 | 1.00 | 20.89 |
| ATOM | 131 | NE | ARG | 242 | 19.452 | 25.616 | 98.299 | 1.00 | 22.47 |

TABLE 5-continued

Coordinates of Lck bound with baicalein

| | Atom Type | Res | # | X | Y | Z | Occ | B |
|---|---|---|---|---|---|---|---|---|
| ATOM | 132 | HE | ARG | 242 | 19.153 | 25.017 | 99.024 | 1.00 | 0.00 |
| ATOM | 133 | CZ | ARG | 242 | 18.839 | 26.785 | 98.163 | 1.00 | 22.81 |
| ATOM | 134 | NH1 | ARG | 242 | 19.200 | 27.604 | 97.196 | 1.00 | 24.25 |
| ATOM | 135 | HH11 | ARG | 242 | 19.938 | 27.350 | 96.556 | 1.00 | 0.00 |
| ATOM | 136 | HH12 | ARG | 242 | 18.738 | 28.483 | 97.077 | 1.00 | 0.00 |
| ATOM | 137 | NH2 | ARG | 242 | 17.833 | 27.107 | 98.950 | 1.00 | 21.93 |
| ATOM | 138 | HH21 | ARG | 242 | 17.519 | 26.453 | 99.652 | 1.00 | 0.00 |
| ATOM | 139 | HH22 | ARG | 242 | 17.361 | 27.974 | 98.839 | 1.00 | 0.00 |
| ATOM | 140 | C | ARG | 242 | 19.859 | 21.913 | 94.552 | 1.00 | 18.84 |
| ATOM | 141 | O | ARG | 242 | 20.876 | 22.362 | 94.071 | 1.00 | 17.20 |
| ATOM | 142 | N | GLU | 243 | 19.685 | 20.617 | 94.796 | 1.00 | 19.60 |
| ATOM | 143 | H | GLU | 243 | 18.834 | 20.321 | 95.191 | 1.00 | 0.00 |
| ATOM | 144 | CA | GLU | 243 | 20.725 | 19.604 | 94.542 | 1.00 | 20.30 |
| ATOM | 145 | CB | GLU | 243 | 20.304 | 18.220 | 95.132 | 1.00 | 21.75 |
| ATOM | 146 | CG | GLU | 243 | 20.072 | 18.236 | 96.694 | 1.00 | 24.42 |
| ATOM | 147 | CD | GLU | 243 | 18.720 | 18.816 | 97.112 | 1.00 | 24.58 |
| ATOM | 148 | OE1 | GLU | 243 | 17.820 | 18.956 | 96.250 | 1.00 | 27.17 |
| ATOM | 149 | OE2 | GLU | 243 | 18.559 | 19.103 | 98.320 | 1.00 | 27.42 |
| ATOM | 150 | C | GLU | 243 | 21.055 | 19.472 | 93.031 | 1.00 | 19.51 |
| ATOM | 151 | O | GLU | 243 | 22.072 | 18.872 | 92.637 | 1.00 | 18.63 |
| ATOM | 152 | N | THR | 244 | 20.193 | 20.019 | 92.172 | 1.00 | 18.99 |
| ATOM | 153 | H | THR | 244 | 19.408 | 20.469 | 92.503 | 1.00 | 0.00 |
| ATOM | 154 | CA | THR | 244 | 20.436 | 19.925 | 90.740 | 1.00 | 18.62 |
| ATOM | 155 | CB | THR | 244 | 19.181 | 20.201 | 89.949 | 1.00 | 18.76 |
| ATOM | 156 | OG1 | THR | 244 | 18.738 | 21.553 | 90.197 | 1.00 | 19.20 |
| ATOM | 157 | HG1 | THR | 244 | 19.416 | 22.161 | 89.904 | 1.00 | 0.00 |
| ATOM | 158 | CG2 | THR | 244 | 18.071 | 19.247 | 90.306 | 1.00 | 18.42 |
| ATOM | 159 | C | THR | 244 | 21.488 | 20.951 | 90.315 | 1.00 | 18.40 |
| ATOM | 160 | O | THR | 244 | 21.956 | 20.926 | 89.166 | 1.00 | 18.16 |
| ATOM | 161 | N | LEU | 245 | 21.917 | 21.817 | 91.239 | 1.00 | 17.97 |
| ATOM | 162 | H | LEU | 245 | 21.573 | 21.739 | 92.152 | 1.00 | 0.00 |
| ATOM | 163 | CA | LEU | 245 | 22.841 | 22.876 | 90.889 | 1.00 | 17.92 |
| ATOM | 164 | CB | LEU | 245 | 22.187 | 24.239 | 91.182 | 1.00 | 18.16 |
| ATOM | 165 | CG | LEU | 245 | 20.835 | 24.509 | 90.508 | 1.00 | 17.74 |
| ATOM | 166 | CD1 | LEU | 245 | 20.064 | 25.581 | 91.285 | 1.00 | 17.10 |
| ATOM | 167 | CD2 | LEU | 245 | 21.049 | 24.956 | 89.057 | 1.00 | 17.77 |
| ATOM | 168 | C | LEU | 245 | 24.172 | 22.835 | 91.515 | 1.00 | 18.40 |
| ATOM | 169 | O | LEU | 245 | 24.323 | 22.497 | 92.689 | 1.00 | 18.77 |
| ATOM | 170 | N | LYS | 246 | 25.187 | 23.095 | 90.708 | 1.00 | 18.18 |
| ATOM | 171 | H | LYS | 246 | 25.012 | 23.183 | 89.763 | 1.00 | 0.00 |
| ATOM | 172 | CA | LYS | 246 | 26.544 | 23.166 | 91.220 | 1.00 | 19.19 |
| ATCM | 173 | CB | LYS | 246 | 27.470 | 22.154 | 90.591 | 1.00 | 20.06 |
| ATOM | 174 | CG | LYS | 246 | 28.908 | 22.308 | 91.131 | 1.00 | 23.43 |
| ATOM | 175 | CD | LYS | 246 | 29.943 | 21.640 | 90.210 | 1.00 | 26.42 |
| ATOM | 176 | CE | LYS | 246 | 31.312 | 21.484 | 90.889 | 1.00 | 28.37 |
| ATOM | 177 | NZ | LYS | 246 | 32.167 | 20.565 | 90.010 | 1.00 | 29.77 |
| ATOM | 178 | HZ1 | LYS | 246 | 32.294 | 20.975 | 89.090 | 1.00 | 0.00 |
| ATOM | 179 | HZ2 | LYS | 246 | 31.720 | 19.635 | 89.963 | 1.00 | 0.00 |
| ATOM | 180 | HZ3 | LYS | 246 | 33.108 | 20.458 | 90.488 | 1.00 | 0.00 |
| ATOM | 181 | C | LYS | 246 | 26.988 | 24.581 | 90.830 | 1.00 | 18.35 |
| ATOM | 182 | O | LYS | 246 | 27.019 | 24.917 | 89.654 | 1.00 | 18.30 |
| ATOM | 183 | N | LEU | 247 | 27.311 | 25.415 | 91.817 | 0.60 | 17.21 |
| ATOM | 184 | H | LEU | 247 | 27.194 | 25.107 | 92.746 | 1.00 | 0.00 |
| ATOM | 185 | CA | LEU | 247 | 27.795 | 26.780 | 91.556 | 0.60 | 16.60 |
| ATOM | 186 | CB | LEU | 247 | 27.346 | 27.740 | 92.668 | 0.60 | 15.40 |
| ATOM | 187 | CG | LEU | 247 | 25.868 | 28.181 | 92.634 | 0.60 | 14.58 |
| ATOM | 188 | CD1 | LEU | 247 | 24.866 | 27.032 | 92.617 | 0.60 | 14.79 |
| ATOM | 189 | CD2 | LEU | 247 | 25.619 | 29.047 | 93.852 | 0.60 | 14.38 |
| ATOM | 190 | C | LEU | 247 | 29.309 | 26.703 | 91.391 | 0.60 | 16.87 |
| ATOM | 191 | O | LEU | 247 | 30.031 | 26.245 | 92.266 | 0.60 | 16.66 |
| ATOM | 192 | N | VAL | 248 | 29.804 | 27.212 | 90.269 | 1.00 | 18.21 |
| ATOM | 193 | H | VAL | 248 | 29.228 | 27.693 | 89.652 | 1.00 | 0.00 |
| ATOM | 194 | CA | VAL | 248 | 31.224 | 27.062 | 89.967 | 1.00 | 19.40 |
| ATOM | 195 | CB | VAL | 248 | 31.404 | 26.400 | 88.558 | 1.00 | 19.30 |
| ATOM | 196 | CG1 | VAL | 248 | 32.856 | 26.357 | 88.176 | 1.00 | 22.10 |
| ATOM | 197 | CG2 | VAL | 248 | 30.887 | 24.987 | 88.600 | 1.00 | 19.06 |
| ATOM | 198 | C | VAL | 248 | 32.119 | 28.285 | 90.065 | 1.00 | 20.08 |
| ATOM | 199 | O | VAL | 248 | 33.182 | 28.187 | 90.642 | 1.00 | 19.92 |
| ATOM | 200 | N | GLU | 249 | 31.668 | 29.402 | 89.489 | 1.00 | 20.82 |
| ATOM | 201 | H | GLU | 249 | 30.815 | 29.403 | 89.044 | 1.00 | 0.00 |
| ATOM | 202 | CA | GLU | 249 | 32.496 | 30.579 | 89.478 | 1.00 | 21.74 |
| ATOM | 203 | CB | GLU | 249 | 33.167 | 30.702 | 88.121 | 1.00 | 22.95 |
| ATOM | 204 | CG | GLU | 249 | 34.045 | 31.911 | 87.972 | 1.00 | 25.43 |
| ATOM | 205 | CD | GLU | 249 | 34.469 | 32.209 | 86.538 | 1.00 | 27.71 |

TABLE 5-continued

Coordinates of Lck bound with baicalein

| | | Atom Type | Res | # | X | Y | Z | Occ | B |
|---|---|---|---|---|---|---|---|---|---|
| ATOM | 206 | OE1 | GLU | 249 | 34.186 | 31.389 | 85.622 | 1.00 | 29.65 |
| ATOM | 207 | OE2 | GLU | 249 | 35.019 | 33.320 | 86.326 | 1.00 | 27.90 |
| ATOM | 208 | C | GLU | 249 | 31.624 | 31.807 | 89.766 | 1.00 | 22.07 |
| ATOM | 209 | O | GLU | 249 | 30.568 | 32.001 | 89.179 | 1.00 | 22.57 |
| ATOM | 210 | N | ARG | 250 | 32.032 | 32.615 | 90.731 | 1.00 | 22.30 |
| ATOM | 211 | H | ARG | 250 | 32.820 | 32.377 | 91.280 | 1.00 | 0.00 |
| ATOM | 212 | CA | ARG | 250 | 31.264 | 33.807 | 91.028 | 1.00 | 22.78 |
| ATOM | 213 | CB | ARG | 250 | 31.425 | 34.258 | 92.464 | 1.00 | 23.48 |
| ATOM | 214 | CG | ARG | 250 | 30.432 | 35.402 | 92.790 | 1.00 | 27.50 |
| ATOM | 215 | CD | ARG | 250 | 30.544 | 35.922 | 94.205 | 1.00 | 30.10 |
| ATOM | 216 | NE | ARG | 250 | 31.919 | 35.874 | 94.660 | 1.00 | 32.45 |
| ATOM | 217 | HE | ARG | 250 | 32.568 | 35.397 | 94.100 | 1.00 | 0.00 |
| ATOM | 218 | CZ | ARG | 250 | 32.373 | 36.415 | 95.784 | 1.00 | 35.24 |
| ATOM | 219 | NH1 | ARG | 250 | 31.560 | 37.103 | 96.590 | 1.00 | 34.99 |
| ATOM | 220 | HH11 | ARG | 250 | 30.592 | 37.215 | 96.350 | 1.00 | 0.00 |
| ATOM | 221 | HH12 | ARG | 250 | 31.914 | 37.518 | 97.425 | 1.00 | 0.00 |
| ATOM | 222 | NH2 | ARG | 250 | 33.627 | 36.135 | 96.169 | 1.00 | 36.41 |
| ATOM | 223 | HH21 | ARG | 250 | 34.184 | 35.516 | 95.629 | 1.00 | 0.00 |
| ATOM | 224 | HH22 | ARG | 250 | 33.978 | 36.538 | 97.014 | 1.00 | 0.00 |
| ATOM | 225 | C | ARG | 250 | 31.620 | 34.893 | 90.027 | 1.00 | 21.50 |
| ATOM | 226 | O | ARG | 250 | 32.784 | 35.157 | 89.765 | 1.00 | 20.89 |
| ATOM | 227 | N | LEU | 251 | 30.586 | 35.400 | 89.368 | 1.00 | 21.67 |
| ATOM | 228 | H | LEU | 251 | 29.701 | 35.056 | 89.534 | 1.00 | 0.00 |
| ATOM | 229 | CA | LEU | 251 | 30.740 | 36.422 | 88.332 | 1.00 | 21.85 |
| ATOM | 230 | CB | LEU | 251 | 29.712 | 36.214 | 87.225 | 1.00 | 20.09 |
| ATOM | 231 | CG | LEU | 251 | 29.789 | 34.823 | 86.606 | 1.00 | 18.17 |
| ATOM | 232 | CD1 | LEU | 251 | 28.744 | 34.740 | 85.572 | 1.00 | 17.75 |
| ATOM | 233 | CD2 | LEU | 251 | 31.196 | 34.553 | 86.041 | 1.00 | 18.47 |
| ATOM | 234 | C | LEU | 251 | 30.536 | 37.785 | 88.894 | 1.00 | 23.03 |
| ATOM | 235 | O | LEU | 251 | 31.095 | 38.757 | 88.384 | 1.00 | 24.26 |
| ATOM | 236 | N | GLY | 252 | 29.707 | 37.859 | 89.924 | 1.00 | 23.64 |
| ATOM | 237 | H | GLY | 252 | 29.281 | 37.023 | 90.276 | 1.00 | 0.00 |
| ATOM | 238 | CA | GLY | 252 | 29.408 | 39.124 | 90.536 | 1.00 | 23.72 |
| ATOM | 239 | C | GLY | 252 | 28.865 | 39.031 | 91.928 | 1.00 | 23.97 |
| ATOM | 240 | O | GLY | 252 | 28.279 | 38.021 | 92.336 | 1.00 | 23.90 |
| ATOM | 241 | N | ALA | 253 | 29.083 | 40.110 | 92.671 | 1.00 | 24.45 |
| ATOM | 242 | H | ALA | 253 | 29.577 | 40.841 | 92.281 | 1.00 | 0.00 |
| ATOM | 243 | CA | ALA | 253 | 28.624 | 40.205 | 94.054 | 1.00 | 25.38 |
| ATOM | 244 | CB | ALA | 253 | 29.667 | 39.731 | 95.030 | 1.00 | 25.25 |
| ATOM | 245 | C | ALA | 253 | 28.205 | 41.626 | 94.388 | 1.00 | 25.55 |
| ATOM | 246 | O | ALA | 253 | 28.875 | 42.607 | 94.045 | 1.00 | 25.34 |
| ATOM | 247 | N | GLY | 254 | 27.054 | 41.717 | 95.025 | 1.00 | 26.07 |
| ATOM | 248 | H | GLY | 254 | 26.565 | 40.923 | 95.250 | 1.00 | 0.00 |
| ATOM | 249 | CA | GLY | 254 | 26.537 | 43.015 | 95.362 | 1.00 | 27.08 |
| ATOM | 250 | C | GLY | 254 | 25.754 | 42.925 | 96.632 | 1.00 | 27.49 |
| ATOM | 251 | O | GLY | 254 | 25.682 | 41.932 | 97.338 | 1.00 | 28.27 |
| ATOM | 252 | N | GLN | 255 | 25.121 | 44.029 | 96.897 | 1.00 | 28.14 |
| ATOM | 253 | H | GLN | 255 | 25.187 | 44.782 | 96.274 | 1.00 | 0.00 |
| ATOM | 254 | CA | GLN | 255 | 24.299 | 44.217 | 98.081 | 1.00 | 28.55 |
| ATOM | 255 | CB | GLN | 255 | 23.729 | 45.576 | 97.929 | 1.00 | 28.83 |
| ATOM | 256 | CG | GLN | 255 | 23.066 | 46.194 | 99.077 | 1.00 | 29.64 |
| ATOM | 257 | CD | GLN | 255 | 22.802 | 47.613 | 98.707 | 1.00 | 30.95 |
| ATOM | 258 | OE1 | GLN | 255 | 22.077 | 48.293 | 99.391 | 1.00 | 32.21 |
| ATOM | 259 | NE2 | GLN | 255 | 23.386 | 48.066 | 97.593 | 1.00 | 30.41 |
| ATOM | 260 | HE21 | GLN | 255 | 23.973 | 47.453 | 97.054 | 1.00 | 0.00 |
| ATOM | 261 | HE22 | GLN | 255 | 23.260 | 48.977 | 97.326 | 1.00 | 0.00 |
| ATOM | 262 | C | GLN | 255 | 23.134 | 43.265 | 98.190 | 1.00 | 28.71 |
| ATOM | 263 | O | GLN | 255 | 22.720 | 42.897 | 99.294 | 1.00 | 28.59 |
| ATOM | 264 | N | PHE | 256 | 22.545 | 42.940 | 97.044 | 1.00 | 28.02 |
| ATOM | 265 | H | PHE | 256 | 22.911 | 43.281 | 96.199 | 1.00 | 0.00 |
| ATOM | 266 | CA | PHE | 256 | 21.365 | 42.079 | 97.041 | 1.00 | 27.76 |
| ATOM | 267 | CB | PHE | 256 | 20.401 | 42.613 | 95.999 | 1.00 | 28.05 |
| ATOM | 268 | CG | PHE | 256 | 20.118 | 44.059 | 96.183 | 1.00 | 27.98 |
| ATOM | 269 | CD1 | PHE | 256 | 19.483 | 44.504 | 97.327 | 1.00 | 27.38 |
| ATOM | 270 | CD2 | PHE | 256 | 20.527 | 44.999 | 95.223 | 1.00 | 27.60 |
| ATOM | 271 | CE1 | PHE | 256 | 19.238 | 45.873 | 97.535 | 1.00 | 27.75 |
| ATOM | 272 | CE2 | PHE | 256 | 20.287 | 46.359 | 95.423 | 1.00 | 27.88 |
| ATOM | 273 | CZ | PHE | 256 | 19.648 | 46.791 | 96.560 | 1.00 | 27.42 |
| ATOM | 274 | C | PHE | 256 | 21.734 | 40.652 | 96.761 | 1.00 | 27.16 |
| ATOM | 275 | O | PHE | 256 | 20.846 | 39.822 | 96.613 | 1.00 | 26.88 |
| ATOM | 276 | N | GLY | 257 | 23.037 | 40.409 | 96.662 | 1.00 | 27.06 |
| ATOM | 277 | H | GLY | 257 | 23.674 | 41.159 | 96.692 | 1.00 | 0.00 |
| ATOM | 278 | CA | GLY | 257 | 23.457 | 39.087 | 96.441 | 1.00 | 27.21 |
| ATOM | 279 | C | GLY | 257 | 24.524 | 38.868 | 95.426 | 1.00 | 26.72 |

TABLE 5-continued

Coordinates of Lck bound with baicalein

| | Atom Type | Res | # | X | Y | Z | Occ | B |
|---|---|---|---|---|---|---|---|---|
| ATOM | 280 | O | GLY | 257 | 25.272 | 39.805 | 95.052 | 1.00 | 26.35 |
| ATOM | 281 | N | GLU | 258 | 24.661 | 37.599 | 95.025 | 1.00 | 25.36 |
| ATOM | 282 | H | GLU | 258 | 24.065 | 36.942 | 95.471 | 1.00 | 0.00 |
| ATOM | 283 | CA | GLU | 258 | 25.660 | 37.202 | 94.075 | 1.00 | 24.17 |
| ATOM | 284 | CB | GLU | 258 | 26.726 | 36.305 | 94.749 | 1.00 | 26.35 |
| ATOM | 285 | CG | GLU | 258 | 26.727 | 36.179 | 96.311 | 1.00 | 30.37 |
| ATOM | 286 | CD | GLU | 258 | 27.962 | 35.427 | 96.813 | 1.00 | 31.55 |
| ATOM | 287 | OE1 | GLU | 258 | 28.994 | 36.071 | 97.039 | 1.00 | 34.39 |
| ATOM | 288 | OE2 | GLU | 258 | 27.910 | 34.193 | 96.903 | 1.00 | 32.88 |
| ATOM | 289 | C | GLU | 258 | 25.094 | 36.561 | 92.784 | 1.00 | 21.78 |
| ATOM | 290 | O | GLU | 258 | 23.912 | 36.202 | 92.719 | 1.00 | 20.75 |
| ATOM | 291 | N | VAL | 259 | 25.948 | 36.508 | 91.753 | 0.77 | 19.03 |
| ATOM | 292 | H | VAL | 259 | 26.785 | 36.942 | 91.858 | 1.00 | 0.00 |
| ATOM | 293 | CA | VAL | 259 | 25.639 | 35.875 | 90.445 | 0.77 | 16.94 |
| ATOM | 294 | CB | VAL | 259 | 25.605 | 36.909 | 89.235 | 0.77 | 16.26 |
| ATOM | 295 | CG1 | VAL | 259 | 25.352 | 36.133 | 87.889 | 0.77 | 15.81 |
| ATOM | 296 | CG2 | VAL | 259 | 24.499 | 37.924 | 89.442 | 0.77 | 15.45 |
| ATOM | 297 | C | VAL | 259 | 26.804 | 34.912 | 90.146 | 0.77 | 15.94 |
| ATOM | 298 | O | VAL | 259 | 27.974 | 35.279 | 90.153 | 0.77 | 13.35 |
| ATOM | 299 | N | TRP | 260 | 26.446 | 33.685 | 89.813 | 1.00 | 16.61 |
| ATOM | 300 | H | TRP | 260 | 25.504 | 33.427 | 89.741 | 1.00 | 0.00 |
| ATOM | 301 | CA | TRP | 260 | 27.448 | 32.627 | 89.547 | 1.00 | 16.20 |
| ATOM | 302 | CB | TRP | 260 | 27.305 | 31.519 | 90.600 | 1.00 | 17.42 |
| ATOM | 303 | CG | TRP | 260 | 27.724 | 31.913 | 91.968 | 1.00 | 19.64 |
| ATOM | 304 | CD2 | TRP | 260 | 28.854 | 31.425 | 92.668 | 1.00 | 19.75 |
| ATOM | 305 | CE2 | TRP | 260 | 28.864 | 32.048 | 93.934 | 1.00 | 21.37 |
| ATOM | 306 | CE3 | TRP | 260 | 29.862 | 30.504 | 92.354 | 1.00 | 20.56 |
| ATOM | 307 | CD1 | TRP | 260 | 27.105 | 32.801 | 92.808 | 1.00 | 20.64 |
| ATOM | 308 | NE1 | TRP | 260 | 27.788 | 32.892 | 93.986 | 1.00 | 20.42 |
| ATOM | 309 | HE1 | TRP | 260 | 27.536 | 33.451 | 94.749 | 1.00 | 0.00 |
| ATOM | 310 | CZ2 | TRP | 260 | 29.842 | 31.778 | 94.898 | 1.00 | 22.04 |
| ATOM | 311 | CZ3 | TRP | 260 | 30.848 | 30.226 | 93.313 | 1.00 | 22.26 |
| ATOM | 312 | CH2 | TRP | 260 | 30.830 | 30.861 | 94.567 | 1.00 | 22.87 |
| ATOM | 313 | C | TRP | 260 | 27.285 | 31.936 | 88.225 | 1.00 | 15.69 |
| ATOM | 314 | O | TRP | 260 | 26.201 | 31.911 | 87.638 | 1.00 | 15.48 |
| ATOM | 315 | N | MET | 261 | 28.367 | 31.401 | 87.715 | 1.00 | 15.54 |
| ATOM | 316 | H | MET | 261 | 29.250 | 31.641 | 88.085 | 1.00 | 0.00 |
| ATOM | 317 | CA | MET | 261 | 28.265 | 30.518 | 86.560 | 1.00 | 15.97 |
| ATOM | 318 | CB | MET | 261 | 29.536 | 30.576 | 85.710 | 1.00 | 16.61 |
| ATOM | 319 | CG | MET | 261 | 29.540 | 29.560 | 84.502 | 1.00 | 16.94 |
| ATOM | 320 | SD | MET | 261 | 30.046 | 27.910 | 84.960 | 1.00 | 18.08 |
| ATOM | 321 | CE | MET | 261 | 31.754 | 28.160 | 85.189 | 1.00 | 16.48 |
| ATOM | 322 | C | MET | 261 | 28.175 | 29.161 | 87.280 | 1.00 | 14.62 |
| ATOM | 323 | O | MET | 261 | 28.829 | 28.975 | 88.297 | 1.00 | 14.27 |
| ATOM | 324 | N | GLY | 262 | 27.299 | 28.280 | 86.813 | 1.00 | 14.08 |
| ATOM | 325 | H | GLY | 262 | 26.759 | 28.483 | 86.021 | 1.00 | 0.00 |
| ATOM | 326 | CA | GLY | 262 | 27.175 | 26.957 | 87.422 | 1.00 | 14.16 |
| ATOM | 327 | C | GLY | 262 | 26.638 | 25.945 | 86.430 | 1.00 | 14.28 |
| ATOM | 328 | O | GLY | 262 | 26.485 | 26.284 | 85.254 | 1.00 | 14.04 |
| ATOM | 329 | N | TYR | 263 | 26.370 | 24.722 | 86.888 | 1.00 | 13.70 |
| ATOM | 330 | H | TYR | 263 | 26.543 | 24.523 | 87.827 | 1.00 | 0.00 |
| ATOM | 331 | CA | TYR | 263 | 25.854 | 23.673 | 86.025 | 1.00 | 13.56 |
| ATOM | 332 | CB | TYR | 263 | 26.879 | 22.576 | 85.855 | 1.00 | 14.70 |
| ATOM | 333 | CG | TYR | 263 | 28.044 | 23.035 | 85.066 | 1.00 | 16.76 |
| ATOM | 334 | CD1 | TYR | 263 | 28.005 | 22.986 | 83.664 | 1.00 | 18.68 |
| ATOM | 335 | CE1 | TYR | 263 | 29.050 | 23.425 | 82.908 | 1.00 | 20.16 |
| ATOM | 336 | CD2 | TYR | 263 | 29.164 | 23.544 | 85.684 | 1.00 | 17.71 |
| ATOM | 337 | CE2 | TYR | 263 | 30.250 | 23.998 | 84.922 | 1.00 | 18.84 |
| ATOM | 338 | CZ | TYR | 263 | 30.182 | 23.944 | 83.550 | 1.00 | 20.56 |
| ATOM | 339 | OH | TYR | 263 | 31.234 | 24.394 | 82.762 | 1.00 | 22.19 |
| ATOM | 340 | HH | TYR | 263 | 31.913 | 24.753 | 83.335 | 1.00 | 0.00 |
| ATOM | 341 | C | TYR | 263 | 24.576 | 23.072 | 86.592 | 1.00 | 13.20 |
| ATOM | 342 | O | TYR | 263 | 24.451 | 22.889 | 87.792 | 1.00 | 12.79 |
| ATOM | 343 | N | TYR | 264 | 23.609 | 22.845 | 85.716 | 1.00 | 13.60 |
| ATOM | 344 | H | TYR | 264 | 23.712 | 23.168 | 84.804 | 1.00 | 0.00 |
| ATOM | 345 | CA | TYR | 264 | 22.349 | 22.231 | 86.106 | 1.00 | 15.04 |
| ATOM | 346 | CB | TYR | 264 | 21.141 | 22.897 | 85.441 | 1.00 | 15.36 |
| ATOM | 347 | CG | TYR | 264 | 19.851 | 22.111 | 85.601 | 1.00 | 16.22 |
| ATOM | 348 | CD1 | TYR | 264 | 19.092 | 22.208 | 86.776 | 1.00 | 16.16 |
| ATOM | 349 | CE1 | TYR | 264 | 17.914 | 21.446 | 86.952 | 1.00 | 16.83 |
| ATOM | 350 | CD2 | TYR | 264 | 19.393 | 21.228 | 84.567 | 1.00 | 16.68 |
| ATOM | 351 | CE2 | TYR | 264 | 18.208 | 20.471 | 84.751 | 1.00 | 16.67 |
| ATOM | 352 | CZ | TYR | 264 | 17.482 | 20.579 | 85.933 | 1.00 | 17.12 |
| ATOM | 353 | OH | TYR | 264 | 16.383 | 19.827 | 86.164 | 1.00 | 17.80 |

TABLE 5-continued

Coordinates of Lck bound with baicalein

| | | Atom Type | Res | # | X | Y | Z | Occ | B |
|---|---|---|---|---|---|---|---|---|---|
| ATOM | 354 | HH | TYR | 264 | 16.004 | 20.002 | 87.000 | 1.00 | 0.00 |
| ATOM | 355 | C | TYR | 264 | 22.486 | 20.756 | 85.629 | 1.00 | 15.41 |
| ATOM | 356 | O | TYR | 264 | 22.770 | 20.509 | 84.459 | 1.00 | 13.45 |
| ATOM | 357 | N | ASN | 265 | 22.226 | 19.822 | 86.552 | 1.00 | 16.41 |
| ATOM | 358 | H | ASN | 265 | 21.985 | 20.109 | 87.454 | 1.00 | 0.00 |
| ATOM | 359 | CA | ASN | 265 | 22.301 | 18.407 | 86.278 | 1.00 | 17.04 |
| ATOM | 360 | CB | ASN | 265 | 21.059 | 17.919 | 85.463 | 1.00 | 19.42 |
| ATOM | 361 | CG | ASN | 265 | 19.867 | 17.653 | 86.347 | 1.00 | 20.60 |
| ATOM | 362 | OD1 | ASN | 265 | 18.869 | 17.109 | 85.902 | 1.00 | 24.45 |
| ATOM | 363 | ND2 | ASN | 265 | 19.980 | 18.009 | 87.621 | 1.00 | 20.00 |
| ATOM | 364 | HD21 | ASN | 265 | 20.806 | 18.395 | 87.946 | 1.00 | 0.00 |
| ATOM | 365 | HD22 | ASN | 265 | 19.212 | 17.816 | 88.196 | 1.00 | 0.00 |
| ATOM | 366 | C | ANS | 265 | 23.603 | 17.965 | 85.627 | 1.00 | 16.04 |
| ATOM | 367 | O | ASN | 265 | 23.602 | 17.246 | 84.619 | 1.00 | 17.31 |
| ATOM | 368 | N | GLY | 266 | 24.688 | 18.508 | 86.135 | 1.00 | 15.75 |
| ATOM | 369 | H | GLY | 266 | 24.501 | 19.058 | 86.775 | 1.00 | 0.00 |
| ATOM | 370 | CA | GLY | 266 | 26.021 | 18.187 | 85.698 | 1.00 | 14.74 |
| ATOM | 371 | C | GLY | 266 | 26.469 | 18.683 | 84.372 | 1.00 | 14.51 |
| ATOM | 372 | O | GLY | 266 | 27.613 | 19.158 | 84.251 | 1.00 | 14.66 |
| ATOM | 373 | N | HIS | 267 | 25.605 | 18.649 | 83.374 | 0.49 | 12.53 |
| ATOM | 374 | H | HIS | 267 | 24.659 | 18.398 | 83.546 | 1.00 | 0.00 |
| ATOM | 375 | CA | HIS | 267 | 26.007 | 19.038 | 82.021 | 0.49 | 1.11 |
| ATOM | 376 | CB | HIS | 267 | 25.625 | 17.863 | 81.050 | 0.49 | 8.96 |
| ATOM | 377 | CG | HIS | 267 | 26.079 | 16.536 | 81.480 | 0.48 | 8.71 |
| ATOM | 378 | CD2 | HIS | 267 | 25.439 | 15.475 | 82.018 | 0.49 | 8.12 |
| ATOM | 379 | ND1 | HIS | 267 | 27.409 | 16.121 | 81.379 | 0.49 | 8.34 |
| ATOM | 380 | HD1 | HIS | 267 | 28.149 | 16.631 | 80.998 | 1.00 | 0.00 |
| ATOM | 381 | CE1 | HIS | 267 | 27.542 | 14.877 | 81.838 | 0.49 | 9.01 |
| ATOM | 382 | NE2 | HIS | 267 | 26.316 | 14.508 | 82.224 | 0.49 | 8.87 |
| ATOM | 383 | HE2 | HIS | 267 | 26.083 | 13.630 | 82.635 | 1.00 | 0.00 |
| ATOM | 384 | C | HIS | 267 | 25.580 | 20.351 | 81.390 | 0.49 | 11.52 |
| ATOM | 385 | O | HIS | 267 | 26.188 | 20.798 | 80.425 | 0.49 | 9.59 |
| ATOM | 386 | N | THR | 268 | 24.630 | 21.041 | 81.994 | 1.00 | 12.84 |
| ATOM | 387 | H | THR | 268 | 24.310 | 20.794 | 82.891 | 1.00 | 0.00 |
| ATOM | 388 | CA | THR | 268 | 24.123 | 22.301 | 81.383 | 1.00 | 13.44 |
| ATOM | 389 | CB | THR | 268 | 22.561 | 22.239 | 81.307 | 1.00 | 14.08 |
| ATOM | 390 | OG1 | THR | 268 | 22.188 | 21.021 | 80.582 | 1.00 | 13.45 |
| ATOM | 391 | HG1 | THR | 268 | 22.532 | 20.276 | 81.070 | 1.00 | 0.00 |
| ATOM | 392 | CG2 | THR | 268 | 21.967 | 23.477 | 80.529 | 1.00 | 12.92 |
| ATOM | 393 | C | THR | 268 | 24.539 | 23.584 | 82.035 | 1.00 | 13.50 |
| ATOM | 394 | O | THR | 268 | 24.197 | 23.892 | 83.163 | 1.00 | 12.72 |
| ATOM | 395 | N | LYS | 269 | 25.247 | 24.401 | 81.297 | 1.00 | 12.85 |
| ATOM | 396 | H | LYS | 269 | 25.447 | 24.144 | 80.336 | 1.00 | 0.00 |
| ATOM | 397 | CA | LYS | 269 | 25.776 | 25.648 | 81.817 | 1.00 | 12.98 |
| ATCM | 398 | CB | LYS | 269 | 26.799 | 26.173 | 80.806 | 1.00 | 15.53 |
| ATOM | 399 | CG | LYS | 269 | 27.789 | 27.092 | 81.414 | 1.00 | 18.34 |
| ATOM | 400 | CD | LYS | 269 | 28.907 | 27.331 | 80.403 | 1.00 | 20.62 |
| ATOM | 401 | CE | LYS | 269 | 30.156 | 27.790 | 81.109 | 1.00 | 22.66 |
| ATOM | 402 | NZ | LYS | 269 | 31.308 | 27.987 | 80.160 | 1.00 | 25.09 |
| ATOM | 403 | HZ1 | LYS | 269 | 31.046 | 28.655 | 79.452 | 1.00 | 0.00 |
| ATOM | 404 | HZ2 | LYS | 269 | 31.492 | 27.047 | 79.710 | 1.00 | 0.00 |
| ATOM | 405 | HZ3 | LYS | 269 | 32.137 | 28.271 | 80.694 | 1.00 | 0.00 |
| ATOM | 406 | C | LYS | 269 | 24.671 | 26.655 | 82.055 | 1.00 | 12.52 |
| ATOM | 407 | O | LYS | 269 | 23.799 | 26.919 | 81.204 | 1.00 | 13.03 |
| ATOM | 408 | N | VAL | 272 | 24.667 | 27.264 | 83.225 | 1.00 | 11.77 |
| ATOM | 409 | H | VAL | 272 | 25.383 | 27.025 | 83.864 | 1.00 | 0.00 |
| ATOM | 410 | CA | VAL | 272 | 23.629 | 28.204 | 83.595 | 1.00 | 10.77 |
| ATOM | 411 | CB | VAL | 272 | 22.489 | 27.529 | 84.421 | 1.00 | 12.38 |
| ATOM | 412 | CG1 | VAL | 272 | 21.805 | 26.412 | 83.572 | 1.00 | 12.23 |
| ATOM | 413 | CG2 | VAL | 272 | 23.062 | 26.886 | 85.763 | 1.00 | 10.39 |
| ATOM | 414 | C | VAL | 272 | 24.173 | 29.339 | 84.442 | 1.00 | 10.82 |
| ATOM | 415 | O | VAL | 272 | 25.272 | 29.261 | 84.980 | 1.00 | 9.60 |
| ATOM | 416 | N | ALA | 273 | 23.440 | 30.453 | 84.462 | 1.00 | 10.55 |
| ATOM | 417 | H | ALA | 273 | 22.677 | 30.523 | 83.855 | 1.00 | 0.00 |
| ATOM | 418 | CA | ALA | 273 | 23.811 | 31.607 | 85.349 | 1.00 | 9.79 |
| ATOM | 419 | CB | ALA | 273 | 23.615 | 32.956 | 84.627 | 1.00 | 10.09 |
| ATOM | 420 | C | ALA | 273 | 22.846 | 31.499 | 86.530 | 1.00 | 10.59 |
| ATOM | 421 | O | ALA | 273 | 21.684 | 31.160 | 86.363 | 1.00 | 9.71 |
| ATOM | 422 | N | VAL | 272 | 23.369 | 31.702 | 87.736 | 1.00 | 12.25 |
| ATOM | 423 | H | VAL | 272 | 24.300 | 31.897 | 87.826 | 1.00 | 0.00 |
| ATOM | 424 | CA | VAL | 272 | 22.552 | 31.581 | 88.973 | 1.00 | 13.38 |
| ATOM | 425 | CB | VAL | 272 | 22.988 | 30.413 | 89.874 | 1.00 | 12.52 |
| ATOM | 426 | CG1 | VAL | 272 | 22.014 | 30.278 | 91.096 | 1.00 | 11.03 |
| ATOM | 427 | CG2 | VAL | 272 | 22.932 | 29.065 | 89.063 | 1.00 | 12.47 |

TABLE 5-continued

Coordinates of Lck bound with baicalein

| | Atom Type | Res | # | X | Y | Z | Occ | B |
|---|---|---|---|---|---|---|---|---|
| ATOM | 428 | C | VAL | 272 | 22.626 | 32.851 | 89.803 | 1.00 | 15.51 |
| ATOM | 429 | O | VAL | 272 | 23.706 | 33.328 | 90.138 | 1.00 | 16.68 |
| ATOM | 430 | N | LYS | 273 | 21.478 | 33.484 | 90.002 | 1.00 | 17.12 |
| ATOM | 431 | H | LYS | 273 | 20.651 | 33.138 | 89.587 | 1.00 | 0.00 |
| ATOM | 432 | CA | LYS | 273 | 21.450 | 34.721 | 90.788 | 1.00 | 18.45 |
| ATOM | 433 | CB | LYS | 273 | 20.639 | 35.815 | 90.095 | 1.00 | 20.94 |
| ATOM | 434 | CG | LYS | 273 | 20.487 | 37.006 | 91.002 | 1.00 | 24.90 |
| ATOM | 435 | CD | LYS | 273 | 20.284 | 38.296 | 90.245 | 1.00 | 28.50 |
| ATOM | 436 | CE | LYS | 273 | 18.974 | 38.278 | 89.464 | 1.00 | 29.47 |
| ATOM | 437 | NZ | LYS | 273 | 18.631 | 39.663 | 89.047 | 1.00 | 29.42 |
| ATOM | 438 | HZ1 | LYS | 273 | 19.400 | 40.037 | 88.466 | 1.00 | 0.00 |
| ATOM | 439 | HZ2 | LYS | 273 | 18.521 | 40.244 | 89.904 | 1.00 | 0.00 |
| ATOM | 440 | HZ3 | LYS | 273 | 17.749 | 39.643 | 88.516 | 1.00 | 0.00 |
| ATOM | 441 | C | LYS | 273 | 20.831 | 34.367 | 92.131 | 1.00 | 17.40 |
| ATOM | 442 | O | LYS | 273 | 19.722 | 33.864 | 92.200 | 1.00 | 17.27 |
| ATOM | 443 | N | SER | 274 | 21.584 | 34.613 | 93.195 | 0.65 | 16.17 |
| ATOM | 444 | H | SER | 274 | 22.478 | 34.991 | 93.070 | 1.00 | 0.00 |
| ATOM | 445 | CA | SER | 274 | 21.147 | 34.272 | 94.546 | 0.65 | 16.14 |
| ATOM | 446 | CB | SER | 274 | 22.251 | 33.517 | 95.299 | 0.65 | 15.87 |
| ATOM | 447 | OG | SER | 274 | 23.419 | 34.316 | 95.446 | 0.65 | 14.96 |
| ATOM | 448 | HG | SER | 274 | 23.191 | 35.116 | 95.962 | 1.00 | 0.00 |
| ATOM | 449 | C | SER | 274 | 20.804 | 35.514 | 95.303 | 0.65 | 16.78 |
| ATOM | 450 | O | SER | 274 | 21.523 | 36.501 | 95.245 | 0.65 | 15.25 |
| ATOM | 451 | N | LEU | 275 | 19.746 | 35.436 | 96.097 | 1.00 | 18.97 |
| ATOM | 452 | H | LEU | 275 | 19.235 | 34.587 | 96.150 | 1.00 | 0.00 |
| ATOM | 453 | CA | LEU | 275 | 19.292 | 36.581 | 96.902 | 1.00 | 21.30 |
| ATOM | 454 | CB | LEU | 275 | 17.759 | 36.635 | 97.007 | 1.00 | 21.14 |
| ATOM | 455 | CG | LEU | 275 | 17.128 | 37.612 | 98.017 | 1.00 | 20.80 |
| ATOM | 456 | CD1 | LEU | 275 | 17.485 | 39.055 | 97.747 | 1.00 | 18.95 |
| ATOM | 457 | CD2 | LEU | 275 | 15.596 | 37.413 | 98.017 | 1.00 | 21.37 |
| ATOM | 458 | C | LEU | 275 | 19.877 | 36.563 | 98.295 | 1.00 | 22.89 |
| ATOM | 459 | O | LEU | 275 | 19.808 | 35.549 | 99.032 | 1.00 | 23.83 |
| ATOM | 460 | N | LYS | 276 | 20.467 | 37.683 | 98.663 | 1.00 | 23.69 |
| ATOM | 461 | H | LYS | 276 | 20.545 | 38.414 | 97.989 | 1.00 | 0.00 |
| ATOM | 462 | CA | LYS | 276 | 21.056 | 37.852 | 99.977 | 1.00 | 25.48 |
| ATOM | 463 | CB | LYS | 276 | 21.926 | 39.130 | 99.991 | 1.00 | 26.00 |
| ATOM | 464 | CG | LYS | 276 | 22.439 | 39.405 | 101.374 | 1.00 | 27.43 |
| ATOM | 465 | CD | LYS | 276 | 23.445 | 40.490 | 101.336 | 1.00 | 28.67 |
| ATOM | 466 | CE | LYS | 276 | 24.072 | 40.620 | 102.708 | 1.00 | 30.90 |
| ATOM | 467 | NZ | LYS | 276 | 25.304 | 41.463 | 102.651 | 1.00 | 31.22 |
| ATOM | 468 | HZ1 | LYS | 276 | 25.040 | 42.403 | 102.318 | 1.00 | 0.00 |
| ATOM | 469 | HZ2 | LYS | 276 | 25.980 | 41.024 | 101.996 | 1.00 | 0.00 |
| ATOM | 470 | HZ3 | LYS | 276 | 25.717 | 41.517 | 103.600 | 1.00 | 0.00 |
| ATOM | 471 | C | LYS | 276 | 19.959 | 37.999 | 100.995 | 1.00 | 25.96 |
| ATOM | 472 | O | LYS | 276 | 19.258 | 39.007 | 101.017 | 1.00 | 26.01 |
| ATOM | 473 | N | ALA | 277 | 19.750 | 36.966 | 101.802 | 1.00 | 27.37 |
| ATOM | 474 | H | ALA | 277 | 20.339 | 36.158 | 101.723 | 1.00 | 0.00 |
| ATOM | 475 | CA | ALA | 277 | 18.668 | 36.936 | 102.784 | 1.00 | 28.79 |
| ATOM | 476 | CB | ALA | 277 | 18.745 | 35.712 | 103.678 | 1.00 | 28.67 |
| ATOM | 477 | C | ALA | 277 | 18.689 | 38.187 | 103.599 | 1.00 | 29.45 |
| ATOM | 478 | O | ALA | 277 | 19.701 | 38.555 | 104.199 | 1.00 | 30.76 |
| ATOM | 479 | N | GLY | 278 | 17.567 | 38.896 | 103.557 | 1.00 | 29.65 |
| ATOM | 480 | H | GLY | 278 | 16.881 | 38.521 | 103.043 | 1.00 | 0.00 |
| ATOM | 481 | CA | GLY | 278 | 17.386 | 40.132 | 104.313 | 1.00 | 28.77 |
| ATOM | 482 | C | GLY | 278 | 17.780 | 41.399 | 103.582 | 1.00 | 28.62 |
| ATOM | 483 | O | GLY | 278 | 17.475 | 42.490 | 104.039 | 1.00 | 28.15 |
| ATOM | 484 | N | SER | 279 | 18.436 | 41.291 | 102.436 | 1.00 | 28.15 |
| ATOM | 485 | H | SER | 279 | 18.650 | 40.408 | 102.065 | 1.00 | 0.00 |
| ATOM | 486 | CA | SER | 279 | 18.851 | 42.517 | 101.731 | 1.00 | 27.01 |
| ATOM | 487 | CB | SER | 279 | 19.936 | 42.179 | 100.736 | 1.00 | 27.49 |
| ATOM | 488 | OG | SER | 279 | 19.420 | 41.370 | 99.681 | 1.00 | 26.83 |
| ATOM | 489 | HG | SER | 279 | 18.735 | 41.844 | 99.224 | 1.00 | 0.00 |
| ATOM | 490 | C | SER | 279 | 17.691 | 43.202 | 101.003 | 1.00 | 26.48 |
| ATOM | 491 | O | SER | 279 | 17.781 | 44.358 | 100.616 | 1.00 | 27.62 |
| ATOM | 492 | N | MET | 280 | 16.646 | 42.430 | 100.723 | 1.00 | 26.30 |
| ATOM | 493 | H | MET | 280 | 16.666 | 41.498 | 101.021 | 1.00 | 0.00 |
| ATOM | 494 | CA | MET | 280 | 15.467 | 42.922 | 100.020 | 1.00 | 24.05 |
| ATOM | 495 | CB | MET | 280 | 15.782 | 43.202 | 98.559 | 1.00 | 25.97 |
| ATOM | 496 | CG | MET | 280 | 16.167 | 41.999 | 97.728 | 1.00 | 26.38 |
| ATOM | 497 | SD | MET | 280 | 16.402 | 42.423 | 95.989 | 1.00 | 29.67 |
| ATOM | 498 | CE | MET | 280 | 14.743 | 42.550 | 95.457 | 1.00 | 24.77 |
| ATOM | 499 | C | MET | 280 | 14.387 | 41.846 | 100.119 | 1.00 | 22.57 |
| ATOM | 500 | O | MET | 280 | 14.635 | 40.707 | 100.539 | 1.00 | 21.90 |
| ATOM | 501 | N | SER | 281 | 13.178 | 42.217 | 99.738 | 1.00 | 20.84 |

TABLE 5-continued

Coordinates of Lck bound with baicalein

| | Atom Type | Res | # | X | Y | Z | Occ | B |
|---|---|---|---|---|---|---|---|---|
| ATOM | 502 | H | SER | 281 | 13.028 | 43.132 | 99.443 | 1.00 | 0.00 |
| ATOM | 503 | CA | SER | 281 | 12.051 | 41.295 | 99.801 | 1.00 | 20.06 |
| ATOM | 504 | CB | SER | 281 | 10.779 | 42.042 | 99.416 | 1.00 | 19.81 |
| ATOM | 505 | OG | SER | 281 | 9.677 | 41.168 | 99.265 | 1.00 | 18.76 |
| ATOM | 506 | HG | SER | 281 | 9.923 | 40.531 | 98.536 | 1.00 | 0.00 |
| ATOM | 507 | C | SER | 281 | 12.198 | 40.085 | 98.849 | 1.00 | 19.13 |
| ATOM | 508 | O | SER | 281 | 12.534 | 40.255 | 97.665 | 1.00 | 19.84 |
| ATOM | 509 | N | PRO | 282 | 11.901 | 38.876 | 99.352 | 0.51 | 17.18 |
| ATOM | 510 | CD | PRO | 282 | 11.451 | 38.518 | 100.707 | 0.51 | 16.30 |
| ATOM | 511 | CA | PRO | 282 | 12.010 | 37.696 | 98.499 | 0.51 | 16.02 |
| ATOM | 512 | CB | PRO | 282 | 11.739 | 36.528 | 99.468 | 0.51 | 15.24 |
| ATOM | 513 | CG | PRO | 282 | 11.947 | 37.095 | 100.818 | 0.51 | 16.40 |
| ATOM | 514 | C | PRO | 282 | 10.927 | 37.792 | 97.421 | 0.51 | 15.05 |
| ATOM | 515 | O | PRO | 282 | 11.116 | 37.328 | 96.316 | 0.51 | 12.78 |
| ATOM | 516 | N | ASP | 283 | 9.791 | 38.409 | 97.762 | 1.00 | 16.35 |
| ATOM | 517 | H | ASP | 283 | 9.679 | 38.752 | 98.676 | 1.00 | 0.00 |
| ATOM | 518 | CA | ASP | 283 | 8.704 | 38.609 | 96.797 | 1.00 | 17.21 |
| ATOM | 519 | CB | ASP | 283 | 7.464 | 39.155 | 97.448 | 1.00 | 17.95 |
| ATOM | 520 | CG | ASP | 283 | 6.313 | 39.330 | 96.458 | 1.00 | 20.22 |
| ATOM | 521 | OD1 | ASP | 283 | 5.853 | 38.300 | 95.949 | 1.00 | 22.87 |
| ATOM | 522 | OD2 | ASP | 283 | 5.847 | 40.472 | 96.181 | 1.00 | 18.84 |
| ATOM | 523 | C | ASP | 283 | 9.188 | 39.560 | 95.684 | 1.00 | 16.65 |
| ATOM | 524 | O | ASP | 283 | 8.899 | 39.331 | 94.533 | 1.00 | 17.48 |
| ATOM | 525 | N | ALA | 284 | 9.895 | 40.634 | 96.037 | 1.00 | 16.53 |
| ATOM | 526 | H | ALA | 284 | 10.049 | 40.808 | 96.989 | 1.00 | 0.00 |
| ATOM | 527 | CA | ALA | 284 | 10.390 | 41.588 | 95.039 | 1.00 | 17.93 |
| ATOM | 528 | CB | ALA | 284 | 11.102 | 42.783 | 95.735 | 1.00 | 17.26 |
| ATOM | 529 | C | ALA | 284 | 11.401 | 40.878 | 94.148 | 1.00 | 16.92 |
| ATOM | 530 | O | ALA | 284 | 11.407 | 41.074 | 92.945 | 1.00 | 18.69 |
| ATOM | 531 | N | PHE | 285 | 12.299 | 40.112 | 94.768 | 1.00 | 17.37 |
| ATOM | 532 | H | PHE | 285 | 12.261 | 40.033 | 95.746 | 1.00 | 0.00 |
| ATOM | 533 | CA | PHE | 285 | 13.311 | 39.364 | 94.021 | 1.00 | 16.37 |
| ATOM | 534 | CB | PHE | 285 | 14.154 | 38.549 | 95.021 | 1.00 | 15.40 |
| ATOM | 535 | CG | PHE | 285 | 15.287 | 37.782 | 94.372 | 1.00 | 13.88 |
| ATOM | 536 | CD1 | PHE | 285 | 16.437 | 38.438 | 93.961 | 1.00 | 14.15 |
| ATOM | 537 | CD2 | PHE | 285 | 15.206 | 36.379 | 94.204 | 1.00 | 12.32 |
| ATOM | 538 | CE1 | PHE | 285 | 17.522 | 37.696 | 93.385 | 1.00 | 15.15 |
| ATOM | 539 | CE2 | PHE | 285 | 16.245 | 35.668 | 93.657 | 1.00 | 11.99 |
| ATOM | 540 | CZ | PHE | 285 | 17.415 | 36.300 | 93.239 | 1.00 | 11.09 |
| ATOM | 541 | C | PHE | 285 | 12.620 | 38.415 | 92.976 | 1.00 | 15.64 |
| ATOM | 542 | O | PHE | 285 | 12.848 | 38.527 | 91.794 | 1.00 | 16.15 |
| ATOM | 543 | N | LEU | 286 | 11.668 | 37.609 | 93.428 | 1.00 | 16.27 |
| ATOM | 544 | H | LEU | 286 | 11.391 | 37.673 | 94.372 | 1.00 | 0.00 |
| ATOM | 545 | CA | LEU | 286 | 11.021 | 36.608 | 92.575 | 1.00 | 16.17 |
| ATOM | 546 | CB | LEU | 286 | 10.331 | 35.544 | 93.443 | 1.00 | 15.71 |
| ATOM | 547 | CG | LEU | 286 | 11.311 | 34.583 | 94.124 | 1.00 | 15.96 |
| ATOM | 548 | CD1 | LEU | 286 | 10.540 | 33.813 | 95.221 | 1.00 | 14.81 |
| ATOM | 549 | CD2 | LEU | 286 | 11.982 | 33.611 | 93.098 | 1.00 | 13.94 |
| ATOM | 550 | C | LEU | 286 | 10.078 | 37.167 | 91.530 | 1.00 | 16.67 |
| ATOM | 551 | O | LEU | 286 | 9.725 | 36.495 | 90.583 | 1.00 | 17.00 |
| ATOM | 552 | N | ALA | 287 | 9.658 | 38.404 | 91.735 | 1.00 | 16.13 |
| ATOM | 553 | H | ALA | 287 | 9.924 | 38.880 | 92.560 | 1.00 | 0.00 |
| ATOM | 554 | CA | ALA | 287 | 8.770 | 39.060 | 90.795 | 1.00 | 16.30 |
| ATOM | 555 | CB | ALA | 287 | 8.405 | 40.462 | 91.331 | 1.00 | 16.21 |
| ATOM | 556 | C | ALA | 287 | 9.412 | 39.149 | 89.401 | 1.00 | 15.67 |
| ATOM | 557 | O | ALA | 287 | 8.742 | 39.108 | 88.390 | 1.00 | 15.68 |
| ATOM | 558 | N | GLU | 288 | 10.721 | 39.229 | 89.353 | 1.00 | 16.11 |
| ATOM | 559 | H | GLU | 288 | 11.247 | 39.254 | 90.186 | 1.00 | 0.00 |
| ATOM | 560 | CA | GLU | 288 | 11.439 | 39.268 | 88.082 | 1.00 | 16.38 |
| ATOM | 561 | CB | GLU | 288 | 12.939 | 39.535 | 88.283 | 1.00 | 16.79 |
| ATOM | 562 | CG | GLU | 288 | 13.637 | 39.629 | 86.956 | 1.00 | 18.62 |
| ATOM | 563 | CD | GLU | 288 | 15.101 | 39.872 | 87.032 | 1.00 | 19.80 |
| ATOM | 564 | OE1 | GLU | 288 | 15.689 | 39.861 | 88.133 | 1.00 | 21.86 |
| ATOM | 565 | OE2 | GLU | 288 | 15.681 | 40.092 | 85.938 | 1.00 | 20.35 |
| ATOM | 566 | C | GLU | 288 | 11.281 | 37.936 | 87.360 | 1.00 | 16.31 |
| ATOM | 567 | O | GLU | 288 | 10.953 | 37.930 | 86.158 | 1.00 | 14.83 |
| ATOM | 568 | N | ALA | 289 | 11.497 | 36.825 | 88.082 | 1.00 | 16.72 |
| ATOM | 569 | H | ALA | 289 | 11.735 | 36.889 | 89.021 | 1.00 | 0.00 |
| ATOM | 570 | CA | ALA | 289 | 11.357 | 35.479 | 87.489 | 1.00 | 16.71 |
| ATOM | 571 | CB | ALA | 289 | 11.696 | 34.420 | 88.543 | 1.00 | 15.77 |
| ATOM | 572 | C | ALA | 289 | 9.892 | 35.293 | 86.972 | 1.00 | 16.97 |
| ATOM | 573 | O | ALA | 289 | 9.687 | 34.829 | 85.851 | 1.00 | 16.49 |
| ATOM | 574 | N | ASN | 290 | 8.886 | 35.685 | 87.771 | 1.00 | 17.38 |
| ATOM | 575 | H | ASN | 290 | 9.110 | 36.064 | 88.648 | 1.00 | 0.00 |

TABLE 5-continued

Coordinates of Lck bound with baicalein

| | Atom Type | Res | # | X | Y | Z | Occ | B |
|---|---|---|---|---|---|---|---|---|
| ATOM | 576 | CA | ASN | 290 | 7.490 | 35.517 | 87.375 | 1.00 | 19.41 |
| ATOM | 577 | CB | ASN | 290 | 6.549 | 35.996 | 88.493 | 1.00 | 20.04 |
| ATOM | 578 | CG | ASN | 290 | 6.616 | 35.081 | 89.745 | 1.00 | 22.33 |
| ATOM | 579 | OD1 | ASN | 290 | 7.071 | 33.940 | 89.658 | 1.00 | 24.23 |
| ATOM | 580 | ND2 | ASN | 290 | 6.184 | 35.580 | 90.887 | 1.00 | 21.73 |
| ATOM | 581 | HD21 | ASN | 290 | 5.825 | 36.489 | 90.889 | 1.00 | 0.00 |
| ATOM | 582 | HD22 | ASN | 290 | 6.220 | 35.009 | 91.669 | 1.00 | 0.00 |
| ATOM | 583 | C | ASN | 290 | 7.235 | 36.287 | 86.078 | 1.00 | 19.90 |
| ATOM | 584 | O | ASN | 290 | 6.551 | 35.789 | 85.156 | 1.00 | 19.27 |
| ATOM | 585 | N | LEU | 291 | 7.762 | 37.514 | 85.996 | 1.00 | 19.50 |
| ATOM | 586 | H | LEU | 291 | 8.191 | 37.906 | 86.773 | 1.00 | 0.00 |
| ATOM | 587 | CA | LEU | 291 | 7.590 | 38.286 | 84.762 | 1.00 | 19.58 |
| ATOM | 588 | CB | LEU | 291 | 8.162 | 39.708 | 84.918 | 1.00 | 18.90 |
| ATOM | 589 | CG | LEU | 291 | 8.051 | 40.542 | 83.631 | 1.00 | 20.77 |
| ATOM | 590 | CD1 | LEU | 291 | 7.764 | 42.009 | 83.988 | 1.00 | 19.65 |
| ATOM | 591 | CD2 | LEU | 291 | 9.341 | 40.458 | 82.771 | 1.00 | 20.89 |
| ATOM | 592 | C | LEU | 291 | 8.302 | 37.544 | 83.584 | 1.00 | 18.72 |
| ATOM | 593 | O | LEU | 291 | 7.758 | 37.485 | 82.479 | 1.00 | 18.65 |
| ATOM | 594 | N | MET | 292 | 9.513 | 37.029 | 83.807 | 1.00 | 18.30 |
| ATOM | 595 | H | MET | 292 | 9.917 | 37.122 | 84.700 | 1.00 | 0.00 |
| ATOM | 596 | CA | MET | 292 | 10.239 | 36.310 | 82.747 | 1.00 | 19.00 |
| ATOM | 597 | CB | MET | 292 | 11.661 | 35.933 | 83.210 | 1.00 | 18.89 |
| ATOM | 598 | CG | MET | 292 | 12.570 | 37.105 | 83.533 | 1.00 | 17.91 |
| ATOM | 599 | SD | MET | 292 | 14.172 | 36.614 | 84.147 | 1.00 | 17.10 |
| ATOM | 600 | CE | MET | 292 | 14.899 | 35.936 | 82.663 | 1.00 | 17.54 |
| ATOM | 601 | C | MET | 292 | 9.472 | 35.064 | 82.208 | 1.00 | 19.83 |
| ATOM | 602 | O | MET | 292 | 9.638 | 34.704 | 81.050 | 1.00 | 20.73 |
| ATOM | 603 | N | LYS | 293 | 8.595 | 34.464 | 83.018 | 1.00 | 20.97 |
| ATOM | 604 | H | LYS | 293 | 8.480 | 34.758 | 83.935 | 1.00 | 0.00 |
| ATOM | 605 | CA | LYS | 293 | 7.783 | 33.306 | 82.551 | 1.00 | 22.64 |
| ATOM | 606 | CB | LYS | 293 | 6.931 | 32.757 | 83.720 | 1.00 | 21.97 |
| ATOM | 607 | CG | LYS | 293 | 7.760 | 32.228 | 84.880 | 1.00 | 23.84 |
| ATOM | 608 | CD | LYS | 293 | 6.865 | 31.831 | 86.080 | 1.00 | 24.39 |
| ATOM | 609 | CE | LYS | 293 | 7.713 | 31.410 | 87.295 | 1.00 | 25.78 |
| ATOM | 610 | NZ | LYS | 293 | 6.885 | 30.980 | 88.483 | 1.00 | 25.56 |
| ATOM | 611 | HZ1 | LYS | 293 | 6.306 | 30.135 | 88.192 | 1.00 | 0.00 |
| ATOM | 612 | HZ2 | LYS | 293 | 6.254 | 31.732 | 88.768 | 1.00 | 0.GO |
| ATOM | 613 | HZ3 | LYS | 293 | 7.507 | 30.691 | 89.254 | 1.00 | 0.00 |
| ATOM | 614 | C | LYS | 293 | 6.868 | 33.714 | 81.371 | 1.00 | 23.05 |
| ATOM | 615 | O | LYS | 293 | 6.613 | 32.952 | 80.450 | 1.00 | 24.13 |
| ATOM | 616 | N | GLN | 294 | 6.442 | 34.965 | 81.401 | 1.00 | 23.60 |
| ATOM | 617 | H | GLN | 294 | 6.724 | 35.537 | 82.132 | 1.00 | 0.00 |
| ATOM | 618 | CA | GLN | 294 | 5.546 | 35.513 | 80.392 | 1.00 | 24.30 |
| ATOM | 619 | CB | GLN | 294 | 4.702 | 36.629 | 81.026 | 1.00 | 25.39 |
| ATOM | 620 | CG | GLN | 294 | 3.842 | 36.204 | 82.199 | 1.00 | 26.65 |
| ATOM | 621 | CD | GLN | 294 | 3.037 | 34.973 | 81.868 | 1.00 | 28.29 |
| ATOM | 622 | OE1 | GLN | 294 | 2.663 | 34.754 | 80.717 | 1.00 | 31.33 |
| ATOM | 623 | NE2 | GLN | 294 | 2.806 | 34.125 | 82.874 | 1.00 | 28.93 |
| ATOM | 624 | HE21 | GLN | 294 | 3.161 | 34.313 | 83.765 | 1.00 | 0.00 |
| ATOM | 625 | HE22 | GLN | 294 | 2.279 | 33.319 | 82.675 | 1.00 | 0.00 |
| ATOM | 626 | C | GLN | 294 | 6.225 | 36.079 | 79.166 | 1.00 | 23.90 |
| ATOM | 627 | O | GLN | 294 | 5.572 | 36.423 | 78.185 | 1.00 | 25.85 |
| ATOM | 628 | N | LEU | 295 | 7.537 | 36.241 | 79.233 | 1.00 | 22.52 |
| ATOM | 629 | H | LEU | 295 | 8.012 | 36.000 | 80.054 | 1.00 | 0.00 |
| ATOM | 630 | CA | LEU | 295 | 8.265 | 36.885 | 78.147 | 1.00 | 20.10 |
| ATOM | 631 | CB | LEU | 295 | 8.930 | 38.176 | 78.646 | 1.00 | 19.31 |
| ATOM | 632 | CG | LEU | 295 | 8.160 | 39.471 | 78.662 | 1.00 | 19.00 |
| ATOM | 633 | CD1 | LEU | 295 | 9.009 | 40.585 | 79.171 | 1.00 | 18.29 |
| ATOM | 634 | CD2 | LEU | 295 | 7.739 | 39.797 | 77.237 | 1.00 | 18.34 |
| ATOM | 635 | C | LEU | 295 | 9.333 | 35.960 | 77.655 | 1.00 | 19.99 |
| ATOM | 636 | O | LEU | 295 | 10.510 | 36.170 | 77.921 | 1.00 | 20.90 |
| ATOM | 637 | N | GLN | 296 | 8.953 | 35.015 | 76.814 | 1.00 | 18.25 |
| ATOM | 638 | H | GLN | 296 | 8.010 | 34.934 | 76.585 | 1.00 | 0.00 |
| ATOM | 639 | CA | GLN | 296 | 9.922 | 34.071 | 76.323 | 1.00 | 17.16 |
| ATOM | 640 | CB | GLN | 296 | 9.386 | 32.654 | 76.541 | 1.00 | 18.33 |
| ATOM | 641 | CG | GLN | 296 | 9.213 | 32.263 | 78.032 | 1.00 | 20.30 |
| ATOM | 642 | CD | GLN | 296 | 8.762 | 30.839 | 78.185 | 1.00 | 20.23 |
| ATOM | 643 | OE1 | GLN | 296 | 9.265 | 29.955 | 77.504 | 1.00 | 21.93 |
| ATOM | 644 | NE2 | GLN | 296 | 7.776 | 30.608 | 79.056 | 1.00 | 21.82 |
| ATOM | 645 | HE21 | GLN | 296 | 7.383 | 31.322 | 79.562 | 1.00 | 0.00 |
| ATOM | 646 | HE22 | GLN | 296 | 7.472 | 29.658 | 79.149 | 1.00 | 0.00 |
| ATOM | 647 | C | GLN | 296 | 10.139 | 34.374 | 74.840 | 1.00 | 15.96 |
| ATOM | 648 | O | GLN | 296 | 9.187 | 34.455 | 74.094 | 1.00 | 14.79 |
| ATOM | 649 | N | HIS | 297 | 11.402 | 34.527 | 74.445 | 1.00 | 13.60 |

TABLE 5-continued

Coordinates of Lck bound with baicalein

| | | Atom Type | Res | # | X | Y | Z | Occ | B |
|---|---|---|---|---|---|---|---|---|---|
| ATOM | 650 | H | HIS | 297 | 12.087 | 34.511 | 75.106 | 1.00 | 0.00 |
| ATOM | 651 | CA | HIS | 297 | 11.730 | 34.786 | 73.057 | 1.00 | 13.93 |
| ATOM | 652 | CB | HIS | 297 | 11.409 | 36.268 | 72.723 | 1.00 | 12.12 |
| ATOM | 653 | CG | HIS | 297 | 11.471 | 36.587 | 71.255 | 1.00 | 10.19 |
| ATOM | 654 | CD2 | HIS | 297 | 10.494 | 36.709 | 70.339 | 1.00 | 9.51 |
| ATOM | 655 | ND1 | HIS | 297 | 12.664 | 36.863 | 70.608 | 1.00 | 9.84 |
| ATOM | 656 | HD1 | HIS | 297 | 13.526 | 36.855 | 71.021 | 1.00 | 0.00 |
| ATOM | 657 | CE1 | HIS | 297 | 12.404 | 37.160 | 69.348 | 1.00 | 8.40 |
| ATOM | 658 | NE2 | HIS | 297 | 11.107 | 37.082 | 69.140 | 1.00 | 9.47 |
| ATOM | 659 | HE2 | HIS | 297 | 10.653 | 37.218 | 68.293 | 1.00 | 0.00 |
| ATOM | 660 | C | HIS | 297 | 13.206 | 34.518 | 72.848 | 1.00 | 12.98 |
| ATOM | 661 | O | HIS | 297 | 13.984 | 34.737 | 73.783 | 1.00 | 13.27 |
| ATOM | 662 | N | GLN | 298 | 13.621 | 34.102 | 71.651 | 1.00 | 12.33 |
| ATOM | 663 | H | GLN | 298 | 12.945 | 33.904 | 70.951 | 1.00 | 0.00 |
| ATOM | 664 | CA | GLN | 298 | 15.052 | 33.849 | 71.406 | 1.00 | 12.21 |
| ATOM | 665 | CB | GLN | 298 | 15.349 | 33.528 | 69.887 | 1.00 | 11.92 |
| ATOM | 666 | CG | GLN | 298 | 14.993 | 32.144 | 69.402 | 1.00 | 13.23 |
| ATOM | 667 | CD | GLN | 298 | 15.636 | 31.008 | 70.211 | 1.00 | 11.23 |
| ATOM | 668 | OE1 | GLN | 298 | 14.914 | 30.197 | 70.743 | 1.00 | 12.55 |
| ATOM | 669 | NE2 | GLN | 298 | 16.986 | 30.964 | 70.302 | 1.00 | 11.53 |
| ATOM | 670 | HE21 | GLN | 298 | 17.503 | 31.657 | 69.833 | 1.00 | 0.00 |
| ATOM | 671 | HE22 | GLN | 298 | 17.376 | 30.239 | 70.798 | 1.00 | 0.00 |
| ATOM | 672 | C | GLN | 298 | 15.927 | 35.039 | 71.738 | 1.00 | 11.01 |
| ATOM | 673 | O | GLN | 298 | 17.099 | 34.884 | 72.071 | 1.00 | 11.00 |
| ATOM | 674 | N | ARG | 299 | 15.382 | 36.242 | 71.616 | 1.00 | 10.60 |
| ATOM | 675 | H | ARG | 299 | 14.474 | 36.310 | 71.328 | 1.00 | 0.00 |
| ATOM | 676 | CA | ARG | 299 | 16.195 | 37.458 | 71.833 | 1.00 | 10.37 |
| ATOM | 677 | CB | ARG | 299 | 15.758 | 38.558 | 70.877 | 1.00 | 10.11 |
| ATOM | 678 | CG | ARG | 299 | 15.961 | 38.189 | 69.375 | 1.00 | 9.53 |
| ATOM | 679 | CD | ARG | 299 | 17.285 | 38.727 | 68.808 | 1.00 | 7.25 |
| ATOM | 680 | NE | ARG | 299 | 18.447 | 38.146 | 69.481 | 1.00 | 7.73 |
| ATOM | 681 | HE | ARG | 299 | 18.999 | 38.728 | 69.992 | 1.00 | 0.00 |
| ATOM | 682 | CZ | ARG | 299 | 18.824 | 36.855 | 69.381 | 1.00 | 8.83 |
| ATOM | 683 | NH1 | ARG | 299 | 18.145 | 35.971 | 68.635 | 1.00 | 6.72 |
| ATOM | 684 | HH11 | ARG | 299 | 17.304 | 36.268 | 68.153 | 1.00 | 0.00 |
| ATOM | 685 | HH12 | ARG | 299 | 18.413 | 35.014 | 68.588 | 1.00 | 0.00 |
| ATOM | 686 | NH2 | ARG | 299 | 19.900 | 36.444 | 70.053 | 1.00 | 7.58 |
| ATOM | 687 | HH21 | ARG | 299 | 20.416 | 37.074 | 70.566 | 1.00 | 0.00 |
| ATOM | 688 | HH22 | ARG | 299 | 20.169 | 35.473 | 69.952 | 1.00 | 0.00 |
| ATOM | 689 | C | ARG | 299 | 16.222 | 37.977 | 73.266 | 1.00 | 10.06 |
| ATOM | 690 | O | ARG | 299 | 16.812 | 39.044 | 73.531 | 1.00 | 11.28 |
| ATOM | 691 | N | LEU | 300 | 15.564 | 37.273 | 74.185 | 1.00 | 7.45 |
| ATOM | 692 | H | LEU | 300 | 15.081 | 36.468 | 73.873 | 1.00 | 0.00 |
| ATOM | 693 | CA | LEU | 300 | 15.544 | 37.633 | 75.603 | 1.00 | 7.74 |
| ATOM | 694 | CB | LEU | 300 | 14.096 | 37.871 | 76.064 | 1.00 | 8.97 |
| ATOM | 695 | CG | LEU | 300 | 13.414 | 39.224 | 75.711 | 1.00 | 8.35 |
| ATOM | 696 | CD1 | LEU | 300 | 13.363 | 39.486 | 74.201 | 1.00 | 7.38 |
| ATOM | 697 | CD2 | LEU | 300 | 11.987 | 39.214 | 76.321 | 1.00 | 7.90 |
| ATOM | 698 | C | LEU | 300 | 16.175 | 36.502 | 76.434 | 1.00 | 8.56 |
| ATOM | 699 | O | LEU | 300 | 15.969 | 35.338 | 76.168 | 1.00 | 8.17 |
| ATOM | 700 | N | VAL | 301 | 16.989 | 36.854 | 77.418 | 1.00 | 8.87 |
| ATOM | 701 | H | VAL | 301 | 17.210 | 37.804 | 77.53 | 1.00 | 0.00 |
| ATOM | 702 | CA | VAL | 301 | 17.622 | 35.879 | 78.281 | 1.00 | 10.50 |
| ATOM | 703 | CB | VAL | 301 | 18.509 | 36.571 | 79.345 | 1.00 | 10.68 |
| ATOM | 704 | CG1 | VAL | 301 | 18.953 | 35.591 | 80.432 | 1.00 | 12.02 |
| ATOM | 705 | CG2 | VAL | 301 | 19.804 | 37.029 | 78.654 | 1.00 | 10.40 |
| ATOM | 706 | C | VAL | 301 | 16.497 | 35.054 | 78.896 | 1.00 | 10.94 |
| ATOM | 707 | O | VAL | 301 | 15.586 | 35.615 | 79.507 | 1.00 | 9.78 |
| ATOM | 708 | N | ARG | 302 | 16.548 | 33.733 | 78.708 | 1.00 | 11.53 |
| ATOM | 709 | H | ARG | 302 | 17.314 | 33.343 | 78.194 | 1.00 | 0.00 |
| ATOM | 710 | CA | ARG | 302 | 15.472 | 32.823 | 79.137 | 1.00 | 11.89 |
| ATOM | 711 | CB | ARG | 302 | 15.442 | 31.552 | 78.208 | 1.00 | 12.74 |
| ATOM | 712 | CG | ARG | 302 | 14.335 | 30.560 | 78.516 | 1.00 | 16.09 |
| ATOM | 713 | CD | ARG | 302 | 14.566 | 29.266 | 77.638 | 1.00 | 20.59 |
| ATOM | 714 | NE | ARG | 302 | 13.561 | 28.203 | 77.885 | 1.00 | 24.26 |
| ATOM | 715 | HE | ARG | 302 | 12.767 | 28.200 | 77.320 | 1.00 | 0.00 |
| ATOM | 716 | CZ | ARG | 302 | 13.696 | 27.284 | 78.829 | 1.00 | 26.07 |
| ATOM | 717 | NH1 | ARG | 302 | 14.761 | 27.288 | 79.605 | 1.00 | 26.29 |
| ATOM | 718 | HH11 | ARG | 302 | 15.477 | 27.994 | 79.490 | 1.00 | 0.00 |
| ATOM | 719 | HH12 | ARG | 302 | 14.876 | 26.599 | 80.318 | 1.00 | 0.00 |
| ATOM | 720 | NH2 | ARG | 302 | 12.817 | 26.327 | 78.942 | 1.00 | 27.65 |
| ATOM | 721 | HH21 | ARG | 302 | 12.042 | 26.277 | 78.279 | 1.00 | 0.00 |
| ATOM | 722 | HH22 | ARG | 302 | 12.906 | 25.615 | 79.624 | 1.00 | 0.00 |
| ATOM | 723 | C | ARG | 302 | 15.580 | 32.334 | 80.551 | 1.00 | 11.53 |

TABLE 5-continued

Coordinates of Lck bound with baicalein

| | Atom Type | Res | # | X | Y | Z | Occ | B |
|---|---|---|---|---|---|---|---|---|
| ATOM | 724 | O | ARG | 302 | 16.668 | 31.943 | 81.004 | 1.00 | 9.98 |
| ATOM | 275 | N | LEU | 303 | 14.463 | 32.384 | 81.284 | 1.00 | 11.79 |
| ATOM | 726 | H | LEU | 303 | 13.659 | 32.815 | 80.904 | 1.00 | 0.00 |
| ATOM | 727 | CA | LEU | 303 | 14.421 | 31.856 | 82.656 | 1.00 | 12.49 |
| ATOM | 728 | CB | LEU | 303 | 13.088 | 32.215 | 83.303 | 1.00 | 11.33 |
| ATOM | 729 | CG | LEU | 303 | 12.848 | 31.565 | 84.707 | 1.00 | 11.90 |
| ATOM | 730 | CD1 | LEU | 303 | 13.783 | 32.187 | 85.716 | 1.00 | 8.32 |
| ATOM | 731 | CD2 | LEU | 303 | 11.361 | 31.786 | 85.148 | 1.00 | 7.11 |
| ATOM | 732 | C | LEU | 303 | 14.502 | 30.317 | 82.534 | 1.00 | 13.89 |
| ATOM | 733 | O | LEU | 303 | 13.772 | 29.719 | 81.729 | 1.00 | 13.84 |
| ATOM | 734 | N | TYR | 304 | 15.377 | 29.713 | 83.323 | 1.00 | 14.91 |
| ATOM | 735 | H | TYR | 304 | 15.909 | 30.251 | 83.935 | 1.00 | 0.00 |
| ATOM | 736 | CA | TYR | 304 | 15.597 | 28.265 | 83.315 | 1.00 | 17.62 |
| ATOM | 737 | CB | TYR | 304 | 17.133 | 28.074 | 83.450 | 1.00 | 21.04 |
| ATOM | 738 | CG | TYR | 304 | 17.653 | 26.712 | 83.121 | 1.00 | 25.64 |
| ATOM | 739 | CD1 | TYR | 304 | 17.432 | 25.615 | 83.984 | 1.00 | 26.94 |
| ATOM | 740 | CE1 | TYR | 304 | 17.831 | 24.318 | 83.621 | 1.00 | 28.45 |
| ATOM | 741 | CD2 | TYR | 304 | 18.290 | 26.479 | 81.910 | 1.00 | 27.68 |
| ATOM | 742 | CE2 | TYR | 304 | 18.676 | 25.170 | 81.534 | 1.00 | 29.00 |
| ATOM | 743 | CZ | TYR | 304 | 18.440 | 24.108 | 82.398 | 1.00 | 28.78 |
| ATOM | 744 | OH | TYR | 304 | 18.786 | 22.836 | 82.031 | 1.00 | 30.70 |
| ATOM | 745 | HH | TYR | 304 | 19.169 | 22.862 | 81.133 | 1.00 | 0.00 |
| ATOM | 746 | C | TYR | 304 | 14.829 | 27.581 | 84.480 | 1.00 | 17.09 |
| ATOM | 747 | O | TYR | 304 | 14.141 | 26.548 | 84.314 | 1.00 | 18.58 |
| ATOM | 748 | N | ALA | 305 | 14.965 | 28.151 | 85.668 | 1.00 | 15.04 |
| ATOM | 749 | H | ALA | 305 | 15.490 | 28.954 | 85.725 | 1.00 | 0.00 |
| ATOM | 750 | CA | ALA | 305 | 14.361 | 27.564 | 86.849 | 1.00 | 13.94 |
| ATOM | 752 | CB | ALA | 305 | 15.166 | 26.252 | 87.248 | 1.00 | 13.36 |
| ATOM | 752 | C | ALA | 305 | 14.429 | 28.539 | 88.035 | 1.00 | 13.02 |
| ATOM | 753 | O | ALA | 305 | 15.021 | 29.610 | 87.962 | 1.00 | 11.46 |
| ATOM | 754 | N | VAL | 306 | 13.856 | 28.100 | 89.151 | 0.75 | 11.87 |
| ATOM | 755 | H | VAL | 306 | 13.385 | 27.228 | 89.118 | 1.00 | 0.00 |
| ATOM | 756 | CA | VAL | 306 | 13.866 | 28.840 | 90.392 | 0.75 | 11.87 |
| ATOM | 757 | CB | VAL | 306 | 12.607 | 29.761 | 90.623 | 0.75 | 12.29 |
| ATOM | 758 | CG1 | VAL | 306 | 12.543 | 30.883 | 89.534 | 0.75 | 13.51 |
| ATOM | 759 | CG2 | VAL | 306 | 11.323 | 28.940 | 90.606 | 0.75 | 12.67 |
| ATOM | 760 | C | VAL | 306 | 13.925 | 27.869 | 91.572 | 0.75 | 13.32 |
| ATOM | 761 | O | VAL | 306 | 13.557 | 26.704 | 91.454 | 0.75 | 12.05 |
| ATOM | 762 | N | VAL | 307 | 14.530 | 28.339 | 92.656 | 1.00 | 14.60 |
| ATOM | 763 | H | VAL | 307 | 14.963 | 29.215 | 92.591 | 1.00 | 0.00 |
| ATOM | 764 | CA | VAL | 307 | 14.582 | 27.563 | 93.904 | 1.00 | 16.74 |
| ATOM | 765 | CB | VAL | 307 | 16.044 | 27.192 | 94.312 | 1.00 | 16.78 |
| ATOM | 766 | CG1 | VAL | 307 | 16.023 | 26.528 | 95.677 | 1.00 | 16.76 |
| ATOM | 767 | CG2 | VAL | 307 | 16.611 | 26.207 | 93.316 | 1.00 | 15.60 |
| ATOM | 768 | C | VAL | 307 | 13.964 | 28.517 | 94.906 | 1.00 | 18.04 |
| ATOM | 769 | O | VAL | 307 | 14.614 | 29.486 | 95.335 | 1.00 | 18.12 |
| ATOM | 770 | N | THR | 308 | 12.709 | 28.283 | 95.267 | 1.00 | 18.92 |
| ATOM | 771 | H | THR | 308 | 12.257 | 27.468 | 94.964 | 1.00 | 0.00 |
| ATOM | 772 | CA | THR | 308 | 11.999 | 29.203 | 96.158 | 1.00 | 20.52 |
| ATOM | 773 | CB | THR | 308 | 10.526 | 29.389 | 95.755 | 1.00 | 20.46 |
| ATOM | 774 | OG1 | THR | 308 | 9.887 | 28.114 | 95.659 | 1.00 | 20.64 |
| ATOM | 775 | HG1 | THR | 308 | 10.316 | 27.566 | 95.046 | 1.00 | 0.00 |
| ATOM | 776 | CG2 | THR | 308 | 10.444 | 30.078 | 94.375 | 1.00 | 20.22 |
| ATOM | 777 | C | THR | 308 | 12.147 | 29.113 | 97.667 | 1.00 | 22.33 |
| ATOM | 778 | O | THR | 308 | 11.377 | 29.771 | 98.405 | 1.00 | 23.07 |
| ATOM | 779 | N | ALA | 309 | 13.148 | 28.356 | 98.135 | 1.00 | 23.01 |
| ATOM | 780 | H | ALA | 309 | 13.665 | 27.825 | 97.495 | 1.00 | 0.00 |
| ATOM | 781 | CA | ALA | 309 | 13.454 | 28.270 | 99.567 | 1.00 | 23.83 |
| ATOM | 782 | CB | ALA | 309 | 13.620 | 26.825 | 99.995 | 1.00 | 23.86 |
| ATOM | 783 | C | ALA | 309 | 14.777 | 29.038 | 99.768 | 1.00 | 24.02 |
| ATOM | 784 | O | ALA | 309 | 15.663 | 28.998 | 98.937 | 1.00 | 24.23 |
| ATOM | 785 | N | GLU | 310 | 14.899 | 29.769 | 100.869 | 1.00 | 25.28 |
| ATOM | 786 | H | GLU | 310 | 14.144 | 29.805 | 101.519 | 1.00 | 0.00 |
| ATOM | 787 | CA | GLU | 310 | 16.114 | 30.553 | 101.145 | 1.00 | 26.05 |
| ATOM | 788 | CB | GLU | 310 | 15.890 | 31.466 | 102.356 | 1.00 | 28.07 |
| ATOM | 789 | CG | GLU | 310 | 14.771 | 32.481 | 102.111 | 1.00 | 30.39 |
| ATOM | 790 | CD | GLU | 310 | 14.490 | 33.404 | 103.304 | 1.00 | 32.85 |
| ATOM | 791 | OE1 | GLU | 310 | 15.000 | 33.123 | 104.421 | 1.00 | 33.86 |
| ATOM | 792 | OE2 | GLU | 310 | 13.721 | 34.374 | 103.102 | 1.00 | 32.05 |
| ATOM | 793 | C | GLU | 310 | 17.433 | 29.713 | 101.327 | 1.00 | 25.89 |
| ATOM | 794 | O | GLU | 310 | 17.454 | 28.687 | 101.983 | 1.00 | 26.04 |
| ATOM | 795 | N | PRO | 311 | 18.536 | 30.160 | 100.664 | 1.00 | 25.34 |
| ATOM | 796 | CD | PRO | 311 | 19.841 | 29.483 | 100.778 | 1.00 | 25.21 |
| ATOM | 797 | CA | PRO | 311 | 18.624 | 31.362 | 99.804 | 1.00 | 24.14 |

TABLE 5-continued

Coordinates of Lck bound with baicalein

| | | Atom Type | Res | # | X | Y | Z | Occ | B |
|---|---|---|---|---|---|---|---|---|---|
| ATOM | 798 | CB | PRO | 311 | 20.147 | 31.570 | 99.702 | 1.00 | 24.95 |
| ATOM | 799 | CG | PRO | 311 | 20.688 | 30.129 | 99.700 | 1.00 | 25.04 |
| ATOM | 800 | C | PRO | 311 | 17.980 | 31.133 | 98.451 | 1.00 | 23.79 |
| ATOM | 801 | O | PRO | 311 | 18.228 | 30.168 | 97.768 | 1.00 | 23.74 |
| ATOM | 802 | N | ILE | 312 | 17.191 | 32.116 | 98.055 | 1.00 | 23.64 |
| ATOM | 803 | H | ILE | 312 | 17.084 | 32.914 | 98.625 | 1.00 | 0.00 |
| ATOM | 804 | CA | ILE | 312 | 16.455 | 32.107 | 96.801 | 1.00 | 21.83 |
| ATOM | 805 | CB | ILE | 312 | 15.386 | 33.023 | 96.853 | 1.00 | 22.79 |
| ATOM | 806 | CG2 | ILE | 312 | 14.599 | 33.251 | 95.541 | 1.00 | 23.26 |
| ATOM | 807 | CG1 | ILE | 312 | 14.472 | 32.917 | 98.042 | 1.00 | 23.87 |
| ATOM | 808 | CD1 | ILE | 312 | 13.448 | 33.987 | 98.277 | 1.00 | 25.06 |
| ATOM | 809 | C | ILE | 312 | 17.316 | 32.224 | 95.567 | 1.00 | 20.27 |
| ATOM | 810 | O | ILE | 312 | 18.241 | 33.046 | 95.499 | 1.00 | 18.18 |
| ATOM | 811 | N | TYR | 313 | 17.070 | 31.337 | 94.615 | 1.00 | 19.30 |
| ATOM | 812 | H | TYR | 313 | 16.402 | 30.624 | 94.757 | 1.00 | 0.00 |
| ATOM | 813 | CA | TYR | 313 | 17.839 | 31.376 | 93.376 | 1.00 | 17.96 |
| ATOM | 814 | CB | TYR | 313 | 18.574 | 30.048 | 93.061 | 1.00 | 19.12 |
| ATOM | 815 | CG | TYR | 313 | 19.719 | 29.607 | 93.952 | 1.00 | 20.79 |
| ATOM | 816 | CD1 | TYR | 313 | 20.334 | 30.459 | 94.834 | 1.00 | 20.06 |
| ATOM | 817 | CE1 | TYR | 313 | 21.406 | 30.022 | 95.614 | 1.00 | 21.24 |
| ATOM | 818 | CD2 | TYR | 313 | 20.201 | 28.296 | 93.862 | 1.00 | 21.80 |
| ATOM | 819 | CE2 | TYR | 313 | 21.268 | 27.858 | 94.635 | 1.00 | 22.33 |
| ATOM | 820 | CZ | TYR | 313 | 21.868 | 28.739 | 95.523 | 1.00 | 22.01 |
| ATOM | 821 | OH | TYR | 313 | 22.890 | 28.331 | 96.337 | 1.00 | 21.94 |
| ATOM | 822 | HH | TYR | 313 | 23.080 | 27.370 | 96.151 | 1.00 | 0.00 |
| ATOM | 823 | C | TYR | 313 | 16.974 | 31.632 | 92.174 | 1.00 | 15.90 |
| ATOM | 824 | O | TYR | 313 | 15.846 | 31.158 | 92.113 | 1.00 | 15.13 |
| ATOM | 825 | N | ILE | 314 | 17.511 | 32.401 | 91.233 | 0.82 | 12.85 |
| ATOM | 826 | H | ILE | 314 | 18.325 | 32.892 | 91.453 | 1.00 | 0.00 |
| ATOM | 827 | CA | ILE | 314 | 16.888 | 32.588 | 89.922 | 0.82 | 11.93 |
| ATOM | 828 | CB | ILE | 314 | 16.602 | 34.077 | 89.560 | 0.82 | 10.24 |
| ATOM | 829 | CG2 | ILE | 314 | 16.266 | 34.170 | 88.084 | 0.82 | 9.30 |
| ATOM | 830 | CG1 | ILE | 314 | 15.392 | 34.544 | 90.392 | 0.82 | 10.36 |
| ATOM | 831 | CD1 | ILE | 314 | 15.054 | 36.024 | 90.271 | 0.82 | 9.00 |
| ATOM | 832 | C | ILE | 314 | 17.953 | 32.006 | 88.984 | 0.82 | 10.44 |
| ATOM | 833 | O | ILE | 314 | 19.121 | 32.400 | 89.017 | 0.82 | 10.94 |
| ATOM | 834 | N | ILE | 315 | 17.583 | 31.020 | 88.186 | 1.00 | 10.44 |
| ATOM | 835 | H | ILE | 315 | 16.671 | 30.676 | 88.243 | 1.00 | 0.00 |
| ATOM | 836 | CA | ILE | 315 | 18.547 | 30.391 | 87.269 | 1.00 | 10.61 |
| ATOM | 837 | CB | ILE | 315 | 18.574 | 28.824 | 87.422 | 1.00 | 8.93 |
| ATOM | 838 | CG2 | ILE | 315 | 19.596 | 28.216 | 86.489 | 1.00 | 7.62 |
| ATOM | 839 | CG1 | ILE | 315 | 18.939 | 28.454 | 88.896 | 1.00 | 10.09 |
| ATOM | 840 | CD1 | ILE | 315 | 17.761 | 28.176 | 89.770 | 1.00 | 7.69 |
| ATOM | 841 | C | ILE | 315 | 18.128 | 30.780 | 85.867 | 1.00 | 9.10 |
| ATOM | 842 | O | ILE | 315 | 16.959 | 30.646 | 85.530 | 1.00 | 6.73 |
| ATOM | 843 | N | THR | 316 | 19.092 | 31.252 | 85.062 | 1.00 | 9.07 |
| ATOM | 844 | H | THR | 316 | 20.021 | 31.314 | 85.391 | 1.00 | 0.00 |
| ATOM | 845 | CA | THR | 316 | 18.768 | 31.620 | 83.683 | 1.00 | 11.43 |
| ATOM | 846 | CB | THR | 316 | 18.765 | 33.155 | 83.519 | 1.00 | 10.96 |
| ATOM | 847 | OG1 | THR | 316 | 20.081 | 33.672 | 83.757 | 1.00 | 10.16 |
| ATOM | 848 | HG1 | THR | 316 | 20.712 | 33.263 | 83.159 | 1.00 | 0.00 |
| ATOM | 849 | CG2 | THR | 316 | 17.770 | 33.817 | 84.457 | 1.00 | 9.76 |
| ATOM | 850 | C | THR | 316 | 19.773 | 31.100 | 82.688 | 1.00 | 11.54 |
| ATOM | 851 | O | THR | 316 | 20.817 | 30.574 | 83.068 | 1.00 | 13.42 |
| ATOM | 852 | N | GLU | 317 | 19.445 | 31.280 | 81.410 | 1.00 | 12.67 |
| ATOM | 853 | H | GLU | 317 | 15.585 | 31.710 | 81.200 | 1.00 | 0.00 |
| ATOM | 854 | CA | GLU | 317 | 20.317 | 30.950 | 80.264 | 1.00 | 12.95 |
| ATOM | 855 | CB | GLU | 317 | 19.665 | 31.540 | 79.002 | 1.00 | 14.12 |
| ATOM | 856 | CG | GLU | 317 | 20.370 | 31.328 | 77.669 | 1.00 | 13.22 |
| ATOM | 857 | CD | GLU | 317 | 19.486 | 31.838 | 76.531 | 1.00 | 13.31 |
| ATOM | 858 | OE1 | GLU | 317 | 18.523 | 32.618 | 76.808 | 1.00 | 10.56 |
| ATOM | 859 | OE2 | GLU | 317 | 19.700 | 31.446 | 75.350 | 1.00 | 12.27 |
| ATOM | 860 | C | GLU | 317 | 21.697 | 31.604 | 80.455 | 1.00 | 12.40 |
| ATOM | 861 | O | GLU | 317 | 21.820 | 32.761 | 80.902 | 1.00 | 11.80 |
| ATOM | 862 | N | TYR | 318 | 22.750 | 30.867 | 80.141 | 1.00 | 11.52 |
| ATOM | 863 | H | TYR | 318 | 22.625 | 29.985 | 79.889 | 1.00 | 0.00 |
| ATOM | 864 | CA | TYR | 318 | 24.098 | 31.396 | 80.275 | 1.00 | 11.33 |
| ATOM | 865 | CB | TYR | 318 | 25.063 | 30.302 | 80.732 | 1.00 | 11.32 |
| ATOM | 866 | CG | TYR | 318 | 26.420 | 30.854 | 81.066 | 1.00 | 12.09 |
| ATOM | 867 | CD1 | TYR | 318 | 26.609 | 31.511 | 82.255 | 1.00 | 13.20 |
| ATOM | 868 | CE1 | TYR | 318 | 27.831 | 32.034 | 82.607 | 1.00 | 14.93 |
| ATOM | 869 | CD2 | TYR | 318 | 27.519 | 30.719 | 80.210 | 1.00 | 12.24 |
| ATOM | 870 | CE2 | TYR | 318 | 28.749 | 31.231 | 80.566 | 1.00 | 12.94 |
| ATOM | 871 | CZ | TYR | 318 | 28.905 | 31.884 | 81.760 | 1.00 | 14.18 |

TABLE 5-continued

Coordinates of Lck bound with baicalein

| | | Atom Type | Res | # | X | Y | Z | Occ | B |
|---|---|---|---|---|---|---|---|---|---|
| ATOM | 872 | OH | TYR | 318 | 30.119 | 32.405 | 82.204 | 1.00 | 16.00 |
| ATOM | 873 | HH | TYR | 318 | 30.800 | 32.202 | 81.510 | 1.00 | 0.00 |
| ATOM | 874 | C | TYR | 318 | 24.582 | 32.045 | 78.983 | 1.00 | 12.58 |
| ATOM | 875 | O | TYR | 318 | 24.377 | 31.526 | 77.870 | 1.00 | 11.61 |
| ATOM | 876 | N | MET | 319 | 25.134 | 33.251 | 79.125 | 1.00 | 13.09 |
| ATOM | 877 | H | MET | 319 | 22.205 | 33.623 | 79.998 | 1.00 | 0.00 |
| ATOM | 878 | CA | MET | 319 | 25.632 | 34.049 | 77.956 | 1.00 | 15.15 |
| ATOM | 879 | CB | MET | 319 | 24.939 | 35.434 | 77.948 | 1.00 | 14.72 |
| ATOM | 880 | CG | MET | 319 | 23.413 | 35.357 | 77.772 | 1.00 | 13.64 |
| ATOM | 881 | SD | MET | 319 | 22.942 | 34.551 | 76.219 | 1.00 | 15.36 |
| ATOM | 882 | CE | MET | 319 | 23.196 | 35.839 | 75.042 | 1.00 | 15.72 |
| ATOM | 883 | C | MET | 319 | 27.146 | 34.196 | 78.097 | 1.00 | 15.28 |
| ATOM | 884 | O | MET | 319 | 27.641 | 34.982 | 78.900 | 1.00 | 16.10 |
| ATOM | 885 | N | GLU | 320 | 27.875 | 33.357 | 77.395 | 1.00 | 15.91 |
| ATOM | 886 | H | GLU | 320 | 27.420 | 32.787 | 76.714 | 1.00 | 0.00 |
| ATOM | 887 | CA | GLU | 320 | 29.323 | 33.302 | 77.491 | 1.00 | 16.21 |
| ATOM | 888 | CB | GLU | 320 | 29.901 | 32.357 | 76.390 | 1.00 | 18.00 |
| ATOM | 889 | CG | GLU | 320 | 31.322 | 31.940 | 76.654 | 1.00 | 23.17 |
| ATOM | 890 | CD | GLU | 320 | 31.452 | 31.043 | 77.892 | 1.00 | 26.45 |
| ATOM | 891 | OE1 | GLU | 320 | 30.694 | 30.027 | 77.958 | 1.00 | 28.89 |
| ATOM | 892 | OE2 | GLU | 320 | 32.297 | 31.326 | 78.796 | 1.00 | 27.99 |
| ATOM | 893 | C | GLU | 320 | 30.101 | 34.627 | 77.498 | 1.00 | 14.92 |
| ATOM | 894 | O | GLU | 320 | 31.012 | 34.826 | 78.300 | 1.00 | 12.59 |
| ATOM | 895 | N | ASN | 321 | 29.732 | 35.554 | 76.642 | 1.00 | 13.95 |
| ATOM | 896 | H | ASN | 321 | 28.954 | 35.403 | 76.055 | 1.00 | 0.00 |
| ATOM | 897 | CA | ASN | 321 | 30.483 | 36.792 | 76.557 | 1.00 | 15.08 |
| ATOM | 898 | CB | ASN | 321 | 30.643 | 37.242 | 75.065 | 1.00 | 13.80 |
| ATOM | 899 | CG | ASN | 321 | 31.723 | 36.447 | 74.352 | 1.00 | 14.87 |
| ATOM | 900 | OD1 | ASN | 321 | 32.847 | 36.357 | 74.846 | 1.00 | 15.54 |
| ATOM | 901 | ND2 | ASN | 321 | 31.375 | 35.804 | 73.259 | 1.00 | 15.95 |
| ATOM | 902 | HD21 | ASN | 321 | 30.436 | 35.843 | 72.917 | 1.00 | 0.00 |
| ATOM | 903 | HD22 | ASN | 321 | 32.050 | 35.282 | 72.763 | 1.00 | 0.00 |
| ATOM | 904 | C | ASN | 321 | 30.067 | 37.897 | 77.487 | 1.00 | 13.89 |
| ATOM | 905 | O | ASN | 321 | 30.544 | 39.036 | 77.360 | 1.00 | 17.50 |
| ATOM | 906 | N | GLY | 322 | 29.171 | 37.584 | 78.401 | 1.00 | 12.35 |
| ATOM | 907 | H | GLY | 322 | 28.800 | 36.669 | 78.416 | 1.00 | 0.00 |
| ATOM | 908 | CA | GLY | 322 | 28.766 | 38.543 | 79.396 | 1.00 | 10.58 |
| ATOM | 909 | C | GLY | 322 | 28.072 | 39.812 | 78.921 | 1.00 | 8.04 |
| ATOM | 910 | O | GLY | 322 | 27.394 | 39.842 | 77.891 | 1.00 | 8.20 |
| ATOM | 911 | N | SER | 323 | 28.283 | 40.881 | 79.648 | 0.43 | 5.18 |
| ATOM | 912 | H | SER | 323 | 28.905 | 40.826 | 80.386 | 1.00 | 0.00 |
| ATOM | 913 | CA | SER | 323 | 27.654 | 42.144 | 79.294 | 0.43 | 3.96 |
| ATOM | 914 | CB | SER | 323 | 27.708 | 43.033 | 80.540 | 0.43 | 3.66 |
| ATOM | 915 | OG | SER | 323 | 29.619 | 44.374 | 80.212 | 0.43 | 5.50 |
| ATOM | 916 | HG | SER | 323 | 26.781 | 44.532 | 79.734 | 1.00 | 0.00 |
| ATOM | 917 | C | SER | 323 | 28.218 | 42.840 | 78.055 | 0.43 | 3.62 |
| ATOM | 918 | O | SER | 323 | 28.419 | 42.909 | 77.865 | 0.43 | 2.00 |
| ATOM | 919 | N | LEU | 324 | 27.343 | 43.399 | 77.229 | 1.00 | 5.56 |
| ATOM | 920 | H | LEU | 324 | 26.381 | 43.282 | 77.440 | 1.00 | 0.00 |
| ATOM | 921 | CA | LEU | 324 | 27.724 | 44.097 | 76.009 | 1.00 | 7.05 |
| ATOM | 922 | CB | LEU | 324 | 26.477 | 44.641 | 75.260 | 1.00 | 5.00 |
| ATOM | 923 | CG | LEU | 324 | 26.764 | 45.359 | 73.952 | 1.00 | 4.87 |
| ATOM | 924 | CD1 | LEU | 324 | 27.440 | 44.377 | 72.901 | 1.00 | 2.16 |
| ATOM | 925 | CD2 | LEU | 324 | 25.448 | 45.916 | 73.406 | 1.00 | 5.99 |
| ATOM | 926 | C | LEU | 324 | 28.691 | 45.257 | 76.316 | 1.00 | 7.97 |
| ATOM | 927 | O | LEU | 324 | 29.777 | 45.346 | 75.758 | 1.00 | 8.93 |
| ATOM | 928 | N | VAL | 525 | 28.372 | 46.015 | 77.353 | 1.00 | 10.95 |
| ATOM | 929 | H | VAL | 525 | 27.541 | 45.798 | 77.856 | 1.00 | 0.00 |
| ATOM | 930 | CA | VAL | 525 | 29.220 | 47.102 | 77.742 | 1.00 | 11.39 |
| ATOM | 931 | CB | VAL | 525 | 28.607 | 47.947 | 78.855 | 1.00 | 12.01 |
| ATOM | 932 | CG1 | VAL | 525 | 28.779 | 47.314 | 80.256 | 1.00 | 12.37 |
| ATOM | 933 | CG2 | VAL | 525 | 29.259 | 49.315 | 78.828 | 1.00 | 14.47 |
| ATOM | 934 | C | VAL | 525 | 30.640 | 46.643 | 78.042 | 1.00 | 12.65 |
| ATOM | 935 | O | VAL | 525 | 31.589 | 47.347 | 77.696 | 1.00 | 12.30 |
| ATOM | 936 | N | ASP | 326 | 30.813 | 45.459 | 78.644 | 1.00 | 12.29 |
| ATOM | 937 | H | ASP | 326 | 30.020 | 44.934 | 78.900 | 1.00 | 0.00 |
| ATOM | 938 | CA | ASP | 326 | 32.158 | 44.899 | 78.914 | 1.00 | 13.17 |
| ATOM | 939 | CB | ASP | 326 | 32.124 | 43.904 | 80.098 | 1.00 | 14.11 |
| ATOM | 940 | CG | ASP | 326 | 31.708 | 44.555 | 81.400 | 1.00 | 16.42 |
| ATOM | 941 | OD1 | ASP | 326 | 32.054 | 45.724 | 81.698 | 1.00 | 16.07 |
| ATOM | 942 | OD2 | ASP | 326 | 31.017 | 43.905 | 82.157 | 1.00 | 18.52 |
| ATOM | 943 | C | ASP | 326 | 32.754 | 44.184 | 77.676 | 1.00 | 12.14 |
| ATOM | 944 | O | ASP | 326 | 33.937 | 44.367 | 77.371 | 1.00 | 12.82 |
| ATOM | 945 | N | PHE | 327 | 31.947 | 43.418 | 76.947 | 1.00 | 11.07 |

TABLE 5-continued

Coordinates of Lck bound with baicalein

| | Atom Type | Res | # | X | Y | Z | Occ | B |
|---|---|---|---|---|---|---|---|---|
| ATOM | 946 | H | PHE | 327 | 31.016 | 43.315 | 77.178 | 1.00 | 0.00 |
| ATOM | 947 | CA | PHE | 327 | 32.467 | 42.723 | 75.775 | 1.00 | 10.27 |
| ATOM | 948 | CB | PHE | 327 | 31.369 | 41.897 | 75.090 | 1.00 | 10.45 |
| ATOM | 949 | CG | PHE | 327 | 31.817 | 41.251 | 73.824 | 1.00 | 11.86 |
| ATOM | 950 | CD1 | PHE | 327 | 32.699 | 40.182 | 73.846 | 1.00 | 10.63 |
| ATOM | 951 | CD2 | PHE | 327 | 31.344 | 41.725 | 72.593 | 1.00 | 12.21 |
| ATOM | 952 | CE1 | PHE | 327 | 33.126 | 39.579 | 72.679 | 1.00 | 11.37 |
| ATOM | 953 | CE2 | PHE | 327 | 31.769 | 41.117 | 71.395 | 1.00 | 13.82 |
| ATOM | 954 | CZ | PHE | 327 | 32.682 | 40.025 | 71.461 | 1.00 | 12.65 |
| ATOM | 955 | C | PHE | 327 | 33.087 | 43.681 | 74.714 | 1.00 | 10.57 |
| ATOM | 956 | O | PHE | 327 | 34.150 | 43.358 | 74.112 | 1.00 | 9.50 |
| ATOM | 957 | N | LEU | 328 | 32.448 | 44.824 | 74.479 | 1.00 | 8.40 |
| ATOM | 958 | H | LEU | 328 | 31.649 | 45.018 | 75.033 | 1.00 | 0.00 |
| ATOM | 959 | CA | LEU | 328 | 32.920 | 45.786 | 73.501 | 0.40 | 8.54 |
| ATOM | 960 | CB | LEU | 328 | 31.932 | 46.962 | 73.384 | 0.40 | 8.34 |
| ATOM | 961 | CG | LEU | 328 | 30.608 | 46.625 | 72.715 | 0.40 | 7.41 |
| ATOM | 962 | CD1 | LEU | 328 | 29.693 | 47.813 | 72.773 | 0.40 | 7.70 |
| ATOM | 963 | CD2 | LEU | 328 | 30.821 | 46.178 | 71.294 | 0.40 | 7.34 |
| ATOM | 964 | C | LEU | 328 | 34.306 | 45.340 | 73.765 | 0.40 | 9.68 |
| ATOM | 965 | O | LEU | 328 | 34.921 | 46.924 | 72.896 | 0.40 | 7.10 |
| ATOM | 966 | N | LYS | 329 | 34.780 | 46.164 | 74.986 | 1.00 | 12.01 |
| ATOM | 967 | H | LYS | 329 | 34.188 | 45.614 | 75.612 | 1.00 | 0.00 |
| ATOM | 968 | CA | LYS | 329 | 36.069 | 46.587 | 74.444 | 1.00 | 13.95 |
| ATOM | 969 | CB | LYS | 329 | 35.962 | 47.128 | 76.878 | 1.00 | 14.87 |
| ATOM | 970 | CG | LYS | 329 | 35.181 | 48.381 | 7.965 | 1.00 | 16.09 |
| ATOM | 971 | CD | LYS | 329 | 35.062 | 48.818 | 78.421 | 1.00 | 17.33 |
| ATOM | 972 | CE | LYS | 329 | 33.978 | 49.857 | 78.582 | 1.00 | 16.66 |
| ATOM | 973 | NZ | LYS | 329 | 33.786 | 50.087 | 80.029 | 1.00 | 19.41 |
| ATOM | 974 | HZ1 | LYS | 329 | 34.685 | 50.415 | 80.447 | 1.00 | 0.00 |
| ATOM | 975 | HZ2 | LYS | 329 | 33.540 | 49.167 | 80.502 | 1.00 | 0.00 |
| ATOM | 976 | HZ3 | LYS | 329 | 33.041 | 50.759 | 80.196 | 1.00 | 0.00 |
| ATOM | 977 | C | LYS | 329 | 37.160 | 45.537 | 75.397 | 1.00 | 15.22 |
| ATOM | 978 | O | LYS | 329 | 38.333 | 45.875 | 75.561 | 1.00 | 16.11 |
| ATOM | 979 | N | THR | 330 | 36.791 | 44.279 | 75.227 | 1.00 | 14.48 |
| ATOM | 980 | H | THR | 330 | 35.811 | 44.042 | 75.189 | 1.00 | 0.00 |
| ATOM | 981 | CA | THR | 330 | 37.778 | 43.204 | 75.124 | 1.00 | 14.80 |
| ATOM | 982 | CB | THR | 330 | 37.085 | 41.833 | 75.256 | 1.00 | 11.82 |
| ATOM | 983 | OG1 | THR | 330 | 36.224 | 41.644 | 74.161 | 1.00 | 11.03 |
| ATOM | 984 | HG1 | THR | 330 | 35.574 | 42.322 | 74.117 | 1.00 | 0.00 |
| ATOM | 985 | CG2 | THR | 330 | 36.272 | 41.774 | 76.512 | 1.00 | 13.75 |
| ATOM | 986 | C | THR | 330 | 38.414 | 43.259 | 73.735 | 1.00 | 14.28 |
| ATOM | 987 | O | THR | 330 | 37.889 | 43.907 | 72.837 | 1.00 | 14.25 |
| ATOM | 988 | N | PRO | 331 | 39.551 | 42.557 | 73.532 | 1.00 | 15.05 |
| ATOM | 989 | CD | PRO | 331 | 40.346 | 41.802 | 74.534 | 1.00 | 15.24 |
| ATOM | 990 | CA | PRO | 331 | 40.233 | 42.542 | 72.217 | 1.00 | 16.13 |
| ATOM | 991 | CB | PRO | 331 | 41.324 | 41.478 | 72.415 | 1.00 | 15.20 |
| ATOM | 992 | CG | PRO | 331 | 41.702 | 41.656 | 73.796 | 1.00 | 15.12 |
| ATOM | 993 | C | PRO | 331 | 39.289 | 42.113 | 71.082 | 1.00 | 15.78 |
| ATOM | 994 | O | PRO | 331 | 39.356 | 42.660 | 69.979 | 1.00 | 16.91 |
| ATOM | 995 | N | SER | 332 | 38.405 | 41.147 | 71.344 | 1.00 | 16.34 |
| ATOM | 996 | H | SER | 332 | 38.412 | 40.695 | 72.202 | 1.00 | 0.00 |
| ATOM | 997 | CA | SER | 332 | 37.493 | 40.648 | 70.307 | 1.00 | 18.02 |
| ATOM | 998 | CB | SER | 332 | 36.749 | 39.383 | 70.800 | 1.00 | 17.23 |
| ATOM | 999 | OG | SER | 332 | 37.667 | 38.307 | 70.913 | 1.00 | 18.30 |
| ATOM | 1000 | HG | SER | 332 | 38.321 | 38.496 | 71.559 | 1.00 | 0.00 |
| ATOM | 1001 | C | SER | 332 | 36.494 | 41.761 | 70.008 | 1.00 | 18.35 |
| ATOM | 1002 | O | SER | 332 | 36.253 | 42.080 | 68.870 | 1.00 | 19.63 |
| ATOM | 1003 | N | GLY | 333 | 35.971 | 42.373 | 71.059 | 1.00 | 17.92 |
| ATOM | 1004 | H | GLY | 333 | 36.275 | 42.093 | 71.951 | 1.00 | 0.00 |
| ATOM | 1005 | CA | GLY | 333 | 34.999 | 43.429 | 70.893 | 1.00 | 18.25 |
| ATOM | 1006 | C | GLY | 333 | 35.568 | 44.606 | 70.108 | 1.00 | 18.39 |
| ATOM | 1007 | O | GLY | 333 | 34.925 | 45.156 | 69.220 | 1.00 | 17.05 |
| ATOM | 1008 | N | ILE | 334 | 36.794 | 44.985 | 70.446 | 1.00 | 18.48 |
| ATOM | 1009 | H | ILE | 334 | 37.264 | 44.463 | 71.158 | 1.00 | 0.00 |
| ATOM | 1010 | CA | ILE | 334 | 37.488 | 46.084 | 69.799 | 1.00 | 18.92 |
| ATOM | 1011 | CB | ILE | 334 | 38.830 | 46.343 | 70.495 | 1.00 | 19.78 |
| ATOM | 1012 | CG2 | ILE | 334 | 39.702 | 47.278 | 69.659 | 1.00 | 20.34 |
| ATOM | 1013 | CG1 | ILE | 334 | 38.562 | 46.897 | 71.908 | 1.00 | 20.14 |
| ATOM | 1014 | CD1 | ILE | 334 | 39.814 | 46.924 | 72.799 | 1.00 | 19.96 |
| ATOM | 1015 | C | ILE | 334 | 37.697 | 45.879 | 68.296 | 1.00 | 20.08 |
| ATOM | 1016 | O | ILE | 334 | 37.618 | 46.814 | 67.521 | 1.00 | 19.73 |
| ATOM | 1017 | N | LYS | 335 | 37.871 | 44.648 | 67.846 | 1.00 | 21.65 |
| ATOM | 1018 | H | LYS | 335 | 37.826 | 43.878 | 68.468 | 1.00 | 0.00 |
| ATOM | 1019 | CA | LYS | 335 | 38.053 | 44.435 | 66.431 | 1.00 | 21.48 |

TABLE 5-continued

Coordinates of Lck bound with baicalein

| | Atom Type | Res | # | X | Y | Z | Occ | B |
|---|---|---|---|---|---|---|---|---|
| ATOM | 1020 | CB | LYS | 335 | 38.831 | 43.131 | 66.225 | 1.00 | 25.00 |
| ATOM | 1021 | CG | LYS | 335 | 40.147 | 43.134 | 66.955 | 1.00 | 27.86 |
| ATOM | 1022 | CD | LYS | 335 | 40.785 | 41.728 | 66.948 | 1.00 | 30.18 |
| ATOM | 1023 | CE | LYS | 335 | 42.063 | 41.751 | 67.744 | 1.00 | 30.33 |
| ATOM | 1024 | NZ | LYS | 335 | 42.318 | 40.431 | 68.376 | 1.00 | 32.64 |
| ATOM | 1025 | HZ1 | LYS | 335 | 42.373 | 39.698 | 67.609 | 1.00 | 0.00 |
| ATOM | 1026 | HZ2 | LYS | 335 | 41.531 | 40.207 | 68.976 | 1.00 | 0.00 |
| ATOM | 1027 | HZ3 | LYS | 335 | 43.179 | 40.448 | 68.887 | 1.00 | 0.00 |
| ATOM | 1028 | C | LYS | 335 | 36.727 | 44.360 | 65.648 | 1.00 | 20.93 |
| ATOM | 1029 | O | LYS | 335 | 36.749 | 44.123 | 64.440 | 1.00 | 20.88 |
| ATOM | 1030 | N | LEU | 336 | 35.577 | 44.566 | 66.286 | 1.00 | 19.05 |
| ATOM | 1031 | H | LEU | 336 | 35.577 | 44.804 | 67.252 | 1.00 | 0.00 |
| ATOM | 1032 | CA | LEU | 336 | 34.334 | 44.447 | 65.558 | 1.00 | 18.36 |
| ATOM | 1033 | CB | LEU | 336 | 33.125 | 44.433 | 66.480 | 1.00 | 18.28 |
| ATOM | 1034 | CG | LEU | 336 | 33.001 | 43.278 | 67.490 | 1.00 | 19.42 |
| ATOM | 1035 | CD1 | LEU | 336 | 31.719 | 43.395 | 68.234 | 1.00 | 19.05 |
| ATOM | 1036 | CD2 | LEU | 336 | 33.080 | 41.886 | 66.808 | 1.00 | 18.37 |
| ATOM | 1037 | C | LEU | 336 | 34.164 | 45.465 | 64.487 | 1.00 | 18.24 |
| ATOM | 1038 | O | LEU | 336 | 34.493 | 46.630 | 64.692 | 1.00 | 18.98 |
| ATOM | 1049 | N | THR | 337 | 33.663 | 45.050 | 63.312 | 1.00 | 18.02 |
| ATOM | 1040 | H | THR | 337 | 33.504 | 44.098 | 63.188 | 1.00 | 0.00 |
| ATOM | 1041 | CA | THR | 337 | 33.399 | 46.002 | 62.218 | 1.00 | 17.73 |
| ATOM | 1042 | CB | THR | 337 | 33.202 | 45.307 | 60.868 | 1.00 | 17.13 |
| ATOM | 1043 | OG1 | THR | 337 | 32.104 | 44.417 | 60.923 | 1.00 | 14.03 |
| ATOM | 1044 | HG1 | THR | 337 | 31.971 | 43.954 | 60.077 | 1.00 | 0.00 |
| ATOM | 1045 | CG2 | THR | 337 | 34.499 | 44.535 | 60.434 | 1.00 | 18.85 |
| ATOM | 1046 | C | THR | 337 | 32.108 | 46.785 | 62.523 | 1.00 | 18.00 |
| ATOM | 1047 | O | THR | 337 | 31.272 | 46.337 | 63.324 | 1.00 | 16.60 |
| ATOM | 1048 | N | ILE | 338 | 31.935 | 47.938 | 61.868 | 1.00 | 16.28 |
| ATOM | 1049 | H | ILE | 338 | 32.638 | 48.286 | 61.288 | 1.00 | 0.00 |
| ATOM | 1050 | CA | ILE | 338 | 30.707 | 48.686 | 62.051 | 1.00 | 16.54 |
| ATOM | 1051 | CB | ILE | 338 | 30.687 | 50.032 | 61.247 | 1.00 | 16.25 |
| ATOM | 1052 | CG2 | ILE | 338 | 30.836 | 49.789 | 59.755 | 1.00 | 17.67 |
| ATOM | 1053 | CG1 | ILE | 338 | 29.403 | 50.801 | 61.550 | 1.00 | 16.81 |
| ATOM | 1054 | CD1 | ILE | 338 | 29.222 | 51.165 | 63.086 | 1.00 | 14.43 |
| ATOM | 1055 | C | ILE | 338 | 29.503 | 47.811 | 61.635 | 1.00 | 15.70 |
| ATOM | 1056 | O | ILE | 338 | 28.415 | 47.945 | 62.212 | 1.00 | 14.80 |
| ATOM | 1057 | N | ASN | 339 | 29.673 | 46.951 | 60.622 | 1.00 | 15.13 |
| ATOM | 1058 | H | ASN | 339 | 30.553 | 46.919 | 60.164 | 1.00 | 0.00 |
| ATOM | 1059 | CA | ASN | 339 | 28.613 | 46.067 | 60.140 | 1.00 | 16.01 |
| ATOM | 1060 | CB | ASN | 339 | 29.065 | 45.322 | 58.829 | 1.00 | 20.30 |
| ATOM | 1061 | CG | ASN | 339 | 28.803 | 43.834 | 58.875 | 1.00 | 23.96 |
| ATOM | 1062 | OD1 | ASN | 339 | 27.847 | 43.339 | 58.193 | 1.00 | 28.96 |
| ATOM | 1063 | ND2 | ASN | 339 | 29.600 | 43.125 | 59.530 | 1.00 | 26.99 |
| ATOM | 1064 | HD21 | ASN | 339 | 30.342 | 43.536 | 60.038 | 1.00 | 0.00 |
| ATOM | 1065 | HD22 | ASN | 339 | 29.472 | 42.154 | 59.553 | 1.00 | 0.00 |
| ATOM | 1066 | C | ASN | 339 | 28.162 | 45.109 | 61.263 | 1.00 | 14.65 |
| ATOM | 1067 | O | ASN | 339 | 26.967 | 44.939 | 61.456 | 1.00 | 13.42 |
| ATOM | 1068 | N | LYS | 340 | 29.107 | 44.555 | 62.042 | 1.00 | 12.58 |
| ATOM | 1069 | H | LYS | 340 | 30.051 | 44.741 | 61.836 | 1.00 | 0.00 |
| ATOM | 1070 | CA | LYS | 340 | 28.753 | 43.663 | 63.143 | 1.00 | 11.12 |
| ATOM | 1071 | CB | LYS | 340 | 29.967 | 42.857 | 63.628 | 1.00 | 11.45 |
| ATOM | 1072 | CG | LYS | 340 | 29.646 | 41.843 | 64.807 | 1.00 | 9.76 |
| ATOM | 1073 | CD | LYS | 340 | 28.494 | 40.883 | 64.410 | 1.00 | 10.06 |
| ATOM | 1074 | CE | LYS | 340 | 28.155 | 39.903 | 65.571 | 1.00 | 9.42 |
| ATOM | 1075 | NZ | LYS | 340 | 26.978 | 39.037 | 65.247 | 1.00 | 8.84 |
| ATOM | 1076 | HZ1 | LYS | 340 | 27.156 | 38.478 | 64.384 | 1.00 | 0.00 |
| ATOM | 1077 | HZ2 | LYS | 340 | 26.135 | 39.643 | 65.072 | 1.00 | 0.00 |
| ATOM | 1078 | HZ3 | LYS | 340 | 26.779 | 38.405 | 66.037 | 1.00 | 0.00 |
| ATOM | 1079 | C | LYS | 340 | 28.110 | 44.475 | 64.288 | 1.00 | 11.51 |
| ATOM | 1080 | O | LYS | 340 | 27.185 | 44.018 | 64.959 | 1.00 | 9.75 |
| ATOM | 1081 | N | LEU | 341 | 28.561 | 45.715 | 64.502 | 1.00 | 11.18 |
| ATOM | 1082 | H | LEU | 341 | 29.292 | 46.059 | 63.973 | 1.00 | 0.00 |
| ATOM | 1083 | CA | LEU | 341 | 27.938 | 46.531 | 65.544 | 1.00 | 10.54 |
| ATOM | 1084 | CB | LEU | 341 | 28.718 | 47.857 | 65.752 | 1.00 | 11.07 |
| ATOM | 1085 | CG | LEU | 341 | 30.147 | 47.704 | 66.261 | 1.00 | 12.07 |
| ATOM | 1086 | CD1 | LEU | 341 | 30.775 | 49.038 | 66.416 | 1.00 | 10.29 |
| ATOM | 1087 | CD2 | LEU | 341 | 30.180 | 46.942 | 67.611 | 1.00 | 13.35 |
| ATOM | 1088 | C | LEU | 341 | 26.462 | 46.850 | 65.167 | 1.00 | 10.23 |
| ATOM | 1089 | O | LEU | 341 | 25.571 | 46.906 | 66.016 | 1.00 | 9.32 |
| ATOM | 1090 | N | LEU | 342 | 26.198 | 47.121 | 63.897 | 1.00 | 9.88 |
| ATOM | 1091 | H | LEU | 342 | 26.914 | 47.132 | 63.219 | 1.00 | 0.00 |
| ATOM | 1092 | CA | LEU | 342 | 24.818 | 47.419 | 63.471 | 1.00 | 9.87 |
| ATOM | 1093 | CB | LEU | 342 | 24.832 | 47.983 | 62.039 | 1.00 | 10.00 |

TABLE 5-continued

Coordinates of Lck bound with baicalein

| | Atom Type | Res | # | X | Y | Z | Occ | B |
|---|---|---|---|---|---|---|---|---|
| ATOM | 1094 | CG | LEU | 342 | 25.471 | 49.405 | 61.872 | 1.00 | 10.18 |
| ATOM | 1095 | CD1 | LEU | 342 | 25.655 | 49.693 | 60.417 | 1.00 | 9.05 |
| ATOM | 1096 | CD2 | LEU | 342 | 24.608 | 50.493 | 62.494 | 1.00 | 8.57 |
| ATOM | 1097 | C | LEU | 342 | 24.004 | 46.159 | 63.571 | 1.00 | 9.73 |
| ATOM | 1098 | O | LEU | 342 | 22.787 | 46.226 | 63.858 | 1.00 | 10.01 |
| ATOM | 1099 | N | ASP | 343 | 24.631 | 45.007 | 63.318 | 1.00 | 10.47 |
| ATOM | 1100 | H | ASP | 343 | 25.589 | 45.057 | 63.017 | 1.00 | 0.00 |
| ATOM | 1101 | CA | ASP | 343 | 23.975 | 43.694 | 63.385 | 1.00 | 11.49 |
| ATOM | 1102 | CB | ASP | 343 | 25.023 | 42.586 | 63.021 | 1.00 | 10.46 |
| ATOM | 1103 | CG | ASP | 343 | 24.560 | 41.209 | 63.337 | 1.00 | 9.89 |
| ATOM | 1104 | OD1 | ASP | 343 | 23.361 | 40.952 | 63.559 | 1.00 | 10.01 |
| ATOM | 1105 | OD2 | ASP | 343 | 25.414 | 40.353 | 63.341 | 1.00 | 9.87 |
| ATOM | 1106 | C | ASP | 343 | 23.507 | 43.550 | 64.823 | 1.00 | 10.45 |
| ATOM | 1107 | O | ASP | 343 | 22.296 | 43.351 | 65.073 | 1.00 | 11.49 |
| ATOM | 1108 | N | MET | 344 | 34.432 | 43.703 | 65.768 | 1.00 | 10.00 |
| ATOM | 1109 | H | MET | 344 | 25.343 | 43.869 | 65.531 | 1.00 | 0.00 |
| ATOM | 1110 | CA | MET | 344 | 24.057 | 43.571 | 67.206 | 1.00 | 11.71 |
| ATOM | 1111 | CB | MET | 344 | 25.303 | 43.694 | 68.056 | 1.00 | 11.96 |
| ATOM | 1112 | CG | MET | 344 | 26.310 | 42.576 | 67.832 | 1.00 | 13.73 |
| ATOM | 1113 | SD | MET | 344 | 27.823 | 43.005 | 68.703 | 1.00 | 17.59 |
| ATOM | 1114 | CE | MET | 344 | 28.003 | 41.540 | 69.759 | 1.00 | 14.82 |
| ATOM | 1115 | C | MET | 344 | 22.987 | 44.577 | 67.621 | 1.00 | 9.78 |
| ATOM | 1116 | O | MET | 344 | 22.157 | 44.276 | 68.410 | 1.00 | 9.95 |
| ATOM | 1117 | N | ALA | 345 | 23.030 | 45.781 | 67.063 | 1.00 | 10.20 |
| ATOM | 1118 | H | ALA | 345 | 23.769 | 45.969 | 66.428 | 1.00 | 0.00 |
| ATOM | 1119 | CA | ALA | 345 | 22.027 | 46.836 | 67.361 | 1.00 | 9.44 |
| ATOM | 1120 | CB | ALA | 345 | 22.418 | 48.134 | 66.692 | 1.00 | 9.14 |
| ATOM | 1121 | C | ALA | 345 | 20.621 | 46.384 | 66.905 | 1.00 | 9.52 |
| ATOM | 1122 | O | ALA | 345 | 19.653 | 46.627 | 67.647 | 1.00 | 8.69 |
| ATOM | 1123 | N | ALA | 346 | 20.495 | 45.826 | 65.687 | 1.00 | 8.91 |
| ATOM | 1124 | H | ALA | 346 | 21.306 | 45.759 | 65.108 | 1.00 | 0.00 |
| ATOM | 1125 | CA | ALA | 346 | 19.223 | 45.285 | 65.183 | 1.00 | 8.58 |
| ATOM | 1126 | CB | ALA | 346 | 19.364 | 44.787 | 63.685 | 1.00 | 10.01 |
| ATOM | 1127 | C | ALA | 346 | 18.741 | 44.122 | 66.058 | 1.00 | 8.08 |
| ATOM | 1128 | O | ALA | 346 | 17.555 | 43.983 | 66.248 | 1.00 | 8.74 |
| ATOM | 1129 | N | GLN | 347 | 19.643 | 43.246 | 66.538 | 1.00 | 10.00 |
| ATOM | 1130 | H | GLN | 347 | 20.582 | 43.317 | 66.251 | 1.00 | 0.00 |
| ATOM | 1131 | CA | GLN | 347 | 19.241 | 42.059 | 67.346 | 1.00 | 10.17 |
| ATOM | 1132 | CB | GLN | 347 | 20.451 | 41.190 | 67.716 | 1.00 | 9.38 |
| ATOM | 1133 | CG | GLN | 347 | 21.211 | 40.606 | 66.467 | 1.00 | 9.87 |
| ATOM | 1134 | CD | GLN | 347 | 22.244 | 39.557 | 66.858 | 1.00 | 10.06 |
| ATOM | 1135 | OE1 | GLN | 347 | 22.227 | 39.055 | 67.967 | 1.00 | 9.68 |
| ATOM | 1136 | NE2 | GLN | 347 | 23.161 | 39.228 | 65.926 | 1.00 | 9.95 |
| ATOM | 1137 | HE21 | GLN | 347 | 23.126 | 39.666 | 65.046 | 1.00 | 0.00 |
| ATOM | 1138 | HE22 | GLN | 347 | 23.822 | 38.563 | 66.162 | 1.00 | 0.00 |
| ATOM | 1139 | C | GLN | 347 | 18.575 | 42.608 | 68.595 | 1.00 | 9.84 |
| ATOM | 1140 | O | GLN | 347 | 17.545 | 42.107 | 69.036 | 1.00 | 10.49 |
| ATOM | 1141 | N | ILE | 348 | 19.139 | 43.684 | 69.141 | 1.00 | 8.69 |
| ATOM | 1142 | H | ILE | 348 | 19.934 | 44.051 | 68.711 | 1.00 | 0.00 |
| ATOM | 1143 | CA | ILE | 348 | 18.592 | 44.271 | 70.359 | 1.00 | 8.56 |
| ATOM | 1144 | CB | ILE | 348 | 19.550 | 45.325 | 70.932 | 1.00 | 9.20 |
| ATOM | 1145 | CG2 | ILE | 348 | 18.898 | 46.054 | 72.135 | 1.00 | 7.96 |
| ATOM | 1146 | CG1 | ILE | 348 | 20.836 | 44.629 | 71.412 | 1.00 | 8.29 |
| ATOM | 1147 | CD1 | ILE | 348 | 22.028 | 45.638 | 71.556 | 1.00 | 7.54 |
| ATOM | 1148 | C | ILE | 348 | 17.258 | 44.902 | 70.071 | 1.00 | 8.45 |
| ATOM | 1149 | O | ILE | 348 | 16.326 | 44.798 | 70.879 | 1.00 | 8.32 |
| ATOM | 1150 | N | ALA | 349 | 17.144 | 45.563 | 68.918 | 1.00 | 10.01 |
| ATOM | 1151 | H | ALA | 349 | 17.934 | 45.634 | 68.331 | 1.00 | 0.00 |
| ATOM | 1152 | CA | ALA | 349 | 15.867 | 46.199 | 68.545 | 1.00 | 9.45 |
| ATOM | 1153 | CB | ALA | 349 | 16.018 | 47.116 | 67.260 | 1.00 | 7.33 |
| ATOM | 1154 | C | ALA | 349 | 14.812 | 45.114 | 68.326 | 1.00 | 9.19 |
| ATOM | 1155 | O | ALA | 349 | 13.657 | 45.334 | 68.685 | 1.00 | 8.63 |
| ATOM | 1056 | N | GLU | 350 | 15.204 | 43.961 | 67.775 | 1.00 | 9.34 |
| ATOM | 1057 | H | GLU | 350 | 16.130 | 43.858 | 67.507 | 1.00 | 0.00 |
| ATOM | 1058 | CA | GLU | 350 | 14.292 | 42.834 | 67.524 | 1.00 | 11.14 |
| ATOM | 1059 | CB | GLU | 350 | 15.050 | 41.660 | 66.814 | 1.00 | 11.17 |
| ATOM | 1060 | CG | GLU | 350 | 14.176 | 40.990 | 66.475 | 1.00 | 13.04 |
| ATOM | 1061 | CD | GLU | 350 | 14.969 | 39.401 | 65.758 | 1.00 | 14.49 |
| ATOM | 1062 | OE1 | GLU | 350 | 15.994 | 39.709 | 65.126 | 1.00 | 15.48 |
| ATOM | 1063 | OE2 | GLU | 350 | 14.511 | 38.275 | 65.833 | 1.00 | 16.30 |
| ATOM | 1064 | C | GLU | 350 | 13.744 | 42.334 | 68.850 | 1.00 | 9.65 |
| ATOM | 1065 | O | GLU | 350 | 12.571 | 42.051 | 68.970 | 1.00 | 12.10 |
| ATOM | 1066 | N | GLY | 351 | 14.612 | 42.238 | 69.845 | 1.00 | 9.53 |
| ATOM | 1067 | H | GLY | 351 | 15.561 | 42.458 | 69.673 | 1.00 | 0.00 |

TABLE 5-continued

Coordinates of Lck bound with baicalein

| | Atom Type | Res | # | X | Y | Z | Occ | B |
|---|---|---|---|---|---|---|---|---|
| ATOM | 1068 | CA | GLY | 351 | 14.218 | 41.802 | 71.181 | 1.00 | 9.30 |
| ATOM | 1069 | C | GLY | 351 | 13.222 | 42.778 | 71.790 | 1.00 | 9.62 |
| ATOM | 1070 | O | GLY | 351 | 13.187 | 42.432 | 72.386 | 1.00 | 8.74 |
| ATOM | 1171 | N | MET | 352 | 13.519 | 44.054 | 71.640 | 1.00 | 9.81 |
| ATOM | 1172 | H | MET | 352 | 14.374 | 44.300 | 71.208 | 1.00 | 0.00 |
| ATOM | 1173 | CA | MET | 352 | 12.622 | 45.078 | 72.179 | 1.00 | 9.70 |
| ATOM | 1174 | CB | MET | 352 | 13.282 | 46.469 | 72.132 | 1.00 | 9.76 |
| ATOM | 1175 | CG | MET | 352 | 14.437 | 46.699 | 73.193 | 1.00 | 10.86 |
| ATOM | 1176 | SD | MET | 352 | 14.082 | 46.366 | 74.915 | 1.00 | 11.04 |
| ATOM | 1177 | CE | MET | 352 | 12.507 | 47.450 | 75.116 | 1.00 | 8.53 |
| ATOM | 1178 | C | MET | 352 | 11.321 | 45.145 | 71.389 | 1.00 | 1.04 |
| ATOM | 1179 | O | MET | 352 | 10.310 | 45.582 | 71.949 | 1.00 | 10.60 |
| ATOM | 1180 | N | ALA | 353 | 11.290 | 44.735 | 70.108 | 1.00 | 10.26 |
| ATOM | 1181 | H | ALA | 353 | 12.121 | 44.444 | 69.664 | 1.00 | 0.00 |
| ATOM | 1182 | CA | ALA | 353 | 10.025 | 44.799 | 69.350 | 1.00 | 9.37 |
| ATOM | 1183 | CB | ALA | 353 | 10.257 | 44.597 | 67.872 | 1.00 | 7.85 |
| ATOM | 1184 | C | ALA | 353 | 9.112 | 43.715 | 69.902 | 1.00 | 10.70 |
| ATOM | 1185 | O | ALA | 353 | 7.882 | 43.903 | 69.892 | 1.00 | 11.32 |
| ATOM | 1186 | N | PHE | 354 | 9.688 | 42.612 | 70.401 | 1.00 | 10.56 |
| ATOM | 1187 | H | PHE | 354 | 10.645 | 42.466 | 70.292 | 1.00 | 0.00 |
| ATOM | 1188 | CA | PHE | 354 | 8.870 | 41.538 | 71.021 | 1.00 | 11.23 |
| ATOM | 1189 | CB | PHE | 354 | 9.714 | 40.298 | 71.350 | 1.00 | 12.35 |
| ATOM | 1190 | CG | PHE | 354 | 8.969 | 39.281 | 72.174 | 1.00 | 13.96 |
| ATOM | 1191 | CD1 | PHE | 354 | 7.946 | 38.502 | 71.615 | 1.00 | 14.28 |
| ATOM | 1192 | CD2 | PHE | 354 | 9.291 | 39.113 | 73.515 | 1.00 | 14.83 |
| ATOM | 1193 | CE1 | PHE | 354 | 7.241 | 37.547 | 72.393 | 1.00 | 14.50 |
| ATOM | 1194 | CE2 | PHE | 354 | 8.599 | 38.168 | 74.298 | 1.00 | 16.37 |
| ATOM | 1195 | CZ | PHE | 354 | 7.569 | 37.383 | 73.725 | 1.00 | 15.49 |
| ATOM | 1196 | C | PHE | 354 | 8.254 | 42.111 | 72.314 | 1.00 | 9.74 |
| ATOM | 1197 | O | PHE | 354 | 7.097 | 42.000 | 72.542 | 1.00 | 11.06 |
| ATOM | 1198 | N | ILE | 355 | 9.077 | 42.692 | 73.171 | 1.00 | 9.37 |
| ATOM | 1199 | H | ILE | 355 | 10.038 | 42.696 | 72.972 | 1.00 | 0.00 |
| ATOM | 1200 | CA | ILE | 355 | 8.649 | 43.313 | 74.415 | 1.00 | 8.88 |
| ATOM | 1201 | CB | ILE | 355 | 9.865 | 43.916 | 75.124 | 1.00 | 8.90 |
| ATOM | 1202 | CG2 | ILE | 355 | 9.441 | 44.930 | 76.212 | 1.00 | 9.41 |
| ATOM | 1203 | CG1 | ILE | 355 | 10.692 | 42.811 | 75.723 | 1.00 | 8.41 |
| ATOM | 1204 | CD1 | ILE | 355 | 12.000 | 43.222 | 76.352 | 1.00 | 6.31 |
| ATOM | 1205 | C | ILE | 355 | 7.542 | 44.359 | 74.140 | 1.00 | 9.03 |
| ATOM | 1206 | O | ILE | 355 | 6.483 | 44.388 | 74.772 | 1.00 | 8.95 |
| ATOM | 1207 | N | GLU | 356 | 7.739 | 45.153 | 73.099 | 1.00 | 9.35 |
| ATOM | 1208 | H | GLU | 356 | 8.542 | 45.016 | 72.579 | 1.00 | 0.00 |
| ATOM | 1209 | CA | GLU | 356 | 6.756 | 46.146 | 72.666 | 1.00 | 8.93 |
| ATOM | 1210 | CB | GLU | 356 | 7.373 | 46.887 | 71.452 | 1.00 | 11.49 |
| ATOM | 1211 | CG | GLU | 356 | 6.408 | 47.712 | 70.519 | 1.00 | 13.98 |
| ATOM | 1212 | CD | GLU | 356 | 7.198 | 48.425 | 69.388 | 1.00 | 15.68 |
| ATOM | 1213 | OE1 | GLU | 356 | 7.361 | 47.930 | 68.195 | 1.00 | 13.77 |
| ATOM | 1214 | OE2 | GLU | 356 | 7.743 | 49.484 | 69.727 | 1.00 | 15.14 |
| ATOM | 1215 | C | GLU | 356 | 5.418 | 45.490 | 72.263 | 1.00 | 9.09 |
| ATOM | 1216 | O | GLU | 356 | 4.345 | 45.974 | 72.711 | 1.00 | 7.29 |
| ATOM | 1217 | N | GLU | 357 | 5.456 | 44.448 | 71.418 | 0.36 | 6.96 |
| ATOM | 1218 | H | GLU | 357 | 6.329 | 44.129 | 71.094 | 1.00 | 0.00 |
| ATOM | 1219 | CA | GLU | 357 | 4.245 | 43.765 | 70.988 | 0.36 | 7.75 |
| ATOM | 1220 | CB | GLU | 357 | 4.580 | 42.788 | 69.835 | 0.36 | 7.54 |
| ATOM | 1221 | CG | GLU | 357 | 3.414 | 41.957 | 69.315 | 0.36 | 9.57 |
| ATOM | 1222 | CD | GLU | 357 | 3.239 | 40.683 | 70.074 | 0.36 | 10.99 |
| ATOM | 1223 | OE1 | GLU | 357 | 4.109 | 40.426 | 70.946 | 0.36 | 11.36 |
| ATOM | 1224 | OE2 | GLU | 357 | 2.268 | 39.922 | 69.814 | 0.36 | 12.68 |
| ATOM | 1225 | C | GLU | 357 | 3.467 | 43.061 | 72.110 | 0.36 | 7.56 |
| ATOM | 1226 | O | GLU | 357 | 2.265 | 42.947 | 72.065 | 0.36 | 5.21 |
| ATOM | 1227 | N | ARG | 358 | 4.177 | 42.648 | 73.148 | 1.00 | 9.97 |
| ATOM | 1228 | H | ARG | 358 | 5.162 | 42.766 | 73.138 | 1.00 | 0.00 |
| ATOM | 1229 | CA | ARG | 358 | 3.576 | 41.924 | 74.284 | 1.00 | 12.56 |
| ATOM | 1230 | CB | ARG | 358 | 4.564 | 40.891 | 74.891 | 1.00 | 13.64 |
| ATOM | 1231 | CG | ARG | 358 | 5.029 | 39.814 | 73.947 | 1.00 | 15.08 |
| ATOM | 1232 | CD | ARG | 358 | 3.859 | 39.007 | 73.392 | 1.00 | 18.78 |
| ATOM | 1233 | NE | ARG | 358 | 2.948 | 38.591 | 74.434 | 1.00 | 20.65 |
| ATOM | 1234 | HE | ARG | 358 | 3.298 | 38.498 | 75.355 | 1.00 | 0.00 |
| ATOM | 1235 | CZ | ARG | 358 | 1.667 | 38.301 | 74.234 | 1.00 | 22.90 |
| ATOM | 1236 | NH1 | ARG | 358 | 1.159 | 38.395 | 73.024 | 1.00 | 23.19 |
| ATOM | 1237 | HH11 | ARG | 358 | 1.743 | 38.636 | 72.252 | 1.00 | 0.00 |
| ATOM | 1238 | HH12 | ARG | 358 | 0.201 | 38.138 | 72.861 | 1.00 | 0.00 |
| ATOM | 1239 | NH2 | ARG | 358 | 0.883 | 37.932 | 75.263 | 1.00 | 23.04 |
| ATOM | 1240 | HH21 | ARG | 358 | 1.277 | 37.881 | 76.184 | 1.00 | 0.00 |
| ATOM | 1241 | HH22 | ARG | 358 | −0.069 | 37.706 | 75.107 | 1.00 | 0.00 |

TABLE 5-continued

Coordinates of Lck bound with baicalein

| | Atom Type | Res | # | X | Y | Z | Occ | B |
|---|---|---|---|---|---|---|---|---|
| ATOM | 1242 | C | ARG | 358 | 3.086 | 42.870 | 75.358 | 1.00 | 13.80 |
| ATOM | 1243 | O | ARG | 358 | 2.726 | 42.452 | 76.461 | 1.00 | 15.30 |
| ATOM | 1244 | N | ASN | 359 | 3.084 | 44.167 | 75.045 | 1.00 | 14.83 |
| ATOM | 1245 | H | ASN | 359 | 3.421 | 44.421 | 74.171 | 1.00 | 0.00 |
| ATOM | 1246 | CA | ASN | 359 | 2.659 | 45.211 | 75.984 | 1.00 | 15.66 |
| ATOM | 1247 | CB | ASN | 359 | 1.180 | 45.015 | 76.397 | 1.00 | 15.14 |
| ATOM | 1248 | CG | ASN | 359 | 0.242 | 45.545 | 75.317 | 1.00 | 16.36 |
| ATOM | 1249 | OD1 | ASN | 359 | 0.722 | 46.154 | 74.396 | 1.00 | 18.56 |
| ATOM | 1250 | ND2 | ASN | 359 | −1.051 | 45.282 | 75.395 | 1.00 | 15.79 |
| ATOM | 1251 | HD21 | ASN | 359 | −1.363 | 44.677 | 76.164 | 1.00 | 0.00 |
| ATOM | 1252 | HD22 | ASN | 359 | −1.643 | 45.563 | 74.722 | 1.00 | 0.00 |
| ATOM | 1253 | C | ASN | 359 | 3.530 | 45.432 | 77.206 | 1.00 | 14.57 |
| ATOM | 1254 | O | ASN | 359 | 3.055 | 45.863 | 78.288 | 1.00 | 14.47 |
| ATOM | 1255 | N | TYR | 360 | 4.796 | 45.094 | 77.083 | 1.00 | 13.67 |
| ATOM | 1256 | H | TYR | 360 | 5.153 | 44.692 | 76.251 | 1.00 | 0.00 |
| ATOM | 1257 | CA | TYR | 360 | 5.680 | 45.293 | 78.227 | 1.00 | 14.74 |
| ATOM | 1258 | CB | TYR | 360 | 6.534 | 44.024 | 78.521 | 1.00 | 14.70 |
| ATOM | 1259 | CG | TYR | 360 | 5.812 | 42.963 | 79.281 | 1.00 | 15.46 |
| ATOM | 1260 | CD1 | TYR | 360 | 4.951 | 42.077 | 78.625 | 1.00 | 16.52 |
| ATOM | 1261 | CE1 | TYR | 360 | 4.288 | 41.049 | 79.321 | 1.00 | 16.07 |
| ATOM | 1262 | CD2 | TYR | 360 | 6.004 | 42.814 | 80.646 | 1.00 | 15.82 |
| ATOM | 1263 | CE2 | TYR | 360 | 5.351 | 41.788 | 81.361 | 1.00 | 16.44 |
| ATOM | 1264 | CZ | TYR | 360 | 4.489 | 40.917 | 80.675 | 1.00 | 18.28 |
| ATOM | 1265 | OH | TYR | 360 | 3.769 | 39.971 | 81.384 | 1.00 | 19.46 |
| ATOM | 1266 | HH | TYR | 360 | 3.227 | 39.467 | 80.758 | 1.00 | 0.00 |
| ATOM | 1267 | C | TYR | 360 | 6.628 | 46.462 | 78.037 | 1.00 | 13.34 |
| ATOM | 1268 | O | TYR | 360 | 6.808 | 46.992 | 76.951 | 1.00 | 12.61 |
| ATOM | 1269 | N | ILE | 361 | 7.158 | 46.943 | 79.136 | 1.00 | 13.85 |
| ATOM | 1270 | H | ILE | 361 | 6.794 | 46.631 | 80.005 | 1.00 | 0.00 |
| ATOM | 1271 | CA | ILE | 361 | 8.187 | 47.936 | 79.039 | 1.00 | 13.79 |
| ATOM | 1272 | CB | ILE | 361 | 7.791 | 49.431 | 79.412 | 1.00 | 15.44 |
| ATOM | 1273 | CG2 | ILE | 361 | 6.741 | 50.044 | 78.397 | 1.00 | 15.19 |
| ATOM | 1274 | CG1 | ILE | 361 | 7.295 | 49.562 | 80.867 | 1.00 | 15.03 |
| ATOM | 1275 | CD1 | ILE | 361 | 7.000 | 51.081 | 81.157 | 1.00 | 18.02 |
| ATOM | 1276 | C | ILE | 361 | 9.355 | 47.428 | 79.834 | 1.00 | 13.92 |
| ATOM | 1277 | O | ILE | 361 | 9.181 | 46.559 | 80.696 | 1.00 | 14.26 |
| ATOM | 1278 | N | HIS | 362 | 10.555 | 47.951 | 79.564 | 1.00 | 12.84 |
| ATOM | 1279 | H | HIS | 362 | 10.566 | 48.670 | 78.905 | 1.00 | 0.00 |
| ATOM | 1280 | CA | HIS | 362 | 11.775 | 47.501 | 80.246 | 1.00 | 12.43 |
| ATOM | 1281 | CB | HIS | 362 | 12.838 | 47.242 | 79.159 | 1.00 | 12.59 |
| ATOM | 1282 | CG | HIS | 362 | 14.036 | 46.490 | 79.675 | 1.00 | 13.04 |
| ATOM | 1283 | CD2 | HIS | 362 | 14.352 | 45.187 | 79.641 | 1.00 | 10.27 |
| ATOM | 1284 | ND1 | HIS | 362 | 15.044 | 47.123 | 80.698 | 1.00 | 11.44 |
| ATOM | 1285 | HD1 | HIS | 362 | 15.071 | 48.077 | 80.555 | 1.00 | 0.00 |
| ATOM | 1286 | CE1 | HIS | 362 | 15.941 | 46.227 | 80.753 | 1.00 | 10.51 |
| ATOM | 1287 | NE2 | HIS | 362 | 15.560 | 45.041 | 80.315 | 1.00 | 11.97 |
| ATOM | 1288 | HE2 | HIS | 362 | 16.033 | 44.204 | 80.456 | 1.00 | 0.00 |
| ATOM | 1289 | C | HIS | 362 | 12.295 | 48.491 | 81.339 | 1.00 | 12.90 |
| ATOM | 1290 | O | HIS | 362 | 12.541 | 48.094 | 82.472 | 1.00 | 10.63 |
| ATOM | 1291 | N | ARG | 363 | 12.467 | 49.762 | 80.948 | 1.00 | 13.44 |
| ATOM | 1292 | H | ARG | 363 | 12.371 | 50.001 | 80.051 | 1.00 | 0.00 |
| ATOM | 1293 | CA | ARG | 363 | 12.933 | 50.788 | 81.895 | 1.00 | 14.98 |
| ATOM | 1294 | CB | ARG | 363 | 12.065 | 50.809 | 83.192 | 1.00 | 16.13 |
| ATOM | 1295 | CG | ARG | 363 | 10.591 | 51.066 | 82.912 | 1.00 | 15.88 |
| ATOM | 1296 | CD | ARG | 363 | 9.809 | 51.480 | 84.164 | 1.00 | 18.00 |
| ATOM | 1297 | NE | ARG | 363 | 9.910 | 50.561 | 85.265 | 1.00 | 18.78 |
| ATOM | 1298 | HE | ARG | 363 | 10.040 | 49.599 | 85.069 | 1.00 | 0.00 |
| ATOM | 1299 | CZ | ARG | 363 | 9.872 | 50.919 | 86.546 | 1.00 | 19.51 |
| ATOM | 1300 | NH1 | ARG | 363 | 9.737 | 52.207 | 86.856 | 1.00 | 19.86 |
| ATOM | 1301 | HH11 | ARG | 363 | 9.663 | 52.881 | 86.145 | 1.00 | 0.00 |
| ATOM | 1302 | HH12 | ARG | 363 | 9.682 | 52.471 | 87.828 | 1.00 | 0.00 |
| ATOM | 1303 | NH2 | ARG | 363 | 9.873 | 49.994 | 87.509 | 1.00 | 15.47 |
| ATOM | 1304 | HH21 | ARG | 363 | 9.938 | 49.014 | 87.272 | 1.00 | 0.00 |
| ATOM | 1305 | HH22 | ARG | 363 | 9.841 | 50.257 | 88.474 | 1.00 | 0.00 |
| ATOM | 1306 | C | ARG | 363 | 14.353 | 50.781 | 82.299 | 1.00 | 14.57 |
| ATOM | 1307 | O | ARG | 363 | 14.754 | 51.728 | 82.982 | 1.00 | 15.11 |
| ATOM | 1308 | N | ASP | 364 | 15.157 | 49.811 | 81.860 | 1.00 | 13.65 |
| ATOM | 1309 | H | ASP | 364 | 14.754 | 49.103 | 81.269 | 1.00 | 0.00 |
| ATOM | 1310 | CA | ASP | 364 | 16.575 | 49.736 | 82.254 | 1.00 | 13.33 |
| ATOM | 1311 | CB | ASP | 364 | 16.732 | 48.695 | 83.351 | 1.00 | 14.48 |
| ATOM | 1312 | CG | ASP | 364 | 17.911 | 49.004 | 84.269 | 1.00 | 16.16 |
| ATOM | 1313 | OD1 | ASP | 364 | 18.552 | 50.051 | 84.073 | 1.00 | 15.11 |
| ATOM | 1314 | OD2 | ASP | 364 | 18.198 | 48.215 | 85.204 | 1.00 | 16.47 |
| ATOM | 1315 | C | ASP | 364 | 17.429 | 49.344 | 81.024 | 1.00 | 13.16 |

TABLE 5-continued

Coordinates of Lck bound with baicalein

| | Atom Type | Res | # | X | Y | Z | Occ | B |
|---|---|---|---|---|---|---|---|---|
| ATOM | 1316 | O | ASP | 364 | 18.421 | 48.595 | 81.147 | 1.00 | 12.80 |
| ATOM | 1317 | N | LEU | 365 | 16.998 | 49.797 | 79.847 | 1.00 | 11.37 |
| ATOM | 1318 | H | LEU | 365 | 16.198 | 50.343 | 79.821 | 1.00 | 0.00 |
| ATOM | 1319 | CA | LEU | 365 | 17.666 | 49.438 | 78.598 | 1.00 | 12.02 |
| ATOM | 1320 | CB | LEU | 365 | 16.710 | 49.644 | 77.405 | 1.00 | 11.92 |
| ATOM | 1321 | CG | LEU | 365 | 17.230 | 49.262 | 76.004 | 1.00 | 10.27 |
| ATOM | 1322 | CD1 | LEU | 365 | 17.664 | 47.847 | 75.909 | 1.00 | 10.68 |
| ATOM | 1323 | CD2 | LEU | 365 | 16.124 | 49.501 | 75.028 | 1.00 | 8.82 |
| ATOM | 1324 | C | LEU | 365 | 18.954 | 50.247 | 78.433 | 1.00 | 12.81 |
| ATOM | 1325 | O | LEU | 365 | 18.952 | 51.485 | 78.276 | 1.00 | 13.57 |
| ATOM | 1326 | N | ARG | 366 | 20.058 | 49.528 | 78.513 | 1.00 | 12.34 |
| ATOM | 1327 | H | ARG | 366 | 19.966 | 48.537 | 78.618 | 1.00 | 0.00 |
| ATOM | 1328 | CA | ARG | 366 | 21.370 | 50.114 | 78.374 | 1.00 | 12.21 |
| ATOM | 1329 | CB | ARG | 366 | 21.765 | 50.742 | 79.687 | 1.00 | 13.86 |
| ATOM | 1330 | CG | ARG | 366 | 21.682 | 49.788 | 80.860 | 1.00 | 15.05 |
| ATOM | 1331 | CD | ARG | 366 | 21.880 | 50.535 | 82.159 | 1.00 | 18.66 |
| ATOM | 1332 | NE | ARG | 366 | 23.189 | 51.163 | 82.247 | 1.00 | 21.34 |
| ATOM | 1333 | HE | ARG | 366 | 23.843 | 50.967 | 81.545 | 1.00 | 0.00 |
| ATOM | 1334 | CZ | ARG | 366 | 23.511 | 52.021 | 83.209 | 1.00 | 23.86 |
| ATOM | 1335 | NH1 | ARG | 366 | 22.615 | 52.338 | 84.156 | 1.00 | 24.39 |
| ATOM | 1336 | HH11 | ARG | 366 | 21.697 | 51.904 | 84.129 | 1.00 | 0.00 |
| ATOM | 1337 | HH12 | ARG | 366 | 22.847 | 52.958 | 84.880 | 1.00 | 0.00 |
| ATOM | 1338 | NH2 | ARG | 366 | 24.731 | 52.548 | 83.260 | 1.00 | 24.20 |
| ATOM | 1339 | HH21 | ARG | 366 | 25.400 | 52.270 | 82.574 | 1.00 | 0.00 |
| ATOM | 1340 | HH22 | ARG | 366 | 24.958 | 53.164 | 83.992 | 1.00 | 0.00 |
| ATOM | 1341 | C | ARG | 366 | 22.316 | 48.959 | 78.066 | 1.00 | 12.29 |
| ATOM | 1342 | O | ARG | 366 | 21.988 | 47.777 | 78.362 | 1.00 | 10.81 |
| ATOM | 1343 | N | ALA | 367 | 23.489 | 49.296 | 77.544 | 1.00 | 10.54 |
| ATOM | 1344 | H | ALA | 367 | 23.714 | 50.225 | 77.449 | 1.00 | 0.00 |
| ATOM | 1345 | CA | ALA | 367 | 24.446 | 48.276 | 77.146 | 1.00 | 11.66 |
| ATOM | 1346 | CB | ALA | 367 | 25.701 | 48.916 | 76.565 | 1.00 | 10.94 |
| ATOM | 1347 | C | ALA | 367 | 24.812 | 47.304 | 78.258 | 1.00 | 10.63 |
| ATOM | 1348 | O | ALA | 367 | 25.092 | 46.142 | 77.969 | 1.00 | 11.07 |
| ATOM | 1349 | N | ALA | 368 | 24.818 | 47.790 | 79.500 | 1.00 | 9.10 |
| ATOM | 1350 | H | ALA | 368 | 24.626 | 48.715 | 79.659 | 1.00 | 0.00 |
| ATOM | 1351 | CA | ALA | 368 | 25.110 | 46.933 | 80.648 | 1.00 | 10.62 |
| ATOM | 1352 | CB | ALA | 368 | 25.190 | 47.777 | 81.928 | 1.00 | 8.98 |
| ATOM | 1353 | C | ALA | 368 | 24.072 | 45.797 | 80.811 | 1.00 | 9.13 |
| ATOM | 1354 | O | ALA | 368 | 24.375 | 44.757 | 81.414 | 1.00 | 10.33 |
| ATOM | 1355 | N | ASN | 369 | 22.890 | 45.975 | 80.237 | 1.00 | 8.90 |
| ATOM | 1356 | H | ASN | 369 | 22.733 | 46.745 | 79.689 | 1.00 | 0.00 |
| ATOM | 1357 | CA | ASN | 369 | 21.812 | 45.004 | 80.409 | 1.00 | 10.35 |
| ATOM | 1358 | CB | ASN | 369 | 20.553 | 45.692 | 80.948 | 1.00 | 10.19 |
| ATOM | 1359 | CG | ASN | 369 | 20.729 | 46.146 | 82.397 | 1.00 | 12.13 |
| ATOM | 1360 | OD1 | ASN | 369 | 21.501 | 45.558 | 83.154 | 1.00 | 11.09 |
| ATOM | 1361 | ND2 | ASN | 369 | 20.061 | 47.235 | 72.772 | 1.00 | 11.96 |
| ATOM | 1362 | HD21 | ASN | 369 | 19.481 | 47.658 | 82.135 | 1.00 | 0.00 |
| ATOM | 1363 | HD22 | ASN | 369 | 20.150 | 47.478 | 83.696 | 1.00 | 0.00 |
| ATOM | 1364 | C | ASN | 369 | 21.487 | 44.227 | 79.155 | 1.00 | 8.81 |
| ATOM | 1365 | O | ASN | 369 | 20.304 | 43.859 | 78.950 | 1.00 | 10.42 |
| ATOM | 1366 | N | ILE | 370 | 22.489 | 44.112 | 78.266 | 1.00 | 9.20 |
| ATOM | 1367 | H | ILE | 370 | 23.292 | 44.594 | 78.426 | 1.00 | 0.00 |
| ATOM | 1368 | CA | ILE | 370 | 22.371 | 43.317 | 77.024 | 1.00 | 8.11 |
| ATOM | 1369 | CB | ILE | 370 | 22.747 | 44.135 | 75.726 | 1.00 | 6.67 |
| ATOM | 1370 | CG2 | ILE | 370 | 22.768 | 43.199 | 74.459 | 1.00 | 5.55 |
| ATOM | 1371 | CG1 | ILE | 370 | 21.744 | 45.268 | 75.522 | 1.00 | 6.71 |
| ATOM | 1372 | CD1 | ILE | 370 | 20.208 | 44.889 | 75.640 | 1.00 | 9.82 |
| ATOM | 1373 | C | ILE | 370 | 23.484 | 42.277 | 77.262 | 1.00 | 9.99 |
| ATOM | 1374 | O | ILE | 370 | 24.622 | 42.649 | 77.684 | 1.00 | 10.00 |
| ATOM | 1375 | N | LEU | 371 | 23.183 | 41.000 | 77.010 | 1.00 | 9.28 |
| ATOM | 1376 | H | LEU | 371 | 22.238 | 40.743 | 76.814 | 1.00 | 0.00 |
| ATOM | 1377 | CA | LEU | 371 | 24.204 | 39.951 | 77.186 | 1.00 | 8.98 |
| ATOM | 1378 | CB | LEU | 371 | 23.694 | 38.795 | 78.122 | 1.00 | 7.65 |
| ATOM | 1379 | CG | LEU | 371 | 23.505 | 39.162 | 79.585 | 1.00 | 8.68 |
| ATOM | 1380 | CD1 | LEU | 371 | 22.867 | 38.040 | 80.471 | 1.00 | 7.61 |
| ATOM | 1381 | CD2 | LEU | 371 | 24.865 | 39.473 | 80.181 | 1.00 | 9.32 |
| ATOM | 1382 | C | LEU | 371 | 24.598 | 39.431 | 75.817 | 1.00 | 8.97 |
| ATOM | 1383 | O | LEU | 371 | 23.808 | 39.488 | 74.885 | 1.00 | 8.19 |
| ATOM | 1384 | N | VAL | 372 | 25.835 | 38.927 | 75.717 | 1.00 | 9.00 |
| ATOM | 1385 | H | VAL | 372 | 26.396 | 38.891 | 76.485 | 1.00 | 0.00 |
| ATOM | 1386 | CA | VAL | 372 | 26.347 | 38.442 | 74.433 | 1.00 | 10.47 |
| ATOM | 1387 | CB | VAL | 372 | 27.635 | 39.235 | 74.076 | 1.00 | 11.00 |
| ATOM | 1388 | CG1 | VAL | 372 | 28.125 | 38.893 | 72.654 | 1.00 | 9.69 |
| ATOM | 1389 | CG2 | VAL | 372 | 27.373 | 40.778 | 74.268 | 1.00 | 10.39 |

TABLE 5-continued

Coordinates of Lck bound with baicalein

| | Atom Type | Res | # | X | Y | Z | Occ | B |
|---|---|---|---|---|---|---|---|---|
| ATOM | 1390 | C | VAL | 372 | 26.719 | 36.967 | 74.557 | 1.00 | 10.63 |
| ATOM | 1391 | O | VAL | 372 | 27.466 | 36.603 | 75.462 | 1.00 | 10.67 |
| ATOM | 1392 | N | SER | 373 | 26.275 | 36.168 | 73.589 | 1.00 | 1.55 |
| ATOM | 1393 | H | SER | 373 | 25.721 | 36.559 | 72.852 | 1.00 | 0.00 |
| ATOM | 1394 | CA | SER | 373 | 26.508 | 34.727 | 73.567 | 1.00 | 11.71 |
| ATOM | 1395 | CB | SER | 373 | 25.459 | 34.035 | 72.697 | 1.00 | 9.39 |
| ATOM | 1396 | OG | SER | 373 | 25.706 | 34.372 | 71.389 | 1.00 | 13.49 |
| ATOM | 1397 | HG | SER | 373 | 25.602 | 35.295 | 71.216 | 1.00 | 0.00 |
| ATOM | 1398 | C | SER | 373 | 27.884 | 34.437 | 72.998 | 1.00 | 12.60 |
| ATOM | 1399 | O | SER | 373 | 28.622 | 35.326 | 72.512 | 1.00 | 11.43 |
| ATOM | 1400 | N | ASP | 374 | 28.215 | 33.152 | 72.971 | 1.00 | 14.07 |
| ATOM | 1401 | H | ASP | 374 | 27.584 | 32.476 | 73.352 | 1.00 | 0.00 |
| ATOM | 1402 | CA | ASP | 374 | 29.499 | 32.703 | 72.427 | 1.00 | 13.79 |
| ATOM | 1403 | CB | ASP | 374 | 29.701 | 31.234 | 72.793 | 1.00 | 15.48 |
| ATOM | 1404 | CG | ASP | 374 | 28.721 | 30.344 | 72.102 | 1.00 | 16.95 |
| ATOM | 1405 | OD1 | ASP | 374 | 27.515 | 30.643 | 72.224 | 1.00 | 15.27 |
| ATOM | 1406 | OD2 | ASP | 374 | 29.178 | 29.390 | 71.412 | 1.00 | 18.87 |
| ATOM | 1407 | C | ASP | 374 | 29.513 | 32.878 | 70.902 | 1.00 | 13.18 |
| ATOM | 1408 | O | ASP | 374 | 30.574 | 32.895 | 70.339 | 1.00 | 12.80 |
| ATOM | 1409 | N | THR | 375 | 28.356 | 32.957 | 70.222 | 1.00 | 13.27 |
| ATOM | 1410 | H | THR | 375 | 27.504 | 32.841 | 70.681 | 1.00 | 0.00 |
| ATOM | 1411 | CA | THR | 375 | 28.356 | 33.144 | 68.743 | 1.00 | 12.59 |
| ATOM | 1412 | CB | THR | 375 | 27.265 | 32.361 | 68.084 | 1.00 | 11.33 |
| ATOM | 1413 | OG1 | THR | 375 | 26.021 | 32.687 | 68.739 | 1.00 | 11.99 |
| ATOM | 1414 | HG1 | THR | 375 | 25.304 | 32.175 | 68.310 | 1.00 | 0.00 |
| ATOM | 1415 | CG2 | THR | 375 | 27.539 | 30.846 | 68.174 | 1.00 | 12.33 |
| ATOM | 1416 | C | THR | 375 | 28.162 | 34.665 | 68.454 | 1.00 | 13.31 |
| ATOM | 1417 | O | THR | 375 | 27.886 | 35.122 | 67.359 | 1.00 | 11.86 |
| ATOM | 1418 | N | LEU | 376 | 28.279 | 35.467 | 69.489 | 1.00 | 13.59 |
| ATOM | 1419 | H | LEU | 376 | 28.433 | 35.066 | 70.376 | 1.00 | 0.00 |
| ATOM | 1420 | CA | LEU | 376 | 28.150 | 36.899 | 69.339 | 1.00 | 13.17 |
| ATOM | 1421 | CB | LEU | 376 | 29.216 | 37.430 | 68.312 | 1.00 | 14.47 |
| ATOM | 1422 | CG | LEU | 376 | 30.606 | 37.786 | 68.872 | 1.00 | 14.28 |
| ATOM | 1423 | CD1 | LEU | 376 | 31.111 | 36.841 | 69.929 | 1.00 | 15.30 |
| ATOM | 1424 | CD2 | LEU | 376 | 31.604 | 37.959 | 67.756 | 1.00 | 15.98 |
| ATOM | 1425 | C | LEU | 376 | 26.745 | 37.354 | 68.961 | 1.00 | 13.40 |
| ATOM | 1426 | O | LEU | 376 | 26.559 | 38.232 | 68.054 | 1.00 | 13.18 |
| ATOM | 1427 | N | SER | 377 | 25.751 | 36.690 | 69.543 | 1.00 | 11.00 |
| ATOM | 1428 | H | SER | 377 | 25.975 | 35.848 | 70.025 | 1.00 | 0.00 |
| ATOM | 1429 | CA | SER | 377 | 24.375 | 37.077 | 69.336 | 1.00 | 11.29 |
| ATOM | 1430 | CB | SER | 377 | 23.440 | 35.886 | 69.068 | 1.00 | 11.10 |
| ATOM | 1431 | OG | SER | 377 | 23.509 | 34.938 | 70.107 | 1.00 | 10.85 |
| ATOM | 1432 | HG | SER | 377 | 24.399 | 34.635 | 70.211 | 1.00 | 0.00 |
| ATOM | 1433 | C | SER | 377 | 24.041 | 37.820 | 70.666 | 1.00 | 10.98 |
| ATOM | 1434 | O | SER | 377 | 24.676 | 37.581 | 71.760 | 1.00 | 9.26 |
| ATOM | 1435 | N | CYS | 378 | 23.100 | 38.768 | 70.584 | 1.00 | 11.28 |
| ATOM | 1436 | H | CYS | 378 | 22.675 | 38.934 | 69.705 | 1.00 | 0.00 |
| ATOM | 1437 | CA | CYS | 378 | 22.706 | 39.575 | 71.751 | 1.00 | 11.29 |
| ATOM | 1438 | CB | CYS | 378 | 22.786 | 41.084 | 71.429 | 1.00 | 10.93 |
| ATOM | 1439 | SG | CYS | 378 | 24.406 | 41.730 | 70.929 | 1.00 | 13.14 |
| ATOM | 1440 | C | CYS | 378 | 21.339 | 39.306 | 72.292 | 1.00 | 11.38 |
| ATOM | 1441 | O | CYS | 378 | 20.377 | 39.122 | 71.529 | 1.00 | 13.08 |
| ATOM | 1442 | N | LYS | 379 | 21.210 | 39.353 | 73.613 | 1.00 | 10.07 |
| ATOM | 1443 | H | LYS | 379 | 21.992 | 39.451 | 74.167 | 1.00 | 0.00 |
| ATOM | 1444 | CA | LYS | 379 | 19.904 | 39.125 | 74.221 | 1.00 | 9.40 |
| ATOM | 1445 | CB | LYS | 379 | 19.781 | 37.689 | 74.827 | 1.00 | 9.37 |
| ATOM | 1446 | CG | LYS | 379 | 19.903 | 36.585 | 73.728 | 1.00 | 7.75 |
| ATOM | 1447 | CD | LYS | 379 | 19.531 | 35.185 | 74.222 | 1.00 | 4.23 |
| ATOM | 1448 | CE | LYS | 379 | 19.866 | 34.202 | 73.087 | 1.00 | 5.59 |
| ATOM | 1449 | NZ | LYS | 379 | 19.067 | 32.967 | 73.188 | 1.00 | 5.62 |
| ATOM | 1450 | HZ1 | LYS | 379 | 18.073 | 33.172 | 73.112 | 1.00 | 0.00 |
| ATOM | 1451 | HZ2 | LYS | 379 | 19.275 | 32.493 | 74.084 | 1.00 | 0.00 |
| ATOM | 1452 | HZ3 | LYS | 379 | 19.360 | 32.315 | 72.408 | 1.00 | 0.00 |
| ATOM | 1453 | C | LYS | 379 | 19.600 | 40.194 | 75.274 | 1.00 | 9.30 |
| ATOM | 1454 | O | LYS | 379 | 20.503 | 40.654 | 75.974 | 1.00 | 8.21 |
| ATOM | 1455 | N | ILE | 380 | 18.321 | 40.543 | 75.392 | 1.00 | 9.58 |
| ATOM | 1456 | H | ILE | 380 | 17.664 | 40.163 | 74.757 | 1.00 | 0.00 |
| ATOM | 1457 | CA | ILE | 380 | 17.911 | 41.495 | 76.414 | 1.00 | 10.10 |
| ATOM | 1458 | CB | ILE | 380 | 16.447 | 42.026 | 76.225 | 1.00 | 10.74 |
| ATOM | 1459 | CG2 | ILE | 380 | 15.168 | 43.100 | 77.279 | 1.00 | 10.12 |
| ATOM | 1460 | CG1 | ILE | 380 | 16.153 | 42.514 | 74.797 | 1.00 | 12.84 |
| ATOM | 1461 | CD1 | ILE | 380 | 16.999 | 43.640 | 74.352 | 1.00 | 10.59 |
| ATOM | 1462 | C | ILE | 380 | 17.890 | 40.758 | 77.790 | 1.00 | 9.51 |
| ATOM | 1463 | O | ILE | 380 | 17.385 | 39.641 | 77.922 | 1.00 | 7.33 |

TABLE 5-continued

Coordinates of Lck bound with baicalein

| | Atom Type | Res | # | X | Y | Z | Occ | B |
|---|---|---|---|---|---|---|---|---|
| ATOM | 1464 | N | ALA | 381 | 18.419 | 41.443 | 78.808 | 1.00 | 9.54 |
| ATOM | 1465 | H | ALA | 381 | 18.795 | 42.318 | 78.627 | 1.00 | 0.00 |
| ATOM | 1466 | CA | ALA | 381 | 18.536 | 40.895 | 80.132 | 1.00 | 11.74 |
| ATOM | 1467 | CB | ALA | 381 | 19.983 | 40.411 | 80.401 | 1.00 | 11.24 |
| ATOM | 1468 | C | ALA | 381 | 18.104 | 41.919 | 81.232 | 1.00 | 13.11 |
| ATOM | 1469 | O | ALA | 381 | 17.749 | 43.064 | 80.948 | 1.00 | 11.41 |
| ATOM | 1470 | N | ASP | 382 | 18.127 | 41.432 | 82.471 | 1.00 | 14.06 |
| ATOM | 1471 | H | ASP | 382 | 18.397 | 40.482 | 82.574 | 1.00 | 0.00 |
| ATOM | 1472 | CA | ASP | 382 | 17.784 | 42.179 | 83.684 | 1.00 | 15.91 |
| ATOM | 1473 | CB | ASP | 382 | 18.798 | 43.275 | 83.932 | 1.00 | 17.25 |
| ATOM | 1474 | CG | ASP | 382 | 18.658 | 43.890 | 85.342 | 1.00 | 20.83 |
| ATOM | 1475 | OD1 | ASP | 382 | 17.583 | 43.755 | 86.026 | 1.00 | 19.86 |
| ATOM | 1476 | OD2 | ASP | 382 | 19.659 | 44.484 | 85.807 | 1.00 | 19.37 |
| ATOM | 1477 | C | ASP | 382 | 16.382 | 42.809 | 83.621 | 1.00 | 16.35 |
| ATOM | 1478 | O | ASP | 382 | 16.225 | 44.010 | 83.331 | 1.00 | 15.93 |
| ATOM | 1479 | N | PHE | 383 | 15.382 | 42.011 | 83.981 | 1.00 | 15.98 |
| ATOM | 1480 | H | PHE | 383 | 15.614 | 41.088 | 84.263 | 1.00 | 0.00 |
| ATOM | 1481 | CA | PHE | 383 | 14.004 | 42.403 | 83.906 | 1.00 | 15.83 |
| ATOM | 1482 | CB | PHE | 383 | 13.244 | 41.139 | 83.430 | 1.00 | 15.14 |
| ATOM | 1483 | CG | PHE | 383 | 13.607 | 40.727 | 82.015 | 1.00 | 13.31 |
| ATOM | 1484 | CD1 | PHE | 383 | 13.054 | 41.413 | 80.939 | 1.00 | 12.31 |
| ATOM | 1485 | CD2 | PHE | 383 | 14.538 | 39.758 | 81.772 | 1.00 | 10.75 |
| ATOM | 1486 | CE1 | PHE | 383 | 13.476 | 41.101 | 79.619 | 1.00 | 10.90 |
| ATOM | 1487 | CE2 | PHE | 383 | 14.959 | 39.449 | 80.453 | 1.00 | 10.72 |
| ATOM | 1488 | CZ | PHE | 383 | 14.418 | 40.131 | 79.423 | 1.00 | 9.14 |
| ATOM | 1489 | C | PHE | 383 | 13.457 | 42.970 | 85.222 | 1.00 | 16.35 |
| ATOM | 1490 | O | PHE | 383 | 12.248 | 43.123 | 85.409 | 1.00 | 17.16 |
| ATOM | 1491 | N | GLY | 384 | 14.366 | 43.300 | 86.122 | 1.00 | 17.08 |
| ATOM | 1492 | H | GLY | 384 | 15.309 | 43.204 | 85.887 | 1.00 | 0.00 |
| ATOM | 1493 | CA | GLY | 384 | 14.009 | 43.788 | 87.431 | 1.00 | 17.82 |
| ATOM | 1494 | C | GLY | 384 | 13.025 | 44.931 | 87.424 | 1.00 | 18.47 |
| ATOM | 1495 | O | GLY | 384 | 12.116 | 45.009 | 88.268 | 1.00 | 17.75 |
| ATOM | 1496 | N | LEU | 385 | 13.193 | 45.841 | 86.469 | 1.00 | 18.23 |
| ATOM | 1497 | H | LEU | 385 | 13.919 | 45.735 | 85.833 | 1.00 | 0.00 |
| ATOM | 1498 | CA | LEU | 385 | 12.271 | 46.976 | 86.398 | 1.00 | 17.70 |
| ATOM | 1499 | CB | LEU | 385 | 13.039 | 48.250 | 86.139 | 1.00 | 18.87 |
| ATOM | 1500 | CG | LEU | 385 | 13.951 | 48.678 | 87.289 | 1.00 | 20.12 |
| ATOM | 1501 | CD1 | LEU | 385 | 14.807 | 49.869 | 86.827 | 1.00 | 19.62 |
| ATOM | 1502 | CD2 | LEU | 385 | 13.089 | 49.061 | 88.487 | 1.00 | 19.61 |
| ATOM | 1503 | C | LEU | 385 | 11.196 | 46.853 | 85.359 | 1.00 | 17.58 |
| ATOM | 1504 | O | LEU | 385 | 10.359 | 47.745 | 85.256 | 1.00 | 16.04 |
| ATOM | 1505 | N | ALA | 386 | 11.212 | 45.757 | 84.586 | 1.00 | 17.12 |
| ATOM | 1506 | H | ALA | 386 | 11.881 | 45.034 | 84.749 | 1.00 | 0.00 |
| ATOM | 1507 | CA | ALA | 386 | 10.225 | 45.539 | 83.515 | 1.00 | 17.26 |
| ATOM | 1508 | CB | ALA | 386 | 10.568 | 44.351 | 82.719 | 1.00 | 15.73 |
| ATOM | 1509 | C | ALA | 386 | 8.804 | 45.440 | 84.108 | 1.00 | 18.15 |
| ATOM | 1510 | O | ALA | 386 | 8.596 | 44.897 | 85.190 | 1.00 | 18.53 |
| ATOM | 1511 | N | ARG | 387 | 7.827 | 45.955 | 83.367 | 1.00 | 17.68 |
| ATOM | 1512 | H | ARG | 387 | 8.077 | 46.359 | 82.483 | 1.00 | 0.00 |
| ATOM | 1513 | CA | ARG | 387 | 6.450 | 45.945 | 83.790 | 1.00 | 17.40 |
| ATOM | 1514 | CB | ARG | 387 | 6.069 | 47.286 | 84.423 | 1.00 | 17.98 |
| ATOM | 1515 | CG | ARG | 387 | 6.909 | 47.730 | 85.632 | 1.00 | 17.84 |
| ATOM | 1516 | CD | ARG | 387 | 6.655 | 46.862 | 86.829 | 1.00 | 16.86 |
| ATOM | 1517 | NE | ARG | 387 | 7.407 | 47.385 | 87.960 | 1.00 | 18.36 |
| ATOM | 1518 | HE | ARG | 387 | 6.985 | 48.085 | 88.478 | 1.00 | 0.00 |
| ATOM | 1519 | CZ | ARG | 387 | 8.582 | 46.904 | 88.372 | 1.00 | 18.83 |
| ATOM | 1520 | NH1 | ARG | 387 | 9.171 | 45.883 | 87.763 | 1.00 | 17.79 |
| ATOM | 1521 | HH11 | ARG | 387 | 8.760 | 45.471 | 86.934 | 1.00 | 0.00 |
| ATOM | 1522 | HH12 | ARG | 387 | 10.079 | 45.562 | 88.049 | 1.00 | 0.00 |
| ATOM | 1523 | NH2 | ARG | 387 | 9.154 | 47.438 | 89.423 | 1.00 | 18.45 |
| ATOM | 1524 | HH21 | ARG | 387 | 8.707 | 48.167 | 89.928 | 1.00 | 0.00 |
| ATOM | 1525 | HH22 | ARG | 387 | 10.046 | 47.085 | 89.739 | 1.00 | 0.00 |
| ATOM | 1526 | C | ARG | 387 | 5.474 | 45.744 | 82.660 | 1.00 | 18.02 |
| ATOM | 1527 | O | ARG | 387 | 5.706 | 46.154 | 81.502 | 1.00 | 17.08 |
| ATOM | 1528 | N | LEU | 388 | 4.359 | 45.125 | 83.028 | 1.00 | 18.45 |
| ATOM | 1529 | H | LEU | 388 | 4.283 | 44.974 | 83.953 | 1.00 | 0.00 |
| ATOM | 1530 | CA | LEU | 388 | 3.260 | 44.903 | 82.115 | 1.00 | 20.75 |
| ATOM | 1531 | CB | LEU | 388 | 2.360 | 43.771 | 82.519 | 1.00 | 21.13 |
| ATOM | 1532 | CG | LEU | 388 | 1.206 | 43.447 | 81.539 | 1.00 | 2.07 |
| ATOM | 1533 | CD1 | LEU | 388 | 1.687 | 43.312 | 80.142 | 1.00 | 21.59 |
| ATOM | 1534 | CD2 | LEU | 388 | 0.579 | 42.114 | 81.955 | 1.00 | 22.97 |
| ATOM | 1535 | C | LEU | 388 | 2.491 | 46.185 | 82.101 | 1.00 | 22.17 |
| ATOM | 1536 | O | LEU | 388 | 2.110 | 46.774 | 83.128 | 1.00 | 21.05 |
| ATOM | 1537 | N | ILE | 389 | 2.248 | 46.632 | 80.894 | 1.00 | 23.75 |

TABLE 5-continued

Coordinates of Lck bound with baicalein

| | Atom Type | Res | # | X | Y | Z | Occ | B |
|---|---|---|---|---|---|---|---|---|
| ATOM | 1538 | H | ILE | 389 | 2.560 | 46.097 | 80.130 | 1.00 | 0.00 |
| ATOM | 1539 | CA | ILE | 389 | 1.572 | 47.864 | 80.686 | 1.00 | 25.32 |
| ATOM | 1540 | CB | ILE | 389 | 2.496 | 48.712 | 79.764 | 1.00 | 25.11 |
| ATOM | 1541 | CG2 | ILE | 389 | 1.780 | 49.331 | 78.617 | 1.00 | 25.25 |
| ATOM | 1542 | CG1 | ILE | 389 | 3.269 | 49.720 | 80.625 | 1.00 | 25.03 |
| ATOM | 1543 | CD1 | ILE | 389 | 3.624 | 49.254 | 82.054 | 1.00 | 36.13 |
| ATOM | 1544 | C | ILE | 389 | 0.135 | 47.570 | 80.266 | 1.00 | 27.97 |
| ATOM | 1545 | O | ILE | 389 | −0.162 | 47.015 | 79.194 | 1.00 | 28.10 |
| ATOM | 1546 | N | GLU | 390 | −0.730 | 47.753 | 81.252 | 1.00 | 29.92 |
| ATOM | 1547 | H | GLU | 390 | −0.364 | 48.010 | 82.127 | 1.00 | 0.00 |
| ATOM | 1548 | CA | GLU | 390 | −2.158 | 47.486 | 81.153 | 1.00 | 32.44 |
| ATOM | 1549 | CB | GLU | 390 | −2.661 | 47.580 | 82.611 | 1.00 | 33.39 |
| ATOM | 1550 | CG | GLU | 390 | −1.601 | 46.310 | 83.277 | 1.00 | 35.46 |
| ATOM | 1551 | CD | GLU | 390 | −1.750 | 46.086 | 84.766 | 1.00 | 37.59 |
| ATOM | 1552 | OE1 | GLU | 390 | −0.970 | 46.722 | 85.539 | 1.00 | 39.67 |
| ATOM | 1553 | OE2 | GLU | 390 | −2.557 | 45.227 | 85.163 | 1.00 | 39.16 |
| ATOM | 1554 | C | GLU | 390 | −2.834 | 48.656 | 80.354 | 1.00 | 33.92 |
| ATOM | 1555 | O | GLU | 390 | −3.575 | 48.388 | 79.396 | 1.00 | 35.01 |
| ATOM | 1556 | N | ASP | 391 | −2.455 | 49.918 | 80.658 | 1.00 | 34.56 |
| ATOM | 1557 | H | ASP | 391 | −1.908 | 49.999 | 81.434 | 1.00 | 0.00 |
| ATOM | 1558 | CA | ASP | 391 | −2.892 | 51.114 | 79.912 | 1.00 | 36.02 |
| ATOM | 1559 | CB | ASP | 391 | −3.600 | 52.101 | 80.827 | 1.00 | 36.05 |
| ATOM | 1560 | CG | ASP | 391 | −4.956 | 51.605 | 81.274 | 1.00 | 36.11 |
| ATOM | 1561 | OD1 | ASP | 391 | −5.905 | 51.754 | 80.469 | 1.00 | 38.70 |
| ATOM | 1562 | OD2 | ASP | 391 | −5.049 | 51.050 | 82.400 | 1.00 | 36.44 |
| ATOM | 1563 | C | ASP | 391 | −1.593 | 51.740 | 79.340 | 1.00 | 37.11 |
| ATOM | 1564 | O | ASP | 391 | −0.495 | 51.372 | 79.775 | 1.00 | 38.91 |
| ATOM | 1565 | N | ASN | 392 | −1.675 | 52.687 | 78.410 | 1.00 | 36.70 |
| ATOM | 1566 | H | ASN | 392 | −2.561 | 53.014 | 78.127 | 1.00 | 0.00 |
| ATOM | 1567 | CA | ASN | 392 | −0.459 | 53.268 | 77.798 | 1.00 | 37.06 |
| ATOM | 1568 | CB | ASN | 392 | −0.816 | 54.562 | 77.009 | 1.00 | 37.93 |
| ATOM | 1569 | CG | ASN | 392 | 0.210 | 54.895 | 75.934 | 1.00 | 39.00 |
| ATOM | 1570 | OD1 | ASN | 392 | 1.407 | 55.17 | 76.216 | 1.00 | 40.82 |
| ATOM | 1571 | ND2 | ASN | 392 | −0.258 | 55.071 | 74.690 | 1.00 | 39.90 |
| ATOM | 1572 | HD21 | ASN | 392 | −1.203 | 55.002 | 74.502 | 1.00 | 0.00 |
| ATOM | 1573 | HD22 | ASN | 392 | 0.406 | 55.314 | 73.985 | 1.00 | 0.00 |
| ATOM | 1574 | C | ASN | 392 | 0.795 | 53.482 | 78.697 | 1.00 | 36.53 |
| ATOM | 1575 | O | ASN | 392 | 1.896 | 53.163 | 78.273 | 1.00 | 36.13 |
| ATOM | 1576 | N | GLU | 393 | 0.593 | 53.937 | 79.942 | 1.00 | 35.32 |
| ATOM | 1577 | H | GLU | 393 | −0.302 | 53.959 | 80.328 | 1.00 | 0.00 |
| ATOM | 1578 | CA | GLU | 393 | 1.767 | 54.126 | 80.815 | 1.00 | 35.27 |
| ATOM | 1579 | CB | GLU | 393 | 2.258 | 55.640 | 80.787 | 1.00 | 34.77 |
| ATOM | 1580 | CG | GLU | 393 | 1.240 | 56.768 | 80.753 | 1.00 | 36.48 |
| ATOM | 1581 | CD | GLU | 393 | 1.834 | 58.199 | 80.932 | 1.00 | 38.45 |
| ATOM | 1582 | OE1 | GLU | 393 | 2.737 | 58.630 | 80.151 | 1.00 | 38.85 |
| ATOM | 1583 | OE2 | GLU | 393 | 1.383 | 58.878 | 81.854 | 1.00 | 38.61 |
| ATOM | 1584 | C | GLU | 393 | 1.851 | 53.608 | 82.240 | 1.00 | 34.53 |
| ATOM | 1585 | O | GLU | 393 | 0.838 | 53.245 | 82.855 | 1.00 | 34.44 |
| ATOM | 1586 | N | PTR | 394 | 3.110 | 53.446 | 82.676 | 1.00 | 32.44 |
| ATOM | 1587 | CA | PTR | 394 | 3.449 | 53.016 | 84.028 | 1.00 | 30.95 |
| ATOM | 1588 | C | PTR | 394 | 3.993 | 54.254 | 84.735 | 1.00 | 30.05 |
| ATOM | 1589 | O | PTR | 394 | 4.850 | 54.975 | 84.237 | 1.00 | 29.07 |
| ATOM | 1590 | CB | PTR | 394 | 4.526 | 51.918 | 84.020 | 1.00 | 31.99 |
| ATOM | 1591 | CG | PTR | 394 | 4.783 | 51.349 | 85.364 | 1.00 | 33.60 |
| ATOM | 1592 | CD1 | PTR | 394 | 3.956 | 50.363 | 85.919 | 1.00 | 34.62 |
| ATOM | 1593 | CD2 | PTR | 394 | 5.874 | 51.784 | 86.121 | 1.00 | 34.79 |
| ATOM | 1594 | CE1 | PTR | 394 | 4.244 | 49.840 | 87.191 | 1.00 | 35.49 |
| ATOM | 1595 | CE2 | PTR | 394 | 6.189 | 51.286 | 87.399 | 1.00 | 36.24 |
| ATOM | 1596 | CZ | PTR | 394 | 5.357 | 50.314 | 87.895 | 1.00 | 37.63 |
| ATOM | 1597 | OH | PTR | 394 | 5.693 | 49.787 | 89.214 | 1.00 | 39.94 |
| ATOM | 1598 | P | PTR | 394 | 6.556 | 50.615 | 90.334 | 1.00 | 42.01 |
| ATOM | 1599 | O1P | PTR | 394 | 7.944 | 50.768 | 89.818 | 1.00 | 42.16 |
| ATOM | 1600 | O2P | PTR | 394 | 6.587 | 49.869 | 91.588 | 1.00 | 41.20 |
| ATOM | 1601 | O3P | PTR | 394 | 5.991 | 51.795 | 90.513 | 1.00 | 42.16 |
| ATOM | 1602 | N | THR | 395 | 3.459 | 54.518 | 85.915 | 1.00 | 29.28 |
| ATOM | 1603 | H | THR | 395 | 2.718 | 53.945 | 86.253 | 1.00 | 0.00 |
| ATOM | 1604 | CA | THR | 395 | 3.901 | 55.669 | 86.722 | 1.00 | 29.07 |
| ATOM | 1605 | CB | THR | 395 | 2.712 | 56.564 | 87.077 | 1.00 | 28.14 |
| ATOM | 1606 | OG1 | THR | 395 | 2.143 | 57.094 | 85.876 | 1.00 | 29.97 |
| ATOM | 1607 | HG1 | THR | 395 | 1.848 | 56.353 | 85.293 | 1.00 | 0.00 |
| ATOM | 1608 | CG2 | THR | 395 | 3.151 | 57.713 | 87.936 | 1.00 | 28.89 |
| ATOM | 1609 | C | THR | 395 | 4.623 | 55.148 | 87.961 | 1.00 | 29.71 |
| ATOM | 1610 | O | THR | 395 | 4.034 | 54.447 | 88.788 | 1.00 | 31.18 |
| ATOM | 1611 | N | ALA | 396 | 5.914 | 55.447 | 88.043 | 1.00 | 30.07 |

TABLE 5-continued

Coordinates of Lck bound with baicalein

| | | Atom Type | Res | # | X | Y | Z | Occ | B |
|---|---|---|---|---|---|---|---|---|---|
| ATOM | 1612 | H | ALA | 396 | 6.334 | 55.935 | 87.324 | 1.00 | 0.00 |
| ATOM | 1613 | CA | ALA | 396 | 6.756 | 54.987 | 89.142 | 1.00 | 32.01 |
| ATOM | 1614 | CB | ALA | 396 | 8.207 | 55.213 | 88.798 | 1.00 | 31.62 |
| ATOM | 1615 | C | ALA | 396 | 6.428 | 55.641 | 90.503 | 1.00 | 33.24 |
| ATOM | 1616 | O | ALA | 396 | 5.353 | 56.221 | 90.666 | 1.00 | 33.39 |
| ATOM | 1617 | N | ALA | 397 | 7.324 | 55.470 | 91.480 | 1.00 | 34.70 |
| ATOM | 1618 | H | ALA | 397 | 8.109 | 54.902 | 91.292 | 1.00 | 0.00 |
| ATOM | 1619 | CA | ALA | 397 | 7.166 | 56.051 | 92.825 | 1.00 | 36.67 |
| ATOM | 1620 | CB | ALA | 397 | 7.782 | 55.119 | 93.863 | 1.00 | 36.18 |
| ATOM | 1621 | C | ALA | 397 | 7.865 | 57.442 | 92.876 | 1.00 | 37.83 |
| ATOM | 1622 | O | ALA | 397 | 9.008 | 57.568 | 92.436 | 1.00 | 38.12 |
| ATOM | 1623 | N | GLU | 398 | 7.215 | 58.481 | 93.417 | 1.00 | 39.68 |
| ATOM | 1624 | H | GLU | 398 | 6.304 | 58.360 | 93.777 | 1.00 | 0.00 |
| ATOM | 1625 | CA | GLU | 398 | 7.857 | 59.807 | 93.441 | 1.00 | 40.68 |
| ATOM | 1626 | CB | GLU | 398 | 7.109 | 60.804 | 94.334 | 1.00 | 42.46 |
| ATOM | 1627 | CG | GLU | 398 | 5.793 | 61.375 | 93.762 | 1.00 | 45.37 |
| ATOM | 1628 | CD | GLU | 398 | 5.841 | 61.585 | 92.255 | 1.00 | 46.64 |
| ATOM | 1629 | OE1 | GLU | 398 | 6.745 | 62.313 | 91.779 | 1.00 | 49.05 |
| ATOM | 1630 | OE2 | GLU | 398 | 4.971 | 61.001 | 91.572 | 1.00 | 48.39 |
| ATOM | 1631 | C | GLU | 398 | 9.335 | 59.777 | 93.862 | 1.00 | 40.35 |
| ATOM | 1632 | O | GLU | 398 | 10.179 | 60.532 | 93.329 | 1.00 | 41.07 |
| ATOM | 1633 | N | GLY | 399 | 9.643 | 58.897 | 94.807 | 1.00 | 39.58 |
| ATOM | 1634 | H | GLY | 399 | 8.948 | 58.336 | 95.192 | 1.00 | 0.00 |
| ATOM | 1635 | CA | GLY | 399 | 11.008 | 58.779 | 95.278 | 1.00 | 38.09 |
| ATOM | 1636 | C | GLY | 399 | 11.892 | 57.938 | 94.370 | 1.00 | 37.48 |
| ATOM | 1637 | O | GLY | 399 | 13.112 | 58.072 | 94.420 | 1.00 | 38.05 |
| ATOM | 1638 | N | ALA | 400 | 11.301 | 57.090 | 93.527 | 1.00 | 36.09 |
| ATOM | 1639 | H | ALA | 400 | 10.329 | 56.980 | 93.545 | 1.00 | 0.00 |
| ATOM | 1640 | CA | ALA | 400 | 12.105 | 56.220 | 92.658 | 1.00 | 35.21 |
| ATOM | 1641 | CB | ALA | 400 | 11.206 | 55.307 | 91.818 | 1.00 | 35.23 |
| ATOM | 1642 | C | ALA | 400 | 13.079 | 57.017 | 91.777 | 1.00 | 34.29 |
| ATOM | 1643 | O | ALA | 400 | 12.726 | 58.049 | 91.216 | 1.00 | 34.75 |
| ATOM | 1644 | N | ALA | 401 | 14.320 | 56.557 | 91.692 | 1.00 | 32.38 |
| ATOM | 1645 | H | ALA | 401 | 14.585 | 55.751 | 92.203 | 1.00 | 0.00 |
| ATOM | 1646 | CA | ALA | 401 | 15.315 | 57.258 | 90.886 | 1.00 | 30.63 |
| ATOM | 1647 | CB | ALA | 401 | 16.392 | 57.803 | 91.772 | 1.00 | 30.02 |
| ATOM | 1648 | C | ALA | 401 | 15.900 | 56.408 | 89.766 | 1.00 | 29.77 |
| ATOM | 1649 | O | ALA | 401 | 16.114 | 55.193 | 89.930 | 1.00 | 30.27 |
| ATOM | 1650 | N | PHE | 402 | 16.161 | 57.037 | 88.621 | 1.00 | 28.46 |
| ATOM | 1651 | H | PHE | 402 | 15.945 | 57.975 | 88.544 | 1.00 | 0.00 |
| ATOM | 1652 | CA | PHE | 402 | 16.698 | 56.300 | 87.457 | 1.00 | 27.06 |
| ATOM | 1653 | CB | PHE | 402 | 15.620 | 56.209 | 86.380 | 1.00 | 27.80 |
| ATOM | 1654 | CG | PHE | 402 | 14.432 | 55.388 | 86.790 | 1.00 | 29.62 |
| ATOM | 1655 | CD1 | PHE | 402 | 13.411 | 55.948 | 87.554 | 1.00 | 30.38 |
| ATOM | 1656 | CD2 | PHE | 402 | 14.356 | 54.048 | 86.455 | 1.00 | 30.17 |
| ATOM | 1657 | CE1 | PHE | 402 | 12.320 | 55.170 | 87.991 | 1.00 | 30.47 |
| ATOM | 1658 | CE2 | PHE | 402 | 13.271 | 53.258 | 86.887 | 1.00 | 31.59 |
| ATOM | 1659 | CZ | PHE | 402 | 12.258 | 53.827 | 87.656 | 1.00 | 30.40 |
| ATOM | 1660 | C | PHE | 402 | 17.949 | 56.988 | 86.899 | 1.00 | 25.40 |
| ATOM | 1661 | O | PHE | 402 | 18.169 | 58.185 | 87.145 | 1.00 | 24.86 |
| ATOM | 1662 | N | PRO | 403 | 18.808 | 56.241 | 86.176 | 1.00 | 23.95 |
| ATOM | 1663 | CD | PRO | 403 | 18.726 | 54.808 | 85.831 | 1.00 | 23.76 |
| ATOM | 1664 | CA | PRO | 403 | 20.033 | 56.824 | 85.610 | 1.00 | 22.76 |
| ATOM | 1665 | CB | PRO | 403 | 20.663 | 55.634 | 84.867 | 1.00 | 22.78 |
| ATOM | 1666 | CG | PRO | 403 | 20.153 | 54.479 | 85.617 | 1.00 | 24.38 |
| ATOM | 1667 | C | PRO | 403 | 19.625 | 57.920 | 84.638 | 1.00 | 21.39 |
| ATOM | 1668 | O | PRO | 403 | 18.910 | 57.701 | 83.671 | 1.00 | 22.19 |
| ATOM | 1669 | N | ILE | 404 | 20.037 | 59.134 | 84.937 | 1.00 | 20.21 |
| ATOM | 1670 | H | ILE | 404 | 20.576 | 59.263 | 85.733 | 1.00 | 0.00 |
| ATOM | 1671 | CA | ILE | 404 | 19.663 | 60.294 | 84.131 | 1.00 | 18.37 |
| ATOM | 1672 | CB | ILE | 404 | 20.235 | 61.592 | 84.764 | 1.00 | 18.97 |
| ATOM | 1673 | CG2 | ILE | 404 | 20.079 | 62.841 | 83.823 | 1.00 | 15.09 |
| ATOM | 1674 | CG1 | ILE | 404 | 19.532 | 61.860 | 86.077 | 1.00 | 20.58 |
| ATOM | 1675 | CD1 | ILE | 404 | 18.014 | 61.932 | 85.941 | 1.00 | 22.19 |
| ATOM | 1676 | C | ILE | 404 | 20.068 | 60.234 | 82.687 | 1.00 | 16.90 |
| ATOM | 1677 | O | ILE | 404 | 19.261 | 60.502 | 81.830 | 1.00 | 17.02 |
| ATOM | 1678 | N | LYS | 405 | 21.322 | 59.885 | 82.407 | 1.00 | 15.86 |
| ATOM | 1679 | H | LYS | 405 | 21.937 | 59.591 | 83.125 | 1.00 | 0.00 |
| ATOM | 1680 | CA | LYS | 405 | 21.786 | 59.832 | 81.020 | 1.00 | 14.58 |
| ATOM | 1681 | CB | LYS | 405 | 23.280 | 59.561 | 80.988 | 1.00 | 13.71 |
| ATOM | 1682 | CG | LYS | 405 | 24.097 | 60.667 | 81.572 | 1.00 | 13.20 |
| ATOM | 1683 | CD | LYS | 405 | 25.578 | 60.465 | 81.428 | 1.00 | 14.48 |
| ATOM | 1684 | CE | LYS | 405 | 26.357 | 61.706 | 81.926 | 1.00 | 15.21 |
| ATOM | 1685 | NZ | LYS | 405 | 27.808 | 61.811 | 81.393 | 1.00 | 16.61 |

TABLE 5-continued

Coordinates of Lck bound with baicalein

| | | Atom Type | Res | # | X | Y | Z | Occ | B |
|---|---|---|---|---|---|---|---|---|---|
| ATOM | 1686 | HZ1 | LYS | 405 | 27.785 | 61.833 | 80.345 | 1.00 | 0.00 |
| ATOM | 1687 | HZ2 | LYS | 405 | 28.335 | 60.965 | 81.696 | 1.00 | 0.00 |
| ATOM | 1688 | HZ3 | LYS | 405 | 28.247 | 62.659 | 81.755 | 1.00 | 0.00 |
| ATOM | 1689 | C | LYS | 405 | 21.022 | 58.892 | 80.080 | 1.00 | 14.15 |
| ATOM | 1690 | O | LYS | 405 | 20.998 | 59.187 | 78.887 | 1.00 | 12.15 |
| ATOM | 1691 | N | TRP | 406 | 20.431 | 57.789 | 80.564 | 1.00 | 13.78 |
| ATOM | 1692 | H | TRP | 406 | 20.476 | 57.599 | 81.536 | 1.00 | 0.00 |
| ATOM | 1693 | CA | TRP | 406 | 19.712 | 56.831 | 79.678 | 1.00 | 14.07 |
| ATOM | 1694 | CB | TRP | 406 | 20.046 | 55.384 | 80.131 | 1.00 | 15.16 |
| ATOM | 1695 | CG | TRP | 406 | 21.647 | 54.915 | 79.659 | 1.00 | 14.16 |
| ATOM | 1696 | CD2 | TRP | 406 | 22.595 | 55.071 | 80.331 | 1.00 | 13.58 |
| ATOM | 1697 | CE2 | TRP | 406 | 23.563 | 54.371 | 79.585 | 1.00 | 13.10 |
| ATOM | 1698 | CE3 | TRP | 406 | 22.978 | 55.732 | 81.514 | 1.00 | 11.90 |
| ATOM | 1699 | CD1 | TRP | 406 | 21.595 | 54.144 | 78.532 | 1.00 | 15.52 |
| ATOM | 1700 | NE1 | TRP | 406 | 22.939 | 53.818 | 78.491 | 1.00 | 14.22 |
| ATOM | 1701 | HE1 | TRP | 406 | 23.352 | 53.271 | 77.800 | 1.00 | 0.00 |
| ATOM | 1702 | CZ2 | TRP | 406 | 24.902 | 54.307 | 79.974 | 1.00 | 12.82 |
| ATOM | 1703 | CZ3 | TRP | 406 | 24.312 | 55.672 | 81.894 | 1.00 | 13.81 |
| ATOM | 1704 | CH2 | TRP | 406 | 25.265 | 54.959 | 81.118 | 1.00 | 13.24 |
| ATOM | 1705 | C | TRP | 406 | 18.203 | 56.946 | 79.702 | 1.00 | 14.74 |
| ATOM | 1706 | O | TRP | 406 | 17.481 | 56.340 | 78.893 | 1.00 | 14.93 |
| ATOM | 1707 | N | THR | 407 | 17.702 | 57.728 | 80.640 | 1.00 | 15.40 |
| ATOM | 1708 | H | THR | 407 | 18.321 | 58.163 | 81.252 | 1.00 | 0.00 |
| ATOM | 1709 | CA | THR | 407 | 16.274 | 57.828 | 80.840 | 1.00 | 15.74 |
| ATOM | 1710 | CB | THR | 407 | 15.967 | 57.886 | 82.355 | 1.00 | 14.87 |
| ATOM | 1711 | OG1 | THR | 407 | 16.709 | 56.821 | 82.983 | 1.00 | 14.96 |
| ATOM | 1712 | HG1 | THR | 407 | 16.435 | 55.969 | 82.662 | 1.00 | 0.00 |
| ATOM | 1713 | CG2 | THR | 407 | 14.484 | 57.729 | 82.616 | 1.00 | 13.65 |
| ATOM | 1714 | C | THR | 407 | 15.573 | 58.962 | 80.088 | 1.00 | 16.37 |
| ATOM | 1715 | O | THR | 407 | 16.028 | 60.099 | 80.073 | 1.00 | 16.48 |
| ATOM | 1716 | N | ALA | 408 | 14.430 | 58.673 | 79.495 | 1.00 | 16.63 |
| ATOM | 1717 | H | ALA | 408 | 14.168 | 57.812 | 79.543 | 1.00 | 0.00 |
| ATOM | 1718 | CA | ALA | 408 | 13.680 | 59.675 | 78.735 | 1.00 | 17.46 |
| ATOM | 1719 | CB | ALA | 408 | 12.452 | 59.032 | 78.079 | 1.00 | 16.99 |
| ATOM | 1720 | C | ALA | 408 | 13.257 | 60.826 | 79.643 | 1.00 | 19.05 |
| ATOM | 1721 | O | ALA | 408 | 12.966 | 60.653 | 80.826 | 1.00 | 19.14 |
| ATOM | 1722 | N | PRO | 409 | 13.176 | 62.032 | 79.092 | 1.00 | 20.91 |
| ATOM | 1723 | CD | PRO | 409 | 13.497 | 62.425 | 77.705 | 1.00 | 19.75 |
| ATOM | 1724 | CA | PRO | 409 | 12.780 | 63.210 | 79.881 | 1.00 | 20.79 |
| ATOM | 1725 | CB | PRO | 409 | 12.691 | 64.315 | 78.814 | 1.00 | 20.81 |
| ATOM | 1726 | CG | PRO | 409 | 13.743 | 63.901 | 77.839 | 1.00 | 20.82 |
| ATOM | 1727 | C | PRO | 409 | 11.463 | 63.109 | 80.673 | 1.00 | 21.93 |
| ATOM | 1728 | O | PRO | 409 | 11.422 | 63.520 | 81.824 | 1.00 | 20.90 |
| ATOM | 1729 | N | GLU | 410 | 10.412 | 62.570 | 80.043 | 1.00 | 22.51 |
| ATOM | 1730 | H | GLU | 410 | 10.490 | 62.301 | 79.120 | 1.00 | 0.00 |
| ATOM | 1731 | CA | GLU | 410 | 9.133 | 62.396 | 80.734 | 1.00 | 22.50 |
| ATOM | 1732 | CB | GLU | 410 | 8.061 | 61.874 | 79.766 | 1.00 | 22.39 |
| ATOM | 1733 | CG | GLU | 410 | 8.288 | 60.408 | 79.288 | 1.00 | 22.75 |
| ATOM | 1734 | CD | GLU | 410 | 9.156 | 60.285 | 78.007 | 1.00 | 21.87 |
| ATOM | 1735 | OE1 | GLU | 410 | 9.854 | 61.254 | 77.591 | 1.00 | 21.50 |
| ATOM | 1736 | OE2 | GLU | 410 | 9.125 | 59.199 | 77.407 | 1.00 | 22.59 |
| ATOM | 1737 | C | GLU | 410 | 9.267 | 61.459 | 81.916 | 1.00 | 23.18 |
| ATOM | 1738 | O | GLU | 410 | 8.530 | 61.612 | 82.896 | 1.00 | 24.73 |
| ATOM | 1739 | N | ALA | 411 | 10.130 | 60.439 | 81.815 | 1.00 | 22.52 |
| ATOM | 1740 | H | ALA | 411 | 10.589 | 60.233 | 80.979 | 1.00 | 0.00 |
| ATOM | 1741 | CA | ALA | 411 | 10.311 | 59.535 | 82.945 | 1.00 | 22.55 |
| ATOM | 1742 | CB | ALA | 411 | 11.019 | 58.272 | 82.506 | 1.00 | 21.87 |
| ATOM | 1743 | C | ALA | 411 | 11.088 | 60.326 | 84.027 | 1.00 | 22.20 |
| ATOM | 1744 | O | ALA | 411 | 10.830 | 60.200 | 85.215 | 1.00 | 21.48 |
| ATOM | 1745 | N | ILE | 412 | 12.054 | 61.142 | 83.637 | 1.00 | 22.22 |
| ATOM | 1746 | H | ILE | 412 | 12.241 | 61.252 | 82.662 | 1.00 | 0.00 |
| ATOM | 1747 | CA | ILE | 412 | 12.860 | 61.899 | 84.632 | 1.00 | 22.95 |
| ATOM | 1748 | CB | ILE | 412 | 14.064 | 62.656 | 83.958 | 1.00 | 22.38 |
| ATOM | 1749 | CG2 | ILE | 412 | 14.666 | 63.716 | 84.953 | 1.00 | 21.62 |
| ATOM | 1750 | CG1 | ILE | 412 | 15.141 | 61.643 | 83.560 | 1.00 | 21.37 |
| ATOM | 1751 | CD1 | ILE | 412 | 16.249 | 62.299 | 82.723 | 1.00 | 21.05 |
| ATOM | 1752 | C | ILE | 412 | 11.965 | 62.967 | 85.349 | 1.00 | 22.94 |
| ATOM | 1753 | O | ILE | 412 | 11.923 | 63.070 | 86.548 | 1.00 | 21.96 |
| ATOM | 1754 | N | ASN | 413 | 11.162 | 63.650 | 84.560 | 1.00 | 23.04 |
| ATOM | 1755 | H | ASN | 413 | 11.079 | 63.416 | 83.636 | 1.00 | 0.00 |
| ATOM | 1756 | CA | ASN | 413 | 10.342 | 64.691 | 85.137 | 1.00 | 24.84 |
| ATOM | 1757 | CB | ASN | 413 | 10.190 | 65.823 | 84.133 | 1.00 | 24.17 |
| ATOM | 1758 | CG | ASN | 413 | 11.540 | 66.387 | 83.699 | 1.00 | 23.80 |
| ATOM | 1759 | OD1 | ASN | 413 | 11.644 | 66.999 | 82.662 | 1.00 | 25.16 |

TABLE 5-continued

Coordinates of Lck bound with baicalein

| | Atom Type | Res | # | X | Y | Z | Occ | B |
|---|---|---|---|---|---|---|---|---|
| ATOM | 1760 | ND2 | ASN | 413 | 12.592 | 66.119 | 84.484 | 1.00 | 25.32 |
| ATOM | 1761 | HD21 | ASN | 413 | 12.486 | 65.528 | 85.273 | 1.00 | 0.00 |
| ATOM | 1762 | HD22 | ASN | 413 | 13.478 | 66.435 | 84.207 | 1.00 | 0.00 |
| ATOM | 1763 | C | ASN | 413 | 8.994 | 64.273 | 85.752 | 1.00 | 25.41 |
| ATOM | 1764 | O | ASN | 413 | 8.595 | 64.845 | 86.767 | 1.00 | 25.27 |
| ATOM | 1765 | N | TYR | 414 | 8.348 | 63.228 | 85.219 | 1.00 | 26.57 |
| ATOM | 1766 | H | TYR | 414 | 8.766 | 62.762 | 84.469 | 1.00 | 0.00 |
| ATOM | 1767 | CA | TYR | 414 | 7.072 | 62.776 | 85.741 | 1.00 | 27.08 |
| ATOM | 1768 | CB | TYR | 414 | 6.008 | 62.876 | 84.681 | 1.00 | 27.94 |
| ATOM | 1769 | CG | TYR | 414 | 6.094 | 64.129 | 83.871 | 1.00 | 29.55 |
| ATOM | 1770 | CD1 | TYR | 414 | 6.174 | 65.360 | 84.484 | 1.00 | 30.68 |
| ATOM | 1771 | CE1 | TYR | 414 | 6.267 | 66.542 | 83.727 | 1.00 | 31.28 |
| ATOM | 1772 | CD2 | TYR | 414 | 3.109 | 64.086 | 82.478 | 1.00 | 30.67 |
| ATOM | 1773 | CE2 | TYR | 414 | 6.203 | 65.232 | 81.713 | 1.00 | 31.40 |
| ATOM | 1774 | CZ | TYR | 414 | 6.276 | 66.465 | 82.341 | 1.00 | 32.01 |
| ATOM | 1775 | OH | TYR | 414 | 6.339 | 67.624 | 81.599 | 1.00 | 33.29 |
| ATOM | 1776 | HH | TYR | 414 | 6.344 | 67.397 | 80.671 | 1.00 | 0.00 |
| ATOM | 1777 | C | TYR | 414 | 6.989 | 61.385 | 86.364 | 1.00 | 26.78 |
| ATOM | 1778 | O | TYR | 414 | 6.014 | 61.123 | 87.063 | 1.00 | 27.79 |
| ATOM | 1779 | N | GLY | 415 | 7.960 | 60.518 | 86.096 | 1.00 | 25.74 |
| ATOM | 1780 | H | GLY | 415 | 8.718 | 60.759 | 85.539 | 1.00 | 0.00 |
| ATOM | 1781 | CA | GLY | 415 | 7.873 | 59.189 | 86.654 | 1.00 | 26.33 |
| ATOM | 1782 | C | GLY | 415 | 7.059 | 58.315 | 85.709 | 1.00 | 25.95 |
| ATOM | 1783 | O | GLY | 415 | 6.793 | 57.136 | 86.013 | 1.00 | 26.86 |
| ATOM | 1784 | N | THR | 416 | 6.694 | 58.892 | 84.560 | 1.00 | 24.42 |
| ATOM | 1785 | H | THR | 416 | 7.012 | 59.793 | 84.381 | 1.00 | 0.00 |
| ATOM | 1786 | CA | THR | 416 | 5.931 | 58.191 | 83.534 | 1.00 | 24.18 |
| ATOM | 1787 | CB | THR | 416 | 4.988 | 59.129 | 82.774 | 1.00 | 25.81 |
| ATOM | 1788 | OG1 | THR | 416 | 5.753 | 60.174 | 82.159 | 1.00 | 27.80 |
| ATOM | 1789 | HG1 | THR | 416 | 6.242 | 60.655 | 82.826 | 1.00 | 0.00 |
| ATOM | 1790 | CG2 | THR | 416 | 3.939 | 59.726 | 83.687 | 1.00 | 27.40 |
| ATOM | 1791 | C | THR | 416 | 6.778 | 57.468 | 82.458 | 1.00 | 22.30 |
| ATOM | 1792 | O | THR | 416 | 7.580 | 58.084 | 81.733 | 1.00 | 21.78 |
| ATOM | 1793 | N | PHE | 417 | 6.537 | 56.168 | 82.353 | 1.00 | 20.15 |
| ATOM | 1794 | H | PHE | 417 | 5.874 | 55.753 | 82.945 | 1.00 | 0.00 |
| ATOM | 1795 | CA | PHE | 417 | 7.248 | 55.316 | 81.402 | 1.00 | 17.59 |
| ATOM | 1796 | CB | PHE | 417 | 7.944 | 54.202 | 82.143 | 1.00 | 16.86 |
| ATOM | 1797 | CG | PHE | 417 | 9.103 | 54.668 | 82.959 | 1.00 | 16.04 |
| ATOM | 1798 | CD1 | PHE | 417 | 8.914 | 55.141 | 84.259 | 1.00 | 15.15 |
| ATOM | 1799 | CD2 | PHE | 417 | 10.393 | 54.547 | 82.466 | 1.00 | 14.04 |
| ATOM | 1800 | CE1 | PHE | 417 | 10.026 | 55.455 | 85.041 | 1.00 | 15.67 |
| ATOM | 1801 | CE2 | PHE | 417 | 11.482 | 54.854 | 83.213 | 1.00 | 13.17 |
| ATOM | 1802 | CZ | PHE | 417 | 11.314 | 55.307 | 84.518 | 1.00 | 13.77 |
| ATOM | 1803 | C | PHE | 417 | 6.320 | 54.682 | 80.377 | 1.00 | 16.67 |
| ATOM | 1804 | O | PHE | 417 | 5.182 | 54.290 | 80.695 | 1.00 | 16.78 |
| ATOM | 1805 | N | THR | 418 | 6.751 | 54.679 | 79.124 | 1.00 | 15.49 |
| ATOM | 1806 | H | THR | 418 | 7.553 | 55.231 | 78.925 | 1.00 | 0.00 |
| ATOM | 1807 | CA | THR | 418 | 6.025 | 54.022 | 78.071 | 1.00 | 14.51 |
| ATOM | 1808 | CB | THR | 418 | 5.177 | 54.979 | 77.153 | 1.00 | 14.65 |
| ATOM | 1809 | OG1 | THR | 418 | 6.052 | 55.699 | 76.330 | 1.00 | 17.27 |
| ATOM | 1810 | HG1 | THR | 418 | 6.569 | 55.143 | 75.787 | 1.00 | 0.00 |
| ATOM | 1811 | CG2 | THR | 418 | 4.278 | 55.946 | 77.993 | 1.00 | 14.44 |
| ATOM | 1812 | C | THR | 418 | 7.052 | 53.298 | 77.220 | 1.00 | 13.93 |
| ATOM | 1813 | O | THR | 418 | 8.252 | 53.492 | 77.394 | 1.00 | 14.85 |
| ATOM | 1814 | N | ILE | 419 | 6.615 | 52.470 | 76.286 | 1.00 | 12.57 |
| ATOM | 1815 | H | ILE | 419 | 5.660 | 52.253 | 76.215 | 1.00 | 0.00 |
| ATOM | 1816 | CA | ILE | 419 | 7.585 | 51.801 | 75.447 | 1.00 | 11.69 |
| ATOM | 1817 | CB | ILE | 419 | 6.886 | 50.857 | 74.443 | 1.00 | 12.13 |
| ATOM | 1818 | CG2 | ILE | 419 | 6.063 | 51.661 | 73.365 | 1.00 | 12.79 |
| ATOM | 1819 | CG1 | ILE | 419 | 7.918 | 49.934 | 73.730 | 1.00 | 11.73 |
| ATOM | 1820 | CD1 | ILE | 419 | 8.541 | 48.904 | 74.610 | 1.00 | 9.42 |
| ATOM | 1821 | C | ILE | 419 | 8.426 | 52.903 | 74.690 | 1.00 | 13.13 |
| ATOM | 1822 | O | ILE | 419 | 9.587 | 52.652 | 74.239 | 1.00 | 13.11 |
| ATOM | 1823 | N | LYS | 420 | 7.872 | 54.123 | 74.585 | 1.00 | 11.67 |
| ATOM | 1824 | H | LYS | 420 | 6.969 | 54.243 | 74.943 | 1.00 | 0.00 |
| ATOM | 1825 | CA | LYS | 420 | 8.544 | 55.241 | 73.902 | 1.00 | 10.91 |
| ATOM | 1826 | CB | LYS | 420 | 7.584 | 56.390 | 73.604 | 1.00 | 11.23 |
| ATOM | 1827 | CG | LYS | 420 | 6.486 | 56.045 | 72.551 | 1.00 | 11.52 |
| ATOM | 1828 | CD | LYS | 420 | 7.036 | 55.644 | 71.161 | 1.00 | 9.01 |
| ATOM | 1829 | CE | LYS | 420 | 5.889 | 55.302 | 70.198 | 1.00 | 7.53 |
| ATOM | 1830 | NZ | LYS | 420 | 6.418 | 54.679 | 68.961 | 1.00 | 11.49 |
| ATOM | 1831 | HZ1 | LYS | 420 | 6.916 | 53.736 | 69.211 | 1.00 | 0.00 |
| ATOM | 1832 | HZ2 | LYS | 420 | 7.114 | 55.244 | 68.474 | 1.00 | 0.00 |
| ATOM | 1833 | HZ3 | LYS | 420 | 5.650 | 54.397 | 68.308 | 1.00 | 0.00 |

TABLE 5-continued

Coordinates of Lck bound with baicalein

| | Atom Type | Res | # | X | Y | Z | Occ | B |
|---|---|---|---|---|---|---|---|---|
| ATOM | 1834 | C | LYS | 420 | 9.681 | 55.767 | 74.784 | 1.00 | 9.88 |
| ATOM | 1835 | O | LYS | 420 | 10.590 | 56.386 | 74.266 | 1.00 | 10.06 |
| ATOM | 1836 | N | SER | 421 | 9.611 | 55.527 | 76.101 | 0.84 | 9.09 |
| ATOM | 1837 | H | SER | 421 | 8.799 | 55.123 | 76.467 | 1.00 | 0.00 |
| ATOM | 1838 | CA | SER | 421 | 10.707 | 55.869 | 77.001 | 0.84 | 8.77 |
| ATOM | 1839 | CB | SER | 421 | 10.315 | 55.735 | 78.481 | 0.84 | 8.81 |
| ATOM | 1840 | OG | SER | 421 | 9.140 | 56.448 | 78.722 | 0.84 | 13.82 |
| ATOM | 1841 | HG | SER | 421 | 8.426 | 56.087 | 78.174 | 1.00 | 0.00 |
| ATOM | 1842 | C | SER | 421 | 11.841 | 54.895 | 76.707 | 0.84 | 8.14 |
| ATOM | 1843 | O | SER | 421 | 12.978 | 55.297 | 76.822 | 0.84 | 6.60 |
| ATOM | 1844 | N | ASP | 422 | 11.538 | 53.610 | 76.467 | 1.00 | 8.44 |
| ATOM | 1845 | H | ASP | 422 | 10.616 | 53.302 | 76.537 | 1.00 | 0.00 |
| ATOM | 1846 | CA | ASP | 422 | 12.586 | 52.630 | 76.138 | 1.00 | 10.22 |
| ATOM | 1847 | CB | ASP | 422 | 11.976 | 51.201 | 76.043 | 1.00 | 11.40 |
| ATOM | 1848 | CG | ASP | 422 | 11.682 | 50.602 | 77.376 | 1.00 | 10.92 |
| ATOM | 1849 | OD1 | ASP | 422 | 12.280 | 51.031 | 78.366 | 1.00 | 10.76 |
| ATOM | 1850 | OD2 | ASP | 422 | 10.852 | 49.700 | 77.441 | 1.00 | 10.13 |
| ATOM | 1851 | C | ASP | 422 | 13.222 | 53.018 | 74.818 | 1.00 | 8.99 |
| ATOM | 1852 | O | ASP | 422 | 14.431 | 52.919 | 74.610 | 1.00 | 10.30 |
| ATOM | 1853 | N | VAL | 423 | 12.422 | 53.504 | 73.890 | 1.00 | 9.20 |
| ATOM | 1854 | H | VAL | 423 | 11.470 | 53.567 | 74.034 | 1.00 | 0.00 |
| ATOM | 1855 | CA | VAL | 423 | 12.993 | 53.914 | 72.546 | 1.00 | 8.86 |
| ATOM | 1856 | CB | VAL | 423 | 11.843 | 54.393 | 71.573 | 1.00 | 7.64 |
| ATOM | 1857 | CG1 | VAL | 423 | 12.441 | 55.170 | 70.424 | 1.00 | 7.46 |
| ATOM | 1858 | CG2 | VAL | 423 | 11.058 | 53.235 | 71.099 | 1.00 | 7.88 |
| ATOM | 1859 | C | VAL | 423 | 14.035 | 54.982 | 72.768 | 1.00 | 7.83 |
| ATOM | 1860 | O | VAL | 423 | 15.092 | 54.921 | 72.178 | 1.00 | 7.82 |
| ATOM | 1861 | N | TRP | 424 | 13.789 | 55.938 | 73.669 | 1.00 | 8.38 |
| ATOM | 1862 | H | TRP | 424 | 12.910 | 55.933 | 74.130 | 1.00 | 0.00 |
| ATOM | 1863 | CA | TRP | 424 | 14.786 | 56.969 | 73.959 | 1.00 | 8.62 |
| ATOM | 1864 | CB | TRP | 424 | 14.194 | 57.924 | 75.045 | 1.00 | 8.70 |
| ATOM | 1865 | CG | TRP | 424 | 15.203 | 58.953 | 75.490 | 1.00 | 9.96 |
| ATOM | 1866 | CD2 | TRP | 424 | 15.180 | 60.348 | 75.143 | 1.00 | 9.10 |
| ATOM | 1867 | CE2 | TRP | 424 | 16.338 | 60.933 | 75.675 | 1.00 | 9.06 |
| ATOM | 1868 | CE3 | TRP | 424 | 14.261 | 61.142 | 74.434 | 1.00 | 9.39 |
| ATOM | 1869 | CD1 | TRP | 424 | 16.331 | 58.755 | 76.233 | 1.00 | 8.59 |
| ATOM | 1870 | NE1 | TRP | 424 | 17.010 | 59.952 | 76.354 | 1.00 | 10.17 |
| ATOM | 1871 | HE1 | TRP | 424 | 17.867 | 60.057 | 76.826 | 1.00 | 0.00 |
| ATOM | 1872 | CZ2 | TRP | 424 | 16.647 | 62.290 | 75.515 | 1.00 | 9.27 |
| ATOM | 1873 | CZ3 | TRP | 424 | 14.537 | 62.532 | 74.265 | 1.00 | 10.62 |
| ATOM | 1874 | CH2 | TRP | 424 | 15.736 | 63.085 | 74.806 | 1.00 | 10.12 |
| ATOM | 1875 | C | TRP | 424 | 16.079 | 56.276 | 74.498 | 1.00 | 8.23 |
| ATOM | 1876 | O | TRP | 424 | 17.179 | 56.608 | 74.052 | 1.00 | 10.11 |
| ATOM | 1877 | N | SER | 425 | 15.940 | 55.381 | 75.480 | 0.74 | 5.82 |
| ATOM | 1878 | H | SER | 425 | 15.028 | 55.179 | 75.809 | 1.00 | 0.00 |
| ATOM | 1879 | CA | SER | 425 | 17.085 | 54.653 | 76.026 | 0.74 | 5.02 |
| ATOM | 1880 | CB | SER | 425 | 16.616 | 53.643 | 77.050 | 0.74 | 3.75 |
| ATOM | 1881 | OG | SER | 425 | 15.933 | 54.307 | 78.060 | 0.74 | 3.99 |
| ATOM | 1882 | HG | SER | 425 | 16.556 | 54.901 | 78.507 | 1.00 | 0.00 |
| ATOM | 1883 | C | SER | 425 | 17.861 | 53.933 | 74.945 | 0.74 | 4.64 |
| ATOM | 1884 | O | SER | 425 | 19.088 | 53.961 | 74.989 | 0.74 | 3.01 |
| ATOM | 1885 | N | PHE | 426 | 17.150 | 53.281 | 73.997 | 1.00 | 6.29 |
| ATOM | 1886 | H | PHE | 426 | 16.184 | 53.252 | 74.086 | 1.00 | 0.00 |
| ATOM | 1887 | CA | PHE | 426 | 17.777 | 52.552 | 72.903 | 1.00 | 7.55 |
| ATOM | 1888 | CB | PHE | 426 | 16.716 | 51.991 | 71.978 | 1.00 | 6.76 |
| ATOM | 1889 | CG | PHE | 426 | 17.270 | 51.155 | 70.856 | 1.00 | 7.91 |
| ATOM | 1890 | CD1 | PHE | 426 | 17.800 | 49.865 | 71.105 | 1.00 | 7.79 |
| ATOM | 1891 | CD2 | PHE | 426 | 17.314 | 51.671 | 69.548 | 1.00 | 6.55 |
| ATOM | 1892 | CE1 | PHE | 426 | 18.370 | 49.129 | 70.068 | 1.00 | 8.02 |
| ATOM | 1893 | CE2 | PHE | 426 | 17.894 | 50.902 | 68.496 | 1.00 | 7.90 |
| ATOM | 1894 | CZ | PHE | 426 | 18.410 | 49.648 | 68.803 | 1.00 | 7.01 |
| ATOM | 1895 | C | PHE | 426 | 18.705 | 53.550 | 72.129 | 1.00 | 8.95 |
| ATOM | 1896 | O | PHE | 426 | 19.850 | 53.184 | 71.739 | 1.00 | 8.87 |
| ATOM | 1897 | N | GLY | 427 | 18.238 | 54.799 | 71.929 | 1.00 | 9.07 |
| ATOM | 1898 | H | GLY | 427 | 17.358 | 55.025 | 72.298 | 1.00 | 0.00 |
| ATOM | 1899 | CA | GLY | 427 | 19.047 | 55.786 | 71.245 | 1.00 | 8.40 |
| ATOM | 1900 | C | GLY | 427 | 20.361 | 55.981 | 71.979 | 1.00 | 8.02 |
| ATOM | 1901 | O | GLY | 427 | 21.423 | 56.041 | 71.379 | 1.00 | 9.37 |
| ATOM | 1902 | N | ILE | 428 | 20.298 | 56.057 | 73.303 | 1.00 | 8.50 |
| ATOM | 1903 | H | ILE | 428 | 19.414 | 55.972 | 73.727 | 1.00 | 0.00 |
| ATOM | 1904 | CA | ILE | 428 | 21.480 | 56.194 | 74.122 | 1.00 | 7.90 |
| ATOM | 1905 | CB | ILE | 428 | 21.131 | 56.449 | 75.613 | 1.00 | 7.92 |
| ATOM | 1906 | CG2 | ILE | 428 | 22.419 | 56.617 | 76.423 | 1.00 | 6.35 |
| ATOM | 1907 | CG1 | ILE | 428 | 20.179 | 57.648 | 75.804 | 1.00 | 8.46 |

TABLE 5-continued

Coordinates of Lck bound with baicalein

| | Atom Type | Res | # | X | Y | Z | Occ | B |
|---|---|---|---|---|---|---|---|---|
| ATOM | 1908 | CD1 | ILE | 428 | 20.689 | 58.992 | 75.260 | 1.00 | 5.14 |
| ATOM | 1909 | C | ILE | 428 | 22.341 | 54.930 | 74.046 | 1.00 | 9.62 |
| ATOM | 1910 | O | ILE | 428 | 23.582 | 55.071 | 73.985 | 1.00 | 10.08 |
| ATOM | 1911 | N | LEU | 429 | 21.711 | 53.738 | 74.035 | 1.00 | 10.59 |
| ATOM | 1912 | H | LEU | 429 | 20.731 | 53.708 | 74.074 | 1.00 | 0.00 |
| ATOM | 1913 | CA | LEU | 429 | 22.426 | 52.422 | 73.897 | 1.00 | 11.07 |
| ATOM | 1914 | CB | LEU | 429 | 21.404 | 51.261 | 74.003 | 1.00 | 11.52 |
| ATOM | 1915 | CG | LEU | 429 | 21.963 | 49.845 | 74.303 | 1.00 | 12.71 |
| ATOM | 1916 | CD1 | LEU | 429 | 20.773 | 48.926 | 74.782 | 1.00 | 10.45 |
| ATOM | 1917 | CD2 | LEU | 429 | 22.600 | 49.271 | 73.048 | 1.00 | 12.44 |
| ATOM | 1918 | C | LEU | 429 | 23.189 | 52.415 | 72.561 | 1.00 | 10.87 |
| ATOM | 1919 | O | LEU | 429 | 24.351 | 51.977 | 72.513 | 1.00 | 11.19 |
| ATOM | 1920 | N | LEU | 430 | 22.593 | 52.955 | 71.493 | 1.00 | 9.40 |
| ATOM | 1921 | H | LEU | 430 | 21.695 | 53.305 | 71.552 | 1.00 | 0.00 |
| ATOM | 1922 | CA | LEU | 430 | 23.308 | 52.675 | 70.205 | 1.00 | 10.07 |
| ATOM | 1923 | CB | LEU | 430 | 22.449 | 53.596 | 69.110 | 1.00 | 10.01 |
| ATOM | 1924 | CG | LEU | 430 | 21.230 | 52.790 | 58.684 | 1.00 | 9.98 |
| ATOM | 1925 | CD1 | LEU | 430 | 20.597 | 53.656 | 67.490 | 1.00 | 10.30 |
| ATOM | 1926 | CD2 | LEU | 430 | 21.610 | 51.391 | 68.037 | 1.00 | 10.24 |
| ATOM | 1927 | C | LEU | 430 | 24.634 | 53.753 | 70.308 | 1.00 | 9.79 |
| ATOM | 1928 | O | LEU | 430 | 25.604 | 53.460 | 69.594 | 1.00 | 8.98 |
| ATOM | 1929 | N | THR | 431 | 24.686 | 54.750 | 71.210 | 1.00 | 10.85 |
| ATOM | 1930 | H | THR | 431 | 23.848 | 54.981 | 71.672 | 1.00 | 0.00 |
| ATOM | 1931 | CA | THR | 431 | 25.940 | 55.542 | 71.408 | 1.00 | 10.11 |
| ATOM | 1932 | CB | THR | 431 | 25.764 | 56.981 | 72.157 | 1.00 | 10.17 |
| ATOM | 1933 | OG1 | THR | 431 | 25.470 | 56.846 | 73.555 | 1.00 | 10.01 |
| ATOM | 1934 | HG1 | THR | 431 | 26.155 | 56.345 | 73.986 | 1.00 | 0.00 |
| ATOM | 1935 | CG2 | THR | 431 | 24.638 | 57.773 | 71.481 | 1.00 | 7.87 |
| ATOM | 1936 | C | THR | 431 | 26.958 | 54.712 | 72.140 | 1.00 | 9.95 |
| ATOM | 1937 | O | THR | 431 | 28.161 | 54.832 | 71.854 | 1.00 | 9.76 |
| ATOM | 1938 | N | GLU | 432 | 26.493 | 53.819 | 73.031 | 1.00 | 10.76 |
| ATOM | 1939 | H | GLU | 432 | 25.525 | 53.798 | 73.214 | 1.00 | 0.00 |
| ATOM | 1940 | CA | GLU | 432 | 27.417 | 52.911 | 73.717 | 1.00 | 10.57 |
| ATOM | 1941 | CB | GLU | 432 | 26.735 | 52.134 | 74.838 | 1.00 | 10.99 |
| ATOM | 1942 | CG | GLU | 432 | 26.172 | 53.011 | 75.931 | 1.00 | 12.19 |
| ATOM | 1943 | CD | GLU | 432 | 25.477 | 52.263 | 76.989 | 1.00 | 11.22 |
| ATOM | 1944 | OE1 | GLU | 432 | 24.287 | 51.924 | 76.800 | 1.00 | 10.87 |
| ATOM | 1945 | OE2 | GLU | 432 | 26.130 | 51.985 | 78.019 | 1.00 | 12.57 |
| ATOM | 1946 | C | GLU | 432 | 27.998 | 51.932 | 72.754 | 1.00 | 10.44 |
| ATOM | 1947 | O | GLU | 432 | 29.195 | 51.635 | 72.822 | 1.00 | 12.01 |
| ATOM | 1948 | N | ILE | 433 | 27.204 | 51.482 | 71.784 | 1.00 | 10.08 |
| ATOM | 1949 | H | ILE | 433 | 26.288 | 51.771 | 71.700 | 1.00 | 0.00 |
| ATOM | 1950 | CA | ILE | 433 | 27.715 | 50.447 | 70.836 | 1.00 | 11.27 |
| ATOM | 1951 | CB | ILE | 433 | 26.530 | 49.890 | 69.980 | 1.00 | 10.42 |
| ATOM | 1952 | CG2 | ILE | 433 | 27.075 | 49.059 | 68.768 | 1.00 | 11.49 |
| ATOM | 1953 | CG1 | ILE | 433 | 25.664 | 49.036 | 70.858 | 1.00 | 8.02 |
| ATOM | 1954 | CD1 | ILE | 433 | 24.386 | 48.577 | 70.114 | 1.00 | 10.54 |
| ATOM | 1955 | C | ILE | 433 | 28.828 | 51.050 | 69.951 | 1.00 | 13.00 |
| ATOM | 1956 | O | ILE | 433 | 29.963 | 50.565 | 69.909 | 1.00 | 14.26 |
| ATOM | 1957 | N | VAL | 434 | 28.523 | 52.174 | 69.320 | 1.00 | 12.95 |
| ATOM | 1958 | H | VAL | 434 | 27.626 | 52.546 | 69.452 | 1.00 | 0.00 |
| ATOM | 1959 | CA | VAL | 434 | 29.454 | 52.799 | 68.399 | 1.00 | 14.03 |
| ATOM | 1960 | CB | VAL | 434 | 28.704 | 53.844 | 67.510 | 1.00 | 14.37 |
| ATOM | 1961 | CG1 | VAL | 434 | 28.604 | 55.191 | 68.207 | 1.00 | 13.37 |
| ATOM | 1962 | CG2 | VAL | 434 | 29.352 | 53.965 | 66.168 | 1.00 | 15.55 |
| ATOM | 1963 | C | VAL | 434 | 30.720 | 53.386 | 69.073 | 1.00 | 14.82 |
| ATOM | 1964 | O | VAL | 434 | 31.732 | 53.629 | 68.424 | 1.00 | 15.31 |
| ATOM | 1965 | N | THR | 435 | 30.691 | 53.593 | 70.372 | 1.00 | 14.86 |
| ATOM | 1966 | H | THR | 435 | 29.853 | 53.411 | 70.871 | 1.00 | 0.00 |
| ATOM | 1967 | CA | THR | 435 | 31.894 | 54.079 | 71.036 | 1.00 | 15.04 |
| ATOM | 1968 | CB | THR | 435 | 31.562 | 55.259 | 72.031 | 1.00 | 14.20 |
| ATOM | 1969 | OG1 | THR | 435 | 30.694 | 54.812 | 73.095 | 1.00 | 14.28 |
| ATOM | 1970 | HG1 | THR | 435 | 29.871 | 54.045 | 72.694 | 1.00 | 0.00 |
| ATOM | 1971 | CG2 | THR | 435 | 30.880 | 56.408 | 71.296 | 1.00 | 14.64 |
| ATOM | 1972 | C | THR | 435 | 32.541 | 52.958 | 71.848 | 1.00 | 15.43 |
| ATOM | 1973 | O | THR | 435 | 33.360 | 53.221 | 72.724 | 1.00 | 15.24 |
| ATOM | 1974 | N | HIS | 436 | 32.157 | 51.707 | 71.589 | 1.00 | 15.88 |
| ATOM | 1975 | H | HIS | 436 | 31.501 | 51.526 | 70.880 | 1.00 | 0.00 |
| ATOM | 1976 | CA | HIS | 436 | 32.731 | 50.558 | 72.324 | 1.00 | 16.19 |
| ATOM | 1977 | CB | HIS | 436 | 34.156 | 50.258 | 71.849 | 1.00 | 18.40 |
| ATOM | 1978 | CG | HIS | 436 | 34.223 | 49.679 | 70.446 | 1.00 | 21.19 |
| ATOM | 1979 | CD2 | HIS | 436 | 34.237 | 50.279 | 69.235 | 1.00 | 22.44 |
| ATOM | 1980 | ND1 | HIS | 436 | 34.293 | 48.306 | 70.203 | 1.00 | 22.10 |
| ATOM | 1981 | HD1 | HIS | 436 | 34.321 | 47.600 | 70.875 | 1.00 | 0.00 |

TABLE 5-continued

Coordinates of Lck bound with baicalein

| | | Atom Type | Res | # | X | Y | Z | Occ | B |
|---|---|---|---|---|---|---|---|---|---|
| ATOM | 1982 | CE1 | HIS | 436 | 34.341 | 48.107 | 68.891 | 1.00 | 22.90 |
| ATOM | 1983 | NE2 | HIS | 436 | 34.309 | 49.272 | 68.275 | 1.00 | 22.45 |
| ATOM | 1984 | HE2 | HIS | 436 | 34.291 | 49.408 | 67.309 | 1.00 | 0.00 |
| ATOM | 1985 | C | HIS | 436 | 32.644 | 50.742 | 73.851 | 1.00 | 16.07 |
| ATOM | 1986 | O | HIS | 436 | 33.623 | 50.626 | 74.568 | 1.00 | 17.17 |
| ATOM | 1987 | N | GLY | 437 | 31.453 | 51.082 | 74.333 | 1.00 | 15.20 |
| ATOM | 1988 | H | GLY | 437 | 30.727 | 51.254 | 73.702 | 1.00 | 0.00 |
| ATOM | 1989 | CA | GLY | 437 | 31.216 | 51.153 | 75.745 | 1.00 | 14.53 |
| ATOM | 1990 | C | GLY | 437 | 31.431 | 52.451 | 76.498 | 1.00 | 15.55 |
| ATOM | 1991 | O | GLY | 437 | 31.304 | 52.476 | 77.727 | 1.00 | 15.47 |
| ATOM | 1992 | N | ARG | 438 | 31.689 | 53.535 | 75.795 | 0.58 | 13.88 |
| ATOM | 1993 | H | ARG | 438 | 31.745 | 53.443 | 74.799 | 1.00 | 0.00 |
| ATOM | 1994 | CA | ARG | 438 | 31.903 | 54.806 | 76.448 | 0.58 | 14.38 |
| ATOM | 1995 | CB | ARG | 438 | 32.420 | 55.835 | 75.401 | 0.58 | 14.66 |
| ATOM | 1996 | CG | ARG | 438 | 33.016 | 57.112 | 75.987 | 0.58 | 17.30 |
| ATOM | 1997 | CD | ARG | 438 | 33.477 | 58.086 | 74.864 | 0.58 | 18.16 |
| ATOM | 1998 | NE | ARG | 438 | 34.281 | 59.183 | 75.398 | 0.58 | 21.31 |
| ATOM | 1999 | HE | ARG | 438 | 34.624 | 59.099 | 76.317 | 1.00 | 0.00 |
| ATOM | 2000 | CZ | ARG | 438 | 34.582 | 60.303 | 74.735 | 0.58 | 21.85 |
| ATOM | 2001 | NH1 | ARG | 438 | 34.152 | 60.497 | 73.502 | 0.58 | 22.70 |
| ATOM | 2002 | HH11 | ARG | 438 | 33.601 | 59.774 | 73.056 | 1.00 | 0.00 |
| ATOM | 2003 | HH12 | ARG | 438 | 34.385 | 61.318 | 73.004 | 1.00 | 0.00 |
| ATOM | 2004 | NH2 | ARG | 438 | 35.311 | 61.246 | 75.300 | 0.58 | 21.08 |
| ATOM | 2005 | HH21 | ARG | 438 | 35.641 | 61.133 | 76.237 | 1.00 | 0.00 |
| ATOM | 2006 | HH22 | ARG | 438 | 35.531 | 62.079 | 74.791 | 1.00 | 0.00 |
| ATOM | 2007 | C | ARG | 438 | 30.630 | 55.341 | 77.124 | 0.58 | 13.27 |
| ATOM | 2008 | O | ARG | 438 | 29.504 | 55.079 | 76.702 | 0.58 | 12.69 |
| ATOM | 2009 | N | ILE | 439 | 30.811 | 56.082 | 78.211 | 1.00 | 14.23 |
| ATOM | 2010 | H | ILE | 439 | 31.716 | 56.200 | 78.548 | 1.00 | 0.00 |
| ATOM | 2011 | CA | ILE | 439 | 29.689 | 56.668 | 78.963 | 1.00 | 13.63 |
| ATOM | 2012 | CB | ILE | 439 | 30.199 | 57.245 | 80.277 | 1.00 | 16.14 |
| ATOM | 2013 | CG2 | ILE | 439 | 29.133 | 58.213 | 80.972 | 1.00 | 16.00 |
| ATOM | 2014 | CG1 | ILE | 439 | 30.526 | 56.084 | 81.235 | 1.00 | 15.62 |
| ATOM | 2015 | CD1 | ILE | 439 | 30.916 | 56.617 | 85.570 | 1.00 | 18.61 |
| ATOM | 2016 | C | ILE | 439 | 29.034 | 57.783 | 78.128 | 1.00 | 12.36 |
| ATOM | 2017 | O | ILE | 439 | 29.780 | 58.633 | 77.498 | 1.00 | 11.19 |
| ATOM | 2018 | N | PRO | 440 | 27.687 | 57.757 | 77.985 | 0.43 | 10.50 |
| ATOM | 2019 | CD | PRO | 440 | 26.725 | 56.786 | 78.514 | 0.43 | 9.39 |
| ATOM | 2020 | CA | PRO | 440 | 27.006 | 58.784 | 77.184 | 0.43 | 9.36 |
| ATOM | 2021 | CB | PRO | 440 | 25.534 | 58.378 | 77.256 | 0.43 | 8.26 |
| ATOM | 2022 | CG | PRO | 440 | 25.449 | 57.562 | 78.481 | 0.43 | 9.41 |
| ATOM | 2023 | C | PRO | 440 | 27.253 | 60.211 | 77.668 | 0.43 | 9.84 |
| ATOM | 2024 | O | PRO | 440 | 27.595 | 60.468 | 78.818 | 0.43 | 8.88 |
| ATOM | 2025 | N | TYR | 441 | 27.130 | 61.164 | 76.760 | 1.00 | 12.41 |
| ATOM | 2026 | H | TYR | 441 | 26.875 | 60.867 | 75.828 | 1.00 | 0.00 |
| ATOM | 2027 | CA | TYR | 441 | 27.296 | 62.610 | 76.984 | 1.00 | 14.28 |
| ATOM | 2028 | CB | TYR | 441 | 26.222 | 63.145 | 77.930 | 1.00 | 13.61 |
| ATOM | 2029 | CG | TYR | 441 | 24.815 | 62.935 | 77.435 | 1.00 | 12.37 |
| ATOM | 2030 | CD1 | TYR | 441 | 24.224 | 63.871 | 76.548 | 1.00 | 10.67 |
| ATOM | 2031 | CE1 | TYR | 441 | 22.898 | 63.698 | 76.110 | 1.00 | 9.82 |
| ATOM | 2032 | CD2 | TYR | 441 | 24.052 | 61.848 | 77.838 | 1.00 | 11.27 |
| ATOM | 2033 | CE2 | TYR | 441 | 22.741 | 61.680 | 77.400 | 1.00 | 10.12 |
| ATOM | 2034 | CZ | TYR | 441 | 22.176 | 62.647 | 76.530 | 1.00 | 10.72 |
| ATOM | 2035 | OH | TYR | 441 | 20.826 | 62.578 | 76.120 | 1.00 | 9.59 |
| ATOM | 2036 | HH | TYR | 441 | 20.630 | 63.220 | 75.544 | 1.00 | 0.00 |
| ATOM | 2037 | C | TYR | 441 | 28.682 | 62.849 | 77.645 | 1.00 | 16.20 |
| ATOM | 2038 | O | TYR | 441 | 28.756 | 63.395 | 78.750 | 1.00 | 17.49 |
| ATOM | 2039 | N | PRO | 442 | 29.773 | 62.515 | 76.924 | 1.00 | 16.78 |
| ATOM | 2040 | CD | PRO | 442 | 29.765 | 62.133 | 75.491 | 1.00 | 17.13 |
| ATOM | 2041 | CA | PRO | 442 | 31.128 | 62.673 | 77.420 | 1.00 | 18.20 |
| ATOM | 2042 | CB | PRO | 442 | 31.992 | 62.375 | 76.183 | 1.00 | 17.79 |
| ATOM | 2043 | CG | PRO | 442 | 31.105 | 61.487 | 75.326 | 1.00 | 18.63 |
| ATOM | 2044 | C | PRO | 442 | 31.466 | 64.073 | 78.021 | 1.00 | 18.36 |
| ATOM | 2045 | O | PRO | 442 | 31.100 | 65.117 | 77.477 | 1.00 | 17.67 |
| ATOM | 2046 | N | GLY | 443 | 32.035 | 64.065 | 79.220 | 1.00 | 18.11 |
| ATOM | 2047 | H | GLY | 443 | 32.158 | 63.188 | 79.674 | 1.00 | 0.00 |
| ATOM | 2048 | CA | GLY | 443 | 32.436 | 65.311 | 79.824 | 1.00 | 18.16 |
| ATOM | 2049 | C | GLY | 443 | 31.320 | 66.130 | 80.423 | 1.00 | 18.07 |
| ATOM | 2050 | O | GLY | 443 | 31.517 | 67.307 | 80.807 | 1.00 | 17.58 |
| ATOM | 2051 | N | MET | 444 | 30.165 | 65.500 | 80.591 | 1.00 | 17.86 |
| ATOM | 2052 | H | MET | 444 | 30.086 | 64.528 | 80.345 | 1.00 | 0.00 |
| ATOM | 2053 | CA | MET | 444 | 29.006 | 66.195 | 81.154 | 1.00 | 17.09 |
| ATOM | 2054 | CB | MET | 444 | 27.894 | 66.393 | 80.092 | 1.00 | 17.38 |
| ATOM | 2055 | CG | MET | 444 | 28.375 | 67.056 | 78.749 | 1.00 | 17.49 |

TABLE 5-continued

Coordinates of Lck bound with baicalein

| | Atom Type | Res | # | X | Y | Z | Occ | B |
|---|---|---|---|---|---|---|---|---|
| ATOM | 2056 | SD | MET | 444 | 27.097 | 67.200 | 77.444 | 1.00 | 17.06 |
| ATOM | 2057 | CE | MET | 444 | 25.812 | 68.000 | 78.238 | 1.00 | 15.65 |
| ATOM | 2058 | C | MET | 444 | 28.394 | 65.559 | 82.397 | 1.00 | 16.30 |
| ATOM | 2059 | O | MET | 444 | 28.254 | 64.373 | 82.484 | 1.00 | 16.36 |
| ATOM | 2060 | N | THR | 445 | 28.047 | 66.422 | 83.353 | 1.00 | 15.71 |
| ATOM | 2061 | H | THR | 445 | 28.272 | 67.353 | 83.236 | 1.00 | 0.00 |
| ATOM | 2062 | CA | THR | 445 | 27.380 | 66.007 | 84.569 | 1.00 | 15.55 |
| ATOM | 2063 | CB | THR | 445 | 27.536 | 67.021 | 85.714 | 1.00 | 16.34 |
| ATOM | 2064 | OG1 | THR | 445 | 26.876 | 68.268 | 85.378 | 1.00 | 14.90 |
| ATOM | 2065 | HG1 | THR | 445 | 25.956 | 68.082 | 85.239 | 1.00 | 0.00 |
| ATOM | 2066 | CG2 | THR | 445 | 29.023 | 67.256 | 86.011 | 1.00 | 17.10 |
| ATOM | 2067 | C | THR | 445 | 25.893 | 65.897 | 84.262 | 1.00 | 15.45 |
| ATOM | 2068 | O | THR | 445 | 25.399 | 66.455 | 83.263 | 1.00 | 14.46 |
| ATOM | 2069 | N | ASN | 446 | 25.155 | 65.243 | 85.149 | 1.00 | 14.83 |
| ATOM | 2070 | H | ASN | 446 | 25.584 | 64.803 | 85.928 | 1.00 | 0.00 |
| ATOM | 2071 | CA | ASN | 446 | 23.717 | 65.065 | 84.943 | 1.00 | 16.50 |
| ATOM | 2072 | CB | ASN | 446 | 23.083 | 64.170 | 86.040 | 1.00 | 17.08 |
| ATOM | 2073 | CG | ASN | 446 | 23.496 | 63.735 | 85.915 | 1.00 | 16.90 |
| ATOM | 2074 | OD1 | ASN | 446 | 23.900 | 62.313 | 84.854 | 1.00 | 17.29 |
| ATOM | 2075 | ND2 | ASN | 446 | 23.424 | 61.992 | 87.004 | 1.00 | 15.29 |
| ATOM | 2076 | HD21 | ASN | 446 | 23.110 | 62.369 | 87.838 | 1.00 | 0.00 |
| ATOM | 2077 | HD22 | ASN | 446 | 23.689 | 61.039 | 86.918 | 1.00 | 0.00 |
| ATOM | 2078 | C | ASN | 446 | 23.014 | 66.414 | 84.829 | 1.00 | 16.32 |
| ATOM | 2079 | O | ASN | 446 | 22.152 | 66.571 | 83.974 | 1.00 | 17.08 |
| ATOM | 2080 | N | PRO | 447 | 23.322 | 67.385 | 85.718 | 1.00 | 15.49 |
| ATOM | 2081 | CD | PRO | 447 | 24.071 | 67.316 | 86.990 | 1.00 | 15.12 |
| ATOM | 2082 | CA | PRO | 447 | 22.634 | 68.667 | 85.583 | 1.00 | 15.54 |
| ATOM | 2083 | CB | PRO | 447 | 23.185 | 69.502 | 86.780 | 1.00 | 15.61 |
| ATOM | 2084 | CG | PRO | 447 | 23.414 | 68.439 | 87.829 | 1.00 | 15.23 |
| ATOM | 2085 | C | PRO | 447 | 22.930 | 69.329 | 84.225 | 1.00 | 15.06 |
| ATOM | 2086 | O | PRO | 447 | 22.081 | 70.066 | 83.702 | 1.00 | 15.54 |
| ATOM | 2087 | N | GLU | 448 | 24.134 | 69.148 | 83.682 | 1.00 | 14.67 |
| ATOM | 2088 | H | GLU | 448 | 24.819 | 68.632 | 84.221 | 1.00 | 0.00 |
| ATOM | 2089 | CA | GLU | 448 | 24.466 | 69.702 | 82.349 | 1.00 | 14.62 |
| ATOM | 2090 | CB | GLU | 448 | 25.953 | 69.575 | 82.021 | 1.00 | 15.50 |
| ATOM | 2091 | CG | GLU | 448 | 26.842 | 70.467 | 82.887 | 1.00 | 17.58 |
| ATOM | 2092 | CD | GLU | 448 | 28.321 | 70.269 | 82.610 | 1.00 | 17.59 |
| ATOM | 2093 | OE1 | GLU | 448 | 28.847 | 69.152 | 82.645 | 1.00 | 18.03 |
| ATOM | 2094 | OE2 | GLU | 448 | 28.984 | 71.246 | 82.375 | 1.00 | 21.71 |
| ATOM | 2095 | C | GLU | 448 | 23.687 | 68.985 | 81.253 | 1.00 | 14.23 |
| ATOM | 2096 | O | GLU | 448 | 23.260 | 69.650 | 80.279 | 1.00 | 14.21 |
| ATOM | 2097 | N | VAL | 449 | 23.477 | 67.657 | 81.396 | 1.00 | 13.24 |
| ATOM | 2098 | H | VAL | 449 | 23.895 | 67.149 | 82.154 | 1.00 | 0.00 |
| ATOM | 2099 | CA | VAL | 449 | 22.733 | 66.874 | 80.371 | 1.00 | 11.33 |
| ATOM | 2100 | CB | VAL | 449 | 22.751 | 65.355 | 80.676 | 1.00 | 10.92 |
| ATOM | 2101 | CG1 | VAL | 449 | 21.759 | 64.606 | 79.761 | 1.00 | 9.98 |
| ATOM | 2102 | CG2 | VAL | 449 | 24.124 | 64.841 | 80.459 | 1.00 | 10.67 |
| ATOM | 2103 | C | VAL | 449 | 21.297 | 67.435 | 80.353 | 1.00 | 10.80 |
| ATOM | 2104 | O | VAL | 449 | 20.757 | 67.785 | 79.290 | 1.00 | 9.17 |
| ATOM | 2105 | N | ILE | 450 | 20.699 | 67.582 | 81.525 | 0.60 | 10.27 |
| ATOM | 2106 | H | ILE | 450 | 21.201 | 67.310 | 82.347 | 1.00 | 0.00 |
| ATOM | 2107 | CA | ILE | 450 | 19.318 | 68.070 | 81.636 | 0.60 | 10.36 |
| ATOM | 2108 | CB | ILE | 450 | 18.852 | 68.003 | 83.145 | 0.60 | 10.57 |
| ATOM | 2109 | CG2 | ILE | 450 | 17.530 | 68.746 | 83.347 | 0.60 | 8.76 |
| ATOM | 2110 | CG1 | ILE | 450 | 18.729 | 66.547 | 83.622 | 0.60 | 9.26 |
| ATOM | 2111 | CD1 | ILE | 450 | 18.485 | 66.413 | 85.115 | 0.60 | 8.85 |
| ATOM | 2112 | C | ILE | 450 | 19.156 | 69.496 | 81.043 | 0.60 | 11.81 |
| ATOM | 2113 | O | ILE | 450 | 18.238 | 69.794 | 80.290 | 0.60 | 9.77 |
| ATOM | 2114 | N | GLN | 451 | 20.075 | 70.381 | 81.375 | 1.00 | 14.21 |
| ATOM | 2115 | H | GLN | 451 | 20.753 | 70.119 | 82.058 | 1.00 | 0.00 |
| ATOM | 2116 | CA | GLN | 451 | 20.045 | 71.769 | 80.918 | 1.00 | 17.34 |
| ATOM | 2117 | CB | GLN | 451 | 21.236 | 72.517 | 81.545 | 1.00 | 21.47 |
| ATOM | 2118 | CG | GLN | 451 | 21.392 | 74.024 | 81.169 | 1.00 | 26.21 |
| ATOM | 2119 | CD | GLN | 451 | 22.577 | 74.719 | 81.872 | 1.00 | 28.91 |
| ATOM | 2120 | OE1 | GLN | 451 | 22.381 | 75.764 | 82.503 | 1.00 | 32.74 |
| ATOM | 2121 | NE2 | GLN | 451 | 23.811 | 74.166 | 81.734 | 1.00 | 30.12 |
| ATOM | 2122 | HE21 | GLN | 451 | 23.924 | 73.346 | 81.208 | 1.00 | 0.00 |
| ATOM | 2123 | HE22 | GLN | 451 | 24.569 | 74.609 | 82.180 | 1.00 | 0.00 |
| ATOM | 2124 | C | GLN | 451 | 20.129 | 71.764 | 79.388 | 1.00 | 16.52 |
| ATOM | 2125 | O | GLN | 451 | 19.365 | 72.452 | 78.693 | 1.00 | 14.37 |
| ATOM | 2126 | N | ASN | 452 | 21.039 | 70.958 | 78.831 | 1.00 | 16.57 |
| ATOM | 2127 | H | ASN | 452 | 21.601 | 70.401 | 79.415 | 1.00 | 0.00 |
| ATOM | 2128 | CA | ASN | 452 | 21.172 | 70.852 | 77.370 | 1.00 | 15.13 |
| ATOM | 2129 | CB | ASN | 452 | 22.340 | 69.964 | 76.998 | 1.00 | 18.12 |

TABLE 5-continued

Coordinates of Lck bound with baicalein

| | | Atom Type | Res | # | X | Y | Z | Occ | B |
|---|---|---|---|---|---|---|---|---|---|
| ATOM | 2130 | CG | ASN | 452 | 23.640 | 70.719 | 76.890 | 1.00 | 19.07 |
| ATOM | 2131 | OD1 | ASN | 452 | 24.577 | 70.231 | 76.280 | 1.00 | 22.53 |
| ATOM | 2132 | ND2 | ASN | 452 | 23.711 | 71.883 | 77.470 | 1.00 | 20.19 |
| ATOM | 2133 | HD21 | ASN | 452 | 22.920 | 72.248 | 77.938 | 1.00 | 0.00 |
| ATOM | 2134 | HD22 | ASN | 452 | 24.549 | 72.383 | 77.420 | 1.00 | 0.00 |
| ATOM | 2135 | C | ASN | 452 | 19.938 | 70.304 | 76.729 | 1.00 | 15.71 |
| ATOM | 2136 | O | ASN | 452 | 19.468 | 70.877 | 75.742 | 1.00 | 14.30 |
| ATOM | 2137 | N | LEU | 453 | 19.384 | 69.203 | 77.255 | 1.00 | 14.50 |
| ATOM | 2138 | H | LEU | 453 | 19.790 | 68.750 | 78.019 | 1.00 | 0.00 |
| ATOM | 2139 | CA | LEU | 453 | 18.183 | 68.626 | 76.618 | 1.00 | 13.57 |
| ATOM | 2140 | CB | LEU | 453 | 17.743 | 67.383 | 77.336 | 1.00 | 13.77 |
| ATOM | 2141 | CG | LEU | 453 | 18.732 | 66.184 | 77.258 | 1.00 | 13.49 |
| ATOM | 2142 | CD1 | LEU | 453 | 18.227 | 65.035 | 78.186 | 1.00 | 12.68 |
| ATOM | 2143 | CD2 | LEU | 453 | 18.854 | 65.760 | 75.758 | 1.00 | 13.52 |
| ATOM | 2144 | C | LEU | 453 | 17.065 | 69.658 | 76.556 | 1.00 | 14.84 |
| ATOM | 2145 | O | LEU | 453 | 16.409 | 69.841 | 75.503 | 1.00 | 11.98 |
| ATOM | 2146 | N | GLU | 454 | 16.924 | 70.441 | 77.620 | 1.00 | 15.35 |
| ATOM | 2147 | H | GLU | 454 | 17.560 | 70.316 | 78.396 | 1.00 | 0.00 |
| ATOM | 2148 | CA | GLU | 454 | 15.858 | 71.411 | 77.679 | 1.00 | 17.03 |
| ATOM | 2149 | CB | GLU | 454 | 15.615 | 71.884 | 79.144 | 1.00 | 19.94 |
| ATOM | 2150 | CG | GLU | 454 | 14.985 | 70.715 | 79.963 | 1.00 | 24.08 |
| ATOM | 2151 | CD | GLU | 454 | 14.761 | 71.065 | 81.432 | 1.00 | 27.77 |
| ATOM | 2152 | OE1 | GLU | 454 | 15.352 | 72.088 | 81.891 | 1.00 | 28.47 |
| ATOM | 2153 | OE2 | GLU | 454 | 14.023 | 70.309 | 82.137 | 1.00 | 29.17 |
| ATOM | 2154 | C | GLU | 454 | 16.000 | 72.557 | 76.705 | 1.00 | 16.00 |
| ATOM | 2155 | O | GLU | 454 | 14.998 | 73.212 | 76.338 | 1.00 | 15.76 |
| ATOM | 2156 | N | ARG | 455 | 17.217 | 72.749 | 76.213 | 1.00 | 14.83 |
| ATOM | 2157 | H | ARG | 455 | 17.969 | 72.208 | 76.433 | 1.00 | 0.00 |
| ATOM | 2158 | CA | ARG | 455 | 17.471 | 73.798 | 75.205 | 1.00 | 14.21 |
| ATOM | 2159 | CB | ARG | 455 | 18.945 | 74.195 | 75.205 | 1.00 | 12.83 |
| ATOM | 2160 | CG | ARG | 455 | 19.385 | 74.797 | 76.491 | 1.00 | 14.18 |
| ATOM | 2161 | CD | ARG | 455 | 20.797 | 75.311 | 76.394 | 1.00 | 15.20 |
| ATOM | 2162 | NE | ARG | 455 | 20.858 | 76.449 | 75.453 | 1.00 | 15.22 |
| ATOM | 2163 | HE | ARG | 455 | 20.039 | 76.716 | 75.045 | 1.00 | 0.00 |
| ATOM | 2164 | CZ | ARG | 455 | 21.991 | 77.073 | 75.099 | 1.00 | 15.26 |
| ATOM | 2165 | NH1 | ARG | 455 | 23.181 | 76.691 | 75.596 | 1.00 | 13.31 |
| ATOM | 2166 | HH11 | ARG | 455 | 23.224 | 75.925 | 76.260 | 1.00 | 0.00 |
| ATOM | 2167 | HH12 | ARG | 455 | 24.015 | 77.148 | 75.325 | 1.00 | 0.00 |
| ATOM | 2168 | NH2 | ARG | 455 | 21.936 | 78.093 | 74.263 | 1.00 | 10.44 |
| ATOM | 2169 | HH21 | ARG | 455 | 21.048 | 78.269 | 73.893 | 1.00 | 0.00 |
| ATOM | 2170 | HH22 | ARG | 455 | 22.767 | 78.543 | 73.973 | 1.00 | 0.00 |
| ATOM | 2171 | C | ARG | 455 | 17.164 | 73.264 | 73.797 | 1.00 | 14.10 |
| ATOM | 2172 | O | ARG | 455 | 17.187 | 74.045 | 72.854 | 1.00 | 14.19 |
| ATOM | 2173 | N | GLY | 456 | 16.888 | 71.963 | 73.641 | 1.00 | 13.08 |
| ATOM | 2174 | H | GLY | 456 | 16.856 | 71.350 | 74.435 | 1.00 | 0.00 |
| ATOM | 2175 | CA | GLY | 456 | 16.655 | 71.410 | 72.314 | 1.00 | 11.81 |
| ATOM | 2176 | C | GLY | 456 | 17.882 | 70.655 | 71.795 | 1.00 | 11.20 |
| ATOM | 2177 | O | GLY | 456 | 17.851 | 70.084 | 70.705 | 1.00 | 11.84 |
| ATOM | 2178 | N | TYR | 457 | 18.989 | 70.699 | 72.522 | 1.00 | 12.16 |
| ATOM | 2179 | H | TYR | 457 | 18.998 | 71.190 | 73.370 | 1.00 | 0.00 |
| ATOM | 2180 | CA | TYR | 457 | 20.209 | 69.959 | 72.102 | 1.00 | 12.52 |
| ATOM | 2181 | CB | TYR | 457 | 21.419 | 70.395 | 72.934 | 1.00 | 12.27 |
| ATOM | 2182 | CG | TYR | 457 | 21.941 | 71.789 | 72.694 | 1.00 | 12.61 |
| ATOM | 2183 | CD1 | TYR | 457 | 21.488 | 72.565 | 71.648 | 1.00 | 13.00 |
| ATOM | 2184 | CE1 | TYR | 457 | 22.003 | 73.873 | 71.428 | 1.00 | 10.90 |
| ATOM | 2185 | CD2 | TYR | 457 | 22.917 | 72.327 | 73.534 | 1.00 | 14.33 |
| ATOM | 2186 | CE2 | TYR | 457 | 23.433 | 73.637 | 73.325 | 1.00 | 13.63 |
| ATOM | 2187 | CZ | TYR | 457 | 22.954 | 74.385 | 72.256 | 1.00 | 13.36 |
| ATOM | 2188 | OH | TYR | 457 | 23.490 | 75.682 | 72.051 | 1.00 | 12.48 |
| ATOM | 2189 | HH | TYR | 457 | 23.056 | 76.028 | 71.276 | 1.00 | 0.00 |
| ATOM | 2190 | C | TYR | 457 | 20.040 | 68.473 | 72.405 | 1.00 | 12.71 |
| ATOM | 2191 | O | TYR | 457 | 19.166 | 68.085 | 73.239 | 1.00 | 13.69 |
| ATOM | 2192 | N | ARG | 458 | 20.904 | 67.652 | 71.789 | 1.00 | 13.49 |
| ATOM | 2193 | H | ARG | 458 | 21.501 | 68.028 | 71.110 | 1.00 | 0.00 |
| ATOM | 2194 | CA | ARG | 458 | 20.915 | 66.191 | 72.008 | 1.00 | 13.16 |
| ATOM | 2195 | CB | ARG | 458 | 20.268 | 65.441 | 70.880 | 1.00 | 11.71 |
| ATOM | 2196 | CG | ARG | 458 | 18.709 | 65.621 | 70.828 | 1.00 | 11.07 |
| ATOM | 2197 | CD | ARG | 458 | 18.021 | 65.277 | 72.148 | 1.00 | 9.84 |
| ATOM | 2198 | NE | ARG | 458 | 16.564 | 65.378 | 72.073 | 1.00 | 8.74 |
| ATOM | 2199 | HE | ARG | 458 | 16.060 | 64.655 | 71.628 | 1.00 | 0.00 |
| ATOM | 2200 | CZ | ARG | 458 | 15.853 | 66.379 | 72.599 | 1.00 | 12.73 |
| ATOM | 2201 | NH1 | ARG | 458 | 16.494 | 67.407 | 73.220 | 1.00 | 11.94 |
| ATOM | 2202 | HH11 | ARG | 458 | 17.500 | 67.356 | 73.289 | 1.00 | 0.00 |
| ATOM | 2203 | HH12 | ARG | 458 | 15.986 | 68.125 | 73.627 | 1.00 | 0.00 |

TABLE 5-continued

Coordinates of Lck bound with baicalein

| | | Atom Type | Res | # | X | Y | Z | Occ | B |
|---|---|---|---|---|---|---|---|---|---|
| ATOM | 2204 | NH2 | ARG | 458 | 14.506 | 66.343 | 72.566 | 1.00 | 8.82 |
| ATOM | 2205 | HH21 | ARG | 458 | 14.051 | 65.546 | 72.181 | 1.00 | 0.00 |
| ATOM | 2206 | HH22 | ARG | 458 | 13.998 | 67.080 | 72.987 | 1.00 | 0.00 |
| ATOM | 2207 | C | ARG | 458 | 22.391 | 65.875 | 72.054 | 1.00 | 13.08 |
| ATOM | 2208 | O | ARG | 458 | 23.229 | 66.727 | 71.790 | 1.00 | 11.74 |
| ATOM | 2209 | N | MET | 459 | 22.726 | 64.648 | 72.421 | 1.00 | 14.15 |
| ATOM | 2210 | H | MET | 459 | 22.049 | 63.953 | 72.631 | 1.00 | 0.00 |
| ATOM | 2211 | CA | MET | 459 | 24.147 | 64.271 | 72.507 | 1.00 | 13.57 |
| ATOM | 2212 | CB | MET | 459 | 24.293 | 62.778 | 72.754 | 1.00 | 12.84 |
| ATOM | 2213 | CG | MET | 459 | 25.611 | 62.458 | 73.301 | 1.00 | 12.57 |
| ATOM | 2214 | SD | MET | 459 | 25.825 | 60.701 | 73.565 | 1.00 | 11.22 |
| ATOM | 2215 | CE | MET | 459 | 24.346 | 60.284 | 74.354 | 1.00 | 11.82 |
| ATOM | 2216 | C | MET | 459 | 24.891 | 64.614 | 71.229 | 1.00 | 13.48 |
| ATOM | 2217 | O | MET | 459 | 24.402 | 64.452 | 70.111 | 1.00 | 13.27 |
| ATOM | 2218 | N | VAL | 460 | 26.073 | 65.163 | 71.439 | 1.00 | 14.06 |
| ATOM | 2219 | H | VAL | 460 | 26.355 | 65.316 | 72.351 | 1.00 | 0.00 |
| ATOM | 2220 | CA | VAL | 460 | 27.033 | 65.478 | 70.372 | 1.00 | 14.67 |
| ATOM | 2221 | CB | VAL | 460 | 28.329 | 66.032 | 70.996 | 1.00 | 16.00 |
| ATOM | 2222 | CG1 | VAL | 460 | 29.478 | 66.082 | 69.965 | 1.00 | 15.59 |
| ATOM | 2223 | CG2 | VAL | 460 | 28.067 | 67.468 | 71.578 | 1.00 | 16.30 |
| ATOM | 2224 | C | VAL | 460 | 27.384 | 64.178 | 69.587 | 1.00 | 14.73 |
| ATOM | 2225 | O | VAL | 460 | 27.482 | 63.121 | 70.180 | 1.00 | 13.78 |
| ATOM | 2226 | N | ARG | 461 | 27.513 | 64.277 | 68.262 | 1.00 | 13.72 |
| ATOM | 2227 | H | ARG | 461 | 27.341 | 65.141 | 67.817 | 1.00 | 0.00 |
| ATOM | 2228 | CA | ARG | 461 | 27.887 | 63.136 | 67.437 | 1.00 | 15.16 |
| ATOM | 2229 | CB | ARG | 461 | 28.252 | 63.549 | 66.007 | 1.00 | 14.21 |
| ATOM | 2230 | CG | ARG | 461 | 27.118 | 64.113 | 65.184 | 1.00 | 12.97 |
| ATOM | 2231 | CD | ARG | 461 | 27.622 | 64.744 | 63.869 | 1.00 | 12.67 |
| ATOM | 2232 | NE | ARG | 461 | 26.480 | 64.972 | 63.004 | 1.00 | 15.35 |
| ATOM | 2233 | HE | ARG | 461 | 26.154 | 64.245 | 62.430 | 1.00 | 0.00 |
| ATOM | 2234 | CZ | ARG | 461 | 25.788 | 66.112 | 62.983 | 1.00 | 15.94 |
| ATOM | 2235 | NH1 | ARG | 461 | 26.156 | 67.119 | 63.790 | 1.00 | 17.18 |
| ATOM | 2236 | HH11 | ARG | 461 | 26.930 | 66.991 | 64.395 | 1.00 | 0.00 |
| ATOM | 2237 | HH12 | ARG | 461 | 25.643 | 67.965 | 63.764 | 1.00 | 0.00 |
| ATOM | 2238 | NH2 | ARG | 461 | 24.763 | 66.267 | 62.153 | 1.00 | 13.66 |
| ATOM | 2239 | HH21 | ARG | 461 | 24.460 | 65.481 | 61.598 | 1.00 | 0.00 |
| ATOM | 2240 | HH22 | ARG | 461 | 24.233 | 67.100 | 62.168 | 1.00 | 0.00 |
| ATOM | 2241 | C | ARG | 461 | 29.099 | 62.443 | 68.010 | 1.00 | 17.07 |
| ATOM | 2242 | O | ARG | 461 | 30.171 | 63.082 | 68.192 | 1.00 | 17.61 |
| ATOM | 2243 | N | PRO | 462 | 28.952 | 61.168 | 68.391 | 1.00 | 19.39 |
| ATOM | 2244 | CD | PRO | 462 | 27.731 | 60.363 | 68.480 | 1.00 | 17.69 |
| ATOM | 2245 | CA | PRO | 462 | 30.112 | 60.451 | 68.925 | 1.00 | 18.10 |
| ATOM | 2246 | CB | PRO | 462 | 29.543 | 59.034 | 69.205 | 1.00 | 17.30 |
| ATOM | 2247 | CG | PRO | 462 | 28.105 | 59.327 | 69.555 | 1.00 | 17.61 |
| ATOM | 2248 | C | PRO | 462 | 31.207 | 60.367 | 67.828 | 1.00 | 19.93 |
| ATOM | 2249 | O | PRO | 462 | 30.922 | 60.499 | 66.658 | 1.00 | 19.44 |
| ATOM | 2250 | N | ASP | 463 | 32.459 | 60.149 | 68.231 | 1.00 | 23.33 |
| ATOM | 2251 | H | ASP | 463 | 32.616 | 60.112 | 69.155 | 1.00 | 0.00 |
| ATOM | 2252 | CA | ASP | 463 | 33.585 | 59.948 | 67.301 | 1.00 | 26.01 |
| ATOM | 2253 | CB | ASP | 463 | 34.873 | 59.667 | 68.066 | 1.00 | 28.38 |
| ATOM | 2254 | CG | ASP | 463 | 35.459 | 60.913 | 68.727 | 1.00 | 30.51 |
| ATOM | 2255 | OD1 | ASP | 463 | 35.179 | 62.027 | 68.228 | 1.00 | 32.98 |
| ATOM | 2256 | OD2 | ASP | 463 | 36.219 | 60.765 | 69.737 | 1.00 | 29.84 |
| ATOM | 2257 | C | ASP | 463 | 33.313 | 58.738 | 66.404 | 1.00 | 26.38 |
| ATOM | 2258 | O | ASP | 463 | 32.779 | 57.719 | 66.862 | 1.00 | 26.76 |
| ATOM | 2259 | N | ASN | 464 | 33.623 | 58.896 | 65.115 | 1.00 | 26.80 |
| ATOM | 2260 | H | ASN | 464 | 33.938 | 59.753 | 64.819 | 1.00 | 0.00 |
| ATOM | 2261 | CA | ASN | 464 | 33.438 | 57.844 | 64.112 | 1.00 | 27.36 |
| ATOM | 2262 | CB | ASN | 464 | 34.506 | 56.752 | 64.295 | 1.00 | 30.82 |
| ATOM | 2263 | CG | ASN | 464 | 35.890 | 57.289 | 64.111 | 1.00 | 32.90 |
| ATOM | 2264 | OD1 | ASN | 464 | 36.160 | 58.011 | 63.146 | 1.00 | 36.42 |
| ATOM | 2265 | ND2 | ASN | 464 | 36.761 | 57.005 | 65.051 | 1.00 | 34.08 |
| ATOM | 2266 | HD21 | ASN | 464 | 36.492 | 56.445 | 65.811 | 1.00 | 0.00 |
| ATOM | 2267 | HD22 | ASN | 464 | 37.682 | 57.318 | 64.929 | 1.00 | 0.00 |
| ATOM | 2268 | C | ASN | 464 | 32.078 | 57.213 | 64.024 | 1.00 | 25.56 |
| ATOM | 2269 | O | ASN | 464 | 31.946 | 56.050 | 63.638 | 1.00 | 27.48 |
| ATOM | 2270 | N | CYS | 465 | 31.057 | 57.959 | 64.390 | 1.00 | 22.51 |
| ATOM | 2271 | H | CYS | 465 | 21.191 | 58.851 | 64.732 | 1.00 | 0.00 |
| ATOM | 2272 | CA | CYS | 465 | 26.694 | 57.421 | 64.290 | 1.00 | 19.66 |
| ATOM | 2273 | CB | CYS | 465 | 28.832 | 58.069 | 65.378 | 1.00 | 18.06 |
| ATOM | 2274 | SG | CYS | 465 | 27.104 | 57.722 | 65.362 | 1.00 | 16.12 |
| ATOM | 2275 | C | CYS | 465 | 29.147 | 57.758 | 62.872 | 1.00 | 19.26 |
| ATOM | 2276 | O | CYS | 465 | 29.262 | 58.921 | 62.452 | 1.00 | 17.98 |
| ATOM | 2277 | N | PRO | 466 | 28.679 | 56.735 | 62.104 | 1.00 | 16.74 |

TABLE 5-continued

Coordinates of Lck bound with baicalein

| | Atom Type | Res | # | X | Y | Z | Occ | B |
|---|---|---|---|---|---|---|---|---|
| ATOM | 2278 | CD | PRO | 466 | 28.696 | 55.287 | 62.444 | 1.00 | 16.46 |
| ATOM | 2279 | CA | PRO | 466 | 28.130 | 56.955 | 60.766 | 1.00 | 14.99 |
| ATOM | 2280 | CB | PRO | 466 | 27.568 | 55.578 | 60.385 | 1.00 | 16.26 |
| ATOM | 2281 | CG | PRO | 466 | 28.481 | 54.604 | 61.110 | 1.00 | 16.27 |
| ATOM | 2282 | C | PRO | 466 | 26.984 | 57.942 | 60.946 | 1.00 | 14.67 |
| ATOM | 2283 | O | PRO | 466 | 26.232 | 57.879 | 61.912 | 1.00 | 13.15 |
| ATOM | 2284 | N | GLU | 467 | 26.840 | 58.869 | 60.003 | 1.00 | 13.55 |
| ATOM | 2285 | H | GLU | 467 | 27.424 | 58.883 | 59.242 | 1.00 | 0.00 |
| ATOM | 2286 | CA | GLU | 467 | 25.757 | 59.870 | 60.122 | 1.00 | 13.09 |
| ATOM | 2287 | CB | GLU | 467 | 25.973 | 61.011 | 59.099 | 1.00 | 12.03 |
| ATOM | 2288 | CG | GLU | 467 | 24.895 | 62.148 | 59.215 | 1.00 | 13.23 |
| ATOM | 2289 | CD | GLU | 467 | 24.979 | 62.955 | 60.507 | 1.00 | 12.03 |
| ATOM | 2290 | OE1 | GLU | 467 | 26.016 | 62.919 | 61.235 | 1.00 | 12.94 |
| ATOM | 2291 | OE2 | GLU | 467 | 24.020 | 63.676 | 60.821 | 1.00 | 13.41 |
| ATOM | 2292 | C | GLU | 467 | 23.334 | 59.295 | 60.019 | 1.00 | 10.71 |
| ATOM | 2293 | O | GLU | 467 | 23.451 | 59.835 | 60.667 | 1.00 | 11.34 |
| ATOM | 2294 | N | GLU | 468 | 24.152 | 58.201 | 59.277 | 0.51 | 8.06 |
| ATOM | 2295 | H | GLU | 468 | 24.915 | 57.819 | 58.768 | 1.00 | 0.00 |
| ATOM | 2296 | CA | GLU | 468 | 22.862 | 57.522 | 59.187 | 0.51 | 6.74 |
| ATOM | 2297 | CB | GLU | 468 | 22.915 | 56.344 | 58.168 | 0.51 | 6.51 |
| ATOM | 2298 | CG | GLU | 468 | 23.066 | 56.792 | 56.741 | 0.51 | 7.59 |
| ATOM | 2299 | CD | GLU | 468 | 23.476 | 55.672 | 55.805 | 0.51 | 6.74 |
| ATOM | 2300 | OE1 | GLU | 468 | 22.612 | 55.096 | 55.142 | 0.51 | 6.63 |
| ATOM | 2301 | OE2 | GLU | 468 | 24.682 | 55.380 | 55.757 | 0.51 | 8.78 |
| ATOM | 2302 | C | GLU | 468 | 22.474 | 56.996 | 60.558 | 0.51 | 6.22 |
| ATOM | 2303 | O | GLU | 468 | 21.324 | 57.122 | 60.927 | 0.51 | 5.42 |
| ATOM | 2304 | N | LEU | 469 | 23.447 | 56.485 | 61.328 | 1.00 | 8.30 |
| ATOM | 2305 | H | LEU | 469 | 24.348 | 56.349 | 60.949 | 1.00 | 0.00 |
| ATOM | 2306 | CA | LEU | 469 | 23.135 | 55.898 | 62.660 | 1.00 | 7.88 |
| ATOM | 2307 | CB | LEU | 469 | 24.355 | 55.137 | 63.192 | 1.00 | 9.09 |
| ATOM | 2308 | CG | LEU | 469 | 24.180 | 54.384 | 64.549 | 1.00 | 9.29 |
| ATOM | 2309 | CD1 | LEU | 469 | 23.098 | 53.300 | 64.409 | 1.00 | 9.82 |
| ATOM | 2310 | CD2 | LEU | 469 | 25.520 | 53.682 | 64.955 | 1.00 | 9.63 |
| ATOM | 2311 | C | LEU | 469 | 22.797 | 57.085 | 63.597 | 1.00 | 8.25 |
| ATOM | 2312 | O | LEU | 469 | 21.879 | 57.050 | 64.413 | 1.00 | 8.45 |
| ATOM | 2313 | N | TYR | 470 | 23.548 | 58.174 | 63.452 | 1.00 | 8.34 |
| ATOM | 2314 | H | TYR | 470 | 24.666 | 58.180 | 62.763 | 1.00 | 0.00 |
| ATOM | 2315 | CA | TYR | 470 | 23.350 | 59.322 | 64.300 | 1.00 | 8.14 |
| ATOM | 2316 | CB | TYR | 470 | 24.444 | 60.370 | 64.072 | 1.00 | 7.31 |
| ATOM | 2317 | CG | TYR | 470 | 24.237 | 61.570 | 65.022 | 1.00 | 7.98 |
| ATOM | 2318 | CD1 | TYR | 470 | 24.447 | 61.434 | 66.388 | 1.00 | 8.38 |
| ATOM | 2319 | CE1 | TYR | 470 | 24.278 | 62.497 | 67.249 | 1.00 | 9.40 |
| ATOM | 2320 | CD2 | TYR | 470 | 23.855 | 62.813 | 64.537 | 1.00 | 7.44 |
| ATOM | 2321 | CE2 | TYR | 470 | 23.681 | 63.914 | 65.379 | 1.00 | 9.16 |
| ATOM | 2322 | CZ | TYR | 470 | 23.905 | 63.745 | 66.728 | 1.00 | 9.80 |
| ATOM | 2323 | OH | TYR | 470 | 23.824 | 64.826 | 67.561 | 1.00 | 11.65 |
| ATOM | 2324 | HH | TYR | 470 | 24.010 | 64.510 | 68.451 | 1.00 | 0.00 |
| ATOM | 2325 | C | TYR | 470 | 21.938 | 59.901 | 64.079 | 1.00 | 8.88 |
| ATOM | 2326 | O | TYR | 470 | 21.299 | 60.296 | 65.065 | 1.00 | 8.58 |
| ATOM | 2327 | N | GLN | 471 | 21.472 | 60.000 | 62.821 | 1.00 | 9.10 |
| ATOM | 2328 | H | GLN | 471 | 22.044 | 59.698 | 62.074 | 1.00 | 0.00 |
| ATOM | 2329 | CA | GLN | 471 | 20.118 | 60.470 | 62.549 | 1.00 | 7.77 |
| ATOM | 2330 | CB | GLN | 471 | 19.953 | 60.735 | 61.046 | 1.00 | 7.69 |
| ATOM | 2331 | CG | GLN | 471 | 20.669 | 62.055 | 60.581 | 1.00 | 8.33 |
| ATOM | 2332 | CD | GLN | 471 | 20.326 | 63.261 | 61.465 | 1.00 | 8.19 |
| ATOM | 2333 | OE1 | GLN | 471 | 19.155 | 63.540 | 61.703 | 1.00 | 10.17 |
| ATOM | 2334 | NE2 | GLN | 471 | 21.347 | 63.976 | 61.952 | 1.00 | 7.78 |
| ATOM | 2335 | HE21 | GLN | 471 | 22.249 | 63.721 | 61.683 | 1.00 | 0.00 |
| ATOM | 2336 | HE22 | GLN | 471 | 21.123 | 64.732 | 62.494 | 1.00 | 0.00 |
| ATOM | 2337 | C | GLN | 471 | 19.062 | 59.479 | 63.087 | 1.00 | 9.41 |
| ATOM | 2338 | O | GLN | 471 | 17.955 | 59.900 | 63.452 | 1.00 | 10.15 |
| ATOM | 2339 | N | LEU | 472 | 19.371 | 58.168 | 63.140 | 1.00 | 9.14 |
| ATOM | 2340 | H | LEU | 472 | 20.207 | 57.850 | 62.739 | 1.00 | 0.00 |
| ATOM | 2341 | CA | LEU | 472 | 18.445 | 57.173 | 63.707 | 1.00 | 8.75 |
| ATOM | 2342 | CB | LEU | 472 | 19.065 | 55.755 | 63.518 | 1.00 | 9.29 |
| ATOM | 2343 | CG | LEU | 472 | 18.028 | 54.582 | 63.676 | 1.00 | 8.04 |
| ATOM | 2344 | CD1 | LEU | 472 | 19.925 | 54.764 | 62.642 | 1.00 | 9.60 |
| ATOM | 2345 | CD2 | LEU | 472 | 18.792 | 53.277 | 63.449 | 1.00 | 8.30 |
| ATOM | 2346 | C | LEU | 472 | 18.331 | 57.500 | 65.226 | 1.00 | 9.52 |
| ATOM | 2347 | O | LEU | 472 | 17.246 | 57.523 | 65.830 | 1.00 | 9.64 |
| ATOM | 2348 | N | MET | 473 | 19.467 | 57.776 | 65.845 | 1.00 | 9.60 |
| ATOM | 2349 | H | MET | 473 | 20.298 | 57.746 | 65.334 | 1.00 | 0.00 |
| ATOM | 2350 | CA | MET | 473 | 19.502 | 58.101 | 67.289 | 1.00 | 9.98 |
| ATOM | 2351 | CB | MET | 473 | 20.911 | 58.423 | 67.731 | 1.00 | 10.72 |

TABLE 5-continued

Coordinates of Lck bound with baicalein

| | Atom Type | Res | # | X | Y | Z | Occ | B |
|---|---|---|---|---|---|---|---|---|
| ATOM | 2352 | CG | MET | 473 | 21.980 | 57.362 | 67.502 | 1.00 | 9.81 |
| ATOM | 2353 | SD | MET | 473 | 23.614 | 58.098 | 67.920 | 1.00 | 10.3 |
| ATOM | 2354 | CE | MET | 473 | 24.706 | 56.441 | 67.790 | 1.00 | 9.35 |
| ATOM | 2355 | C | MET | 473 | 18.646 | 59.317 | 67.535 | 1.00 | 10.75 |
| ATOM | 2356 | O | MET | 473 | 17.902 | 59.689 | 68.512 | 1.00 | 10.41 |
| ATOM | 2357 | N | ARG | 474 | 18.753 | 60.316 | 66.667 | 1.00 | 10.94 |
| ATOM | 2358 | H | ARG | 474 | 19.385 | 60.217 | 65.915 | 1.00 | 0.00 |
| ATOM | 2359 | CA | ARG | 474 | 17.940 | 61.535 | 66.823 | 1.00 | 11.36 |
| ATOM | 2360 | CB | ARG | 474 | 18.303 | 62.556 | 65.723 | 1.00 | 11.13 |
| ATOM | 2361 | CG | ARG | 474 | 19.761 | 62.885 | 65.645 | 1.00 | 12.27 |
| ATOM | 2362 | CD | ARG | 474 | 20.280 | 63.622 | 66.871 | 1.00 | 15.07 |
| ATOM | 2363 | NE | ARG | 474 | 19.523 | 64.842 | 67.105 | 1.00 | 18.00 |
| ATOM | 2364 | HE | ARG | 474 | 18.529 | 64.761 | 67.144 | 1.00 | 0.00 |
| ATOM | 2365 | CZ | ARG | 474 | 20.051 | 66.038 | 67.382 | 1.00 | 17.57 |
| ATOM | 2366 | NH1 | ARG | 474 | 21.354 | 66.221 | 67.468 | 1.00 | 14.03 |
| ATOM | 2367 | HH11 | ARG | 474 | 21.962 | 65.408 | 67.310 | 1.00 | 0.00 |
| ATOM | 2368 | HH12 | ARG | 474 | 21.742 | 67.087 | 67.670 | 1.00 | 0.00 |
| ATOM | 2369 | NH2 | ARG | 474 | 19.247 | 67.051 | 67.676 | 1.00 | 18.14 |
| ATOM | 2370 | HH21 | ARG | 474 | 18.243 | 66.900 | 67.698 | 1.00 | 0.00 |
| ATOM | 2371 | HH22 | ARG | 474 | 19.617 | 67.938 | 67.892 | 1.00 | 0.00 |
| ATOM | 2372 | C | ARG | 474 | 16.415 | 61.240 | 66.757 | 1.00 | 11.37 |
| ATOM | 2373 | O | ARG | 474 | 15.650 | 61.920 | 67.417 | 1.00 | 10.31 |
| ATOM | 2374 | N | LEU | 475 | 15.953 | 60.282 | 65.943 | 1.00 | 11.18 |
| ATOM | 2375 | H | LEU | 475 | 16.591 | 59.774 | 65.376 | 1.00 | 0.00 |
| ATOM | 2376 | CA | LEU | 475 | 14.527 | 59.932 | 65.922 | 1.00 | 12.79 |
| ATOM | 2377 | CB | LEU | 475 | 14.194 | 58.822 | 64.888 | 1.00 | 13.87 |
| ATOM | 2378 | CG | LEU | 475 | 14.387 | 59.074 | 63.420 | 1.00 | 14.86 |
| ATOM | 2379 | CD1 | LEU | 475 | 13.775 | 57.930 | 62.668 | 1.00 | 14.51 |
| ATOM | 2380 | CD2 | LEU | 475 | 13.706 | 60.357 | 62.995 | 1.00 | 15.10 |
| ATOM | 2381 | C | LEU | 475 | 14.148 | 59.387 | 67.275 | 1.00 | 12.61 |
| ATOM | 2382 | O | LEU | 475 | 13.043 | 59.657 | 67.719 | 1.00 | 14.25 |
| ATOM | 2383 | N | CYS | 476 | 15.035 | 58.607 | 67.918 | 1.00 | 10.73 |
| ATOM | 2384 | H | CYS | 476 | 15.872 | 58.377 | 67.514 | 1.00 | 0.00 |
| ATOM | 2385 | CA | CYS | 476 | 14.701 | 58.060 | 69.269 | 1.00 | 12.37 |
| ATOM | 2386 | CB | CYS | 476 | 15.790 | 57.089 | 69.714 | 1.00 | 8.82 |
| ATOM | 2387 | SG | CYS | 476 | 16.072 | 55.707 | 68.616 | 1.00 | 7.97 |
| ATOM | 2388 | C | CYS | 476 | 14.617 | 59.158 | 70.324 | 1.00 | 12.17 |
| ATOM | 2389 | O | CYS | 476 | 14.115 | 58.956 | 71.431 | 1.00 | 12.13 |
| ATOM | 2390 | N | TRP | 477 | 15.205 | 60.312 | 70.017 | 1.00 | 12.09 |
| ATOM | 2391 | H | TRP | 477 | 15.622 | 60.422 | 69.147 | 1.00 | 0.00 |
| ATOM | 2392 | CA | TRP | 477 | 15.267 | 61.382 | 71.001 | 1.00 | 13.19 |
| ATOM | 2393 | CB | TRP | 477 | 16.678 | 61.903 | 71.147 | 1.00 | 11.65 |
| ATOM | 2394 | CG | TRP | 477 | 17.754 | 60.867 | 71.605 | 1.00 | 10.54 |
| ATOM | 2395 | CD2 | TRP | 477 | 19.124 | 60.870 | 71.200 | 1.00 | 9.57 |
| ATOM | 2396 | CE2 | TRP | 477 | 19.732 | 59.737 | 71.774 | 1.00 | 10.09 |
| ATOM | 2397 | CE3 | TRP | 477 | 19.899 | 61.736 | 70.393 | 1.00 | 11.15 |
| ATOM | 2398 | CD1 | TRP | 477 | 17.584 | 59.782 | 72.402 | 1.00 | 9.27 |
| ATOM | 2399 | NE1 | TRP | 477 | 18.765 | 59.091 | 72.509 | 1.00 | 10.31 |
| ATOM | 2400 | HE1 | TRP | 477 | 18.913 | 58.256 | 73.024 | 1.00 | 0.00 |
| ATOM | 2401 | CZ2 | TRP | 477 | 21.110 | 59.417 | 71.561 | 1.00 | 8.15 |
| ATOM | 2402 | CZ3 | TRP | 477 | 21.298 | 61.407 | 70.158 | 1.00 | 9.07 |
| ATOM | 2403 | CH2 | TRP | 477 | 21.856 | 60.250 | 70.768 | 1.00 | 9.11 |
| ATOM | 2404 | C | TRP | 477 | 14.336 | 62.551 | 70.677 | 1.00 | 13.58 |
| ATOM | 2405 | O | TRP | 477 | 14.575 | 63.670 | 71.085 | 1.00 | 13.35 |
| ATOM | 2406 | N | LYS | 478 | 13.253 | 62.273 | 69.962 | 1.00 | 15.40 |
| ATOM | 2407 | H | LYS | 478 | 13.127 | 61.359 | 69.612 | 1.00 | 0.00 |
| ATOM | 2408 | CA | LYS | 478 | 12.284 | 63.324 | 69.690 | 1.00 | 16.64 |
| ATOM | 2409 | CB | LYS | 478 | 11.262 | 62.841 | 68.667 | 1.00 | 18.34 |
| ATOM | 2410 | CG | LYS | 478 | 11.842 | 62.886 | 67.252 | 1.00 | 18.98 |
| ATOM | 2411 | CD | LYS | 478 | 10.888 | 62.395 | 66.250 | 1.00 | 20.55 |
| ATOM | 2412 | CE | LYS | 478 | 11.399 | 62.605 | 64.850 | 1.00 | 20.73 |
| ATOM | 2413 | NZ | LYS | 478 | 11.614 | 64.011 | 64.539 | 1.00 | 22.67 |
| ATOM | 2414 | HZ1 | LYS | 478 | 12.293 | 64.439 | 65.199 | 1.00 | 0.00 |
| ATOM | 2415 | HZ2 | LYS | 478 | 10.708 | 64.507 | 64.593 | 1.00 | 0.00 |
| ATOM | 2416 | HZ3 | LYS | 478 | 11.994 | 64.102 | 63.562 | 1.00 | 0.00 |
| ATOM | 2417 | C | LYS | 478 | 11.604 | 63.755 | 70.967 | 1.00 | 16.06 |
| ATOM | 2418 | O | LYS | 478 | 11.436 | 62.966 | 71.914 | 1.00 | 15.93 |
| ATOM | 2419 | N | GLU | 479 | 11.222 | 65.029 | 71.034 | 1.00 | 17.41 |
| ATOM | 2420 | H | GLU | 479 | 11.366 | 65.612 | 70.270 | 1.00 | 0.00 |
| ATOM | 2421 | CA | GLU | 479 | 10.579 | 65.589 | 72.248 | 1.00 | 18.64 |
| ATOM | 2422 | CB | GLU | 479 | 10.303 | 67.075 | 72.067 | 1.00 | 20.53 |
| ATOM | 2423 | CG | GLU | 479 | 9.655 | 67.740 | 73.287 | 1.00 | 23.52 |
| ATOM | 2424 | CD | GLU | 479 | 10.661 | 68.130 | 74.324 | 1.00 | 25.50 |
| ATOM | 2425 | OE1 | GLU | 479 | 11.824 | 67.732 | 74.196 | 1.00 | 28.33 |

TABLE 5-continued

Coordinates of Lck bound with baicalein

| Atom Type | Res | # | X | Y | Z | Occ | B |
|---|---|---|---|---|---|---|---|
| ATOM 2426 OE2 | GLU | 479 | 10.994 | 68.856 | 75.262 | 1.00 | 27.52 |
| ATOM 2427 C | GLU | 479 | 9.306 | 64.889 | 72.601 | 1.00 | 18.51 |
| ATOM 2428 O | GLU | 479 | 9.069 | 64.550 | 73.746 | 1.00 | 17.34 |
| ATOM 2429 N | ARG | 480 | 8.437 | 64.687 | 71.619 | 1.00 | 18.65 |
| ATOM 2430 H | ARG | 480 | 8.703 | 64.883 | 70.678 | 1.00 | 0.00 |
| ATOM 2431 CA | ARG | 480 | 7.184 | 63.959 | 71.868 | 1.00 | 20.62 |
| ATOM 2432 CB | ARG | 480 | 6.112 | 64.390 | 70.874 | 1.00 | 21.72 |
| ATOM 2433 CG | ARG | 480 | 5.730 | 65.861 | 70.922 | 1.00 | 24.84 |
| ATOM 2434 CD | ARG | 480 | 4.352 | 66.080 | 70.256 | 1.00 | 25.50 |
| ATOM 2435 NE | ARG | 480 | 4.400 | 65.990 | 68.800 | 1.00 | 29.04 |
| ATOM 2436 HE | ARG | 480 | 5.242 | 66.207 | 68.343 | 1.00 | 0.00 |
| ATOM 2437 CZ | ARG | 480 | 3.377 | 65.589 | 68.043 | 1.00 | 30.65 |
| ATOM 2438 NH1 | ARG | 480 | 2.237 | 65.238 | 68.635 | 1.00 | 31.09 |
| ATOM 2439 HH11 | ARG | 480 | 2.139 | 65.261 | 69.614 | 1.00 | 0.00 |
| ATOM 2440 HH12 | ARG | 480 | 1.464 | 64.945 | 68.054 | 1.00 | 0.00 |
| ATOM 2441 NH2 | ARG | 480 | 3.466 | 65.586 | 66.706 | 1.00 | 30.31 |
| ATOM 2442 HH21 | ARG | 480 | 4.328 | 65.853 | 66.271 | 1.00 | 0.00 |
| ATOM 2443 HH22 | ARG | 480 | 2.697 | 65.280 | 66.154 | 1.00 | 0.00 |
| ATOM 2444 C | ARG | 480 | 9.316 | 62.481 | 71.852 | 1.00 | 19.07 |
| ATOM 2445 O | ARG | 480 | 7.700 | 61.936 | 70.755 | 1.00 | 20.51 |
| ATOM 2446 N | PRO | 481 | 7.025 | 61.762 | 72.928 | 1.00 | 18.14 |
| ATOM 2447 CD | PRO | 481 | 6.736 | 62.279 | 74.287 | 1.00 | 17.58 |
| ATOM 2448 CA | PRO | 481 | 7.136 | 60.296 | 72.937 | 1.00 | 17.76 |
| ATOM 2449 CB | PRO | 481 | 6.348 | 59.923 | 74.207 | 1.00 | 17.25 |
| ATOM 2450 CG | PRO | 481 | 6.973 | 60.994 | 75.181 | 1.00 | 17.81 |
| ATOM 2451 C | PRO | 481 | 6.448 | 59.695 | 71.713 | 1.00 | 17.64 |
| ATOM 2452 O | PRO | 481 | 7.023 | 58.892 | 70.973 | 1.00 | 16.34 |
| ATOM 2453 N | GLU | 482 | 5.222 | 60.152 | 71.464 | 1.00 | 17.82 |
| ATOM 2454 H | GLU | 482 | 4.821 | 60.816 | 82.021 | 1.00 | 0.00 |
| ATOM 2455 CA | GLU | 482 | 4.463 | 59.612 | 70.333 | 1.00 | 19.06 |
| ATOM 2456 CB | GLU | 482 | 3.028 | 60.117 | 70.375 | 1.00 | 20.92 |
| ATOM 2457 CG | GLU | 482 | 2.914 | 61.610 | 70.132 | 1.00 | 25.47 |
| ATOM 2458 CD | GLU | 482 | 2.915 | 62.492 | 71.402 | 1.00 | 28.47 |
| ATOM 2459 OE1 | GLU | 482 | 3.434 | 62.104 | 72.480 | 1.00 | 28.35 |
| ATOM 2460 OE2 | GLU | 482 | 2.354 | 63.601 | 71.368 | 1.00 | 31.00 |
| ATOM 2461 C | GLU | 482 | 5.109 | 59.852 | 68.970 | 1.00 | 17.12 |
| ATOM 2462 O | GLU | 482 | 4.718 | 59.217 | 68.000 | 1.00 | 16.34 |
| ATOM 2463 N | ASP | 483 | 6.139 | 60.716 | 68.912 | 1.00 | 16.79 |
| ATOM 2464 H | ASP | 483 | 6.417 | 61.180 | 69.699 | 1.00 | 0.00 |
| ATOM 2465 CA | ASP | 483 | 6.825 | 61.001 | 67.617 | 1.00 | 14.99 |
| ATOM 2466 CB | ASP | 483 | 7.319 | 62.420 | 67.557 | 1.00 | 17.88 |
| ATOM 2467 CG | ASP | 483 | 6.178 | 63.423 | 67.336 | 1.00 | 20.62 |
| ATOM 2468 OD1 | ASP | 483 | 5.094 | 63.020 | 66.835 | 1.00 | 17.81 |
| ATOM 2469 OD2 | ASP | 483 | 6.403 | 64.626 | 67.680 | 1.00 | 21.07 |
| ATOM 2470 C | ASP | 483 | 8.021 | 60.113 | 67.407 | 1.00 | 13.06 |
| ATOM 2471 O | ASP | 483 | 8.596 | 60.056 | 66.325 | 1.00 | 10.84 |
| ATOM 2472 N | ARG | 484 | 8.472 | 59.475 | 68.470 | 1.00 | 12.04 |
| ATOM 2473 H | ARG | 484 | 8.090 | 59.684 | 69.353 | 1.00 | 0.00 |
| ATOM 2474 CA | ARG | 484 | 9.638 | 58.577 | 68.372 | 1.00 | 11.64 |
| ATOM 2475 CB | ARG | 484 | 10.127 | 58.272 | 69.791 | 1.00 | 11.86 |
| ATOM 2476 CG | ARG | 484 | 10.529 | 59.505 | 70.597 | 1.00 | 8.96 |
| ATOM 2477 CD | ARG | 484 | 10.835 | 59.128 | 71.987 | 1.00 | 10.66 |
| ATOM 2478 NE | ARG | 484 | 10.909 | 60.324 | 72.820 | 1.00 | 10.54 |
| ATOM 2479 HE | ARG | 484 | 11.146 | 61.155 | 72.388 | 1.00 | 0.00 |
| ATOM 2480 CZ | ARG | 484 | 10.694 | 60.367 | 74.145 | 1.00 | 11.89 |
| ATOM 2481 NH1 | ARG | 484 | 10.400 | 59.260 | 74.868 | 1.00 | 11.93 |
| ATOM 2482 HH11 | ARG | 484 | 10.359 | 58.362 | 74.400 | 1.00 | 0.00 |
| ATOM 2483 HH12 | ARG | 484 | 10.262 | 59.311 | 75.844 | 1.00 | 0.00 |
| ATOM 2484 NH2 | ARG | 484 | 10.665 | 61.573 | 74.754 | 1.00 | 11.76 |
| ATOM 2485 HH21 | ARG | 484 | 10.786 | 62.378 | 74.194 | 1.00 | 0.00 |
| ATOM 2486 HH22 | ARG | 484 | 10.501 | 61.611 | 75.723 | 1.00 | 0.00 |
| ATOM 2487 C | ARG | 484 | 9.127 | 57.304 | 67.653 | 1.00 | 11.50 |
| ATOM 2488 O | ARG | 484 | 7.977 | 56.968 | 67.780 | 1.00 | 11.00 |
| ATOM 2489 N | PRO | 485 | 10.027 | 56.602 | 66.921 | 1.00 | 12.30 |
| ATOM 2490 CD | PRO | 485 | 11.481 | 56.851 | 66.891 | 1.00 | 10.62 |
| ATOM 2491 CA | PRO | 485 | 9.676 | 55.372 | 66.167 | 1.00 | 12.36 |
| ATOM 2492 CB | PRO | 485 | 10.896 | 55.113 | 65.317 | 1.00 | 10.15 |
| ATOM 2493 CG | PRO | 485 | 12.018 | 55.524 | 66.220 | 1.00 | 11.99 |
| ATOM 2494 C | PRO | 485 | 9.390 | 54.122 | 67.020 | 1.00 | 12.67 |
| ATOM 2495 O | PRO | 485 | 9.669 | 54.115 | 68.216 | 1.00 | 13.64 |
| ATOM 2496 N | THR | 486 | 8.763 | 53.119 | 66.404 | 1.00 | 13.75 |
| ATOM 2497 H | THR | 486 | 8.455 | 53.250 | 65.480 | 1.00 | 0.00 |
| ATOM 2498 CA | THR | 486 | 8.519 | 51.843 | 67.072 | 1.00 | 12.48 |
| ATOM 2499 CB | THR | 486 | 7.430 | 50.981 | 66.336 | 1.00 | 12.02 |

TABLE 5-continued

Coordinates of Lck bound with baicalein

| | | Atom Type | Res | # | X | Y | Z | Occ | B |
|---|---|---|---|---|---|---|---|---|---|
| ATOM | 2500 | OG1 | THR | 486 | 7.893 | 50.712 | 64.989 | 1.00 | 11.75 |
| ATOM | 2501 | HG1 | THR | 486 | 8.701 | 50.222 | 65.038 | 1.00 | 0.00 |
| ATOM | 2502 | CG2 | THR | 486 | 6.090 | 51.735 | 66.280 | 1.00 | 13.84 |
| ATOM | 2503 | C | THR | 486 | 9.820 | 51.032 | 67.033 | 1.00 | 11.53 |
| ATOM | 2504 | O | THR | 486 | 10.752 | 51.315 | 66.262 | 1.00 | 9.94 |
| ATOM | 2505 | N | PHE | 487 | 9.864 | 49.978 | 67.837 | 1.00 | 10.88 |
| ATOM | 2506 | H | PHE | 487 | 9.133 | 49.791 | 68.469 | 1.00 | 0.00 |
| ATOM | 2507 | CA | PHE | 487 | 11.026 | 49.108 | 67.814 | 1.00 | 11.89 |
| ATOM | 2508 | CB | PHE | 487 | 11.127 | 48.238 | 69.098 | 1.00 | 8.69 |
| ATOM | 2509 | CG | PHE | 487 | 11.748 | 48.969 | 70.204 | 1.00 | 8.74 |
| ATOM | 2510 | CD1 | PHE | 487 | 13.129 | 49.256 | 70.178 | 1.00 | 7.83 |
| ATOM | 2511 | CD2 | PHE | 487 | 11.000 | 49.340 | 71.291 | 1.00 | 7.92 |
| ATOM | 2512 | CE1 | PHE | 487 | 13.747 | 49.876 | 71.243 | 1.00 | 8.02 |
| ATOM | 2513 | CE2 | PHE | 487 | 11.591 | 49.978 | 73.274 | 1.00 | 9.07 |
| ATOM | 2514 | CZ | PHE | 487 | 12.991 | 50.243 | 72.358 | 1.00 | 9.86 |
| ATOM | 2515 | C | PHE | 487 | 11.062 | 48.276 | 66.579 | 1.00 | 11.78 |
| ATOM | 2516 | O | PHE | 487 | 12.164 | 48.019 | 66.111 | 1.00 | 12.19 |
| ATOM | 2517 | N | ASP | 488 | 9.896 | 47.939 | 66.015 | 1.00 | 13.38 |
| ATOM | 2518 | H | ASP | 488 | 9.039 | 48.143 | 66.456 | 1.00 | 0.00 |
| ATOM | 2519 | CA | ASP | 488 | 9.909 | 47.200 | 64.749 | 1.00 | 13.80 |
| ATOM | 2520 | CB | ASP | 488 | 8.521 | 46.708 | 64.316 | 1.00 | 17.66 |
| ATOM | 2521 | CG | ASP | 488 | 8.640 | 45.651 | 63.220 | 1.00 | 19.13 |
| ATOM | 2522 | OD1 | ASP | 488 | 9.201 | 44.572 | 63.511 | 1.00 | 22.81 |
| ATOM | 2523 | OD2 | ASP | 488 | 8.391 | 45.939 | 62.056 | 1.00 | 23.29 |
| ATOM | 2524 | C | ASP | 488 | 10.507 | 48.083 | 63.633 | 1.00 | 13.45 |
| ATOM | 2525 | O | ASP | 488 | 11.266 | 47.593 | 62.805 | 1.00 | 12.80 |
| ATOM | 2526 | N | TYR | 489 | 10.161 | 49.377 | 63.618 | 1.00 | 12.26 |
| ATOM | 2527 | H | TYR | 489 | 9.522 | 49.709 | 64.266 | 1.00 | 0.00 |
| ATOM | 2528 | CA | TYR | 489 | 10.752 | 50.314 | 62.634 | 1.00 | 12.39 |
| ATOM | 2529 | CB | TYR | 489 | 10.145 | 51.714 | 62.789 | 1.00 | 13.11 |
| ATOM | 2530 | CG | TYR | 489 | 10.827 | 52.707 | 62.892 | 1.00 | 14.56 |
| ATOM | 2531 | CD1 | TYR | 489 | 10.415 | 50.868 | 60.578 | 1.00 | 14.33 |
| ATOM | 2532 | CE1 | TYR | 489 | 11.052 | 53.765 | 59.723 | 1.00 | 15.93 |
| ATOM | 2533 | CD2 | TYR | 489 | 11.092 | 53.479 | 62.346 | 1.00 | 15.27 |
| ATOM | 2534 | CE2 | TYR | 489 | 12.547 | 54.398 | 61.497 | 1.00 | 16.72 |
| ATOM | 2535 | CZ | TYR | 489 | 12.109 | 54.530 | 60.185 | 1.00 | 17.30 |
| ATOM | 2536 | OH | TYR | 489 | 12.718 | 55.450 | 59.352 | 1.00 | 17.14 |
| ATOM | 2537 | HH | TYR | 489 | 12.325 | 55.422 | 58.482 | 1.00 | 0.00 |
| ATOM | 2538 | C | TYR | 489 | 12.282 | 50.393 | 62.812 | 1.00 | 11.55 |
| ATOM | 2539 | O | TYR | 489 | 13.023 | 50.220 | 61.855 | 1.00 | 13.45 |
| ATOM | 2540 | N | LEU | 490 | 12.754 | 50.541 | 64.041 | 1.00 | 10.80 |
| ATOM | 2541 | H | LEU | 490 | 12.100 | 50.625 | 64.767 | 1.00 | 0.00 |
| ATOM | 2542 | CA | LEU | 490 | 14.195 | 50.580 | 64.353 | 1.00 | 10.38 |
| ATOM | 2543 | CB | LEU | 490 | 14.698 | 50.738 | 65.880 | 1.00 | 8.09 |
| ATOM | 2544 | CG | LEU | 490 | 14.000 | 52.154 | 66.363 | 1.00 | 8.32 |
| ATOM | 2545 | CD1 | LEU | 490 | 13.887 | 52.249 | 67.916 | 1.00 | 5.44 |
| ATOM | 2546 | CD2 | LEU | 490 | 15.055 | 53.199 | 65.814 | 1.00 | 5.30 |
| ATOM | 2547 | C | LEU | 490 | 14.884 | 49.289 | 63.878 | 1.00 | 10.97 |
| ATOM | 2548 | O | LEU | 490 | 15.938 | 49.341 | 63.262 | 1.00 | 10.64 |
| ATOM | 2549 | N | ARG | 491 | 14.280 | 48.136 | 64.159 | 1.00 | 11.32 |
| ATOM | 2550 | H | ARG | 491 | 13.450 | 48.133 | 64.679 | 1.00 | 0.00 |
| ATOM | 2551 | CA | ARG | 491 | 14.848 | 46.845 | 63.734 | 1.00 | 11.44 |
| ATOM | 2552 | CB | ARG | 491 | 13.951 | 45.666 | 64.186 | 1.00 | 13.32 |
| ATOM | 2553 | CG | ARG | 491 | 14.506 | 44.319 | 63.617 | 1.00 | 14.73 |
| ATOM | 2554 | CD | ARG | 491 | 13.451 | 43.228 | 63.537 | 1.00 | 17.35 |
| ATOM | 2555 | NE | ARG | 491 | 12.232 | 43.699 | 63.869 | 1.00 | 18.07 |
| ATOM | 2556 | HE | ARG | 491 | 11.466 | 43.954 | 63.454 | 1.00 | 0.00 |
| ATOM | 2557 | CZ | ARG | 491 | 12.031 | 43.774 | 61.554 | 1.00 | 18.62 |
| ATOM | 2558 | NH1 | ARG | 491 | 12.972 | 43.390 | 60.697 | 1.00 | 19.26 |
| ATOM | 2559 | HH11 | ARG | 491 | 13.848 | 43.041 | 61.055 | 1.00 | 0.00 |
| ATOM | 2560 | HH12 | ARG | 491 | 12.824 | 43.466 | 59.726 | 1.00 | 0.00 |
| ATOM | 2561 | NH2 | ARG | 491 | 10.876 | 44.276 | 61.105 | 1.00 | 17.15 |
| ATOM | 2562 | HH21 | ARG | 491 | 10.165 | 44.534 | 61.751 | 1.00 | 0.00 |
| ATOM | 2563 | HH22 | ARG | 491 | 10.718 | 44.319 | 60.124 | 1.00 | 0.00 |
| ATOM | 2564 | C | ARG | 491 | 15.006 | 46.838 | 62.223 | 1.00 | 10.44 |
| ATOM | 2565 | O | ARG | 491 | 16.085 | 46.598 | 61.724 | 1.00 | 10.55 |
| ATOM | 2566 | N | SER | 492 | 13.941 | 47.186 | 61.510 | 0.71 | 9.61 |
| ATOM | 2567 | H | SER | 492 | 13.115 | 47.461 | 61.983 | 1.00 | 0.00 |
| ATOM | 2568 | CA | SER | 492 | 13.931 | 47.187 | 60.061 | 0.71 | 7.95 |
| ATOM | 2569 | CB | SER | 492 | 12.569 | 47.647 | 59.583 | 0.71 | 6.61 |
| ATOM | 2570 | OG | SER | 492 | 12.491 | 47.458 | 58.219 | 0.71 | 7.55 |
| ATOM | 2571 | HG | SER | 492 | 12.615 | 46.522 | 57.969 | 1.00 | 0.00 |
| ATOM | 2572 | C | SER | 492 | 15.018 | 48.060 | 59.465 | 0.71 | 9.13 |
| ATOM | 2573 | O | SER | 492 | 15.691 | 47.698 | 58.526 | 0.71 | 6.83 |

TABLE 5-continued

Coordinates of Lck bound with baicalein

| | Atom Type | Res | # | X | Y | Z | Occ | B |
|---|---|---|---|---|---|---|---|---|
| ATOM | 2574 | N | VAL | 493 | 15.165 | 49.270 | 59.991 | 1.00 | 10.30 |
| ATOM | 2575 | H | VAL | 493 | 14.536 | 49.557 | 60.685 | 1.00 | 0.00 |
| ATOM | 2576 | CA | VAL | 493 | 16.168 | 50.186 | 59.483 | 1.00 | 10.64 |
| ATOM | 2577 | CB | VAL | 493 | 15.977 | 51.613 | 60.075 | 1.00 | 12.23 |
| ATOM | 2578 | CG1 | VAL | 493 | 17.072 | 52.540 | 59.623 | 1.00 | 12.45 |
| ATOM | 2579 | CG2 | VAL | 493 | 14.632 | 52.189 | 59.638 | 1.00 | 12.84 |
| ATOM | 2580 | C | VAL | 493 | 17.569 | 49.662 | 59.790 | 1.00 | 10.28 |
| ATOM | 2581 | O | VAL | 493 | 18.507 | 49.770 | 58.982 | 1.00 | 9.79 |
| ATOM | 2582 | N | LEU | 494 | 17.775 | 49.135 | 60.984 | 1.00 | 10.94 |
| ATOM | 2583 | H | LEU | 494 | 17.048 | 49.097 | 61.629 | 1.00 | 0.00 |
| ATOM | 2584 | CA | LEU | 494 | 19.111 | 48.647 | 61.337 | 1.00 | 11.73 |
| ATOM | 2585 | CB | LEU | 494 | 19.201 | 48.384 | 62.855 | 1.00 | 11.95 |
| ATOM | 2586 | CG | LEU | 494 | 19.294 | 49.640 | 63.711 | 1.00 | 12.33 |
| ATOM | 2587 | CD1 | LEU | 494 | 18.973 | 49.352 | 65.166 | 1.00 | 10.17 |
| ATOM | 2588 | CD2 | LEU | 494 | 20.647 | 50.280 | 63.625 | 1.00 | 11.34 |
| ATOM | 2589 | C | LEU | 494 | 19.538 | 47.449 | 60.489 | 1.00 | 12.40 |
| ATOM | 2590 | O | LEU | 494 | 20.727 | 47.340 | 60.156 | 1.00 | 10.84 |
| ATOM | 2591 | N | GLU | 495 | 18.582 | 46.559 | 60.160 | 1.00 | 13.98 |
| ATOM | 2592 | H | GLU | 495 | 17.656 | 46.682 | 60.494 | 1.00 | 0.00 |
| ATOM | 2593 | CA | GLU | 495 | 18.864 | 45.415 | 59.269 | 1.00 | 15.38 |
| ATOM | 2594 | CB | GLU | 495 | 17.614 | 44.527 | 59.152 | 1.00 | 16.78 |
| ATOM | 2595 | CG | GLU | 495 | 17.463 | 43.616 | 60.373 | 1.00 | 18.88 |
| ATOM | 2596 | CD | GLU | 495 | 16.186 | 42.824 | 60.367 | 1.00 | 21.48 |
| ATOM | 2597 | OE1 | GLU | 495 | 15.413 | 42.869 | 59.384 | 1.00 | 23.92 |
| ATOM | 2598 | OE2 | GLU | 495 | 15.929 | 42.165 | 61.384 | 1.00 | 24.12 |
| ATOM | 2599 | C | GLU | 495 | 19.292 | 45.974 | 57.975 | 1.00 | 15.60 |
| ATOM | 2600 | O | GLU | 495 | 20.228 | 45.481 | 57.275 | 1.00 | 15.26 |
| ATOM | 2601 | N | ASP | 496 | 18.625 | 47.026 | 57.399 | 1.00 | 14.62 |
| ATOM | 2602 | H | ASP | 496 | 17.890 | 47.421 | 57.932 | 1.00 | 0.00 |
| ATOM | 2603 | CA | ASP | 496 | 18.977 | 47.612 | 56.112 | 1.00 | 15.07 |
| ATOM | 2604 | CB | ASP | 496 | 17.961 | 48.704 | 55.725 | 1.00 | 16.88 |
| ATOM | 2605 | CG | ASP | 496 | 16.709 | 48.126 | 55.136 | 1.00 | 15.54 |
| ATOM | 2606 | OD1 | ASP | 496 | 16.717 | 46.938 | 54.781 | 1.00 | 16.07 |
| ATOM | 2607 | OD2 | ASP | 496 | 15.709 | 48.849 | 55.029 | 1.00 | 16.89 |
| ATOM | 2608 | C | ASP | 496 | 20.381 | 48.197 | 56.180 | 1.00 | 15.68 |
| ATOM | 2609 | O | ASP | 496 | 21.170 | 47.982 | 55.307 | 1.00 | 15.05 |
| ATOM | 2610 | N | PHE | 497 | 20.709 | 48.900 | 57.260 | 1.00 | 15.30 |
| ATOM | 2611 | H | PHE | 497 | 20.034 | 48.975 | 57.972 | 1.00 | 0.00 |
| ATOM | 2612 | CA | PHE | 497 | 22.043 | 49.464 | 57.425 | 1.00 | 16.88 |
| ATOM | 2613 | CB | PHE | 497 | 22.120 | 50.184 | 58.785 | 1.00 | 16.05 |
| ATOM | 2614 | CG | PHE | 497 | 21.429 | 51.484 | 58.829 | 1.00 | 15.61 |
| ATOM | 2615 | CD1 | PHE | 497 | 20.767 | 51.994 | 57.716 | 1.00 | 15.21 |
| ATOM | 2616 | CD2 | PHE | 497 | 21.466 | 52.249 | 60.016 | 1.00 | 14.82 |
| ATOM | 2617 | CE1 | PHE | 497 | 20.149 | 53.271 | 57.769 | 1.00 | 15.88 |
| ATOM | 2618 | CE2 | PHE | 497 | 20.868 | 53.493 | 60.079 | 1.00 | 15.70 |
| ATOM | 2619 | CZ | PHE | 497 | 20.206 | 54.015 | 58.959 | 1.00 | 14.48 |
| ATOM | 2620 | C | PHE | 497 | 23.136 | 48.396 | 57.408 | 1.00 | 17.62 |
| ATOM | 2621 | O | PHE | 497 | 24.213 | 48.591 | 56.859 | 1.00 | 16.67 |
| ATOM | 2622 | N | PHE | 498 | 22.817 | 47.268 | 58.027 | 1.00 | 19.79 |
| ATOM | 2623 | H | PHE | 498 | 21.921 | 47.186 | 58.442 | 1.00 | 0.00 |
| ATOM | 2624 | CA | PHE | 498 | 23.685 | 46.095 | 58.120 | 1.00 | 22.82 |
| ATOM | 2625 | CB | PHE | 498 | 23.122 | 45.198 | 59.243 | 1.00 | 23.80 |
| ATOM | 2626 | CG | PHE | 498 | 23.585 | 43.797 | 59.224 | 1.00 | 25.04 |
| ATOM | 2627 | CD1 | PHE | 498 | 24.923 | 43.483 | 59.070 | 1.00 | 25.58 |
| ATOM | 2628 | CD2 | PHE | 498 | 22.666 | 42.754 | 59.438 | 1.00 | 26.56 |
| ATOM | 2629 | CE1 | PHE | 498 | 25.342 | 42.149 | 59.124 | 1.00 | 26.20 |
| ATOM | 2630 | CE2 | PHE | 498 | 23.080 | 41.445 | 59.485 | 1.00 | 26.68 |
| ATOM | 2631 | CZ | PHE | 498 | 24.428 | 41.145 | 59.325 | 1.00 | 26.54 |
| ATOM | 2632 | C | PHE | 498 | 23.821 | 45.373 | 56.780 | 1.00 | 24.19 |
| ATOM | 2633 | O | PHE | 498 | 24.937 | 45.151 | 56.330 | 1.00 | 24.92 |
| ATOM | 2634 | N | THR | 499 | 22.704 | 45.090 | 56.105 | 1.00 | 26.59 |
| ATOM | 2635 | H | THR | 499 | 21.834 | 45.340 | 56.450 | 1.00 | 0.00 |
| ATOM | 2636 | CA | THR | 499 | 22.745 | 44.322 | 54.827 | 1.00 | 28.99 |
| ATOM | 2637 | CB | THR | 499 | 21.385 | 43.831 | 54.394 | 1.00 | 28.75 |
| ATOM | 2638 | OG1 | THR | 499 | 20.485 | 44.924 | 54.326 | 1.00 | 28.67 |
| ATOM | 2639 | HG1 | THR | 499 | 19.608 | 44.591 | 54.039 | 1.00 | 0.00 |
| ATOM | 2640 | CG2 | THR | 499 | 20.934 | 42.818 | 55.419 | 1.00 | 29.90 |
| ATOM | 2641 | C | THR | 499 | 23.373 | 45.180 | 53.771 | 1.00 | 31.44 |
| ATOM | 2642 | O | THR | 499 | 23.767 | 44.712 | 52.710 | 1.00 | 33.07 |
| ATOM | 2643 | N | ALA | 500 | 23.536 | 46.454 | 54.115 | 1.00 | 32.29 |
| ATOM | 2644 | H | ALA | 500 | 23.205 | 46.742 | 54.973 | 1.00 | 0.00 |
| ATOM | 2645 | CA | ALA | 500 | 24.156 | 47.412 | 53.219 | 1.00 | 33.44 |
| ATOM | 2646 | CB | ALA | 500 | 23.586 | 48.781 | 53.488 | 1.00 | 33.24 |
| ATOM | 2647 | C | ALA | 500 | 25.672 | 47.397 | 53.471 | 1.00 | 34.61 |

TABLE 5-continued

Coordinates of Lck bound with baicalein

| | Atom Type | Res | # | X | Y | Z | Occ | B |
|---|---|---|---|---|---|---|---|---|
| ATOM | 2648 | O | ALA | 500 | 25.454 | 47.198 | 52.542 | 1.00 | 35.09 |
| ATOM | 2649 | N | THR | 501 | 26.072 | 47.605 | 54.726 | 1.00 | 34.50 |
| ATOM | 2650 | H | THR | 501 | 25.412 | 47.785 | 55.416 | 1.00 | 0.00 |
| ATOM | 2651 | CA | THR | 501 | 27.498 | 47.618 | 55.077 | 1.00 | 34.67 |
| ATOM | 2652 | CB | THR | 501 | 27.738 | 48.118 | 56.563 | 1.00 | 35.17 |
| ATOM | 2653 | OG1 | THR | 501 | 27.094 | 47.226 | 57.495 | 1.00 | 35.60 |
| ATOM | 2654 | HG1 | THR | 501 | 27.431 | 46.329 | 57.377 | 1.00 | 0.00 |
| ATOM | 2655 | CG2 | THR | 501 | 27.207 | 49.526 | 56.752 | 1.00 | 34.68 |
| ATOM | 2656 | C | THR | 501 | 28.136 | 46.213 | 54.947 | 1.00 | 34.73 |
| ATOM | 2657 | O | THR | 501 | 27.646 | 45.400 | 54.130 | 1.00 | 34.94 |
| ATOM | 2658 | OT | THR | 501 | 29.115 | 45.943 | 55.688 | 1.00 | 33.77 |
| ATOM | 2659 | OH2 | TIP3 | 3 | 22.738 | 64.822 | 58.592 | 1.00 | 15.53 |
| ATOM | 2660 | H1 | TIP3 | 3 | 22.748 | 65.749 | 58.595 | 1.00 | 0.00 |
| ATOM | 2661 | H2 | TIP3 | 3 | 22.748 | 64.551 | 57.669 | 1.00 | 0.00 |
| ATOM | 2662 | OH2 | TIP3 | 4 | 14.883 | 51.936 | 79.416 | 1.00 | 14.47 |
| ATOM | 2663 | H1 | TIP3 | 4 | 14.862 | 52.877 | 79.420 | 1.00 | 0.00 |
| ATOM | 2664 | H2 | TIP3 | 4 | 14.862 | 51.679 | 78.493 | 1.00 | 0.00 |
| ATOM | 2665 | OH2 | TIP3 | 5 | 24.454 | 79.051 | 73.982 | 1.00 | 12.98 |
| ATOM | 2666 | H1 | TIP3 | 5 | 24.446 | 80.041 | 73.982 | 1.00 | 0.00 |
| ATOM | 2667 | H2 | TIP3 | 5 | 24.444 | 78.848 | 73.053 | 1.00 | 0.00 |
| ATOM | 2668 | OH2 | TIP3 | 6 | 19.428 | 60.997 | 77.482 | 1.00 | 12.67 |
| ATOM | 2669 | H1 | TIP3 | 6 | 19.448 | 61.973 | 77.444 | 1.00 | 0.00 |
| ATOM | 2670 | H2 | TIP3 | 6 | 19.448 | 60.778 | 76.519 | 1.00 | 0.00 |
| ATOM | 2671 | OH2 | TIP3 | 7 | 20.640 | 63.060 | 73.307 | 1.00 | 14.36 |
| ATOM | 2672 | H1 | TIP3 | 7 | 20.601 | 64.003 | 73.311 | 1.00 | 0.00 |
| ATOM | 2673 | H2 | TIP3 | 7 | 20.602 | 62.807 | 72.385 | 1.00 | 0.00 |
| ATOM | 2674 | OH2 | TIP3 | 8 | 20.561 | 66.735 | 62.784 | 1.00 | 15.57 |
| ATOM | 2675 | H1 | TIP3 | 8 | 20.539 | 67.675 | 62.745 | 1.00 | 0.00 |
| ATOM | 2676 | H2 | TIP3 | 8 | 20.540 | 66.475 | 61.821 | 1.00 | 0.00 |
| ATOM | 2677 | OH2 | TIP3 | 9 | 33.216 | 40.290 | 77.882 | 1.00 | 25.89 |
| ATOM | 2678 | H1 | TIP3 | 9 | 33.233 | 41.252 | 77.901 | 1.00 | 0.00 |
| ATOM | 2679 | H2 | TIP3 | 9 | 33.233 | 40.055 | 76.973 | 1.00 | 0.00 |
| ATOM | 2680 | OH2 | TIP3 | 10 | 18.163 | 62.372 | 79.868 | 1.00 | 14.70 |
| ATOM | 2681 | H1 | TIP3 | 10 | 18.142 | 63.350 | 79.878 | 1.00 | 0.00 |
| ATOM | 2682 | H2 | TIP3 | 10 | 18.142 | 62.157 | 78.948 | 1.00 | 0.00 |
| ATOM | 2683 | OH2 | TIP3 | 11 | 24.947 | 20.089 | 88.279 | 1.00 | 14.42 |
| ATOM | 2684 | H1 | TIP3 | 11 | 24.976 | 21.033 | 88.245 | 1.00 | 1.00 |
| ATOM | 2685 | H2 | TIP3 | 11 | 25.053 | 19.964 | 87.397 | 1.00 | 0.00 |
| ATOM | 2686 | OH2 | TIP3 | 12 | 13.339 | 34.229 | 76.687 | 1.00 | 13.97 |
| ATOM | 2687 | H1 | TIP3 | 12 | 13.324 | 35.111 | 76.678 | 1.00 | 0.00 |
| ATOM | 2688 | H2 | TIP3 | 12 | 13.324 | 33.908 | 75.755 | 1.00 | 0.00 |
| ATOM | 2689 | OH2 | TIP3 | 14 | 20.258 | 71.446 | 85.731 | 1.00 | 23.57 |
| ATOM | 2690 | H1 | TIP3 | 14 | 20.252 | 72.429 | 85.751 | 1.00 | 0.00 |
| ATOM | 2691 | H2 | TIP3 | 14 | 20.252 | 71.234 | 84.822 | 1.00 | 0.00 |
| ATOM | 2692 | OH2 | TIP3 | 15 | 3.886 | 51.947 | 76.257 | 1.00 | 17.45 |
| ATOM | 2693 | H1 | TIP3 | 15 | 3.905 | 52.878 | 76.239 | 1.00 | 0.00 |
| ATOM | 2694 | H2 | TIP3 | 15 | 3.905 | 51.680 | 75.315 | 1.00 | 0.00 |
| ATOM | 2695 | OH2 | TIP3 | 16 | 25.198 | 50.668 | 80.081 | 1.00 | 15.97 |
| ATOM | 2696 | H1 | TIP3 | 16 | 25.180 | 51.641 | 80.082 | 1.00 | 0.00 |
| ATOM | 2697 | H2 | TIP3 | 16 | 25.179 | 50.444 | 79.155 | 1.00 | 0.00 |
| ATOM | 2698 | OH2 | TIP3 | 17 | 26.816 | 31.804 | 75.396 | 1.00 | 12.38 |
| ATOM | 2699 | H1 | TIP3 | 17 | 26.820 | 32.695 | 75.454 | 1.00 | 0.00 |
| ATOM | 2700 | H2 | TIP3 | 17 | 26.820 | 31.493 | 74.525 | 1.00 | 0.00 |
| ATOM | 2701 | OH2 | TIP3 | 18 | 35.732 | 44.202 | 79.604 | 1.00 | 34.00 |
| ATOM | 2702 | H1 | TIP3 | 18 | 35.748 | 45.170 | 79.609 | 1.00 | 0.00 |
| ATOM | 2703 | H2 | TIP3 | 18 | 35.748 | 43.974 | 78.682 | 1.00 | 0.00 |
| ATOM | 2704 | OH2 | TIP3 | 19 | 25.557 | 69.892 | 62.927 | 1.00 | 22.48 |
| ATOM | 2705 | H1 | TIP3 | 19 | 25.556 | 70.841 | 62.938 | 1.00 | 0.00 |
| ATOM | 2706 | H2 | TIP3 | 19 | 25.556 | 69.643 | 62.011 | 1.00 | 0.00 |
| ATOM | 2707 | OH2 | TIP3 | 21 | 19.002 | 57.617 | 59.594 | 1.00 | 16.36 |
| ATOM | 2708 | H1 | TIP3 | 21 | 18.984 | 58.582 | 59.618 | 1.00 | 0.00 |
| ATOM | 2709 | H2 | TIP3 | 21 | 18.983 | 57.385 | 58.690 | 1.00 | 0.00 |
| ATOM | 2710 | OH2 | TIP3 | 22 | 10.260 | 44.334 | 57.353 | 1.00 | 40.18 |
| ATOM | 2711 | H1 | TIP3 | 22 | 10.246 | 45.292 | 57.343 | 1.00 | 0.00 |
| ATOM | 2712 | H2 | TIP3 | 22 | 10.246 | 44.095 | 54.417 | 1.00 | 0.00 |
| ATOM | 2713 | OH2 | TIP3 | 23 | 22.430 | 28.315 | 79.143 | 1.00 | 19.83 |
| ATOM | 2714 | H1 | TIP3 | 23 | 22.432 | 29.244 | 79.049 | 1.00 | 0.00 |
| ATOM | 2715 | H2 | TIP3 | 23 | 22.445 | 28.097 | 78.183 | 1.00 | 0.00 |
| ATOM | 2716 | OH2 | TIP3 | 24 | 2.955 | 57.144 | 68.104 | 1.00 | 26.15 |
| ATOM | 2717 | H1 | TIP3 | 24 | 2.929 | 58.101 | 68.108 | 1.00 | 0.00 |
| ATOM | 2718 | H2 | TIP3 | 24 | 2.929 | 56.904 | 67.181 | 1.00 | 0.00 |
| ATOM | 2719 | OH2 | TIP3 | 26 | 22.768 | 46.638 | 85.487 | 1.00 | 35.59 |
| ATOM | 2720 | H1 | TIP3 | 26 | 22.756 | 47.605 | 85.482 | 1.00 | 0.00 |
| ATOM | 2721 | H2 | TIP3 | 26 | 22.756 | 46.409 | 84.556 | 1.00 | 0.00 |

TABLE 5-continued

Coordinates of Lck bound with baicalein

| | | Atom Type | Res | # | X | Y | Z | Occ | B |
|---|---|---|---|---|---|---|---|---|---|
| ATOM | 2722 | OH2 | TIP3 | 28 | 28.122 | 56.611 | 74.469 | 1.00 | 19.64 |
| ATOM | 2723 | H1 | TIP3 | 28 | 28.126 | 57.565 | 74.436 | 1.00 | 0.00 |
| ATOM | 2724 | H2 | TIP3 | 28 | 28.127 | 56.369 | 73.512 | 1.00 | 0.00 |
| ATOM | 2725 | OH2 | TIP3 | 29 | 16.459 | 58.662 | 60.558 | 1.00 | 19.59 |
| ATOM | 2726 | H1 | TIP3 | 29 | 16.746 | 59.622 | 60.564 | 1.00 | 0.00 |
| ATOM | 2727 | H2 | TIP3 | 29 | 16.746 | 58.425 | 59.636 | 1.00 | 0.00 |
| ATOM | 2728 | OH2 | TIP3 | 30 | 28.184 | 53.392 | 79.068 | 1.00 | 18.45 |
| ATOM | 2729 | H1 | TIP3 | 30 | 28.192 | 54.357 | 79.099 | 1.00 | 0.00 |
| ATOM | 2730 | H2 | TIP3 | 30 | 28.192 | 53.161 | 78.169 | 1.00 | 0.00 |
| ATOM | 2731 | OH2 | TIP3 | 31 | 17.493 | 32.065 | 67.051 | 1.00 | 14.12 |
| ATOM | 2732 | H1 | TIP3 | 31 | 17.455 | 33.015 | 67.088 | 1.00 | 0.00 |
| ATOM | 2733 | H2 | TIP3 | 31 | 17.455 | 31.817 | 66.159 | 1.00 | 0.00 |
| ATOM | 2734 | OH2 | TIP3 | 32 | 2.575 | 52.072 | 89.806 | 1.00 | 36.50 |
| ATOM | 2735 | H1 | TIP3 | 32 | 2.575 | 53.019 | 89.790 | 1.00 | 0.00 |
| ATOM | 2736 | H2 | TIP3 | 32 | 2.575 | 51.821 | 88.865 | 1.00 | 0.00 |
| ATOM | 2737 | OH2 | TIP3 | 33 | 26.201 | 53.175 | 58.259 | 1.00 | 44.31 |
| ATOM | 2738 | H1 | TIP3 | 33 | 26.211 | 54.141 | 58.273 | 1.00 | 0.00 |
| ATOM | 2739 | H2 | TIP3 | 33 | 26.211 | 52.945 | 57.345 | 1.00 | 0.00 |
| ATOM | 2740 | OH2 | TIP3 | 35 | 24.006 | 42.035 | 83.271 | 1.00 | 37.01 |
| ATOM | 2741 | H1 | TIP3 | 35 | 23.999 | 42.988 | 83.287 | 1.00 | 0.00 |
| ATOM | 2742 | H2 | TIP3 | 35 | 23.999 | 41.790 | 82.359 | 1.00 | 0.00 |
| ATOM | 2743 | OH2 | TIP3 | 36 | 15.488 | 54.418 | 81.756 | 1.00 | 22.18 |
| ATOM | 2744 | H1 | TIP3 | 36 | 15.514 | 55.373 | 81.755 | 1.00 | 0.00 |
| ATOM | 2745 | H2 | TIP3 | 36 | 15.515 | 54.178 | 80.829 | 1.00 | 0.00 |
| ATOM | 2746 | OH2 | TIP3 | 38 | 8.520 | 65.982 | 69.122 | 1.00 | 25.05 |
| ATOM | 2747 | H1 | TIP3 | 38 | 8.504 | 66.943 | 69.123 | 1.00 | 0.00 |
| ATOM | 2748 | H2 | TIP3 | 38 | 8.504 | 65.746 | 68.196 | 1.00 | 0.00 |
| ATOM | 2749 | OH2 | TIP3 | 39 | 27.252 | 50.914 | 81.982 | 1.00 | 21.34 |
| ATOM | 2750 | H1 | TIP3 | 39 | 27.228 | 51.874 | 81.970 | 1.00 | 0.00 |
| ATOM | 2751 | H2 | TIP3 | 39 | 27.228 | 50.677 | 81.044 | 1.00 | 0.00 |
| ATOM | 2752 | OH2 | TIP3 | 40 | 4.097 | 54.839 | 66.839 | 1.00 | 18.26 |
| ATOM | 2753 | H1 | TIP3 | 40 | 4.080 | 55.808 | 66.804 | 1.00 | 0.00 |
| ATOM | 2754 | H2 | TIP3 | 40 | 4.080 | 54.612 | 65.879 | 1.00 | 0.00 |
| ATOM | 2755 | OH2 | TIP3 | 42 | 23.741 | 18.849 | 90.940 | 1.00 | 28.88 |
| ATOM | 2756 | H1 | TIP3 | 42 | 23.711 | 19.803 | 90.982 | 1.00 | 0.00 |
| ATOM | 2757 | H2 | TIP3 | 42 | 23.711 | 18.606 | 90.053 | 1.00 | 0.00 |
| ATOM | 2758 | OH2 | TIP3 | 43 | 6.086 | 57.516 | 65.421 | 1.00 | 28.23 |
| ATOM | 2759 | H1 | TIP3 | 43 | 6.069 | 58.469 | 65.415 | 1.00 | 0.00 |
| ATOM | 2760 | H2 | TIP3 | 43 | 6.069 | 57.272 | 64.489 | 1.00 | 0.00 |
| ATOM | 2761 | OH2 | TIP3 | 44 | 16.783 | 62.302 | 62.218 | 1.00 | 30.17 |
| ATOM | 2762 | H1 | TIP3 | 44 | 16.782 | 63.243 | 62.206 | 1.00 | 0.00 |
| ATOM | 2763 | H2 | TIP3 | 44 | 16.782 | 62.045 | 61.280 | 1.00 | 0.00 |
| ATOM | 2764 | OH2 | TIP3 | 46 | 6.110 | 51.172 | 62.526 | 1.00 | 37.28 |
| ATOM | 2765 | H1 | TIP3 | 46 | 6.119 | 52.113 | 62.516 | 1.00 | 0.00 |
| ATOM | 2766 | H2 | TIP3 | 46 | 6.119 | 50.914 | 61.591 | 1.00 | 0.00 |
| ATOM | 2767 | OH2 | TIP3 | 47 | 13.245 | 23.477 | 95.259 | 1.00 | 21.56 |
| ATOM | 2768 | H1 | TIP3 | 47 | 13.243 | 24.403 | 95.263 | 1.00 | 0.00 |
| ATOM | 2769 | H2 | TIP3 | 47 | 13.242 | 23.204 | 94.337 | 1.00 | 0.00 |
| ATOM | 2770 | OH2 | TIP3 | 49 | 13.972 | 25.241 | 81.262 | 1.00 | 27.98 |
| ATOM | 2771 | H1 | TIP3 | 49 | 13.967 | 25.206 | 81.269 | 1.00 | 0.00 |
| ATOM | 2772 | H2 | TIP3 | 49 | 13.967 | 25.010 | 80.340 | 1.00 | 0.00 |
| ATOM | 2773 | OH2 | TIP3 | 50 | 0.949 | 40.492 | 77.426 | 1.00 | 31.88 |
| ATOM | 2774 | H1 | TIP3 | 50 | 0.924 | 41.448 | 77.433 | 1.00 | 0.00 |
| ATOM | 2775 | H2 | TIP3 | 50 | 0.924 | 40.251 | 76.505 | 1.00 | 0.00 |
| ATOM | 2776 | OH2 | TIP3 | 51 | −0.990 | 51.240 | 82.226 | 1.00 | 33.94 |
| ATOM | 2777 | H1 | TIP3 | 51 | −1.016 | 52.158 | 82.235 | 1.00 | 0.00 |
| ATOM | 2778 | H2 | TIP3 | 51 | −1.015 | 50.953 | 81.337 | 1.00 | 0.00 |
| ATOM | 2779 | OH2 | TIP3 | 53 | 28.463 | 37.192 | 63.890 | 1.00 | 18.57 |
| ATOM | 2780 | H1 | TIP3 | 53 | 28.443 | 38.135 | 63.872 | 1.00 | 0.00 |
| ATOM | 2781 | H2 | TIP3 | 53 | 28.443 | 36.938 | 62.948 | 1.00 | 0.00 |
| ATOM | 2782 | OH2 | TIP3 | 55 | 6.841 | 45.328 | 67.946 | 1.00 | 21.13 |
| ATOM | 2783 | H1 | TIP3 | 55 | 6.846 | 46.229 | 67.983 | 1.00 | 0.00 |
| ATOM | 2784 | H2 | TIP3 | 55 | 6.852 | 45.050 | 67.057 | 1.00 | 0.00 |
| ATOM | 2785 | OH2 | TIP3 | 56 | 10.523 | 40.705 | 67.116 | 1.00 | 28.31 |
| ATOM | 2786 | H1 | TIP3 | 56 | 10.534 | 41.653 | 67.117 | 1.00 | 0.00 |
| ATOM | 2787 | H2 | TIP3 | 56 | 10.534 | 40.455 | 66.190 | 1.00 | 0.00 |
| ATOM | 2788 | OH2 | TIP3 | 57 | 13.810 | 69.139 | 73.892 | 1.00 | 30.11 |
| ATOM | 2789 | H1 | TIP3 | 57 | 13.803 | 70.085 | 73.906 | 1.00 | 0.00 |
| ATOM | 2790 | H2 | TIP3 | 57 | 13.803 | 68.887 | 72.978 | 1.00 | 0.00 |
| ATOM | 2791 | OH2 | TIP3 | 59 | 29.252 | 34.626 | 65.041 | 1.00 | 23.19 |
| ATOM | 2792 | H1 | TIP3 | 59 | 29.271 | 35.536 | 65.055 | 1.00 | 0.00 |
| ATOM | 2793 | H2 | TIP3 | 59 | 29.271 | 34.335 | 64.129 | 1.00 | 0.00 |
| ATOM | 2794 | OH2 | TIP3 | 60 | 7.419 | 54.240 | 63.866 | 1.00 | 23.79 |
| ATOM | 2795 | H1 | TIP3 | 60 | 7.403 | 55.225 | 63.865 | 1.00 | 0.00 |

TABLE 5-continued

Coordinates of Lck bound with baicalein

| | Atom Type | Res | # | X | Y | Z | Occ | B |
|---|---|---|---|---|---|---|---|---|
| ATOM | 2796 | H2 | TIP3 | 60 | 7.403 | 54.030 | 62.938 | 1.00 | 0.00 |
| ATOM | 2797 | OH2 | TIP3 | 61 | 18.015 | 52.938 | 80.829 | 1.00 | 18.25 |
| ATOM | 2798 | H1 | TIP3 | 61 | 18.017 | 53.897 | 80.831 | 1.00 | 0.00 |
| ATOM | 2799 | H2 | TIP3 | 61 | 18.018 | 52.701 | 79.904 | 1.00 | 0.00 |
| ATOM | 2800 | OH2 | TIP3 | 62 | 26.999 | 65.665 | 74.277 | 1.00 | 24.15 |
| ATOM | 2801 | H1 | TIP3 | 62 | 27.006 | 66.645 | 74.262 | 1.00 | 0.00 |
| ATOM | 2802 | H2 | TIP3 | 62 | 27.011 | 65.450 | 73.342 | 1.00 | 0.00 |
| ATOM | 2803 | OH2 | TIP3 | 63 | 12.745 | 31.730 | 74.642 | 1.00 | 28.80 |
| ATOM | 2804 | H1 | TIP3 | 63 | 12.737 | 32.710 | 74.615 | 1.00 | 0.00 |
| ATOM | 2805 | H2 | TIP3 | 63 | 12.736 | 31.516 | 73.692 | 1.00 | 0.00 |
| ATOM | 2806 | OH2 | TIP3 | 66 | 6.976 | 52.113 | 70.071 | 1.00 | 26.87 |
| ATOM | 2807 | H1 | TIP3 | 66 | 6.995 | 53.066 | 70.067 | 1.00 | 0.00 |
| ATOM | 2808 | H2 | TIP3 | 66 | 6.992 | 51.875 | 69.136 | 1.00 | 1.00 |
| ATOM | 2809 | OH2 | TIP3 | 67 | 8.613 | 37.119 | 67.362 | 1.00 | 39.59 |
| ATOM | 2810 | H1 | TIP3 | 67 | 8.606 | 38.083 | 67.354 | 1.00 | 0.00 |
| ATOM | 2811 | H2 | TIP3 | 67 | 8.606 | 36.886 | 66.428 | 1.00 | 0.00 |
| ATOM | 2812 | OH2 | TIP3 | 68 | 30.480 | 60.079 | 72.375 | 1.00 | 22.20 |
| ATOM | 2813 | H1 | TIP3 | 68 | 30.480 | 60.986 | 72.384 | 1.00 | 0.00 |
| ATOM | 2814 | H2 | TIP3 | 68 | 30.480 | 59.785 | 71.459 | 1.00 | 0.00 |
| ATOM | 2815 | OH2 | TIP3 | 69 | 36.671 | 38.871 | 74.755 | 1.00 | 19.57 |
| ATOM | 2816 | H1 | TIP3 | 69 | 36.374 | 39.808 | 74.797 | 1.00 | 0.00 |
| ATOM | 2817 | H2 | TIP3 | 69 | 36.377 | 38.622 | 73.869 | 1.00 | 0.00 |
| ATOM | 2818 | OH2 | TIP3 | 70 | 33.004 | 60.276 | 71.094 | 1.00 | 27.30 |
| ATOM | 2819 | H1 | TIP3 | 70 | 33.024 | 61.240 | 71.067 | 1.00 | 0.00 |
| ATOM | 2820 | H2 | TIP3 | 70 | 33.045 | 60.040 | 70.188 | 1.00 | 0.00 |
| ATOM | 2821 | OH2 | TIP3 | 71 | 11.647 | 33.316 | 69.667 | 1.00 | 30.96 |
| ATOM | 2822 | H1 | TIP3 | 71 | 11.650 | 34.274 | 69.664 | 1.00 | 0.00 |
| ATOM | 2823 | H2 | TIP3 | 71 | 11.650 | 33.077 | 68.737 | 1.00 | 0.00 |
| ATOM | 2824 | OH2 | TIP3 | 72 | 13.689 | 55.943 | 79.324 | 1.00 | 20.16 |
| ATOM | 2825 | H1 | TIP3 | 72 | 13.582 | 56.827 | 79.262 | 1.00 | 0.00 |
| ATOM | 2826 | H2 | TIP3 | 72 | 13.656 | 55.738 | 78.378 | 1.00 | 0.00 |
| ATOM | 2827 | OH2 | TIP3 | 73 | 32.794 | 40.600 | 80.852 | 1.00 | 45.22 |
| ATOM | 2828 | H1 | TIP3 | 73 | 32.794 | 41.553 | 80.855 | 1.00 | 0.00 |
| ATOM | 2829 | H2 | TIP3 | 73 | 32.794 | 40.356 | 79.928 | 1.00 | 0.00 |
| ATOM | 2830 | OH2 | TIP3 | 74 | 11.646 | 38.076 | 66.165 | 1.00 | 32.76 |
| ATOM | 2831 | H1 | TIP3 | 74 | 11.616 | 39.023 | 66.150 | 1.00 | 0.00 |
| ATOM | 2832 | H2 | TIP3 | 74 | 11.616 | 37.825 | 65.225 | 1.00 | 0.00 |
| ATOM | 2833 | OH2 | TIP3 | 75 | 12.916 | 69.629 | 76.340 | 1.00 | 29.73 |
| ATOM | 2834 | H1 | TIP3 | 75 | 12.926 | 70.607 | 76.308 | 1.00 | 0.00 |
| ATOM | 2835 | H2 | TIP3 | 75 | 12.925 | 69.413 | 75.384 | 1.00 | 0.00 |
| ATOM | 2836 | OH2 | TIP3 | 76 | 22.163 | 18.753 | 82.161 | 1.00 | 17.90 |
| ATOM | 2837 | H1 | TIP3 | 76 | 22.180 | 19.714 | 82.129 | 1.00 | 0.00 |
| ATOM | 2838 | H2 | TIP3 | 76 | 22.181 | 18.522 | 81.200 | 1.00 | 0.00 |
| ATOM | 2839 | OH2 | TIP3 | 81 | 12.458 | 55.090 | 56.596 | 1.00 | 41.28 |
| ATOM | 2840 | H1 | TIP3 | 81 | 12.457 | 56.040 | 56.600 | 1.00 | 0.00 |
| ATOM | 2841 | H2 | TIP3 | 81 | 12.457 | 54.842 | 55.673 | 1.00 | 0.00 |
| ATOM | 2842 | OH2 | TIP3 | 83 | 26.183 | 23.911 | 78.578 | 1.00 | 27.25 |
| ATOM | 2843 | H1 | TIP3 | 83 | 26.183 | 24.867 | 78.571 | 1.00 | 0.00 |
| ATOM | 2844 | H2 | TIP3 | 83 | 26.183 | 23.670 | 77.645 | 1.00 | 0.00 |
| ATOM | 2845 | OH2 | TIP3 | 85 | 18.833 | 52.723 | 83.292 | 1.00 | 23.73 |
| ATOM | 2846 | H1 | TIP3 | 85 | 18.830 | 53.708 | 83.264 | 1.00 | 0.00 |
| ATOM | 2847 | H2 | TIP3 | 85 | 18.830 | 52.513 | 82.339 | 1.00 | 0.00 |
| ATOM | 2848 | OH2 | TIP3 | 86 | 27.197 | 39.988 | 61.230 | 1.00 | 18.55 |
| ATOM | 2849 | H1 | TIP3 | 86 | 27.184 | 40.933 | 61.225 | 1.00 | 0.00 |
| ATOM | 2850 | H2 | TIP3 | 86 | 27.184 | 39.734 | 60.299 | 1.00 | 0.00 |
| ATOM | 2851 | OH2 | TIP3 | 87 | 23.632 | 52.527 | 54.458 | 1.00 | 41.27 |
| ATOM | 2852 | H1 | TIP3 | 87 | 23.650 | 53.485 | 54.461 | 1.00 | 0.00 |
| ATOM | 2853 | H2 | TIP3 | 87 | 23.649 | 52.290 | 53.535 | 1.00 | 0.00 |
| ATOM | 2854 | OH2 | TIP3 | 88 | 23.454 | 43.217 | 94.180 | 1.00 | 31.15 |
| ATOM | 2855 | H1 | TIP3 | 88 | 23.492 | 44.161 | 94.168 | 1.00 | 0.00 |
| ATOM | 2856 | H2 | TIP3 | 88 | 23.492 | 42.963 | 93.242 | 1.00 | 0.00 |
| ATOM | 2857 | OH2 | TIP3 | 89 | 11.981 | 45.264 | 99.148 | 1.00 | 37.29 |
| ATOM | 2858 | H1 | TIP3 | 89 | 11.983 | 46.215 | 99.149 | 1.00 | 0.00 |
| ATOM | 2859 | H2 | TIP3 | 89 | 11.983 | 45.018 | 98.222 | 1.00 | 0.00 |
| ATOM | 2860 | OH2 | TIP3 | 90 | 16.685 | 60.770 | 88.818 | 1.00 | 38.79 |
| ATOM | 2861 | H1 | TIP3 | 90 | 16.693 | 61.714 | 88.829 | 1.00 | 0.00 |
| ATOM | 2862 | H2 | TIP3 | 90 | 16.693 | 60.516 | 87.902 | 1.00 | 0.00 |
| ATOM | 2863 | OH2 | TIP3 | 92 | 4.124 | 43.934 | 85.682 | 1.00 | 30.60 |
| ATOM | 2864 | H1 | TIP3 | 92 | 4.093 | 44.876 | 85.684 | 1.00 | 0.00 |
| ATOM | 2865 | H2 | TIP3 | 92 | 4.093 | 43.677 | 84.758 | 1.00 | 0.00 |
| ATOM | 2866 | OH2 | TIP3 | 93 | 19.336 | 23.884 | 101.162 | 1.00 | 42.89 |
| ATOM | 2867 | H1 | TIP3 | 93 | 19.346 | 24.841 | 101.182 | 1.00 | 0.00 |
| ATOM | 2868 | H2 | TIP3 | 93 | 19.346 | 23.644 | 100.253 | 1.00 | 0.00 |
| ATOM | 2869 | OH2 | TIP3 | 95 | 9.558 | 42.547 | 87.570 | 1.00 | 35.33 |

TABLE 5-continued

Coordinates of Lck bound with baicalein

| | Atom Type | Res | # | X | Y | Z | Occ | B |
|---|---|---|---|---|---|---|---|---|
| ATOM | 2870 | H1 | TIP3 | 95 | 9.561 | 43.490 | 87.281 | 1.00 | 0.00 |
| ATOM | 2871 | H2 | TIP3 | 95 | 9.561 | 42.291 | 86.354 | 1.00 | 0.00 |
| ATOM | 2872 | OH2 | TIP3 | 96 | 29.977 | 58.577 | 74.535 | 1.00 | 16.50 |
| ATOM | 2873 | H1 | TIP3 | 96 | 30.006 | 59.542 | 74.519 | 1.00 | 0.00 |
| ATOM | 2874 | H2 | TIP3 | 96 | 30.007 | 58.348 | 73.594 | 1.00 | 0.00 |
| ATOM | 2875 | OH2 | TIP3 | 98 | 40.680 | 39.007 | 69.571 | 1.00 | 30.44 |
| ATOM | 2876 | H1 | TIP3 | 98 | 40.679 | 39.970 | 69.563 | 1.00 | 0.00 |
| ATOM | 2877 | H2 | TIP3 | 98 | 40.688 | 38.776 | 68.631 | 1.00 | 0.00 |
| ATOM | 2878 | OH2 | TIP3 | 100 | 24.749 | 67.658 | 74.498 | 1.00 | 23.99 |
| ATOM | 2879 | H1 | TIP3 | 100 | 24.740 | 68.620 | 74.471 | 1.00 | 0.00 |
| ATOM | 2880 | H2 | TIP3 | 100 | 24.740 | 67.424 | 73.545 | 1.00 | 0.00 |
| ATOM | 2881 | OH2 | TIP3 | 101 | −2.152 | 44.216 | 77.951 | 1.00 | 38.18 |
| ATOM | 2882 | H1 | TIP3 | 101 | −2.148 | 45.176 | 77.946 | 1.00 | 0.00 |
| ATOM | 2883 | H2 | TIP3 | 101 | −2.149 | 43.978 | 77.020 | 1.00 | 0.00 |
| ATOM | 2884 | OH2 | TIP3 | 102 | 9.408 | 69.245 | 78.064 | 1.00 | 48.45 |
| ATOM | 2885 | H1 | TIP3 | 102 | 9.405 | 70.197 | 78.068 | 1.00 | 0.00 |
| ATOM | 2886 | H2 | TIP3 | 102 | 9.404 | 69.000 | 77.142 | 1.00 | 0.00 |
| ATOM | 2887 | OH2 | TIP3 | 103 | 35.609 | 63.960 | 74.623 | 1.00 | 41.70 |
| ATOM | 2888 | H1 | TIP3 | 103 | 35.582 | 64.970 | 74.707 | 1.00 | 0.00 |
| ATOM | 2889 | H2 | TIP3 | 103 | 35.582 | 63.777 | 73.772 | 1.00 | 0.00 |
| ATOM | 2890 | OH2 | TIP3 | 104 | 25.370 | 43.788 | 104.479 | 1.00 | 43.83 |
| ATOM | 2891 | H1 | TIP3 | 104 | 25.356 | 44.731 | 104.480 | 1.00 | 0.00 |
| ATOM | 2892 | H2 | TIP3 | 104 | 25.356 | 43.533 | 103.553 | 1.00 | 0.00 |
| ATOM | 2893 | OH2 | TIP3 | 105 | 19.202 | 55.100 | 89.579 | 1.00 | 42.56 |
| ATOM | 2894 | H1 | TIP3 | 105 | 19.199 | 56.069 | 89.567 | 1.00 | 0.00 |
| ATOM | 2895 | H2 | TIP3 | 105 | 19.199 | 54.873 | 88.641 | 1.00 | 0.00 |
| ATOM | 2896 | OH2 | TIP3 | 107 | 23.724 | 29.152 | 76.813 | 1.00 | 26.60 |
| ATOM | 2897 | H1 | TIP3 | 107 | 23.753 | 30.0893 | 76.840 | 1.00 | 0.00 |
| ATOM | 2898 | H2 | TIP3 | 107 | 23.755 | 28.8887 | 75.914 | 1.00 | 0.00 |
| ATOM | 2899 | OH2 | TIP3 | 108 | 14.128 | 45.865 | 83.742 | 1.00 | 14.12 |
| ATOM | 2900 | H1 | TIP3 | 108 | 14.117 | 46.808 | 83.712 | 1.00 | 0.00 |
| ATOM | 2901 | H2 | TIP3 | 108 | 14.117 | 45.610 | 82.788 | 1.00 | 0.00 |
| ATOM | 2902 | OH2 | TIP3 | 109 | 17.447 | 34.386 | 100.053 | 1.00 | 30.32 |
| ATOM | 2903 | H1 | TIP3 | 109 | 17.450 | 35.350 | 100.074 | 1.00 | 0.00 |
| ATOM | 2904 | H2 | TIP3 | 109 | 17.450 | 34.153 | 99.146 | 1.00 | 0.00 |
| ATOM | 2905 | OH2 | TIP3 | 110 | 30.306 | 41.360 | 81.954 | 1.00 | 23.77 |
| ATOM | 2906 | H1 | TIP3 | 110 | 30.289 | 42.292 | 81.984 | 1.00 | 0.00 |
| ATOM | 2907 | H2 | TIP3 | 110 | 30.299 | 41.117 | 81.057 | 1.00 | 0.00 |
| ATOM | 2908 | OH2 | TIP3 | 111 | 16.483 | 52.860 | 84.814 | 1.00 | 19.42 |
| ATOM | 2909 | H1 | TIP3 | 111 | 16.496 | 53.832 | 84.830 | 1.00 | 0.00 |
| ATOM | 2910 | H2 | TIP3 | 111 | 16.496 | 52.637 | 83.901 | 1.00 | 0.00 |
| ATOM | 2911 | OH2 | TIP3 | 112 | 22.845 | 77.271 | 79.714 | 1.00 | 39.39 |
| ATOM | 2912 | H1 | TIP3 | 112 | 22.835 | 78.215 | 79.701 | 1.00 | 0.00 |
| ATOM | 2913 | H2 | TIP3 | 112 | 22.835 | 77.016 | 78.776 | 1.00 | 0.00 |
| ATOM | 2914 | OH2 | TIP3 | 113 | 26.147 | 57.098 | 57.389 | 1.00 | 24.60 |
| ATOM | 2915 | H1 | TIP3 | 113 | 26.162 | 58.072 | 57.401 | 1.00 | 0.00 |
| ATOM | 2916 | H2 | TIP3 | 113 | 26.162 | 56.876 | 56.473 | 1.00 | 0.00 |
| ATOM | 2917 | OH2 | TIP3 | 114 | 32.984 | 52.137 | 66.207 | 1.00 | 43.56 |
| ATOM | 2918 | H1 | TIP3 | 114 | 32.991 | 53.098 | 66.205 | 1.00 | 0.00 |
| ATOM | 2919 | H2 | TIP3 | 114 | 32.991 | 51.902 | 65.278 | 1.00 | 0.00 |
| ATOM | 2920 | OH2 | TIP3 | 115 | 24.296 | 74.629 | 76.785 | 1.00 | 23.18 |
| ATOM | 2921 | H1 | TIP3 | 115 | 24.388 | 75.597 | 76.747 | 1.00 | 0.00 |
| ATOM | 2922 | H2 | TIP3 | 115 | 24.387 | 74.403 | 75.822 | 1.00 | 0.00 |
| ATOM | 2923 | OH2 | TIP3 | 116 | 33.581 | 41.966 | 62.306 | 1.00 | 34.03 |
| ATOM | 2924 | H1 | TIP3 | 116 | 33.582 | 42.896 | 62.285 | 1.00 | 0.00 |
| ATOM | 2925 | H2 | TIP3 | 116 | 33.582 | 41.698 | 61.361 | 1.00 | 0.00 |
| ATOM | 2926 | OH2 | TIP3 | 117 | 1.196 | 49.476 | 87.433 | 1.00 | 41.83 |
| ATOM | 2927 | H1 | TIP3 | 117 | 1.200 | 50.447 | 87.429 | 1.00 | 0.00 |
| ATOM | 2928 | H2 | TIP3 | 117 | 1.200 | 49.251 | 86.503 | 1.00 | 0.00 |
| ATOM | 2929 | OH2 | TIP3 | 118 | 8.458 | 47.328 | 92.995 | 1.00 | 35.82 |
| ATOM | 2930 | H1 | TIP3 | 118 | 8.470 | 48.289 | 92.990 | 1.00 | 0.00 |
| ATOM | 2931 | H2 | TIP3 | 118 | 8.470 | 47.092 | 92.063 | 1.00 | 0.00 |
| ATOM | 2932 | OH2 | TIP3 | 119 | 13.027 | 30.925 | 72.205 | 1.00 | 26.37 |
| ATOM | 2933 | H1 | TIP3 | 119 | 13.043 | 31.885 | 72.241 | 1.00 | 0.00 |
| ATOM | 2934 | H2 | TIP3 | 119 | 13.042 | 30.688 | 71.312 | 1.00 | 0.00 |
| ATOM | 2935 | OH2 | TIP3 | 120 | 11.352 | 66.626 | 68.472 | 1.00 | 24.97 |
| ATOM | 2936 | H1 | TIP3 | 120 | 11.345 | 67.549 | 68.484 | 1.00 | 0.00 |
| ATOM | 2937 | H2 | TIP3 | 120 | 11.344 | 66.350 | 67.558 | 1.00 | 0.00 |
| ATOM | 2938 | OH2 | TIP3 | 121 | 15.530 | 39.003 | 102.194 | 1.00 | 28.13 |
| ATOM | 2939 | H1 | TIP3 | 121 | 15.630 | 39.954 | 102.234 | 1.00 | 0.00 |
| ATOM | 2940 | H2 | TIP3 | 121 | 15.630 | 38.756 | 101.304 | 1.00 | 0.00 |
| ATOM | 2941 | OH2 | TIP3 | 122 | 29.002 | 57.023 | 57.274 | 1.00 | 34.92 |
| ATOM | 2942 | H1 | TIP3 | 122 | 29.021 | 57.990 | 57.316 | 1.00 | 0.00 |
| ATOM | 2943 | H2 | TIP3 | 122 | 29.021 | 56.795 | 56.386 | 1.00 | 0.00 |

TABLE 5-continued

Coordinates of Lck bound with baicalein

| | Atom Type | Res | # | X | Y | Z | Occ | B |
|---|---|---|---|---|---|---|---|---|
| ATOM | 2944 | OH2 | TIP3 | 123 | 17.093 | 28.979 | 80.374 | 1.00 | 32.54 |
| ATOM | 2945 | H1 | TIP3 | 123 | 17.092 | 29.965 | 80.419 | 1.00 | 0.00 |
| ATOM | 2946 | H2 | TIP3 | 123 | 17.092 | 28.770 | 79.488 | 1.00 | 0.00 |
| ATOM | 2947 | OH2 | TIP3 | 124 | 37.795 | 32.814 | 88.817 | 1.00 | 43.25 |
| ATOM | 2948 | H1 | TIP3 | 124 | 37.802 | 33.775 | 88.815 | 1.00 | 0.00 |
| ATOM | 2949 | H2 | TIP3 | 124 | 37.802 | 32.579 | 87.888 | 1.00 | 0.00 |
| ATOM | 2950 | OH2 | TIP3 | 128 | 4.423 | 47.650 | 75.188 | 1.00 | 32.38 |
| ATOM | 2951 | H1 | TIP3 | 128 | 4.390 | 48.597 | 75.171 | 1.00 | 0.00 |
| ATOM | 2952 | H2 | TIP3 | 128 | 4.390 | 47.400 | 74.246 | 1.00 | 0.00 |
| ATOM | 2953 | OH2 | TIP3 | 130 | 7.680 | 27.996 | 92.217 | 1.00 | 32.43 |
| ATOM | 2954 | H1 | TIP3 | 130 | 7.681 | 28.949 | 92.200 | 1.00 | 0.00 |
| ATOM | 2955 | H2 | TIP3 | 130 | 7.681 | 27.752 | 91.275 | 1.00 | 0.00 |
| ATOM | 2956 | OH2 | TIP3 | 131 | 11.904 | 33.642 | 80.265 | 1.00 | 19.52 |
| ATOM | 2957 | H1 | TIP3 | 131 | 11.918 | 34.594 | 80.282 | 1.00 | 0.00 |
| ATOM | 2958 | H2 | TIP3 | 131 | 11.918 | 33.396 | 79.354 | 1.00 | 0.00 |
| ATOM | 2959 | OH2 | TIP3 | 132 | 32.717 | 37.141 | 100.133 | 1.00 | 44.14 |
| ATOM | 2960 | H1 | TIP3 | 132 | 32.711 | 38.095 | 100.120 | 1.00 | 0.00 |
| ATOM | 2961 | H2 | TIP3 | 132 | 32.711 | 36.898 | 99.194 | 1.00 | 0.00 |
| ATOM | 2962 | OH2 | TIP3 | 133 | 3.150 | 56.961 | 74.053 | 1.00 | 37.97 |
| ATOM | 2963 | H1 | TIP3 | 133 | 3.141 | 57.929 | 74.054 | 1.00 | 0.00 |
| ATOM | 2964 | H2 | TIP3 | 133 | 3.141 | 56.733 | 73.127 | 1.00 | 0.00 |
| ATOM | 2965 | OH2 | TIP3 | 134 | 9.900 | 25.245 | 82.428 | 1.00 | 42.37 |
| ATOM | 2966 | H1 | TIP3 | 134 | 9.891 | 26.192 | 82.426 | 1.00 | 0.00 |
| ATOM | 2967 | H2 | TIP3 | 134 | 9.891 | 24.993 | 81.500 | 1.00 | 0.00 |
| ATOM | 2968 | OH2 | TIP3 | 137 | 23.962 | 49.318 | 84.630 | 1.00 | 48.99 |
| ATOM | 2969 | H1 | TIP3 | 137 | 23.962 | 50.286 | 84.633 | 1.00 | 0.00 |
| ATOM | 2970 | H2 | TIP3 | 137 | 23.962 | 49.092 | 83.704 | 1.00 | 0.00 |
| ATOM | 2971 | OH2 | TIP3 | 139 | 32.254 | 60.280 | 78.527 | 1.00 | 38.95 |
| ATOM | 2972 | H1 | TIP3 | 139 | 32.272 | 61.234 | 78.544 | 1.00 | 0.00 |
| ATOM | 2973 | H2 | TIP3 | 139 | 32.264 | 60.046 | 77.608 | 1.00 | 0.00 |
| ATOM | 2974 | OH2 | TIP3 | 140 | 22.676 | 31.792 | 73.445 | 1.00 | 37.61 |
| ATOM | 2975 | H1 | TIP3 | 140 | 22.674 | 32.745 | 73.460 | 1.00 | 0.00 |
| ATOM | 2976 | H2 | TIP3 | 140 | 22.674 | 31.547 | 72.532 | 1.00 | 0.00 |
| ATOM | 2977 | OH2 | TIP3 | 142 | 5.857 | 35.075 | 75.747 | 1.00 | 36.54 |
| ATOM | 2978 | H1 | TIP3 | 142 | 5.832 | 36.047 | 75.745 | 1.00 | 0.00 |
| ATOM | 2979 | H2 | TIP3 | 142 | 5.832 | 34.851 | 74.818 | 1.00 | 0.00 |
| ATOM | 2980 | OH2 | TIP3 | 143 | 11.576 | 41.514 | 63.703 | 1.00 | 43.08 |
| ATOM | 2981 | H1 | TIP3 | 143 | 11.566 | 41.935 | 62.962 | 1.00 | 0.00 |
| ATOM | 2982 | H2 | TIP3 | 143 | 11.597 | 41.122 | 62.039 | 1.00 | 0.00 |
| ATOM | 2983 | OH2 | TIP3 | 146 | 9.560 | 68.340 | 86.338 | 1.00 | 36.92 |
| ATOM | 2984 | H1 | TIP3 | 146 | 9.553 | 69.281 | 86.336 | 1.00 | 0.00 |
| ATOM | 2985 | H2 | TIP3 | 146 | 9.553 | 68.083 | 85.410 | 1.00 | 0.00 |
| ATOM | 2986 | OH2 | TIP3 | 147 | 36.270 | 28.632 | 92.302 | 1.00 | 43.33 |
| ATOM | 2987 | H1 | TIP3 | 147 | 36.280 | 29.595 | 92.299 | 1.00 | 0.00 |
| ATOM | 2988 | H2 | TIP3 | 147 | 36.280 | 28.398 | 91.372 | 1.00 | 0.00 |
| ATOM | 2989 | OH2 | TIP3 | 149 | 11.528 | 39.703 | 62.020 | 1.00 | 43.78 |
| ATOM | 2990 | H1 | TIP3 | 149 | 11.553 | 41.262 | 62.227 | 1.00 | 0.00 |
| ATOM | 2991 | H2 | TIP3 | 149 | 11.566 | 40.343 | 61.457 | 1.00 | 0.00 |
| ATOM | 2992 | OH2 | TIP3 | 150 | 33.046 | 32.972 | 71.878 | 1.00 | 45.35 |
| ATOM | 2993 | H1 | TIP3 | 150 | 33.048 | 33.917 | 71.875 | 1.00 | 0.00 |
| ATOM | 2994 | H2 | TIP3 | 150 | 33.048 | 32.718 | 70.949 | 1.00 | 0.00 |
| ATOM | 2995 | OH2 | TIP3 | 151 | 24.840 | 30.312 | 97.085 | 1.00 | 46.28 |
| ATOM | 2996 | H1 | TIP3 | 151 | 24.849 | 31.266 | 97.080 | 1.00 | 0.00 |
| ATOM | 2997 | H2 | TIP3 | 151 | 24.849 | 30.069 | 96.154 | 1.00 | 0.00 |
| ATOM | 2998 | OH2 | TIP3 | 152 | 24.327 | 24.865 | 95.644 | 1.00 | 38.09 |
| ATOM | 2999 | H1 | TIP3 | 152 | 24.318 | 25.812 | 95.673 | 1.00 | 0.00 |
| ATOM | 3000 | H2 | TIP3 | 152 | 24.318 | 24.614 | 94.745 | 1.00 | 0.00 |
| ATOM | 3001 | OH2 | TIP3 | 153 | 28.285 | 24.394 | 94.612 | 1.00 | 36.63 |
| ATOM | 3002 | H1 | TIP3 | 153 | 28.288 | 25.348 | 94.615 | 1.00 | 0.00 |
| ATOM | 3003 | H2 | TIP3 | 153 | 28.614 | 17.935 | 93.688 | 1.00 | 0.00 |
| ATOM | 3004 | OH2 | TIP3 | 156 | 28.614 | 17.935 | 90.242 | 1.00 | 42.16 |
| ATOM | 3005 | H1 | TIP3 | 156 | 28.630 | 18.887 | 90.244 | 1.00 | 0.00 |
| ATOM | 3006 | H2 | TIP3 | 156 | 28.630 | 17.689 | 89.317 | 1.00 | 0.00 |
| ATOM | 3007 | OH2 | TIP3 | 157 | 3.781 | 28.407 | 86.909 | 1.00 | 38.91 |
| ATOM | 3008 | H1 | TIP3 | 157 | 4.150 | 29.205 | 87.025 | 1.00 | 0.00 |
| ATOM | 3009 | H2 | TIP3 | 157 | 4.146 | 28.060 | 86.114 | 1.00 | 0.00 |
| ATOM | 3010 | OH2 | TIP3 | 158 | 28.102 | 61.891 | 63.159 | 1.00 | 35.82 |
| ATOM | 3011 | H1 | TIP3 | 158 | 28.129 | 62.839 | 63.159 | 1.00 | 0.00 |
| ATOM | 3012 | H2 | TIP3 | 158 | 28.126 | 61.664 | 62.240 | 1.00 | 0.00 |
| ATOM | 3013 | OH2 | TIP3 | 161 | 16.354 | 46.577 | 86.239 | 1.00 | 33.52 |
| ATOM | 3014 | H1 | TIP3 | 161 | 16.350 | 47.543 | 86.260 | 1.00 | 0.00 |
| ATOM | 3015 | H2 | TIP3 | 161 | 16.350 | 46.347 | 85.331 | 1.00 | 0.00 |
| ATOM | 3016 | OH2 | TIP3 | 162 | 0.729 | 45.361 | 71.372 | 1.00 | 29.26 |
| ATOM | 3017 | H1 | TIP3 | 162 | 0.732 | 46.329 | 71.355 | 1.00 | 0.00 |

TABLE 5-continued

Coordinates of Lck bound with baicalein

| | Atom Type | Res | # | X | Y | Z | Occ | B |
|---|---|---|---|---|---|---|---|---|
| ATOM | 3018 | H2 | TIP3 | 162 | 0.732 | 45.133 | 70.429 | 1.00 | 0.00 |
| ATOM | 3019 | OH2 | TIP3 | 163 | 36.272 | 39.784 | 66.800 | 1.00 | 41.30 |
| ATOM | 3020 | H1 | TIP3 | 163 | 36.276 | 40.738 | 66.797 | 1.00 | 0.00 |
| ATOM | 3021 | H2 | TIP3 | 163 | 36.276 | 39.541 | 65.870 | 1.00 | 0.00 |
| ATOM | 3022 | OH2 | TIP3 | 164 | 3.745 | 39.853 | 84.182 | 1.00 | 40.87 |
| ATOM | 3023 | H1 | TIP3 | 164 | 3.754 | 40.795 | 84.191 | 1.00 | 0.00 |
| ATOM | 3024 | H2 | TIP3 | 164 | 3.754 | 39.597 | 83.266 | 1.00 | 0.00 |
| ATOM | 3025 | OH2 | TIP3 | 166 | 5.657 | 32.765 | 77.970 | 1.00 | 45.85 |
| ATOM | 3026 | H1 | TIP3 | 166 | 5.667 | 33.717 | 77.969 | 1.00 | 0.00 |
| ATOM | 3027 | H2 | TIP3 | 166 | 5.667 | 32.520 | 77.042 | 1.00 | 0.00 |
| ATOM | 3028 | OH2 | TIP3 | 167 | 27.639 | 29.253 | 75.503 | 1.00 | 44.27 |
| ATOM | 3029 | H1 | TIP3 | 167 | 27.633 | 30.199 | 75.503 | 1.00 | 0.00 |
| ATOM | 3030 | H2 | TIP3 | 167 | 27.633 | 29.001 | 74.576 | 1.00 | 0.00 |
| ATOM | 3031 | OH2 | TIP3 | 169 | 22.367 | 15.272 | 83.181 | 1.00 | 27.84 |
| ATOM | 3032 | H1 | TIP3 | 169 | 22.355 | 16.231 | 83.166 | 1.00 | 0.00 |
| ATOM | 3033 | H2 | TIP3 | 169 | 22.355 | 15.034 | 82.241 | 1.00 | 0.00 |
| ATOM | 3034 | OH2 | TIP3 | 170 | 26.170 | 75.473 | 75.510 | 1.00 | 36.16 |
| ATOM | 3035 | H1 | TIP3 | 170 | 26.112 | 76.398 | 75.559 | 1.00 | 0.00 |
| ATOM | 3036 | H2 | TIP3 | 170 | 26.112 | 75.198 | 74.629 | 1.00 | 0.00 |
| ATOM | 3037 | OH2 | TIP3 | 171 | 29.118 | 59.510 | 58.054 | 1.00 | 23.91 |
| ATOM | 3038 | H1 | TIP3 | 171 | 29.118 | 60.446 | 58.080 | 1.00 | 0.00 |
| ATOM | 3039 | H2 | TIP3 | 171 | 29.118 | 59.247 | 57.153 | 1.00 | 0.00 |
| ATOM | 3040 | OH2 | TIP3 | 174 | 34.575 | 32.511 | 92.231 | 1.00 | 34.24 |
| ATOM | 3041 | H1 | TIP3 | 174 | 34.555 | 33.485 | 92.222 | 1.00 | 0.00 |
| ATOM | 3042 | H2 | TIP3 | 174 | 34.555 | 32.290 | 91.295 | 1.00 | 0.00 |
| ATOM | 3043 | OH2 | TIP3 | 177 | 31.067 | 50.221 | 85.657 | 1.00 | 39.98 |
| ATOM | 3044 | H1 | TIP3 | 177 | 21.073 | 51.165 | 85.660 | 1.00 | 0.00 |
| ATOM | 3045 | H2 | TIP3 | 177 | 21.073 | 49.967 | 84.733 | 1.00 | 0.00 |
| ATOM | 3046 | OH2 | TIP3 | 180 | 8.241 | 65.336 | 63.826 | 1.00 | 47.81 |
| ATOM | 3047 | H1 | TIP3 | 180 | 8.234 | 66.280 | 63.824 | 1.00 | 0.00 |
| ATOM | 3048 | H2 | TIP3 | 180 | 8.234 | 65.081 | 62.898 | 1.00 | 0.00 |
| ATOM | 3049 | OH2 | TIP3 | 181 | 11.722 | 71.686 | 76.900 | 1.00 | 49.95 |
| ATOM | 3050 | H1 | TIP3 | 181 | 11.754 | 72.621 | 76.884 | 1.00 | 0.00 |
| ATOM | 3051 | H2 | TIP3 | 181 | 11.754 | 71.422 | 75.959 | 1.00 | 0.00 |
| ATOM | 3052 | OH2 | TIP3 | 183 | 29.809 | 66.200 | 75.194 | 1.00 | 31.78 |
| ATOM | 3053 | H1 | TIP3 | 183 | 29.815 | 67.166 | 75.191 | 1.00 | 0.00 |
| ATOM | 3054 | H2 | TIP3 | 183 | 29.815 | 65.970 | 74.264 | 1.00 | 0.00 |
| ATOM | 3055 | OH2 | TIP3 | 185 | 1.065 | 39.061 | 80.129 | 1.00 | 44.91 |
| ATOM | 3056 | H1 | TIP3 | 185 | 1.050 | 40.021 | 80.126 | 1.00 | 0.00 |
| ATOM | 3057 | H2 | TIP3 | 185 | 1.050 | 38.824 | 79.199 | 1.00 | 0.00 |
| ATOM | 3058 | OH2 | TIP3 | 186 | 3.777 | 52.072 | 69.980 | 1.00 | 50.94 |
| ATOM | 3059 | H1 | TIP3 | 186 | 3.782 | 53.027 | 69.962 | 1.00 | 0.00 |
| ATOM | 3060 | H2 | TIP3 | 186 | 3.782 | 51.830 | 69.037 | 1.00 | 0.00 |
| ATOM | 3061 | OH2 | TIP3 | 187 | 5.731 | 39.762 | 68.968 | 1.00 | 38.69 |
| ATOM | 3062 | H1 | TIP3 | 187 | 5.713 | 40.710 | 68.982 | 1.00 | 0.00 |
| ATOM | 3063 | H2 | TIP3 | 187 | 5.712 | 39.513 | 68.055 | 1.00 | 0.00 |
| ATOM | 3064 | OH2 | TIP3 | 188 | 6.844 | 43.382 | 65.561 | 1.00 | 51.28 |
| ATOM | 3065 | H1 | TIP3 | 188 | 6.831 | 44.343 | 65.561 | 1.00 | 0.00 |
| ATOM | 3066 | H2 | TIP3 | 188 | 6.831 | 43.146 | 64.634 | 1.00 | 0.00 |
| ATOM | 3067 | OH2 | TIP3 | 189 | 18.784 | 43.926 | 106.548 | 1.00 | 44.75 |
| ATOM | 3068 | H1 | TIP3 | 189 | 18.798 | 44.890 | 106.554 | 1.00 | 0.00 |
| ATOM | 3069 | H2 | TIP3 | 189 | 18.798 | 43.694 | 105.626 | 1.00 | 0.00 |
| ATOM | 3070 | OH2 | TIP3 | 194 | 34.849 | 34.095 | 76.228 | 1.00 | 42.16 |
| ATOM | 3071 | H1 | TIP3 | 194 | 34.857 | 35.053 | 76.229 | 1.00 | 0.00 |
| ATOM | 3072 | H2 | TIP3 | 194 | 34.857 | 33.856 | 75.302 | 1.00 | 0.00 |
| ATOM | 3073 | OH2 | TIP3 | 195 | −0.680 | 35.228 | 82.391 | 1.00 | 40.44 |
| ATOM | 3074 | H1 | TIP3 | 195 | −0.684 | 36.184 | 82.398 | 1.00 | 0.00 |
| ATOM | 3075 | H2 | TIP3 | 195 | −0.684 | 34.987 | 81.471 | 1.00 | 0.00 |
| ATOM | 3076 | OH2 | TIP3 | 197 | 7.585 | 59.067 | 90.533 | 1.00 | 40.83 |
| ATOM | 3077 | H1 | TIP3 | 197 | 7.589 | 60.023 | 90.528 | 1.00 | 0.00 |
| ATOM | 3078 | H2 | TIP3 | 197 | 7.589 | 58.826 | 89.602 | 1.00 | 0.00 |
| ATOM | 3079 | OH2 | TIP3 | 200 | 29.717 | 63.190 | 72.340 | 1.00 | 37.01 |
| ATOM | 3080 | H1 | TIP3 | 200 | 29.753 | 64.178 | 72.344 | 1.00 | 0.00 |
| ATOM | 3081 | H2 | TIP3 | 200 | 29.753 | 62.983 | 71.415 | 1.00 | 0.00 |
| ATOM | 3082 | OH2 | TIP3 | 201 | 37.857 | 57.465 | 69.079 | 1.00 | 44.88 |
| ATOM | 3083 | H1 | TIP3 | 201 | 37.858 | 58.413 | 69.077 | 1.00 | 0.00 |
| ATOM | 3084 | H2 | TIP3 | 201 | 37.858 | 57.215 | 68.151 | 1.00 | 0.00 |
| ATOM | 3085 | OH2 | TIP3 | 202 | 34.945 | 35.755 | 72.365 | 1.00 | 41.40 |
| ATOM | 3086 | H1 | TIP3 | 202 | 34.947 | 36.702 | 72.377 | 1.00 | 0.00 |
| ATOM | 3087 | H2 | TIP3 | 202 | 34.947 | 35.504 | 71.449 | 1.00 | 0.00 |
| ATOM | 3088 | OH2 | TIP3 | 204 | 3.367 | 28.454 | 84.689 | 1.00 | 50.09 |
| ATOM | 3089 | H1 | TIP3 | 204 | 3.392 | 29.379 | 84.744 | 1.00 | 0.00 |
| ATOM | 3090 | H2 | TIP3 | 204 | 3.392 | 28.179 | 83.815 | 1.00 | 0.00 |
| ATOM | 3091 | OH2 | TIP3 | 205 | 31.931 | 53.554 | 61.016 | 1.00 | 48.98 |

TABLE 5-continued

Coordinates of Lck bound with baicalein

| | Atom Type | Res | # | X | Y | Z | Occ | B |
|---|---|---|---|---|---|---|---|---|
| ATOM | 3092 | H1 | TIP3 | 205 | 31.923 | 54.508 | 61.030 | 1.00 | 0.00 |
| ATOM | 3093 | H2 | TIP3 | 205 | 31.923 | 53.311 | 60.102 | 1.00 | 0.00 |
| ATOM | 3094 | OH2 | TIP3 | 206 | 28.842 | 38.466 | 99.026 | 1.00 | 38.42 |
| ATOM | 3095 | H1 | TIP3 | 206 | 28.840 | 39.440 | 99.039 | 1.00 | 0.00 |
| ATOM | 3096 | H2 | TIP3 | 206 | 28.840 | 38.245 | 98.111 | 1.00 | 0.00 |
| ATOM | 3097 | OH2 | TIP3 | 207 | 3.844 | 28.023 | 96.474 | 1.00 | 37.67 |
| ATOM | 3098 | H1 | TIP3 | 207 | 3.838 | 28.981 | 96.462 | 1.00 | 0.00 |
| ATOM | 3099 | H2 | TIP3 | 207 | 3.838 | 27.784 | 95.536 | 1.00 | 0.00 |
| ATOM | 3100 | OH2 | TIP3 | 208 | 5.007 | 57.485 | 96.461 | 1.00 | 42.93 |
| ATOM | 3101 | H1 | TIP3 | 208 | 4.990 | 58.439 | 96.475 | 1.00 | 0.00 |
| ATOM | 3102 | H2 | TIP3 | 208 | 4.990 | 57.242 | 95.547 | 1.00 | 0.00 |
| ATOM | 3103 | OH2 | TIP3 | 212 | 29.679 | 41.117 | 60.857 | 1.00 | 38.66 |
| ATOM | 3104 | H1 | TIP3 | 212 | 29.676 | 42.092 | 60.862 | 1.00 | 0.00 |
| ATOM | 3105 | H2 | TIP3 | 212 | 29.675 | 40.922 | 59.897 | 1.00 | 0.00 |
| ATOM | 3106 | OH2 | TIP3 | 213 | 31.614 | 21.247 | 87.320 | 1.00 | 46.06 |
| ATOM | 3107 | H1 | TIP3 | 213 | 31.617 | 22.200 | 87.305 | 1.00 | 0.00 |
| ATOM | 3108 | H2 | TIP3 | 213 | 31.617 | 21.003 | 86.379 | 1.00 | 0.00 |
| ATOM | 3119 | OH2 | TIP3 | 215 | 5.863 | 29.181 | 94.415 | 1.00 | 45.31 |
| ATOM | 3110 | H1 | TIP3 | 215 | 5.856 | 30.140 | 94.427 | 1.00 | 0.00 |
| ATOM | 3111 | H2 | TIP3 | 215 | 5.856 | 28.943 | 93.499 | 1.00 | 0.00 |
| ATOM | 3112 | OH2 | TIP3 | 218 | 31.334 | 49.047 | 55.917 | 1.00 | 45.99 |
| ATOM | 3113 | H1 | TIP3 | 218 | 31.336 | 49.989 | 55.905 | 1.00 | 0.00 |
| ATOM | 3114 | H2 | TIP3 | 218 | 31.336 | 48.790 | 54.980 | 1.00 | 0.00 |
| ATOM | 3115 | OH2 | TIP3 | 219 | 31.833 | 65.255 | 66.839 | 1.00 | 38.18 |
| ATOM | 3116 | H1 | TIP3 | 219 | 31.844 | 66.227 | 66.847 | 1.00 | 0.00 |
| ATOM | 3117 | H2 | TIP3 | 219 | 31.844 | 65.031 | 65.919 | 1.00 | 0.00 |
| ATOM | 3118 | OH2 | TIP3 | 223 | 14.630 | 19.309 | 88.243 | 1.00 | 26.28 |
| ATOM | 3129 | H1 | TIP3 | 223 | 14.603 | 20.263 | 88.235 | 1.00 | 0.00 |
| ATOM | 3120 | H2 | TIP3 | 223 | 14.603 | 19.066 | 87.309 | 1.00 | 0.00 |
| ATOM | 3121 | OH2 | TIP3 | 224 | 3.173 | 49.592 | 72.023 | 1.00 | 43.32 |
| ATOM | 3122 | H1 | TIP3 | 224 | 3.173 | 50.555 | 72.013 | 1.00 | 0.00 |
| ATOM | 3123 | H2 | TIP3 | 224 | 3.173 | 49.359 | 71.087 | 1.00 | 0.00 |
| ATOM | 3124 | OH2 | TIP3 | 225 | 2.989 | 38.449 | 95.328 | 1.00 | 48.51 |
| ATOM | 3125 | H1 | TIP3 | 225 | 2.987 | 39.405 | 95.342 | 1.00 | 0.00 |
| ATOM | 3126 | H2 | TIP3 | 225 | 2.986 | 38.209 | 94.415 | 1.00 | 0.00 |
| ATOM | 3127 | OH2 | TIP3 | 228 | 36.022 | 41.179 | 63.166 | 1.00 | 35.50 |
| ATOM | 3128 | H1 | TIP3 | 228 | 36.019 | 42.133 | 63.154 | 1.00 | 0.00 |
| ATOM | 3139 | H2 | TIP3 | 228 | 36.049 | 40.936 | 62.229 | 1.00 | 0.00 |
| ATOM | 3130 | OH2 | TIP3 | 229 | 13.132 | 67.094 | 76.080 | 1.00 | 37.20 |
| ATOM | 3131 | H1 | TIP3 | 229 | 13.108 | 68.067 | 76.064 | 1.00 | 0.00 |
| ATOM | 3132 | H2 | TIP3 | 229 | 13.121 | 66.865 | 75.147 | 1.00 | 0.00 |
| ATOM | 3133 | OH2 | TIP3 | 200 | 24.694 | 26.099 | 78.276 | 1.00 | 44.32 |
| ATOM | 3134 | H1 | TIP3 | 230 | 24.725 | 27.040 | 78.264 | 1.00 | 0.00 |
| ATOM | 3135 | H2 | TIP3 | 230 | 24.725 | 25.842 | 77.338 | 1.00 | 0.00 |
| ATOM | 3136 | OH2 | TIP3 | 231 | 29.513 | 19.508 | 86.524 | 1.00 | 42.10 |
| ATOM | 3137 | H1 | TIP3 | 231 | 29.513 | 20.473 | 86.521 | 1.00 | 0.00 |
| ATOM | 3138 | H2 | TIP3 | 231 | 29.513 | 19.277 | 85.594 | 1.00 | 0.00 |
| ATOM | 3149 | OH2 | TIP3 | 233 | 0.163 | 49.406 | 74.295 | 1.00 | 42.56 |
| ATOM | 3140 | H1 | TIP3 | 233 | 0.171 | 50.374 | 74.290 | 1.00 | 0.00 |
| ATOM | 3141 | H2 | TIP3 | 233 | 0.171 | 49.179 | 73.364 | 1.00 | 0.00 |
| ATOM | 3142 | OH2 | TIP3 | 236 | 34.366 | 49.149 | 60.593 | 1.00 | 36.82 |
| ATOM | 3143 | H1 | TIP3 | 236 | 34.356 | 50.114 | 60.580 | 1.00 | 0.00 |
| ATOM | 3144 | H2 | TIP3 | 236 | 34.356 | 48.918 | 59.654 | 1.00 | 0.00 |
| ATOM | 3145 | OH2 | TIP3 | 237 | 18.051 | 51.168 | 87.274 | 1.00 | 39.76 |
| ATOM | 3146 | H1 | TIP3 | 237 | 18.059 | 52.110 | 87.258 | 1.00 | 0.00 |
| ATOM | 3147 | H2 | TIP3 | 237 | 18.059 | 50.911 | 86.333 | 1.00 | 0.00 |
| ATOM | 3148 | OH2 | TIP3 | 239 | 29.757 | 43.217 | 90.673 | 1.00 | 43.28 |
| ATOM | 3159 | H1 | TIP3 | 239 | 29.753 | 44.168 | 90.682 | 1.00 | 0.00 |
| ATOM | 3150 | H2 | TIP3 | 239 | 29.753 | 42.970 | 89.755 | 1.00 | 0.00 |
| ATOM | 3151 | OH2 | TIP3 | 240 | 17.585 | 53.225 | 91.151 | 1.00 | 45.05 |
| ATOM | 3152 | H1 | TIP3 | 240 | 17.585 | 54.183 | 91.148 | 1.00 | 0.00 |
| ATOM | 3153 | H2 | TIP3 | 240 | 17.585 | 52.986 | 90.221 | 1.00 | 0.00 |
| ATOM | 3154 | OH2 | TIP3 | 242 | 34.142 | 34.192 | 99.567 | 1.00 | 41.49 |
| ATOM | 3155 | H1 | TIP3 | 242 | 34.143 | 35.133 | 99.577 | 1.00 | 0.00 |
| ATOM | 3156 | H2 | TIP3 | 242 | 34.143 | 33.934 | 98.650 | 1.00 | 0.00 |
| ATOM | 3157 | OH2 | TIP3 | 244 | −3.666 | 24.202 | 91.704 | 1.00 | 43.26 |
| ATOM | 3158 | H1 | TIP3 | 244 | −3.649 | 25.161 | 91.695 | 1.00 | 0.00 |
| ATOM | 3169 | H2 | TIP3 | 244 | −3.649 | 23.964 | 90.769 | 1.00 | 0.00 |
| ATOM | 3160 | OH2 | TIP3 | 249 | 35.236 | 35.723 | 87.883 | 1.00 | 49.44 |
| ATOM | 3161 | H1 | TIP3 | 249 | 35.233 | 36.677 | 87.888 | 1.00 | 0.00 |
| ATOM | 3162 | H2 | TIP3 | 249 | 35.233 | 35.480 | 86.961 | 1.00 | 0.00 |
| ATOM | 3163 | OH2 | TIP3 | 251 | 13.730 | 38.753 | 104.272 | 1.00 | 37.86 |
| ATOM | 3164 | H1 | TIP3 | 251 | 13.749 | 39.706 | 104.269 | 1.00 | 0.00 |
| ATOM | 3165 | H2 | TIP3 | 251 | 13.749 | 38.508 | 103.342 | 1.00 | 0.00 |

TABLE 5-continued

Coordinates of Lck bound with baicalein

| | Atom Type | Res | # | X | Y | Z | Occ | B |
|---|---|---|---|---|---|---|---|---|
| ATOM | 3166 | OH2 | TIP3 | 253 | 12.155 | 67.868 | 87.648 | 1.00 | 49.30 |
| ATOM | 3167 | H1 | TIP3 | 253 | 12.145 | 68.830 | 87.643 | 1.00 | 0.00 |
| ATOM | 3168 | H2 | TIP3 | 253 | 12.145 | 67.634 | 86.716 | 1.00 | 0.00 |
| ATOM | 3169 | OH2 | TIP3 | 255 | 24.052 | 54.570 | 85.478 | 1.00 | 43.94 |
| ATOM | 3170 | H1 | TIP3 | 255 | 24.056 | 55.525 | 85.481 | 1.00 | 0.00 |
| ATOM | 3171 | H2 | TIP3 | 255 | 24.056 | 54.328 | 84.554 | 1.00 | 0.00 |
| ATOM | 3172 | OH2 | TIP3 | 256 | 28.639 | 42.086 | 83.778 | 1.00 | 39.97 |
| ATOM | 3173 | H1 | TIP3 | 256 | 28.643 | 43.044 | 83.759 | 1.00 | 0.00 |
| ATOM | 3174 | H2 | TIP3 | 256 | 28.643 | 41.847 | 82.834 | 1.00 | 0.00 |
| ATOM | 3175 | OH2 | TIP3 | 260 | 28.422 | 34.137 | 100.602 | 1.00 | 51.29 |
| ATOM | 3176 | H1 | TIP3 | 260 | 28.431 | 35.090 | 100.593 | 1.00 | 0.00 |
| ATOM | 3177 | H2 | TIP3 | 260 | 28.431 | 33.893 | 99.667 | 1.00 | 0.00 |
| ATOM | 3178 | OH2 | TIP3 | 266 | 7.006 | 36.941 | 93.893 | 1.00 | 42.16 |
| ATOM | 3189 | H1 | TIP3 | 266 | 7.002 | 37.886 | 93.882 | 1.00 | 0.00 |
| ATOM | 3180 | H2 | TIP3 | 266 | 7.002 | 36.687 | 92.956 | 1.00 | 0.00 |
| ATOM | 3181 | OH2 | TIP3 | 269 | −0.225 | 64.883 | 67.924 | 1.00 | 46.69 |
| ATOM | 3182 | H1 | TIP3 | 269 | −0.202 | 65.840 | 67.929 | 1.00 | 0.00 |
| ATOM | 3183 | H2 | TIP3 | 269 | −0.202 | 64.643 | 67.002 | 1.00 | 0.00 |
| ATOM | 3184 | OH2 | TIP3 | 270 | 14.103 | 46.158 | 53.992 | 1.00 | 38.27 |
| ATOM | 3185 | H1 | TIP3 | 270 | 14.095 | 47.101 | 53.989 | 1.00 | 0.00 |
| ATOM | 3186 | H2 | TIP3 | 270 | 14.095 | 45.902 | 53.063 | 1.00 | 0.00 |
| ATOM | 3187 | OH2 | TIP3 | 271 | 35.595 | 52.905 | 75.973 | 1.00 | 33.90 |
| ATOM | 3188 | H1 | TIP3 | 271 | 35.568 | 53.881 | 75.967 | 1.00 | 0.00 |
| ATOM | 3199 | H2 | TIP3 | 271 | 35.568 | 52.686 | 75.041 | 1.00 | 0.00 |
| ATOM | 3190 | OH2 | TIP3 | 272 | 9.014 | 48.174 | 60.097 | 1.00 | 41.41 |
| ATOM | 3191 | H1 | TIP3 | 272 | 9.016 | 49.148 | 60.090 | 1.00 | 0.00 |
| ATOM | 3192 | H2 | TIP3 | 272 | 9.016 | 47.952 | 59.163 | 1.00 | 0.00 |
| ATOM | 3193 | OH2 | TIP3 | 276 | 3.993 | 37.937 | 70.251 | 1.00 | 39.07 |
| ATOM | 3194 | H1 | TIP3 | 276 | 4.015 | 38.830 | 70.226 | 1.00 | 0.00 |
| ATOM | 3195 | H2 | TIP3 | 276 | 4.004 | 37.736 | 69.329 | 1.00 | 0.00 |
| ATOM | 3196 | OH2 | TIP3 | 277 | −2.077 | 21.227 | 94.519 | 1.00 | 27.79 |
| ATOM | 3197 | H1 | TIP3 | 277 | −2.093 | 22.183 | 94.531 | 1.00 | 0.00 |
| ATOM | 3198 | H2 | TIP3 | 277 | −2.094 | 20.986 | 93.605 | 1.00 | 0.00 |
| ATOM | 3199 | OH2 | TIP3 | 303 | 34.610 | 25.604 | 92.283 | 1.00 | 39.62 |
| ATOM | 3200 | H1 | TIP3 | 303 | 34.606 | 26.571 | 92.295 | 1.00 | 0.00 |
| ATOM | 3201 | H2 | TIP3 | 303 | 34.606 | 25.375 | 91.367 | 1.00 | 0.00 |
| ATOM | 3202 | OH2 | TIP3 | 310 | 32.154 | 40.044 | 63.511 | 1.00 | 40.04 |
| ATOM | 3203 | H1 | TIP3 | 310 | 32.163 | 41.007 | 63.509 | 1.00 | 0.00 |
| ATOM | 3204 | H2 | TIP3 | 310 | 32.163 | 39.810 | 62.582 | 1.00 | 0.00 |
| ATOM | 3205 | OH2 | TIP3 | 313 | 31.325 | 63.788 | 63.564 | 1.00 | 44.31 |
| ATOM | 3206 | H1 | TIP3 | 313 | 31.312 | 64.698 | 63.566 | 1.00 | 0.00 |
| ATOM | 3207 | H2 | TIP3 | 313 | 31.312 | 63.497 | 62.641 | 1.00 | 0.00 |
| ATOM | 3208 | OH2 | TIP3 | 325 | 26.451 | 64.212 | 87.620 | 1.00 | 38.85 |
| ATOM | 3219 | H1 | TIP3 | 325 | 26.458 | 65.173 | 87.628 | 1.00 | 0.00 |
| ATOM | 3210 | H2 | TIP3 | 325 | 26.458 | 63.976 | 86.700 | 1.00 | 0.00 |
| ATOM | 3211 | OH2 | TIP3 | 340 | 22.037 | 58.979 | 87.692 | 1.00 | 39.17 |
| ATOM | 3212 | H1 | TIP3 | 340 | 22.035 | 59.932 | 87.695 | 1.00 | 0.00 |
| ATOM | 3213 | H2 | TIP3 | 340 | 22.035 | 58.735 | 86.768 | 1.00 | 0.00 |
| ATOM | 3214 | OH2 | TIP3 | 342 | 8.991 | 56.736 | 62.029 | 1.00 | 44.02 |
| ATOM | 3215 | H1 | TIP3 | 342 | 8.994 | 57.709 | 62.023 | 1.00 | 0.00 |
| ATOM | 3216 | H2 | TIP3 | 342 | 8.994 | 56.513 | 61.097 | 1.00 | 0.00 |
| ATOM | 3217 | OH2 | TIP3 | 349 | 21.450 | 48.837 | 89.164 | 1.00 | 43.52 |
| ATOM | 3218 | H1 | TIP3 | 349 | 21.457 | 49.796 | 89.158 | 1.00 | 0.00 |
| ATOM | 3229 | H2 | TIP3 | 349 | 21.457 | 48.600 | 88.231 | 1.00 | 0.00 |
| ATOM | 3220 | OH2 | TIP3 | 358 | 8.768 | 55.698 | 57.689 | 1.00 | 45.43 |
| ATOM | 3221 | H1 | TIP3 | 358 | 8.773 | 56.661 | 57.694 | 1.00 | 0.00 |
| ATOM | 3222 | H2 | TIP3 | 358 | 8.773 | 55.464 | 56.767 | 1.00 | 0.00 |
| ATOM | 3223 | OH2 | TIP3 | 377 | 15.491 | 35.840 | 101.679 | 1.00 | 32.23 |
| ATOM | 3224 | H1 | TIP3 | 377 | 15.491 | 36.794 | 101.718 | 1.00 | 0.00 |
| ATOM | 3225 | H2 | TIP3 | 377 | 15.491 | 35.597 | 100.789 | 1.00 | 0.00 |
| ATOM | 3226 | OH2 | TIP3 | 390 | 26.883 | 27.457 | 73.706 | 1.00 | 43.62 |
| ATOM | 3227 | H1 | TIP3 | 390 | 26.892 | 28.425 | 73.727 | 1.00 | 0.00 |
| ATOM | 3228 | H2 | TIP3 | 390 | 26.892 | 27.229 | 72.798 | 1.00 | 0.00 |
| ATOM | 3239 | OH2 | TIP3 | 391 | −0.663 | 50.621 | 70.815 | 1.00 | 34.21 |
| ATOM | 3230 | H1 | TIP3 | 391 | −0.653 | 51.577 | 70.814 | 1.00 | 0.00 |
| ATOM | 3231 | H2 | TIP3 | 391 | −0.653 | 50.380 | 69.887 | 1.00 | 0.00 |
| ATOM | 3232 | OH2 | TIP3 | 393 | 32.944 | 45.838 | 55.436 | 1.00 | 38.53 |
| ATOM | 3233 | H1 | TIP3 | 393 | 32.948 | 46.777 | 55.433 | 1.00 | 0.00 |
| ATOM | 3234 | H2 | TIP3 | 393 | 32.948 | 45.578 | 54.507 | 1.00 | 0.00 |
| ATOM | 3235 | OH2 | TIP3 | 398 | 13.375 | 41.983 | 103.297 | 1.00 | 35.66 |
| ATOM | 3236 | H1 | TIP3 | 398 | 13.371 | 42.930 | 103.304 | 1.00 | 0.00 |
| ATOM | 3237 | H2 | TIP3 | 398 | 13.371 | 41.732 | 102.377 | 1.00 | 0.00 |
| ATOM | 3238 | OH2 | TIP3 | 304 | 1.283 | 60.549 | 66.767 | 1.00 | 40.47 |
| ATOM | 3239 | H1 | TIP3 | 304 | 1.290 | 61.484 | 66.773 | 1.00 | 0.00 |

TABLE 5-continued

Coordinates of Lck bound with baicalein

| | Atom Type | Res | # | X | Y | Z | Occ | B |
|---|---|---|---|---|---|---|---|---|
| ATOM | 3240 | H2 | TIP3 | 304 | 1.290 | 60.285 | 65.846 | 1.00 | 0.00 |
| ATOM | 3241 | OH2 | TIP3 | 316 | 16.119 | 46.405 | 89.865 | 1.00 | 42.56 |
| ATOM | 3242 | H1 | TIP3 | 316 | 16.132 | 47.364 | 89.876 | 1.00 | 0.00 |
| ATOM | 3243 | H2 | TIP3 | 316 | 16.132 | 46.167 | 88.948 | 1.00 | 0.00 |
| ATOM | 3244 | OH2 | TIP3 | 317 | 35.169 | 65.417 | 76.492 | 1.00 | 39.35 |
| ATOM | 3245 | H1 | TIP3 | 317 | 35.198 | 66.343 | 76.413 | 1.00 | 0.00 |
| ATOM | 3246 | H2 | TIP3 | 317 | 35.194 | 65.155 | 75.501 | 1.00 | 0.00 |
| ATOM | 3247 | OH2 | TIP3 | 330 | 34.450 | 38.176 | 76.641 | 1.00 | 33.32 |
| ATOM | 3248 | H1 | TIP3 | 330 | 34.432 | 39.140 | 76.655 | 1.00 | 0.00 |
| ATOM | 3259 | H2 | TIP3 | 330 | 34.432 | 37.943 | 75.727 | 1.00 | 0.00 |
| ATOM | 3250 | OH2 | TIP3 | 347 | 20.622 | 45.053 | 101.668 | 1.00 | 38.93 |
| ATOM | 3251 | H1 | TIP3 | 347 | 20.639 | 46.016 | 101.674 | 1.00 | 0.00 |
| ATOM | 3252 | H2 | TIP3 | 347 | 20.639 | 44.819 | 100.746 | 1.00 | 0.00 |
| ATOM | 3253 | OH2 | TIP3 | 351 | 37.829 | 65.419 | 72.893 | 1.00 | 40.12 |
| ATOM | 3254 | H1 | TIP3 | 351 | 37.843 | 66.378 | 72.898 | 1.00 | 0.00 |
| ATOM | 3255 | H2 | TIP3 | 351 | 37.843 | 65.181 | 71.971 | 1.00 | 0.00 |
| ATOM | 3256 | OH2 | TIP3 | 354 | 21.222 | 39.600 | 93.220 | 1.00 | 46.01 |
| ATOM | 3257 | H1 | TIP3 | 354 | 21.223 | 40.559 | 93.215 | 1.00 | 0.00 |
| ATOM | 3258 | H2 | TIP3 | 354 | 21.224 | 39.363 | 92.290 | 1.00 | 0.00 |
| ATOM | 3269 | OH2 | TIP3 | 366 | 15.649 | 43.126 | 46.430 | 1.00 | 42.53 |
| ATOM | 3260 | H1 | TIP3 | 366 | 15.652 | 44.084 | 56.427 | 1.00 | 0.00 |
| ATOM | 3261 | H2 | TIP3 | 366 | 15.652 | 42.887 | 55.500 | 1.00 | 0.00 |
| ATOM | 3262 | OH2 | TIP3 | 367 | 30.830 | 61.416 | 63.417 | 1.00 | 41.70 |
| ATOM | 3263 | H1 | TIP3 | 367 | 30.828 | 62.392 | 63.417 | 1.00 | 0.00 |
| ATOM | 3264 | H2 | TIP3 | 367 | 30.834 | 61.212 | 62.490 | 1.00 | 0.00 |
| ATOM | 3265 | OH2 | TIP3 | 380 | 23.839 | 38.640 | 104.721 | 1.00 | 40.58 |
| ATOM | 3266 | H1 | TIP3 | 380 | 23.843 | 39.621 | 104.725 | 1.00 | 0.00 |
| ATOM | 3267 | H2 | TIP3 | 380 | 23.844 | 38.427 | 103.793 | 1.00 | 0.00 |
| ATOM | 3268 | OH2 | TIP3 | 381 | 33.878 | 47.634 | 81.556 | 1.00 | 37.01 |
| ATOM | 3269 | H1 | TIP3 | 381 | 33.898 | 48.603 | 81.573 | 1.00 | 0.00 |
| ATOM | 3270 | H2 | TIP3 | 381 | 33.898 | 47.408 | 80.643 | 1.00 | 0.00 |
| ATOM | 3271 | S | SO4 | 901 | 20.230 | 32.853 | 69.408 | 1.00 | 16.74 |
| ATOM | 3272 | O1 | SO4 | 901 | 19.842 | 32.091 | 70.582 | 1.00 | 17.66 |
| ATOM | 3273 | O2 | SO4 | 901 | 19.030 | 33.293 | 68.733 | 1.00 | 17.53 |
| ATOM | 3274 | O3 | SO4 | 901 | 20.993 | 33.877 | 69.742 | 1.00 | 18.50 |
| ATOM | 3275 | O4 | SO4 | 901 | 21.008 | 31.936 | 68.530 | 1.00 | 18.75 |
| ATOM | 3276 | S | SO4 | 902 | 39.385 | 38.288 | 73.453 | 1.00 | 44.58 |
| ATOM | 3277 | O1 | SO4 | 902 | 38.420 | 37.298 | 73.146 | 1.00 | 44.98 |
| ATOM | 3278 | O2 | SO4 | 902 | 40.448 | 38.235 | 72.646 | 1.00 | 43.37 |
| ATOM | 3279 | O3 | SO4 | 902 | 38.756 | 39.591 | 73.520 | 1.00 | 43.91 |
| ATOM | 3280 | O4 | SO4 | 902 | 39.807 | 38.008 | 74.899 | 1.00 | 45.91 |
| ATOM | 3281 | S | SO4 | 903 | 14.891 | 67.067 | 81.000 | 1.00 | 51.63 |
| ATOM | 3282 | O1 | SO4 | 903 | 15.115 | 65.733 | 80.601 | 1.00 | 50.79 |
| ATOM | 3283 | O2 | SO4 | 903 | 13.718 | 67.663 | 80.451 | 1.00 | 50.45 |
| ATOM | 3284 | O3 | SO4 | 903 | 14.807 | 67.078 | 82.460 | 1.00 | 50.64 |
| ATOM | 3285 | O4 | SO4 | 903 | 16.051 | 67.833 | 80.531 | 1.00 | 50.67 |
| ATOM | 3286 | C1 | DTT | 1 | 16.130 | 35.259 | 66.098 | 1.00 | 28.41 |
| ATOM | 3287 | C2 | DTT | 1 | 15.362 | 34.118 | 66.149 | 1.00 | 27.01 |
| ATOM | 3288 | O3 | DTT | 1 | 16.194 | 33.575 | 65.224 | 1.00 | 28.30 |
| ATOM | 3289 | O6 | DTT | 1 | 15.894 | 36.464 | 66.317 | 1.00 | 28.97 |
| ATOM | 3290 | C1 | DTT | 2 | 17.884 | 37.942 | 85.285 | 1.00 | 32.78 |
| ATOM | 3291 | C2 | DTT | 2 | 17.695 | 38.313 | 83.794 | 1.00 | 32.82 |
| ATOM | 3292 | O3 | DTT | 2 | 18.897 | 38.890 | 83.322 | 1.00 | 33.86 |
| ATOM | 3293 | O6 | DTT | 2 | 18.103 | 39.123 | 86.070 | 1.00 | 35.27 |
| ATOM | 3294 | C1 | BAI | 1 | 23.417 | 38.153 | 84.880 | 1.00 | 25.90 |
| ATOM | 3295 | C2 | BAI | 1 | 24.772 | 38.198 | 84.668 | 1.00 | 25.45 |
| ATOM | 3296 | C3 | BAI | 1 | 25.393 | 37.353 | 83.750 | 1.00 | 24.85 |
| ATOM | 3297 | C4 | BAI | 1 | 24.673 | 36.351 | 83.006 | 1.00 | 24.86 |
| ATOM | 3298 | C5 | BAI | 1 | 23.261 | 36.220 | 83.172 | 1.00 | 24.31 |
| ATOM | 3299 | C6 | BAI | 1 | 22.601 | 37.144 | 84.139 | 1.00 | 25.75 |
| ATOM | 3300 | O8 | BAI | 1 | 26.743 | 37.458 | 83.580 | 1.00 | 25.60 |
| ATOM | 3301 | C9 | BAI | 1 | 27.465 | 36.663 | 82.654 | 1.00 | 24.70 |
| ATOM | 3302 | C10 | BAI | 1 | 26.832 | 35.694 | 81.969 | 1.00 | 24.35 |
| ATOM | 3303 | C11 | BAI | 1 | 25.366 | 35.495 | 82.105 | 1.00 | 24.14 |
| ATOM | 3304 | O13 | BAI | 1 | 24.989 | 34.636 | 81.438 | 1.00 | 26.77 |
| ATOM | 3305 | O14 | BAI | 1 | 21.290 | 37.013 | 84.370 | 1.00 | 26.75 |
| ATOM | 3306 | O15 | BAI | 1 | 22.726 | 38.887 | 85.706 | 1.00 | 28.53 |
| ATOM | 3307 | O16 | BAI | 1 | 22.419 | 35.366 | 82.603 | 1.00 | 25.24 |
| ATOM | 3308 | C20 | BAI | 1 | 28.855 | 36.902 | 82.491 | 1.00 | 24.01 |
| ATOM | 3309 | C21 | BAI | 1 | 29.653 | 36.041 | 81.723 | 1.00 | 21.71 |
| ATOM | 3310 | C22 | BAI | 1 | 31.008 | 36.307 | 81.593 | 1.00 | 22.54 |
| ATOM | 3311 | C23 | BAI | 1 | 31.606 | 37.405 | 82.231 | 1.00 | 22.25 |

TABLE 5-continued

Coordinates of Lck bound with baicalein

| | | Atom Type | Res | # | X | Y | Z | Occ | B |
|---|---|---|---|---|---|---|---|---|---|
| ATOM | 3312 | C24 | BAI | 1 | 30.860 | 38.273 | 82.996 | 1.00 | 22.57 |
| ATOM | 3313 | C25 | BAI | 1 | 27.479 | 38.036 | 83.140 | 1.00 | 24.07 |
| END | | | | | | | | | |

TABLE 6

Coordinates of Lck bound with damnacanthal

| | | Atom Type | Res | # | X | Y | Z | Occ | B |
|---|---|---|---|---|---|---|---|---|---|
| ATOM | 1 | CB | LYS | 231 | 1.427 | 26.880 | 89.991 | 1.00 | 38.67 |
| ATOM | 2 | CG | LYS | 231 | 0.473 | 26.776 | 88.817 | 1.00 | 40.51 |
| ATOM | 3 | CD | LYS | 231 | 0.998 | 25.829 | 87.752 | 1.00 | 44.40 |
| ATOM | 4 | CE | LYS | 231 | 0.045 | 25.778 | 86.568 | 1.00 | 47.72 |
| ATOM | 5 | NZ | LYS | 231 | 0.595 | 25.008 | 85.400 | 1.00 | 51.52 |
| ATOM | 6 | HZ1 | LYS | 231 | 0.789 | 24.028 | 85.690 | 1.00 | 0.00 |
| ATOM | 7 | HZ2 | LYS | 231 | 1.477 | 25.454 | 85.075 | 1.00 | 0.00 |
| ATOM | 8 | HZ3 | LYS | 231 | −0.099 | 25.009 | 84.626 | 1.00 | 0.00 |
| ATOM | 9 | C | LYS | 231 | 1.848 | 27.511 | 92.360 | 1.00 | 34.63 |
| ATOM | 10 | O | LYS | 231 | 2.919 | 28.123 | 92.464 | 1.00 | 30.30 |
| ATOM | 11 | HT1 | LYS | 231 | 1.736 | 29.555 | 90.512 | 1.00 | 0.00 |
| ATOM | 12 | HT2 | LYS | 231 | 0.418 | 29.732 | 91.568 | 1.00 | 0.00 |
| ATOM | 13 | N | LYS | 231 | 0.799 | 29.185 | 90.770 | 1.00 | 41.10 |
| ATOM | 14 | HT3 | LYS | 231 | 0.157 | 29.268 | 89.956 | 1.00 | 0.00 |
| ATOM | 15 | CA | LYS | 231 | 0.922 | 27.738 | 91.166 | 1.00 | 38.10 |
| ATOM | 16 | N | PRO | 232 | 1.421 | 26.651 | 93.302 | 1.00 | 32.50 |
| ATOM | 17 | CD | PRO | 232 | 0.129 | 25.956 | 93.371 | 1.00 | 31.93 |
| ATOM | 18 | CA | PRO | 232 | 2.231 | 26.342 | 94.483 | 1.00 | 28.62 |
| ATOM | 19 | CB | PRO | 232 | 1.316 | 25.423 | 95.309 | 1.00 | 25.08 |
| ATOM | 20 | CG | PRO | 232 | 0.417 | 24.870 | 94.361 | 1.00 | 25.21 |
| ATOM | 21 | C | PRO | 232 | 3.489 | 25.652 | 93.987 | 1.00 | 26.57 |
| ATOM | 22 | O | PRO | 232 | 3.520 | 25.074 | 92.892 | 1.00 | 23.89 |
| ATOM | 23 | N | TRP | 233 | 4.546 | 25.758 | 94.768 | 1.00 | 26.20 |
| ATOM | 24 | H | TRP | 233 | 4.478 | 26.211 | 95.634 | 1.00 | 0.00 |
| ATOM | 25 | CA | TRP | 233 | 5.824 | 25.209 | 94.363 | 1.00 | 23.97 |
| ATOM | 26 | CB | TRP | 233 | 6.906 | 25.565 | 95.388 | 1.00 | 18.91 |
| ATOM | 27 | CG | TRP | 233 | 6.864 | 24.768 | 96.641 | 1.00 | 18.57 |
| ATOM | 28 | CD2 | TRP | 233 | 7.297 | 23.416 | 96.806 | 1.00 | 18.98 |
| ATOM | 29 | CE2 | TRP | 233 | 7.049 | 23.066 | 98.145 | 1.00 | 20.07 |
| ATOM | 30 | CE3 | TRP | 233 | 7.878 | 22.463 | 95.948 | 1.00 | 16.20 |
| ATOM | 31 | CD1 | TRP | 233 | 6.402 | 25.173 | 97.841 | 1.00 | 18.75 |
| ATOM | 32 | NE1 | TRP | 233 | 6.514 | 24.168 | 98.760 | 1.00 | 13.75 |
| ATOM | 33 | HE1 | TRP | 233 | 6.256 | 24.225 | 99.699 | 1.00 | 0.00 |
| ATOM | 34 | CZ2 | TRP | 233 | 7.338 | 21.782 | 98.657 | 1.00 | 16.30 |
| ATOM | 35 | CZ3 | TRP | 233 | 8.174 | 21.196 | 96.463 | 1.00 | 15.25 |
| ATOM | 36 | CH2 | TRP | 233 | 7.901 | 20.873 | 97.808 | 1.00 | 11.72 |
| ATOM | 37 | C | TRP | 233 | 5.845 | 23.715 | 93.986 | 1.00 | 24.83 |
| ATOM | 38 | O | TRP | 233 | 6.643 | 23.328 | 93.142 | 1.00 | 22.87 |
| ATOM | 39 | N | TRP | 234 | 4.955 | 22.895 | 94.556 | 1.00 | 24.77 |
| ATOM | 40 | H | TRP | 234 | 4.299 | 23.236 | 95.199 | 1.00 | 0.00 |
| ATOM | 41 | CA | TRP | 234 | 4.957 | 21.452 | 94.213 | 1.00 | 24.87 |
| ATOM | 42 | CB | TRP | 234 | 4.323 | 20.585 | 95.305 | 1.00 | 18.13 |
| ATOM | 43 | CG | TRP | 234 | 2.959 | 21.022 | 95.678 | 1.00 | 14.29 |
| ATOM | 44 | CD2 | TRP | 234 | 2.626 | 21.912 | 96.735 | 1.00 | 11.77 |
| ATOM | 45 | CE2 | TRP | 234 | 1.234 | 22.054 | 96.749 | 1.00 | 11.68 |
| ATOM | 46 | CE3 | TRP | 234 | 3.374 | 22.648 | 97.671 | 1.00 | 15.65 |
| ATOM | 47 | CD1 | TRP | 234 | 1.797 | 20.660 | 95.086 | 1.00 | 10.81 |
| ATOM | 48 | NE1 | TRP | 234 | 0.751 | 21.266 | 95.729 | 1.00 | 12.41 |
| ATOM | 49 | HE1 | TRP | 234 | −0.191 | 21.156 | 95.500 | 1.00 | 0.00 |
| ATOM | 50 | CZ2 | TRP | 234 | 0.552 | 22.888 | 97.645 | 1.00 | 15.58 |
| ATOM | 51 | CZ3 | TRP | 234 | 2.700 | 23.506 | 98.569 | 1.00 | 15.13 |
| ATOM | 52 | CH2 | TRP | 234 | 1.308 | 23.613 | 98.546 | 1.00 | 14.31 |
| ATOM | 53 | C | TRP | 234 | 4.288 | 21.159 | 92.894 | 1.00 | 27.03 |
| ATOM | 54 | O | TRP | 234 | 4.389 | 20.049 | 92.378 | 1.00 | 28.98 |
| ATOM | 55 | N | GLU | 235 | 3.683 | 22.187 | 92.309 | 1.00 | 30.25 |
| ATOM | 56 | H | GLU | 235 | 3.692 | 23.067 | 92.740 | 1.00 | 0.00 |
| ATOM | 57 | CA | GLU | 235 | 2.997 | 22.048 | 91.029 | 1.00 | 31.13 |
| ATOM | 58 | CB | GLU | 235 | 1.538 | 22.490 | 91.140 | 1.00 | 31.13 |
| ATOM | 59 | CG | GLU | 235 | 0.636 | 21.616 | 91.994 | 1.00 | 31.06 |
| ATOM | 60 | CD | GLU | 235 | −0.842 | 21.859 | 91.709 | 1.00 | 36.26 |

TABLE 6-continued

Coordinates of Lck bound with damnacanthal

| | | Atom Type | Res | # | X | Y | Z | Occ | B |
|---|---|---|---|---|---|---|---|---|---|
| ATOM | 61 | OE1 | GLU | 235 | -1.175 | 22.712 | 90.860 | 1.00 | 39.57 |
| ATOM | 62 | OE2 | GLU | 235 | -1.692 | 21.188 | 92.314 | 1.00 | 38.42 |
| ATOM | 63 | C | GLU | 235 | 3.672 | 22.907 | 89.971 | 1.00 | 30.39 |
| ATOM | 64 | O | GLU | 235 | 3.398 | 22.778 | 88.783 | 1.00 | 34.51 |
| ATOM | 65 | N | ASP | 236 | 4.537 | 23.801 | 90.418 | 1.00 | 29.59 |
| ATOM | 66 | H | ASP | 236 | 4.721 | 23.851 | 91.379 | 1.00 | 0.00 |
| ATOM | 67 | CA | ASP | 236 | 5.247 | 24.737 | 89.531 | 1.00 | 28.65 |
| ATOM | 68 | CB | ASP | 236 | 5.996 | 25.744 | 90.416 | 1.00 | 27.24 |
| ATOM | 69 | CG | ASP | 236 | 6.449 | 26.972 | 89.672 | 1.00 | 28.39 |
| ATOM | 70 | OD1 | ASP | 236 | 6.204 | 27.075 | 88.450 | 1.00 | 27.44 |
| ATOM | 71 | OD2 | ASP | 236 | 7.059 | 27.835 | 90.338 | 1.00 | 28.94 |
| ATOM | 72 | C | ASP | 236 | 6.240 | 24.035 | 88.603 | 1.00 | 28.13 |
| ATOM | 73 | O | ASP | 236 | 7.163 | 23.358 | 89.065 | 1.00 | 27.10 |
| ATOM | 74 | N | ALA | 237 | 6.078 | 24.245 | 87.304 | 1.00 | 26.66 |
| ATOM | 75 | H | ALA | 237 | 5.338 | 24.807 | 86.992 | 1.00 | 0.00 |
| ATOM | 76 | CA | ALA | 237 | 6.975 | 23.661 | 86.307 | 1.00 | 26.34 |
| ATOM | 77 | CB | ALA | 237 | 6.442 | 23.919 | 84.916 | 1.00 | 29.79 |
| ATOM | 78 | C | ALA | 237 | 8.417 | 24.188 | 86.398 | 1.00 | 23.49 |
| ATOM | 79 | O | ALA | 237 | 9.333 | 23.541 | 85.908 | 1.00 | 21.90 |
| ATOM | 80 | N | TRP | 238 | 8.593 | 25.360 | 87.007 | 1.00 | 22.18 |
| ATOM | 81 | H | TRP | 238 | 7.811 | 25.818 | 87.380 | 1.00 | 0.00 |
| ATOM | 82 | CA | TRP | 238 | 9.904 | 26.024 | 87.160 | 1.00 | 21.07 |
| ATOM | 83 | CB | TRP | 238 | 9.763 | 27.549 | 86.965 | 1.00 | 21.39 |
| ATOM | 84 | CG | TRP | 238 | 9.881 | 27.968 | 85.453 | 1.00 | 25.02 |
| ATOM | 85 | CD2 | TRP | 238 | 8.827 | 28.390 | 84.595 | 1.00 | 24.54 |
| ATOM | 86 | CE2 | TRP | 238 | 9.403 | 28.669 | 83.324 | 1.00 | 25.33 |
| ATOM | 87 | CE3 | TRP | 238 | 7.452 | 28.549 | 84.765 | 1.00 | 23.37 |
| ATOM | 88 | CD1 | TRP | 238 | 11.029 | 28.003 | 84.680 | 1.00 | 24.50 |
| ATOM | 89 | NE1 | TRP | 238 | 10.743 | 28.420 | 83.403 | 1.00 | 19.22 |
| ATOM | 90 | HE1 | TRP | 238 | 11.386 | 28.521 | 82.678 | 1.00 | 0.00 |
| ATOM | 91 | CZ2 | TRP | 238 | 8.656 | 29.108 | 82.256 | 1.00 | 27.40 |
| ATOM | 92 | CZ3 | TRP | 238 | 6.701 | 28.984 | 83.685 | 1.00 | 26.56 |
| ATOM | 93 | CH2 | TRP | 238 | 7.307 | 29.256 | 82.444 | 1.00 | 31.01 |
| ATOM | 94 | C | TRP | 238 | 10.641 | 25.740 | 88.482 | 1.00 | 19.28 |
| ATOM | 95 | O | TRP | 238 | 11.800 | 26.079 | 88.606 | 1.00 | 18.70 |
| ATOM | 96 | N | GLU | 239 | 9.956 | 25.225 | 89.496 | 1.00 | 15.50 |
| ATOM | 97 | H | GLU | 239 | 8.994 | 25.056 | 89.424 | 1.00 | 0.00 |
| ATOM | 98 | CA | GLU | 239 | 10.660 | 24.907 | 90.743 | 1.00 | 13.71 |
| ATOM | 99 | CB | GLU | 239 | 9.635 | 24.659 | 91.879 | 1.00 | 12.75 |
| ATOM | 100 | CG | GLU | 239 | 10.242 | 24.435 | 93.249 | 1.00 | 12.94 |
| ATOM | 101 | CD | GLU | 239 | 10.459 | 25.731 | 94.027 | 1.00 | 14.63 |
| ATOM | 102 | OE1 | GLU | 239 | 9.696 | 26.701 | 93.812 | 1.00 | 14.73 |
| ATOM | 103 | OE2 | GLU | 239 | 11.410 | 25.807 | 94.838 | 1.00 | 17.90 |
| ATOM | 104 | C | GLU | 239 | 11.539 | 23.620 | 90.551 | 1.00 | 11.61 |
| ATOM | 105 | O | GLU | 239 | 11.122 | 22.659 | 89.906 | 1.00 | 9.57 |
| ATOM | 106 | N | VAL | 240 | 12.789 | 23.688 | 90.994 | 1.00 | 11.30 |
| ATOM | 107 | H | VAL | 240 | 13.127 | 24.530 | 91.364 | 1.00 | 0.00 |
| ATOM | 108 | CA | VAL | 240 | 13.686 | 22.547 | 90.951 | 1.00 | 13.32 |
| ATOM | 109 | CB | VAL | 240 | 14.875 | 22.678 | 89.949 | 1.00 | 14.04 |
| ATOM | 110 | CG1 | VAL | 240 | 14.364 | 22.873 | 88.535 | 1.00 | 15.77 |
| ATOM | 111 | CG2 | VAL | 240 | 15.893 | 23.786 | 90.394 | 1.00 | 16.94 |
| ATOM | 112 | C | VAL | 240 | 14.282 | 22.360 | 92.316 | 1.00 | 15.05 |
| ATOM | 113 | O | VAL | 240 | 14.348 | 23.303 | 93.101 | 1.00 | 14.24 |
| ATOM | 114 | N | PRO | 241 | 14.706 | 21.120 | 92.635 | 1.00 | 15.03 |
| ATOM | 115 | CD | PRO | 241 | 14.431 | 19.852 | 91.917 | 1.00 | 16.06 |
| ATOM | 116 | CA | PRO | 241 | 15.318 | 20.865 | 93.941 | 1.00 | 14.36 |
| ATOM | 117 | CB | PRO | 241 | 15.404 | 19.333 | 93.974 | 1.00 | 15.16 |
| ATOM | 118 | CG | PRO | 241 | 14.255 | 18.881 | 93.050 | 1.00 | 12.77 |
| ATOM | 119 | C | PRO | 241 | 16.718 | 21.530 | 93.921 | 1.00 | 16.91 |
| ATOM | 120 | O | PRO | 241 | 17.390 | 21.564 | 92.880 | 1.00 | 15.35 |
| ATOM | 121 | N | ARG | 242 | 17.127 | 22.101 | 95.056 | 1.00 | 21.08 |
| ATOM | 122 | H | ARG | 242 | 16.552 | 22.064 | 95.849 | 1.00 | 0.00 |
| ATOM | 123 | CA | ARG | 242 | 18.421 | 22.793 | 95.169 | 1.00 | 21.52 |
| ATOM | 124 | CB | ARG | 242 | 18.607 | 23.393 | 96.560 | 1.00 | 16.18 |
| ATOM | 125 | CG | ARG | 242 | 19.771 | 24.404 | 96.568 | 1.00 | 24.52 |
| ATOM | 126 | CD | ARG | 242 | 20.192 | 24.933 | 97.939 | 1.00 | 25.96 |
| ATOM | 127 | NE | ARG | 242 | 19.075 | 25.411 | 98.749 | 1.00 | 27.78 |
| ATOM | 128 | HE | ARG | 242 | 18.722 | 24.817 | 99.443 | 1.00 | 0.00 |
| ATOM | 129 | CZ | ARG | 242 | 18.511 | 26.599 | 98.602 | 1.00 | 27.12 |
| ATOM | 130 | NH1 | ARG | 242 | 18.961 | 27.436 | 97.672. | 1.00 | 33.19 |
| ATOM | 131 | HH11 | ARG | 242 | 19.725 | 27.167 | 97.085 | 1.00 | 0.00 |
| ATOM | 132 | HH12 | ARG | 242 | 18.536 | 28.334 | 97.560 | 1.00 | 0.00 |
| ATOM | 133 | NH2 | ARG | 242 | 17.475 | 26.932 | 99.355 | 1.00 | 30.80 |
| ATOM | 134 | HH21 | ARG | 242 | 17.121 | 26.287 | 100.032 | 1.00 | 0.00 |

TABLE 6-continued

Coordinates of Lck bound with damnacanthal

| | | Atom Type | Res | # | X | Y | Z | Occ | B |
|---|---|---|---|---|---|---|---|---|---|
| ATOM | 135 | HH22 | ARG | 242 | 17.046 | 27.829 | 99.247 | 1.00 | 0.00 |
| ATOM | 136 | C | ARG | 242 | 19.646 | 21.904 | 94.829 | 1.00 | 21.32 |
| ATOM | 137 | O | ARG | 242 | 20.690 | 22.408 | 94.383 | 1.00 | 20.76 |
| ATOM | 138 | N | GLU | 243 | 19.471 | 20.589 | 94.979 | 1.00 | 19.29 |
| ATOM | 139 | H | GLU | 243 | 18.600 | 20.262 | 95.285 | 1.00 | 0.00 |
| ATOM | 140 | CA | GLU | 243 | 20.514 | 19.585 | 94.712 | 1.00 | 21.02 |
| ATOM | 141 | CB | GLU | 243 | 20.077 | 18.201 | 95.248 | 1.00 | 26.54 |
| ATOM | 142 | CG | GLU | 243 | 19.968 | 18.084 | 96.784 | 1.00 | 31.62 |
| ATOM | 143 | CD | GLU | 243 | 18.743 | 18.787 | 97.361 | 1.00 | 32.10 |
| ATOM | 144 | OE1 | GLU | 243 | 17.772 | 18.966 | 96.599 | 1.00 | 28.25 |
| ATOM | 145 | OE2 | GLU | 243 | 18.752 | 19.168 | 98.567 | 1.00 | 31.44 |
| ATOM | 146 | C | GLU | 243 | 20.831 | 19.455 | 93.217 | 1.00 | 22.07 |
| ATOM | 147 | O | GLU | 243 | 21.787 | 18.777 | 92.844 | 1.00 | 24.53 |
| ATOM | 148 | N | THR | 244 | 19.966 | 20.008 | 92.357 | 1.00 | 21.56 |
| ATOM | 149 | H | THR | 244 | 19.162 | 20.458 | 92.691 | 1.00 | 0.00 |
| ATOM | 150 | CA | THR | 244 | 20.195 | 19.957 | 90.908 | 1.00 | 16.31 |
| ATOM | 151 | CB | THR | 244 | 18.882 | 20.224 | 90.138 | 1.00 | 19.16 |
| ATOM | 152 | OG1 | THR | 244 | 18.353 | 21.508 | 90.512 | 1.00 | 12.78 |
| ATOM | 153 | HG1 | THR | 244 | 17.538 | 21.671 | 90.032 | 1.00 | 0.00 |
| ATOM | 154 | CG2 | THR | 244 | 17.821 | 19.077 | 90.421 | 1.00 | 14.64 |
| ATOM | 155 | C | THR | 244 | 21.213 | 21.020 | 90.479 | 1.00 | 14.23 |
| ATOM | 156 | O | THR | 244 | 21.658 | 21.032 | 89.340 | 1.00 | 13.16 |
| ATOM | 157 | N | LEU | 245 | 21.646 | 21.852 | 91.416 | 1.00 | 12.58 |
| ATOM | 158 | H | LEU | 245 | 21.366 | 21.744 | 92.349 | 1.00 | 0.00 |
| ATOM | 159 | CA | LEU | 245 | 22.550 | 22.944 | 91.064 | 1.00 | 12.96 |
| ATOM | 160 | CB | LEU | 245 | 21.885 | 24.286 | 91.406 | 1.00 | 11.93 |
| ATOM | 161 | CG | LEU | 245 | 20.525 | 24.551 | 90.766 | 1.00 | 12.85 |
| ATOM | 162 | CD1 | LEU | 245 | 19.753 | 25.620 | 91.560 | 1.00 | 12.04 |
| ATOM | 163 | CD2 | LEU | 245 | 20.709 | 24.937 | 89.312 | 1.00 | 5.30 |
| ATOM | 164 | C | LEU | 245 | 23.895 | 22.923 | 91.738 | 1.00 | 13.48 |
| ATOM | 165 | O | LEU | 245 | 24.009 | 22.645 | 92.901 | 1.00 | 18.88 |
| ATOM | 166 | N | LYS | 246 | 24.926 | 23.261 | 90.998 | 1.00 | 12.85 |
| ATOM | 167 | H | LYS | 246 | 24.816 | 23.486 | 90.051 | 1.00 | 0.00 |
| ATOM | 168 | CA | LYS | 246 | 26.245 | 23.301 | 91.596 | 1.00 | 14.06 |
| ATOM | 169 | CB | LYS | 246 | 27.162 | 22.184 | 91.073 | 1.00 | 18.78 |
| ATOM | 170 | CG | LYS | 246 | 28.495 | 22.198 | 91.801 | 1.00 | 26.05 |
| ATOM | 171 | CD | LYS | 246 | 29.532 | 21.294 | 91.160 | 1.00 | 35.90 |
| ATOM | 172 | CE | LYS | 246 | 30.834 | 21.261 | 91.978 | 1.00 | 39.06 |
| ATOM | 173 | NZ | LYS | 246 | 31.638 | 20.039 | 91.647 | 1.00 | 45.58 |
| ATOM | 174 | HZ1 | LYS | 246 | 31.878 | 20.045 | 90.635 | 1.00 | 0.00 |
| ATOM | 175 | HZ2 | LYS | 246 | 31.082 | 19.188 | 91.867 | 1.00 | 0.00 |
| ATOM | 176 | HZ3 | LYS | 246 | 32.512 | 20.036 | 92.210 | 1.00 | 0.00 |
| ATOM | 177 | C | LYS | 246 | 26.759 | 24.628 | 91.141 | 1.00 | 12.93 |
| ATOM | 178 | O | LYS | 246 | 26.802 | 24.867 | 89.946 | 1.00 | 11.85 |
| ATOM | 179 | N | LEU | 247 | 27.021 | 25.508 | 92.105 | 0.60 | 10.72 |
| ATOM | 180 | H | LEU | 247 | 26.862 | 25.235 | 93.032 | 1.00 | 0.00 |
| ATOM | 181 | CA | LEU | 247 | 27.531 | 26.862 | 91.898 | 0.60 | 9.52 |
| ATOM | 182 | CB | LEU | 247 | 27.156 | 27.713 | 93.115 | 0.60 | 7.16 |
| ATOM | 183 | CG | LEU | 247 | 25.730 | 28.305 | 93.159 | 0.60 | 3.16 |
| ATOM | 184 | CD1 | LEU | 247 | 24.683 | 27.310 | 92.819 | 0.60 | 5.77 |
| ATOM | 185 | CD2 | LEU | 247 | 25.459 | 28.878 | 94.495 | 0.60 | 2.00 |
| ATOM | 186 | C | LEU | 247 | 29.048 | 26.771 | 91.746 | 0.60 | 12.46 |
| ATOM | 187 | O | LEU | 247 | 29.744 | 26.373 | 92.662 | 0.60 | 14.30 |
| ATOM | 188 | N | VAL | 248 | 29.568 | 27.175 | 90.599 | 1.00 | 17.24 |
| ATOM | 189 | H | VAL | 248 | 29.005 | 27.571 | 89.902 | 1.00 | 0.00 |
| ATOM | 190 | CA | VAL | 248 | 30.991 | 27.030 | 90.372 | 1.00 | 19.34 |
| ATOM | 191 | CB | VAL | 248 | 31.248 | 26.269 | 89.058 | 1.00 | 19.25 |
| ATOM | 192 | CG1 | VAL | 248 | 32.754 | 26.192 | 88.778 | 1.00 | 18.08 |
| ATOM | 193 | CG2 | VAL | 248 | 30.628 | 24.866 | 89.166 | 1.00 | 17.64 |
| ATOM | 194 | C | VAL | 248 | 31.894 | 28.258 | 90.466 | 1.00 | 21.34 |
| ATOM | 195 | O | VAL | 248 | 32.929 | 28.188 | 91.123 | 1.00 | 20.76 |
| ATOM | 196 | N | GLU | 249 | 31.467 | 29.376 | 89.887 | 1.00 | 20.64 |
| ATOM | 197 | H | GLU | 249 | 30.594 | 29.386 | 89.441 | 1.00 | 0.00 |
| ATOM | 198 | CA | GLU | 249 | 32.256 | 30.607 | 89.888 | 1.00 | 19.54 |
| ATOM | 199 | CB | GLU | 249 | 32.952 | 30.738 | 88.533 | 1.00 | 22.41 |
| ATOM | 200 | CG | GLU | 249 | 33.770 | 32.006 | 88.392 | 1.00 | 33.75 |
| ATOM | 201 | CD | GLU | 249 | 34.230 | 32.271 | 86.975 | 1.00 | 37.32 |
| ATOM | 202 | OE1 | GLU | 249 | 34.379 | 31.304 | 86.197 | 1.00 | 45.17 |
| ATOM | 203 | OE2 | GLU | 249 | 34.446 | 33.466 | 86.640 | 1.00 | 42.51 |
| ATOM | 204 | C | GLU | 249 | 31.387 | 31.862 | 90.114 | 1.00 | 17.77 |
| ATOM | 205 | O | GLU | 249 | 30.510 | 32.174 | 89.312 | 1.00 | 20.06 |
| ATOM | 206 | N | ARG | 250 | 31.630 | 32.580 | 91.194 | 1.00 | 18.14 |
| ATOM | 207 | H | ARG | 250 | 32.320 | 32.292 | 91.827 | 1.00 | 0.00 |
| ATOM | 208 | CA | ARG | 250 | 30.892 | 33.808 | 91.479 | 1.00 | 19.12 |

TABLE 6-continued

Coordinates of Lck bound with damnacanthal

| | | Atom Type | Res | # | X | Y | Z | Occ | B |
|---|---|---|---|---|---|---|---|---|---|
| ATOM | 209 | CB | ARG | 250 | 31.298 | 34.364 | 92.845 | 1.00 | 20.62 |
| ATOM | 210 | CG | ARG | 250 | 30.177 | 35.104 | 93.517 | 1.00 | 29.85 |
| ATOM | 211 | CD | ARG | 250 | 30.681 | 36.178 | 94.445 | 1.00 | 35.79 |
| ATOM | 212 | NE | ARG | 250 | 31.136 | 35.664 | 95.725 | 1.00 | 44.44 |
| ATOM | 213 | HE | ARG | 250 | 30.472 | 35.278 | 96.333 | 1.00 | 0.00 |
| ATOM | 214 | CZ | ARG | 250 | 32.405 | 35.690 | 96.115 | 1.00 | 47.95 |
| ATOM | 215 | NH1 | ARG | 250 | 33.344 | 36.177 | 95.312 | 1.00 | 50.75 |
| ATOM | 216 | HH11 | ARG | 250 | 33.097 | 36.527 | 94.408 | 1.00 | 0.00 |
| ATOM | 217 | HH12 | ARG | 250 | 34.298 | 36.194 | 95.611 | 1.00 | 0.00 |
| ATOM | 218 | NH2 | ARG | 250 | 32.718 | 35.354 | 97.354 | 1.00 | 51.08 |
| ATOM | 219 | HH21 | ARG | 250 | 32.000 | 35.081 | 97.995 | 1.00 | 0.00 |
| ATOM | 220 | HH22 | ARG | 250 | 33.673 | 35.372 | 97.651 | 1.00 | 0.00 |
| ATOM | 221 | C | ARG | 250 | 31.232 | 34.828 | 90.401 | 1.00 | 19.32 |
| ATOM | 222 | O | ARG | 250 | 32.402 | 35.016 | 90.069 | 1.00 | 20.20 |
| ATOM | 223 | N | LEU | 251 | 30.204 | 35.429 | 89.808 | 1.00 | 18.99 |
| ATOM | 224 | H | LEU | 251 | 29.290 | 35.215 | 90.090 | 1.00 | 0.00 |
| ATOM | 225 | CA | LEU | 251 | 30.385 | 36.404 | 88.743 | 1.00 | 20.72 |
| ATOM | 226 | CB | LEU | 251 | 29.320 | 36.225 | 87.654 | 1.00 | 19.61 |
| ATOM | 227 | CG | LEU | 251 | 29.240 | 34.858 | 86.952 | 1.00 | 20.53 |
| ATOM | 228 | CD1 | LEU | 251 | 28.048 | 34.878 | 86.038 | 1.00 | 17.56 |
| ATOM | 229 | CD2 | LEU | 251 | 30.552 | 34.563 | 86.189 | 1.00 | 17.43 |
| ATOM | 230 | C | LEU | 251 | 30.238 | 37.807 | 89.282 | 1.00 | 20.77 |
| ATOM | 231 | O | LEU | 251 | 30.697 | 38.768 | 88.654 | 1.00 | 23.66 |
| ATOM | 232 | N | GLY | 252 | 29.542 | 37.913 | 90.405 | 1.00 | 17.99 |
| ATOM | 233 | H | GLY | 252 | 29.195 | 37.103 | 90.835 | 1.00 | 0.00 |
| ATOM | 234 | CA | GLY | 252 | 29.287 | 39.194 | 91.003 | 1.00 | 19.11 |
| ATOM | 235 | C | GLY | 252 | 28.580 | 39.099 | 92.331 | 1.00 | 20.69 |
| ATOM | 236 | O | GLY | 252 | 28.026 | 38.070 | 92.721 | 1.00 | 16.87 |
| ATOM | 237 | N | ALA | 253 | 28.582 | 40.222 | 93.028 | 1.00 | 24.04 |
| ATOM | 238 | H | ALA | 253 | 28.996 | 41.031 | 92.660 | 1.00 | 0.00 |
| ATOM | 239 | CA | ALA | 253 | 27.980 | 40.282 | 94.334 | 1.00 | 22.56 |
| ATOM | 240 | CB | ALA | 253 | 28.968 | 39.792 | 95.396 | 1.00 | 21.19 |
| ATOM | 241 | C | ALA | 253 | 27.568 | 41.705 | 94.611 | 1.00 | 24.96 |
| ATOM | 242 | O | ALA | 253 | 28.209 | 42.667 | 94.175 | 1.00 | 25.58 |
| ATOM | 243 | N | GLY | 254 | 26.485 | 41.829 | 95.346 | 1.00 | 23.79 |
| ATOM | 244 | H | GLY | 254 | 26.008 | 41.032 | 95.658 | 1.00 | 0.00 |
| ATOM | 245 | CA | GLY | 254 | 26.009 | 43.130 | 95.686 | 1.00 | 21.01 |
| ATOM | 246 | C | GLY | 254 | 25.366 | 43.049 | 97.037 | 1.00 | 22.59 |
| ATOM | 247 | O | GLY | 254 | 25.487 | 42.071 | 97.772 | 1.00 | 21.62 |
| ATOM | 248 | N | GLN | 255 | 24.642 | 44.110 | 97.347 | 1.00 | 27.14 |
| ATOM | 249 | H | GLN | 255 | 24.566 | 44.839 | 96.696 | 1.00 | 0.00 |
| ATOM | 250 | CA | GLN | 255 | 23.943 | 44.263 | 98.610 | 1.00 | 28.97 |
| ATOM | 251 | CB | GLN | 255 | 23.377 | 45.681 | 98.589 | 1.00 | 32.66 |
| ATOM | 252 | CG | GLN | 255 | 22.520 | 46.138 | 99.723 | 1.00 | 36.70 |
| ATOM | 253 | CD | GLN | 255 | 21.895 | 47.495 | 99.406 | 1.00 | 40.26 |
| ATOM | 254 | OE1 | GLN | 255 | 22.101 | 48.070 | 98.325 | 1.00 | 40.10 |
| ATOM | 255 | NE2 | GLN | 255 | 21.109 | 48.001 | 100.335 | 1.00 | 43.96 |
| ATOM | 256 | HE21 | GLN | 255 | 20.956 | 47.509 | 101.169 | 1.00 | 0.00 |
| ATOM | 257 | HE22 | GLN | 255 | 20.697 | 48.870 | 100.154 | 1.00 | 0.00 |
| ATOM | 258 | C | GLN | 255 | 22.814 | 43.233 | 98.742 | 1.00 | 28.32 |
| ATOM | 259 | O | GLN | 255 | 22.503 | 42.757 | 99.833 | 1.00 | 28.39 |
| ATOM | 260 | N | PHE | 256 | 22.278 | 42.795 | 97.611 | 1.00 | 28.48 |
| ATOM | 261 | H | PHE | 256 | 22.634 | 43.066 | 96.739 | 1.00 | 0.00 |
| ATOM | 262 | CA | PHE | 256 | 21.144 | 41.899 | 97.682 | 1.00 | 26.49 |
| ATOM | 263 | CB | PHE | 256 | 20.001 | 42.486 | 96.842 | 1.00 | 26.36 |
| ATOM | 264 | CG | PHE | 256 | 19.618 | 43.853 | 97.284 | 1.00 | 24.34 |
| ATOM | 265 | CD1 | PHE | 256 | 19.142 | 44.055 | 98.574 | 1.00 | 23.85 |
| ATOM | 266 | CD2 | PHE | 256 | 19.800 | 44.960 | 96.443 | 1.00 | 28.14 |
| ATOM | 267 | CE1 | PHE | 256 | 18.863 | 45.367 | 99.028 | 1.00 | 23.49 |
| ATOM | 268 | CE2 | PHE | 256 | 19.526 | 46.243 | 96.881 | 1.00 | 24.89 |
| ATOM | 269 | CZ | PHE | 256 | 19.059 | 46.430 | 98.183 | 1.00 | 27.06 |
| ATOM | 270 | C | PHE | 256 | 21.381 | 40.434 | 97.405 | 1.00 | 24.59 |
| ATOM | 271 | O | PHE | 256 | 20.476 | 39.617 | 97.547 | 1.00 | 21.81 |
| ATOM | 272 | N | GLY | 257 | 22.629 | 40.113 | 97.056 | 1.00 | 23.00 |
| ATOM | 273 | H | GLY | 257 | 23.307 | 40.814 | 96.959 | 1.00 | 0.00 |
| ATOM | 274 | CA | GLY | 257 | 22.979 | 38.730 | 96.821 | 1.00 | 21.04 |
| ATOM | 275 | C | GLY | 257 | 24.162 | 38.540 | 95.902 | 1.00 | 20.70 |
| ATOM | 276 | O | GLY | 257 | 25.013 | 39.410 | 95.754 | 1.00 | 20.90 |
| ATOM | 277 | N | GLU | 258 | 24.155 | 37.419 | 95.207 | 1.00 | 19.42 |
| ATOM | 278 | H | GLU | 258 | 23.401 | 36.797 | 95.283 | 1.00 | 0.00 |
| ATOM | 279 | CA | GLU | 258 | 25.244 | 37.084 | 94.328 | 1.00 | 21.66 |
| ATOM | 280 | CB | GLU | 258 | 26.176 | 36.087 | 95.054 | 1.00 | 24.83 |
| ATOM | 281 | CG | GLU | 258 | 26.950 | 36.656 | 96.257 | 1.00 | 27.48 |
| ATOM | 282 | CD | GLU | 258 | 27.637 | 35.570 | 97.100 | 1.00 | 35.23 |

TABLE 6-continued

Coordinates of Lck bound with damnacanthal

| | | Atom Type | Res | # | X | Y | Z | Occ | B |
|---|---|---|---|---|---|---|---|---|---|
| ATOM | 283 | OE1 | GLU | 258 | 27.259 | 34.379 | 97.021 | 1.00 | 37.07 |
| ATOM | 284 | OE2 | GLU | 258 | 28.546 | 35.914 | 97.877 | 1.00 | 36.98 |
| ATOM | 285 | C | GLU | 258 | 24.737 | 36.456 | 93.047 | 1.00 | 20.99 |
| ATOM | 286 | O | GLU | 258 | 23.614 | 35.999 | 92.982 | 1.00 | 21.51 |
| ATOM | 287 | N | VAL | 259 | 25.561 | 36.499 | 92.020 | 1.00 | 18.78 |
| ATOM | 288 | H | VAL | 259 | 26.410 | 36.971 | 92.143 | 1.00 | 20.00 |
| ATOM | 289 | CA | VAL | 259 | 25.253 | 35.862 | 90.759 | 1.00 | 16.87 |
| ATOM | 290 | CB | VAL | 259 | 25.149 | 36.872 | 89.636 | 1.00 | 18.38 |
| ATOM | 291 | CG1 | VAL | 259 | 24.723 | 36.176 | 88.328 | 1.00 | 18.11 |
| ATOM | 292 | CG2 | VAL | 259 | 24.151 | 37.971 | 90.040 | 1.00 | 18.84 |
| ATOM | 293 | C | VAL | 259 | 26.452 | 34.901 | 90.527 | 1.00 | 16.12 |
| ATOM | 294 | O | VAL | 259 | 27.608 | 35.298 | 90.644 | 1.00 | 12.39 |
| ATOM | 295 | N | TRP | 260 | 26.139 | 33.624 | 90.287 | 1.00 | 17.33 |
| ATOM | 296 | H | TRP | 260 | 25.194 | 33.370 | 90.233 | 1.00 | 0.00 |
| ATOM | 297 | CA | TRP | 260 | 27.133 | 32.570 | 90.098 | 1.00 | 12.51 |
| ATOM | 298 | CB | TRP | 260 | 26.927 | 31.516 | 91.168 | 1.00 | 12.85 |
| ATOM | 299 | CG | TRP | 260 | 27.366 | 31.905 | 92.502 | 1.00 | 15.01 |
| ATOM | 300 | CD2 | TRP | 260 | 28.507 | 31.404 | 93.201 | 1.00 | 14.63 |
| ATOM | 301 | CE2 | TRP | 260 | 28.552 | 32.057 | 94.452 | 1.00 | 16.82 |
| ATOM | 302 | CE3 | TRP | 260 | 29.495 | 30.462 | 92.891 | 1.00 | 16.25 |
| ATOM | 303 | CD1 | TRP | 260 | 26.767 | 32.806 | 93.334 | 1.00 | 16.56 |
| ATOM | 304 | NE1 | TRP | 260 | 27.477 | 32.904 | 94.509 | 1.00 | 18.88 |
| ATOM | 305 | HE1 | TRP | 260 | 27.251 | 33.483 | 95.261 | 1.00 | 0.00 |
| ATOM | 306 | CZ2 | TRP | 260 | 29.549 | 31.802 | 95.398 | 1.00 | 14.41 |
| ATOM | 307 | CZ3 | TRP | 260 | 30.486 | 30.207 | 93.831 | 1.00 | 16.18 |
| ATOM | 308 | CH2 | TRP | 260 | 30.508 | 30.886 | 95.073 | 1.00 | 16.70 |
| ATOM | 309 | C | TRP | 260 | 26.977 | 31.855 | 88.773 | 1.00 | 12.47 |
| ATOM | 310 | O | TRP | 260 | 25.873 | 31.740 | 88.249 | 1.00 | 12.03 |
| ATOM | 311 | N | MET | 261 | 28.080 | 31.420 | 88.192 | 1.00 | 10.87 |
| ATOM | 312 | H | MET | 261 | 28.961 | 31.616 | 88.573 | 1.00 | 0.00 |
| ATOM | 313 | CA | MET | 261 | 27.987 | 30.646 | 86.980 | 1.00 | 11.42 |
| ATOM | 314 | CB | MET | 261 | 29.277 | 30.672 | 86.160 | 1.00 | 12.56 |
| ATOM | 315 | CG | MET | 261 | 29.255 | 29.743 | 84.939 | 1.00 | 12.64 |
| ATOM | 316 | SD | MET | 261 | 29.760 | 28.005 | 85.379 | 1.00 | 18.83 |
| ATOM | 317 | CE | MET | 261 | 31.623 | 28.181 | 85.322 | 1.00 | 17.09 |
| ATOM | 318 | C | MET | 261 | 27.767 | 29.294 | 87.624 | 1.00 | 10.62 |
| ATOM | 319 | O | MET | 261 | 28.298 | 29.031 | 88.720 | 1.00 | 9.30 |
| ATOM | 320 | N | GLY | 262 | 26.949 | 28.458 | 87.000 | 1.00 | 13.90 |
| ATOM | 321 | H | GLY | 262 | 26.543 | 28.702 | 86.142 | 1.00 | 0.00 |
| ATOM | 322 | CA | GLY | 262 | 26.667 | 27.167 | 87.619 | 1.00 | 12.58 |
| ATOM | 323 | C | GLY | 262 | 26.256 | 26.080 | 86.648 | 1.00 | 13.49 |
| ATOM | 324 | O | GLY | 262 | 26.227 | 26.320 | 85.439 | 1.00 | 12.64 |
| ATOM | 325 | N | TYR | 263 | 25.988 | 24.879 | 87.174 | 1.00 | 10.81 |
| ATOM | 326 | H | TYR | 263 | 26.088 | 24.741 | 88.139 | 1.00 | 0.00 |
| ATOM | 327 | CA | TYR | 263 | 25.545 | 23.745 | 86.356 | 1.00 | 10.52 |
| ATOM | 328 | CB | TYR | 263 | 26.616 | 22.650 | 86.293 | 1.00 | 6.87 |
| ATOM | 329 | CG | TYR | 263 | 27.749 | 23.057 | 85.410 | 1.00 | 6.90 |
| ATOM | 330 | CD1 | TYR | 263 | 27.629 | 22.973 | 84.030 | 1.00 | 7.37 |
| ATOM | 331 | CE1 | TYR | 263 | 28.612 | 23.450 | 83.205 | 1.00 | 14.24 |
| ATOM | 332 | CD2 | TYR | 263 | 28.899 | 23.614 | 85.948 | 1.00 | 10.06 |
| ATOM | 333 | CE2 | TYR | 263 | 29.914 | 24.102 | 85.125 | 1.00 | 13.25 |
| ATOM | 334 | CZ | TYR | 263 | 29.757 | 24.016 | 83.772 | 1.00 | 17.58 |
| ATOM | 335 | OH | TYR | 263 | 30.736 | 24.485 | 82.942 | 1.00 | 27.53 |
| ATOM | 336 | HH | TYR | 263 | 31.458 | 24.839 | 83.466 | 1.00 | 0.00 |
| ATOM | 337 | C | TYR | 263 | 24.269 | 23.136 | 86.884 | 1.00 | 11.34 |
| ATOM | 338 | O | TYR | 263 | 24.091 | 22.973 | 88.071 | 1.00 | 15.69 |
| ATOM | 339 | N | TYR | 264 | 23.377 | 22.796 | 85.986 | 1.00 | 10.66 |
| ATOM | 340 | H | TYR | 264 | 23.538 | 22.955 | 85.033 | 1.00 | 0.00 |
| ATOM | 341 | CA | TYR | 264 | 22.138 | 22.178 | 86.404 | 1.00 | 13.68 |
| ATOM | 342 | CB | TYR | 264 | 20.962 | 22.833 | 85.669 | 1.00 | 11.86 |
| ATOM | 343 | CG | TYR | 264 | 19.675 | 22.069 | 85.802 | 1.00 | 15.62 |
| ATOM | 344 | CD1 | TYR | 264 | 18.915 | 22.152 | 86.952 | 1.00 | 17.84 |
| ATOM | 345 | CE1 | TYR | 264 | 17.751 | 21.361 | 87.109 | 1.00 | 17.03 |
| ATOM | 346 | CD2 | TYR | 264 | 19.250 | 21.191 | 84.785 | 1.00 | 13.90 |
| ATOM | 347 | CE2 | TYR | 264 | 18.137 | 20.427 | 84.930 | 1.00 | 14.42 |
| ATOM | 348 | CZ | TYR | 264 | 17.392 | 20.502 | 86.093 | 1.00 | 14.31 |
| ATOM | 349 | OH | TYR | 264 | 16.374 | 19.627 | 86.277 | 1.00 | 18.53 |
| ATOM | 350 | HH | TYR | 264 | 16.314 | 19.041 | 85.519 | 1.00 | 0.00 |
| ATOM | 351 | C | TYR | 264 | 22.312 | 20.686 | 86.011 | 1.00 | 13.71 |
| ATOM | 352 | O | TYR | 264 | 22.673 | 20.394 | 84.885 | 1.00 | 8.35 |
| ATOM | 353 | N | ASN | 265 | 22.003 | 19.779 | 86.934 | 1.00 | 15.03 |
| ATOM | 354 | H | ASN | 265 | 21.656 | 20.076 | 87.801 | 1.00 | 0.00 |
| ATOM | 355 | CA | ASN | 265 | 22.160 | 18.324 | 86.713 | 1.00 | 13.57 |
| ATOM | 356 | CB | ASN | 265 | 20.976 | 17.728 | 85.906 | 1.00 | 12.16 |

TABLE 6-continued

Coordinates of Lck bound with damnacanthal

| Atom | | Atom Type | Res | # | X | Y | Z | Occ | B |
|---|---|---|---|---|---|---|---|---|---|
| ATOM | 357 | CG | ASN | 265 | 19.679 | 17.609 | 86.717 | 1.00 | 10.35 |
| ATOM | 358 | OD1 | ASN | 265 | 18.634 | 17.328 | 86.145 | 1.00 | 16.05 |
| ATOM | 359 | ND2 | ASN | 265 | 19.733 | 17.825 | 88.023 | 1.00 | 5.99 |
| ATOM | 360 | HD21 | ASN | 265 | 20.586 | 18.054 | 88.447 | 1.00 | 0.00 |
| ATOM | 361 | HD22 | ASN | 265 | 18.899 | 17.746 | 88.529 | 1.00 | 0.00 |
| ATOM | 362 | C | ASN | 265 | 23.493 | 18.011 | 86.036 | 1.00 | 10.83 |
| ATOM | 363 | O | ASN | 265 | 23.559 | 17.372 | 84.983 | 1.00 | 9.35 |
| ATOM | 364 | N | GLY | 266 | 24.522 | 18.665 | 86.523 | 1.00 | 12.93 |
| ATOM | 365 | H | GLY | 266 | 24.383 | 19.315 | 87.243 | 1.00 | 0.00 |
| ATOM | 366 | CA | GLY | 266 | 25.862 | 18.442 | 86.012 | 1.00 | 11.38 |
| ATOM | 367 | C | GLY | 266 | 26.278 | 18.947 | 84.656 | 1.00 | 6.70 |
| ATOM | 368 | O | GLY | 266 | 27.394 | 19.393 | 84.543 | 1.00 | 11.16 |
| ATOM | 369 | N | HIS | 267 | 25.415 | 18.943 | 83.648 | 0.49 | 4.11 |
| ATOM | 370 | H | HIS | 267 | 24.486 | 18.663 | 83.789 | 1.00 | 0.00 |
| ATOM | 371 | CA | HIS | 267 | 25.839 | 19.357 | 82.311 | 0.49 | 2.04 |
| ATOM | 372 | CB | HIS | 267 | 25.495 | 18.254 | 81.315 | 0.49 | 2.00 |
| ATOM | 373 | CG | HIS | 267 | 26.043 | 16.918 | 81.692 | 0.49 | 2.00 |
| ATOM | 374 | CD2 | HIS | 267 | 25.423 | 15.755 | 82.021 | 0.49 | 2.00 |
| ATOM | 375 | ND1 | HIS | 267 | 27.393 | 16.666 | 81.773 | 0.49 | 2.00 |
| ATOM | 376 | HD1 | HIS | 267 | 28.098 | 17.315 | 81.590 | 1.00 | 0.00 |
| ATOM | 377 | CE1 | HIS | 267 | 27.589 | 15.412 | 82.136 | 0.49 | 2.00 |
| ATOM | 378 | NE2 | HIS | 267 | 26.400 | 14.841 | 82.291 | 0.49 | 2.00 |
| ATOM | 379 | HE2 | HIS | 267 | 26.249 | 13.914 | 82.556 | 1.00 | 0.00 |
| ATOM | 380 | C | HIS | 267 | 25.348 | 20.638 | 81.703 | 0.49 | 3.34 |
| ATOM | 381 | O | HIS | 267 | 25.841 | 21.036 | 80.656 | 0.49 | 2.00 |
| ATOM | 382 | N | THR | 268 | 24.384 | 21.292 | 82.331 | 1.00 | 10.56 |
| ATOM | 383 | H | THR | 268 | 24.034 | 20.964 | 83.187 | 1.00 | 20.00 |
| ATOM | 384 | CA | THR | 268 | 23.807 | 22.493 | 81.711 | 1.00 | 13.07 |
| ATOM | 385 | CB | THR | 268 | 22.273 | 22.385 | 81.622 | 1.00 | 10.60 |
| ATOM | 386 | OG1 | THR | 268 | 21.936 | 21.173 | 80.938 | 1.00 | 13.53 |
| ATOM | 387 | HG1 | THR | 268 | 22.288 | 20.423 | 81.423 | 1.00 | 0.00 |
| ATOM | 388 | CG2 | THR | 268 | 21.709 | 23.557 | 80.825 | 1.00 | 9.40 |
| ATOM | 389 | C | THR | 268 | 24.224 | 23.761 | 82.420 | 1.00 | 13.67 |
| ATOM | 390 | O | THR | 268 | 23.848 | 24.008 | 83.552 | 1.00 | 14.62 |
| ATOM | 391 | N | LYS | 269 | 25.101 | 24.494 | 81.760 | 1.00 | 11.80 |
| ATOM | 392 | H | LYS | 269 | 25.421 | 24.203 | 80.881 | 1.00 | 0.00 |
| ATOM | 393 | CA | LYS | 269 | 25.607 | 25.729 | 82.307 | 1.00 | 13.99 |
| ATOM | 394 | CB | LYS | 269 | 26.679 | 26.265 | 81.377 | 1.00 | 17.28 |
| ATOM | 395 | CG | LYS | 269 | 27.493 | 27.418 | 81.932 | 1.00 | 17.58 |
| ATOM | 396 | CD | LYS | 269 | 28.566 | 27.697 | 80.868 | 1.00 | 22.60 |
| ATOM | 397 | CE | LYS | 269 | 29.758 | 28.479 | 81.431 | 1.00 | 21.38 |
| ATOM | 398 | NZ | LYS | 269 | 31.022 | 28.211 | 80.663 | 1.00 | 22.85 |
| ATOM | 399 | HZ1 | LYS | 269 | 30.891 | 28.491 | 79.670 | 1.00 | 0.00 |
| ATOM | 400 | HZ2 | LYS | 269 | 31.248 | 27.197 | 80.710 | 1.00 | 0.00 |
| ATOM | 401 | HZ3 | LYS | 269 | 31.802 | 28.759 | 81.077 | 1.00 | 0.00 |
| ATOM | 402 | C | LYS | 269 | 24.439 | 26.734 | 82.433 | 1.00 | 13.44 |
| ATOM | 403 | O | LYS | 269 | 23.718 | 26.957 | 81.476 | 1.00 | 15.32 |
| ATOM | 404 | N | VAL | 270 | 24.313 | 27.345 | 83.605 | 1.00 | 11.46 |
| ATOM | 405 | H | VAL | 270 | 24.968 | 27.159 | 84.310 | 1.00 | 0.00 |
| ATOM | 406 | CA | VAL | 270 | 23.237 | 28.294 | 83.911 | 1.00 | 10.20 |
| ATOM | 407 | CB | VAL | 270 | 22.048 | 27.552 | 84.686 | 1.00 | 10.70 |
| ATOM | 408 | CG1 | VAL | 270 | 21.458 | 26.389 | 83.851 | 1.00 | 2.00 |
| ATOM | 409 | CG2 | VAL | 270 | 22.582 | 26.966 | 85.998 | 1.00 | 5.86 |
| ATOM | 410 | C | VAL | 270 | 23.801 | 29.368 | 84.854 | 1.00 | 7.03 |
| ATOM | 411 | O | VAL | 270 | 24.884 | 29.197 | 85.392 | 1.00 | 6.14 |
| ATOM | 412 | N | ALA | 271 | 23.084 | 30.505 | 84.943 | 1.00 | 9.57 |
| ATOM | 413 | H | ALA | 271 | 22.285 | 30.616 | 84.386 | 1.00 | 0.00 |
| ATOM | 414 | CA | ALA | 271 | 23.453 | 31.600 | 85.851 | 1.00 | 7.37 |
| ATOM | 415 | CB | ALA | 271 | 23.256 | 33.013 | 85.137 | 1.00 | 9.19 |
| ATOM | 416 | C | ALA | 271 | 22.486 | 31.466 | 87.008 | 1.00 | 7.59 |
| ATOM | 417 | O | ALA | 271 | 21.289 | 31.365 | 86.819 | 1.00 | 10.80 |
| ATOM | 418 | N | VAL | 272 | 23.037 | 31.555 | 88.229 | 1.00 | 12.87 |
| ATOM | 419 | H | VAL | 272 | 24.003 | 31.695 | 88.313 | 1.00 | 0.00 |
| ATOM | 420 | CA | VAL | 272 | 22.245 | 31.450 | 89.456 | 1.00 | 13.48 |
| ATOM | 421 | CB | VAL | 272 | 22.764 | 30.290 | 90.349 | 1.00 | 12.53 |
| ATOM | 422 | CG1 | VAL | 272 | 21.869 | 30.163 | 91.606 | 1.00 | 6.36 |
| ATOM | 423 | CG2 | VAL | 272 | 22.731 | 28.952 | 89.530 | 1.00 | 6.88 |
| ATOM | 424 | C | VAL | 272 | 22.269 | 32.739 | 90.277 | 1.00 | 12.67 |
| ATOM | 425 | O | VAL | 272 | 23.332 | 33.200 | 90.664 | 1.00 | 10.50 |
| ATOM | 426 | N | DAM | 273 | 21.096 | 33.316 | 90.530 | 1.00 | 14.15 |
| ATOM | 427 | CA | DAM | 273 | 20.964 | 34.571 | 91.294 | 1.00 | 11.05 |
| ATOM | 428 | C | DAM | 273 | 20.565 | 34.158 | 92.693 | 1.00 | 12.72 |
| ATOM | 429 | O | DAM | 273 | 19.528 | 33.508 | 92.874 | 1.00 | 15.51 |
| ATOM | 430 | CB | DAM | 273 | 19.892 | 35.459 | 90.655 | 1.00 | 7.73 |

TABLE 6-continued

Coordinates of Lck bound with damnacanthal

| | | Atom Type | Res | # | X | Y | Z | Occ | B |
|---|---|---|---|---|---|---|---|---|---|
| ATOM | 431 | CG | DAM | 273 | 20.186 | 35.872 | 89.221 | 1.00 | 10.50 |
| ATOM | 432 | CD | DAM | 273 | 19.085 | 36.736 | 88.690 | 1.00 | 12.73 |
| ATOM | 433 | CE | DAM | 273 | 19.173 | 36.960 | 87.163 | 1.00 | 18.26 |
| ATOM | 434 | NZ | DAM | 273 | 20.444 | 37.569 | 86.678 | 1.00 | 17.87 |
| ATOM | 435 | H | DAM | 273 | 20.286 | 32.874 | 90.214 | 1.00 | 20.00 |
| ATOM | 436 | C1 | DAM | 273 | 22.572 | 37.412 | 85.485 | 1.00 | 23.69 |
| ATOM | 437 | C2 | DAM | 273 | 23.303 | 36.704 | 84.533 | 1.00 | 25.50 |
| ATOM | 438 | C3 | DAM | 273 | 24.603 | 37.100 | 84.190 | 1.00 | 22.64 |
| ATOM | 439 | C4 | DAM | 273 | 25.154 | 38.223 | 84.815 | 1.00 | 20.62 |
| ATOM | 440 | C5 | DAM | 273 | 24.412 | 38.938 | 85.749 | 1.00 | 19.92 |
| ATOM | 441 | C6 | DAM | 273 | 23.130 | 38.535 | 86.082 | 1.00 | 23.05 |
| ATOM | 442 | C8 | DAM | 273 | 25.385 | 36.344 | 83.190 | 1.00 | 25.18 |
| ATOM | 443 | C9 | DAM | 273 | 26.818 | 36.653 | 83.104 | 1.00 | 24.17 |
| ATOM | 444 | C10 | DAM | 273 | 27.360 | 37.769 | 83.738 | 1.00 | 24.11 |
| ATOM | 445 | C11 | DAM | 273 | 26.518 | 38.675 | 84.526 | 1.00 | 20.53 |
| ATOM | 446 | C12 | DAM | 273 | 27.647 | 35.804 | 82.374 | 1.00 | 23.66 |
| ATOM | 447 | C13 | DAM | 273 | 29.008 | 36.060 | 82.281 | 1.00 | 22.58 |
| ATOM | 448 | C14 | DAM | 273 | 29.548 | 37.173 | 82.910 | 1.00 | 23.39 |
| ATOM | 449 | C15 | DAM | 273 | 28.725 | 38.028 | 83.633 | 1.00 | 23.25 |
| ATOM | 450 | O20 | DAM | 273 | 26.941 | 39.743 | 84.951 | 1.00 | 23.97 |
| ATOM | 451 | O21 | DAM | 273 | 24.896 | 35.476 | 82.478 | 1.00 | 26.28 |
| ATOM | 452 | O22 | DAM | 273 | 22.674 | 35.615 | 83.942 | 1.00 | 31.23 |
| ATOM | 453 | C23 | DAM | 273 | 22.333 | 35.828 | 82.584 | 1.00 | 26.87 |
| ATOM | 454 | C27 | DAM | 273 | 21.189 | 36.948 | 85.862 | 1.00 | 22.67 |
| ATOM | 455 | O31 | DAM | 273 | 22.399 | 39.242 | 87.014 | 1.00 | 32.41 |
| ATOM | 456 | N | SER | 274 | 21.404 | 34.469 | 93.673 | 0.65 | 10.33 |
| ATOM | 457 | H | SER | 274 | 22.215 | 34.984 | 93.479 | 1.00 | 0.00 |
| ATOM | 458 | CA | SER | 274 | 21.150 | 34.063 | 95.040 | 0.65 | 9.85 |
| ATOM | 459 | CB | SER | 274 | 22.368 | 33.307 | 95.581 | 0.65 | 9.18 |
| ATOM | 460 | OG | SER | 274 | 22.084 | 32.697 | 96.822 | 0.65 | 11.31 |
| ATOM | 461 | HG | SER | 274 | 21.834 | 33.370 | 97.460 | 1.00 | 0.00 |
| ATOM | 462 | C | SER | 274 | 20.797 | 35.218 | 95.937 | 0.65 | 12.70 |
| ATOM | 463 | O | SER | 274 | 21.613 | 36.103 | 96.207 | 0.65 | 11.70 |
| ATOM | 464 | N | LEU | 275 | 19.566 | 35.198 | 96.438 | 1.00 | 17.48 |
| ATOM | 465 | H | LEU | 275 | 18.950 | 34.462 | 96.241 | 1.00 | 0.00 |
| ATOM | 466 | CA | LEU | 275 | 19.138 | 36.285 | 97.288 | 1.00 | 16.72 |
| ATOM | 467 | CB | LEU | 275 | 17.612 | 36.385 | 97.279 | 1.00 | 14.67 |
| ATOM | 468 | CG | LEU | 275 | 17.037 | 37.287 | 98.366 | 1.00 | 12.14 |
| ATOM | 469 | CD1 | LEU | 275 | 17.171 | 38.747 | 97.935 | 1.00 | 10.52 |
| ATOM | 470 | CD2 | LEU | 275 | 15.610 | 36.921 | 98.601 | 1.00 | 12.79 |
| ATOM | 471 | C | LEU | 275 | 19.720 | 36.151 | 98.710 | 1.00 | 18.20 |
| ATOM | 472 | O | LEU | 275 | 19.711 | 35.077 | 99.317 | 1.00 | 17.86 |
| ATOM | 473 | N | LYS | 276 | 20.348 | 37.224 | 99.166 | 1.00 | 21.14 |
| ATOM | 474 | H | LYS | 276 | 20.429 | 38.012 | 98.589 | 1.00 | 0.00 |
| ATOM | 475 | CA | LYS | 276 | 20.934 | 37.295 | 100.503 | 1.00 | 27.00 |
| ATOM | 476 | CB | LYS | 276 | 21.818 | 38.562 | 100.584 | 1.00 | 29.21 |
| ATOM | 477 | CG | LYS | 276 | 22.402 | 38.956 | 101.955 | 1.00 | 34.49 |
| ATOM | 478 | CD | LYS | 276 | 23.455 | 40.066 | 101.782 | 1.00 | 40.45 |
| ATOM | 479 | CE | LYS | 276 | 24.077 | 40.536 | 103.104 | 1.00 | 45.65 |
| ATOM | 480 | NZ | LYS | 276 | 25.345 | 41.366 | 102.925 | 1.00 | 50.81 |
| ATOM | 481 | HZ1 | LYS | 276 | 25.128 | 42.216 | 102.366 | 1.00 | 0.00 |
| ATOM | 482 | HZ2 | LYS | 276 | 26.063 | 40.800 | 102.430 | 1.00 | 0.00 |
| ATOM | 483 | HZ3 | LYS | 276 | 25.709 | 41.648 | 103.857 | 1.00 | 0.00 |
| ATOM | 484 | C | LYS | 276 | 19.734 | 37.430 | 101.439 | 1.00 | 28.06 |
| ATOM | 485 | O | LYS | 276 | 19.022 | 38.429 | 101.390 | 1.00 | 27.43 |
| ATOM | 486 | N | GLN | 277 | 19.561 | 36.518 | 102.398 | 1.00 | 29.80 |
| ATOM | 487 | H | GLN | 277 | 20.430 | 36.023 | 102.669 | 1.00 | 20.00 |
| ATOM | 488 | CA | GLN | 277 | 18.384 | 36.669 | 103.257 | 1.00 | 32.45 |
| ATOM | 489 | CB | GLN | 277 | 17.883 | 35.404 | 103.947 | 1.00 | 30.63 |
| ATOM | 490 | CG | GLN | 277 | 18.889 | 34.714 | 104.693 | 1.00 | 36.73 |
| ATOM | 491 | CD | GLN | 277 | 19.334 | 33.462 | 103.948 | 1.00 | 38.68 |
| ATOM | 492 | OE1 | GLN | 277 | 20.050 | 33.550 | 102.920 | 1.00 | 41.83 |
| ATOM | 493 | NE2 | GLN | 277 | 18.845 | 32.296 | 104.375 | 1.00 | 35.63 |
| ATOM | 494 | HE21 | GLN | 277 | 18.228 | 32.273 | 105.136 | 1.00 | 0.00 |
| ATOM | 495 | HE22 | GLN | 277 | 19.127 | 31.487 | 103.901 | 1.00 | 0.00 |
| ATOM | 496 | C | GLN | 277 | 18.472 | 37.853 | 104.183 | 1.00 | 32.92 |
| ATOM | 497 | O | GLN | 277 | 19.564 | 38.291 | 104.513 | 1.00 | 34.52 |
| ATOM | 498 | N | GLY | 278 | 17.300 | 38.482 | 104.322 | 1.00 | 30.87 |
| ATOM | 499 | H | GLY | 278 | 16.514 | 38.115 | 103.866 | 1.00 | 0.00 |
| ATOM | 500 | CA | GLY | 278 | 17.141 | 39.684 | 105.118 | 1.00 | 29.53 |
| ATOM | 501 | C | GLY | 278 | 17.465 | 40.939 | 104.334 | 1.00 | 28.71 |
| ATOM | 502 | O | GLY | 278 | 17.079 | 42.035 | 104.715 | 1.00 | 31.78 |
| ATOM | 503 | N | SER | 279 | 18.159 | 40.794 | 103.216 | 1.00 | 28.35 |
| ATOM | 504 | H | SER | 279 | 18.415 | 39.905 | 102.892 | 1.00 | 0.00 |

TABLE 6-continued

Coordinates of Lck bound with damnacanthal

| | | Atom Type | Res | # | X | Y | Z | Occ | B |
|---|---|---|---|---|---|---|---|---|---|
| ATOM | 505 | CA | SER | 279 | 18.548 | 41.980 | 102.456 | 1.00 | 30.71 |
| ATOM | 506 | CB | SER | 279 | 19.618 | 41.631 | 101.402 | 1.00 | 31.52 |
| ATOM | 507 | OG | SER | 279 | 19.130 | 40.839 | 100.329 | 1.00 | 30.25 |
| ATOM | 508 | HG | SER | 279 | 18.788 | 40.010 | 100.672 | 1.00 | 0.00 |
| ATOM | 509 | C | SER | 279 | 17.364 | 42.723 | 101.829 | 1.00 | 30.84 |
| ATOM | 510 | O | SER | 279 | 17.364 | 43.962 | 101.761 | 1.00 | 32.06 |
| ATOM | 511 | N | MET | 280 | 16.395 | 41.954 | 101.340 | 1.00 | 27.31 |
| ATOM | 512 | H | MET | 280 | 16.487 | 40.980 | 101.400 | 1.00 | 0.00 |
| ATOM | 513 | CA | MET | 280 | 15.193 | 42.478 | 100.715 | 1.00 | 25.90 |
| ATOM | 514 | CB | MET | 280 | 15.433 | 42.896 | 99.268 | 1.00 | 24.92 |
| ATOM | 515 | CG | MET | 280 | 15.564 | 41.724 | 98.299 | 1.00 | 25.68 |
| ATOM | 516 | SD | MET | 280 | 15.904 | 42.158 | 96.598 | 1.00 | 23.49 |
| ATOM | 517 | CE | MET | 280 | 14.237 | 42.260 | 95.982 | 1.00 | 16.80 |
| ATOM | 518 | C | MET | 280 | 14.129 | 41.376 | 100.758 | 1.00 | 26.00 |
| ATOM | 519 | O | MET | 280 | 14.385 | 40.253 | 101.189 | 1.00 | 25.87 |
| ATOM | 520 | N | SER | 281 | 12.908 | 41.730 | 100.364 | 1.00 | 25.12 |
| ATOM | 521 | H | SER | 281 | 12.740 | 42.643 | 100.050 | 1.00 | 0.00 |
| ATOM | 522 | CA | SER | 281 | 11.806 | 40.791 | 100.387 | 1.00 | 21.31 |
| ATOM | 523 | CB | SER | 281 | 10.506 | 41.513 | 100.115 | 1.00 | 23.45 |
| ATOM | 524 | OG | SER | 281 | 9.530 | 40.595 | 99.681 | 1.00 | 25.57 |
| ATOM | 525 | HG | SER | 281 | 9.388 | 39.933 | 100.361 | 1.00 | 0.00 |
| ATOM | 526 | C | SER | 281 | 11.966 | 39.701 | 99.346 | 1.00 | 18.03 |
| ATOM | 527 | O | SER | 281 | 12.198 | 39.993 | 98.181 | 1.00 | 22.71 |
| ATOM | 528 | N | PRO | 282 | 11.797 | 38.434 | 99.746 | 0.51 | 11.55 |
| ATOM | 529 | CD | PRO | 282 | 11.694 | 37.981 | 101.137 | 0.51 | 8.66 |
| ATOM | 530 | CA | PRO | 282 | 11.900 | 37.300 | 98.852 | 0.51 | 9.27 |
| ATOM | 531 | CB | PRO | 282 | 11.808 | 36.109 | 99.808 | 0.51 | 5.55 |
| ATOM | 532 | CG | PRO | 282 | 11.084 | 36.649 | 100.969 | 0.51 | 9.16 |
| ATOM | 533 | C | PRO | 282 | 10.793 | 37.358 | 97.790 | 0.51 | 9.15 |
| ATOM | 534 | O | PRO | 282 | 11.021 | 36.976 | 96.642 | 0.51 | 5.77 |
| ATOM | 535 | N | ASP | 283 | 9.661 | 37.978 | 98.139 | 1.00 | 12.43 |
| ATOM | 536 | H | ASP | 283 | 9.564 | 38.331 | 99.048 | 1.00 | 0.00 |
| ATOM | 537 | CA | ASP | 283 | 8.539 | 38.154 | 97.202 | 1.00 | 13.00 |
| ATOM | 538 | CB | ASP | 283 | 7.260 | 38.567 | 97.947 | 1.00 | 19.51 |
| ATOM | 539 | CG | ASP | 283 | 6.091 | 38.906 | 97.003 | 1.00 | 24.50 |
| ATOM | 540 | OD1 | ASP | 283 | 5.812 | 40.099 | 96.765 | 1.00 | 27.16 |
| ATOM | 541 | OD2 | ASP | 283 | 5.407 | 37.982 | 96.506 | 1.00 | 28.32 |
| ATOM | 542 | C | ASP | 283 | 8.943 | 39.196 | 96.142 | 1.00 | 12.73 |
| ATOM | 543 | O | ASP | 283 | 8.649 | 39.000 | 94.975 | 1.00 | 13.24 |
| ATOM | 544 | N | ALA | 284 | 9.625 | 40.282 | 96.543 | 1.00 | 10.11 |
| ATOM | 545 | H | ALA | 284 | 9.818 | 40.407 | 97.496 | 1.00 | 0.00 |
| ATOM | 546 | CA | ALA | 284 | 10.102 | 41.308 | 95.594 | 1.00 | 12.04 |
| ATOM | 547 | CB | ALA | 284 | 10.885 | 42.470 | 96.366 | 1.00 | 10.41 |
| ATOM | 548 | C | ALA | 284 | 11.062 | 40.627 | 94.617 | 1.00 | 13.73 |
| ATOM | 549 | O | ALA | 284 | 10.937 | 40.780 | 93.406 | 1.00 | 14.81 |
| ATOM | 550 | N | PHE | 285 | 12.014 | 39.857 | 95.166 | 1.00 | 14.06 |
| ATOM | 551 | H | PHE | 285 | 12.069 | 39.776 | 96.141 | 1.00 | 0.00 |
| ATOM | 552 | CA | PHE | 285 | 12.990 | 39.121 | 94.353 | 1.00 | 12.64 |
| ATOM | 553 | CB | PHE | 285 | 13.896 | 38.255 | 95.251 | 1.00 | 9.31 |
| ATOM | 554 | CG | PHE | 285 | 15.084 | 37.652 | 94.523 | 1.00 | 8.77 |
| ATOM | 555 | CD1 | PHE | 285 | 16.011 | 38.478 | 93.887 | 1.00 | 8.47 |
| ATOM | 556 | CD2 | PHE | 285 | 15.273 | 36.276 | 94.490 | 1.00 | 14.02 |
| ATOM | 557 | CE1 | PHE | 285 | 17.111 | 37.956 | 93.226 | 1.00 | 10.68 |
| ATOM | 558 | CE2 | PHE | 285 | 16.375 | 35.720 | 93.839 | 1.00 | 16.12 |
| ATOM | 559 | CZ | PHE | 285 | 17.301 | 36.549 | 93.201 | 1.00 | 19.89 |
| ATOM | 560 | C | PHE | 285 | 12.316 | 38.223 | 93.329 | 1.00 | 11.62 |
| ATOM | 561 | O | PHE | 285 | 12.457 | 38.411 | 92.136 | 1.00 | 18.14 |
| ATOM | 562 | N | LEU | 286 | 11.521 | 37.289 | 93.822 | 1.00 | 13.05 |
| ATOM | 563 | H | LEU | 286 | 11.394 | 37.242 | 94.792 | 1.00 | 0.00 |
| ATOM | 564 | CA | LEU | 286 | 10.817 | 36.318 | 93.010 | 1.00 | 14.32 |
| ATOM | 565 | CB | LEU | 286 | 10.089 | 35.358 | 93.953 | 1.00 | 14.02 |
| ATOM | 566 | CG | LEU | 286 | 10.953 | 34.368 | 94.768 | 1.00 | 10.88 |
| ATOM | 567 | CD1 | LEU | 286 | 10.100 | 33.469 | 95.715 | 1.00 | 11.11 |
| ATOM | 568 | CD2 | LEU | 286 | 11.736 | 33.428 | 93.749 | 1.00 | 9.24 |
| ATOM | 569 | C | LEU | 286 | 9.871 | 36.877 | 91.948 | 1.00 | 18.50 |
| ATOM | 570 | O | LEU | 286 | 9.608 | 36.251 | 90.916 | 1.00 | 16.87 |
| ATOM | 571 | N | ALA | 287 | 9.393 | 38.109 | 92.174 | 1.00 | 17.63 |
| ATOM | 572 | H | ALA | 287 | 9.650 | 38.592 | 92.987 | 1.00 | 0.00 |
| ATOM | 573 | CA | ALA | 287 | 8.490 | 38.761 | 91.234 | 1.00 | 14.28 |
| ATOM | 574 | CB | ALA | 287 | 7.993 | 40.157 | 91.802 | 1.00 | 17.74 |
| ATOM | 575 | C | ALA | 287 | 9.212 | 38.958 | 89.902 | 1.00 | 14.40 |
| ATOM | 576 | O | ALA | 287 | 8.600 | 39.007 | 88.819 | 1.00 | 12.93 |
| ATOM | 577 | N | GLU | 288 | 10.529 | 39.090 | 89.953 | 1.00 | 16.64 |
| ATOM | 578 | H | GLU | 288 | 11.013 | 39.112 | 90.810 | 1.00 | 20.00 |

TABLE 6-continued

Coordinates of Lck bound with damnacanthal

| | Atom Type | Res | # | X | Y | Z | Occ | B |
|---|---|---|---|---|---|---|---|---|
| ATOM | 579 | CA | GLU | 288 | 11.249 | 39.212 | 88.712 | 1.00 | 19.67 |
| ATOM | 580 | CB | GLU | 288 | 12.637 | 39.784 | 88.916 | 1.00 | 20.68 |
| ATOM | 581 | CG | GLU | 288 | 12.755 | 41.172 | 88.286 | 1.00 | 28.20 |
| ATOM | 582 | CD | GLU | 288 | 11.749 | 42.187 | 88.830 | 1.00 | 29.18 |
| ATOM | 583 | OE1 | GLU | 288 | 10.613 | 42.219 | 88.316 | 1.00 | 36.49 |
| ATOM | 584 | OE2 | GLU | 288 | 12.086 | 42.974 | 89.750 | 1.00 | 25.68 |
| ATOM | 585 | C | GLU | 288 | 11.237 | 37.884 | 87.953 | 1.00 | 20.13 |
| ATOM | 586 | O | GLU | 288 | 11.078 | 37.895 | 86.740 | 1.00 | 17.94 |
| ATOM | 587 | N | ALA | 289 | 11.320 | 36.746 | 88.652 | 1.00 | 21.94 |
| ATOM | 588 | H | ALA | 289 | 11.434 | 36.759 | 89.625 | 1.00 | 0.00 |
| ATOM | 589 | CA | ALA | 289 | 11.239 | 35.451 | 87.945 | 1.00 | 20.03 |
| ATOM | 590 | CB | ALA | 289 | 11.487 | 34.273 | 88.892 | 1.00 | 19.69 |
| ATOM | 591 | C | ALA | 289 | 9.823 | 35.378 | 87.320 | 1.00 | 18.98 |
| ATOM | 592 | O | ALA | 289 | 9.690 | 35.037 | 86.139 | 1.00 | 18.44 |
| ATOM | 593 | N | ASN | 290 | 8.789 | 35.742 | 88.100 | 1.00 | 19.45 |
| ATOM | 594 | H | ASN | 290 | 8.951 | 36.002 | 89.031 | 1.00 | 0.00 |
| ATOM | 595 | CA | ASN | 290 | 7.407 | 35.765 | 87.601 | 1.00 | 19.93 |
| ATOM | 596 | CB | ASN | 290 | 6.420 | 36.345 | 88.639 | 1.00 | 25.31 |
| ATOM | 597 | CG | ASN | 290 | 6.236 | 35.441 | 89.887 | 1.00 | 33.50 |
| ATOM | 598 | OD1 | ASN | 290 | 6.187 | 35.928 | 91.038 | 1.00 | 33.10 |
| ATOM | 599 | ND2 | ASN | 290 | 6.153 | 34.134 | 89.667 | 1.00 | 38.42 |
| ATOM | 600 | HD21 | ASN | 290 | 6.208 | 33.787 | 88.752 | 1.00 | 0.00 |
| ATOM | 601 | HD22 | ASN | 290 | 6.037 | 33.551 | 90.445 | 1.00 | 0.00 |
| ATOM | 602 | C | ASN | 290 | 7.341 | 36.614 | 86.318 | 1.00 | 20.65 |
| ATOM | 603 | O | ASN | 290 | 6.667 | 36.249 | 85.349 | 1.00 | 21.08 |
| ATOM | 604 | N | LEU | 291 | 8.059 | 37.737 | 86.264 | 1.00 | 19.69 |
| ATOM | 605 | H | LEU | 291 | 8.616 | 38.028 | 87.015 | 1.00 | 0.00 |
| ATOM | 606 | CA | LEU | 291 | 7.995 | 38.540 | 85.035 | 1.00 | 18.75 |
| ATOM | 607 | CB | LEU | 291 | 8.660 | 39.917 | 85.199 | 1.00 | 19.51 |
| ATOM | 608 | CG | LEU | 291 | 8.509 | 40.769 | 83.928 | 1.00 | 25.16 |
| ATOM | 609 | CD1 | LEU | 291 | 8.043 | 42.191 | 84.220 | 1.00 | 22.89 |
| ATOM | 610 | CD2 | LEU | 291 | 9.785 | 40.753 | 83.167 | 1.00 | 27.85 |
| ATOM | 611 | C | LEU | 291 | 8.628 | 37.795 | 83.868 | 1.00 | 19.30 |
| ATOM | 612 | O | LEU | 291 | 8.092 | 37.761 | 82.758 | 1.00 | 21.13 |
| ATOM | 613 | N | MET | 292 | 9.800 | 37.217 | 84.094 | 1.00 | 22.55 |
| ATOM | 614 | H | MET | 292 | 10.231 | 37.277 | 84.972 | 1.00 | 0.00 |
| ATOM | 615 | CA | MET | 292 | 10.454 | 36.484 | 83.023 | 1.00 | 18.32 |
| ATOM | 616 | CB | MET | 292 | 11.798 | 35.942 | 83.497 | 1.00 | 15.80 |
| ATOM | 617 | CG | MET | 292 | 12.838 | 37.042 | 83.781 | 1.00 | 16.01 |
| ATOM | 618 | SD | MET | 292 | 14.370 | 36.392 | 84.455 | 1.00 | 21.35 |
| ATOM | 619 | CE | MET | 292 | 15.202 | 36.010 | 83.038 | 1.00 | 17.21 |
| ATOM | 620 | C | MET | 292 | 9.528 | 35.392 | 82.458 | 1.00 | 18.54 |
| ATOM | 621 | O | MET | 292 | 9.506 | 35.183 | 81.239 | 1.00 | 18.66 |
| ATOM | 622 | N | LYS | 293 | 8.686 | 34.771 | 83.294 | 1.00 | 16.27 |
| ATOM | 623 | H | LYS | 293 | 8.668 | 34.984 | 84.250 | 1.00 | 0.00 |
| ATOM | 624 | CA | LYS | 293 | 7.766 | 33.740 | 82.745 | 1.00 | 18.16 |
| ATOM | 625 | CB | LYS | 293 | 6.904 | 33.088 | 83.819 | 1.00 | 19.46 |
| ATOM | 626 | CG | LYS | 293 | 7.647 | 32.255 | 84.813 | 1.00 | 27.50 |
| ATOM | 627 | CD | LYS | 293 | 6.721 | 31.846 | 86.004 | 1.00 | 35.17 |
| ATOM | 628 | CE | LYS | 293 | 7.560 | 31.605 | 87.292 | 1.00 | 35.58 |
| ATOM | 629 | NZ | LYS | 293 | 6.778 | 30.876 | 88.368 | 1.00 | 41.06 |
| ATOM | 630 | HZ1 | LYS | 293 | 6.473 | 29.949 | 88.008 | 1.00 | 0.00 |
| ATOM | 631 | HZ2 | LYS | 293 | 5.943 | 31.438 | 88.631 | 1.00 | 0.00 |
| ATOM | 632 | HZ3 | LYS | 293 | 7.382 | 30.741 | 89.204 | 1.00 | 0.00 |
| ATOM | 633 | C | LYS | 293 | 6.851 | 34.291 | 81.651 | 1.00 | 17.96 |
| ATOM | 634 | O | LYS | 293 | 6.636 | 33.667 | 80.604 | 1.00 | 16.62 |
| ATOM | 635 | N | GLN | 294 | 6.371 | 35.499 | 81.843 | 1.00 | 22.00 |
| ATOM | 636 | H | GLN | 294 | 6.598 | 36.011 | 82.647 | 1.00 | 0.00 |
| ATOM | 637 | CA | GLN | 294 | 5.488 | 36.082 | 80.842 | 1.00 | 24.83 |
| ATOM | 638 | CB | GLN | 294 | 4.609 | 37.168 | 81.473 | 1.00 | 26.59 |
| ATOM | 639 | CG | GLN | 294 | 3.762 | 36.646 | 82.632 | 1.00 | 29.43 |
| ATOM | 640 | CD | GLN | 294 | 2.823 | 35.523 | 82.211 | 1.00 | 35.56 |
| ATOM | 641 | OE1 | GLN | 294 | 2.230 | 35.557 | 81.124 | 1.00 | 37.02 |
| ATOM | 642 | NE2 | GLN | 294 | 2.664 | 34.523 | 83.083 | 1.00 | 38.01 |
| ATOM | 643 | HE21 | GLN | 294 | 3.140 | 34.540 | 83.940 | 1.00 | 0.00 |
| ATOM | 644 | HE22 | GLN | 294 | 2.064 | 33.793 | 82.829 | 1.00 | 0.00 |
| ATOM | 645 | C | GLN | 294 | 6.156 | 36.636 | 79.606 | 1.00 | 26.21 |
| ATOM | 646 | O | GLN | 294 | 5.467 | 37.026 | 78.688 | 1.00 | 30.71 |
| ATOM | 647 | N | LEU | 295 | 7.483 | 36.589 | 79.525 | 1.00 | 26.20 |
| ATOM | 648 | H | LEU | 295 | 8.006 | 36.162 | 80.235 | 1.00 | 0.00 |
| ATOM | 649 | CA | LEU | 295 | 8.181 | 37.167 | 78.389 | 1.00 | 25.29 |
| ATOM | 650 | CB | LEU | 295 | 8.876 | 38.460 | 78.813 | 1.00 | 23.53 |
| ATOM | 651 | CG | LEU | 295 | 8.027 | 39.652 | 79.196 | 1.00 | 20.70 |
| ATOM | 652 | CD1 | LEU | 295 | 8.967 | 40.769 | 79.625 | 1.00 | 20.71 |

TABLE 6-continued

Coordinates of Lck bound with damnacanthal

| | | Atom Type | Res | # | X | Y | Z | Occ | B |
|---|---|---|---|---|---|---|---|---|---|
| ATOM | 653 | CD2 | LEU | 295 | 7.169 | 40.036 | 77.993 | 1.00 | 18.34 |
| ATOM | 654 | C | LEU | 295 | 9.232 | 36.231 | 77.853 | 1.00 | 25.61 |
| ATOM | 655 | O | LEU | 295 | 10.456 | 36.514 | 77.923 | 1.00 | 28.41 |
| ATOM | 656 | N | GLN | 296 | 8.767 | 35.174 | 77.212 | 1.00 | 20.20 |
| ATOM | 657 | H | GLN | 296 | 7.805 | 35.043 | 77.081 | 1.00 | 0.00 |
| ATOM | 658 | CA | GLN | 296 | 9.691 | 34.208 | 76.703 | 1.00 | 16.20 |
| ATOM | 659 | CB | GLN | 296 | 9.150 | 32.791 | 76.927 | 1.00 | 16.60 |
| ATOM | 660 | CG | GLN | 296 | 9.139 | 32.405 | 78.418 | 1.00 | 20.36 |
| ATOM | 661 | CD | GLN | 296 | 8.595 | 31.003 | 78.641 | 1.00 | 25.11 |
| ATOM | 662 | OE1 | GLN | 296 | 9.075 | 30.040 | 78.043 | 1.00 | 30.17 |
| ATOM | 663 | NE2 | GLN | 296 | 7.580 | 30.891 | 79.476 | 1.00 | 26.60 |
| ATOM | 664 | HE21 | GLN | 296 | 7.216 | 31.688 | 79.915 | 1.00 | 0.00 |
| ATOM | 665 | HE22 | GLN | 296 | 7.218 | 29.994 | 79.630 | 1.00 | 0.00 |
| ATOM | 666 | C | GLN | 296 | 9.896 | 34.496 | 75.289 | 1.00 | 12.22 |
| ATOM | 667 | O | GLN | 296 | 8.947 | 34.548 | 74.554 | 1.00 | 15.87 |
| ATOM | 668 | N | HIS | 297 | 11.151 | 34.645 | 74.896 | 1.00 | 13.19 |
| ATOM | 669 | H | HIS | 297 | 11.879 | 34.552 | 75.546 | 1.00 | 0.00 |
| ATOM | 670 | CA | HIS | 297 | 11.493 | 34.947 | 73.507 | 1.00 | 12.98 |
| ATOM | 671 | CB | HIS | 297 | 11.112 | 36.414 | 73.225 | 1.00 | 11.49 |
| ATOM | 672 | CG | HIS | 297 | 11.277 | 36.810 | 71.801 | 1.00 | 8.99 |
| ATOM | 673 | CD2 | HIS | 297 | 10.398 | 36.833 | 70.776 | 1.00 | 6.66 |
| ATOM | 674 | ND1 | HIS | 297 | 12.504 | 37.127 | 71.261 | 1.00 | 10.86 |
| ATOM | 675 | HD1 | HIS | 297 | 13.336 | 37.199 | 71.767 | 1.00 | 0.00 |
| ATOM | 676 | CE1 | HIS | 297 | 12.391 | 37.319 | 69.959 | 1.00 | 2.00 |
| ATOM | 677 | NE2 | HIS | 297 | 11.104 | 37.147 | 69.643 | 1.00 | 13.12 |
| ATOM | 678 | HE2 | HIS | 297 | 10.726 | 37.231 | 68.747 | 1.00 | 0.00 |
| ATOM | 679 | C | HIS | 297 | 13.007 | 34.717 | 73.330 | 1.00 | 11.69 |
| ATOM | 680 | O | HIS | 297 | 13.760 | 34.864 | 74.295 | 1.00 | 17.62 |
| ATOM | 681 | N | GLN | 298 | 13.443 | 34.343 | 72.125 | 1.00 | 10.99 |
| ATOM | 682 | H | GLN | 298 | 12.809 | 34.229 | 71.387 | 1.00 | 0.00 |
| ATOM | 683 | CA | GLN | 298 | 14.871 | 34.095 | 71.874 | 1.00 | 12.42 |
| ATOM | 684 | CB | GLN | 298 | 15.147 | 33.740 | 70.399 | 1.00 | 15.26 |
| ATOM | 685 | CG | GLN | 298 | 14.843 | 32.342 | 69.896 | 1.00 | 19.71 |
| ATOM | 686 | CD | GLN | 298 | 15.543 | 31.184 | 70.646 | 1.00 | 18.63 |
| ATOM | 687 | OE1 | GLN | 298 | 14.865 | 30.381 | 71.234 | 1.00 | 22.28 |
| ATOM | 688 | NE2 | GLN | 298 | 16.895 | 31.135 | 70.645 | 1.00 | 15.43 |
| ATOM | 689 | HE21 | GLN | 298 | 17.410 | 31.824 | 70.176 | 1.00 | 0.00 |
| ATOM | 690 | HE22 | GLN | 298 | 17.321 | 30.395 | 71.125 | 1.00 | 0.00 |
| ATOM | 691 | C | GLN | 298 | 15.772 | 35.333 | 72.250 | 1.00 | 9.35 |
| ATOM | 692 | O | GLN | 298 | 16.881 | 35.162 | 72.768 | 1.00 | 7.95 |
| ATOM | 693 | N | ARG | 299 | 15.277 | 36.544 | 72.000 | 1.00 | 10.32 |
| ATOM | 694 | H | ARG | 299 | 14.379 | 36.632 | 71.617 | 1.00 | 0.00 |
| ATOM | 695 | CA | ARG | 299 | 16.050 | 37.788 | 72.285 | 1.00 | 10.31 |
| ATOM | 696 | CB | ARG | 299 | 15.589 | 38.927 | 71.367 | 1.00 | 7.33 |
| ATOM | 697 | CG | ARG | 299 | 15.723 | 38.657 | 69.915 | 1.00 | 5.83 |
| ATOM | 698 | CD | ARG | 299 | 17.169 | 38.846 | 69.313 | 1.00 | 6.17 |
| ATOM | 699 | NE | ARG | 299 | 18.266 | 38.237 | 70.068 | 1.00 | 9.50 |
| ATOM | 700 | HE | ARG | 299 | 18.706 | 38.791 | 70.744 | 1.00 | 0.00 |
| ATOM | 701 | CZ | ARG | 299 | 18.721 | 36.977 | 69.910 | 1.00 | 9.61 |
| ATOM | 702 | NH1 | ARG | 299 | 18.143 | 36.157 | 69.039 | 1.00 | 2.09 |
| ATOM | 703 | HH11 | ARG | 299 | 17.365 | 36.473 | 68.495 | 1.00 | 0.00 |
| ATOM | 704 | HH12 | ARG | 299 | 18.486 | 35.224 | 68.927 | 1.00 | 0.00 |
| ATOM | 705 | NH2 | ARG | 299 | 19.859 | 36.600 | 70.500 | 1.00 | 2.69 |
| ATOM | 706 | HH21 | ARG | 299 | 20.373 | 37.252 | 71.058 | 1.00 | 0.00 |
| ATOM | 707 | HH22 | ARG | 299 | 20.197 | 35.666 | 70.383 | 1.00 | 0.00 |
| ATOM | 708 | C | ARG | 299 | 16.028 | 38.272 | 73.740 | 1.00 | 7.33 |
| ATOM | 709 | O | ARG | 299 | 16.578 | 39.326 | 74.041 | 1.00 | 8.57 |
| ATOM | 710 | N | LEU | 300 | 15.365 | 37.538 | 74.628 | 1.00 | 6.35 |
| ATOM | 711 | H | LEU | 300 | 14.912 | 36.722 | 74.330 | 1.00 | 0.00 |
| ATOM | 712 | CA | LEU | 300 | 15.274 | 37.891 | 76.052 | 1.00 | 6.83 |
| ATOM | 713 | CB | LEU | 300 | 13.796 | 38.082 | 76.482 | 1.00 | 7.12 |
| ATOM | 714 | CG | LEU | 300 | 13.147 | 39.477 | 76.195 | 1.00 | 9.57 |
| ATOM | 715 | CD1 | LEU | 300 | 13.233 | 39.840 | 74.746 | 1.00 | 2.00 |
| ATOM | 716 | CD2 | LEU | 300 | 11.696 | 39.525 | 76.713 | 1.00 | 6.74 |
| ATOM | 717 | C | LEU | 300 | 15.897 | 36.763 | 76.852 | 1.00 | 7.85 |
| ATOM | 718 | O | LEU | 300 | 15.658 | 35.587 | 76.512 | 1.00 | 9.41 |
| ATOM | 719 | N | VAL | 301 | 16.644 | 37.093 | 77.912 | 1.00 | 8.46 |
| ATOM | 720 | H | VAL | 301 | 16.761 | 38.036 | 78.153 | 1.00 | 0.00 |
| ATOM | 721 | CA | VAL | 301 | 17.301 | 36.075 | 78.733 | 1.00 | 10.15 |
| ATOM | 722 | CB | VAL | 301 | 18.262 | 36.702 | 79.864 | 1.00 | 8.78 |
| ATOM | 723 | CG1 | VAL | 301 | 18.957 | 35.614 | 80.662 | 1.00 | 8.66 |
| ATOM | 724 | CG2 | VAL | 301 | 19.383 | 37.508 | 79.236 | 1.00 | 13.52 |
| ATOM | 725 | C | VAL | 301 | 16.173 | 35.162 | 79.294 | 1.00 | 12.25 |
| ATOM | 726 | O | VAL | 301 | 15.191 | 35.626 | 79.854 | 1.00 | 13.87 |

TABLE 6-continued

Coordinates of Lck bound with damnacanthal

| | | Atom Type | Res | # | X | Y | Z | Occ | B |
|---|---|---|---|---|---|---|---|---|---|
| ATOM | 727 | N | ARG | 302 | 16.368 | 33.857 | 79.218 | 1.00 | 14.33 |
| ATOM | 728 | H | ARG | 302 | 17.223 | 33.500 | 78.898 | 1.00 | 0.00 |
| ATOM | 729 | CA | ARG | 302 | 15.305 | 32.920 | 79.613 | 1.00 | 11.26 |
| ATOM | 730 | CB | ARG | 302 | 15.249 | 31.740 | 78.612 | 1.00 | 11.25 |
| ATOM | 731 | CG | ARG | 302 | 14.218 | 30.619 | 78.925 | 1.00 | 11.50 |
| ATOM | 732 | CD | ARG | 302 | 14.253 | 29.557 | 77.787 | 1.00 | 16.07 |
| ATOM | 733 | NE | ARG | 302 | 13.273 | 28.470 | 77.975 | 1.00 | 19.19 |
| ATOM | 734 | HE | ARG | 302 | 12.550 | 28.385 | 77.320 | 1.00 | 0.00 |
| ATOM | 735 | CZ | ARG | 302 | 13.311 | 27.592 | 78.987 | 1.00 | 25.10 |
| ATOM | 736 | NH1 | ARG | 302 | 14.273 | 27.658 | 79.911 | 1.00 | 20.92 |
| ATOM | 737 | HH11 | ARG | 302 | 14.975 | 28.368 | 79.852 | 1.00 | 0.00 |
| ATOM | 738 | HH12 | ARG | 302 | 14.291 | 26.998 | 80.662 | 1.00 | 0.00 |
| ATOM | 739 | NH2 | ARG | 302 | 12.381 | 26.644 | 79.086 | 1.00 | 29.45 |
| ATOM | 740 | HH21 | ARG | 302 | 11.652 | 26.586 | 78.404 | 1.00 | 0.00 |
| ATOM | 741 | HH22 | ARG | 302 | 12.412 | 25.990 | 79.842 | 1.00 | 0.00 |
| ATOM | 742 | C | ARG | 302 | 15.361 | 32.420 | 81.013 | 1.00 | 12.39 |
| ATOM | 743 | O | ARG | 302 | 16.428 | 32.082 | 81.512 | 1.00 | 13.92 |
| ATOM | 744 | N | LEU | 303 | 14.222 | 32.474 | 81.691 | 1.00 | 11.03 |
| ATOM | 745 | H | LEU | 303 | 13.423 | 32.874 | 81.289 | 1.00 | 0.00 |
| ATOM | 746 | CA | LEU | 303 | 14.143 | 31.940 | 83.043 | 1.00 | 9.50 |
| ATOM | 747 | CB | LEU | 303 | 12.789 | 32.201 | 83.668 | 1.00 | 12.86 |
| ATOM | 748 | CG | LEU | 303 | 12.515 | 31.581 | 85.047 | 1.00 | 12.34 |
| ATOM | 749 | CD1 | LEU | 303 | 13.357 | 32.221 | 86.090 | 1.00 | 18.36 |
| ATOM | 750 | CD2 | LEU | 303 | 11.012 | 31.763 | 85.415 | 1.00 | 11.34 |
| ATOM | 751 | C | LEU | 303 | 14.304 | 30.420 | 82.881 | 1.00 | 10.58 |
| ATOM | 752 | O | LEU | 303 | 13.765 | 29.804 | 81.943 | 1.00 | 9.92 |
| ATOM | 753 | N | TYR | 304 | 15.124 | 29.851 | 83.733 | 1.00 | 11.10 |
| ATOM | 754 | H | TYR | 304 | 15.583 | 30.394 | 84.407 | 1.00 | 0.00 |
| ATOM | 755 | CA | TYR | 304 | 15.375 | 28.414 | 83.706 | 1.00 | 12.90 |
| ATOM | 756 | CB | TYR | 304 | 16.874 | 28.168 | 83.850 | 1.00 | 15.13 |
| ATOM | 757 | CG | TYR | 304 | 17.341 | 26.786 | 83.477 | 1.00 | 20.24 |
| ATOM | 758 | CD1 | TYR | 304 | 17.779 | 26.513 | 82.186 | 1.00 | 21.79 |
| ATOM | 759 | CE1 | TYR | 304 | 18.183 | 25.239 | 81.824 | 1.00 | 23.27 |
| ATOM | 760 | CD2 | TYR | 304 | 17.347 | 25.742 | 84.419 | 1.00 | 19.38 |
| ATOM | 761 | CE2 | TYR | 304 | 17.760 | 24.462 | 84.064 | 1.00 | 21.75 |
| ATOM | 762 | CZ | TYR | 304 | 18.176 | 24.229 | 82.768 | 1.00 | 25.53 |
| ATOM | 763 | OH | TYR | 304 | 18.568 | 22.986 | 82.398 | 1.00 | 26.24 |
| ATOM | 764 | HH | TYR | 304 | 18.497 | 22.391 | 83.148 | 1.00 | 0.00 |
| ATOM | 765 | C | TYR | 304 | 14.609 | 27.761 | 84.850 | 1.00 | 11.51 |
| ATOM | 766 | O | TYR | 304 | 13.897 | 26.817 | 84.640 | 1.00 | 9.84 |
| ATOM | 767 | N | ALA | 305 | 14.692 | 28.329 | 86.045 | 1.00 | 8.68 |
| ATOM | 768 | H | ALA | 305 | 15.218 | 29.148 | 86.164 | 1.00 | 0.00 |
| ATOM | 769 | CA | ALA | 305 | 14.014 | 27.761 | 87.200 | 1.00 | 9.38 |
| ATOM | 770 | CB | ALA | 305 | 14.650 | 26.445 | 87.570 | 1.00 | 8.60 |
| ATOM | 771 | C | ALA | 305 | 14.152 | 28.702 | 88.385 | 1.00 | 8.22 |
| ATOM | 772 | O | ALA | 305 | 14.820 | 29.754 | 88.278 | 1.00 | 8.45 |
| ATOM | 773 | N | VAL | 306 | 13.546 | 28.276 | 89.495 | 0.75 | 7.52 |
| ATOM | 774 | H | VAL | 306 | 13.038 | 27.440 | 89.449 | 1.00 | 0.00 |
| ATOM | 775 | CA | VAL | 306 | 13.574 | 28.958 | 90.795 | 0.75 | 6.68 |
| ATOM | 776 | CB | VAL | 306 | 12.270 | 29.752 | 91.100 | 0.75 | 5.90 |
| ATOM | 777 | CG1 | VAL | 306 | 11.960 | 30.818 | 90.002 | 0.75 | 3.47 |
| ATOM | 778 | CG2 | VAL | 306 | 11.102 | 28.792 | 91.282 | 0.75 | 2.00 |
| ATOM | 779 | C | VAL | 306 | 13.694 | 27.929 | 91.947 | 0.75 | 7.87 |
| ATOM | 780 | O | VAL | 306 | 13.321 | 26.738 | 91.826 | 0.75 | 6.88 |
| ATOM | 781 | N | VAL | 307 | 14.242 | 28.383 | 93.059 | 1.00 | 12.10 |
| ATOM | 782 | H | VAL | 307 | 14.608 | 29.292 | 93.090 | 1.00 | 0.00 |
| ATOM | 783 | CA | VAL | 307 | 14.319 | 27.558 | 94.258 | 1.00 | 15.71 |
| ATOM | 784 | CB | VAL | 307 | 15.761 | 27.184 | 94.688 | 1.00 | 16.80 |
| ATOM | 785 | CG1 | VAL | 307 | 15.707 | 26.401 | 96.020 | 1.00 | 11.91 |
| ATOM | 786 | CG2 | VAL | 307 | 16.436 | 26.364 | 93.613 | 1.00 | 20.31 |
| ATOM | 787 | C | VAL | 307 | 13.710 | 28.506 | 95.280 | 1.00 | 18.31 |
| ATOM | 788 | O | VAL | 307 | 14.387 | 29.400 | 95.754 | 1.00 | 20.75 |
| ATOM | 789 | N | THR | 308 | 12.424 | 28.312 | 95.575 | 1.00 | 20.77 |
| ATOM | 790 | H | THR | 308 | 11.954 | 27.552 | 95.174 | 1.00 | 0.00 |
| ATOM | 791 | CA | THR | 308 | 11.664 | 29.180 | 96.475 | 1.00 | 20.38 |
| ATOM | 792 | CB | THR | 308 | 10.182 | 29.274 | 96.025 | 1.00 | 20.02 |
| ATOM | 793 | OG1 | THR | 308 | 9.645 | 27.966 | 95.871 | 1.00 | 19.76 |
| ATOM | 794 | HG1 | THR | 308 | 8.728 | 28.027 | 95.593 | 1.00 | 0.00 |
| ATOM | 795 | CG2 | THR | 308 | 10.090 | 29.984 | 96.641 | 1.00 | 17.73 |
| ATOM | 796 | C | THR | 308 | 11.793 | 29.027 | 97.989 | 1.00 | 23.55 |
| ATOM | 797 | O | THR | 308 | 11.107 | 29.721 | 98.769 | 1.00 | 25.08 |
| ATOM | 798 | N | ALA | 309 | 12.760 | 28.210 | 98.396 | 1.00 | 26.18 |
| ATOM | 799 | H | ALA | 309 | 13.285 | 27.728 | 97.724 | 1.00 | 0.00 |
| ATOM | 800 | CA | ALA | 309 | 13.094 | 27.983 | 99.800 | 1.00 | 27.29 |

TABLE 6-continued

Coordinates of Lck bound with damnacanthal

| Atom Type | | # | Res | X | Y | Z | Occ | B |
|---|---|---|---|---|---|---|---|---|
| ATOM | 801 | CB | ALA | 309 | 13.280 | 26.481 | 100.063 | 1.00 | 29.08 |
| ATOM | 802 | C | ALA | 309 | 14.427 | 28.700 | 100.009 | 1.00 | 29.01 |
| ATOM | 803 | O | ALA | 309 | 15.291 | 28.647 | 99.141 | 1.00 | 28.07 |
| ATOM | 804 | N | GLU | 310 | 14.616 | 29.317 | 101.178 | 1.00 | 31.36 |
| ATOM | 805 | H | GLU | 310 | 13.915 | 29.281 | 101.862 | 1.00 | 0.00 |
| ATOM | 806 | CA | GLU | 310 | 15.852 | 30.060 | 101.486 | 1.00 | 34.84 |
| ATOM | 807 | CB | GLU | 310 | 15.632 | 30.932 | 102.729 | 1.00 | 37.12 |
| ATOM | 808 | CG | GLU | 310 | 14.617 | 32.060 | 102.521 | 1.00 | 46.57 |
| ATOM | 809 | CD | GLU | 310 | 14.487 | 33.002 | 103.720 | 1.00 | 51.34 |
| ATOM | 810 | OE1 | GLU | 310 | 15.053 | 32.681 | 104.783 | 1.00 | 55.17 |
| ATOM | 811 | OE2 | GLU | 310 | 13.819 | 34.064 | 103.597 | 1.00 | 52.97 |
| ATOM | 812 | C | GLU | 310 | 17.160 | 29.270 | 101.648 | 1.00 | 35.74 |
| ATOM | 813 | O | GLU | 310 | 17.182 | 28.156 | 102.152 | 1.00 | 38.27 |
| ATOM | 814 | N | PRO | 311 | 18.270 | 29.822 | 101.074 | 1.00 | 35.50 |
| ATOM | 815 | CD | PRO | 311 | 19.578 | 29.111 | 101.099 | 1.00 | 34.24 |
| ATOM | 816 | CA | PRO | 311 | 18.337 | 31.079 | 100.359 | 1.00 | 34.17 |
| ATOM | 817 | CB | PRO | 311 | 19.845 | 31.380 | 100.319 | 1.00 | 37.54 |
| ATOM | 818 | CG | PRO | 311 | 20.455 | 30.007 | 100.226 | 1.00 | 35.11 |
| ATOM | 819 | C | PRO | 311 | 17.712 | 30.831 | 98.953 | 1.00 | 29.99 |
| ATOM | 820 | O | PRO | 311 | 17.839 | 29.733 | 98.378 | 1.00 | 30.46 |
| ATOM | 821 | N | ILE | 312 | 16.952 | 31.792 | 98.482 | 1.00 | 24.15 |
| ATOM | 822 | H | ILE | 312 | 16.873 | 32.623 | 98.994 | 1.00 | 0.00 |
| ATOM | 823 | CA | ILE | 312 | 16.218 | 31.704 | 97.247 | 1.00 | 19.42 |
| ATOM | 824 | CB | ILE | 312 | 15.080 | 32.722 | 97.294 | 1.00 | 22.51 |
| ATOM | 825 | CG2 | ILE | 312 | 14.392 | 32.851 | 95.956 | 1.00 | 26.60 |
| ATOM | 826 | CG1 | ILE | 312 | 14.143 | 32.339 | 98.441 | 1.00 | 23.19 |
| ATOM | 827 | CD1 | ILE | 312 | 13.532 | 33.505 | 99.074 | 1.00 | 27.86 |
| ATOM | 828 | C | ILE | 312 | 17.061 | 31.930 | 96.016 | 1.00 | 18.49 |
| ATOM | 829 | O | ILE | 312 | 17.942 | 32.800 | 95.966 | 1.00 | 17.29 |
| ATOM | 830 | N | TYR | 313 | 16.739 | 31.176 | 94.979 | 1.00 | 18.68 |
| ATOM | 831 | H | TYR | 313 | 16.005 | 30.531 | 95.049 | 1.00 | 0.00 |
| ATOM | 832 | CA | TYR | 313 | 17.457 | 31.282 | 93.722 | 1.00 | 14.42 |
| ATOM | 833 | CB | TYR | 313 | 18.159 | 29.972 | 93.398 | 1.00 | 16.93 |
| ATOM | 834 | CG | TYR | 313 | 19.268 | 29.529 | 94.312 | 1.00 | 16.29 |
| ATOM | 835 | CD1 | TYR | 313 | 20.003 | 30.428 | 95.092 | 1.00 | 18.75 |
| ATOM | 836 | CE1 | TYR | 313 | 21.086 | 29.977 | 95.865 | 1.00 | 16.90 |
| ATOM | 837 | CD2 | TYR | 313 | 19.640 | 28.181 | 94.336 | 1.00 | 19.69 |
| ATOM | 838 | CE2 | TYR | 313 | 20.703 | 27.736 | 95.099 | 1.00 | 22.56 |
| ATOM | 839 | CZ | TYR | 313 | 21.416 | 28.620 | 95.885 | 1.00 | 21.65 |
| ATOM | 840 | OH | TYR | 313 | 22.440 | 28.102 | 96.621 | 1.00 | 23.28 |
| ATOM | 841 | HH | TYR | 313 | 22.488 | 27.152 | 96.491 | 1.00 | 0.00 |
| ATOM | 842 | C | TYR | 313 | 16.560 | 31.489 | 92.548 | 1.00 | 9.32 |
| ATOM | 843 | O | TYR | 313 | 15.424 | 31.010 | 92.549 | 1.00 | 11.65 |
| ATOM | 844 | N | ILE | 314 | 17.074 | 32.216 | 91.564 | 0.82 | 5.34 |
| ATOM | 845 | H | ILE | 314 | 17.938 | 32.658 | 91.697 | 1.00 | 0.00 |
| ATOM | 846 | CA | ILE | 314 | 16.409 | 32.393 | 90.277 | 0.82 | 6.71 |
| ATOM | 847 | CB | ILE | 314 | 16.039 | 33.900 | 89.929 | 0.82 | 9.46 |
| ATOM | 848 | CG2 | ILE | 314 | 15.622 | 33.972 | 88.462 | 0.82 | 6.84 |
| ATOM | 849 | CG1 | ILE | 314 | 14.964 | 34.431 | 90.924 | 0.82 | 8.87 |
| ATOM | 850 | CD1 | ILE | 314 | 14.481 | 35.877 | 90.732 | 0.82 | 7.08 |
| ATOM | 851 | C | ILE | 314 | 17.533 | 31.880 | 89.336 | 0.82 | 9.29 |
| ATOM | 852 | O | ILE | 314 | 18.676 | 32.352 | 89.383 | 0.82 | 9.05 |
| ATOM | 853 | N | ILE | 315 | 17.210 | 30.948 | 88.460 | 1.00 | 9.56 |
| ATOM | 854 | H | ILE | 315 | 16.284 | 30.638 | 88.377 | 1.00 | 0.00 |
| ATOM | 855 | CA | ILE | 315 | 18.231 | 30.372 | 87.608 | 1.00 | 7.43 |
| ATOM | 856 | CB | ILE | 315 | 18.305 | 28.780 | 87.821 | 1.00 | 8.14 |
| ATOM | 857 | CG2 | ILE | 315 | 19.319 | 28.109 | 86.889 | 1.00 | 3.98 |
| ATOM | 858 | CG1 | ILE | 315 | 18.692 | 28.436 | 89.278 | 1.00 | 5.24 |
| ATOM | 859 | CD1 | ILE | 315 | 17.541 | 28.086 | 90.179 | 1.00 | 4.00 |
| ATOM | 860 | C | ILE | 315 | 17.848 | 30.782 | 86.213 | 1.00 | 6.77 |
| ATOM | 861 | O | ILE | 315 | 16.691 | 30.685 | 85.858 | 1.00 | 7.51 |
| ATOM | 862 | N | THR | 316 | 18.817 | 31.277 | 85.440 | 1.00 | 9.28 |
| ATOM | 863 | H | THR | 316 | 19.735 | 31.348 | 85.775 | 1.00 | 0.00 |
| ATOM | 864 | CA | THR | 316 | 18.520 | 31.716 | 84.093 | 1.00 | 9.15 |
| ATOM | 865 | CB | THR | 316 | 18.612 | 33.272 | 83.958 | 1.00 | 12.34 |
| ATOM | 866 | OG1 | THR | 316 | 19.980 | 33.675 | 84.068 | 1.00 | 11.44 |
| ATOM | 867 | HG1 | THR | 316 | 20.040 | 34.630 | 83.986 | 1.00 | 0.00 |
| ATOM | 868 | CG2 | THR | 316 | 17.813 | 34.028 | 85.046 | 1.00 | 5.37 |
| ATOM | 869 | C | THR | 316 | 19.504 | 31.191 | 83.047 | 1.00 | 12.32 |
| ATOM | 870 | O | THR | 316 | 20.568 | 30.667 | 83.372 | 1.00 | 10.57 |
| ATOM | 871 | N | GLU | 317 | 19.139 | 31.409 | 81.790 | 1.00 | 12.98 |
| ATOM | 872 | H | GLU | 317 | 18.250 | 31.783 | 81.619 | 1.00 | 0.00 |
| ATOM | 873 | CA | GLU | 317 | 19.979 | 31.128 | 80.630 | 1.00 | 16.03 |
| ATOM | 874 | CB | GLU | 317 | 19.293 | 31.811 | 79.429 | 1.00 | 10.12 |

TABLE 6-continued

Coordinates of Lck bound with damnacanthal

| | | Atom Type | Res | # | X | Y | Z | Occ | B |
|---|---|---|---|---|---|---|---|---|---|
| ATOM | 875 | CG | GLU | 317 | 19.998 | 31.758 | 78.100 | 1.00 | 11.28 |
| ATOM | 876 | CD | GLU | 317 | 19.084 | 32.151 | 76.936 | 1.00 | 12.65 |
| ATOM | 877 | OE1 | GLU | 317 | 18.129 | 32.939 | 77.142 | 1.00 | 11.20 |
| ATOM | 878 | OE2 | GLU | 317 | 19.307 | 31.664 | 75.805 | 1.00 | 13.40 |
| ATOM | 879 | C | GLU | 317 | 21.377 | 31.805 | 80.909 | 1.00 | 18.65 |
| ATOM | 880 | O | GLU | 317 | 21.461 | 32.950 | 81.424 | 1.00 | 20.28 |
| ATOM | 881 | N | TYR | 318 | 22.466 | 31.093 | 80.688 | 1.00 | 17.79 |
| ATOM | 882 | H | TYR | 318 | 22.439 | 30.154 | 80.478 | 1.00 | 20.00 |
| ATOM | 883 | CA | TYR | 318 | 23.771 | 31.698 | 80.934 | 1.00 | 13.22 |
| ATOM | 884 | CB | TYR | 318 | 24.780 | 30.627 | 81.302 | 1.00 | 11.06 |
| ATOM | 885 | CG | TYR | 318 | 26.126 | 31.205 | 81.621 | 1.00 | 15.71 |
| ATOM | 886 | CD1 | TYR | 318 | 27.187 | 31.029 | 80.749 | 1.00 | 20.59 |
| ATOM | 887 | CE1 | TYR | 318 | 28.443 | 31.496 | 81.061 | 1.00 | 23.75 |
| ATOM | 888 | CD2 | TYR | 318 | 26.343 | 31.898 | 82.803 | 1.00 | 15.45 |
| ATOM | 889 | CE2 | TYR | 318 | 27.579 | 32.373 | 83.127 | 1.00 | 16.55 |
| ATOM | 890 | CZ | TYR | 318 | 28.635 | 32.168 | 82.246 | 1.00 | 21.09 |
| ATOM | 891 | OH | TYR | 318 | 29.904 | 32.572 | 82.569 | 1.00 | 26.61 |
| ATOM | 892 | HH | TYR | 318 | 30.503 | 32.353 | 81.851 | 1.00 | 0.00 |
| ATOM | 893 | C | TYR | 318 | 24.219 | 32.466 | 76.984 | 1.00 | 13.52 |
| ATOM | 894 | O | TYR | 318 | 24.045 | 31.971 | 78.563 | 1.00 | 12.69 |
| ATOM | 895 | N | MET | 319 | 24.791 | 33.662 | 79.852 | 1.00 | 11.72 |
| ATOM | 896 | H | MET | 319 | 24.946 | 34.021 | 80.750 | 1.00 | 0.00 |
| ATOM | 897 | CA | MET | 319 | 25.197 | 34.458 | 78.673 | 1.00 | 12.09 |
| ATOM | 898 | CB | MET | 319 | 24.502 | 35.826 | 78.686 | 1.00 | 10.63 |
| ATOM | 899 | CG | MET | 319 | 22.956 | 35.714 | 78.545 | 1.00 | 8.40 |
| ATOM | 900 | SD | MET | 319 | 22.427 | 34.886 | 77.036 | 1.00 | 11.75 |
| ATOM | 901 | CE | MET | 319 | 23.110 | 35.793 | 75.678 | 1.00 | 7.34 |
| ATOM | 902 | C | MET | 319 | 26.695 | 34.572 | 78.764 | 1.00 | 11.26 |
| ATOM | 903 | O | MET | 319 | 27.226 | 35.352 | 79.546 | 1.00 | 15.48 |
| ATOM | 904 | N | GLU | 320 | 27.368 | 33.724 | 78.008 | 1.00 | 13.13 |
| ATOM | 905 | H | GLU | 320 | 26.884 | 33.140 | 77.388 | 1.00 | 0.00 |
| ATOM | 906 | CA | GLU | 320 | 28.810 | 33.622 | 78.060 | 1.00 | 13.42 |
| ATOM | 907 | CB | GLU | 320 | 29.321 | 32.731 | 76.927 | 1.00 | 19.76 |
| ATOM | 908 | CG | GLU | 320 | 30.837 | 32.583 | 76.879 | 1.00 | 28.29 |
| ATOM | 909 | CD | GLU | 320 | 31.331 | 31.458 | 77.773 | 1.00 | 36.39 |
| ATOM | 910 | OE1 | GLU | 320 | 31.439 | 30.290 | 77.271 | 1.00 | 39.37 |
| ATOM | 911 | OE2 | GLU | 320 | 31.579 | 31.738 | 78.968 | 1.00 | 38.78 |
| ATOM | 912 | C | GLU | 320 | 29.615 | 34.908 | 78.119 | 1.00 | 14.66 |
| ATOM | 913 | O | GLU | 320 | 30.462 | 35.046 | 79.001 | 1.00 | 14.91 |
| ATOM | 914 | N | ASN | 321 | 29.335 | 35.874 | 77.244 | 1.00 | 14.99 |
| ATOM | 915 | H | ASN | 321 | 28.601 | 35.777 | 76.603 | 1.00 | 0.00 |
| ATOM | 916 | CA | ASN | 321 | 30.136 | 37.093 | 77.244 | 1.00 | 13.97 |
| ATOM | 917 | CB | ASN | 321 | 30.383 | 37.581 | 75.819 | 1.00 | 12.92 |
| ATOM | 918 | CG | ASN | 321 | 31.394 | 36.725 | 75.076 | 1.00 | 10.32 |
| ATOM | 919 | OD1 | ASN | 321 | 32.565 | 36.705 | 75.415 | 1.00 | 16.59 |
| ATOM | 920 | ND2 | ASN | 321 | 30.955 | 36.071 | 74.025 | 1.00 | 14.07 |
| ATOM | 921 | HD21 | ASN | 321 | 30.016 | 36.150 | 73.756 | 1.00 | 0.00 |
| ATOM | 922 | HD22 | ASN | 321 | 31.597 | 35.516 | 73.537 | 1.00 | 0.00 |
| ATOM | 923 | C | ASN | 321 | 29.701 | 38.224 | 78.159 | 1.00 | 12.35 |
| ATOM | 924 | O | ASN | 321 | 30.193 | 39.325 | 78.005 | 1.00 | 14.08 |
| ATOM | 925 | N | GLY | 322 | 28.783 | 37.949 | 79.097 | 1.00 | 13.03 |
| ATOM | 926 | H | GLY | 322 | 28.396 | 37.049 | 79.124 | 1.00 | 0.00 |
| ATOM | 927 | CA | GLY | 322 | 28.332 | 38.939 | 80.086 | 1.00 | 8.29 |
| ATOM | 928 | C | GLY | 322 | 27.694 | 40.241 | 79.590 | 1.00 | 7.25 |
| ATOM | 929 | O | GLY | 322 | 27.093 | 40.265 | 78.551 | 1.00 | 2.51 |
| ATOM | 930 | N | SER | 323 | 27.786 | 41.299 | 80.371 | 0.43 | 4.82 |
| ATOM | 931 | H | SER | 323 | 28.254 | 41.232 | 81.230 | 1.00 | 0.00 |
| ATOM | 932 | CA | SER | 323 | 27.206 | 42.584 | 79.993 | 0.43 | 5.83 |
| ATOM | 933 | CB | SER | 323 | 27.476 | 43.591 | 81.114 | 0.43 | 3.19 |
| ATOM | 934 | OG | SER | 323 | 26.932 | 44.851 | 80.803 | 0.43 | 6.64 |
| ATOM | 935 | HG | SER | 323 | 25.983 | 44.770 | 80.685 | 1.00 | 0.00 |
| ATOM | 936 | C | SER | 323 | 27.751 | 43.133 | 78.659 | 0.43 | 5.72 |
| ATOM | 937 | O | SER | 323 | 28.964 | 43.089 | 78.422 | 0.43 | 2.00 |
| ATOM | 938 | N | LEU | 324 | 26.865 | 43.624 | 77.782 | 1.00 | 9.48 |
| ATOM | 939 | H | LEU | 324 | 25.906 | 43.604 | 77.981 | 1.00 | 0.00 |
| ATOM | 940 | CA | LEU | 324 | 27.325 | 44.208 | 76.490 | 1.00 | 12.06 |
| ATOM | 941 | CB | LEU | 324 | 26.156 | 44.704 | 75.598 | 1.00 | 8.34 |
| ATOM | 942 | CG | LEU | 324 | 26.473 | 45.608 | 74.370 | 1.00 | 7.44 |
| ATOM | 943 | CD1 | LEU | 324 | 27.415 | 44.914 | 73.353 | 1.00 | 6.92 |
| ATOM | 944 | CD2 | LEU | 324 | 25.198 | 46.042 | 73.650 | 1.00 | 3.10 |
| ATOM | 945 | C | LEU | 324 | 28.308 | 45.380 | 76.784 | 1.00 | 14.56 |
| ATOM | 946 | C | LEU | 324 | 29.303 | 45.548 | 76.086 | 1.00 | 14.05 |
| ATOM | 947 | N | VAL | 325 | 28.039 | 46.142 | 77.840 | 1.00 | 13.64 |
| ATOM | 948 | H | VAL | 325 | 27.255 | 45.961 | 78.399 | 1.00 | 0.00 |

TABLE 6-continued

Coordinates of Lck bound with damnacanthal

| Atom Type | | Res | # | X | Y | Z | Occ | B |
|---|---|---|---|---|---|---|---|---|
| ATOM | 949 | CA | VAL | 325 | 28.906 | 47.253 | 78.176 | 1.00 | 16.20 |
| ATOM | 950 | CB | VAL | 325 | 28.321 | 48.152 | 79.321 | 1.00 | 14.20 |
| ATOM | 951 | CG1 | VAL | 325 | 28.370 | 47.442 | 80.669 | 1.00 | 13.67 |
| ATOM | 952 | CG2 | VAL | 325 | 29.109 | 49.447 | 79.383 | 1.00 | 19.24 |
| ATOM | 953 | C | VAL | 325 | 30.337 | 46.767 | 78.502 | 1.00 | 17.95 |
| ATOM | 954 | O | VAL | 325 | 31.294 | 47.415 | 78.086 | 1.00 | 21.28 |
| ATOM | 955 | N | ASP | 326 | 30.481 | 45.647 | 79.219 | 1.00 | 15.93 |
| ATOM | 956 | H | ASP | 326 | 29.691 | 45.165 | 79.541 | 1.00 | 0.00 |
| ATOM | 957 | CA | ASP | 326 | 31.809 | 45.114 | 79.540 | 1.00 | 14.78 |
| ATOM | 958 | CB | ASP | 326 | 31.766 | 44.037 | 80.610 | 1.00 | 17.75 |
| ATOM | 959 | CG | ASP | 326 | 31.447 | 44.568 | 81.963 | 1.00 | 19.86 |
| ATOM | 960 | OD1 | ASP | 326 | 31.705 | 45.747 | 82.242 | 1.00 | 26.60 |
| ATOM | 961 | OD2 | ASP | 326 | 30.913 | 43.786 | 82.766 | 1.00 | 26.10 |
| ATOM | 962 | C | ASP | 326 | 32.400 | 44.474 | 78.308 | 1.00 | 17.33 |
| ATOM | 963 | O | ASP | 326 | 33.585 | 44.657 | 78.012 | 1.00 | 21.69 |
| ATOM | 964 | N | PHE | 327 | 31.558 | 43.784 | 77.554 | 1.00 | 15.24 |
| ATOM | 965 | H | PHE | 327 | 30.611 | 43.721 | 77.798 | 1.00 | 0.00 |
| ATOM | 966 | CA | PHE | 327 | 32.020 | 43.115 | 76.362 | 1.00 | 12.27 |
| ATOM | 967 | CB | PHE | 327 | 30.917 | 42.243 | 75.756 | 1.00 | 13.66 |
| ATOM | 968 | CG | PHE | 327 | 31.332 | 41.600 | 74.453 | 1.00 | 12.44 |
| ATOM | 969 | CD1 | PHE | 327 | 32.251 | 40.572 | 74.437 | 1.00 | 9.39 |
| ATOM | 970 | CD2 | PHE | 327 | 30.868 | 42.097 | 73.260 | 1.00 | 14.52 |
| ATOM | 971 | CE1 | PHE | 327 | 32.684 | 40.053 | 73.234 | 1.00 | 8.11 |
| ATOM | 972 | CE2 | PHE | 327 | 31.299 | 41.592 | 72.061 | 1.00 | 9.78 |
| ATOM | 973 | CZ | PHE | 327 | 32.190 | 40.579 | 72.048 | 1.00 | 11.96 |
| ATOM | 974 | C | PHE | 327 | 32.654 | 44.029 | 75.280 | 1.00 | 12.12 |
| ATOM | 975 | O | PHE | 327 | 33.712 | 43.681 | 74.691 | 1.00 | 12.18 |
| ATOM | 976 | N | LEU | 328 | 32.112 | 45.229 | 75.158 | 0.40 | 6.21 |
| ATOM | 977 | H | LEU | 328 | 31.365 | 45.491 | 75.736 | 1.00 | 0.00 |
| ATOM | 978 | CA | LEU | 328 | 32.600 | 46.184 | 74.176 | 0.40 | 4.56 |
| ATOM | 979 | CB | LEU | 328 | 31.622 | 47.350 | 74.084 | 0.40 | 2.00 |
| ATOM | 980 | CG | LEU | 328 | 30.634 | 47.455 | 72.914 | 0.40 | 2.00 |
| ATOM | 981 | CD1 | LEU | 328 | 30.602 | 46.229 | 72.079 | 0.40 | 5.60 |
| ATOM | 982 | CD2 | LEU | 328 | 29.265 | 47.851 | 73.411 | 0.40 | 2.00 |
| ATOM | 983 | C | LEU | 328 | 34.006 | 46.658 | 74.487 | 0.40 | 5.58 |
| ATOM | 984 | O | LEU | 328 | 34.725 | 47.075 | 73.600 | 0.40 | 2.00 |
| ATOM | 985 | N | LYS | 329 | 34.429 | 46.484 | 75.728 | 1.00 | 10.57 |
| ATOM | 986 | H | LYS | 329 | 33.836 | 46.051 | 76.377 | 1.00 | 0.00 |
| ATOM | 987 | CA | LYS | 329 | 35.739 | 46.905 | 76.187 | 1.00 | 12.94 |
| ATOM | 988 | CB | LYS | 329 | 35.633 | 47.480 | 77.597 | 1.00 | 14.05 |
| ATOM | 989 | CG | LYS | 329 | 34.788 | 48.754 | 77.694 | 1.00 | 13.69 |
| ATOM | 990 | CD | LYS | 329 | 34.482 | 49.083 | 79.134 | 1.00 | 11.83 |
| ATOM | 991 | CE | LYS | 329 | 33.506 | 50.274 | 79.132 | 1.00 | 12.27 |
| ATOM | 992 | NZ | LYS | 329 | 33.348 | 50.777 | 80.498 | 1.00 | 16.71 |
| ATOM | 993 | HZ1 | LYS | 329 | 34.271 | 51.086 | 80.863 | 1.00 | 0.00 |
| ATOM | 994 | HZ2 | LYS | 329 | 32.971 | 50.021 | 81.104 | 1.00 | 0.00 |
| ATOM | 995 | HZ3 | LYS | 329 | 32.689 | 51.581 | 80.497 | 1.00 | 0.00 |
| ATOM | 996 | C | LYS | 329 | 36.826 | 45.812 | 76.128 | 1.00 | 16.63 |
| ATOM | 997 | O | LYS | 329 | 38.023 | 46.123 | 76.273 | 1.00 | 20.19 |
| ATOM | 998 | N | THR | 330 | 36.431 | 44.563 | 75.864 | 1.00 | 17.59 |
| ATOM | 999 | H | THR | 330 | 35.481 | 44.376 | 75.715 | 1.00 | 0.00 |
| ATOM | 1000 | CA | THR | 330 | 37.387 | 43.439 | 75.787 | 1.00 | 14.08 |
| ATOM | 1001 | CB | THR | 330 | 36.661 | 42.040 | 75.906 | 1.00 | 12.04 |
| ATOM | 1002 | OG1 | THR | 330 | 35.864 | 41.803 | 74.737 | 1.00 | 11.61 |
| ATOM | 1003 | HG1 | THR | 330 | 35.205 | 42.496 | 74.653 | 1.00 | 0.00 |
| ATOM | 1004 | CG2 | THR | 330 | 35.786 | 41.949 | 77.143 | 1.00 | 11.33 |
| ATOM | 1005 | C | THR | 330 | 38.117 | 43.464 | 74.430 | 1.00 | 12.83 |
| ATOM | 1006 | O | THR | 330 | 37.638 | 44.095 | 73.476 | 1.00 | 11.76 |
| ATOM | 1007 | N | PRO | 331 | 39.275 | 42.772 | 74.310 | 1.00 | 10.34 |
| ATOM | 1008 | CD | PRO | 331 | 40.023 | 42.108 | 75.379 | 1.00 | 7.87 |
| ATOM | 1009 | CA | PRO | 331 | 40.031 | 42.722 | 73.051 | 1.00 | 11.43 |
| ATOM | 1010 | CB | PRO | 331 | 41.002 | 41.580 | 73.292 | 1.00 | 8.60 |
| ATOM | 1011 | CG | PRO | 331 | 41.304 | 41.698 | 74.700 | 1.00 | 9.00 |
| ATOM | 1012 | C | PRO | 331 | 39.081 | 42.392 | 71.884 | 1.00 | 14.84 |
| ATOM | 1013 | O | PRO | 331 | 39.164 | 42.990 | 70.821 | 1.00 | 18.33 |
| ATOM | 1014 | N | SER | 332 | 38.170 | 41.435 | 72.098 | 1.00 | 18.29 |
| ATOM | 1015 | H | SER | 332 | 38.153 | 40.969 | 72.960 | 1.00 | 0.00 |
| ATOM | 1016 | CA | SER | 332 | 37.184 | 41.049 | 71.086 | 1.00 | 17.41 |
| ATOM | 1017 | CB | SER | 332 | 36.420 | 39.799 | 71.521 | 1.00 | 22.00 |
| ATOM | 1018 | OG | SER | 332 | 37.179 | 38.635 | 71.350 | 1.00 | 24.77 |
| ATOM | 1019 | HG | SER | 332 | 37.980 | 38.695 | 71.876 | 1.00 | 0.00 |
| ATOM | 1020 | C | SER | 332 | 36.165 | 42.136 | 70.797 | 1.00 | 17.88 |
| ATOM | 1021 | O | SER | 332 | 35.970 | 42.464 | 69.663 | 1.00 | 17.54 |
| ATOM | 1022 | N | GLY | 333 | 35.501 | 42.683 | 71.809 | 1.00 | 18.25 |

TABLE 6-continued

Coordinates of Lck bound with damnacanthal

| | Atom Type | Res | # | X | Y | Z | Occ | B |
|---|---|---|---|---|---|---|---|---|
| ATOM | 1023 | H | GLY | 333 | 35.680 | 42.388 | 72.726 | 1.00 | 0.00 |
| ATOM | 1024 | CA | GLY | 333 | 34.500 | 43.728 | 71.560 | 1.00 | 18.84 |
| ATOM | 1025 | C | GLY | 333 | 35.083 | 44.891 | 70.780 | 1.00 | 18.38 |
| ATOM | 1026 | O | GLY | 333 | 34.550 | 45.378 | 69.771 | 1.00 | 16.17 |
| ATOM | 1027 | N | ILE | 334 | 36.278 | 45.266 | 71.230 | 1.00 | 21.21 |
| ATOM | 1028 | H | ILE | 334 | 36.655 | 44.797 | 72.003 | 1.00 | 0.00 |
| ATOM | 1029 | CA | ILE | 334 | 37.072 | 46.333 | 70.650 | 1.00 | 20.69 |
| ATOM | 1030 | CB | ILE | 334 | 38.380 | 46.439 | 71.457 | 1.00 | 22.67 |
| ATOM | 1031 | CG2 | ILE | 334 | 39.567 | 46.975 | 70.617 | 1.00 | 22.59 |
| ATOM | 1032 | CG1 | ILE | 334 | 38.123 | 47.250 | 72.696 | 1.00 | 15.69 |
| ATOM | 1033 | CD1 | ILE | 334 | 39.396 | 47.528 | 73.436 | 1.00 | 25.48 |
| ATOM | 1034 | C | ILE | 334 | 37.354 | 46.244 | 69.142 | 1.00 | 22.55 |
| ATOM | 1035 | O | ILE | 334 | 37.533 | 47.274 | 68.481 | 1.00 | 25.70 |
| ATOM | 1036 | N | LYS | 335 | 37.411 | 45.039 | 68.595 | 1.00 | 20.07 |
| ATOM | 1037 | H | LYS | 335 | 37.255 | 44.251 | 69.156 | 1.00 | 0.00 |
| ATOM | 1038 | CA | LYS | 335 | 37.698 | 44.825 | 67.185 | 1.00 | 20.39 |
| ATOM | 1039 | CB | LYS | 335 | 38.485 | 43.526 | 67.033 | 1.00 | 23.98 |
| ATOM | 1040 | CG | LYS | 335 | 39.850 | 43.494 | 67.703 | 1.00 | 30.82 |
| ATOM | 1041 | CD | LYS | 335 | 40.424 | 42.074 | 67.692 | 1.00 | 34.74 |
| ATOM | 1042 | CE | LYS | 335 | 41.639 | 41.961 | 68.599 | 1.00 | 38.24 |
| ATOM | 1043 | NZ | LYS | 335 | 42.129 | 40.555 | 68.744 | 1.00 | 36.18 |
| ATOM | 1044 | HZ1 | LYS | 335 | 42.395 | 40.182 | 67.810 | 1.00 | 0.00 |
| ATOM | 1045 | HZ2 | LYS | 335 | 41.375 | 39.965 | 69.150 | 1.00 | 0.00 |
| ATOM | 1046 | HZ3 | LYS | 335 | 42.957 | 40.540 | 69.373 | 1.00 | 0.00 |
| ATOM | 1047 | C | LYS | 335 | 36.462 | 44.717 | 66.291 | 1.00 | 20.96 |
| ATOM | 1048 | O | LYS | 335 | 36.575 | 44.603 | 65.071 | 1.00 | 19.84 |
| ATOM | 1049 | N | LEU | 336 | 35.281 | 44.662 | 66.885 | 1.00 | 20.94 |
| ATOM | 1050 | H | LEU | 336 | 35.215 | 44.701 | 67.862 | 1.00 | 0.00 |
| ATOM | 1051 | CA | LEU | 336 | 34.052 | 44.542 | 66.092 | 1.00 | 20.60 |
| ATOM | 1052 | CB | LEU | 336 | 32.833 | 44.589 | 67.020 | 1.00 | 19.79 |
| ATOM | 1053 | CG | LEU | 336 | 32.781 | 43.485 | 68.106 | 1.00 | 21.02 |
| ATOM | 1054 | CD1 | LEU | 336 | 31.487 | 43.592 | 68.879 | 1.00 | 21.95 |
| ATOM | 1055 | CD2 | LEU | 336 | 32.937 | 42.098 | 67.478 | 1.00 | 13.72 |
| ATOM | 1056 | C | LEU | 336 | 33.928 | 45.625 | 65.003 | 1.00 | 19.76 |
| ATOM | 1057 | O | LEU | 336 | 34.239 | 46.779 | 65.214 | 1.00 | 20.01 |
| ATOM | 1058 | N | THR | 337 | 33.413 | 45.247 | 63.847 | 1.00 | 18.96 |
| ATOM | 1059 | H | THR | 337 | 33.159 | 44.311 | 63.704 | 1.00 | 0.00 |
| ATOM | 1060 | CA | THR | 337 | 33.212 | 46.197 | 62.771 | 1.00 | 20.51 |
| ATOM | 1061 | CB | THR | 337 | 33.026 | 45.455 | 61.446 | 1.00 | 18.54 |
| ATOM | 1062 | OG1 | THR | 337 | 31.864 | 44.613 | 61.536 | 1.00 | 23.67 |
| ATOM | 1063 | HG1 | THR | 337 | 31.743 | 44.145 | 60.707 | 1.00 | 0.00 |
| ATOM | 1064 | CG2 | THR | 337 | 34.258 | 44.589 | 61.141 | 1.00 | 21.12 |
| ATOM | 1065 | C | THR | 337 | 31.906 | 46.969 | 63.074 | 1.00 | 17.47 |
| ATOM | 1066 | O | THR | 337 | 31.135 | 46.560 | 63.944 | 1.00 | 16.29 |
| ATOM | 1067 | N | ILE | 338 | 31.692 | 48.066 | 62.349 | 1.00 | 13.93 |
| ATOM | 1068 | H | ILE | 338 | 32.343 | 48.350 | 61.673 | 1.00 | 0.00 |
| ATOM | 1069 | CA | ILE | 338 | 30.482 | 48.863 | 62.551 | 1.00 | 13.48 |
| ATOM | 1070 | CB | ILE | 338 | 30.522 | 50.187 | 61.736 | 1.00 | 11.87 |
| ATOM | 1071 | CG2 | ILE | 338 | 30.768 | 49.876 | 60.276 | 1.00 | 10.99 |
| ATOM | 1072 | CG1 | ILE | 338 | 29.217 | 50.983 | 61.901 | 1.00 | 8.89 |
| ATOM | 1073 | CD1 | ILE | 338 | 28.874 | 51.296 | 63.341 | 1.00 | 9.37 |
| ATOM | 1074 | C | ILE | 338 | 29.300 | 47.970 | 62.109 | 1.00 | 12.62 |
| ATOM | 1075 | O | ILE | 338 | 28.204 | 48.118 | 62.637 | 1.00 | 12.13 |
| ATOM | 1076 | N | ASN | 339 | 29.555 | 47.057 | 61.157 | 1.00 | 12.51 |
| ATOM | 1077 | H | ASN | 339 | 30.454 | 47.018 | 60.770 | 1.00 | 0.00 |
| ATOM | 1078 | CA | ASN | 339 | 28.555 | 46.096 | 60.650 | 1.00 | 13.59 |
| ATOM | 1079 | CB | ASN | 339 | 29.185 | 45.177 | 59.586 | 1.00 | 23.90 |
| ATOM | 1080 | CG | ASN | 339 | 28.333 | 43.897 | 59.284 | 1.00 | 31.18 |
| ATOM | 1081 | OD1 | ASN | 339 | 28.459 | 42.851 | 59.952 | 1.00 | 38.99 |
| ATOM | 1082 | ND2 | ASN | 339 | 27.485 | 43.982 | 58.272 | 1.00 | 29.51 |
| ATOM | 1083 | HD21 | ASN | 339 | 27.417 | 44.814 | 57.759 | 1.00 | 0.00 |
| ATOM | 1084 | HD22 | ASN | 339 | 26.944 | 43.192 | 58.068 | 1.00 | 0.00 |
| ATOM | 1085 | C | ASN | 339 | 28.044 | 45.235 | 61.797 | 1.00 | 13.31 |
| ATOM | 1086 | O | ASN | 339 | 26.833 | 45.121 | 62.009 | 1.00 | 11.39 |
| ATOM | 1087 | N | LYS | 340 | 28.982 | 44.709 | 62.586 | 1.00 | 8.10 |
| ATOM | 1088 | H | LYS | 340 | 29.929 | 44.902 | 62.421 | 1.00 | 0.00 |
| ATOM | 1089 | CA | LYS | 340 | 28.633 | 43.858 | 63.683 | 1.00 | 8.78 |
| ATOM | 1090 | CB | LYS | 340 | 29.830 | 43.037 | 64.183 | 1.00 | 11.82 |
| ATOM | 1091 | CG | LYS | 340 | 29.508 | 42.134 | 65.409 | 1.00 | 9.86 |
| ATOM | 1092 | CD | LYS | 340 | 28.400 | 41.173 | 65.030 | 1.00 | 9.45 |
| ATOM | 1093 | CE | LYS | 340 | 27.996 | 40.305 | 66.182 | 1.00 | 11.87 |
| ATOM | 1094 | NZ | LYS | 340 | 26.918 | 39.393 | 65.710 | 1.00 | 8.00 |
| ATOM | 1095 | HZ1 | LYS | 340 | 27.275 | 38.809 | 64.927 | 1.00 | 0.00 |
| ATOM | 1096 | HZ2 | LYS | 340 | 26.107 | 39.955 | 65.381 | 1.00 | 0.00 |

TABLE 6-continued

Coordinates of Lck bound with damnacanthal

| | Atom Type | Res | # | X | Y | Z | Occ | B |
|---|---|---|---|---|---|---|---|---|
| ATOM | 1097 | HZ3 | LYS | 340 | 26.618 | 38.777 | 66.492 | 1.00 | 0.00 |
| ATOM | 1098 | C | LYS | 340 | 27.972 | 44.622 | 64.807 | 1.00 | 10.59 |
| ATOM | 1099 | O | LYS | 340 | 27.069 | 44.086 | 65.463 | 1.00 | 11.30 |
| ATOM | 1100 | N | LEU | 341 | 28.412 | 45.861 | 65.053 | 1.00 | 9.98 |
| ATOM | 1101 | H | LEU | 341 | 29.159 | 46.234 | 64.540 | 1.00 | 0.00 |
| ATOM | 1102 | CA | LEU | 341 | 27.787 | 46.675 | 66.088 | 1.00 | 7.87 |
| ATOM | 1103 | CB | LEU | 341 | 28.585 | 47.929 | 66.287 | 1.00 | 9.26 |
| ATOM | 1104 | CG | LEU | 341 | 30.003 | 47.807 | 66.843 | 1.00 | 7.04 |
| ATOM | 1105 | CD1 | LEU | 341 | 30.659 | 49.162 | 66.721 | 1.00 | 2.00 |
| ATOM | 1106 | CD2 | LEU | 341 | 29.917 | 47.340 | 68.304 | 1.00 | 8.42 |
| ATOM | 1107 | C | LEU | 341 | 26.293 | 47.002 | 65.700 | 1.00 | 9.21 |
| ATOM | 1108 | O | LEU | 341 | 25.415 | 46.904 | 66.532 | 1.00 | 9.96 |
| ATOM | 1109 | N | LEU | 342 | 26.039 | 47.239 | 64.409 | 1.00 | 10.94 |
| ATOM | 1110 | H | LEU | 342 | 26.784 | 47.216 | 63.773 | 1.00 | 0.00 |
| ATOM | 1111 | CA | LEU | 342 | 24.703 | 47.535 | 63.868 | 1.00 | 13.26 |
| ATOM | 1112 | CB | LEU | 342 | 24.774 | 47.992 | 62.375 | 1.00 | 9.26 |
| ATOM | 1113 | CG | LEU | 342 | 25.308 | 49.432 | 62.132 | 1.00 | 13.42 |
| ATOM | 1114 | CD1 | LEU | 342 | 25.648 | 49.716 | 60.665 | 1.00 | 2.69 |
| ATOM | 1115 | CD2 | LEU | 342 | 24.317 | 50.467 | 62.687 | 1.00 | 7.30 |
| ATOM | 1116 | C | LEU | 342 | 23.830 | 46.283 | 63.971 | 1.00 | 14.03 |
| ATOM | 1117 | O | LEU | 342 | 22.617 | 46.371 | 64.243 | 1.00 | 12.33 |
| ATOM | 1118 | N | ASP | 343 | 24.475 | 45.134 | 63.749 | 1.00 | 12.14 |
| ATOM | 1119 | H | ASP | 343 | 25.431 | 45.160 | 63.535 | 1.00 | 0.00 |
| ATOM | 1120 | CA | ASP | 343 | 23.835 | 43.832 | 63.807 | 1.00 | 12.09 |
| ATOM | 1121 | CB | ASP | 343 | 24.868 | 42.705 | 63.502 | 1.00 | 15.93 |
| ATOM | 1122 | CG | ASP | 343 | 24.357 | 41.309 | 63.876 | 1.00 | 17.58 |
| ATOM | 1123 | OD1 | ASP | 343 | 23.140 | 41.102 | 64.109 | 1.00 | 20.16 |
| ATOM | 1124 | OD2 | ASP | 343 | 25.182 | 40.408 | 63.975 | 1.00 | 19.00 |
| ATOM | 1125 | C | ASP | 343 | 23.321 | 43.710 | 65.210 | 1.00 | 13.02 |
| ATOM | 1126 | O | ASP | 343 | 22.109 | 43.506 | 65.435 | 1.00 | 15.35 |
| ATOM | 1127 | N | MET | 344 | 24.218 | 43.914 | 66.163 | 1.00 | 13.20 |
| ATOM | 1128 | H | MET | 344 | 25.145 | 44.136 | 65.934 | 1.00 | 0.00 |
| ATOM | 1129 | CA | MET | 344 | 23.841 | 43.812 | 67.567 | 1.00 | 13.80 |
| ATOM | 1130 | CB | MET | 344 | 25.077 | 43.967 | 68.467 | 1.00 | 15.77 |
| ATOM | 1131 | CG | MET | 344 | 26.146 | 42.915 | 68.237 | 1.00 | 16.15 |
| ATOM | 1132 | SD | MET | 344 | 27.609 | 43.146 | 69.249 | 1.00 | 18.87 |
| ATOM | 1133 | CE | MET | 344 | 27.139 | 42.459 | 70.615 | 1.00 | 12.49 |
| ATOM | 1134 | C | MET | 344 | 22.744 | 44.809 | 67.970 | 1.00 | 11.36 |
| ATOM | 1135 | O | MET | 344 | 21.814 | 44.467 | 68.727 | 1.00 | 11.21 |
| ATOM | 1136 | N | ALA | 345 | 22.854 | 46.039 | 67.471 | 1.00 | 8.42 |
| ATOM | 1137 | H | ALA | 345 | 23.607 | 46.273 | 66.889 | 1.00 | 0.00 |
| ATOM | 1138 | CA | ALA | 345 | 21.856 | 47.059 | 67.782 | 1.00 | 6.84 |
| ATOM | 1139 | CB | ALA | 345 | 22.207 | 48.403 | 67.088 | 1.00 | 6.71 |
| ATOM | 1140 | C | ALA | 345 | 20.495 | 46.538 | 67.294 | 1.00 | 5.21 |
| ATOM | 1141 | O | ALA | 345 | 19.517 | 46.702 | 67.958 | 1.00 | 8.24 |
| ATOM | 1142 | N | ALA | 346 | 20.454 | 45.960 | 66.111 | 1.00 | 6.74 |
| ATOM | 1143 | H | ALA | 346 | 21.274 | 45.890 | 65.580 | 1.00 | 0.00 |
| ATOM | 1144 | CA | ALA | 346 | 19.218 | 45.410 | 65.548 | 1.00 | 13.01 |
| ATOM | 1145 | CB | ALA | 346 | 19.410 | 44.984 | 64.082 | 1.00 | 11.86 |
| ATOM | 1146 | C | ALA | 346 | 18.638 | 44.255 | 66.383 | 1.00 | 12.42 |
| ATOM | 1147 | O | ALA | 346 | 17.425 | 44.213 | 66.583 | 1.00 | 12.13 |
| ATOM | 1148 | N | GLN | 347 | 19.508 | 43.381 | 66.914 | 1.00 | 10.84 |
| ATOM | 1149 | H | GLN | 347 | 20.464 | 43.479 | 66.722 | 1.00 | 0.00 |
| ATOM | 1150 | CA | GLN | 347 | 19.090 | 42.268 | 67.783 | 1.00 | 11.18 |
| ATOM | 1151 | CB | GLN | 347 | 20.299 | 41.385 | 68.187 | 1.00 | 11.43 |
| ATOM | 1152 | CG | GLN | 347 | 21.105 | 40.829 | 66.997 | 1.00 | 11.39 |
| ATOM | 1153 | CD | GLN | 347 | 22.089 | 39.700 | 67.400 | 1.00 | 11.75 |
| ATOM | 1154 | OE1 | GLN | 347 | 22.090 | 39.247 | 68.522 | 1.00 | 7.79 |
| ATOM | 1155 | NE2 | GLN | 347 | 22.976 | 39.328 | 66.483 | 1.00 | 15.92 |
| ATOM | 1156 | HE21 | GLN | 347 | 22.985 | 39.763 | 65.605 | 1.00 | 0.00 |
| ATOM | 1157 | HE22 | GLN | 347 | 23.604 | 38.616 | 66.724 | 1.00 | 0.00 |
| ATOM | 1158 | C | GLN | 347 | 18.426 | 42.813 | 69.059 | 1.00 | 10.02 |
| ATOM | 1159 | O | GLN | 347 | 17.493 | 42.215 | 69.569 | 1.00 | 9.62 |
| ATOM | 1160 | N | ILE | 348 | 18.970 | 43.897 | 69.610 | 1.00 | 8.94 |
| ATOM | 1161 | H | ILE | 348 | 19.764 | 44.304 | 69.205 | 1.00 | 0.00 |
| ATOM | 1162 | CA | ILE | 348 | 18.408 | 44.510 | 70.824 | 1.00 | 8.70 |
| ATOM | 1163 | CB | ILE | 348 | 19.338 | 45.612 | 71.400 | 1.00 | 15.50 |
| ATOM | 1164 | CG2 | ILE | 348 | 18.655 | 46.307 | 72.603 | 1.00 | 15.51 |
| ATOM | 1165 | CG1 | ILE | 348 | 20.742 | 45.021 | 71.740 | 1.00 | 13.53 |
| ATOM | 1166 | CD1 | ILE | 348 | 21.818 | 46.078 | 72.148 | 1.00 | 9.43 |
| ATOM | 1167 | C | ILE | 348 | 17.039 | 45.114 | 70.459 | 1.00 | 8.65 |
| ATOM | 1168 | O | ILE | 348 | 16.095 | 44.925 | 71.205 | 1.00 | 8.67 |
| ATOM | 1169 | N | ALA | 349 | 16.952 | 45.802 | 69.303 | 1.00 | 8.87 |
| ATOM | 1170 | H | ALA | 349 | 17.752 | 45.917 | 68.749 | 1.00 | 0.00 |

TABLE 6-continued

Coordinates of Lck bound with damnacanthal

| | | Atom Type | Res | # | X | Y | Z | Occ | B |
|---|---|---|---|---|---|---|---|---|---|
| ATOM | 1171 | CA | ALA | 349 | 15.678 | 46.402 | 68.826 | 1.00 | 11.26 |
| ATOM | 1172 | CB | ALA | 349 | 15.848 | 47.178 | 67.509 | 1.00 | 2.00 |
| ATOM | 1173 | C | ALA | 349 | 14.635 | 45.279 | 68.614 | 1.00 | 11.43 |
| ATOM | 1174 | O | ALA | 349 | 13.472 | 45.460 | 68.925 | 1.00 | 7.75 |
| ATOM | 1175 | N | GLU | 350 | 15.115 | 44.111 | 68.145 | 1.00 | 13.21 |
| ATOM | 1176 | H | GLU | 350 | 16.071 | 44.025 | 67.949 | 1.00 | 0.00 |
| ATOM | 1177 | CA | GLU | 350 | 14.258 | 42.956 | 67.914 | 1.00 | 12.62 |
| ATOM | 1178 | CB | GLU | 350 | 15.021 | 41.849 | 67.227 | 1.00 | 8.14 |
| ATOM | 1179 | CG | GLU | 350 | 14.154 | 40.729 | 66.778 | 1.00 | 9.08 |
| ATOM | 1180 | CD | GLU | 350 | 14.978 | 39.609 | 66.120 | 1.00 | 15.55 |
| ATOM | 1181 | OE1 | GLU | 350 | 15.959 | 39.878 | 65.377 | 1.00 | 14.89 |
| ATOM | 1182 | OE2 | GLU | 350 | 14.623 | 38.461 | 66.338 | 1.00 | 11.67 |
| ATOM | 1183 | C | GLU | 350 | 13.674 | 42.473 | 69.227 | 1.00 | 11.14 |
| ATOM | 1184 | O | GLU | 350 | 12.466 | 42.257 | 69.327 | 1.00 | 14.22 |
| ATOM | 1185 | N | GLY | 351 | 14.537 | 42.412 | 70.256 | 1.00 | 11.35 |
| ATOM | 1186 | H | GLY | 351 | 15.479 | 42.632 | 70.100 | 1.00 | 0.00 |
| ATOM | 1187 | CA | GLY | 351 | 14.114 | 42.030 | 71.593 | 1.00 | 10.67 |
| ATOM | 1188 | C | GLY | 351 | 13.065 | 42.993 | 72.171 | 1.00 | 13.00 |
| ATOM | 1189 | O | GLY | 351 | 12.085 | 42.540 | 72.794 | 1.00 | 12.17 |
| ATOM | 1190 | N | MET | 352 | 13.329 | 44.305 | 72.049 | 1.00 | 9.47 |
| ATOM | 1191 | H | MET | 352 | 14.171 | 44.597 | 71.642 | 1.00 | 0.00 |
| ATOM | 1192 | CA | MET | 352 | 12.382 | 45.329 | 72.512 | 1.00 | 7.52 |
| ATOM | 1193 | CB | MET | 352 | 13.021 | 46.723 | 75.528 | 1.00 | 12.04 |
| ATOM | 1194 | CG | MET | 352 | 14.162 | 46.901 | 73.483 | 1.00 | 5.69 |
| ATOM | 1195 | SD | MET | 352 | 13.724 | 46.665 | 75.211 | 1.00 | 12.58 |
| ATOM | 1196 | CE | MET | 352 | 12.311 | 47.861 | 75.444 | 1.00 | 3.64 |
| ATOM | 1197 | C | MET | 352 | 11.127 | 45.379 | 71.627 | 1.00 | 5.74 |
| ATOM | 1198 | O | MET | 352 | 10.135 | 45.860 | 72.072 | 1.00 | 5.79 |
| ATOM | 1199 | N | ALA | 353 | 11.161 | 44.911 | 70.375 | 1.00 | 5.05 |
| ATOM | 1200 | H | ALA | 353 | 11.991 | 44.572 | 69.980 | 1.00 | 0.00 |
| ATOM | 1201 | CA | ALA | 353 | 9.937 | 44.912 | 69.600 | 1.00 | 4.26 |
| ATOM | 1202 | CB | ALA | 353 | 10.185 | 44.692 | 68.132 | 1.00 | 4.67 |
| ATOM | 1203 | C | ALA | 353 | 9.021 | 43.816 | 70.171 | 1.00 | 10.30 |
| ATOM | 1204 | O | ALA | 353 | 7.797 | 43.938 | 70.060 | 1.00 | 9.26 |
| ATOM | 1205 | N | PHE | 354 | 9.598 | 42.708 | 70.679 | 1.00 | 12.48 |
| ATOM | 1206 | H | PHE | 354 | 10.569 | 42.586 | 70.631 | 1.00 | 0.00 |
| ATOM | 1207 | CA | PHE | 354 | 8.767 | 41.657 | 71.319 | 1.00 | 14.04 |
| ATOM | 1208 | CB | PHE | 354 | 9.553 | 40.396 | 71.700 | 1.00 | 9.45 |
| ATOM | 1209 | CG | PHE | 354 | 8.746 | 39.398 | 72.538 | 1.00 | 8.70 |
| ATOM | 1210 | CD1 | PHE | 354 | 7.786 | 38.587 | 71.945 | 1.00 | 6.97 |
| ATOM | 1211 | CD2 | PHE | 354 | 8.960 | 39.285 | 73.893 | 1.00 | 6.24 |
| ATOM | 1212 | CE1 | PHE | 354 | 7.023 | 37.642 | 72.202 | 1.00 | 5.55 |
| ATOM | 1213 | CE2 | PHE | 354 | 8.231 | 38.370 | 74.648 | 1.00 | 8.25 |
| ATOM | 1214 | CZ | PHE | 354 | 7.247 | 37.534 | 74.036 | 1.00 | 4.45 |
| ATOM | 1215 | C | PHE | 354 | 8.187 | 42.268 | 72.622 | 1.00 | 12.12 |
| ATOM | 1216 | O | PHE | 354 | 7.001 | 42.142 | 72.863 | 1.00 | 11.91 |
| ATOM | 1217 | N | ILE | 355 | 9.036 | 42.870 | 73.460 | 1.00 | 11.90 |
| ATOM | 1218 | H | ILE | 355 | 9.993 | 42.899 | 73.251 | 1.00 | 0.00 |
| ATOM | 1219 | CA | ILE | 355 | 8.569 | 43.493 | 74.694 | 1.00 | 11.76 |
| ATOM | 1220 | CB | ILE | 355 | 9.703 | 44.189 | 75.406 | 1.00 | 10.56 |
| ATOM | 1221 | CG2 | ILE | 355 | 9.179 | 45.177 | 76.502 | 1.00 | 8.15 |
| ATOM | 1222 | CG1 | ILE | 355 | 10.607 | 43.137 | 76.044 | 1.00 | 9.35 |
| ATOM | 1223 | CD1 | ILE | 355 | 11.899 | 43.766 | 76.683 | 1.00 | 10.94 |
| ATOM | 1224 | C | ILE | 355 | 7.388 | 44.489 | 74.403 | 1.00 | 10.12 |
| ATOM | 1225 | O | ILE | 355 | 6.349 | 44.454 | 75.036 | 1.00 | 11.21 |
| ATOM | 1226 | N | GLU | 356 | 7.565 | 45.254 | 73.346 | 1.00 | 13.55 |
| ATOM | 1227 | H | GLU | 356 | 8.398 | 45.169 | 72.837 | 1.00 | 0.00 |
| ATOM | 1228 | CA | GLU | 356 | 6.595 | 46.228 | 72.880 | 1.00 | 13.41 |
| ATOM | 1229 | CB | GLU | 356 | 7.231 | 47.064 | 71.737 | 1.00 | 10.17 |
| ATOM | 1230 | CG | GLU | 356 | 6.325 | 47.658 | 70.658 | 1.00 | 19.16 |
| ATOM | 1231 | CD | GLU | 356 | 7.117 | 48.473 | 69.595 | 1.00 | 23.88 |
| ATOM | 1232 | OE1 | GLU | 356 | 7.229 | 48.050 | 68.380 | 1.00 | 20.75 |
| ATOM | 1233 | OE2 | GLU | 356 | 7.669 | 49.520 | 70.008 | 1.00 | 23.00 |
| ATOM | 1234 | C | GLU | 356 | 5.292 | 45.502 | 72.464 | 1.00 | 12.85 |
| ATOM | 1235 | O | GLU | 356 | 4.229 | 46.004 | 72.872 | 1.00 | 14.22 |
| ATOM | 1236 | N | GLU | 357 | 5.353 | 44.454 | 71.608 | 0.36 | 7.88 |
| ATOM | 1237 | H | GLU | 357 | 6.218 | 44.210 | 71.218 | 1.00 | 0.00 |
| ATOM | 1238 | CA | GLU | 357 | 4.173 | 43.645 | 71.222 | 0.36 | 6.12 |
| ATOM | 1239 | CB | GLU | 357 | 4.635 | 42.507 | 70.251 | 0.36 | 7.14 |
| ATOM | 1240 | CG | GLU | 357 | 3.798 | 41.176 | 70.230 | 0.36 | 8.15 |
| ATOM | 1241 | CD | GLU | 357 | 4.554 | 39.931 | 69.715 | 0.36 | 13.28 |
| ATOM | 1242 | OE1 | GLU | 357 | 5.546 | 40.093 | 68.956 | 0.36 | 15.24 |
| ATOM | 1243 | OE2 | GLU | 357 | 4.116 | 38.789 | 70.046 | 0.36 | 13.24 |
| ATOM | 1244 | C | GLU | 357 | 3.416 | 43.075 | 72.472 | 0.36 | 5.81 |

TABLE 6-continued

Coordinates of Lck bound with damnacanthal

| | Atom Type | Res | # | X | Y | Z | Occ | B |
|---|---|---|---|---|---|---|---|---|
| ATOM | 1245 | O | GLU | 357 | 2.197 | 43.008 | 72.466 | 0.36 | 2.00 |
| ATOM | 1246 | N | ARG | 358 | 4.101 | 42.746 | 73.565 | 1.00 | 9.62 |
| ATOM | 1247 | H | ARG | 358 | 5.073 | 42.869 | 73.600 | 1.00 | 0.00 |
| ATOM | 1248 | CA | ARG | 358 | 3.405 | 42.193 | 74.736 | 1.00 | 9.72 |
| ATOM | 1249 | CB | ARG | 358 | 4.354 | 41.216 | 75.478 | 1.00 | 10.56 |
| ATOM | 1250 | CG | ARG | 358 | 4.984 | 40.159 | 74.597 | 1.00 | 13.86 |
| ATOM | 1251 | CD | ARG | 358 | 3.919 | 39.447 | 73.815 | 1.00 | 17.79 |
| ATOM | 1252 | NE | ARG | 358 | 2.935 | 38.904 | 74.721 | 1.00 | 22.39 |
| ATOM | 1253 | HE | ARG | 358 | 3.179 | 38.823 | 75.666 | 1.00 | 0.00 |
| ATOM | 1254 | CZ | ARG | 358 | 1.728 | 38.510 | 74.359 | 1.00 | 21.51 |
| ATOM | 1255 | NH1 | ARG | 358 | 1.350 | 38.606 | 73.092 | 1.00 | 20.13 |
| ATOM | 1256 | HH11 | ARG | 358 | 1.979 | 38.977 | 72.409 | 1.00 | 0.00 |
| ATOM | 1257 | HH12 | ARG | 358 | 0.436 | 38.307 | 72.819 | 1.00 | 0.00 |
| ATOM | 1258 | NH2 | ARG | 328 | 0.909 | 38.025 | 75.270 | 1.00 | 26.31 |
| ATOM | 1259 | HH21 | ARG | 358 | 1.204 | 37.959 | 76.223 | 1.00 | 0.00 |
| ATOM | 1260 | HH22 | ARG | 358 | −0.008 | 37.723 | 75.008 | 1.00 | 0.00 |
| ATOM | 1261 | C | ARG | 358 | 2.865 | 43.256 | 75.681 | 1.00 | 8.12 |
| ATOM | 1262 | O | ARG | 358 | 2.456 | 42.958 | 76.817 | 1.00 | 9.63 |
| ATOM | 1263 | N | ASN | 359 | 3.006 | 44.503 | 75.286 | 1.00 | 9.42 |
| ATOM | 1264 | H | ASN | 359 | 3.402 | 44.723 | 74.417 | 1.00 | 0.00 |
| ATOM | 1265 | CA | ASN | 359 | 2.556 | 45.567 | 76.176 | 1.00 | 11.06 |
| ATOM | 1266 | CB | ASN | 359 | 1.065 | 45.412 | 76.521 | 1.00 | 8.68 |
| ATOM | 1267 | CG | ASN | 359 | 0.217 | 45.865 | 75.402 | 1.00 | 12.93 |
| ATOM | 1268 | OD1 | ASN | 359 | 0.737 | 46.474 | 74.478 | 1.00 | 19.48 |
| ATOM | 1269 | ND2 | ASN | 359 | −1.081 | 45.598 | 75.450 | 1.00 | 16.98 |
| ATOM | 1270 | HD21 | ASN | 359 | −1.453 | 45.112 | 76.215 | 1.00 | 0.00 |
| ATOM | 1271 | HD22 | ASN | 359 | −1.633 | 45.904 | 74.702 | 1.00 | 0.00 |
| ATOM | 1272 | C | ASN | 359 | 3.347 | 45.724 | 77.454 | 1.00 | 11.30 |
| ATOM | 1273 | O | ASN | 359 | 2.796 | 46.123 | 78.460 | 1.00 | 15.14 |
| ATOM | 1274 | N | TYR | 360 | 4.625 | 45.361 | 77.438 | 1.00 | 13.12 |
| ATOM | 1275 | H | TYR | 360 | 5.014 | 44.948 | 76.639 | 1.00 | 0.00 |
| ATOM | 1276 | CA | TYR | 360 | 5.471 | 45.572 | 78.612 | 1.00 | 15.69 |
| ATOM | 1277 | CB | TYR | 360 | 6.303 | 44.329 | 78.920 | 1.00 | 21.12 |
| ATOM | 1278 | CG | TYR | 360 | 5.537 | 43.213 | 79.593 | 1.00 | 25.00 |
| ATOM | 1279 | CD1 | TYR | 360 | 4.724 | 42.350 | 78.855 | 1.00 | 24.99 |
| ATOM | 1280 | CE1 | TYR | 360 | 4.042 | 41.330 | 79.466 | 1.00 | 25.45 |
| ATOM | 1281 | CD2 | TYR | 360 | 5.635 | 43.007 | 80.962 | 1.00 | 27.51 |
| ATOM | 1282 | CE2 | TYR | 360 | 4.944 | 41.991 | 81.574 | 1.00 | 25.16 |
| ATOM | 1283 | CZ | TYR | 360 | 4.144 | 41.159 | 80.816 | 1.00 | 27.31 |
| ATOM | 1284 | OH | TYR | 360 | 3.362 | 40.199 | 81.434 | 1.00 | 35.06 |
| ATOM | 1285 | HH | TYR | 360 | 2.871 | 39.710 | 80.770 | 1.00 | 0.00 |
| ATOM | 1286 | C | TYR | 360 | 6.438 | 46.747 | 78.325 | 1.00 | 14.58 |
| ATOM | 1287 | O | TYR | 360 | 6.593 | 47.169 | 77.191 | 1.00 | 10.89 |
| ATOM | 1288 | N | ILE | 361 | 7.089 | 47.237 | 79.368 | 1.00 | 16.39 |
| ATOM | 1289 | H | ILE | 361 | 6.895 | 46.884 | 80.261 | 1.00 | 0.00 |
| ATOM | 1290 | CA | ILE | 361 | 8.096 | 48.293 | 79.255 | 1.00 | 18.35 |
| ATOM | 1291 | CB | ILE | 361 | 7.651 | 49.651 | 79.890 | 1.00 | 18.26 |
| ATOM | 1292 | CG2 | ILE | 361 | 6.406 | 50.192 | 79.212 | 1.00 | 18.04 |
| ATOM | 1293 | CG1 | ILE | 361 | 7.467 | 49.481 | 81.385 | 1.00 | 20.72 |
| ATOM | 1294 | CD1 | ILE | 361 | 6.705 | 50.604 | 82.028 | 1.00 | 22.93 |
| ATOM | 1295 | C | ILE | 361 | 9.322 | 47.830 | 80.045 | 1.00 | 18.74 |
| ATOM | 1296 | O | ILE | 361 | 9.191 | 47.262 | 81.121 | 1.00 | 22.57 |
| ATOM | 1297 | N | HIS | 362 | 10.511 | 48.085 | 79.525 | 1.00 | 16.58 |
| ATOM | 1298 | H | HIS | 362 | 10.590 | 48.526 | 78.653 | 1.00 | 0.00 |
| ATOM | 1299 | CA | HIS | 362 | 11.708 | 47.716 | 80.238 | 1.00 | 13.83 |
| ATOM | 1300 | CB | HIS | 362 | 12.874 | 47.748 | 79.278 | 1.00 | 16.55 |
| ATOM | 1301 | CG | HIS | 362 | 14.054 | 47.012 | 79.781 | 1.00 | 13.27 |
| ATOM | 1302 | CD2 | HIS | 362 | 14.474 | 45.746 | 79.553 | 1.00 | 13.27 |
| ATOM | 1303 | ND1 | HIS | 362 | 14.898 | 47.527 | 80.750 | 1.00 | 13.99 |
| ATOM | 1304 | HD1 | HIS | 362 | 14.846 | 48.427 | 81.122 | 1.00 | 0.00 |
| ATOM | 1305 | CE1 | HIS | 362 | 15.780 | 46.615 | 81.090 | 1.00 | 18.74 |
| ATOM | 1306 | NE2 | HIS | 362 | 15.544 | 45.518 | 80.380 | 1.00 | 19.58 |
| ATOM | 1307 | HE2 | HIS | 362 | 16.049 | 44.686 | 80.437 | 1.00 | 0.00 |
| ATOM | 1308 | C | HIS | 362 | 12.022 | 48.633 | 81.424 | 1.00 | 13.59 |
| ATOM | 1309 | O | HIS | 362 | 12.200 | 48.189 | 82.545 | 1.00 | 15.38 |
| ATOM | 1310 | N | ALA | 363 | 12.042 | 49.936 | 81.210 | 1.00 | 15.49 |
| ATOM | 1311 | H | ALA | 363 | 11.831 | 50.315 | 80.332 | 1.00 | 0.00 |
| ATOM | 1312 | CA | ALA | 363 | 12.395 | 50.827 | 82.340 | 1.00 | 22.96 |
| ATOM | 1313 | CB | ALA | 363 | 11.399 | 50.742 | 83.486 | 1.00 | 27.17 |
| ATOM | 1314 | C | ALA | 363 | 13.837 | 50.779 | 82.888 | 1.00 | 23.53 |
| ATOM | 1315 | O | ALA | 363 | 14.065 | 51.215 | 84.003 | 1.00 | 25.57 |
| ATOM | 1316 | N | ASP | 364 | 14.751 | 50.126 | 82.169 | 1.00 | 20.75 |
| ATOM | 1317 | H | ASP | 364 | 14.470 | 48.618 | 81.380 | 1.00 | 0.00 |
| ATOM | 1318 | CA | ASP | 364 | 16.183 | 50.135 | 82.514 | 1.00 | 16.43 |

TABLE 6-continued

Coordinates of Lck bound with damnacanthal

| | Atom Type | Res | # | X | Y | Z | Occ | B |
|---|---|---|---|---|---|---|---|---|
| ATOM | 1319 | CB | ASP | 364 | 16.568 | 49.432 | 83.818 | 1.00 | 18.19 |
| ATOM | 1320 | CG | ASP | 364 | 17.874 | 49.997 | 84.400 | 1.00 | 22.48 |
| ATOM | 1321 | OD1 | ASP | 364 | 18.376 | 51.017 | 83.864 | 1.00 | 27.11 |
| ATOM | 1322 | OD2 | ASP | 364 | 18.414 | 49.434 | 85.369 | 1.00 | 21.66 |
| ATOM | 1323 | C | ASP | 364 | 17.003 | 49.643 | 81.352 | 1.00 | 11.31 |
| ATOM | 1324 | O | ASP | 364 | 17.940 | 48.884 | 81.486 | 1.00 | 11.08 |
| ATOM | 1325 | N | LEU | 365 | 16.617 | 50.135 | 80.199 | 1.00 | 9.94 |
| ATOM | 1326 | H | LEU | 365 | 15.855 | 50.751 | 80.174 | 1.00 | 0.00 |
| ATOM | 1327 | CA | LEU | 365 | 17.251 | 49.820 | 78.973 | 1.00 | 14.34 |
| ATOM | 1328 | CB | LEU | 365 | 16.270 | 50.020 | 77.821 | 1.00 | 5.26 |
| ATOM | 1329 | CG | LEU | 365 | 16.867 | 49.599 | 76.479 | 1.00 | 5.25 |
| ATOM | 1330 | CD1 | LEU | 365 | 17.117 | 48.074 | 76.508 | 1.00 | 2.16 |
| ATOM | 1331 | CD2 | LEU | 365 | 15.985 | 49.994 | 75.329 | 1.00 | 6.16 |
| ATOM | 1332 | C | LEU | 365 | 18.527 | 50.676 | 78.757 | 1.00 | 19.01 |
| ATOM | 1333 | O | LEU | 365 | 18.481 | 51.905 | 78.488 | 1.00 | 18.55 |
| ATOM | 1334 | N | ARG | 366 | 19.642 | 49.970 | 78.894 | 1.00 | 18.68 |
| ATOM | 1335 | H | ARG | 366 | 19.560 | 49.029 | 79.155 | 1.00 | 0.00 |
| ATOM | 1336 | CA | ARG | 366 | 20.976 | 50.467 | 78.692 | 1.00 | 15.87 |
| ATOM | 1337 | CB | ARG | 366 | 21.419 | 51.325 | 79.851 | 1.00 | 12.39 |
| ATOM | 1338 | CG | ARG | 366 | 21.405 | 50.678 | 81.206 | 1.00 | 16.05 |
| ATOM | 1339 | CD | ARG | 366 | 21.994 | 51.689 | 82.159 | 1.00 | 19.92 |
| ATOM | 1340 | NE | ARG | 366 | 22.228 | 51.119 | 83.450 | 1.00 | 24.76 |
| ATOM | 1341 | HE | ARG | 366 | 21.688 | 50.347 | 83.718 | 1.00 | 0.00 |
| ATOM | 1342 | CZ | ARG | 366 | 23.139 | 51.577 | 84.309 | 1.00 | 35.30 |
| ATOM | 1343 | NH1 | ARG | 366 | 23.893 | 52.664 | 84.037 | 1.00 | 36.53 |
| ATOM | 1344 | HH11 | ARG | 366 | 23.776 | 53.150 | 83.171 | 1.00 | 0.00 |
| ATOM | 1345 | HH12 | ARG | 366 | 24.568 | 52.983 | 84.702 | 1.00 | 0.00 |
| ATOM | 1346 | NH2 | ARG | 366 | 23.330 | 50.913 | 85.443 | 1.00 | 34.57 |
| ATOM | 1347 | HH21 | ARG | 366 | 22.796 | 50.090 | 85.636 | 1.00 | 0.00 |
| ATOM | 1348 | HH22 | ARG | 366 | 24.008 | 51.236 | 86.104 | 1.00 | 0.00 |
| ATOM | 1349 | C | ARG | 366 | 21.896 | 49.241 | 78.458 | 1.00 | 15.49 |
| ATOM | 1350 | O | ARG | 366 | 21.537 | 48.066 | 78.808 | 1.00 | 12.42 |
| ATOM | 1351 | N | ALA | 367 | 23.055 | 49.516 | 77.861 | 1.00 | 9.54 |
| ATOM | 1352 | H | ALA | 367 | 23.287 | 50.446 | 77.659 | 1.00 | 0.00 |
| ATOM | 1353 | CA | ALA | 367 | 23.989 | 48.489 | 77.497 | 1.00 | 10.32 |
| ATOM | 1354 | CB | ALA | 367 | 25.209 | 49.106 | 76.842 | 1.00 | 8.00 |
| ATOM | 1355 | C | ALA | 367 | 24.355 | 47.495 | 78.648 | 1.00 | 12.09 |
| ATOM | 1356 | O | ALA | 367 | 24.513 | 46.281 | 78.416 | 1.00 | 11.23 |
| ATOM | 1357 | N | ALA | 368 | 24.434 | 48.009 | 79.870 | 1.00 | 9.24 |
| ATOM | 1358 | H | ALA | 368 | 24.297 | 48.970 | 80.001 | 1.00 | 0.00 |
| ATOM | 1359 | CA | ALA | 368 | 24.715 | 47.204 | 81.017 | 1.00 | 10.40 |
| ATOM | 1360 | CB | ALA | 368 | 24.768 | 48.080 | 82.280 | 1.00 | 4.89 |
| ATOM | 1361 | C | ALA | 368 | 23.610 | 46.126 | 81.163 | 1.00 | 14.35 |
| ATOM | 1362 | O | ALA | 368 | 23.806 | 45.144 | 81.868 | 1.00 | 15.21 |
| ATOM | 1363 | N | ASN | 369 | 22.437 | 46.352 | 80.554 | 1.00 | 14.59 |
| ATOM | 1364 | H | ASN | 369 | 22.297 | 47.171 | 80.035 | 1.00 | 0.00 |
| ATOM | 1365 | CA | ASN | 369 | 21.363 | 45.393 | 80.654 | 1.00 | 13.50 |
| ATOM | 1366 | CB | ASN | 369 | 20.084 | 46.023 | 81.205 | 1.00 | 17.94 |
| ATOM | 1367 | CG | ASN | 369 | 20.220 | 46.349 | 82.665 | 1.00 | 16.63 |
| ATOM | 1368 | OD1 | ASN | 369 | 20.988 | 45.695 | 83.339 | 1.00 | 21.52 |
| ATOM | 1369 | ND2 | ASN | 369 | 19.611 | 47.442 | 83.127 | 1.00 | 18.93 |
| ATOM | 1370 | HD21 | ASN | 369 | 19.092 | 48.008 | 82.518 | 1.00 | 0.00 |
| ATOM | 1371 | HD22 | ASN | 369 | 19.707 | 47.644 | 84.080 | 1.00 | 0.00 |
| ATOM | 1372 | C | ASN | 369 | 21.126 | 44.533 | 79.421 | 1.00 | 14.57 |
| ATOM | 1373 | O | ASN | 369 | 20.047 | 43.952 | 79.255 | 1.00 | 14.57 |
| ATOM | 1374 | N | ILE | 370 | 22.124 | 44.509 | 78.533 | 1.00 | 15.35 |
| ATOM | 1375 | H | ILE | 370 | 22.909 | 45.079 | 78.671 | 1.00 | 0.00 |
| ATOM | 1376 | CA | ILE | 370 | 22.091 | 43.666 | 77.364 | 1.00 | 10.86 |
| ATOM | 1377 | CB | ILE | 370 | 22.461 | 44.388 | 76.105 | 1.00 | 10.11 |
| ATOM | 1378 | CG2 | ILE | 370 | 22.509 | 43.381 | 74.927 | 1.00 | 12.62 |
| ATOM | 1379 | CG1 | ILE | 370 | 21.493 | 45.559 | 75.847 | 1.00 | 13.98 |
| ATOM | 1380 | CD1 | ILE | 370 | 19.979 | 45.249 | 75.875 | 1.00 | 18.21 |
| ATOM | 1381 | C | ILE | 370 | 23.177 | 42.624 | 77.665 | 1.00 | 11.26 |
| ATOM | 1382 | O | ILE | 370 | 24.221 | 42.968 | 78.231 | 1.00 | 12.28 |
| ATOM | 1383 | N | LEU | 370 | 22.884 | 41.349 | 77.400 | 1.00 | 12.64 |
| ATOM | 1384 | H | LEU | 371 | 21.988 | 41.138 | 77.104 | 1.00 | 20.00 |
| ATOM | 1385 | CA | LEU | 371 | 23.828 | 40.245 | 77.647 | 1.00 | 11.76 |
| ATOM | 1386 | CB | LEU | 371 | 23.182 | 39.125 | 78.497 | 1.00 | 9.60 |
| ATOM | 1387 | CG | LEU | 371 | 23.592 | 39.015 | 79.965 | 1.00 | 8.92 |
| ATOM | 1388 | CD1 | LEU | 371 | 24.424 | 40.210 | 80.416 | 1.00 | 16.55 |
| ATOM | 1389 | CD2 | LEU | 371 | 22.406 | 38.839 | 80.844 | 1.00 | 18.69 |
| ATOM | 1390 | C | LEU | 371 | 24.266 | 39.696 | 76.304 | 1.00 | 11.56 |
| ATOM | 1391 | O | LEU | 371 | 23.506 | 39.746 | 75.353 | 1.00 | 11.42 |
| ATOM | 1392 | N | VAL | 372 | 25.505 | 39.229 | 76.242 | 1.00 | 11.47 |

TABLE 6-continued

Coordinates of Lck bound with damnacanthal

| | Atom Type | Res | # | X | Y | Z | Occ | B |
|---|---|---|---|---|---|---|---|---|
| ATOM | 1393 | H | VAL | 372 | 26.065 | 39.224 | 77.046 | 1.00 | 0.00 |
| ATOM | 1394 | CA | VAL | 372 | 26.062 | 38.723 | 75.017 | 1.00 | 14.19 |
| ATOM | 1395 | CB | VAL | 372 | 27.354 | 39.471 | 74.636 | 1.00 | 14.59 |
| ATOM | 1396 | CG1 | VAL | 372 | 27.766 | 39.047 | 73.258 | 1.00 | 7.72 |
| ATOM | 1397 | CG2 | VAL | 372 | 27.140 | 41.015 | 74.693 | 1.00 | 12.70 |
| ATOM | 1398 | C | VAL | 372 | 26.392 | 37.238 | 75.139 | 1.00 | 13.07 |
| ATOM | 1399 | O | VAL | 372 | 27.064 | 36.831 | 76.076 | 1.00 | 8.92 |
| ATOM | 1400 | N | SER | 373 | 25.966 | 36.465 | 74.155 | 1.00 | 11.67 |
| ATOM | 1401 | H | SER | 373 | 25.474 | 36.857 | 73.404 | 1.00 | 0.00 |
| ATOM | 1402 | CA | SER | 373 | 26.210 | 35.029 | 74.154 | 1.00 | 12.43 |
| ATOM | 1403 | CB | SER | 373 | 25.164 | 34.327 | 73.299 | 1.00 | 10.41 |
| ATOM | 1404 | OG | SER | 373 | 25.437 | 34.577 | 71.956 | 1.00 | 7.77 |
| ATOM | 1405 | HG | SER | 373 | 26.310 | 34.243 | 71.739 | 1.00 | 0.00 |
| ATOM | 1406 | C | SER | 373 | 27.609 | 34.715 | 73.588 | 1.00 | 15.00 |
| ATOM | 1407 | O | SER | 373 | 28.268 | 35.587 | 73.001 | 1.00 | 14.30 |
| ATOM | 1408 | N | ASP | 374 | 27.962 | 33.425 | 73.612 | 1.00 | 14.76 |
| ATOM | 1409 | H | ASP | 374 | 27.335 | 32.754 | 73.955 | 1.00 | 0.00 |
| ATOM | 1410 | CA | ASP | 374 | 29.269 | 32.979 | 73.137 | 1.00 | 14.97 |
| ATOM | 1411 | CB | ASP | 374 | 29.534 | 31.535 | 73.563 | 1.00 | 14.18 |
| ATOM | 1412 | CG | ASP | 374 | 28.633 | 30.584 | 72.860 | 1.00 | 20.92 |
| ATOM | 1413 | OD1 | ASP | 374 | 27.427 | 30.596 | 73.161 | 1.00 | 23.50 |
| ATOM | 1414 | OD2 | ASP | 374 | 29.079 | 29.918 | 71.915 | 1.00 | 26.77 |
| ATOM | 1415 | C | ASP | 374 | 29.349 | 33.121 | 71.637 | 1.00 | 13.65 |
| ATOM | 1416 | O | ASP | 374 | 30.428 | 33.074 | 71.053 | 1.00 | 10.83 |
| ATOM | 1417 | N | THR | 375 | 28.191 | 33.187 | 70.983 | 1.00 | 16.46 |
| ATOM | 1418 | H | THR | 375 | 27.337 | 33.102 | 71.456 | 1.00 | 0.00 |
| ATOM | 1419 | CA | THR | 375 | 28.200 | 33.391 | 69.531 | 1.00 | 14.52 |
| ATOM | 1420 | CB | THR | 375 | 27.112 | 32.587 | 68.775 | 1.00 | 13.77 |
| ATOM | 1421 | OG1 | THR | 375 | 25.805 | 32.978 | 69.227 | 1.00 | 10.94 |
| ATOM | 1422 | HG1 | THR | 375 | 25.138 | 32.475 | 68.753 | 1.00 | 0.00 |
| ATOM | 1423 | CG2 | THR | 375 | 27.317 | 31.089 | 68.954 | 1.00 | 13.55 |
| ATOM | 1424 | C | THR | 375 | 28.018 | 34.889 | 69.215 | 1.00 | 14.28 |
| ATOM | 1425 | O | THR | 375 | 27.752 | 35.230 | 68.068 | 1.00 | 7.56 |
| ATOM | 1426 | N | LEU | 376 | 28.193 | 35.768 | 70.209 | 1.00 | 13.36 |
| ATOM | 1427 | H | LEU | 376 | 28.437 | 35.456 | 71.105 | 1.00 | 0.00 |
| ATOM | 1428 | CA | LEU | 376 | 28.025 | 37.208 | 69.984 | 1.00 | 16.96 |
| ATOM | 1429 | CB | LEU | 376 | 29.137 | 37.770 | 69.048 | 1.00 | 16.06 |
| ATOM | 1430 | CG | LEU | 376 | 30.554 | 37.242 | 69.425 | 1.00 | 15.98 |
| ATOM | 1431 | CD1 | LEU | 376 | 31.665 | 37.878 | 68.541 | 1.00 | 15.60 |
| ATOM | 1432 | CD2 | LEU | 376 | 30.808 | 37.469 | 70.885 | 1.00 | 2.83 |
| ATOM | 1433 | C | LEU | 376 | 26.611 | 37.641 | 69.520 | 1.00 | 18.03 |
| ATOM | 1434 | O | LEU | 376 | 26.463 | 38.430 | 68.577 | 1.00 | 20.72 |
| ATOM | 1435 | N | SER | 377 | 25.590 | 37.024 | 70.120 | 1.00 | 17.29 |
| ATOM | 1436 | H | SER | 377 | 25.776 | 36.291 | 70.743 | 1.00 | 0.00 |
| ATOM | 1437 | CA | SER | 377 | 24.177 | 37.390 | 69.893 | 1.00 | 14.20 |
| ATOM | 1438 | CB | SER | 377 | 23.250 | 36.167 | 69.558 | 1.00 | 12.08 |
| ATOM | 1439 | OG | SER | 377 | 23.190 | 35.172 | 70.600 | 1.00 | 9.52 |
| ATOM | 1440 | HG | SER | 377 | 22.609 | 34.458 | 70.328 | 1.00 | 0.00 |
| ATOM | 1441 | C | SER | 377 | 23.783 | 38.091 | 71.213 | 1.00 | 7.73 |
| ATOM | 1442 | O | SER | 377 | 24.356 | 37.798 | 72.271 | 1.00 | 8.70 |
| ATOM | 1443 | H | CYS | 378 | 22.897 | 39.073 | 71.141 | 1.00 | 11.83 |
| ATOM | 1444 | H | CYS | 378 | 22.495 | 39.314 | 70.281 | 1.00 | 0.00 |
| ATOM | 1445 | CA | CYS | 378 | 22.499 | 39.821 | 72.350 | 1.00 | 12.27 |
| ATOM | 1446 | CB | CYS | 378 | 22.521 | 41.347 | 72.089 | 1.00 | 13.15 |
| ATOM | 1447 | SG | CYS | 378 | 24.141 | 41.872 | 71.488 | 1.00 | 14.52 |
| ATOM | 1448 | C | CYS | 378 | 21.117 | 39.468 | 72.811 | 1.00 | 9.12 |
| ATOM | 1449 | O | CYS | 378 | 20.240 | 39.246 | 71.986 | 1.00 | 10.07 |
| ATOM | 1450 | N | LYS | 379 | 20.910 | 39.531 | 74.123 | 1.00 | 10.21 |
| ATOM | 1451 | H | LYS | 379 | 21.653 | 39.765 | 74.718 | 1.00 | 0.00 |
| ATOM | 1452 | CA | LYS | 379 | 19.610 | 39.264 | 74.720 | 1.00 | 7.80 |
| ATOM | 1453 | CB | LYS | 379 | 19.581 | 37.877 | 75.381 | 1.00 | 2.69 |
| ATOM | 1454 | CG | LYS | 379 | 19.713 | 36.777 | 74.348 | 1.00 | 3.92 |
| ATOM | 1455 | CD | LYS | 379 | 19.384 | 35.359 | 74.846 | 1.00 | 4.28 |
| ATOM | 1456 | CE | LYS | 379 | 19.784 | 34.383 | 73.706 | 1.00 | 6.33 |
| ATOM | 1457 | NZ | LYS | 379 | 18.842 | 33.243 | 73.605 | 1.00 | 16.80 |
| ATOM | 1458 | HZ1 | LYS | 379 | 17.885 | 33.600 | 73.409 | 1.00 | 0.00 |
| ATOM | 1459 | HZ2 | LYS | 379 | 18.839 | 32.715 | 74.501 | 1.00 | 0.00 |
| ATOM | 1460 | HZ3 | LYS | 379 | 19.142 | 32.613 | 72.834 | 1.00 | 0.00 |
| ATOM | 1461 | C | LYS | 379 | 19.391 | 40.370 | 75.756 | 1.00 | 8.86 |
| ATOM | 1462 | O | LYS | 379 | 20.347 | 40.910 | 76.331 | 1.00 | 8.59 |
| ATOM | 1463 | N | ILE | 380 | 18.137 | 40.701 | 75.983 | 1.00 | 9.36 |
| ATOM | 1464 | H | ILE | 380 | 17.417 | 40.248 | 75.497 | 1.00 | 0.00 |
| ATOM | 1465 | H | ILE | 380 | 17.784 | 41.730 | 76.944 | 1.00 | 10.48 |
| ATOM | 1466 | CB | ILE | 380 | 16.432 | 42.366 | 76.552 | 1.00 | 7.72 |

TABLE 6-continued

Coordinates of Lck bound with damnacanthal

| | | Atom Type | Res | # | X | Y | Z | Occ | B |
|---|---|---|---|---|---|---|---|---|---|
| ATOM | 1467 | CG2 | ILE | 380 | 15.907 | 43.269 | 77.662 | 1.00 | 5.01 |
| ATOM | 1468 | CG1 | ILE | 380 | 16.557 | 43.014 | 75.193 | 1.00 | 11.15 |
| ATOM | 1469 | CD1 | ILE | 380 | 15.313 | 43.500 | 74.691 | 1.00 | 17.80 |
| ATOM | 1470 | C | ILE | 380 | 17.663 | 40.985 | 78.262 | 1.00 | 10.66 |
| ATOM | 1471 | O | ILE | 380 | 17.185 | 39.865 | 78.318 | 1.00 | 7.84 |
| ATOM | 1472 | N | ALA | 381 | 18.036 | 41.659 | 79.331 | 1.00 | 11.32 |
| ATOM | 1473 | H | ALA | 381 | 18.328 | 42.590 | 79.241 | 1.00 | 0.00 |
| ATOM | 1474 | CA | ALA | 381 | 18.029 | 41.081 | 80.613 | 1.00 | 16.46 |
| ATOM | 1475 | CB | ALA | 381 | 19.476 | 40.671 | 81.023 | 1.00 | 20.08 |
| ATOM | 1476 | C | ALA | 381 | 17.511 | 42.124 | 81.572 | 1.00 | 18.77 |
| ATOM | 1477 | O | ALA | 381 | 17.120 | 43.227 | 81.175 | 1.00 | 15.47 |
| ATOM | 1478 | N | ALA | 382 | 17.727 | 41.773 | 82.831 | 1.00 | 25.66 |
| ATOM | 1479 | H | ALA | 382 | 18.178 | 40.922 | 83.009 | 1.00 | 0.00 |
| ATOM | 1480 | CA | ALA | 382 | 17.337 | 42.573 | 83.983 | 1.00 | 29.42 |
| ATOM | 1481 | CB | ALA | 382 | 18.374 | 43.732 | 84.216 | 1.00 | 22.81 |
| ATOM | 1482 | C | ALA | 382 | 15.886 | 43.045 | 83.769 | 1.00 | 31.21 |
| ATOM | 1483 | O | ALA | 382 | 15.577 | 43.930 | 82.968 | 1.00 | 36.10 |
| ATOM | 1484 | N | PHE | 383 | 14.968 | 42.332 | 84.388 | 1.00 | 31.81 |
| ATOM | 1485 | H | PHE | 383 | 15.216 | 41.568 | 84.949 | 1.00 | 0.00 |
| ATOM | 1486 | CA | PHE | 383 | 13.587 | 42.682 | 84.237 | 1.00 | 32.87 |
| ATOM | 1487 | CB | PHE | 383 | 12.834 | 41.455 | 83.730 | 1.00 | 33.14 |
| ATOM | 1488 | CG | PHE | 383 | 13.381 | 40.887 | 82.419 | 1.00 | 29.04 |
| ATOM | 1489 | CD1 | PHE | 383 | 12.913 | 41.345 | 81.190 | 1.00 | 24.21 |
| ATOM | 1490 | CD2 | PHE | 383 | 14.366 | 39.900 | 82.429 | 1.00 | 22.63 |
| ATOM | 1491 | CE1 | PHE | 383 | 13.421 | 40.826 | 79.999 | 1.00 | 23.40 |
| ATOM | 1492 | CE2 | PHE | 383 | 14.872 | 39.373 | 81.230 | 1.00 | 19.28 |
| ATOM | 1493 | CZ | PHE | 383 | 14.412 | 39.825 | 80.032 | 1.00 | 17.80 |
| ATOM | 1494 | C | PHE | 383 | 13.095 | 43.174 | 85.599 | 1.00 | 36.38 |
| ATOM | 1495 | O | PHE | 383 | 11.966 | 42.950 | 86.022 | 1.00 | 39.76 |
| ATOM | 1496 | N | GLY | 384 | 13.943 | 43.930 | 86.271 | 1.00 | 40.50 |
| ATOM | 1497 | H | GLY | 384 | 14.812 | 44.163 | 85.883 | 1.00 | 0.00 |
| ATOM | 1498 | CA | GLY | 384 | 13.577 | 44.410 | 87.584 | 1.00 | 38.87 |
| ATOM | 1499 | C | GLY | 384 | 12.375 | 45.325 | 87.587 | 1.00 | 37.62 |
| ATOM | 1500 | O | GLY | 384 | 11.428 | 45.127 | 88.336 | 1.00 | 37.89 |
| ATOM | 1501 | N | ALA | 385 | 12.413 | 46.293 | 86.688 | 1.00 | 37.15 |
| ATOM | 1502 | H | ALA | 385 | 13.151 | 46.321 | 86.043 | 1.00 | 0.00 |
| ATOM | 1503 | CA | ALA | 385 | 11.406 | 47.324 | 86.610 | 1.00 | 36.51 |
| ATOM | 1504 | CB | ALA | 385 | 12.091 | 48.681 | 86.497 | 1.00 | 38.17 |
| ATOM | 1505 | C | ALA | 385 | 10.538 | 47.127 | 85.441 | 1.00 | 37.86 |
| ATOM | 1506 | O | ALA | 385 | 9.854 | 48.072 | 85.028 | 1.00 | 35.66 |
| ATOM | 1507 | N | ALA | 386 | 10.688 | 45.976 | 84.785 | 1.00 | 38.75 |
| ATOM | 1508 | H | ALA | 386 | 11.353 | 45.312 | 85.061 | 1.00 | 0.00 |
| ATOM | 1509 | CA | ALA | 386 | 9.830 | 45.720 | 83.629 | 1.00 | 39.48 |
| ATOM | 1510 | CB | ALA | 386 | 10.150 | 44.416 | 82.986 | 1.00 | 38.07 |
| ATOM | 1511 | C | ALA | 386 | 8.411 | 45.730 | 84.187 | 1.00 | 40.18 |
| ATOM | 1512 | O | ALA | 386 | 8.143 | 45.311 | 85.325 | 1.00 | 38.21 |
| ATOM | 1513 | N | ALA | 387 | 7.497 | 46.257 | 83.406 | 1.00 | 41.46 |
| ATOM | 1514 | H | ALA | 387 | 7.721 | 46.577 | 82.507 | 1.00 | 0.00 |
| ATOM | 1515 | CA | ALA | 387 | 6.127 | 46.365 | 83.891 | 1.00 | 42.57 |
| ATOM | 1516 | CB | ALA | 387 | 5.926 | 47.729 | 84.584 | 1.00 | 43.43 |
| ATOM | 1517 | C | ALA | 387 | 5.159 | 46.223 | 82.742 | 1.00 | 40.87 |
| ATOM | 1518 | O | ALA | 387 | 5.487 | 46.587 | 81.608 | 1.00 | 39.52 |
| ATOM | 1519 | N | LEU | 388 | 3.998 | 45.645 | 83.037 | 1.00 | 38.41 |
| ATOM | 1520 | H | LEU | 388 | 3.821 | 45.330 | 83.948 | 1.00 | 0.00 |
| ATOM | 1521 | CA | LEU | 388 | 2.977 | 45.470 | 82.026 | 1.00 | 36.49 |
| ATOM | 1522 | CB | LEU | 388 | 2.190 | 44.192 | 82.285 | 1.00 | 37.61 |
| ATOM | 1523 | CG | LEU | 388 | 0.838 | 44.168 | 81.574 | 1.00 | 33.79 |
| ATOM | 1524 | CD1 | LEU | 388 | 0.748 | 42.997 | 80.622 | 1.00 | 30.56 |
| ATOM | 1525 | CD2 | LEU | 388 | −0.237 | 44.117 | 82.627 | 1.00 | 34.52 |
| ATOM | 1526 | C | LEU | 388 | 2.042 | 46.659 | 82.115 | 1.00 | 34.42 |
| ATOM | 1527 | O | LEU | 388 | 1.392 | 46.830 | 83.144 | 1.00 | 38.80 |
| ATOM | 1528 | N | PRO | 403 | 19.023 | 56.521 | 86.612 | 1.00 | 29.11 |
| ATOM | 1529 | CD | PRO | 403 | 18.267 | 55.372 | 86.092 | 1.00 | 28.32 |
| ATOM | 1530 | CD | PRO | 403 | 20.053 | 56.934 | 85.658 | 1.00 | 23.31 |
| ATOM | 1531 | CB | PRO | 403 | 20.291 | 55.673 | 84.807 | 1.00 | 18.38 |
| ATOM | 1532 | CG | PRO | 403 | 19.312 | 54.646 | 85.307 | 1.00 | 22.38 |
| ATOM | 1533 | C | PRO | 403 | 19.531 | 58.040 | 84.765 | 1.00 | 22.12 |
| ATOM | 1534 | O | PRO | 403 | 19.001 | 57.744 | 83.715 | 1.00 | 24.17 |
| ATOM | 1535 | N | ILE | 404 | 19.735 | 59.300 | 85.149 | 1.00 | 20.28 |
| ATOM | 1536 | H | ILE | 404 | 20.208 | 59.484 | 85.988 | 1.00 | 0.00 |
| ATOM | 1537 | CA | ILE | 404 | 19.276 | 60.416 | 84.359 | 1.00 | 15.85 |
| ATOM | 1538 | CB | ILE | 404 | 19.833 | 61.737 | 84.901 | 1.00 | 20.04 |
| ATOM | 1539 | CG2 | ILE | 404 | 19.596 | 62.884 | 83.911 | 1.00 | 21.19 |
| ATOM | 1540 | CG1 | ILE | 404 | 19.239 | 62.037 | 86.271 | 1.00 | 24.93 |

TABLE 6-continued

Coordinates of Lck bound with damnacanthal

| | | Atom Type | Res | # | X | Y | Z | Occ | B |
|---|---|---|---|---|---|---|---|---|---|
| ATOM | 1541 | CD1 | ILE | 404 | 17.713 | 62.226 | 86.267 | 1.00 | 25.87 |
| ATOM | 1542 | C | ILE | 404 | 19.677 | 60.367 | 82.888 | 1.00 | 14.36 |
| ATOM | 1543 | O | ILE | 404 | 18.822 | 60.506 | 82.027 | 1.00 | 19.25 |
| ATOM | 1544 | N | LYS | 405 | 20.946 | 60.097 | 82.602 | 1.00 | 10.24 |
| ATOM | 1545 | H | LYS | 405 | 21.576 | 59.869 | 83.317 | 1.00 | 0.00 |
| ATOM | 1546 | CA | LYS | 405 | 21.427 | 60.134 | 81.218 | 1.00 | 8.92 |
| ATOM | 1547 | CB | LYS | 405 | 22.935 | 59.922 | 81.150 | 1.00 | 14.00 |
| ATOM | 1548 | CG | LYS | 405 | 23.808 | 61.027 | 81.787 | 1.00 | 14.27 |
| ATOM | 1549 | CD | LYS | 405 | 25.303 | 60.817 | 81.418 | 1.00 | 15.56 |
| ATOM | 1550 | CE | LYS | 405 | 26.240 | 61.899 | 82.058 | 1.00 | 19.90 |
| ATOM | 1551 | NZ | LYS | 405 | 27.678 | 61.975 | 81.482 | 1.00 | 18.82 |
| ATOM | 1552 | HZ1 | LYS | 405 | 27.634 | 62.194 | 80.466 | 1.00 | 0.00 |
| ATOM | 1553 | HZ2 | LYS | 405 | 28.155 | 61.061 | 81.619 | 1.00 | 0.00 |
| ATOM | 1554 | HZ3 | LYS | 405 | 28.210 | 62.721 | 81.975 | 1.00 | 0.00 |
| ATOM | 1555 | C | LYS | 405 | 20.753 | 59.269 | 80.185 | 1.00 | 10.27 |
| ATOM | 1556 | O | LYS | 405 | 20.901 | 59.529 | 78.987 | 1.00 | 5.68 |
| ATOM | 1557 | N | TRP | 406 | 20.042 | 58.229 | 80.649 | 1.00 | 11.23 |
| ATOM | 1558 | H | TRP | 406 | 19.997 | 58.072 | 81.615 | 1.00 | 0.00 |
| ATOM | 1559 | CA | TRP | 406 | 19.315 | 57.298 | 79.765 | 1.00 | 13.61 |
| ATOM | 1560 | CB | TRP | 406 | 19.537 | 55.839 | 80.218 | 1.00 | 14.00 |
| ATOM | 1561 | CG | TRP | 406 | 20.858 | 55.261 | 79.806 | 1.00 | 13.93 |
| ATOM | 1562 | CD2 | TRP | 406 | 22.097 | 55.377 | 80.505 | 1.00 | 12.60 |
| ATOM | 1563 | CE2 | TRP | 406 | 23.076 | 54.710 | 79.736 | 1.00 | 10.08 |
| ATOM | 1564 | CE3 | TRP | 406 | 22.476 | 55.980 | 81.697 | 1.00 | 14.36 |
| ATOM | 1565 | CD1 | TRP | 406 | 21.123 | 54.551 | 78.669 | 1.00 | 14.19 |
| ATOM | 1566 | NE1 | TRP | 406 | 22.454 | 54.219 | 78.616 | 1.00 | 12.54 |
| ATOM | 1567 | HE1 | TRP | 406 | 22.886 | 53.717 | 77.900 | 1.00 | 0.00 |
| ATOM | 1568 | CZ2 | TRP | 406 | 24.397 | 54.631 | 80.126 | 1.00 | 10.48 |
| ATOM | 1569 | CZ3 | TRP | 406 | 23.790 | 55.899 | 82.084 | 1.00 | 14.48 |
| ATOM | 1570 | CH2 | TRP | 406 | 24.737 | 55.231 | 81.300 | 1.00 | 14.28 |
| ATOM | 1571 | C | TRP | 406 | 17.807 | 57.539 | 79.780 | 1.00 | 15.76 |
| ATOM | 1572 | O | TRP | 406 | 17.095 | 57.119 | 78.869 | 1.00 | 15.01 |
| ATOM | 1573 | N | THR | 407 | 17.324 | 48.204 | 80.824 | 1.00 | 17.40 |
| ATOM | 1574 | H | THR | 407 | 17.936 | 58.548 | 81.508 | 1.00 | 0.00 |
| ATOM | 1575 | CA | THR | 407 | 15.898 | 58.442 | 80.988 | 1.00 | 18.09 |
| ATOM | 1576 | CB | THR | 407 | 15.542 | 58.617 | 82.475 | 1.00 | 21.23 |
| ATOM | 1577 | OG1 | THR | 407 | 16.361 | 57.751 | 83.259 | 1.00 | 20.17 |
| ATOM | 1578 | HG1 | THR | 407 | 17.285 | 57.972 | 83.121 | 1.00 | 0.00 |
| ATOM | 1579 | CG2 | THR | 407 | 14.105 | 58.199 | 82.721 | 1.00 | 18.73 |
| ATOM | 1580 | C | THR | 407 | 15.296 | 59.577 | 80.191 | 1.00 | 18.53 |
| ATOM | 1581 | O | THR | 407 | 15.799 | 60.676 | 80.229 | 1.00 | 24.14 |
| ATOM | 1582 | N | ALA | 408 | 14.146 | 59.313 | 79.572 | 1.00 | 18.34 |
| ATOM | 1583 | H | ALA | 408 | 13.757 | 58.420 | 79.676 | 1.00 | 0.00 |
| ATOM | 1584 | CA | ALA | 408 | 13.413 | 60.260 | 78.742 | 1.00 | 16.68 |
| ATOM | 1585 | CB | ALA | 408 | 12.249 | 59.539 | 78.023 | 1.00 | 14.23 |
| ATOM | 1586 | C | ALA | 408 | 12.883 | 61.410 | 79.590 | 1.00 | 16.88 |
| ATOM | 1587 | O | ALA | 408 | 12.673 | 61.243 | 80.767 | 1.00 | 13.96 |
| ATOM | 1588 | N | PRO | 409 | 12.714 | 62.602 | 79.005 | 1.00 | 22.03 |
| ATOM | 1589 | CD | PRO | 409 | 13.236 | 62.994 | 77.688 | 1.00 | 20.99 |
| ATOM | 1590 | CA | PRO | 409 | 12.211 | 63.797 | 79.714 | 1.00 | 26.55 |
| ATOM | 1591 | CB | PRO | 409 | 12.177 | 64.835 | 78.618 | 1.00 | 28.05 |
| ATOM | 1592 | CG | PRO | 409 | 13.423 | 64.479 | 77.869 | 1.00 | 27.35 |
| ATOM | 1593 | C | PRO | 409 | 10.875 | 63.693 | 80.438 | 1.00 | 28.86 |
| ATOM | 1594 | O | PRO | 409 | 10.760 | 64.187 | 81.548 | 1.00 | 31.04 |
| ATOM | 1595 | N | GLU | 410 | 9.873 | 63.051 | 79.832 | 1.00 | 30.48 |
| ATOM | 1596 | H | GLU | 410 | 9.992 | 62.676 | 78.934 | 1.00 | 0.00 |
| ATOM | 1597 | CA | GLU | 410 | 8.587 | 62.899 | 80.499 | 1.00 | 28.11 |
| ATOM | 1598 | CB | GLU | 410 | 7.566 | 62.118 | 79.673 | 1.00 | 29.15 |
| ATOM | 1599 | CG | GLU | 410 | 7.752 | 62.043 | 78.183 | 1.00 | 32.93 |
| ATOM | 1600 | CD | GLU | 410 | 8.863 | 61.091 | 77.742 | 1.00 | 34.62 |
| ATOM | 1601 | OE1 | GLU | 410 | 8.753 | 59.854 | 77.950 | 1.00 | 30.49 |
| ATOM | 1602 | OE2 | GLU | 410 | 9.832 | 61.609 | 77.150 | 1.00 | 34.57 |
| ATOM | 1603 | C | GLU | 410 | 8.814 | 62.066 | 81.727 | 1.00 | 29.87 |
| ATOM | 1604 | O | GLU | 410 | 8.057 | 62.188 | 82.681 | 1.00 | 33.43 |
| ATOM | 1605 | N | ALA | 411 | 9.781 | 61.139 | 81.660 | 1.00 | 30.35 |
| ATOM | 1606 | H | ALA | 411 | 10.311 | 61.052 | 80.840 | 1.00 | 0.00 |
| ATOM | 1607 | CA | ALA | 411 | 10.083 | 60.237 | 82.779 | 1.00 | 31.10 |
| ATOM | 1608 | CB | ALA | 411 | 10.913 | 58.990 | 82.293 | 1.00 | 30.02 |
| ATOM | 1609 | C | ALA | 411 | 10.806 | 60.912 | 83.918 | 1.00 | 29.45 |
| ATOM | 1610 | O | ALA | 411 | 10.625 | 60.520 | 85.061 | 1.00 | 29.04 |
| ATOM | 1611 | N | ILE | 412 | 11.718 | 61.836 | 83.595 | 1.00 | 30.12 |
| ATOM | 1612 | H | ILE | 412 | 11.897 | 62.043 | 82.654 | 1.00 | 0.00 |
| ATOM | 1613 | CA | ILE | 412 | 12.470 | 62.560 | 84.637 | 1.00 | 32.26 |
| ATOM | 1614 | CB | ILE | 412 | 13.709 | 63.326 | 84.039 | 1.00 | 30.69 |

TABLE 6-continued

Coordinates of Lck bound with damnacanthal

| | Atom Type | Res | # | X | Y | Z | Occ | B |
|---|---|---|---|---|---|---|---|---|
| ATOM | 1615 | CG2 | ILE | 412 | 14.351 | 64.207 | 85.100 | 1.00 | 29.17 |
| ATOM | 1616 | CG1 | ILE | 412 | 14.758 | 62.320 | 83.556 | 1.00 | 34.88 |
| ATOM | 1617 | CD1 | ILE | 412 | 15.931 | 62.910 | 82.752 | 1.00 | 31.80 |
| ATOM | 1618 | C | ILE | 412 | 11.527 | 63.575 | 85.335 | 1.00 | 31.91 |
| ATOM | 1619 | O | ILE | 412 | 11.557 | 63.753 | 86.544 | 1.00 | 30.38 |
| ATOM | 1620 | N | ASN | 413 | 10.670 | 64.185 | 84.536 | 1.00 | 32.85 |
| ATOM | 1621 | H | ASN | 413 | 10.669 | 63.963 | 83.582 | 1.00 | 0.00 |
| ATOM | 1622 | CA | ASN | 413 | 9.717 | 65.178 | 84.997 | 1.00 | 36.45 |
| ATOM | 1623 | CB | ASN | 413 | 9.506 | 66.198 | 83.881 | 1.00 | 34.71 |
| ATOM | 1624 | CG | ASN | 413 | 10.810 | 66.851 | 83.464 | 1.00 | 36.15 |
| ATOM | 1625 | OD1 | ASN | 413 | 11.667 | 67.095 | 84.293 | 1.00 | 35.59 |
| ATOM | 1626 | ND2 | ASN | 413 | 10.975 | 67.108 | 82.184 | 1.00 | 39.63 |
| ATOM | 1627 | HD21 | ASN | 413 | 10.270 | 66.878 | 81.543 | 1.00 | 0.00 |
| ATOM | 1628 | HD22 | ASN | 413 | 11.816 | 67.529 | 81.912 | 1.00 | 0.00 |
| ATOM | 1629 | C | ASN | 413 | 8.368 | 64.724 | 85.609 | 1.00 | 37.51 |
| ATOM | 1630 | O | ASN | 413 | 7.807 | 65.453 | 86.448 | 1.00 | 40.43 |
| ATOM | 1631 | N | TYR | 414 | 7.821 | 63.574 | 85.185 | 1.00 | 37.85 |
| ATOM | 1632 | H | TYR | 414 | 8.268 | 63.047 | 84.490 | 1.00 | 0.00 |
| ATOM | 1633 | CA | TYR | 414 | 6.544 | 63.070 | 85.745 | 1.00 | 38.65 |
| ATOM | 1634 | CB | TYR | 414 | 5.433 | 63.014 | 84.708 | 1.00 | 36.09 |
| ATOM | 1635 | CG | TYR | 414 | 5.559 | 63.991 | 83.583 | 1.00 | 37.31 |
| ATOM | 1636 | CD1 | TYR | 414 | 5.906 | 65.318 | 83.803 | 1.00 | 39.88 |
| ATOM | 1637 | CE1 | TYR | 414 | 6.068 | 66.195 | 82.733 | 1.00 | 42.07 |
| ATOM | 1638 | CD2 | TYR | 414 | 5.373 | 63.571 | 82.286 | 1.00 | 40.85 |
| ATOM | 1639 | CE2 | TYR | 414 | 5.528 | 64.422 | 81.233 | 1.00 | 43.09 |
| ATOM | 1640 | CZ | TYR | 414 | 5.877 | 65.719 | 81.450 | 1.00 | 43.34 |
| ATOM | 1641 | OH | TYR | 414 | 6.056 | 66.510 | 80.344 | 1.00 | 48.48 |
| ATOM | 1642 | HH | TYR | 414 | 6.298 | 67.397 | 80.620 | 1.00 | 0.00 |
| ATOM | 1643 | C | TYR | 414 | 6.608 | 61.671 | 86.344 | 1.00 | 39.27 |
| ATOM | 1644 | O | TYR | 414 | 5.766 | 61.283 | 87.164 | 1.00 | 40.18 |
| ATOM | 1645 | N | GLY | 415 | 7.600 | 60.905 | 85.933 | 1.00 | 36.55 |
| ATOM | 1646 | H | GLY | 415 | 8.275 | 61.249 | 85.311 | 1.00 | 0.00 |
| ATOM | 1647 | CA | GLY | 415 | 7.667 | 59.554 | 86.419 | 1.00 | 35.66 |
| ATOM | 1648 | C | GLY | 415 | 6.751 | 58.790 | 85.485 | 1.00 | 35.43 |
| ATOM | 1649 | O | GLY | 415 | 6.340 | 57.699 | 85.803 | 1.00 | 38.94 |
| ATOM | 1650 | N | THR | 416 | 6.503 | 59.371 | 84.324 | 1.00 | 34.92 |
| ATOM | 1651 | H | THR | 416 | 6.908 | 60.244 | 84.143 | 1.00 | 0.00 |
| ATOM | 1652 | CA | THR | 416 | 5.667 | 58.806 | 83.287 | 1.00 | 34.01 |
| ATOM | 1653 | CB | THR | 416 | 5.018 | 59.988 | 82.609 | 1.00 | 34.46 |
| ATOM | 1654 | OG1 | THR | 416 | 3.850 | 60.355 | 83.328 | 1.00 | 37.83 |
| ATOM | 1655 | HG1 | THR | 416 | 3.433 | 61.107 | 82.900 | 1.00 | 0.00 |
| ATOM | 1656 | CG2 | THR | 416 | 4.625 | 59.689 | 81.162 | 1.00 | 36.27 |
| ATOM | 1657 | C | THR | 416 | 6.400 | 57.922 | 82.274 | 1.00 | 32.09 |
| ATOM | 1658 | O | THR | 416 | 6.952 | 58.440 | 81.311 | 1.00 | 34.11 |
| ATOM | 1659 | N | PHE | 417 | 6.431 | 56.615 | 82.538 | 1.00 | 29.06 |
| ATOM | 1660 | H | PHE | 417 | 5.980 | 56.281 | 83.341 | 1.00 | 0.00 |
| ATOM | 1661 | CA | PHE | 417 | 7.108 | 55.641 | 81.686 | 1.00 | 30.69 |
| ATOM | 1662 | CB | PHE | 417 | 7.781 | 54.579 | 82.549 | 1.00 | 36.50 |
| ATOM | 1663 | CG | PHE | 417 | 9.231 | 54.784 | 82.781 | 1.00 | 45.54 |
| ATOM | 1664 | CD1 | PHE | 417 | 9.674 | 55.709 | 83.722 | 1.00 | 49.71 |
| ATOM | 1665 | CD2 | PHE | 417 | 10.167 | 53.957 | 82.149 | 1.00 | 48.15 |
| ATOM | 1666 | CE1 | PHE | 417 | 11.053 | 55.813 | 84.046 | 1.00 | 49.08 |
| ATOM | 1667 | CE2 | PHE | 417 | 11.504 | 54.047 | 82.455 | 1.00 | 49.74 |
| ATOM | 1668 | CZ | PHE | 417 | 11.953 | 54.977 | 83.408 | 1.00 | 50.79 |
| ATOM | 1669 | C | PHE | 417 | 6.231 | 54.869 | 80.671 | 1.00 | 25.80 |
| ATOM | 1670 | O | PHE | 417 | 5.196 | 54.277 | 81.023 | 1.00 | 26.52 |
| ATOM | 1671 | N | THR | 418 | 6.626 | 54.858 | 79.415 | 1.00 | 19.44 |
| ATOM | 1672 | H | THR | 418 | 7.417 | 55.363 | 79.133 | 1.00 | 0.00 |
| ATOM | 1673 | CA | THR | 418 | 5.884 | 54.091 | 78.436 | 1.00 | 18.51 |
| ATOM | 1674 | CB | THR | 418 | 4.922 | 54.953 | 77.598 | 1.00 | 20.98 |
| ATOM | 1675 | OG1 | THR | 418 | 5.664 | 55.665 | 76.621 | 1.00 | 21.29 |
| ATOM | 1676 | HG1 | THR | 418 | 6.307 | 56.230 | 77.056 | 1.00 | 0.00 |
| ATOM | 1677 | CG2 | THR | 418 | 4.097 | 55.924 | 78.503 | 1.00 | 17.54 |
| ATOM | 1678 | C | THR | 418 | 6.944 | 53.451 | 77.572 | 1.00 | 13.71 |
| ATOM | 1679 | O | THR | 418 | 8.124 | 53.622 | 77.846 | 1.00 | 12.02 |
| ATOM | 1680 | N | ILE | 419 | 6.534 | 52.701 | 76.555 | 1.00 | 11.32 |
| ATOM | 1681 | H | ILE | 419 | 5.575 | 52.585 | 76.390 | 1.00 | 0.00 |
| ATOM | 1682 | CA | ILE | 419 | 7.475 | 52.038 | 75.667 | 1.00 | 13.15 |
| ATOM | 1683 | CB | ILE | 419 | 6.747 | 51.070 | 74.675 | 1.00 | 12.62 |
| ATOM | 1684 | CG2 | ILE | 419 | 5.972 | 51.872 | 73.545 | 1.00 | 11.11 |
| ATOM | 1685 | CG1 | ILE | 419 | 7.763 | 50.085 | 74.036 | 1.00 | 11.14 |
| ATOM | 1686 | CD1 | ILE | 419 | 8.364 | 49.106 | 75.032 | 1.00 | 9.37 |
| ATOM | 1687 | C | ILE | 419 | 8.246 | 53.147 | 74.915 | 1.00 | 15.67 |
| ATOM | 1688 | O | ILE | 419 | 9.382 | 52.948 | 74.441 | 1.00 | 15.66 |

TABLE 6-continued

Coordinates of Lck bound with damnacanthal

| | | Atom Type | Res | # | X | Y | Z | Occ | B |
|---|---|---|---|---|---|---|---|---|---|
| ATOM | 1689 | N | LYS | 420 | 7.638 | 54.330 | 74.840 | 1.00 | 14.75 |
| ATOM | 1690 | H | LYS | 420 | 6.752 | 54.455 | 75.239 | 1.00 | 0.00 |
| ATOM | 1691 | CA | LYS | 420 | 8.275 | 55.464 | 74.165 | 1.00 | 8.63 |
| ATOM | 1692 | CB | LYS | 420 | 7.301 | 56.613 | 74.000 | 1.00 | 6.78 |
| ATOM | 1693 | CG | LYS | 420 | 6.218 | 56.307 | 72.931 | 1.00 | 7.84 |
| ATOM | 1694 | CD | LYS | 420 | 6.840 | 55.736 | 71.662 | 1.00 | 6.67 |
| ATOM | 1695 | CE | LYS | 420 | 5.789 | 55.493 | 70.622 | 1.00 | 4.94 |
| ATOM | 1696 | NZ | LYS | 420 | 6.308 | 54.986 | 69.312 | 1.00 | 9.91 |
| ATOM | 1697 | HZ1 | LYS | 420 | 6.798 | 54.081 | 69.460 | 1.00 | 0.00 |
| ATOM | 1698 | HZ2 | LYS | 420 | 6.972 | 55.679 | 68.911 | 1.00 | 0.00 |
| ATOM | 1699 | HZ3 | LYS | 420 | 5.514 | 54.847 | 68.655 | 1.00 | 0.00 |
| ATOM | 1700 | C | LYS | 420 | 9.478 | 55.917 | 71.934 | 1.00 | 6.49 |
| ATOM | 1701 | O | LYS | 420 | 10.400 | 56.475 | 74.323 | 1.00 | 9.33 |
| ATOM | 1702 | N | SER | 421 | 9.414 | 55.711 | 76.262 | 0.84 | 6.66 |
| ATOM | 1703 | H | SER | 421 | 8.584 | 55.434 | 76.658 | 1.00 | 0.00 |
| ATOM | 1704 | CA | SER | 421 | 10.507 | 56.082 | 77.170 | 0.84 | 10.26 |
| ATOM | 1705 | CB | SER | 421 | 10.075 | 55.947 | 78.650 | 0.84 | 9.32 |
| ATOM | 1706 | OG | SER | 421 | 8.919 | 56.713 | 78.902 | 0.84 | 14.08 |
| ATOM | 1707 | HG | SER | 421 | 9.100 | 57.637 | 78.714 | 1.00 | 0.00 |
| ATOM | 1708 | C | SER | 421 | 11.664 | 55.103 | 76.917 | 0.84 | 10.15 |
| ATOM | 1709 | O | SER | 421 | 12.826 | 55.442 | 77.086 | 0.84 | 11.46 |
| ATOM | 1710 | N | ASP | 422 | 11.340 | 53.860 | 76.597 | 1.00 | 10.53 |
| ATOM | 1711 | H | ASP | 422 | 10.403 | 53.578 | 76.545 | 1.00 | 0.00 |
| ATOM | 1712 | CA | ASP | 422 | 12.393 | 52.907 | 76.320 | 1.00 | 10.34 |
| ATOM | 1713 | CB | ASP | 422 | 11.825 | 51.512 | 76.192 | 1.00 | 12.41 |
| ATOM | 1714 | CG | ASP | 422 | 11.533 | 50.894 | 77.500 | 1.00 | 12.19 |
| ATOM | 1715 | OD1 | ASP | 422 | 12.091 | 51.279 | 78.529 | 1.00 | 14.41 |
| ATOM | 1716 | OD2 | ASP | 422 | 10.728 | 49.980 | 77.493 | 1.00 | 16.95 |
| ATOM | 1717 | C | ASP | 422 | 13.037 | 53.257 | 75.006 | 1.00 | 10.36 |
| ATOM | 1718 | O | ASP | 422 | 14.191 | 52.953 | 74.794 | 1.00 | 13.02 |
| ATOM | 1719 | N | VAL | 423 | 12.242 | 53.804 | 74.088 | 1.00 | 12.66 |
| ATOM | 1720 | H | VAL | 423 | 11.297 | 53.971 | 74.288 | 1.00 | 0.00 |
| ATOM | 1721 | CA | VAL | 423 | 12.758 | 54.162 | 72.778 | 1.00 | 11.18 |
| ATOM | 1722 | CB | VAL | 423 | 11.622 | 54.575 | 71.818 | 1.00 | 8.66 |
| ATOM | 1723 | CG1 | VAL | 423 | 12.165 | 55.327 | 70.599 | 1.00 | 8.14 |
| ATOM | 1724 | CG2 | VAL | 423 | 10.849 | 53.281 | 71.345 | 1.00 | 4.43 |
| ATOM | 1725 | C | VAL | 423 | 13.867 | 55.217 | 79.920 | 1.00 | 9.98 |
| ATOM | 1726 | O | VAL | 423 | 14.950 | 55.034 | 72.414 | 1.00 | 11.08 |
| ATOM | 1727 | N | TRP | 424 | 13.627 | 56.226 | 73.758 | 1.00 | 10.60 |
| ATOM | 1728 | H | TRP | 424 | 12.763 | 56.280 | 74.217 | 1.00 | 0.00 |
| ATOM | 1729 | CA | TRP | 424 | 14.618 | 57.270 | 74.021 | 1.00 | 8.71 |
| ATOM | 1730 | CB | TRP | 424 | 14.029 | 58.261 | 75.054 | 1.00 | 5.30 |
| ATOM | 1731 | CG | TRP | 424 | 14.980 | 59.289 | 75.519 | 1.00 | 10.19 |
| ATOM | 1732 | CD2 | TRP | 424 | 14.955 | 60.696 | 75.175 | 1.00 | 10.57 |
| ATOM | 1733 | CE2 | TRP | 424 | 16.125 | 61.282 | 75.733 | 1.00 | 6.33 |
| ATOM | 1734 | CE3 | TRP | 424 | 14.054 | 61.517 | 74.455 | 1.00 | 10.25 |
| ATOM | 1735 | CD1 | TRP | 424 | 16.099 | 59.089 | 76.269 | 1.00 | 8.86 |
| ATOM | 1736 | NE1 | TRP | 424 | 16.800 | 60.285 | 76.389 | 1.00 | 9.00 |
| ATOM | 1737 | HE1 | TRP | 424 | 17.643 | 60.397 | 76.867 | 1.00 | 0.00 |
| ATOM | 1738 | CZ2 | TRP | 424 | 16.432 | 62.645 | 75.595 | 1.00 | 8.83 |
| ATOM | 1739 | CZ3 | TRP | 424 | 14.365 | 62.919 | 74.312 | 1.00 | 9.91 |
| ATOM | 1740 | CH2 | TRP | 424 | 15.554 | 63.449 | 74.886 | 1.00 | 11.23 |
| ATOM | 1741 | C | TRP | 424 | 15.880 | 56.598 | 74.592 | 1.00 | 5.72 |
| ATOM | 1742 | O | TRP | 424 | 17.024 | 56.944 | 74.218 | 1.00 | 5.55 |
| ATOM | 1743 | N | SER | 425 | 15.663 | 55.706 | 75.560 | 0.74 | 3.90 |
| ATOM | 1744 | H | SER | 425 | 14.743 | 55.531 | 75.847 | 1.00 | 0.00 |
| ATOM | 1745 | CA | SER | 425 | 16.726 | 54.971 | 76.220 | 0.74 | 2.00 |
| ATOM | 1746 | CB | SER | 425 | 16.141 | 54.034 | 77.298 | 0.74 | 5.72 |
| ATOM | 1747 | OG | SER | 425 | 15.524 | 54.761 | 78.355 | 0.74 | 4.92 |
| ATOM | 1748 | HG | SER | 425 | 16.173 | 55.332 | 78.773 | 1.00 | 0.00 |
| ATOM | 1749 | C | SER | 425 | 17.530 | 54.188 | 75.214 | 0.74 | 2.68 |
| ATOM | 1750 | O | SER | 425 | 18.738 | 54.119 | 75.317 | 0.74 | 2.00 |
| ATOM | 1751 | N | PHE | 426 | 16.849 | 53.631 | 74.212 | 1.00 | 5.48 |
| ATOM | 1752 | H | PHE | 426 | 15.874 | 53.725 | 74.181 | 1.00 | 0.00 |
| ATOM | 1753 | CA | PHE | 426 | 17.503 | 52.876 | 73.144 | 1.00 | 8.11 |
| ATOM | 1754 | CB | PHE | 426 | 16.481 | 52.279 | 72.191 | 1.00 | 8.29 |
| ATOM | 1755 | CG | PHE | 426 | 17.097 | 51.382 | 71.124 | 1.00 | 14.71 |
| ATOM | 1756 | CD1 | PHE | 426 | 17.594 | 50.118 | 71.464 | 1.00 | 11.84 |
| ATOM | 1757 | CD2 | PHE | 426 | 17.163 | 51.794 | 69.789 | 1.00 | 12.26 |
| ATOM | 1758 | CE1 | PHE | 426 | 18.149 | 49.270 | 70.473 | 1.00 | 13.18 |
| ATOM | 1759 | CE2 | PHE | 426 | 17.701 | 50.970 | 68.809 | 1.00 | 9.93 |
| ATOM | 1760 | CZ | PHE | 426 | 18.205 | 49.689 | 69.153 | 1.00 | 11.55 |
| ATOM | 1761 | C | PHE | 426 | 18.465 | 53.780 | 72.310 | 1.00 | 8.81 |
| ATOM | 1762 | O | PHE | 426 | 19.531 | 53.321 | 71.849 | 1.00 | 7.83 |

TABLE 6-continued

Coordinates of Lck bound with damnacanthal

| | | Atom Type | Res | # | X | Y | Z | Occ | B |
|---|---|---|---|---|---|---|---|---|---|
| ATOM | 1763 | N | GLY | 427 | 18.066 | 55.035 | 72.077 | 1.00 | 7.90 |
| ATOM | 1764 | H | GLY | 427 | 17.199 | 55.347 | 72.409 | 1.00 | 0.00 |
| ATOM | 1765 | CA | GLY | 427 | 18.938 | 55.940 | 71.320 | 1.00 | 10.14 |
| ATOM | 1766 | C | GLY | 427 | 20.209 | 56.180 | 72.123 | 1.00 | 8.28 |
| ATOM | 1767 | O | GLY | 427 | 21.291 | 56.250 | 71.560 | 1.00 | 10.33 |
| ATOM | 1768 | N | ILE | 428 | 20.073 | 56.275 | 73.442 | 1.00 | 8.04 |
| ATOM | 1769 | H | ILE | 428 | 19.180 | 56.220 | 73.841 | 1.00 | 0.00 |
| ATOM | 1770 | CA | ILE | 428 | 21.211 | 56.460 | 74.327 | 1.00 | 11.04 |
| ATOM | 1771 | CB | ILE | 428 | 20.779 | 56.676 | 75.806 | 1.00 | 9.44 |
| ATOM | 1772 | CG2 | ILE | 428 | 21.982 | 56.994 | 76.638 | 1.00 | 8.60 |
| ATOM | 1773 | CG1 | ILE | 428 | 19.749 | 57.817 | 75.914 | 1.00 | 11.62 |
| ATOM | 1774 | CD1 | ILE | 428 | 20.297 | 59.194 | 75.630 | 1.00 | 15.00 |
| ATOM | 1775 | C | ILE | 428 | 22.086 | 55.190 | 74.253 | 1.00 | 12.85 |
| ATOM | 1776 | O | ILE | 428 | 23.300 | 55.266 | 74.126 | 1.00 | 14.25 |
| ATOM | 1777 | N | LEU | 429 | 21.441 | 54.026 | 74.371 | 1.00 | 12.74 |
| ATOM | 1778 | H | LEU | 429 | 20.470 | 54.027 | 74.502 | 1.00 | 0.00 |
| ATOM | 1779 | CA | LEU | 429 | 22.127 | 52.724 | 74.313 | 1.00 | 8.76 |
| ATOM | 1780 | CB | LEU | 429 | 21.100 | 51.591 | 74.506 | 1.00 | 8.76 |
| ATOM | 1781 | CG | LEU | 429 | 21.565 | 50.138 | 74.744 | 1.00 | 11.17 |
| ATOM | 1782 | CD1 | LEU | 429 | 20.355 | 49.192 | 75.012 | 1.00 | 4.53 |
| ATOM | 1783 | CD2 | LEU | 429 | 22.355 | 49.663 | 73.536 | 1.00 | 8.11 |
| ATOM | 1784 | C | LEU | 429 | 22.937 | 52.622 | 72.990 | 1.00 | 7.34 |
| ATOM | 1785 | O | LEU | 429 | 24.063 | 52.130 | 72.990 | 1.00 | 8.13 |
| ATOM | 1786 | N | LEU | 430 | 22.397 | 53.177 | 71.901 | 1.00 | 6.14 |
| ATOM | 1787 | H | LEU | 430 | 21.517 | 53.604 | 71.954 | 1.00 | 0.00 |
| ATOM | 1788 | CA | LEU | 430 | 23.083 | 53.165 | 70.632 | 1.00 | 5.92 |
| ATOM | 1789 | CB | LEU | 430 | 22.233 | 53.714 | 69.484 | 1.00 | 4.23 |
| ATOM | 1790 | CG | LEU | 430 | 21.034 | 52.953 | 68.895 | 1.00 | 11.20 |
| ATOM | 1791 | CD1 | LEU | 430 | 20.377 | 53.892 | 67.843 | 1.00 | 6.80 |
| ATOM | 1792 | CD2 | LEU | 430 | 21.439 | 51.536 | 68.230 | 1.00 | 7.90 |
| ATOM | 1793 | C | LEU | 430 | 24.425 | 53.933 | 70.674 | 1.00 | 8.34 |
| ATOM | 1794 | O | LEU | 430 | 25.340 | 53.587 | 69.911 | 1.00 | 6.98 |
| ATOM | 1795 | N | THR | 431 | 24.502 | 54.983 | 71.531 | 1.00 | 12.24 |
| ATOM | 1796 | H | THR | 431 | 23.712 | 55.244 | 72.048 | 1.00 | 0.00 |
| ATOM | 1797 | CA | THR | 431 | 25.745 | 55.757 | 71.718 | 1.00 | 10.30 |
| ATOM | 1798 | CB | THR | 431 | 25.590 | 57.143 | 72.476 | 1.00 | 8.13 |
| ATOM | 1799 | OG1 | THR | 431 | 25.320 | 57.000 | 73.889 | 1.00 | 8.89 |
| ATOM | 1800 | HG1 | THR | 431 | 24.502 | 56.513 | 74.011 | 1.00 | 0.00 |
| ATOM | 1801 | CG2 | THR | 431 | 24.581 | 58.029 | 71.851 | 1.00 | 10.09 |
| ATOM | 1802 | C | THR | 431 | 26.700 | 54.853 | 72.492 | 1.00 | 12.65 |
| ATOM | 1803 | O | THR | 431 | 27.896 | 54.863 | 72.252 | 1.00 | 14.59 |
| ATOM | 1804 | N | GLU | 432 | 26.188 | 54.079 | 73.435 | 1.00 | 14.47 |
| ATOM | 1805 | H | GLU | 432 | 25.234 | 54.130 | 73.653 | 1.00 | 0.00 |
| ATOM | 1806 | CA | GLU | 432 | 27.033 | 53.135 | 74.169 | 1.00 | 13.73 |
| ATOM | 1807 | CB | GLU | 432 | 26.244 | 52.417 | 75.239 | 1.00 | 11.90 |
| ATOM | 1808 | CG | GLU | 432 | 25.739 | 53.342 | 76.282 | 1.00 | 14.90 |
| ATOM | 1809 | CD | GLU | 432 | 25.126 | 52.568 | 77.415 | 1.00 | 16.89 |
| ATOM | 1810 | OE1 | GLU | 432 | 23.941 | 52.213 | 77.316 | 1.00 | 17.07 |
| ATOM | 1811 | OE2 | GLU | 432 | 25.843 | 52.260 | 78.388 | 1.00 | 22.24 |
| ATOM | 1812 | C | GLU | 432 | 27.619 | 52.106 | 73.193 | 1.00 | 14.48 |
| ATOM | 1813 | O | GLU | 432 | 28.791 | 51.782 | 73.281 | 1.00 | 14.60 |
| ATOM | 1814 | N | ILE | 433 | 26.836 | 51.649 | 72.221 | 1.00 | 14.14 |
| ATOM | 1815 | H | ILE | 433 | 25.907 | 51.950 | 72.138 | 1.00 | 0.00 |
| ATOM | 1816 | CA | ILE | 433 | 27.368 | 50.688 | 71.266 | 1.00 | 14.33 |
| ATOM | 1817 | CB | ILE | 433 | 26.241 | 50.139 | 70.344 | 1.00 | 12.46 |
| ATOM | 1818 | CG2 | ILE | 433 | 26.817 | 49.345 | 69.167 | 1.00 | 11.72 |
| ATOM | 1819 | CG1 | ILE | 433 | 25.265 | 49.297 | 71.156 | 1.00 | 5.76 |
| ATOM | 1820 | CD1 | ILE | 433 | 24.261 | 48.627 | 70.250 | 1.00 | 6.88 |
| ATOM | 1821 | C | ILE | 433 | 28.531 | 51.252 | 70.398 | 1.00 | 15.57 |
| ATOM | 1822 | O | ILE | 433 | 29.630 | 50.720 | 70.415 | 1.00 | 15.17 |
| ATOM | 1823 | N | VAL | 434 | 28.291 | 52.361 | 69.701 | 1.00 | 13.93 |
| ATOM | 1824 | H | VAL | 434 | 27.424 | 52.808 | 69.791 | 1.00 | 0.00 |
| ATOM | 1825 | CA | VAL | 434 | 29.280 | 52.950 | 68.793 | 1.00 | 13.97 |
| ATOM | 1826 | CB | VAL | 434 | 28.550 | 53.883 | 67.823 | 1.00 | 10.82 |
| ATOM | 1827 | CG1 | VAL | 434 | 28.266 | 55.285 | 68.494 | 1.00 | 9.41 |
| ATOM | 1828 | CG2 | VAL | 434 | 29.242 | 53.942 | 66.515 | 1.00 | 13.81 |
| ATOM | 1829 | C | VAL | 434 | 30.546 | 53.574 | 69.461 | 1.00 | 15.00 |
| ATOM | 1830 | O | VAL | 434 | 31.580 | 53.753 | 68.827 | 1.00 | 16.08 |
| ATOM | 1831 | N | THR | 435 | 30.494 | 53.824 | 70.761 | 1.00 | 13.41 |
| ATOM | 1832 | H | THR | 435 | 29.670 | 53.662 | 71.266 | 1.00 | 0.00 |
| ATOM | 1833 | CA | THR | 435 | 31.662 | 54.343 | 71.457 | 1.00 | 11.79 |
| ATOM | 1834 | CB | THR | 435 | 31.275 | 55.452 | 72.409 | 1.00 | 14.82 |
| ATOM | 1835 | OG1 | THR | 435 | 30.426 | 54.902 | 73.402 | 1.00 | 9.72 |
| ATOM | 1836 | HG1 | THR | 435 | 29.643 | 54.534 | 72.986 | 1.00 | 0.00 |

TABLE 6-continued

Coordinates of Lck bound with damnacanthal

| | Atom Type | Res | # | X | Y | Z | Occ | B |
|---|---|---|---|---|---|---|---|---|
| ATOM | 1837 | CG2 | THR | 435 | 30.543 | 56.665 | 71.657 | 1.00 | 6.39 |
| ATOM | 1838 | C | THR | 435 | 32.323 | 53.207 | 72.288 | 1.00 | 14.88 |
| ATOM | 1839 | O | THR | 435 | 33.158 | 53.446 | 73.148 | 1.00 | 12.06 |
| ATOM | 1840 | N | HIS | 436 | 31.864 | 51.971 | 72.072 | 1.00 | 16.31 |
| ATOM | 1841 | H | HIS | 436 | 31.163 | 51.820 | 71.404 | 1.00 | 0.00 |
| ATOM | 1842 | CA | HIS | 436 | 32.383 | 50.819 | 72.812 | 1.00 | 16.08 |
| ATOM | 1843 | CB | HIS | 436 | 33.856 | 50.574 | 72.424 | 1.00 | 17.56 |
| ATOM | 1844 | CG | HIS | 436 | 34.023 | 50.183 | 70.978 | 1.00 | 18.98 |
| ATOM | 1845 | CD2 | HIS | 436 | 34.137 | 50.938 | 69.874 | 1.00 | 19.92 |
| ATOM | 1846 | ND1 | HIS | 436 | 33.959 | 48.870 | 70.560 | 1.00 | 24.86 |
| ATOM | 1847 | HD1 | HIS | 436 | 33.879 | 48.092 | 71.143 | 1.00 | 0.00 |
| ATOM | 1848 | CE1 | HIS | 436 | 34.024 | 48.838 | 69.230 | 1.00 | 26.38 |
| ATOM | 1849 | NE2 | HIS | 436 | 34.128 | 50.082 | 68.789 | 1.00 | 22.11 |
| ATOM | 1850 | HE2 | HIS | 436 | 34.188 | 50.350 | 67.853 | 1.00 | 0.00 |
| ATOM | 1851 | C | HIS | 436 | 32.222 | 50.905 | 74.322 | 1.00 | 12.65 |
| ATOM | 1852 | O | HIS | 436 | 33.133 | 50.577 | 75.050 | 1.00 | 16.58 |
| ATOM | 1853 | N | GLY | 437 | 31.091 | 51.403 | 74.798 | 1.00 | 10.82 |
| ATOM | 1854 | H | GLY | 437 | 30.394 | 51.712 | 74.182 | 1.00 | 0.00 |
| ATOM | 1855 | CA | GLY | 437 | 30.883 | 51.491 | 76.236 | 1.00 | 7.12 |
| ATOM | 1856 | C | GLY | 437 | 31.140 | 52.832 | 76.906 | 1.00 | 7.11 |
| ATOM | 1857 | O | GLY | 437 | 31.168 | 52.918 | 78.152 | 1.00 | 14.52 |
| ATOM | 1858 | N | ARG | 438 | 31.312 | 53.896 | 76.148 | 0.58 | 6.90 |
| ATOM | 1859 | H | ARG | 438 | 31.287 | 53.844 | 75.170 | 1.00 | 0.00 |
| ATOM | 1860 | CA | ARG | 438 | 31.542 | 55.161 | 76.811 | 0.58 | 5.73 |
| ATOM | 1861 | CB | ARG | 438 | 32.133 | 56.178 | 75.827 | 0.58 | 8.70 |
| ATOM | 1862 | CG | ARG | 438 | 32.771 | 57.397 | 76.490 | 0.58 | 13.85 |
| ATOM | 1863 | CD | ARG | 438 | 33.300 | 58.440 | 75.469 | 0.58 | 12.62 |
| ATOM | 1864 | NE | ARG | 438 | 33.993 | 59.513 | 76.192 | 0.58 | 17.82 |
| ATOM | 1865 | HE | ARG | 438 | 34.115 | 59.399 | 77.157 | 1.00 | 0.00 |
| ATOM | 1866 | CZ | ARG | 438 | 34.468 | 60.627 | 75.644 | 0.58 | 17.36 |
| ATOM | 1867 | NH1 | ARG | 438 | 34.350 | 60.847 | 74.350 | 0.58 | 22.02 |
| ATOM | 1868 | HH11 | ARG | 438 | 33.898 | 60.171 | 73.767 | 1.00 | 0.00 |
| ATOM | 1869 | HH12 | ARG | 438 | 34.712 | 61.689 | 73.951 | 1.00 | 0.00 |
| ATOM | 1870 | NH2 | ARG | 438 | 35.021 | 61.555 | 76.405 | 0.58 | 18.21 |
| ATOM | 1871 | HH21 | ARG | 438 | 35.082 | 61.419 | 77.394 | 1.00 | 0.00 |
| ATOM | 1872 | HH22 | ARG | 438 | 35.378 | 62.393 | 75.991 | 1.00 | 0.00 |
| ATOM | 1873 | C | ARG | 438 | 30.250 | 55.686 | 77.445 | 0.58 | 6.44 |
| ATOM | 1874 | O | ARG | 438 | 29.153 | 55.513 | 76.912 | 0.58 | 6.39 |
| ATOM | 1875 | N | ILE | 439 | 30.387 | 56.264 | 78.632 | 1.00 | 8.61 |
| ATOM | 1876 | H | ILE | 439 | 31.273 | 56.287 | 79.051 | 1.00 | 0.00 |
| ATOM | 1877 | CA | ILE | 439 | 29.292 | 56.872 | 79.355 | 1.00 | 10.63 |
| ATOM | 1878 | CB | ILE | 439 | 29.788 | 57.521 | 80.666 | 1.00 | 12.63 |
| ATOM | 1879 | CG2 | ILE | 439 | 28.714 | 58.409 | 81.282 | 1.00 | 13.74 |
| ATOM | 1880 | CG1 | ILE | 439 | 30.161 | 56.428 | 81.683 | 1.00 | 17.30 |
| ATOM | 1881 | CD1 | ILE | 439 | 31.045 | 56.922 | 82.849 | 1.00 | 16.03 |
| ATOM | 1882 | C | ILE | 439 | 28.718 | 57.967 | 78.429 | 1.00 | 8.36 |
| ATOM | 1883 | O | ILE | 439 | 29.486 | 58.690 | 77.800 | 1.00 | 11.71 |
| ATOM | 1884 | N | PRO | 440 | 27.397 | 58.034 | 78.267 | 0.43 | 3.38 |
| ATOM | 1885 | CD | PRO | 440 | 26.374 | 57.203 | 78.916 | 0.43 | 2.00 |
| ATOM | 1886 | CA | PRO | 440 | 26.793 | 59.053 | 77.400 | 0.43 | 2.64 |
| ATOM | 1887 | CB | PRO | 440 | 25.311 | 58.674 | 77.405 | 0.43 | 2.00 |
| ATOM | 1888 | CG | PRO | 440 | 25.130 | 58.027 | 78.720 | 0.43 | 2.07 |
| ATOM | 1889 | C | PRO | 440 | 27.025 | 60.509 | 77.878 | 0.43 | 3.23 |
| ATOM | 1890 | O | PRO | 440 | 27.354 | 60.751 | 79.031 | 0.43 | 2.00 |
| ATOM | 1891 | N | TYR | 441 | 26.942 | 61.437 | 76.925 | 1.00 | 8.54 |
| ATOM | 1892 | H | TYR | 441 | 26.764 | 61.141 | 76.008 | 1.00 | 0.00 |
| ATOM | 1893 | CA | TYR | 441 | 27.097 | 62.883 | 77.133 | 1.00 | 11.74 |
| ATOM | 1894 | CB | TYR | 441 | 26.018 | 63.387 | 78.087 | 1.00 | 9.27 |
| ATOM | 1895 | CG | TYR | 441 | 24.659 | 63.217 | 77.545 | 1.00 | 10.34 |
| ATOM | 1896 | CD1 | TYR | 441 | 24.135 | 64.164 | 76.657 | 1.00 | 6.73 |
| ATOM | 1897 | CE1 | TYR | 441 | 22.839 | 64.029 | 76.188 | 1.00 | 9.51 |
| ATOM | 1898 | TYR | 441 | 441 | 23.847 | 62.129 | 77.947 | 1.00 | 11.08 |
| ATOM | 1899 | CE2 | TYR | 441 | 22.558 | 61.998 | 77.485 | 1.00 | 10.14 |
| ATOM | 1900 | CZ | TYR | 441 | 22.057 | 62.956 | 76.609 | 1.00 | 8.87 |
| ATOM | 1901 | OH | TYR | 441 | 20.772 | 62.891 | 76.186 | 1.00 | 8.94 |
| ATOM | 1902 | HH | TYR | 441 | 20.593 | 63.624 | 75.593 | 1.00 | 0.00 |
| ATOM | 1903 | C | TYR | 441 | 28.432 | 63.142 | 77.776 | 1.00 | 15.26 |
| ATOM | 1904 | O | TYR | 441 | 28.473 | 63.684 | 78.880 | 1.00 | 15.64 |
| ATOM | 1905 | N | PRO | 442 | 29.520 | 62.635 | 77.161 | 1.00 | 16.80 |
| ATOM | 1906 | CD | PRO | 442 | 29.534 | 62.016 | 75.815 | 1.00 | 15.29 |
| ATOM | 1907 | CA | PRO | 442 | 30.880 | 62.812 | 77.688 | 1.00 | 18.13 |
| ATOM | 1908 | CB | PRO | 442 | 31.744 | 62.774 | 76.406 | 1.00 | 15.01 |
| ATOM | 1909 | CG | PRO | 442 | 31.003 | 61.692 | 75.561 | 1.00 | 13.63 |
| ATOM | 1910 | C | PRO | 442 | 31.113 | 64.139 | 78.396 | 1.00 | 16.74 |

TABLE 6-continued

Coordinates of Lck bound with damnacanthal

| | | Atom Type | Res | # | X | Y | Z | Occ | B |
|---|---|---|---|---|---|---|---|---|---|
| ATOM | 1911 | O | PRO | 442 | 30.834 | 65.180 | 77.855 | 1.00 | 18.34 |
| ATOM | 1912 | N | GLY | 443 | 31.654 | 64.100 | 79.594 | 1.00 | 18.15 |
| ATOM | 1913 | H | GLY | 443 | 31.824 | 63.241 | 80.034 | 1.00 | 0.00 |
| ATOM | 1914 | CA | GLY | 443 | 31.999 | 65.355 | 80.263 | 1.00 | 21.52 |
| ATOM | 1915 | C | GLY | 443 | 30.903 | 66.244 | 80.791 | 1.00 | 20.07 |
| ATOM | 1916 | O | GLY | 443 | 31.156 | 67.387 | 81.182 | 1.00 | 23.05 |
| ATOM | 1917 | N | MET | 444 | 29.689 | 65.719 | 80.839 | 1.00 | 18.84 |
| ATOM | 1918 | H | MET | 444 | 29.535 | 64.809 | 80.509 | 1.00 | 0.00 |
| ATOM | 1919 | CA | MET | 444 | 28.568 | 66.461 | 81.372 | 1.00 | 16.56 |
| ATOM | 1920 | CB | MET | 444 | 27.496 | 66.632 | 80.295 | 1.00 | 17.05 |
| ATOM | 1921 | CG | MET | 444 | 27.986 | 67.394 | 79.087 | 1.00 | 17.26 |
| ATOM | 1922 | SD | MET | 444 | 26.911 | 67.163 | 77.672 | 1.00 | 19.62 |
| ATOM | 1923 | CE | MET | 444 | 25.395 | 67.838 | 78.273 | 1.00 | 11.57 |
| ATOM | 1924 | C | MET | 444 | 27.974 | 65.750 | 82.590 | 1.00 | 15.08 |
| ATOM | 1925 | O | MET | 444 | 27.916 | 64.529 | 82.645 | 1.00 | 14.54 |
| ATOM | 1926 | N | THR | 445 | 27.535 | 66.537 | 83.567 | 1.00 | 17.21 |
| ATOM | 1927 | H | THR | 445 | 27.646 | 67.508 | 83.494 | 1.00 | 0.00 |
| ATOM | 1928 | CA | THR | 445 | 26.889 | 66.007 | 84.753 | 1.00 | 19.53 |
| ATOM | 1929 | CB | THR | 445 | 27.042 | 66.992 | 85.925 | 1.00 | 22.94 |
| ATOM | 1930 | OG1 | THR | 445 | 26.476 | 68.258 | 85.537 | 1.00 | 24.68 |
| ATOM | 1931 | HG1 | THR | 445 | 26.939 | 68.593 | 84.766 | 1.00 | 0.00 |
| ATOM | 1932 | CG2 | THR | 445 | 28.547 | 67.138 | 86.310 | 1.00 | 17.56 |
| ATOM | 1933 | C | THR | 445 | 25.394 | 65.870 | 84.439 | 1.00 | 15.72 |
| ATOM | 1934 | O | THR | 445 | 24.940 | 66.324 | 83.403 | 1.00 | 16.59 |
| ATOM | 1935 | N | ASN | 446 | 24.630 | 65.261 | 85.338 | 1.00 | 15.13 |
| ATOM | 1936 | H | ASN | 446 | 25.027 | 64.906 | 86.161 | 1.00 | 0.00 |
| ATOM | 1937 | CA | ASN | 446 | 23.181 | 65.103 | 85.127 | 1.00 | 15.90 |
| ATOM | 1938 | CB | ASN | 446 | 22.522 | 64.315 | 86.289 | 1.00 | 20.41 |
| ATOM | 1939 | CG | ASN | 446 | 22.845 | 62.816 | 86.252 | 1.00 | 20.37 |
| ATOM | 1940 | OD1 | ASN | 446 | 23.172 | 62.267 | 85.195 | 1.00 | 21.12 |
| ATOM | 1941 | ND2 | ASN | 446 | 22.778 | 62.161 | 87.395 | 1.00 | 20.02 |
| ATOM | 1942 | HD21 | ASN | 446 | 22.531 | 62.634 | 88.217 | 1.00 | 0.00 |
| ATOM | 1943 | HD22 | ASN | 446 | 22.983 | 61.204 | 87.380 | 1.00 | 0.00 |
| ATOM | 1944 | C | ASN | 446 | 22.445 | 66.452 | 84.904 | 1.00 | 17.07 |
| ATOM | 1945 | O | ASN | 446 | 21.694 | 66.582 | 83.941 | 1.00 | 15.01 |
| ATOM | 1946 | N | PRO | 447 | 22.707 | 67.481 | 85.752 | 1.00 | 17.68 |
| ATOM | 1947 | CD | PRO | 447 | 23.669 | 67.505 | 86.872 | 1.00 | 15.21 |
| ATOM | 1948 | CA | PRO | 447 | 22.056 | 68.790 | 85.621 | 1.00 | 15.95 |
| ATOM | 1949 | CB | PRO | 447 | 22.712 | 69.604 | 86.729 | 1.00 | 20.00 |
| ATOM | 1950 | CG | PRO | 447 | 23.091 | 68.550 | 87.752 | 1.00 | 19.84 |
| ATOM | 1951 | C | PRO | 447 | 22.370 | 69.392 | 84.268 | 1.00 | 16.76 |
| ATOM | 1952 | O | PRO | 447 | 21.478 | 69.810 | 83.562 | 1.00 | 17.96 |
| ATOM | 1953 | N | GLU | 448 | 23.645 | 69.359 | 83.879 | 1.00 | 19.04 |
| ATOM | 1954 | H | GLU | 448 | 24.328 | 68.987 | 84.476 | 1.00 | 0.00 |
| ATOM | 1955 | CA | GLU | 448 | 24.065 | 69.869 | 82.566 | 1.00 | 15.82 |
| ATOM | 1956 | CB | GLU | 448 | 25.559 | 69.665 | 82.357 | 1.00 | 16.00 |
| ATOM | 1957 | CG | GLU | 448 | 26.435 | 70.703 | 83.106 | 1.00 | 18.95 |
| ATOM | 1958 | CD | GLU | 448 | 27.915 | 70.464 | 82.888 | 1.00 | 20.90 |
| ATOM | 1959 | OE1 | GLU | 448 | 28.424 | 69.364 | 83.231 | 1.00 | 22.13 |
| ATOM | 1960 | OE2 | GLU | 448 | 28.566 | 71.346 | 82.317 | 1.00 | 20.25 |
| ATOM | 1961 | C | GLU | 448 | 23.303 | 69.184 | 81.431 | 1.00 | 14.57 |
| ATOM | 1962 | O | GLU | 448 | 22.897 | 69.837 | 80.459 | 1.00 | 9.78 |
| ATOM | 1963 | N | VAL | 449 | 23.088 | 67.865 | 81.581 | 1.00 | 15.89 |
| ATOM | 1964 | H | VAL | 449 | 23.417 | 67.406 | 82.382 | 1.00 | 0.00 |
| ATOM | 1965 | CA | VAL | 449 | 22.369 | 67.081 | 80.573 | 1.00 | 13.35 |
| ATOM | 1966 | CB | VAL | 449 | 22.445 | 65.543 | 80.890 | 1.00 | 13.24 |
| ATOM | 1967 | CG1 | VAL | 449 | 21.425 | 64.784 | 80.022 | 1.00 | 9.89 |
| ATOM | 1968 | CG2 | VAL | 449 | 23.848 | 65.062 | 80.575 | 1.00 | 6.37 |
| ATOM | 1969 | C | VAL | 449 | 20.913 | 67.536 | 80.436 | 1.00 | 8.73 |
| ATOM | 1970 | O | VAL | 449 | 20.417 | 67.706 | 79.340 | 1.00 | 8.99 |
| ATOM | 1971 | N | ILE | 450 | 20.244 | 67.679 | 81.566 | 0.60 | 8.18 |
| ATOM | 1972 | H | ILE | 450 | 20.681 | 67.450 | 82.413 | 1.00 | 0.00 |
| ATOM | 1973 | CA | ILE | 450 | 18.880 | 68.163 | 81.617 | 0.60 | 9.57 |
| ATOM | 1974 | CB | ILE | 450 | 18.319 | 68.036 | 83.089 | 0.60 | 9.57 |
| ATOM | 1975 | CG2 | ILE | 450 | 16.907 | 68.690 | 83.228 | 0.60 | 9.81 |
| ATOM | 1976 | CG1 | ILE | 450 | 18.225 | 66.550 | 83.474 | 0.60 | 5.11 |
| ATOM | 1977 | CD1 | ILE | 450 | 17.921 | 66.332 | 84.936 | 0.60 | 8.84 |
| ATOM | 1978 | C | ILE | 450 | 18.813 | 69.605 | 81.085 | 0.60 | 9.79 |
| ATOM | 1979 | O | ILE | 450 | 17.959 | 69.909 | 80.255 | 0.60 | 7.33 |
| ATOM | 1980 | N | GLN | 451 | 19.765 | 70.464 | 81.470 | 1.00 | 13.18 |
| ATOM | 1981 | H | GLN | 451 | 20.473 | 70.175 | 82.083 | 1.00 | 0.00 |
| ATOM | 1982 | CA | GLN | 451 | 19.770 | 71.862 | 80.981 | 1.00 | 16.68 |
| ATOM | 1983 | CB | GLN | 451 | 21.006 | 72.671 | 81.430 | 1.00 | 19.04 |
| ATOM | 1984 | CG | GLN | 451 | 21.292 | 72.703 | 82.919 | 1.00 | 26.52 |

TABLE 6-continued

Coordinates of Lck bound with damnacanthal

| | | Atom Type | Res | # | X | Y | Z | Occ | B |
|---|---|---|---|---|---|---|---|---|---|
| ATOM | 1985 | CD | GLN | 451 | 22.732 | 73.096 | 83.232 | 1.00 | 33.01 |
| ATOM | 1986 | OE1 | GLN | 451 | 23.174 | 72.986 | 84.398 | 1.00 | 36.74 |
| ATOM | 1987 | NE2 | GLN | 451 | 23.481 | 73.556 | 82.209 | 1.00 | 32.52 |
| ATOM | 1988 | HE21 | GLN | 451 | 23.094 | 73.626 | 81.311 | 1.00 | 0.00 |
| ATOM | 1989 | HE22 | GLN | 451 | 24.406 | 73.810 | 82.404 | 1.00 | 0.00 |
| ATOM | 1990 | C | GLN | 451 | 19.852 | 71.813 | 79.487 | 1.00 | 17.45 |
| ATOM | 1991 | O | GLN | 451 | 19.132 | 72.536 | 78.800 | 1.00 | 24.28 |
| ATOM | 1992 | N | ASN | 452 | 20.751 | 70.971 | 78.972 | 1.00 | 14.54 |
| ATOM | 1993 | H | ASN | 452 | 21.305 | 70.402 | 79.545 | 1.00 | 0.00 |
| ATOM | 1994 | CA | ASN | 452 | 20.895 | 70.912 | 77.540 | 1.00 | 11.01 |
| ATOM | 1995 | CB | ASN | 452 | 22.136 | 70.127 | 77.151 | 1.00 | 15.21 |
| ATOM | 1996 | CG | ASN | 452 | 23.370 | 71.000 | 77.065 | 1.00 | 16.92 |
| ATOM | 1997 | OD1 | ASN | 452 | 24.264 | 70.743 | 76.255 | 1.00 | 22.55 |
| ATOM | 1998 | ND2 | ASN | 452 | 23.405 | 72.056 | 77.855 | 1.00 | 17.56 |
| ATOM | 1999 | HD21 | ASN | 452 | 22.655 | 72.242 | 78.458 | 1.00 | 0.00 |
| ATOM | 2000 | HD22 | ASN | 452 | 24.198 | 72.629 | 77.809 | 1.00 | 0.00 |
| ATOM | 2001 | C | ASN | 452 | 19.664 | 70.401 | 76.820 | 1.00 | 12.68 |
| ATOM | 2002 | O | ASN | 452 | 19.286 | 90.924 | 75.769 | 1.00 | 15.75 |
| ATOM | 2003 | N | LEU | 453 | 19.030 | 69.362 | 77.364 | 1.00 | 12.79 |
| ATOM | 2004 | H | LEU | 453 | 19.344 | 68.953 | 78.197 | 1.00 | 0.00 |
| ATOM | 2005 | CA | LEU | 453 | 17.852 | 68.836 | 76.699 | 1.00 | 8.79 |
| ATOM | 2006 | CB | LEU | 453 | 17.356 | 67.586 | 77.425 | 1.00 | 12.86 |
| ATOM | 2007 | CG | LEU | 453 | 18.339 | 66.402 | 77.324 | 1.00 | 10.55 |
| ATOM | 2008 | CD1 | LEU | 453 | 17.803 | 65.280 | 78.182 | 1.00 | 10.97 |
| ATOM | 2009 | CD2 | LEU | 453 | 18.607 | 66.024 | 75.816 | 1.00 | 6.50 |
| ATOM | 2010 | C | LEU | 453 | 16.763 | 69.881 | 76.629 | 1.00 | 8.81 |
| ATOM | 2011 | O | LEU | 453 | 16.109 | 70.024 | 75.624 | 1.00 | 10.61 |
| ATOM | 2012 | N | GLU | 454 | 16.584 | 70.613 | 77.722 | 1.00 | 11.68 |
| ATOM | 2013 | H | GLU | 454 | 17.151 | 70.463 | 78.508 | 1.00 | 0.00 |
| ATOM | 2014 | CA | GLU | 454 | 15.555 | 71.649 | 77.792 | 1.00 | 11.12 |
| ATOM | 2015 | CB | GLU | 454 | 15.492 | 72.243 | 79.205 | 1.00 | 16.61 |
| ATOM | 2016 | CG | GLU | 454 | 15.172 | 71.152 | 80.229 | 1.00 | 23.86 |
| ATOM | 2017 | CD | GLU | 454 | 14.986 | 71.654 | 81.644 | 1.00 | 31.23 |
| ATOM | 2018 | OE1 | GLU | 454 | 15.568 | 72.709 | 81.982 | 1.00 | 37.87 |
| ATOM | 2019 | OE2 | GLU | 454 | 14.248 | 70.997 | 82.420 | 1.00 | 32.86 |
| ATOM | 2020 | C | GLU | 454 | 15.710 | 72.725 | 76.730 | 1.00 | 12.89 |
| ATOM | 2021 | O | GLU | 454 | 14.723 | 73.255 | 76.271 | 1.00 | 12.34 |
| ATOM | 2022 | N | ARG | 455 | 16.932 | 72.997 | 76.267 | 1.00 | 12.57 |
| ATOM | 2023 | H | ARG | 455 | 17.714 | 72.520 | 76.616 | 1.00 | 0.00 |
| ATOM | 2024 | CA | ARG | 455 | 17.122 | 74.015 | 75.228 | 1.00 | 7.74 |
| ATOM | 2025 | CB | ARG | 455 | 18.586 | 74.518 | 75.215 | 1.00 | 11.08 |
| ATOM | 2026 | CG | ARG | 455 | 19.206 | 74.720 | 76.592 | 1.00 | 14.73 |
| ATOM | 2027 | CD | ARG | 455 | 20.573 | 75.471 | 76.580 | 1.00 | 19.45 |
| ATOM | 2028 | NE | ARG | 455 | 20.626 | 76.556 | 75.576 | 1.00 | 18.04 |
| ATOM | 2029 | HE | ARG | 455 | 19.792 | 76.816 | 75.134 | 1.00 | 0.00 |
| ATOM | 2030 | CZ | ARG | 455 | 21.756 | 77.208 | 75.234 | 1.00 | 16.10 |
| ATOM | 2031 | NH1 | ARG | 455 | 22.929 | 76.914 | 75.821 | 1.00 | 12.05 |
| ATOM | 2032 | HH11 | ARG | 455 | 22.973 | 76.203 | 76.522 | 1.00 | 0.00 |
| ATOM | 2033 | HH12 | ARG | 455 | 23.758 | 77.407 | 75.556 | 1.00 | 0.00 |
| ATOM | 2034 | NH2 | ARG | 455 | 21.729 | 78.111 | 74.281 | 1.00 | 6.76 |
| ATOM | 2035 | HH21 | ARG | 455 | 20.871 | 78.315 | 73.809 | 1.00 | 0.00 |
| ATOM | 2036 | HH22 | ARG | 455 | 22.566 | 78.595 | 74.027 | 1.00 | 0.00 |
| ATOM | 2037 | C | ARG | 455 | 16.858 | 73.407 | 73.866 | 1.00 | 8.45 |
| ATOM | 2038 | O | ARG | 455 | 17.054 | 74.075 | 72.826 | 1.00 | 3.82 |
| ATOM | 2039 | N | GLY | 456 | 16.548 | 72.099 | 73.851 | 1.00 | 6.71 |
| ATOM | 2040 | H | GLY | 456 | 16.459 | 71.607 | 74.694 | 1.00 | 0.00 |
| ATOM | 2041 | CA | GLY | 456 | 16.345 | 71.415 | 72.590 | 1.00 | 7.75 |
| ATOM | 2042 | C | GLY | 456 | 17.616 | 70.751 | 71.999 | 1.00 | 9.65 |
| ATOM | 2043 | O | GLY | 456 | 17.586 | 70.219 | 70.881 | 1.00 | 6.89 |
| ATOM | 2044 | N | TYR | 457 | 18.749 | 70.849 | 72.684 | 1.00 | 11.47 |
| ATOM | 2045 | H | TYR | 457 | 18.775 | 71.350 | 73.526 | 1.00 | 0.00 |
| ATOM | 2046 | CA | TYR | 457 | 19.980 | 70.213 | 72.199 | 1.00 | 11.23 |
| ATOM | 2047 | CB | TYR | 457 | 21.217 | 70.653 | 73.051 | 1.00 | 7.76 |
| ATOM | 2048 | CG | TYR | 457 | 21.761 | 72.070 | 72.830 | 1.00 | 10.70 |
| ATOM | 2049 | CD1 | TYR | 457 | 21.358 | 72.855 | 71.739 | 1.00 | 12.23 |
| ATOM | 2050 | CE1 | TYR | 457 | 21.899 | 74.118 | 71.527 | 1.00 | 14.77 |
| ATOM | 2051 | CD2 | TYR | 457 | 22.711 | 72.591 | 73.692 | 1.00 | 11.31 |
| ATOM | 2052 | CE2 | TYR | 457 | 23.254 | 73.830 | 73.492 | 1.00 | 12.61 |
| ATOM | 2053 | CZ | TYR | 457 | 22.852 | 74.593 | 72.411 | 1.00 | 13.75 |
| ATOM | 2054 | OH | TYR | 457 | 23.421 | 75.829 | 72.230 | 1.00 | 19.63 |
| ATOM | 2055 | HH | TYR | 457 | 23.049 | 76.241 | 71.447 | 1.00 | 0.00 |
| ATOM | 2056 | C | TYR | 457 | 19.842 | 68.703 | 72.490 | 1.00 | 10.48 |
| ATOM | 2057 | O | TYR | 457 | 19.125 | 68.323 | 73.408 | 1.00 | 8.08 |
| ATOM | 2058 | N | ARG | 458 | 20.595 | 67.883 | 71.161 | 1.00 | 8.53 |

TABLE 6-continued

Coordinates of Lck bound with damnacanthal

| | | Atom Type | Res | # | X | Y | Z | Occ | B |
|---|---|---|---|---|---|---|---|---|---|
| ATOM | 2059 | H | ARG | 458 | 21.134 | 68.237 | 71.023 | 1.00 | 0.00 |
| ATOM | 2060 | CA | ARG | 458 | 20.640 | 66.435 | 72.039 | 1.00 | 7.79 |
| ATOM | 2061 | CB | ARG | 458 | 19.942 | 65.638 | 70.916 | 1.00 | 7.03 |
| ATOM | 2062 | CG | ARG | 458 | 18.429 | 65.775 | 70.828 | 1.00 | 6.00 |
| ATOM | 2063 | CD | ARG | 458 | 17.742 | 65.444 | 72.201 | 1.00 | 9.85 |
| ATOM | 2064 | NE | ARG | 458 | 16.279 | 65.488 | 72.134 | 1.00 | 10.07 |
| ATOM | 2065 | HE | ARG | 458 | 15.820 | 64.747 | 71.688 | 1.00 | 0.00 |
| ATOM | 2066 | CZ | ARG | 458 | 15.533 | 66.466 | 72.637 | 1.00 | 9.20 |
| ATOM | 2067 | NH1 | ARG | 458 | 16.114 | 67.505 | 73.260 | 1.00 | 4.42 |
| ATOM | 2068 | HH11 | ARG | 458 | 17.110 | 67.543 | 73.346 | 1.00 | 0.00 |
| ATOM | 2069 | HH12 | ARG | 458 | 15.551 | 68.240 | 73.638 | 1.00 | 0.00 |
| ATOM | 2070 | NH2 | ARG | 458 | 14.221 | 66.466 | 72.414 | 1.00 | 6.41 |
| ATOM | 2071 | HH21 | ARG | 458 | 13.806 | 65.735 | 71.873 | 1.00 | 0.00 |
| ATOM | 2072 | HH22 | ARG | 458 | 13.650 | 67.197 | 72.788 | 1.00 | 0.00 |
| ATOM | 2073 | C | ARG | 458 | 22.122 | 66.058 | 72.210 | 1.00 | 10.26 |
| ATOM | 2074 | O | ARG | 458 | 23.002 | 66.938 | 72.232 | 1.00 | 9.19 |
| ATOM | 2075 | N | MET | 459 | 22.427 | 64.769 | 72.464 | 1.00 | 11.60 |
| ATOM | 2076 | H | MET | 459 | 21.722 | 64.095 | 72.558 | 1.00 | 0.00 |
| ATOM | 2077 | CA | MET | 459 | 23.809 | 64.376 | 72.600 | 1.00 | 11.86 |
| ATOM | 2078 | CB | MET | 459 | 23.923 | 62.840 | 72.891 | 1.00 | 11.92 |
| ATOM | 2079 | CG | MET | 459 | 25.275 | 62.452 | 73.471 | 1.00 | 9.39 |
| ATOM | 2080 | SD | MET | 459 | 25.599 | 60.643 | 73.701 | 1.00 | 10.88 |
| ATOM | 2081 | CE | MET | 459 | 24.258 | 60.233 | 74.708 | 1.00 | 5.41 |
| ATOM | 2082 | C | MET | 459 | 24.648 | 64.786 | 71.375 | 1.00 | 10.28 |
| ATOM | 2083 | O | MET | 459 | 24.218 | 64.648 | 70.231 | 1.00 | 8.39 |
| ATOM | 2084 | N | VAL | 460 | 25.845 | 65.308 | 71.634 | 1.00 | 10.90 |
| ATOM | 2085 | H | VAL | 460 | 26.115 | 65.457 | 72.564 | 1.00 | 0.00 |
| ATOM | 2086 | CA | VAL | 460 | 26.792 | 65.675 | 70.571 | 1.00 | 9.71 |
| ATOM | 2087 | CB | VAL | 460 | 28.157 | 66.217 | 71.207 | 1.00 | 11.89 |
| ATOM | 2088 | CG1 | VAL | 460 | 29.323 | 66.45 | 70.201 | 1.00 | 9.68 |
| ATOM | 2089 | CG2 | VAL | 460 | 27.981 | 67.696 | 71.627 | 1.00 | 10.02 |
| ATOM | 2090 | C | VAL | 460 | 27.129 | 64.362 | 69.789 | 1.00 | 7.51 |
| ATOM | 2091 | O | VAL | 460 | 27.237 | 63.330 | 70.399 | 1.00 | 9.59 |
| ATOM | 2092 | N | ARG | 461 | 27.249 | 64.422 | 68.456 | 1.00 | 10.16 |
| ATOM | 2093 | H | ARG | 461 | 27.101 | 65.277 | 68.002 | 1.00 | 0.00 |
| ATOM | 2094 | CA | ARG | 461 | 27.590 | 63.274 | 67.640 | 1.00 | 15.46 |
| ATOM | 2095 | CB | ARG | 461 | 27.985 | 63.700 | 66.213 | 1.00 | 14.45 |
| ATOM | 2096 | CG | ARG | 461 | 26.864 | 64.345 | 65.452 | 1.00 | 14.41 |
| ATOM | 2097 | CD | ARG | 461 | 27.309 | 64.737 | 64.061 | 1.00 | 11.37 |
| ATOM | 2098 | NE | ARG | 461 | 26.171 | 65.043 | 63.205 | 1.00 | 12.89 |
| ATOM | 2099 | HE | ARG | 461 | 25.889 | 64.349 | 62.575 | 1.00 | 0.00 |
| ATOM | 2100 | CZ | ARG | 461 | 25.478 | 66.184 | 63.201 | 1.00 | 17.45 |
| ATOM | 2101 | NH1 | ARG | 461 | 25.798 | 67.169 | 64.042 | 1.00 | 16.20 |
| ATOM | 2102 | HH11 | ARG | 461 | 26.560 | 67.055 | 64.679 | 1.00 | 0.00 |
| ATOM | 2103 | HH12 | ARG | 461 | 25.276 | 68.022 | 64.035 | 1.00 | 0.00 |
| ATOM | 2104 | NH2 | ARG | 461 | 24.558 | 66.383 | 62.237 | 1.00 | 13.36 |
| ATOM | 2105 | HH21 | ARG | 461 | 24.404 | 65.682 | 61.541 | 1.00 | 0.00 |
| ATOM | 2106 | HH22 | ARG | 461 | 24.029 | 67.232 | 62.218 | 1.00 | 0.00 |
| ATOM | 2107 | C | ARG | 461 | 28.797 | 62.553 | 68.210 | 1.00 | 19.40 |
| ATOM | 2108 | O | ARG | 461 | 29.834 | 63.163 | 68.441 | 1.00 | 23.20 |
| ATOM | 2109 | N | PRO | 462 | 28.639 | 61.266 | 68.532 | 1.00 | 19.22 |
| ATOM | 2110 | CD | PRO | 462 | 27.425 | 60.449 | 68.627 | 1.00 | 18.02 |
| ATOM | 2111 | CA | PRO | 462 | 29.794 | 60.570 | 69.086 | 1.00 | 19.64 |
| ATOM | 2112 | CG | PRO | 462 | 29.239 | 59.169 | 69.408 | 1.00 | 18.72 |
| ATOM | 2113 | CG | PRO | 462 | 27.830 | 59.393 | 69.659 | 1.00 | 18.66 |
| ATOM | 2114 | C | PRO | 462 | 30.883 | 60.477 | 68.014 | 1.00 | 20.12 |
| ATOM | 2115 | O | PRO | 462 | 30.592 | 60.520 | 66.817 | 1.00 | 15.52 |
| ATOM | 2116 | N | ASP | 463 | 32.134 | 60.447 | 68.470 | 1.00 | 24.76 |
| ATOM | 2117 | H | ASP | 463 | 32.304 | 60.542 | 69.430 | 1.00 | 0.00 |
| ATOM | 2118 | CA | ASP | 463 | 33.268 | 60.277 | 67.582 | 1.00 | 28.90 |
| ATOM | 2119 | CB | ASP | 463 | 34.553 | 60.114 | 68.411 | 1.00 | 36.40 |
| ATOM | 2120 | CG | ASP | 463 | 34.985 | 61.382 | 69.119 | 1.00 | 37.04 |
| ATOM | 2121 | OD1 | ASP | 463 | 34.146 | 62.197 | 69.559 | 1.00 | 38.10 |
| ATOM | 2122 | OD2 | ASP | 463 | 36.208 | 61.533 | 69.268 | 1.00 | 41.04 |
| ATOM | 2123 | C | ASP | 463 | 33.037 | 58.951 | 66.839 | 1.00 | 27.32 |
| ATOM | 2124 | O | ASP | 463 | 32.514 | 57.987 | 67.430 | 1.00 | 23.86 |
| ATOM | 2125 | N | ALA | 464 | 33.382 | 58.922 | 65.554 | 1.00 | 28.40 |
| ATOM | 2126 | H | ALA | 464 | 33.750 | 59.731 | 65.141 | 1.00 | 0.00 |
| ATOM | 2127 | CA | ALA | 464 | 33.239 | 57.724 | 64.706 | 1.00 | 29.37 |
| ATOM | 2128 | CB | ALA | 464 | 34.169 | 56.611 | 65.177 | 1.00 | 31.50 |
| ATOM | 2129 | C | ALA | 464 | 31.808 | 57.175 | 64.568 | 1.00 | 29.20 |
| ATOM | 2130 | O | ALA | 464 | 31.621 | 55.966 | 64.335 | 1.00 | 32.98 |
| ATOM | 2131 | N | CYS | 465 | 30.809 | 58.008 | 64.783 | 1.00 | 22.67 |
| ATOM | 2132 | H | CYS | 465 | 30.980 | 58.938 | 65.042 | 1.00 | 0.00 |

TABLE 6-continued

Coordinates of Lck bound with damnacanthal

| | Atom Type | Res | # | X | Y | Z | Occ | B |
|---|---|---|---|---|---|---|---|---|
| ATOM | 2133 | CA | CYS | 465 | 29.446 | 57.553 | 64.638 | 1.00 | 20.51 |
| ATOM | 2134 | CB | CYS | 465 | 28.583 | 58.156 | 65.727 | 1.00 | 20.41 |
| ATOM | 2135 | SG | CYS | 465 | 26.859 | 57.726 | 65.663 | 1.00 | 14.64 |
| ATOM | 2136 | C | CYS | 465 | 28.950 | 57.893 | 63.216 | 1.00 | 19.00 |
| ATOM | 2137 | O | CYS | 465 | 29.087 | 59.038 | 62.791 | 1.00 | 19.85 |
| ATOM | 2138 | N | PRO | 466 | 28.477 | 56.881 | 62.472 | 1.00 | 14.13 |
| ATOM | 2139 | CD | PRO | 466 | 28.269 | 55.465 | 62.863 | 1.00 | 12.05 |
| ATOM | 2140 | CA | PRO | 466 | 27.973 | 57.117 | 61.112 | 1.00 | 11.52 |
| ATOM | 2141 | CB | PRO | 466 | 27.552 | 55.721 | 60.639 | 1.00 | 16.84 |
| ATOM | 2142 | CG | PRO | 466 | 28.330 | 54.730 | 61.543 | 1.00 | 13.65 |
| ATOM | 2143 | C | PRO | 466 | 26.788 | 58.077 | 61.217 | 1.00 | 9.94 |
| ATOM | 2144 | O | PRO | 466 | 25.985 | 57.992 | 62.126 | 1.00 | 10.28 |
| ATOM | 2145 | N | GLU | 467 | 26.717 | 59.024 | 60.301 | 1.00 | 11.08 |
| ATOM | 2146 | H | GLU | 467 | 27.366 | 59.061 | 59.568 | 1.00 | 0.00 |
| ATOM | 2147 | CA | GLU | 467 | 25.680 | 60.015 | 60.373 | 1.00 | 13.60 |
| ATOM | 2148 | CB | GLU | 467 | 25.958 | 61.113 | 59.357 | 1.00 | 8.50 |
| ATOM | 2149 | CG | GLU | 467 | 24.976 | 62.271 | 59.388 | 1.00 | 12.41 |
| ATOM | 2150 | CD | GLU | 467 | 24.868 | 63.004 | 60.715 | 1.00 | 8.19 |
| ATOM | 2151 | OE1 | GLU | 467 | 23.861 | 63.721 | 60.901 | 1.00 | 12.02 |
| ATOM | 2152 | OE2 | GLU | 467 | 25.772 | 62.929 | 61.558 | 1.00 | 5.91 |
| ATOM | 2153 | C | GLU | 467 | 24.249 | 59.411 | 60.306 | 1.00 | 13.65 |
| ATOM | 2154 | O | GLU | 467 | 23.357 | 59.878 | 61.011 | 1.00 | 18.46 |
| ATOM | 2155 | N | GLU | 468 | 24.064 | 58.327 | 59.559 | 0.51 | 8.16 |
| ATOM | 2156 | H | GLU | 468 | 24.811 | 57.961 | 59.042 | 1.00 | 0.00 |
| ATOM | 2157 | CA | GLU | 468 | 22.761 | 57.647 | 59.479 | 0.51 | 5.89 |
| ATOM | 2158 | CB | GLU | 468 | 22.837 | 56.476 | 58.511 | 0.51 | 3.63 |
| ATOM | 2159 | CG | GLU | 468 | 22.961 | 56.853 | 57.081 | 0.51 | 4.18 |
| ATOM | 2160 | CD | GLU | 468 | 23.335 | 55.661 | 56.225 | 0.51 | 13.23 |
| ATOM | 2161 | OE1 | GLU | 468 | 22.414 | 55.019 | 55.659 | 0.51 | 13.94 |
| ATOM | 2162 | OE2 | GLU | 468 | 24.548 | 55.346 | 56.147 | 0.51 | 9.65 |
| ATOM | 2163 | C | GLU | 468 | 22.296 | 57.120 | 60.853 | 0.51 | 3.31 |
| ATOM | 2164 | O | GLU | 468 | 21.140 | 57.221 | 61.222 | 0.51 | 2.00 |
| ATOM | 2165 | N | LEU | 469 | 23.242 | 56.631 | 61.635 | 1.00 | 7.04 |
| ATOM | 2166 | H | LEU | 469 | 24.172 | 56.624 | 61.327 | 1.00 | 0.00 |
| ATOM | 2167 | CA | LEU | 469 | 22.945 | 56.093 | 62.961 | 1.00 | 7.79 |
| ATOM | 2168 | CB | LEU | 469 | 24.148 | 55.295 | 63.534 | 1.00 | 8.52 |
| ATOM | 2169 | CG | LEU | 469 | 23.828 | 54.581 | 64.843 | 1.00 | 8.80 |
| ATOM | 2170 | CD1 | LEU | 469 | 22.747 | 53.517 | 64.602 | 1.00 | 9.54 |
| ATOM | 2171 | CD1 | LEU | 469 | 25.086 | 53.912 | 65.358 | 1.00 | 7.73 |
| ATOM | 2172 | C | LEU | 469 | 22.612 | 57.252 | 63.857 | 1.00 | 6.93 |
| ATOM | 2173 | O | LEU | 469 | 21.648 | 57.209 | 64.630 | 1.00 | 10.27 |
| ATOM | 2174 | N | TYR | 470 | 23.437 | 58.291 | 63.773 | 1.00 | 8.67 |
| ATOM | 2175 | H | TYR | 470 | 24.219 | 58.266 | 63.183 | 1.00 | 0.00 |
| ATOM | 2176 | CA | TYR | 470 | 23.176 | 59.487 | 64.570 | 1.00 | 7.86 |
| ATOM | 2177 | CB | TYR | 470 | 24.185 | 60.622 | 64.289 | 1.00 | 3.41 |
| ATOM | 2178 | CG | TYR | 470 | 23.996 | 61.765 | 65.276 | 1.00 | 4.57 |
| ATOM | 2179 | CD1 | TYR | 470 | 24.196 | 61.567 | 66.622 | 1.00 | 3.33 |
| ATOM | 2180 | CE1 | TYR | 470 | 24.035 | 62.627 | 67.531 | 1.00 | 11.52 |
| ATOM | 2181 | CD2 | TYR | 470 | 23.616 | 63.047 | 64.835 | 1.00 | 8.00 |
| ATOM | 2182 | CE2 | TYR | 470 | 23.444 | 64.116 | 65.713 | 1.00 | 6.63 |
| ATOM | 2183 | CZ | TYR | 470 | 23.657 | 63.908 | 67.046 | 1.00 | 11.17 |
| ATOM | 2184 | OH | TYR | 470 | 23.556 | 64.941 | 67.897 | 1.00 | 11.56 |
| ATOM | 2185 | HH | TYR | 470 | 23.332 | 65.737 | 67.410 | 1.00 | 0.00 |
| ATOM | 2186 | C | TYR | 470 | 21.758 | 60.004 | 64.304 | 1.00 | 7.15 |
| ATOM | 2187 | O | TYR | 470 | 21.088 | 60.353 | 65.235 | 1.00 | 10.78 |
| ATOM | 2188 | N | GLN | 471 | 21.301 | 60.031 | 63.048 | 1.00 | 8.45 |
| ATOM | 2189 | H | GLN | 471 | 21.863 | 59.717 | 62.309 | 1.00 | 0.00 |
| ATOM | 2190 | CA | GLN | 471 | 19.962 | 60.527 | 62.758 | 1.00 | 10.54 |
| ATOM | 2191 | CB | GLN | 471 | 19.816 | 60.843 | 61.261 | 1.00 | 10.19 |
| ATOM | 2192 | CG | GLN | 471 | 20.670 | 62.141 | 60.833 | 1.00 | 10.80 |
| ATOM | 2193 | CD | GLN | 471 | 20.271 | 63.416 | 61.669 | 1.00 | 15.05 |
| ATOM | 2194 | OE1 | GLN | 471 | 19.100 | 63.636 | 61.941 | 1.00 | 18.25 |
| ATOM | 2195 | NE2 | GLN | 471 | 21.262 | 64.215 | 62.100 | 1.00 | 12.38 |
| ATOM | 2196 | HE21 | GLN | 471 | 22.194 | 63.996 | 61.892 | 1.00 | 0.00 |
| ATOM | 2197 | HE22 | GLN | 471 | 21.011 | 65.006 | 62.619 | 1.00 | 0.00 |
| ATOM | 2198 | C | GLN | 471 | 18.886 | 59.569 | 63.298 | 1.00 | 13.94 |
| ATOM | 2199 | O | GLN | 471 | 17.804 | 59.998 | 63.652 | 1.00 | 12.11 |
| ATOM | 2200 | N | LEU | 472 | 19.225 | 58.276 | 63.418 | 1.00 | 13.41 |
| ATOM | 2201 | H | LEU | 472 | 20.122 | 57.979 | 63.158 | 1.00 | 0.00 |
| ATOM | 2202 | CA | LEU | 472 | 18.279 | 57.283 | 63.934 | 1.00 | 10.14 |
| ATOM | 2203 | CB | LEU | 472 | 18.769 | 55.841 | 63.685 | 1.00 | 9.90 |
| ATOM | 2204 | CG | LEU | 472 | 17.631 | 54.817 | 63.901 | 1.00 | 15.08 |
| ATOM | 2205 | CD1 | LEU | 472 | 16.563 | 55.038 | 62.746 | 1.00 | 14.31 |
| ATOM | 2206 | CD2 | LEU | 472 | 18.198 | 53.379 | 63.874 | 1.00 | 8.58 |

TABLE 6-continued

Coordinates of Lck bound with damnacanthal

| | Atom Type | Res | # | X | Y | Z | Occ | B |
|---|---|---|---|---|---|---|---|---|
| ATOM | 2207 | C | LEU | 472 | 18.211 | 57.546 | 65.435 | 1.00 | 7.85 |
| ATOM | 2208 | O | LEU | 472 | 17.150 | 57.496 | 66.036 | 1.00 | 7.83 |
| ATOM | 2209 | N | MET | 473 | 19.339 | 57.889 | 66.034 | 1.00 | 7.95 |
| ATOM | 2210 | H | MET | 473 | 20.185 | 57.952 | 65.544 | 1.00 | 0.00 |
| ATOM | 2211 | CA | MET | 473 | 19.292 | 58.172 | 67.449 | 1.00 | 6.39 |
| ATOM | 2212 | CB | MET | 473 | 20.687 | 58.382 | 68.008 | 1.00 | 6.49 |
| ATOM | 2213 | CG | MET | 473 | 21.706 | 57.302 | 67.739 | 1.00 | 6.74 |
| ATOM | 2214 | SD | MET | 473 | 23.333 | 58.080 | 68.081 | 1.00 | 8.43 |
| ATOM | 2215 | CE | MET | 473 | 24.525 | 56.717 | 67.884 | 1.00 | 9.95 |
| ATOM | 2216 | C | MET | 473 | 18.445 | 59.446 | 69.694 | 1.00 | 8.34 |
| ATOM | 2217 | O | MET | 473 | 17.741 | 59.522 | 68.696 | 1.00 | 10.16 |
| ATOM | 2218 | N | ARG | 474 | 18.547 | 60.442 | 66.796 | 1.00 | 11.47 |
| ATOM | 2219 | H | ARG | 474 | 19.149 | 60.342 | 66.029 | 1.00 | 0.00 |
| ATOM | 2220 | CA | ARG | 474 | 17.776 | 61.701 | 66.920 | 1.00 | 10.12 |
| ATOM | 2221 | CB | ARG | 474 | 18.109 | 62.670 | 65.775 | 1.00 | 13.05 |
| ATOM | 2222 | CG | ARG | 474 | 19.568 | 63.078 | 65.628 | 1.00 | 11.74 |
| ATOM | 2223 | CD | ARG | 474 | 20.073 | 63.924 | 66.743 | 1.00 | 14.72 |
| ATOM | 2224 | NE | ARG | 474 | 19.503 | 65.278 | 66.786 | 1.00 | 19.37 |
| ATOM | 2225 | HE | ARG | 474 | 18.633 | 65.421 | 66.360 | 1.00 | 0.00 |
| ATOM | 2226 | CZ | ARG | 474 | 20.098 | 66.336 | 67.373 | 1.00 | 21.15 |
| ATOM | 2227 | NH1 | ARG | 474 | 21.297 | 66.275 | 67.928 | 1.00 | 8.45 |
| ATOM | 2228 | HH11 | ARG | 474 | 21.806 | 65.414 | 67.925 | 1.00 | 0.00 |
| ATOM | 2229 | HH12 | ARG | 474 | 21.694 | 67.089 | 68.351 | 1.00 | 0.00 |
| ATOM | 2230 | NH2 | ARG | 474 | 19.369 | 67.394 | 67.661 | 1.00 | 27.75 |
| ATOM | 2231 | HH21 | ARG | 474 | 18.393 | 67.403 | 67.444 | 1.00 | 0.00 |
| ATOM | 2232 | HH22 | ARG | 474 | 19.792 | 68.189 | 68.096 | 1.00 | 0.00 |
| ATOM | 2233 | C | ARG | 474 | 16.256 | 61.365 | 66.863 | 1.00 | 12.12 |
| ATOM | 2234 | O | ARG | 474 | 15.496 | 62.012 | 67.533 | 1.00 | 11.46 |
| ATOM | 2235 | N | LEU | 475 | 15.812 | 60.444 | 65.991 | 1.00 | 11.99 |
| ATOM | 2236 | H | LEU | 475 | 16.422 | 60.024 | 65.349 | 1.00 | 0.00 |
| ATOM | 2237 | CA | LEU | 475 | 14.369 | 60.053 | 65.998 | 1.00 | 15.09 |
| ATOM | 2238 | CB | LEU | 475 | 14.066 | 58.912 | 65.011 | 1.00 | 17.14 |
| ATOM | 2239 | CG | LEU | 475 | 14.251 | 59.086 | 63.524 | 1.00 | 23.52 |
| ATOM | 2240 | CD1 | LEU | 475 | 13.598 | 57.869 | 62.850 | 1.00 | 23.36 |
| ATOM | 2241 | CD2 | LEU | 475 | 13.660 | 60.400 | 63.035 | 1.00 | 24.42 |
| ATOM | 2242 | C | LEU | 475 | 13.965 | 59.560 | 67.394 | 1.00 | 13.05 |
| ATOM | 2243 | O | LEU | 475 | 12.910 | 59.916 | 67.911 | 1.00 | 10.62 |
| ATOM | 2244 | N | CYS | 476 | 14.822 | 58.735 | 68.003 | 1.00 | 11.37 |
| ATOM | 2245 | H | CYS | 476 | 15.644 | 58.459 | 67.547 | 1.00 | 0.00 |
| ATOM | 2246 | CA | CYS | 476 | 14.561 | 58.224 | 69.356 | 1.00 | 9.89 |
| ATOM | 2247 | CB | CYS | 476 | 15.692 | 57.274 | 69.821 | 1.00 | 6.53 |
| ATOM | 2248 | SG | CYS | 476 | 15.859 | 55.743 | 68.813 | 1.00 | 11.51 |
| ATOM | 2249 | C | CYS | 476 | 14.469 | 59.339 | 70.392 | 1.00 | 9.54 |
| ATOM | 2250 | O | CYS | 476 | 13.904 | 59.123 | 71.474 | 1.00 | 10.53 |
| ATOM | 2251 | N | TRP | 477 | 15.124 | 60.477 | 70.123 | 1.00 | 10.66 |
| ATOM | 2252 | H | TRP | 477 | 15.606 | 60.584 | 69.277 | 1.00 | 0.00 |
| ATOM | 2253 | CA | TRP | 477 | 15.130 | 61.572 | 71.083 | 1.00 | 7.55 |
| ATOM | 2254 | CB | TRP | 477 | 16.563 | 62.116 | 71.267 | 1.00 | 10.44 |
| ATOM | 2255 | CG | TRP | 477 | 17.635 | 61.071 | 71.632 | 1.00 | 7.24 |
| ATOM | 2256 | CD2 | TRP | 477 | 18.992 | 61.045 | 71.170 | 1.00 | 6.78 |
| ATOM | 2257 | CE2 | TRP | 477 | 19.624 | 59.950 | 71.801 | 1.00 | 9.03 |
| ATOM | 2258 | CE3 | TRP | 477 | 19.731 | 61.840 | 70.279 | 1.00 | 5.65 |
| ATOM | 2259 | CD1 | TRP | 477 | 17.501 | 60.011 | 72.490 | 1.00 | 7.00 |
| ATOM | 2260 | NE1 | TRP | 477 | 18.688 | 59.345 | 72.605 | 1.00 | 9.09 |
| ATOM | 2261 | HE1 | TRP | 477 | 18.846 | 58.564 | 73.168 | 1.00 | 0.00 |
| ATOM | 2262 | CZ2 | TRP | 477 | 20.978 | 59.618 | 71.571 | 1.00 | 2.00 |
| ATOM | 2263 | CZ3 | TRP | 477 | 21.075 | 61.514 | 70.046 | 1.00 | 4.44 |
| ATOM | 2264 | CH2 | TRP | 477 | 21.679 | 60.400 | 70.705 | 1.00 | 4.53 |
| ATOM | 2265 | C | TRP | 477 | 14.139 | 62.709 | 70.698 | 1.00 | 10.77 |
| ATOM | 2266 | O | TRP | 477 | 14.295 | 63.873 | 71.086 | 1.00 | 10.36 |
| ATOM | 2267 | N | LYS | 478 | 13.133 | 62.387 | 69.897 | 1.00 | 14.32 |
| ATOM | 2268 | H | LYS | 478 | 13.064 | 61.492 | 69.503 | 1.00 | 0.00 |
| ATOM | 2269 | CA | LYS | 478 | 12.115 | 63.390 | 69.602 | 1.00 | 14.94 |
| ATOM | 2270 | CB | LYS | 478 | 11.115 | 62.882 | 68.565 | 1.00 | 13.40 |
| ATOM | 2271 | CG | LYS | 478 | 11.736 | 62.870 | 67.186 | 1.00 | 14.36 |
| ATOM | 2272 | CD | LYS | 478 | 10.722 | 62.773 | 66.160 | 1.00 | 18.47 |
| ATOM | 2273 | CE | LYS | 478 | 11.072 | 63.645 | 65.035 | 1.00 | 28.65 |
| ATOM | 2274 | NZ | LYS | 478 | 10.858 | 62.798 | 63.814 | 1.00 | 36.20 |
| ATOM | 2275 | HZ1 | LYS | 478 | 9.864 | 62.494 | 63.772 | 1.00 | 0.00 |
| ATOM | 2276 | HZ2 | LYS | 478 | 11.474 | 61.962 | 63.860 | 1.00 | 0.00 |
| ATOM | 2277 | HZ3 | LYS | 478 | 11.088 | 63.351 | 62.964 | 1.00 | 0.00 |
| ATOM | 2278 | C | LYS | 478 | 11.430 | 63.771 | 70.911 | 1.00 | 12.87 |
| ATOM | 2279 | O | LYS | 478 | 11.257 | 62.935 | 71.796 | 1.00 | 10.94 |
| ATOM | 2280 | N | GLU | 479 | 11.280 | 65.083 | 71.095 | 1.00 | 17.33 |

TABLE 6-continued

Coordinates of Lck bound with damnacanthal

| | Atom Type | Res | # | X | Y | Z | Occ | B |
|---|---|---|---|---|---|---|---|---|
| ATOM | 2281 | H | GLU | 479 | 11.604 | 65.699 | 70.406 | 1.00 | 0.00 |
| ATOM | 2282 | CA | GLU | 479 | 10.653 | 65.662 | 72.278 | 1.00 | 19.33 |
| ATOM | 2283 | CB | GLU | 479 | 10.365 | 67.142 | 72.071 | 1.00 | 23.73 |
| ATOM | 2284 | CG | GLU | 479 | 9.620 | 67.744 | 73.254 | 1.00 | 33.47 |
| ATOM | 2285 | CD | GLU | 479 | 10.509 | 67.898 | 74.474 | 1.00 | 39.43 |
| ATOM | 2286 | OE1 | GLU | 479 | 11.743 | 67.948 | 74.304 | 1.00 | 47.84 |
| ATOM | 2287 | OE2 | GLU | 479 | 9.990 | 67.985 | 75.606 | 1.00 | 44.04 |
| ATOM | 2288 | C | GLU | 479 | 9.344 | 64.992 | 72.659 | 1.00 | 18.42 |
| ATOM | 2289 | O | GLU | 479 | 9.117 | 64.693 | 73.820 | 1.00 | 18.20 |
| ATOM | 2290 | N | ARG | 480 | 8.459 | 64.815 | 71.688 | 1.00 | 20.37 |
| ATOM | 2291 | H | ARG | 480 | 8.645 | 65.110 | 70.772 | 1.00 | 0.00 |
| ATOM | 2292 | CA | ARG | 480 | 7.177 | 64.162 | 72.000 | 1.00 | 21.17 |
| ATOM | 2293 | CB | ARG | 480 | 6.055 | 64.646 | 71.081 | 1.00 | 23.40 |
| ATOM | 2294 | CG | ARG | 480 | 5.708 | 66.125 | 71.217 | 1.00 | 22.73 |
| ATOM | 2295 | CD | ARG | 480 | 4.333 | 66.350 | 70.616 | 1.00 | 26.63 |
| ATOM | 2296 | NE | ARG | 480 | 4.263 | 65.842 | 69.259 | 1.00 | 33.73 |
| ATOM | 2297 | HE | ARG | 480 | 5.100 | 65.558 | 68.837 | 1.00 | 0.00 |
| ATOM | 2298 | CZ | ARG | 480 | 3.145 | 65.733 | 68.545 | 1.00 | 42.85 |
| ATOM | 2299 | NH1 | ARG | 480 | 1.981 | 66.095 | 69.073 | 1.00 | 48.97 |
| ATOM | 2300 | HH11 | ARG | 480 | 1.944 | 66.450 | 70.007 | 1.00 | 0.00 |
| ATOM | 2301 | HH12 | ARG | 480 | 1.141 | 66.013 | 68.536 | 1.00 | 0.00 |
| ATOM | 2302 | NH2 | ARG | 480 | 3.194 | 65.330 | 67.276 | 1.00 | 44.92 |
| ATOM | 2303 | HH21 | ARG | 480 | 4.074 | 65.108 | 66.856 | 1.00 | 0.00 |
| ATOM | 2304 | HH22 | ARG | 480 | 2.351 | 65.250 | 66.744 | 1.00 | 0.00 |
| ATOM | 2305 | C | ARG | 480 | 7.267 | 62.626 | 71.939 | 1.00 | 15.72 |
| ATOM | 2306 | O | ARG | 480 | 7.662 | 62.067 | 70.942 | 1.00 | 11.24 |
| ATOM | 2307 | N | PRO | 481 | 6.887 | 61.946 | 73.021 | 1.00 | 13.81 |
| ATOM | 2308 | CD | PRO | 481 | 6.436 | 62.532 | 74.294 | 1.00 | 11.82 |
| ATOM | 2309 | CA | PRO | 481 | 6.921 | 60.476 | 73.089 | 1.00 | 12.48 |
| ATOM | 2310 | CB | PRO | 481 | 6.072 | 60.197 | 74.313 | 1.00 | 8.37 |
| ATOM | 2311 | CG | PRO | 481 | 6.444 | 61.358 | 75.223 | 1.00 | 8.93 |
| ATOM | 2312 | C | PRO | 481 | 6.335 | 59.801 | 71.847 | 1.00 | 13.76 |
| ATOM | 2313 | O | PRO | 481 | 6.962 | 58.942 | 71.237 | 1.00 | 16.40 |
| ATOM | 2314 | N | GLU | 482 | 5.163 | 60.287 | 71.448 | 1.00 | 17.88 |
| ATOM | 2315 | H | GLU | 482 | 4.798 | 61.043 | 71.951 | 1.00 | 0.00 |
| ATOM | 2316 | CA | GLU | 482 | 4.350 | 59.814 | 70.331 | 1.00 | 17.70 |
| ATOM | 2317 | CB | GLU | 482 | 2.965 | 60.491 | 70.380 | 1.00 | 23.28 |
| ATOM | 2318 | CG | GLU | 482 | 2.974 | 62.039 | 70.526 | 1.00 | 29.97 |
| ATOM | 2319 | CD | GLU | 482 | 3.183 | 62.541 | 71.974 | 1.00 | 32.40 |
| ATOM | 2320 | OE1 | GLU | 482 | 3.453 | 61.744 | 72.892 | 1.00 | 35.80 |
| ATOM | 2321 | OE2 | GLU | 482 | 3.085 | 63.762 | 72.198 | 1.00 | 42.53 |
| ATOM | 2322 | C | GLU | 482 | 4.965 | 59.974 | 68.969 | 1.00 | 19.24 |
| ATOM | 2323 | O | GLU | 482 | 4.527 | 59.354 | 67.995 | 1.00 | 20.02 |
| ATOM | 2324 | N | ASP | 483 | 5.995 | 60.806 | 68.889 | 1.00 | 17.10 |
| ATOM | 2325 | H | ASP | 483 | 6.307 | 61.289 | 69.683 | 1.00 | 0.00 |
| ATOM | 2326 | CA | ASP | 483 | 6.675 | 61.014 | 67.627 | 1.00 | 13.00 |
| ATOM | 2327 | CB | ASP | 483 | 7.171 | 62.456 | 67.539 | 1.00 | 19.12 |
| ATOM | 2328 | CG | ASP | 483 | 6.048 | 63.432 | 67.314 | 1.00 | 22.52 |
| ATOM | 2329 | OD1 | ASP | 483 | 5.028 | 63.028 | 66.715 | 1.00 | 26.00 |
| ATOM | 2330 | OD2 | ASP | 483 | 6.186 | 64.585 | 67.758 | 1.00 | 23.38 |
| ATOM | 2331 | C | ASP | 483 | 7.867 | 60.075 | 67.488 | 1.00 | 9.89 |
| ATOM | 2332 | O | ASP | 483 | 8.423 | 59.979 | 66.416 | 1.00 | 11.09 |
| ATOM | 2333 | N | ARG | 484 | 8.317 | 59.473 | 68.584 | 1.00 | 9.75 |
| ATOM | 2334 | H | ARG | 484 | 7.894 | 59.633 | 69.453 | 1.00 | 0.00 |
| ATOM | 2335 | CA | ARG | 484 | 9.473 | 58.546 | 68.497 | 1.00 | 8.35 |
| ATOM | 2336 | CB | ARG | 484 | 10.003 | 58.244 | 69.879 | 1.00 | 4.43 |
| ATOM | 2337 | CG | ARG | 484 | 10.089 | 59.446 | 70.733 | 1.00 | 2.01 |
| ATOM | 2338 | CD | ARG | 484 | 10.645 | 59.170 | 72.033 | 1.00 | 2.45 |
| ATOM | 2339 | NE | ARG | 484 | 10.680 | 60.401 | 72.759 | 1.00 | 4.87 |
| ATOM | 2340 | HE | ARG | 484 | 10.869 | 61.211 | 72.244 | 1.00 | 0.00 |
| ATOM | 2341 | CZ | ARG | 484 | 10.481 | 60.554 | 74.062 | 1.00 | 12.17 |
| ATOM | 2342 | NH1 | ARG | 484 | 10.244 | 59.504 | 74.850 | 1.00 | 10.96 |
| ATOM | 2343 | HH11 | ARG | 484 | 10.214 | 58.583 | 74.461 | 1.00 | 0.00 |
| ATOM | 2344 | HH12 | ARG | 484 | 10.096 | 59.638 | 75.830 | 1.00 | 0.00 |
| ATOM | 2345 | NH2 | ARG | 484 | 10.446 | 61.793 | 74.560 | 1.00 | 6.08 |
| ATOM | 2346 | HH21 | ARG | 484 | 10.568 | 62.579 | 73.954 | 1.00 | 0.00 |
| ATOM | 2347 | HH22 | ARG | 484 | 10.297 | 61.934 | 75.539 | 1.00 | 0.00 |
| ATOM | 2348 | C | ARG | 484 | 8.962 | 57.277 | 67.784 | 1.00 | 13.73 |
| ATOM | 2349 | O | ARG | 484 | 7.777 | 56.944 | 67.861 | 1.00 | 18.51 |
| ATOM | 2350 | N | PRO | 485 | 9.830 | 56.599 | 67.027 | 1.00 | 14.55 |
| ATOM | 2351 | CD | PRO | 485 | 11.254 | 56.875 | 66.817 | 1.00 | 9.98 |
| ATOM | 2352 | CA | PRO | 485 | 9.435 | 55.389 | 66.290 | 1.00 | 15.61 |
| ATOM | 2353 | CB | PRO | 485 | 10.655 | 55.127 | 65.417 | 1.00 | 14.71 |
| ATOM | 2354 | CG | PRO | 485 | 11.756 | 55.522 | 66.365 | 1.00 | 13.34 |

TABLE 6-continued

Coordinates of Lck bound with damnacanthal

| | Atom Type | Res | # | X | Y | Z | Occ | B |
|---|---|---|---|---|---|---|---|---|
| ATOM | 2355 | C | PRO | 485 | 9.177 | 54.174 | 67.134 | 1.00 | 15.17 |
| ATOM | 2356 | O | PRO | 485 | 9.535 | 54.137 | 68.315 | 1.00 | 16.48 |
| ATOM | 2357 | N | THR | 486 | 8.544 | 53.175 | 66.525 | 1.00 | 14.31 |
| ATOM | 2358 | H | THR | 486 | 8.210 | 53.275 | 65.609 | 1.00 | 0.00 |
| ATOM | 2359 | CA | THR | 486 | 8.343 | 51.908 | 67.232 | 1.00 | 15.50 |
| ATOM | 2360 | CB | THR | 486 | 7.281 | 51.028 | 66.536 | 1.00 | 12.99 |
| ATOM | 2361 | OG1 | THR | 486 | 7.773 | 50.607 | 65.260 | 1.00 | 12.20 |
| ATOM | 2362 | HG1 | THR | 486 | 8.580 | 50.101 | 65.379 | 1.00 | 0.00 |
| ATOM | 2363 | CG2 | THR | 486 | 5.920 | 51.856 | 66.334 | 1.00 | 13.92 |
| ATOM | 2364 | C | THR | 486 | 9.677 | 51.122 | 67.270 | 1.00 | 13.41 |
| ATOM | 2365 | O | THR | 486 | 10.617 | 51.371 | 66.502 | 1.00 | 10.75 |
| ATOM | 2366 | N | PHE | 487 | 9.760 | 50.122 | 68.130 | 1.00 | 15.57 |
| ATOM | 2367 | H | PHE | 487 | 9.028 | 49.916 | 68.748 | 1.00 | 0.00 |
| ATOM | 2368 | CA | PHE | 487 | 10.970 | 49.323 | 68.144 | 1.00 | 14.98 |
| ATOM | 2369 | CB | PHE | 487 | 11.065 | 48.490 | 69.411 | 1.00 | 14.95 |
| ATOM | 2370 | CG | PHE | 487 | 11.678 | 49.242 | 70.555 | 1.00 | 11.58 |
| ATOM | 2371 | CD1 | PHE | 487 | 13.056 | 49.490 | 70.577 | 1.00 | 6.66 |
| ATOM | 2372 | CD2 | PHE | 487 | 10.898 | 49.668 | 71.603 | 1.00 | 3.84 |
| ATOM | 2373 | CE1 | PHE | 487 | 13.633 | 50.131 | 71.640 | 1.00 | 5.82 |
| ATOM | 2374 | CE2 | PHE | 487 | 11.445 | 50.307 | 72.658 | 1.00 | 7.65 |
| ATOM | 2375 | CZ | PHE | 487 | 12.836 | 50.553 | 72.698 | 1.00 | 9.92 |
| ATOM | 2376 | C | PHE | 487 | 11.063 | 48.474 | 66.890 | 1.00 | 15.46 |
| ATOM | 2377 | O | PHE | 487 | 12.169 | 48.244 | 66.397 | 1.00 | 16.03 |
| ATOM | 2378 | N | ASP | 488 | 9.907 | 48.103 | 66.326 | 1.00 | 18.67 |
| ATOM | 2379 | H | ASP | 488 | 9.042 | 48.342 | 66.720 | 1.00 | 0.00 |
| ATOM | 2380 | CA | ASP | 488 | 9.966 | 47.314 | 65.079 | 1.00 | 18.23 |
| ATOM | 2381 | CB | ASP | 488 | 8.657 | 46.623 | 64.717 | 1.00 | 22.41 |
| ATOM | 2382 | CG | ASP | 488 | 8.928 | 45.487 | 63.757 | 1.00 | 27.02 |
| ATOM | 2383 | OD1 | ASP | 488 | 9.791 | 44.601 | 64.049 | 1.00 | 28.09 |
| ATOM | 2384 | OD2 | ASP | 488 | 8.412 | 45.561 | 62.651 | 1.00 | 31.11 |
| ATOM | 2385 | C | ASP | 488 | 10.483 | 48.124 | 63.904 | 1.00 | 14.03 |
| ATOM | 2386 | O | ASP | 488 | 11.111 | 47.576 | 62.979 | 1.00 | 10.24 |
| ATOM | 2387 | N | TYR | 489 | 10.131 | 49.395 | 63.873 | 1.00 | 13.15 |
| ATOM | 2388 | H | TYR | 489 | 9.490 | 49.744 | 64.527 | 1.00 | 0.00 |
| ATOM | 2389 | CA | TYR | 489 | 10.682 | 50.309 | 62.872 | 1.00 | 11.70 |
| ATOM | 2390 | CB | TYR | 489 | 10.078 | 51.695 | 63.043 | 1.00 | 10.04 |
| ATOM | 2391 | CG | TYR | 489 | 10.704 | 52.726 | 62.128 | 1.00 | 11.58 |
| ATOM | 2392 | CD1 | TYR | 489 | 10.363 | 52.780 | 60.781 | 1.00 | 9.03 |
| ATOM | 2393 | CE1 | TYR | 489 | 10.983 | 53.670 | 59.930 | 1.00 | 14.47 |
| ATOM | 2394 | CD2 | TYR | 489 | 11.700 | 53.610 | 62.600 | 1.00 | 9.55 |
| ATOM | 2395 | CE2 | TYR | 489 | 12.337 | 54.521 | 61.730 | 1.00 | 13.61 |
| ATOM | 2396 | CZ | TYR | 489 | 11.970 | 54.546 | 60.411 | 1.00 | 15.49 |
| ATOM | 2397 | OH | TYR | 489 | 12.536 | 55.456 | 59.556 | 1.00 | 16.82 |
| ATOM | 2398 | HH | TYR | 489 | 13.166 | 55.998 | 60.036 | 1.00 | 0.00 |
| ATOM | 2399 | C | TYR | 489 | 12.225 | 50.389 | 63.099 | 1.00 | 8.96 |
| ATOM | 2400 | O | TYR | 489 | 12.993 | 50.318 | 62.165 | 1.00 | 14.67 |
| ATOM | 2401 | N | LEU | 490 | 12.662 | 50.522 | 64.337 | 1.00 | 10.83 |
| ATOM | 2402 | H | LEU | 490 | 12.025 | 50.569 | 65.080 | 1.00 | 0.00 |
| ATOM | 2403 | CA | LEU | 490 | 14.101 | 50.603 | 64.635 | 1.00 | 9.83 |
| ATOM | 2404 | CB | LEU | 490 | 14.328 | 50.875 | 66.131 | 1.00 | 7.67 |
| ATOM | 2405 | CG | LEU | 490 | 13.830 | 52.287 | 66.597 | 1.00 | 10.39 |
| ATOM | 2406 | CD1 | LEU | 490 | 13.899 | 52.408 | 68.116 | 1.00 | 7.46 |
| ATOM | 2407 | CD2 | LEU | 490 | 14.718 | 53.380 | 65.946 | 1.00 | 5.53 |
| ATOM | 2408 | C | LEU | 490 | 14.803 | 49.321 | 64.181 | 1.00 | 11.08 |
| ATOM | 2409 | O | LEU | 490 | 15.826 | 49.385 | 63.506 | 1.00 | 13.76 |
| ATOM | 2410 | N | ARG | 491 | 14.237 | 48.160 | 64.525 | 1.00 | 11.39 |
| ATOM | 2411 | H | ARG | 491 | 13.423 | 48.145 | 65.070 | 1.00 | 0.00 |
| ATOM | 2412 | CA | ARG | 491 | 14.825 | 46.901 | 64.092 | 1.00 | 12.01 |
| ATOM | 2413 | CB | ARG | 491 | 13.979 | 45.674 | 64.494 | 1.00 | 11.95 |
| ATOM | 2414 | CG | ARG | 491 | 14.600 | 44.407 | 63.903 | 1.00 | 9.99 |
| ATOM | 2415 | CD | ARG | 491 | 13.573 | 43.334 | 63.662 | 1.00 | 14.00 |
| ATOM | 2416 | NE | ARG | 491 | 12.337 | 43.856 | 63.102 | 1.00 | 18.21 |
| ATOM | 2417 | HE | ARG | 491 | 11.677 | 44.207 | 63.733 | 1.00 | 0.00 |
| ATOM | 2418 | CZ | ARG | 491 | 12.021 | 43.900 | 61.810 | 1.00 | 21.38 |
| ATOM | 2419 | NH1 | ARG | 491 | 12.864 | 43.477 | 60.889 | 1.00 | 25.13 |
| ATOM | 2420 | HH11 | ARG | 491 | 13.757 | 43.116 | 61.157 | 1.00 | 0.00 |
| ATOM | 2421 | HH12 | ARG | 491 | 12.610 | 43.517 | 59.923 | 1.00 | 0.00 |
| ATOM | 2422 | NH2 | ARG | 491 | 10.781 | 44.248 | 61.449 | 1.00 | 22.39 |
| ATOM | 2423 | HH21 | ARG | 491 | 10.101 | 44.472 | 62.147 | 1.00 | 0.00 |
| ATOM | 2424 | HH22 | ARG | 491 | 10.534 | 44.284 | 60.481 | 1.00 | 0.00 |
| ATOM | 2425 | C | ARG | 491 | 14.982 | 46.859 | 62.598 | 1.00 | 10.27 |
| ATOM | 2426 | O | ARG | 491 | 16.055 | 46.587 | 62.071 | 1.00 | 15.22 |
| ATOM | 2427 | N | SER | 492 | 13.899 | 47.165 | 61.904 | 0.71 | 11.31 |
| ATOM | 2428 | H | SER | 492 | 13.077 | 47.439 | 62.361 | 1.00 | 0.00 |

TABLE 6-continued

Coordinates of Lck bound with damnacanthal

| | | Atom Type | Res | # | X | Y | Z | Occ | B |
|---|---|---|---|---|---|---|---|---|---|
| ATOM | 2429 | CA | SER | 492 | 13.912 | 47.100 | 60.460 | 0.71 | 8.82 |
| ATOM | 2430 | CB | SER | 492 | 12.520 | 47.370 | 59.930 | 0.71 | 7.77 |
| ATOM | 2431 | OG | SER | 492 | 12.506 | 47.365 | 58.540 | 0.71 | 16.77 |
| ATOM | 2432 | HG | SER | 492 | 12.796 | 46.508 | 58.220 | 1.00 | 0.00 |
| ATOM | 2433 | C | SER | 492 | 14.939 | 48.022 | 59.826 | 0.71 | 9.26 |
| ATOM | 2434 | O | SER | 492 | 15.584 | 47.636 | 58.858 | 0.71 | 8.01 |
| ATOM | 2435 | N | VAL | 493 | 15.058 | 49.245 | 60.356 | 1.00 | 12.44 |
| ATOM | 2436 | H | VAL | 493 | 14.481 | 49.507 | 61.103 | 1.00 | 0.00 |
| ATOM | 2437 | CA | VAL | 493 | 16.040 | 50.229 | 59.851 | 1.00 | 12.28 |
| ATOM | 2438 | CB | VAL | 493 | 15.847 | 51.661 | 60.494 | 1.00 | 13.19 |
| ATOM | 2439 | CG1 | VAL | 493 | 16.981 | 52.595 | 59.989 | 1.00 | 9.40 |
| ATOM | 2440 | CG2 | VAL | 493 | 14.433 | 52.266 | 60.112 | 1.00 | 10.17 |
| ATOM | 2441 | C | VAL | 493 | 17.492 | 49.753 | 60.171 | 1.00 | 10.87 |
| ATOM | 2442 | O | VAL | 493 | 18.387 | 49.838 | 59.344 | 1.00 | 11.38 |
| ATOM | 2443 | N | LEU | 494 | 17.726 | 49.311 | 61.393 | 1.00 | 10.18 |
| ATOM | 2444 | H | LEU | 494 | 17.015 | 49.305 | 62.067 | 1.00 | 0.00 |
| ATOM | 2445 | CA | LEU | 494 | 19.059 | 48.823 | 61.753 | 1.00 | 10.45 |
| ATOM | 2446 | CB | LEU | 494 | 19.113 | 48.540 | 63.256 | 1.00 | 10.18 |
| ATOM | 2447 | CG | LEU | 494 | 19.070 | 49.827 | 64.110 | 1.00 | 6.58 |
| ATOM | 2448 | CD1 | LEU | 494 | 18.687 | 49.419 | 65.556 | 1.00 | 7.69 |
| ATOM | 2449 | CD2 | LEU | 494 | 20.423 | 50.558 | 64.079 | 1.00 | 2.00 |
| ATOM | 2450 | C | LEU | 494 | 19.415 | 47.587 | 60.882 | 1.00 | 11.13 |
| ATOM | 2451 | O | LEU | 494 | 20.543 | 47.448 | 60.429 | 1.00 | 9.96 |
| ATOM | 2452 | N | GLU | 495 | 18.438 | 46.736 | 60.553 | 1.00 | 12.18 |
| ATOM | 2453 | H | GLU | 495 | 17.525 | 46.854 | 60.887 | 1.00 | 0.00 |
| ATOM | 2454 | CA | GLU | 495 | 18.761 | 45.588 | 59.658 | 1.00 | 13.56 |
| ATOM | 2455 | CB | GLU | 495 | 17.576 | 44.622 | 59.552 | 1.00 | 13.17 |
| ATOM | 2456 | CG | GLU | 495 | 17.331 | 43.935 | 60.896 | 1.00 | 17.69 |
| ATOM | 2457 | CD | GLU | 495 | 16.216 | 42.894 | 60.881 | 1.00 | 21.75 |
| ATOM | 2458 | OE1 | GLU | 495 | 15.655 | 42.625 | 59.810 | 1.00 | 21.72 |
| ATOM | 2459 | OE2 | GLU | 495 | 15.919 | 42.321 | 61.946 | 1.00 | 24.58 |
| ATOM | 2460 | C | GLU | 495 | 19.208 | 46.094 | 58.274 | 1.00 | 13.54 |
| ATOM | 2461 | O | GLU | 495 | 20.038 | 45.478 | 57.590 | 1.00 | 16.65 |
| ATOM | 2462 | N | ASP | 496 | 18.566 | 47.151 | 57.809 | 1.00 | 12.54 |
| ATOM | 2463 | H | ASP | 496 | 17.826 | 47.544 | 58.317 | 1.00 | 0.00 |
| ATOM | 2464 | CA | ASP | 496 | 18.944 | 47.746 | 56.544 | 1.00 | 13.92 |
| ATOM | 2465 | CB | ASP | 496 | 17.915 | 48.818 | 56.145 | 1.00 | 13.25 |
| ATOM | 2466 | CG | ASP | 496 | 16.633 | 48.213 | 55.526 | 1.00 | 15.41 |
| ATOM | 2467 | OD1 | ASP | 496 | 16.650 | 47.047 | 55.083 | 1.00 | 14.74 |
| ATOM | 2468 | OD2 | ASP | 496 | 15.602 | 48.906 | 55.460 | 1.00 | 15.26 |
| ATOM | 2469 | C | ASP | 496 | 20.382 | 48.363 | 56.674 | 1.00 | 11.34 |
| ATOM | 2470 | O | ASP | 496 | 21.188 | 48.211 | 55.801 | 1.00 | 11.21 |
| ATOM | 2471 | N | PHE | 497 | 20.690 | 48.986 | 57.798 | 1.00 | 10.46 |
| ATOM | 2472 | H | PHE | 497 | 20.026 | 49.039 | 58.516 | 1.00 | 0.00 |
| ATOM | 2473 | CA | PHE | 497 | 21.976 | 49.599 | 58.018 | 1.00 | 12.48 |
| ATOM | 2474 | CB | PHE | 497 | 21.951 | 50.351 | 59.382 | 1.00 | 9.24 |
| ATOM | 2475 | CG | PHE | 497 | 21.195 | 51.719 | 59.363 | 1.00 | 7.70 |
| ATOM | 2476 | CD1 | PHE | 497 | 20.588 | 52.196 | 58.222 | 1.00 | 7.48 |
| ATOM | 2477 | CD2 | PHE | 497 | 21.190 | 52.531 | 60.507 | 1.00 | 2.61 |
| ATOM | 2478 | CE1 | PHE | 497 | 20.002 | 53.483 | 58.210 | 1.00 | 8.76 |
| ATOM | 2479 | CE2 | PHE | 497 | 20.618 | 53.798 | 60.510 | 1.00 | 3.09 |
| ATOM | 2480 | CZ | PHE | 497 | 20.027 | 54.281 | 59.357 | 1.00 | 5.08 |
| ATOM | 2481 | C | PHE | 497 | 23.050 | 48.476 | 57.982 | 1.00 | 15.30 |
| ATOM | 2482 | O | PHE | 497 | 24.041 | 48.550 | 57.269 | 1.00 | 15.58 |
| ATOM | 2483 | N | PHE | 498 | 22.741 | 47.366 | 58.651 | 1.00 | 20.82 |
| ATOM | 2484 | H | PHE | 498 | 21.884 | 47.320 | 59.123 | 1.00 | 0.00 |
| ATOM | 2485 | CA | PHE | 498 | 23.623 | 46.189 | 58.724 | 1.00 | 21.74 |
| ATOM | 2486 | CB | PHE | 498 | 22.999 | 45.227 | 59.767 | 1.00 | 25.20 |
| ATOM | 2487 | CG | PHE | 498 | 23.449 | 43.815 | 59.700 | 1.00 | 27.68 |
| ATOM | 2488 | CD1 | PHE | 498 | 24.775 | 43.482 | 59.552 | 1.00 | 31.32 |
| ATOM | 2489 | CD2 | PHE | 498 | 22.509 | 42.798 | 59.898 | 1.00 | 29.47 |
| ATOM | 2490 | CE1 | PHE | 498 | 25.188 | 42.157 | 59.600 | 1.00 | 28.74 |
| ATOM | 2491 | CE2 | PHE | 498 | 22.889 | 41.474 | 59.949 | 1.00 | 28.00 |
| ATOM | 2492 | CZ | PHE | 498 | 24.240 | 41.147 | 59.797 | 1.00 | 29.96 |
| ATOM | 2493 | C | PHE | 498 | 23.820 | 45.571 | 57.350 | 1.00 | 23.89 |
| ATOM | 2494 | O | PHE | 498 | 24.963 | 45.469 | 56.898 | 1.00 | 24.54 |
| ATOM | 2495 | N | THR | 499 | 22.734 | 45.312 | 56.606 | 1.00 | 25.07 |
| ATOM | 2496 | H | THR | 499 | 21.839 | 45.553 | 56.925 | 1.00 | 0.00 |
| ATOM | 2497 | CA | THR | 499 | 22.881 | 44.665 | 55.307 | 1.00 | 26.19 |
| ATOM | 2498 | CB | THR | 499 | 21.562 | 44.003 | 54.803 | 1.00 | 26.16 |
| ATOM | 2499 | OG1 | THR | 499 | 20.584 | 45.013 | 54.597 | 1.00 | 26.40 |
| ATOM | 2500 | HG1 | THR | 499 | 20.801 | 45.638 | 53.942 | 1.00 | 0.00 |
| ATOM | 2501 | CG2 | THR | 499 | 21.012 | 42.983 | 55.808 | 1.00 | 24.92 |
| ATOM | 2502 | C | THR | 499 | 23.385 | 45.640 | 54.244 | 1.00 | 29.54 |

TABLE 6-continued

Coordinates of Lck bound with damnacanthal

| | | Atom Type | Res | # | X | Y | Z | Occ | B |
|---|---|---|---|---|---|---|---|---|---|
| ATOM | 2503 | O | THR | 499 | 23.397 | 45.308 | 53.077 | 1.00 | 33.72 |
| ATOM | 2504 | N | ALA | 500 | 23.724 | 46.863 | 54.657 | 1.00 | 31.43 |
| ATOM | 2505 | H | ALA | 500 | 23.616 | 47.112 | 55.599 | 1.00 | 0.00 |
| ATOM | 2506 | CA | ALA | 500 | 24.262 | 47.857 | 53.719 | 1.00 | 35.30 |
| ATOM | 2507 | CB | ALA | 500 | 23.556 | 49.215 | 53.861 | 1.00 | 37.13 |
| ATOM | 2508 | C | ALA | 500 | 25.762 | 47.999 | 54.008 | 1.00 | 37.61 |
| ATOM | 2509 | O | ALA | 500 | 26.538 | 48.325 | 53.108 | 1.00 | 40.06 |
| ATOM | 2510 | N | THR | 501 | 26.159 | 47.777 | 55.267 | 1.00 | 0.00 |
| ATOM | 2511 | H | THR | 501 | 25.500 | 47.575 | 55.964 | 1.00 | 0.00 |
| ATOM | 2512 | CA | THR | 501 | 27.581 | 47.831 | 55.631 | 1.00 | 34.96 |
| ATOM | 2513 | CB | THR | 501 | 27.824 | 48.380 | 57.055 | 1.00 | 31.14 |
| ATOM | 2514 | OG1 | THR | 501 | 27.262 | 47.478 | 58.015 | 1.00 | 29.78 |
| ATOM | 2515 | HG1 | THR | 501 | 26.318 | 47.393 | 57.861 | 1.00 | 0.00 |
| ATOM | 2516 | CG2 | THR | 501 | 27.259 | 49.800 | 57.231 | 1.00 | 19.32 |
| ATOM | 2517 | C | THR | 501 | 28.163 | 46.396 | 55.580 | 1.00 | 36.09 |
| ATOM | 2518 | O | THR | 501 | 27.817 | 45.633 | 54.645 | 1.00 | 34.78 |
| ATOM | 2519 | OT | THR | 501 | 28.921 | 46.043 | 56.494 | 1.00 | 38.87 |
| ATOM | 2520 | OH2 | TIP3 | 2 | 19.112 | 28.199 | 79.276 | 1.00 | 10.12 |
| ATOM | 2521 | H1 | TIP3 | 2 | 19.112 | 29.156 | 79.276 | 1.00 | 0.00 |
| ATOM | 2522 | H2 | TIP3 | 2 | 19.112 | 27.959 | 78.349 | 1.00 | 0.00 |
| ATOM | 2523 | OH2 | TIP3 | 3 | 26.211 | 73.069 | 71.067 | 1.00 | 13.91 |
| ATOM | 2524 | H1 | TIP3 | 3 | 26.211 | 72.026 | 71.067 | 1.00 | 0.00 |
| ATOM | 2525 | H2 | TIP3 | 3 | 26.211 | 72.829 | 70.140 | 1.00 | 0.00 |
| ATOM | 2526 | OH2 | TIP3 | 4 | 13.559 | 45.759 | 83.729 | 1.00 | 7.26 |
| ATOM | 2527 | H1 | TIP3 | 4 | 13.559 | 46.716 | 83.729 | 1.00 | 0.00 |
| ATOM | 2528 | H2 | TIP3 | 4 | 13.559 | 45.519 | 82.802 | 1.00 | 0.00 |
| ATOM | 2529 | OH2 | TIP3 | 5 | 24.464 | 78.783 | 74.137 | 1.00 | 13.54 |
| ATOM | 2530 | H1 | TIP3 | 5 | 24.464 | 79.740 | 74.137 | 1.00 | 0.00 |
| ATOM | 2531 | H2 | TIP3 | 5 | 24.464 | 78.543 | 73.210 | 1.00 | 0.00 |
| ATOM | 2532 | OH2 | TIP3 | 6 | 19.278 | 61.230 | 77.735 | 1.00 | 7.78 |
| ATOM | 2533 | H1 | TIP3 | 6 | 19.278 | 62.187 | 77.735 | 1.00 | 0.00 |
| ATOM | 2534 | H2 | TIP3 | 6 | 19.278 | 60.990 | 76.808 | 1.00 | 0.00 |
| ATOM | 2535 | OH2 | TIP3 | 7 | 14.866 | 52.441 | 79.967 | 1.00 | 13.64 |
| ATOM | 2536 | H1 | TIP3 | 7 | 14.866 | 53.398 | 79.967 | 1.00 | 0.00 |
| ATOM | 2537 | H2 | TIP3 | 7 | 14.866 | 52.201 | 79.040 | 1.00 | 0.00 |
| ATOM | 2538 | OH2 | TIP3 | 9 | 27.897 | 56.354 | 74.808 | 1.00 | 14.80 |
| ATOM | 2539 | H1 | TIP3 | 9 | 27.897 | 57.311 | 74.808 | 1.00 | 0.00 |
| ATOM | 2540 | H2 | TIP3 | 9 | 27.897 | 56.114 | 73.881 | 1.00 | 0.00 |
| ATOM | 2541 | OH2 | TIP3 | 10 | 13.356 | 71.274 | 72.206 | 1.00 | 29.42 |
| ATOM | 2542 | H1 | TIP3 | 10 | 13.356 | 72.231 | 72.206 | 1.00 | 0.00 |
| ATOM | 2543 | H2 | TIP3 | 10 | 13.356 | 71.034 | 71.279 | 1.00 | 0.00 |
| ATOM | 2544 | OH2 | TIP3 | 11 | 13.031 | 34.540 | 77.033 | 1.00 | 15.62 |
| ATOM | 2545 | H1 | TIP3 | 11 | 13.031 | 35.497 | 77.033 | 1.00 | 0.00 |
| ATOM | 2546 | H2 | TIP3 | 11 | 13.031 | 34.300 | 76.106 | 1.00 | 0.00 |
| ATOM | 2547 | OH2 | TIP3 | 12 | 22.204 | 46.704 | 86.286 | 1.00 | 26.59 |
| ATOM | 2548 | H1 | TIP3 | 12 | 22.204 | 47.661 | 86.286 | 1.00 | 0.00 |
| ATOM | 2549 | H2 | TIP3 | 12 | 22.204 | 46.464 | 85.359 | 1.00 | 0.00 |
| ATOM | 2550 | OH2 | TIP3 | 13 | 26.475 | 31.942 | 75.843 | 1.00 | 15.66 |
| ATOM | 2551 | H1 | TIP3 | 13 | 26.475 | 32.899 | 75.843 | 1.00 | 0.00 |
| ATOM | 2552 | H2 | TIP3 | 13 | 26.475 | 31.702 | 74.916 | 1.00 | 0.00 |
| ATOM | 2553 | OH2 | TIP3 | 14 | 39.095 | 38.454 | 73.923 | 1.00 | 18.17 |
| ATOM | 2554 | H1 | TIP3 | 14 | 39.095 | 39.411 | 73.923 | 1.00 | 0.00 |
| ATOM | 2555 | H2 | TIP3 | 14 | 39.095 | 38.214 | 72.996 | 1.00 | 0.00 |
| ATOM | 2556 | OH2 | TIP3 | 15 | 13.376 | 56.487 | 79.559 | 1.00 | 11.18 |
| ATOM | 2557 | H1 | TIP3 | 15 | 13.376 | 57.444 | 79.559 | 1.00 | 0.00 |
| ATOM | 2558 | H2 | TIP3 | 15 | 13.376 | 56.247 | 78.632 | 1.00 | 0.00 |
| ATOM | 2559 | OH2 | TIP3 | 16 | 19.647 | 65.219 | 58.554 | 1.00 | 14.56 |
| ATOM | 2560 | H1 | TIP3 | 16 | 19.647 | 66.176 | 58.554 | 1.00 | 0.00 |
| ATOM | 2561 | H2 | TIP3 | 16 | 19.647 | 64.979 | 57.627 | 1.00 | 0.00 |
| ATOM | 2562 | OH2 | TIP3 | 17 | 16.561 | 33.113 | 75.214 | 1.00 | 5.67 |
| ATOM | 2563 | H1 | TIP3 | 17 | 16.561 | 34.070 | 75.214 | 1.00 | 0.00 |
| ATOM | 2564 | H2 | TIP3 | 17 | 16.561 | 32.873 | 74.287 | 1.00 | 0.00 |
| ATOM | 2565 | OH2 | TIP3 | 19 | 3.802 | 51.792 | 76.668 | 1.00 | 10.92 |
| ATOM | 2566 | H1 | TIP3 | 19 | 3.802 | 52.749 | 76.668 | 1.00 | 0.00 |
| ATOM | 2567 | H2 | TIP3 | 19 | 3.802 | 51.552 | 75.741 | 1.00 | 0.00 |
| ATOM | 2568 | OH2 | TIP3 | 20 | 28.173 | 53.411 | 79.335 | 1.00 | 9.17 |
| ATOM | 2569 | H1 | TIP3 | 20 | 28.173 | 54.368 | 79.335 | 1.00 | 0.00 |
| ATOM | 2570 | H2 | TIP3 | 20 | 28.173 | 53.171 | 78.408 | 1.00 | 0.00 |
| ATOM | 2571 | OH2 | TIP3 | 21 | 22.126 | 19.123 | 82.638 | 1.00 | 8.31 |
| ATOM | 2572 | H1 | TIP3 | 21 | 22.126 | 20.080 | 82.638 | 1.00 | 0.00 |
| ATOM | 2573 | H2 | TIP3 | 21 | 22.126 | 18.883 | 81.711 | 1.00 | 0.00 |
| ATOM | 2574 | OH2 | TIP3 | 23 | 32.214 | 60.241 | 71.488 | 1.00 | 22.58 |
| ATOM | 2575 | H1 | TIP3 | 23 | 32.214 | 61.198 | 71.488 | 1.00 | 0.00 |
| ATOM | 2576 | H2 | TIP3 | 23 | 32.214 | 60.001 | 70.561 | 1.00 | 0.00 |

TABLE 6-continued

Coordinates of Lck bound with damnacanthal

| Atom | | Type | Res | # | X | Y | Z | Occ | B |
|---|---|---|---|---|---|---|---|---|---|
| ATOM | 2577 | OH2 | TIP3 | 24 | 5.766 | 57.695 | 65.769 | 1.00 | 31.05 |
| ATOM | 2578 | H1 | TIP3 | 24 | 5.766 | 58.652 | 65.769 | 1.00 | 0.00 |
| ATOM | 2579 | H2 | TIP3 | 24 | 5.766 | 57.455 | 64.842 | 1.00 | 0.00 |
| ATOM | 2580 | OH2 | TIP3 | 25 | 22.949 | 20.838 | 78.649 | 1.00 | 7.72 |
| ATOM | 2581 | H1 | TIP3 | 25 | 22.949 | 21.795 | 78.649 | 1.00 | 0.00 |
| ATOM | 2582 | H2 | TIP3 | 25 | 22.949 | 20.598 | 77.722 | 1.00 | 0.00 |
| ATOM | 2583 | OH2 | TIP3 | 26 | 2.733 | 57.289 | 67.930 | 1.00 | 22.68 |
| ATOM | 2584 | H1 | TIP3 | 26 | 2.733 | 58.246 | 67.930 | 1.00 | 0.00 |
| ATOM | 2585 | H2 | TIP3 | 26 | 2.733 | 57.049 | 67.003 | 1.00 | 0.00 |
| ATOM | 2586 | OH2 | TIP3 | 27 | 22.989 | 59.076 | 84.529 | 1.00 | 26.58 |
| ATOM | 2587 | H1 | TIP3 | 27 | 22.989 | 60.033 | 84.529 | 1.00 | 0.00 |
| ATOM | 2588 | H2 | TIP3 | 27 | 22.989 | 58.836 | 83.602 | 1.00 | 0.00 |
| ATOM | 2589 | OH2 | TIP3 | 28 | 6.600 | 45.426 | 68.417 | 1.00 | 15.86 |
| ATOM | 2590 | H1 | TIP3 | 28 | 6.600 | 46.383 | 68.417 | 1.00 | 0.00 |
| ATOM | 2591 | H2 | TIP3 | 28 | 6.600 | 45.186 | 67.490 | 1.00 | 0.00 |
| ATOM | 2592 | OH2 | TIP3 | 29 | 35.794 | 38.871 | 75.084 | 1.00 | 22.04 |
| ATOM | 2593 | H1 | TIP3 | 29 | 35.794 | 39.828 | 75.084 | 1.00 | 0.00 |
| ATOM | 2594 | H2 | TIP3 | 29 | 35.794 | 38.631 | 74.157 | 1.00 | 0.00 |
| ATOM | 2595 | OH2 | TIP3 | 30 | 34.627 | 37.253 | 69.864 | 1.00 | 50.13 |
| ATOM | 2596 | H1 | TIP3 | 30 | 34.627 | 38.210 | 69.864 | 1.00 | 0.00 |
| ATOM | 2597 | H2 | TIP3 | 30 | 34.627 | 37.013 | 68.937 | 1.00 | 0.00 |
| ATOM | 2598 | OH2 | TIP3 | 31 | 7.373 | 21.436 | 91.964 | 1.00 | 23.28 |
| ATOM | 2599 | H1 | TIP3 | 31 | 7.373 | 22.393 | 91.964 | 1.00 | 0.00 |
| ATOM | 2600 | H2 | TIP3 | 31 | 7.373 | 21.196 | 91.037 | 1.00 | 0.00 |
| ATOM | 2601 | OH2 | TIP3 | 32 | −1.814 | 21.280 | 94.994 | 1.00 | 22.97 |
| ATOM | 2602 | H1 | TIP3 | 32 | −1.814 | 22.237 | 94.994 | 1.00 | 0.00 |
| ATOM | 2603 | H2 | TIP3 | 32 | −1.814 | 21.040 | 94.067 | 1.00 | 0.00 |
| ATOM | 2604 | OH2 | TIP3 | 33 | 26.254 | 70.814 | 72.279 | 1.00 | 20.94 |
| ATOM | 2605 | H1 | TIP3 | 33 | 26.254 | 71.771 | 72.279 | 1.00 | 0.00 |
| ATOM | 2606 | H2 | TIP3 | 33 | 26.254 | 70.574 | 71.352 | 1.00 | 0.00 |
| ATOM | 2607 | OH2 | TIP3 | 34 | 32.329 | 34.138 | 72.344 | 1.00 | 38.70 |
| ATOM | 2608 | H1 | TIP3 | 34 | 32.329 | 35.095 | 72.344 | 1.00 | 0.00 |
| ATOM | 2609 | H2 | TIP3 | 34 | 32.329 | 33.898 | 71.417 | 1.00 | 0.00 |
| ATOM | 2610 | OH2 | TIP3 | 35 | 20.413 | 62.930 | 73.590 | 1.00 | 10.41 |
| ATOM | 2611 | H1 | TIP3 | 35 | 20.413 | 63.887 | 73.590 | 1.00 | 0.00 |
| ATOM | 2612 | H2 | TIP3 | 35 | 20.413 | 62.690 | 72.663 | 1.00 | 0.00 |
| ATOM | 2613 | OH2 | TIP3 | 902 | 3.977 | 45.581 | 68.420 | 1.00 | 41.91 |
| ATOM | 2614 | H1 | TIP3 | 902 | 3.977 | 46.538 | 68.420 | 1.00 | 0.00 |
| ATOM | 2615 | H2 | TIP3 | 902 | 3.977 | 45.341 | 67.493 | 1.00 | 0.00 |
| ATOM | 2616 | OH2 | TIP3 | 903 | 29.925 | 35.589 | 64.801 | 1.00 | 67.56 |
| ATOM | 2617 | H1 | TIP3 | 903 | 29.925 | 36.546 | 64.801 | 1.00 | 0.00 |
| ATOM | 2618 | H2 | TIP3 | 903 | 29.925 | 35.349 | 63.874 | 1.00 | 0.00 |
| ATOM | 2619 | OH2 | TIP3 | 904 | 19.000 | 39.034 | 84.271 | 1.00 | 26.89 |
| ATOM | 2620 | H1 | TIP3 | 904 | 19.000 | 39.991 | 84.271 | 1.00 | 0.00 |
| ATOM | 2621 | H2 | TIP3 | 904 | 19.000 | 38.794 | 83.344 | 1.00 | 0.00 |
| ATOM | 2622 | OH2 | TIP3 | 905 | 22.754 | 58.929 | 87.160 | 1.00 | 41.79 |
| ATOM | 2623 | H1 | TIP3 | 905 | 22.754 | 59.886 | 87.160 | 1.00 | 0.00 |
| ATOM | 2624 | H2 | TIP3 | 905 | 22.754 | 58.689 | 86.233 | 1.00 | 0.00 |
| ATOM | 2625 | OH2 | TIP3 | 906 | 25.318 | 54.478 | 89.399 | 1.00 | 48.02 |
| ATOM | 2626 | H1 | TIP3 | 906 | 25.318 | 55.435 | 86.399 | 1.00 | 0.00 |
| ATOM | 2627 | H2 | TIP3 | 906 | 25.318 | 54.238 | 85.472 | 1.00 | 0.00 |
| ATOM | 2628 | OH2 | TIP3 | 907 | 11.415 | 67.392 | 87.402 | 1.00 | 45.43 |
| ATOM | 2629 | H1 | TIP3 | 907 | 11.415 | 68.349 | 87.402 | 1.00 | 0.00 |
| ATOM | 2630 | H2 | TIP3 | 907 | 11.415 | 67.152 | 86.475 | 1.00 | 0.00 |
| ATOM | 2631 | OH2 | TIP3 | 908 | 2.211 | 53.015 | 75.319 | 1.00 | 25.26 |
| ATOM | 2632 | H1 | TIP3 | 908 | 2.211 | 53.972 | 75.319 | 1.00 | 0.00 |
| ATOM | 2633 | H2 | TIP3 | 908 | 2.211 | 52.775 | 74.392 | 1.00 | 0.00 |
| ATOM | 2634 | OH2 | TIP3 | 909 | 27.215 | 63.461 | 86.684 | 1.00 | 37.88 |
| ATOM | 2635 | H1 | TIP3 | 909 | 27.215 | 64.418 | 86.684 | 1.00 | 0.00 |
| ATOM | 2636 | H2 | TIP3 | 909 | 27.215 | 63.221 | 85.757 | 1.00 | 0.00 |
| ATOM | 2637 | OH2 | TIP3 | 910 | 12.718 | 25.990 | 76.741 | 1.00 | 33.62 |
| ATOM | 2638 | H1 | TIP3 | 910 | 12.718 | 26.947 | 76.741 | 1.00 | 0.00 |
| ATOM | 2639 | H2 | TIP3 | 910 | 12.718 | 25.750 | 75.814 | 1.00 | 0.00 |
| ATOM | 2640 | OH2 | TIP3 | 911 | 12.392 | 63.522 | 61.586 | 1.00 | 46.35 |
| ATOM | 2641 | H1 | TIP3 | 911 | 12.392 | 64.479 | 61.586 | 1.00 | 0.00 |
| ATOM | 2642 | H2 | TIP3 | 911 | 12.392 | 63.282 | 60.659 | 1.00 | 0.00 |
| ATOM | 2643 | OH2 | TIP3 | 912 | 10.143 | 24.894 | 82.530 | 1.00 | 36.93 |
| ATOM | 2644 | H1 | TIP3 | 912 | 10.143 | 25.851 | 82.530 | 1.00 | 0.00 |
| ATOM | 2645 | H2 | TIP3 | 912 | 10.143 | 24.654 | 81.603 | 1.00 | 0.00 |
| ATOM | 2646 | OH2 | TIP3 | 913 | 13.911 | 21.585 | 84.456 | 1.00 | 37.37 |
| ATOM | 2647 | H1 | TIP3 | 913 | 13.911 | 22.542 | 84.456 | 1.00 | 0.00 |
| ATOM | 2648 | H2 | TIP3 | 913 | 13.911 | 21.345 | 83.529 | 1.00 | 0.00 |
| ATOM | 2649 | OH2 | TIP3 | 914 | 24.550 | 30.957 | 97.509 | 1.00 | 31.43 |
| ATOM | 2650 | H1 | TIP3 | 914 | 24.550 | 31.914 | 97.509 | 1.00 | 0.00 |

TABLE 6-continued

Coordinates of Lck bound with damnacanthal

| | Atom Type | Res | # | X | Y | Z | Occ | B |
|---|---|---|---|---|---|---|---|---|
| ATOM | 2651 | H2 | TIP3 | 914 | 24.550 | 30.717 | 96.582 | 1.00 | 0.00 |
| ATOM | 2652 | OH2 | TIP3 | 915 | 12.547 | 36.425 | 79.544 | 1.00 | 47.28 |
| ATOM | 2653 | H1 | TIP3 | 915 | 12.547 | 37.382 | 79.544 | 1.00 | 0.00 |
| ATOM | 2654 | H2 | TIP3 | 915 | 12.547 | 36.185 | 78.617 | 1.00 | 0.00 |
| ATOM | 2655 | OH2 | TIP3 | 916 | 11.722 | 33.718 | 69.714 | 1.00 | 45.94 |
| ATOM | 2656 | H1 | TIP3 | 916 | 11.722 | 34.675 | 69.714 | 1.00 | 0.00 |
| ATOM | 2657 | H2 | TIP3 | 916 | 11.722 | 33.478 | 68.787 | 1.00 | 0.00 |
| ATOM | 2658 | OH2 | TIP3 | 917 | 42.845 | 37.058 | 69.840 | 1.00 | 69.82 |
| ATOM | 2659 | H1 | TIP3 | 917 | 42.845 | 36.015 | 68.840 | 1.00 | 0.00 |
| ATOM | 2660 | H2 | TIP3 | 917 | 42.845 | 36.818 | 68.913 | 1.00 | 0.00 |
| ATOM | 2661 | OH2 | TIP3 | 918 | 11.997 | 44.553 | 99.892 | 1.00 | 24.31 |
| ATOM | 2662 | H1 | TIP3 | 918 | 11.997 | 45.510 | 99.892 | 1.00 | 0.00 |
| ATOM | 2663 | H2 | TIP3 | 918 | 11.997 | 44.313 | 98.965 | 1.00 | 0.00 |
| ATOM | 2664 | OH2 | TIP3 | 919 | 13.938 | 69.177 | 74.324 | 1.00 | 32.00 |
| ATOM | 2665 | H1 | TIP3 | 919 | 13.938 | 70.134 | 74.324 | 1.00 | 0.00 |
| ATOM | 2666 | H2 | TIP3 | 919 | 13.938 | 68.937 | 73.397 | 1.00 | 0.00 |
| ATOM | 2667 | OH2 | TIP3 | 920 | 13.410 | 68.438 | 77.533 | 1.00 | 35.40 |
| ATOM | 2668 | H1 | TIP3 | 920 | 13.410 | 68.395 | 77.533 | 1.00 | 0.00 |
| ATOM | 2669 | H2 | TIP3 | 920 | 13.410 | 68.198 | 76.606 | 1.00 | 0.00 |
| ATOM | 2670 | OH2 | TIP3 | 921 | 26.444 | 65.850 | 74.397 | 1.00 | 28.46 |
| ATOM | 2671 | H1 | TIP3 | 921 | 26.444 | 66.807 | 74.397 | 1.00 | 0.00 |
| ATOM | 2672 | H2 | TIP3 | 921 | 26.444 | 65.610 | 73.470 | 1.00 | 0.00 |
| ATOM | 2673 | OH2 | TIP3 | 922 | 28.767 | 62.703 | 72.382 | 1.00 | 11.65 |
| ATOM | 2674 | H1 | TIP3 | 922 | 28.767 | 63.660 | 72.382 | 1.00 | 0.00 |
| ATOM | 2675 | H2 | TIP3 | 922 | 28.767 | 62.463 | 71.455 | 1.00 | 0.00 |
| ATOM | 2676 | OH2 | TIP3 | 923 | 25.938 | 56.867 | 57.692 | 1.00 | 23.34 |
| ATOM | 2677 | H1 | TIP3 | 923 | 25.938 | 57.824 | 57.692 | 1.00 | 0.00 |
| ATOM | 2678 | H2 | TIP3 | 923 | 25.938 | 56.627 | 56.765 | 1.00 | 0.00 |
| ATOM | 2679 | OH2 | TIP3 | 924 | 20.381 | 66.725 | 62.772 | 1.00 | 12.70 |
| ATOM | 2680 | H1 | TIP3 | 924 | 20.381 | 67.682 | 62.772 | 1.00 | 0.00 |
| ATOM | 2681 | H2 | TIP3 | 924 | 20.381 | 66.485 | 61.845 | 1.00 | 0.00 |
| ATOM | 2682 | OH2 | TIP3 | 925 | 16.636 | 62.383 | 62.449 | 1.00 | 25.25 |
| ATOM | 2683 | H1 | TIP3 | 925 | 16.636 | 63.340 | 62.449 | 1.00 | 0.00 |
| ATOM | 2684 | H2 | TIP3 | 925 | 16.636 | 62.143 | 61.522 | 1.00 | 0.00 |
| ATOM | 2685 | OH2 | TIP3 | 926 | 17.534 | 68.718 | 67.540 | 1.00 | 42.52 |
| ATOM | 2686 | H1 | TIP3 | 926 | 17.534 | 69.675 | 67.540 | 1.00 | 0.00 |
| ATOM | 2687 | H2 | TIP3 | 926 | 17.534 | 68.478 | 66.613 | 1.00 | 0.00 |
| ATOM | 2688 | OH2 | TIP3 | 927 | 11.120 | 66.752 | 68.562 | 1.00 | 31.26 |
| ATOM | 2689 | H1 | TIP3 | 927 | 11.120 | 67.709 | 68.562 | 1.00 | 0.00 |
| ATOM | 2690 | H2 | TIP3 | 927 | 11.120 | 66.512 | 67.635 | 1.00 | 0.00 |
| ATOM | 2691 | OH2 | TIP3 | 928 | 8.343 | 65.846 | 68.974 | 1.00 | 21.20 |
| ATOM | 2692 | H1 | TIP3 | 928 | 8.343 | 66.803 | 68.974 | 1.00 | 0.00 |
| ATOM | 2693 | H2 | TIP3 | 928 | 8.343 | 65.606 | 68.047 | 1.00 | 0.00 |
| ATOM | 2694 | OH2 | TIP3 | 929 | 9.792 | 67.479 | 78.506 | 1.00 | 32.47 |
| ATOM | 2695 | H1 | TIP3 | 929 | 9.792 | 68.436 | 78.506 | 1.00 | 0.00 |
| ATOM | 2696 | H2 | TIP3 | 929 | 9.792 | 67.239 | 77.579 | 1.00 | 0.00 |
| ATOM | 2697 | OH2 | TIP3 | 930 | −0.783 | 60.222 | 69.699 | 1.00 | 40.10 |
| ATOM | 2698 | H1 | TIP3 | 930 | −0.783 | 61.179 | 69.699 | 1.00 | 0.00 |
| ATOM | 2699 | H2 | TIP3 | 930 | −0.783 | 59.982 | 68.772 | 1.00 | 0.00 |
| ATOM | 2700 | OH2 | TIP3 | 931 | 3.209 | 57.518 | 73.689 | 1.00 | 44.52 |
| ATOM | 2701 | H1 | TIP3 | 931 | 3.209 | 58.475 | 73.689 | 1.00 | 0.00 |
| ATOM | 2702 | H2 | TIP3 | 931 | 3.209 | 57.278 | 72.762 | 1.00 | 0.00 |
| ATOM | 2703 | OH2 | TIP3 | 932 | 7.702 | 53.996 | 63.934 | 1.00 | 18.89 |
| ATOM | 2704 | H1 | TIP3 | 932 | 7.702 | 54.953 | 63.934 | 1.00 | 0.00 |
| ATOM | 2705 | H2 | TIP3 | 932 | 7.702 | 53.756 | 63.007 | 1.00 | 0.00 |
| ATOM | 2706 | OH2 | TIP3 | 933 | 4.531 | 48.455 | 67.309 | 1.00 | 29.32 |
| ATOM | 2707 | H1 | TIP3 | 933 | 4.531 | 49.412 | 67.309 | 1.00 | 0.00 |
| ATOM | 2708 | H2 | TIP3 | 933 | 4.531 | 48.215 | 66.382 | 1.00 | 0.00 |
| ATOM | 2709 | OH2 | TIP3 | 934 | 4.608 | 45.799 | 64.678 | 1.00 | 41.61 |
| ATOM | 2710 | H1 | TIP3 | 934 | 4.608 | 46.756 | 64.678 | 1.00 | 0.00 |
| ATOM | 2711 | H2 | TIP3 | 934 | 4.608 | 45.559 | 63.751 | 1.00 | 0.00 |
| ATOM | 2712 | OH2 | TIP3 | 935 | 12.361 | 55.277 | 56.911 | 1.00 | 28.76 |
| ATOM | 2713 | H1 | TIP3 | 935 | 12.361 | 56.234 | 56.911 | 1.00 | 0.00 |
| ATOM | 2714 | H2 | TIP3 | 935 | 12.361 | 55.037 | 55.984 | 1.00 | 0.00 |
| ATOM | 2715 | OH2 | TIP3 | 936 | 11.471 | 44.610 | 57.925 | 1.00 | 43.76 |
| ATOM | 2716 | H1 | TIP3 | 936 | 11.471 | 45.567 | 57.925 | 1.00 | 0.00 |
| ATOM | 2717 | H2 | TIP3 | 936 | 11.471 | 44.370 | 56.998 | 1.00 | 0.00 |
| ATOM | 2718 | OH2 | TIP3 | 937 | 16.215 | 39.893 | 58.610 | 1.00 | 27.98 |
| ATOM | 2719 | H1 | TIP3 | 937 | 16.215 | 40.850 | 58.610 | 1.00 | 0.00 |
| ATOM | 2720 | H2 | TIP3 | 937 | 16.215 | 39.653 | 57.683 | 1.00 | 0.00 |
| ATOM | 2721 | OH2 | TIP3 | 938 | 25.322 | 53.255 | 58.207 | 1.00 | 23.88 |
| ATOM | 2722 | H1 | TIP3 | 938 | 25.322 | 54.212 | 58.207 | 1.00 | 0.00 |
| ATOM | 2723 | H2 | TIP3 | 938 | 25.322 | 53.015 | 57.280 | 1.00 | 0.00 |
| ATOM | 2724 | OH2 | TIP3 | 939 | 21.201 | 46.368 | 52.244 | 1.00 | 41.58 |

TABLE 6-continued

Coordinates of Lck bound with damnacanthal

| | | Atom Type | Res | # | X | Y | Z | Occ | B |
|---|---|---|---|---|---|---|---|---|---|
| ATOM | 2725 | H1 | TIP3 | 939 | 21.201 | 47.325 | 52.244 | 1.00 | 0.00 |
| ATOM | 2726 | H2 | TIP3 | 939 | 21.201 | 46.128 | 51.317 | 1.00 | 0.00 |
| ATOM | 2727 | OH2 | TIP3 | 940 | 28.123 | 42.893 | 53.585 | 1.00 | 52.96 |
| ATOM | 2728 | H1 | TIP3 | 940 | 28.123 | 43.850 | 53.585 | 1.00 | 0.00 |
| ATOM | 2729 | H2 | TIP3 | 940 | 28.123 | 42.653 | 52.658 | 1.00 | 0.00 |
| ATOM | 2730 | OH2 | TIP3 | 941 | 38.859 | 50.436 | 80.121 | 1.00 | 30.78 |
| ATOM | 2731 | H1 | TIP3 | 941 | 38.859 | 51.393 | 80.121 | 1.00 | 0.00 |
| ATOM | 2732 | H2 | TIP3 | 941 | 38.859 | 50.196 | 79.194 | 1.00 | 0.00 |
| ATOM | 2733 | OH2 | TIP3 | 942 | 18.459 | 41.669 | 89.903 | 1.00 | 26.88 |
| ATOM | 2734 | H1 | TIP3 | 942 | 18.459 | 42.626 | 89.903 | 1.00 | 0.00 |
| ATOM | 2735 | H2 | TIP3 | 942 | 18.459 | 41.429 | 88.976 | 1.00 | 0.00 |
| ATOM | 2736 | OH2 | TIP3 | 943 | 10.063 | 36.916 | 107.716 | 1.00 | 45.59 |
| ATOM | 2737 | H1 | TIP3 | 943 | 10.063 | 37.873 | 107.716 | 1.00 | 0.00 |
| ATOM | 2738 | H2 | TIP3 | 943 | 10.063 | 36.676 | 106.789 | 1.00 | 0.00 |
| ATOM | 2739 | OH2 | TIP3 | 944 | 37.990 | 36.769 | 70.136 | 1.00 | 44.88 |
| ATOM | 2740 | H1 | TIP3 | 944 | 37.990 | 37.726 | 70.136 | 1.00 | 0.00 |
| ATOM | 2741 | H2 | TIP3 | 944 | 37.990 | 36.529 | 69.209 | 1.00 | 0.00 |
| ATOM | 2742 | OH2 | TIP3 | 945 | 23.161 | 29.511 | 77.682 | 1.00 | 21.17 |
| ATOM | 2743 | H1 | TIP3 | 945 | 23.161 | 30.468 | 77.682 | 1.00 | 0.00 |
| ATOM | 2744 | H2 | TIP3 | 945 | 23.161 | 29.271 | 76.755 | 1.00 | 0.00 |
| ATOM | 2745 | OH2 | TIP3 | 946 | 30.162 | 71.027 | 77.691 | 1.00 | 51.01 |
| ATOM | 2746 | H1 | TIP3 | 946 | 30.162 | 71.984 | 77.691 | 1.00 | 0.00 |
| ATOM | 2747 | H2 | TIP3 | 946 | 30.162 | 70.787 | 76.764 | 1.00 | 0.00 |
| ATOM | 2748 | OH2 | TIP3 | 947 | 16.595 | 42.125 | 92.194 | 1.00 | 20.14 |
| ATOM | 2749 | H1 | TIP3 | 947 | 16.595 | 43.082 | 92.194 | 1.00 | 0.00 |
| ATOM | 2750 | H2 | TIP3 | 947 | 16.595 | 41.885 | 91.267 | 1.00 | 0.00 |
| ATOM | 2751 | OH2 | TIP3 | 948 | 33.326 | 41.725 | 63.735 | 1.00 | 34.82 |
| ATOM | 2752 | H1 | TIP3 | 948 | 33.326 | 42.682 | 63.735 | 1.00 | 0.00 |
| ATOM | 2753 | H2 | TIP3 | 948 | 33.326 | 41.485 | 62.808 | 1.00 | 0.00 |
| ATOM | 2754 | OH2 | TIP3 | 949 | 3.342 | 32.254 | 81.251 | 1.00 | 59.47 |
| ATOM | 2755 | H1 | TIP3 | 949 | 3.342 | 33.211 | 81.251 | 1.00 | 0.00 |
| ATOM | 2756 | H2 | TIP3 | 949 | 3.342 | 32.014 | 80.324 | 1.00 | 0.00 |
| ATOM | 2757 | OH2 | TIP3 | 950 | 10.798 | 37.536 | 105.225 | 1.00 | 60.29 |
| ATOM | 2758 | H1 | TIP3 | 950 | 10.798 | 38.493 | 105.225 | 1.00 | 0.00 |
| ATOM | 2759 | H2 | TIP3 | 950 | 10.798 | 37.296 | 104.298 | 1.00 | 0.00 |
| ATOM | 2760 | OH2 | TIP3 | 951 | 38.244 | 59.441 | 68.131 | 1.00 | 56.10 |
| ATOM | 2761 | H1 | TIP3 | 951 | 38.244 | 60.398 | 68.131 | 1.00 | 0.00 |
| ATOM | 2762 | H2 | TIP3 | 951 | 38.244 | 59.201 | 67.204 | 1.00 | 0.00 |
| ATOM | 2763 | OH2 | TIP3 | 952 | 4.587 | 42.314 | 89.272 | 1.00 | 44.38 |
| ATOM | 2764 | H1 | TIP3 | 952 | 4.587 | 43.271 | 89.272 | 1.00 | 0.00 |
| ATOM | 2765 | H2 | TIP3 | 952 | 4.587 | 42.074 | 88.345 | 1.00 | 0.00 |
| ATOM | 2766 | OH2 | TIP3 | 953 | 27.081 | 20.290 | 78.278 | 1.00 | 27.86 |
| ATOM | 2767 | H1 | TIP3 | 953 | 27.081 | 21.247 | 78.278 | 1.00 | 0.00 |
| ATOM | 2768 | H2 | TIP3 | 953 | 27.081 | 20.050 | 77.351 | 1.00 | 0.00 |
| ATOM | 2769 | OH2 | TIP3 | 955 | −0.652 | 31.568 | 89.309 | 1.00 | 34.23 |
| ATOM | 2770 | H1 | TIP3 | 955 | −0.652 | 32.525 | 89.309 | 1.00 | 0.00 |
| ATOM | 2771 | H2 | TIP3 | 955 | −0.652 | 31.328 | 88.382 | 1.00 | 0.00 |
| ATOM | 2772 | OH2 | TIP3 | 956 | 30.004 | 41.225 | 82.705 | 1.00 | 35.02 |
| ATOM | 2773 | H1 | TIP3 | 956 | 30.004 | 42.182 | 82.705 | 1.00 | 0.00 |
| ATOM | 2774 | H2 | TIP3 | 956 | 30.004 | 40.985 | 81.778 | 1.00 | 0.00 |
| ATOM | 2775 | OH2 | TIP3 | 957 | 32.830 | 40.624 | 78.555 | 1.00 | 35.46 |
| ATOM | 2776 | H1 | TIP3 | 957 | 32.830 | 41.581 | 78.555 | 1.00 | 0.00 |
| ATOM | 2777 | H2 | TIP3 | 957 | 32.830 | 40.384 | 77.628 | 1.00 | 0.00 |
| ATOM | 2778 | OH2 | TIP3 | 958 | 23.297 | 42.589 | 84.800 | 1.00 | 37.53 |
| ATOM | 2779 | H1 | TIP3 | 958 | 23.297 | 43.546 | 84.800 | 1.00 | 0.00 |
| ATOM | 2780 | H2 | TIP3 | 958 | 23.297 | 42.349 | 83.873 | 1.00 | 0.00 |
| ATOM | 2781 | OH2 | TIP3 | 959 | 21.348 | 42.245 | 91.264 | 1.00 | 36.91 |
| ATOM | 2782 | H1 | TIP3 | 959 | 21.348 | 43.202 | 91.264 | 1.00 | 0.00 |
| ATOM | 2783 | H2 | TIP3 | 959 | 21.348 | 42.005 | 90.337 | 1.00 | 0.00 |
| ATOM | 2784 | S | SO4 | 901 | 20.077 | 32.993 | 69.827 | 1.00 | 8.33 |
| ATOM | 2785 | O1 | SO4 | 901 | 19.658 | 32.468 | 71.037 | 1.00 | 12.44 |
| ATOM | 2786 | O2 | SO4 | 901 | 18.988 | 33.437 | 69.067 | 1.00 | 7.14 |
| ATOM | 2787 | O3 | SO4 | 901 | 20.947 | 34.096 | 70.157 | 1.00 | 9.66 |
| ATOM | 2788 | O4 | SO4 | 901 | 20.793 | 31.996 | 69.016 | 1.00 | 8.00 |
| ATOM END | | | | | | | | | |

TABLE 7

Coordinates of Lck bound with PD153035

| | | Atom Type | Res | # | X | Y | Z | Occ | B |
|---|---|---|---|---|---|---|---|---|---|
| ATOM | 1 | CB | LYS | 231 | 1.308 | 26.760 | 90.013 | 1.00 | 25.95 |
| ATOM | 2 | CG | LYS | 231 | 0.543 | 26.788 | 88.714 | 1.00 | 26.69 |
| ATOM | 3 | CD | LYS | 231 | 1.112 | 25.687 | 87.830 | 1.00 | 27.64 |
| ATOM | 4 | CE | LYS | 231 | 0.322 | 25.469 | 86.562 | 1.00 | 28.05 |
| ATOM | 5 | NZ | LYS | 231 | 1.078 | 24.533 | 85.684 | 1.00 | 28.29 |
| ATOM | 9 | C | LYS | 231 | 1.852 | 27.635 | 92.257 | 1.00 | 24.68 |
| ATOM | 10 | O | LYS | 231 | 2.891 | 28.263 | 92.373 | 1.00 | 24.83 |
| ATOM | 13 | N | LYS | 231 | 1.230 | 29.199 | 90.447 | 1.00 | 25.47 |
| ATOM | 15 | CA | LYS | 231 | 0.972 | 27.850 | 91.033 | 1.00 | 25.33 |
| ATOM | 16 | N | PRO | 232 | 1.418 | 26.779 | 93.211 | 1.00 | 24.19 |
| ATOM | 17 | CD | PRO | 232 | 0.146 | 26.026 | 93.224 | 1.00 | 24.14 |
| ATOM | 18 | CA | PRO | 232 | 2.198 | 26.489 | 94.425 | 1.00 | 23.56 |
| ATOM | 19 | CB | PRO | 232 | 1.299 | 25.503 | 95.180 | 1.00 | 23.89 |
| ATOM | 20 | CG | PRO | 232 | 0.509 | 24.844 | 94.082 | 1.00 | 24.01 |
| ATOM | 21 | C | PRO | 232 | 3.499 | 25.820 | 93.969 | 1.00 | 22.59 |
| ATOM | 22 | O | PRO | 232 | 3.522 | 25.185 | 92.917 | 1.00 | 21.81 |
| ATOM | 23 | N | TRP | 233 | 4.552 | 25.931 | 94.769 | 1.00 | 22.02 |
| ATOM | 25 | CA | TRP | 233 | 5.858 | 25.367 | 94.390 | 1.00 | 21.66 |
| ATOM | 26 | CB | TRP | 233 | 6.949 | 25.702 | 95.437 | 1.00 | 20.86 |
| ATOM | 27 | CG | TRP | 233 | 6.841 | 24.981 | 96.757 | 1.00 | 19.60 |
| ATOM | 28 | CD2 | TRP | 233 | 7.280 | 23.644 | 97.048 | 1.00 | 19.16 |
| ATOM | 29 | CE2 | TRP | 233 | 6.975 | 23.388 | 98.409 | 1.00 | 19.16 |
| ATOM | 30 | CE3 | TRP | 233 | 7.893 | 22.638 | 96.294 | 1.00 | 19.01 |
| ATOM | 31 | CD1 | TRP | 233 | 6.310 | 25.465 | 97.915 | 1.00 | 19.20 |
| ATOM | 32 | NE1 | TRP | 233 | 6.390 | 24.516 | 98.912 | 1.00 | 19.09 |
| ATOM | 34 | CZ2 | TRP | 233 | 7.260 | 22.163 | 99.026 | 1.00 | 18.61 |
| ATOM | 35 | CZ3 | TRP | 233 | 8.177 | 21.421 | 96.904 | 1.00 | 18.42 |
| ATOM | 36 | CH2 | TRP | 233 | 7.858 | 21.194 | 98.263 | 1.00 | 18.49 |
| ATOM | 37 | C | TRP | 233 | 5.892 | 23.868 | 94.015 | 1.00 | 21.78 |
| ATOM | 38 | O | TRP | 233 | 6.698 | 23.468 | 93.158 | 1.00 | 21.60 |
| ATOM | 39 | N | TRP | 234 | 5.016 | 23.060 | 94.630 | 1.00 | 21.88 |
| ATOM | 41 | CA | TRP | 234 | 4.954 | 21.616 | 94.362 | 1.00 | 22.22 |
| ATOM | 42 | CB | TRP | 234 | 4.325 | 20.865 | 95.553 | 1.00 | 21.89 |
| ATOM | 43 | CG | TRP | 234 | 2.940 | 21.307 | 95.917 | 1.00 | 21.33 |
| ATOM | 44 | CD2 | TRP | 234 | 2.562 | 22.278 | 96.907 | 1.00 | 21.26 |
| ATOM | 45 | CE2 | TRP | 234 | 1.153 | 22.326 | 96.918 | 1.00 | 21.16 |
| ATOM | 46 | CE3 | TRP | 234 | 3.287 | 23.103 | 97.787 | 1.00 | 20.85 |
| ATOM | 47 | CD1 | TRP | 234 | 1.760 | 20.837 | 95.377 | 1.00 | 21.60 |
| ATOM | 48 | NE1 | TRP | 234 | 0.694 | 21.455 | 95.984 | 1.00 | 21.20 |
| ATOM | 50 | CZ2 | TRP | 234 | 0.451 | 23.176 | 97.783 | 1.00 | 21.29 |
| ATOM | 51 | CZ3 | TRP | 234 | 2.575 | 23.943 | 98.637 | 1.00 | 21.10 |
| ATOM | 52 | CH2 | TRP | 234 | 1.173 | 23.966 | 98.632 | 1.00 | 20.96 |
| ATOM | 53 | C | TRP | 234 | 4.276 | 21.279 | 93.016 | 1.00 | 22.92 |
| ATOM | 54 | O | TRP | 234 | 4.276 | 20.128 | 92.557 | 1.00 | 22.48 |
| ATOM | 55 | N | GLU | 235 | 3.712 | 22.301 | 92.388 | 1.00 | 24.00 |
| ATOM | 57 | CA | GLU | 235 | 3.092 | 22.179 | 91.075 | 1.00 | 24.88 |
| ATOM | 58 | CB | GLU | 235 | 1.615 | 22.573 | 91.112 | 1.00 | 25.12 |
| ATOM | 59 | CG | GLU | 235 | 0.747 | 21.638 | 91.915 | 1.00 | 25.47 |
| ATOM | 60 | CD | GLU | 235 | −0.730 | 21.824 | 91.650 | 1.00 | 25.68 |
| ATOM | 61 | OE1 | GLU | 235 | −1.126 | 22.784 | 90.935 | 1.00 | 26.26 |
| ATOM | 62 | OE2 | GLU | 235 | −1.492 | 20.985 | 92.179 | 1.00 | 26.26 |
| ATOM | 63 | C | GLU | 235 | 3.819 | 23.126 | 90.120 | 1.00 | 25.33 |
| ATOM | 64 | O | GLU | 235 | 3.576 | 23.105 | 88.919 | 1.00 | 25.36 |
| ATOM | 65 | N | ASP | 236 | 4.716 | 23.954 | 90.650 | 1.00 | 25.69 |
| ATOM | 67 | CA | ASP | 236 | 5.432 | 24.895 | 89.794 | 1.00 | 26.27 |
| ATOM | 68 | CB | ASP | 236 | 6.148 | 25.987 | 90.609 | 1.00 | 26.83 |
| ATOM | 69 | CG | ASP | 236 | 6.428 | 27.222 | 89.790 | 1.00 | 27.36 |
| ATOM | 70 | OD1 | ASP | 236 | 7.260 | 28.043 | 90.229 | 1.00 | 28.12 |
| ATOM | 71 | OD2 | ASP | 236 | 7.260 | 28.043 | 90.229 | 1.00 | 28.12 |
| ATOM | 72 | C | ASP | 236 | 6.411 | 24.231 | 88.828 | 1.00 | 26.24 |
| ATOM | 73 | O | ASP | 236 | 7.270 | 23.439 | 89.219 | 1.00 | 26.32 |
| ATOM | 74 | N | GLU | 237 | 6.291 | 24.626 | 87.567 | 1.00 | 25.96 |
| ATOM | 76 | CA | GLU | 237 | 7.136 | 24.146 | 86.487 | 1.00 | 25.67 |
| ATOM | 77 | CB | GLU | 237 | 6.604 | 24.691 | 85.161 | 1.00 | 26.29 |
| ATOM | 78 | CG | GLU | 237 | 5.075 | 24.584 | 85.010 | 1.00 | 27.43 |
| ATOM | 79 | CD | GLU | 237 | 4.318 | 25.863 | 85.383 | 1.00 | 28.00 |
| ATOM | 80 | OE1 | GLU | 237 | 4.351 | 26.302 | 86.553 | 1.00 | 28.57 |
| ATOM | 81 | OE2 | GLU | 237 | 3.652 | 26.417 | 84.484 | 1.00 | 28.97 |
| ATOM | 82 | C | GLU | 237 | 8.600 | 24.587 | 86.666 | 1.00 | 24.89 |
| ATOM | 83 | O | GLU | 237 | 9.514 | 23.914 | 86.194 | 1.00 | 25.08 |
| ATOM | 84 | N | TRP | 238 | 8.815 | 25.661 | 87.427 | 1.00 | 23.85 |
| ATOM | 86 | CA | TRP | 238 | 10.151 | 26.217 | 87.626 | 1.00 | 22.63 |
| ATOM | 87 | CB | TRP | 238 | 10.110 | 27.736 | 87.465 | 1.00 | 22.91 |
| ATOM | 88 | CG | TRP | 238 | 9.889 | 28.179 | 86.056 | 1.00 | 23.06 |

TABLE 7-continued

Coordinates of Lck bound with PD153035

| | | Atom Type | Res | # | X | Y | Z | Occ | B |
|---|---|---|---|---|---|---|---|---|---|
| ATOM | 89 | CD2 | TRP | 238 | 8.634 | 28.497 | 85.448 | 1.00 | 23.12 |
| ATOM | 90 | CE2 | TRP | 238 | 8.896 | 28.856 | 84.111 | 1.00 | 23.38 |
| ATOM | 91 | CE3 | TRP | 238 | 7.310 | 28.500 | 85.906 | 1.00 | 22.97 |
| ATOM | 92 | CD1 | TRP | 238 | 10.840 | 28.356 | 85.092 | 1.00 | 23.04 |
| ATOM | 93 | NE1 | TRP | 238 | 10.251 | 28.766 | 83.915 | 1.00 | 23.51 |
| ATOM | 95 | CZ2 | TRP | 238 | 7.888 | 29.225 | 83.230 | 1.00 | 23.48 |
| ATOM | 96 | CZ3 | TRP | 238 | 6.313 | 28.860 | 85.038 | 1.00 | 22.98 |
| ATOM | 97 | CH2 | TRP | 238 | 6.602 | 29.216 | 83.706 | 1.00 | 23.53 |
| ATOM | 98 | C | TRP | 238 | 10.916 | 25.860 | 88.897 | 1.00 | 21.67 |
| ATOM | 99 | O | TRP | 238 | 12.141 | 25.981 | 88.932 | 1.00 | 21.55 |
| ATOM | 100 | N | GLU | 239 | 10.210 | 25.461 | 89.948 | 1.00 | 20.22 |
| ATOM | 102 | CA | GLU | 239 | 10.868 | 25.106 | 91.203 | 1.00 | 19.17 |
| ATOM | 103 | CB | GLU | 239 | 9.825 | 24.788 | 92.285 | 1.00 | 18.77 |
| ATOM | 104 | CG | GLU | 239 | 10.406 | 24.547 | 93.665 | 1.00 | 18.02 |
| ATOM | 105 | CD | GLU | 239 | 10.767 | 25.835 | 94.388 | 1.00 | 17.60 |
| ATOM | 106 | OE1 | GLU | 239 | 10.133 | 26.880 | 94.112 | 1.00 | 17.55 |
| ATOM | 107 | OE2 | GLU | 239 | 11.665 | 25.812 | 95.252 | 1.00 | 17.17 |
| ATOM | 108 | C | GLU | 239 | 11.766 | 23.883 | 91.011 | 1.00 | 18.60 |
| ATOM | 109 | O | GLU | 239 | 11.345 | 22.907 | 90.378 | 1.00 | 18.07 |
| ATOM | 110 | N | VAL | 240 | 13.020 | 23.967 | 91.471 | 1.00 | 18.01 |
| ATOM | 112 | CA | VAL | 240 | 13.923 | 22.817 | 91.388 | 1.00 | 17.50 |
| ATOM | 113 | CB | VAL | 240 | 15.018 | 22.896 | 90.241 | 1.00 | 16.88 |
| ATOM | 114 | CG1 | VAL | 240 | 14.379 | 23.051 | 88.894 | 1.00 | 16.76 |
| ATOM | 115 | CG2 | VAL | 240 | 16.070 | 23.992 | 90.534 | 1.00 | 16.73 |
| ATOM | 116 | C | VAL | 240 | 14.634 | 22.589 | 92.709 | 1.00 | 17.52 |
| ATOM | 117 | O | VAL | 240 | 14.843 | 23.530 | 93.485 | 1.00 | 17.61 |
| ATOM | 118 | N | PRO | 241 | 14.908 | 21.312 | 93.040 | 1.00 | 17.40 |
| ATOM | 119 | CD | PRO | 241 | 14.386 | 20.089 | 92.391 | 1.00 | 17.64 |
| ATOM | 120 | CA | PRO | 241 | 15.607 | 20.984 | 94.290 | 1.00 | 17.91 |
| ATOM | 121 | CB | PRO | 241 | 15.736 | 19.452 | 94.210 | 1.00 | 17.56 |
| ATOM | 122 | CG | PRO | 241 | 14.469 | 19.046 | 93.533 | 1.00 | 17.25 |
| ATOM | 123 | C | PRO | 241 | 16.982 | 21.659 | 94.272 | 1.00 | 18.22 |
| ATOM | 124 | O | PRO | 241 | 17.662 | 21.625 | 93.245 | 1.00 | 18.11 |
| ATOM | 125 | N | ARG | 242 | 17.408 | 22.258 | 95.383 | 1.00 | 18.55 |
| ATOM | 127 | CA | ARG | 242 | 18.719 | 22.925 | 95.387 | 1.00 | 19.12 |
| ATOM | 128 | CB | ARG | 242 | 19.003 | 23.612 | 96.723 | 1.00 | 19.74 |
| ATOM | 129 | CG | ARG | 242 | 20.164 | 24.638 | 96.647 | 1.00 | 20.08 |
| ATOM | 130 | CD | ARG | 242 | 20.560 | 25.199 | 98.016 | 1.00 | 20.60 |
| ATOM | 131 | NE | ARG | 242 | 19.418 | 25.660 | 98.814 | 1.00 | 20.26 |
| ATOM | 133 | CZ | ARG | 242 | 18.897 | 26.883 | 98.741 | 1.00 | 20.86 |
| ATOM | 134 | NH1 | ARG | 242 | 19.407 | 27.762 | 97.902 | 1.00 | 20.72 |
| ATOM | 137 | NH2 | ARG | 242 | 17.924 | 27.255 | 99.566 | 1.00 | 20.67 |
| ATOM | 140 | C | ARG | 242 | 19.886 | 21.977 | 95.001 | 1.00 | 19.11 |
| ATOM | 141 | O | ARG | 242 | 20.882 | 22.409 | 94.415 | 1.00 | 18.87 |
| ATOM | 142 | N | GLU | 243 | 19.686 | 20.679 | 95.231 | 1.00 | 18.81 |
| ATOM | 144 | CA | GLU | 243 | 20.666 | 19.634 | 94.919 | 1.00 | 18.48 |
| ATOM | 145 | CB | GLU | 243 | 20.183 | 18.268 | 95.430 | 1.00 | 19.18 |
| ATOM | 146 | CG | GLU | 243 | 19.988 | 18.174 | 96.943 | 1.00 | 20.67 |
| ATOM | 147 | CD | GLU | 243 | 18.784 | 18.966 | 97.436 | 1.00 | 20.86 |
| ATOM | 148 | OE1 | GLU | 243 | 17.746 | 18.966 | 96.739 | 1.00 | 21.24 |
| ATOM | 149 | OE2 | GLU | 243 | 18.870 | 19.585 | 98.523 | 1.00 | 22.29 |
| ATOM | 150 | C | GLU | 243 | 21.021 | 19.528 | 93.429 | 1.00 | 17.63 |
| ATOM | 151 | O | GLU | 243 | 22.104 | 19.069 | 93.066 | 1.00 | 17.73 |
| ATOM | 152 | N | THR | 244 | 20.146 | 20.042 | 92.574 | 1.00 | 16.63 |
| ATOM | 154 | CA | THR | 244 | 20.370 | 19.996 | 91.124 | 1.00 | 15.86 |
| ATOM | 155 | CB | THR | 244 | 19.079 | 20.361 | 90.332 | 1.00 | 15.28 |
| ATOM | 156 | OG1 | THR | 244 | 18.608 | 21.662 | 90.728 | 1.00 | 15.76 |
| ATOM | 158 | CG2 | THR | 244 | 17.987 | 19.330 | 90.550 | 1.00 | 15.04 |
| ATOM | 159 | C | THR | 244 | 21.463 | 20.976 | 90.710 | 1.00 | 15.41 |
| ATOM | 160 | O | THR | 244 | 22.004 | 20.891 | 89.624 | 1.00 | 15.09 |
| ATOM | 161 | N | LEU | 245 | 21.819 | 21.892 | 91.608 | 1.00 | 15.28 |
| ATOM | 163 | CA | LEU | 245 | 22.787 | 22.918 | 91.303 | 1.00 | 15.43 |
| ATOM | 164 | CB | LEU | 245 | 22.149 | 24.296 | 91.546 | 1.00 | 15.17 |
| ATOM | 165 | CG | LEU | 245 | 20.772 | 24.632 | 90.954 | 1.00 | 14.94 |
| ATOM | 166 | CD1 | LEU | 245 | 20.170 | 25.864 | 91.661 | 1.00 | 15.11 |
| ATOM | 167 | CD2 | LEU | 245 | 20.881 | 24.815 | 89.450 | 1.00 | 15.27 |
| ATOM | 168 | C | LEU | 245 | 24.134 | 22.900 | 92.027 | 1.00 | 15.50 |
| ATOM | 169 | O | LEU | 245 | 24.211 | 22.774 | 93.255 | 1.00 | 15.39 |
| ATOM | 170 | N | LYS | 246 | 25.167 | 23.191 | 91.255 | 1.00 | 15.76 |
| ATOM | 172 | CA | LYS | 246 | 26.521 | 23.277 | 91.781 | 1.00 | 16.17 |
| ATOM | 173 | CB | LYS | 246 | 27.437 | 22.204 | 91.178 | 1.00 | 16.84 |
| ATOM | 174 | CG | LYS | 246 | 28.873 | 22.319 | 91.640 | 1.00 | 17.48 |
| ATOM | 175 | CD | LYS | 246 | 29.822 | 21.640 | 90.663 | 1.00 | 19.20 |
| ATOM | 176 | CE | LYS | 246 | 31.168 | 21.341 | 91.338 | 1.00 | 19.77 |

TABLE 7-continued

Coordinates of Lck bound with PD153035

| Atom | | | | | | | | |
|---|---|---|---|---|---|---|---|---|
| | Type | Res | # | X | Y | Z | Occ | B |
| ATOM | 177 | NZ | LYS | 246 | 31.986 | 20.397 | 90.497 | 1.00 | 20.33 |
| ATOM | 181 | C | LYS | 246 | 27.008 | 24.652 | 91.322 | 1.00 | 15.92 |
| ATOM | 182 | O | LYS | 246 | 27.060 | 24.910 | 90.122 | 1.00 | 15.86 |
| ATOM | 183 | N | LEU | 247 | 27.291 | 25.518 | 92.285 | 0.60 | 15.87 |
| ATOM | 185 | CA | LEU | 247 | 27.787 | 26.879 | 92.030 | 0.60 | 15.95 |
| ATOM | 186 | CB | LEU | 247 | 27.412 | 27.804 | 93.185 | 0.60 | 15.50 |
| ATOM | 187 | CG | LEU | 247 | 26.004 | 28.413 | 93.207 | 0.60 | 15.74 |
| ATOM | 188 | CD1 | LEU | 247 | 24.899 | 27.396 | 93.067 | 0.60 | 15.84 |
| ATOM | 189 | CD2 | LEU | 247 | 25.872 | 29.212 | 94.502 | 0.60 | 15.52 |
| ATOM | 190 | C | LEU | 247 | 29.308 | 26.816 | 91.853 | 0.60 | 16.33 |
| ATOM | 191 | O | LEU | 247 | 30.037 | 26.430 | 92.761 | 0.60 | 15.75 |
| ATOM | 192 | N | VAL | 248 | 29.777 | 27.234 | 90.685 | 1.00 | 16.99 |
| ATOM | 194 | CA | VAL | 248 | 31.187 | 27.166 | 90.323 | 1.00 | 17.42 |
| ATOM | 195 | CB | VAL | 248 | 31.330 | 26.570 | 88.912 | 1.00 | 17.24 |
| ATOM | 196 | CG1 | VAL | 248 | 32.745 | 26.779 | 88.365 | 1.00 | 17.55 |
| ATOM | 197 | CG2 | VAL | 248 | 30.994 | 25.096 | 88.934 | 1.00 | 17.30 |
| ATOM | 198 | C | VAL | 248 | 32.071 | 28.404 | 90.445 | 1.00 | 18.24 |
| ATOM | 199 | O | VAL | 248 | 33.167 | 28.327 | 90.997 | 1.00 | 18.51 |
| ATOM | 200 | N | GLU | 249 | 31.620 | 29.531 | 89.923 | 1.00 | 18.60 |
| ATOM | 202 | CA | GLU | 249 | 32.425 | 30.740 | 89.955 | 1.00 | 19.49 |
| ATOM | 203 | CB | GLU | 249 | 33.102 | 30.888 | 88.597 | 1.00 | 19.87 |
| ATOM | 204 | CG | GLU | 249 | 33.839 | 32.186 | 88.355 | 1.00 | 20.44 |
| ATOM | 205 | CD | GLU | 249 | 34.357 | 32.298 | 86.927 | 1.00 | 20.72 |
| ATOM | 206 | OE1 | GLU | 249 | 33.896 | 31.536 | 86.040 | 1.00 | 21.25 |
| ATOM | 207 | OE2 | GLU | 249 | 35.226 | 33.157 | 86.681 | 1.00 | 21.07 |
| ATOM | 208 | C | GLU | 249 | 31.551 | 31.961 | 90.235 | 1.00 | 19.97 |
| ATOM | 209 | O | GLU | 249 | 30.490 | 32.110 | 89.648 | 1.00 | 19.90 |
| ATOM | 210 | N | ARG | 250 | 31.970 | 32.811 | 91.154 | 1.00 | 20.52 |
| ATOM | 212 | CA | ARG | 250 | 31.182 | 34.001 | 91.432 | 1.00 | 20.99 |
| ATOM | 213 | CB | ARG | 250 | 31.426 | 34.523 | 92.847 | 1.00 | 23.07 |
| ATOM | 214 | CG | ARG | 250 | 30.479 | 35.656 | 93.211 | 1.00 | 23.47 |
| ATOM | 215 | CD | ARG | 250 | 30.580 | 36.086 | 94.674 | 1.00 | 24.86 |
| ATOM | 216 | NE | ARG | 250 | 31.936 | 35.955 | 95.183 | 1.00 | 25.99 |
| ATOM | 218 | CZ | ARG | 250 | 32.383 | 36.509 | 96.302 | 1.00 | 26.36 |
| ATOM | 219 | NH1 | ARG | 250 | 31.586 | 37.266 | 97.057 | 1.00 | 26.68 |
| ATOM | 222 | NH2 | ARG | 250 | 33.626 | 36.248 | 96.698 | 1.00 | 26.86 |
| ATOM | 225 | C | ARG | 250 | 31.554 | 35.038 | 90.390 | 1.00 | 20.61 |
| ATOM | 226 | O | ARG | 250 | 32.742 | 35.292 | 90.159 | 1.00 | 20.60 |
| ATOM | 227 | N | LEU | 251 | 30.544 | 35.583 | 89.718 | 1.00 | 19.72 |
| ATOM | 229 | CA | LEU | 251 | 30.743 | 36.576 | 88.677 | 1.00 | 19.14 |
| ATOM | 230 | CB | LEU | 251 | 29.806 | 36.312 | 87.496 | 1.00 | 18.96 |
| ATOM | 231 | CG | LEU | 251 | 29.825 | 34.901 | 86.930 | 1.00 | 18.57 |
| ATOM | 232 | CD1 | LEU | 251 | 28.736 | 34.756 | 85.904 | 1.00 | 18.34 |
| ATOM | 233 | CD2 | LEU | 251 | 31.169 | 34.631 | 86.327 | 1.00 | 18.74 |
| ATOM | 234 | C | LEU | 251 | 30.473 | 37.983 | 89.187 | 1.00 | 19.10 |
| ATOM | 235 | O | LEU | 251 | 30.889 | 38.957 | 88.540 | 1.00 | 18.81 |
| ATOM | 236 | N | GLY | 252 | 29.702 | 38.079 | 90.273 | 1.00 | 18.81 |
| ATOM | 238 | CA | GLY | 252 | 29.371 | 39.376 | 90.843 | 1.00 | 18.71 |
| ATOM | 239 | C | GLY | 252 | 28.812 | 39.279 | 92.248 | 1.00 | 18.63 |
| ATOM | 240 | O | GLY | 252 | 28.263 | 38.254 | 92.635 | 1.00 | 18.14 |
| ATOM | 241 | N | ALA | 253 | 28.999 | 40.339 | 93.036 | 1.00 | 18.80 |
| ATOM | 243 | CA | ALA | 253 | 28.492 | 40.390 | 94.403 | 1.00 | 19.28 |
| ATOM | 244 | CB | ALA | 253 | 29.495 | 39.795 | 95.393 | 1.00 | 19.53 |
| ATOM | 245 | C | ALA | 253 | 28.139 | 41.814 | 94.800 | 1.00 | 19.68 |
| ATOM | 246 | O | ALA | 253 | 28.832 | 42.768 | 94.450 | 1.00 | 19.58 |
| ATOM | 247 | N | GLY | 254 | 27.020 | 41.943 | 95.486 | 1.00 | 20.09 |
| ATOM | 249 | CA | GLY | 254 | 26.590 | 43.242 | 95.918 | 1.00 | 20.72 |
| ATOM | 250 | C | GLY | 254 | 25.753 | 43.221 | 97.169 | 1.00 | 21.17 |
| ATOM | 251 | O | GLY | 254 | 25.666 | 42.244 | 97.907 | 1.00 | 21.36 |
| ATOM | 252 | N | GLN | 255 | 25.100 | 44.348 | 97.357 | 1.00 | 21.76 |
| ATOM | 254 | CA | GLN | 255 | 24.235 | 44.608 | 98.480 | 1.00 | 22.22 |
| ATOM | 255 | CB | GLN | 255 | 23.636 | 45.972 | 98.250 | 1.00 | 22.70 |
| ATOM | 256 | CG | GLN | 255 | 23.032 | 46.647 | 99.422 | 1.00 | 23.40 |
| ATOM | 257 | CD | GLN | 255 | 22.605 | 48.035 | 99.022 | 1.00 | 23.38 |
| ATOM | 258 | OE1 | GLN | 255 | 21.768 | 48.630 | 99.665 | 1.00 | 24.47 |
| ATOM | 259 | NE2 | GLN | 255 | 23.172 | 48.547 | 97.921 | 1.00 | 24.09 |
| ATOM | 262 | C | GLN | 255 | 23.107 | 43.605 | 98.558 | 1.00 | 22.24 |
| ATOM | 263 | O | GLN | 255 | 22.741 | 43.155 | 99.644 | 1.00 | 22.21 |
| ATOM | 264 | N | PHE | 256 | 22.545 | 43.266 | 97.403 | 1.00 | 22.01 |
| ATOM | 266 | CA | PHE | 256 | 21.394 | 42.356 | 97.368 | 1.00 | 21.69 |
| ATOM | 267 | CB | PHE | 256 | 20.398 | 42.865 | 96.321 | 1.00 | 21.98 |
| ATOM | 268 | CG | PHE | 256 | 20.054 | 44.317 | 96.492 | 1.00 | 22.30 |
| ATOM | 269 | CD1 | PHE | 256 | 19.527 | 44.780 | 97.697 | 1.00 | 22.20 |
| ATOM | 270 | CD2 | PHE | 256 | 20.334 | 45.238 | 95.476 | 1.00 | 22.23 |

TABLE 7-continued

Coordinates of Lck bound with PD153035

| | | Atom Type | Res | # | X | Y | Z | Occ | B |
|---|---|---|---|---|---|---|---|---|---|
| ATOM | 271 | CE1 | PHE | 256 | 19.270 | 46.146 | 97.899 | 1.00 | 22.35 |
| ATOM | 272 | CE2 | PHE | 256 | 20.084 | 46.608 | 95.657 | 1.00 | 22.42 |
| ATOM | 273 | CZ | PHE | 256 | 19.564 | 47.062 | 96.869 | 1.00 | 22.41 |
| ATOM | 274 | C | PHE | 256 | 21.696 | 40.879 | 97.169 | 1.00 | 21.24 |
| ATOM | 275 | O | PHE | 256 | 20.780 | 40.058 | 97.105 | 1.00 | 21.09 |
| ATOM | 276 | N | GLY | 257 | 22.975 | 40.556 | 97.010 | 1.00 | 20.46 |
| ATOM | 278 | CA | GLY | 257 | 23.335 | 39.162 | 96.829 | 1.00 | 19.62 |
| ATOM | 279 | C | GLY | 257 | 24.460 | 38.944 | 95.851 | 1.00 | 18.79 |
| ATOM | 280 | O | GLY | 257 | 25.214 | 39.882 | 95.561 | 1.00 | 18.61 |
| ATOM | 281 | N | GLU | 258 | 24.539 | 37.726 | 95.305 | 1.00 | 18.08 |
| ATOM | 283 | CA | GLU | 258 | 25.603 | 37.376 | 94.348 | 1.00 | 17.42 |
| ATOM | 284 | CB | GLU | 258 | 26.609 | 36.428 | 95.000 | 1.00 | 17.90 |
| ATOM | 285 | CG | GLU | 258 | 27.180 | 36.928 | 96.318 | 1.00 | 18.62 |
| ATOM | 286 | CD | GLU | 258 | 28.091 | 35.900 | 96.996 | 1.00 | 19.45 |
| ATOM | 287 | OE1 | GLU | 258 | 27.868 | 34.675 | 96.853 | 1.00 | 19.93 |
| ATOM | 288 | OE2 | GLU | 258 | 29.030 | 36.311 | 97.706 | 1.00 | 19.56 |
| ATOM | 289 | C | GLU | 258 | 25.097 | 36.719 | 93.073 | 1.00 | 16.66 |
| ATOM | 290 | O | GLU | 258 | 24.002 | 36.186 | 93.034 | 1.00 | 16.55 |
| ATOM | 291 | N | VAL | 259 | 25.928 | 36.745 | 92.046 | 0.77 | 15.68 |
| ATOM | 293 | CA | VAL | 259 | 25.624 | 36.135 | 90.751 | 0.77 | 14.88 |
| ATOM | 294 | CB | VAL | 259 | 25.507 | 37.209 | 89.655 | 0.77 | 14.45 |
| ATOM | 295 | CG1 | VAL | 259 | 25.336 | 36.559 | 88.278 | 0.77 | 14.76 |
| ATOM | 296 | CG2 | VAL | 259 | 24.309 | 38.138 | 89.987 | 0.77 | 14.64 |
| ATOM | 297 | C | VAL | 259 | 26.771 | 35.148 | 90.461 | 0.77 | 14.68 |
| ATOM | 298 | O | VAL | 259 | 27.939 | 35.522 | 90.490 | 0.77 | 13.91 |
| ATOM | 299 | N | TRP | 260 | 26.400 | 33.898 | 90.200 | 1.00 | 14.40 |
| ATOM | 301 | CA | TRP | 260 | 27.323 | 32.790 | 89.966 | 1.00 | 14.33 |
| ATOM | 302 | CB | TRP | 260 | 27.133 | 31.748 | 91.073 | 1.00 | 14.78 |
| ATOM | 303 | CG | TRP | 260 | 27.555 | 32.155 | 92.437 | 1.00 | 16.33 |
| ATOM | 304 | CD2 | TRP | 260 | 28.700 | 31.677 | 93.149 | 1.00 | 16.87 |
| ATOM | 305 | CE2 | TRP | 260 | 28.693 | 32.300 | 94.409 | 1.00 | 17.24 |
| ATOM | 306 | CE3 | TRP | 260 | 29.730 | 30.780 | 92.841 | 1.00 | 16.82 |
| ATOM | 307 | CD1 | TRP | 260 | 26.917 | 33.023 | 93.273 | 1.00 | 16.69 |
| ATOM | 308 | NE1 | TRP | 260 | 27.590 | 33.111 | 94.457 | 1.00 | 16.95 |
| ATOM | 310 | CZ2 | TRP | 260 | 29.682 | 32.054 | 95.374 | 1.00 | 17.57 |
| ATOM | 311 | CZ3 | TRP | 260 | 30.711 | 30.530 | 93.795 | 1.00 | 17.21 |
| ATOM | 312 | CH2 | TRP | 260 | 30.683 | 31.169 | 95.048 | 1.00 | 17.49 |
| ATOM | 313 | C | TRP | 260 | 27.127 | 32.023 | 88.661 | 1.00 | 13.83 |
| ATOM | 314 | O | TRP | 260 | 25.995 | 31.922 | 88.151 | 1.00 | 12.91 |
| ATOM | 315 | N | MET | 261 | 28.239 | 31.540 | 88.098 | 1.00 | 12.89 |
| ATOM | 317 | CA | MET | 261 | 28.189 | 30.657 | 86.934 | 1.00 | 12.62 |
| ATOM | 318 | CB | MET | 261 | 29.502 | 30.698 | 86.114 | 1.00 | 12.93 |
| ATOM | 319 | CG | MET | 261 | 29.644 | 29.655 | 84.949 | 1.00 | 13.46 |
| ATOM | 320 | SD | MET | 261 | 30.012 | 27.929 | 85.492 | 1.00 | 14.60 |
| ATOM | 321 | CE | MET | 261 | 30.840 | 27.279 | 84.169 | 1.00 | 15.42 |
| ATOM | 322 | C | MET | 261 | 28.070 | 29.297 | 87.648 | 1.00 | 12.41 |
| ATOM | 323 | O | MET | 261 | 28.741 | 29.055 | 88.657 | 1.00 | 12.17 |
| ATOM | 324 | N | GLY | 262 | 27.230 | 28.411 | 87.131 | 1.00 | 12.22 |
| ATOM | 326 | CA | GLY | 262 | 27.082 | 27.113 | 87.770 | 1.00 | 12.09 |
| ATOM | 327 | C | GLY | 262 | 26.613 | 26.065 | 86.788 | 1.00 | 12.05 |
| ATOM | 328 | O | GLY | 262 | 26.551 | 26.325 | 85.590 | 1.00 | 11.57 |
| ATOM | 329 | N | TYR | 263 | 26.327 | 24.874 | 87.288 | 1.00 | 12.15 |
| ATOM | 331 | CA | TYR | 263 | 25.841 | 23.798 | 86.450 | 1.00 | 12.23 |
| ATOM | 332 | CB | TYR | 263 | 26.887 | 22.699 | 86.323 | 1.00 | 13.24 |
| ATOM | 333 | CG | TYR | 263 | 28.071 | 23.083 | 85.484 | 1.00 | 14.31 |
| ATOM | 334 | CD1 | TYR | 263 | 29.196 | 23.687 | 86.056 | 1.00 | 14.52 |
| ATOM | 335 | CE1 | TYR | 263 | 30.258 | 24.087 | 85.270 | 1.00 | 15.11 |
| ATOM | 336 | CD2 | TYR | 263 | 28.040 | 22.900 | 84.113 | 1.00 | 14.62 |
| ATOM | 337 | CE2 | TYR | 263 | 29.078 | 23.287 | 83.322 | 1.00 | 15.61 |
| ATOM | 338 | CZ | TYR | 263 | 30.186 | 23.888 | 83.894 | 1.00 | 15.67 |
| ATOM | 339 | OH | TYR | 263 | 31.208 | 24.253 | 83.052 | 1.00 | 16.54 |
| ATOM | 341 | C | TYR | 263 | 24.612 | 23.190 | 87.079 | 1.00 | 12.04 |
| ATOM | 342 | O | TYR | 263 | 24.540 | 23.003 | 88.305 | 1.00 | 11.84 |
| ATOM | 343 | N | TYR | 264 | 23.640 | 22.899 | 86.229 | 1.00 | 11.85 |
| ATOM | 345 | CA | TYR | 264 | 22.382 | 22.249 | 86.625 | 1.00 | 11.57 |
| ATOM | 346 | CB | TYR | 264 | 21.198 | 22.899 | 85.887 | 1.00 | 12.23 |
| ATOM | 347 | CG | TYR | 264 | 19.892 | 22.137 | 86.055 | 1.00 | 12.04 |
| ATOM | 348 | CD1 | TYR | 264 | 19.174 | 22.232 | 87.234 | 1.00 | 11.93 |
| ATOM | 349 | CE1 | TYR | 264 | 18.005 | 21.512 | 87.432 | 1.00 | 12.26 |
| ATOM | 350 | CD2 | TYR | 264 | 19.401 | 21.289 | 85.048 | 1.00 | 12.07 |
| ATOM | 351 | CE2 | TYR | 264 | 18.217 | 20.556 | 85.231 | 1.00 | 12.44 |
| ATOM | 352 | CZ | TYR | 264 | 17.528 | 20.680 | 86.433 | 1.00 | 12.55 |
| ATOM | 353 | OH | TYR | 264 | 16.341 | 20.011 | 86.659 | 1.00 | 12.47 |
| ATOM | 355 | C | TYR | 264 | 22.477 | 20.775 | 86.194 | 1.00 | 11.05 |

TABLE 7-continued

Coordinates of Lck bound with PD153035

| | | Atom Type | Res | # | X | Y | Z | Occ | B |
|---|---|---|---|---|---|---|---|---|---|
| ATOM | 356 | O | TYR | 264 | 22.725 | 20.502 | 85.029 | 1.00 | 10.86 |
| ATOM | 357 | N | ASN | 265 | 22.236 | 19.855 | 87.111 | 1.00 | 10.97 |
| ATOM | 359 | CA | ASN | 265 | 22.290 | 18.415 | 86.802 | 1.00 | 10.97 |
| ATOM | 360 | CB | ASN | 265 | 21.065 | 17.989 | 85.994 | 1.00 | 11.36 |
| ATOM | 361 | CG | ASN | 265 | 19.854 | 17.783 | 86.834 | 1.00 | 11.87 |
| ATOM | 362 | OD1 | ASN | 265 | 19.878 | 17.972 | 88.034 | 1.00 | 12.34 |
| ATOM | 363 | ND2 | ASN | 265 | 18.738 | 17.457 | 86.169 | 1.00 | 12.51 |
| ATOM | 366 | C | ASN | 265 | 23.549 | 17.993 | 86.091 | 1.00 | 10.61 |
| ATOM | 367 | O | ASN | 265 | 23.500 | 17.287 | 85.074 | 1.00 | 11.07 |
| ATOM | 368 | N | GLY | 266 | 24.647 | 18.576 | 86.553 | 1.00 | 10.11 |
| ATOM | 370 | CA | GLY | 266 | 25.951 | 18.265 | 86.036 | 1.00 | 9.94 |
| ATOM | 371 | C | GLY | 266 | 26.450 | 18.845 | 84.733 | 1.00 | 9.65 |
| ATOM | 372 | O | GLY | 266 | 27.550 | 9.391 | 84.689 | 1.00 | 10.19 |
| ATOM | 373 | N | HIS | 267 | 25.629 | 18.814 | 83.697 | 0.49 | 8.97 |
| ATOM | 375 | CA | HIS | 267 | 26.073 | 19.256 | 82.384 | 0.49 | 8.86 |
| ATOM | 376 | CB | HIS | 267 | 25.743 | 18.152 | 81.391 | 0.49 | 8.59 |
| ATOM | 377 | CG | HIS | 267 | 26.420 | 16.859 | 81.695 | 0.49 | 8.64 |
| ATOM | 378 | CD2 | HIS | 267 | 27.712 | 16.481 | 81.515 | 0.49 | 8.96 |
| ATOM | 379 | ND1 | HIS | 267 | 25.775 | 15.763 | 82.233 | 0.49 | 8.91 |
| ATOM | 381 | CE1 | HIS | 267 | 26.637 | 14.766 | 82.352 | 0.49 | 8.64 |
| ATOM | 382 | NE2 | HIS | 267 | 27.810 | 15.177 | 81.928 | 0.49 | 9.11 |
| ATOM | 384 | C | HIS | 267 | 25.631 | 20.598 | 81.827 | 0.49 | 8.89 |
| ATOM | 385 | O | HIS | 267 | 26.255 | 21.144 | 80.901 | 0.49 | 8.45 |
| ATOM | 386 | N | THR | 268 | 24.574 | 21.151 | 82.393 | 1.00 | 9.26 |
| ATOM | 388 | CA | THR | 268 | 24.045 | 22.416 | 81.855 | 1.00 | 9.61 |
| ATOM | 389 | CB | THR | 268 | 22.499 | 22.366 | 81.765 | 1.00 | 9.46 |
| ATOM | 390 | OG1 | THR | 268 | 22.137 | 21.174 | 81.048 | 1.00 | 9.92 |
| ATOM | 392 | CG2 | THR | 268 | 21.955 | 23.595 | 80.949 | 1.00 | 8.90 |
| ATOM | 393 | C | THR | 268 | 24.502 | 23.693 | 82.534 | 1.00 | 9.88 |
| ATOM | 394 | O | THR | 268 | 24.229 | 23.926 | 83.701 | 1.00 | 10.26 |
| ATOM | 395 | N | LYS | 269 | 25.237 | 24.508 | 81.781 | 1.00 | 10.07 |
| ATOM | 397 | CA | LYS | 269 | 25.762 | 25.765 | 82.285 | 1.00 | 10.47 |
| ATOM | 398 | CB | LYS | 269 | 26.825 | 26.279 | 81.301 | 1.00 | 11.48 |
| ATOM | 399 | CG | LYS | 269 | 27.526 | 27.525 | 81.710 | 1.00 | 13.36 |
| ATOM | 400 | CD | LYS | 269 | 29.045 | 27.390 | 81.717 | 1.00 | 14.42 |
| ATOM | 401 | CE | LYS | 269 | 29.729 | 27.779 | 80.425 | 1.00 | 16.07 |
| ATOM | 402 | NZ | LYS | 269 | 31.124 | 28.308 | 80.703 | 1.00 | 16.45 |
| ATOM | 406 | C | LYS | 269 | 24.600 | 26.746 | 82.484 | 1.00 | 10.01 |
| ATOM | 407 | O | LYS | 269 | 23.758 | 26.907 | 81.614 | 1.00 | 10.03 |
| ATOM | 408 | N | VAL | 270 | 24.528 | 27.336 | 83.669 | 1.00 | 9.45 |
| ATOM | 410 | CA | VAL | 270 | 23.477 | 28.290 | 84.005 | 1.00 | 9.31 |
| ATOM | 411 | CB | VAL | 270 | 22.357 | 27.634 | 84.909 | 1.00 | 9.04 |
| ATOM | 412 | CG1 | VAL | 270 | 21.698 | 26.450 | 84.210 | 1.00 | 8.38 |
| ATOM | 413 | CG2 | VAL | 270 | 22.922 | 27.186 | 86.276 | 1.00 | 9.11 |
| ATOM | 414 | C | VAL | 270 | 24.061 | 29.446 | 84.822 | 1.00 | 9.53 |
| ATOM | 415 | O | VAL | 270 | 25.189 | 29.359 | 85.338 | 1.00 | 9.52 |
| ATOM | 416 | N | ALA | 271 | 23.292 | 30.531 | 84.914 | 1.00 | 9.60 |
| ATOM | 418 | CA | ALA | 271 | 23.645 | 31.689 | 85.745 | 1.00 | 9.88 |
| ATOM | 419 | CB | ALA | 271 | 23.319 | 33.003 | 84.994 | 1.00 | 10.49 |
| ATOM | 420 | C | ALA | 271 | 22.730 | 31.556 | 86.958 | 1.00 | 10.18 |
| ATOM | 421 | O | ALA | 271 | 21.581 | 31.162 | 86.814 | 1.00 | 9.65 |
| ATOM | 422 | N | VAL | 272 | 23.236 | 31.850 | 88.149 | 1.00 | 10.92 |
| ATOM | 424 | CA | VAL | 272 | 22.457 | 31.769 | 89.393 | 1.00 | 11.83 |
| ATOM | 425 | CB | VAL | 272 | 23.012 | 30.672 | 90.323 | 1.00 | 11.58 |
| ATOM | 426 | CG1 | VAL | 272 | 22.217 | 30.614 | 91.620 | 1.00 | 11.64 |
| ATOM | 427 | CG2 | VAL | 272 | 22.996 | 29.304 | 89.631 | 1.00 | 11.65 |
| ATOM | 428 | C | VAL | 272 | 22.553 | 33.077 | 90.203 | 1.00 | 12.85 |
| ATOM | 429 | O | VAL | 272 | 23.661 | 33.578 | 90.420 | 1.00 | 13.20 |
| ATOM | 430 | N | LYS | 273 | 21.412 | 33.671 | 90.566 | 1.00 | 13.36 |
| ATOM | 432 | CA | LYS | 273 | 21.416 | 34.865 | 91.422 | 1.00 | 14.05 |
| ATOM | 433 | CB | LYS | 273 | 20.609 | 36.037 | 90.813 | 1.00 | 14.43 |
| ATOM | 434 | CG | LYS | 273 | 20.583 | 37.302 | 91.680 | 1.00 | 15.25 |
| ATOM | 435 | CD | LYS | 273 | 20.387 | 38.601 | 90.861 | 1.00 | 15.85 |
| ATOM | 436 | CE | LYS | 273 | 18.952 | 38.787 | 90.343 | 1.00 | 16.05 |
| ATOM | 437 | NZ | LYS | 273 | 18.692 | 40.215 | 89.867 | 1.00 | 15.90 |
| ATOM | 441 | C | LYS | 273 | 20.853 | 34.458 | 92.771 | 1.00 | 14.28 |
| ATOM | 442 | O | LYS | 273 | 19.771 | 33.878 | 92.856 | 1.00 | 14.12 |
| ATOM | 443 | N | SER | 274 | 21.624 | 34.706 | 93.820 | 0.65 | 14.69 |
| ATOM | 445 | CA | SER | 274 | 21.218 | 34.376 | 95.175 | 0.65 | 15.38 |
| ATOM | 446 | CB | SER | 274 | 22.336 | 33.621 | 95.916 | 0.65 | 15.34 |
| ATOM | 447 | OG | SER | 274 | 23.538 | 34.370 | 95.921 | 0.65 | 15.09 |
| ATOM | 449 | C | SER | 274 | 20.910 | 35.661 | 95.901 | 0.65 | 15.86 |
| ATOM | 450 | O | SER | 274 | 21.595 | 36.671 | 95.716 | 0.65 | 15.80 |
| ATOM | 451 | N | LEU | 275 | 19.851 | 35.624 | 96.696 | 1.00 | 16.73 |

TABLE 7-continued

Coordinates of Lck bound with PD153035

| | | Atom Type | Res | # | X | Y | Z | Occ | B |
|---|---|---|---|---|---|---|---|---|---|
| ATOM | 453 | CA | LEU | 275 | 19.424 | 36.776 | 97.476 | 1.00 | 17.83 |
| ATOM | 454 | CB | LEU | 275 | 17.899 | 36.767 | 97.640 | 1.00 | 17.48 |
| ATOM | 455 | CG | LEU | 275 | 17.268 | 37.741 | 98.644 | 1.00 | 17.48 |
| ATOM | 456 | CD1 | LEU | 275 | 17.491 | 39.168 | 98.203 | 1.00 | 16.74 |
| ATOM | 457 | CD2 | LEU | 275 | 15.783 | 37.434 | 98.824 | 1.00 | 17.26 |
| ATOM | 458 | C | LEU | 275 | 20.071 | 36.762 | 98.848 | 1.00 | 18.63 |
| ATOM | 459 | O | LEU | 275 | 20.046 | 35.751 | 99.539 | 1.00 | 19.04 |
| ATOM | 460 | N | LYS | 276 | 20.661 | 37.888 | 99.236 | 1.00 | 19.63 |
| ATOM | 462 | CA | LYS | 276 | 21.262 | 38.003 | 100.558 | 1.00 | 20.55 |
| ATOM | 463 | CB | LYS | 276 | 22.191 | 39.207 | 100.613 | 1.00 | 20.86 |
| ATOM | 464 | CG | LYS | 276 | 22.776 | 39.412 | 101.977 | 1.00 | 21.25 |
| ATOM | 465 | CD | LYS | 276 | 23.808 | 40.471 | 101.961 | 1.00 | 21.85 |
| ATOM | 466 | CE | LYS | 276 | 24.463 | 40.502 | 103.312 | 1.00 | 22.37 |
| ATOM | 467 | NZ | LYS | 276 | 25.548 | 41.512 | 103.347 | 1.00 | 22.76 |
| ATOM | 471 | C | LYS | 276 | 20.145 | 38.147 | 101.595 | 1.00 | 20.94 |
| ATOM | 472 | O | LYS | 276 | 19.436 | 39.148 | 101.603 | 1.00 | 20.97 |
| ATOM | 473 | N | ALA | 277 | 20.000 | 37.147 | 102.461 | 1.00 | 21.39 |
| ATOM | 475 | CA | ALA | 277 | 18.948 | 37.124 | 103.489 | 1.00 | 21.94 |
| ATOM | 476 | CB | ALA | 277 | 19.121 | 35.919 | 104.418 | 1.00 | 21.71 |
| ATOM | 477 | C | ALA | 277 | 18.868 | 38.402 | 104.305 | 1.00 | 22.01 |
| ATOM | 478 | O | ALA | 277 | 19.846 | 38.801 | 104.937 | 1.00 | 22.40 |
| ATOM | 479 | N | GLY | 278 | 17.700 | 39.043 | 104.258 | 1.00 | 21.92 |
| ATOM | 481 | CA | GLY | 278 | 17.480 | 40.283 | 104.986 | 1.00 | 21.83 |
| ATOM | 482 | C | GLY | 278 | 17.839 | 41.557 | 104.232 | 1.00 | 21.82 |
| ATOM | 483 | O | GLY | 278 | 17.485 | 42.647 | 104.670 | 1.00 | 21.69 |
| ATOM | 484 | N | SER | 279 | 18.500 | 41.432 | 103.082 | 1.00 | 21.81 |
| ATOM | 486 | CA | SER | 279 | 18.899 | 42.605 | 102.304 | 1.00 | 21.64 |
| ATOM | 487 | CB | SER | 279 | 20.023 | 42.244 | 101.327 | 1.00 | 22.31 |
| ATOM | 488 | OG | SER | 279 | 19.548 | 41.479 | 100.225 | 1.00 | 22.41 |
| ATOM | 490 | C | SER | 279 | 17.740 | 43.258 | 101.550 | 1.00 | 21.46 |
| ATOM | 491 | O | SER | 279 | 17.800 | 44.438 | 101.182 | 1.00 | 21.53 |
| ATOM | 492 | N | MET | 280 | 16.717 | 42.465 | 101.260 | 1.00 | 20.56 |
| ATOM | 494 | CA | MET | 280 | 15.546 | 42.960 | 100.559 | 1.00 | 19.86 |
| ATOM | 495 | CB | MET | 280 | 15.839 | 43.221 | 99.083 | 1.00 | 20.17 |
| ATOM | 496 | CG | MET | 280 | 16.000 | 42.000 | 98.241 | 1.00 | 20.52 |
| ATOM | 497 | SD | MET | 280 | 16.263 | 42.363 | 96.502 | 1.00 | 21.51 |
| ATOM | 498 | CE | MET | 280 | 14.586 | 42.686 | 95.983 | 1.00 | 21.07 |
| ATOM | 499 | C | MET | 280 | 14.464 | 41.900 | 100.710 | 1.00 | 19.27 |
| ATOM | 500 | O | MET | 280 | 14.735 | 40.772 | 101.132 | 1.00 | 18.78 |
| ATOM | 501 | N | SER | 281 | 13.238 | 42.271 | 100.379 | 1.00 | 18.62 |
| ATOM | 503 | CA | SER | 281 | 12.134 | 41.348 | 100.507 | 1.00 | 17.95 |
| ATOM | 504 | CB | SER | 281 | 10.832 | 42.072 | 100.168 | 1.00 | 17.81 |
| ATOM | 505 | OG | SER | 281 | 9.827 | 41.134 | 99.883 | 1.00 | 16.79 |
| ATOM | 507 | C | SER | 281 | 12.271 | 40.135 | 99.590 | 1.00 | 17.47 |
| ATOM | 508 | O | SER | 281 | 12.596 | 40.279 | 98.423 | 1.00 | 17.79 |
| ATOM | 509 | N | PRO | 282 | 11.936 | 38.937 | 100.091 | 0.51 | 17.18 |
| ATOM | 510 | CD | PRO | 282 | 11.623 | 38.572 | 101.478 | 0.51 | 16.60 |
| ATOM | 511 | CA | PRO | 282 | 12.034 | 37.737 | 99.254 | 0.51 | 16.43 |
| ATOM | 512 | CB | PRO | 282 | 11.735 | 36.611 | 100.236 | 0.51 | 16.73 |
| ATOM | 513 | CG | PRO | 282 | 12.136 | 37.161 | 101.536 | 0.51 | 17.03 |
| ATOM | 514 | C | PRO | 282 | 10.999 | 37.782 | 98.138 | 0.51 | 15.95 |
| ATOM | 515 | O | PRO | 282 | 11.243 | 37.285 | 97.043 | 0.51 | 15.70 |
| ATOM | 516 | N | ASP | 283 | 9.868 | 38.442 | 98.415 | 1.00 | 15.55 |
| ATOM | 518 | CA | ASP | 283 | 8.761 | 38.586 | 97.454 | 1.00 | 14.63 |
| ATOM | 519 | CB | ASP | 283 | 7.527 | 39.205 | 98.157 | 1.00 | 14.94 |
| ATOM | 520 | CG | ASP | 283 | 6.310 | 39.310 | 97.231 | 1.00 | 15.52 |
| ATOM | 521 | OD1 | ASP | 283 | 5.986 | 38.315 | 96.540 | 1.00 | 16.17 |
| ATOM | 522 | OD2 | ASP | 283 | 5.693 | 40.389 | 97.151 | 1.00 | 15.32 |
| ATOM | 523 | C | ASP | 283 | 9.235 | 39.517 | 96.348 | 1.00 | 13.96 |
| ATOM | 524 | O | ASP | 283 | 8.968 | 39.297 | 95.176 | 1.00 | 13.97 |
| ATOM | 525 | N | ALA | 284 | 9.908 | 40.592 | 96.759 | 1.00 | 13.60 |
| ATOM | 527 | CA | ALA | 284 | 10.453 | 41.602 | 95.854 | 1.00 | 12.78 |
| ATOM | 528 | CB | ALA | 284 | 11.177 | 42.687 | 96.683 | 1.00 | 12.79 |
| ATOM | 529 | C | ALA | 284 | 11.432 | 40.932 | 94.887 | 1.00 | 12.08 |
| ATOM | 530 | O | ALA | 284 | 11.328 | 41.078 | 93.676 | 1.00 | 11.84 |
| ATOM | 531 | N | PHE | 285 | 12.338 | 40.133 | 95.443 | 1.00 | 11.82 |
| ATOM | 533 | CA | PHE | 285 | 13.354 | 39.418 | 94.667 | 1.00 | 11.49 |
| ATOM | 534 | CB | PHE | 285 | 14.209 | 38.582 | 95.634 | 1.00 | 11.62 |
| ATOM | 535 | CG | PHE | 285 | 15.317 | 37.812 | 94.968 | 1.00 | 11.60 |
| ATOM | 536 | CD1 | PHE | 285 | 16.458 | 38.466 | 94.524 | 1.00 | 11.53 |
| ATOM | 537 | CD2 | PHE | 285 | 15.237 | 36.420 | 94.821 | 1.00 | 11.58 |
| ATOM | 538 | CE1 | PHE | 285 | 17.525 | 37.749 | 93.939 | 1.00 | 11.84 |
| ATOM | 539 | CE2 | PHE | 285 | 16.289 | 35.692 | 94.248 | 1.00 | 11.35 |
| ATOM | 540 | CZ | PHE | 285 | 17.439 | 36.353 | 93.803 | 1.00 | 11.31 |

TABLE 7-continued

Coordinates of Lck bound with PD153035

| | | Atom Type | Res | # | X | Y | Z | Occ | B |
|---|---|---|---|---|---|---|---|---|---|
| ATOM | 541 | C | PHE | 285 | 12.733 | 38.494 | 93.608 | 1.00 | 11.38 |
| ATOM | 542 | O | PHE | 285 | 13.102 | 38.526 | 92.441 | 1.00 | 11.63 |
| ATOM | 543 | N | LEU | 286 | 11.770 | 37.684 | 94.028 | 1.00 | 11.28 |
| ATOM | 545 | CA | LEU | 286 | 11.124 | 36.725 | 93.140 | 1.00 | 11.32 |
| ATOM | 546 | CB | LEU | 286 | 10.385 | 35.671 | 93.968 | 1.00 | 11.15 |
| ATOM | 547 | CG | LEU | 286 | 11.391 | 34.756 | 94.673 | 1.00 | 11.04 |
| ATOM | 548 | CD1 | LEU | 286 | 10.790 | 34.061 | 95.883 | 1.00 | 10.91 |
| ATOM | 549 | CD2 | LEU | 286 | 11.964 | 33.765 | 93.657 | 1.00 | 11.40 |
| ATOM | 550 | C | LEU | 286 | 10.231 | 37.351 | 92.087 | 1.00 | 11.26 |
| ATOM | 551 | O | LEU | 286 | 9.969 | 36.749 | 91.023 | 1.00 | 10.75 |
| ATOM | 552 | N | ALA | 287 | 9.830 | 38.598 | 92.340 | 1.00 | 11.37 |
| ATOM | 554 | CA | ALA | 287 | 8.994 | 39.311 | 91.379 | 1.00 | 11.39 |
| ATOM | 555 | CB | ALA | 287 | 8.729 | 40.729 | 91.860 | 1.00 | 11.31 |
| ATOM | 556 | C | ALA | 287 | 9.700 | 39.314 | 90.022 | 1.00 | 11.45 |
| ATOM | 557 | O | ALA | 287 | 9.056 | 39.198 | 88.971 | 1.00 | 11.42 |
| ATOM | 558 | N | GLU | 288 | 11.029 | 39.375 | 90.062 | 1.00 | 11.61 |
| ATOM | 560 | CA | GLU | 288 | 11.835 | 39.355 | 88.848 | 1.00 | 12.41 |
| ATOM | 561 | CB | GLU | 288 | 13.321 | 39.493 | 89.206 | 1.00 | 12.35 |
| ATOM | 562 | CG | GLU | 288 | 14.258 | 39.549 | 88.004 | 1.00 | 13.25 |
| ATOM | 563 | CD | GLU | 288 | 15.669 | 39.956 | 88.414 | 1.00 | 13.61 |
| ATOM | 564 | OE1 | GLU | 288 | 15.791 | 40.690 | 89.417 | 1.00 | 14.16 |
| ATOM | 565 | OE2 | GLU | 288 | 16.644 | 39.567 | 87.745 | 1.00 | 14.44 |
| ATOM | 566 | C | GLU | 288 | 11.630 | 38.050 | 88.052 | 1.00 | 12.39 |
| ATOM | 567 | O | GLU | 288 | 11.517 | 38.063 | 86.839 | 1.00 | 12.30 |
| ATOM | 568 | N | ALA | 289 | 11.631 | 36.919 | 88.751 | 1.00 | 12.95 |
| ATOM | 570 | CA | ALA | 289 | 11.449 | 35.630 | 88.072 | 1.00 | 13.21 |
| ATOM | 571 | CB | ALA | 289 | 11.841 | 34.487 | 89.010 | 1.00 | 13.39 |
| ATOM | 572 | C | ALA | 289 | 9.998 | 35.461 | 87.555 | 1.00 | 13.33 |
| ATOM | 573 | O | ALA | 289 | 9.759 | 34.883 | 86.478 | 1.00 | 12.38 |
| ATOM | 574 | N | ASN | 290 | 9.040 | 35.988 | 88.320 | 1.00 | 13.44 |
| ATOM | 576 | CA | ASN | 290 | 7.638 | 35.918 | 87.926 | 1.00 | 13.93 |
| ATOM | 577 | CB | ASN | 290 | 6.738 | 36.405 | 89.071 | 1.00 | 14.01 |
| ATOM | 578 | CG | ASN | 290 | 6.677 | 35.387 | 90.212 | 1.00 | 14.58 |
| ATOM | 579 | OD1 | ASN | 290 | 7.027 | 34.219 | 90.017 | 1.00 | 15.13 |
| ATOM | 580 | ND2 | ASN | 290 | 6.220 | 35.807 | 91.382 | 1.00 | 14.51 |
| ATOM | 583 | C | ASN | 290 | 7.381 | 36.645 | 86.607 | 1.00 | 14.09 |
| ATOM | 584 | O | ASN | 290 | 6.651 | 36.151 | 85.749 | 1.00 | 13.59 |
| ATOM | 585 | N | LEU | 291 | 8.039 | 37.785 | 86.420 | 1.00 | 14.63 |
| ATOM | 587 | CA | LEU | 291 | 7.907 | 38.534 | 85.165 | 1.00 | 15.17 |
| ATOM | 588 | CB | LEU | 291 | 8.622 | 39.873 | 85.268 | 1.00 | 15.21 |
| ATOM | 589 | CG | LEU | 291 | 8.431 | 40.702 | 83.993 | 1.00 | 15.48 |
| ATOM | 590 | CD1 | LEU | 291 | 8.128 | 42.140 | 84.384 | 1.00 | 15.88 |
| ATOM | 591 | CD2 | LEU | 291 | 9.644 | 40.602 | 83.085 | 1.00 | 15.79 |
| ATOM | 592 | C | LEU | 291 | 8.514 | 37.777 | 83.973 | 1.00 | 15.34 |
| ATOM | 593 | O | LEU | 291 | 7.994 | 37.845 | 82.857 | 1.00 | 15.39 |
| ATOM | 594 | N | MET | 292 | 9.685 | 37.170 | 84.210 | 1.00 | 15.23 |
| ATOM | 596 | CA | MET | 292 | 10.410 | 36.432 | 83.190 | 1.00 | 15.40 |
| ATOM | 597 | CB | MET | 292 | 11.798 | 36.003 | 83.688 | 1.00 | 14.56 |
| ATOM | 598 | CG | MET | 292 | 12.747 | 37.173 | 83.994 | 1.00 | 13.49 |
| ATOM | 599 | SD | MET | 292 | 14.388 | 36.548 | 84.497 | 1.00 | 11.74 |
| ATOM | 600 | CE | MET | 292 | 15.014 | 36.073 | 82.943 | 1.00 | 11.63 |
| ATOM | 601 | C | MET | 292 | 9.620 | 35.239 | 82.694 | 1.00 | 16.20 |
| ATOM | 602 | O | MET | 292 | 9.766 | 34.871 | 81.537 | 1.00 | 15.95 |
| ATOM | 603 | N | LYS | 293 | 8.774 | 34.658 | 83.554 | 1.00 | 17.20 |
| ATOM | 605 | CA | LYS | 293 | 7.920 | 33.530 | 83.155 | 1.00 | 18.79 |
| ATOM | 606 | CB | LYS | 293 | 7.030 | 33.049 | 84.323 | 1.00 | 18.90 |
| ATOM | 607 | CG | LYS | 293 | 7.743 | 32.415 | 85.507 | 1.00 | 20.00 |
| ATOM | 608 | CD | LYS | 293 | 6.785 | 32.281 | 86.707 | 1.00 | 20.52 |
| ATOM | 609 | CE | LYS | 293 | 7.435 | 31.683 | 87.944 | 1.00 | 20.47 |
| ATOM | 610 | NZ | LYS | 293 | 6.475 | 31.584 | 89.112 | 1.00 | 21.45 |
| ATOM | 614 | C | LYS | 293 | 7.005 | 34.014 | 82.024 | 1.00 | 19.24 |
| ATOM | 615 | O | LYS | 293 | 6.694 | 33.263 | 81.114 | 1.00 | 19.72 |
| ATOM | 616 | N | GLN | 294 | 6.568 | 35.272 | 82.105 | 1.00 | 19.78 |
| ATOM | 618 | CA | GLN | 294 | 5.682 | 35.829 | 81.084 | 1.00 | 19.87 |
| ATOM | 619 | CB | GLN | 294 | 4.707 | 36.832 | 81.714 | 1.00 | 20.82 |
| ATOM | 620 | CG | GLN | 294 | 3.686 | 36.230 | 82.709 | 1.00 | 22.14 |
| ATOM | 621 | CD | GLN | 294 | 3.043 | 34.943 | 82.225 | 1.00 | 23.20 |
| ATOM | 622 | OE1 | GLN | 294 | 2.671 | 34.805 | 81.053 | 1.00 | 24.12 |
| ATOM | 623 | NE2 | GLN | 294 | 2.894 | 33.984 | 83.143 | 1.00 | 24.36 |
| ATOM | 626 | C | GLN | 294 | 6.370 | 36.480 | 79.879 | 1.00 | 19.58 |
| ATOM | 627 | O | GLN | 294 | 5.701 | 37.007 | 78.982 | 1.00 | 19.59 |
| ATOM | 628 | N | LEU | 295 | 7.699 | 36.509 | 79.877 | 1.00 | 18.71 |
| ATOM | 630 | CA | LEU | 295 | 8.448 | 37.113 | 78.775 | 1.00 | 18.31 |
| ATOM | 631 | CB | LEU | 295 | 9.127 | 38.392 | 79.254 | 1.00 | 18.98 |

TABLE 7-continued

Coordinates of Lck bound with PD153035

| | | Atom Type | Res | # | X | Y | Z | Occ | B |
|---|---|---|---|---|---|---|---|---|---|
| ATOM | 632 | CG | LEU | 295 | 8.298 | 39.650 | 79.291 | 1.00 | 19.30 |
| ATOM | 633 | CD1 | LEU | 295 | 9.131 | 40.787 | 79.844 | 1.00 | 19.50 |
| ATOM | 634 | CD2 | LEU | 295 | 7.833 | 39.947 | 77.877 | 1.00 | 19.56 |
| ATOM | 635 | C | LEU | 295 | 9.487 | 36.173 | 78.215 | 1.00 | 17.42 |
| ATOM | 636 | O | LEU | 295 | 10.688 | 36.326 | 78.462 | 1.00 | 17.68 |
| ATOM | 637 | N | GLN | 296 | 9.027 | 35.234 | 77.406 | 1.00 | 16.74 |
| ATOM | 639 | CA | GLN | 296 | 9.895 | 34.237 | 76.808 | 1.00 | 15.75 |
| ATOM | 640 | CB | GLN | 296 | 9.361 | 32.852 | 77.091 | 1.00 | 15.87 |
| ATOM | 641 | CG | GLN | 296 | 9.187 | 32.565 | 78.559 | 1.00 | 15.99 |
| ATOM | 642 | CD | GLN | 296 | 8.721 | 31.154 | 78.785 | 1.00 | 15.69 |
| ATOM | 643 | OE1 | GLN | 296 | 9.229 | 30.230 | 78.171 | 1.00 | 16.14 |
| ATOM | 644 | NE2 | GLN | 296 | 7.775 | 30.976 | 79.686 | 1.00 | 15.75 |
| ATOM | 647 | C | GLN | 296 | 10.013 | 34.434 | 75.320 | 1.00 | 15.18 |
| ATOM | 648 | O | GLN | 296 | 9.003 | 34.448 | 74.609 | 1.00 | 15.08 |
| ATOM | 649 | N | HIS | 297 | 11.259 | 34.504 | 74.848 | 1.00 | 13.95 |
| ATOM | 651 | CA | HIS | 297 | 11.558 | 34.736 | 73.430 | 1.00 | 12.66 |
| ATOM | 652 | CB | HIS | 297 | 11.226 | 36.206 | 73.096 | 1.00 | 12.42 |
| ATOM | 653 | CG | HIS | 297 | 11.363 | 36.553 | 71.649 | 1.00 | 12.40 |
| ATOM | 654 | CD2 | HIS | 297 | 10.453 | 36.559 | 70.639 | 1.00 | 12.31 |
| ATOM | 655 | ND1 | HIS | 297 | 12.557 | 36.964 | 71.089 | 1.00 | 12.39 |
| ATOM | 657 | CE1 | HIS | 297 | 12.375 | 37.208 | 69.802 | 1.00 | 12.51 |
| ATOM | 658 | NE2 | HIS | 297 | 11.113 | 36.971 | 69.502 | 1.00 | 12.21 |
| ATOM | 660 | C | HIS | 297 | 13.048 | 34.498 | 73.266 | 1.00 | 11.79 |
| ATOM | 661 | O | HIS | 297 | 13.807 | 34.713 | 74.226 | 1.00 | 11.38 |
| ATOM | 662 | N | GLN | 298 | 13.481 | 34.107 | 72.061 | 1.00 | 10.98 |
| ATOM | 664 | CA | GLN | 298 | 14.916 | 33.863 | 71.798 | 1.00 | 10.82 |
| ATOM | 665 | CB | GLN | 298 | 15.187 | 33.527 | 70.319 | 1.00 | 11.48 |
| ATOM | 666 | CG | GLN | 298 | 14.756 | 32.159 | 69.846 | 1.00 | 12.18 |
| ATOM | 667 | CD | GLN | 298 | 15.406 | 30.985 | 70.603 | 1.00 | 12.06 |
| ATOM | 668 | OE1 | GLN | 298 | 14.705 | 30.114 | 71.087 | 1.00 | 11.83 |
| ATOM | 669 | NE2 | GLN | 298 | 16.743 | 30.939 | 70.649 | 1.00 | 12.12 |
| ATOM | 672 | C | GLN | 298 | 15.826 | 35.054 | 72.148 | 1.00 | 10.15 |
| ATOM | 673 | O | GLN | 298 | 16.955 | 34.872 | 72.613 | 1.00 | 10.20 |
| ATOM | 674 | N | ARG | 299 | 15.328 | 36.268 | 7.920 | 1.00 | 9.13 |
| ATOM | 676 | CA | ARG | 299 | 16.094 | 37.485 | 72.175 | 1.00 | 8.09 |
| ATOM | 677 | CB | ARG | 299 | 15.651 | 38.606 | 71.215 | 1.00 | 7.54 |
| ATOM | 678 | CG | ARG | 299 | 15.875 | 38.298 | 69.739 | 1.00 | 7.33 |
| ATOM | 679 | CD | ARG | 299 | 17.246 | 38.757 | 69.166 | 1.00 | 7.84 |
| ATOM | 680 | NE | ARG | 299 | 18.397 | 38.138 | 69.829 | 1.00 | 7.80 |
| ATOM | 682 | CZ | ARG | 299 | 18.767 | 36.858 | 69.716 | 1.00 | 8.23 |
| ATOM | 683 | NH1 | ARG | 299 | 18.099 | 36.000 | 68.941 | 1.00 | 7.97 |
| ATOM | 686 | NH2 | ARG | 299 | 19.798 | 36.417 | 70.435 | 1.00 | 8.36 |
| ATOM | 689 | C | ARG | 299 | 16.140 | 37.985 | 73.623 | 1.00 | 7.50 |
| ATOM | 690 | O | ARG | 299 | 16.712 | 39.055 | 73.902 | 1.00 | 7.42 |
| ATOM | 691 | N | LEU | 300 | 15.465 | 37.274 | 74.522 | 1.00 | 7.21 |
| ATOM | 693 | CA | LEU | 300 | 15.464 | 37.587 | 75.947 | 1.00 | 7.24 |
| ATOM | 694 | CB | LEU | 300 | 14.049 | 37.908 | 76.451 | 1.00 | 7.35 |
| ATOM | 695 | CG | LEU | 300 | 13.475 | 39.313 | 76.213 | 1.00 | 6.77 |
| ATOM | 696 | CD1 | LEU | 300 | 13.428 | 39.685 | 74.738 | 1.00 | 6.40 |
| ATOM | 697 | CD2 | LEU | 300 | 12.096 | 39.380 | 76.844 | 1.00 | 6.69 |
| ATOM | 698 | C | LEU | 300 | 16.044 | 36.414 | 76.753 | 1.00 | 7.53 |
| ATOM | 699 | O | LEU | 300 | 15.725 | 35.266 | 76.497 | 1.00 | 7.08 |
| ATOM | 700 | N | VAL | 301 | 16.935 | 36.718 | 77.693 | 1.00 | 7.75 |
| ATOM | 702 | CA | VAL | 301 | 17.575 | 35.704 | 78.521 | 1.00 | 8.85 |
| ATOM | 703 | CB | VAL | 301 | 18.408 | 36.342 | 79.609 | 1.00 | 9.21 |
| ATOM | 704 | CG1 | VAL | 301 | 19.032 | 35.256 | 80.491 | 1.00 | 9.66 |
| ATOM | 705 | CG2 | VAL | 301 | 19.464 | 37.214 | 78.997 | 1.00 | 8.66 |
| ATOM | 706 | C | VAL | 301 | 16.452 | 34.916 | 79.174 | 1.00 | 9.58 |
| ATOM | 707 | O | VAL | 301 | 15.580 | 35.503 | 79.818 | 1.00 | 9.31 |
| ATOM | 708 | N | ARG | 302 | 16.506 | 33.592 | 79.055 | 1.00 | 10.55 |
| ATOM | 710 | CA | ARG | 302 | 15.416 | 32.763 | 79.575 | 1.00 | 11.94 |
| ATOM | 711 | CB | ARG | 302 | 15.155 | 31.560 | 78.646 | 1.00 | 14.06 |
| ATOM | 712 | CG | ARG | 302 | 13.913 | 30.752 | 79.128 | 1.00 | 16.90 |
| ATOM | 713 | CD | ARG | 302 | 13.019 | 30.274 | 78.050 | 1.00 | 19.53 |
| ATOM | 714 | NE | ARG | 302 | 12.780 | 31.193 | 76.948 | 1.00 | 20.50 |
| ATOM | 716 | CZ | ARG | 302 | 12.458 | 30.752 | 75.745 | 1.00 | 21.60 |
| ATOM | 717 | NH1 | ARG | 302 | 12.314 | 29.440 | 75.539 | 1.00 | 22.21 |
| ATOM | 720 | NH2 | ARG | 302 | 12.459 | 31.584 | 74.725 | 1.00 | 21.91 |
| ATOM | 723 | C | ARG | 302 | 15.507 | 32.275 | 80.987 | 1.00 | 11.64 |
| ATOM | 724 | O | ARG | 302 | 16.549 | 31.774 | 81.395 | 1.00 | 11.68 |
| ATOM | 725 | N | LEU | 303 | 14.407 | 32.416 | 81.733 | 1.00 | 10.98 |
| ATOM | 727 | CA | LEU | 303 | 14.332 | 31.908 | 83.101 | 1.00 | 10.96 |
| ATOM | 728 | CB | LEU | 303 | 13.006 | 32.290 | 83.770 | 1.00 | 10.45 |
| ATOM | 729 | CG | LEU | 303 | 12.705 | 31.721 | 85.161 | 1.00 | 10.59 |

TABLE 7-continued

Coordinates of Lck bound with PD153035

| | | Atom Type | Res | # | X | Y | Z | Occ | B |
|---|---|---|---|---|---|---|---|---|---|
| ATOM | 730 | CD1 | LEU | 303 | 13.655 | 32.270 | 86.202 | 1.00 | 10.64 |
| ATOM | 731 | CD2 | LEU | 303 | 11.255 | 31.972 | 85.585 | 1.00 | 10.93 |
| ATOM | 732 | C | LEU | 303 | 14.381 | 30.372 | 82.998 | 1.00 | 10.89 |
| ATOM | 733 | O | LEU | 303 | 13.719 | 29.789 | 82.149 | 1.00 | 11.21 |
| ATOM | 734 | N | TYR | 304 | 15.207 | 29.747 | 83.829 | 1.00 | 10.87 |
| ATOM | 736 | CA | TYR | 304 | 15.322 | 28.304 | 83.871 | 1.00 | 10.95 |
| ATOM | 737 | CB | TYR | 304 | 16.789 | 27.866 | 83.992 | 1.00 | 11.07 |
| ATOM | 738 | CG | TYR | 304 | 17.548 | 27.888 | 82.706 | 1.00 | 11.08 |
| ATOM | 739 | CD1 | TYR | 304 | 16.997 | 28.461 | 81.554 | 1.00 | 10.97 |
| ATOM | 740 | CE1 | TYR | 304 | 17.686 | 28.459 | 80.360 | 1.00 | 11.58 |
| ATOM | 741 | CD2 | TYR | 304 | 18.819 | 27.326 | 82.629 | 1.00 | 11.19 |
| ATOM | 742 | CE2 | TYR | 304 | 19.526 | 27.318 | 81.437 | 1.00 | 11.79 |
| ATOM | 743 | CZ | TYR | 304 | 18.951 | 27.879 | 80.294 | 1.00 | 11.61 |
| ATOM | 744 | OH | TYR | 304 | 19.602 | 27.777 | 79.087 | 1.00 | 11.67 |
| ATOM | 746 | C | TYR | 304 | 14.573 | 27.727 | 85.061 | 1.00 | 10.93 |
| ATOM | 747 | O | TYR | 304 | 13.755 | 26.841 | 84.906 | 1.00 | 11.09 |
| ATOM | 748 | N | ALA | 305 | 14.898 | 28.199 | 86.258 | 1.00 | 10.92 |
| ATOM | 750 | CA | ALA | 305 | 14.299 | 27.666 | 87.477 | 1.00 | 11.17 |
| ATOM | 751 | CB | ALA | 305 | 15.034 | 26.361 | 87.864 | 1.00 | 10.75 |
| ATOM | 752 | C | ALA | 305 | 14.411 | 28.668 | 88.628 | 1.00 | 11.24 |
| ATOM | 753 | O | ALA | 305 | 15.005 | 29.729 | 88.470 | 1.00 | 11.27 |
| ATOM | 754 | N | VAL | 306 | 13.848 | 28.285 | 89.770 | 0.75 | 11.75 |
| ATOM | 756 | CA | VAL | 306 | 13.878 | 29.026 | 91.029 | 0.75 | 12.71 |
| ATOM | 757 | CB | VAL | 306 | 12.590 | 29.867 | 91.279 | 0.75 | 12.97 |
| ATOM | 758 | CG1 | VAL | 306 | 12.480 | 31.038 | 90.310 | 0.75 | 12.24 |
| ATOM | 759 | CG2 | VAL | 306 | 11.348 | 28.958 | 91.175 | 0.75 | 12.43 |
| ATOM | 760 | C | VAL | 306 | 13.955 | 28.049 | 92.196 | 0.75 | 13.71 |
| ATOM | 761 | O | VAL | 306 | 13.542 | 26.882 | 92.077 | 0.75 | 13.44 |
| ATOM | 762 | N | VAL | 307 | 14.515 | 28.515 | 93.310 | 1.00 | 14.74 |
| ATOM | 764 | CA | VAL | 307 | 14.569 | 27.732 | 94.558 | 1.00 | 16.03 |
| ATOM | 765 | CB | VAL | 307 | 15.996 | 27.281 | 94.965 | 1.00 | 15.74 |
| ATOM | 766 | CG1 | VAL | 307 | 15.926 | 26.529 | 96.277 | 1.00 | 15.85 |
| ATOM | 767 | CG2 | VAL | 307 | 16.594 | 26.382 | 93.869 | 1.00 | 16.07 |
| ATOM | 768 | C | VAL | 307 | 14.044 | 28.727 | 95.576 | 1.00 | 16.83 |
| ATOM | 769 | O | VAL | 307 | 14.719 | 29.725 | 95.896 | 1.00 | 16.88 |
| ATOM | 770 | N | THR | 308 | 12.786 | 28.526 | 95.951 | 1.00 | 18.01 |
| ATOM | 772 | CA | THR | 308 | 12.071 | 29.414 | 96.866 | 1.00 | 19.56 |
| ATOM | 773 | CB | THR | 308 | 10.527 | 29.414 | 96.574 | 1.00 | 19.54 |
| ATOM | 774 | OG1 | THR | 308 | 10.028 | 28.067 | 96.575 | 1.00 | 19.34 |
| ATOM | 775 | CG2 | THR | 308 | 10.247 | 30.067 | 95.186 | 1.00 | 19.57 |
| ATOM | 777 | C | THR | 308 | 12.325 | 29.305 | 98.357 | 1.00 | 20.50 |
| ATOM | 778 | O | THR | 308 | 11.611 | 29.939 | 99.123 | 1.00 | 20.99 |
| ATOM | 779 | N | ALA | 309 | 13.334 | 28.531 | 98.769 | 1.00 | 21.44 |
| ATOM | 781 | CA | ALA | 309 | 13.691 | 28.399 | 100.186 | 1.00 | 22.11 |
| ATOM | 782 | CB | ALA | 309 | 13.846 | 26.928 | 100.592 | 1.00 | 22.03 |
| ATOM | 783 | C | ALA | 309 | 15.003 | 29.162 | 100.388 | 1.00 | 22.74 |
| ATOM | 784 | O | ALA | 309 | 15.882 | 29.171 | 99.507 | 1.00 | 22.83 |
| ATOM | 785 | N | GLU | 310 | 15.099 | 29.875 | 101.505 | 1.00 | 23.46 |
| ATOM | 787 | CA | GLU | 310 | 16.292 | 30.674 | 101.798 | 1.00 | 24.08 |
| ATOM | 788 | CB | GLU | 310 | 16.034 | 31.557 | 103.029 | 1.00 | 25.25 |
| ATOM | 789 | CG | GLU | 310 | 14.855 | 32.521 | 102.803 | 1.00 | 26.66 |
| ATOM | 790 | CD | GLU | 310 | 14.579 | 33.474 | 103.942 | 1.00 | 27.82 |
| ATOM | 791 | OE1 | GLU | 310 | 15.198 | 33.344 | 105.024 | 1.00 | 28.46 |
| ATOM | 792 | OE2 | GLU | 310 | 13.711 | 34.357 | 103.742 | 1.00 | 28.44 |
| ATOM | 793 | C | GLU | 310 | 17.544 | 29.805 | 101.938 | 1.00 | 23.91 |
| ATOM | 794 | O | GLU | 310 | 17.535 | 28.800 | 102.649 | 1.00 | 24.38 |
| ATOM | 795 | N | PRO | 311 | 18.641 | 30.183 | 101.262 | 1.00 | 23.09 |
| ATOM | 796 | CD | PRO | 311 | 19.942 | 29.493 | 101.353 | 1.00 | 23.02 |
| ATOM | 797 | CA | PRO | 311 | 18.713 | 31.373 | 100.399 | 1.00 | 22.27 |
| ATOM | 798 | CB | PRO | 311 | 20.217 | 31.610 | 100.289 | 1.00 | 22.56 |
| ATOM | 799 | CG | PRO | 311 | 20.783 | 30.196 | 100.295 | 1.00 | 22.83 |
| ATOM | 800 | C | PRO | 311 | 18.049 | 31.222 | 99.027 | 1.00 | 21.67 |
| ATOM | 801 | O | PRO | 311 | 18.306 | 30.268 | 98.296 | 1.00 | 21.75 |
| ATOM | 802 | N | ILE | 312 | 17.210 | 32.192 | 98.678 | 1.00 | 20.47 |
| ATOM | 804 | CA | ILE | 312 | 16.497 | 32.166 | 97.415 | 1.00 | 19.07 |
| ATOM | 805 | CB | ILE | 312 | 15.418 | 33.261 | 97.428 | 1.00 | 19.30 |
| ATOM | 806 | CG2 | ILE | 312 | 14.638 | 33.256 | 96.105 | 1.00 | 19.56 |
| ATOM | 807 | CG1 | ILE | 312 | 14.513 | 33.048 | 98.656 | 1.00 | 19.27 |
| ATOM | 808 | CD1 | ILE | 312 | 13.598 | 34.209 | 98.961 | 1.00 | 19.44 |
| ATOM | 809 | C | ILE | 312 | 17.414 | 32.350 | 96.198 | 1.00 | 17.98 |
| ATOM | 810 | O | ILE | 312 | 18.350 | 33.152 | 96.222 | 1.00 | 17.71 |
| ATOM | 811 | N | TYR | 313 | 17.180 | 31.547 | 95.162 | 1.00 | 16.37 |
| ATOM | 813 | CA | TYR | 313 | 17.936 | 31.617 | 93.908 | 1.00 | 14.87 |
| ATOM | 814 | CB | TYR | 313 | 18.690 | 30.300 | 93.589 | 1.00 | 14.92 |

TABLE 7-continued

Coordinates of Lck bound with PD153035

| | | Atom Type | Res | # | X | Y | Z | Occ | B |
|---|---|---|---|---|---|---|---|---|---|
| ATOM | 815 | CG | TYR | 313 | 19.821 | 29.858 | 94.495 | 1.00 | 14.74 |
| ATOM | 816 | CD1 | TYR | 313 | 20.324 | 30.664 | 95.493 | 1.00 | 14.80 |
| ATOM | 817 | CE1 | TYR | 313 | 21.370 | 30.203 | 96.316 | 1.00 | 15.16 |
| ATOM | 818 | CD2 | TYR | 313 | 20.382 | 28.581 | 94.331 | 1.00 | 14.81 |
| ATOM | 819 | CE2 | TYR | 313 | 21.401 | 28.127 | 95.126 | 1.00 | 15.12 |
| ATOM | 820 | CZ | TYR | 313 | 21.890 | 28.928 | 96.114 | 1.00 | 15.00 |
| ATOM | 821 | OH | TYR | 313 | 22.889 | 28.476 | 96.939 | 1.00 | 15.74 |
| ATOM | 823 | C | TYR | 313 | 16.999 | 31.807 | 92.722 | 1.00 | 13.64 |
| ATOM | 824 | O | TYR | 313 | 15.890 | 31.283 | 92.721 | 1.00 | 13.57 |
| ATOM | 825 | N | ILE | 314 | 17.497 | 32.502 | 91.711 | 0.82 | 12.02 |
| ATOM | 827 | CA | ILE | 314 | 16.821 | 32.660 | 90.439 | 0.82 | 10.55 |
| ATOM | 828 | CB | ILE | 314 | 16.564 | 34.145 | 90.056 | 0.82 | 10.14 |
| ATOM | 829 | CG2 | ILE | 314 | 16.167 | 34.263 | 88.582 | 0.82 | 9.80 |
| ATOM | 830 | CG1 | ILE | 314 | 15.502 | 34.755 | 90.960 | 0.82 | 9.73 |
| ATOM | 831 | CD1 | ILE | 314 | 15.419 | 36.288 | 90.875 | 0.82 | 9.95 |
| ATOM | 832 | C | ILE | 314 | 17.866 | 32.073 | 89.466 | 0.82 | 9.99 |
| ATOM | 833 | O | ILE | 314 | 19.026 | 32.523 | 89.408 | 0.82 | 9.44 |
| ATOM | 834 | N | ILE | 315 | 17.473 | 31.078 | 88.691 | 1.00 | 9.17 |
| ATOM | 836 | CA | ILE | 315 | 18.425 | 30.483 | 87.765 | 1.00 | 8.13 |
| ATOM | 837 | CB | ILE | 315 | 18.531 | 28.935 | 88.002 | 1.00 | 8.35 |
| ATOM | 838 | CG2 | ILE | 315 | 19.575 | 28.311 | 87.070 | 1.00 | 7.53 |
| ATOM | 839 | CG1 | ILE | 315 | 18.875 | 28.645 | 89.476 | 1.00 | 8.06 |
| ATOM | 840 | CD1 | ILE | 315 | 17.680 | 28.507 | 90.419 | 1.00 | 8.37 |
| ATOM | 841 | C | ILE | 315 | 18.042 | 30.792 | 86.316 | 1.00 | 8.47 |
| ATOM | 842 | O | ILE | 315 | 16.891 | 30.606 | 85.932 | 1.00 | 8.68 |
| ATOM | 843 | N | THR | 316 | 19.009 | 31.222 | 85.496 | 1.00 | 8.15 |
| ATOM | 845 | CA | THR | 316 | 18.707 | 31.533 | 84.099 | 1.00 | 7.99 |
| ATOM | 846 | CB | THR | 316 | 18.694 | 33.062 | 83.842 | 1.00 | 8.20 |
| ATOM | 847 | OG1 | THR | 316 | 20.045 | 33.540 | 83.922 | 1.00 | 8.51 |
| ATOM | 849 | CG2 | THR | 316 | 17.859 | 33.805 | 84.864 | 1.00 | 7.16 |
| ATOM | 850 | C | THR | 316 | 19.721 | 30.991 | 83.109 | 1.00 | 8.36 |
| ATOM | 851 | O | THR | 316 | 20.749 | 30.419 | 83.481 | 1.00 | 7.87 |
| ATOM | 852 | N | GLU | 317 | 19.407 | 31.224 | 81.833 | 1.00 | 8.54 |
| ATOM | 854 | CA | GLU | 317 | 20.244 | 30.893 | 80.683 | 1.00 | 8.64 |
| ATOM | 855 | CB | GLU | 317 | 19.533 | 31.405 | 79.427 | 1.00 | 8.05 |
| ATOM | 856 | CG | GLU | 317 | 20.234 | 31.279 | 78.081 | 1.00 | 7.55 |
| ATOM | 857 | CD | GLU | 317 | 19.372 | 31.826 | 76.920 | 1.00 | 7.38 |
| ATOM | 858 | OE1 | GLU | 317 | 18.483 | 32.662 | 77.157 | 1.00 | 7.83 |
| ATOM | 859 | OE2 | GLU | 317 | 19.593 | 31.463 | 75.755 | 1.00 | 7.77 |
| ATOM | 860 | C | GLU | 317 | 21.569 | 31.656 | 80.896 | 1.00 | 9.16 |
| ATOM | 861 | O | GLU | 317 | 21.564 | 32.825 | 81.332 | 1.00 | 9.34 |
| ATOM | 862 | N | TYR | 318 | 22.681 | 30.967 | 80.660 | 1.00 | 9.50 |
| ATOM | 864 | CA | TYR | 318 | 24.033 | 31.519 | 80.808 | 1.00 | 10.42 |
| ATOM | 865 | CB | TYR | 318 | 25.028 | 30.413 | 81.213 | 1.00 | 10.86 |
| ATOM | 866 | CG | TYR | 318 | 26.398 | 30.938 | 81.596 | 1.00 | 11.62 |
| ATOM | 867 | CD1 | TYR | 318 | 26.588 | 31.575 | 82.810 | 1.00 | 12.07 |
| ATOM | 868 | CE1 | TYR | 318 | 27.835 | 32.092 | 83.174 | 1.00 | 12.42 |
| ATOM | 869 | CD2 | TYR | 318 | 27.499 | 30.819 | 80.733 | 1.00 | 11.92 |
| ATOM | 870 | CE2 | TYR | 318 | 28.762 | 31.343 | 81.089 | 1.00 | 11.97 |
| ATOM | 871 | CZ | TYR | 318 | 28.914 | 31.978 | 82.312 | 1.00 | 12.53 |
| ATOM | 872 | OH | TYR | 318 | 30.133 | 32.526 | 82.704 | 1.00 | 13.18 |
| ATOM | 874 | C | TYR | 318 | 24.484 | 32.169 | 79.499 | 1.00 | 10.38 |
| ATOM | 875 | O | TYR | 318 | 24.341 | 31.601 | 78.422 | 1.00 | 10.43 |
| ATOM | 876 | N | MET | 319 | 25.051 | 33.361 | 79.609 | 1.00 | 10.88 |
| ATOM | 878 | CA | MET | 319 | 25.511 | 34.123 | 78.447 | 1.00 | 11.09 |
| ATOM | 879 | CB | MET | 319 | 24.766 | 35.464 | 78.389 | 1.00 | 10.81 |
| ATOM | 880 | CG | MET | 319 | 23.194 | 35.299 | 78.260 | 1.00 | 10.34 |
| ATOM | 881 | SD | MET | 319 | 22.751 | 34.665 | 76.705 | 1.00 | 10.19 |
| ATOM | 882 | CE | MET | 319 | 23.128 | 36.043 | 75.519 | 1.00 | 9.74 |
| ATOM | 883 | C | MET | 319 | 27.027 | 34.281 | 78.584 | 1.00 | 11.45 |
| ATOM | 884 | O | MET | 319 | 27.540 | 35.136 | 79.322 | 1.00 | 11.99 |
| ATOM | 885 | N | GLU | 320 | 27.730 | 33.432 | 77.854 | 1.00 | 11.57 |
| ATOM | 887 | CA | GLU | 320 | 29.184 | 33.340 | 77.919 | 1.00 | 11.89 |
| ATOM | 888 | CB | GLU | 320 | 29.703 | 32.424 | 76.798 | 1.00 | 13.12 |
| ATOM | 889 | CG | GLU | 320 | 31.172 | 32.053 | 76.932 | 1.00 | 15.65 |
| ATOM | 890 | CD | GLU | 320 | 31.453 | 31.330 | 78.227 | 1.00 | 16.68 |
| ATOM | 891 | OE1 | GLU | 320 | 31.244 | 30.103 | 78.266 | 1.00 | 18.66 |
| ATOM | 892 | OE2 | GLU | 320 | 31.891 | 31.973 | 79.207 | 1.00 | 18.52 |
| ATOM | 893 | C | GLU | 320 | 29.990 | 34.629 | 77.939 | 1.00 | 11.13 |
| ATOM | 894 | O | GLU | 320 | 30.941 | 34.739 | 78.687 | 1.00 | 11.21 |
| ATOM | 895 | N | ASN | 321 | 29.604 | 35.590 | 77.115 | 1.00 | 10.35 |
| ATOM | 897 | CA | ASN | 321 | 30.358 | 36.820 | 77.010 | 1.00 | 9.39 |
| ATOM | 898 | CB | ASN | 321 | 30.528 | 37.205 | 75.532 | 1.00 | 9.23 |
| ATOM | 899 | CG | ASN | 321 | 31.599 | 36.366 | 74.846 | 1.00 | 9.76 |

TABLE 7-continued

Coordinates of Lck bound with PD153035

| | | Atom Type | Res | # | X | Y | Z | Occ | B |
|---|---|---|---|---|---|---|---|---|---|
| ATOM | 900 | OD1 | ASN | 321 | 32.705 | 36.200 | 75.391 | 1.00 | 9.25 |
| ATOM | 901 | ND2 | ASN | 321 | 31.282 | 35.823 | 73.668 | 1.00 | 8.81 |
| ATOM | 904 | C | ASN | 321 | 29.949 | 37.982 | 77.893 | 1.00 | 8.57 |
| ATOM | 905 | O | ASN | 321 | 30.437 | 39.085 | 77.709 | 1.00 | 8.46 |
| ATOM | 906 | N | GLY | 322 | 29.053 | 37.720 | 78.847 | 1.00 | 7.34 |
| ATOM | 908 | CA | GLY | 322 | 28.637 | 38.734 | 79.802 | 1.00 | 6.50 |
| ATOM | 909 | C | GLY | 322 | 27.957 | 39.975 | 79.272 | 1.00 | 5.80 |
| ATOM | 910 | O | GLY | 322 | 27.339 | 39.908 | 78.232 | 1.00 | 6.05 |
| ATOM | 911 | N | SER | 323 | 27.993 | 41.066 | 80.037 | 0.43 | 5.40 |
| ATOM | 913 | CA | SER | 323 | 27.337 | 42.313 | 79.647 | 0.43 | 5.30 |
| ATOM | 914 | CB | SER | 323 | 27.323 | 43.328 | 80.807 | 0.43 | 5.06 |
| ATOM | 915 | OG | SER | 323 | 28.639 | 43.672 | 81.175 | 0.43 | 5.29 |
| ATOM | 917 | C | SER | 323 | 28.010 | 42.909 | 78.430 | 0.43 | 5.52 |
| ATOM | 918 | O | SER | 323 | 29.238 | 42.855 | 78.290 | 0.43 | 4.55 |
| ATOM | 919 | N | LEU | 324 | 27.188 | 43.487 | 77.560 | 1.00 | 6.10 |
| ATOM | 921 | CA | LEU | 324 | 27.665 | 44.095 | 76.328 | 1.00 | 6.27 |
| ATOM | 922 | CB | LEU | 324 | 26.486 | 44.654 | 75.512 | 1.00 | 5.94 |
| ATOM | 923 | CG | LEU | 324 | 26.810 | 45.438 | 74.231 | 1.00 | 5.58 |
| ATOM | 924 | CD1 | LEU | 324 | 27.480 | 44.576 | 73.171 | 1.00 | 5.60 |
| ATOM | 925 | CD2 | LEU | 324 | 25.533 | 46.028 | 73.665 | 1.00 | 5.75 |
| ATOM | 926 | C | LEU | 324 | 28.636 | 45.232 | 76.662 | 1.00 | 7.06 |
| ATOM | 927 | O | LEU | 324 | 29.654 | 45.415 | 75.963 | 1.00 | 7.18 |
| ATOM | 928 | N | VAL | 325 | 28.313 | 46.005 | 77.699 | 1.00 | 7.66 |
| ATOM | 930 | CA | VAL | 325 | 29.180 | 47.113 | 78.074 | 1.00 | 8.23 |
| ATOM | 931 | CB | VAL | 325 | 28.561 | 47.997 | 79.177 | 1.00 | 8.68 |
| ATOM | 932 | CG1 | VAL | 325 | 28.758 | 47.406 | 80.550 | 1.00 | 8.68 |
| ATOM | 933 | CG2 | VAL | 325 | 29.129 | 49.400 | 79.093 | 1.00 | 9.29 |
| ATOM | 934 | C | VAL | 325 | 30.606 | 46.612 | 78.418 | 1.00 | 8.90 |
| ATOM | 935 | O | VAL | 325 | 31.594 | 47.239 | 78.012 | 1.00 | 9.22 |
| ATOM | 936 | N | ASP | 326 | 30.714 | 45.442 | 79.048 | 1.00 | 8.75 |
| ATOM | 938 | CA | ASP | 326 | 32.016 | 44.868 | 79.389 | 1.00 | 8.84 |
| ATOM | 939 | CB | ASP | 326 | 31.897 | 43.835 | 80.510 | 1.00 | 9.27 |
| ATOM | 940 | CG | ASP | 326 | 31.554 | 44.455 | 81.842 | 1.00 | 10.19 |
| ATOM | 941 | OD1 | ASP | 326 | 31.980 | 45.590 | 82.113 | 1.00 | 10.50 |
| ATOM | 942 | OD2 | ASP | 326 | 30.872 | 43.800 | 82.635 | 1.00 | 10.15 |
| ATOM | 943 | C | ASP | 326 | 32.677 | 44.215 | 78.173 | 1.00 | 9.00 |
| ATOM | 944 | O | ASP | 326 | 33.840 | 44.509 | 77.857 | 1.00 | 9.40 |
| ATOM | 945 | N | PHE | 327 | 31.904 | 43.423 | 77.427 | 1.00 | 8.23 |
| ATOM | 947 | CA | PHE | 327 | 32.410 | 42.748 | 76.249 | 1.00 | 8.00 |
| ATOM | 948 | CB | PHE | 327 | 31.292 | 41.951 | 75.588 | 1.00 | 8.17 |
| ATOM | 949 | CG | PHE | 327 | 31.719 | 41.270 | 74.342 | 1.00 | 8.32 |
| ATOM | 950 | CD1 | PHE | 327 | 32.642 | 40.222 | 74.388 | 1.00 | 8.05 |
| ATOM | 951 | CD2 | PHE | 327 | 31.220 | 41.678 | 73.111 | 1.00 | 7.97 |
| ATOM | 952 | CE1 | PHE | 327 | 33.053 | 39.594 | 73.216 | 1.00 | 7.79 |
| ATOM | 953 | CE2 | PHE | 327 | 31.628 | 41.054 | 71.937 | 1.00 | 8.21 |
| ATOM | 954 | CZ | PHE | 327 | 32.558 | 39.998 | 72.004 | 1.00 | 8.58 |
| ATOM | 955 | C | PHE | 327 | 33.027 | 43.676 | 75.196 | 1.00 | 8.16 |
| ATOM | 956 | O | PHE | 327 | 34.060 | 43.349 | 74.601 | 1.00 | 7.75 |
| ATOM | 957 | N | LEU | 328 | 32.378 | 44.815 | 74.947 | 0.40 | 7.57 |
| ATOM | 959 | CA | LEU | 328 | 32.853 | 45.767 | 73.940 | 0.40 | 7.45 |
| ATOM | 960 | CB | LEU | 328 | 31.850 | 46.916 | 73.763 | 0.40 | 6.83 |
| ATOM | 961 | CG | LEU | 328 | 30.499 | 46.640 | 73.088 | 0.40 | 5.98 |
| ATOM | 962 | CD1 | LEU | 328 | 29.617 | 47.885 | 73.156 | 0.40 | 6.09 |
| ATOM | 963 | CD2 | LEU | 328 | 30.695 | 46.224 | 71.654 | 0.40 | 5.97 |
| ATOM | 964 | C | LEU | 328 | 34.238 | 46.324 | 74.259 | 0.40 | 7.78 |
| ATOM | 965 | O | LEU | 328 | 34.895 | 46.907 | 73.403 | 0.40 | 7.42 |
| ATOM | 966 | N | LYS | 329 | 34.644 | 46.177 | 75.514 | 1.00 | 8.52 |
| ATOM | 968 | CA | LYS | 329 | 35.957 | 46.644 | 75.984 | 1.00 | 9.34 |
| ATOM | 969 | CB | LYS | 329 | 35.843 | 47.207 | 77.395 | 1.00 | 9.71 |
| ATOM | 970 | CG | LYS | 329 | 34.854 | 48.366 | 77.490 | 1.00 | 9.78 |
| ATOM | 971 | CD | LYS | 329 | 34.846 | 48.890 | 78.884 | 1.00 | 10.12 |
| ATOM | 972 | CE | LYS | 329 | 33.855 | 50.024 | 79.047 | 1.00 | 10.74 |
| ATOM | 973 | NZ | LYS | 329 | 33.687 | 50.243 | 80.504 | 1.00 | 11.73 |
| ATOM | 977 | C | LYS | 329 | 37.068 | 45.579 | 75.946 | 1.00 | 10.03 |
| ATOM | 978 | O | LYS | 329 | 38.244 | 45.872 | 76.213 | 1.00 | 9.73 |
| ATOM | 979 | N | THR | 330 | 36.698 | 44.345 | 75.636 | 1.00 | 10.26 |
| ATOM | 981 | CA | THR | 330 | 37.680 | 43.271 | 75.561 | 1.00 | 9.97 |
| ATOM | 982 | CB | THR | 330 | 37.014 | 41.891 | 75.677 | 1.00 | 9.65 |
| ATOM | 983 | OG1 | THR | 330 | 36.170 | 41.694 | 74.550 | 1.00 | 9.41 |
| ATOM | 985 | CG2 | THR | 330 | 36.211 | 41.763 | 76.947 | 1.00 | 9.80 |
| ATOM | 986 | C | THR | 330 | 38.343 | 43.305 | 74.205 | 1.00 | 10.55 |
| ATOM | 987 | O | THR | 330 | 37.812 | 43.883 | 73.257 | 1.00 | 10.44 |
| ATOM | 988 | N | PRO | 331 | 39.471 | 42.598 | 74.052 | 1.00 | 10.98 |
| ATOM | 989 | CD | PRO | 331 | 40.281 | 41.925 | 75.089 | 1.00 | 10.53 |

TABLE 7-continued

Coordinates of Lck bound with PD153035

| | | Atom Type | Res | # | X | Y | Z | Occ | B |
|---|---|---|---|---|---|---|---|---|---|
| ATOM | 990 | CA | PRO | 331 | 40.151 | 42.586 | 72.754 | 1.00 | 10.99 |
| ATOM | 991 | CB | PRO | 331 | 41.291 | 41.586 | 72.964 | 1.00 | 10.97 |
| ATOM | 992 | CG | PRO | 331 | 41.602 | 41.735 | 74.386 | 1.00 | 11.03 |
| ATOM | 993 | C | PRO | 331 | 39.212 | 42.131 | 71.629 | 1.00 | 11.70 |
| ATOM | 994 | O | PRO | 331 | 39.258 | 42.674 | 70.532 | 1.00 | 12.26 |
| ATOM | 995 | N | SER | 332 | 38.323 | 41.175 | 71.905 | 1.00 | 12.36 |
| ATOM | 997 | CA | SER | 332 | 37.394 | 40.708 | 70.862 | 1.00 | 13.12 |
| ATOM | 998 | CB | SER | 332 | 36.556 | 39.498 | 71.345 | 1.00 | 13.44 |
| ATOM | 999 | OG | SER | 332 | 37.322 | 38.315 | 71.359 | 1.00 | 14.99 |
| ATOM | 1001 | C | SER | 332 | 36.427 | 41.817 | 70.451 | 1.00 | 13.06 |
| ATOM | 1002 | O | SER | 332 | 36.145 | 42.002 | 69.262 | 1.00 | 12.97 |
| ATOM | 1003 | N | GLY | 333 | 35.871 | 42.477 | 71.467 | 1.00 | 13.57 |
| ATOM | 1005 | CA | GLY | 333 | 34.915 | 43.551 | 71.259 | 1.00 | 14.17 |
| ATOM | 1006 | C | GLY | 333 | 35.479 | 44.739 | 70.514 | 1.00 | 14.54 |
| ATOM | 1007 | O | GLY | 333 | 34.807 | 45.361 | 69.663 | 1.00 | 14.49 |
| ATOM | 1008 | N | ILE | 334 | 36.713 | 45.080 | 70.856 | 1.00 | 14.96 |
| ATOM | 1010 | CA | ILE | 334 | 37.383 | 46.186 | 70.217 | 1.00 | 15.74 |
| ATOM | 1011 | CB | ILE | 334 | 38.734 | 46.485 | 70.929 | 1.00 | 15.79 |
| ATOM | 1012 | CG2 | ILE | 334 | 39.573 | 47.484 | 70.123 | 1.00 | 16.44 |
| ATOM | 1013 | CG1 | ILE | 334 | 38.439 | 47.026 | 72.329 | 1.00 | 16.36 |
| ATOM | 1014 | CD1 | ILE | 334 | 39.637 | 47.015 | 73.272 | 1.00 | 16.42 |
| ATOM | 1015 | C | ILE | 334 | 37.550 | 45.965 | 68.722 | 1.00 | 16.16 |
| ATOM | 1016 | O | ILE | 334 | 37.371 | 46.886 | 67.943 | 1.00 | 16.10 |
| ATOM | 1017 | N | LYS | 335 | 37.787 | 44.729 | 68.300 | 1.00 | 16.72 |
| ATOM | 1019 | CA | LYS | 335 | 37.973 | 44.468 | 66.870 | 1.00 | 17.23 |
| ATOM | 1020 | CB | LYS | 335 | 38.765 | 43.187 | 66.660 | 1.00 | 18.16 |
| ATOM | 1021 | CG | LYS | 335 | 40.075 | 43.175 | 67.404 | 1.00 | 19.86 |
| ATOM | 1022 | CD | LYS | 335 | 40.680 | 41.793 | 67.426 | 1.00 | 20.64 |
| ATOM | 1023 | CE | LYS | 335 | 41.900 | 41.803 | 68.281 | 1.00 | 21.41 |
| ATOM | 1024 | NZ | LYS | 335 | 42.066 | 40.495 | 68.900 | 1.00 | 21.98 |
| ATOM | 1028 | C | LYS | 335 | 36.699 | 44.420 | 66.031 | 1.00 | 16.74 |
| ATOM | 1029 | O | LYS | 335 | 36.776 | 44.365 | 64.815 | 1.00 | 16.44 |
| ATOM | 1030 | N | LEU | 336 | 35.537 | 44.462 | 66.670 | 1.00 | 16.67 |
| ATOM | 1032 | CA | LEU | 336 | 34.257 | 44.409 | 65.931 | 1.00 | 16.25 |
| ATOM | 1033 | CB | LEU | 336 | 33.064 | 44.439 | 66.878 | 1.00 | 15.95 |
| ATOM | 1034 | CG | LEU | 336 | 32.995 | 43.325 | 67.925 | 1.00 | 16.53 |
| ATOM | 1035 | CD1 | LEU | 336 | 31.750 | 43.491 | 68.773 | 1.00 | 16.61 |
| ATOM | 1036 | CD2 | LEU | 336 | 33.071 | 41.937 | 67.269 | 1.00 | 16.33 |
| ATOM | 1037 | C | LEU | 336 | 34.098 | 45.554 | 64.934 | 1.00 | 15.86 |
| ATOM | 1038 | O | LEU | 336 | 34.363 | 46.713 | 65.258 | 1.00 | 15.98 |
| ATOM | 1039 | N | THR | 337 | 33.612 | 45.203 | 63.745 | 1.00 | 15.26 |
| ATOM | 1041 | CA | THR | 337 | 33.370 | 46.141 | 62.665 | 1.00 | 15.15 |
| ATOM | 1042 | CB | THR | 337 | 33.218 | 45.392 | 61.326 | 1.00 | 15.14 |
| ATOM | 1043 | OG1 | THR | 337 | 32.056 | 44.534 | 61.389 | 1.00 | 15.61 |
| ATOM | 1045 | CG2 | THR | 337 | 34.477 | 44.554 | 61.039 | 1.00 | 15.61 |
| ATOM | 1046 | C | THR | 337 | 32.043 | 46.856 | 62.936 | 1.00 | 14.41 |
| ATOM | 1047 | O | THR | 337 | 31.187 | 46.317 | 63.649 | 1.00 | 14.28 |
| ATOM | 1048 | N | ILE | 338 | 31.866 | 48.040 | 62.344 | 1.00 | 13.83 |
| ATOM | 1050 | CA | ILE | 338 | 30.626 | 48.786 | 62.523 | 1.00 | 13.58 |
| ATOM | 1051 | CB | ILE | 338 | 30.647 | 50.180 | 61.814 | 1.00 | 13.62 |
| ATOM | 1052 | CG2 | ILE | 338 | 30.800 | 50.019 | 60.336 | 1.00 | 14.09 |
| ATOM | 1053 | CG1 | ILE | 338 | 29.349 | 50.944 | 62.107 | 1.00 | 13.54 |
| ATOM | 1054 | CD1 | ILE | 338 | 29.078 | 51.137 | 63.571 | 1.00 | 13.19 |
| ATOM | 1055 | C | ILE | 338 | 29.445 | 47.930 | 62.039 | 1.00 | 13.08 |
| ATOM | 1056 | O | ILE | 338 | 28.349 | 48.063 | 62.546 | 1.00 | 12.98 |
| ATOM | 1057 | N | ASN | 339 | 29.699 | 47.025 | 61.093 | 1.00 | 13.04 |
| ATOM | 1059 | CA | ASN | 339 | 28.685 | 46.106 | 60.568 | 1.00 | 12.95 |
| ATOM | 1060 | CB | ASN | 339 | 29.300 | 45.311 | 59.415 | 1.00 | 13.97 |
| ATOM | 1061 | CG | ASN | 339 | 28.849 | 43.866 | 59.377 | 1.00 | 15.62 |
| ATOM | 1062 | OD1 | ASN | 339 | 27.855 | 43.505 | 58.756 | 1.00 | 16.45 |
| ATOM | 1063 | ND2 | ASN | 339 | 29.632 | 43.009 | 60.041 | 1.00 | 17.19 |
| ATOM | 1066 | C | ASN | 339 | 28.168 | 45.171 | 61.682 | 1.00 | 11.98 |
| ATOM | 1067 | O | ASN | 339 | 26.959 | 44.992 | 61.866 | 1.00 | 11.65 |
| ATOM | 1068 | N | LYS | 340 | 29.087 | 44.598 | 62.466 | 1.00 | 10.92 |
| ATOM | 1070 | CA | LYS | 340 | 28.667 | 43.710 | 63.539 | 1.00 | 9.76 |
| ATOM | 1071 | CB | LYS | 340 | 29.834 | 42.859 | 64.051 | 1.00 | 9.43 |
| ATOM | 1072 | CG | LYS | 340 | 29.487 | 42.007 | 65.249 | 1.00 | 8.51 |
| ATOM | 1073 | CD | LYS | 340 | 28.553 | 40.901 | 64.827 | 1.00 | 7.92 |
| ATOM | 1074 | CE | LYS | 340 | 28.103 | 40.083 | 66.014 | 1.00 | 8.23 |
| ATOM | 1075 | NZ | LYS | 340 | 26.997 | 39.117 | 65.619 | 1.00 | 8.02 |
| ATOM | 1079 | C | LYS | 340 | 28.028 | 44.491 | 64.695 | 1.00 | 9.13 |
| ATOM | 1080 | O | LYS | 340 | 27.134 | 43.984 | 65.382 | 1.00 | 8.52 |
| ATOM | 1081 | N | LEU | 341 | 28.473 | 45.730 | 64.922 | 1.00 | 8.72 |
| ATOM | 1083 | CA | LEU | 341 | 27.870 | 46.527 | 65.990 | 1.00 | 8.15 |

TABLE 7-continued

Coordinates of Lck bound with PD153035

| | Atom Type | Res | # | X | Y | Z | Occ | B |
|---|---|---|---|---|---|---|---|---|
| ATOM | 1084 | CB | LEU | 341 | 28.670 | 47.836 | 66.214 | 1.00 | 8.69 |
| ATOM | 1085 | CG | LEU | 341 | 30.126 | 47.663 | 66.696 | 1.00 | 8.51 |
| ATOM | 1086 | CD1 | LEU | 341 | 30.838 | 49.008 | 66.734 | 1.00 | 9.28 |
| ATOM | 1087 | CD2 | LEU | 341 | 30.173 | 47.043 | 68.074 | 1.00 | 8.74 |
| ATOM | 1088 | C | LEU | 341 | 26.390 | 46.836 | 65.625 | 1.00 | 7.66 |
| ATOM | 1089 | O | LEU | 341 | 25.516 | 46.858 | 66.485 | 1.00 | 7.42 |
| ATOM | 1090 | N | LEU | 342 | 26.140 | 47.105 | 64.348 | 1.00 | 7.55 |
| ATOM | 1092 | CA | LEU | 342 | 24.788 | 47.411 | 63.855 | 1.00 | 7.67 |
| ATOM | 1093 | CB | LEU | 342 | 24.864 | 47.858 | 62.395 | 1.00 | 8.04 |
| ATOM | 1094 | CG | LEU | 342 | 25.484 | 49.264 | 62.272 | 1.00 | 8.00 |
| ATOM | 1095 | CD1 | LEU | 342 | 25.975 | 49.570 | 60.857 | 1.00 | 7.89 |
| ATOM | 1096 | CD2 | LEU | 342 | 24.465 | 50.288 | 62.759 | 1.00 | 8.34 |
| ATOM | 1097 | C | LEU | 342 | 23.918 | 46.153 | 63.960 | 1.00 | 7.52 |
| ATOM | 1098 | O | LEU | 342 | 22.754 | 46.215 | 64.321 | 1.00 | 6.70 |
| ATOM | 1099 | N | ASP | 343 | 24.535 | 45.016 | 63.631 | 1.00 | 7.76 |
| ATOM | 1101 | CA | ASP | 343 | 23.897 | 43.688 | 63.683 | 1.00 | 7.17 |
| ATOM | 1102 | CB | ASP | 343 | 24.957 | 42.610 | 63.318 | 1.00 | 7.20 |
| ATOM | 1103 | CG | ASP | 343 | 24.520 | 41.198 | 63.656 | 1.00 | 7.46 |
| ATOM | 1104 | OD1 | ASP | 343 | 23.309 | 40.985 | 63.857 | 1.00 | 7.35 |
| ATOM | 1105 | OD2 | ASP | 343 | 25.396 | 40.298 | 63.742 | 1.00 | 7.52 |
| ATOM | 1106 | C | ASP | 343 | 23.381 | 43.543 | 65.103 | 1.00 | 7.15 |
| ATOM | 1107 | O | ASP | 343 | 22.180 | 43.394 | 65.315 | 1.00 | 6.79 |
| ATOM | 1108 | N | MET | 344 | 24.278 | 43.623 | 66.081 | 1.00 | 6.70 |
| ATOM | 1110 | CA | MET | 344 | 23.922 | 43.536 | 67.504 | 1.00 | 7.09 |
| ATOM | 1111 | CB | MET | 344 | 25.178 | 43.680 | 68.366 | 1.00 | 7.76 |
| ATOM | 1112 | CG | MET | 344 | 26.192 | 42.539 | 68.236 | 1.00 | 8.00 |
| ATOM | 1113 | SD | MET | 344 | 27.700 | 43.114 | 69.084 | 1.00 | 10.54 |
| ATOM | 1114 | CE | MET | 344 | 27.872 | 42.026 | 70.247 | 1.00 | 8.70 |
| ATOM | 1115 | C | MET | 344 | 22.867 | 44.562 | 67.942 | 1.00 | 6.95 |
| ATOM | 1116 | O | MET | 344 | 21.970 | 44.246 | 68.701 | 1.00 | 6.68 |
| ATOM | 1117 | N | ALA | 345 | 22.978 | 45.787 | 67.436 | 1.00 | 7.20 |
| ATOM | 1119 | CA | ALA | 345 | 22.003 | 46.846 | 67.771 | 1.00 | 6.73 |
| ATOM | 1120 | CB | ALA | 345 | 22.425 | 48.175 | 67.134 | 1.00 | 6.77 |
| ATOM | 1121 | C | ALA | 345 | 20.608 | 46.428 | 67.264 | 1.00 | 6.46 |
| ATOM | 1122 | O | ALA | 345 | 19.597 | 46.660 | 67.935 | 1.00 | 6.70 |
| ATOM | 1123 | N | ALA | 346 | 20.569 | 45.849 | 66.066 | 1.00 | 5.91 |
| ATOM | 1125 | CA | ALA | 346 | 19.329 | 45.347 | 65.511 | 1.00 | 6.15 |
| ATOM | 1126 | CB | ALA | 346 | 19.507 | 44.900 | 64.079 | 1.00 | 6.12 |
| ATOM | 1127 | C | ALA | 346 | 18.824 | 44.184 | 66.380 | 1.00 | 5.95 |
| ATOM | 1128 | O | ALA | 346 | 17.637 | 44.121 | 66.651 | 1.00 | 6.41 |
| ATOM | 1129 | N | GLN | 347 | 19.707 | 43.291 | 66.852 | 1.00 | 5.78 |
| ATOM | 1131 | CA | GLN | 347 | 19.266 | 42.176 | 67.716 | 1.00 | 5.22 |
| ATOM | 1132 | CB | GLN | 347 | 20.454 | 41.271 | 68.104 | 1.00 | 4.44 |
| ATOM | 1133 | CG | GLN | 347 | 20.991 | 40.499 | 66.899 | 1.00 | 3.12 |
| ATOM | 1134 | CD | GLN | 347 | 22.134 | 39.533 | 67.245 | 1.00 | 2.93 |
| ATOM | 1135 | OE1 | GLN | 347 | 22.231 | 39.055 | 68.378 | 1.00 | 3.01 |
| ATOM | 1136 | NE2 | GLN | 347 | 23.002 | 39.283 | 66.280 | 1.00 | 2.11 |
| ATOM | 1139 | C | GLN | 347 | 18.565 | 42.696 | 68.981 | 1.00 | 5.16 |
| ATOM | 1140 | O | GLN | 347 | 17.524 | 42.168 | 69.416 | 1.00 | 5.25 |
| ATOM | 1141 | N | ILE | 348 | 19.114 | 43.772 | 69.547 | 1.00 | 4.88 |
| ATOM | 1143 | CA | ILE | 348 | 18.573 | 44.358 | 70.769 | 1.00 | 5.25 |
| ATOM | 1144 | CB | ILE | 348 | 19.562 | 45.428 | 71.367 | 1.00 | 5.35 |
| ATOM | 1145 | CG2 | ILE | 348 | 18.968 | 46.145 | 72.587 | 1.00 | 5.41 |
| ATOM | 1146 | CG1 | ILE | 348 | 20.886 | 44.753 | 71.759 | 1.00 | 5.28 |
| ATOM | 1147 | CD1 | ILE | 348 | 22.012 | 45.785 | 72.044 | 1.00 | 6.37 |
| ATOM | 1148 | C | ILE | 348 | 17.208 | 44.979 | 70.472 | 1.00 | 5.26 |
| ATOM | 1149 | O | ILE | 348 | 16.299 | 44.873 | 71.291 | 1.00 | 4.75 |
| ATOM | 1150 | N | ALA | 349 | 17.102 | 45.627 | 69.310 | 1.00 | 6.02 |
| ATOM | 1152 | CA | ALA | 349 | 15.847 | 46.272 | 68.880 | 1.00 | 6.05 |
| ATOM | 1153 | CB | ALA | 349 | 16.054 | 46.997 | 67.555 | 1.00 | 6.10 |
| ATOM | 1154 | C | ALA | 349 | 14.797 | 45.145 | 68.724 | 1.00 | 6.33 |
| ATOM | 1155 | O | ALA | 349 | 13.648 | 45.271 | 69.143 | 1.00 | 5.78 |
| ATOM | 1156 | N | GLU | 350 | 15.231 | 44.025 | 68.159 | 1.00 | 5.94 |
| ATOM | 1158 | CA | GLU | 350 | 14.346 | 42.874 | 67.968 | 1.00 | 5.77 |
| ATOM | 1159 | CB | GLU | 350 | 15.088 | 41.753 | 67.243 | 1.00 | 6.61 |
| ATOM | 1160 | CG | GLU | 350 | 14.200 | 40.614 | 66.768 | 1.00 | 7.22 |
| ATOM | 1161 | CD | GLU | 350 | 15.001 | 39.527 | 66.039 | 1.00 | 7.46 |
| ATOM | 1162 | OE1 | GLU | 350 | 16.049 | 39.838 | 65.435 | 1.00 | 7.85 |
| ATOM | 1163 | OE2 | GLU | 350 | 14.584 | 38.355 | 66.067 | 1.00 | 7.23 |
| ATOM | 1164 | C | GLU | 350 | 13.775 | 42.364 | 69.293 | 1.00 | 5.63 |
| ATOM | 1165 | O | GLU | 350 | 12.572 | 42.086 | 69.393 | 1.00 | 5.59 |
| ATOM | 1166 | N | GLY | 351 | 14.617 | 42.260 | 70.314 | 1.00 | 4.60 |
| ATOM | 1168 | CA | GLY | 351 | 14.138 | 41.806 | 71.618 | 1.00 | 4.84 |
| ATOM | 1169 | C | GLY | 351 | 13.208 | 42.825 | 72.281 | 1.00 | 5.42 |

TABLE 7-continued

Coordinates of Lck bound with PD153035

| | | Atom Type | Res | # | X | Y | Z | Occ | B |
|---|---|---|---|---|---|---|---|---|---|
| ATOM | 1170 | O | GLY | 351 | 12.161 | 42.482 | 72.828 | 1.00 | 4.89 |
| ATOM | 1171 | N | MET | 352 | 13.573 | 44.098 | 72.177 | 1.00 | 5.42 |
| ATOM | 1173 | CA | MET | 352 | 12.758 | 45.171 | 72.712 | 1.00 | 6.24 |
| ATOM | 1174 | CB | MET | 352 | 13.574 | 46.484 | 72.631 | 1.00 | 6.46 |
| ATOM | 1175 | CG | MET | 352 | 14.845 | 46.422 | 73.593 | 1.00 | 7.23 |
| ATOM | 1176 | SD | MET | 352 | 14.138 | 46.384 | 75.213 | 1.00 | 8.16 |
| ATOM | 1177 | CE | MET | 352 | 15.342 | 46.039 | 76.305 | 1.00 | 9.38 |
| ATOM | 1178 | C | MET | 352 | 11.383 | 45.246 | 71.956 | 1.00 | 6.56 |
| ATOM | 1179 | O | MET | 352 | 10.346 | 45.606 | 72.546 | 1.00 | 6.65 |
| ATOM | 1180 | N | ALA | 353 | 11.342 | 44.822 | 70.692 | 1.00 | 6.90 |
| ATOM | 1182 | CA | ALA | 353 | 10.092 | 44.838 | 69.913 | 1.00 | 7.58 |
| ATOM | 1183 | CB | ALA | 353 | 10.347 | 44.657 | 68.424 | 1.00 | 7.40 |
| ATOM | 1184 | C | ALA | 353 | 9.118 | 43.766 | 70.403 | 1.00 | 8.05 |
| ATOM | 1185 | O | ALA | 353 | 7.906 | 43.887 | 70.195 | 1.00 | 8.11 |
| ATOM | 1186 | N | PHE | 354 | 9.661 | 42.683 | 70.964 | 1.00 | 8.40 |
| ATOM | 1188 | CA | PHE | 354 | 8.824 | 41.615 | 71.518 | 1.00 | 8.56 |
| ATOM | 1189 | CB | PHE | 354 | 9.649 | 40.349 | 71.797 | 1.00 | 9.18 |
| ATOM | 1190 | CG | PHE | 354 | 8.934 | 39.339 | 72.675 | 1.00 | 9.56 |
| ATOM | 1191 | CD1 | PHE | 354 | 7.941 | 38.520 | 72.148 | 1.00 | 10.21 |
| ATOM | 1192 | CD2 | PHE | 354 | 9.247 | 39.225 | 74.022 | 1.00 | 10.11 |
| ATOM | 1193 | CE1 | PHE | 354 | 7.260 | 37.592 | 72.964 | 1.00 | 9.63 |
| ATOM | 1194 | CE2 | PHE | 354 | 8.572 | 38.302 | 74.851 | 1.00 | 10.44 |
| ATOM | 1195 | CZ | PHE | 354 | 7.573 | 37.485 | 74.307 | 1.00 | 9.73 |
| ATOM | 1196 | C | PHE | 354 | 8.231 | 42.126 | 72.817 | 1.00 | 8.25 |
| ATOM | 1197 | O | PHE | 354 | 7.062 | 41.919 | 73.109 | 1.00 | 7.98 |
| ATOM | 1198 | N | ILE | 355 | 9.066 | 42.787 | 73.605 | 1.00 | 7.98 |
| ATOM | 1200 | CA | ILE | 355 | 8.661 | 43.363 | 74.878 | 1.00 | 8.22 |
| ATOM | 1201 | CB | ILE | 355 | 9.875 | 44.043 | 75.553 | 1.00 | 8.08 |
| ATOM | 1202 | CG2 | ILE | 355 | 9.442 | 45.031 | 76.603 | 1.00 | 8.82 |
| ATOM | 1203 | CG1 | ILE | 355 | 10.833 | 42.964 | 76.079 | 1.00 | 8.20 |
| ATOM | 1204 | CD1 | ILE | 355 | 12.028 | 43.503 | 76.890 | 1.00 | 8.28 |
| ATOM | 1205 | C | ILE | 355 | 7.524 | 44.372 | 74.639 | 1.00 | 8.53 |
| ATOM | 1206 | O | ILE | 355 | 6.526 | 44.358 | 75.337 | 1.00 | 8.27 |
| ATOM | 1207 | N | GLU | 356 | 7.705 | 45.215 | 73.623 | 1.00 | 8.92 |
| ATOM | 1209 | CA | GLU | 356 | 6.737 | 46.232 | 73.198 | 1.00 | 9.48 |
| ATOM | 1210 | CB | GLU | 356 | 7.359 | 47.041 | 72.049 | 1.00 | 9.89 |
| ATOM | 1211 | CG | GLU | 356 | 6.448 | 47.771 | 71.071 | 1.00 | 10.68 |
| ATOM | 1212 | CD | GLU | 356 | 7.258 | 48.506 | 69.997 | 1.00 | 11.39 |
| ATOM | 1213 | OE1 | GLU | 356 | 7.350 | 48.060 | 68.816 | 1.00 | 11.93 |
| ATOM | 1214 | OE2 | GLU | 356 | 7.806 | 49.558 | 70.338 | 1.00 | 12.54 |
| ATOM | 1215 | C | GLU | 356 | 5.412 | 45.568 | 72.777 | 1.00 | 9.82 |
| ATOM | 1216 | O | GLU | 356 | 4.367 | 45.946 | 73.260 | 1.00 | 9.73 |
| ATOM | 1217 | N | GLU | 357 | 5.480 | 44.541 | 71.933 | 0.36 | 10.16 |
| ATOM | 1219 | CA | GLU | 357 | 4.281 | 43.833 | 71.479 | 0.36 | 10.35 |
| ATOM | 1220 | CB | GLU | 357 | 4.646 | 42.821 | 70.372 | 0.36 | 10.59 |
| ATOM | 1221 | CG | GLU | 357 | 3.488 | 41.996 | 69.805 | 0.36 | 10.38 |
| ATOM | 1222 | CD | GLU | 357 | 3.188 | 40.752 | 70.628 | 0.36 | 10.62 |
| ATOM | 1223 | OE1 | GLU | 357 | 4.101 | 40.263 | 71.320 | 0.36 | 10.79 |
| ATOM | 1224 | OE2 | GLU | 357 | 2.037 | 40.254 | 70.599 | 0.36 | 10.96 |
| ATOM | 1225 | C | GLU | 357 | 3.518 | 43.152 | 72.629 | 0.36 | 10.48 |
| ATOM | 1226 | O | GLU | 357 | 2.297 | 43.018 | 72.570 | 0.36 | 10.06 |
| ATOM | 1227 | N | ARG | 358 | 4.232 | 42.703 | 73.661 | 1.00 | 10.72 |
| ATOM | 1229 | CA | ARG | 358 | 3.592 | 42.049 | 74.815 | 1.00 | 11.24 |
| ATOM | 1230 | CB | ARG | 358 | 4.556 | 41.046 | 75.491 | 1.00 | 11.48 |
| ATOM | 1231 | CG | ARG | 358 | 5.039 | 39.910 | 74.587 | 1.00 | 11.83 |
| ATOM | 1232 | CD | ARG | 358 | 3.868 | 39.143 | 73.964 | 1.00 | 13.16 |
| ATOM | 1233 | NE | ARG | 358 | 2.933 | 38.673 | 74.980 | 1.00 | 13.74 |
| ATOM | 1235 | CZ | ARG | 358 | 1.670 | 38.321 | 74.737 | 1.00 | 14.25 |
| ATOM | 1236 | NH1 | ARG | 358 | 1.182 | 38.378 | 73.507 | 1.00 | 14.63 |
| ATOM | 1239 | NH2 | ARG | 358 | 0.881 | 37.977 | 75.742 | 1.00 | 14.77 |
| ATOM | 1242 | C | ARG | 358 | 3.091 | 43.050 | 75.870 | 1.00 | 11.37 |
| ATOM | 1243 | O | ARG | 358 | 2.717 | 42.663 | 76.974 | 1.00 | 11.10 |
| ATOM | 1244 | N | ASN | 359 | 3.071 | 44.337 | 75.533 | 1.00 | 11.81 |
| ATOM | 1246 | CA | ASN | 359 | 2.635 | 45.374 | 76.485 | 1.00 | 12.13 |
| ATOM | 1247 | CB | ASN | 359 | 1.160 | 45.193 | 76.900 | 1.00 | 12.06 |
| ATOM | 1248 | CG | ASN | 359 | 0.208 | 45.568 | 75.810 | 1.00 | 12.35 |
| ATOM | 1249 | OD1 | ASN | 359 | 0.621 | 46.048 | 74.765 | 1.00 | 12.82 |
| ATOM | 1250 | ND2 | ASN | 359 | −1.091 | 45.327 | 76.035 | 1.00 | 12.10 |
| ATOM | 1253 | C | ASN | 359 | 3.492 | 45.479 | 77.744 | 1.00 | 12.50 |
| ATOM | 1254 | O | ASN | 359 | 2.975 | 45.734 | 78.835 | 1.00 | 12.85 |
| ATOM | 1255 | N | TYR | 360 | 4.788 | 45.185 | 77.614 | 1.00 | 12.44 |
| ATOM | 1257 | CA | TYR | 360 | 5.693 | 45.314 | 78.749 | 1.00 | 12.20 |
| ATOM | 1258 | CB | TYR | 360 | 6.495 | 44.010 | 79.001 | 1.00 | 13.16 |
| ATOM | 1259 | CG | TYR | 360 | 5.791 | 42.954 | 79.832 | 1.00 | 14.12 |

TABLE 7-continued

Coordinates of Lck bound with PD153035

| | Atom Type | Res | # | X | Y | Z | Occ | B |
|---|---|---|---|---|---|---|---|---|
| ATOM | 1260 | CD1 | TYR | 360 | 4.844 | 42.115 | 79.258 | 1.00 | 14.78 |
| ATOM | 1261 | CE1 | TYR | 360 | 4.172 | 41.152 | 80.012 | 1.00 | 15.20 |
| ATOM | 1262 | CD2 | TYR | 360 | 6.063 | 42.811 | 81.192 | 1.00 | 14.70 |
| ATOM | 1263 | CE2 | TYR | 360 | 5.395 | 41.852 | 81.958 | 1.00 | 15.23 |
| ATOM | 1264 | CZ | TYR | 360 | 4.446 | 41.034 | 81.357 | 1.00 | 15.41 |
| ATOM | 1265 | OH | TYR | 360 | 3.738 | 40.137 | 82.128 | 1.00 | 16.13 |
| ATOM | 1267 | C | TYR | 360 | 6.664 | 46.464 | 78.465 | 1.00 | 11.31 |
| ATOM | 1268 | O | TYR | 360 | 6.716 | 46.958 | 77.360 | 1.00 | 11.07 |
| ATOM | 1269 | N | ILE | 361 | 7.291 | 46.963 | 79.511 | 1.00 | 10.74 |
| ATOM | 1271 | CA | ILE | 361 | 8.354 | 47.961 | 79.393 | 1.00 | 10.32 |
| ATOM | 1272 | CB | ILE | 361 | 8.025 | 49.364 | 79.987 | 1.00 | 9.88 |
| ATOM | 1273 | CG2 | ILE | 361 | 7.102 | 50.175 | 79.029 | 1.00 | 10.16 |
| ATOM | 1274 | CG1 | ILE | 361 | 7.474 | 49.225 | 81.393 | 1.00 | 10.11 |
| ATOM | 1275 | CD1 | ILE | 361 | 7.153 | 50.528 | 82.086 | 1.00 | 10.10 |
| ATOM | 1276 | C | ILE | 361 | 9.480 | 47.353 | 80.223 | 1.00 | 10.22 |
| ATOM | 1277 | O | ILE | 361 | 9.213 | 46.567 | 81.129 | 1.00 | 10.06 |
| ATOM | 1278 | N | HIS | 362 | 10.712 | 47.794 | 79.977 | 1.00 | 10.06 |
| ATOM | 1280 | CA | HIS | 362 | 11.878 | 47.278 | 80.673 | 1.00 | 9.92 |
| ATOM | 1281 | CB | HIS | 362 | 12.978 | 46.998 | 79.636 | 1.00 | 10.18 |
| ATOM | 1282 | CG | HIS | 362 | 14.133 | 46.235 | 80.176 | 1.00 | 10.80 |
| ATOM | 1283 | CD2 | HIS | 362 | 14.364 | 44.893 | 80.240 | 1.00 | 10.36 |
| ATOM | 1284 | ND1 | HIS | 362 | 15.208 | 46.831 | 80.832 | 1.00 | 10.49 |
| ATOM | 1286 | CE1 | HIS | 362 | 16.020 | 45.895 | 81.271 | 1.00 | 1.00 |
| ATOM | 1287 | NE2 | HIS | 362 | 15.539 | 44.721 | 80.932 | 1.00 | 10.96 |
| ATOM | 1289 | C | HIS | 362 | 12.363 | 48.278 | 81.738 | 1.00 | 9.82 |
| ATOM | 1290 | O | HIS | 362 | 12.716 | 47.906 | 82.850 | 1.00 | 9.16 |
| ATOM | 1291 | N | ARG | 363 | 12.424 | 49.553 | 81.368 | 1.00 | 9.83 |
| ATOM | 1293 | CA | ARG | 363 | 12.862 | 50.611 | 82.273 | 1.00 | 9.90 |
| ATOM | 1294 | CB | ARG | 363 | 12.044 | 50.587 | 83.568 | 1.00 | 10.08 |
| ATOM | 1295 | CG | ARG | 363 | 10.576 | 50.777 | 83.316 | 1.00 | 10.74 |
| ATOM | 1296 | CD | ARG | 363 | 9.922 | 51.370 | 84.538 | 1.00 | 11.23 |
| ATOM | 1297 | NE | ARG | 363 | 9.938 | 50.453 | 85.659 | 1.00 | 11.39 |
| ATOM | 1299 | CZ | ARG | 363 | 9.881 | 50.812 | 86.928 | 1.00 | 11.65 |
| ATOM | 1300 | NH1 | ARG | 363 | 9.804 | 52.106 | 87.259 | 1.00 | 12.47 |
| ATOM | 1303 | NH2 | ARG | 363 | 9.830 | 49.876 | 87.860 | 1.00 | 11.63 |
| ATOM | 1306 | C | ARG | 363 | 14.335 | 50.703 | 82.663 | 1.00 | 9.47 |
| ATOM | 1307 | O | ARG | 363 | 14.714 | 51.672 | 83.321 | 1.00 | 9.48 |
| ATOM | 1308 | N | ASP | 364 | 15.148 | 49.721 | 82.276 | 1.00 | 8.99 |
| ATOM | 1310 | CA | ASP | 364 | 16.578 | 49.714 | 82.640 | 1.00 | 8.75 |
| ATOM | 1311 | CB | ASP | 364 | 16.794 | 48.748 | 83.809 | 1.00 | 8.65 |
| ATOM | 1312 | CG | ASP | 364 | 17.979 | 49.129 | 84.722 | 1.00 | 9.13 |
| ATOM | 1313 | OD1 | ASP | 364 | 18.664 | 50.149 | 84.513 | 1.00 | 9.46 |
| ATOM | 1314 | OD2 | ASP | 364 | 18.186 | 48.405 | 85.702 | 1.00 | 8.81 |
| ATOM | 1315 | C | ASP | 364 | 17.408 | 49.317 | 81.414 | 1.00 | 8.33 |
| ATOM | 1316 | O | ASP | 364 | 18.382 | 48.550 | 81.501 | 1.00 | 8.68 |
| ATOM | 1317 | N | LEU | 365 | 16.952 | 49.779 | 80.258 | 1.00 | 7.78 |
| ATOM | 1319 | CA | LEU | 365 | 17.591 | 49.511 | 78.998 | 1.00 | 7.94 |
| ATOM | 1320 | CB | LEU | 365 | 16.611 | 49.765 | 77.826 | 1.00 | 7.18 |
| ATOM | 1321 | CG | LEU | 365 | 17.102 | 49.432 | 76.399 | 1.00 | 6.82 |
| ATOM | 1322 | CD1 | LEU | 365 | 17.684 | 48.059 | 76.400 | 1.00 | 6.45 |
| ATOM | 1323 | CD2 | LEU | 365 | 16.023 | 49.533 | 75.302 | 1.00 | 6.33 |
| ATOM | 1324 | C | LEU | 365 | 18.912 | 50.327 | 78.855 | 1.00 | 8.69 |
| ATOM | 1325 | O | LEU | 365 | 18.919 | 51.570 | 78.832 | 1.00 | 8.75 |
| ATOM | 1326 | N | ARG | 366 | 20.021 | 49.597 | 78.857 | 1.00 | 8.83 |
| ATOM | 1328 | CA | ARG | 366 | 21.385 | 50.144 | 78.722 | 1.00 | 9.21 |
| ATOM | 1329 | CB | ARG | 366 | 21.828 | 50.824 | 80.027 | 1.00 | 10.18 |
| ATOM | 1330 | CG | ARG | 366 | 21.654 | 49.943 | 81.243 | 1.00 | 12.47 |
| ATOM | 1331 | CD | ARG | 366 | 21.776 | 50.744 | 82.519 | 1.00 | 14.53 |
| ATOM | 1332 | NE | ARG | 366 | 23.106 | 51.333 | 82.659 | 1.00 | 15.73 |
| ATOM | 1334 | CZ | ARG | 366 | 23.453 | 52.127 | 83.659 | 1.00 | 16.32 |
| ATOM | 1335 | NH1 | ARG | 366 | 22.566 | 52.421 | 84.602 | 1.00 | 16.74 |
| ATOM | 1338 | NH2 | ARG | 366 | 24.690 | 52.602 | 83.732 | 1.00 | 17.17 |
| ATOM | 1341 | C | ARG | 366 | 22.317 | 48.963 | 78.433 | 1.00 | 8.94 |
| ATOM | 1342 | O | ARG | 366 | 21.986 | 47.839 | 78.761 | 1.00 | 8.16 |
| ATOM | 1343 | N | ALA | 367 | 23.528 | 49.258 | 77.956 | 1.00 | 8.27 |
| ATOM | 1345 | CA | ALA | 367 | 24.515 | 48.229 | 77.596 | 1.00 | 8.06 |
| ATOM | 1346 | CB | ALA | 367 | 25.765 | 48.889 | 77.034 | 1.00 | 7.37 |
| ATOM | 1347 | C | ALA | 367 | 24.875 | 47.268 | 78.734 | 1.00 | 7.86 |
| ATOM | 1348 | O | ALA | 367 | 25.205 | 46.101 | 78.505 | 1.00 | 8.24 |
| ATOM | 1349 | N | ALA | 368 | 24.786 | 47.738 | 79.967 | 1.00 | 7.62 |
| ATOM | 1351 | CA | ALA | 368 | 25.086 | 46.894 | 81.107 | 1.00 | 7.74 |
| ATOM | 1352 | CB | ALA | 368 | 25.097 | 47.717 | 82.385 | 1.00 | 7.62 |
| ATOM | 1353 | C | ALA | 368 | 24.035 | 45.778 | 81.211 | 1.00 | 7.71 |
| ATOM | 1354 | O | ALA | 368 | 24.314 | 44.713 | 81.754 | 1.00 | 7.83 |

TABLE 7-continued

Coordinates of Lck bound with PD153035

| | Atom Type | Res | # | X | Y | Z | Occ | B |
|---|---|---|---|---|---|---|---|---|
| ATOM | 1355 | N | ASN | 369 | 22.836 | 46.028 | 80.680 | 1.00 | 7.60 |
| ATOM | 1357 | CA | ASN | 369 | 21.753 | 45.057 | 80.754 | 1.00 | 7.51 |
| ATOM | 1358 | CB | ASN | 369 | 20.499 | 45.723 | 81.347 | 1.00 | 7.51 |
| ATOM | 1359 | CG | ASN | 369 | 20.677 | 46.059 | 82.814 | 1.00 | 8.09 |
| ATOM | 1360 | OD1 | ASN | 369 | 21.379 | 45.342 | 83.547 | 1.00 | 8.05 |
| ATOM | 1361 | ND2 | ASN | 369 | 20.041 | 47.138 | 83.265 | 1.00 | 7.48 |
| ATOM | 1364 | C | ASN | 369 | 21.464 | 44.262 | 79.479 | 1.00 | 7.57 |
| ATOM | 1365 | O | ASN | 369 | 20.368 | 43.729 | 79.301 | 1.00 | 8.11 |
| ATOM | 1366 | N | ILE | 370 | 22.457 | 44.200 | 78.588 | 1.00 | 7.20 |
| ATOM | 1368 | CA | ILE | 370 | 22.371 | 43.424 | 77.359 | 1.00 | 6.20 |
| ATOM | 1369 | CB | ILE | 370 | 22.677 | 44.299 | 76.090 | 1.00 | 6.75 |
| ATOM | 1370 | CG2 | ILE | 370 | 22.620 | 43.457 | 74.838 | 1.00 | 6.53 |
| ATOM | 1371 | CG1 | ILE | 370 | 21.627 | 45.446 | 75.952 | 1.00 | 6.76 |
| ATOM | 1372 | CD1 | ILE | 370 | 20.135 | 44.988 | 76.031 | 1.00 | 6.91 |
| ATOM | 1373 | C | ILE | 370 | 23.438 | 42.294 | 77.557 | 1.00 | 6.63 |
| ATOM | 1374 | O | ILE | 370 | 24.569 | 42.605 | 77.973 | 1.00 | 5.60 |
| ATOM | 1375 | N | LEU | 371 | 23.042 | 41.011 | 77.464 | 1.00 | 6.38 |
| ATOM | 1377 | CA | LEU | 371 | 24.047 | 39.929 | 77.610 | 1.00 | 6.61 |
| ATOM | 1378 | CB | LEU | 371 | 23.643 | 38.838 | 78.625 | 1.00 | 6.41 |
| ATOM | 1379 | CG | LEU | 371 | 23.487 | 39.388 | 80.032 | 1.00 | 7.08 |
| ATOM | 1380 | CD1 | LEU | 371 | 22.922 | 38.371 | 81.070 | 1.00 | 6.95 |
| ATOM | 1381 | CD2 | LEU | 371 | 24.832 | 39.943 | 80.496 | 1.00 | 6.96 |
| ATOM | 1382 | C | LEU | 371 | 24.463 | 39.376 | 76.255 | 1.00 | 6.75 |
| ATOM | 1383 | O | LEU | 371 | 23.675 | 39.373 | 75.308 | 1.00 | 7.26 |
| ATOM | 1384 | N | VAL | 372 | 25.727 | 38.963 | 76.151 | 1.00 | 6.40 |
| ATOM | 1386 | CA | VAL | 372 | 26.278 | 38.501 | 74.891 | 1.00 | 6.30 |
| ATOM | 1387 | CB | VAL | 372 | 27.567 | 39.289 | 74.547 | 1.00 | 6.63 |
| ATOM | 1388 | CG1 | VAL | 372 | 28.041 | 38.970 | 73.141 | 1.00 | 6.36 |
| ATOM | 1389 | CG2 | VAL | 372 | 27.345 | 40.822 | 74.751 | 1.00 | 6.84 |
| ATOM | 1390 | C | VAL | 372 | 26.598 | 37.018 | 75.034 | 1.00 | 6.59 |
| ATOM | 1391 | O | VAL | 372 | 27.221 | 36.630 | 76.011 | 1.00 | 6.20 |
| ATOM | 1392 | N | SER | 373 | 26.245 | 36.234 | 74.017 | 1.00 | 6.94 |
| ATOM | 1394 | CA | SER | 373 | 26.439 | 34.771 | 74.051 | 1.00 | 7.49 |
| ATOM | 1395 | CB | SER | 373 | 25.380 | 34.083 | 73.213 | 1.00 | 7.34 |
| ATOM | 1396 | OG | SER | 373 | 25.594 | 34.330 | 71.834 | 1.00 | 7.95 |
| ATOM | 1398 | C | SER | 373 | 27.787 | 34.413 | 73.461 | 1.00 | 8.14 |
| ATOM | 1399 | O | SER | 373 | 28.459 | 35.267 | 72.861 | 1.00 | 7.58 |
| ATOM | 1400 | N | ASP | 374 | 28.116 | 33.125 | 73.515 | 1.00 | 9.02 |
| ATOM | 1402 | CA | ASP | 374 | 29.399 | 32.660 | 72.963 | 1.00 | 9.70 |
| ATOM | 1403 | CB | ASP | 374 | 29.579 | 31.167 | 73.226 | 1.00 | 10.33 |
| ATOM | 1404 | CG | ASP | 374 | 28.569 | 30.337 | 72.486 | 1.00 | 11.26 |
| ATOM | 1405 | OD1 | ASP | 374 | 27.368 | 30.596 | 72.705 | 1.00 | 11.98 |
| ATOM | 1406 | OD2 | ASP | 374 | 28.957 | 29.518 | 71.628 | 1.00 | 11.99 |
| ATOM | 1407 | C | ASP | 374 | 29.482 | 32.934 | 71.461 | 1.00 | 10.00 |
| ATOM | 1408 | O | ASP | 374 | 30.566 | 33.140 | 70.945 | 1.00 | 10.28 |
| ATOM | 1409 | N | THR | 375 | 28.334 | 32.925 | 70.763 | 1.00 | 10.10 |
| ATOM | 1411 | CA | THR | 375 | 28.256 | 33.200 | 69.315 | 1.00 | 10.17 |
| ATOM | 1412 | CB | THR | 375 | 27.127 | 32.370 | 68.610 | 1.00 | 10.49 |
| ATOM | 1413 | OG1 | THR | 375 | 25.836 | 32.716 | 69.166 | 1.00 | 10.16 |
| ATOM | 1415 | CG2 | THR | 375 | 27.363 | 30.866 | 68.786 | 1.00 | 10.27 |
| ATOM | 1416 | C | THR | 375 | 28.045 | 34.711 | 68.970 | 1.00 | 9.95 |
| ATOM | 1417 | O | THR | 375 | 27.700 | 35.073 | 67.835 | 1.00 | 10.42 |
| ATOM | 1418 | N | LEU | 376 | 28.234 | 35.582 | 69.951 | 1.00 | 9.60 |
| ATOM | 1420 | CA | LEU | 376 | 28.091 | 37.028 | 69.740 | 1.00 | 9.77 |
| ATOM | 1421 | CB | LEU | 376 | 29.134 | 37.573 | 68.758 | 1.00 | 9.91 |
| ATOM | 1422 | CG | LEU | 376 | 30.506 | 37.931 | 69.367 | 1.00 | 10.36 |
| ATOM | 1423 | CD1 | LEU | 376 | 30.905 | 37.036 | 70.509 | 1.00 | 9.91 |
| ATOM | 1424 | CD2 | LEU | 376 | 31.553 | 37.935 | 68.260 | 1.00 | 10.52 |
| ATOM | 1425 | C | LEU | 376 | 26.691 | 37.471 | 69.331 | 1.00 | 9.28 |
| ATOM | 1426 | O | LEU | 376 | 26.508 | 38.317 | 68.446 | 1.00 | 9.39 |
| ATOM | 1427 | N | SER | 377 | 25.713 | 36.796 | 69.906 | 1.00 | 8.95 |
| ATOM | 1429 | CA | SER | 377 | 24.347 | 37.186 | 69.676 | 1.00 | 8.62 |
| ATOM | 1430 | CB | SER | 377 | 23.432 | 35.961 | 69.497 | 1.00 | 8.20 |
| ATOM | 1431 | OG | SER | 377 | 23.436 | 35.163 | 70.662 | 1.00 | 8.95 |
| ATOM | 1433 | C | SER | 377 | 24.059 | 37.911 | 71.000 | 1.00 | 7.89 |
| ATOM | 1434 | O | SER | 377 | 24.713 | 37.644 | 72.026 | 1.00 | 7.66 |
| ATOM | 1435 | N | CYS | 378 | 23.048 | 38.779 | 70.996 | 1.00 | 7.19 |
| ATOM | 1437 | CA | CYS | 378 | 22.723 | 39.542 | 72.179 | 1.00 | 7.05 |
| ATOM | 1438 | CB | CYS | 378 | 22.798 | 41.048 | 71.877 | 1.00 | 7.60 |
| ATOM | 1439 | SG | CYS | 378 | 24.416 | 41.665 | 71.420 | 1.00 | 9.25 |
| ATOM | 1440 | C | CYS | 378 | 21.298 | 39.263 | 72.618 | 1.00 | 6.86 |
| ATOM | 1441 | O | CYS | 378 | 20.405 | 39.061 | 71.792 | 1.00 | 6.31 |
| ATOM | 1442 | N | LYS | 379 | 21.072 | 39.458 | 73.902 | 1.00 | 6.69 |
| ATOM | 1444 | CA | LYS | 379 | 19.744 | 39.259 | 74.482 | 1.00 | 6.83 |

TABLE 7-continued

Coordinates of Lck bound with PD153035

| | Atom Type | Res | # | X | Y | Z | Occ | B |
|---|---|---|---|---|---|---|---|---|
| ATOM | 1445 | CB | LYS | 379 | 19.595 | 37.808 | 75.014 | 1.00 | 6.22 |
| ATOM | 1446 | CG | LYS | 379 | 19.827 | 36.697 | 73.964 | 1.00 | 5.63 |
| ATOM | 1447 | CD | LYS | 379 | 19.457 | 35.305 | 74.450 | 1.00 | 5.68 |
| ATOM | 1448 | CE | LYS | 379 | 19.727 | 34.291 | 73.316 | 1.00 | 5.90 |
| ATOM | 1449 | NZ | LYS | 379 | 19.013 | 33.051 | 73.616 | 1.00 | 6.67 |
| ATOM | 1453 | C | LYS | 379 | 19.466 | 40.236 | 75.608 | 1.00 | 6.98 |
| ATOM | 1454 | O | LYS | 379 | 20.376 | 40.601 | 76.362 | 1.00 | 7.26 |
| ATOM | 1455 | N | ILE | 380 | 18.216 | 40.688 | 75.707 | 1.00 | 6.64 |
| ATOM | 1457 | CA | ILE | 380 | 17.840 | 41.572 | 76.812 | 1.00 | 6.59 |
| ATOM | 1458 | CB | ILE | 380 | 16.392 | 42.134 | 76.666 | 1.00 | 6.06 |
| ATOM | 1459 | CG2 | ILE | 380 | 16.114 | 43.108 | 77.818 | 1.00 | 6.31 |
| ATOM | 1460 | CG1 | ILE | 380 | 16.091 | 42.605 | 75.228 | 1.00 | 5.92 |
| ATOM | 1461 | CD1 | ILE | 380 | 17.070 | 43.648 | 74.628 | 1.00 | 5.48 |
| ATOM | 1462 | C | ILE | 380 | 17.877 | 40.789 | 78.136 | 1.00 | 6.77 |
| ATOM | 1463 | O | ILE | 380 | 17.432 | 39.629 | 78.207 | 1.00 | 6.69 |
| ATOM | 1464 | N | ALA | 381 | 18.369 | 41.437 | 79.194 | 1.00 | 7.11 |
| ATOM | 1466 | CA | ALA | 381 | 18.490 | 40.826 | 80.505 | 1.00 | 7.98 |
| ATOM | 1467 | CB | ALA | 381 | 19.932 | 40.313 | 80.738 | 1.00 | 7.95 |
| ATOM | 1468 | C | ALA | 381 | 18.114 | 41.804 | 81.592 | 1.00 | 8.49 |
| ATOM | 1469 | O | ALA | 381 | 17.805 | 42.966 | 81.318 | 1.00 | 8.10 |
| ATOM | 1470 | N | ASP | 382 | 18.169 | 41.324 | 82.837 | 1.00 | 9.11 |
| ATOM | 1472 | CA | ASP | 382 | 17.867 | 42.144 | 84.021 | 1.00 | 10.47 |
| ATOM | 1473 | CB | ASP | 382 | 18.944 | 43.222 | 84.217 | 1.00 | 11.36 |
| ATOM | 1474 | CG | ASP | 382 | 19.997 | 42.819 | 85.230 | 1.00 | 12.50 |
| ATOM | 1475 | OD1 | ASP | 382 | 19.657 | 42.737 | 86.433 | 1.00 | 13.26 |
| ATOM | 1476 | OD2 | ASP | 382 | 21.165 | 42.602 | 84.842 | 1.00 | 13.32 |
| ATOM | 1477 | C | ASP | 382 | 16.477 | 42.795 | 84.003 | 1.00 | 10.69 |
| ATOM | 1478 | O | ASP | 382 | 16.344 | 44.022 | 83.925 | 1.00 | 10.60 |
| ATOM | 1479 | N | PHE | 383 | 15.468 | 41.965 | 84.242 | 1.00 | 10.80 |
| ATOM | 1481 | CA | PHE | 383 | 14.081 | 42.387 | 84.222 | 1.00 | 11.07 |
| ATOM | 1482 | CB | PHE | 383 | 13.244 | 41.228 | 83.667 | 1.00 | 10.71 |
| ATOM | 1483 | CG | PHE | 383 | 13.651 | 40.806 | 82.281 | 1.00 | 10.49 |
| ATOM | 1484 | CD1 | PHE | 383 | 13.099 | 41.413 | 81.163 | 1.00 | 9.84 |
| ATOM | 1485 | CD2 | PHE | 383 | 14.641 | 39.850 | 82.091 | 1.00 | 10.27 |
| ATOM | 1486 | CE1 | PHE | 383 | 13.539 | 41.082 | 79.892 | 1.00 | 9.97 |
| ATOM | 1487 | CE2 | PHE | 383 | 15.071 | 39.526 | 80.828 | 1.00 | 10.16 |
| ATOM | 1488 | CZ | PHE | 383 | 14.524 | 40.139 | 79.729 | 1.00 | 9.98 |
| ATOM | 1489 | C | PHE | 383 | 13.534 | 42.850 | 85.577 | 1.00 | 11.41 |
| ATOM | 1490 | O | PHE | 383 | 12.333 | 42.865 | 85.773 | 1.00 | 11.87 |
| ATOM | 1491 | N | GLY | 384 | 14.411 | 43.240 | 86.498 | 1.00 | 11.41 |
| ATOM | 1493 | CA | GLY | 384 | 13.973 | 43.653 | 87.818 | 1.00 | 11.94 |
| ATOM | 1494 | C | GLY | 384 | 13.022 | 44.835 | 87.848 | 1.00 | 11.95 |
| ATOM | 1495 | O | GLY | 384 | 12.128 | 44.913 | 88.703 | 1.00 | 11.51 |
| ATOM | 1496 | N | LEU | 385 | 13.222 | 45.767 | 86.926 | 1.00 | 12.20 |
| ATOM | 1498 | CA | LEU | 385 | 12.362 | 46.946 | 86.863 | 1.00 | 12.64 |
| ATOM | 1499 | CB | LEU | 385 | 13.212 | 48.186 | 86.616 | 1.00 | 12.36 |
| ATOM | 1500 | CG | LEU | 385 | 14.090 | 48.581 | 87.802 | 1.00 | 12.74 |
| ATOM | 1501 | CD1 | LEU | 385 | 14.924 | 49.813 | 87.416 | 1.00 | 12.83 |
| ATOM | 1502 | CD2 | LEU | 385 | 13.222 | 48.859 | 89.020 | 1.00 | 12.85 |
| ATOM | 1503 | C | LEU | 385 | 11.273 | 46.817 | 85.797 | 1.00 | 12.86 |
| ATOM | 1504 | O | LEU | 385 | 10.437 | 47.706 | 85.662 | 1.00 | 12.91 |
| ATOM | 1505 | N | ALA | 386 | 11.265 | 45.701 | 85.063 | 1.00 | 13.37 |
| ATOM | 1507 | CA | ALA | 386 | 10.266 | 45.495 | 84.013 | 1.00 | 14.36 |
| ATOM | 1508 | CB | ALA | 386 | 10.606 | 44.258 | 83.211 | 1.00 | 14.26 |
| ATOM | 1509 | C | ALA | 386 | 8.838 | 45.402 | 84.618 | 1.00 | 15.09 |
| ATOM | 1510 | O | ALA | 386 | 8.663 | 44.955 | 85.754 | 1.00 | 14.73 |
| ATOM | 1511 | N | ARG | 387 | 7.842 | 45.827 | 83.849 | 1.00 | 16.20 |
| ATOM | 1513 | CA | ARG | 387 | 6.458 | 45.874 | 84.308 | 1.00 | 17.50 |
| ATOM | 1514 | CB | ARG | 387 | 6.143 | 47.235 | 84.960 | 1.00 | 16.88 |
| ATOM | 1515 | CG | ARG | 387 | 7.027 | 47.663 | 86.118 | 1.00 | 16.50 |
| ATOM | 1516 | CD | ARG | 387 | 6.664 | 46.904 | 87.362 | 1.00 | 15.62 |
| ATOM | 1517 | NE | ARG | 387 | 7.381 | 47.396 | 88.527 | 1.00 | 15.11 |
| ATOM | 1519 | CZ | ARG | 387 | 8.521 | 46.874 | 88.981 | 1.00 | 14.98 |
| ATOM | 1520 | NH1 | ARG | 387 | 9.082 | 45.833 | 88.371 | 1.00 | 14.75 |
| ATOM | 1523 | NH2 | ARG | 387 | 9.103 | 47.394 | 90.046 | 1.00 | 14.76 |
| ATOM | 1526 | C | ARG | 387 | 5.501 | 45.752 | 83.143 | 1.00 | 18.48 |
| ATOM | 1527 | O | ARG | 387 | 5.745 | 46.270 | 82.042 | 1.00 | 18.41 |
| ATOM | 1528 | N | LEU | 388 | 4.369 | 45.123 | 83.429 | 1.00 | 20.17 |
| ATOM | 1530 | CA | LEU | 388 | 3.332 | 44.940 | 82.436 | 1.00 | 21.90 |
| ATOM | 1531 | CB | LEU | 388 | 2.440 | 43.757 | 82.802 | 1.00 | 22.05 |
| ATOM | 1532 | CG | LEU | 388 | 1.707 | 43.102 | 81.616 | 1.00 | 22.26 |
| ATOM | 1533 | CD1 | LEU | 388 | 0.793 | 41.996 | 82.106 | 1.00 | 22.44 |
| ATOM | 1534 | CD2 | LEU | 388 | 0.915 | 44.113 | 80.870 | 1.00 | 22.51 |
| ATOM | 1535 | C | LEU | 388 | 2.525 | 46.228 | 82.429 | 1.00 | 23.19 |

TABLE 7-continued

Coordinates of Lck bound with PD153035

| | | Atom Type | Res | # | X | Y | Z | Occ | B |
|---|---|---|---|---|---|---|---|---|---|
| ATOM | 1536 | O | LEU | 388 | 2.119 | 46.727 | 83.473 | 1.00 | 23.17 |
| ATOM | 1537 | N | ILE | 389 | 2.328 | 46.788 | 81.244 | 1.00 | 24.75 |
| ATOM | 1539 | CA | ILE | 389 | 1.570 | 48.031 | 81.099 | 1.00 | 26.68 |
| ATOM | 1540 | CB | ILE | 389 | 2.243 | 48.924 | 79.999 | 1.00 | 26.55 |
| ATOM | 1541 | CG2 | ILE | 389 | 1.225 | 49.520 | 79.045 | 1.00 | 27.05 |
| ATOM | 1542 | CG1 | ILE | 389 | 3.070 | 50.029 | 80.670 | 1.00 | 27.07 |
| ATOM | 1543 | CD1 | ILE | 389 | 3.701 | 49.661 | 82.025 | 1.00 | 27.04 |
| ATOM | 1544 | C | ILE | 389 | 0.068 | 47.685 | 80.848 | 1.00 | 28.00 |
| ATOM | 1545 | O | ILE | 389 | −0.303 | 47.228 | 79.779 | 1.00 | 28.28 |
| ATOM | 1546 | N | GLU | 390 | −0.754 | 47.821 | 81.887 | 1.00 | 29.33 |
| ATOM | 1548 | CA | GLU | 390 | −2.200 | 47.511 | 81.820 | 1.00 | 30.84 |
| ATOM | 1549 | CB | GLU | 390 | −2.778 | 47.354 | 83.236 | 1.00 | 31.29 |
| ATOM | 1550 | CG | GLU | 390 | −1.699 | 47.409 | 84.322 | 1.00 | 31.97 |
| ATOM | 1551 | CD | GLU | 390 | −1.708 | 46.218 | 85.268 | 1.00 | 32.28 |
| ATOM | 1552 | OE1 | GLU | 390 | −2.753 | 45.549 | 85.413 | 1.00 | 32.70 |
| ATOM | 1553 | OE2 | GLU | 390 | −0.669 | 46.003 | 85.939 | 1.00 | 32.85 |
| ATOM | 1554 | C | GLU | 390 | −2.897 | 48.629 | 81.032 | 1.00 | 31.44 |
| ATOM | 1555 | O | GLU | 390 | −3.819 | 48.370 | 80.268 | 1.00 | 31.88 |
| ATOM | 1556 | N | ASP | 391 | −2.439 | 49.860 | 81.238 | 1.00 | 32.14 |
| ATOM | 1558 | CA | ASP | 391 | −2.901 | 51.036 | 80.528 | 1.00 | 32.70 |
| ATOM | 1559 | CB | ASP | 391 | −3.583 | 52.001 | 81.481 | 1.00 | 33.48 |
| ATOM | 1560 | CG | ASP | 391 | −5.007 | 51.595 | 81.801 | 1.00 | 34.11 |
| ATOM | 1561 | OD1 | ASP | 391 | −5.891 | 51.771 | 80.930 | 1.00 | 34.39 |
| ATOM | 1562 | OD2 | ASP | 391 | −5.234 | 51.118 | 82.931 | 1.00 | 33.89 |
| ATOM | 1563 | C | ASP | 391 | −1.591 | 51.638 | 80.042 | 1.00 | 32.96 |
| ATOM | 1564 | O | ASP | 391 | −0.564 | 51.462 | 80.702 | 1.00 | 33.68 |
| ATOM | 1565 | N | ASN | 392 | −1.629 | 52.384 | 78.944 | 1.00 | 32.69 |
| ATOM | 1567 | CA | ASN | 392 | −0.432 | 52.994 | 78.355 | 1.00 | 32.36 |
| ATOM | 1568 | CB | ASN | 392 | −0.840 | 54.202 | 77.503 | 1.00 | 32.55 |
| ATOM | 1569 | CG | ASN | 392 | 0.326 | 54.780 | 76.713 | 1.00 | 32.90 |
| ATOM | 1570 | OD1 | ASN | 392 | 1.225 | 54.041 | 76.303 | 1.00 | 32.96 |
| ATOM | 1571 | ND2 | ASN | 392 | 0.321 | 56.098 | 76.496 | 1.00 | 33.07 |
| ATOM | 1574 | C | ASN | 392 | 0.754 | 53.428 | 79.242 | 1.00 | 32.03 |
| ATOM | 1575 | O | ASN | 392 | 1.897 | 53.463 | 78.763 | 1.00 | 32.11 |
| ATOM | 1576 | N | GLU | 393 | 0.533 | 53.674 | 80.532 | 1.00 | 31.46 |
| ATOM | 1578 | CA | GLU | 393 | 1.621 | 54.195 | 81.348 | 1.00 | 30.97 |
| ATOM | 1579 | CB | GLU | 393 | 1.426 | 55.708 | 81.327 | 1.00 | 30.95 |
| ATOM | 1580 | CG | GLU | 393 | 2.395 | 56.586 | 82.025 | 1.00 | 30.99 |
| ATOM | 1581 | CD | GLU | 393 | 1.923 | 58.028 | 81.933 | 1.00 | 30.95 |
| ATOM | 1582 | OE1 | GLU | 393 | 1.342 | 58.506 | 82.924 | 1.00 | 31.01 |
| ATOM | 1583 | OE2 | GLU | 393 | 2.084 | 58.662 | 80.861 | 1.00 | 30.91 |
| ATOM | 1584 | C | GLU | 393 | 1.815 | 53.676 | 82.785 | 1.00 | 30.72 |
| ATOM | 1585 | O | GLU | 393 | 0.851 | 53.412 | 83.514 | 1.00 | 30.85 |
| ATOM | 1586 | N | TYR | 394 | 30.82 | 53.502 | 83.166 | 1.00 | 29.92 |
| ATOM | 1588 | CA | TYR | 394 | 3.465 | 53.045 | 84.501 | 1.00 | 28.91 |
| ATOM | 1589 | CB | TYR | 394 | 4.520 | 51.924 | 84.405 | 1.00 | 28.28 |
| ATOM | 1590 | CG | TYR | 394 | 5.009 | 51.396 | 85.742 | 1.00 | 27.47 |
| ATOM | 1591 | CD1 | TYR | 394 | 4.408 | 50.291 | 86.336 | 1.00 | 27.15 |
| ATOM | 1592 | CE1 | TYR | 394 | 4.809 | 49.840 | 87.592 | 1.00 | 27.23 |
| ATOM | 1593 | CD2 | TYR | 394 | 6.034 | 52.037 | 86.435 | 1.00 | 27.20 |
| ATOM | 1594 | CE2 | TYR | 394 | 6.445 | 51.599 | 87.694 | 1.00 | 27.15 |
| ATOM | 1595 | CZ | TYR | 394 | 5.825 | 50.503 | 88.265 | 1.00 | 27.07 |
| ATOM | 1596 | OH | TYR | 394 | 6.202 | 50.089 | 89.521 | 1.00 | 27.62 |
| ATOM | 1598 | C | TYR | 394 | 4.073 | 54.247 | 85.230 | 1.00 | 28.72 |
| ATOM | 1599 | O | TYR | 394 | 4.932 | 54.939 | 84.675 | 1.00 | 28.32 |
| ATOM | 1600 | N | THR | 395 | 3.623 | 54.498 | 86.456 | 1.00 | 28.56 |
| ATOM | 1602 | CA | THR | 395 | 4.137 | 55.608 | 87.251 | 1.00 | 28.63 |
| ATOM | 1603 | CB | THR | 395 | 2.994 | 56.551 | 87.718 | 1.00 | 28.41 |
| ATOM | 1604 | OG1 | THR | 395 | 2.277 | 57.029 | 86.575 | 1.00 | 28.19 |
| ATOM | 1606 | CG2 | THR | 395 | 3.556 | 57.729 | 88.483 | 1.00 | 28.26 |
| ATOM | 1607 | C | THR | 395 | 4.854 | 55.091 | 88.481 | 1.00 | 28.95 |
| ATOM | 1608 | O | THR | 395 | 4.261 | 54.432 | 59.320 | 1.00 | 29.11 |
| ATOM | 1609 | N | ALA | 396 | 6.121 | 55.449 | 88.596 | 1.00 | 29.39 |
| ATOM | 1611 | CA | ALA | 396 | 6.964 | 55.037 | 89.721 | 1.00 | 30.35 |
| ATOM | 1612 | CB | ALA | 396 | 8.412 | 55.311 | 89.379 | 1.00 | 30.16 |
| ATOM | 1613 | C | ALA | 396 | 6.587 | 55.771 | 91.005 | 1.00 | 30.96 |
| ATOM | 1614 | O | ALA | 396 | 5.543 | 56.410 | 91.070 | 1.00 | 31.03 |
| ATOM | 1615 | N | ALA | 397 | 7.457 | 55.707 | 92.004 | 1.00 | 31.85 |
| ATOM | 1617 | CA | ALA | 397 | 7.208 | 56.383 | 93.275 | 1.00 | 32.89 |
| ATOM | 1618 | CB | ALA | 397 | 7.592 | 55.485 | 94.437 | 1.00 | 33.15 |
| ATOM | 1619 | C | ALA | 397 | 7.987 | 57.685 | 93.357 | 1.00 | 33.49 |
| ATOM | 1620 | O | ALA | 397 | 9.087 | 57.795 | 92.800 | 1.00 | 33.65 |
| ATOM | 1621 | N | GLU | 398 | 7.424 | 58.673 | 94.048 | 1.00 | 34.04 |
| ATOM | 1623 | CA | GLU | 398 | 8.087 | 59.967 | 94.175 | 1.00 | 34.44 |

TABLE 7-continued

Coordinates of Lck bound with PD153035

| | | Atom Type | Res | # | X | Y | Z | Occ | B |
|---|---|---|---|---|---|---|---|---|---|
| ATOM | 1624 | CB | GLU | 398 | 7.323 | 60.908 | 95.115 | 1.00 | 35.85 |
| ATOM | 1625 | CG | GLU | 398 | 6.065 | 61.543 | 94.524 | 1.00 | 37.46 |
| ATOM | 1626 | CD | GLU | 398 | 6.214 | 61.900 | 93.051 | 1.00 | 38.12 |
| ATOM | 1627 | OE1 | GLU | 398 | 7.251 | 62.506 | 92.683 | 1.00 | 38.92 |
| ATOM | 1628 | OE2 | GLU | 398 | 5.291 | 61.553 | 92.269 | 1.00 | 38.88 |
| ATOM | 1629 | C | GLU | 398 | 9.531 | 59.860 | 94.630 | 1.00 | 33.95 |
| ATOM | 1630 | O | GLU | 398 | 10.349 | 60.725 | 94.320 | 1.00 | 34.09 |
| ATOM | 1631 | N | GLY | 399 | 9.829 | 58.812 | 95.399 | 1.00 | 33.54 |
| ATOM | 1633 | CA | GLY | 399 | 11.185 | 58.596 | 95.881 | 1.00 | 32.47 |
| ATOM | 1634 | C | GLY | 399 | 12.034 | 57.791 | 94.910 | 1.00 | 31.73 |
| ATOM | 1635 | O | GLY | 399 | 13.265 | 57.854 | 94.948 | 1.00 | 31.85 |
| ATOM | 1636 | N | ALA | 400 | 11.391 | 57.003 | 94.059 | 1.00 | 30.98 |
| ATOM | 1638 | CA | ALA | 400 | 12.099 | 56.200 | 93.065 | 1.00 | 30.01 |
| ATOM | 1639 | CB | ALA | 400 | 11.078 | 55.569 | 92.104 | 1.00 | 30.36 |
| ATOM | 1640 | C | ALA | 400 | 13.127 | 57.048 | 92.294 | 1.00 | 29.13 |
| ATOM | 1641 | O | ALA | 400 | 12.782 | 58.109 | 91.797 | 1.00 | 29.04 |
| ATOM | 1642 | N | ALA | 401 | 14.389 | 56.614 | 92.261 | 1.00 | 27.86 |
| ATOM | 1644 | CA | ALA | 401 | 15.466 | 57.327 | 91.553 | 1.00 | 26.66 |
| ATOM | 1645 | CB | ALA | 401 | 16.629 | 57.668 | 92.506 | 1.00 | 27.24 |
| ATOM | 1646 | C | ALA | 401 | 15.991 | 56.494 | 90.383 | 1.00 | 25.51 |
| ATOM | 1647 | O | ALA | 401 | 16.111 | 55.267 | 90.486 | 1.00 | 25.45 |
| ATOM | 1648 | N | PHE | 402 | 16.291 | 57.158 | 89.272 | 1.00 | 23.80 |
| ATOM | 1650 | CA | PHE | 402 | 16.776 | 56.480 | 88.075 | 1.00 | 22.16 |
| ATOM | 1651 | CB | PHE | 402 | 15.645 | 56.395 | 87.029 | 1.00 | 22.50 |
| ATOM | 1652 | CG | PHE | 402 | 14.423 | 55.654 | 87.508 | 1.00 | 22.93 |
| ATOM | 1653 | CD1 | PHE | 402 | 13.372 | 56.333 | 88.141 | 1.00 | 23.23 |
| ATOM | 1654 | CD2 | PHE | 402 | 14.327 | 54.273 | 87.331 | 1.00 | 23.20 |
| ATOM | 1655 | CE1 | PHE | 402 | 12.247 | 55.642 | 88.590 | 1.00 | 22.96 |
| ATOM | 1656 | CE2 | PHE | 402 | 13.219 | 53.583 | 87.774 | 1.00 | 23.53 |
| ATOM | 1657 | CZ | PHE | 402 | 12.179 | 54.261 | 88.403 | 1.00 | 23.53 |
| ATOM | 1658 | C | PHE | 402 | 17.988 | 57.161 | 87.421 | 1.00 | 20.67 |
| ATOM | 1659 | O | PHE | 402 | 18.100 | 58.394 | 87.447 | 1.00 | 20.39 |
| ATOM | 1660 | N | PRO | 403 | 18.855 | 56.372 | 86.756 | 1.00 | 19.14 |
| ATOM | 1661 | CD | PRO | 403 | 18.629 | 54.948 | 86.439 | 1.00 | 18.64 |
| ATOM | 1662 | CA | PRO | 403 | 20.052 | 56.855 | 86.064 | 1.00 | 18.18 |
| ATOM | 1663 | CB | PRO | 403 | 20.554 | 55.628 | 85.311 | 1.00 | 18.40 |
| ATOM | 1664 | CG | PRO | 403 | 19.994 | 54.492 | 86.087 | 1.00 | 18.56 |
| ATOM | 1665 | C | PRO | 403 | 19.623 | 57.943 | 85.078 | 1.00 | 17.14 |
| ATOM | 1666 | O | PRO | 403 | 18.989 | 57.675 | 84.048 | 1.00 | 16.76 |
| ATOM | 1667 | N | ILE | 404 | 19.982 | 59.168 | 85.417 | 1.00 | 16.12 |
| ATOM | 1669 | CA | ILE | 404 | 19.653 | 60.345 | 84.635 | 1.00 | 15.21 |
| ATOM | 1670 | CB | ILE | 404 | 20.262 | 61.626 | 85.316 | 1.00 | 14.93 |
| ATOM | 1671 | CG2 | ILE | 404 | 20.057 | 62.868 | 84.431 | 1.00 | 14.60 |
| ATOM | 1672 | CG1 | ILE | 404 | 19.641 | 61.836 | 86.691 | 1.00 | 14.75 |
| ATOM | 1673 | CD1 | ILE | 404 | 18.183 | 62.316 | 86.655 | 1.00 | 15.56 |
| ATOM | 1674 | C | ILE | 404 | 20.069 | 60.296 | 83.179 | 1.00 | 14.61 |
| ATOM | 1675 | O | ILE | 404 | 19.283 | 60.624 | 82.306 | 1.00 | 14.69 |
| ATOM | 1676 | N | LYS | 405 | 21.301 | 59.872 | 82.893 | 1.00 | 13.99 |
| ATOM | 1678 | CA | LYS | 405 | 21.762 | 59.858 | 81.498 | 1.00 | 13.23 |
| ATOM | 1679 | CB | LYS | 405 | 23.276 | 59.644 | 81.378 | 1.00 | 13.20 |
| ATOM | 1680 | CG | LYS | 405 | 24.115 | 60.812 | 81.962 | 1.00 | 13.09 |
| ATOM | 1681 | CD | LYS | 405 | 25.596 | 60.615 | 81.671 | 1.00 | 13.09 |
| ATOM | 1682 | CE | LYS | 405 | 26.436 | 61.749 | 82.262 | 1.00 | 13.08 |
| ATOM | 1683 | NZ | LYS | 405 | 27.826 | 61.777 | 81.718 | 1.00 | 12.98 |
| ATOM | 1687 | C | LYS | 405 | 21.040 | 58.917 | 80.555 | 1.00 | 12.64 |
| ATOM | 1688 | O | LYS | 405 | 21.012 | 59.180 | 79.368 | 1.00 | 12.27 |
| ATOM | 1689 | N | TRP | 406 | 20.446 | 57.841 | 81.076 | 1.00 | 12.70 |
| ATOM | 1691 | CA | TRP | 406 | 19.739 | 56.851 | 80.237 | 1.00 | 12.42 |
| ATOM | 1692 | CB | TRP | 406 | 20.059 | 55.425 | 80.721 | 1.00 | 12.61 |
| ATOM | 1693 | CG | TRP | 406 | 21.353 | 54.924 | 80.268 | 1.00 | 12.29 |
| ATOM | 1694 | CD2 | TRP | 406 | 22.612 | 55.113 | 80.907 | 1.00 | 12.43 |
| ATOM | 1695 | CE2 | TRP | 406 | 23.582 | 54.465 | 80.115 | 1.00 | 12.41 |
| ATOM | 1696 | CE3 | TRP | 406 | 23.022 | 55.775 | 82.069 | 1.00 | 12.52 |
| ATOM | 1697 | CD1 | TRP | 406 | 21.593 | 54.184 | 79.150 | 1.00 | 12.71 |
| ATOM | 1698 | NE1 | TRP | 406 | 22.930 | 53.911 | 79.046 | 1.00 | 12.21 |
| ATOM | 1700 | CZ2 | TRP | 406 | 24.924 | 54.446 | 80.455 | 1.00 | 12.43 |
| ATOM | 1701 | CZ3 | TRP | 406 | 24.361 | 55.760 | 82.406 | 1.00 | 12.81 |
| ATOM | 1702 | CH2 | TRP | 406 | 25.297 | 55.104 | 81.603 | 1.00 | 12.22 |
| ATOM | 1703 | C | TRP | 406 | 18.227 | 56.947 | 80.162 | 1.00 | 12.52 |
| ATOM | 1704 | O | TRP | 406 | 17.607 | 56.330 | 79.307 | 1.00 | 12.28 |
| ATOM | 1705 | N | THR | 407 | 17.652 | 57.658 | 81.119 | 1.00 | 12.20 |
| ATOM | 1707 | CA | THR | 407 | 16.215 | 57.798 | 81.279 | 1.00 | 12.03 |
| ATOM | 1708 | CB | THR | 407 | 15.905 | 57.855 | 82.775 | 1.00 | 12.03 |
| ATOM | 1709 | OG1 | THR | 407 | 16.615 | 56.811 | 83.453 | 1.00 | 11.86 |

TABLE 7-continued

Coordinates of Lck bound with PD153035

| | | Atom Type | Res | # | X | Y | Z | Occ | B |
|---|---|---|---|---|---|---|---|---|---|
| ATOM | 1711 | CG2 | THR | 407 | 14.392 | 57.718 | 83.035 | 1.00 | 12.13 |
| ATOM | 1712 | C | THR | 407 | 15.573 | 59.029 | 80.604 | 1.00 | 12.33 |
| ATOM | 1713 | O | THR | 407 | 16.049 | 60.158 | 80.770 | 1.00 | 12.18 |
| ATOM | 1714 | N | ALA | 408 | 14.443 | 58.793 | 79.940 | 1.00 | 12.10 |
| ATOM | 1716 | CA | ALA | 408 | 13.681 | 59.816 | 79.227 | 1.00 | 12.58 |
| ATOM | 1717 | CB | ALA | 408 | 12.448 | 59.167 | 78.542 | 1.00 | 12.36 |
| ATOM | 1718 | C | ALA | 408 | 13.229 | 60.945 | 80.159 | 1.00 | 12.53 |
| ATOM | 1719 | O | ALA | 408 | 12.869 | 60.690 | 81.302 | 1.00 | 12.39 |
| ATOM | 1720 | N | PRO | 409 | 13.141 | 62.187 | 79.639 | 1.00 | 13.12 |
| ATOM | 1721 | CD | PRO | 409 | 13.334 | 62.558 | 78.229 | 1.00 | 12.95 |
| ATOM | 1722 | CA | PRO | 409 | 12.731 | 63.362 | 80.415 | 1.00 | 13.24 |
| ATOM | 1723 | CB | PRO | 409 | 12.586 | 64.457 | 79.342 | 1.00 | 12.99 |
| ATOM | 1724 | CG | PRO | 409 | 13.630 | 64.030 | 78.330 | 1.00 | 13.06 |
| ATOM | 1725 | C | PRO | 409 | 11.440 | 63.144 | 81.184 | 1.00 | 13.65 |
| ATOM | 1726 | O | PRO | 409 | 11.390 | 63.413 | 82.367 | 1.00 | 13.34 |
| ATOM | 1727 | N | GLU | 410 | 10.437 | 62.570 | 80.529 | 1.00 | 14.33 |
| ATOM | 1729 | CA | GLU | 410 | 9.146 | 62.352 | 87.179 | 1.00 | 15.08 |
| ATOM | 1730 | CB | GLU | 410 | 8.114 | 61.849 | 80.174 | 1.00 | 15.16 |
| ATOM | 1731 | CG | GLU | 410 | 8.319 | 60.398 | 79.727 | 1.00 | 15.59 |
| ATOM | 1732 | CD | GLU | 410 | 9.222 | 60.243 | 78.510 | 1.00 | 15.76 |
| ATOM | 1733 | OE1 | GLU | 410 | 9.946 | 61.198 | 78.134 | 1.00 | 15.99 |
| ATOM | 1734 | OE2 | GLU | 410 | 9.201 | 59.154 | 77.920 | 1.00 | 15.80 |
| ATOM | 1735 | C | GLU | 410 | 9.223 | 61.414 | 82.384 | 1.00 | 15.57 |
| ATOM | 1736 | O | GLU | 410 | 8.451 | 61.540 | 83.340 | 1.00 | 15.59 |
| ATOM | 1737 | N | ALA | 411 | 10.148 | 60.462 | 82.329 | 1.00 | 16.06 |
| ATOM | 1739 | CA | ALA | 411 | 10.334 | 59.519 | 83.416 | 1.00 | 16.53 |
| ATOM | 1740 | CB | ALA | 411 | 11.041 | 58.269 | 82.912 | 1.00 | 16.14 |
| ATOM | 1741 | C | ALA | 411 | 11.114 | 60.195 | 84.556 | 1.00 | 16.96 |
| ATOM | 1742 | O | ALA | 411 | 10.793 | 60.004 | 85.732 | 1.00 | 17.30 |
| ATOM | 1743 | N | ILE | 412 | 12.118 | 61.004 | 84.209 | 1.00 | 17.43 |
| ATOM | 1745 | CA | ILE | 412 | 12.908 | 61.741 | 85.220 | 1.00 | 17.79 |
| ATOM | 1746 | CB | ILE | 412 | 14.118 | 62.488 | 84.556 | 1.00 | 17.95 |
| ATOM | 1747 | CG2 | ILE | 412 | 14.749 | 63.537 | 85.525 | 1.00 | 18.18 |
| ATOM | 1748 | CG1 | ILE | 412 | 15.188 | 61.485 | 84.120 | 1.00 | 17.76 |
| ATOM | 1749 | CD1 | ILE | 412 | 16.101 | 62.042 | 83.022 | 1.00 | 18.11 |
| ATOM | 1750 | C | ILE | 412 | 12.051 | 62.792 | 85.953 | 1.00 | 18.12 |
| ATOM | 1751 | O | ILE | 412 | 12.082 | 62.893 | 87.168 | 1.00 | 17.83 |
| ATOM | 1752 | N | ASN | 413 | 11.266 | 63.540 | 85.191 | 1.00 | 18.70 |
| ATOM | 1754 | CA | ASN | 413 | 10.428 | 64.611 | 85.720 | 1.00 | 19.65 |
| ATOM | 1755 | CB | ASN | 413 | 10.198 | 65.655 | 84.619 | 1.00 | 19.48 |
| ATOM | 1756 | CG | ASN | 413 | 11.487 | 66.326 | 84.181 | 1.00 | 18.97 |
| ATOM | 1757 | OD1 | ASN | 413 | 12.385 | 66.531 | 84.979 | 1.00 | 19.09 |
| ATOM | 1758 | ND2 | ASN | 413 | 11.588 | 66.634 | 82.924 | 1.00 | 18.83 |
| ATOM | 1761 | C | ASN | 413 | 9.076 | 64.232 | 86.330 | 1.00 | 20.31 |
| ATOM | 1762 | O | ASN | 413 | 8.716 | 64.745 | 87.386 | 1.00 | 20.45 |
| ATOM | 1763 | N | TYR | 414 | 8.332 | 63.348 | 85.654 | 1.00 | 21.18 |
| ATOM | 1765 | CA | TYR | 414 | 6.999 | 62.946 | 86.099 | 1.00 | 21.89 |
| ATOM | 1766 | CB | TYR | 414 | 6.011 | 63.050 | 84.936 | 1.00 | 23.25 |
| ATOM | 1767 | CG | TYR | 414 | 6.100 | 64.351 | 84.174 | 1.00 | 24.45 |
| ATOM | 1768 | CD1 | TYR | 414 | 6.118 | 65.569 | 84.848 | 1.00 | 25.29 |
| ATOM | 1769 | CE1 | TYR | 414 | 6.267 | 66.768 | 84.167 | 1.00 | 25.70 |
| ATOM | 1770 | CD2 | TYR | 414 | 6.229 | 64.366 | 82.789 | 1.00 | 25.19 |
| ATOM | 1771 | CE2 | TYR | 414 | 6.382 | 65.567 | 82.094 | 1.00 | 25.82 |
| ATOM | 1772 | CZ | TYR | 414 | 6.401 | 66.765 | 82.799 | 1.00 | 26.40 |
| ATOM | 1773 | OH | TYR | 414 | 6.582 | 67.967 | 82.148 | 1.00 | 26.44 |
| ATOM | 1775 | C | TYR | 414 | 6.916 | 61.550 | 86.703 | 1.00 | 21.76 |
| ATOM | 1776 | O | TYR | 414 | 5.889 | 61.190 | 87.288 | 1.00 | 22.06 |
| ATOM | 1777 | N | GLY | 415 | 7.992 | 60.781 | 86.597 | 1.00 | 21.24 |
| ATOM | 1779 | CA | GLY | 415 | 7.979 | 59.427 | 87.131 | 1.00 | 20.69 |
| ATOM | 1780 | C | GLY | 415 | 7.201 | 58.503 | 86.198 | 1.00 | 20.02 |
| ATOM | 1781 | O | GLY | 415 | 6.994 | 57.335 | 86.523 | 1.00 | 20.31 |
| ATOM | 1782 | N | THR | 416 | 6.770 | 59.025 | 85.049 | 1.00 | 19.17 |
| ATOM | 1784 | CA | THR | 416 | 6.005 | 58.253 | 84.080 | 1.00 | 18.25 |
| ATOM | 1785 | CB | THR | 416 | 4.997 | 59.147 | 83.325 | 1.00 | 18.64 |
| ATOM | 1786 | OG1 | THR | 416 | 5.704 | 60.178 | 82.632 | 1.00 | 19.19 |
| ATOM | 1788 | CG2 | THR | 416 | 3.990 | 59.783 | 84.280 | 1.00 | 18.40 |
| ATOM | 1789 | C | THR | 416 | 6.861 | 57.525 | 83.035 | 1.00 | 17.51 |
| ATOM | 1790 | O | THR | 416 | 7.644 | 58.147 | 82.299 | 1.00 | 17.60 |
| ATOM | 1791 | N | PHE | 417 | 6.588 | 56.233 | 82.885 | 1.00 | 16.09 |
| ATOM | 1793 | CA | PHE | 417 | 7.290 | 55.363 | 81.954 | 1.00 | 15.19 |
| ATOM | 1794 | CB | PHE | 417 | 7.975 | 54.249 | 82.738 | 1.00 | 15.18 |
| ATOM | 1795 | CG | PHE | 417 | 9.174 | 54.680 | 83.527 | 1.00 | 14.52 |
| ATOM | 1796 | CD1 | PHE | 417 | 10.450 | 54.563 | 82.966 | 1.00 | 13.78 |
| ATOM | 1797 | CD2 | PHE | 417 | 9.050 | 55.137 | 84.838 | 1.00 | 14.06 |

TABLE 7-continued

Coordinates of Lck bound with PD153035

| Atom Type | | Res | # | X | Y | Z | Occ | B |
|---|---|---|---|---|---|---|---|---|
| ATOM | 1798 | CE1 | PHE | 417 | 11.579 | 54.871 | 83.697 | 1.00 | 13.91 |
| ATOM | 1799 | CE2 | PHE | 417 | 10.186 | 55.455 | 85.589 | 1.00 | 14.53 |
| ATOM | 1800 | CZ | PHE | 417 | 11.451 | 55.325 | 85.014 | 1.00 | 14.27 |
| ATOM | 1801 | C | PHE | 417 | 6.361 | 54.678 | 80.948 | 1.00 | 14.66 |
| ATOM | 1802 | O | PHE | 417 | 5.272 | 54.224 | 81.311 | 1.00 | 14.35 |
| ATOM | 1803 | N | THR | 418 | 6.764 | 54.646 | 79.684 | 1.00 | 13.93 |
| ATOM | 1805 | CA | THR | 418 | 6.001 | 53.947 | 78.647 | 1.00 | 13.38 |
| ATOM | 1806 | CB | THR | 418 | 5.217 | 54.894 | 77.685 | 1.00 | 13.72 |
| ATOM | 1807 | OG1 | THR | 418 | 6.146 | 55.624 | 76.887 | 1.00 | 14.12 |
| ATOM | 1809 | CG2 | THR | 418 | 4.332 | 55.885 | 78.458 | 1.00 | 13.66 |
| ATOM | 1810 | C | THR | 418 | 7.014 | 53.252 | 77.763 | 1.00 | 12.65 |
| ATOM | 1811 | O | THR | 418 | 8.218 | 53.354 | 77.992 | 1.00 | 12.74 |
| ATOM | 1812 | N | ILE | 419 | 6.548 | 52.538 | 76.753 | 1.00 | 11.63 |
| ATOM | 1814 | CA | ILE | 419 | 7.505 | 51.882 | 75.878 | 1.00 | 10.78 |
| ATOM | 1815 | CB | ILE | 419 | 6.804 | 50.982 | 74.828 | 1.00 | 10.41 |
| ATOM | 1816 | CG2 | ILE | 419 | 5.994 | 51.798 | 73.804 | 1.00 | 10.68 |
| ATOM | 1817 | CG1 | ILE | 419 | 7.842 | 50.047 | 74.182 | 1.00 | 10.40 |
| ATOM | 1818 | CD1 | ILE | 419 | 8.375 | 49.011 | 75.159 | 1.00 | 9.94 |
| ATOM | 1819 | C | ILE | 419 | 8.373 | 52.991 | 75.219 | 1.00 | 10.71 |
| ATOM | 1820 | O | ILE | 419 | 9.525 | 52.763 | 74.865 | 1.00 | 10.31 |
| ATOM | 1821 | N | LYS | 420 | 7.818 | 54.202 | 75.117 | 1.00 | 9.96 |
| ATOM | 1823 | CA | LYS | 420 | 8.535 | 55.336 | 74.499 | 1.00 | 9.30 |
| ATOM | 1824 | CB | LYS | 420 | 7.571 | 56.496 | 74.210 | 1.00 | 8.93 |
| ATOM | 1825 | CG | LYS | 420 | 6.439 | 56.101 | 73.216 | 1.00 | 8.80 |
| ATOM | 1826 | CD | LYS | 420 | 6.971 | 55.800 | 71.800 | 1.00 | 8.59 |
| ATOM | 1827 | CE | LYS | 420 | 5.913 | 55.205 | 70.864 | 1.00 | 8.62 |
| ATOM | 1828 | NZ | LYS | 420 | 6.492 | 54.812 | 69.512 | 1.00 | 8.32 |
| ATOM | 1832 | C | LYS | 420 | 9.736 | 55.782 | 75.334 | 1.00 | 8.83 |
| ATOM | 1833 | O | LYS | 420 | 10.703 | 56.303 | 74.770 | 1.00 | 9.39 |
| ATOM | 1834 | N | SER | 421 | 9.672 | 55.572 | 76.652 | 0.84 | 8.27 |
| ATOM | 1836 | CA | SER | 421 | 10.761 | 55.894 | 77.559 | 0.84 | 8.13 |
| ATOM | 1837 | CB | SER | 421 | 10.366 | 55.756 | 79.030 | 0.84 | 8.50 |
| ATOM | 1838 | OG | SER | 421 | 9.171 | 56.511 | 79.312 | 0.84 | 9.56 |
| ATOM | 1840 | C | SER | 421 | 11.885 | 54.894 | 77.246 | 0.84 | 7.81 |
| ATOM | 1841 | O | SER | 421 | 13.039 | 55.278 | 77.138 | 0.84 | 7.58 |
| ATOM | 1842 | N | ASP | 422 | 11.520 | 53.630 | 77.008 | 1.00 | 7.66 |
| ATOM | 1844 | CA | ASP | 422 | 12.502 | 52.602 | 76.666 | 1.00 | 7.21 |
| ATOM | 1845 | CB | ASP | 422 | 11.848 | 51.214 | 76.513 | 1.00 | 7.54 |
| ATOM | 1846 | CG | ASP | 422 | 11.610 | 50.509 | 77.852 | 1.00 | 7.01 |
| ATOM | 1847 | OD1 | ASP | 422 | 12.188 | 50.880 | 78.891 | 1.00 | 7.56 |
| ATOM | 1848 | OD2 | ASP | 422 | 10.854 | 49.529 | 77.849 | 1.00 | 7.65 |
| ATOM | 1849 | C | ASP | 422 | 13.189 | 52.995 | 75.363 | 1.00 | 7.34 |
| ATOM | 1850 | O | ASP | 422 | 14.394 | 52.865 | 75.246 | 1.00 | 7.51 |
| ATOM | 1851 | N | VAL | 423 | 12.427 | 53.492 | 74.391 | 1.00 | 6.89 |
| ATOM | 1853 | CA | VAL | 423 | 12.973 | 53.917 | 73.105 | 1.00 | 6.77 |
| ATOM | 1854 | CB | VAL | 423 | 11.845 | 54.393 | 72.140 | 1.00 | 7.10 |
| ATOM | 1855 | CG1 | VAL | 423 | 12.421 | 55.131 | 70.955 | 1.00 | 6.61 |
| ATOM | 1856 | CG2 | VAL | 423 | 11.059 | 53.209 | 71.607 | 1.00 | 7.04 |
| ATOM | 1857 | C | VAL | 423 | 14.067 | 54.996 | 73.256 | 1.00 | 6.87 |
| ATOM | 1858 | O | VAL | 423 | 15.107 | 54.938 | 72.583 | 1.00 | 6.06 |
| ATOM | 1859 | N | TRP | 424 | 13.825 | 55.963 | 74.145 | 1.00 | 6.58 |
| ATOM | 1861 | CA | TRP | 424 | 14.813 | 57.003 | 74.436 | 1.00 | 5.92 |
| ATOM | 1862 | CB | TRP | 424 | 14.259 | 57.930 | 75.520 | 1.00 | 6.24 |
| ATOM | 1863 | CG | TRP | 424 | 15.204 | 58.993 | 75.926 | 1.00 | 6.56 |
| ATOM | 1864 | CD2 | TRP | 424 | 15.150 | 60.384 | 75.555 | 1.00 | 6.31 |
| ATOM | 1865 | CE2 | TRP | 424 | 16.281 | 61.013 | 76.111 | 1.00 | 6.74 |
| ATOM | 1866 | CE3 | TRP | 424 | 14.219 | 61.160 | 74.821 | 1.00 | 7.02 |
| ATOM | 1867 | CD1 | TRP | 424 | 16.341 | 58.849 | 76.685 | 1.00 | 6.82 |
| ATOM | 1868 | NE1 | TRP | 424 | 16.992 | 60.063 | 76.794 | 1.00 | 6.96 |
| ATOM | 1870 | CZ2 | TRP | 424 | 16.534 | 62.382 | 75.953 | 1.00 | 6.58 |
| ATOM | 1871 | CZ3 | TRP | 424 | 14.474 | 62.539 | 74.675 | 1.00 | 6.75 |
| ATOM | 1872 | CH2 | TRP | 424 | 15.618 | 63.118 | 75.240 | 1.00 | 6.34 |
| ATOM | 1873 | C | TRP | 424 | 16.092 | 56.282 | 74.968 | 1.00 | 5.35 |
| ATOM | 1874 | O | TRP | 424 | 17.202 | 56.556 | 74.514 | 1.00 | 5.83 |
| ATOM | 1875 | N | SER | 425 | 15.922 | 55.408 | 75.951 | 0.74 | 4.31 |
| ATOM | 1877 | CA | SER | 425 | 17.047 | 54.661 | 76.533 | 0.74 | 3.83 |
| ATOM | 1878 | CB | SER | 425 | 16.557 | 53.661 | 77.582 | 0.74 | 3.11 |
| ATOM | 1879 | OG | SER | 425 | 15.847 | 54.301 | 78.621 | 0.74 | 2.00 |
| ATOM | 1881 | C | SER | 425 | 17.836 | 53.926 | 75.453 | 0.74 | 3.85 |
| ATOM | 1882 | O | SER | 425 | 19.063 | 53.863 | 75.510 | 0.74 | 3.22 |
| ATOM | 1883 | N | PHE | 426 | 17.120 | 53.346 | 74.482 | 1.00 | 4.49 |
| ATOM | 1885 | CA | PHE | 426 | 17.741 | 52.647 | 73.352 | 1.00 | 4.39 |
| ATOM | 1886 | CB | PHE | 426 | 16.658 | 52.030 | 72.439 | 1.00 | 3.97 |
| ATOM | 1887 | CG | PHE | 426 | 17.210 | 51.252 | 71.275 | 1.00 | 3.54 |

TABLE 7-continued

Coordinates of Lck bound with PD153035

| | | Atom Type | Res | # | X | Y | Z | Occ | B |
|---|---|---|---|---|---|---|---|---|---|
| ATOM | 1888 | CD1 | PHE | 426 | 17.836 | 50.005 | 71.476 | 1.00 | 3.85 |
| ATOM | 1889 | CD2 | PHE | 426 | 17.159 | 51.771 | 69.986 | 1.00 | 3.68 |
| ATOM | 1890 | CE1 | PHE | 426 | 18.412 | 49.316 | 70.389 | 1.00 | 3.60 |
| ATOM | 1891 | CE2 | PHE | 426 | 17.725 | 51.096 | 68.907 | 1.00 | 3.45 |
| ATOM | 1892 | CZ | PHE | 426 | 18.361 | 49.867 | 69.114 | 1.00 | 3.30 |
| ATOM | 1893 | C | PHE | 426 | 18.635 | 53.626 | 72.542 | 1.00 | 5.10 |
| ATOM | 1894 | O | PHE | 426 | 19.686 | 53.221 | 72.022 | 1.00 | 4.71 |
| ATOM | 1895 | N | GLY | 427 | 18.195 | 54.886 | 72.414 | 1.00 | 5.06 |
| ATOM | 1897 | CA | GLY | 427 | 18.991 | 55.883 | 71.690 | 1.00 | 5.46 |
| ATOM | 1898 | C | GLY | 427 | 20.336 | 56.077 | 72.397 | 1.00 | 5.37 |
| ATOM | 1899 | O | GLY | 427 | 21.394 | 56.080 | 71.757 | 1.00 | 5.94 |
| ATOM | 1900 | N | ILE | 428 | 20.299 | 56.134 | 73.723 | 1.00 | 5.50 |
| ATOM | 1902 | CA | ILE | 428 | 21.498 | 56.288 | 74.558 | 1.00 | 6.01 |
| ATOM | 1903 | CB | ILE | 428 | 21.151 | 56.505 | 76.068 | 1.00 | 5.55 |
| ATOM | 1904 | CG2 | ILE | 428 | 22.427 | 56.574 | 76.931 | 1.00 | 5.31 |
| ATOM | 1905 | CG1 | ILE | 428 | 20.295 | 57.773 | 76.267 | 1.00 | 5.78 |
| ATOM | 1906 | CD1 | ILE | 428 | 20.939 | 59.075 | 75.754 | 1.00 | 5.45 |
| ATOM | 1907 | C | ILE | 428 | 22.321 | 54.988 | 74.405 | 1.00 | 6.77 |
| ATOM | 1908 | O | ILE | 428 | 23.542 | 55.018 | 74.193 | 1.00 | 6.62 |
| ATOM | 1909 | N | LEU | 429 | 21.636 | 53.847 | 74.440 | 1.00 | 6.93 |
| ATOM | 1911 | CA | LEU | 429 | 22.317 | 52.556 | 74.268 | 1.00 | 7.19 |
| ATOM | 1912 | CB | LEU | 429 | 21.304 | 51.392 | 74.314 | 1.00 | 7.27 |
| ATOM | 1913 | CG | LEU | 429 | 21.934 | 50.026 | 74.654 | 1.00 | 7.92 |
| ATOM | 1914 | CD1 | LEU | 429 | 20.921 | 49.036 | 75.241 | 1.00 | 8.24 |
| ATOM | 1915 | CD2 | LEU | 429 | 22.553 | 49.460 | 73.420 | 1.00 | 8.62 |
| ATOM | 1916 | C | LEU | 429 | 23.142 | 52.516 | 72.979 | 1.00 | 6.99 |
| ATOM | 1917 | O | LEU | 429 | 24.277 | 52.016 | 72.978 | 1.00 | 6.52 |
| ATOM | 1918 | N | LEU | 430 | 22.560 | 52.987 | 71.876 | 1.00 | 6.79 |
| ATOM | 1920 | CA | LEU | 430 | 23.253 | 53.025 | 70.605 | 1.00 | 6.92 |
| ATOM | 1921 | CB | LEU | 430 | 22.404 | 53.709 | 69.513 | 1.00 | 7.16 |
| ATOM | 1922 | CG | LEU | 430 | 21.091 | 53.057 | 69.067 | 1.00 | 7.35 |
| ATOM | 1923 | CD1 | LEU | 430 | 20.421 | 53.899 | 67.993 | 1.00 | 7.87 |
| ATOM | 1924 | CD2 | LEU | 430 | 21.338 | 51.631 | 68.557 | 1.00 | 7.33 |
| ATOM | 1925 | C | LEU | 430 | 24.582 | 53.778 | 70.765 | 1.00 | 7.18 |
| ATOM | 1926 | O | LEU | 430 | 25.574 | 53.384 | 70.147 | 1.00 | 6.55 |
| ATOM | 1927 | N | THR | 431 | 24.611 | 54.849 | 71.575 | 1.00 | 6.99 |
| ATOM | 1929 | CA | THR | 431 | 25.893 | 55.560 | 71.787 | 1.00 | 6.92 |
| ATOM | 1930 | CB | THR | 431 | 25.756 | 56.885 | 72.591 | 1.00 | 6.02 |
| ATOM | 1931 | OG1 | THR | 431 | 25.501 | 56.625 | 73.975 | 1.00 | 5.93 |
| ATOM | 1933 | CG2 | THR | 431 | 24.605 | 57.753 | 72.016 | 1.00 | 5.81 |
| ATOM | 1934 | C | THR | 431 | 26.934 | 54.636 | 72.471 | 1.00 | 7.02 |
| ATOM | 1935 | O | THR | 431 | 28.119 | 54.655 | 72.108 | 1.00 | 6.78 |
| ATOM | 1936 | N | GLU | 432 | 26.507 | 53.868 | 73.468 | 1.00 | 7.21 |
| ATOM | 1938 | CA | GLU | 432 | 27.441 | 52.930 | 74.141 | 1.00 | 8.29 |
| ATOM | 1939 | CB | GLU | 432 | 26.774 | 52.199 | 75.293 | 1.00 | 8.21 |
| ATOM | 1940 | CG | GLU | 432 | 26.185 | 53.113 | 76.340 | 1.00 | 8.66 |
| ATOM | 1941 | CD | GLU | 432 | 25.415 | 52.328 | 77.369 | 1.00 | 9.09 |
| ATOM | 1942 | OE1 | GLU | 432 | 24.269 | 51.913 | 77.062 | 1.00 | 8.35 |
| ATOM | 1943 | OE2 | GLU | 432 | 25.965 | 52.094 | 78.453 | 1.00 | 9.32 |
| ATOM | 1944 | C | GLU | 432 | 28.021 | 51.893 | 73.183 | 1.00 | 8.20 |
| ATOM | 1945 | O | GLU | 432 | 29.157 | 51.412 | 73.376 | 1.00 | 8.40 |
| ATOM | 1946 | N | ILE | 433 | 27.229 | 51.498 | 72.192 | 1.00 | 8.64 |
| ATOM | 1948 | CA | ILE | 433 | 27.656 | 50.492 | 71.211 | 1.00 | 9.11 |
| ATOM | 1949 | CB | ILE | 433 | 26.436 | 50.004 | 70.362 | 1.00 | 8.93 |
| ATOM | 1950 | CG2 | ILE | 433 | 26.845 | 49.446 | 69.003 | 1.00 | 8.87 |
| ATOM | 1951 | CG1 | ILE | 433 | 25.602 | 49.020 | 71.175 | 1.00 | 8.30 |
| ATOM | 1952 | CD1 | ILE | 433 | 24.335 | 48.594 | 70.436 | 1.00 | 8.90 |
| ATOM | 1953 | C | ILE | 433 | 28.777 | 51.043 | 70.327 | 1.00 | 9.77 |
| ATOM | 1954 | O | ILE | 433 | 29.907 | 50.528 | 70.327 | 1.00 | 9.88 |
| ATOM | 1955 | N | VAL | 434 | 28.504 | 52.193 | 69.727 | 1.00 | 9.77 |
| ATOM | 1957 | CA | VAL | 434 | 29.434 | 52.858 | 68.821 | 1.00 | 10.50 |
| ATOM | 1958 | CB | VAL | 434 | 28.661 | 53.960 | 68.029 | 1.00 | 10.82 |
| ATOM | 1959 | CG1 | VAL | 434 | 28.576 | 55.239 | 68.821 | 1.00 | 10.35 |
| ATOM | 1960 | CG2 | VAL | 434 | 29.273 | 54.161 | 66.669 | 1.00 | 12.02 |
| ATOM | 1961 | C | VAL | 434 | 30.712 | 53.428 | 69.480 | 1.00 | 10.11 |
| ATOM | 1962 | O | VAL | 434 | 31.702 | 53.672 | 68.799 | 1.00 | 10.62 |
| ATOM | 1963 | N | THR | 435 | 30.704 | 53.612 | 70.793 | 1.00 | 9.95 |
| ATOM | 1965 | CA | THR | 435 | 31.873 | 54.144 | 71.488 | 1.00 | 10.67 |
| ATOM | 1966 | CB | THR | 435 | 31.499 | 55.329 | 72.425 | 1.00 | 10.55 |
| ATOM | 1967 | OG1 | THR | 435 | 30.708 | 54.846 | 73.510 | 1.00 | 10.51 |
| ATOM | 1969 | CG2 | THR | 435 | 30.711 | 56.441 | 71.672 | 1.00 | 10.52 |
| ATOM | 1970 | C | THR | 435 | 32.526 | 53.031 | 72.326 | 1.00 | 10.97 |
| ATOM | 1971 | O | THR | 435 | 33.313 | 53.303 | 73.233 | 1.00 | 10.72 |
| ATOM | 1972 | N | HIS | 436 | 32.157 | 51.779 | 72.037 | 1.00 | 11.43 |

TABLE 7-continued

Coordinates of Lck bound with PD153035

| | | Atom Type | Res | # | X | Y | Z | Occ | B |
|---|---|---|---|---|---|---|---|---|---|
| ATOM | 1974 | CA | HIS | 436 | 32.664 | 50.606 | 72.756 | 1.00 | 12.41 |
| ATOM | 1975 | CB | HIS | 436 | 34.087 | 50.223 | 72.313 | 1.00 | 12.85 |
| ATOM | 1976 | CG | HIS | 436 | 34.169 | 49.708 | 70.902 | 1.00 | 13.97 |
| ATOM | 1977 | CD2 | HIS | 436 | 34.081 | 50.356 | 69.717 | 1.00 | 14.37 |
| ATOM | 1978 | ND1 | HIS | 436 | 34.341 | 48.374 | 70.600 | 1.00 | 14.10 |
| ATOM | 1980 | CE1 | HIS | 436 | 34.348 | 48.216 | 69.283 | 1.00 | 14.35 |
| ATOM | 1981 | NE2 | HIS | 436 | 34.190 | 49.408 | 68.726 | 1.00 | 14.84 |
| ATOM | 1983 | C | HIS | 436 | 32.561 | 50.735 | 74.268 | 1.00 | 12.43 |
| ATOM | 1984 | O | HIS | 436 | 33.515 | 50.480 | 75.012 | 1.00 | 12.65 |
| ATOM | 1985 | N | GLY | 437 | 31.381 | 51.158 | 74.709 | 1.00 | 12.51 |
| ATOM | 1987 | CA | GLY | 437 | 31.088 | 51.253 | 76.115 | 1.00 | 12.44 |
| ATOM | 1988 | C | GLY | 437 | 31.343 | 52.504 | 76.899 | 1.00 | 12.40 |
| ATOM | 1989 | O | GLY | 437 | 31.262 | 52.426 | 78.115 | 1.00 | 12.51 |
| ATOM | 1990 | N | ARG | 438 | 31.590 | 53.639 | 76.230 | 0.58 | 12.17 |
| ATOM | 1992 | CA | ARG | 438 | 31.854 | 54.915 | 76.900 | 0.58 | 12.14 |
| ATOM | 1993 | CB | ARG | 438 | 32.437 | 55.939 | 75.902 | 0.58 | 12.65 |
| ATOM | 1994 | CG | ARG | 438 | 32.867 | 57.298 | 76.517 | 0.58 | 13.06 |
| ATOM | 1995 | CD | ARG | 438 | 33.318 | 58.306 | 75.437 | 0.58 | 13.35 |
| ATOM | 1996 | NE | ARG | 438 | 34.139 | 59.409 | 75.953 | 0.58 | 14.15 |
| ATOM | 1998 | CZ | ARG | 438 | 34.491 | 60.477 | 75.235 | 0.58 | 14.45 |
| ATOM | 1999 | NH1 | ARG | 438 | 34.100 | 60.592 | 73.971 | 0.58 | 14.57 |
| ATOM | 2002 | NH2 | ARG | 438 | 35.280 | 61.414 | 75.754 | 0.58 | 14.64 |
| ATOM | 2005 | C | ARG | 438 | 30.605 | 55.487 | 77.553 | 0.58 | 12.04 |
| ATOM | 2006 | O | ARG | 438 | 29.495 | 55.266 | 77.088 | 0.58 | 11.47 |
| ATOM | 2007 | N | ILE | 439 | 30.800 | 56.194 | 78.662 | 1.00 | 12.04 |
| ATOM | 2009 | CA | ILE | 439 | 29.707 | 56.829 | 79.407 | 1.00 | 10.83 |
| ATOM | 2010 | CB | ILE | 439 | 30.210 | 57.393 | 80.727 | 1.00 | 11.06 |
| ATOM | 2011 | CG2 | ILE | 439 | 29.110 | 58.211 | 81.459 | 1.00 | 10.88 |
| ATOM | 2012 | CG1 | ILE | 439 | 30.749 | 56.233 | 81.566 | 1.00 | 10.95 |
| ATOM | 2013 | CD1 | ILE | 439 | 31.344 | 56.666 | 82.860 | 1.00 | 11.38 |
| ATOM | 2014 | C | ILE | 439 | 29.109 | 57.915 | 78.542 | 1.00 | 11.23 |
| ATOM | 2015 | O | ILE | 439 | 29.848 | 58.692 | 77.917 | 1.00 | 10.77 |
| ATOM | 2016 | N | PRO | 440 | 27.767 | 57.892 | 78.380 | 0.43 | 10.97 |
| ATOM | 2017 | CD | PRO | 440 | 26.835 | 56.886 | 78.925 | 0.43 | 10.59 |
| ATOM | 2018 | CA | PRO | 440 | 27.053 | 58.885 | 77.563 | 0.43 | 10.05 |
| ATOM | 2019 | CB | PRO | 440 | 25.589 | 58.417 | 77.636 | 0.43 | 10.44 |
| ATOM | 2020 | CG | PRO | 440 | 25.515 | 57.606 | 78.877 | 0.43 | 11.07 |
| ATOM | 2021 | C | PRO | 440 | 27.246 | 60.317 | 78.051 | 0.43 | 10.35 |
| ATOM | 2022 | O | PRO | 440 | 27.509 | 60.552 | 79.222 | 0.43 | 9.52 |
| ATOM | 2023 | N | TYR | 441 | 27.126 | 61.262 | 77.125 | 1.00 | 10.49 |
| ATOM | 2025 | CA | TYR | 441 | 27.301 | 62.690 | 77.409 | 1.00 | 10.78 |
| ATOM | 2026 | CB | TYR | 441 | 26.215 | 63.200 | 78.376 | 1.00 | 10.00 |
| ATOM | 2027 | CG | TYR | 441 | 24.785 | 62.994 | 77.906 | 1.00 | 10.08 |
| ATOM | 2028 | CD1 | TYR | 441 | 24.207 | 63.866 | 76.978 | 1.00 | 9.61 |
| ATOM | 2029 | CE1 | TYR | 441 | 22.904 | 63.697 | 76.543 | 1.00 | 9.58 |
| ATOM | 2030 | CD2 | TYR | 441 | 24.006 | 61.932 | 78.397 | 1.00 | 9.60 |
| ATOM | 2031 | CE2 | TYR | 441 | 22.686 | 61.749 | 77.971 | 1.00 | 9.31 |
| ATOM | 2032 | CZ | TYR | 441 | 22.142 | 62.642 | 77.040 | 1.00 | 9.08 |
| ATOM | 2033 | OH | TYR | 441 | 20.857 | 62.544 | 76.593 | 1.00 | 8.63 |
| ATOM | 2035 | C | TYR | 441 | 28.687 | 62.904 | 78.050 | 1.00 | 11.26 |
| ATOM | 2036 | O | TYR | 441 | 28.777 | 63.289 | 79.204 | 1.00 | 11.93 |
| ATOM | 2037 | N | PRO | 442 | 29.771 | 62.618 | 77.307 | 1.00 | 12.34 |
| ATOM | 2038 | CD | PRO | 442 | 29.717 | 62.160 | 75.902 | 1.00 | 11.98 |
| ATOM | 2039 | CA | PRO | 442 | 31.158 | 62.768 | 77.758 | 1.00 | 12.52 |
| ATOM | 2040 | CB | PRO | 442 | 31.955 | 62.593 | 76.468 | 1.00 | 12.26 |
| ATOM | 2041 | CG | PRO | 442 | 31.101 | 61.660 | 75.662 | 1.00 | 12.69 |
| ATOM | 2042 | C | PRO | 442 | 31.445 | 64.166 | 78.350 | 1.00 | 12.85 |
| ATOM | 2043 | O | PRO | 442 | 31.109 | 65.173 | 77.749 | 1.00 | 13.60 |
| ATOM | 2044 | N | GLY | 443 | 32.056 | 64.201 | 79.523 | 1.00 | 13.21 |
| ATOM | 2046 | CA | GLY | 443 | 32.416 | 65.463 | 80.149 | 1.00 | 13.66 |
| ATOM | 2047 | C | GLY | 443 | 31.289 | 66.232 | 80.798 | 1.00 | 14.06 |
| ATOM | 2048 | O | GLY | 443 | 31.485 | 67.361 | 81.241 | 1.00 | 14.31 |
| ATOM | 2049 | N | MET | 444 | 30.130 | 65.599 | 80.941 | 1.00 | 13.76 |
| ATOM | 2051 | CA | MET | 444 | 28.996 | 66.291 | 81.515 | 1.00 | 13.45 |
| ATOM | 2052 | CB | MET | 444 | 27.908 | 66.537 | 80.443 | 1.00 | 13.55 |
| ATOM | 2053 | CG | MET | 444 | 28.343 | 67.245 | 79.145 | 1.00 | 13.33 |
| ATOM | 2054 | SD | MET | 444 | 27.037 | 67.317 | 77.838 | 1.00 | 13.08 |
| ATOM | 2055 | CE | MET | 444 | 25.682 | 67.995 | 78.769 | 1.00 | 12.65 |
| ATOM | 2056 | C | MET | 444 | 28.389 | 65.605 | 82.730 | 1.00 | 13.28 |
| ATOM | 2057 | O | MET | 444 | 28.232 | 64.378 | 82.778 | 1.00 | 13.25 |
| ATOM | 2058 | N | THR | 445 | 28.003 | 66.433 | 83.693 | 1.00 | 12.83 |
| ATOM | 2060 | CA | THR | 445 | 27.343 | 65.985 | 84.908 | 1.00 | 12.63 |
| ATOM | 2061 | CB | THR | 445 | 27.552 | 66.988 | 86.063 | 1.00 | 13.45 |
| ATOM | 2062 | OG1 | THR | 445 | 26.871 | 68.228 | 85.766 | 1.00 | 13.61 |

TABLE 7-continued

Coordinates of Lck bound with PD153035

| | Atom Type | Res | # | X | Y | Z | Occ | B |
|---|---|---|---|---|---|---|---|---|
| ATOM | 2064 | CG2 | THR | 445 | 29.066 | 67.270 | 86.252 | 1.00 | 13.51 |
| ATOM | 2065 | C | THR | 445 | 25.830 | 65.904 | 84.632 | 1.00 | 12.36 |
| ATOM | 2066 | O | THR | 445 | 25.348 | 66.377 | 83.589 | 1.00 | 11.73 |
| ATOM | 2067 | N | ASN | 446 | 25.109 | 65.280 | 85.559 | 1.00 | 11.85 |
| ATOM | 2069 | CA | ASN | 446 | 23.649 | 65.154 | 85.442 | 1.00 | 11.88 |
| ATOM | 2070 | CB | ASN | 446 | 23.113 | 64.250 | 86.565 | 1.00 | 11.35 |
| ATOM | 2071 | CG | ASN | 446 | 23.535 | 62.802 | 86.378 | 1.00 | 11.83 |
| ATOM | 2072 | OD1 | ASN | 446 | 23.981 | 62.423 | 85.297 | 1.00 | 11.86 |
| ATOM | 2073 | ND2 | ASN | 446 | 23.417 | 62.000 | 87.418 | 1.00 | 12.04 |
| ATOM | 2076 | C | ASN | 446 | 22.904 | 66.508 | 85.314 | 1.00 | 11.64 |
| ATOM | 2077 | O | ASN | 446 | 22.040 | 66.649 | 84.452 | 1.00 | 11.35 |
| ATOM | 2078 | N | PRO | 447 | 23.277 | 67.534 | 86.115 | 1.00 | 11.20 |
| ATOM | 2079 | CD | PRO | 447 | 24.160 | 67.509 | 87.296 | 1.00 | 11.31 |
| ATOM | 2080 | CA | PRO | 447 | 22.601 | 68.833 | 86.003 | 1.00 | 11.30 |
| ATOM | 2081 | CB | PRO | 447 | 23.220 | 69.640 | 87.146 | 1.00 | 11.59 |
| ATOM | 2082 | CG | PRO | 447 | 23.605 | 68.599 | 88.142 | 1.00 | 11.49 |
| ATOM | 2083 | C | PRO | 447 | 22.912 | 69.466 | 84.621 | 1.00 | 10.83 |
| ATOM | 2084 | O | PRO | 447 | 22.054 | 70.101 | 84.019 | 1.00 | 10.80 |
| ATOM | 2085 | N | GLU | 448 | 24.110 | 69.222 | 84.095 | 1.00 | 10.47 |
| ATOM | 2087 | CA | GLU | 448 | 24.496 | 69.749 | 82.793 | 1.00 | 10.36 |
| ATOM | 2088 | CB | GLU | 448 | 25.989 | 69.553 | 82.524 | 1.00 | 10.91 |
| ATOM | 2089 | CG | GLU | 448 | 26.891 | 70.526 | 83.279 | 1.00 | 12.04 |
| ATOM | 2090 | CD | GLU | 448 | 28.368 | 70.314 | 82.947 | 1.00 | 12.94 |
| ATOM | 2091 | OE1 | GLU | 448 | 28.875 | 69.179 | 83.091 | 1.00 | 12.84 |
| ATOM | 2092 | OE2 | GLU | 448 | 29.024 | 71.294 | 82.516 | 1.00 | 14.23 |
| ATOM | 2093 | C | GLU | 448 | 23.695 | 69.084 | 81.686 | 1.00 | 10.02 |
| ATOM | 2094 | O | GLU | 448 | 23.274 | 69.745 | 80.737 | 1.00 | 10.12 |
| ATOM | 2095 | N | VAL | 449 | 23.492 | 67.772 | 81.817 | 1.00 | 9.62 |
| ATOM | 2097 | CA | VAL | 449 | 22.712 | 67.001 | 80.844 | 1.00 | 9.43 |
| ATOM | 2098 | CB | VAL | 449 | 22.703 | 65.487 | 81.209 | 1.00 | 8.95 |
| ATOM | 2099 | CG1 | VAL | 449 | 21.702 | 64.762 | 80.356 | 1.00 | 9.24 |
| ATOM | 2100 | CG2 | VAL | 449 | 24.091 | 64.874 | 80.977 | 1.00 | 9.06 |
| ATOM | 2101 | C | VAL | 449 | 21.262 | 67.525 | 80.804 | 1.00 | 9.35 |
| ATOM | 2102 | O | VAL | 449 | 20.734 | 67.832 | 79.732 | 1.00 | 8.53 |
| ATOM | 2103 | N | ILE | 450 | 20.645 | 67.645 | 81.972 | 0.60 | 9.74 |
| ATOM | 2105 | CA | ILE | 450 | 19.273 | 68.149 | 82.081 | 0.60 | 10.85 |
| ATOM | 2106 | CB | ILE | 450 | 18.827 | 68.142 | 83.584 | 0.60 | 10.83 |
| ATOM | 2107 | CG2 | ILE | 450 | 17.414 | 68.744 | 83.739 | 0.60 | 11.11 |
| ATOM | 2108 | CG1 | ILE | 450 | 18.863 | 66.699 | 84.121 | 0.60 | 10.67 |
| ATOM | 2109 | CD1 | ILE | 450 | 18.845 | 66.555 | 85.639 | 0.60 | 10.79 |
| ATOM | 2110 | C | ILE | 450 | 19.114 | 69.564 | 81.460 | 0.60 | 11.24 |
| ATOM | 2111 | O | ILE | 450 | 18.187 | 69.835 | 80.701 | 0.60 | 10.75 |
| ATOM | 2112 | N | GLN | 451 | 20.063 | 70.437 | 81.756 | 1.00 | 12.34 |
| ATOM | 2114 | CA | GLN | 451 | 20.075 | 71.812 | 81.264 | 1.00 | 13.32 |
| ATOM | 2115 | CB | GLN | 451 | 21.296 | 72.542 | 81.853 | 1.00 | 14.81 |
| ATOM | 2116 | CG | GLN | 451 | 21.467 | 74.005 | 81.445 | 1.00 | 17.11 |
| ATOM | 2117 | CD | GLN | 451 | 22.706 | 74.632 | 82.085 | 1.00 | 18.04 |
| ATOM | 2118 | OE1 | GLN | 451 | 23.822 | 74.446 | 81.589 | 1.00 | 19.01 |
| ATOM | 2119 | NE2 | GLN | 451 | 22.523 | 75.314 | 83.218 | 1.00 | 19.01 |
| ATOM | 2122 | C | GLN | 451 | 20.125 | 71.836 | 79.745 | 1.00 | 13.13 |
| ATOM | 2123 | O | GLN | 451 | 19.352 | 72.552 | 79.105 | 1.00 | 12.87 |
| ATOM | 2124 | N | ASN | 452 | 21.005 | 71.026 | 79.168 | 1.00 | 12.87 |
| ATOM | 2126 | CA | ASN | 452 | 21.143 | 70.970 | 77.734 | 1.00 | 12.61 |
| ATOM | 2127 | CB | ASN | 452 | 22.427 | 70.255 | 77.343 | 1.00 | 12.96 |
| ATOM | 2128 | CG | ASN | 452 | 23.650 | 71.157 | 77.513 | 1.00 | 13.59 |
| ATOM | 2129 | OD1 | ASN | 452 | 23.831 | 71.838 | 78.506 | 1.00 | 14.62 |
| ATOM | 2130 | ND2 | ASN | 452 | 24.519 | 71.111 | 76.539 | 1.00 | 14.49 |
| ATOM | 2133 | C | ASN | 452 | 19.918 | 70.363 | 77.039 | 1.00 | 12.68 |
| ATOM | 2134 | O | ASN | 452 | 19.420 | 70.897 | 76.030 | 1.00 | 12.27 |
| ATOM | 2135 | N | LEU | 453 | 19.392 | 69.274 | 77.603 | 1.00 | 12.54 |
| ATOM | 2137 | CA | LEU | 453 | 18.213 | 68.662 | 77.015 | 1.00 | 12.29 |
| ATOM | 2138 | CB | LEU | 453 | 17.801 | 67.440 | 77.816 | 1.00 | 12.16 |
| ATOM | 2139 | CG | LEU | 453 | 18.798 | 66.272 | 77.750 | 1.00 | 11.95 |
| ATOM | 2140 | CD1 | LEU | 453 | 18.297 | 65.136 | 78.615 | 1.00 | 11.64 |
| ATOM | 2141 | CD2 | LEU | 453 | 18.986 | 65.833 | 76.287 | 1.00 | 11.74 |
| ATOM | 2142 | C | LEU | 453 | 17.070 | 69.696 | 76.986 | 1.00 | 12.46 |
| ATOM | 2143 | O | LEU | 453 | 16.399 | 69.844 | 75.959 | 1.00 | 12.21 |
| ATOM | 2144 | N | GLU | 454 | 16.899 | 70.435 | 78.080 | 1.00 | 12.76 |
| ATOM | 2146 | CA | GLU | 454 | 15.840 | 71.430 | 78.146 | 1.00 | 12.92 |
| ATOM | 2147 | CB | GLU | 454 | 15.670 | 71.931 | 79.580 | 1.00 | 14.20 |
| ATOM | 2148 | CG | GLU | 454 | 15.039 | 70.854 | 80.485 | 1.00 | 15.55 |
| ATOM | 2149 | CD | GLU | 454 | 15.054 | 71.196 | 81.951 | 1.00 | 16.66 |
| ATOM | 2150 | OE1 | GLU | 454 | 15.643 | 72.226 | 82.344 | 1.00 | 17.49 |
| ATOM | 2151 | OE2 | GLU | 454 | 14.487 | 70.406 | 82.738 | 1.00 | 17.65 |

TABLE 7-continued

Coordinates of Lck bound with PD153035

| | Atom Type | Res | # | X | Y | Z | Occ | B |
|---|---|---|---|---|---|---|---|---|
| ATOM | 2152 | C | GLU | 454 | 15.955 | 72.563 | 77.136 | 1.00 | 12.66 |
| ATOM | 2153 | O | GLU | 454 | 14.951 | 73.219 | 76.819 | 1.00 | 12.56 |
| ATOM | 2154 | N | ARG | 455 | 17.169 | 72.786 | 76.621 | 1.00 | 11.79 |
| ATOM | 2156 | CA | ARG | 455 | 17.426 | 73.810 | 75.596 | 1.00 | 10.89 |
| ATOM | 2157 | CB | ARG | 455 | 18.914 | 74.203 | 75.614 | 1.00 | 10.77 |
| ATOM | 2158 | CG | ARG | 455 | 19.425 | 74.793 | 76.913 | 1.00 | 11.07 |
| ATOM | 2159 | CD | ARG | 455 | 20.819 | 75.347 | 76.687 | 1.00 | 10.97 |
| ATOM | 2160 | NE | ARG | 455 | 20.812 | 76.479 | 75.748 | 1.00 | 10.23 |
| ATOM | 2162 | CZ | ARG | 455 | 21.913 | 77.155 | 75.396 | 1.00 | 10.34 |
| ATOM | 2163 | NH1 | ARG | 455 | 23.100 | 76.791 | 75.904 | 1.00 | 9.38 |
| ATOM | 2166 | NH2 | ARG | 455 | 21.819 | 78.240 | 74.616 | 1.00 | 10.04 |
| ATOM | 2169 | C | ARG | 455 | 17.118 | 73.254 | 74.192 | 1.00 | 10.29 |
| ATOM | 2170 | O | ARG | 455 | 17.035 | 74.003 | 73.206 | 1.00 | 10.06 |
| ATOM | 2171 | N | GLY | 456 | 16.928 | 71.937 | 74.111 | 1.00 | 9.51 |
| ATOM | 2173 | CA | GLY | 456 | 16.667 | 71.277 | 72.841 | 1.00 | 8.64 |
| ATOM | 2174 | C | GLY | 456 | 17.882 | 70.545 | 72.267 | 1.00 | 8.15 |
| ATOM | 2175 | O | GLY | 456 | 17.807 | 69.966 | 71.175 | 1.00 | 8.10 |
| ATOM | 2176 | N | TYR | 457 | 19.020 | 70.660 | 72.949 | 1.00 | 7.81 |
| ATOM | 2178 | CA | TYR | 457 | 20.267 | 69.989 | 72.529 | 1.00 | 7.42 |
| ATOM | 2179 | CB | TYR | 457 | 21.467 | 70.517 | 73.316 | 1.00 | 7.53 |
| ATOM | 2180 | CG | TYR | 457 | 21.880 | 71.962 | 73.102 | 1.00 | 8.35 |
| ATOM | 2181 | CD1 | TYR | 457 | 21.477 | 72.697 | 71.982 | 1.00 | 8.58 |
| ATOM | 2182 | CE1 | TYR | 457 | 21.985 | 73.997 | 71.751 | 1.00 | 9.19 |
| ATOM | 2183 | CD2 | TYR | 457 | 22.777 | 72.551 | 73.981 | 1.00 | 9.02 |
| ATOM | 2184 | CE2 | TYR | 457 | 23.287 | 73.815 | 73.765 | 1.00 | 9.20 |
| ATOM | 2185 | CZ | TYR | 457 | 22.897 | 74.532 | 72.655 | 1.00 | 9.65 |
| ATOM | 2186 | OH | TYR | 457 | 23.478 | 75.769 | 72.476 | 1.00 | 10.17 |
| ATOM | 2188 | C | TYR | 457 | 20.126 | 68.517 | 72.901 | 1.00 | 6.84 |
| ATOM | 2189 | O | TYR | 457 | 19.364 | 68.179 | 73.800 | 1.00 | 6.35 |
| ATOM | 2190 | N | ARG | 458 | 20.874 | 67.673 | 72.200 | 1.00 | 6.75 |
| ATOM | 2192 | CA | ARG | 458 | 20.928 | 66.229 | 72.460 | 1.00 | 6.42 |
| ATOM | 2193 | CB | ARG | 458 | 20.198 | 65.423 | 71.365 | 1.00 | 5.68 |
| ATOM | 2194 | CG | ARG | 458 | 18.663 | 65.713 | 71.252 | 1.00 | 5.29 |
| ATOM | 2195 | CD | ARG | 458 | 17.933 | 65.328 | 72.561 | 1.00 | 5.36 |
| ATOM | 2196 | NE | ARG | 458 | 16.466 | 65.462 | 72.531 | 1.00 | 5.25 |
| ATOM | 2198 | CZ | ARG | 458 | 15.791 | 66.478 | 73.083 | 1.00 | 6.23 |
| ATOM | 2199 | NH1 | ARG | 458 | 16.430 | 67.485 | 73.698 | 1.00 | 6.36 |
| ATOM | 2202 | NH2 | ARG | 458 | 14.472 | 66.442 | 73.134 | 1.00 | 5.78 |
| ATOM | 2205 | C | ARG | 458 | 22.438 | 65.922 | 72.489 | 1.00 | 6.91 |
| ATOM | 2206 | O | ARG | 458 | 23.289 | 66.802 | 72.251 | 1.00 | 6.73 |
| ATOM | 2207 | N | MET | 459 | 22.783 | 64.687 | 72.806 | 1.00 | 7.14 |
| ATOM | 2209 | CA | MET | 459 | 24.184 | 64.310 | 72.904 | 1.00 | 6.83 |
| ATOM | 2210 | CB | MET | 459 | 24.303 | 62.811 | 73.185 | 1.00 | 6.97 |
| ATOM | 2211 | CG | MET | 459 | 25.656 | 62.444 | 73.748 | 1.00 | 7.00 |
| ATOM | 2212 | SD | MET | 459 | 25.838 | 60.657 | 74.008 | 1.00 | 7.43 |
| ATOM | 2213 | CE | MET | 459 | 24.265 | 60.254 | 74.838 | 1.00 | 7.06 |
| ATOM | 2214 | C | MET | 459 | 24.944 | 64.639 | 71.647 | 1.00 | 7.00 |
| ATOM | 2215 | O | MET | 459 | 24.454 | 64.441 | 70.539 | 1.00 | 6.89 |
| ATOM | 2216 | N | VAL | 460 | 26.113 | 65.248 | 71.843 | 1.00 | 7.73 |
| ATOM | 2218 | CA | VAL | 460 | 27.005 | 65.598 | 70.753 | 1.00 | 8.96 |
| ATOM | 2219 | CB | VAL | 460 | 28.322 | 66.237 | 71.307 | 1.00 | 9.06 |
| ATOM | 2220 | CG1 | VAL | 460 | 29.403 | 66.295 | 70.207 | 1.00 | 8.52 |
| ATOM | 2221 | CG2 | VAL | 460 | 28.026 | 67.647 | 71.907 | 1.00 | 9.08 |
| ATOM | 2222 | C | VAL | 460 | 27.344 | 64.291 | 70.038 | 1.00 | 9.89 |
| ATOM | 2223 | O | VAL | 460 | 27.462 | 63.251 | 70.676 | 1.00 | 10.19 |
| ATOM | 2224 | N | ARG | 461 | 27.426 | 64.352 | 68.713 | 1.00 | 11.39 |
| ATOM | 2226 | CA | ARG | 461 | 27.746 | 63.206 | 67.874 | 1.00 | 13.13 |
| ATOM | 2227 | CB | ARG | 461 | 28.095 | 63.658 | 66.467 | 1.00 | 12.99 |
| ATOM | 2228 | CG | ARG | 461 | 26.967 | 64.204 | 65.612 | 1.00 | 12.82 |
| ATOM | 2229 | CD | ARG | 461 | 27.516 | 64.704 | 64.269 | 1.00 | 12.84 |
| ATOM | 2230 | NE | ARG | 461 | 26.421 | 65.052 | 63.365 | 1.00 | 11.61 |
| ATOM | 2232 | CZ | ARG | 461 | 25.814 | 66.238 | 63.329 | 1.00 | 11.45 |
| ATOM | 2233 | NH1 | ARG | 461 | 26.199 | 67.214 | 64.157 | 1.00 | 10.99 |
| ATOM | 2236 | NH2 | ARG | 461 | 24.824 | 66.454 | 62.455 | 1.00 | 10.55 |
| ATOM | 2239 | C | ARG | 461 | 29.000 | 62.530 | 68.418 | 1.00 | 14.21 |
| ATOM | 2240 | O | ARG | 461 | 30.059 | 63.158 | 68.472 | 1.00 | 14.58 |
| ATOM | 2241 | N | PRO | 462 | 28.901 | 61.246 | 68.810 | 1.00 | 14.83 |
| ATOM | 2242 | CD | PRO | 462 | 27.679 | 60.426 | 68.891 | 1.00 | 15.14 |
| ATOM | 2243 | CA | PRO | 462 | 30.061 | 60.514 | 69.336 | 1.00 | 15.80 |
| ATOM | 2244 | CB | PRO | 462 | 29.473 | 59.134 | 69.670 | 1.00 | 15.31 |
| ATOM | 2245 | CG | PRO | 462 | 28.014 | 59.444 | 69.983 | 1.00 | 15.45 |
| ATOM | 2246 | C | PRO | 462 | 31.118 | 60.386 | 68.240 | 1.00 | 16.48 |
| ATOM | 2247 | O | PRO | 462 | 30.783 | 60.355 | 67.064 | 1.00 | 16.50 |
| ATOM | 2248 | N | ASP | 463 | 32.382 | 60.294 | 68.659 | 1.00 | 17.97 |

TABLE 7-continued

Coordinates of Lck bound with PD153035

| | | Atom Type | Res | # | X | Y | Z | Occ | B |
|---|---|---|---|---|---|---|---|---|---|
| ATOM | 2250 | CA | ASP | 463 | 33.529 | 60.138 | 67.767 | 1.00 | 18.96 |
| ATOM | 2251 | CB | ASP | 463 | 34.792 | 59.885 | 68.607 | 1.00 | 20.06 |
| ATOM | 2252 | CG | ASP | 463 | 35.368 | 61.157 | 69.224 | 1.00 | 21.16 |
| ATOM | 2253 | OD1 | ASP | 463 | 35.101 | 62.264 | 68.682 | 1.00 | 22.46 |
| ATOM | 2254 | OD2 | ASP | 463 | 36.106 | 61.036 | 70.224 | 1.00 | 21.40 |
| ATOM | 2255 | C | ASP | 463 | 33.292 | 58.944 | 66.855 | 1.00 | 18.96 |
| ATOM | 2256 | O | ASP | 463 | 32.873 | 57.900 | 67.330 | 1.00 | 19.15 |
| ATOM | 2257 | N | ASN | 464 | 33.538 | 59.122 | 65.561 | 1.00 | 19.09 |
| ATOM | 2259 | CA | ASN | 464 | 33.390 | 58.070 | 64.564 | 1.00 | 18.99 |
| ATOM | 2260 | CB | ASN | 464 | 34.452 | 57.016 | 64.760 | 1.00 | 20.41 |
| ATOM | 2261 | SG | ASN | 464 | 35.819 | 57.607 | 64.701 | 1.00 | 20.72 |
| ATOM | 2262 | OD1 | ASN | 464 | 36.550 | 57.559 | 65.677 | 1.00 | 21.66 |
| ATOM | 2263 | ND2 | ASN | 464 | 36.085 | 58.368 | 63.636 | 1.00 | 21.88 |
| ATOM | 2266 | C | ASN | 464 | 32.043 | 57.398 | 64.399 | 1.00 | 18.21 |
| ATOM | 2267 | O | ASN | 464 | 31.956 | 56.276 | 63.906 | 1.00 | 18.56 |
| ATOM | 2268 | N | CYS | 465 | 30.994 | 58.066 | 64.830 | 1.00 | 16.74 |
| ATOM | 2270 | CA | CYS | 465 | 29.656 | 57.513 | 64.695 | 1.00 | 15.08 |
| ATOM | 2271 | CB | CYS | 465 | 28.745 | 58.085 | 65.806 | 1.00 | 14.87 |
| ATOM | 2272 | SG | CYS | 465 | 26.998 | 57.628 | 65.754 | 1.00 | 13.34 |
| ATOM | 2273 | C | CYS | 465 | 29.109 | 57.845 | 63.315 | 1.00 | 14.11 |
| ATOM | 2274 | O | CYS | 465 | 29.236 | 58.966 | 62.840 | 1.00 | 13.93 |
| ATOM | 2275 | N | PRO | 466 | 28.608 | 56.834 | 62.598 | 1.00 | 13.18 |
| ATOM | 2276 | CD | PRO | 466 | 28.585 | 55.425 | 63.003 | 1.00 | 13.33 |
| ATOM | 2277 | CA | PRO | 466 | 28.037 | 57.034 | 61.257 | 1.00 | 12.25 |
| ATOM | 2278 | CB | PRO | 466 | 27.573 | 55.626 | 60.863 | 1.00 | 12.56 |
| ATOM | 2279 | CG | PRO | 466 | 28.499 | 54.719 | 61.709 | 1.00 | 12.87 |
| ATOM | 2280 | C | PRO | 466 | 26.836 | 57.971 | 61.403 | 1.00 | 11.38 |
| ATOM | 2281 | O | PRO | 466 | 25.998 | 57.752 | 62.282 | 1.00 | 10.89 |
| ATOM | 2282 | N | GLU | 467 | 26.766 | 59.013 | 60.560 | 1.00 | 10.30 |
| ATOM | 2284 | CA | GLU | 467 | 25.672 | 59.980 | 60.665 | 1.00 | 9.23 |
| ATOM | 2285 | CB | GLU | 467 | 25.788 | 61.094 | 59.619 | 1.00 | 9.32 |
| ATOM | 2286 | CG | GLU | 467 | 24.660 | 62.178 | 59.758 | 1.00 | 8.83 |
| ATOM | 2287 | CD | GLU | 467 | 24.837 | 63.084 | 60.994 | 1.00 | 8.38 |
| ATOM | 2288 | OE1 | GLU | 467 | 25.833 | 62.914 | 61.710 | 1.00 | 8.79 |
| ATOM | 2289 | OE2 | GLU | 467 | 24.005 | 64.002 | 61.232 | 1.00 | 8.36 |
| ATOM | 2290 | C | GLU | 467 | 24.275 | 59.350 | 60.564 | 1.00 | 8.49 |
| ATOM | 2291 | O | GLU | 467 | 23.329 | 59.838 | 61.193 | 1.00 | 8.63 |
| ATOM | 2292 | N | GLU | 468 | 24.134 | 58.282 | 59.780 | 0.51 | 7.32 |
| ATOM | 2294 | CA | GLU | 468 | 22.821 | 57.636 | 59.664 | 0.51 | 6.35 |
| ATOM | 2295 | CB | GLU | 468 | 22.840 | 56.515 | 58.646 | 0.51 | 6.23 |
| ATOM | 2296 | CG | GLU | 468 | 22.947 | 57.017 | 57.244 | 0.51 | 6.48 |
| ATOM | 2297 | CD | GLU | 468 | 23.403 | 55.949 | 56.298 | 0.51 | 6.21 |
| ATOM | 2298 | OE1 | GLU | 468 | 22.563 | 55.359 | 55.605 | 0.51 | 6.33 |
| ATOM | 2299 | OE2 | GLU | 468 | 24.614 | 55.703 | 56.234 | 0.51 | 6.39 |
| ATOM | 2300 | C | GLU | 468 | 22.354 | 57.113 | 61.004 | 0.51 | 5.80 |
| ATOM | 2301 | O | GLU | 468 | 21.190 | 57.241 | 61.350 | 0.51 | 5.11 |
| ATOM | 2302 | N | LEU | 469 | 23.283 | 56.537 | 61.760 | 1.00 | 5.78 |
| ATOM | 2304 | CA | LEU | 469 | 22.998 | 56.007 | 63.086 | 1.00 | 6.03 |
| ATOM | 2305 | CB | LEU | 469 | 24.177 | 55.176 | 63.620 | 1.00 | 5.90 |
| ATOM | 2306 | CG | LEU | 469 | 23.879 | 54.462 | 64.950 | 1.00 | 6.11 |
| ATOM | 2307 | CD1 | LEU | 469 | 22.721 | 53.487 | 64.771 | 1.00 | 6.34 |
| ATOM | 2308 | CD2 | LEU | 469 | 25.108 | 53.694 | 65.447 | 1.00 | 6.49 |
| ATOM | 2309 | C | LEU | 469 | 22.727 | 57.169 | 64.027 | 1.00 | 6.10 |
| ATOM | 2310 | O | LEU | 469 | 21.842 | 57.102 | 64.869 | 1.00 | 6.48 |
| ATOM | 2311 | N | TYR | 470 | 23.488 | 58.251 | 63.881 | 1.00 | 6.40 |
| ATOM | 2313 | CA | TYR | 470 | 23.278 | 59.411 | 64.749 | 1.00 | 5.73 |
| ATOM | 2314 | CB | TYR | 470 | 24.312 | 60.517 | 64.467 | 1.00 | 5.58 |
| ATOM | 2315 | CG | TYR | 470 | 24.173 | 61.677 | 65.434 | 1.00 | 5.41 |
| ATOM | 2316 | CD1 | TYR | 470 | 24.378 | 61.500 | 66.795 | 1.00 | 5.27 |
| ATOM | 2317 | CE1 | TYR | 470 | 24.227 | 62.567 | 67.707 | 1.00 | 5.74 |
| ATOM | 2318 | CD2 | TYR | 470 | 23.803 | 62.957 | 64.979 | 1.00 | 5.59 |
| ATOM | 2319 | CE2 | TYR | 470 | 23.644 | 64.017 | 65.863 | 1.00 | 5.81 |
| ATOM | 2320 | CZ | TYR | 470 | 23.856 | 63.826 | 67.221 | 1.00 | 5.86 |
| ATOM | 2321 | OH | TYR | 470 | 23.719 | 64.886 | 68.117 | 1.00 | 6.77 |
| ATOM | 2323 | C | TYR | 470 | 21.837 | 59.970 | 64.548 | 1.00 | 5.80 |
| ATOM | 2324 | O | TYR | 470 | 21.161 | 60.290 | 65.511 | 1.00 | 5.91 |
| ATOM | 2325 | N | GLN | 471 | 21.384 | 60.071 | 63.301 | 1.00 | 5.89 |
| ATOM | 2327 | CA | GLN | 471 | 20.027 | 60.569 | 63.030 | 1.00 | 6.26 |
| ATOM | 2328 | CB | GLN | 471 | 19.840 | 60.872 | 61.543 | 1.00 | 6.43 |
| ATOM | 2329 | CG | GLN | 471 | 20.516 | 62.222 | 61.074 | 1.00 | 6.08 |
| ATOM | 2330 | CD | GLN | 471 | 20.222 | 63.403 | 61.998 | 1.00 | 6.31 |
| ATOM | 2331 | OE1 | GLN | 471 | 19.070 | 63.645 | 62.341 | 1.00 | 6.80 |
| ATOM | 2332 | NE2 | GLN | 471 | 21.286 | 64.114 | 62.457 | 1.00 | 5.92 |
| ATOM | 2335 | C | GLN | 471 | 18.960 | 59.587 | 63.553 | 1.00 | 6.51 |

TABLE 7-continued

Coordinates of Lck bound with PD153035

| | Atom Type | Res | # | X | Y | Z | Occ | B |
|---|---|---|---|---|---|---|---|---|
| ATOM | 2336 | O | GLN | 471 | 17.872 | 59.995 | 63.970 | 1.00 | 6.89 |
| ATOM | 2337 | N | LEU | 472 | 19.290 | 58.291 | 63.571 | 1.00 | 6.78 |
| ATOM | 2339 | CA | LEU | 472 | 18.365 | 57.279 | 64.108 | 1.00 | 6.76 |
| ATOM | 2340 | CB | LEU | 472 | 18.830 | 55.859 | 63.766 | 1.00 | 7.31 |
| ATOM | 2341 | CG | LEU | 472 | 17.800 | 54.757 | 64.075 | 1.00 | 7.68 |
| ATOM | 2342 | CD1 | LEU | 472 | 16.604 | 54.925 | 63.161 | 1.00 | 7.64 |
| ATOM | 2343 | CD2 | LEU | 472 | 18.409 | 53.355 | 63.911 | 1.00 | 7.89 |
| ATOM | 2344 | C | LEU | 472 | 18.267 | 57.486 | 65.634 | 1.00 | 7.05 |
| ATOM | 2345 | O | LEU | 472 | 17.188 | 57.390 | 66.227 | 1.00 | 6.47 |
| ATOM | 2346 | N | MET | 473 | 19.399 | 57.801 | 66.268 | 1.00 | 7.45 |
| ATOM | 2348 | CA | MET | 473 | 19.414 | 58.085 | 67.697 | 1.00 | 7.69 |
| ATOM | 2349 | CB | MET | 473 | 20.822 | 58.412 | 68.152 | 1.00 | 7.78 |
| ATOM | 2350 | CG | MET | 473 | 21.857 | 57.295 | 67.990 | 1.00 | 8.31 |
| ATOM | 2351 | SD | MET | 473 | 23.498 | 58.049 | 68.268 | 1.00 | 8.39 |
| ATOM | 2352 | CE | MET | 473 | 24.619 | 56.555 | 68.231 | 1.00 | 7.41 |
| ATOM | 2353 | C | MET | 473 | 18.531 | 59.320 | 67.997 | 1.00 | 7.72 |
| ATOM | 2354 | O | MET | 473 | 17.745 | 59.318 | 68.962 | 1.00 | 7.10 |
| ATOM | 2355 | N | ARG | 474 | 18.660 | 60.353 | 67.159 | 1.00 | 8.16 |
| ATOM | 2357 | CA | ARG | 474 | 17.892 | 61.600 | 67.338 | 1.00 | 8.92 |
| ATOM | 2358 | CB | ARG | 474 | 18.193 | 62.612 | 66.221 | 1.00 | 9.47 |
| ATOM | 2359 | CG | ARG | 474 | 19.654 | 63.089 | 66.130 | 1.00 | 10.68 |
| ATOM | 2360 | CD | ARG | 474 | 20.148 | 63.823 | 67.357 | 1.00 | 12.21 |
| ATOM | 2361 | NE | ARG | 474 | 19.444 | 65.076 | 67.628 | 1.00 | 13.70 |
| ATOM | 2363 | CZ | ARG | 474 | 20.035 | 66.249 | 67.878 | 1.00 | 13.78 |
| ATOM | 2364 | NH1 | ARG | 474 | 21.364 | 66.359 | 67.880 | 1.00 | 13.18 |
| ATOM | 2367 | NH2 | ARG | 474 | 19.286 | 67.298 | 68.234 | 1.00 | 14.13 |
| ATOM | 2370 | C | ARG | 474 | 16.376 | 61.291 | 67.332 | 1.00 | 9.11 |
| ATOM | 2371 | O | ARG | 474 | 15.632 | 61.896 | 68.088 | 1.00 | 8.98 |
| ATOM | 2372 | N | LEU | 475 | 15.941 | 60.348 | 66.486 | 1.00 | 9.35 |
| ATOM | 2374 | CA | LEU | 475 | 14.518 | 59.949 | 66.423 | 1.00 | 9.43 |
| ATOM | 2375 | CB | LEU | 475 | 14.266 | 58.868 | 65.352 | 1.00 | 9.79 |
| ATOM | 2376 | CG | LEU | 475 | 14.500 | 59.057 | 63.844 | 1.00 | 10.15 |
| ATOM | 2377 | CD1 | LEU | 475 | 13.954 | 57.839 | 63.125 | 1.00 | 10.59 |
| ATOM | 2378 | CD2 | LEU | 475 | 13.804 | 60.279 | 63.294 | 1.00 | 11.03 |
| ATOM | 2379 | C | LEU | 475 | 14.101 | 59.437 | 67.797 | 1.00 | 9.27 |
| ATOM | 2380 | O | LEU | 475 | 13.023 | 59.777 | 68.296 | 1.00 | 9.27 |
| ATOM | 2381 | N | CYS | 476 | 14.977 | 58.657 | 68.430 | 1.00 | 8.96 |
| ATOM | 2383 | CA | CYS | 476 | 14.729 | 58.137 | 69.774 | 1.00 | 8.65 |
| ATOM | 2384 | CB | CYS | 476 | 15.861 | 57.167 | 70.168 | 1.00 | 8.90 |
| ATOM | 2385 | SG | CYS | 476 | 15.983 | 55.678 | 69.106 | 1.00 | 8.05 |
| ATOM | 2386 | C | CYS | 476 | 14.615 | 59.231 | 70.845 | 1.00 | 8.94 |
| ATOM | 2387 | O | CYS | 476 | 13.994 | 59.017 | 71.886 | 1.00 | 8.20 |
| ATOM | 2388 | N | TRP | 477 | 15.248 | 60.385 | 70.598 | 1.00 | 9.64 |
| ATOM | 2390 | CA | TRP | 477 | 15.254 | 61.475 | 71.551 | 1.00 | 11.06 |
| ATOM | 2391 | CB | TRP | 477 | 16.673 | 62.047 | 71.708 | 1.00 | 10.56 |
| ATOM | 2392 | CG | TRP | 477 | 17.752 | 60.994 | 72.070 | 1.00 | 10.74 |
| ATOM | 2393 | CD2 | TRP | 477 | 19.112 | 60.979 | 71.611 | 1.00 | 10.93 |
| ATOM | 2394 | CE2 | TRP | 477 | 19.738 | 59.846 | 72.184 | 1.00 | 10.96 |
| ATOM | 2395 | CE3 | TRP | 477 | 19.868 | 61.815 | 70.772 | 1.00 | 10.66 |
| ATOM | 2396 | CD1 | TRP | 477 | 17.611 | 59.895 | 72.887 | 1.00 | 10.75 |
| ATOM | 2397 | NE1 | TRP | 477 | 18.802 | 59.204 | 72.959 | 1.00 | 11.10 |
| ATOM | 2399 | CZ2 | TRP | 477 | 21.081 | 59.533 | 71.941 | 1.00 | 10.99 |
| ATOM | 2400 | CZ3 | TRP | 477 | 21.200 | 61.502 | 70.537 | 1.00 | 11.06 |
| ATOM | 2401 | CH2 | TRP | 477 | 21.792 | 60.372 | 71.116 | 1.00 | 10.96 |
| ATOM | 2402 | C | TRP | 477 | 14.244 | 62.592 | 71.252 | 1.00 | 12.23 |
| ATOM | 2403 | O | TRP | 477 | 14.386 | 63.713 | 71.738 | 1.00 | 12.44 |
| ATOM | 2404 | N | LYS | 478 | 13.220 | 62.287 | 70.456 | 1.00 | 13.67 |
| ATOM | 2406 | CA | LYS | 478 | 12.203 | 63.294 | 70.167 | 1.00 | 14.46 |
| ATOM | 2407 | CB | LYS | 478 | 11.177 | 62.782 | 69.150 | 1.00 | 14.97 |
| ATOM | 2408 | CG | LYS | 478 | 11.740 | 62.758 | 67.744 | 1.00 | 15.30 |
| ATOM | 2409 | CD | LYS | 478 | 10.696 | 62.559 | 66.708 | 1.00 | 16.07 |
| ATOM | 2410 | CE | LYS | 478 | 11.271 | 62.665 | 65.316 | 1.00 | 16.23 |
| ATOM | 2411 | NZ | LYS | 478 | 11.607 | 64.045 | 64.920 | 1.00 | 17.45 |
| ATOM | 2415 | C | LYS | 478 | 11.572 | 63.754 | 71.477 | 1.00 | 14.68 |
| ATOM | 2416 | O | LYS | 478 | 11.541 | 63.020 | 72.440 | 1.00 | 14.31 |
| ATOM | 2417 | N | GLU | 479 | 11.222 | 65.039 | 71.548 | 1.00 | 15.19 |
| ATOM | 2419 | CA | GLU | 479 | 10.648 | 65.631 | 72.761 | 1.00 | 15.85 |
| ATOM | 2420 | CB | GLU | 479 | 10.397 | 67.128 | 72.501 | 1.00 | 16.31 |
| ATOM | 2421 | CG | GLU | 479 | 9.782 | 67.907 | 73.655 | 1.00 | 17.24 |
| ATOM | 2422 | CD | GLU | 479 | 10.709 | 68.087 | 74.847 | 1.00 | 18.01 |
| ATOM | 2423 | OE1 | GLU | 479 | 11.919 | 67.758 | 74.743 | 1.00 | 19.06 |
| ATOM | 2424 | OE2 | GLU | 479 | 10.225 | 68.557 | 75.898 | 1.00 | 18.39 |
| ATOM | 2425 | C | GLU | 479 | 9.353 | 64.913 | 73.181 | 1.00 | 15.88 |
| ATOM | 2426 | O | GLU | 479 | 9.208 | 64.470 | 74.326 | 1.00 | 15.48 |

TABLE 7-continued

Coordinates of Lck bound with PD153035

| | Atom Type | Res | # | X | Y | Z | Occ | B |
|---|---|---|---|---|---|---|---|---|
| ATOM | 2427 | N | ARG | 480 | 8.400 | 64.837 | 72.258 | 1.00 | 15.84 |
| ATOM | 2429 | CA | ARG | 480 | 7.131 | 64.136 | 72.519 | 1.00 | 16.19 |
| ATOM | 2430 | CB | ARG | 480 | 6.078 | 64.560 | 71.473 | 1.00 | 17.18 |
| ATOM | 2431 | CG | ARG | 480 | 5.189 | 65.775 | 71.801 | 1.00 | 19.32 |
| ATOM | 2432 | CD | ARG | 480 | 4.491 | 66.351 | 70.542 | 1.00 | 20.87 |
| ATOM | 2433 | NE | ARG | 480 | 3.538 | 65.474 | 69.842 | 1.00 | 21.81 |
| ATOM | 2435 | CZ | ARG | 480 | 3.415 | 65.439 | 68.516 | 1.00 | 22.77 |
| ATOM | 2436 | NH1 | ARG | 480 | 4.200 | 66.213 | 67.765 | 1.00 | 23.44 |
| ATOM | 2439 | NH2 | ARG | 480 | 2.462 | 64.736 | 67.926 | 1.00 | 23.38 |
| ATOM | 2442 | C | ARG | 480 | 7.329 | 62.606 | 72.446 | 1.00 | 15.51 |
| ATOM | 2443 | O | ARG | 480 | 7.781 | 62.096 | 71.438 | 1.00 | 14.74 |
| ATOM | 2444 | N | PRO | 481 | 6.983 | 61.878 | 73.522 | 1.00 | 15.00 |
| ATOM | 2445 | CD | PRO | 481 | 6.550 | 62.369 | 74.835 | 1.00 | 15.20 |
| ATOM | 2446 | CA | PRO | 481 | 7.128 | 60.414 | 73.528 | 1.00 | 15.02 |
| ATOM | 2447 | CB | PRO | 481 | 6.420 | 60.035 | 74.823 | 1.00 | 15.19 |
| ATOM | 2448 | CG | PRO | 481 | 6.772 | 61.168 | 75.716 | 1.00 | 15.23 |
| ATOM | 2449 | C | PRO | 481 | 6.442 | 59.762 | 72.322 | 1.00 | 14.83 |
| ATOM | 2450 | O | PRO | 481 | 7.022 | 58.922 | 71.630 | 1.00 | 14.27 |
| ATOM | 2451 | N | GLU | 482 | 5.224 | 60.213 | 72.019 | 1.00 | 14.55 |
| ATOM | 2453 | CA | GLU | 482 | 4.456 | 59.683 | 70.901 | 1.00 | 14.59 |
| ATOM | 2454 | CB | GLU | 482 | 2.996 | 60.208 | 70.952 | 1.00 | 15.67 |
| ATOM | 2455 | CG | GLU | 482 | 2.838 | 61.725 | 70.835 | 1.00 | 17.38 |
| ATOM | 2456 | CD | GLU | 482 | 3.086 | 62.542 | 72.129 | 1.00 | 18.14 |
| ATOM | 2457 | OE1 | GLU | 482 | 3.438 | 62.009 | 73.205 | 1.00 | 17.50 |
| ATOM | 2458 | OE2 | GLU | 482 | 2.908 | 63.778 | 72.047 | 1.00 | 19.84 |
| ATOM | 2459 | C | GLU | 482 | 5.090 | 59.926 | 69.530 | 1.00 | 13.83 |
| ATOM | 2460 | O | GLU | 482 | 4.695 | 59.313 | 68.542 | 1.00 | 13.64 |
| ATOM | 2461 | N | ASP | 483 | 6.094 | 60.804 | 69.471 | 1.00 | 13.03 |
| ATOM | 2463 | CA | ASP | 483 | 6.778 | 61.083 | 68.204 | 1.00 | 11.83 |
| ATOM | 2464 | CB | ASP | 483 | 7.274 | 62.529 | 68.165 | 1.00 | 12.29 |
| ATOM | 2465 | CG | ASP | 483 | 6.134 | 63.541 | 67.981 | 1.00 | 12.65 |
| ATOM | 2466 | OD1 | ASP | 483 | 5.025 | 63.137 | 67.565 | 1.00 | 12.58 |
| ATOM | 2467 | OD2 | ASP | 483 | 6.378 | 64.744 | 68.231 | 1.00 | 12.94 |
| ATOM | 2468 | C | ASP | 483 | 7.940 | 60.143 | 67.935 | 1.00 | 11.02 |
| ATOM | 2469 | O | ASP | 483 | 8.403 | 60.005 | 66.800 | 1.00 | 10.49 |
| ATOM | 2470 | N | ARG | 484 | 8.436 | 59.528 | 68.994 | 1.00 | 10.24 |
| ATOM | 2472 | CA | ARG | 484 | 9.559 | 58.574 | 68.894 | 1.00 | 9.48 |
| ATOM | 2473 | CB | ARG | 484 | 10.057 | 58.249 | 70.302 | 1.00 | 8.79 |
| ATOM | 2474 | CG | ARG | 484 | 10.575 | 59.453 | 71.086 | 1.00 | 7.85 |
| ATOM | 2475 | CD | ARG | 484 | 10.852 | 59.115 | 72.548 | 1.00 | 6.75 |
| ATOM | 2476 | NE | ARG | 484 | 10.872 | 60.350 | 73.332 | 1.00 | 6.16 |
| ATOM | 2478 | CZ | ARG | 484 | 10.667 | 60.414 | 74.643 | 1.00 | 5.79 |
| ATOM | 2479 | NH1 | ARG | 484 | 10.451 | 59.295 | 75.343 | 1.00 | 5.77 |
| ATOM | 2482 | NH2 | ARG | 484 | 10.598 | 61.607 | 72.250 | 1.00 | 5.83 |
| ATOM | 2485 | C | ARG | 484 | 9.083 | 57.291 | 68.175 | 1.00 | 9.50 |
| ATOM | 2486 | O | ARG | 484 | 7.970 | 56.847 | 68.383 | 1.00 | 8.85 |
| ATOM | 2487 | N | PRO | 485 | 9.966 | 56.641 | 67.398 | 1.00 | 8.94 |
| ATOM | 2488 | CD | PRO | 485 | 11.411 | 56.908 | 67.339 | 1.00 | 8.82 |
| ATOM | 2489 | CA | PRO | 485 | 9.618 | 55.419 | 66.656 | 1.00 | 8.84 |
| ATOM | 2490 | CB | PRO | 485 | 10.859 | 55.170 | 65.808 | 1.00 | 8.74 |
| ATOM | 2491 | CG | PRO | 485 | 11.959 | 55.630 | 66.728 | 1.00 | 9.27 |
| ATOM | 2492 | C | PRO | 485 | 9.285 | 54.197 | 67.518 | 1.00 | 8.54 |
| ATOM | 2493 | O | PRO | 485 | 9.429 | 54.219 | 68.747 | 1.00 | 8.05 |
| ATOM | 2494 | N | THR | 486 | 8.755 | 53.167 | 66.860 | 1.00 | 8.54 |
| ATOM | 2496 | CA | THR | 486 | 8.445 | 51.885 | 67.510 | 1.00 | 8.49 |
| ATOM | 2497 | CB | THR | 486 | 7.321 | 51.114 | 66.745 | 1.00 | 8.14 |
| ATOM | 2498 | OG1 | THR | 486 | 7.768 | 50.830 | 65.416 | 1.00 | 7.88 |
| ATOM | 2500 | CG2 | THR | 486 | 6.023 | 51.966 | 66.650 | 1.00 | 8.68 |
| ATOM | 2501 | C | THR | 486 | 9.755 | 51.045 | 67.467 | 1.00 | 8.96 |
| ATOM | 2502 | O | THR | 486 | 10.660 | 51.329 | 66.676 | 1.00 | 8.42 |
| ATOM | 2503 | N | PHE | 487 | 9.846 | 50.013 | 68.297 | 1.00 | 9.63 |
| ATOM | 2505 | CA | PHE | 487 | 11.055 | 49.176 | 68.274 | 1.00 | 9.63 |
| ATOM | 2506 | CB | PHE | 487 | 11.157 | 48.308 | 69.525 | 1.00 | 9.13 |
| ATOM | 2507 | CG | PHE | 487 | 11.804 | 49.001 | 70.675 | 1.00 | 9.15 |
| ATOM | 2508 | CD1 | PHE | 487 | 13.147 | 49.330 | 70.624 | 1.00 | 8.61 |
| ATOM | 2509 | CD2 | PHE | 487 | 11.071 | 49.310 | 71.816 | 1.00 | 8.40 |
| ATOM | 2510 | CE1 | PHE | 487 | 13.768 | 49.966 | 71.723 | 1.00 | 8.64 |
| ATOM | 2511 | CE2 | PHE | 487 | 11.659 | 49.930 | 72.892 | 1.00 | 8.87 |
| ATOM | 2512 | CZ | PHE | 487 | 13.021 | 50.268 | 72.857 | 1.00 | 9.06 |
| ATOM | 2513 | C | PHE | 487 | 11.112 | 48.347 | 67.008 | 1.00 | 10.20 |
| ATOM | 2514 | O | PHE | 487 | 12.183 | 48.007 | 66.489 | 1.00 | 9.77 |
| ATOM | 2515 | N | ASP | 488 | 9.938 | 48.037 | 66.474 | 1.00 | 10.32 |
| ATOM | 2517 | CA | ASP | 488 | 9.914 | 47.301 | 65.241 | 1.00 | 10.71 |
| ATOM | 2518 | CB | ASP | 488 | 8.502 | 46.828 | 64.914 | 1.00 | 12.00 |

TABLE 7-continued

Coordinates of Lck bound with PD153035

| | | Atom Type | Res | # | X | Y | Z | Occ | B |
|---|---|---|---|---|---|---|---|---|---|
| ATOM | 2519 | CG | ASP | 488 | 8.475 | 45.979 | 63.671 | 1.00 | 12.83 |
| ATOM | 2520 | OD1 | ASP | 488 | 9.191 | 44.942 | 63.635 | 1.00 | 13.99 |
| ATOM | 2521 | OD2 | ASP | 488 | 7.765 | 46.364 | 62.720 | 1.00 | 14.43 |
| ATOM | 2522 | C | ASP | 488 | 10.489 | 48.177 | 64.106 | 1.00 | 10.45 |
| ATOM | 2523 | O | ASP | 488 | 11.189 | 47.667 | 63.210 | 1.00 | 10.01 |
| ATOM | 2524 | N | TYR | 489 | 10.173 | 49.480 | 64.130 | 1.00 | 9.74 |
| ATOM | 2526 | CA | TYR | 489 | 10.714 | 50.418 | 63.128 | 1.00 | 9.78 |
| ATOM | 2527 | CB | TYR | 489 | 10.188 | 51.859 | 63.346 | 1.00 | 9.45 |
| ATOM | 2528 | CG | TYR | 489 | 10.785 | 52.856 | 62.374 | 1.00 | 9.93 |
| ATOM | 2529 | CD1 | TYR | 489 | 10.370 | 52.896 | 61.051 | 1.00 | 9.44 |
| ATOM | 2530 | CE1 | TYR | 489 | 10.971 | 53.773 | 60.133 | 1.00 | 9.95 |
| ATOM | 2531 | CD2 | TYR | 489 | 11.821 | 53.731 | 62.772 | 1.00 | 9.63 |
| ATOM | 2532 | CE2 | TYR | 489 | 12.416 | 54.597 | 61.874 | 1.00 | 9.47 |
| ATOM | 2533 | CZ | TYR | 489 | 11.987 | 54.612 | 60.557 | 1.00 | 10.07 |
| ATOM | 2534 | OH | TYR | 489 | 12.570 | 55.482 | 59.658 | 1.00 | 9.94 |
| ATOM | 2536 | C | TYR | 489 | 12.262 | 50.431 | 63.265 | 1.00 | 9.41 |
| ATOM | 2537 | O | TYR | 489 | 12.995 | 50.336 | 62.285 | 1.00 | 10.08 |
| ATOM | 2538 | N | LEU | 490 | 12.730 | 50.569 | 64.488 | 1.00 | 9.28 |
| ATOM | 2540 | CA | LEU | 490 | 14.165 | 50.589 | 64.778 | 1.00 | 9.18 |
| ATOM | 2541 | CB | LEU | 490 | 14.390 | 50.773 | 66.282 | 1.00 | 9.75 |
| ATOM | 2542 | CG | LEU | 490 | 14.106 | 52.220 | 66.708 | 1.00 | 9.99 |
| ATOM | 2543 | CD1 | LEU | 490 | 14.060 | 52.390 | 68.223 | 1.00 | 10.04 |
| ATOM | 2544 | CD2 | LEU | 490 | 15.190 | 53.111 | 66.071 | 1.00 | 9.95 |
| ATOM | 2545 | C | LEU | 490 | 14.863 | 49.324 | 64.281 | 1.00 | 9.20 |
| ATOM | 2546 | O | LEU | 490 | 15.885 | 49.389 | 63.628 | 1.00 | 8.18 |
| ATOM | 2547 | N | ARG | 491 | 14.278 | 48.171 | 64.567 | 1.00 | 9.19 |
| ATOM | 2549 | CA | ARG | 491 | 14.849 | 46.909 | 64.142 | 1.00 | 9.01 |
| ATOM | 2550 | CB | ARG | 491 | 13.963 | 45.737 | 64.618 | 1.00 | 9.83 |
| ATOM | 2551 | CG | ARG | 491 | 14.487 | 44.370 | 64.104 | 1.00 | 10.30 |
| ATOM | 2552 | CD | ARG | 491 | 13.385 | 43.301 | 64.040 | 1.00 | 11.60 |
| ATOM | 2553 | NE | ARG | 491 | 12.196 | 43.762 | 63.310 | 1.00 | 12.52 |
| ATOM | 2555 | CZ | ARG | 491 | 12.077 | 43.839 | 61.984 | 1.00 | 13.31 |
| ATOM | 2556 | NH1 | ARG | 491 | 13.074 | 43.477 | 61.188 | 1.00 | 14.40 |
| ATOM | 2559 | NH2 | ARG | 491 | 10.938 | 44.285 | 61.458 | 1.00 | 13.53 |
| ATOM | 2562 | C | ARG | 491 | 14.966 | 46.862 | 62.639 | 1.00 | 8.71 |
| ATOM | 2563 | O | ARG | 491 | 15.997 | 46.489 | 62.081 | 1.00 | 8.64 |
| ATOM | 2564 | N | SER | 492 | 13.928 | 47.330 | 61.968 | 0.71 | 7.84 |
| ATOM | 2566 | CA | SER | 492 | 13.920 | 47.276 | 60.526 | 0.71 | 7.30 |
| ATOM | 2567 | CB | SER | 492 | 12.523 | 47.614 | 60.011 | 0.71 | 7.35 |
| ATOM | 2568 | OG | SER | 492 | 12.475 | 47.441 | 58.621 | 0.71 | 8.12 |
| ATOM | 2570 | C | SER | 492 | 14.986 | 48.140 | 59.864 | 0.71 | 7.02 |
| ATOM | 2571 | O | SER | 492 | 15.665 | 47.689 | 58.961 | 0.71 | 6.58 |
| ATOM | 2572 | N | VAL | 493 | 15.162 | 49.360 | 60.353 | 1.00 | 7.30 |
| ATOM | 2574 | CA | VAL | 493 | 16.153 | 50.275 | 59.795 | 1.00 | 7.68 |
| ATOM | 2575 | CB | VAL | 493 | 16.039 | 51.708 | 60.408 | 1.00 | 7.49 |
| ATOM | 2576 | CG1 | VAL | 493 | 17.236 | 52.566 | 60.009 | 1.00 | 7.22 |
| ATOM | 2577 | CG2 | VAL | 493 | 14.751 | 52.369 | 59.954 | 1.00 | 7.83 |
| ATOM | 2578 | C | VAL | 493 | 17.536 | 49.731 | 60.098 | 1.00 | 7.67 |
| ATOM | 2579 | O | VAL | 493 | 18.391 | 49.716 | 59.230 | 1.00 | 8.47 |
| ATOM | 2580 | N | LEU | 494 | 17.757 | 49.343 | 61.346 | 1.00 | 8.23 |
| ATOM | 2582 | CA | LEU | 494 | 19.061 | 48.826 | 61.730 | 1.00 | 8.96 |
| ATOM | 2583 | CB | LEU | 494 | 19.137 | 48.551 | 63.220 | 1.00 | 8.51 |
| ATOM | 2584 | CG | LEU | 494 | 19.241 | 49.795 | 64.110 | 1.00 | 8.31 |
| ATOM | 2585 | CD1 | LEU | 494 | 18.851 | 49.428 | 65.504 | 1.00 | 7.89 |
| ATOM | 2586 | CD2 | LEU | 494 | 20.639 | 50.458 | 64.049 | 1.00 | 7.91 |
| ATOM | 2587 | C | LEU | 494 | 19.472 | 47.626 | 60.891 | 1.00 | 9.63 |
| ATOM | 2588 | O | LEU | 494 | 20.647 | 47.513 | 60.535 | 1.00 | 9.42 |
| ATOM | 2589 | N | GLU | 495 | 18.507 | 46.756 | 60.540 | 1.00 | 10.22 |
| ATOM | 2591 | CA | GLU | 495 | 18.826 | 45.616 | 59.675 | 1.00 | 10.89 |
| ATOM | 2592 | CB | GLU | 495 | 17.663 | 44.605 | 59.590 | 1.00 | 10.67 |
| ATOM | 2593 | CG | GLU | 495 | 17.385 | 43.883 | 60.894 | 1.00 | 10.53 |
| ATOM | 2594 | CD | GLU | 495 | 16.305 | 42.830 | 60.778 | 1.00 | 11.00 |
| ATOM | 2595 | OE1 | GLU | 495 | 15.815 | 42.562 | 59.666 | 1.00 | 11.53 |
| ATOM | 2596 | OE2 | GLU | 495 | 15.918 | 42.283 | 61.821 | 1.00 | 10.64 |
| ATOM | 2597 | C | GLU | 495 | 19.229 | 46.101 | 58.272 | 1.00 | 11.38 |
| ATOM | 2598 | O | GLU | 495 | 20.122 | 45.535 | 57.662 | 1.00 | 11.40 |
| ATOM | 2599 | N | ASP | 496 | 18.567 | 47.135 | 57.763 | 1.00 | 11.91 |
| ATOM | 2601 | CA | ASP | 496 | 18.906 | 47.698 | 56.453 | 1.00 | 12.93 |
| ATOM | 2602 | CB | ASP | 496 | 17.914 | 48.813 | 56.049 | 1.00 | 12.55 |
| ATOM | 2603 | CG | ASP | 496 | 16.579 | 48.265 | 55.555 | 1.00 | 12.22 |
| ATOM | 2604 | OD1 | ASP | 496 | 16.480 | 47.042 | 55.285 | 1.00 | 11.99 |
| ATOM | 2605 | OD2 | ASP | 496 | 15.607 | 49.045 | 55.452 | 1.00 | 11.82 |
| ATOM | 2606 | C | ASP | 496 | 20.322 | 48.277 | 56.531 | 1.00 | 13.85 |
| ATOM | 2607 | O | ASP | 496 | 21.108 | 48.125 | 55.614 | 1.00 | 14.31 |

TABLE 7-continued

Coordinates of Lck bound with PD153035

| | | Atom Type | Res | # | X | Y | Z | Occ | B |
|---|---|---|---|---|---|---|---|---|---|
| ATOM | 2608 | N | PHE | 497 | 20.636 | 48.920 | 57.655 | 1.00 | 14.83 |
| ATOM | 2610 | CA | PHE | 497 | 21.948 | 49.508 | 57.886 | 1.00 | 16.25 |
| ATOM | 2611 | CB | PHE | 497 | 21.984 | 50.154 | 59.284 | 1.00 | 14.74 |
| ATOM | 2612 | CG | PHE | 497 | 21.364 | 51.542 | 59.357 | 1.00 | 13.40 |
| ATOM | 2613 | CD1 | PHE | 497 | 20.728 | 52.109 | 58.242 | 1.00 | 13.33 |
| ATOM | 2614 | CD2 | PHE | 497 | 21.381 | 52.260 | 60.545 | 1.00 | 13.01 |
| ATOM | 2615 | CE1 | PHE | 497 | 20.121 | 53.362 | 58.316 | 1.00 | 12.61 |
| ATOM | 2616 | CE2 | PHE | 497 | 20.767 | 53.526 | 60.627 | 1.00 | 12.66 |
| ATOM | 2617 | CZ | PHE | 497 | 20.138 | 54.074 | 59.514 | 1.00 | 12.36 |
| ATOM | 2618 | C | PHE | 497 | 23.004 | 48.389 | 57.818 | 1.00 | 18.07 |
| ATOM | 2619 | O | PHE | 497 | 23.996 | 48.484 | 57.094 | 1.00 | 17.93 |
| ATOM | 2620 | N | PHE | 498 | 22.703 | 47.299 | 58.521 | 1.00 | 20.19 |
| ATOM | 2622 | CA | PHE | 498 | 23.561 | 46.116 | 58.624 | 1.00 | 22.44 |
| ATOM | 2623 | CB | PHE | 498 | 22.957 | 45.188 | 59.718 | 1.00 | 22.82 |
| ATOM | 2624 | CG | PHE | 498 | 23.414 | 43.746 | 59.687 | 1.00 | 23.69 |
| ATOM | 2625 | CD1 | PHE | 498 | 24.741 | 43.402 | 59.500 | 1.00 | 23.79 |
| ATOM | 2626 | CD2 | PHE | 498 | 22.473 | 42.725 | 59.845 | 1.00 | 24.01 |
| ATOM | 2627 | CE1 | PHE | 498 | 25.126 | 42.045 | 59.465 | 1.00 | 23.69 |
| ATOM | 2628 | CE2 | PHE | 498 | 22.838 | 41.387 | 59.813 | 1.00 | 23.95 |
| ATOM | 2629 | CZ | PHE | 498 | 24.167 | 41.043 | 59.617 | 1.00 | 23.78 |
| ATOM | 2630 | C | PHE | 498 | 23.724 | 45.444 | 57.254 | 1.00 | 23.43 |
| ATOM | 2631 | O | PHE | 498 | 24.846 | 45.264 | 56.782 | 1.00 | 23.54 |
| ATOM | 2632 | N | THR | 499 | 22.613 | 45.248 | 56.553 | 1.00 | 24.85 |
| ATOM | 2634 | CA | THR | 499 | 22.627 | 44.592 | 55.244 | 1.00 | 25.87 |
| ATOM | 2635 | CB | THR | 499 | 21.206 | 44.132 | 54.798 | 1.00 | 25.96 |
| ATOM | 2636 | OG1 | THR | 499 | 20.316 | 45.245 | 54.783 | 1.00 | 26.38 |
| ATOM | 2638 | CG2 | THR | 499 | 20.640 | 43.080 | 55.741 | 1.00 | 25.62 |
| ATOM | 2639 | C | THR | 499 | 23.261 | 45.486 | 54.195 | 1.00 | 26.47 |
| ATOM | 2640 | O | THR | 499 | 23.496 | 45.055 | 53.065 | 1.00 | 26.63 |
| ATOM | 2641 | N | ALA | 500 | 23.522 | 46.739 | 54.570 | 1.00 | 27.08 |
| ATOM | 2643 | CA | ALA | 500 | 24.163 | 47.708 | 53.680 | 1.00 | 27.79 |
| ATOM | 2644 | CB | ALA | 500 | 23.655 | 49.124 | 53.962 | 1.00 | 27.62 |
| ATOM | 2645 | C | ALA | 500 | 25.676 | 47.659 | 53.872 | 1.00 | 28.38 |
| ATOM | 2646 | O | ALA | 500 | 26.429 | 47.511 | 52.904 | 1.00 | 28.49 |
| ATOM | 2647 | N | THR | 501 | 26.103 | 47.788 | 55.129 | 1.00 | 28.89 |
| ATOM | 2649 | CA | THR | 501 | 27.510 | 47.763 | 55.500 | 1.00 | 29.53 |
| ATOM | 2650 | CB | THR | 501 | 27.733 | 48.332 | 56.923 | 1.00 | 29.95 |
| ATOM | 2651 | OG1 | THR | 501 | 27.207 | 47.420 | 57.900 | 1.00 | 30.26 |
| ATOM | 2653 | CG2 | THR | 501 | 27.092 | 49.706 | 57.085 | 1.00 | 30.35 |
| ATOM | 2654 | C | THR | 501 | 28.083 | 46.334 | 55.473 | 1.00 | 29.54 |
| ATOM | 2655 | O | THR | 501 | 27.576 | 45.469 | 54.717 | 1.00 | 29.73 |
| ATOM | 2656 | OT | THR | 501 | 29.044 | 46.092 | 56.239 | 1.00 | 29.73 |
| ATOM | 2657 | S | SO4 | 901 | 20.154 | 32.836 | 69.838 | 1.00 | 11.34 |
| ATOM | 2658 | O1 | SO4 | 901 | 19.905 | 32.207 | 71.054 | 1.00 | 11.32 |
| ATOM | 2659 | O2 | SO4 | 901 | 18.916 | 33.175 | 69.246 | 1.00 | 11.06 |
| ATOM | 2660 | O3 | SO4 | 901 | 20.958 | 34.002 | 70.094 | 1.00 | 11.36 |
| ATOM | 2661 | O4 | SO4 | 901 | 20.855 | 32.012 | 68.973 | 1.00 | 11.13 |
| ATOM | 2662 | S | SO4 | 902 | 39.547 | 38.046 | 74.000 | 1.00 | 21.58 |
| ATOM | 2663 | O1 | SO4 | 902 | 38.689 | 36.864 | 73.957 | 1.00 | 22.15 |
| ATOM | 2664 | O2 | SO4 | 902 | 38.689 | 39.190 | 73.960 | 1.00 | 20.89 |
| ATOM | 2665 | O3 | SO4 | 902 | 40.316 | 38.029 | 75.223 | 1.00 | 21.41 |
| ATOM | 2666 | O4 | SO4 | 902 | 40.396 | 38.016 | 72.860 | 1.00 | 21.15 |
| ATOM | 2667 | S | SO4 | 903 | 10.706 | 44.478 | 57.695 | 1.00 | 27.60 |
| ATOM | 2668 | O1 | SO4 | 903 | 9.878 | 43.419 | 58.225 | 1.00 | 26.77 |
| ATOM | 2669 | O2 | SO4 | 903 | 9.990 | 45.735 | 57.951 | 1.00 | 26.97 |
| ATOM | 2670 | O3 | SO4 | 903 | 11.990 | 44.457 | 58.377 | 1.00 | 26.55 |
| ATOM | 2671 | O4 | SO4 | 903 | 10.892 | 44.348 | 56.254 | 1.00 | 26.37 |
| ATOM | 2672 | OH2 | TIP | 2 | 20.636 | 62.958 | 73.833 | 1.00 | 11.29 |
| ATOM | 2675 | OH2 | TIP | 5 | 19.398 | 60.900 | 78.187 | 1.00 | 6.67 |
| ATOM | 2678 | OH2 | TIP | 6 | 4.442 | 54.735 | 67.622 | 1.00 | 10.83 |
| ATOM | 2681 | OH2 | TIP | 7 | 14.721 | 51.844 | 79.689 | 1.00 | 8.18 |
| ATOM | 2684 | OH2 | TIP | 8 | 20.361 | 66.719 | 63.177 | 1.00 | 12.72 |
| ATOM | 2687 | OH2 | TIP | 9 | 16.747 | 62.231 | 62.930 | 1.00 | 15.70 |
| ATOM | 2690 | OH2 | TIP | 10 | 26.680 | 31.890 | 75.751 | 1.00 | 17.57 |
| ATOM | 2693 | OH2 | TIP | 11 | 16.671 | 58.761 | 61.106 | 1.00 | 10.84 |
| ATOM | 2696 | OH2 | TIP | 12 | 32.958 | 40.137 | 78.354 | 1.00 | 18.97 |
| ATOM | 2699 | OH2 | TIP | 13 | 25.128 | 50.571 | 80.484 | 1.00 | 8.49 |
| ATOM | 2702 | OH2 | TIP | 14 | 23.048 | 20.687 | 78.556 | 1.00 | 15.90 |
| ATOM | 2705 | OH2 | TIP | 15 | 28.441 | 53.344 | 79.223 | 1.00 | 10.68 |
| ATOM | 2708 | OH2 | TIP | 16 | 19.020 | 52.625 | 83.694 | 1.00 | 14.53 |
| ATOM | 2711 | OH2 | TIP | 17 | 27.358 | 50.660 | 82.547 | 1.00 | 12.17 |
| ATOM | 2714 | OH2 | TIP | 18 | 16.551 | 32.874 | 75.309 | 1.00 | 9.44 |
| ATOM | 2717 | OH2 | TIP | 19 | 30.188 | 41.207 | 82.437 | 1.00 | 16.54 |
| ATOM | 2720 | OH2 | TIP | 20 | 30.288 | 60.008 | 72.956 | 1.00 | 17.53 |

TABLE 7-continued

Coordinates of Lck bound with PD153035

| | | Atom Type | Res | # | X | Y | Z | Occ | B |
|---|---|---|---|---|---|---|---|---|---|
| ATOM | 2723 | OH2 | TIP | 22 | 19.943 | 41.713 | 93.216 | 1.00 | 24.43 |
| ATOM | 2726 | OH2 | TIP | 25 | 29.431 | 66.197 | 75.578 | 1.00 | 19.72 |
| ATOM | 2729 | OH2 | TIP | 26 | 29.030 | 34.838 | 65.212 | 1.00 | 15.67 |
| ATOM | 2732 | OH2 | TIP | 27 | 15.913 | 36.149 | 67.158 | 1.00 | 11.60 |
| ATOM | 2735 | OH2 | TIP | 28 | 22.338 | 28.300 | 79.589 | 1.00 | 9.38 |
| ATOM | 2738 | OH2 | TIP | 29 | 20.436 | 36.517 | 83.380 | 1.00 | 9.22 |
| ATOM | 2741 | OH2 | TIP | 30 | 35.542 | 44.295 | 80.109 | 1.00 | 24.17 |
| ATOM | 2744 | OH2 | TIP | 32 | 31.295 | 38.714 | 83.284 | 1.00 | 18.72 |
| ATOM | 2747 | OH2 | TIP | 34 | 28.108 | 56.490 | 75.113 | 1.00 | 13.28 |
| ATOM | 2750 | OH2 | TIP | 36 | 18.137 | 62.091 | 80.294 | 1.00 | 12.50 |
| ATOM | 2753 | OH2 | TIP | 38 | 6.588 | 45.437 | 68.379 | 1.00 | 14.19 |
| ATOM | 2756 | OH2 | TIP | 39 | 6.558 | 52.095 | 70.657 | 1.00 | 19.40 |
| ATOM | 2759 | OH2 | TIP | 40 | 16.010 | 39.242 | 85.032 | 1.00 | 16.36 |
| ATOM | 2762 | OH2 | TIP | 41 | 13.492 | 23.841 | 95.714 | 1.00 | 19.61 |
| ATOM | 2765 | OH2 | TIP | 42 | 34.460 | 69.013 | 71.205 | 1.00 | 7.81 |
| ATOM | 2768 | OH2 | TIP | 43 | 16.422 | 52.518 | 82.251 | 1.00 | 11.04 |
| ATOM | 2771 | OH2 | TIP | 44 | 26.967 | 65.546 | 74.806 | 1.00 | 11.07 |
| ATOM | 2774 | OH2 | TIP | 45 | 3.624 | 51.963 | 76.646 | 1.00 | 15.54 |
| ATOM | 2777 | OH2 | TIP | 46 | 23.263 | 43.066 | 94.829 | 1.00 | 21.16 |
| ATOM | 2780 | OH2 | TIP | 47 | 29.767 | 18.255 | 81.278 | 1.00 | 18.69 |
| ATOM | 2783 | OH2 | TIP | 49 | 13.244 | 34.456 | 77.141 | 1.00 | 13.30 |
| ATOM | 2786 | OH2 | TIP | 50 | 26.838 | 40.111 | 61.429 | 1.00 | 18.07 |
| ATOM | 2789 | OH2 | TIP | 51 | 25.957 | 56.915 | 57.918 | 1.00 | 17.98 |
| ATOM | 2792 | OH2 | TIP | 52 | 11.454 | 66.564 | 68.883 | 1.00 | 19.34 |
| ATOM | 2795 | OH2 | TIP | 53 | 14.315 | 45.854 | 84.185 | 1.00 | 7.72 |
| ATOM | 2798 | OH2 | TIP | 54 | 19.976 | 55.816 | 55.699 | 1.00 | 16.12 |
| ATOM | 2801 | OH2 | TIP | 56 | 28.971 | 59.363 | 58.602 | 1.00 | 20.83 |
| ATOM | 2804 | OH2 | TIP | 57 | 36.087 | 39.908 | 75.044 | 1.00 | 16.53 |
| ATOM | 2807 | OH2 | TIP | 58 | 29.787 | 58.456 | 75.095 | 1.00 | 16.17 |
| ATOM | 2810 | OH2 | TIP | 59 | 17.909 | 53.040 | 81.251 | 1.00 | 21.37 |
| ATOM | 2813 | OH2 | TIP | 60 | 12.351 | 44.999 | 99.823 | 1.00 | 21.75 |
| ATOM | 2816 | OH2 | TIP | 61 | 25.921 | 23.902 | 78.945 | 1.00 | 16.75 |
| ATOM | 2819 | OH2 | TIP | 62 | 29.162 | 62.668 | 72.531 | 1.00 | 15.68 |
| ATOM | 2822 | OH2 | TIP | 63 | 23.731 | 29.160 | 77.239 | 1.00 | 19.74 |
| ATOM | 2825 | OH2 | TIP | 64 | 14.063 | 69.335 | 74.259 | 1.00 | 21.19 |
| ATOM | 2828 | OH2 | TIP | 65 | 12.813 | 36.434 | 79.883 | 1.00 | 20.72 |
| ATOM | 2831 | OH2 | TIP | 66 | 6.229 | 57.725 | 66.114 | 1.00 | 17.37 |
| ATOM | 2834 | OH2 | TIP | 67 | −1.926 | 43.494 | 77.984 | 1.00 | 22.35 |
| ATOM | 2837 | OH2 | TIP | 68 | 20.726 | 41.571 | 88.544 | 1.00 | 20.17 |
| ATOM | 2840 | OH2 | TIP | 69 | 14.561 | 57.344 | 59.759 | 1.00 | 15.41 |
| ATOM | 2843 | OH2 | TIP | 71 | 7.793 | 54.148 | 64.368 | 1.00 | 15.04 |
| ATOM | 2846 | OH2 | TIP | 73 | 5.917 | 50.219 | 63.649 | 1.00 | 23.00 |
| ATOM | 2849 | OH2 | TIP | 74 | 4.433 | 59.466 | 78.107 | 1.00 | 17.52 |
| ATOM | 2852 | OH2 | TIP | 77 | 15.334 | 38.624 | 102.811 | 1.00 | 19.66 |
| ATOM | 2855 | OH2 | TIP | 79 | 4.150 | 43.814 | 86.201 | 1.00 | 19.42 |
| ATOM | 2858 | OH2 | TIP | 81 | 26.850 | 63.882 | 87.882 | 1.00 | 22.25 |
| ATOM | 2861 | OH2 | TIP | 21 | 32.711 | 60.178 | 71.581 | 1.00 | 19.46 |
| ATOM | 2864 | OH2 | TIP | 24 | 16.723 | 46.041 | 86.276 | 1.00 | 17.23 |
| ATOM | 2867 | OH2 | TIP | 70 | 27.767 | 19.473 | 88.929 | 1.00 | 19.90 |
| ATOM | 2870 | OH2 | TIP | 76 | 28.065 | 61.964 | 56.849 | 1.00 | 19.67 |
| ATOM | 2873 | OH2 | TIP | 82 | 32.539 | 53.218 | 66.232 | 1.00 | 28.73 |
| ATOM | 2876 | OH2 | TIP | 84 | 7.192 | 37.984 | 93.756 | 1.00 | 23.74 |
| ATOM | 2879 | OH2 | TIP | 85 | 1.468 | 39.132 | 80.638 | 1.00 | 19.46 |
| ATOM | 2882 | OH2 | TIP | 90 | 12.086 | 33.689 | 80.387 | 1.00 | 19.28 |
| ATOM | 2885 | OH2 | TIP | 91 | 33.189 | 42.100 | 63.303 | 1.00 | 17.33 |
| ATOM | 2888 | OH2 | TIP | 92 | 22.378 | 15.248 | 83.723 | 1.00 | 20.89 |
| ATOM | 2891 | OH2 | TIP | 94 | 15.697 | 33.621 | 66.151 | 1.00 | 21.18 |
| ATOM | 2894 | OH2 | TIP | 96 | 24.217 | 74.468 | 77.321 | 1.00 | 19.61 |
| ATOM | 2897 | OH2 | TIP | 103 | 24.545 | 39.776 | 86.184 | 1.00 | 16.26 |
| ATOM | 2900 | OH2 | TIP | 104 | 14.550 | 45.671 | 57.370 | 1.00 | 20.72 |
| ATOM | 2903 | OH2 | TIP | 108 | 18.413 | 68.772 | 63.020 | 1.00 | 20.81 |
| ATOM | 2906 | OH2 | TIP | 111 | 4.698 | 47.747 | 75.835 | 1.00 | 16.17 |
| ATOM | 2909 | OH2 | TIP | 112 | 6.695 | 58.009 | 77.649 | 1.00 | 18.72 |
| ATOM | 2912 | OH2 | TIP | 115 | 4.547 | 48.462 | 67.644 | 1.00 | 20.17 |
| ATOM | 2915 | OH2 | TIP | 117 | 6.324 | 29.409 | 94.809 | 1.00 | 24.83 |
| ATOM | 2918 | OH2 | TIP | 118 | 2.647 | 52.805 | 68.498 | 1.00 | 22.98 |
| ATOM | 2921 | OH2 | TIP | 119 | 10.513 | 40.633 | 67.600 | 1.00 | 20.47 |
| ATOM | 2924 | OH2 | TIP | 120 | 14.737 | 64.028 | 64.335 | 1.00 | 25.32 |
| ATOM | 2927 | OH2 | TIP | 121 | 12.083 | 21.523 | 95.972 | 1.00 | 19.51 |
| ATOM | 2930 | OH2 | TIP | 122 | 28.375 | 37.244 | 64.062 | 1.00 | 16.38 |
| ATOM | 2933 | OH2 | TIP | 126 | 24.567 | 67.622 | 74.932 | 1.00 | 22.73 |
| ATOM | 2936 | OH2 | TIP | 127 | 22.534 | 41.060 | 93.087 | 1.00 | 23.51 |
| ATOM | 2939 | OH2 | TIP | 128 | 11.174 | 42.733 | 89.922 | 1.00 | 22.66 |
| ATOM | 2942 | OH2 | TIP | 129 | 19.211 | 15.807 | 83.654 | 1.00 | 21.46 |

TABLE 7-continued

Coordinates of Lck bound with PD153035

| | Atom Type | Res | # | X | Y | Z | Occ | B |
|---|---|---|---|---|---|---|---|---|
| ATOM | 2945 | OH2 | TIP | 131 | 26.969 | 29.258 | 75.896 | 1.00 | 22.07 |
| ATOM | 2948 | OH2 | TIP | 133 | 22.317 | 46.468 | 85.971 | 1.00 | 22.76 |
| ATOM | 2951 | OH2 | TIP | 137 | 17.361 | 52.004 | 88.074 | 1.00 | 17.42 |
| ATOM | 2954 | OH2 | TIP | 142 | 25.264 | 41.436 | 84.273 | 1.00 | 23.65 |
| ATOM | 2957 | OH2 | TIP | 143 | 6.370 | 40.189 | 88.966 | 1.00 | 22.91 |
| ATOM | 2960 | OH2 | TIP | 145 | 0.766 | 45.312 | 71.852 | 1.00 | 24.06 |
| ATOM | 2963 | OH2 | TIP | 146 | 39.332 | 48.330 | 76.231 | 1.00 | 25.86 |
| ATOM | 2966 | OH2 | TIP | 148 | 24.119 | 25.468 | 95.927 | 1.00 | 24.00 |
| ATOM | 2969 | OH2 | TIP | 150 | 29.750 | 42.799 | 91.178 | 1.00 | 24.59 |
| ATOM | 2972 | OH2 | TIP | 157 | 32.389 | 33.469 | 68.814 | 1.00 | 21.71 |
| ATOM | 2975 | OH2 | TIP | 158 | 9.944 | 35.817 | 104.042 | 1.00 | 25.85 |
| ATOM | 2978 | OH2 | TIP | 159 | 23.651 | 49.151 | 85.460 | 1.00 | 28.88 |
| ATOM | 2981 | OH2 | TIP | 162 | 25.550 | 52.977 | 57.713 | 1.00 | 25.60 |
| ATOM | 2984 | OH2 | TIP | 169 | 27.829 | 61.531 | 63.380 | 1.00 | 23.47 |
| ATOM | 2987 | OH2 | TIP | 170 | 1.344 | 40.263 | 77.913 | 1.00 | 21.04 |
| ATOM | 2990 | OH2 | TIP | 174 | 34.578 | 35.495 | 71.101 | 1.00 | 24.24 |
| ATOM | 2993 | OH2 | TIP | 176 | 29.470 | 19.626 | 86.799 | 1.00 | 25.31 |
| ATOM | 2996 | OH2 | TIP | 177 | 14.738 | 19.492 | 88.838 | 1.00 | 20.92 |
| ATOM | 2999 | OH2 | TIP | 179 | 28.072 | 42.482 | 84.011 | 1.00 | 22.09 |
| ATOM | 3002 | OH2 | TIP | 180 | 2.688 | 52.178 | 90.642 | 1.00 | 25.65 |
| ATOM | 3005 | OH2 | TIP | 181 | 16.393 | 64.386 | 68.595 | 1.00 | 25.44 |
| ATOM | 3008 | OH2 | TIP | 183 | 28.823 | 52.721 | 81.739 | 1.00 | 24.27 |
| ATOM | 3011 | OH2 | TIP | 184 | 19.307 | 69.148 | 65.426 | 1.00 | 22.57 |
| ATOM | 3014 | OH2 | TIP | 185 | 15.707 | 35.835 | 102.108 | 1.00 | 24.77 |
| ATOM | 3017 | OH2 | TIP | 192 | 38.610 | 44.616 | 79.884 | 1.00 | 22.08 |
| ATOM | 3020 | OH2 | TIP | 194 | 35.148 | 36.450 | 73.473 | 1.00 | 25.96 |
| ATOM | 3023 | OH2 | TIP | 196 | 41.353 | 44.217 | 69.859 | 1.00 | 22.19 |
| ATOM | 3026 | OH2 | TIP | 197 | 23.323 | 54.286 | 86.238 | 1.00 | 26.51 |
| ATOM | 3029 | OH2 | TIP | 198 | 34.576 | 32.395 | 92.747 | 1.00 | 24.63 |
| ATOM | 3032 | OH2 | TIP | 200 | 9.798 | 42.416 | 87.466 | 1.00 | 23.40 |
| ATOM | 3035 | OH2 | TIP | 201 | 16.924 | 68.352 | 67.191 | 1.00 | 25.75 |
| ATOM | 3038 | OH2 | TIP | 203 | 25.785 | 46.724 | 95.381 | 1.00 | 20.62 |
| ATOM | 3041 | OH2 | TIP | 206 | 6.416 | 34.582 | 94.453 | 1.00 | 25.48 |
| ATOM | 3044 | OH2 | TIP | 207 | 21.227 | 50.258 | 85.990 | 1.00 | 23.73 |
| ATOM | 3047 | OH2 | TIP | 210 | 20.023 | 45.373 | 89.042 | 1.00 | 26.96 |
| ATOM | 3050 | OH2 | TIP | 211 | 12.218 | 37.941 | 66.392 | 1.00 | 23.86 |
| ATOM | 3053 | OH2 | TIP | 216 | 28.627 | 18.306 | 91.282 | 1.00 | 23.74 |
| ATOM | 3056 | OH2 | TIP | 219 | 32.118 | 59.607 | 78.828 | 1.00 | 25.19 |
| ATOM | 3059 | OH2 | TIP | 220 | 23.073 | 42.471 | 82.864 | 1.00 | 23.38 |
| ATOM | 3062 | OH2 | TIP | 221 | 7.979 | 28.059 | 92.887 | 1.00 | 23.44 |
| ATOM | 3065 | OH2 | TIP | 224 | 29.053 | 38.506 | 99.068 | 1.00 | 23.90 |
| ATOM | 3068 | OH2 | TIP | 225 | 18.916 | 43.533 | 91.563 | 1.00 | 25.38 |
| ATOM | 3071 | OH2 | TIP | 226 | 38.182 | 59.033 | 66.728 | 1.00 | 29.31 |
| ATOM | 3074 | OH2 | TIP | 229 | 4.022 | 52.099 | 70.962 | 1.00 | 24.37 |
| ATOM | 3077 | OH2 | TIP | 230 | 26.270 | 38.823 | 59.182 | 1.00 | 24.89 |
| ATOM | 3080 | OH2 | TIP | 231 | 27.599 | 24.559 | 95.028 | 1.00 | 21.60 |
| ATOM | 3083 | OH2 | TIP | 234 | 8.116 | 40.306 | 68.349 | 1.00 | 29.49 |
| ATOM | 3086 | OH2 | TIP | 235 | 6.842 | 43.263 | 66.563 | 1.00 | 25.74 |
| ATOM | 3089 | OH2 | TIP | 236 | 2.951 | 17.859 | 93.343 | 1.00 | 24.64 |
| ATOM | 3092 | OH2 | TIP | 237 | 7.818 | 28.500 | 98.343 | 1.00 | 25.42 |
| ATOM | 3095 | OH2 | TIP | 238 | 11.384 | 46.608 | 91.377 | 1.00 | 19.66 |
| ATOM | 3098 | OH2 | TIP | 241 | 11.010 | 27.883 | 73.874 | 1.00 | 25.81 |
| ATOM | 3101 | OH2 | TIP | 242 | 31.747 | 34.779 | 65.927 | 1.00 | 25.60 |
| ATOM | 3104 | OH2 | TIP | 243 | 17.296 | 43.252 | 86.927 | 1.00 | 21.32 |
| ATOM | 3107 | OH2 | TIP | 244 | 24.965 | 31.775 | 97.224 | 1.00 | 26.49 |
| ATOM | 3110 | OH2 | TIP | 245 | 8.234 | 31.105 | 72.802 | 1.00 | 29.02 |
| ATOM | 3113 | OH2 | TIP | 246 | 31.689 | 53.720 | 61.829 | 1.00 | 28.50 |
| ATOM | 3116 | OH2 | TIP | 247 | 7.714 | 37.139 | 67.959 | 1.00 | 30.08 |
| ATOM | 3119 | OH2 | TIP | 250 | 15.975 | 38.481 | 62.991 | 1.00 | 26.80 |
| ATOM | 3122 | OH2 | TIP | 253 | 3.307 | 40.953 | 85.176 | 1.00 | 26.34 |
| ATOM | 3125 | OH2 | TIP | 254 | 15.048 | 40.468 | 92.044 | 1.00 | 22.92 |
| ATOM | 3128 | OH2 | TIP | 255 | 33.580 | 56.525 | 79.695 | 1.00 | 23.08 |
| ATOM | 3131 | OH2 | TIP | 256 | 34.459 | 57.490 | 71.733 | 1.00 | 23.41 |
| ATOM | 3134 | OH2 | TIP | 257 | 34.589 | 37.917 | 77.028 | 1.00 | 19.31 |
| ATOM | 3137 | OH2 | TIP | 258 | 7.817 | 21.360 | 91.944 | 1.00 | 20.66 |
| ATOM | 3140 | OH2 | TIP | 260 | 1.220 | 52.891 | 87.564 | 1.00 | 26.19 |
| ATOM | 3143 | OH2 | TIP | 262 | 23.634 | 58.180 | 87.630 | 1.00 | 27.29 |
| ATOM | 3146 | OH2 | TIP | 263 | 33.963 | 33.436 | 75.974 | 1.00 | 27.86 |
| ATOM | 3149 | OH2 | TIP | 265 | 4.159 | 48.450 | 90.318 | 1.00 | 28.16 |
| ATOM | 3152 | OH2 | TIP | 266 | 25.613 | 65.499 | 89.881 | 1.00 | 29.75 |
| ATOM | 3155 | OH2 | TIP | 267 | 31.607 | 52.081 | 80.963 | 1.00 | 25.49 |
| ATOM | 3158 | OH2 | TIP | 268 | 0.476 | 48.700 | 88.391 | 1.00 | 27.78 |
| ATOM | 3161 | OH2 | TIP | 270 | 43.041 | 37.091 | 69.449 | 1.00 | 23.90 |
| ATOM | 3164 | OH2 | TIP | 271 | 33.640 | 36.013 | 79.595 | 1.00 | 22.66 |

TABLE 7-continued

Coordinates of Lck bound with PD153035

| | | Atom Type | Res | # | X | Y | Z | Occ | B |
|---|---|---|---|---|---|---|---|---|---|
| ATOM | 3167 | OH2 | TIP | 273 | 15.864 | 43.194 | 57.148 | 1.00 | 21.50 |
| ATOM | 3170 | OH2 | TIP | 280 | 12.971 | 27.117 | 80.224 | 1.00 | 30.25 |
| ATOM | 3173 | OH2 | TIP | 283 | 6.084 | 34.988 | 76.625 | 1.00 | 24.99 |
| ATOM | 3176 | OH2 | TIP | 284 | 31.620 | 64.963 | 67.152 | 1.00 | 27.00 |
| ATOM | 3179 | OH2 | TIP | 288 | 13.812 | 39.274 | 104.677 | 1.00 | 27.71 |
| ATOM | 3182 | OH2 | TIP | 290 | 0.510 | 29.834 | 86.786 | 1.00 | 23.36 |
| ATOM | 3185 | OH2 | TIP | 292 | 3.403 | 38.670 | 95.574 | 1.00 | 26.25 |
| ATOM | 3188 | OH2 | TIP | 293 | 31.420 | 39.759 | 61.170 | 1.00 | 27.39 |
| ATOM | 3191 | OH2 | TIP | 296 | 9.730 | 37.947 | 66.645 | 1.00 | 27.59 |
| ATOM | 3194 | OH2 | TIP | 297 | 35.236 | 53.852 | 70.093 | 1.00 | 26.50 |
| ATOM | 3197 | OH2 | TIP | 300 | 3.108 | 49.864 | 75.076 | 1.00 | 22.96 |
| ATOM | 3200 | OH2 | TIP | 301 | 33.566 | 24.839 | 84.441 | 1.00 | 25.81 |
| ATOM | 3203 | OH2 | TIP | 302 | 33.762 | 54.002 | 81.380 | 1.00 | 26.91 |
| ATOM | 3206 | OH2 | TIP | 304 | 13.352 | 66.605 | 76.653 | 1.00 | 26.34 |
| ATOM | 3209 | OH2 | TIP | 305 | -3.359 | 52.415 | 84.798 | 1.00 | 25.69 |
| ATOM | 3212 | OH2 | TIP | 306 | 22.379 | 67.124 | 65.597 | 1.00 | 23.82 |
| ATOM | 3215 | OH2 | TIP | 308 | 32.387 | 68.649 | 76.981 | 1.00 | 27.12 |
| ATOM | 3218 | OH2 | TIP | 309 | 35.326 | 41.412 | 80.520 | 1.00 | 26.52 |
| ATOM | 3221 | OH2 | TIP | 310 | 3.433 | 38.312 | 77.886 | 1.00 | 24.43 |
| ATOM | 3224 | OH2 | TIP | 311 | -1.819 | 20.914 | 94.996 | 1.00 | 23.55 |
| ATOM | 3227 | OH2 | TIP | 312 | 15.556 | 20.641 | 97.822 | 1.00 | 29.06 |
| ATOM | 3230 | OH2 | TIP | 313 | 20.777 | 39.337 | 94.407 | 1.00 | 21.91 |
| ATOM | 3233 | OH2 | TIP | 314 | 35.671 | 49.740 | 64.558 | 1.00 | 29.25 |
| ATOM | 3236 | OH2 | TIP | 315 | 21.425 | 42.197 | 105.134 | 1.00 | 27.51 |
| ATOM | 3239 | OH2 | TIP | 316 | 12.324 | 60.390 | 60.079 | 1.00 | 27.45 |
| ATOM | 3242 | OH2 | TIP | 317 | 36.717 | 58.918 | 71.759 | 1.00 | 28.39 |
| ATOM | 3245 | OH2 | TIP | 318 | 36.457 | 40.128 | 67.298 | 1.00 | 21.69 |
| ATOM | 3248 | OH2 | TIP | 319 | 7.255 | 35.680 | 70.058 | 1.00 | 27.43 |
| ATOM | 3251 | OH2 | TIP | 320 | 30.841 | 70.291 | 80.575 | 1.00 | 23.02 |
| ATOM | 3254 | OH2 | TIP | 321 | 14.925 | 40.014 | 61.264 | 1.00 | 26.70 |
| ATOM | 3257 | OH2 | TIP | 322 | 31.382 | 27.308 | 96.035 | 1.00 | 29.30 |
| ATOM | 3260 | OH2 | TIP | 326 | 12.664 | 69.319 | 76.790 | 1.00 | 28.70 |
| ATOM | 3263 | OH2 | TIP | 328 | 24.561 | 28.442 | 74.415 | 1.00 | 22.89 |
| ATOM | 3266 | OH2 | TIP | 401 | -1.370 | 40.894 | 78.706 | 1.00 | 29.74 |
| ATOM | 3269 | OH2 | TIP | 402 | -2.963 | 40.727 | 83.815 | 1.00 | 25.79 |
| ATOM | 3272 | OH2 | TIP | 403 | 4.480 | 62.397 | 78.449 | 1.00 | 24.96 |
| ATOM | 3275 | OH2 | TIP | 404 | 28.503 | 42.194 | 86.865 | 1.00 | 24.37 |
| ATOM | 3278 | OH2 | TIP | 405 | 25.601 | 41.678 | 90.752 | 1.00 | 29.31 |
| ATOM | 3281 | OH2 | TIP | 406 | 26.920 | 40.776 | 88.387 | 1.00 | 22.18 |
| ATOM | 3284 | C1 | TES | 1 | 28.026 | 36.745 | 83.206 | 1.00 | 26.23 |
| ATOM | 3285 | C2 | TES | 1 | 27.098 | 35.935 | 82.522 | 1.00 | 28.23 |
| ATOM | 3286 | C3 | TES | 1 | 25.732 | 36.087 | 82.772 | 1.00 | 30.73 |
| ATOM | 3287 | C4 | TES | 1 | 25.332 | 37.036 | 83.738 | 1.00 | 32.50 |
| ATOM | 3288 | C5 | TES | 1 | 26.199 | 37.867 | 84.438 | 1.00 | 29.42 |
| ATOM | 3289 | C6 | TES | 1 | 27.611 | 37.743 | 84.158 | 1.00 | 26.82 |
| ATOM | 3290 | N9 | TES | 1 | 24.734 | 35.299 | 82.196 | 1.00 | 30.85 |
| ATOM | 3291 | C10 | TES | 1 | 23.467 | 35.429 | 82.580 | 1.00 | 32.47 |
| ATOM | 3292 | N11 | TES | 1 | 23.121 | 36.306 | 83.522 | 1.00 | 35.70 |
| ATOM | 3293 | C12 | TES | 1 | 24.037 | 36.980 | 83.968 | 1.00 | 35.86 |
| ATOM | 3294 | N14 | TES | 1 | 23.620 | 37.794 | 85.123 | 1.00 | 46.57 |
| ATOM | 3295 | C15 | TES | 1 | 22.214 | 37.861 | 85.791 | 1.00 | 38.82 |
| ATOM | 3296 | C17 | TES | 1 | 21.808 | 36.654 | 86.239 | 1.00 | 36.09 |
| ATOM | 3297 | C18 | TES | 1 | 20.479 | 36.587 | 86.764 | 1.00 | 33.24 |
| ATOM | 3298 | C19 | TES | 1 | 19.654 | 37.758 | 86.754 | 1.00 | 33.24 |
| ATOM | 3299 | C20 | TES | 1 | 20.175 | 39.021 | 86.274 | 1.00 | 35.21 |
| ATOM | 3300 | C21 | TES | 1 | 21.537 | 39.046 | 85.763 | 1.00 | 37.90 |
| ATOM | 3301 | BR6 | TES | 1 | 19.826 | 34.948 | 87.523 | 1.00 | 26.28 |
| ATOM | 3302 | O27 | TES | 1 | 28.634 | 38.634 | 84.699 | 1.00 | 25.71 |
| ATOM | 3303 | O28 | TES | 1 | 29.364 | 36.561 | 82.920 | 1.00 | 24.71 |
| ATOM | 3304 | C29 | TES | 1 | 29.806 | 35.929 | 81.654 | 1.00 | 22.79 |
| ATOM | 3305 | C33 | TES | 1 | 28.561 | 39.105 | 86.058 | 1.00 | 24.42 |
| ATOM | 3306 | H1 | TES | 1 | 24.353 | 38.267 | 85.518 | 1.00 | 20.00 |
| END | | | | | | | | | |

TABLE 8

Table of the statistics of diffraction data and refined complex structures

|  | Reso | Rsym (*) | Complete | unique | observed | Rref | Rfree |
|---|---|---|---|---|---|---|---|
| AMP-PNP1 | 1.6O | 5.9 (14.5%) | 98 (96%) | 38,529 | 258,235 | 20.0% | 23.0% |
| AMP-PNP2 | 2.2O | 4.2 (21.6%) | 96 (95%) | 15,024 | 54,174 | 23.7% | 27.0% |
| Staurosporine | 2.0O | 5.9 (12.1%) | 99 (100%) | 20,010 | 161,934 | 19.5% | 23.7% |
| PP2 | 2.0O | 8.2 (19.8%) | 93 (90%) | 19,946 | 53,618 | 18.9% | 25.4% |

Note: Rsyms in the parentheses are for the highest resolution shell. Fobs greater than 1σ are used in the structural refinement. In all the structures residues 231 to 501 of Lck are included in the final refined model with water molecules added. The N- and C- terminal segments (GS-225-230 and 502-509) are however disordered (GS are the two extra residues left from the thrombin cleavage). The RMS bond length and angles for the AMP-PNP/Lck complex, staurosporine and PP2 are 0.018O/ 2.1°, 0.109O/2.0°, 0.018O/1.8°, respectively. AMP-PNP1 and AMP-PNP2 correspond to Table 2 and Table 3 respectively.

TABLE 9

Table of the statistics of the refined complex structures

|  | Reso | Rref | Rfree | bond | bond angle |
|---|---|---|---|---|---|
| damnacanthal | 2.2O | 22.8% | 25.2% | 0.017O | 1.8° |
| baicalein | 2.1O | 20.9% | 22.5% | 0.018O | 1.7° |
| PD153035 | 2.0O | 23.2% | 25.9% | 0.018O | 2.2° |

What is claimed is:

1. A crystal of a protein-ligand complex comprising a protein-ligand complex of a truncated lck and a ligand, wherein the crystal effectively diffracts X-rays for the determination of the atomic coordinates of the protein-ligand complex to a resolution of greater than 5.0 Angstroms; and wherein the truncated lck: (a) comprises amino acids 225 to 508 of SEQ ID NO: 1 or an amino acid sequence that differs from amino acids 225 to 508 of SEQ ID NO: 1 by only conservative substitutions; and (b) retains the globular core of the corresponding full-length lck.

2. The crystal of claim 1, wherein the truncated lck comprises an amino acid sequence of amino acids 251 to 371 of SEQ ID NO: 1, or an amino acid sequence that differs from amino acids 251 to 371 of SEQ ID NO: 1 by only conservative substitutions.

3. The crystal of claim 1 or 2, wherein the ligand is baicalein.

4. The crystal of claim 1 or 2, wherein the ligand is damnacanthal.

5. The crystal of claim 1 or 2, wherein the ligand is PD153035.

6. The crystal of claim 3 having space group of $P2_12_12_1$ and a unit cell of dimensions of a=42.2 Å, b=73.9 Å, and c=91.7 Å.

7. The crystal of claim 3 having space group of $P2_12_12_1$ and a unit cell of dimensions of a=41.9 Å, b=73.6 Å, and c=92.3 Å.

8. The crystal of claim 4 having space group of $P2_12_12_1$ and a unit cell of dimensions of a=41.9 Å, b=73.6 Å, and c=92.3 Å.

9. The crystal of claim 5 having space group of $P2_12_12_1$ and a unit cell of dimensions of a=42.1 Å, b=73.8 Å, and c=92.3 Å.

10. The crystal of claim 1 wherein the kinase has secondary structural elements that include five beta strands and one helix in the N-terminal lobe designated as strands 1, 2,3, 4 and 5 and alpha helix C and two beta strands and seven alpha helices in the C-terminal domain designated as strands 6 & 8, and alpha helices D, E, F, G, H and I.

11. A method of using the crystal of claim 1 in an inhibitor screening assay comprising:
   (a) selecting a potential inhibitor by performing rational drug design with the three-dimensional structure determined for the crystal, wherein said selecting is performed in conjunction with computer modeling;
   (b) contacting the potential inhibitor with a kinase; and
   (c) detecting the ability of the potential inhibitor for inhibiting the kinase.

12. The method of claim 11, wherein detecting the ability of the potential inhibitor for inhibiting the kinase in step (c) is performed using an enzyme inhibition assay.

13. The method of claim 11, wherein detecting the ability of the potential inhibitor for inhibiting the kinase in step (c) is performed using a cellular-based assay.

14. The method of claim 11, further comprising:
   (d) growing a supplemental crystal comprising a protein-ligand complex formed between the kinase and a first potential inhibitor from step (a), wherein the supplemental crystal effectively diffracts X-rays for the determination of the atomic coordinates of the protein-ligand complex to a resolution of greater than 5.0 Angstroms;
   (e) determining the three-dimensional structure of the supplemental crystal;
   (f) selecting a second potential inhibitor by performing rational drug design with the three-dimensional structure determined for the supplemental crystal, wherein said selecting is performed in conjunction with computer modeling;
   (g) contacting the second potential inhibitor with a kinase; and
   (h) detecting the ability of the second potential inhibitor for inhibiting the kinase.

15. A method for identifying a potential inhibitor of a kinase comprising:
   (a) selecting or designing a potential inhibitor by performing rational drug design with the three-dimensional structure coordinates of any of Tables 1–7, wherein said selecting is performed in conjunction with computer modeling;
   (b) contacting the potential inhibitor with a kinase; and
   (c) detecting the ability of the potential inhibitor for inhibiting the kinase.

16. The method of claim 15, wherein detecting the ability of the potential inhibitor for inhibiting the kinase in step (c) is performed using an enzyme inhibition assay.

17. The method of claim 15, wherein detecting the ability of the potential inhibitor for inhibiting the kinase in step (c) is performed using a cellular-based assay.

18. The method of claim 15, wherein the potential inhibitor is designed de novo.

19. The method of claim 15, wherein the potential inhibitor is designed from a known inhibitor.

20. The method of claim 15 further comprising:
   (d) selecting an second potential inhibitor by performing rational drug design with the three-dimensional structure coordinates of any of Tables 1–7 and the potential inhibitor of step (a), wherein said selecting is performed in conjunction with computer modeling;
   (e) contacting the potential inhibitor with a kinase; and
   (f) detecting the ability of the potential inhibitor for inhibiting the kinase.

21. A method of using truncated lck to grow a crystal of a protein-ligand complex comprising:
   (a) contacting truncated lck with a ligand, wherein the truncated lck forms a protein-ligand complex with the ligand; and
   (b) growing the crystal of the protein-ligand complex; wherein the crystal effectively diffracts X-rays for the determination of the atomic coordinates of the protein-ligand complex to a resolution of greater than 5.0 Angstroms.

22. The method of claim 21, wherein said growing is performed by hanging drop vapor diffusion.

23. The method of claim 21, wherein said ligand is PP2, staurosporine, AMP-PNP, baicalein, damncanthal, or PD153035.

24. The method of claim 21, wherein said ligand is PP2.

25. A method of growing a crystal of a truncated lck-ligand complex wherein the crystal effectively diffracts X-rays for the determination of the atomic coordinates of the protein-ligand complex to a resolution of greater than 5.0 Angstroms, comprising:
   (a) contacting a truncated lck solution with a ligand, wherein the truncated lck forms a protein-ligand complex with the ligand; and
   (b) growing the crystal of the protein-ligand complex; wherein the crystal effectively diffracts X-rays for the determination of the atomic coordinates of the protein-ligand complex to a resolution of greater than 5.0 Angstroms.

26. The method of claim 25, wherein the growing is performed by hanging drop vapor diffusion.

27. The method of claim 25, wherein the ligand is PP2, staurosporine, AMP-PNP, baicalein, damnacanthal, or PD153035.

28. A method of producing a crystal of a truncated lck-ligand complex wherein the crystal effectively diffracts X-rays for the determination of the atomic coordinates of the protein-ligand complex to a resolution of greater than 5.0 Angstroms, comprising contacting a truncated lck crystal with a ligand, wherein the truncated lck forms a protein-ligand complex with the ligand within the crystal, and wherein the crystal effectively diffracts X-rays for the determination of the atomic coordinates of the protein-ligand complex to a resolution of greater than 5.0 Angstroms.

29. The method of claim 28, wherein the ligand is PP2, staurosporine, AMP-PNP, baicalein, damnacanthal, or PD153035.

30. A method of using the three-dimensional structure coordinates of any one of Tables 1–7, comprising:
  (a) determining structure factors from the coordinates; and
  (b) applying said structure factor information to a set of X-ray diffraction data obtained from a crystal of a protein homologous to SEQ ID NO: 1;
  (c) solving the three-dimensional structure of the protein homologous to SEQ ID NO: 1.

31. A computer readable data storage material encoded with computer readable data comprising structure coordinates of any one or more of Tables 1–7.

32. A computer readable data storage material encoded with computer readable data comprising structure coordinates of the active site of any one or more of Tables 1–7.

33. A method for identifying a potential inhibitor of a kinase comprising:
  (a) selecting or designing a potential inhibitor by performing rational drug design with a computer readable data storage material encoded with computer readable data comprising structure coordinates of any one or more of Tables 1–7, wherein said selecting is performed in conjunction with computer modeling;
  (b) contacting the potential inhibitor with a kinase; and
  (c) detecting the ability of the potential inhibitor for inhibiting the kinase.

34. The method of claim 33, wherein the computer readable data storage material is encoded with computer readable data comprising structure coordinates of the active site of any one or more of Tables 1–7.

35. A method for identifying a potential inhibitor of a kinase that covalently binds with Lys 273 of SEQ ID NO.: 1 or a homologous lysine residue in a kinase comprising:
  (a) selecting or designing a potential inhibitor by performing rational drug design with the three-dimensional structure coordinates of Table 6, wherein said selecting is performed in conjunction with computer modeling;
  (b) contacting the potential inhibitor with a kinase; and
  (c) detecting the ability of the potential inhibitor for inhibiting the kinase.

36. The method of claim 35, wherein the three-dimensional structure coordinates in step (a) further comprise one or more structure coordinates of Tables 1–5 or 7.

* * * * *